(12) United States Patent
Altenbach et al.

(10) Patent No.: US 9,981,910 B2
(45) Date of Patent: May 29, 2018

(54) SUBSTITUTED PYRROLIDINES AND METHODS OF USE

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Sylvain Couty, Gentilly (FR); Elsa De Lemos, Paris (FR); Nicolas Desroy, Massy (FR); Béranger Duthion, Paris (FR); Gregory A. Gfesser, Lindenhurst, IL (US); Stephen N. Greszler, Vernon Hills, IL (US); Christopher Gaëtan Housseman, Montreuil (FR); John R. Koenig, Chicago, IL (US); Philip R. Kym, Libertyville, IL (US); Bo Liu, Waukegan, IL (US); Marc J. Scanio, Libertyville, IL (US); Xenia Searle, Grayslake, IL (US); Xueqing Wang, Northbrook, IL (US); Ming C. Yeung, Grayslake, IL (US); Gang Zhao, Northbrook, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days. days.

(21) Appl. No.: 15/726,075

(22) Filed: Oct. 5, 2017

(65) Prior Publication Data

US 2018/0099931 A1    Apr. 12, 2018

Related U.S. Application Data

(60) Provisional application No. 62/405,598, filed on Oct. 7, 2016.

(51) Int. Cl.
| | | |
|---|---|---|
| C07D 207/14 | (2006.01) |
| C07D 207/48 | (2006.01) |
| C07D 413/06 | (2006.01) |
| C07D 401/12 | (2006.01) |
| C07D 403/12 | (2006.01) |
| C07D 417/12 | (2006.01) |
| A61K 31/401 | (2006.01) |
| A61K 31/427 | (2006.01) |
| A61K 31/4439 | (2006.01) |
| A61K 31/506 | (2006.01) |
| A61K 31/5377 | (2006.01) |

(52) U.S. Cl.
CPC ......... *C07D 207/14* (2013.01); *C07D 207/48* (2013.01)

(58) Field of Classification Search
None
See application file for complete search history.

(56) References Cited

U.S. PATENT DOCUMENTS

| | | |
|---|---|---|
| 8,999,976 B2 | 4/2015 | Binch et al. |
| 2016/0120841 A1 | 5/2016 | Altenbach et al. |
| 2016/0122331 A1 | 5/2016 | Kym et al. |
| 2017/0015675 A1 | 1/2017 | Altenbach et al. |
| 2017/0101405 A1 | 4/2017 | Akkari et al. |
| 2017/0101406 A1 | 4/2017 | Akkari et al. |
| 2017/0217627 A1 | 8/2017 | Earnshaw et al. |
| 2017/0233564 A1 | 8/2017 | Li et al. |

FOREIGN PATENT DOCUMENTS

| | | | |
|---|---|---|---|
| WO | 2005120497 A2 | 12/2005 | |
| WO | 2006002421 A2 | 1/2006 | |
| WO | 2008147952 A1 | 12/2008 | |
| WO | WO-2009003009 A1 * | 12/2008 | ........... C07D 401/14 |
| WO | 2009074575 A1 | 6/2009 | |
| WO | 2009076593 A1 | 6/2009 | |
| WO | 2010048573 A1 | 4/2010 | |
| WO | 2011072241 A1 | 6/2011 | |
| WO | 2011113894 A1 | 9/2011 | |

(Continued)

OTHER PUBLICATIONS

Quinton, P.M., 1990. Cystic fibrosis: a disease in electrolyte transport. FASEB J. 4, 2709-2717.
Kerem, B., Rommens, J.M., Buchanan, J.A., Markiewicz, D., Cox, T.K., Chakravarti, A., Buchwald, M., Tsui, L.C., 1989. Identification of the cystic fibrosis gene: genetic analysis. Science 245, 1073-1080.
Bobadilla, J.L., Macek, M., Jr, Fine, J.P., Farrell, P.M., 2002. Cystic fibrosis: a worldwide analysis of CFTR mutations-correlation with incidence data and application to screening. Hum. Mutat. 19, 575-606. doi:10.1002/humu.10041.

(Continued)

*Primary Examiner* — Michael Barker
(74) *Attorney, Agent, or Firm* — Quarles & Brady LLP

(57) ABSTRACT

The invention discloses compounds of Formula (I)

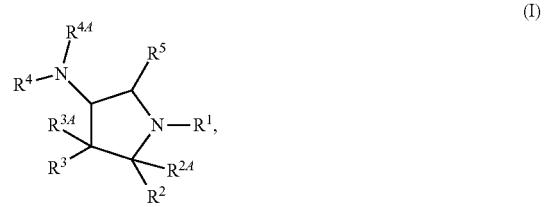

wherein $R^1$, $R^2$, $R^{2A}$, $R^3$, $R^{3A}$, $R^4$, $R^{4A}$, and $R^5$ are as defined herein. The present invention relates to compounds and their use in the treatment of cystic fibrosis, methods for their production, pharmaceutical compositions comprising the same, and methods of treating cystic fibrosis by administering a compound of the invention.

23 Claims, No Drawings

(56) References Cited

FOREIGN PATENT DOCUMENTS

| WO | 2012048181 A1 | 4/2012 |
|---|---|---|
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014180562 A1 | 11/2014 |
| WO | 2015018823 A1 | 2/2015 |
| WO | 2015138909 A1 | 9/2015 |
| WO | 2015138934 A1 | 9/2015 |
| WO | 2016193812 A1 | 12/2016 |

OTHER PUBLICATIONS

Pasyk, E.A., Foskett, J.K., 1995. Mutant (F508delCFTR) Cystic Fibrosis Transmembrane Conductance Regulator Cl-channel is functional when retained in Endoplasmic Reticulum of mammalian cells. J. Biol. Chem. 270, 12347-12350.

Morello, J.-P., Bouvier, M., Petäjä-Repo, U.E., Bichet, D.G., 2000. Pharmacological chaperones: a new twist on receptor folding. Trends Pharmacol. Sci. 21, 466-469. doi:10.1016/S0165-6147(00)01575-3.

Shastry, B.S., 2003. Neurodegenerative disorders of protein aggregation. Neurochem. Int. 43, 1-7. doi:10.1016/S0197-0186(02)00196-1.

Zhang, W., Fujii, N., Naren, A.P., 2012. Recent advances and new perspectives in targeting CFTR for therapy of cystic fibrosis and enterotoxin-induced secretory diarrheas. (Future Med. Chem. 4, 329-345. doi:10.4155/fmc.12.1).

IUPAC 1974 Recommendations for Section E, Fundamental Stereochemistry, in Pure Appl. Chem., 1976, 45: 13-30.

Yan, X.-X., Peng, Q., Zhang, Y., Zhang, K., Hong, W., Hou, X.-L. and Wu, Y.-D., Angew. Chem., Int. Ed. 2006, 45 1979-1983.

S. M. Berge et al. J. Pharmaceutical Sciences, 1977, 66: 1-19.

Veit G et al, (2012) Mol Biol Cell. 23(21): 4188-4202.

* cited by examiner

SUBSTITUTED PYRROLIDINES AND METHODS OF USE

CROSS-REFERENCE TO RELATED APPLICATIONS

This application claims priority to U.S. Provisional Application No. 62/405,598, filed Oct. 7, 2016, which is incorporated herein by its entirety for all purposes.

BACKGROUND OF THE INVENTION

Technical Field

The invention relates to substituted pyridine compounds that are modulators of the Cystic Fibrosis Transmembrane Conductance Regulator (CFTR) protein, useful in treating diseases and conditions mediated and modulated by CFTR. The invention also relates to compositions containing compounds of the invention, processes for their preparation, and methods of treatment using them.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi: 10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). F508delCFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if F508delCFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (F508delCFTR) Cystic Fibrosis Transmembrane Conductance Regulator Cl⁻ channel is functional when retained in Endoplasmic Reticulum of mammalian cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjögren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjogren's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjögren's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjögren's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the F508delCFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petaja-Repo, U. E., Bichet, D. G., 2000. Pharmacological chaperones: a new twist on receptor folding. Trends Pharmacol. Sci. 21, 466-469. doi: 10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. (Future Med. Chem. 4, 329-345. doi: 10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurohypophyseal DI (vasopressin hormone N2-receptor), nephrogenic DI (aquaporin II), Charcot-Marie Tooth syndrome (peripheral myelin protein 22), Pelizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebellar ataxia type I, spinal and bulbar muscular atrophy, dentatorubral pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjögren's syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect, the invention provides for compounds of Formula (I)

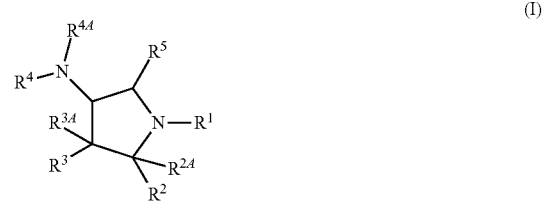

wherein
  $R^1$ is selected from the group consisting of $SO_2R^6$, $C(O)R^6$, $C(O)OR^6$, and $C(O)NR^7R^8$;
  $R^2$ is $C(O)OH$ or a bioisostere thereof;
  $R^{2A}$ is selected from the group consisting of hydrogen, $C_1$-$C_6$ alkyl, $C_1$-$C_6$ haloalkyl, and $C_3$-$C_6$ cycloalkyl;
  $R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen, $C_1$-$C_6$ alkyl, and $C_1$-$C_6$ haloalkyl; or $R^4$ and $R^{4A}$, together with the carbon to which they are attached, form 4-12 membered heterocyclyl; wherein the 4-12 membered heterocyclyl is optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl; $R^{21}$, at each occurrence, is independently selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein each R$^{21}$ C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of OH, oxo, CN, NO$_2$, F, Cl, Br and I;

R$^{22}$ and R$^{23}$, at each occurrence, are each independently hydrogen or C$_1$-C$_6$ alkyl;

R$^{24}$, at each occurrence, is independently selected from the group consisting of C$_1$-C$_6$ alkyl, C$_1$-C$_6$ haloalkyl, C$_1$-C$_6$ alkoxy-C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; and R$^{25}$ and R$^{26}$, at each occurrence, are each independently hydrogen or C$_1$-C$_6$ alkyl.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of Formula (I)

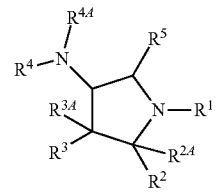

wherein R$^1$, R$^2$, R$^{2A}$, R$^3$, R$^{3A}$, R$^4$, R$^{4A}$, and R$^5$ are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_6$ alkenyl" means an alkenyl group containing 2-6 carbon atoms. Non-limiting examples of C$_2$-C$_6$ alkenyl include buta-1,3-dienyl, ethenyl, 2-propenyl, 2-methyl-2-propenyl, 3-butenyl, 4-pentenyl, and 5-hexenyl.

The term "C$_1$-C$_6$ alkoxy" as used herein, means a C$_1$-C$_6$ alkyl group, as defined herein, appended to the parent molecular moiety through an oxygen atom. Non-limiting examples of alkoxy include methoxy, ethoxy, propoxy, 2-propoxy, butoxy, tert-butoxy, pentyloxy, and hexyloxy.

The term "alkyl" as used herein, means a saturated, straight or branched hydrocarbon chain radical. In some instances, the number of carbon atoms in an alkyl moiety is indicated by the prefix "C$_x$-C$_y$," wherein x is the minimum and y is the maximum number of carbon atoms in the substituent. Thus, for example, "C$_1$-C$_6$ alkyl" means an alkyl substituent containing from 1 to 6 carbon atoms and "C$_1$-C$_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —$CH_2$—, —$CH_2CH_2$—, —$C(CH_3)_2$—$CH_2CH_2CH_2$—, —$C(CH_3)_2$—$CH_2CH_2$—, —$CH_2CH_2CH_2CH_2$—, and —$CH_2CH(CH_3)CH_2$—.

The term, "alkenylene" as used herein, means a divalent radical derived from a straight or branched hydrocarbon chain containing at least one carbon-carbon double bond. The term, "$C_2$-$C_6$ alkenylene" as used herein, means a divalent radical derived from a straight or branched hydrocarbon chain containing from 2 to 6 carbons and containing at least one carbon-carbon double bond.

The term, "alkynylene" as used herein, means a divalent radical derived from straight or branched chain hydrocarbon radical containing at least one carbon-carbon triple bond. The term, "$C_2$-$C_6$ alkynylene" as used herein, means a divalent radical derived from straight or branched chain hydrocarbon radical containing from 2 to 6 carbon atoms and containing at least one carbon-carbon triple bond.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_3$-$C_{11}$ cycloalkyl" as used herein, means a hydrocarbon ring radical containing 3-11 carbon atoms, zero heteroatoms, and zero double bonds. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_{11}$ monocyclic cycloalkyl), and even more typically 3-6 carbon ring atoms ($C_3$-$C_6$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. Examples of a spirocyclic cycloalkyl include spiro[2.5]octanyl and spiro[4.5]decanyl. In a bridged cycloalkyl, the rings share at least two non-adjacent atoms. Examples of bridged cycloalkyls include, but are not limited to bicyclo[1.1.1]pentanyl, bicyclo[2.2.2]octyl, bicyclo[3.2.1]octyl, bicyclo[3.1.1]heptyl, bicyclo[2.2.1]heptyl, bicyclo[3.2.2]nonyl, bicyclo[3.3.1]nonyl, and bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[4.3.1.1$^{3,8}$]undecyl (homoadamantyl). In a fused ring cycloalkyl, the rings share one common bond.

Examples of fused-ring cycloalkyl include, but not limited to, decalin (decahydronaphthyl), bicyclo[3.1.0]hexanyl, and bicyclo[2.2.0]octyl.

The term "$C_3$-$C_6$ cycloalkyl" as used herein, means a hydrocarbon ring radical containing 3-6 carbon atoms, zero heteroatoms, and zero double bonds. The $C_3$-$C_6$ cycloalkyl group may be a single-ring (monocyclic) or have two rings (bicyclic).

The term "$C_4$-$C_{11}$ cycloalkenyl" as used herein, means a non-aromatic hydrocarbon ring radical containing 4-11 carbon atoms, zero heteroatoms, and one or more double bonds. The $C_4$-$C_{11}$ cycloalkenyl group may be a single-ring (monocyclic) or have two or more rings (polycyclic or bicyclic). Examples of monocyclic cycloalkenyl include cyclobutenyl, cyclopentenyl, cyclohexenyl, cyclohexadienyl, cycloheptyl, cyclooctenyl, and cyclooctadienyl. Examples of bicyclic cycloalkenyl include bicyclo[2.2.1]hept-2-enyl.

The term "$C_4$-$C_8$ monocyclic cycloalkenyl" as used herein, means cyclobutenyl, cyclopentenyl, cyclohexenyl, cyclohexadienyl, cycloheptyl, cycloheptadienyl, cyclooctenyl, and cyclooctadienyl.

The term "$C_4$-$C_7$ monocyclic cycloalkenyl" as used herein, means cyclobutenyl, cyclopentenyl, cyclohexenyl, cyclohexadienyl, and cycloheptyl.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "haloalkoxy" as used herein, means an alkoxy group, as defined herein, in which one, two, three, four, five or six hydrogen atoms are replaced by halogen. The term "$C_1$-$C_6$ haloalkoxy" means a $C_1$-$C_6$ alkoxy group, as defined herein, in which one, two, three, four, five, or six hydrogen atoms are replaced by halogen.

The term "4-12 membered heterocycle" as used herein, means a hydrocarbon ring radical of 4-12 carbon ring atoms wherein at least one carbon atom is replaced by a heteroatom(s) independently selected from the group consisting of O, N, and S. The 4-12 membered heterocycle ring may be a single ring (monocyclic) or have two or more rings (bicyclic or polycyclic). In certain embodiments, the monocyclic heterocycle is a four-, five-, six-, seven-, or eight-membered hydrocarbon ring wherein at least one carbon ring atom is replaced by a heteroatom(s) independently selected from the group consisting of O, N, and S. In certain embodiments, the monocyclic heterocycle is a 4-7 membered hydrocarbon ring wherein at least one carbon ring atom is replaced by a heteroatom(s). A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S. Examples of monocyclic heterocycles include, but are not limited to, azetidinyl, azepanyl, aziridinyl, 1,4-diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxazepanyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups may be in a bridged, fused, or spiro orientation, or combinations thereof. In a spirocyclic heterocycle, one atom is common to two different rings. Non limiting examples of the spirocyclic heterocycle include 6-oxaspiro[2.5]octanyl, 2-azaspiro[3.3]heptyl, 5-azaspiro[2.4]heptyl, 5-azaspiro[2.5]octyl, 2-azaspiro[3.5]nonyl, 2-azaspiro[3.4]octyl, 3-azaspiro[5.5]undecyl, 5-azaspiro[3.4]octyl, 2-oxaspiro[3.3]heptyl, 2-oxa-6-azaspiro[3.3]heptyl, 6-oxa-2-azaspiro[3.4]octyl, 6-azaspiro[3.4]octyl, 7-azaspiro[3.5]nonyl, 8-azaspiro[4.5]decyl, 1-oxa-7-azaspiro[4.4]nonyl, 1-oxa-7-azaspiro[3.5]nonyl, 1-oxa-8-azaspiro[4.5]decyl, 1-oxa-3,8-diazaspiro[4.5]decyl, 1-oxa-4,9-diazaspiro[5.5]undecyl, 2-oxa-7-azaspiro[3.5]nonyl, 5-oxa-2-azaspiro[3.5]nonyl, 6-oxa-2-azaspiro[3.5]nonyl, 7-oxa-2-azaspiro[3.5]nonyl, 8-oxa-2-azaspiro[4.5]decyl, 2,7-diazaspiro[4.4]nonyl, 1,4-dioxa-8-azaspiro[4.5]decyl, 1,3,8-triazaspiro[4.5]decyl. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a $C_3-C_6$ monocyclic cycloalkyl, or a 4-6 membered monocyclic heterocycle fused to a $C_4-C_7$ monocyclic cycloalkenyl, or a 4-6 membered monocyclic heterocycle fused to a 4-7 membered monocyclic heterocycle. Examples of fused bicyclic heterocycles include, but are not limited to, 1,2-dihydrophthalazinyl, 3,4-dihydro-2H-benzo[b][1,4]dioxepinyl, chromanyl, chromenyl, isochromanyl, 2,3-dihydrobenzo[b][1,4]dioxinyl, isoindolinyl, 2,3-dihydrobenzo[b]thienyl, hexahydro-1H-cyclopenta[c]furanyl, 3-oxabicyclo[3.1.0]hexanyl, 3-azabicyclo[3.1.0]hexyl, benzopyranyl, benzothiopyranyl, indolinyl, decahydropyrrolo[3,4-b]azepinyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido [1,2-a]pyrazin-2-yl, hexahydropyrano[3,4-b][1,4]oxazin-1(5H)-yl, hexahydropyrrolo[3,4-c]pyrrol-2(1H)-yl, hexahydrocyclopenta[c]pyrrol-3a(1H)-yl, hexahydro-1H-oxazolo[3,4-a]pyrazinyl, octahydropyrrolo[3,4-b][1,4]oxazinyl, octahydroimidazo[1,5-a]pyrazinyl, octahydropyrrolo[1,2-a]pyrazinyl, octahydro-1H-pyrrolo[3,2-c]pyridinyl, and octahydropyrrolo[3,4-c]pyrrolyl. In a bridged heterocycle, the rings share at least two non-adjacent atoms. Examples of such bridged heterocycles include, but are not limited to, 8-oxabicyclo[3.2.1]octanyl, 7-oxabicyclo[2.2.1]heptanyl, azabicyclo[2.2.1]heptyl (including 2-azabicyclo[2.2.1]hept-2-yl), 8-azabicyclo[3.2.1]oct-8-yl, octahydro-2,5-epoxypentalene, 8-oxa-3-azabicyclo[3.2.1]octyl, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quaternized. Non limiting examples of the polycyclic heterocycle include 6,7-dihydro-[1,3]dioxolo[4,5-f]benzofuranyl.

The term "4-6 membered heterocycle" as used herein, means a hydrocarbon ring radical of 4-6 carbon ring atoms wherein at least one carbon atom is replaced by a heteroatom (s) independently selected from the group consisting of O, N, and S. A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1N; 1 Sand 1 N; 1 S and 2N; 1 Sand 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl.

The term "5-11 membered heteroaryl" as used herein, means a monocyclic heteroaryl and a bicyclic heteroaryl. The "5-7 membered heteroaryl" is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridazinonyl, pyridinonyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_6$ monocyclic cycloalkyl, or a monocyclic heteroaryl fused to $C_4$-$C_7$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, 4H-furo[3,2-b]pyrrolyl, benzofuranyl, benzothienyl, benzoisoxazolyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 4,5,6,7-tetrahydropyrazolo[1,5-a]pyridinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The nitrogen atom in the heteroaryl rings may optionally be oxidized and may optionally be alkylated.

The term "6-10 membered aryl", as used herein, means a hydrocarbon ring radical containing 6-10 carbon atoms, zero heteroatoms, and one or more aromatic rings. The 6-10 membered aryl group may be a single-ring (monocyclic) or have two rings (bicyclic). The bicyclic aryl is naphthyl, or a phenyl fused to a monocyclic cycloalkyl, or a phenyl fused to a monocyclic cycloalkenyl. Representative examples of 6-10 membered aryl groups include, but are not limited to, phenyl, indenyl, tetrahydronaphthalenyl, dihydroindenyl (indanyl), naphthyl, and the like.

The aryls, the cycloalkyls, the cycloalkenyls, the heterocycles, and the heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term "one or more" refers to one to eight. In one embodiment it refers to one to eight. In one embodiment it refers to one to seven. In one embodiment it refers to one to six. In one embodiment it refers to one to five. In one embodiment it refers to one to four. In one embodiment it refers to one or three. In another embodiment it refers to one to three. In a further embodiment it refers to one to two. In yet other embodiment it refers to two. In yet other further embodiment it refers to one.

The term "bioisostere", as used herein, means a moiety with substantially similar physical or chemical properties that imparts similar biological properties to the compound having Formula (I). Examples of —C(O)OH bioisosteres include —P(O)(OH)$_2$, —P(O)(OH)(H), —P(O)(OH)(O—$C_1$-$C_6$ alkyl), —P(O)(CH$_3$)(OH), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$) =NC(O)R$^{G3a}$, —C(O)NHS(O)(R$^{G3a}$)=NR$^{G3b}$,

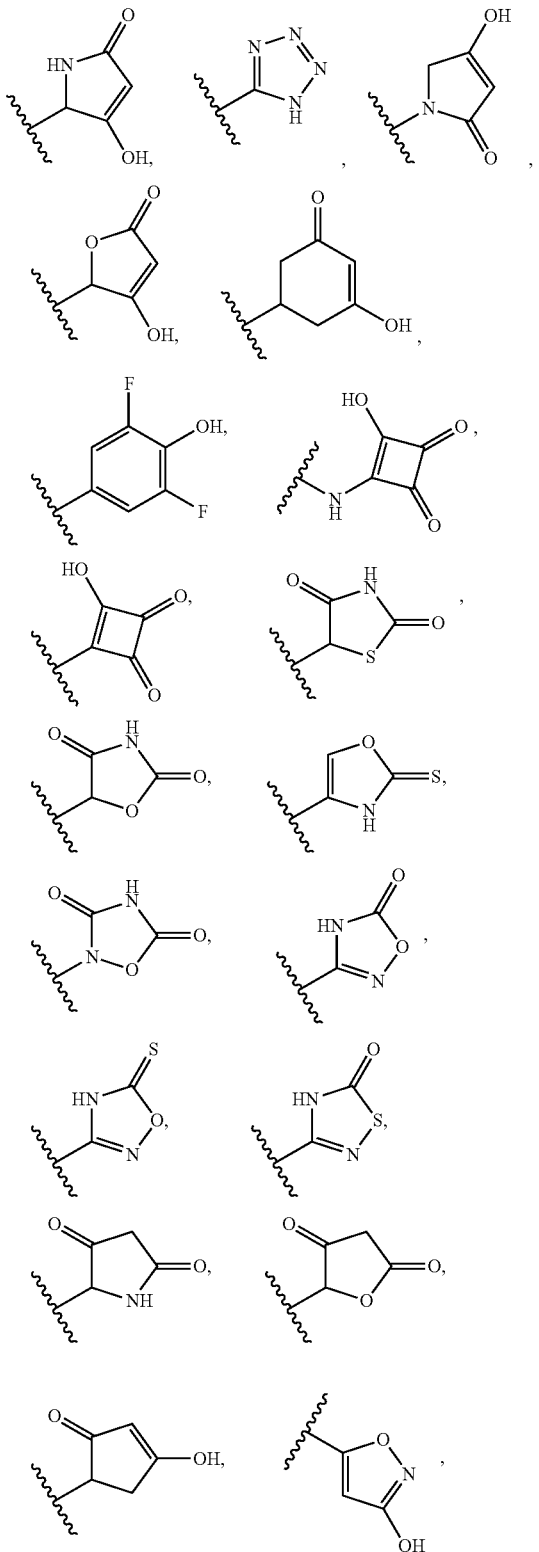

and ; wherein

R$^{G3a}$, at each occurrence, is independently C$_1$-C$_6$ alkyl, C$_1$-C$_6$ alkyl-O—C$_1$-C$_6$ alkyl, C$_1$-C$_6$ haloalkyl, or G$^A$;
R$^{G3b}$ is hydrogen, C$_1$-C$_6$ alkyl, or C$_1$-C$_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected RU groups; wherein
R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, —NO$_2$, —OR$^j$, —OC(O)R$^k$, —OC(O)N(R$^j$)$_2$, —S(O)$_2$R, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
R$^j$, at each occurrence, is independently selected from the group consisting of hydrogen, C$_1$-C$_6$ alkyl, or C$_1$-C$_6$ haloalkyl; and
R$^k$, at each occurrence, is independently selected from the group consisting of C$_1$-C$_6$ alkyl or C$_1$-C$_6$ haloalkyl.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to Phe508del (F508del), Ile507del, or Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120de123, N287Y, 4326dellTC, or 4279insA mutations. More particularly, Class VI mutation(s) refers to Rescued F508del mutations.

Compounds

Compounds of the invention have the general Formula (I) as described above.

Particular values of variable groups are as follows. Such values may be used where appropriate with any of the other values, definitions, claims or embodiments defined hereinbefore or hereinafter.

Formula (I)

One embodiment pertains to compounds of Formula (I),

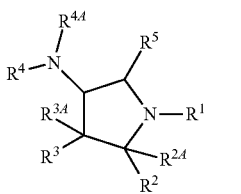

(I)

wherein
- $R^1$ is selected from the group consisting of $SO_2R^6$, $C(O)R^6$, $C(O)OR^6$, and $C(O)NR^7R^8$;
- $R^2$ is $C(O)OH$ or a bioisostere thereof;
- $R^{2A}$ is selected from the group consisting of hydrogen, $C_1$-$C_6$ alkyl, $C_1$-$C_6$ haloalkyl, and $C_3$-$C_6$ cycloalkyl;
- $R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and
- $R^{3A}$ is selected from the group consisting of hydrogen, $C_1$-$C_6$ alkyl, and $C_1$-$C_6$ haloalkyl; or
- $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;
- $R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and
- $R^{4A}$ is selected from the group consisting of hydrogen, $C_1$-$C_6$ alkyl, and $C_1$-$C_6$ haloalkyl; or
- $R^4$ and $R^{4A}$, together with the carbon to which they are attached, form 4-12 membered heterocyclyl; wherein the 4-12 membered heterocyclyl is optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;
- $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;
- $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;
- $R^7$ and $R^8$ are each independently hydrogen or $C_1$-$C_6$ alkyl;
- $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^9C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

Another embodiment pertains to compounds of Formula (I), wherein $R^1$ is selected from the group consisting of $SO_2R^6$, $C(O)R^6$, $C(O)OR^6$, and $C(O)NR^7R^8$;

$R^2$ is C(O)OH or a bioisostere thereof, $R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$-$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^{4A}$ is selected from the group consisting of hydrogen, $C_1$-$C_6$ alkyl, and $C_1$-$C_6$ haloalkyl;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (I), $R^1$ is selected from the group consisting of $SO_2R^6$, $C(O)R^6$, $C(O)OR^6$, and $C(O)NR^7R^8$. In another embodiment of Formula (I), $R^1$ is $C(O)R^6$ or $C(O)OR^6$. In another embodiment of Formula (I), $R^1$ is $SO_2R^6$. In another embodiment of Formula (I), $R^1$ is $C(O)R^6$. In another embodiment of Formula (I), $R^1$ is $C(O)OR^6$. In another embodiment of Formula (I), $R^1$ is $C(O)NR^7R^8$.

In one embodiment of Formula (I), $R^2$ is C(O)OH or a bioisostere thereof. In another embodiment of Formula (I), $R^2$ is —$P(O)(OH)_2$, —P(O)(OH)(H), —P(O)(OH)(O—$C_1$-$C_6$ alkyl), —$P(O)(CH_3)(OH)$, —$B(OH)_2$, —$SO_3H$, —CH(OH)$CF_3$, —C(O)NH(OH), —C(O)NH(CN), —C(O)NHSO$_2R^{G3a}$, —SO$_2$NHC(O)$R^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$

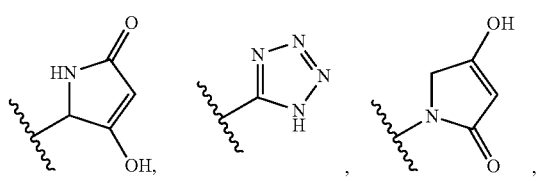

-continued

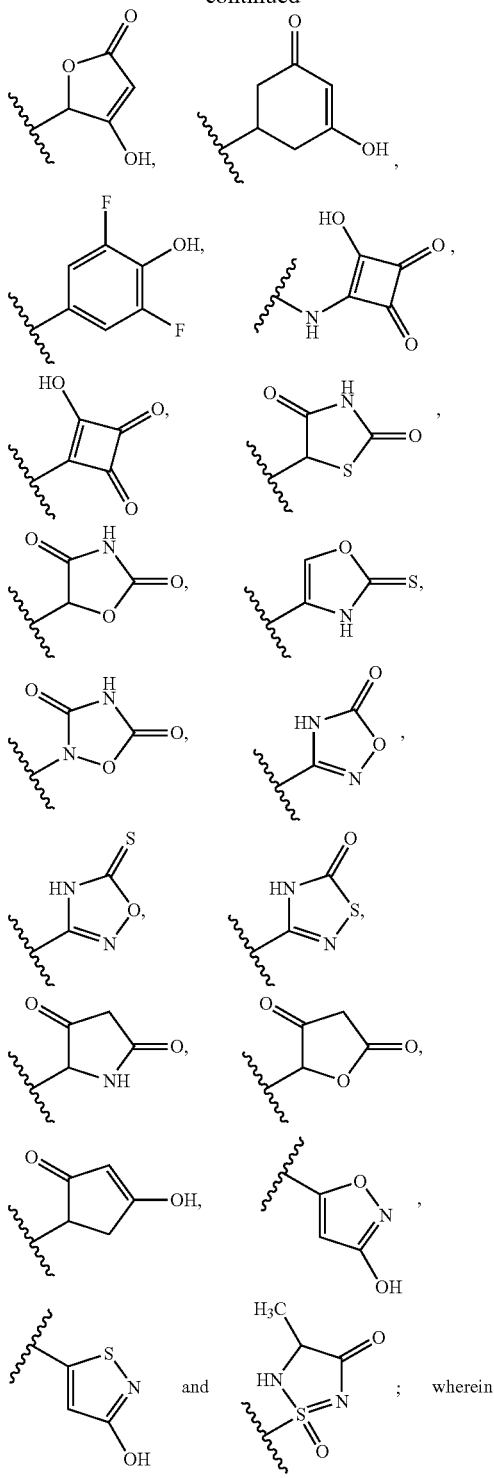

$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected RU groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —$NO_2$, —$OR^j$, —$OC(O)R^k$, —$OC(O)N(R^j)_2$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, or —$N(R^j)C(O)N(R^j)_2$;
$R^j$, at each occurrence, is independently selected from the group consisting of hydrogen, $C_1$-$C_6$ alkyl, or $C_1$-$C_6$ haloalkyl; and
$R^k$, at each occurrence, is independently selected from the group consisting of $C_1$-$C_6$ alkyl or $C_1$-$C_6$ haloalkyl. In another embodiment of Formula (I), $R^2$ is —$P(O)(OH)_2$, —$P(O)(OH)(H)$, —$B(OH)_2$, —$SO_3H$, —$CH(OH)CF_3$, —$C(O)NH(OH)$, —$C(O)NH(CN)$, —$C(O)NHSO_2R^{G3a}$, —$SO_2NHC(O)R^{G3a}$, —$C(O)NHSO_2NHR^{G3a}$, —$C(O)NHSO_2N(R^{G3a})_2$, —$SO_2NH_2$, —$SO_2NHR^{G3a}$, —$SO_2N(R^{G3a})_2$, —$C(O)NHS(O)(R^{G3a})$=$NC(O)R^{G3a}$, —$C(O)NHS(O)(R^{G3a})$=$NR^{G3b}$, or

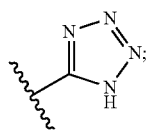

wherein
$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected RU groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —$NO_2$, —$OR^j$, —$OC(O)R^k$, —$OC(O)N(R^j)_2$, —$S(O)_2R^j$, —$S(O)_2N(R^j)_2$, —$C(O)R^k$, —$C(O)OR^j$, —$C(O)N(R^j)_2$, —$N(R^j)_2$, —$N(R^j)C(O)R^k$, —$N(R^j)S(O)_2R^k$, —$N(R^j)C(O)O(R^k)$, or —$N(R^j)C(O)N(R^j)_2$;
$R^j$, at each occurrence, is independently selected from the group consisting of hydrogen, $C_1$-$C_6$ alkyl, or $C_1$-$C_6$ haloalkyl; and
$R^k$, at each occurrence, is independently selected from the group consisting of $C_1$-$C_6$ alkyl or $C_1$-$C_6$ haloalkyl.

In another embodiment of Formula (I), $R^2$ is C(O)OH. In another embodiment of Formula (I), $R^2$ is —$C(O)NHSO_2R^{G3a}$ or —$C(O)NHSO_2N(R^{G3a})_2$; $R^{G3a}$, at each occurrence, is independently $C_1$-$C_6$ alkyl, $C_1$-$C_6$ alkyl-O—$C_1$-$C_6$ alkyl, or $G^A$; and $G^A$, at each occurrence, is independently cycloalkyl, which is independently unsubstituted or substituted with 1, 2, or 3 independently selected $R^u$ groups; wherein $R^u$, at each occurrence, is independently $C_1$-$C_6$ alkyl. In another embodiment of Formula (I), $R^2$ is —$C(O)NHSO_2R^{G3a}$; $R^{G3a}$, at each occurrence, is independently $C_1$-$C_6$ alkyl, $C_1$-$C_6$ alkyl-O—$C_1$-$C_6$ alkyl, or $G^A$; and $G^A$, at each occurrence, is independently cycloalkyl, which is independently unsubstituted or substituted with 1, 2, or 3 independently selected $R^u$ groups; wherein $R^u$, at each occurrence, is independently $C_1$-$C_6$ alkyl. In another embodiment of Formula (I), $R^2$ is —$C(O)NHSO_2N(R^{G3a})_2$; and $R^{G3a}$, at each occurrence, is independently $C_1$-$C_6$ alkyl.

In one embodiment of Formula (I), $R^{2A}$ is selected from the group consisting of hydrogen, $C_1$-$C_6$ alkyl, $C_1$-$C_6$ haloalkyl, and $C_3$-$C_6$ cycloalkyl. In another embodiment of Formula (I), $R^{2A}$ is hydrogen or $C_1$-$C_6$ alkyl. In another embodiment of Formula (I), $R^{2A}$ is hydrogen. In another embodiment of Formula (I), $R^{2A}$ is $C_1$-$C_6$ alkyl. In another embodiment of Formula (I), $R^{2A}$ is $CH_3$.

In one embodiment of Formula (I), $R^2$ is C(O)OH; and $R^{2A}$ is hydrogen.

In one embodiment of Formula (I),
$R^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or

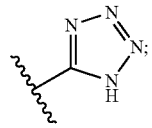 [SMILES: *c1nnn[nH]1]

$R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;
$R^{G3b}$ is hydrogen, $C_1$-$C_6$ alkyl, or $C_1$-$C_6$ haloalkyl or $G^A$;
$G^A$, at each occurrence, is independently cycloalkyl, cycloalkenyl, aryl, or heteroaryl, each of which is independently unsubstituted or substituted with 1, 2, or 3 independently selected $R^u$ groups; wherein
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
$R^j$, at each occurrence, is independently selected from the group consisting of hydrogen, $C_1$-$C_6$ alkyl, or $C_1$-$C_6$ haloalkyl;
$R^k$, at each occurrence, is independently selected from the group consisting of $C_1$-$C_6$ alkyl or $C_1$-$C_6$ haloalkyl; and $R^{2A}$ is hydrogen. In one embodiment of Formula (I), $R^2$ is —C(O)NHSO$_2$R$^{G3a}$ or —C(O)NHSO$_2$N(R$^{G3a}$)$_2$;
$R^{G3a}$, at each occurrence, is independently $C_1$-$C_6$ alkyl, $C_1$-$C_6$ alkyl-O—$C_1$-$C_6$ alkyl, or $G^A$;
$G^A$, at each occurrence, is independently cycloalkyl, which is independently unsubstituted or substituted with 1, 2, or 3 independently selected $R^u$ groups;
$R^u$, at each occurrence, is independently $C_1$-$C_6$ alkyl; and $R^{2A}$ is hydrogen.

In one embodiment of Formula (I), $R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, NO$_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I; and $R^{3A}$ is independently selected from the group consisting of hydrogen, $C_1$-$C_6$ alkyl, and $C_1$-$C_6$ haloalkyl. In another embodiment of Formula (I), $R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with one or more $C_1$-$C_6$ alkyl; and $R^{3A}$ is independently hydrogen. In another embodiment of Formula (I), $R^3$ is $C_1$-$C_6$ alkyl; wherein the $R^3$ $C_1$-$C_6$ alkyl is optionally substituted with one or more $C_1$-$C_6$ alkoxy; and $R^{3A}$ is independently hydrogen. In another embodiment of Formula (I), $R^3$ is $C_3$-$C_6$ cycloalkyl; wherein the $R^3$ $C_3$-$C_6$ cycloalkyl is optionally substituted with one or more $C_1$-$C_6$ alkyl; and $R^{3A}$ is hydrogen. In one embodiment of Formula (I), $R^3$ is $CH_3$, and $R^{3A}$ is hydrogen. In one embodiment of Formula (I), $R^3$ is C(CH$_3$)$_3$, and $R^{3A}$ is hydrogen. In one embodiment of Formula (I), $R^3$ is C(OCH$_3$)(CH$_3$)$_2$, and $R^{3A}$ is hydrogen. In one embodiment of Formula (I), $R^3$ is cyclopropyl wherein the $R^3$ cyclopropyl is optionally substituted with one $CH_3$; and $R^{3A}$ is hydrogen. In one embodiment of Formula (I), $R^3$ is bicyclo[1.1.1]pentanyl, and $R^{3A}$ is hydrogen.

In one embodiment of Formula (I), $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I. In another embodiment of Formula (I), $R^3$ and $R^{3A}$, together with the carbon to which they are attached, form $C_3$-$C_6$ cycloalkyl, which is unsubstituted. In another embodiment of Formula (I), $R^3$ and $R^{3A}$ together with the carbon to which they are attached, form cyclopropyl.

In one embodiment of Formula (I), $R^4$ is selected from the group consisting of $L^1$-$C_6$-$C_{10}$ aryl, $L^1$-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen, $C_1$-$C_6$ alkyl, and $C_1$-$C_6$ haloalkyl. In another embodiment of Formula (I), $R^4$ is selected from the group consisting of $L^1$-$C_6$-$C_{10}$ aryl, $L^1$-5-11 membered heteroaryl, $L^1$-4-12 membered heterocyclyl, and $L^1$-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, OR$^9$, C(O)OR$^9$, SR$^9$, NR$^{10}$R$^{11}$, Si(R$^9$)$_3$, SF$_5$, SO$_2$R$^9$, OH, CN, F, Cl, and Br; wherein $L^1$ is absent or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen, and $C_1$-$C_6$ alkyl. In another embodiment of Formula (I), $R^4$ is $L^1$-$C_6$-$C_{10}$ aryl; wherein the $R^4$ $C_6$-$C_{10}$ aryl is optionally substituted with one or more substituents independently selected from the group consisting of $R^9$, OR$^9$, C(O)OR$^9$, SR$^9$, NR$^{10}$R$^{11}$, Si(R$^9$)$_3$, SF$_5$, SO$_2$R$^9$, OH, CN, F, Cl, and Br; wherein $L^1$ is $C_1$-$C_6$ alkylene; and $R^{4A}$ is hydrogen. In another embodiment of Formula (I), $R^4$ is $L^1$-5-11 membered heteroaryl; wherein the $R^4$ 5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4A}$ is hydrogen. In another embodiment of Formula (I), $R^4$ is $L^1$-4-12 membered heterocyclyl; wherein the $R^4$ 4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4A}$ is hydrogen. In another embodiment of Formula (I), $R^4$ is $L^1$-$C_3$-$C_{11}$ cycloalkyl; wherein the $R^4$ $L^1$-$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4A}$ is hydrogen. In one embodiment of Formula (I), $R^4$ and $R^{4A}$, together with the carbon to which they are attached, form 4-12 membered heterocyclyl; wherein the 4-12 membered heterocyclyl is optionally substituted with one or more substituents independently selected from the group consisting of $R^9$, $OR^9$, $C(O)OR^9$, $C(O)NR^{10}R^{11}$ $SR^9$, $NR^{10}R^{11}$, $Si(R^9)_3$, $SF_5$, $SO_2R^9$, OH, oxo, CN, $NO_2$, F, Cl, Br and I. In another embodiment of Formula (I), $R^4$ and $R^{4A}$, together with the carbon to which they are attached, form 4-12 membered heterocyclyl; wherein the 4-12 membered heterocyclyl is optionally substituted with one or more substituents independently selected from the group consisting of $OR^9$, and Cl.

In one embodiment of Formula (I), $R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$-$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; $R^{4A}$ is selected from the group consisting of hydrogen, $C_1$-$C_6$ alkyl, and $C_1$-$C_6$ haloalkyl; and x is 0 or 1. In another embodiment of Formula (I), $R^4$ is selected from the group consisting of $(C_1$-$C_6$ alkylene$)_x$-$C_6$-$C_{10}$ aryl, $(C_1$-$C_6$ alkylene)-5-11 membered heteroaryl, $(C_1$-$C_6$ alkylene$)_x$-4-12 membered heterocyclyl, and $(C_1$-$C_6$ alkylene$)_x$-$C_3$-$C_{11}$ cycloalkyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, and the $C_3$-$C_{11}$ cycloalkyl of $(C_1$-$C_6$ alkylene$)_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4A}$ is hydrogen; and x is 0 or 1. In another embodiment of Formula (I), $R^4$ is $(C_1$-$C_6$ alkylene$)_x$-$C_6$-$C_{10}$ aryl; wherein the $R^4$ $(C_1$-$C_6$ alkylene$)_x$-$C_6$-$C_{10}$ membered aryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4A}$ is hydrogen; and x is 0 or 1.

In another embodiment of Formula (I), $R^4$ is $(C_1$-$C_6$ alkylene$)_x$-5-11 membered heteroaryl; wherein the $R^4$ $(C_1$-$C_6$ alkylene$)_x$-5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4A}$ is hydrogen; and x is 0 or 1. In another embodiment of Formula (I), $R^4$ is $(C_1$-$C_6$ alkylene$)_x$-4-12 membered heterocyclyl; wherein the $R^4$ $(C_1$-$C_6$ alkylene$)_x$-4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4A}$ is hydrogen; and x is 0 or 1. In another embodiment of Formula (I), $R^4$ is $(C_1$-$C_6$ alkylene$)_x$-$C_3$-$C_{11}$ cycloalkyl; wherein the $R^4$ $(C_1$-$C_6$ alkylene$)_x$-$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4A}$ is hydrogen; and x is 0 or 1.

In one embodiment of Formula (I), $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (I), $R^5$ is selected from the group consisting of $C_6$-$C_{10}$ membered aryl, 4-6 membered monocyclic heterocycle fused to a phenyl group, and 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is selected from the group consisting of $C_6$-$C_{10}$ membered aryl, 4-6 membered monocyclic heterocycle fused to a phenyl group, and 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl)$_2$, OH, oxo, CN, NO$_2$, F, Cl, Br and I; and $R^{13}$ and $R^{14}$, at each occurrence, are each independently $C_1$-$C_6$ alkyl.

In one embodiment of Formula (I), $R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, NO$_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I; and $R^{13}$ and $R^{14}$, at each occurrence, are each independently hydrogen or $C_1$-$C_6$ alkyl. In another embodiment of Formula (I), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13R14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^3$ and $R^{14}$, at each occurrence, are each independently $C_1$-$C_6$ alkyl. In another embodiment of Formula (I), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I; and $R^{13}$ and $R^{14}$, at each occurrence, are each independently $C_1$-$C_6$ alkyl.

In another embodiment of Formula (I), $R^5$ is $C_6$-$C_{10}$ membered aryl; wherein the $R^5$ $C_6$-$C_{10}$ membered aryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is 4-6 membered monocyclic heterocycle fused to a phenyl group; wherein the $R^5$ 4-6 membered monocyclic heterocycle fused to a phenyl group is optionally substituted with one or more substituents independently selected from the group consisting of $R^{12}$, $OR^{12}$, $NR^{13}R^{14}$ OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl)$_2$, OH, oxo, CN, NO$_2$, OH, F, Cl, Br and I; and $R^{13}$ and $R^{14}$, at each occurrence, are each independently $C_1$-$C_6$ alkyl.

In another embodiment of Formula (I), $R^5$ is phenyl, which is unsubstituted. In another embodiment of Formula (I), $R^5$ is phenyl; wherein the $R^5$ phenyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (I), $R^5$ is phenyl; which is substituted with one $R^{12}$; and $R^{12}$ is $C_1$-$C_6$ alkyl. In another embodiment of Formula (I), $R^5$ is phenyl; which is substituted with one $R^{12}$; and $R^{12}$ is $CH_3$ or $CH(CH_3)_2$. In another embodiment of Formula (I), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (I), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (I), $R^5$ is pyridinyl; wherein the $R^5$ pyridinyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl.

In one embodiment of Formula (I), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, NO$_2$, F, Cl, Br and I; wherein the $R^6$ 6-10 membered aryl, 5-11 membered heteroaryl, $C_3$-$C_1$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (I), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl is optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; $R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (I), $R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$, $SR^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl. In another embodiment of Formula (I), $R^6$ is $C_1$-$C_6$ alkyl; wherein the $R^6$ $C_1$-$C_6$ alkyl is substituted with one $R^{15}$; and $R^{15}$, at each occurrence, is independently 6-10 membered aryl. In another embodiment of Formula (I), $R^6$ is $C_2$ alkyl; wherein the $R^6$ $C_2$ alkyl is substituted with one $R^{15}$; and $R^{15}$, at each occurrence, is independently phenyl. In another embodiment of Formula (I), $R^6$ is $C_1$-$C_6$ alkyl; wherein the $R^6$ $C_1$-$C_6$ alkyl is unsubstituted. In another embodiment of Formula (I), $R^6$ is —$CH_3$. In another embodiment of Formula (I), $R^6$ is —$CH(CH_3)_2$. In one embodiment of Formula (I), $R^6$ is 4-12 membered heterocyclyl; wherein the $R^6$ 4-12 membered heterocyclyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (I), $R^6$ is 4-12 membered heterocyclyl; wherein the $R^6$ 4-12 membered heterocyclyl is unsubstituted. In another embodiment of Formula (I), $R^6$ is tetrahydrofuranyl. In another embodiment of Formula (I), $R^6$ is tetrahydropyranyl. In one embodiment of Formula (I), $R^6$ is $C_3$-$C_{11}$ cycloalkyl; wherein the $R^6$ $C_3$-$C_{11}$cycloalkyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (I), $R^6$ is $C_3$-$C_{11}$ cycloalkyl; wherein the $R^6$ $C_3$-$C_{11}$cycloalkyl is optionally substituted with one or more F. In another embodiment of Formula (I), $R^6$ is $C_3$-$C_{11}$ cycloalkyl; wherein the $C_3$-$C_{11}$ cycloalkyl is unsubstituted. In another embodiment of Formula (I), $R^6$ is cyclohexyl; wherein the $R^6$ cyclohexyl is substituted with two F. In another embodiment of Formula (I), $R^6$ is cyclopentyl. In another embodiment of Formula (I), $R^6$ is cyclohexyl.

In one embodiment of Formula (I), $R^1$ is $C(O)OR^6$; $R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$, $SR^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_1$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl.

In one embodiment of Formula (I), $R^1$ is $C(O)OR^6$; and $R^6$ is $C_1$-$C_6$ alkyl; wherein the $R^6$ is unsubstituted $C_1$-$C_6$ alkyl.

In one embodiment of Formula (I), $R^1$ is $C(O)R^6$; $R^6$ is 4-12 membered heterocyclyl; wherein the $R^6$ 4-12 membered heterocyclyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_1$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (I), $R^1$ is $C(O)R^6$; and $R^6$ is 4-12 membered heterocyclyl; wherein the $R^6$ 4-12 membered heterocyclyl is unsubstituted.

In one embodiment of Formula (I), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I; $R^{21}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_1$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl. In another embodiment of Formula (I), $R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl; $R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl, and $C_3$-$C_{11}$ cycloalkyl is optionally substituted with one or more CN; $R^{22}$ and $R^{23}$, at each occurrence, are each independently $C_1$-$C_6$ alkyl; and $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl.

In one embodiment of Formula (I), $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br, and I. In another embodiment of Formula (I), $R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy.

In one embodiment of Formula (I), $R^4$ is $(C_1$-$C_6$ alkylene)$_x$-$C_6$-$C_{10}$ aryl; wherein the $R^4$ $(C_1$-$C_6$ alkylene)$_x$-$C_6$-$C_{10}$ membered aryl is optionally substituted with one or more substituents independently selected from the group consisting of $R^9$ and $OR^9$; $R^{4A}$ is hydrogen; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl. In one embodiment of Formula (I), $R^4$ is $L^1$-$C_6$-$C_{10}$ aryl; wherein the $R^4$ $C_6$-$C_{10}$ membered aryl is optionally substituted with one or more substituents independently selected from the group consisting of $R^9$ and $OR^9$; wherein $L^1$ is absent, or is $C_1$-$C_6$ alkylene; $R^{4A}$ is hydrogen; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (I), $R^4$ is $CH_2$-phenyl; wherein the $R^4$ $CH_2$-phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (I), $R^4$ is phenyl; wherein the $R^4$ phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In another embodiment of Formula (I), $R^4$ is $(C_1$-$C_6$ alkylene)$_x$-5-11 membered heteroaryl; wherein the $R^4$ $(C_1$-$C_6$ alkylene)$_x$-5-11 membered heteroaryl is optionally substituted with one or more substituents independently selected from the group consisting of $R^9$ and $OR^9$; $R^{4A}$ is hydrogen; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$;

and $R^{24}$, at each occurrence, is independently $C_1$-$C_6$ alkyl. In another embodiment of Formula (I), $R^4$ is $L^1$-5-11 membered heteroaryl; wherein the $R^4$ 5-11 membered heteroaryl is optionally substituted with one or more substituents independently selected from the group consisting of $R^9$ and $OR^9$; $L^1$ is absent, or is $C_1$-$C_6$ alkylene; $R^{4A}$ is hydrogen; $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (I), $R^4$ is $CH_2$-pyridinyl; wherein the $R^4$ $CH_2$— pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (I), $R^4$ is pyridinyl; wherein the $R^4$ pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (I), $R^4$ is $CH_2$-quinolinyl; wherein the $R^4$ $CH_2$— quinolinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In one embodiment of Formula (I), $R^4$ is selected from the group consisting of

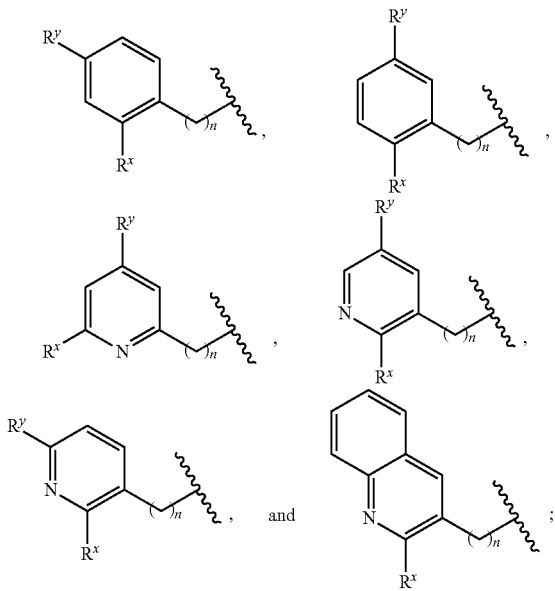

wherein $R^x$ is selected from the group consisting of $CH_3$ and $OCH_3$, and $R^y$ is selected from the group consisting of $CF_3$, $CH_3$, $C(CH_3)_3$, cyclopropyl, cyclobutyl substituted with $CH_3$, and bicyclo[1.1.1]pentyl; and n is 0 or 1.

One embodiment pertains to compounds of Formula (I),

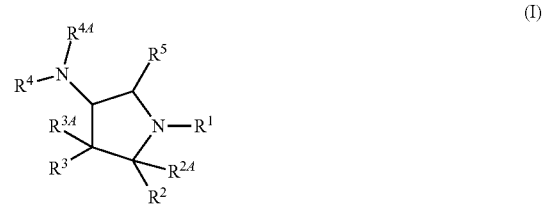

wherein $R^1$ is selected from the group consisting of $SO_2R^6$, $C(O)R^6$, $C(O)OR^6$, and $C(O)NR^7R^8$;

$R^2$ is $C(O)OH$ or a bioisostere thereof;

$R^{2A}$ is selected from the group consisting of hydrogen and $C_1$-$C_6$ alkyl;

$R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with $C_1$-$C_6$ alkyl; and $R^{3A}$ is hydrogen; or $R^3$ and $R^{3A}$, together with the carbon to which they are attached, form $C_3$-$C_6$ cycloalkyl;

$R^4$ is selected from the group consisting of $(C_1$-$C_6$ alkylene)$_x$-$C_6$-$C_{10}$ aryl, $(C_1$-$C_6$ alkylene)$_x$-5-11 membered heteroaryl, $(C_1$-$C_6$ alkylene)$_x$-4-12 membered heterocyclyl, and $(C_1$-$C_6$ alkylene)$_x$-$C_3$-$C_{11}$ cycloalkyl; wherein the $R^4$ $C_6$-$C_{10}$ membered aryl of $(C_1$-$C_6$ alkylene)$_x$-$C_6$-$C_{10}$ membered aryl, the 5-11 membered heteroaryl of $(C_1$-$C_6$ alkylene)$_x$-5-11 membered heteroaryl, the 4-12 membered heterocyclyl of $(C_1$-$C_6$ alkylene)$_x$-4-12 membered heterocyclyl, and the $C_3$-$C_{11}$ cycloalkyl of $(C_1$-$C_6$ alkylene)$_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br;

$R^{4A}$ is hydrogen;

$R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and x is 0 or 1.

One embodiment pertains to compounds of Formula (I),

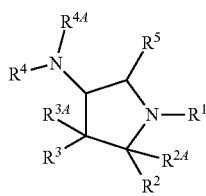

(I)

wherein
$R^1$ is selected from the group consisting of $SO_2R^6$, $C(O)R^6$, $C(O)OR^6$, and $C(O)NR^7R^8$;

$R^2$ is $C(O)OH$ or a bioisostere thereof;

$R^{2A}$ is selected from the group consisting of hydrogen and $C_1$-$C_6$ alkyl;

$R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with $C_1$-$C_6$ alkyl; and $R^{3A}$ is hydrogen; or $R^3$ and $R^{3A}$, together with the carbon to which they are attached, form $C_3$-$C_6$ cycloalkyl;

$R^4$ is selected from the group consisting of $L^1$-$C_6$-$C_{10}$ aryl, $L^1$-5-11 membered heteroaryl, $L^1$-4-12 membered heterocyclyl, and $L^1$-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen and $C_1$-$C_6$ alkyl; or $R^4$ and $R^{4A}$, together with the carbon to which they are attached, form 4-12 membered heterocyclyl; wherein the 4-12 membered heterocyclyl is optionally substituted with one or more substituents independently selected from the group consisting of $OR^9$, and Cl;

$R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, OH, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and $R^{25}$ and $R^{26}$, at each occurrence, are each independently hydrogen or $C_1$-$C_6$ alkyl.

Exemplary compounds of Formula (I) include, but are not limited to:

rac-(2R,3R,4R,5R)-3-tert-buty-1-(cyclohexanecarbonyl)-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(cyclohexanecarbonyl)-4-{[6-methoxy-4-(trifluoromethyl)pyridin-2-yl]amino}-5-phenylpyrrolidine-2-carboxylic acid;

(2R,3R,4R,5R)-3-tert-butyl-1-(cyclohexanecarbonyl)-4-{[6-methyl-4-(trifluoromethyl)pyridin-2-yl]amino}-5-phenylpyrrolidine-2-carboxylic acid;

(2S,3S,4S,5S)-3-tert-butyl-1-(cyclohexanecarbonyl)-4-{[6-methyl-4-(trifluoromethyl)pyridin-2-yl]amino}-5-phenylpyrrolidine-2-carboxylic acid;

rac-(2R,3R,4R,5R)-1-(cyclohexanecarbonyl)-3-(2-methoxypropan-2-yl)-4-{[6-methyl-4-(trifluoromethyl)pyridin-2-yl]amino}-5-phenylpyrrolidine-2-carboxylic acid;

rac-(2R,3R,4R,5R)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[2-methoxy-4-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid;

(2S,3S,4S,5S)-3-tert-butyl-4-({[2-methoxy-4-(trifluoromethyl)phenyl]methyl}amino)-5-phenyl-1-[(2R*)-2-phenylpropanoyl]pyrrolidine-2-carboxylic acid;

(2S,3S,4S,5S)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-1-(cyclohexanecarbonyl)-5-[2-(difluoromethoxy)phenyl]-4-({[2-methoxy-5-(trifluoromethyl)pyridin-3-yl]methyl}amino)pyrrolidine-2-carboxylic acid;

(2S,3S,4S,5S)-1-(benzenesulfonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-[(oxan-2-yl)acetyl]-5-phenylpyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid;

(2S,3S,4S,5S)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2S*,3S*)-3-(propan-2-yl)oxolane-2-carbonyl]pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-fluorophenyl)pyrrolidine-2-carboxylic acid;

(2S,3S,4S,5S)-3-tert-butyl-1-(cyclohexanecarbonyl)-4-{[(2-methoxy-5-phenylpyridin-3-yl)methyl]amino}-5-phenylpyrrolidine-2-carboxylic acid;

(2S,3S,4S,5S)-3-tert-butyl-1-(cyclohexanecarbonyl)-5-(4-fluorophenyl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1S)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(1R)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-methoxy-3-phenylpropanoyl]-5-phenylpyrrolidine-2-carboxylic acid;

(2S,3S,4S,5S)-3-tert-butyl-1-(cyclohexanecarbonyl)-4-[({2-methoxy-5-[1-(trifluoromethyl)cyclopropyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(2S)-oxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(cis-4-hydroxy-4-propylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-[2-(dimethylamino)pyridin-3-yl]pyrrolidine-2-carboxylic acid;

(2S,3S,4S,5S)-3-tert-butyl-1-[(2R*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid;

(2S,3S,4S,5S)-3-tert-butyl-4-{[(6-tert-butyl-2-methoxypyridin-3-yl)methyl]amino}-1-[(2S)-oxane-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R)-oxane-2-carbonyl]-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(2-methoxypropan-2-yl)-5-(2-methoxypyridin-3-yl)pyrrolidine-2-carboxylic acid;

(2S,3S,4S,5S)-4-{[(5-tert-butyl-2-methoxyphenyl)methyl]amino}-1-(cyclohexanecarbonyl)-5-[2-(dimethylamino)pyridin-3-yl]-3-(2-methoxypropan-2-yl)pyrrolidine-2-carboxylic acid;

(2S,3S,4S,5S)-3-tert-butyl-4-{[(5-tert-butyl-2-methoxyphenyl)methyl]amino}-1-[(1R*)-3,3-difluorocyclohexane-1-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(1S*)-3,3-difluorocyclohexane-1-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(2R)-oxane-2-carbonyl]pyrrolidine-2-carboxylic acid;

(2S,3S,4S,5S)-1-(bicyclo[3.1.0]hexane-6-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-1-(cyclohexanecarbonyl)-4-({[2-methoxy-5-(trimethylsilyl)pyridin-3-yl]methyl}amino)-5-phenylpyrrolidine-2-carboxylic acid;

(2S,3S,4S,5S)-3-tert-butyl-4-{[(2-tert-butyl-5-methoxypyridin-4-yl)methyl]amino}-1-(cyclohexanecarbonyl)-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-[(2R)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2S)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2R)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-[(1R*)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(2,2,6,6-tetramethyloxane-4-carbonyl)pyrrolidine-2-carboxylic acid;

(2S,3S,4S,5S)-3-tert-butyl-4-[(5-tert-butyl-2-methoxypyridin-3-yl)amino]-1-(cyclohexanecarbonyl)-5-phenylpyrrolidine-2-carboxylic acid;

(2S,3S,4S,5S)-3-(bicyclo[1.1.1]pentan-1-yl)-1-(cyclohexanecarbonyl)-4-({[2-hydroxy-5-(trifluoromethyl)phenyl]methyl}amino)-5-phenylpyrrolidine-2-carboxylic acid;

(2S,3S,4S,5S)-3-(bicyclo[1.1.1]pentan-1-yl)-1-(cyclohexanecarbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-N-(methanesulfonyl)-5-phenylpyrrolidine-2-carboxamide;

(2S,3S,4S,5S)-3-tert-butyl-4-{[(5-tert-butyl-2-methoxyphenyl)methyl]amino}-5-[2-(difluoromethoxy)phenyl]-1-[(2S)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(2S*)-oxane-2-carbonyl]-5-[2-(propan-2-yl)phenyl]pyrrolidine-2-carboxylic acid;

(2S,3S,4S,5S)-3-tert-butyl-4-({[4-(3-chlorophenyl)oxan-4-yl]methyl}amino)-1-(cyclohexanecarbonyl)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-{[(propan-2-yl)oxy]carbonyl}pyrrolidine-2-carboxylic acid;

(2S,3S,4S,5S)-1-(bicyclo[3.1.0]hexane-6-carbonyl)-3-tert-butyl-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1R)-3,3-difluorocyclohexane-1-carbonyl]-5-phenylpyrrolidine-2-carboxylic acid;

(2S,3S,4S,5S)-3-tert-butyl-4-{[(5-cyclobutyl-2-methoxypyridin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-[(1R)-3,3-difluorocyclohexane-1-carbonyl]-5-phenylpyrrolidine-2-carboxylic acid;

(2S,3S,4S,5S)-3-(bicyclo[1.1.1]pentan-1-yl)-4-{[(6-tert-butyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-(bicyclo[1.1.1]pentan-1-yl)-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-[(2R)-oxane-2-carbonyl]-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-[2-(propan-2-yl)phenyl]pyrrolidine-2-carboxylic acid;

(2S,3S,4S,5S)-3-tert-butyl-1-[(1R)-3,3-difluorocyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-(bicyclo[1.1.1]pentan-1-yl)-4l-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-{[(propan-2-yl)oxy]carbonyl}pyrrolidine-2-carboxylic acid;

(2S,3S,4S,5S)-3-tert-butyl-4-({[2-methoxy-4-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-{[6-methyl-4-(trifluoromethyl)pyridin-2-yl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxane-2-carbonyl]-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-[(2R)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-(3-chlorophenyl)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-1-(cyclohexanecarbonyl)-4-({[2-methoxy-4-(trifluoromethyl)phenyl]methyl}amino)-5-(2-methylphenyl)pyrrolidine-2-carboxylic acid;

(2S,3S,4S,5S)-3-tert-butyl-4-{[(5-cyclobutyl-2-methoxypyridin-3-yl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-4-{[(6-methoxy-2,3-dihydro-1H-inden-5-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-5-(2-cyclopropylphenyl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-(2-methylphenyl)pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylphenyl)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxolane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-(2-cyclopropylpyridin-3-yl)-1-[(2S)-oxolane-2-carbonyl]pyrrolidine-2-carboxylic acid;

(2S,3S,4S,5S)-3-tert-butyl-1-(ethoxycarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-1-(cyclopenanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-{[(5-tert-butyl-2-methoxyphenyl)methyl]amino}-1-{[(propan-2-yl)oxy]carbonyl}pyrrolidine-2-carboxylic acid;

(2S,3S,4S,5S)-3-tert-butyl-4-{[(2-methoxyquinolin-3-yl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-4-{[(5-cyclopropyl-2-methoxypyridin-3-yl)methyl]amino}-1-[(2S)-oxolane-2-carbonyl]-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-{[(5-tert-butyl-2-methoxyphenyl)methyl]amino}-1-(cyclobutanecarbonyl)pyrrolidine-2-carboxylic acid;

(2S,3S,4S,5S)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid;

(2S,3S,4S,5S)-3-tert-butyl-4-{[(5-tert-butyl-2-methoxyphenyl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-1-(cyclohexanecarbonyl)-4-{[(5-cyclopropyl-2-methoxypyridin-3-yl)methyl]amino}-5-(2-methylphenyl)pyrrolidine-2-carboxylic acid;

(2S,3S,4S,5S)-5-(2-bromophenyl)-3-tert-butyl-4-{[(5-cyclobutyl-2-methoxypyridin-3-yl)methyl]amino}-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylphenyl)-1-[(2S)-oxolane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-cyclopropylphenyl)-1-[(2S)-oxolane-2-carbonyl]pyrrolidine-2-carboxylic acid;

(2S,3S,4S,5S)-3-tert-butyl-4-({[2-methoxy-5-(1-methylcyclobutyl)phenyl]methyl}amino)-5-(2-methylphenyl)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methylphenyl)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-ethylphenyl)-1-[(2S)-oxolane-2-carbonyl]pyrrolidine-2-carboxylic acid;

(2S,3S,4S,5S)-3-tert-butyl-5-(2-cyclopropylphenyl)-4-({[2-methoxy-5-(1-methylcyclobutyl)phenyl]methyl}amino)-1-[(2S)-oxolane-2-carbonyl]pyrrolidine-2-carboxylic acid;

(2S,3S,4S,5S)-5-(2-bromophenyl)-3-tert-butyl-4-{[(5-tert-butyl-2-methoxyphenyl)methyl]amino}-1-[(2S)-oxane-2-carbonyl]pyrrolidine-2-carboxylic acid;

(2S,3S,4S,5S)-3-tert-butyl-1-(cyclohexanecarbonyl)-4-{[2-methoxy-5-(trifluoromethyl)pyridin-3-yl]amino}-5-phenylpyrrolidine-2-carboxylic acid;

(2S,3S,4S,5S)-3-tert-butyl-4-{[(5-cyclopropyl-2-methoxypyridin-3-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-5-(2-cyclopropylphenyl)-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-[2-(propan-2-yl)phenyl]pyrrolidine-2-carboxylic acid;

(2S,3S,4S,5S)-3-tert-butyl-1-(cyclohexanecarbonyl)-5-(2,2-dimethyl-2,3-dihydro-1-benzofuran-7-yl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-cyclobutyl-2-methoxypyridin-3-yl)methyl](methyl)amino}-1-[(2S)-oxane-2-carbonyl]-5-[2-(propan-2-yl)phenyl]pyrrolidine-2-carboxylic acid;

rac-(2R,3R,4R,5R)-3-tert-butyl-1-(cyclohexanecarbonyl)-4-[(4,6-dimethoxypyrimidin-2-yl)amino]-5-phenylpyrrolidine-2-carboxylic acid;

rac-(2R,3R,4R,5R)-3-tert-butyl-4-[(4-chloro-6-methoxypyrimidin-2-yl)amino]-1-(cyclohexanecarbonyl)-5-phenylpyrrolidine-2-carboxylic acid;

rac-(2R,3R,4R,5R)-3-tert-butyl-1-(cyclohexanecarbonyl)-4-{[1-(2,2-difluoro-2H-1,3-benzodioxol-5-yl)ethyl]amino}-5-phenylpyrrolidine-2-carboxylic acid;

rac-(2R,3R,4R,5R)-3-tert-butyl-1-(cyclohexanecarbonyl)-4-{[(5-methoxy-1,3-dimethyl-1H-pyrazol-4-yl)methyl]amino}-5-phenylpyrrolidine-2-carboxylic acid;

rac-(2R,3R,4R,5R)-3-tert-butyl-1-(cyclohexanecarbonyl)-5-phenyl-4-{[4-(trifluoromethyl)pyrimidin-2-yl]amino}pyrrolidine-2-carboxylic acid;

rac-(2R,3R,4R,5R)-3-tert-butyl-1-(cyclohexanecarbonyl)-4-({[2-methoxy-5-(trifluoromethyl)phenyl]methyl}amino)-5-phenylpyrrolidine-2-carboxylic acid;

rac-(2R,3R,4R,5R)-1-(cyclohexanecarbonyl)-3-cyclopropyl-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(cyclohexanecarbonyl)-4-({1-[2-methoxy-5-(trifluoromethyl)phenyl]ethyl}amino)-5-phenylpyrrolidine-2-carboxylic acid;

rac-(2S,3S,4S,5S)-3-tert-butyl-1-(cyclohexanecarbonyl)-4-[(2,6-dimethoxypyrimidin-4-yl)amino]-5-phenylpyrrolidine-2-carboxylic acid;

rac-(2R,3R,4R,5R)-3-tert-butyl-4-{[6-methoxy-4-(trifluoromethyl)pyridin-2-yl]amino}-5-phenyl-1-{[(propan-2-yl)oxy]carbonyl}pyrrolidine-2-carboxylic acid;

rac-(2R,3R,4R,5S)-3-tert-butyl-1-(cyclohexanecarbonyl)-4-({[2-(difluoromethoxy)phenyl]methyl}amino)-5-(pyridin-2-yl)pyrrolidine-2-carboxylic acid;

rac-(2R,3R,4R,5R)-3-tert-butyl-4-{[(5-chloro-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[4-methyl-6-(trifluoromethyl)pyrimidin-2-yl]amino}-5-phenyl-1-{[(propan-2-yl)oxy]carbonyl}pyrrolidine-2-carboxylic acid;

rac-(2R,3R,4R,5R)-3-tert-butyl-1-(cyclohexanecarbonyl)-4-({[2-(difluoromethoxy)-5-methoxyphenyl]methyl}amino)-5-phenylpyrrolidine-2-carboxylic acid;

rac-(2R,3R,4R,5R)-3-tert-butyl-1-(cyclohexanecarbonyl)-4-{[2-methoxy-5-(trifluoromethyl)pyridin-3-yl]amino}-5-phenylpyrrolidine-2-carboxylic acid;

rac-(2R,3R,4R,5S)-3-tert-butyl-1-(cyclohexanecarbonyl)-4-({[2-(difluoromethoxy)phenyl]methyl}amino)-5-(6-methoxypyridin-2-yl)pyrrolidine-2-carboxylic acid;

rac-(4R,6R,7R)-5-(cyclohexanecarbonyl)-7-{[6-methyl-4-(trifluoromethyl)pyridin-2-yl]amino}-6-phenyl-5-azaspiro[2.4]heptane-4-carboxylic acid;

rac-(2R,3R,4R,5S)-3-tert-butyl-4-({[2-(difluoromethoxy)phenyl]methyl}amino)-5-(6-methoxypyridin-2-yl)-1-(oxane-2-carbonyl)pyrrolidine-2-carboxylic acid;

rac-(2R,3R,4R,5S)-3-tert-butyl-1-(cyclohexanecarbonyl)-5-(6-methoxypyridin-2-yl)-4-({[2-methoxy-5-(trifluoromethyl)phenyl]methyl}amino)pyrrolidine-2-carboxylic acid;

(2S,3S,4S,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-4-{[6-(difluoromethoxy)pyridin-2-yl]amino}-5-phenylpyrrolidine-2-carboxylic acid;

rac-(2R,3R,4R,5R)-3-tert-butyl-1-(cyclohexanecarbonyl)-5-[2-(dimethylamino)phenyl]-4-({[2-methoxy-5-(trifluoromethyl)phenyl]methyl}amino)pyrrolidine-2-carboxylic acid;

rac-(2R,3R,4R,5S)-3-tert-butyl-5-(6-methoxypyridin-2-yl)-4-({[2-methoxy-5-(trifluoromethyl)phenyl]methyl}amino)-1-[oxane-2-carbonyl]pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-(3-oxabicyclo[3.1.0]hexane-6-carbonyl)pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-[oxane-2-carbonyl]pyrrolidine-2-carboxylic acid;

rac-(2R,3R,4R,5R)-3-tert-butyl-5-[2-(dimethylamino)phenyl]-1-[(2,2-dimethyloxane-4-carbonyl]-4-({[2-methoxy-4-(trifluoromethyl)phenyl]methyl}amino)pyrrolidine-2-carboxylic acid;

rac-(2R,3R,4R,5R)-3-tert-butyl-1-[(3R)-1-(methoxycarbonyl)piperidine-3-carbonyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-1-(cyclohexanecarbonyl)-4-({[5-(methanesulfonyl)-2-methoxyphenyl]methyl}amino)-5-phenylpyrrolidine-2-carboxylic acid;

rac-(2R,3R,4R,5R)-3-tert-butyl-1-[(1R,3R)-3-methoxycyclohexane-1-carbonyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-4-({[2-methoxy-5-(trifluoromethyl)phenyl]methyl}amino)-1-[(2S*)-2-phenoxypropanoyl]-5-phenylpyrrolidine-2-carboxylic acid;

(2R*,3R*,4R*,5R*)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid;

(2S,3S,4S,5S)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-5-phenyl-4-({[2-(propan-2-yl)phenyl]methyl}amino)pyrrolidine-2-carboxylic acid;

rac-(2R,3R,4R,5R)-3-tert-butyl-4-{[(5-chloro-2-methoxypyridin-3-yl)methyl]amino}-1-(cyclohexanecarbonyl)-5-phenylpyrrolidine-2-carboxylic acid;

rac-(2R,3R,4R,5R)-3-tert-butyl-4-{[6-methyl-4-(trifluoromethyl)pyridin-2-yl]amino}-5-phenyl-1-(spiro[2.5]octane-6-carbonyl)pyrrolidine-2-carboxylic acid;

rac-(2R,3R,4R,5R)-1-(cyclohexanecarbonyl)-3-(2-methoxypropan-2-yl)-4-{[6-methoxy-4-(trifluoromethyl)pyridin-2-yl]amino}-5-phenylpyrrolidine-2-carboxylic acid;

(2S,3S,4S,5S)-3-tert-butyl-1-(cyclohexanecarbonyl)-5-(2-methoxypyridin-3-yl)-4-({[2-methoxy-4-(trifluoromethyl)phenyl]methyl}amino)pyrrolidine-2-carboxylic acid;

rac-(2S,3S,4S,5R)-3-tert-butyl-4-{[(5-chloro-2-methoxyphenyl)methyl]amino}-1-(cyclohexanecarbonyl)-5-(3-methoxypyridin-2-yl)pyrrolidine-2-carboxylic acid;

rac-(2R,3R,4R,5R)-3-tert-butyl-1-(2-methoxy-2-methylpropanoyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-{[(3-methoxynaphthalen-2-yl)methyl]amino}-5-phenylpyrrolidine-2-carboxylic acid;

(2S,3S,4S,5S)-3-tert-butyl-1-(cyclohexanecarbonyl)-5-[2-(difluoromethoxy)phenyl]-4-({[2-methoxy-4-(trifluoromethyl)phenyl]methyl}amino)pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-4-(trifluoromethyl)phenyl]methyl}amino)pyrrolidine-2-carboxylic acid;

(2R,3R,4R,5R)-3-tert-butyl-4-({[2-methoxy-4-(trifluoromethyl)phenyl]methyl}amino)-5-phenyl-1-[(2R)-2-phenylpropanoyl]pyrrolidine-2-carboxylic acid;

(2S,3S,4S,5S)-4-{[(1-benzofuran-2-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2,3-dihydro-1,4-benzodioxin-6-yl)methyl]amino}-5-phenylpyrrolidine-2-carboxylic acid;

(2S,3S,4S,5S)-3-tert-butyl-1-(cyclohexanecarbonyl)-4-{[(4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-{[(6-methoxy-2,3-dihydro-1H-inden-5-yl)methyl]amino}-5-phenylpyrrolidine-2-carboxylic acid;

(2S,3S,4S,5S)-3-tert-butyl-1-(cyclohexanecarbonyl)-4-({[2-(cyclopropylmethoxy)-4-fluorophenyl]methyl}amino)-5-phenylpyrrolidine-2-carboxylic acid;

(2S,3S,4S,5S)-3-tert-butyl-4-{[(5-chloro-2-hydroxyphenyl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(trifluoromethyl)phenyl]methyl}amino)pyrrolidine-2-carboxylic acid;

(2S,3S,4S,5S)-3-tert-butyl-1-(cyclohexanecarbonyl)-5-phenyl-4-{[6-(propan-2-yl)-4-(trifluoromethyl)pyridin-2-yl]amino}pyrrolidine-2-carboxylic acid;

(2S,3S,4S,5S)-3-tert-butyl-4-[(3-cyano-4-methoxyquinolin-2-yl)amino]-1-(cyclohexanecarbonyl)-5-phenylpyrrolidine-2-carboxylic acid;

(2S,3S,4S,5S)-3-tert-butyl-1-(cyclohexanecarbonyl)-5-phenyl-4-[3-(trifluoromethyl)anilino]pyrrolidine-2-carboxylic acid;

(2S,3S,4S,5S)-3-tert-butyl-4-{[(5-chloro-2-methoxyphenyl)methyl]amino}-1-(cyclohexanecarbonyl)-5-(2-methoxyphenyl)pyrrolidine-2-carboxylic acid;

(2S,3S,4S,5S)-3-tert-butyl-4-{[(5-tert-butyl-2-methoxyphenyl)methyl]amino}-1-[(1S,3S)-3-methoxycyclohexane-1-carbonyl]-5-phenylpyrrolidine-2-carboxylic acid;

(2S,3S,4S,5S)-3-tert-butyl-1-[(1R,3R)-3-methoxycyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-[(1S,3S)-3-methoxycyclohexane-1-carbonyl]-4-({[2-methoxy-5-(trifluoromethyl)phenyl]methyl}amino)-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-4-{[(4-tert-butyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(pyridine-3-carbonyl)pyrrolidine-2-carboxylic acid;

(2S,3S,4S,5S)-1-benzoyl-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1$\lambda^6$-thiane-3-carbonyl)-5-phenylpyrrolidine-2-carboxylic acid;

(2S,3S,4S,5S)-3-tert-butyl-4-{[6-cyclobutyl-4-(trifluoromethyl)pyridin-2-yl]amino}-1-(cyclohexanecarbonyl)-5-phenylpyrrolidine-2-carboxylic acid;

(2S,3S,4S,5S)-3-tert-butyl-4-{[(5-cyclobutyl-2-methoxyphenyl)methyl]amino}-1-(cyclohexanecarbonyl)-5-phenylpyrrolidine-2-carboxylic acid;

(2S,3S,4S,5S)-4-{[(5-benzyl-2-methoxypyridin-3-yl)methyl]amino}-3-tert-butyl-1-(cyclohexanecarbonyl)-5-phenylpyrrolidine-2-carboxylic acid;

(2S,3S,4S,5S)-4-({[5-(butan-2-yl)-2-methoxypyridin-3-yl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[5-(cyclohexylmethyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-{[(5-cyclohexyl-2-methoxypyridin-3-yl)methyl]amino}-5-phenylpyrrolidine-2-carboxylic acid;

(2S,3S,4S,5S)-3-tert-butyl-1-(cyclohexanecarbonyl)-4-{[(5-cyclopentyl-2-methoxypyridin-3-yl)methyl]amino}-5-phenylpyrrolidine-2-carboxylic acid;

(2S,3S,4S,5S)-3-tert-butyl-1-(cyclohexanecarbonyl)-4-({[5-(2-ethylbutyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(1-phenylethyl)pyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(2-methylpropyl)pyridin-3-yl]methyl}amino)-5-phenylpyrrolidine-2-carboxylic acid;

(2S,3S,4S,5S)-3-tert-butyl-4-[({5-[(3-cyanophenyl)methyl]-2-methoxypyridin-3-yl}methyl)amino]-1-(cyclohexanecarbonyl)-5-phenylpyrrolidine-2-carboxylic acid;

(2S,3S,4S,5S)-3-tert-butyl-4-{[(4-methoxy[1,1'-biphenyl]-3-yl)methyl]amino}-1-[(1R,3R)-3-methoxycyclohexane-1-carbonyl]-5-phenylpyrrolidine-2-carboxylic acid;

(2S,3S,4S,5S)-3-tert-butyl-1-[(1R,3R)-3-methoxycyclohexane-1-carbonyl]-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-hydroxyphenyl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{[(propan-2-yl)oxy]carbonyl}pyrrolidine-2-carboxylic acid;

(2S,3S,4S,5S)-3-tert-butyl-4-(5-tert-butyl-2-methoxyanilino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-phenylpyrrolidine-2-carboxylic acid;

(2S,3S,4S,5S)-3-tert-butyl-4-({[2-methoxy-5-(trifluoromethyl)phenyl]methyl}amino)-1-[(oxan-2-yl)acetyl]-5-phenylpyrrolidine-2-carboxylic acid;

(2S,3S,4S,5S)-3-tert-butyl-1-(cyclohexanecarbonyl)-4-[({5-[(dimethylamino)methyl]-2-methoxyphenyl}methyl)amino]-5-phenylpyrrolidine-2-carboxylic acid;

(2S,3S,4S,5S)-3-tert-butyl-1-(cyclohexanecarbonyl)-4-({[2-methoxy-5-(pentafluoro-$\lambda^6$-sulfanyl)phenyl]methyl}amino)-5-phenylpyrrolidine-2-carboxylic acid;

(2S,3S,4S,5S)-1-(cyclohexanecarbonyl)-4-{[(4-methoxy[1,1'-biphenyl]-3-yl)methyl]amino}-3-(2-methoxypropan-2-yl)-5-phenylpyrrolidine-2-carboxylic acid;

(2S,3S,4S,5S)-3-tert-butyl-4-({[5-(2-cyanopropan-2-yl)-2-methoxyphenyl]methyl}amino)-1-(cyclohexanecarbonyl)-5-phenylpyrrolidine-2-carboxylic acid;

(2S,3S,4S,5S)-3-tert-butyl-1-(cyclohexanecarbonyl)-4-({[4-(2-hydroxypropan-2-yl)-2-methoxyphenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(5-cyano-2-methoxybenzoyl)-5-phenylpyrrolidine-2-carboxylic acid;

(2S,3S,4S,5S)-3-tert-butyl-4-{[(5-tert-butyl-2-methoxyphenyl)methyl]amino}-1-[(1,3-dihydro-2H-isoindol-2-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(thiophen-3-yl)acetyl]pyrrolidine-2-carboxylic acid;

(2S,3S,4S,5S)-3-tert-butyl-4-{[(5-tert-butyl-2-methoxyphenyl)methyl]amino}-1-(8-fluoroquinoline-2-carbonyl)-5-phenylpyrrolidine-2-carboxylic acid;

(2S,3S,4S,5S)-3-tert-butyl-1-(cyclohexanecarbonyl)-4-({[2-methoxy-5-(2-methylpropyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-cyclopropyl-2-methoxyacetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2-cyclopropyl-2-methoxyacetyl]-5-phenylpyrrolidine-2-carboxylic acid;

(2S,3S,4S,5S)-3-tert-butyl-1-(cyclohexanecarbonyl)-4-[({2-methoxy-5-[(1S,3s)-tricyclo[3.3.1.1$^{3,7}$]decan-1-yl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(1H-imidazol-4-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclopentyl)acetyl]-5-phenylpyrrolidine-2-carboxylic acid;

(2S,3S,4S,5S)-1-[(azepan-1-yl)acetyl]-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(1-ethyl-4-oxo-1,4-dihydropyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(4-methyl-4H-furo[3,2-b]pyrrole-5-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(4-chloro-1H-pyrazol-1-yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2R*,3R*)-3-(propan-2-yl)oxolane-2-carbonyl]pyrrolidine-2-carboxylic acid;

(2S,3S,4S,5S)-3-tert-butyl-4-({[2-methoxy-5-(trifluoromethyl)phenyl]methyl}amino)-5-phenyl-1-[(2R*,3R*)-3-(propan-2-yl)oxolane-2-carbonyl]pyrrolidine-2-carboxylic acid;

(2S,3S,4S,5S)-3-tert-butyl-4-({[2-methoxy-5-(trifluoromethyl)phenyl]methyl}amino)-5-phenyl-1-[(2S*,3S*)-3-(propan-2-yl)oxolane-2-carbonyl]pyrrolidine-2-carboxylic acid;

(2S,3S,4S,5S)-3-tert-butyl-4-{[(5-tert-butyl-2-methoxyphenyl)methyl]amino}-1-[(3aR*,6aS*)-hexahydro-1H-cyclopenta[c]furan-1-carbonyl]-5-phenylpyrrolidine-2-carboxylic acid;

(2S,3S,4S,5S)-3-tert-butyl-1-[(3aR*,6aS*)-hexahydro-1H-cyclopenta[c]furan-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-5-(4-fluorophenyl)-4-({[2-methoxy-5-(propan-2-yl)phenyl]methyl}amino)pyrrolidine-2-carboxylic acid;

(2S,3S,4S,5S)-3-tert-butyl-1-(cyclohexanecarbonyl)-5-(2-fluorophenyl)-4-({[2-methoxy-5-(trifluoromethyl)pyridin-3-yl]methyl}amino)pyrrolidine-2-carboxylic acid;

(2S,3S,4S,5S)-3-tert-butyl-1-(cyclohexanecarbonyl)-5-(2-fluorophenyl)-4-({[2-methoxy-5-(propan-2-yl)phenyl]methyl}amino)pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(4-fluorophenyl)pyrrolidine-2-carboxylic acid;

(2S,3S,4S,5S)-3-tert-butyl-1-(cyclohexanecarbonyl)-4-({[2-methoxy-5-(2-methoxypropan-2-yl)pyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(pyrimidin-5-yl)phenyl]methyl}amino)-5-phenylpyrrolidine-2-carboxylic acid;

(2S,3S,4S,5S)-4-{[(5-cyclobutyl-2-methoxypyridin-3-yl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclopentyl-2-methoxypyridin-3-yl)methyl]amino}-3-(2-methoxypropan-2-yl)-5-phenylpyrrolidine-2-carboxylic acid;

(2S,3S,4S,5S)-4-({[5-(bicyclo[2.2.1]heptan-2-yl)-2-methoxyphenyl]methyl}amino)-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-({[5-(cyclohexylmethyl)-2-methoxyphenyl]methyl}amino)-3-(2-methoxypropan-2-yl)-5-phenylpyrrolidine-2-carboxylic acid;

(2S,3S,4S,5S)-3-tert-butyl-4-{[(5-tert-butyl-2-methoxyphenyl)methyl]amino}-1-[(cyclopentyloxy)carbonyl]-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(trifluoromethyl)pyridin-3-yl]methyl}amino)pyrrolidine-2-carboxylic acid;

(2S,3S,4S,5S)-3-tert-butyl-1-(cyclohexanecarbonyl)-4-({[2-methoxy-5-(pyrrolidin-1-yl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(piperidin-1-yl)phenyl]methyl}amino)-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(pyridazin-4-yl)phenyl]methyl}amino)-5-phenylpyrrolidine-2-carboxylic acid;

(2S,3S,4S,5S)-3-tert-butyl-1-(cyclohexanecarbonyl)-4-{[(2'-fluoro-4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[5-(2,4-dimethyl-1,3-thiazol-5-yl)-2-methoxyphenyl]methyl}amino)-5-phenylpyrrolidine-2-carboxylic acid;

(2S,3S,4S,5S)-3-tert-butyl-4-{[(2'-cyano-4-methoxy[1,1'-biphenyl]-3-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[5-(3,6-dihydro-2H-pyran-4-yl)-2-methoxyphenyl]methyl}amino)-5-phenylpyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-(4-fluorophenyl)pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-1-(cyclohexanecarbonyl)-4-{[(5-cyclopentyl-2-methoxypyridin-3-yl)methyl]amino}-5-[2-(dimethylamino)pyridin-3-yl]pyrrolidine-2-carboxylic acid;

(2S,3S,4S,5S)-4-({[5-(bicyclo[2.2.1]heptan-2-yl)-2-methoxypyridin-3-yl]methyl}amino)-3-tert-butyl-1-(cyclohexanecarbonyl)-5-[2-(dimethylamino)pyridin-3-yl]pyrrolidine-2-carboxylic acid;

(2S,3S,4S,5S)-4-{[(6-bromo-3-methoxypyridin-2-yl)methyl]amino}-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-1-(cyclohexanecarbonyl)-4-({[2-methoxy-5-(trifluoromethyl)phenyl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-phenoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-[1-(methanesulfonyl)piperidine-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(trans)-2-(pyridin-3-yl)cyclopropane-1-carbonyl]pyrrolidine-2-carboxylic acid;

(2S,3S,4S,5S)-3-tert-butyl-1-(cyclohexanecarbonyl)-4-({[5-(2-fluorophenyl)-2-methoxypyridin-3-yl]methyl}amino)-5-phenylpyrrolidine-2-carboxylic acid;

(2S,3S,4S,5S)-3-tert-butyl-4-[({2-methoxy-5-[1-(trifluoromethyl)cyclopropyl]phenyl}methyl)amino]-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-(pyrazolo[1,5-a]pyridine-3-carbonyl)pyrrolidine-2-carboxylic acid;

(2S,3S,4S,5S)-3-tert-butyl-4-{[(5-tert-butyl-2-methoxyphenyl)methyl]amino}-1-[5-ethyl-1-(6-methoxypyridazin-3-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-tert-butyl-5-(propan-2-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-(2-fluorophenyl)-3,5-dimethyl-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclobutyl)acetyl]-5-phenylpyrrolidine-2-carboxylic acid;

(2S,3S,4S,5S)-1-[2-(azetidine-1-carbonyl)cyclohexane-1-carbonyl]-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(prop-2-en-1-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(cis-4-ethyl-4-hydroxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(propan-2-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(phenoxycarbonyl)-5-phenylpyrrolidine-2-carboxylic acid;

(2S,3S,4S,5S)-3-tert-butyl-4-{[(5-tert-butyl-2-methoxyphenyl)methyl]amino}-1-{[(2-chlorophenyl)methoxy]carbonyl}-5-phenylpyrrolidine-2-carboxylic acid;

(2S,3S,4S,5S)-3-tert-butyl-4-({[5-(1-cyanocyclobutyl)-2-methoxyphenyl]methyl}amino)-1-(cyclohexanecarbonyl)-5-phenylpyrrolidine-2-carboxylic acid;

(2S,3S,4S,5S)-3-tert-butyl-4-[(4-chloro-2,3-dihydro-1H-inden-2-yl)amino]-1-(cyclohexanecarbonyl)-5-phenylpyrrolidine-2-carboxylic acid;

(2S,3S,4S,5S)-3-tert-butyl-4-[(5-chloro-2,3-dihydro-1H-inden-2-yl)amino]-1-(cyclohexanecarbonyl)-5-phenylpyrrolidine-2-carboxylic acid;

(2S,3S,4S,5S)-3-tert-butyl-4-[(5-chloro-2,3-dihydro-1H-inden-1-yl)amino]-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-(3,4-difluorophenyl)-2-methoxyacetyl]-5-phenylpyrrolidine-2-carboxylic acid;

(2S,3S,4S,5S)-3-tert-butyl-4-{[(5-tert-butyl-2-methoxyphenyl)methyl]amino}-1-[cyclohexyl(methoxy)acetyl]-5-phenylpyrrolidine-2-carboxylic acid;

(2S,3S,4S,5S)-1-(bicyclo[3.1.0]hexane-6-carbonyl)-3-tert-butyl-4-({[2-methoxy-5-(trifluoromethyl)phenyl]methyl}amino)-5-phenylpyrrolidine-2-carboxylic acid;

(2S,3S,4S,5S)-1-(bicyclo[3.1.0]hexane-3-carbonyl)-3-tert-butyl-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)phenyl]methyl}amino)-5-phenyl-1-[3-(trifluoromethyl)cyclopentane-1-carbonyl]pyrrolidine-2-carboxylic acid;

(2S,3S,4S,5S)-3-tert-butyl-1-(5,5-dimethyloxolane-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(2R)-2,3-dihydro-1,4-benzodioxine-2-carbonyl]-5-phenylpyrrolidine-2-carboxylic acid;

(2S,3S,4S,5S)-3-tert-butyl-4-{[(2-cyclobutyl-5-methoxypyridin-4-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2-cyclopentyl-5-methoxypyridin-4-yl)methyl]amino}-5-phenylpyrrolidine-2-carboxylic acid;

(2S,3S,4S,5S)-3-tert-butyl-1-(cyclohexanecarbonyl)-4-[({3-methoxy-6-[1-(trifluoromethyl)cyclopropyl]pyridin-2-yl}methyl)amino]-5-phenylpyrrolidine-2-carboxylic acid;

(2S,3S,4S,5S)-3-tert-butyl-1-(cyclohexanecarbonyl)-4-({[2-methoxy-5-(trimethylsilyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(8-oxabicyclo[3.2.1]octane-3-carbonyl)-5-phenylpyrrolidine-2-carboxylic acid;

(2R,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid;

(2S,3S,4S,5S)-3-(2-methoxypropan-2-yl)-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-[(2S*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid;

(2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-[(2S)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-(oxane-2-carbonyl)-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-phenyl-1-[(2R*,3R*)-3-phenyloxolane-2-carbonyl]pyrrolidine-2-carboxyic acid;

(2S,3S,4S,5S)-3-tert-butyl-4-{[(5-tert-butyl-2-methoxyphenyl)methyl]amino}-5-phenyl-1-[(2S*,3S*)-3-phenyloxolane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-(3,3-difluorocyclohexane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2S*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-5-phenyl-1-[(2R)-2-phenylpropanoyl]pyrrolidine-2-carboxylic acid;

(2S,3S,4S,5S)-3-tert-butyl-1-(3,3-difluorocyclohexane-1-carbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-1-(cyclohexanecarbonyl)-4-[({2-methoxy-5-[(trifluoromethyl)sulfanyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(propan-2-yl)phenyl]pyrrolidine-2-carboxylic acid;

(2S,3S,4S,5S)-1-(bicyclo[3.1.0]hexane-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-[2-(propan-2-yl)phenyl]pyrrolidine-2-carboxylic acid;

(2S,3S,4S,5S)-3-tert-butyl-1-(cyclohexanecarbonyl)-4-{[(2-methoxynaphthalen-1-yl)methyl]amino}-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trimethylsilyl)pyridin-3-yl]methyl}amino)-5-phenylpyrrolidine-2-carboxylic acid;

(2S,3S,4S,5S)-3-tert-butyl-1-[(1R)-3,3-difluorocyclohexane-1-carbonyl]-4-{[(6-methoxy-2,3-dihydro-1H-inden-5-yl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(3S*)-1-methyl-2-oxopiperidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1λ⁶-thiolane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-oxane-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-{(2S*)-2-[(2S*)-oxan-2-yl]propanoyl}-5-phenylpyrrolidine-2-carboxylic acid;

(2S,3S,4S,5S)-3-tert-butyl-4-{[(5-tert-butyl-2-methoxyphenyl)methyl]amino}-1-{(2R*)-2-[(2R*)-oxan-2-yl]propanoyl}-5-phenylpyrrolidine-2-carboxylic acid;

(2S,3S,4S,5S)-3-tert-butyl-4-{[(6-tert-butyl-2-methoxypyridin-3-yl)methyl]amino}-1-(3-methoxycyclohexane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1R*,3S*)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(2,3-dihydro-1,4-benzodioxine-6-carbonyl)-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[4-(cyclohexyloxy)benzoyl]-5-[2-(dimethylamino)pyridin-3-yl]pyrrolidine-2-carboxylic acid;

(2S,3S,4S,5S)-1-(bicyclo[3.1.0]hexane-6-carbonyl)-3-tert-butyl-4-{[(5-tert-butyl-2-methoxyphenyl)methyl]amino}-5-[2-(dimethylamino)pyridin-3-yl]pyrrolidine-2-carboxylic acid;

(2S,3S,4S,5S)-3-(bicyclo[1.1.1]pentan-1-yl)-4-{[(5-tert-butyl-2-methoxyphenyl)methyl]amino}-1-(cyclohexanecarbonyl)-5-phenylpyrrolidine-2-carboxylic acid;

(2R,3R,4R,5R)-3-tert-butyl-4-{[(5-tert-butyl-2-methoxyphenyl)methyl]amino}-1-(cyclohexanecarbonyl)-N-(methane sulfonyl)-5-phenylpyrrolidine-2-carboxamide;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-[(2S*)-2,3-dihydro-1,4-benzodioxine-2-carbonyl]-5-phenylpyrrolidine-2-carboxylic acid;

(2S,3S,4S,5S)-3-tert-butyl-4-{[(5-cyclobutyl-2-methoxypyridin-3-yl)methyl]amino}-1-(3,4-dihydro-1H-2-benzopyran-3-carbonyl)-5-phenylpyrrolidine-2-carboxylic acid;

(2S,3S,4S,5S)-3-tert-butyl-4-{[(2-tert-butyl-4-methoxypyrimidin-5-yl)methyl]amino}-1-(cyclohexanecarbonyl)-5-phenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-phenyl-1-{[(propan-2-yl)oxy]carbonyl}pyrrolidine-2-carboxylic acid;

rac-(2S,3S,4S,5S)-3-tert-butyl-4-{[(5-tert-butyl-2-methoxyphenyl)methyl]amino}-1-(cyclohexanecarbonyl)-2-methyl-5-phenylpyrrolidine-2-carboxylic acid;

(2S,3S,4S,5S)-3-tert-butyl-1-(cyclohexanecarbonyl)-4-({[5-methoxy-2-(pyrrolidin-1-yl)pyridin-4-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(1,1,1-trifluoro-2-methylpropan-2-yl)phenyl]methyl}amino)-5-phenylpyrrolidine-2-carboxylic acid;

(2S,3S,4S,5S)-3-tert-butyl-4-{[(5-cyclobutyl-2-methoxypyridin-3-yl)methyl]amino}-5-phenyl-1-{[propan-2-yl)oxy]carbonyl}pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(2S)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(2R*)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)oxolane-3-carbonyl]pyrrolidine-2-carboxylic acid;

(2S,3S,4S,5S)-3-tert-butyl-4-({[4-(2-chlorophenyl)oxan-4-yl]methyl}amino)-1-(cyclohexanecarbonyl)-5-phenylpyrrolidine-2-carboxylic acid;

(2S,3S,4S,5S)-4-{[(5-tert-butyl-2-methoxyphenyl)methyl]amino}-5-[2-(dimethylamino)pyridin-3-yl]-3-(2- methoxypropan-2-yl)-1-{[(propan-2-yl)oxy]
carbonyl}pyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-{[(propan-2-yl)oxy]carbonyl}pyrrolidine-2-carboxylic acid;

(2S,3S,4S,5S)-1-(bicyclo[3.1.0]hexane-6-carbonyl)-3-tert-butyl-5-[2-(dimethylamino)pyridin-3-yl]-4-{[6-methyl-4-(trifluoromethyl)pyridin-2-yl]amino}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(1S*,2S*,3S*,4R*)-3-(trifluoromethyl)-7-oxabicyclo[2.2.1]heptane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-(2-methoxypyridin-3-yl)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(difluoromethoxy)pyridin-3-yl]pyrrolidine-2-carboxylic acid;

(2S,3S,4S,5S)-3-(bicyclo[1.1.1]pentan-1-yl)-4l-{[(5-tert-butyl-2-methoxyphenyl)methyl]amino}-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(difluoromethoxy)pyridin-3-yl]pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(difluoromethoxy)phenyl]pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(6-tert-butyl-2-methoxypyridin-3-yl)methyl]amino}-5-(2-fluorophenyl)-1-[(2S)-oxane-2-carbonyl]pyrrolidine-2-carboxylic acid;

(2S,3S,4S,5S)-1-(tert-butoxycarbonyl)-3-tert-butyl-4-{[(5-tert-butyl-2-methoxyphenyl)methyl]amino}-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R)-2-phenylpropanoyl]pyrrolidine-2-carboxylic acid;

(2S,3S,4S,5S)-3-tert-butyl-4-{[(6-tert-butyl-2-methoxypyridin-3-yl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid;

(2S,3S,4S,5S)-3-(bicyclo[1.1.1]pentan-1-yl)-4-{[(5-cyclobutyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-3-tert-butyl-1-(cyclohexanecarbonyl)-4-({[2-methoxy-5-(1-methylcyclobutyl)phenyl]methyl}amino)-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2R)-2-phenylpropanoyl]pyrrolidine-2-carboxylic acid;

(2S,3S,4S,5S)-3-tert-butyl-5-(2-methoxypyridin-3-yl)-4-({[2-methoxy-5-(trifluoromethyl)pyridin-3-yl]methyl}amino)-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-phenylpyrrolidine-2-carboxylic acid;

(2S,3S,4S,5S)-3-tert-butyl-4-{[(6-cyclobutyl-2-methoxypyridin-3-yl)methyl]amino}-1-(cyclohexanecarbonyl)-5-phenylpyrrolidine-2-carboxylic acid;

(2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-{[(oxetan-3-yl)oxy]carbonyl}-5-phenylpyrrolidine-2-carboxylic acid;

(2S,3S,4S,5S)-3-tert-butyl-5-[2-(dimethylamino)pyridin-3-yl]-4-({[2-methoxy-5-(pentafluoro-$\lambda^6$-sulfanyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-phenyl-1-[(3R)-1-{[(propan-2-yl)oxy]carbonyl}piperidine-3-carbonyl]pyrrolidine-2-carboxylic acid;

(2S,3S,4S,5S)-3-tert-butyl-4-{[(6-tert-butyl-2-chloropyridin-3-yl)methyl]amino}-1-[(1R)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-(1-phenylcyclopropane-1-carbonyl)pyrrolidine-2-carboxylic acid;

(2S,3S,4S,5S)-3-tert-butyl-4-{[(6-methoxy-2,3-dihydro-1H-inden-5-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(2-methoxyquinolin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(3-methoxy-5,5,8,8-tetramethyl-5,6,7,8-tetrahydronaphthalen-2-yl)methyl]amino}-1-{[(propan-2-yl)oxy]carbonyl}pyrrolidine-2-carboxylic acid;

(2S,3S,4S,5S)-3-tert-butyl-5-(3-chlorophenyl)-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-2-phenylbutanoyl]pyrrolidine-2-carboxylic acid;

(2S,3S,4S,5S)-3-tert-butyl-4-{[(5-tert-butyl-2-methoxyphenyl)methyl]amino}-1-[(7R)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid;

(2S,3S,4S,5S)-3-tert-butyl-1-[(1R,3R)-3-methoxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-[(1R*)-3,3-difluorocyclohexane-1-carbonyl]-5-(2-methoxypyridin-3-yl)-4-({[2-methoxy-5-(trifluoromethyl)phenyl]methyl}amino)pyrrolidine-2-carboxylic acid;

(2S,3S,4S,5S)-3-tert-butyl-1-[(1R*)-3,3-difluorocyclo-
hexane-1-carbonyl]-5-(2-methoxypyridin-3-yl)-4-({[2-
methoxy-4-(trifluoromethyl)phenyl]methyl}amino)pyr-
rolidine-2-carboxylic acid;

(2S,3S,4S,5S)-3-tert-butyl-1-(cyclohexanecarbonyl)-4-({[2-
methoxy-5-(trifluoromethyl)pyridin-3-yl]
methyl}amino)-5-(2-methylphenyl)pyrrolidine-2-carbox-
ylic acid;

(2S,3S,4S,5S)-3-tert-butyl-4-{[(5-cyclobutyl-2-methoxy-
pyridin-3-yl)methyl]amino}-5-phenyl-1-[(1R*,3S*)-3-
(trifluoromethyl)cyclohexane-1-carbonyl]pyrrolidine-2-
carboxylic acid;

(2S,3S,4S,5S)-3-tert-butyl-4-{[(5-cyclobutyl-2-methoxy-
pyridin-3-yl)methyl]amino}-5-phenyl-1-[(1S*,3R*)-3-
(trifluoromethyl)cyclohexane-1-carbonyl]pyrrolidine-2-
carboxylic acid;

(2S,3S,4S,5S)-3-tert-butyl-4-{[(5-tert-butyl-2-methoxyphe-
nyl)methyl]amino}-5-(2-methylphenyl)-1-[(2S)-oxolane-
2-carbonyl]pyrrolidine-2-carboxylic acid;

(2S,3S,4S,5S)-3-tert-butyl-4-({[2-methoxy-5-(trifluorom-
ethyl)pyridin-3-yl]methyl}amino)-5-(2-methylphenyl)-1-
[(2S)-oxolane-2-carbonyl]pyrrolidine-2-carboxylic acid;

(2S,3S,4S,5S)-3-tert-butyl-5-phenyl-4-[(2-phenylethyl)
amino]-1-1-{[(propan-2-yl)oxy]carbonyl}pyrrolidine-2-
carboxylic acid;

(2S,3S,4S,5S)-3-tert-butyl-4-[(2-methyl-2-phenylpropyl)
amino]-5-phenyl-1-{[(propan-2-yl)oxy]
carbonyl}pyrrolidine-2-carboxylic acid;

(2S,3S,4S,5S)-3-tert-butyl-4-{[(5-cyclobutyl-2-methoxy-
pyridin-3-yl)methyl]amino}-5-(2-methylphenyl)-1-[(2S)-
oxolane-2-carbonyl]pyrrolidine-2-carboxylic acid;

(2S,3S,4S,5S)-3-tert-butyl-4-{[(5-cyclobutyl-2-methoxy-
pyridin-3-yl)methyl]amino}-5-(2-methylphenyl)-1-
[(2R)-oxane-2-carbonyl]pyrrolidine-2-carboxylic acid;

(2S,3S,4S,5S)-3-tert-butyl-4-({[4-(2-methoxyphenyl)oxan-
4-yl]methyl}amino)-5-phenyl-1-{[propan-2-yl)oxy]
carbonyl}pyrrolidine-2-carboxylic acid;

(2S,3S,4S,5S)-3-tert-butyl-5-phenyl-1-{[(propan-2-yl)oxy]
carbonyl}-4-[({1-[4-(trifluoromethyl)phenyl]piperidin-3-
yl}methyl)amino]pyrrolidine-2-carboxylic acid;

(2S,3S,4S,5S)-3-tert-butyl-5-(2-cyclopropylpyridin-3-yl)-4-
({[2-methoxy-5-(trifluoromethyl)phenyl]methyl}amino)-
1-[(2S)-oxolane-2-carbonyl]pyrrolidine-2-carboxylic
acid;

(2S,3S,4S,5S)-3-tert-butyl-4-({[2-methoxy-5-(trifluorom-
ethyl)pyridin-3-yl]methyl}amino)-1-[rel-(1R,2S,4S)-7-
oxabicyclo[2.2.1]heptan-2-carbonyl]-5-[2-(propan-2-yl)
phenyl]pyrrolidine-2-carboxylic acid;

(2S,3S,4S,5S)-3-tert-butyl-1-(cyclopropanecarbonyl)-4-
({[2-methoxy-5-(trifluoromethyl)pyridin-3-yl]
methyl}amino)-5-[2-(propan-2-yl)phenyl]pyrrolidine-2-
carboxylic acid;

(2S,3S,4S,5S)-1-(bicyclo[1.1.1]pentane-1-carbonyl)-3-tert-
butyl-4-({[2-methoxy-5-(trifluoromethyl)pyridin-3-yl]
methyl}amino)-5-[2-(propan-2-yl)phenyl]pyrrolidine-2-
carboxylic acid;

(2S,3S,4S,5S)-3-tert-butyl-1-(cyclobutanecarbonyl)-4-({[2-
methoxy-5-(trifluoromethyl)pyridin-3-yl]
methyl}amino)-5-[2-(propan-2-yl)phenyl]pyrrolidine-2-
carboxylic acid;

(2S,3S,4S,5S)-5-[2-(azetidin-1-yl)pyridin-3-yl]-4-{[(5-
bromo-2-ethoxyphenyl)methyl]amino}-3-tert-butyl-1-
{[(propan-2-yl)oxy]carbonyl}pyrrolidine-2-carboxylic
acid;

(2S,3S,4S,5S)-5-[2-(azetidin-1-yl)pyridin-3-yl]-3-tert-bu-
tyl-4-({[2-methoxy-4-(trifluoromethyl)phenyl]
methyl}amino)-1-{[(propan-2-yl)oxy]
carbonyl}pyrrolidine-2-carboxylic acid;

(2S,3S,4S,5S)-3-tert-butyl-5-(2-cyclopropylphenyl)-4-({3-
[(2-methoxypyridin-3-yl)amino]cyclobutyl}amino)-1-
{[(propan-2-yl)oxy]carbonyl}pyrrolidine-2-carboxylic
acid;

(2S,3S,4S,5S)-3-tert-butyl-4-{[(5-tert-butyl-2-methoxyphe-
nyl)methyl]amino}-1-(cyclobutanecarbonyl)-5-[2-(trif-
luoromethyl)phenyl]pyrrolidine-2-carboxylic acid;

(2S,3S,4S,5S)-3-tert-butyl-1-(cyclobutanecarbonyl)-4-{[(5-
cyclobutyl-2-methoxypyridin-3-yl)methyl]amino}-5-[2-
(trifluoromethyl)phenyl]pyrrolidine-2-carboxylic acid;

(2S,3S,4S,5S)-3-tert-butyl-1-(cyclobutanecarbonyl)-4-({[2-
methoxy-5-(1-methylcyclobutyl)phenyl]methyl}amino)-
5-[2-(trifluoromethyl)phenyl]pyrrolidine-2-carboxylic
acid;

(2S,3S,4S,5S)-3-tert-butyl-1-(cyclobutanecarbonyl)-4-({[2-
methoxy-5-(trifluoromethyl)pyridin-3-yl]
methyl}amino)-5-[2-(trifluoromethyl)phenyl]pyrroli-
dine-2-carboxylic acid;

(2S,3S,4S,5S)-3-tert-butyl-4-{[(5-cyclobutyl-2-methoxy-
pyridin-3-yl)methyl]amino}-5-[2-(dimethylamino)pyri-
din-3-yl]-1-[(2S)-oxolane-2-carbonyl]pyrrolidine-2-car-
boxylic acid;

(2S,3S,4S,5S)-3-tert-butyl-5-(2-chlorophenyl)-4-({[2-
methoxy-5-(trifluoromethyl)pyridin-3-yl]
methyl}amino)-1-[(2S)-oxolane-2-carbonyl]pyrrolidine-
2-carboxylic acid;

(2S,3S,4S,5S)-3-tert-butyl-5-[2-(dimethylamino)pyridin-3-
yl]-4-({[2-methoxy-5-(1-methylcyclobutyl)phenyl]
methyl}amino)-1-[(2S)-oxolane-2-carbonyl]pyrrolidine-
2-carboxylic acid;

(2S,3S,4S,5S)-3-tert-butyl-4-{[(5-tert-butyl-2-methoxyphe-
nyl)methyl]amino}-5-[2-(dimethylamino)pyridin-3-yl]-
1-[(2S)-oxolane-2-carbonyl]pyrrolidine-2-carboxylic
acid;

(2S,3S,4S,5S)-3-tert-butyl-4-{[(5-tert-butyl-2-hydroxyphe-
nyl)methyl]amino}-1-[(2S)-oxolane-2-carbonyl]-5-[2-
(propan-2-yl)phenyl]pyrrolidine-2-carboxylic acid;

(2S,3S,4S,5S)-3-tert-butyl-4-{[(5-cyclobutyl-2-methoxy-
pyridin-3-yl)methyl]amino}-1-[(2S)-oxolane-2-carbo-
nyl]-5-[2-(trifluoromethyl)phenyl]pyrrolidine-2-carbox-
ylic acid;

(2S,3S,4S,5S)-4-{[(5-bromo-2-methoxypyridin-3-yl)
methyl]amino}-3-tert-butyl-5-(2-methylphenyl)-1-[(2S)-
oxane-2-carbonyl]pyrrolidine-2-carboxylic acid;

(2S,3S,4S,5S)-5-(2-bromophenyl)-3-tert-butyl-4-({[2-
methoxy-5-(trifluoromethyl)pyridin-3-yl]
methyl}amino)-1-[(2S)-oxane-2-carbonyl]pyrrolidine-2-
carboxylic acid;

(2S,3S,4S,5S)-5-(2-bromophenyl)-3-tert-butyl-4-({[2-
methoxy-4-(trifluoromethyl)phenyl]methyl}amino)-1-
[(2S)-oxane-2-carbonyl]pyrrolidine-2-carboxylic acid;

(2S,3S,4S,5S)-5-(2-bromophenyl)-3-tert-butyl-4-({[2-
methoxy-5-(trifluoromethyl)phenyl]methyl}amino)-1-
[(2S)-oxane-2-carbonyl]pyrrolidine-2-carboxylic acid;

(2S,3S,4S,5S)-5-(2-bromophenyl)-3-tert-butyl-4-{[(5-cy-
clobutyl-2-methoxypyridin-3-yl)methyl]amino}-1-[(2S)-
oxane-2-carbonyl]pyrrolidine-2-carboxylic acid;

(2S,3S,4S,5S)-5-(2-bromophenyl)-3-tert-butyl-4-({[2-
methoxy-5-(trifluoromethyl)phenyl]methyl}amino)-1-
[(2S)-oxolane-2-carbonyl]pyrrolidine-2-carboxylic acid;

(2S,3S,4S,5S)-5-(2-bromophenyl)-3-tert-butyl-4-{[(5-cy-
clopropyl-2-methoxypyridin-3-yl)methyl]amino}-1-
[(2S)-oxolane-2-carbonyl]pyrrolidine-2-carboxylic acid;

(2S,3S,4S,5S)-5-(2-bromophenyl)-3-tert-butyl-4-{[(5-tert-butyl-2-methoxyphenyl)methyl]amino}-1-[(2S)-oxolane-2-carbonyl]pyrrolidine-2-carboxylic acid;
(2S,3S,4S,5S)-5-(2-bromophenyl)-3-tert-butyl-4-({[2-methoxy-5-(1-methylcyclobutyl)phenyl]methyl}amino)-1-[(2S)-oxolane-2-carbonyl]pyrrolidine-2-carboxylic acid;
(2S,3S,4S,5S)-3-tert-butyl-4-{[(5-cyclobutyl-2-methoxypyridin-3-yl)methyl]amino}-5-(2-cyclopropylphenyl)-1-[(2S)-oxane-2-carbonyl]pyrrolidine-2-carboxylic acid;
(2S,3S,4S,5S)-3-tert-butyl-4-{[(5-cyclobutyl-2-methoxypyridin-3-yl)methyl]amino}-5-(2-ethylphenyl)-1-[(2S)-oxane-2-carbonyl]pyrrolidine-2-carboxylic acid;
(2S,3S,4S,5S)-3-tert-butyl-5-(2,3-dihydro-1-benzofuran-7-yl)-4-({[2-methoxy-5-(trifluoromethyl)pyridin-3-yl]methyl}amino)-1-[(2S)-oxane-2-carbonyl]pyrrolidine-2-carboxylic acid;
(2S,3S,4S,5S)-3-tert-butyl-5-(2,3-dihydro-1-benzofuran-7-yl)-4-({[2-methoxy-5-(trifluoromethyl)phenyl]methyl}amino)-1-[(2S)-oxane-2-carbonyl]pyrrolidine-2-carboxylic acid;
(2S,3S,4S,5S)-3-tert-butyl-5-(2,3-dihydro-1-benzofuran-7-yl)-4-({[2-methoxy-4-(trifluoromethyl)phenyl]methyl}amino)-1-[(2S)-oxane-2-carbonyl]pyrrolidine-2-carboxylic acid;
(2S,3S,4S,5S)-3-tert-butyl-4-{[(5-cyclobutyl-2-methoxypyridin-3-yl)methyl]amino}-5-(2,3-dihydro-1-benzofuran-7-yl)-1-[(2S)-oxane-2-carbonyl]pyrrolidine-2-carboxylic acid;
(2S,3S,4S,5S)-3-tert-butyl-5-(2,3-dihydro-1-benzofuran-7-yl)-4-{[(3-methoxy-5,6,7,8-tetrahydronaphthalen-2-yl)methyl]amino}-1-[(2S)-oxane-2-carbonyl]pyrrolidine-2-carboxylic acid;
(2S,3S,4S,5S)-3-tert-butyl-4-{[(5-cyclobutyl-2-methoxypyridin-3-yl)methyl]amino}-1-(6-methoxypyridine-2-sulfonyl)-5-[2-(propan-2-yl)phenyl]pyrrolidine-2-carboxylic acid;
(2S,3S,4S,5S)-3-tert-butyl-4-({[2-methoxy-5-(1-methylcyclobutyl)phenyl]methyl}amino)-1-[(2S)-oxane-2-carbonyl]-5-[2-(propan-2-yl)phenyl]pyrrolidine-2-carboxylic acid;
(2S,3S,4S,5S)-3-tert-butyl-4-{[(2,2-dimethyl-2,3-dihydro-1-benzofuran-7-yl)methyl]amino}-1-[(2S)-oxolane-2-carbonyl]-5-[2-(propan-2-yl)phenyl]pyrrolidine-2-carboxylic acid;
(2S,3S,4S,5S)-3-tert-butyl-4-{[(2,2-dimethyl-2,3-dihydro-1-benzofuran-7-yl)methyl]amino}-1-[(2S)-oxane-2-carbonyl]-5-[2-(propan-2-yl)phenyl]pyrrolidine-2-carboxylic acid;
(2S,3S,4S,5S)-3-tert-butyl-4-{[(5-cyclobutyl-2-methoxypyridin-3-yl)methyl]amino}-1-(cyclohexanecarbonyl)-5-(2,2-dimethyl-2,3-dihydro-1-benzofuran-7-yl)pyrrolidine-2-carboxylic acid;
(2S,3S,4S,5S)-3-tert-butyl-4-(4-chloro-7-methoxy-1,3-dihydro-2H-isoindol-2-yl)-1-[(2S)-oxane-2-carbonyl]-5-[2-(propan-2-yl)phenyl]pyrrolidine-2-carboxylic acid;
(2S,3S,4S,5S)-3-tert-butyl-4-({2-[2-methoxy-5-(trifluoromethyl)phenoxy]ethyl}amino)-1-{[(propan-2-yl)oxy]carbonyl}-5-{2-[(propan-2-yl)oxy]pyridin-3-yl}pyrrolidine-2-carboxylic acid;
(2S,3S,4S,5S)-3-tert-butyl-4-{[(5-tert-butyl-2-methoxyphenyl)methyl]amino}-1-(cyclohexanecarbonyl)-5-(2-hydroxyphenyl)pyrrolidine-2-carboxylic acid;
rac-(2R,3R,4R,5R)-3-tert-butyl-4-[(5-chloropyridin-2-yl)amino]-1-(cyclohexanecarbonyl)-5-phenylpyrrolidine-2-carboxylic acid;
rac-(2R,3R,4R,5R)-3-tert-butyl-4-{[6-chloro-4-(trifluoromethyl)pyridin-2-yl]amino}-1-(cyclohexanecarbonyl)-5-phenylpyrrolidine-2-carboxylic acid;
rac-(2R,3R,4R,5R)-3-tert-butyl-4-{[(3-chloro-2,4-dimethoxyphenyl)methyl]amino}-1-(cyclohexanecarbonyl)-5-phenylpyrrolidine-2-carboxylic acid;
rac-(2R,3R,4R,5R)-3-tert-butyl-1-(cyclohexanecarbonyl)-5-phenyl-4-[({2-[(propan-2-yl)oxy]phenyl}methyl)amino]pyrrolidine-2-carboxylic acid;
rac-(2R,3R,4R,5R)-3-tert-butyl-1-(cyclohexanecarbonyl)-4-({[2-(2-methylpropoxy)phenyl]methyl}amino)-5-phenylpyrrolidine-2-carboxylic acid;
rac-(2R,3R,4R,5R)-3-tert-butyl-1-(cyclohexanecarbonyl)-4-{[(2-methoxypyridin-3-yl)methyl]amino}-5-phenylpyrrolidine-2-carboxylic acid;
rac-(2R,3R,4R,5R)-3-tert-butyl-4-{[(3-chloro-2-methoxyphenyl)methyl]amino}-1-(cyclohexanecarbonyl)-5-phenylpyrrolidine-2-carboxylic acid;
rac-(2R,3R,4R,5R)-3-tert-butyl-4-({[5-chloro-2-(difluoromethoxy)phenyl]methyl}amino)-1-(cyclohexanecarbonyl)-5-phenylpyrrolidine-2-carboxylic acid;
rac-(2R,3R,4R,5R)-3-tert-butyl-4-{[(5-chloro-2-ethoxyphenyl)methyl]amino}-1-(cyclohexanecarbonyl)-5-phenylpyrrolidine-2-carboxylic acid;
rac-(2R,3R,4R,5R)-3-tert-butyl-4-{[(2-chloro-6-methoxyphenyl)methyl]amino}-1-(cyclohexanecarbonyl)-5-phenylpyrrolidine-2-carboxylic acid;
(2R,3R,4R,5R)-1-[di(propan-2-yl)carbamoyl]-3-methyl-4-{[6-methyl-4-(trifluoromethyl)pyridin-2-yl]amino}-5-phenylpyrrolidine-2-carboxylic acid;
rac-(2R,3R,4R,5R)-4-{[(5-chloro-2-methoxyphenyl)methyl]amino}-1-(cyclohexanecarbonyl)-3-cyclopropyl-5-phenylpyrrolidine-2-carboxylic acid;
rac-(2R,3R,4R,5R)-3-tert-butyl-4-{[6-methyl-4-(trifluoromethyl)pyridin-2-yl]amino}-5-phenyl-1-{[(propan-2-yl)oxy]carbonyl}pyrrolidine-2-carboxylic acid;
rac-(2R,3R,4R,5R)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;
rac-(2R,3R,4R,5R)-3-tert-butyl-4-({[2-chloro-5-(trifluoromethyl)pyridin-3-yl]methyl}amino)-1-(cyclohexanecarbonyl)-5-phenylpyrrolidine-2-carboxylic acid;
rac-(2R,3R,4R,5R)-3-tert-butyl-4-({[2-chloro-5-(trifluoromethyl)pyridin-3-yl]methyl}amino)-1-(cyclohexanecarbonyl)-5-(2-methoxyphenyl)pyrrolidine-2-carboxylic acid;
rac-(2R,3R,4R,5R)-3-tert-butyl-1-(cyclohexanecarbonyl)-5-(2-methoxyphenyl)-4-({[2-methoxy-5-(trifluoromethyl)phenyl]methyl}amino)pyrrolidine-2-carboxylic acid;
rac-(2R,3R,4R,5R)-3-tert-butyl-1-(cyclohexanecarbonyl)-4-({[2-(difluoromethoxy)-4-methoxyphenyl]methyl}amino)-5-phenylpyrrolidine-2-carboxylic acid;
rac-(2R,3R,4R,5S)-3-tert-butyl-4-{[(5-chloro-2-methoxyphenyl)methyl]amino}-1-(cyclohexanecarbonyl)-5-(6-methoxypyridin-2-yl)pyrrolidine-2-carboxylic acid;
rac-(2R,3R,4R,5R)-3-tert-butyl-5-[2-(dimethylamino)phenyl]-4-({[2-methoxy-5-(trifluoromethyl)phenyl]methyl}amino)-1-[oxane-2-carbonyl]pyrrolidine-2-carboxylic acid;
rac-(2R,3R,4R,5R)-3-tert-butyl-5-[2-(dimethylamino)phenyl]-4-({[2-methoxy-5-(trifluoromethyl)phenyl]methyl}amino)-1-[oxane-3-carbonyl]pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-[oxane-3-carbonyl]pyrrolidine-2-carboxylic acid;

rac-(2R,3R,4R,5R)-3-tert-butyl-4-{[(4-chloro-2-methoxyphenyl)methyl]amino}-5-[2-(dimethylamino)phenyl]-1-[oxane-3-carbonyl]pyrrolidine-2-carboxylic acid;

rac-(2R,3R,4R,5R)-3-tert-butyl-5-[2-(dimethylamino)phenyl]-1-[2,2-dimethyloxane-4-carbonyl]-4-({[2-methoxy-5-(trifluoromethyl)phenyl]methyl}amino)pyrrolidine-2-carboxylic acid;

rac-(2R,3R,4R,5R)-3-tert-butyl-4-{[(5-chloro-2-methoxyphenyl)methyl]amino}-5-[2-(dimethylamino)phenyl]-1-[2,2-dimethyloxane-4-carbonyl]pyrrolidine-2-carboxylic acid;

rac-(2R,3R,4R,5R)-3-tert-butyl-4-{[(4-chloro-2-methoxyphenyl)methyl]amino}-5-[2-(dimethylamino)phenyl]-1-[2,2-dimethyloxane-4-carbonyl]pyrrolidine-2-carboxylic acid;

rac-(2R,3R,4R,5R)-3-tert-butyl-1-[(3S)-1-(methoxycarbonyl)piperidine-3-carbonyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-4-{[(5-chloro-2-methoxyphenyl)methyl]amino}-5-[2-(dimethylamino)pyridin-3-yl]-1-{[(propan-2-yl)oxy]carbonyl}pyrrolidine-2-carboxylic acid;

rac-(2R,3R,4R,5R)-3-tert-butyl-4-{[(4-chloro-2-methoxyphenyl)methyl]amino}-5-[2-(dimethylamino)pyridin-3-yl]-1-{[(propan-2-yl)oxy]carbonyl}pyrrolidine-2-carboxylic acid;

rac-(2R,3R,4R,5R)-3-tert-butyl-1-(cyclohexanecarbonyl)-4-{[(5-fluoro-2-methoxypyridin-3-yl)methyl]amino}-5-phenylpyrrolidine-2-carboxylic acid;

rac-(2R,3R,4R,5R)-3-tert-butyl-1-(cyclohexanecarbonyl)-5-phenyl-4-({[2-(trifluoromethyl)phenyl]methyl}amino)pyrrolidine-2-carboxylic acid;

rac-(2R,3R,4R,5R)-3-tert-butyl-4-({[2-methoxy-5-(trifluoromethyl)phenyl]methyl}amino)-5-phenyl-1-(phenylacetyl)pyrrolidine-2-carboxylic acid;

rac-(2S,3S,4S,5S)-3-tert-butyl-5-[2-(dimethylamino)pyridin-3-yl]-1-[(2R)-2-methoxy-2-phenylacetyl]-4-({[2-methoxy-5-(trifluoromethyl)phenyl]methyl}amino)pyrrolidine-2-carboxylic acid;

rac-(2R,3R,4R,5R)-3-tert-butyl-4-({[2-methoxy-5-(trifluoromethyl)phenyl]methyl}amino)-1-[(2R,3R)-2-methyloxane-3-carbonyl]-5-phenylpyrrolidine-2-carboxylic acid;

rac-(2R,3R,4R,5R)-3-tert-butyl-4-({[2-methoxy-5-(trifluoromethyl)phenyl]methyl}amino)-1-[(2S,3S)-2-methyloxane-3-carbonyl]-5-phenylpyrrolidine-2-carboxylic acid;

rac-(2R,3R,4R,5R)-3-(tert-butyl)-4-((2-methoxy-5-(trifluoromethyl)benzyl)amino)-1-((1R,3R)-3-methoxycyclohexanecarbonyl)-5-phenylpyrrolidine-2-carboxylic acid;

rac-(2R,3R,4R,5R)-3-(tert-butyl)-4-((2-methoxy-4-(trifluoromethyl)benzyl)amino)-1-((1R,3R)-3-methoxycyclohexanecarbonyl)-5-phenylpyrrolidine-2-carboxylic acid;

rac-(2R,3R,4R,5R)-3-(tert-butyl)-4-((4-chloro-2-methoxybenzyl)amino)-1-((1R,3R)-3-methoxycyclohexanecarbonyl)-5-phenylpyrrolidine-2-carboxylic acid;

rac-(2R,3R,4R,5R)-3-tert-butyl-4-{[(4-fluoro-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[(2-methoxy-5-methylphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-({[2-methoxy-4-(trifluoromethoxy)phenyl]methyl}amino)-5-phenyl-1-{[(propan-2-yl)oxy]carbonyl}pyrrolidine-2-carboxylic acid;

rac-(2R,3R,4R,5R)-3-tert-butyl-4-{[(5-fluoro-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[(5-tert-butyl-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-({[2-methoxy-5-(propan-2-yl)phenyl]methyl}amino)-5-phenyl-1-{[(propan-2-yl)oxy]carbonyl}pyrrolidine-2-carboxylic acid;

rac-(2R,3R,4R,5R)-3-tert-butyl-4-{[(4-chloro-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[(2-methoxyphenyl)methyl]amino}-5-phenyl-1-{[(propan-2-yl)oxy]carbonyl}pyrrolidine-2-carboxylic acid;

rac-(2S,3S,4S,5S)-3-tert-butyl-4-{[(4-chloro-2-methoxyphenyl)methyl]amino}-5-[2-(dimethylamino)pyridin-3-yl]-1-[(2R)-2-methoxy-2-phenylacetyl]pyrrolidine-2-carboxylic acid;

rac-(2S,3S,4S,5S)-3-tert-butyl-5-[2-(dimethylamino)pyridin-3-yl]-1-[(2R)-2-methoxy-2-phenylacetyl]-4-({[2-methoxy-4-(trifluoromethyl)phenyl]methyl}amino)pyrrolidine-2-carboxylic acid;

rac-(2R,3R,4R,5R)-3-tert-butyl-4-({[2-methoxy-4-(trifluoromethyl)phenyl]methyl}amino)-1-((2S)-oxane-2-carbonyl)-5-phenylpyrrolidine-2-carboxylic acid;

rac-(2S,3S,4S,5S)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid;

rac-(2R,3R,4R,5R)-3-tert-butyl-1-(cyclohexanecarbonyl)-5-[2-(dimethylamino)pyridin-3-yl]-4-({[2-methoxy-4-(trifluoromethyl)phenyl]methyl}amino)pyrrolidine-2-carboxylic acid;

rac-(2R,3R,4R,5R)-3-tert-butyl-1-(cyclohexanecarbonyl)-5-[2-(dimethylamino)pyridin-3-yl]-4-({[2-methoxy-5-(trifluoromethyl)pyridin-3-yl]methyl}amino)pyrrolidine-2-carboxylic acid;

rac-(2S,3S,4S,5R)-3-tert-butyl-1-(cyclohexanecarbonyl)-4-{[6-methyl-4-(trifluoromethyl)pyridin-2-yl]amino}-5-(pyridin-2-yl)pyrrolidine-2-carboxylic acid;

(2S*,3S*,4S*,5S*)-3-tert-butyl-4-{[(4-chloro-2-methoxyphenyl)methyl]amino}-1-[(2R)-2-methoxy-2-phenylacetyl]-5-phenylpyrrolidine-2-carboxylic acid;

rac-(2R,3R,4R,5R)-3-tert-butyl-4-{[6-methyl-4-(trifluoromethyl)pyridin-2-yl]amino}-5-phenyl-1-(phenylacetyl)pyrrolidine-2-carboxylic acid;

rac-(2R,3R,4R,5R)-3-tert-butyl-5-[2-(dimethylamino)phenyl]-4-({[2-methoxy-5-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-4-({[2-methoxy-4-(trifluoromethyl)phenyl]methyl}amino)-1-[(2S*)-2-phenoxypropanoyl]-5-phenylpyrrolidine-2-carboxylic acid;

rac-(2S,3S,4S,5S)-3-tert-butyl-4-({[2-methoxy-5-(trifluoromethyl)phenyl]methyl}amino)-1-(oxolane-2-carbonyl)-5-phenylpyrrolidine-2-carboxylic acid;

rac-(2S,3S,4S,5S)-3-tert-butyl-4-({[2-methoxy-4-(trifluoromethyl)phenyl]methyl}amino)-1-(oxolane-2-carbonyl)-5-phenylpyrrolidine-2-carboxylic acid;

rac-(2S,3S,4S,5S)-3-tert-butyl-4-{[(5-chloro-2-methoxyphenyl)methyl]amino}-1-(oxolane-2-carbonyl)-5-phenylpyrrolidine-2-carboxylic acid;

(2S,3S,4S,5S)-3-tert-butyl-5-[2-(dimethylamino)phenyl]-1-[(2R)-2-methoxy-2-phenylacetyl]-4-({[2-methoxy-5-(trifluoromethyl)phenyl]methyl}amino)pyrrolidine-2-carboxylic acid;

(2S,3S,4S,5S)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid;

(2R,3R,4R,5R)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid;

(2S,3S,4S,5S)-3-tert-butyl-1-[(2S)-2-methoxy-2-phenylacetyl]-4-({[2-methoxy-4-(trifluoromethyl)phenyl]methyl}amino)-5-phenylpyrrolidine-2-carboxylic acid;

rac-(2R,3R,4R,5R)-3-tert-butyl-4-({[2-methoxy-5-(trifluoromethyl)phenyl]methyl}amino)-1-[(2R)-2-phenoxypropanoyl]-5-phenylpyrrolidine-2-carboxylic acid;

rac-(2R,3R,4R,5R)-3-tert-butyl-4-({[2-methoxy-4-(trifluoromethyl)phenyl]methyl}amino)-1-[(2R*)-2-phenoxypropanoyl]-5-phenylpyrrolidine-2-carboxylic acid;

rac-(2R,3R,4R,5R)-3-tert-butyl-1-(4,4-difluorocyclohexane-1-carbonyl)-4-({[2-methoxy-5-(trifluoromethyl)phenyl]methyl}amino)-5-phenylpyrrolidine-2-carboxylic acid;

rac-(2R,3R,4R,5R)-3-tert-butyl-1-(4,4-difluorocyclohexane-1-carbonyl)-4-({[2-methoxy-4-(trifluoromethyl)phenyl]methyl}amino)-5-phenylpyrrolidine-2-carboxylic acid;

rac-(2R,3R,4R,5R)-3-tert-butyl-4-({[2-methoxy-5-(trifluoromethyl)phenyl]methyl}amino)-5-phenyl-1-(spiro[2.5]octane-6-carbonyl)pyrrolidine-2-carboxylic acid;

rac-(2R,3R,4R,5R)-3-tert-butyl-4-{[(5-cyano-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-({[2-methyl-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-4-({[2-methoxy-5-(propan-2-yl)phenyl]methyl}amino)-5-phenylpyrrolidine-2-carboxylic acid;

rac-(2R,3R,4R,5R)-3-tert-butyl-4-{[(4-cyano-2-methoxyphenyl)methyl]amino}-1-(cyclohexanecarbonyl)-5-phenylpyrrolidine-2-carboxylic acid;

rac-(2R,3R,4R,5R)-3-tert-butyl-4-({[5-chloro-2-(trifluoromethoxy)phenyl]methyl}amino)-1-(cyclohexanecarbonyl)-5-phenylpyrrolidine-2-carboxylic acid;

rac-(2R,3R,4R,5R)-3-tert-butyl-1-(cyclohexanecarbonyl)-5-phenyl-4-({[2-(trifluoromethoxy)phenyl]methyl}amino)pyrrolidine-2-carboxylic acid;

rac-(2R,3R,4R,5R)-3-tert-butyl-1-(cyclohexanecarbonyl)-4-({[2-methoxy-6-(trifluoromethyl)pyridin-3-yl]methyl}amino)-5-phenylpyrrolidine-2-carboxylic acid;

rac-(2R,3R,4R,5R)-4-{[(5-chloro-2-methoxyphenyl)methyl]amino}-1-(cyclohexanecarbonyl)-3-(2-methoxypropan-2-yl)-5-phenylpyrrolidine-2-carboxylic acid;

rac-(2R,3R,4R,5R)-3-tert-butyl-4-({[2-methoxy-4-(trifluoromethyl)phenyl]methyl}amino)-5-phenyl-1-[(2S*)-2-phenylpropanoyl]pyrrolidine-2-carboxylic acid;

(2S,3S,4S,5S)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid;

(2R,3R,4R,5R)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid;

(2S,3S,4S,5S)-3-tert-butyl-1-[(2R)-2-methoxy-2-phenylacetyl]-4-({[2-methoxy-5-(trifluoromethyl)pyridin-3-yl]methyl}amino)-5-phenylpyrrolidine-2-carboxylic acid;

(2S,3S,4S,5S)-3-tert-butyl-1-[(2R)-2-methoxy-2-phenylacetyl]-5-(2-methoxypyridin-3-yl)-4-({[2-methoxy-4-(trifluoromethyl)phenyl]methyl}amino)pyrrolidine-2-carboxylic acid;

rac-(2R,3R,4R,5R)-3-tert-butyl-1-(1,4-dioxane-2-carbonyl)-4-({[2-methoxy-5-(trifluoromethyl)phenyl]methyl}amino)-5-phenylpyrrolidine-2-carboxylic acid;

rac-(2R,3R,4R,5R)-3-tert-butyl-4-{[(5-chloro-2-methoxyphenyl)methyl]amino}-1-(1,4-dioxane-2-carbonyl)-5-phenylpyrrolidine-2-carboxylic acid;

(2S,3S,4S,5S)-3-tert-butyl-5-[2-(dimethylamino)pyridin-3-yl]-1-[(2R)-2-methoxy-2-phenylacetyl]-4-({[2-methoxy-4-(trifluoromethyl)phenyl]methyl}amino)pyrrolidine-2-carboxylic acid;

rac-(2R,3R,4R,5R)-1-(cyclohexanecarbonyl)-3-(2-methoxypropan-2-yl)-4-({[2-methoxy-4-(trifluoromethyl)phenyl]methyl}amino)-5-phenylpyrrolidine-2-carboxylic acid;

rac-(2R,3R,4R,5R)-1-(cyclohexanecarbonyl)-3-(2-methoxypropan-2-yl)-4-{[2-methoxy-5-(trifluoromethyl)pyridin-3-yl]amino}-5-phenylpyrrolidine-2-carboxylic acid;

rac-(2R,3R,4R,5R)-3-tert-butyl-4-{[(5-tert-butyl-2-methoxyphenyl)methyl]amino}-1-[(cyclobutyloxy)carbonyl]-5-phenylpyrrolidine-2-carboxylic acid;

(2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-5-(2-methoxypyridin-3-yl)-4-({[2-methoxy-4-(trifluoromethyl)phenyl]methyl}amino)-1-[(2S)-oxane-2-carbonyl]pyrrolidine-2-carboxylic acid;

(2S,3S,4S,5S)-3-tert-butyl-1-(cyclohexanecarbonyl)-4-({[2-methoxy-5-(trifluoromethyl)phenyl]methyl}amino)-5-(2-methylpyridin-3-yl)pyrrolidine-2-carboxylic acid;

(2S,3S,4S,5S)-3-tert-butyl-1-(cyclohexanecarbonyl)-4-({[2-methoxy-4-(trifluoromethyl)phenyl]methyl}amino)-5-(2-methylpyridin-3-yl)pyrrolidine-2-carboxylic acid;

(2S,3S,4S,5S)-3-tert-butyl-4-{[(5-chloro-2-methoxyphenyl)methyl]amino}-1-(cyclohexanecarbonyl)-5-(2-methylpyridin-3-yl)pyrrolidine-2-carboxylic acid;

(2S,3S,4S,5S)-3-tert-butyl-4-{[(4-chloro-2-methoxyphenyl)methyl]amino}-1-(cyclohexanecarbonyl)-5-(2-methylpyridin-3-yl)pyrrolidine-2-carboxylic acid;

(2S,3S,4S,5S)-3-tert-butyl-4-{[(5-chloro-2-methoxyphenyl)methyl]amino}-1-(cyclohexanecarbonyl)-5-phenylpyrrolidine-2-carboxylic acid;

(2S,3S,4S,5S)-3-tert-butyl-5-(2-methoxypyridin-3-yl)-4-({[2-methoxy-4-(trifluoromethyl)phenyl]methyl}amino)-1-[(2R*)oxane-2-carbony]pyrrolidine-2-carboxylic acid;

(2S,3S,4S,5S)-3-tert-butyl-4-{[(4-chloro-2-methoxyphenyl)methyl]amino}-1-(cyclohexanecarbonyl)-5-phenylpyrrolidine-2-carboxylic acid;

(2S,3S,4S,5S)-4-{[(1-benzofuran-3-yl)methyl]amino}-3-tert-butyl-1-(cyclohexanecarbonyl)-5-phenylpyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-phenylpyrrolidine-2-carboxylic acid;

(2S,3S,4S,5S)-3-tert-butyl-4-{[(4-chloro-2-fluoro-5-methoxyphenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2,5-dichlorophenyl)methyl]amino}-5-phenylpyrrolidine-2-carboxylic acid;

(2S,3S,4S,5S)-3-tert-butyl-1-(cyclohexanecarbonyl)-4-{[(2-fluoro-5-methoxyphenyl)methyl]amino}-5-phenylpyrrolidine-2-carboxylic acid;

(2S,3S,4S,5S)-3-tert-butyl-4-({[5-chloro-2-(difluoromethoxy)phenyl]methyl}amino)-1-(cyclohexanecarbonyl)-5-phenylpyrrolidine-2-carboxylic acid;

(2S,3S,4S,5S)-4-({[3,5-bis(trifluoromethyl)phenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[4-methoxy-2-(trifluoromethyl)phenyl]methyl}amino)-5-phenylpyrrolidine-2-carboxylic acid;

(2S,3S,4S,5S)-4-{[(2-bromo-5-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3,5-dichlorophenyl)methyl]amino}-5-phenylpyrrolidine-2-carboxylic acid;

(2S,3S,4S,5S)-3-tert-butyl-1-(cyclohexanecarbonyl)-4-{[(4-fluoro-3-methoxyphenyl)methyl]amino}-5-phenylpyrrolidine-2-carboxylic acid;

(2S,3S,4S,5S)-3-tert-butyl-1-(cyclohexanecarbonyl)-4-{[(2,4-dichlorophenyl)methyl]amino}-5-phenylpyrrolidine-2-carboxylic acid;

(2S,3S,4S,5S)-4-{[(2-bromo-4-fluoro-5-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3,5-difluorophenyl)methyl]amino}-5-phenylpyrrolidine-2-carboxylic acid;

(2S,3S,4S,5S)-3-tert-butyl-1-(cyclohexanecarbonyl)-4-{[(6-methoxy-2H-1,3-benzodioxol-5-yl)methyl]amino}-5-phenylpyrrolidine-2-carboxylic acid;

(2S,3S,4S,5S)-3-tert-butyl-1-(cyclohexanecarbonyl)-4-{[(2,5-dimethylphenyl)methyl]amino}-5-phenylpyrrolidine-2-carboxylic acid;

(2S,3S,4S,5S)-3-tert-butyl-1-(cyclohexanecarbonyl)-4-{[(4-fluoro-2-methoxyphenyl)methyl]amino}-5-phenylpyrrolidine-2-carboxylic acid;

(2S,3S,4S,5S)-3-tert-butyl-1-(cyclohexanecarbonyl)-4-{[(4-ethoxy-2-methylphenyl)methyl]amino}-5-phenylpyrrolidine-2-carboxylic acid;

(2S,3S,4S,5S)-3-tert-butyl-1-[(2R)-2-methoxypropanoyl]-4-({[2-methoxy-5-(trifluoromethyl)phenyl]methyl}amino)-5-phenylpyrrolidine-2-carboxylic acid;

(2S,3S,4S,5S)-3-tert-butyl-4-{[(3-tert-butylphenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-5-phenyl-4-({[3-(trifluoromethyl)phenyl]methyl}amino)pyrrolidine-2-carboxylic acid;

(2S,3S,4S,5S)-3-tert-butyl-4-{[(2-methoxy-4-methylphenyl)methyl]amino}-5-(2-methoxypyridin-3-yl)-1-[(2S)-oxane-2-carbonyl]pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-[2-(difluoromethoxy)phenyl]pyrrolidine-2-carboxylic acid;

(2S,3S,4S,5S)-3-tert-butyl-1-(cyclohexanecarbonyl)-4-{[(3-methoxy-5,6,7,8-tetrahydronaphthalen-2-yl)methyl]amino}-5-phenylpyrrolidine-2-carboxylic acid;

(2S,3S,4S,5S)-4-{[(5-bromo-2-ethoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[4-methoxy-3-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-{[(4,5-difluoro-2-methoxyphenyl)methyl]amino}-5-phenylpyrrolidine-2-carboxylic acid;

(2S,3S,4S,5S)-3-tert-butyl-1-(cyclohexanecarbonyl)-4-{[(6-ethoxy-2,3-dihydro-1H-inden-5-yl)methyl]amino}-5-phenylpyrrolidine-2-carboxylic acid;

(2S,3S,4S,5S)-3-tert-butyl-1-(cyclohexanecarbonyl)-4-{[(4-fluoro-3-phenoxyphenyl)methyl]amino}-5-phenylpyrrolidine-2-carboxylic acid;

(2S,3S,4S,5S)-3-tert-butyl-1-(cyclohexanecarbonyl)-4-{[(2,4-dimethylphenyl)methyl]amino}-5-phenylpyrrolidine-2-carboxylic acid;

(2S,3S,4S,5S)-3-tert-butyl-1-(cyclohexanecarbonyl)-4-{[(3,5-dimethylphenyl)methyl]amino}-5-phenylpyrrolidine-2-carboxylic acid;

(2S,3S,4S,5S)-3-tert-butyl-1-(cyclohexanecarbonyl)-4-{[(3,5-di-tert-butylphenyl)methyl]amino}-5-phenylpyrrolidine-2-carboxylic acid;

(2S,3S,4S,5S)-3-tert-butyl-5-(2-methoxyphenyl)-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(4-tert-butyl-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-5-(2-methoxyphenyl)-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-chloro-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-1-(cyclohexanecarbonyl)-4-{[(2-methoxy-4-methylphenyl)methyl]amino}-5-(2-methoxypyridin-3-yl)pyrrolidine-2-carboxylic acid;

(2S,3S,4S,5S)-3-tert-butyl-4-({[5-chloro-2-(cyclopropylmethoxy)phenyl]methyl}amino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methoxyphenyl)pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-(2-methoxyphenyl)pyrrolidine-2-carboxylic acid;

rac-(2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid;

rac-(2S,3S,4S,5S)-3-tert-butyl-4-{[(5-chloro-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-[(2-chloro-6-fluoro-4-methylquinolin-3-yl)amino]-1-(cyclohexanecarbonyl)-5-phenylpyrrolidine-2-carboxylic acid;

(2S,3S,4S,5S)-3-tert-butyl-4-[(2-chloro-5-cyanopyridin-3-yl)amino]-1-(cyclohexanecarbonyl)-5-phenylpyrrolidine-2-carboxylic acid;

(2S,3S,4S,5S)-3-tert-butyl-4-[(3-cyano-6-methylpyridin-2-yl)amino]-1-(cyclohexanecarbonyl)-5-phenylpyrrolidine-2-carboxylic acid;

(2S,3S,4S,5S)-3-tert-butyl-4-{[3-cyano-4-(methoxymethyl)-6-methylpyridin-2-yl]amino}-1-(cyclohexanecarbonyl)-5-phenylpyrrolidine-2-carboxylic acid;

(2S,3S,4S,5S)-4-[3,5-bis(trifluoromethyl)anilino]-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1R,3R)-3-methoxycyclohexane-1-carbonyl]-5-phenylpyrrolidine-2-carboxylic acid;

(2S,3S,4S,5S)-1-(cyclohexanecarbonyl)-3-(2-methoxypropan-2-yl)-4-({[2-methoxy-4-(trifluoromethyl)phenyl]methyl}amino)-5-phenylpyrrolidine-2-carboxylic acid;

rac-(2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-1-benzoyl-3-tert-butyl-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1λ⁶-thiane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-1H-pyrazole-3-sulfonyl)-5-phenylpyrrolidine-2-carboxylic acid;

(2S,3S,4S,5S)-1-(benzenesulfonyl)-3-tert-butyl-4-({[2-methoxy-5-(trifluoromethyl)phenyl]methyl}amino)-5-phenylpyrrolidine-2-carboxylic acid;

(2S,3S,4S,5S)-3-tert-butyl-1-(2,3-dihydro-1,4-benzodioxine-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(propan-2-yl)pyridin-3-yl]methyl}amino)-5-phenylpyrrolidine-2-carboxylic acid;

(2S,3S,4S,5S)-4-{[(5-bromo-2-methoxypyridin-3-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-[({2-methoxy-5-[(2R)-3-methoxy-2-methyl-3-oxopropyl]pyridin-3-yl}methyl)amino]-5-phenylpyrrolidine-2-carboxylic acid;

(2S,3S,4S,5S)-3-tert-butyl-4-{[(4-methoxy[1,1'-biphenyl]-3-yl)methyl]amino}-5-phenyl-1-{[(propan-2-yl)oxy]carbonyl}pyrrolidine-2-carboxylic acid;

(2S,3S,4S,5S)-3-tert-butyl-4-({[2-methoxy-4-(trifluoromethyl)phenyl]methyl}amino)-1-[(2-methylpropoxy)carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(oxan-4-yl)acetyl]-5-phenylpyrrolidine-2-carboxylic acid;

(2S,3S,4S,5S)-3-tert-butyl-1-(3,4-dihydro-2H-1-benzopyran-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-1H-2-benzopyran-1-carbonyl)-5-phenylpyrrolidine-2-carboxylic acid;

(2S,3S,4S,5S)-3-tert-butyl-1-(cyclohexanecarbonyl)-5-phenyl-4-({[2-(propan-2-yl)phenyl]methyl}amino)pyrrolidine-2-carboxylic acid;

(2S,3S,4S,5S)-3-tert-butyl-4-[(6-chloro-3,4-dihydro-2H-1-benzopyran-4-yl)amino]-1-(cyclohexanecarbonyl)-5-phenylpyrrolidine-2-carboxylic acid;

(2S,3S,4S,5S)-3-tert-butyl-1-(cyclohexanecarbonyl)-4-({[2-methoxy-5-(propan-2-yl)phenyl]methyl}amino)-5-phenylpyrrolidine-2-carboxylic acid;

(2S,3S,4S,5S)-3-tert-butyl-4-({[2-methoxy-5-(propan-2-yl)phenyl]methyl}amino)-5-phenyl-1-{[(propan-2-yl)oxy]carbonyl}pyrrolidine-2-carboxylic acid;

(2S,3S,4S,5S)-4-{[(5-bromo-2-methoxypyridin-3-yl)methyl]amino}-3-tert-butyl-5-phenyl-1-{[(propan-2-yl)oxy]carbonyl}pyrrolidine-2-carboxylic acid;

(2S,3S,4S,5S)-4-{[(5-bromo-2-methoxyphenyl)methyl]amino}-3-tert-butyl-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1-ethyl-2-methyl-1H-indol-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(1S,2R,4R)-4-(2-cyanoethyl)-2-methylcyclopentane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methyloxane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(4-cyanocyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(6,6-dimethyloxan-3-yl)acetyl]-5-phenylpyrrolidine-2-carboxylic acid;

(2S,3S,4S,5S)-1-[(bicyclo[1.1.1]pentan-1-yl)acetyl]-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-{[(1R)-3,4-dihydro-1H-2-benzopyran-11-yl]acetyl}-5-phenylpyrrolidine-2-carboxylic acid;

(2S,3S,4S,5S)-3-tert-butyl-4-{[(5-tert-butyl-2-methoxyphenyl)methyl]amino}-1-[(oxan-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(phenylacetyl)pyrrolidine-2-carboxylic acid;

(2S,3S,4S,5S)-3-tert-butyl-4-{[(5-tert-butyl-2-methoxyphenyl)methyl]amino}-1-[(4-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(thiophen-2-yl)acetyl]pyrrolidine-2-carboxylic acid;

(2S,3S,4S,5S)-3-tert-butyl-4-{[(5-tert-butyl-2-methoxyphenyl)methyl]amino}-1-[(2-chlorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(pyridin-3-yl)acetyl]pyrrolidine-2-carboxylic acid;

(2S,3S,4S,5S)-1-(1-benzofuran-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[3-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(pyrrolidin-1-yl)acetyl]pyrrolidine-2-carboxylic acid;

(2S,3S,4S,5S)-3-tert-butyl-4-{[(5-tert-butyl-2-methoxyphenyl)methyl]amino}-1-[(4,4-difluorocyclohexyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[1-(pyridin-2-yl)cyclopropane-1-carbonyl]pyrrolidine-2-carboxylic acid;

(2S,3S,4S,5S)-3-tert-butyl-1-(cyclohexanecarbonyl)-4-({[2-methoxy-5-(trifluoromethoxy)phenyl]methyl}amino)-5-phenylpyrrolidine-2-carboxylic acid;

(2S,3S,4S,5S)-4-{[(5-benzyl-2-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(5-cyclohexyl-2-methoxyphenyl)methyl]amino}-5-phenylpyrrolidine-2-carboxylic acid;

(2S,3S,4S,5S)-3-tert-butyl-1-(cyclohexanecarbonyl)-4-{[(5-cyclopentyl-2-methoxyphenyl)methyl]amino}-5-phenylpyrrolidine-2-carboxylic acid;

(2S,3S,4S,5S)-4-({[5-(bicyclo[2.2.1]heptan-2-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(4-hydroxyphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-hydroxyphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(2,6-dimethylpyridine-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2-methylpyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,5-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,6-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,5-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(4-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methoxy-1-methyl-1H-pyrazole-5-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2,5-dimethylthiophen-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(morpholin-4-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclohexyl)acetyl]-5-phenylpyrrolidine-2-carboxylic acid;

(2S,3S,4S,5S)-1-(bicyclo[2.2.1]hept-5-ene-2-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(cyclohex-2-en-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,4-dihydro-2H-1-benzopyran-4-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methoxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(2-phenylpropanoyl)pyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)-1,3-dioxane-5-carbonyl]pyrrolidine-2-carboxylic acid;

(2S,3S,4S,5S)-3-tert-butyl-4-{[(5-tert-butyl-2-methoxyphenyl)methyl]amino}-1-[(3-oxo-2,3-dihydro-1H-inden-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,3-difluorocyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,2-difluorocyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,3-difluoro-1-methylcyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-methyl-4-oxo-3,4-dihydrophthalazin-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(2, 3-dihydro-1-benzofuran-7-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[5-chloro-6-oxo-1-(propan-2-yl)-1,6-dihydropyridine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{4-[pyridin-2-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-phenyl-1-{3-[(1H-1,2,4-triazol-1-yl)methyl]benzoyl}pyrrolidine-2-carboxylic acid;

(2S,3S,4S,5S)-3-tert-butyl-4-{[(5-tert-butyl-2-methoxyphenyl)methyl]amino}-1-(1-methyl-3-phenyl-1H-pyrazole-5-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-5-phenyl-1H-pyrazole-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[5-methyl-1-(2-methylphenyl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3,5-dimethyl-1-phenyl-1H-pyrazole-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-2H-1,5-benzodioxepine-7-carbonyl)-5-phenylpyrrolidine-2-carboxylic acid;

(2S,3S,4S,5S)-1-(2,1-benzoxazole-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-2H-1-benzopyran-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2,3-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(cyclopent-1-en-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(oxolan-2-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(5-chloro-3-fluoropyridin-2-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(R*)-2-(4-chloro-3-methyl-1H-pyrazol-1-yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[5-oxo-1-(propan-2-yl)pyrrolidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1-cyclopropyl-5-oxopyrrolidine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3-cyanophenyl)acetyl]-5-phenylpyrrolidine-2-carboxylic acid;

(2S,3S,4S,5S)-3-tert-butyl-1-[(3aR,6aS)-hexahydro-1H-cyclopenta[c]furan-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(methoxymethyl)phenyl]methyl}amino)-5-phenylpyrrolidine-2-carboxylic acid;

(2S,3S,4S,5S)-3-tert-butyl-1-(cyclohexanecarbonyl)-5-(4-fluorophenyl)-4-[({2-methoxy-5-[(1S,3s)-tricyclo[3.3.1.1$^{3,7}$]decan-1-yl]phenyl}methyl)amino]pyrrolidine-2-carboxylic acid;

(2S,3S,4S,5S)-3-tert-butyl-1-(cyclohexanecarbonyl)-4-{[(2-methoxyquinolin-3-yl)methyl]amino}-5-phenylpyrrolidine-2-carboxylic acid;

(2S,3S,4S,5S)-3-tert-butyl-1-(cyclohexanecarbonyl)-5-(2-fluorophenyl)-4-{[(4-methoxy[1,1'-biphenyl]-3-yl)methyl]amino}pyrrolidine-2-carboxylic acid;

(2S,3S,4S,5S)-3-tert-butyl-1-(cyclohexanecarbonyl)-4-({[2-methoxy-5-(pyrrolidin-1-yl)pyridin-3-yl]methyl}amino)-5-phenylpyrrolidine-2-carboxylic acid;

(2S,3S,4S,5S)-4-{[(5-bromo-2-methoxypyridin-3-yl)methyl]amino}-1-(cyclohexanecarbonyl)-3-(2-methoxypropan-2-yl)-5-phenylpyrrolidine-2-carboxylic acid;

(2S,3S,4S,5S)-4-{[(5-bromo-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-3-tert-butyl-1-(cyclohexanecarbonyl)-4-{[(4-methoxy-4'-methyl[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(2-methoxypyridin-3-yl)phenyl]methyl}amino)-5-phenylpyrrolidine-2-carboxylic acid;

(2S,3S,4S,5S)-4-({[5-(bicyclo[2.2.1]heptan-2-yl)-2-methoxypyridin-3-yl]methyl}amino)-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclohexyl-2-methoxypyridin-3-yl)methyl]amino}-3-(2-methoxypropan-2-yl)-5-phenylpyrrolidine-2-carboxylic acid;

(2S,3S,4S,5S)-1-(cyclohexanecarbonyl)-4-({[5-(cyclohexylmethyl)-2-methoxypyridin-3-yl]methyl}amino)-3-(2-methoxypropan-2-yl)-5-phenylpyrrolidine-2-carboxylic acid;

(2S,3S,4S,5S)-1-(cyclohexanecarbonyl)-3-(2-methoxypropan-2-yl)-4-({[2-methoxy-5-(propan-2-yl)pyridin-3-yl]methyl}amino)-5-phenylpyrrolidine-2-carboxylic acid;

(2S,3S,4S,5S)-4-{[(5-cyclobutyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclopentyl-2-methoxyphenyl)methyl]amino}-3-(2-methoxypropan-2-yl)-5-phenylpyrrolidine-2-carboxylic acid;

(2S,3S,4S,5S)-1-(cyclohexanecarbonyl)-4-{[(5-cyclohexyl-2-methoxyphenyl)methyl]amino}-3-(2-methoxypropan-2-yl)-5-phenylpyrrolidine-2-carboxylic acid;

(2S,3S,4S,5S)-1-(cyclohexanecarbonyl)-3-(2-methoxypropan-2-yl)-4-({[2-methoxy-5-(propan-2-yl)phenyl]methyl}amino)-5-phenylpyrrolidine-2-carboxylic acid;

(2S,3S,4S,5S)-3-tert-butyl-1-(cyclohexanecarbonyl)-4-{[(5-cyclopropyl-2-methoxypyridin-3-yl)methyl]amino}-5-phenylpyrrolidine-2-carboxylic acid;

(2S,3S,4S,5S)-3-tert-butyl-1-(cyclohexanecarbonyl)-5-(2-fluorophenyl)-4-({[2-methoxy-5-(trifluoromethyl)phenyl]methyl}amino)pyrrolidine-2-carboxylic acid;

(2S,3S,4S,5S)-3-tert-butyl-1-(cyclohexanecarbonyl)-5-(2-fluorophenyl)-4-({[2-methoxy-4-(trifluoromethyl)phenyl]methyl}amino)pyrrolidine-2-carboxylic acid;

(2S,3S,4S,5S)-4-{[(5-bromo-2-methoxyphenyl)methyl]amino}-3-tert-butyl-1-(cyclohexanecarbonyl)-5-(2-fluorophenyl)pyrrolidine-2-carboxylic acid;

(2S,3S,4S,5S)-4-{[(5-bromo-2-methoxypyridin-3-yl)methyl]amino}-3-tert-butyl-1-(cyclohexanecarbonyl)-5-(2-fluorophenyl)pyrrolidine-2-carboxylic acid;

(2S,3S,4S,5S)-3-tert-butyl-4-{[(5-tert-butyl-2-methoxyphenyl)methyl]amino}-1-[(2-methylpropoxy)carbonyl]-5-phenylpyrrolidine-2-carboxylic acid;

(2S,3S,4S,5S)-3-tert-butyl-1-[(2R*)-2,3-dihydro-1-benzofuran-2-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-[(2S*)-2,3-dihydro-1-benzofuran-2-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(2-methoxy-3-methylbutanoyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R*,3S*)-3-methyloxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2S*,3R*)-3-methyloxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-(3-chlorophenyl)-2-methoxyacetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2-(3-chlorophenyl)-2-methoxyacetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-phenylpyrrolidine-2-carboxylic acid;

(2S,3S,4S,5S)-3-tert-butyl-1-(2-methoxy-3-methylbutanoyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)phenyl]methyl}amino)-1-[(2R*,3S*)-3-methyloxolane-2-carbonyl]-5-phenylpyrrolidine-2-carboxylic acid;

(2S,3S,4S,5S)-3-tert-butyl-1-(cyclohexanecarbonyl)-4-({[2-methoxy-5-(thiophen-2-yl)phenyl]methyl}amino)-5-phenylpyrrolidine-2-carboxylic acid;

(2S,3S,4S,5S)-3-tert-butyl-1-(cyclohexanecarbonyl)-4-({[5-(furan-3-yl)-2-methoxyphenyl]methyl}amino)-5-phenylpyrrolidine-2-carboxylic acid;

(2S,3S,4S,5S)-3-tert-butyl-1-(cyclohexanecarbonyl)-4-{[(3',4-dimethoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(6-methylpyridin-3-yl)phenyl]methyl}amino)-5-phenylpyrrolidine-2-carboxylic acid;

(2S,3S,4S,5S)-3-tert-butyl-1-(cyclohexanecarbonyl)-4-{[(4-methoxy-2'-methyl[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(4-methylpyridin-3-yl)phenyl]methyl}amino)-5-phenylpyrrolidine-2-carboxylic acid;

(2S,3S,4S,5S)-3-tert-butyl-4-{[(3'-cyano-4-methoxy[1,1'-biphenyl]-3-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(4'-fluoro-4-methoxy-2'-methyl[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-{[(2',4'-difluoro-4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(pyridin-3-yl)phenyl]methyl}amino)-5-phenylpyrrolidine-2-carboxylic acid;

(2S,3S,4S,5S)-3-tert-butyl-1-(cyclohexanecarbonyl)-4-({[5-(3,5-dimethyl-1,2-oxazol-4-yl)-2-methoxyphenyl]methyl}amino)-5-phenylpyrrolidine-2-carboxylic acid;

(2S,3S,4S,5S)-3-tert-butyl-1-(cyclohexanecarbonyl)-4-{[(2',3'-difluoro-4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[5-(5-fluoropyridin-3-yl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(2-methylpyridin-3-yl)phenyl]methyl}amino)-5-phenylpyrrolidine-2-carboxylic acid;

(2S,3S,4S,5S)-3-tert-butyl-4-{[(4'-cyano-4-methoxy[1,1'-biphenyl]-3-yl)methyl]amino}-1-(cyclohexanecarbonyl)-5-phenylpyrrolidine-2-carboxylic acid;

(2S,3S,4S,5S)-3-tert-butyl-4-({[5-(1-cyclobutyl-1H-pyrazol-4-yl)-2-methoxyphenyl]methyl}amino)-1-(cyclohexanecarbonyl)-5-phenylpyrrolidine-2-carboxylic acid;

(2S,3S,4S,5S)-3-tert-butyl-1-(cyclohexanecarbonyl)-4-({[5-(furan-2-yl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[5-(difluoromethoxy)-2-methoxyphenyl]methyl}amino)-5-phenylpyrrolidine-2-carboxylic acid;

(2S,3S,4S,5S)-3-tert-butyl-1-(cyclohexanecarbonyl)-4-({[5-(2,5-dihydrofuran-3-yl)-2-methoxyphenyl]methyl}amino)-5-phenylpyrrolidine-2-carboxylic acid;

(2S,3S,4S,5S)-4-{[(5-tert-butyl-2-methoxyphenyl)methyl]amino}-1-(cyclohexanecarbonyl)-5-(2-methoxyphenyl)-3-(2-methoxypropan-2-yl)pyrrolidine-2-carboxylic acid;

(2S,3S,4S,5S)-1-(cyclohexanecarbonyl)-5-(2-methoxyphenyl)-3-(2-methoxypropan-2-yl)-4-({[2-methoxy-5-(trifluoromethyl)phenyl]methyl}amino)pyrrolidine-2-carboxylic acid;

(2S,3S,4S,5S)-3-tert-butyl-1-(cyclohexanecarbonyl)-4-{[(3-methoxy-6-phenylpyridin-2-yl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2-methoxy-3,3-dimethylbutanoyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-methoxy-3,3-dimethylbutanoyl]-5-phenylpyrrolidine-2-carboxylic acid;

(2S,3S,4S,5S)-3-tert-butyl-1-(3,4-dihydro-1H-2-benzopyran-3-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-1H-2-benzopyran-3-carbonyl)-5-phenylpyrrolidine-2-carboxylic acid;

(2S,3S,4S,5S)-3-tert-butyl-4-{[(5-tert-butyl-2-methoxypyridin-3-yl)methyl]amino}-1-[(2,6-difluorophenyl)acetyl]-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(1-methylcyclopropyl)-5-phenylpyrrolidine-2-carboxylic acid;

(2S,3S,4S,5S)-1-(cyclohexanecarbonyl)-4-({[2-methoxy-4-(trifluoromethyl)phenyl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(4,4,4-trifluoro-2-methylbutanoyl)pyrrolidine-2-carboxylic acid;

(2S,3S,4S,5S)-3-tert-butyl-4-{[(5-tert-butyl-2-methoxyphenyl)methyl]amino}-1-[2-(3-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-(3-methylcyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(4-fluorophenyl)cyclopropane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-methoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-(2,2-dimethylcyclopropane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(4-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-methoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2-chlorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-(cyclobutanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2,3-dihydro-1-benzothiophene-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[1-(cyclopropanecarbonyl)piperidine-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(8-methoxy-1,2,3,4-tetrahydronaphthalene-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(oxane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-phenoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-(6-fluoro-3,4-dihydro-2H-1-benzopyran-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclopent-3-ene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R)-oxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2,3-dimethylphenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(phenylsulfanyl)propanoyl]pyrrolidine-2-carboxylic acid;

(2S,3S,4S,5S)-3-tert-butyl-4-{[(5-tert-butyl-2-methoxyphenyl)methyl]amino}-5-phenyl-1-[(2S)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-(2,2-difluorocyclopropane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2-ethylbutanoyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(3-chlorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(pyridin-4-yl)cyclopropane-1-carbonyl]pyrrolidine-2-carboxylic acid;

(2S,3S,4S,5S)-3-tert-butyl-4-{[(5-tert-butyl-2-methoxyphenyl)methyl]amino}-1-(cyclopentanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclopropanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-difluorocyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3-fluorocyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-difluorocyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2, 3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[trans-2-phenylcyclopropane-1-carbonyl]pyrrolidine-2-carboxylic acid;

(2S,3S,4S,5S)-3-tert-butyl-1-(cyclohexanecarbonyl)-4-({[2-methoxy-5-(oxan-4-yl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(3-methoxyphenyl)pyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(2-methylphenyl)pyridin-3-yl]methyl}amino)-5-phenylpyrrolidine-2-carboxylic acid;

(2S,3S,4S,5S)-3-tert-butyl-1-(cyclohexanecarbonyl)-4-({[5-(4-fluoro-2-methylphenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[5-(2,4-difluorophenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-{[(6-methoxy[3,3'-bipyridin]-5-yl)methyl]amino}-5-phenylpyrrolidine-2-carboxylic acid;

(2S,3S,4S,5S)-3-tert-butyl-1-(cyclohexanecarbonyl)-4-({[5-(2,3-difluorophenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(4-methylphenyl)pyridin-3-yl]methyl}amino)-5-phenylpyrrolidine-2-carboxylic acid;

(2S,3S,4S,5S)-3-tert-butyl-1-(cyclohexanecarbonyl)-4-{[(6-methoxy-2'-methyl[3,3'-bipyridin]-5-yl)methyl]amino}-5-phenylpyrrolidine-2-carboxylic acid;

(2S,3S,4S,5S)-3-tert-butyl-1-(cyclohexanecarbonyl)-4-({[5-(3,6-dihydro-2H-pyran-4-yl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[5-(2,5-dihydrofuran-3-yl)-2-methoxypyridin-3-yl]methyl}amino)-5-phenylpyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-(2-fluorophenyl)pyrrolidine-2-carboxylic acid;

(2S,3S,4S,5S)-3-tert-butyl-1-(cyclohexanecarbonyl)-4-{[(5-cyclopropyl-2-methoxyphenyl)methyl]amino}-5-phenylpyrrolidine-2-carboxylic acid;

(2S,3S,4S,5S)-3-tert-butyl-1-(cyclohexanecarbonyl)-5-(2-fluorophenyl)-4-[({2-methoxy-5-[1-(trifluoromethyl)cyclopropyl]phenyl}methyl)amino]pyrrolidine-2-carboxylic acid;

(2S,3S,4S,5S)-3-tert-butyl-4-{[(5-tert-butyl-2-methoxyphenyl)methyl]amino}-1-[1-(4-fluorophenyl)-5-methyl-1H-pyrazole-4-carbonyl]-5-phenylpyrrolidine-2-carboxylic acid;

(2S,3S,4S,5S)-3-tert-butyl-1-(1-tert-butyl-5-cyano-1H-pyrazole-4-carbonyl)-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[1-(2,4-difluorophenyl)-5-methyl-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-(4-methoxyphenyl)-5-methyl-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-5-phenyl-1H-pyrazole-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[5-ethyl-1-(4-fluorophenyl)-3-methyl-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-tert-butyl-5-(trifluoromethyl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(5-methyl-1-phenyl-1H-pyrazole-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-ethyl-3,5-dimethyl-1H-pyrazole-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2-methyl-4,5,6,7-tetrahydropyrazolo[1,5-a]pyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(4,5,6,7-tetrahydropyrazolo[1,5-a]pyridine-3-carbonyl)pyrrolidine-2-carboxylic acid;

(2S,3S,4S,5S)-3-tert-butyl-4-{[(5-tert-butyl-2-methoxyphenyl)methyl]amino}-1-(5-methoxy-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1R)-4-methoxy-1-methyl-2,3-dihydro-1H-indene-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(4-chloro-1-methyl-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(5-chloro-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(3-phenyl-2,3-dihydro-1-benzofuran-3-carbonyl)pyrrolidine-2-carboxylic acid;

(2S,3S,4S,5S)-3-tert-butyl-4-{[(5-tert-butyl-2-methoxyphenyl)methyl]amino}-1-(3-hydroxy-3-methylpentanoyl)-5-phenylpyrrolidine-2-carboxylic acid;

(2S,3S,4S,5S)-3-tert-butyl-4-{[(5-tert-butyl-2-methoxyphenyl)methyl]amino}-1-(3-hydroxy-3,4-dimethylpentanoyl)-5-phenylpyrrolidine-2-carboxylic acid;

(2S,3S,4S,5S)-3-tert-butyl-4-{[(6-tert-butyl-3-methoxypyridin-2-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[4-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-1-[(1s,3R,5S)-3,5-dimethylcyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(4,7,7-trimethylbicyclo[4.1.0]heptane-3-carbonyl)pyrrolidine-2-carboxylic acid;

(2S,3S,4S,5S)-3-tert-butyl-4-{[(5-tert-butyl-2-methoxyphenyl)methyl]amino}-1-(4,4-difluorocyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(prop-2-en-1-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(trans-4-ethyl-4-hydroxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(propan-2-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(trans-4-hydroxy-4-propylcyclohexane-1-carbonyl)-5-phenylpyrrolidine-2-carboxylic acid;

(2S,3S,4S,5S)-1-(butoxycarbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{[(prop-2-yn-1-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(pentyloxy)carbonyl]-5-phenylpyrrolidine-2-carboxylic acid;

(2S,3S,4S,5S)-3-tert-butyl-4-{[(5-tert-butyl-2-methoxyphenyl)methyl]amino}-1-({[(1S,2R,5S)-5-methyl-2-(propan-2-yl)cyclohexyl]oxy}carbonyl)-5-phenylpyrrolidine-2-carboxylic acid;

(2S,3S,4S,5S)-1-{[(but-3-en-1-yl)oxy]carbonyl}-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(methoxycarbonyl)-5-phenylpyrrolidine-2-carboxylic acid;

(2S,3S,4S,5S)-3-tert-butyl-4-{[(5-tert-butyl-2-methoxyphenyl)methyl]amino}-1-{[(but-2-yn-1-yl)oxy]carbonyl}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(propoxycarbonyl)pyrrolidine-2-carboxylic acid;

(2S,3S,4S,5S)-3-tert-butyl-4-{[(5-tert-butyl-2-methoxyphenyl)methyl]amino}-5-phenyl-1-{[(prop-2-en-1-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(2,2-dimethylpropoxy)carbonyl]-5-phenylpyrrolidine-2-carboxylic acid;

(2S,3R,4R,5S)-3-tert-butyl-4-{[(5-tert-butyl-2-methoxyphenyl)methyl]amino}-1-[(2R)-2-methoxy-2-phenylacetyl]-5-phenylpyrrolidine-2-carboxylic acid;

(2S,3S,4S,5S)-3-tert-butyl-1-(cyclohexanecarbonyl)-4-{[(1-methoxycyclohexyl)methyl]amino}-5-phenylpyrrolidine-2-carboxylic acid;

(2S,3R,4R,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-(3,4-difluorophenyl)-2-methoxyacetyl]-5-phenylpyrrolidine-2-carboxylic acid;

(2S,3S,4S,5S)-3-tert-butyl-4-({[2-methoxy-5-(trifluoromethyl)phenyl]methyl}amino)-1-(6-methyl-3,4-dihydro-2H-1-benzopyran-2-carbonyl)-5-phenylpyrrolidine-2-carboxylic acid;

(2S,3S,4S,5S)-3-tert-butyl-1-(7-fluoro-3,4-dihydro-2H-1-benzopyran-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-[2-(4-chlorophenoxy)-3-methylbutanoyl]-4-({[2-methoxy-5-(trifluoromethyl)phenyl]methyl}amino)-5-phenylpyrrolidine-2-carboxylic acid;

(2S,3S,4S,5S)-3-tert-butyl-4-({[5-(1-cyanocyclopropyl)-2-methoxyphenyl]methyl}amino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(8-methoxy-3,4-dihydro-2H-1-benzopyran-3-carbonyl)-5-phenylpyrrolidine-2-carboxylic acid;

(2S,3S,4S,5S)-4-({[2-(bicyclo[2.2.1]heptan-2-yl)-5-methoxypyridin-4-yl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2-cyclohexyl-5-methoxypyridin-4-yl)methyl]amino}-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[5-(2-fluorophenyl)-2-methoxypyridin-3-yl]methyl}amino)pyrrolidine-2-carboxylic acid;

(2S,3S,4S,5S)-3-tert-butyl-1-(cyclohexanecarbonyl)-4-({[5-(2,4-difluorophenyl)-2-methoxypyridin-3-yl]methyl}amino)-5-[2-(dimethylamino)pyridin-3-yl]pyrrolidine-2-carboxylic acid;

(2S,3S,4S,5S)-3-tert-butyl-1-(cyclohexanecarbonyl)-4-{[(2,6-dimethoxyphenyl)methyl]amino}-5-phenylpyrrolidine-2-carboxylic acid;

(2S,3S,4S,5S)-3-tert-butyl-1-(cyclohexanecarbonyl)-4-({[3-methoxy-6-(trifluoromethyl)pyridin-2-yl]methyl}amino)-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[5-(4-fluoro-2-methylphenyl)-2-methoxypyridin-3-yl]methyl}amino)pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(4-methylphenyl)pyridin-3-yl]methyl}amino)pyrrolidine-2-carboxylic acid;

(2S,3S,4S,5S)-3-tert-butyl-4-{[(5-tert-butyl-2-methoxyphenyl)methyl]amino}-1-(2-fluorocyclohex-1-ene-1-carbonyl)-5-phenylpyrrolidine-2-carboxylic acid;

(2S,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid;

(2S,3R,4R,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(6-chloro-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[3-methyl-2-(2-methylphenoxy)butanoyl]-5-phenylpyrrolidine-2-carboxylic acid;

(2S,3S,4S,5S)-3-tert-butyl-1-(cyclohexanecarbonyl)-4-({[2-(2-fluoro-4-methylphenyl)-5-methoxypyridin-4-yl]methyl}amino)-5-phenylpyrrolidine-2-carboxylic acid;

(2S,3S,4S,5S)-3-tert-butyl-1-(cyclohexanecarbonyl)-4-({[2-(2-fluorophenyl)-5-methoxypyridin-4-yl]methyl}amino)-5-phenylpyrrolidine-2-carboxylic acid;

(2S,3S,4S,5S)-3-tert-butyl-1-(cyclohexanecarbonyl)-4-({[5-methoxy-2-(3-methoxyphenyl)pyridin-4-yl]methyl}amino)-5-phenylpyrrolidine-2-carboxylic acid;

(2S,3S,4S,5S)-4-{[(5-tert-butyl-2-methoxyphenyl)methyl]amino}-3-(2-methoxypropan-2-yl)-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-4-[({2-methoxy-5-[1-(methoxymethyl)cyclopropyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-[2-(dimethylamino)pyridin-3-yl]pyrrolidine-2-carboxylic acid;

(2S,3S,4S,5S)-3-tert-butyl-1-(cyclohexanecarbonyl)-4-({[5-(2,2-difluoro-1-methylcyclopropyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-5-(2-fluorophenyl)-4-{[(2-methoxy-5-phenylpyridin-3-yl)methyl]amino}pyrrolidine-2-carboxylic acid;

(2S,3S,4S,5S)-3-tert-butyl-1-(cyclohexanecarbonyl)-5-(2-fluorophenyl)-4-({[5-(2-fluorophenyl)-2-methoxypyridin-3-yl]methyl}amino)pyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-[(2R*,5S*)-5-phenyloxolane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-[(2-methylphenyl)acetyl]-5-[2-(propan-2-yl)phenyl]pyrrolidine-2-carboxylic acid;

(2S,3S,4S,5S)-3-tert-butyl-4-{[(6-tert-butyl-2-methoxypyridin-3-yl)methyl]amino}-1-(3,3-dimethylcyclopentane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2-methylphenyl)acetyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1R*,3aR*,6a*)-hexahydro-1H-cyclopenta[c]furan-1-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1S*,3aS*,6aR*)-hexahydro-1H-cyclopenta[c]furan-1-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R)-2-methoxy-2-phenylacetyl]-5-phenylpyrrolidine-2-carboxylic acid;

(2S,3S,4S,5S)-3-tert-butyl-1-(5,5-dimethyloxolane-2-carbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-1-(7-fluoro-3,4-dihydro-2H-1-benzopyran-2-carbonyl)-4-({[2-methoxy-5-(trifluoromethyl)pyridin-3-yl]methyl}amino)-5-phenylpyrrolidine-2-carboxylic acid;

(2S,3S,4S,5S)-1-(cyclohexanecarbonyl)-3-(2-methoxypropan-2-yl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-1-(cyclohexanecarbonyl)-5-[2-(dimethylamino)pyridin-3-yl]-3-(2-methoxypropan-2-yl)-4-({[2-methoxy-5-(trifluoromethyl)phenyl]methyl}amino)pyrrolidine-2-carboxylic acid;

(2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-[2-(dimethylamino)pyridin-3-yl]pyrrolidine-2-carboxylic acid;

(2S,3S,4S,5S)-1-{(4E)-2-[(2E)-but-2-en-1-yl]hex-4-enoyl}-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-1-(cyclohexanecarbonyl)-4-({[2-methoxy-5-(1-methylcyclopropyl)pyridin-3-yl]methyl}amino)-5-phenylpyrrolidine-2-carboxylic acid;

(2S,3S,4S,5S)-3-tert-butyl-1-[(1S)-3,3-difluorocyclohexane-1-carbonyl]-4-({[2-methoxy-5-(trimethylsilyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(6-oxaspiro[2.5]octane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(oxetane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3R*)-1-methyl-2-oxopiperidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-1H-pyrazole-3-carbonyl)-5-phenylpyrrolidine-2-carboxylic acid;

(2S,3S,4S,5S)-3-tert-butyl-4-({[2-methoxy-5-(trifluoromethyl)pyridin-3-yl]methyl}amino)-1-(7-methyl-2,3-dihydro-1-benzofuran-2-carbonyl)-5-phenylpyrrolidine-2-carboxylic acid;

(2S,3S,4S,5S)-3-tert-butyl-5-[2-(dimethylamino)pyridin-3-yl]-4l-{[(4-methoxy[1,1'-biphenyl]-3-yl)methyl]amino}-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1S*,3S*)-3-methoxycyclohexane 1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,3R*)-3-methoxycyclohexne-1-carbonyl]pyrrolidine-2-carboxylic acid;

(2S,3S,4S,5S)-3-tert-butyl-5-[2-(dimethylamino)pyridin-3-yl]-4l-{[(4-methoxy[1,1'-biphenyl]-3-yl)methyl]amino}-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-[(2R)-oxane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S*)-7-fluoro-3,4-dihydro-2H-1-benzopyran-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R*)-7-fluoro-3,4-dihydro-2H-1-benzopyran-2-carbonyl]pyrrolidine-2-carboxylic acid;

(2S,3S,4S,5S)-3-tert-butyl-4-{[(5-tert-butyl-2-methoxyphenyl)methyl]amino}-1-{(2R*)-2[(2S*)-oxan-2-yl]propanoyl}-5-phenylpyrrolidine-2-carboxylic acid;

(2S,3S,4S,5S)-3-tert-butyl-4-{[(5-tert-butyl-2-methoxyphenyl)methyl]amino}-1-{(2S*)-2-[(2R*)-oxan-2-yl]propanoyl}-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1S*,3R*)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(oxan-2-yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(trifluoromethyl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(trifluoromethyl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-[(2S)-oxane-2-carbonyl]pyrrolidine-2-carboxylic acid;

(2S,3S,4S,5S)-3-tert-butyl-1-(cyclohexanecarbonyl)-5-[2-(dimethylamino)pyridin-3-yl]-4-{[2-methoxy-5-(trifluoromethyl)pyridin-3-yl]amino}pyrrolidine-2-carboxylic acid;

(2S,3S,4S,5S)-3-tert-butyl-1-(cyclohexanecarbonyl)-4-({[2-methoxy-5-(1-methylcyclobutyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[4-hydroxy-4-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(4-phenoxybenzoyl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{4-[(oxan-4-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{4-[(pyridin-2-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[4-(trifluoromethoxy)benzoyl]pyrrolidine-2-carboxylic acid;

(2S,3S,4S,5S)-3-tert-butyl-4-{[(5-tert-butyl-2-methoxyphenyl)methyl]amino}-1-(4,4-difluorocyclohexane-1-carbonyl)-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(3,5-dimethylcyclohexane-1-carbonyl)pyrrolidine-2-carboxylic acid;

(2S,3S,4S,5S)-3-(bicyclo[1.1.1]pentan-1-yl)-1-(cyclohexanecarbonyl)-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1,4-benzodioxine-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1,4-benzodioxine-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3S*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-cyclobutyl-2-methoxy-pyridin-3-yl)methyl]amino}-1-[(2R*)-2,3-dihydro-1,4-benzodioxine-2-carbonyl]-5-phenylpyrrolidine-2-carboxylic acid;

(2S,3S,4S,5S)-3-tert-butyl-4-{[(5-cyclobutyl-2-methoxy-pyridin-3-yl)methyl]amino}-1-(2,3-dihydro-1,4-benzodioxine-6-carbonyl)-5-phenylpyrrolidine-2-carboxylic acid;

(2S,3S,4S,5S)-3-tert-butyl-4-{[(5-cyclobutyl-2-methoxy-pyridin-3-yl)methyl]amino}-1-(6-fluoro-3,4-dihydro-2H-1-benzopyran-2-carbonyl)-5-phenylpyrrolidine-2-carboxylic acid;

(2S,3S,4S,5S)-3-tert-butyl-4-{[(2-tert-butyl-4-methoxypyrimidin-5-yl)methyl]amino}-1-[(1R*)-3,3-difluorocyclohexane-1-carbonyl]-5-phenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2R)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1R,3R)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(3R*)-3,4-dihydro-1H-2-benzopyran-3-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(3S*)-3,4-dihydro-1H-2-benzopyran-3-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S*)-6-fluoro-3,4-dihydro-2H-1-benzopyran-2-carbonyl]pyrrolidine-2-carboxylic acid;

(2S,3S,4S,5S)-1-(bicyclo[3.1.0]hexane-6-carbonyl)-3-tert-butyl-5-[2-(dimethylamino)pyridin-3-yl]-4-{2-methoxy-5-(trifluoromethyl)pyridin-3-yl]amino}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxyphenyl)pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(1R,2R)-2-(trifluoromethyl)cyclohexane-1-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxypyridin-3-yl)pyrrolidine-2-carboxylic acid;

(2S,3S,4S,5S)-3-tert-butyl-4-({[2-methoxy-4-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-(3,3-difluorocyclohexane-1-carbonyl)-5-[2-(dimethylamino)pyridin-3-yl]-4-{[2-methoxy-5-(trifluoromethyl)pyridin-3-yl]amino}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-[(2S*)-oxane-2-carbonyl]pyrrolidine-2-carboxylic acid;

(2S,3S,4S,5S)-3-tert-butyl-4-{[(5-cyclobutyl-2-methoxy-pyridin-3-yl)methyl]amino}-5-[2-(dimethylamino)pyridin-3-yl]-1-(oxane-2-carbonyl)pyrrolidine-2-carboxylic acid;

(2S,3S,4S,5S)-3-tert-butyl-4-{[(5-cyclobutyl-2-methoxy-pyridin-3-yl)methyl]amino}-1-(3,3-difluorocyclohexane-1-carbonyl)-5-phenylpyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2R)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-[(2R)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-[(2S)-oxane-2-carbonyl]pyrrolidine-2-carboxylic acid;

(2S,3S,4S,5S)-3-tert-butyl-4-{[(6-cyclobutyl-3-methoxy-pyridazin-4-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[3-(3-chlorophenyl)oxetane-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3-fluorobicyclo[1.1.1]pentane-1-carbonyl)-5-phenylpyrrolidine-2-carboxylic acid;

(2S,3S,4S,5S)-3-tert-butyl-1-(cyclohexanecarbonyl)-4-({[1-(2,2-difluoro-2H-1,3-benzodioxol-5-yl)cyclopropyl]methyl}amino)-5-phenylpyrrolidine-2-carboxylic acid;

(2S,3S,4S,5S)-3-tert-butyl-4-{[2-(4-chlorophenyl)-2-methylpropyl]amino}-1-(cyclohexanecarbonyl)-5-phenylpyrrolidine-2-carboxylic acid;

(2S,3S,4S,5S)-4-({[5-(bicyclo[1.1.1]pentan-1-yl)-2-methoxyphenyl]methyl}amino)-5-[2-(dimethylamino)pyridin-3-yl]-3-(2-methoxypropan-2-yl)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[2-(trifluoromethyl)cyclohexane-1-carbonyl]pyrrolidine-2-carboxylic acid;

(2S,3S,4S,5S)-3-tert-butyl-1-(3,3-difluorocyclohexane-1-carbonyl)-5-[2-(dimethylamino)pyridin-3-yl]-4-{[6-methyl-4-(trifluoromethyl)pyridin-2-yl]amino}pyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[(2S*)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(1S*,2S*,3S*,4R*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-1-(3,3-difluorocyclohexane-1-carbonyl)-4-({[2-methoxy-4-(trifluoromethyl)phenyl]methyl}amino)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1S)-3,3-difluorocyclohexane-1-carbonyl]-5-phyenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-5-(2-methoxypyridin-3-yl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-5-(2-methoxypyridin-3-yl)-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1R,3S)-3-hydroxycyclohexane-1-carbonyl]-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1S,3S)-3-methoxycyclohexane-1-carbonyl]-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-fluorophenyl)pyrrolidine-2-carboxylic acid;

(2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-[2-(dimethylamino)pyridin-3-yl]pyrrolidine-2-carboxylic acid;

(2S,3S,4S,5S)-3-tert-butyl-4-{[(6-tert-butyl-2-methoxypyridin-3-yl)methyl]amino}-5-(2-fluorophenyl)-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(dimethylamino)pyridin-3-yl]pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)pyridin-3-yl]-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(1S*,2R*,4R*)-7-oxabicyclo[2.2.1]heptane-2-carbonyl]pyrrolidine-2-carboxylic acid;

(2S,3S,4S,5S)-3-tert-butyl-4-({[2-methoxy-5-(trifluoromethoxy)phenyl]methyl}amino)-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethoxy)phenyl]methyl}amino)pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-(2-fluorophenyl)pyrrolidine-2-carboxylic acid;

(2S,3S,4S,5S)-3-tert-butyl-4-{[(5-tert-butyl-2-methoxyphenyl)methyl]amino}-1-[(1R,3S)-3-hydroxy-3-methylcyclohexane-1-carbonyl]-5-phenylpyrrolidine-2-carboxylic acid;

(2S,3S,4S,5S)-3-tert-butyl-1-(cyclohexanecarbonyl)-5-(2-methoxypyridin-3-yl)-4-[({2-methoxy-5-[(trifluoromethyl)sulfanyl]phenyl}methyl)amino]pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-[2-(difluoromethoxy)phenyl]pyrrolidine-2-carboxylic acid;

(2S,3S,4S,5S)-3-tert-butyl-4-[({2-methoxy-5-[(trifluoromethyl)sulfanyl]phenyl}methyl)amino]-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-cyclobutyl-2-methoxypyridin-3-yl)methyl]amino}-5-(2-fluorophenyl)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-[(1R,3R)-3-fluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(1R,3R)-3-hydroxy-3-methylcyclohexane-1-carbonyl]-5-phenylpyrrolidine-2-carboxylic acid;

(2S,3S,4S,5S)-3-tert-butyl-4-[({2-methoxy-5-[(1S,3s)-tricyclo[3.3.1.1$^{3,7}$]decan-1-yl]phenyl}methyl)amino]-5-phenyl-1-{[(propan-2-yl)oxy]carbonyl}pyrrolidine-2-carboxylic acid;

(2S,3S,4S,5S)-3-tert-butyl-4-({[2-methoxy-5-(pentafluoro-$\lambda^6$-sulfanyl)phenyl]methyl}amino)-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1R,2S,4S)-7-oxabicyclo[2.2.1]heptane-2-carbonyl]-5-[2-(propan-2-yl)phenyl]pyrrolidine-2-carboxylic acid;

(2S,3S,4S,5S)-3-tert-butyl-4-({[2-methoxy-5-(1-methylcyclobutyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-[(1R,3S)-3-hydroxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-2-phenylpropanoyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(1R,3R)-3-(trifluoromethoxy)cyclohexane-1-carbonyl]pyrrolidine-2-carboxylic acid;

(2S,3S,4S,5S)-3-tert-butyl-5-(2-methoxypyridin-3-yl)-4-({[2-methoxy-5-(trifluoromethyl)phenyl]methyl}amino)-1-[(2R)-2-phenylpropanoyl]pyrrolidine-2-carboxylic acid;

(2S,3S,4S,5S)-3-tert-butyl-5-(2-methoxypyridin-3-yl)-4-({[2-methoxy-5-(trifluoromethoxy)phenyl]methyl}amino)-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[(1R,2S,4S)-7-oxabicyclo[2.2.1]heptane-2-carbonyl]-5-phenylpyrrolidine-2-carboxylic acid;

(2S,3S,4S,5S)-3-(bicyclo[1.1.1]pentan-1-yl)-5-(2-fluorophenyl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-1-(cyclohexanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-5-(2-fluorophenyl)-4-({[2-methoxy-5-(1-methylcyclobutyl)phenyl]methyl}amino)-1-[(2S)-oxane-2-carbonyl]pyrrolidine-2-carboxylic acid;

(2S,3S,4S,5S)-3-tert-butyl-5-[2-(dimethylamino)pyridin-3-yl]-4l-{[(4-methoxy[1,1'-biphenyl]-3-yl)methyl]amino}-1-{[(propan-2-yl)oxy]carbonyl}pyrrolidine-2-carboxylic acid;

(2S,3S,4S,5S)-3-tert-butyl-4-{[(6-cyclobutyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-cyclobutyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-5-(trifluoromethoxy)phenyl]methyl}amino)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4R,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid;

(2S,3S,4R,5S)-3-tert-butyl-4-{[(6-methoxy-2,3-dihydro-1H-inden-5-yl)methyl]amino}-5-phenyl-1-{[(propan-2-yl)oxy]carbonyl}pyrrolidine-2-carboxylic acid;

(2S,3S,4R,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-({[2-methoxy-4-(trifluoromethyl)phenyl]methyl}amino)-1-(3-methylbutanoyl)-5-phenylpyrrolidine-2-carboxylic acid;

(2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-{[(propan-2-yl)oxy]carbonyl}pyrrolidine-2-carboxylic acid;

(2S,3S,4S,5S)-3-tert-butyl-4-({[2-methoxy-5-(trifluoromethoxy)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-4-(trifluoromethyl)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(3-methoxynaphthalen-2-yl)methyl]amino}-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4l-{[(6-methoxy-2,3-dihydro-1H-inden-5-yl)methyl]amino}-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-(3-methylbutanoyl)-5-phenylpyrrolidine-2-carboxylic acid;

(2S,3S,4S,5S)-3-tert-butyl-5-[2-(dimethylamino)pyridin-3-yl]-4l-{[(3-methoxy-5,6,7,8-tetrahydronaphthalen-2-yl)methyl]amino}-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-5-(2-fluorophenyl)-1-[(2R)-oxane-2-carbonyl]pyrrolidine-2-carboxylic acid;

(2S,3S,4S,5S)-3-tert-butyl-4-{[(5-chloro-2-methoxyphenyl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-chloro-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1S)-6-methoxy-1-methyl-2,3-dihydro-1H-indene-1-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(1R)-6-methoxy-1-methyl-2,3-dihydro-1H-indene-1-carbonyl]-5-(2-methoxypyridin-3-yl)pyrrolidine-2-carboxylic acid;

(2S,3S,4S,5S)-3-tert-butyl-1-[(1S,3S)-3-methoxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-[(1R)-3,3-difluorocyclohexane-1-carbonyl]-5-(2-methoxypyridin-3-yl)-4-({[2-methoxy-5-(trifluoromethyl)pyridin-3-yl]methyl}amino)pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-3-tert-butyl-4-{[(6-methoxy-2,3-dihydro-1H-inden-5-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-1-(cyclohexanecarbonyl)-5-(2-methylphenyl)-4-{[6-methyl-4-(trifluoromethyl)pyridin-2-yl]amino}pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methylphenyl)pyrrolidine-2-carboxylic acid;

(2S,3S,4S,5S)-3-tert-butyl-5-[2-(dimethylamino)pyridin-3-yl]-4-({[2-methoxy-5-(pyrrolidin-1-yl)pyridin-3-yl]methyl}amino)-1-{[(propan-2-yl)oxy]carbonyl}pyrrolidine-2-carboxylic acid;

(2S,3S,4S,5S)-3-tert-butyl-4-({[2-methoxy-5-(1-methylcyclobutyl)phenyl]methyl}amino)-5-(2-methylphenyl)-1-[(2S)-oxolane-2-carbonyl]pyrrolidine-2-carboxylic acid;

(2S,3S,4S,5S)-3-tert-butyl-4-{[(2-methoxyquinolin-3-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)phenyl]methyl}amino)-5-(2-methylphenyl)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methylphenyl)-1-{[(propan-2-yl)oxy]carbonyl}pyrrolidine-2-carboxylic acid;

(2S,3S,4S,5S)-4-[({1-[(benzyloxy)carbonyl]piperidin-3-yl}methyl)amino]-3-tert-butyl-5-phenyl-1-{[(propan-2-yl)oxy]carbonyl}pyrrolidine-2-carboxylic acid;

(2S,3S,4S,5S)-3-tert-butyl-5-phenyl-1-{[(propan-2-yl)oxy]carbonyl}-4-({[3-(trifluoromethyl)cyclohexyl]methyl}amino)pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-[(2S)-oxane-2-carbonyl]pyrrolidine-2-carboxylic acid;

(2S,3S,4S,5S)-3-tert-butyl-5-(2-cyclopropylpyridin-3-yl)-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-3-tert-butyl-5-(2-cyclopropylpyridin-3-yl)-4-({[2-methoxy-4-(trifluoromethyl)phenyl]methyl}amino)-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylpyridin-3-yl)-1-[(2S)-oxolane-2-carbonyl]pyrrolidine-2-carboxylic acid;

(2S,3S,4S,5S)-3-tert-butyl-1-(3,3-difluorocyclopentane-1-carbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-1-[(2S)-2-methoxypropanoyl]-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-(oxane-4-carbonyl)-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-({[2-methoxy-5-(1-methylcyclobutyl)phenyl]methyl}amino)-1-[(2S)-oxolane-2-carbonyl]-5-[2-(propan-2-yl)phenyl]pyrrolidine-2-carboxylic acid;

(2S,3S,4S,5S)-4-{[(5-bromo-2-methoxypyridin-3-yl)methyl]amino}-3-tert-butyl-1-[(2S)-oxolane-2-carbonyl]-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-[(2S)-oxolane-2-carbonyl]-5-[2-(propan-2-yl)phenyl]pyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-[2-(difluoromethyl)phenyl]-1-[(2S)-oxolane-2-carbonyl]pyrrolidine-2-carboxylic acid;

(2S,3S,4S,5S)-3-tert-butyl-4-{[(2-methoxyquinolin-3-yl)methyl]amino}-1-(oxane-4-carbonyl)-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(2-methoxyquinolin-3-yl)methyl]amino}-1-[(2S)-oxolane-2-carbonyl]pyrrolidine-2-carboxylic acid;

(2S,3S,4S,5S)-3-tert-butyl-5-[2-(dimethylamino)pyridin-3-yl]-4-{[(2-methoxyquinolin-3-yl)methyl]amino}-1-(oxane-4-carbonyl)pyrrolidine-2-carboxylic acid;

rac-(2R,3R,4R,5R)-3-tert-butyl-4-{[(2-chlorophenyl)methyl]amino}-1-(cyclopentylacetyl)-5-phenylpyrrolidine-2-carboxylic acid;

rac-(2R,3R,4R,5R)-3-tert-butyl-1-(cyclopentylacetyl)-4-{[(2-methylphenyl)methyl]amino}-5-phenylpyrrolidine-2-carboxylic acid;

rac-(2R,3R,4R,5R)-3-tert-butyl-1-(cyclopentylacetyl)-4-{[(2,4-dichlorophenyl)methyl]amino}-5-phenylpyrrolidine-2-carboxylic acid;

rac-(2R,3R,4R,5R)-3-tert-butyl-1-(cyclohexanecarbonyl)-5-phenyl-4-{[4-(trifluoromethyl)pyridin-2-yl]amino}pyrrolidine-2-carboxylic acid;

rac-(2R,3R,4R,5R)-3-tert-butyl-1-(cyclohexanecarbonyl)-5-phenyl-4-{[5-(trifluoromethyl)pyridin-2-yl]amino}pyrrolidine-2-carboxylic acid;

rac-(2R,3R,4R,5R)-3-tert-butyl-4-[(4-chloropyridin-2-yl)amino]-1-(cyclohexanecarbonyl)-5-phenylpyrrolidine-2-carboxylic acid;

rac-(2R,3R,4R,5R)-3-tert-butyl-1-(cyclohexanecarbonyl)-4-({[2-(difluoromethoxy)phenyl]methyl}amino)-5-phenylpyrrolidine-2-carboxylic acid;

rac-(2R,3R,4R,5R)-3-tert-butyl-1-(cyclohexanecarbonyl)-4-[(6-methoxypyridin-2-yl)amino]-5-phenylpyrrolidine-2-carboxylic acid;

rac-(2R,3R,4R,5R)-3-tert-butyl-4-{[(3-chloro-2-hydroxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-[({6-[(oxan-4-yl)oxy]pyridin-2-yl}methyl)amino]-5-phenylpyrrolidine-2-carboxylic acid;

rac-(2R,3R,4R,5R)-3-tert-butyl-1-(cyclohexanecarbonyl)-4-{[(2,5-dimethoxyphenyl)methyl]amino}-5-phenylpyrrolidine-2-carboxylic acid;

rac-(2R,3R,4R,5R)-3-tert-butyl-1-(cyclohexanecarbonyl)-4-{[(2-methoxyphenyl)methyl]amino}-5-phenylpyrrolidine-2-carboxylic acid;

rac-(2R,3R,4R,5R)-3-tert-butyl-1-(cyclohexanecarbonyl)-4-{[(2,3-dimethoxyphenyl)methyl]amino}-5-phenylpyrrolidine-2-carboxylic acid;

rac-(2R,3R,4R,5R)-3-tert-butyl-1-(cyclohexanecarbonyl)-4-{[(3-methoxyphenyl)methyl]amino}-5-phenylpyrrolidine-2-carboxylic acid;

rac-(2R,3R,4R,5R)-3-tert-butyl-4-{[(3-chloro-2,4-dimethoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[(4-methoxypyridin-3-yl)methyl]amino}-5-phenylpyrrolidine-2-carboxylic acid;

rac-(2R,3R,4R,5R)-3-tert-butyl-1-(cyclohexanecarbonyl)-4-{[6-methoxy-4-(trifluoromethyl)pyridin-2-yl](methyl)amino}-5-phenylpyrrolidine-2-carboxylic acid;

rac-(2R,3R,4R,5R)-3-tert-butyl-1-(cyclohexanecarbonyl)-4-[(2,2-difluoro-2H-1,3-benzodioxol-5-yl)amino]-5-phenylpyrrolidine-2-carboxylic acid;

rac-(2R,3R,4R,5R)-3-tert-butyl-1-(cyclohexanecarbonyl)-4-{[(6-methoxypyridin-2-yl)methyl]amino}-5-phenylpyrrolidine-2-carboxylic acid;

rac-(2R,3R,4R,5R)-3-tert-butyl-4-{[(5-chloro-2,4-dimethoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[(3-methoxypyridin-2-yl)methyl]amino}-5-phenylpyrrolidine-2-carboxylic acid;

rac-(2R,3R,4R,5R)-3-tert-butyl-1-(cyclohexanecarbonyl)-4-{[(4-methoxypyrimidin-2-yl)methyl]amino}-5-phenylpyrrolidine-2-carboxylic acid;

rac-(2R,3R,4R,5R)-3-tert-butyl-1-(cyclohexanecarbonyl)-4-{[6-oxo-4-(trifluoromethyl)-1,6-dihydropyridin-2-yl]amino}-5-phenylpyrrolidine-2-carboxylic acid;

rac-(2R,3R,4R,5R)-3-tert-butyl-1-(cyclohexanecarbonyl)-4-({[1-(2-methoxyethyl)-1H-imidazol-2-yl]methyl}amino)-5-phenylpyrrolidine-2-carboxylic acid;

rac-(2R,3R,4R,5R)-3-tert-butyl-1-(cyclohexanecarbonyl)-4-{[(6-methoxypyridin-3-yl)methyl]amino}-5-phenylpyrrolidine-2-carboxylic acid;

rac-(2R,3R,4R,5R)-3-tert-butyl-4-{[(5-chloro-2,3-dimethoxyphenyl)methyl]amino}-1-(cyclohexanecarbonyl)-5-phenylpyrrolidine-2-carboxylic acid;

rac-(2R,3R,4R,5R)-3-tert-butyl-4-{[(5-chloro-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-({[2-(morpholin-4-yl)pyridin-3-yl]methyl}amino)-5-phenylpyrrolidine-2-carboxylic acid;

rac-(2R,3R,4R,5R)-3-tert-butyl-1-(cyclohexanecarbonyl)-4-{[(2,4-dimethoxypyrimidin-5-yl)methyl]amino}-5-phenylpyrrolidine-2-carboxylic acid;

rac-(2R,3R,4R,5R)-3-tert-butyl-4-{[(4-chloro-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[1-oxo-4-(trifluoromethyl)-1λ$^5$-pyridin-2-yl]amino}-5-phenylpyrrolidine-2-carboxylic acid;

rac-(2R,3R,4R,5R)-3-tert-butyl-1-(cyclohexanecarbonyl)-4-{[6-methyl-1-oxo-4-(trifluoromethyl)-1-pyridin-2-yl]amino}-5-phenylpyrrolidine-2-carboxylic acid;

rac-(2R,3R,4R,5R)-1-(cyclohexanecarbonyl)-3-cyclopropyl-5-phenyl-4-{[4-(trifluoromethyl)pyridin-2-yl]amino}pyrrolidine-2-carboxylic acid;

rac-(2R,3R,4R,5R)-4-({[2-(difluoromethoxy)phenyl]methyl}amino)-1-[di(propan-2-yl)carbamoyl]-3-methyl-5-phenylpyrrolidine-2-carboxylic acid;

rac-(2R,3R,4R,5R)-3-tert-butyl-1-(cyclohexanecarbonyl)-4-({[2-methoxy-4-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-4-({[2-(dimethylamino)-5-(trifluoromethyl)pyridin-3-yl]methyl}amino)-5-phenylpyrrolidine-2-carboxylic acid;

rac-(2R,3R,4R,5R)-4-{[(5-chloro-2-methoxyphenyl)methyl]amino}-1-[di(propan-2-yl)carbamoyl]-3-methyl-5-phenylpyrrolidine-2-carboxylic acid;

rac-(2R,3R,4R,5R)-3-tert-butyl-5-phenyl-1-{[(propan-2-yl)oxy]carbonyl}-4-{[4-(trifluoromethyl)pyridin-2-yl]amino}pyrrolidine-2-carboxylic acid;

rac-(2R,3R,4R,5R)-4-{[(4-chloro-2-methoxyphenyl)methyl]amino}-1-[di(propan-2-yl)carbamoyl]-3-methyl-5-phenylpyrrolidine-2-carboxylic acid;

rac-(2R,3R,4R,5R)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid;

rac-(2R,3R,4R,5R)-3-tert-butyl-1-(cyclohexanecarbonyl)-5-[2-(dimethylamino)pyridin-3-yl]-4-({[2-methoxy-5-(trifluoromethyl)phenyl]methyl}amino)pyrrolidine-2-carboxylic acid;

rac-(2R,3R,4R,5R)-3-tert-butyl-4-[(4-cyanopyridin-2-yl)amino]-1-(cyclohexanecarbonyl)-5-phenylpyrrolidine-2-carboxylic acid;

rac-(2R,3R,4R,5R)-3-tert-butyl-5-phenyl-1-{[(propan-2-yl)oxy]carbonyl}-4-{[6-(trifluoromethyl)pyridin-2-yl]amino}pyrrolidine-2-carboxylic acid;

rac-(2R,3R,4R,5R)-3-tert-butyl-1-(cyclohexanecarbonyl)-4-{[(2,2-difluoro-2H-1,3-benzodioxol-4-yl)methyl]amino}-5-(2-methoxyphenyl)pyrrolidine-2-carboxylic acid;

rac-(2R,3R,4R,5R)-3-tert-butyl-1-(cyclohexanecarbonyl)-5-[2-(dimethylamino)pyridin-3-yl]-4-{[6-methyl-4-(trifluoromethyl)pyridin-2-yl]amino}pyrrolidine-2-carboxylic acid;

rac-(2R,3R,4R)-3-cyclopropyl-1-[di(propan-2-yl)carbamoyl]-4-{[6-methyl-4-(trifluoromethyl)pyridin-2-yl]amino}-5-phenylpyrrolidine-2-carboxylic acid;

rac-(2R,3R,4R,5R)-4-{[(5-chloro-2-methoxyphenyl)methyl]amino}-3-cyclopropyl-1-[di(propan-2-yl)carbamoyl]-5-phenylpyrrolidine-2-carboxylic acid;

rac-(2R,3R,4R,5R)-3-tert-butyl-1-(cyclohexanecarbonyl)-N-(2-methoxyethanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(2-methylpropane-2-sulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(1-methylcyclopropane-1-sulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(cyclopropanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(ethanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(dimethylsulfamoyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-[ethyl(methyl)sulfamoyl]-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(methanesulfonyl)-4-{[6-methyl-4-(trifluoromethyl)pyridin-2-yl]amino}-5-phenylpyrrolidine-2-carboxamide;

rac-(4R,6R,7R)-5-(cyclohexanecarbonyl)-7-({[2-(difluoromethoxy)phenyl]methyl}amino)-6-phenyl-5-azaspiro[2.4]heptane-4-carboxylic acid;

rac-(2R,3R,4R,5S)-3-tert-butyl-4-({[2-(difluoromethoxy)phenyl]methyl}amino)-5-(6-methoxypyridin-2-yl)-1-[(1R,5S,6S)-3-oxabicyclo[3.1.O]hexane-6-carbonyl]pyrrolidine-2-carboxylic acid;

rac-(2R,3R,4R,5S)-3-tert-butyl-4-({[2-(difluoromethoxy)phenyl]methyl}amino)-1-[di(propan-2-yl)carbamoyl]-5-(6-methoxypyridin-2-yl)pyrrolidine-2-carboxylic acid;

rac-(2R,3R,4R,5S)-3-tert-butyl-1-(cyclohexanecarbonyl)-4-({[2-methoxy-5-(trifluoromethyl)phenyl]methyl}amino)-5-(pyridin-2-yl)pyrrolidine-2-carboxylic acid;

rac-(2R,3R,4R,5S)-3-tert-butyl-4-{[(5-chloro-2-methoxyphenyl)methyl]amino}-1-(cyclohexanecarbonyl)-5-(pyridin-2-yl)pyrrolidine-2-carboxylic acid;

rac-(2R,3R,4R,5S)-3-tert-butyl-5-(6-methoxypyridin-2-yl)-4-{[6-methyl-4-(trifluoromethyl)pyridin-2-yl]amino}-1-(3-oxabicyclo[3.1.0]hexane-6-carbonyl)pyrrolidine-2-carboxylic acid;

rac-(2R,3R,4R,5S)-3-tert-butyl-5-(6-methoxypyridin-2-yl)-4-{[6-methyl-4-(trifluoromethyl)pyridin-2-yl]amino}-1-(oxane-2-carbonyl)pyrrolidine-2-carboxylic acid;

rac-(2R,3R,4R,5R)-3-tert-butyl-1-(cyclohexanecarbonyl)-4-({[2-(2-methoxyethoxy)-5-(trifluoromethyl)phenyl]methyl}amino)-5-phenylpyrrolidine-2-carboxylic acid;

rac-(2S,3S,4S,5S)-3-tert-butyl-1-(cyclohexanecarbonyl)-4-({[1-(2-methoxyethyl)-2-oxo-5-(trifluoromethyl)-1,2-dihydropyridin-3-yl]methyl}amino)-5-phenylpyrrolidine-2-carboxylic acid;

rac-(2R,3R,4R,5R)-3-tert-butyl-1-(cyclohexanecarbonyl)-4-({[2-(2-hydroxyethoxy)-5-(trifluoromethyl)phenyl]methyl}amino)-5-phenylpyrrolidine-2-carboxylic acid;

rac-(2R,3R,4R,5S)-3-tert-butyl-4-{[(4-chloro-2-methoxyphenyl)methyl]amino}-1-(cyclohexanecarbonyl)-5-(6-methoxypyridin-2-yl)pyrrolidine-2-carboxylic acid;

(2R,3R,4R,5R)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

rac-(2S,3S,4S,5R)-3-tert-butyl-5-(6-methoxypyridin-2-yl)-4-({[2-methoxy-5-(trifluoromethyl)phenyl]methyl}amino)-1-(oxane-3-carbonyl)pyrrolidine-2-carboxylic acid;

rac-(2S,3S,4S,5R)-3-tert-butyl-5-(6-methoxypyridin-2-yl)-4-({[2-methoxy-5-(trifluoromethyl)phenyl]methyl}amino)-1-[(3R*)-3-methyloxane-3-carbonyl]pyrrolidine-2-carboxylic acid;

rac-(2R,3R,4R,5R)-3-tert-butyl-5-[2-(dimethylamino)phenyl]-4-({[2-methoxy-5-(trifluoromethyl)phenyl]methyl}amino)-1-(3-oxabicyclo[3.1.0]hexane-6-carbonyl)pyrrolidine-2-carboxylic acid;

rac-(2R,3R,4R,5R)-3-tert-butyl-4-({[2-chloro-5-(2-methoxyethoxy)pyridin-4-yl]methyl}amino)-1-(cyclohexanecarbonyl)-5-phenylpyrrolidine-2-carboxylic acid;

rac-(2R,3R,4R,5R)-3-tert-butyl-4-{[(2-chloro-5-hydroxypyridin-4-yl)methyl]amino}-1-(cyclohexanecarbonyl)-5-phenylpyrrolidine-2-carboxylic acid;

rac-(2R,3R,4R,5R)-4-({[2-amino-5-(trifluoromethyl)pyridin-3-yl]methyl}amino)-3-tert-butyl-1-(cyclohexanecarbonyl)-5-phenylpyrrolidine-2-carboxylic acid;

(2R,3R,4R,5R)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid;

rac-(2S,3S,4S,5R)-3-tert-butyl-4-{[6-(difluoromethoxy)pyridin-2-yl]amino}-5-(6-methoxypyridin-2-yl)-1-(3-methyloxane-3-carbonyl)pyrrolidine-2-carboxylic acid;

rac-(2S,3S,4S,5S)-3-tert-butyl-5-[2-(dimethylamino)phenyl]-4-({[2-methoxy-5-(trifluoromethyl)phenyl]methyl}amino)-1-(3-methyloxane-3-carbonyl)pyrrolidine-2-carboxylic acid;

(2S,3S,4S,5S)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(cyclohexanecarbonyl)-4-({[2-hydroxy-5-(methanesulfonyl)phenyl]methyl}amino)-5-phenylpyrrolidine-2-carboxylic acid;

rac-(2R,3R,4R,5R)-3-tert-butyl-1-(cyclohexanecarbonyl)-4-({[2-(2-methoxyethoxy)-5-(trifluoromethyl)pyridin-3-yl]methyl}amino)-5-phenylpyrrolidine-2-carboxylic acid;

rac-(2R,3R,4R,5R)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid;

rac-(2R,3R,4R,5R)-3-tert-butyl-4-{[(4-chloro-2-methoxyphenyl)methyl]amino}-1-(cyclohexanecarbonyl)-5-(pyridin-2-yl)pyrrolidine-2-carboxylic acid;

rac-(2R,3R,4R,5R)-3-tert-butyl-4-{[(2-cyanophenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-[({2-[3-(methanesulfonyl)propoxy]-5-(trifluoromethyl)phenyl}methyl)amino]-5-phenylpyrrolidine-2-carboxylic acid;

rac-(2R,3R,4R,5R)-3-tert-butyl-1-(cyclohexanecarbonyl)-4-({[2-(3-fluoropropoxy)-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-5-phenyl-4-[({2-[2-(trifluoromethoxy)ethoxy]-5-(trifluoromethyl)phenyl}methyl)amino]pyrrolidine-2-carboxylic acid;

rac-(2R,3R,4R,5R)-3-tert-butyl-1-(cyclohexanecarbonyl)-4-({[2-(2-hydroxyethoxy)-5-(trifluoromethyl)pyridin-3-yl]methyl}amino)-5-phenylpyrrolidine-2-carboxylic acid;

rac-(2R,3R,4R,5R)-3-tert-butyl-5-[2-(dimethylamino)pyridin-3-yl]-1-[(2R*)-2-methoxy-2-phenylacetyl]-4-({[2-methoxy-5-(trifluoromethyl)phenyl]methyl}amino)pyrrolidine-2-carboxylic acid;

rac-(2R,3R,4R,5R)-3-tert-butyl-5-[2-(dimethylamino)pyridin-3-yl]-1-[(2R)-2-methoxy-2-phenylacetyl]-4-{[6-methyl-4-(trifluoromethyl)pyridin-2-yl]amino}pyrrolidine-2-carboxylic acid;

rac-(2R,3R,4R,5R)-3-tert-butyl-5-[2-(dimethylamino)pyridin-3-yl]-1-[(2S)-2-methoxy-2-phenylacetyl]-4-{[6-methyl-4-(trifluoromethyl)pyridin-2-yl]amino}pyrrolidine-2-carboxylic acid;

rac-(2R,3R,4R,5R)-3-tert-butyl-4-{[(2,4-dimethoxyphenyl)methyl]amino}-5-phenyl-1-{[propan-2-yl)oxy]carbonyl}pyrrolidine-2-carboxylic acid;

rac-(2R,3R,4R,5R)-3-tert-butyl-4-{[(3-methoxy[1,1'-biphenyl]-4-yl)methyl]amino}-5-phenyl-1-{[(propan-2-yl)oxy]carbonyl}pyrrolidine-2-carboxylic acid;

rac-(2R,3R,4R,5R)-3-tert-butyl-5-[2-(dimethylamino)pyridin-3-yl]-4-{[6-methyl-4-(trifluoromethyl)pyridin-2-yl]amino}-1-{[(propan-2-yl)oxy]carbonyl}pyrrolidine-2-carboxylic acid;

rac-(2R,3R,4R,5R)-3-tert-butyl-4-{[(5-chloro-2-methoxyphenyl)methyl]amino}-1-(cyclohexanecarbonyl)-5-[2-(dimethylamino)pyridin-3-yl]pyrrolidine-2-carboxylic acid;

(2R,3R,4R,5R)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid;

rac-(2R,3R,4R,5R)-3-tert-butyl-4-{[(5-chloro-2-methoxyphenyl)methyl]amino}-1-[(cyclobutyloxy)carbonyl]-5-phenylpyrrolidine-2-carboxylic acid;

rac-(2S,3S,4S,5R)-3-tert-butyl-1-(cyclohexanecarbonyl)-5-(6-methoxypyridin-2-yl)-4-{[6-methyl-4-(trifluoromethyl)pyridin-2-yl]amino}pyrrolidine-2-carboxylic acid;

(2R,3R,4R,5R)-3-tert-butyl-5-[2-(dimethylamino)phenyl]-1-[(2R)-2-methoxy-2-phenylacetyl]-4-({[2-methoxy-5-(trifluoromethyl)phenyl]methyl}amino)pyrrolidine-2-carboxylic acid;

(2R,3R,4R,5R)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid;

(2S,3S,4S,5S)-3-tert-butyl-4-({[2-methoxy-5-(trifluoromethyl)phenyl]methyl}amino)-5-phenyl-1-[(2R)-3,3,3-trifluoro-2-methoxy-2-phenylpropanoyl]pyrrolidine-2-carboxylic acid;

(2R,3R,4R,5R)-3-tert-butyl-1-[(2S)-2-methoxy-2-phenylacetyl]-4-({[2-methoxy-4-(trifluoromethyl)phenyl]methyl}amino)-5-phenylpyrrolidine-2-carboxylic acid;

(2R,3R,4R,5R)-3-tert-butyl-4-({[2-methoxy-5-(trifluoromethyl)phenyl]methyl}amino)-5-phenyl-1-[(2R)-3,3,3-trifluoro-2-methoxy-2-phenylpropanoyl]pyrrolidine-2-carboxylic acid;

(2S,3S,4S,5S)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(4,4-difluorocyclohexane-1-carbonyl)-4-{[6-methyl-4-(trifluoromethyl)pyridin-2-yl]amino}-5-phenylpyrrolidine-2-carboxylic acid;

rac-(2R,3R,4R,5R)-3-tert-butyl-4-({[2-methoxy-4-(trifluoromethyl)phenyl]methyl}amino)-5-phenyl-1-(spiro[2.5]octane-6-carbonyl)pyrrolidine-2-carboxylic acid;

rac-(2R,3R,4R,5R)-3-tert-butyl-1-(cyclohexanecarbonyl)-4-({[5-methoxy-2-(trifluoromethyl)phenyl]methyl}amino)-5-phenylpyrrolidine-2-carboxylic acid;

rac-(2R,3R,4R,5R)-3-tert-butyl-4-{[(5-tert-butyl-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-({[5-fluoro-2-(methanesulfonyl)phenyl]methyl}amino)-5-phenylpyrrolidine-2-carboxylic acid;

rac-(2R,3R,4R,5R)-4-{[(5-bromo-2-cyanophenyl)methyl]amino}-3-tert-butyl-1-(cyclohexanecarbonyl)-5-phenylpyrrolidine-2-carboxylic acid;

rac-(2R,3R,4R,5R)-1-[(1R,2S,4S)-bicyclo[2.2.1]heptane-2-carbonyl]-3-tert-butyl-4-{[6-methyl-4-(trifluoromethyl)pyridin-2-yl]amino}-5-phenylpyrrolidine-2-carboxylic acid;

rac-(2R,3R,4R,5R)-4-[(5-chloro-3-methoxypyridin-2-yl)amino]-1-(cyclohexanecarbonyl)-3-(2-methoxypropan-2-yl)-5-phenylpyrrolidine-2-carboxylic acid;

rac-(2R,3R,4R,5R)-3-tert-butyl-4-[[2-methoxy-4-(trifluoromethyl)phenyl]methylamino]-5-phenyl-1-[(2R*)-2-phenylpropanoyl]pyrrolidine-2-carboxylic acid;

rac-(2R,3R,4R,5R)-3-tert-butyl-1-(1,4-dioxane-2-carbonyl)-4-({[2-methoxy-4-(trifluoromethyl)phenyl]methyl}amino)-5-phenylpyrrolidine-2-carboxylic acid;

rac-(2R,3R,4R,5R)-3-tert-butyl-1-[(cyclobutyloxy)carbonyl]-4-({[2-methoxy-4-(trifluoromethyl)phenyl]methyl}amino)-5-phenylpyrrolidine-2-carboxylic acid;

rac-(2R,3R,4R,5R)-4-{[(4-chloro-2-methoxyphenyl)methyl]amino}-1-(cyclohexanecarbonyl)-3-(2-methoxypropan-2-yl)-5-phenylpyrrolidine-2-carboxylic acid;

rac-(2R,3R,4R,5R)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid;

(2R,3R,4R,5R)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid;

(2S,3S,4S,5S)-4-{[(5-bromo-2-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3-methoxy-5,8,8-tetramethyl-5,6,7,8-tetrahydronaphthalen-2-yl)methyl]amino}-5-phenylpyrrolidine-2-carboxylic acid;

(2S,3S,4S,5S)-3-tert-butyl-1-(cyclohexanecarbonyl)-4-{[(3,4-dihydro-2H-1-benzopyran-6-yl)methyl]amino}-5-phenylpyrrolidine-2-carboxylic acid;

(2S,3S,4S,5S)-3-tert-butyl-4-{[(4-cyano-2-fluorophenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2,3-dihydro-1-benzofuran-5-yl)methyl]amino}-5-phenylpyrrolidine-2-carboxylic acid;

(2S,3S,4S,5S)-3-tert-butyl-1-(cyclohexanecarbonyl)-4-({[4-fluoro-2-(trifluoromethyl)phenyl]methyl}amino)-5-phenylpyrrolidine-2-carboxylic acid;

(2S,3S,4S,5S)-3-tert-butyl-4-[({5-chloro-2-[(propan-2-yl)oxy]phenyl}methyl)amino]-1-(cyclohexanecarbonyl)-5-phenylpyrrolidine-2-carboxylic acid;

(2S,3S,4S,5S)-3-tert-butyl-4-{[(3-cyano-4-fluorophenyl)methyl]amino}-1-(cyclohexanecarbonyl)-5-phenylpyrrolidine-2-carboxylic acid;

(2S,3S,4S,5S)-3-tert-butyl-4-{[(3-chloro-4-methoxyphenyl)methyl]amino}-1-(cyclohexanecarbonyl)-5-phenylpyrrolidine-2-carboxylic acid;

(2S,3S,4S,5S)-3-tert-butyl-4-{[(2-cyano-4-fluorophenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[3-fluoro-4-(trifluoromethoxy)phenyl]methyl}amino)-5-phenylpyrrolidine-2-carboxylic acid;

(2S,3S,4S,5S)-3-tert-butyl-1-(cyclohexanecarbonyl)-4-{[(3,4-dihydro-2H-1,5-benzodioxepin-7-yl)methyl]amino}-5-phenylpyrrolidine-2-carboxylic acid;

(2S,3S,4S,5S)-3-tert-butyl-1-(cyclohexanecarbonyl)-4-{[(3,4-dichlorophenyl)methyl]amino}-5-phenylpyrrolidine-2-carboxylic acid;

(2S,3S,4S,5S)-4-({[5-bromo-2-(difluoromethoxy)phenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2,2-difluoro-2H-1,3-benzodioxol-5-yl)methyl]amino}-5-phenylpyrrolidine-2-carboxylic acid;

(2S,3S,4S,5S)-3-tert-butyl-1-(cyclohexanecarbonyl)-4-{[(3,5-dimethoxyphenyl)methyl]amino}-5-phenylpyrrolidine-2-carboxylic acid;

(2S,3S,4S,5S)-3-tert-butyl-1-(cyclohexanecarbonyl)-4-{[(3,4-dimethylphenyl)methyl]amino}-5-phenylpyrrolidine-2-carboxylic acid;

(2S,3S,4S,5S)-4-{[(1-benzofuran-5-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[2-fluoro-4-(trifluoromethyl)phenyl]methyl}amino)-5-phenylpyrrolidine-2-carboxylic acid;

(2S,3S,4S,5S)-3-tert-butyl-1-[1-(methanesulfonyl)cyclopropane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-5-phenyl-4-({[4-(trifluoromethyl)phenyl]methyl}amino)pyrrolidine-2-carboxylic acid;

(2S,3S,4S,5S)-3-tert-butyl-1-(cyclohexanecarbonyl)-4-({[2-(difluoromethyl)phenyl]methyl}amino)-5-phenylpyrrolidine-2-carboxylic acid;

(2S,3S,4S,5S)-3-tert-butyl-4-{[(7-chloro-2H-1,3-benzodioxol-5-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[4-(difluoromethoxy)-3,5-dimethylphenyl]methyl}amino)-5-phenylpyrrolidine-2-carboxylic acid;

(2S,3S,4S,5S)-3-tert-butyl-4-{[(6-chloro-2H-1,3-benzodioxol-5-yl)methyl]amino}-1-(cyclohexanecarbonyl)-5-phenylpyrrolidine-2-carboxylic acid;

rac-(2S,3S,4S,5R)-3-tert-butyl-4-{[(4-chloro-2-methoxyphenyl)methyl]amino}-1-(cyclohexanecarbonyl)-5-(3-methoxypyridin-2-yl)pyrrolidine-2-carboxylic acid;

(2S,3S,4S,5S)-3-tert-butyl-4-[(4-carbamoyl-6-chloropyridin-2-yl)amino]-1-(cyclohexanecarbonyl)-5-phenylpyrrolidine-2-carboxylic acid;

(2S,3S,4S,5S)-3-tert-butyl-4-[(6-chloro-3-cyano-5-fluoropyridin-2-yl)amino]-1-(cyclohexanecarbonyl)-5-phenylpyrrolidine-2-carboxylic acid;

(2S,3S,4S,5S)-3-tert-butyl-4-[(6-chloro-4-cyanopyridin-2-yl)amino]-1-(cyclohexanecarbonyl)-5-phenylpyrrolidine-2-carboxylic acid;

(2S,3S,4S,5S)-3-tert-butyl-4-{[6-chloro-4-(2-hydroxypropan-2-yl)pyridin-2-yl]amino}-1-(cyclohexanecarbonyl)-5-phenylpyrrolidine-2-carboxylic acid;

(2S,3S,4S,5S)-3-tert-butyl-4-[(3-cyano-4,6-dimethylpyridin-2-yl)amino]-1-(cyclohexanecarbonyl)-5-phenylpyrrolidine-2-carboxylic acid;

(2S,3S,4S,5S)-3-tert-butyl-4-[(7-chloro-3-ethylquinolin-2-yl)amino]-1-(cyclohexanecarbonyl)-5-phenylpyrrolidine-2-carboxylic acid;

(2S,3S,4S,5S)-4-[(6-anilino-3-cyanopyridin-2-yl)amino]-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-[(7-methoxy-4-methylquinolin-2-yl)amino]-5-phenylpyrrolidine-2-carboxylic acid;

(2S,3S,4S,5S)-3-tert-butyl-1-(cyclohexanecarbonyl)-4-[(4-ethoxyquinolin-2-yl)amino]-5-phenylpyrrolidine-2-carboxylic acid;

(2S,3S,4S,5S)-3-tert-butyl-1-(cyclohexanecarbonyl)-4-({5-[(2-oxopyridin-1 (2H)-yl)methyl]pyridin-2-yl}amino)-5-phenylpyrrolidine-2-carboxylic acid;

(2S,3S,4S,5S)-3-tert-butyl-1-(cyclohexanecarbonyl)-4-[(7-methoxy-3-methylisoquinolin-1-yl)amino]-5-phenylpyrrolidine-2-carboxylic acid;

(2S,3S,4S,5S)-3-tert-butyl-4-{[5-(tert-butylcarbamoyl)pyridin-2-yl]amino}-1-(cyclohexanecarbonyl)-5-phenylpyrrolidine-2-carboxylic acid;

(2S,3S,4S,5S)-3-tert-butyl-1-(cyclohexanecarbonyl)-4-[(isoquinolin-3-yl)amino]-5-phenylpyrrolidine-2-carboxylic acid;

(2S,3S,4S,5S)-3-tert-butyl-1-(cyclohexanecarbonyl)-4-[(1,3-dimethyl-2,4-dioxo-1,2,3,4-tetrahydropyrido[4,3-d]pyrimidin-5-yl)amino]-5-phenylpyrrolidine-2-carboxylic acid;

(2S,3S,4S,5S)-3-tert-butyl-4-{[5-(2-cyanopropan-2-yl)pyridin-2-yl]amino}-1-(cyclohexanecarbonyl)-5-phenylpyrrolidine-2-carboxylic acid;

(2S,3S,4S,5S)-3-tert-butyl-4-{[5-(1-cyanocyclopropyl)pyridin-2-yl]amino}-1-(cyclohexanecarbonyl)-5-phenylpyrrolidine-2-carboxylic acid;

(2S,3S,4S,5S)-4-{[3-(benzyloxy)pyridin-2-yl]amino}-3-tert-butyl-1-(cyclohexanecarbonyl)-5-phenylpyrrolidine-2-carboxylic acid;

(2S,3S,4S,5S)-3-tert-butyl-4-{[5-(tert-butylcarbamoyl)pyridin-3-yl]amino}-1-(cyclohexanecarbonyl)-5-phenylpyrrolidine-2-carboxylic acid;

(2S,3S,4S,5S)-3-tert-butyl-1-(cyclohexanecarbonyl)-4-[(isoquinolin-4-yl)amino]-5-phenylpyrrolidine-2-carboxylic acid;

(2S,3S,4S,5S)-3-tert-butyl-4-({[2-methoxy-4-(trifluoromethyl)phenyl]methyl}amino)-5-phenyl-1-(pyridine-3-carbonyl)pyrrolidine-2-carboxylic acid;

(2S,3S,4S,5R)-3-tert-butyl-5-(3-chloropyridin-2-yl)-1-(cyclohexanecarbonyl)-4-({[2-methoxy-5-(trifluoromethyl)phenyl]methyl}amino)pyrrolidine-2-carboxylic acid;

(2R,3R,4R,5R)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(4-chlorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(cyclohexylacetyl)-5-phenylpyrrolidine-2-carboxylic acid;

(2S,3S,4S,5S)-4-({[5-(butan-2-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[5-(cyclohexylmethyl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[5-(2-ethylbutyl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(1-phenylethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(3,4-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,4-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3-methylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-4-oxo-1,4-dihydropyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-1H-indole-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(6-fluoro-2H,4H-1,3-benzodioxine-8-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)oxane-4-carbonyl]pyrrolidine-2-carboxylic acid;

(2S,3S,4S,5S)-3-tert-butyl-1-(cyclohexanecarbonyl)-4-{[(2-hydroxyquinolin-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(morpholin-4-yl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(S*)-2-(4-chloro-3-methyl-1H-pyrazol-1-yl)propanoyl]-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(tricyclo[3.3.1.1$^{3,7}$]decan-1-yl)phenyl]methyl}amino)pyrrolidine-2-carboxylic acid;

(2S,3S,4S,5S)-3-tert-butyl-1-(cyclohexanecarbonyl)-4-({[2-methoxy-5-(4-methylpiperazin-1-yl)phenyl]methyl}amino)-5-phenylpyrrolidine-2-carboxylic acid;

(2S,3S,4S,5S)-3-tert-butyl-1-[(1S)-3,3-difluorocyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(1-methyl-1H-pyrazol-4-yl)phenyl]methyl}amino)-5-phenylpyrrolidine-2-carboxylic acid;

(2S,3S,4S,5S)-3-tert-butyl-1-(cyclohexanecarbonyl)-4-({[5-(1-cyclopropyl-1H-pyrazol-4-yl)-2-methoxyphenyl]methyl}amino)-5-phenylpyrrolidine-2-carboxylic acid;

(2S,3S,4S,5S)-3-tert-butyl-1-(cyclohexanecarbonyl)-5-(2-fluorophenyl)-4-[({2-methoxy-5-[(1S,3S)-tricyclo[3.3.1.1$^{3,7}$]decan-1-yl]phenyl}methyl)amino]pyrrolidine-2-carboxylic acid;

(2S,3S,4S,5S)-1-(cyclohexanecarbonyl)-4-({[2-methoxy-5-(trifluoromethyl)pyridin-3-yl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(3,5-dimethylphenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(1,2,3,4-tetrahydronaphthalene-2-carbonyl)pyrrolidine-2-carboxylic acid;

(2S,3S,4S,5S)-3-tert-butyl-4-{[(5-tert-butyl-2-methoxyphenyl)methyl]amino}-5-phenyl-1-[(1R,5S)-tricyclo[3.2.1.0$^{2,4}$]octane-3-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[2-(thiophen-2-yl)cyclopropane-1-carbonyl]pyrrolidine-2-carboxylic acid;

(2S,3S,4S,5S)-3-tert-butyl-4-{[(5-tert-butyl-2-methoxyphenyl)methyl]amino}-1-[1-(3-methylphenyl)-5-(propan-2-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(2-methylcyclohexane-1-carbonyl)-5-phenylpyrrolidine-2-carboxylic acid;

(2S,3S,4S,5S)-3-tert-butyl-1-(3,5-dimethylcyclohexane-1-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(3,3-dimethylcyclopentane-1-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)phenyl]methyl}amino)-1-(3-methylcyclopentane-1-carbonyl)-5-phenylpyrrolidine-2-carboxylic acid;

(2R,3R,4R,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-{(2R,3R)-3-[(1H-pyrazol-1-yl)methyl]oxolane-2-carbonyl}pyrrolidine-2-carboxylic acid;

(2S,3S,4S,5S)-3-tert-butyl-1-(3,5-dimethylcyclohexane-1-carbonyl)-4-({[2-methoxy-5-(trifluoromethyl)pyridin-3-yl]methyl}amino)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2,2-dimethylcyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(2-methylcyclohexane-1-carbonyl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[3-(trifluoromethyl)cyclohexane-1-carbonyl]pyrrolidine-2-carboxylic acid;

(2S,3S,4S,5S)-3-(tert-butyl)-4-(((5-cyclobutyl-2-methoxypyridin-3-yl)methyl)amino)-1-(3,5-dimethylcyclohexanecarbonyl)-5-phenylpyrrolidine-2-carboxylic acid;

(2S,3S,4S,5S)-3-tert-butyl-4-{[(5-cyclobutyl-2-methoxypyridin-3-yl)methyl]amino}-1-(2-methylcyclohexane-1-carbonyl)-5-phenylpyrrolidine-2-carboxylic acid;

(2S,3S,4S,5S)-3-tert-butyl-4-{[(5-cyclobutyl-2-methoxypyridin-3-yl)methyl]amino}-5-phenyl-1-[3-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R*)-6-fluoro-3,4-dihydro-2H-1-benzopyran-2-carbonyl]pyrrolidine-2-carboxylic acid;

(2S,3S,4S,5S)-3-tert-butyl-5-[2-(dimethylamino)pyridin-3-yl]-1-(cis-4-hydroxy-4-propylcyclohexane-1-carbonyl)-4-{2-methoxy-5-(trifluoromethyl)pyridin-3-yl]amino}pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(1S,2S)-2-(trifluoromethyl)cyclohexane-1-carbonyl]pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(2R)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-phenyl-1-[2-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-1-[(2R)-2-methoxy-2-phenylacetyl]-2-methyl-5-phenylpyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-[di(propan-2-yl)carbamoyl]-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(difluoromethoxy)pyridin-3-yl]-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-{[(propan-2-yl)oxy]carbonyl}-5-[2-(propan-2-yl)phenyl]pyrrolidine-2-carboxylic acid;

(2S,3S,4S,5S)-3-(bicyclo[1.1.1]pentan-1-yl)-4-({[2-methoxy-5-(trifluoromethyl)pyridin-3-yl]methyl}amino)-5-phenyl-1-{[(propan-2-yl)oxy]carbonyl}pyrrolidine-2-carboxylic acid;

(2S,3S,4S,5S)-3-(bicyclo[1.1.1]pentan-1-yl)-4-{[(5-tert-bu-tyl-2-methoxyphenyl)methyl]amino}-5-(2-fluorophe-nyl)-1-{[(propan-2-yl)oxy]carbonyl}pyrrolidine-2-car-boxylic acid;

(2S,3S,4S,5S)-3-tert-butyl-5-[2-(dimethylamino)pyridin-3-yl]-4-[({2-methoxy-5-[(3S,5S)-tricyclo[3.3.1.1³,⁷]decan-1-yl]phenyl}methyl)amino]-1-{[(propan-2-yl)oxy]carbonyl}pyrrolidine-2-carboxylic acid;

(2S,3S,4S,5S)-3-tert-butyl-4-{[(5-cyclobutyl-2-methoxy-pyridin-3-yl)methyl]amino}-5-[2-(dimethylamino)pyri-din-3-yl]-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-[({2-methoxy-5-[(trifluoromethyl)sulfanyl]phenyl}methyl)amino]-1-{[(propan-2-yl)oxy]carbonyl}pyrrolidine-2-carboxylic acid;

(2S,3S,4S,5S)-3-tert-butyl-4-{[(6-methoxy-2,3-dihydro-1H-inden-5-yl)methyl]amino}-5-phenyl-1-{[(propan-2-yl)oxy]carbonyl}pyrrolidine-2-carboxylic acid;

(2S,3S,4S,5S)-3-tert-butyl-4-{[(3-methoxy-5,5,8,8-tetram-ethyl-5,6,7,8-tetrahydronaphthalen-2-yl)methyl]amino}-5-phenyl-1-{[(propan-2-yl)oxy]carbonyl}pyrrolidine-2-carboxylic acid;

rac-(2S,3S,4S,5S)-3-tert-butyl-4-{[(5-tert-butyl-2-methoxy-phenyl)methyl]amino}-1-(cyclohexanecarbonyl)-5-(1-methyl-2-oxo-1,2-dihydropyridin-3-yl)pyrrolidine-2-car-boxylic acid;

(2S,3S,4S,5S)-3-tert-butyl-4-{[(5-tert-butyl-2-methoxyphe-nyl)methyl]amino}-1-{[(propan-2-yl)oxy]carbonyl}-5-{2-[(propan-2-yl)oxy]pyridin-3-yl}pyrrolidine-2-carbox-ylic acid;

(2S,3S,4S,5S)-3-tert-butyl-4-{[(5-tert-butyl-2-methoxyphe-nyl)methyl]amino}-1-[(7S)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid;

(2S,3S,4S,5S)-3-tert-butyl-4-({[2-methoxy-5-(trifluo-romethoxy)phenyl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-5-[2-(dimethylamino)pyridin-3-yl]-4-({[2-methoxy-5-(2-methylbutan-2-yl)phenyl]methyl}amino)-1-{[(propan-2-yl)oxy]carbonyl}pyrrolidine-2-carboxylic acid;

(2S,3S,4S,5S)-3-tert-butyl-4-({[2-methoxy-5-(1-methylcy-clobutyl)phenyl]methyl}amino)-5-(2-methoxypyridin-3-yl)-1-[(2S)-oxane-2-carbonyl]pyrrolidine-2-carboxylic acid;

(2S,3S,4S,5S)-3-tert-butyl-4-({[2-methoxy-5-(1-methylcy-clobutyl)phenyl]methyl}amino)-5-(2-methoxypyridin-3-yl)-1-[(2R)-oxane-2-carbonyl]pyrrolidine-2-carboxylic acid;

(2S,3S,4S,5S)-3-tert-butyl-5-phenyl-1-{[(propan-2-yl)oxy]carbonyl}-4-({[1-(propan-2-yl)piperidin-4-yl]methyl}amino)pyrrolidine-2-carboxylic acid;

(2R,3R,4R,5R)-3-tert-butyl-5-(2-chlorophenyl)-4-{[(5-cy-clobutyl-2-methoxypyridin-3-yl)methyl]amino}-1-[(2S)-oxolane-2-carbonyl]pyrrolidine-2-carboxylic acid;

(2S,3S,4S,5S)-3-tert-butyl-4-({[2-hydroxy-5-(methoxycar-bonyl)phenyl]methyl}amino)-1-[(2S)-oxolane-2-carbo-nyl]-5-[2-(propan-2-yl)phenyl]pyrrolidine-2-carboxylic acid;

and pharmaceutically acceptable salts thereof.

Formula (II)
One embodiment pertains to compounds of Formula (II),

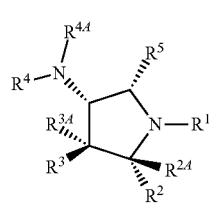

(II)

wherein
R¹ is selected from the group consisting of SO₂R⁶, C(O)R⁶, C(O)OR⁶, and C(O)NR⁷R⁸;
R² is C(O)OH or a bioisostere thereof;
R²ᴬ is selected from the group consisting of hydrogen, C₁-C₆ alkyl, C₁-C₆ haloalkyl, and C₃-C₆ cycloalkyl;
R³ is selected from the group consisting of C₁-C₆ alkyl, C₃-C₆ cycloalkyl, phenyl, and 5-6 membered het-eroaryl; wherein the R³ C₁-C₆ alkyl is optionally sub-stituted with one or more substituents independently selected from the group consisting of C₁-C₆ alkoxy, OH, oxo, CN, NO₂, F, Cl, Br and I; wherein the R³ C₃-C₆ cycloalkyl, phenyl, and 5-6 membered het-eroaryl are optionally substituted with one or more substituents independently selected from the group consisting of C₁-C₆ alkyl, C₁-C₆ alkoxy, C₁-C₆ haloalkyl, OH, oxo, CN, NO₂, F, Cl, Br and I; and
R³ᴬ is selected from the group consisting of hydrogen, C₁-C₆ alkyl, and C₁-C₆ haloalkyl; or
R³ and R³ᴬ, together with the carbon to which they are attached, form C₃-C₆ cycloalkyl; wherein the C₃-C₆ cycloalkyl formed from R³ and R³ᴬ and the carbon to which they are attached is optionally substituted with one or more substituents independently selected from the group consisting of C₁-C₆ alkyl, C₁-C₆ alkoxy, C₁-C₆ haloalkyl, OH, oxo, CN, NO₂, F, Cl, Br and I;
R⁴ is selected from the group consisting of L¹-C₆-C₁₀ aryl, L¹-5-11 membered heteroaryl, L-4-12 membered heterocyclyl, L¹-C₃-C₁₁ cycloalkyl, and L¹-C₄-C₁₁ cycloalkenyl; wherein the R⁴ C₆-C₁₀ aryl, 5-11 mem-bered heteroaryl, 4-12 membered heterocyclyl, C₃-C₁₁ cycloalkyl, and C₄-C₁₁ cycloalkenyl are optionally sub-stituted with one or more substituents independently selected from the group consisting of R⁹, OR⁹, C(O)OR⁹, C(O)NR¹⁰R¹¹, SR⁹, NR¹⁰R¹¹, Si(R⁹)₃, SF₅, SO₂R⁹, OH, oxo, CN, NO₂, F, Cl, Br and I; wherein L¹ is absent, or is selected from the group consisting of C₁-C₆ alkylene, C₂-C₆ alkenylene, C₂-C₆ alkynylene, and C₁-C₆ alkylene-O—; wherein the L¹ C₁-C₆ alky-lene, C₂-C₆ alkenylene, and C₂-C₆ alkynylene, alone or as part of a group, are optionally substituted with one or more substituents independently selected from the group consisting of C₁-C₆ alkoxy, OH, and oxo; and
R⁴ᴬ is selected from the group consisting of hydrogen, C₁-C₆ alkyl, and C₁-C₆ haloalkyl; or
R⁴ and R⁴ᴬ, together with the carbon to which they are attached, form 4-12 membered heterocyclyl; wherein the 4-12 membered heterocyclyl is optionally substi-tuted with one or more substituents independently selected from the group consisting of R⁹, OR⁹, C(O)OR⁹, C(O)NR¹⁰R¹¹, SR⁹, NR¹⁰R¹¹, Si(R⁹)₃, SF₅, SO₂R⁹, OH, oxo, CN, NO₂, F, Cl, Br and I;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

Another embodiment pertains to compounds of Formula (II), wherein $R^1$ is selected from the group consisting of $SO_2R^6$, $C(O)R^6$, $C(O)OR^6$, and $C(O)NR^7R^8$;

$R^2$ is C(O)OH or a bioisostere thereof;

$R^{2A}$ is selected from the group consisting of hydrogen, $C_1$-$C_6$ alkyl, $C_1$-$C_6$ haloalkyl, and $C_3$-$C_6$ cycloalkyl;

$R^3$ is selected from the group consisting of $C_1$-$C_6$ alkyl, $C_3$-$C_6$ cycloalkyl, phenyl, and 5-6 membered heteroaryl; wherein the $R^3$ $C_1$-$C_6$ alkyl is optionally substituted with one or more substituents independently selected from the group consisting of $C_1$-$C_6$ alkoxy, OH, oxo, CN, $NO_2$, F, Cl, Br and I; wherein the $R^3$ $C_3$-$C_6$ cycloalkyl, phenyl, and 5-6 membered heteroaryl are optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{3.4}$ is selected from the group consisting of hydrogen, $C_1$-$C_6$ alkyl, and $C_1$-$C_6$ haloalkyl; or $R^3$ and $R^{3.4}$, together with the carbon to which they are attached, form $C_3$-$C_6$ cycloalkyl; wherein the $C_3$-$C_6$ cycloalkyl formed from $R^3$ and $R^{3.4}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, ($C_1$-$C_6$ alkylene)$_x$-$C_3$-$C_{11}$ cycloalkyl, and ($C_1$-$C_6$ alkylene)$_x$-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$-$C_3$-$C_{11}$ cycloalkyl, and the $C_4$-$C_{11}$ cycloalkenyl of ($C_1$-$C_6$ alkylene)$_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^{4.4}$ is selected from the group consisting of hydrogen, $C_1$-$C_6$ alkyl, and $C_1$-$C_6$ haloalkyl;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{31}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (II), $R^1$ is selected from the group consisting of $SO_2R^6$, $C(O)R^6$, $C(O)OR^6$, and $C(O)NR^7R^8$. In another embodiment of Formula (II), $R^1$ is $C(O)R^6$ or $C(O)OR^6$. In another embodiment of Formula (II), $R^1$ is $SO_2R^6$. In another embodiment of Formula (II), $R^1$ is $C(O)R^6$. In another embodiment of Formula (II), $R^1$ is $C(O)OR^6$. In another embodiment of Formula (II), $R^1$ is $C(O)NR^7R^8$.

In one embodiment of Formula (II), $R^2$ is C(O)OH or a bioisostere thereof. In another embodiment of Formula (II), $R^2$ is —P(O)(OH)$_2$, —P(O)(OH)(H), —P(O)(OH)(O—$C_1$-$C_6$ alkyl), —P(O)(CH$_3$)(OH), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$,

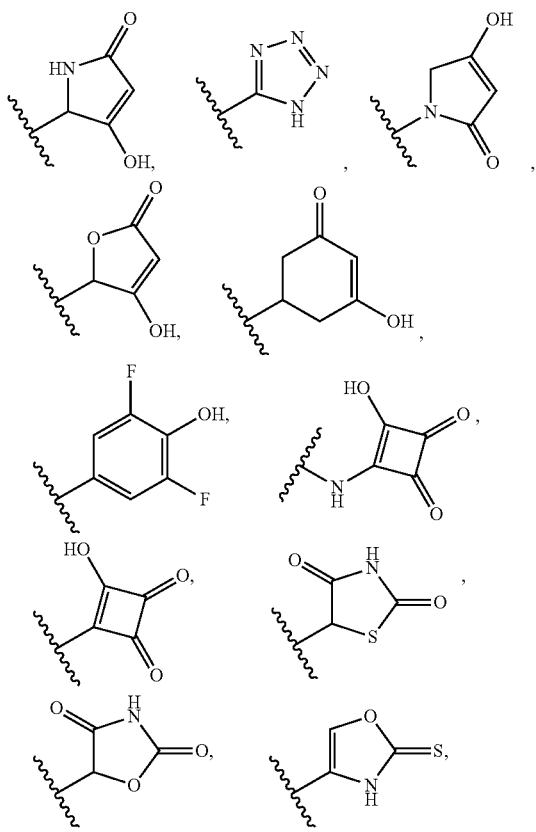

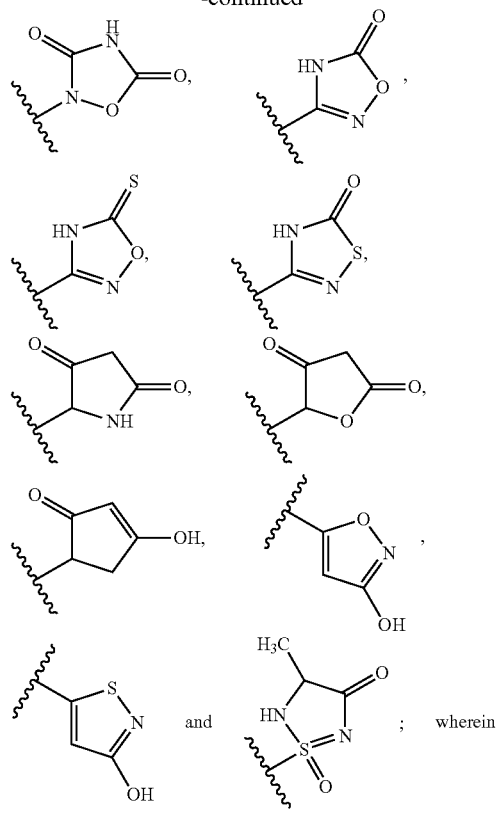

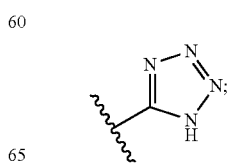
; wherein $R^{G3a}$, at each occurrence, is independently $C_1$-$C_6$ alkyl, $C_1$-$C_6$ alkyl-O—$C_1$-$C_6$ alkyl, $C_1$-$C_6$ haloalkyl, or $G^A$;

$R^{G3b}$ is hydrogen, $C_1$-$C_6$ alkyl, or $C_1$-$C_6$ haloalkyl or $G^A$;

$G^A$, at each occurrence, is independently cycloalkyl, cycloalkenyl, aryl, or heteroaryl, each of which is independently unsubstituted or substituted with 1, 2, or 3 independently selected RU groups; wherein $R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;

$R^j$, at each occurrence, is independently selected from the group consisting of hydrogen, $C_1$-$C_6$ alkyl, or $C_1$-$C_6$ haloalkyl; and $R^k$, at each occurrence, is independently selected from the group consisting of $C_1$-$C_6$ alkyl or $C_1$-$C_6$ haloalkyl. In another embodiment of Formula (II), $R^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or wherein
R$^{G3a}$, at each occurrence, is independently C$_1$-C$_6$ alkyl, C$_1$-C$_6$ alkyl-O—C$_1$-C$_6$ alkyl, C$_1$-C$_6$ haloalkyl, or G$^A$;
R$^{G3b}$ is hydrogen, C$_1$-C$_6$ alkyl, or C$_1$-C$_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected R$^u$ groups; wherein
R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
R$^j$, at each occurrence, is independently selected from the group consisting of hydrogen, C$_1$-C$_6$ alkyl, or C$_1$-C$_6$ haloalkyl; and
R$^k$, at each occurrence, is independently selected from the group consisting of C$_1$-C$_6$ alkyl or C$_1$-C$_6$ haloalkyl.

In another embodiment of Formula (II), R$^2$ is C(O)OH. In another embodiment of Formula (II), R$^2$ is —C(O)NHSO$_2$R$^{G3a}$ or —C(O)NHSO$_2$N(R$^{G3a}$)$_2$; R$^{G3a}$, at each occurrence, is independently C$_1$-C$_6$ alkyl, C$_1$-C$_6$ alkyl-O—C$_1$-C$_6$ alkyl, or G$^A$; and G$^A$, at each occurrence, is independently cycloalkyl, which is independently unsubstituted or substituted with 1, 2, or 3 independently selected R$^u$ groups; wherein R$^u$, at each occurrence, is independently C$_1$-C$_6$ alkyl. In another embodiment of Formula (II), R$^2$ is —C(O)NHSO$_2$R$^{G3a}$; R$^{G3a}$, at each occurrence, is independently C$_1$-C$_6$ alkyl, C$_1$-C$_6$ alkyl-O—C$_1$-C$_6$ alkyl, or G$^A$; and G$^A$, at each occurrence, is independently cycloalkyl, which is independently unsubstituted or substituted with 1, 2, or 3 independently selected R$^u$ groups; wherein R$^u$, at each occurrence, is independently C$_1$-C$_6$ alkyl. In another embodiment of Formula (II), R$^2$ is —C(O)NHSO$_2$N(R$^{G3a}$)$_2$; and R$^{G3a}$, at each occurrence, is independently C$_1$-C$_6$ alkyl.

In one embodiment of Formula (II), R$^{2A}$ is selected from the group consisting of hydrogen, C$_1$-C$_6$ alkyl, C$_1$-C$_6$ haloalkyl, and C$_3$-C$_6$ cycloalkyl. In another embodiment of Formula (II), R$^{2A}$ is hydrogen or C$_1$-C$_6$ alkyl. In another embodiment of Formula (II), R$^{2A}$ is hydrogen. In another embodiment of Formula (II), R$^{2A}$ is C$_1$-C$_6$ alkyl. In another embodiment of Formula (II), R$^{2A}$ is CH$_3$.

In one embodiment of Formula (II), R$^2$ is C(O)OH; and R$^{2A}$ is hydrogen.

In one embodiment of Formula (II),
R$^2$ is —P(O)(OH)$_2$, —P(O)(OH)(H), —B(OH)$_2$, —SO$_3$H, —CH(OH)CF$_3$, —C(O)NH(OH), —C(O)NH(CN), —C(O)NHSO$_2$R$^{G3a}$, —SO$_2$NHC(O)R$^{G3a}$, —C(O)NHSO$_2$NHR$^{G3a}$, —C(O)NHSO$_2$N(R$^{G3a}$)$_2$, —SO$_2$NH$_2$, —SO$_2$NHR$^{G3a}$, —SO$_2$N(R$^{G3a}$)$_2$, —C(O)NHS(O)(R$^{G3a}$)=NC(O)R$^{G3a}$, —C(O)NHS(O)(R$^{G3a}$)=NR$^{G3b}$, or

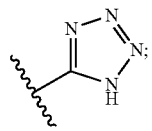

R$^{G3a}$, at each occurrence, is independently C$_1$-C$_6$ alkyl, C$_1$-C$_6$ alkyl-O—C$_1$-C$_6$ alkyl, C$_1$-C$_6$ haloalkyl, or G$^A$;
R$^{G3b}$ is hydrogen, C$_1$-C$_6$ alkyl, or C$_1$-C$_6$ haloalkyl or G$^A$;
G$^A$, at each occurrence, is independently cycloalkyl, cycloalkenyl, aryl, or heteroaryl, each of which is independently unsubstituted or substituted with 1, 2, or 3 independently selected R$^u$ groups; wherein
R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, —NO$_2$, —OR$^j$, —OC(O)R$^k$, —OC(O)N(R$^j$)$_2$, —S(O)$_2$R$^j$, —S(O)$_2$N(R$^j$)$_2$, —C(O)R$^k$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), or —N(R$^j$)C(O)N(R$^j$)$_2$;
R$^j$, at each occurrence, is independently selected from the group consisting of hydrogen, C$_1$-C$_6$ alkyl, or C$_1$-C$_6$ haloalkyl;
R$^k$, at each occurrence, is independently selected from the group consisting of C$_1$-C$_6$ alkyl or C$_1$-C$_6$ haloalkyl; and
R$^{2A}$ is hydrogen. In one embodiment of Formula (II), R$^2$ is —C(O)NHSO$_2$R$^{G3a}$ or —C(O)NHSO$_2$N(R$^{G3a}$)$_2$;
R$^{G3a}$, at each occurrence, is independently C$_1$-C$_6$ alkyl, C$_1$-C$_6$ alkyl-O—C$_1$-C$_6$ alkyl, or G$^A$;
G$^A$, at each occurrence, is independently cycloalkyl, which is independently unsubstituted or substituted with 1, 2, or 3 independently selected R$^u$ groups;
R$^u$, at each occurrence, is independently C$_1$-C$_6$ alkyl; and
R$^{2A}$ is hydrogen.

In one embodiment of Formula (II), R$^3$ is selected from the group consisting of C$_1$-C$_6$ alkyl, C$_3$-C$_6$ cycloalkyl, phenyl, and 5-6 membered heteroaryl; wherein the R$^3$ C$_1$-C$_6$ alkyl is optionally substituted with one or more substituents independently selected from the group consisting of C$_1$-C$_6$ alkoxy, OH, oxo, CN, NO$_2$, F, Cl, Br and I; wherein the R$^3$ C$_3$-C$_6$ cycloalkyl, phenyl, and 5-6 membered heteroaryl are optionally substituted with one or more substituents independently selected from the group consisting of C$_1$-C$_6$ alkyl, C$_1$-C$_6$ alkoxy, C$_1$-C$_6$ haloalkyl, OH, oxo, CN, NO$_2$, F, Cl, Br and I; and R$^{3A}$ is independently selected from the group consisting of hydrogen, C$_1$-C$_6$ alkyl, and C$_1$-C$_6$ haloalkyl. In another embodiment of Formula (II), R$^3$ is selected from the group consisting of C$_1$-C$_6$ alkyl and C$_3$-C$_6$ cycloalkyl; wherein the R$^3$ C$_1$-C$_6$ alkyl is optionally substituted with one or more C$_1$-C$_6$ alkoxy; wherein the R$^3$ C$_3$-C$_6$ cycloalkyl is optionally substituted with one or more C$_1$-C$_6$ alkyl; and R$^{3A}$ is independently hydrogen. In another embodiment of Formula (II), R$^3$ is C$_1$-C$_6$ alkyl; wherein the R$^3$ C$_1$-C$_6$ alkyl is optionally substituted with one or more C$_1$-C$_6$ alkoxy; and R$^{3A}$ is independently hydrogen. In another embodiment of Formula (II), R$^3$ is C$_3$-C$_6$ cycloalkyl; wherein the R$^3$ C$_3$-C$_6$ cycloalkyl is optionally substituted with one or more C$_1$-C$_6$ alkyl; and R$^{3A}$ is hydrogen. In one embodiment of Formula (II), R$^3$ is CH$_3$, and R$^{3A}$ is hydrogen. In one embodiment of Formula (II), R$^3$ is C(CH$_3$)$_3$, and R$^{3A}$ is hydrogen. In one embodiment of Formula (II), R$^3$ is C(OCH$_3$)(CH$_3$)$_2$, and R$^{3A}$ is hydrogen. In one embodiment of Formula (II), R$^3$ is cyclopropyl wherein the R$^3$ cyclopropyl is optionally substituted with one CH$_3$; and R$^{3A}$ is hydrogen. In one embodiment of Formula (II), R$^3$ is bicyclo[1.1.1]pentanyl, and R$^{3A}$ is hydrogen.

In one embodiment of Formula (II), R$^3$ and R$^{3A}$, together with the carbon to which they are attached, form C$_3$-C$_6$ cycloalkyl; wherein the C$_3$-C$_6$ cycloalkyl formed from R$^3$ and R$^{3A}$ and the carbon to which they are attached is optionally substituted with one or more substituents independently selected from the group consisting of C$_1$-C$_6$ alkyl, C$_1$-C$_6$ alkoxy, C$_1$-C$_6$ haloalkyl, OH, oxo, CN, NO$_2$, F, Cl, Br and I. In another embodiment of Formula (II), R$^3$ and R$^{3A}$, together with the carbon to which they are attached, form C$_3$-C$_6$ cycloalkyl, which is unsubstituted. In another embodiment of Formula (II), $R^3$ and $R^{3,4}$, together with the carbon to which they are attached, form cyclopropyl.

In one embodiment of Formula (II), $R^4$ is selected from the group consisting of $L^1$-$C_6$-$C_{10}$ aryl, L-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4,4}$ is selected from the group consisting of hydrogen, $C_1$-$C_6$ alkyl, and $C_1$-$C_6$ haloalkyl. In another embodiment of Formula (II), $R^4$ is $L^1$ is absent, or is selected from the group consisting of $L^1$-$C_6$-$C_{10}$ aryl, $L^1$-5-11 membered heteroaryl, $L^1$-4-12 membered heterocyclyl, and L-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4,4}$ is selected from the group consisting of hydrogen, and $C_1$-$C_6$ alkyl. In another embodiment of Formula (II), $R^4$ is $L^1$-$C_6$-$C_{10}$ aryl; wherein the $R^4$ $C_6$-$C_{10}$ aryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4,4}$ is hydrogen. In another embodiment of Formula (II), $R^4$ is $L^1$-5-11 membered heteroaryl; wherein the $R^4$ 5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4,4}$ is hydrogen. In another embodiment of Formula (II), $R^4$ is $L^1$-4-12 membered heterocyclyl; wherein the $R^4$ 4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4,4}$ is hydrogen. In another embodiment of Formula (II), $R^4$ is $L^1$-$C_3$-$C_{11}$ cycloalkyl; wherein the $R^4$ $L^1$-$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4,4}$ is hydrogen. In one embodiment of Formula (II), $R^4$ and $R^{4,4}$, together with the carbon to which they are attached, form 4-12 membered heterocyclyl; wherein the 4-12 membered heterocyclyl is optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I. In another embodiment of Formula (II), $R^4$ and $R^{4,4}$, together with the carbon to which they are attached, form 4-12 membered heterocyclyl; wherein the 4-12 membered heterocyclyl is optionally substituted with one or more substituents independently selected from the group consisting of $OR^9$, and Cl.

In one embodiment of Formula (II), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, ($C_1$-$C_6$ alkylene)$_x$-$C_3$-$C_{11}$ cycloalkyl, and ($C_1$-$C_6$ alkylene)$_x$-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$$C_3$-$C_{11}$ cycloalkyl, and the $C_4$-$C_{11}$ cycloalkenyl of ($C_1$-$C_6$ alkylene)$_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; $R^{4,4}$ is selected from the group consisting of hydrogen, $C_1$-$C_6$ alkyl, and $C_1$-$C_6$ haloalkyl; and x is 0 or 1. In another embodiment of Formula (II), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, and ($C_1$-$C_6$ alkylene)$_x$-$C_3$-$C_{11}$ cycloalkyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, and the $C_3$-$C_{11}$ cycloalkyl of ($C_1$-$C_6$ alkylene)$_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4,4}$ is hydrogen; and x is 0 or 1. In another embodiment of Formula (II), $R^4$ is ($C_1$-$C_6$ alkylene)$_x$-$C_6$-$C_{10}$ aryl; wherein the $R^4$ ($C_1$-$C_6$ alkylene)$_x$-$C_6$-$C_{10}$ membered aryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4,4}$ is hydrogen; and x is 0 or 1.

In another embodiment of Formula (II), $R^4$ is ($C_1$-$C_6$ alkylene)$_x$-5-11 membered heteroaryl; wherein the $R^4$ ($C_1$-$C_6$ alkylene)$_x$-5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4,4}$ is hydrogen; and x is 0 or 1. In another embodiment of Formula (II), $R^4$ is ($C_1$-$C_6$ alkylene)$_x$-4-12 membered heterocyclyl; wherein the $R^4$ ($C_1$-$C_6$ alkylene)$_x$-4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4,4}$ is hydrogen; and x is 0 or 1. In another embodiment of Formula (II), $R^4$ is ($C_1$-$C_6$ alkylene)$_x$-$C_3$-$C_{11}$ cycloalkyl; wherein the $R^4$ ($C_1$-$C_6$ alkylene)$_x$$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4,4}$ is hydrogen; and x is 0 or 1.

In one embodiment of Formula (II), $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (II), $R^5$ is selected from the group consisting of $C_6$-$C_{10}$ membered aryl, 4-6 membered monocyclic heterocycle fused to a phenyl group, and 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is selected from the group consisting of $C_6$-$C_{10}$ membered aryl, 4-6 membered monocyclic heterocycle fused to a phenyl group, and 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently $C_1$-$C_6$ alkyl.

In one embodiment of Formula (II), $R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^2$, $OR^{12}$, $NR^{13}R^{14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (II), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently $C_1$-$C_6$ alkyl.

In another embodiment of Formula (II), $R^5$ is $C_6$-$C_{10}$ membered aryl; wherein the $R^5$ $C_6$-$C_{10}$ membered aryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is 4-6 membered monocyclic heterocycle fused to a phenyl group; wherein the $R^5$ 4-6 membered monocyclic heterocycle fused to a phenyl group is optionally substituted with one or more substituents independently selected from the group consisting of $R^{12}$, $OR^{12}$, $NR^{13}R^{14}$ OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, OH, F, Cl, Br and I; and $R^{13}$ and $R^{14}$, at each occurrence, are each independently $C_1$-$C_6$ alkyl.

In another embodiment of Formula (II), $R^5$ is phenyl, which is unsubstituted. In another embodiment of Formula (II), $R^5$ is phenyl; wherein the $R^5$ phenyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (II), $R^5$ is phenyl; which is substituted with one $R^{12}$; and $R^{12}$ is $C_1$-$C_6$ alkyl. In another embodiment of Formula (II), $R^5$ is phenyl; which is substituted with one $R^{12}$; and $R^{12}$ is $CH_3$ or $CH(CH_3)_2$. In another embodiment of Formula (II), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (II), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (II), $R^5$ is pyridinyl; wherein the $R^5$ pyridinyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl.

In one embodiment of Formula (II), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_1$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (II), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl is optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; $R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (II), $R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$, $SR^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl. In another embodiment of Formula (II), $R^6$ is $C_1$-$C_6$ alkyl; wherein the $R^6$ $C_1$-$C_6$ alkyl is substituted with one $R^{15}$; and $R^{15}$, at each occurrence, is independently 6-10 membered aryl. In another embodiment of Formula (II), $R^6$ is $C_2$ alkyl; wherein the $R^6$ $C_2$ alkyl is substituted with one $R^{15}$; and $R^{15}$, at each occurrence, is independently phenyl. In another embodiment of Formula (II), $R^6$ is $C_1$-$C_6$ alkyl; wherein the $R^6$ $C_1$-$C_6$ alkyl is unsubstituted. In another embodiment of Formula (II), $R^6$ is —$CH_3$. In another embodiment of Formula (II), $R^6$ is —$CH(CH_3)_2$. In one embodiment of Formula (II), $R^6$ is 4-12 membered heterocyclyl; wherein the $R^6$ 4-12 membered heterocyclyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (II), $R^6$ is 4-12 membered heterocyclyl; wherein the $R^6$ 4-12 membered heterocyclyl is unsubstituted. In another embodiment of Formula (II), $R^6$ is tetrahydrofuranyl. In another embodiment of Formula (II), $R^6$ is tetrahydropyranyl. In one embodiment of Formula (II), $R^6$ is $C_3$-$C_{11}$ cycloalkyl; wherein the $R^6$ $C_3$-$C_{11}$ cycloalkyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_1$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (II), $R^6$ is $C_3$-$C_{11}$ cycloalkyl; wherein the $R^6$ $C_3$-$C_{11}$ cycloalkyl is optionally substituted with one or more F. In another embodiment of Formula (II), $R^6$ is $C_3$-$C_{11}$ cycloalkyl; wherein the $C_3$-$C_{11}$ cycloalkyl is unsubstituted. In another embodiment of Formula (II), $R^6$ is cyclohexyl; wherein the $R^6$ cyclohexyl is substituted with two F. In another embodiment of Formula (II), $R^6$ is cyclopentyl. In another embodiment of Formula (II), $R^6$ is cyclohexyl.

In one embodiment of Formula (II), $R^1$ is $C(O)OR^6$; $R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$, $SR^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl.

In one embodiment of Formula (II), $R^1$ is $C(O)OR^6$; and $R^6$ is $C_1$-$C_6$ alkyl; wherein the $R^6$ is unsubstituted $C_1$-$C_6$ alkyl.

In one embodiment of Formula (II), $R^1$ is $C(O)R^6$; $R^6$ is 4-12 membered heterocyclyl; wherein the $R^6$ 4-12 membered heterocyclyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (II), $R^1$ is $C(O)R^6$; and $R^6$ is 4-12 membered heterocyclyl; wherein the $R^6$ 4-12 membered heterocyclyl is unsubstituted.

In one embodiment of Formula (II), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I; $R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl. In another embodiment of Formula (II), $R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl; $R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl, and $C_3$-$C_{11}$ cycloalkyl is optionally substituted with one or more CN; $R^{22}$ and $R^{23}$, at each occurrence, are each independently $C_1$-$C_6$ alkyl; and $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl.

In one embodiment of Formula (II), $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br, and I. In another embodiment of Formula (II), $R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy.

In one embodiment of Formula (II), $R^4$ is ($C_1$-$C_6$ alkylene)$_x$-$C_6$-$C_{10}$ aryl; wherein the $R^4$ ($C_1$-$C_6$ alkylene)$_x$-$C_6$-$C_{10}$ membered aryl is optionally substituted with one or more substituents independently selected from the group consisting of $R^9$ and $OR^9$; $R^{4.4}$ is hydrogen; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl. In one embodiment of Formula (II), $R^4$ is $L^1$-$C_6$-$C_{10}$ aryl; wherein the $R^4$ $C_6$-$C_{10}$ membered aryl is optionally substituted with one or more substituents independently selected from the group consisting of $R^9$ and $OR^9$; wherein $L^1$ is absent, or is $C_1$-$C_6$ alkylene; $R^{4A}$ is hydrogen; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (II), $R^4$ is $CH_2$-phenyl; wherein the $R^4$ $CH_2$-phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (II), $R^4$ is phenyl; wherein the $R^4$ phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In another embodiment of Formula (II), $R^4$ is $(C_1$-$C_6$ alkylene$)_x$-5-11 membered heteroaryl; wherein the $R^4$ $(C_1$-$C_6$ alkylene$)_x$-5-11 membered heteroaryl is optionally substituted with one or more substituents independently selected from the group consisting of $R^9$ and $OR^9$; $R^{4A}$ is hydrogen; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl. In another embodiment of Formula (II), $R^4$ is $L^1$-5-11 membered heteroaryl; wherein the $R^4$ 5-11 membered heteroaryl is optionally substituted with one or more substituents independently selected from the group consisting of $R^9$ and $OR^9$; $L^1$ is absent, or is $C_1$-$C_6$ alkylene; $R^{4A}$ is hydrogen; $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (II), $R^4$ is $CH_2$-pyridinyl; wherein the $R^4$ $CH_2$— pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (II), $R^4$ is pyridinyl; wherein the $R^4$ pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (II), $R^4$ is $CH_2$-quinolinyl; wherein the $R^4$ $CH_2$— quinolinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In one embodiment of Formula (II), $R^4$ is selected from the group consisting of

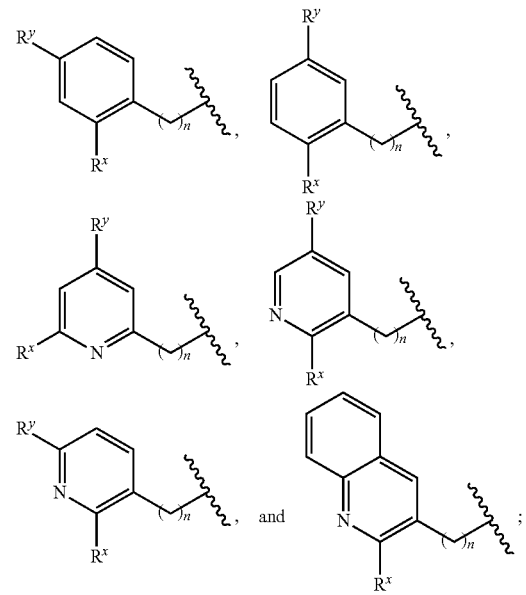

wherein $R^x$ is selected from the group consisting of $CH_3$ and $OCH_3$, and $R^y$ is selected from the group consisting of $CF_3$, $CH_3$, $C(CH_3)_3$, cyclopropyl, cyclobutyl substituted with $CH_3$, and bicyclo[1.1.1]pentyl; and n is 0 or 1.

One embodiment pertains to compounds of Formula (II),

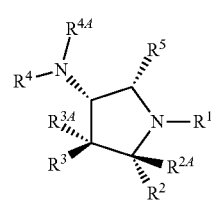

(II)

wherein
$R^1$ is selected from the group consisting of $SO_2R^6$, $C(O)R^6$, $C(O)OR^6$, and $C(O)NR^7R^8$;
$R^2$ is $C(O)OH$ or a bioisostere thereof,
$R^{2A}$ is selected from the group consisting of hydrogen and $C_1$-$C_6$ alkyl;
$R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with $C_1$-$C_6$ alkyl; and $R^{3A}$ is hydrogen; or $R^3$ and $R^{3A}$, together with the carbon to which they are attached, form $C_3$-$C_6$ cycloalkyl;

$R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, and $(C_1$-$C_6$ alkylene$)_x$-$C_3$-$C_{11}$ cycloalkyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, and the $C_3$-$C_{11}$ cycloalkyl of $(C_1$-$C_6$ alkylene$)_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br;

$R^{4A}$ is hydrogen;

$R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^5$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and x is 0 or 1.

One embodiment pertains to compounds of Formula (II), (II)

wherein $R^1$ is selected from the group consisting of $SO_2R^6$, $C(O)R^6$, $C(O)OR^6$, and $C(O)NR^7R^8$;

$R^2$ is C(O)OH or a bioisostere thereof;

$R^{2A}$ is selected from the group consisting of hydrogen and $C_1$-$C_6$ alkyl;

$R^3$ is selected from the group consisting of $C_1$-$C_6$ alkyl and $C_3$-$C_6$ cycloalkyl; wherein the $R^3$ $C_1$-$C_6$ alkyl is optionally substituted with one or more $C_1$-$C_6$ alkoxy; wherein the $R^3$ $C_3$-$C_6$ cycloalkyl is optionally substituted with $C_1$-$C_6$ alkyl; and $R^{3A}$ is hydrogen; or $R^3$ and $R^{3A}$, together with the carbon to which they are attached, form $C_3$-$C_6$ cycloalkyl;

$R^4$ is selected from the group consisting of $L^1$-$C_6$-$C_{10}$ aryl, $L^1$-5-11 membered heteroaryl, $L^1$-4-12 membered heterocyclyl, and $L^1$-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{44}$ is selected from the group consisting of hydrogen and $C_1$-$C_6$ alkyl; or $R^4$ and $R^{44}$, together with the carbon to which they are attached, form 4-12 membered heterocyclyl; wherein the 4-12 membered heterocyclyl is optionally substituted with one or more substituents independently selected from the group consisting of $OR^9$, and Cl;

$R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, OH, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^2$ $C_3$-$C_{11}$ cycloalkyl and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and $R^{25}$ and $R^{26}$, at each occurrence, are each independently hydrogen or $C_1$-$C_6$ alkyl.

Exemplary compounds of Formula (II) include, but are not limited to:

Examples 4; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; I-20; I-34; I-39; I-42; I-43; I-44; I-46; I-47; I-48; I-49; I-50; I-51; I-52; I-53; I-54; I-55; I-56; I-57; I-58; I-59; I-60; I-61; I-62; I-63; I-64; I-65; I-66; I-67; I-68; I-69; I-70; I-71; I-72; I-73; I-74; I-75; I-76; I-77; I-78; I-79; I-80; I-81; I-82; I-83; I-84; I-85; I-86; I-87; I-88; I-89; I-90; I-91; I-92; I-93; I-94; I-95; I-96; I-97; I-98; I-99; I-100; I-101; I-102; I-103; I-104; I-105; I-106; I-107; I-108; I-109; I-110; I-111; I-112; I-113; I-114; I-115; I-116; I-117; I-118; I-119; I-120; I-121; I-123; I-124; I-125; I-126; I-127; I-128; I-129; I-130; I-131; I-132; I-133; I-134; I-135; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-168; I-169; I-170; I-171; I-172; I-174; I-175; I-176; I-177; I-178; I-179; I-180; I-181; I-182; I-183; I-184; I-185; I-186; I-187; I-188; I-189; I-190; I-191; I-192; I-193; I-194; I-195; I-196; I-197; I-198; I-199; I-200; I-201; I-202; I-204; I-205; I-206; I-207; I-208; I-209; I-210; I-211; I-212; I-213; I-214; I-215; I-216; I-217; I-218; I-219; I-220; I-221; I-222; I-223; I-224; I-225; I-226; I-227; I-228; I-229; I-230; I-231; I-232; I-233; I-234; I-235; I-236; I-237; I-238; I-239; I-240; I-241; I-242; I-243; I-244; I-245; I-246; I-247; I-248; I-249; I-250; I-251; I-252; I-253; I-254; I-255; I-256; I-257; I-258; I-259; I-260; I-261; I-262; I-263; I-264; I-265; I-266; I-267; I-268; I-269; I-270; I-271; I-272; I-273; I-274; I-275; I-276; I-277; I-278; I-279; I-280; I-281; I-282; I-283; I-284; I-285; I-286; I-287; I-288; I-289; I-290; I-291; I-292; I-293; I-294; I-295; I-296; I-297; I-298; I-299; I-309; I-310; II-54; II-62; II-63; II-65; II-81; II-83; II-84; II-87; II-91; II-92; II-93; II-94; II-95; II-96; II-97; II-98; II-99; II-100; II-101; II-102; II-103; II-104; II-105; II-106;

II-107; II-108; II-109; II-110; II-111; II-112; II-113; II-114; II-115; II-116; II-117; II-118; II-119; II-120; II-121; II-122; II-123; II-124; II-125; II-126; II-127; II-128; II-129; II-130; II-131; II-132; II-133; II-134; II-135; II-136; II-137; II-138; II-139; II-140; II-141; II-144; II-145; II-146; II-147; II-148; II-149; II-150; II-152; II-153; II-154; II-155; II-156; II-157; II-158; II-159; II-160; II-161; II-162; II-163; II-164; II-165; II-166; II-167; II-168; II-169; II-170; II-171; II-172; II-173; II-174; II-175; II-176; II-177; II-178; II-179; II-180; II-181; II-182; II-183; II-184; II-185; II-186; II-187; II-188; II-189; II-190; II-191; II-192; II-193; II-194; II-195; II-196; II-197; II-198; II-199; II-200; II-201; II-202; II-203; II-204; II-205; II-206; II-207; II-208; II-209; II-210; II-211; II-212; II-213; II-214; II-215; II-216; II-217; II-218; II-219; II-220; II-221; II-222; II-223; II-224; II-225; II-226; II-227; II-228; II-229; II-230; II-231; II-232; II-233; II-234; II-235; II-236; II-237; II-238; II-239; II-240; II-241; II-242; II-243; II-244; II-245; II-246; II-247; II-248; II-249; II-250; II-251; II-252; II-253; II-254; II-255; II-256; II-257; II-258; II-259; II-260; II-261; II-262; II-263; II-264; II-265; II-266; II-267; II-268; II-269; II-270; II-271; II-272; II-273; II-274; II-275; II-276; II-277; II-278; II-279; II-280; II-281; II-282; II-283; II-284; II-285; II-286; II-287; II-288; II-289; II-290; II-291; II-292; II-293; II-294; II-295; II-296; II-297; II-298; II-299; II-300; II-301; II-302; II-303; II-304; II-305; II-306; II-307; II-308; II-309; II-310; II-311; II-312; II-313; II-314; II-315; II-316; II-317; II-318; II-319; II-320; II-321; II-322; II-323; II-324; II-325; II-326; II-327; II-328; II-329; II-330; II-331; II-332; II-333; II-334; II-335; II-336; II-337; II-339; II-340; II-341; II-342; II-343; II-344; II-345; II-346; II-347; II-348; II-349; II-350; II-351; II-352; II-353; II-354; II-355; II-356; II-357; II-358; II-359; II-360; II-361; II-362; II-363; II-364; II-365; II-366; II-367; II-368; II-369; II-370; II-371; II-372; II-373; II-374; II-375; II-376; II-377; II-378; II-379; II-380; II-381; II-382; II-383; II-384; II-385; II-386; II-387; II-388; II-389; II-390; II-391; II-392; II-394; II-396; II-397; II-398; II-399; II-400; II-401; II-402; II-403; II-404; II-405; II-406; II-407; II-408; II-409; II-410; II-411; II-414; II-415; II-416; II-417; II-418; II-419; II-420; II-421; II-422; II-423; II-424; II-425; II-426; II-427; II-428; II-429; II-430; II-431; II-432; II-433; II-434; II-435; II-436; II-437; II-438; II-439; II-440; II-441; II-442; II-443; II-444; II-445; II-446; II-447; II-448; II-449; II-450; II-451; II-452; II-453; II-454; II-455; II-456; II-457; II-458; II-459; II-460; II-461; II-462; II-463; II-464; II-465; II-466; II-467; II-468; II-469; II-470; II-471; II-472; II-473; II-474; II-475; II-476; II-477; II-478; II-479; II-480; II-481; II-482; II-483; II-484; II-485; II-486; II-487; II-488; II-489; II-490; II-491; II-492; II-493; II-494; II-495; II-496; II-497; II-498; II-499; II-500; II-501; II-502; II-503; II-504; II-505; II-506; II-507; II-508; II-509; II-510; II-511; II-512; II-513; II-514; II-515; II-516; II-517; II-518; II-519; II-520; II-521; II-522; II-523; II-524; II-525; II-526; II-527; II-528; II-529; II-530; II-531; II-532; II-533; II-534; II-535; II-536; II-537; II-538; II-539; II-540; II-541; II-542; II-543; II-544; II-545; II-546; II-547; II-548; II-549; II-550; II-551; II-552; II-553; II-557; II-558; II-559; II-560; II-561; II-562; II-563; II-564; II-565; II-566; II-567; II-568; II-569; II-570; II-571; II-572; II-573; II-574; II-575; II-576; II-577; II-578; II-579; II-580; II-581; II-582; II-583; II-584; II-585; II-586; II-587; II-588; II-589; II-590; II-591; II-592; II-593; II-594; II-595; II-596; II-597; II-598; II-599; II-600; III-78; III-100; III-103; III-118; III-119; III-120; III-121; III-122; III-123; III-124; III-125; III-126; III-127; III-128; III-129; III-130; III-131; III-132; III-133; III-134; III-135; III-136; III-137; III-138; III-139; III-140; III-141; III-142; III-144; III-145; III-146; III-147; III-148; III-149; III-150; III-151; III-152; III-153; III-154; III-155; III-156; III-157; III-158; III-159; III-160; III-161; III-162; III-163; III-164; III-166; III-167; III-168; III-169; III-170; III-171; III-172; III-173; III-174; III-175; III-176; III-177; III-178; III-179; III-180; III-181; III-182; III-183; III-184; III-185; III-186; III-187; III-188; III-189; III-190; III-191; III-192; III-193; III-194; III-195; III-196; III-197; III-198; III-200; III-201; III-202; III-203; III-204; II-205; III-206; III-207; III-208; III-209; III-210; III-211; III-212; III-213; III-214; III-215; III-216; III-217; III-218; III-219; III-220; III-221; III-222; III-223; III-224; III-225; III-226; III-227; III-228; III-229; III-230; III-231; III-232; III-233; III-234; III-235; III-237; and pharmaceutically acceptable salts thereof.

Formula (III)

One embodiment pertains to compounds of Formula (III),

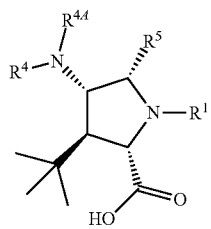

(III)

wherein
R$^1$ is selected from the group consisting of SO$_2$R$^6$, C(O)R$^6$, C(O)OR$^6$, and C(O)NR$^7$R$^8$;
R$^4$ is selected from the group consisting of L$^1$-C$_6$-C$_{10}$ aryl, L$^1$-5-11 membered heteroaryl, L-4-12 membered heterocyclyl, L$^1$-C$_3$-C$_{11}$ cycloalkyl, and L$^1$-C$_4$-C$_{11}$ cycloalkenyl; wherein the R$^4$ C$_6$-C$_{10}$ aryl, 5-11 membered heteroaryl, 4-12 membered heterocyclyl, C$_3$-C$_{11}$ cycloalkyl, and C$_4$-C$_{11}$ cycloalkenyl are optionally substituted with one or more substituents independently selected from the group consisting of R$^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; wherein L$^1$ is absent, or is selected from the group consisting of C$_1$-C$_6$ alkylene, C$_2$-C$_6$ alkenylene, C$_2$-C$_6$ alkynylene, and C$_1$-C$_6$ alkylene-O—; wherein the L$^1$ C$_1$-C$_6$ alkylene, C$_2$-C$_6$ alkenylene, and C$_2$-C$_6$ alkynylene, alone or as part of a group, are optionally substituted with one or more substituents independently selected from the group consisting of C$_1$-C$_6$ alkoxy, OH, and oxo; and
R$^{4A}$ is selected from the group consisting of hydrogen, C$_1$-C$_6$ alkyl, and C$_1$-C$_6$ haloalkyl; or
R$^4$ and R$^{4A}$, together with the carbon to which they are attached, form 4-12 membered heterocyclyl; wherein the 4-12 membered heterocyclyl is optionally substituted with one or more substituents independently selected from the group consisting of R$^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I;
R$^5$ is selected from the group consisting of C$_6$-C$_{10}$ membered aryl, 5-11 membered heteroaryl, 4-6 membered monocyclic heterocycle fused to a phenyl group, C$_3$-C$_{11}$ cycloalkyl, and C$_4$-C$_{11}$ cycloalkenyl; wherein the R$^5$ C$_6$-C$_{10}$ membered aryl, 5-11 membered heteroaryl, 4-6 membered monocyclic heterocycle fused to a phenyl group, C$_3$-C$_{11}$ cycloalkyl, and C$_4$-C$_{11}$ cycloalkenyl are optionally substituted with one or more substituents independently selected from the group consisting of R$^{12}$, OR$^{12}$, NR$^{13}$R$^{14}$, OH, oxo, CN, NO$_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

Another embodiment pertains to compounds of Formula (III), wherein $R^1$ is selected from the group consisting of $SO_2R^6$, $C(O)R^6$, $C(O)OR^6$, and $C(O)NR^7R^8$;

$R^4$ is selected from the group consisting of $(C_1$-$C_6$ alkylene$)_x$-$C_6$-$C_{10}$ aryl, $(C_1$-$C_6$ alkylene$)_x$-5-11 membered heteroaryl, $(C_1$-$C_6$ alkylene$)_x$-4-12 membered heterocyclyl, $(C_1$-$C_6$ alkylene$)_x$-$C_3$-$C_{11}$ cycloalkyl, and $(C_1$-$C_6$ alkylene$)_x$-$C_4$-$C_{11}$ cycloalkenyl; wherein the $R^4$ $C_6$-$C_{10}$ membered aryl of $(C_1$-$C_6$ alkylene$)_x$-$C_6$-$C_{10}$ membered aryl, the 5-11 membered heteroaryl of $(C_1$-$C_6$ alkylene$)_x$-5-11 membered heteroaryl, the 4-12 membered heterocyclyl of $(C_1$-$C_6$ alkylene$)_x$-4-12 membered heterocyclyl, the $C_3$-$C_{11}$ cycloalkyl of $(C_1$-$C_6$ alkylene$)_x$-$C_3$-$C_{11}$ cycloalkyl, and the $C_4$-$C_{11}$ cycloalkenyl of $(C_1$-$C_6$ alkylene$)_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I;

$R^{4A}$ is selected from the group consisting of hydrogen, $C_1$-$C_6$ alkyl, and $C_1$-$C_6$ haloalkyl;

$R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of R's, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, $OR^{21}$, $C(O)R^{21}$, $OC(O)R^{21}$, $C(O)OR^{21}$, $C(O)NR^{22}R^{23}$, $SO_2R^{21}$, $NR^{22}R^{23}$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, $OR^{24}$, $C(O)R^{24}$, $OC(O)R^{24}$, $C(O)OR^{24}$, $SO_2R^{24}$, $NR^{25}R^{26}$, OH, oxo, CN, $NO_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^9$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl;

$R^{25}$ and $R^{26}$, at each occurrence, are each independently hydrogen or $C_1$-$C_6$ alkyl; and x is 0 or 1.

In one embodiment of Formula (III), $R^1$ is selected from the group consisting of $SO_2R^6$, $C(O)R^6$, $C(O)OR^6$, and $C(O)NR^7R^8$. In another embodiment of Formula (III), $R^1$ is $C(O)R^6$ or $C(O)OR^6$. In another embodiment of Formula (III), $R^1$ is $SO_2R^6$. In another embodiment of Formula (III), $R^1$ is $C(O)R^6$. In another embodiment of Formula (III), $R^1$ is $C(O)OR^6$. In another embodiment of Formula (III), $R^1$ is $C(O)NR^7R^8$.

In one embodiment of Formula (III), $R^4$ is selected from the group consisting of $L^1$-$C_6$-$C_{10}$ aryl, L-5-11 membered heteroaryl, $L^1$-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4.4}$ is selected from the group consisting of hydrogen, $C_1$-$C_6$ alkyl, and $C_1$-$C_6$ haloalkyl. In another embodiment of Formula (III), $R^4$ is $L^1$ is absent, or is selected from the group consisting of $L^1$-$C_6$-$C_{10}$ aryl, $L^1$-5-11 membered heteroaryl, $L^1$-4-12 membered heterocyclyl, and L-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4.4}$ is selected from the group consisting of hydrogen, and $C_1$-$C_6$ alkyl. In another embodiment of Formula (III), $R^4$ is $L^1$-$C_6$-$C_{10}$ aryl; wherein the $R^4$ $C_6$-$C_{10}$ aryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4.4}$ is hydrogen. In another embodiment of Formula (III), $R^4$ is $L^1$-5-11 membered heteroaryl; wherein the $R^4$ 5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4.4}$ is hydrogen. In another embodiment of Formula (III), $R^4$ is $L^1$-4-12 membered heterocyclyl; wherein the $R^4$ 4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4.4}$ is hydrogen. In another embodiment of Formula (III), $R^4$ is $L^1$-$C_3$-$C_{11}$ cycloalkyl; wherein the $R^4$ $L^1$-$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is $C_1$-$C_6$ alkylene; and $R^{4.4}$ is hydrogen. In one embodiment of Formula (III), $R^4$ and $R^{4.4}$, together with the carbon to which they are attached, form 4-12 membered heterocyclyl; wherein the 4-12 membered heterocyclyl is optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I. In another embodiment of Formula (III), $R^4$ and $R^{4.4}$, together with the carbon to which they are attached, form 4-12 membered heterocyclyl; wherein the 4-12 membered heterocyclyl is optionally substituted with one or more substituents independently selected from the group consisting of $OR^9$, and Cl.

In one embodiment of Formula (III), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)-4-12 membered heterocyclyl, ($C_1$-$C_6$ alkylene)-$C_3$-$C_{11}$ cycloalkyl, and ($C_1$-$C_6$ alkylene)-$C_4$-$C_{11}$ cycloalkenyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, the $C_3$-$C_{11}$ cycloalkyl of ($C_1$-$C_6$ alkylene)$_x$-$C_3$-$C_{11}$ cycloalkyl, and the $C_4$-$C_{11}$cycloalkenyl of ($C_1$-$C_6$ alkylene)$_x$-$C_4$-$C_{11}$ cycloalkenyl are optionally substituted with one or more substituents independently selected from the group consisting of $R^9$, $OR^9$, $C(O)OR^9$, $C(O)NR^{10}R^{11}$, $SR^9$, $NR^{10}R^{11}$, $Si(R^9)_3$, $SF_5$, $SO_2R^9$, OH, oxo, CN, $NO_2$, F, Cl, Br and I; $R^{4.4}$ is selected from the group consisting of hydrogen, $C_1$-$C_6$ alkyl, and $C_1$-$C_6$ haloalkyl; and x is 0 or 1. In another embodiment of Formula (III), $R^4$ is selected from the group consisting of ($C_1$-$C_6$ alkylene)$_x$-$C_6$-$C_{10}$ aryl, ($C_1$-$C_6$ alkylene)$_x$-5-11 membered heteroaryl, ($C_1$-$C_6$ alkylene)$_x$-4-12 membered heterocyclyl, and ($C_1$-$C_6$ alkylene)$_x$-$C_3$-$C_{11}$ cycloalkyl; wherein the $R^4$ $C_6$-$C_{10}$ membered aryl of ($C_1$-$C_6$ alkylene)$_x$-$C_6$-$C_{10}$ membered aryl, the 5-11 membered heteroaryl of ($C_1$-$C_6$ alkylene)$_x$-5-11 membered heteroaryl, the 4-12 membered heterocyclyl of ($C_1$-$C_6$ alkylene)$_x$-4-12 membered heterocyclyl, and the $C_3$-$C_{11}$ cycloalkyl of ($C_1$-$C_6$ alkylene)$_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4.4}$ is hydrogen; and x is 0 or 1. In another embodiment of Formula (III), $R^4$ is ($C_1$-$C_6$ alkylene)$_x$-$C_6$-$C_{10}$ aryl; wherein the $R^4$ ($C_1$-$C_6$ alkylene)$_x$-$C_6$-$C_{10}$ membered aryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4.4}$ is hydrogen; and x is 0 or 1.

In another embodiment of Formula (III), $R^4$ is ($C_1$-$C_6$ alkylene)$_x$-5-11 membered heteroaryl; wherein the $R^4$ ($C_1$-$C_6$ alkylene)$_x$-5-11 membered heteroaryl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4.4}$ is hydrogen; and x is 0 or 1. In another embodiment of Formula (III), $R^4$ is ($C_1$-$C_6$ alkylene)$_x$-4-12 membered heterocyclyl; wherein the $R^4$ ($C_1$-$C_6$ alkylene)$_x$-4-12 membered heterocyclyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4.4}$ is hydrogen; and x is 0 or 1. In another embodiment of Formula (III), $R^4$ is ($C_1$-$C_6$ alkylene)$_x$-$C_3$-$C_{11}$ cycloalkyl; wherein the $R^4$ ($C_1$-$C_6$ alkylene)$_x$-$C_3$-$C_{11}$ cycloalkyl is optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; $R^{4.4}$ is hydrogen; and x is 0 or 1.

In one embodiment of Formula (III), $R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$cycloalkenyl are optionally substituted with one or more substituents independently selected from the group consisting of $R^{12}$, $OR^{12}$, $NR^{13}R^{14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (III), $R^5$ is selected from the group consisting of $C_6$-$C_{10}$ membered aryl, 4-6 membered monocyclic heterocycle fused to a phenyl group, 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is selected from the group consisting of $C_6$-$C_{10}$ membered aryl, 4-6 membered monocyclic heterocycle fused to a phenyl group, and 5-11 membered heteroaryl; wherein the $R^5$ $C_6$-$C_{10}$ membered aryl, 4-6 membered monocyclic heterocycle fused to a phenyl group, and 5-11 membered heteroaryl are optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I; and $R^{13}$ and $R^{14}$, at each occurrence, are each independently $C_1$-$C_6$ alkyl.

In one embodiment of Formula (III), $R^5$ is selected from the group consisting of $C_6$-$C_{10}$ membered aryl, 5-11 membered heteroaryl, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, $C_3$-$C_{11}$ cycloalkyl, and $C_4$-$C_{11}$ cycloalkenyl are optionally substituted with one or more substituents independently selected from the group consisting of $R^{12}$, $OR^2$, $NR^{13R14}$, OH, oxo, CN, $NO_2$, F, Cl, Br and I; $R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_1$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently hydrogen or $C_1$-$C_6$ alkyl. In another embodiment of Formula (III), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I; and $R^{13}$ and $R^{14}$, at each occurrence, are each independently $C_1$-$C_6$ alkyl.

In another embodiment of Formula (III), $R^5$ is $C_6$-$C_{10}$ membered aryl; wherein the $R^5$ $C_6$-$C_{10}$ membered aryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is 4-6 membered monocyclic heterocycle fused to a phenyl group; wherein the $R^5$ 4-6 membered monocyclic heterocycle fused to a phenyl group is optionally substituted with one or more substituents independently selected from the group consisting of $R^{12}$, $OR^{12}$, $NR^{13}R^{14}$ OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is 5-11 membered heteroaryl; wherein the $R^5$ 5-11 membered heteroaryl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^{12}$ $C_3$-$C_{11}$ cycloalkyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, OH, F, Cl, Br and I; and $R^{13}$ and $R^{14}$, at each occurrence, are each independently $C_1$-$C_6$ alkyl.

In another embodiment of Formula (III), $R^5$ is phenyl, which is unsubstituted. In another embodiment of Formula (III), $R^5$ is phenyl; wherein the $R^5$ phenyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl. In another embodiment of Formula (III), $R^5$ is phenyl; which is substituted with one $R^{12}$; and $R^{12}$ is $C_1$-$C_6$ alkyl. In another embodiment of Formula (III), $R^5$ is phenyl; which is substituted with one $R^{12}$; and $R^{12}$ is $CH_3$ or $CH(CH_3)_2$. In another embodiment of Formula (III), $R^5$ is pyridinyl; which is substituted with one or more substituents independently selected from the group consisting of $R^{12}$, $OR^{12}$, and $NR^{13}R^{14}$; $R^{12}$ is independently $C_1$-$C_6$ alkyl; and $R^{13}$ and $R^{14}$, at each occurrence, are each independently $C_1$-$C_6$ alkyl. In another embodiment of Formula (III), $R^5$ is pyridinyl; which is substituted with one or more substituents independently selected from the group consisting of $R^{12}$, $OR^{12}$, and $NR^{13}R^{14}$; $R^{12}$ is independently $CH_3$ or $CH(CH_3)_2$; and $R^{13}$ and $R^{14}$, at each occurrence, are each independently $CH_3$. In another embodiment of Formula (III), $R^5$ is pyridinyl; wherein the $R^5$ pyridinyl is optionally substituted with one or more substituents independently selected from the group consisting of $R^{12}$, $OR^{12}$, $NR^{13}R^{14}$, OH, F, Cl, and Br; $R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and $R^{13}$ and $R^{14}$, at each occurrence, are each independently $C_1$-$C_6$ alkyl.

In one embodiment of Formula (III), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, $OR^{15}$, $SR^{15}$, $NR^{16}R^{17}$, OH, CN, $NO_2$, F, Cl, Br and I; wherein the $R^6$ 6-10 membered aryl, 5-11 membered heteroaryl, $C_3$-$C_1$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $OC(O)R^{18}$, $C(O)OR^{18}$, $SO_2R^{18}$, $NR^{19}R^{20}$, OH, oxo, CN, $NO_2$, F, Cl, Br and I; $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I; $R^{16}$ and $R^{17}$, at each occurrence, are each independently hydrogen or $C_1$-$C_6$ alkyl; and $R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (III), $R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl is optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_1$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; $R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (III), $R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$ $SR^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl. In another embodiment of Formula (III), $R^6$ is $C_1$-$C_6$ alkyl; wherein the $R^6$ $C_1$-$C_6$ alkyl is substituted with one $R^{15}$; and $R^{15}$, at each occurrence, is independently 6-10 membered aryl. In another embodiment of Formula (III), $R^6$ is $C_2$ alkyl; wherein the $R^6$ $C_2$ alkyl is substituted with one $R^{15}$; and $R^{15}$, at each occurrence, is independently phenyl. In another embodiment of Formula (III), $R^6$ is $C_1$-$C_6$ alkyl; wherein the $R^6$ $C_1$-$C_6$ alkyl is unsubstituted. In another embodiment of Formula (III), $R^6$ is —$CH_3$. In another embodiment of Formula (III), $R^6$ is —$CH(CH_3)_2$. In one embodiment of Formula (III), $R^6$ is 4-12 membered heterocyclyl; wherein the $R^6$ 4-12 membered heterocyclyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (III), $R^6$ is 4-12 membered heterocyclyl; wherein the $R^6$ 4-12 membered heterocyclyl is unsubstituted. In another embodiment of Formula (III), $R^6$ is tetrahydrofuranyl. In another embodiment of Formula (III), $R^6$ is tetrahydropyranyl. In one embodiment of Formula (III), $R^6$ is $C_3$-$C_{11}$ cycloalkyl; wherein the $R^6$ $C_3$-$C_{11}$ cycloalkyl is optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl. In another embodiment of Formula (III), $R^6$ is $C_3$-$C_{11}$ cycloalkyl; wherein the $R^6$ $C_3$-$C_{11}$ cycloalkyl is optionally substituted with one or more F. In another embodiment of Formula (III), $R^6$ is $C_3$-$C_{11}$ cycloalkyl; wherein the $C_3$-$C_{11}$ cycloalkyl is unsubstituted. In another embodiment of Formula (III), $R^6$ is cyclohexyl; wherein the $R^6$ cyclohexyl is substituted with two F. In another embodiment of Formula (III), $R^6$ is cyclopentyl. In another embodiment of Formula (III), $R^6$ is cyclohexyl.

In one embodiment of Formula (III), $R^1$ is C(O)O$R^6$; $R^6$ is $C_1$-$C_6$ alkyl; wherein the $R^6$ $C_1$-$C_6$ alkyl is optionally substituted with one or more substituents independently selected from the group consisting of $R^{15}$, O$R^{15}$, S$R^{15}$, OH, and F; and $R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_1$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl.

In one embodiment of Formula (III), $R^1$ is C(O)O$R^6$; and $R^6$ is $C_1$-$C_6$ alkyl; wherein the $R^6$ is unsubstituted $C_1$-$C_6$ alkyl.

In one embodiment of Formula (III), $R^1$ is C(O)O$R^6$; $R^6$ is 4-12 membered heterocyclyl; wherein the $R^6$ 4-12 membered heterocyclyl is optionally substituted with one or more substituents independently selected from the group consisting of $R^{18}$, O$R^{18}$, C(O)$R^{18}$, C(O)O$R^{18}$, SO$_2R^{18}$, OH, oxo, CN, F, and Cl; and $R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_1$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl.

In one embodiment of Formula (III), $R^1$ is C(O)$R^6$; and $R^6$ is 4-12 membered heterocyclyl; wherein the $R^6$ 4-12 membered heterocyclyl is unsubstituted.

In one embodiment of Formula (III), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, O$R^{21}$, C(O)$R^{21}$, OC(O)$R^{21}$, C(O)O$R^{21}$, C(O)N$R^{22}R^{23}$, SO$_2R^{21}$, N$R^{22}R^{23}$, OH, oxo, CN, NO$_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, O$R^{24}$, C(O)$R^{24}$, OC(O)$R^{24}$, C(O)O$R^{24}$, SO$_2R^{24}$, N$R^{25}R^{26}$, OH, oxo, CN, NO$_2$, F, Cl, Br and I; $R^{21}$ at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, NO$_2$, F, Cl, Br and I; $R^{22}$ and $R^{23}$, at each occurrence, are each independently hydrogen or $C_1$-$C_6$ alkyl; $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_1$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl. In another embodiment of Formula (III), $R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, O$R^{21}$, C(O)O$R^{21}$, N$R^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, O$R^{24}$, CN, F, and Cl; $R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl, and $C_3$-$C_{11}$ cycloalkyl is optionally substituted with one or more CN; $R^{22}$ and $R^{23}$, at each occurrence, are each independently $C_1$-$C_6$ alkyl; and $R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl.

In one embodiment of Formula (III), $R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br, and I. In another embodiment of Formula (III), $R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy.

In one embodiment of Formula (III), $R^4$ is ($C_1$-$C_6$ alkylene)$_x$-$C_6$-$C_{10}$ aryl; wherein the $R^4$ ($C_1$-$C_6$ alkylene)$_x$-$C_6$-$C_{10}$ membered aryl is optionally substituted with one or more substituents independently selected from the group consisting of $R^9$ and O$R^9$; $R^{4A}$ is hydrogen; x is 0 or 1; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl. In one embodiment of Formula (III), $R^4$ is $L^1$-$C_6$-$C_{10}$ aryl; wherein the $R^4$ $C_6$-$C_{10}$ membered aryl is optionally substituted with one or more substituents independently selected from the group consisting of $R^9$ and O$R^9$; wherein $L^1$ is absent, or is $C_1$-$C_6$ alkylene; $R^{4A}$ is hydrogen; and $R^9$, at each occurrence, is independently selected from the group consisting of $C_1$-$C_6$ alkyl and $C_3$-$C_{11}$ cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (III), $R^4$ is $CH_2$-phenyl; wherein the $R^4$ $CH_2$-phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (III), $R^4$ is phenyl; wherein the $R^4$ phenyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In another embodiment of Formula (III), $R^4$ is $(C_1$-$C_6$ alkylene)$_x$-5-11 membered heteroaryl; wherein the $R^4$ $(C_1$-$C_6$ alkylene)$_x$-5-11 membered heteroaryl is optionally substituted with one or more substituents independently selected from the group consisting of $R^9$ and $OR^9$; $R^{4A}$ is hydrogen; x is 0 or 1; and $R^9$, at each occurrence, is independently selected from the group consisting of $C_1$-$C_6$ alkyl and $C_3$-$C_{11}$cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl. In another embodiment of Formula (III), $R^4$ is $L^1$-5-11 membered heteroaryl; wherein the $R^4$ 5-11 membered heteroaryl is optionally substituted with one or more substituents independently selected from the group consisting of $R^9$ and $OR^9$; $L^1$ is absent, or is $C_1$-$C_6$ alkylene; $R^{4A}$ is hydrogen; $R^9$, at each occurrence, is independently selected from the group consisting of $C_1$-$C_6$ alkyl and $C_3$-$C_{11}$cycloalkyl; wherein each $R^9$ $C_1$-$C_6$ alkyl is optionally substituted with one or more F; wherein each $R^9$ cycloalkyl is optionally substituted with one or more $R^{24}$; and $R^{24}$, at each occurrence, is independently $C_1$-$C_6$ alkyl.

In another embodiment of Formula (III), $R^4$ is $CH_2$-pyridinyl; wherein the $R^4$ $CH_2$— pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$. In another embodiment of Formula (III), $R^4$ is pyridinyl; wherein the $R^4$ pyridinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1] pentyl is optionally substituted with one or more $CH_3$. In another embodiment of Formula (III), $R^4$ is $CH_2$-quinolinyl; wherein the $R^4$ $CH_2$— quinolinyl is optionally substituted with one or more substituents independently selected from the group consisting of $R^9$ and $OR^9$; $R^{4A}$ is hydrogen; and $R^9$, at each occurrence, is independently selected from the group consisting of $CH_3$, $CF_3$, cyclopropyl, cyclobutyl, and bicyclo[1.1.1]pentyl; wherein each $R^9$ cyclopropyl, cyclobutyl, and bicyclo[1.1.1]pentyl is optionally substituted with one or more $CH_3$.

In one embodiment of Formula (III), $R^4$ is selected from the group consisting of

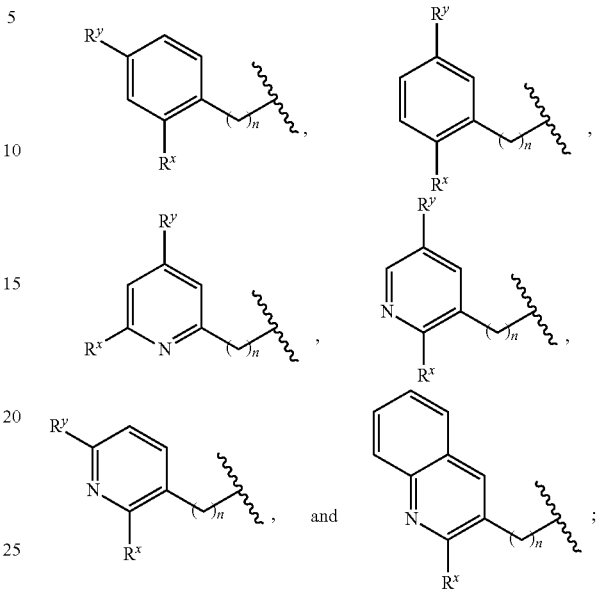

wherein $R^x$ is selected from the group consisting of $CH_3$ and $OCH_3$, and $R^y$ is selected from the group consisting of $CF_3$, $CH_3$, $C(CH_3)_3$, cyclopropyl, cyclobutyl substituted with $CH_3$, and bicyclo[1.1.1]pentyl; and n is 0 or 1.

One embodiment pertains to compounds of Formula (III),

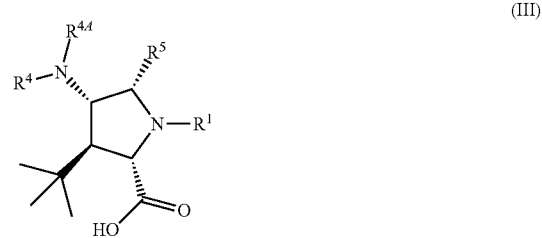

(III)

wherein
$R^1$ is selected from the group consisting of $SO_2R^6$, $C(O)R^6$, $C(O)OR^6$, and $C(O)NR^7R^8$;
$R^4$ is selected from the group consisting of $(C_1$-$C_6$ alkylene)$_x$-$C_6$-$C_{10}$ aryl, $(C_1$-$C_6$ alkylene)$_x$-5-11 membered heteroaryl, $(C_1$-$C_6$ alkylene)$_x$-4-12 membered heterocyclyl, and $(C_1$-$C_6$ alkylene)$_x$-$C_3$-$C_{11}$ cycloalkyl; wherein the $R^4$ $C_6$-$C_{10}$ membered aryl of $(C_1$-$C_6$ alkylene)$_x$-$C_6$-$C_{10}$ membered aryl, the 5-11 membered heteroaryl of $(C_1$-$C_6$ alkylene)$_x$-5-11 membered heteroaryl, the 4-12 membered heterocyclyl of $(C_1$-$C_6$ alkylene)-4-12 membered heterocyclyl, and the $C_3$-$C_{11}$ cycloalkyl of $(C_1$-$C_6$ alkylene)$_x$-$C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br;
$R^{4A}$ is hydrogen;
$R^5$ is selected from the group consisting of $C_6$-$C_{10}$ membered aryl and 5-11 membered heteroaryl; wherein the $R^5$ $C_6$-$C_{10}$ membered aryl and 5-11 membered heteroaryl are optionally substituted with one or more substituents independently selected from the group consisting of $R^{12}$, $OR^{12}$, $NR^{13}R^{14}$, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^5$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ membered aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and x is 0 or 1.

One embodiment pertains to compounds of Formula (III),

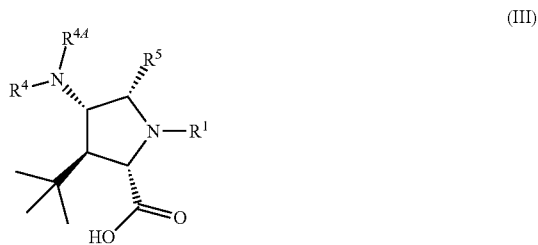

(III)

wherein $R^1$ is selected from the group consisting of $SO_2R^6$, $C(O)R^6$, $C(O)OR^6$, and $C(O)NR^7R^8$;

$R^4$ is selected from the group consisting of $L^1$-$C_6$-$C_{10}$ aryl, $L^1$-5-11 membered heteroaryl, $L^1$-4-12 membered heterocyclyl, and $L^1$-$C_3$-$C_{11}$ cycloalkyl; wherein the $R^4$ $C_6$-$C_{10}$ aryl, 5-11 membered heteroaryl, 4-12 membered heterocyclyl, and $C_3$-$C_{11}$ cycloalkyl are optionally substituted with one or more substituents independently selected from the group consisting of $R^9$, $OR^9$, $C(O)OR^9$, $SR^9$, $NR^{10}R^{11}$, $Si(R^9)_3$, $SF_5$, $SO_2R^9$, OH, CN, F, Cl, and Br; wherein $L^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the $L^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{44}$ is selected from the group consisting of hydrogen and $C_1$-$C_6$ alkyl; or $R^4$ and $R^{44}$, together with the carbon to which they are attached, form 4-12 membered heterocyclyl; wherein the 4-12 membered heterocyclyl is optionally substituted with one or more substituents independently selected from the group consisting of $OR^9$, and Cl;

$R^5$ is selected from the group consisting of $C_6$-$C_{10}$ membered aryl, 5-11 membered heteroaryl, and 4-6 membered monocyclic heterocycle fused to a phenyl group; wherein the $R^5$ $C_6$-$C_{10}$ membered aryl, 5-11 membered heteroaryl, and 4-6 membered monocyclic heterocycle fused to a phenyl group are optionally substituted with one or more substituents independently selected from the group consisting of $R^{12}$, $OR^{12}$, $NR^{13}R^{14}$, OH, F, Cl, and Br;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, $C_2$-$C_6$ alkynyl, are optionally substituted with one or more substituents independently selected from the group consisting of $R^{15}$, $OR^{15}$, $SR^{15}$, OH, and F; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^{18}$, $OR^{18}$, $C(O)R^{18}$, $C(O)OR^{18}$, $SO_2R^{18}$, OH, oxo, CN, F, and Cl;

$R^7$ and $R^8$ are each independently hydrogen or $C_1$-$C_6$ alkyl;

$R^9$, at each occurrence, is independently selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein each $R^9$ $C_1$-$C_6$ alkyl is optionally substituted with one or more substituents independently selected from the group consisting of $R^{21}$, $OR^{21}$, $C(O)OR^{21}$, $NR^{22}R^{23}$, OH, CN, and F; wherein each $R^9$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $R^{24}$, $OR^{24}$, CN, F, and Cl;

$R^{10}$ and $R^{11}$, at each occurrence, are each independently selected from the group consisting of hydrogen and 5-6 membered heteroaryl; wherein each $R^{10}$ and $R^{11}$ 5-6 membered heteroaryl is optionally substituted with one or more $C_1$-$C_6$ alkoxy;

$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; wherein each $R^2$ $C_3$-$C_{11}$ cycloalkyl and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently $C_1$-$C_6$ alkyl;

$R^{15}$, at each occurrence, is independently selected from the group consisting of $C_1$-$C_6$ alkyl, $C_2$-$C_6$ alkenyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, and 4-12 membered heterocyclyl is optionally substituted with one or more substituents independently selected from the group consisting of $C_1$-$C_6$ alkyl, OH, CN, F, and Cl;

$R^{18}$, at each occurrence, is independently selected from the group consisting of $C_1$-$C_6$ alkyl, $C_2$-$C_6$ alkenyl, $C_6$-$C_{10}$ membered aryl, 5-11 membered heteroaryl, $C_3$-$C_{11}$ cycloalkyl, and 4-12 membered heterocyclyl; wherein each $R^{18}$ $C_1$-$C_6$ alkyl and $C_6$-$C_{10}$ aryl is optionally substituted with one or more substituents independently selected from the group consisting of $C_1$-$C_6$ alkyl, $C_1$-$C_6$ alkoxy, 5-6 membered heteroaryl, CN, F, and Cl;

$R^{21}$, at each occurrence, is independently selected from the group consisting of $C_1$-$C_6$ alkyl, 6-10 membered aryl, and $C_3$-$C_{11}$ cycloalkyl; wherein each $R^{21}$ $C_1$-$C_6$ alkyl, 6-10 membered aryl and $C_3$-$C_{11}$ cycloalkyl is optionally substituted with CN;

$R^{22}$ and $R^{23}$, at each occurrence, are each independently $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, and $C_3$-$C_{11}$ cycloalkyl; and $R^{25}$ and $R^{26}$, at each occurrence, are each independently hydrogen or $C_1$-$C_6$ alkyl.

Exemplary compounds of Formula (III) include, but are not limited to:

Examples 4; 7; 8; 9; 10; 11; 12; 13; 14; 15; 16; 17; 18; 19; 20; 21; 23; 24; 25; 26; 27; 28; 29; 30; 31; 32; 33; 34; 35; 36; 37; 38; 39; 42; 43; 44; 45; 46; 47; 48; 49; 50; 51; 52; 53; 54; 55; 56; 57; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; I-20; I-34; I-39; I-42; I-43; I-44; I-46; I-47; I-48; I-49; I-50; I-51; I-52; I-53; I-54; I-55; I-56; I-57; I-58; I-59; I-60; I-64; I-65; I-66; I-67; I-68; I-69; I-70; I-71; I-72; I-73; I-74; I-75; I-76; I-77; I-78; I-79; I-80; I-81; I-82; I-83; I-84; I-85; I-86; I-88; I-89; I-90; I-91; I-92; I-93; I-94; I-95; I-96; I-97; I-98; I-99; I-100; I-101; I-102; I-103; I-104; I-105; I-106; I-107; I-108; I-109; I-110; I-111; I-112; I-113; I-114; I-119; I-120; I-121; I-123; I-124; I-125; I-126; I-127; I-128; I-129; I-130; I-131; I-132; I-133; I-134; I-135; I-136; I-137; I-138; I-139; I-140; I-141; I-142; I-143; I-144; I-145; I-146; I-147; I-148; I-149; I-150; I-151; I-152; I-153; I-154; I-155; I-156; I-157; I-158; I-159; I-160; I-161; I-162; I-163; I-164; I-165; I-166; I-167; I-168; I-169; I-170; I-171; I-172; I-175; I-176; I-177; I-178; I-179; I-180; I-181; I-182; I-183; I-184; I-185; I-186; I-187; I-188; I-189; I-190; I-191; I-192; I-193; I-194; I-195; I-196; I-197; I-198; I-199; I-200; I-201; I-202; I-204; I-205; I-206; I-207; I-208; I-209; I-210; I-212; I-213; I-214; I-215; I-216; I-217; I-218; I-219; I-221; I-222; I-223; I-224; I-225; I-226; I-227; I-228; I-229; I-230; I-231; I-232; I-233; I-234; I-235; I-236; I-237; I-238; I-239; I-240; I-241; I-242; I-243; I-244; I-245; I-246; I-247; I-248; I-249; I-250; I-251; I-252; I-253; I-254; I-255; I-256; I-257; I-258; I-259; I-260; I-261; I-262; I-263; I-264; I-265; I-266; I-267; I-268; I-269; I-270; I-271; I-272; I-273; I-274; I-275; I-276; I-277; I-278; I-279; I-280; I-281; I-282; I-283; I-284; I-285; I-286; I-287; I-288; I-289; I-290; I-291; I-292; I-293; I-294; I-295; I-296; I-297; I-298; I-299; I-300; I-301; I-302; I-303; I-304; I-305; I-306; I-307; I-308; I-309; I-310; II-54; II-62; II-63; II-65; II-81; II-83; II-84; II-87; II-91; II-92; II-93; II-94; II-95; II-96; II-97; II-98; II-99; II-100; II-101; II-102; II-103; II-104; II-105; II-106; II-107; II-108; II-109; II-110; II-111; II-112; II-113; II-114; II-115; II-116; II-117; II-118; II-119; II-120; II-121; II-122; II-123; II-124; II-125; II-126; II-127; II-128; II-129; II-130; II-131; II-132; II-133; II-134; II-135; II-136; II-137; II-138; II-139; II-140; II-141; II-144; II-145; II-146; II-147; II-148; II-149; II-152; II-153; II-154; II-155; II-156; II-157; II-158; II-159; II-160; II-161; II-162; II-163; II-164; II-165; II-166; II-167; II-168; II-169; II-170; II-171; II-172; II-173; II-174; II-175; II-176; II-177; II-178; II-179; II-180; II-181; II-182; II-183; II-184; II-185; II-186; II-187; II-188; II-189; II-190; II-191; II-192; II-193; II-194; II-195; II-196; II-197; II-198; II-199; II-200; II-201; II-202; II-203; II-204; II-205; II-206; II-207; II-208; II-209; II-210; II-211; II-212; II-213; II-214; II-215; II-216; II-217; II-218; II-219; II-220; II-221; II-222; II-223; II-224; II-225; II-226; II-227; II-228; II-229; II-230; II-231; II-232; II-233; II-234; II-235; II-236; II-237; II-238; II-239; II-240; II-241; II-242; II-243; II-244; II-245; II-246; II-249; II-250; II-259; II-260; II-261; II-262; II-263; II-264; II-265; II-266; II-267; II-268; II-269; II-270; II-271; II-272; II-273; II-274; II-275; II-276; II-277; II-278; II-279; II-280; II-281; II-282; II-283; II-284; II-285; II-286; II-287; II-288; II-289; II-290; II-291; II-292; II-293; II-296; II-297; II-298; II-299; II-300; II-301; II-302; II-303; II-304; II-305; II-306; II-307; II-308; II-309; II-310; II-311; II-312; II-313; II-314; II-315; II-316; II-317; II-318; II-319; II-320; II-321; II-322; II-323; II-324; II-325; II-326; II-327; II-328; II-329; II-330; II-331; II-332; II-333; II-334; II-335; II-336; II-337; II-339; II-340; II-341; II-342; II-343; II-344; II-345; II-346; II-347; II-348; II-349; II-350; II-351; II-352; II-353; II-354; II-355; II-356; II-357; II-358; II-359; II-360; II-361; II-362; II-363; II-364; II-365; II-366; II-367; II-368; II-369; II-370; II-371; II-372; II-373; II-374; II-375; II-376; II-377; II-378; II-379; II-380; II-381; II-382; II-383; II-384; II-385; II-386; II-387; II-388; II-389; II-390;

II-391; II-392; II-394; II-396; II-397; II-398; II-399; II-400; II-401; II-402; II-403; II-404; II-405; II-406; II-407; II-408; II-409; II-410; II-411; II-414; II-415; II-416; II-417; II-418; II-420; II-421; II-422; II-423; II-424; II-425; II-426; II-427; II-428; II-429; II-430; II-431; II-432; II-433; II-434; II-435; II-438; II-439; II-440; II-441; II-442; II-443; II-444; II-445; II-446; II-447; II-448; II-449; II-450; II-451; II-452; II-453; II-454; II-455; II-456; II-457; II-458; II-459; II-460; II-461; II-462; II-463; II-464; II-465; II-466; II-467; II-468; II-469; II-470; II-471; II-472; II-473; II-474; II-475; II-476; II-477; II-478; II-479; II-480; II-481; II-482; II-483; II-484; II-485; II-486; II-487; II-488; II-489; II-490; II-491; II-492; II-493; II-494; II-495; II-496; II-497; II-498; II-499; II-500; II-502; II-503; II-504; II-505; II-506; II-507; II-508; II-509; II-510; II-511; II-512; II-513; II-514; II-515; II-516; II-517; II-518; II-519; II-520; II-521; II-522; II-523; II-524; II-525; II-526; II-527; II-528; II-529; II-530; II-531; II-532; II-533; II-534; II-535; II-536; II-537; II-538; II-539; II-540; II-541; II-542; II-543; II-544; II-545; II-546; II-547; II-548; II-549; II-550; II-551; II-552; II-553; II-557; II-558; II-559; II-560; II-561; II-562; II-563; II-564; II-565; II-566; II-567; II-568; II-569; II-570; II-571; II-572; II-573; II-574; II-575; II-576; II-577; II-578; II-579; II-580; II-581; II-582; II-583; II-584; II-585; II-586; II-587; II-588; II-589; II-590; II-591; II-592; II-593; II-594; II-595; II-596; II-597; II-598; II-599; II-600; III-78; III-100; III-103; III-118; III-119; III-120; III-121; III-122; III-123; III-124; III-125; III-126; III-127; III-128; III-129; III-130; III-131; III-132; III-133; III-134; III-135; III-136; III-137; III-138; III-139; III-140; III-141; III-142; III-144; III-145; III-146; III-147; III-148; III-149; III-150; III-151; III-152; III-153; III-154; III-155; III-156; III-157; III-158; III-159; III-160; III-161; III-162; III-163; III-164; III-166; III-167; III-168; III-169; III-170; III-171; III-172; III-173; III-174; III-175; III-176; III-177; III-178; III-179; III-180; III-181; III-182; III-183; III-184; III-185; III-186; III-187; III-188; III-189; III-190; III-191; III-192; III-193; III-194; III-195; III-196; III-197; III-198; III-200; III-201; III-202; III-203; III-204; III-205; III-206; III-207; III-208; III-209; III-210; III-211; III-212; III-213; III-214; III-215; III-216; III-217; III-218; III-219; III-220; III-221; III-222; III-223; III-224; III-225; III-226; III-227; III-229; III-230; III-231; III-232; III-233; III-234; III-235; III-237; and pharmaceutically acceptable salts thereof.

Compounds of the invention are named by using Name 2015 Pack 2 naming algorithm by Advanced Chemical Development or Struct=Name naming algorithm as part of CHEMDRAW® ULTRA v. 12.0.2.1076 or Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by precipitation or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by precipitation or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula (I) for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula (I) may generally be prepared by conventional techniques known to those skilled in the art or by processes analogous to those described in the accompanying Examples using an appropriate isotopically-labelled reagents in place of the non-labelled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of Formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of Formula (I) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of Formula (I), or a pharmaceutically acceptable salt thereof together with a pharmaceutically acceptable carrier. The phrase "pharmaceutical composition" refers to a composition suitable for administration in medical or veterinary use.

The term "pharmaceutically acceptable carrier" as used herein, means a non-toxic, inert solid, semi-solid or liquid filler, diluent, encapsulating material or formulation auxiliary of any type.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of Formula (I), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention, or a pharmaceutically acceptable salt thereof, or pharmaceutical compositions comprising a compound of the invention, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV, V, and/or VI mutation.

One embodiment is directed to the use of a compound according to Formula (I) or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to Formula (I) or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to Formula (I) or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

In one embodiment, the present invention provides pharmaceutical compositions comprising a compound of the invention, or a pharmaceutically acceptable salt thereof, and one or more additional therapeutic agents. In one embodiment, the present invention provides pharmaceutical compositions comprising a compound of the invention, or a pharmaceutically acceptable salt thereof, one potentiator, and one or more additional correctors. In one embodiment, the present invention provides pharmaceutical compositions comprising a compound of the invention, and another therapeutic agent. In a particular embodiment, the other therapeutic agent is a cystic fibrosis treatment agent. In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents wherein the additional therapeutic agents are selected from the group consisting of CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In one embodiment, the present invention provides a method for treating cystic fibrosis in a subject comprising administering a compound of the invention, or a pharmaceutically acceptable salt thereof, and, and another therapeutic agent. In a particular embodiment, the other therapeutic agent is a cystic fibrosis treatment agent. In one embodiment, the present invention provides a method for treating cystic fibrosis in a subject comprising administering a therapeutically effective amount of a compound of the invention, or a pharmaceutically acceptable salt thereof. In a particular embodiment, the additional therapeutic agent(s) are one potentiator, and one or more additional correctors. In another embodiment, the additional therapeutic agent(s) is selected from the group consisting of CFTR modulators and CFTR amplifiers. In another embodiment, the other therapeutic agent(s) is a CFTR modulator. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or pharmaceutically acceptable salts thereof, that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjögren's syndrome. In one embodiment, the CFTR mediated disease is cystic fibrosis. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, GLPG2451, GLPG1837, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, WO2014/180562, WO2015018823, WO 2016193812 and U.S. application Ser. No. 15/502,892.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
GLPG1837;
GLP-2451;
PTI-808;
CTP-656;
NVS-QBW251;
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;

[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl) sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl) [3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl) [3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl) [3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl) [3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2851, GLPG2222, GLPG2665, GLPG2737, GLPG3221, PTI-801, VX-152, VX-440, VX-445, VX-659, FDL169, FDL304, FD2052160, and FD2035659. Examples of correctors are also disclosed in U.S. application Ser. Nos. 14/925,649, 14/926,727, 15/205,512, 15/287,922, 15/287,911, 15/287,922, 15/287,911, and 15/492,094.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
PTI-801;
VX-983;
GLPG2665;
GLPG2851;
GLPG2222;
GLPG2737;
GLPG3221;
VX-152;
VX-440;
VX-659;
VX-445;
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-J][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers are PTI130 and PTI-428. Examples of amplifiers are also disclosed in publications: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in publication: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

In one embodiment, the present invention provides pharmaceutical compositions comprising a compound of the invention, or a pharmaceutically acceptable salt thereof, and one or more additional therapeutic agents. In a particular embodiment, the additional therapeutic agents are selected from the group consisting of CFTR modulators and CFTR amplifiers. In a further embodiment, the additional therapeutic agents are CFTR modulators. In one embodiment, the present invention provides pharmaceutical compositions comprising a compound of the invention, or a pharmaceutically acceptable salt thereof, one potentiator, and one or more additional correctors.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (*Protective Groups in Organic Synthesis Third Edition*; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). Microwave heating was performed with a Biotage® Initiator.

NMR Spectra were recorded on a Bruker Advance 300 or 400 NMR spectrometer (300 MHz). Chemical shifts (δ ppm) for $^1$H NMR spectra were reported in parts per million (ppm) relative to tetramethylsilane (δ ppm 0.00) or the appropriate residual solvent peak, i.e. $CHCl_3$ (δ ppm 7.27), as internal reference. Multiplicities were given as singlet (s), doublet (d), triplet (t), quartet (q), quintuplet (quin), multiplet (m) and broad (br).

Electrospray MS spectra were obtained on Waters Acquity UPLC systems coupled to Waters SQD or SQD2 mass spectrometers. Columns used: Waters Acquity UPLC BEH C18 1.7 μm, 2.1 mm ID×50 mm L or Waters Acquity UPLC BEH C18 1.7 μm, 2.1 mm ID×30 mm L. The methods used acetonitrile/$H_2O$ gradients (both acetonitrile and $H_2O$ contained either 0.1% formic acid or 0.05% $NH_4OH$).

For the compounds purified by preparative chromatography, an XBridge™ Prep Guard Column, C18 19×10 mm 5 μm (Waters) with a XBridge™ Prep OBD Column, C18 30×100 mm 5 μm (Waters) and a gradient of 0.1% formic acid in water (A) and acetonitrile (B) at a flow rate of 50 mL/minute were used. Alternatively, a gradient of 0.1% diethylamine in water (A) and acetonitrile (B) at a flow rate of 50 mL/minute was used on the same references of guard column and column. After elution, the solvent was removed under vacuum to provide the dry product.

Racemic mixtures separation and determination of enantiomeric purity were performed on a Waters Alliance 2690 system with UV detection. Column used: Chiralpak® IA (4.6×250 mm, 5 μm). Solvents used: isopropyl alcohol and heptane.

Reverse Phase Purification Methods

Trifluoroacetic Acid Method

Samples were purified by preparative HPLC on a Phenomenex® Luna® C8(2) 5 um 100 Å AXIA™ column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A).

Prep LC/MS Method TFA6

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA7

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minutes (0-0.5 minutes 25% A, 0.5-8.0 minutes linear gradient 25-100% A, 8.0-9.0 minutes 100% A, 7.0-8.9 minutes 100% A, 9.0-9.1 minutes linear gradient 100-25% A, 9.1-10 minute 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA8

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 40 mL/minute (0-0.5 minute 35% A, 0.5-8.0 minute linear gradient 35-100% A, 8.0-9.0 minute 100% A, 7.0-8.9 minute 100% A, 9.0-9.1 minute linear gradient 100-35% A, 9.1-10 minute 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method TFA10

Samples were purified by reverse phase preparative HPLC on a Phenomenex® Luna® C8(2) 5 um 100 Å AXIA™ column (50 mm×21.2 mm). A gradient of acetonitrile (A) and 0.1% trifluoroacetic acid in water (B) was used, at a flow rate of 30 mL/minute (0-0.2 minute 5% A, 0.2-3.0 minute linear gradient 5-100% A, 4.1-4.5 minute 100-5% A, 4.5-5.0 minute 5% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA6

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 25% A, 0.5-8.0 minute linear gradient 25-100% A, 8.0-9.0 minute 100% A, 7.0-8.9 minute 100% A, 9.0-9.1 minute linear gradient 100-25% A, 9.1-10 minute 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Prep LC/MS Method AA8

Samples were purified by reverse phase preparative HPLC on a Phenomenex® Luna® C8(2) 5 um 100 Å AXIA™ column (50 mm×21.2 mm). A gradient of acetonitrile (A) and 0.1% ammonium acetate in water (B) was used, at a flow rate of 40 mL/minute (0-0.5 minute 35% A, 0.5-8.0 minute linear gradient 35-100% A, 8.0-9.0 minute 100% A, 7.0-8.9 minute 100% A, 9.0-9.1 minute linear gradient 100-35% A, 9.1-10 minute 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0.

Reverse Phase Purification, Ammonium Acetate Method

Samples were purified by preparative HPLC on a Phenomenex® Luna® C8(2) 5 um 100 Å AXIA™ column (30 mm×75 mm). A gradient of acetonitrile (A) and 10 mM ammonium acetate in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A).

Prep HPLC Purification, Ammonium Carbonate Method

The gradient was 40% increased to 70% B within 9.0 minutes (25.0 mL/minutes flow rate). Mobile phase A was water (0.01% $NH_3$)+10 mm ($NH_4HCO_3$), and mobile phase B was HPLC grade acetonitrile. The column used for the chromatography was X-bridge Prep C18 10 um OBD, 19*250 mm. Detection methods were diode array (DAD) and evaporative light scattering (ELSD) detection as well as positive/negative electrospray ionization.

Buffer for Reductive Amination

The buffer for reductive amination pH=4 buffer was prepared by dissolving 36 gram sodium acetate, and 48 gram acetic acid in 900 mL methyl alcohol.

Stereochemistry of final compounds was arbitrarily assigned in some cases, based on the order of elution and/or activity with respect to existing analogs.

List of abbreviations used in the experimental section:

| Abbreviation | Definition |
|---|---|
| DCM | dichloromethane |
| MeCN | acetonitrile |
| TFA | trifluoroacetic acid |
| THF | tetrahydrofuran |
| NMR | nuclear magnetic resonance |
| DMSO | dimethyl sulfoxide |
| LC/MS or LCMS | liquid chromatography - mass spectrometry |
| MeOH | methanol |
| s | singlet |
| br s | broad singlet |
| d | duplet or doublet |
| dd | double duplet or doublet of doublets |
| m | multiplet |
| min | minute |
| mL or ml | milliliter |
| μL | microliter |
| g | gram |
| mg | milligram |
| mmol | millimoles |
| HPLC | high pressure liquid chromatography |
| NBS | N-bromosuccinimide |
| ppm | parts per million |
| $Pd_2(dba)_3$ | tris(dibenzylideneacetone)dipalladium(0) |
| Xantphos | 4,5-bis(diphenylphosphino)-9,9-dimethylxanthene |
| MW | molecular weight |
| DBU | 1,8-diazabicycioundec-7-ene |
| EDC or EDCI | N-(3-dimethylaminopropyl)-N'-ethylcarbodiimide |
| HOBt | 1-hydroxybenzotriazole |

Synthetic Preparation of the Compounds of the Invention

Schemes

The compounds of the present disclosure can be better understood in connection with the following synthetic schemes and methods which illustrate a means by which the compounds can be prepared. The compounds of this disclosure can be prepared by a variety of synthetic procedures. Representative procedures are shown in, but are not limited to, Schemes 1-7.

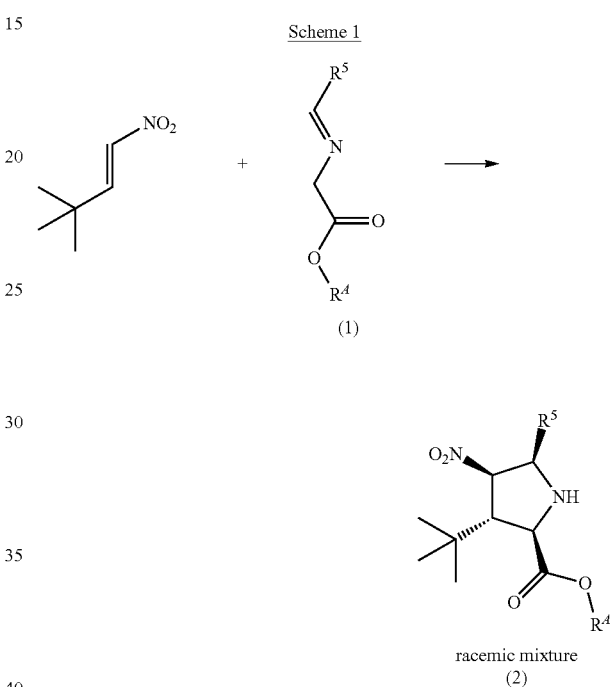

Scheme 1

As shown in Scheme 1, core compounds of formula (2) can be prepared from compounds of formula (1). Compounds of formula (1), wherein $R^4$ is typically $C_1$-$C_6$ alkyl and $R^5$ is as described herein, can be treated first with lithium bromide, followed by (E)-3, 3-dimethyl-1-nitrobut-1-ene in the presence of a base such as, but not limited to, 1,8-diazabicyclo[5.4.0]undec-7-ene, triethylamine, or potassium carbonate in a solvent such as but not limited to toluene, or tetrahydrofuran to provide a racemic mixture of compounds of formula (2). The reaction is typically performed at a reduced temperature, such as −78° C., before quenching with aqueous saturated ammonium chloride.

Alternatively, a mixture of compounds of formula (1) and (E)-3, 3-dimethyl-1-nitrobut-1-ene, wherein $R^4$ is typically $C_1$-$C_6$ alkyl and $R^5$ is as described herein, can be treated with acetyl(oxo)silver in the presence of molecular sieves and a base such as, but not limited to, 1,8-diazabicyclo[5.4.0] undec-7-ene, triethylamine, or potassium carbonate in a solvent such as but not limited to toluene or tetrahydrofuran to provide a racemic mixture of core compounds of formula (2). The reaction is typically performed in an ice bath before warming to room temperature and quenching with aqueous saturated aqueous ammonium chloride.

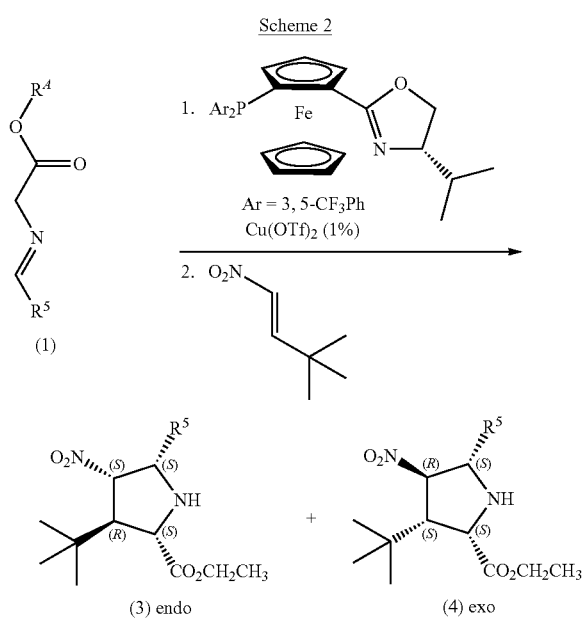

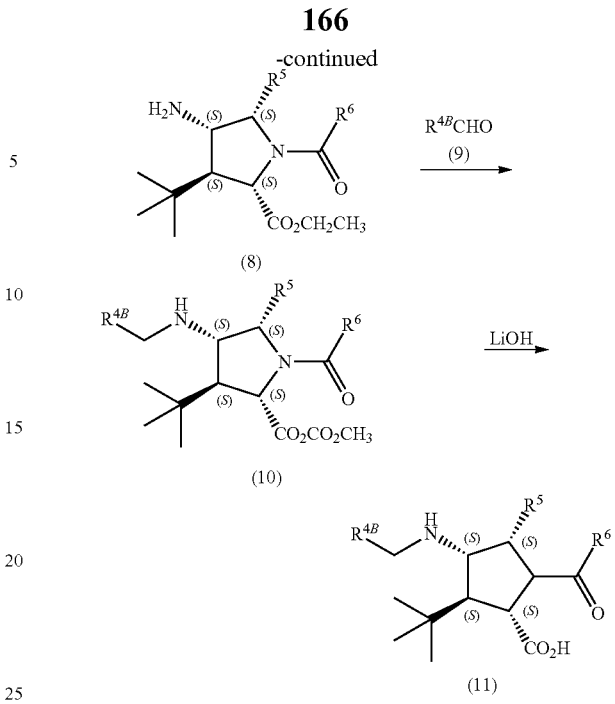

As shown in Scheme 2, core compounds of formula (3) and (4) can be prepared from compounds of formula (1). Compounds of formula (1), wherein $R^A$ is typically $C_1$-$C_6$ alkyl and $R^5$ is as described herein, can be added to a prepared mixture of (2-(bis(3,5-bis(trifluoromethyl)phenyl) phosphino)-3-((S)-4-isopropyl-4,5-dihydrooxazol-2-yl)cyclopenta-2,4-dien-1-yl)(cyclopenta-2,4-dien-1-yl)iron and copper (I) triflate dimer in a solvent such as, but not limited to, tetrahydrofuran, under an inert gas such as but not limited to argon or nitrogen, followed by the addition of (E)-3, 3-dimethyl-1-nitrobut-1-ene, and a base such as, but not limited to potassium tert-butoxide, to provide core compounds of formula (3) and (4). The reaction is typically performed at reduced temperature, such as but not limited to 0° C. Core compounds (3) and (4) may be obtained as a mixture or may be separated by precipitation or chromatography. Core compound (3) is typically the major isomer.

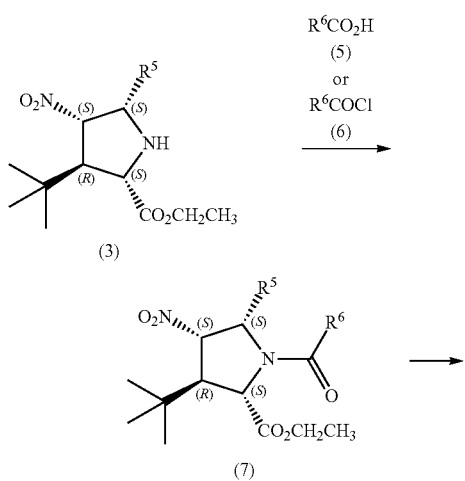

As shown in Scheme 3, compounds of formula (11) can be prepared from compounds of formula (3). Carboxylic acids of formula (5) can be coupled with amine cores of formula (3) to provide compounds of formula (7). Examples of conditions known to generate compounds of formula (7) from a mixture of a carboxylic acid and an amine include, but are not limited to, adding a coupling reagent such as, but not limited to, 1-chloro-N,N,2-trimethylprop-1-en-1-amine (Ghosez reagent), N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-yl-methylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4, 6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (3) optionally in the presence of a base such as a tertiary amine base such as but not limited to triethylamine or N,N-diisopropylethylamine or an aromatic base such as pyridine, at room temperature or heated in a solvent such as dichloromethane to provide compounds of formula (7).

Reduction of the nitro group in compounds of formula (7) to compounds of formula (8) can be accomplished by treating the former with zinc in acetic acid at an elevated temperature. The reaction is typically performed in a solvent such as, but not limited to ethyl acetate.

Alternatively, compounds of formula (8) can be prepared by treating compounds of formula (7) with hydrogen gas in the presence of a catalyst such as, but not limited to, Raney®-nickel. The reaction is typically performed at ambient temperature in a solvent such as, but not limited to water, tetrahydrofuran, or mixtures thereof.

Reductive amination of compounds of formula (8) to compounds of formula (10) can be accomplished via reaction with an aldehyde of formula (9), wherein $R^{4B}$ is a ring as described for $R^4$ of Formula (I), in the presence of a reducing agent such as, but not limited to sodium cyanoborohydride, or sodium triacetoxyborohydride. The reaction may be performed in the presence of acetic acid or zinc(II) chloride in a sodium acetate/acetic acid buffer, and is typically performed at ambient temperature in a solvent such as, but not limited to methanol, or dichloroethane.

Esters of formula (10) can be hydrolyzed in an aqueous hydroxide solution to provide acids of formula (11) which are representative of Formula (I). The reaction is typically performed in a solvent such as but not limited to methanol, tetrahydrofuran, or mixtures thereof, and may be performed at ambient temperature or an elevated temperature.

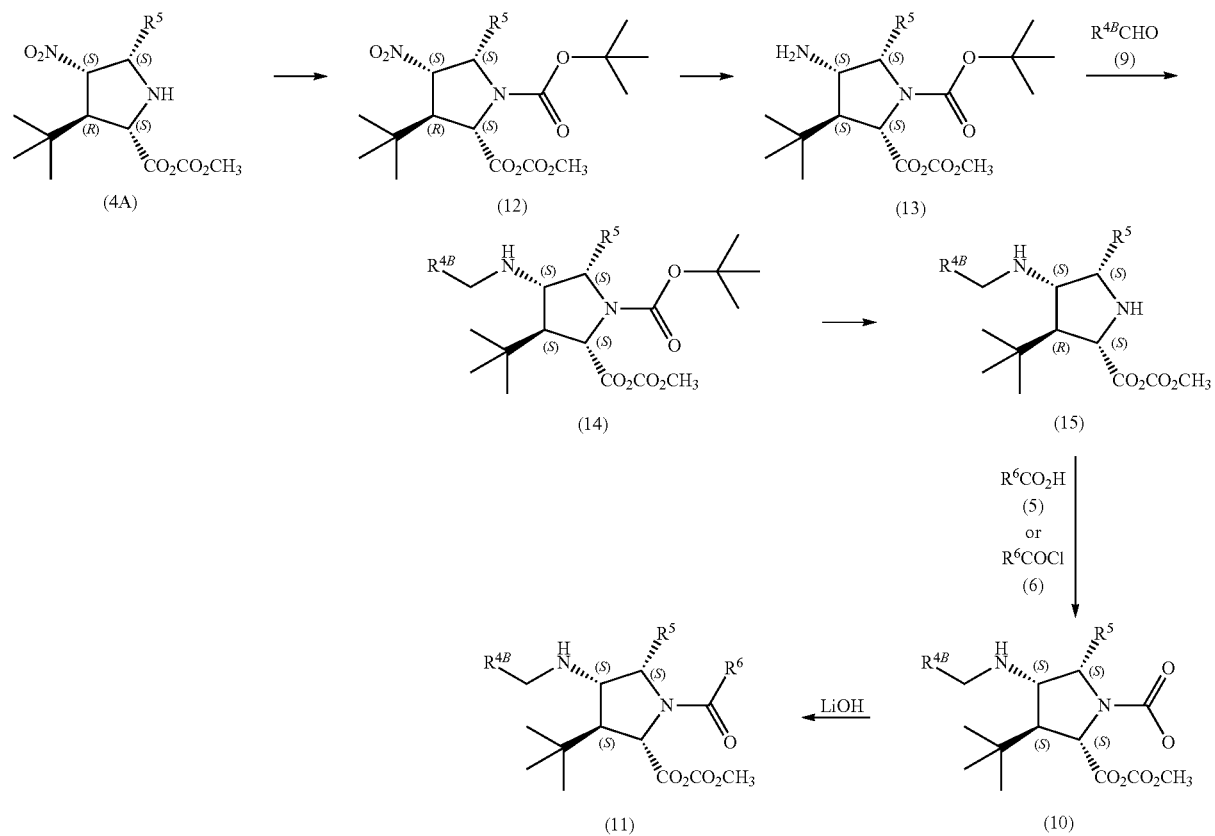

Scheme 4

As shown in Scheme 4, compounds of formula (11) can be prepared from compounds of formula (4A). Protection of the pyrrolidine nitrogen of compounds of formula (4A) to provide compounds of formula (12) can be accomplished by treating the former with di-tert-butyl dicarbonate. The reaction is typically performed at an elevated temperature in a solvent such as but not limited to tetrahydrofuran.

Reduction of the nitro group in compounds of formula (12) to compounds of formula (13) can be accomplished by treating the former with zinc in acetic acid at an elevated temperature. The reaction is typically performed in a solvent such as, but not limited to ethyl acetate.

Alternatively, compounds of formula (13) can be prepared by treating compounds of formula (12) with hydrogen gas in the presence of a catalyst such as, but not limited to, Raney®-Nickel. The reaction is typically performed at ambient temperature in a solvent such as, but not limited to water, tetrahydrofuran, or mixtures thereof.

Reductive amination of compounds of formula (13) to compounds of formula (14) can be accomplished via reaction with an aldehyde of formula (9), wherein $R^{4B}$ is a ring as described for $R^4$, in the presence of a reducing agent such as, but not limited to sodium cyanoborohydride. The reaction may be performed in the presence of acetic acid or zinc(II) chloride in a sodium acetate/acetic acid buffer, and is typically performed at ambient temperature in a solvent such as, but not limited to methanol.

Removal of the BOC protecting group in compounds of formula (14) to provide compounds of formula (15) can be accomplished by treating the former with an acid such as, but not limited to, trifluoroacetic acid. The reaction is typically performed at ambient temperature in a solvent such as, but not limited to, dichloromethane.

Carboxylic acids of formula (5) can be coupled with amines of formula (15) to provide compounds of formula (10). Examples of conditions known to generate compounds of formula (10) from a mixture of a carboxylic acid and an amine include, but are not limited to, adding a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino)pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (15) optionally in the presence of a base such as a tertiary amine base such as but not limited to triethylamine or N,N-diisopropylethylamine or an aromatic base such as pyridine, at room temperature or heated in a solvent such as dichloromethane to provide compounds of formula (10).

Esters of formula (10) can be hydrolyzed in an aqueous hydroxide solution to provide acids of formula (11) which are representative of Formula (I). The reaction is typically performed in a solvent such as but not limited to methanol, tetrahydrofuran, or mixtures thereof, and may be performed at ambient temperature or an elevated temperature.

Scheme 5

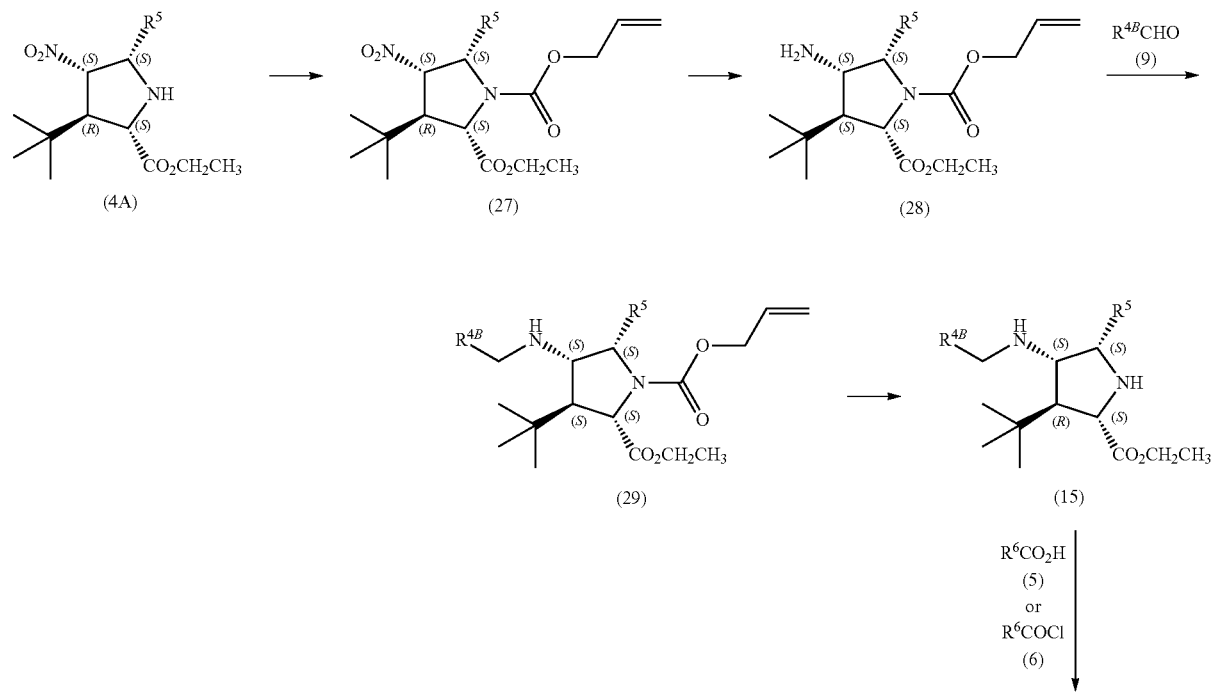

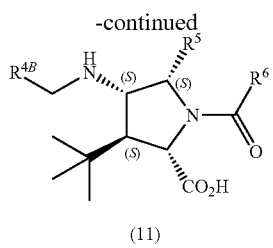 (11)

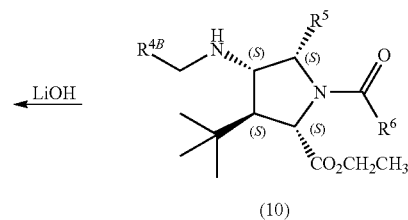 (10)

LiOH

As shown in Scheme 5, compounds of formula (11) can be prepared from compounds of formula (4A). Protection of the pyrrolidine nitrogen of compounds of formula (4A) to provide compounds of formula (27) can be accomplished by treating the former with allyl carbonochloridate in the presence of saturated sodium aqueous NaHCO$_3$ solution. The reaction is typically performed at ambient temperature in a solvent such as, but not limited to, toluene.

Reduction of the nitro group in compounds of formula (27) to compounds of formula (28) can be accomplished by treating the former with zinc in acetic acid at an elevated temperature. The reaction is typically performed in a solvent such as, but not limited to, ethyl acetate.

Alternatively, compounds of formula (28) can be prepared by treating compounds of formula (27) with hydrogen gas in the presence of a catalyst such as, but not limited to, Raney®-Nickel. The reaction is typically performed at ambient temperature in a solvent such as, but not limited to water, tetrahydrofuran, or mixtures thereof.

Removal of the allyl protecting group in compounds of formula (29) to provide compounds of formula (15) can be accomplished by treating the former with 1,3-dimethylpyrimidine-2,4,6(1H,3H,5H)-trione in the presence of tetrakis(triphenylphosphine)palladium(0). The reaction is typically performed at ambient temperature in a solvent such as, but not limited to, ethyl acetate, dichloromethane, or mixtures thereof.

Carboxylic acids of formula (5) can be coupled with amines of formula (15) to provide compounds of formula (10). Examples of conditions known to generate compounds of formula (10) from a mixture of a carboxylic acid and an amine include, but are not limited to, adding a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino)pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation.

Alternatively, carboxylic acids of formula (5) can be converted to the corresponding acid chlorides of formula (6) by reaction with thionyl chloride, PCl$_3$, PCl$_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides of formula (6) (or commercially available acid chlorides of formula (6)) can then reacted with core amines of formula (15) optionally in the presence of a base such as a tertiary amine base such as but not limited to triethylamine or N,N-diisopropylethylamine or an aromatic base such as pyridine, at room temperature or heated in a solvent such as dichloromethane to provide compounds of formula (10).

Esters of formula (10) can be hydrolyzed in an aqueous hydroxide solution to provide acids of formula (11) which are representative of Formula (I). The reaction is typically performed in a solvent such as but not limited to methanol, tetrahydrofuran, or mixtures thereof, and may be performed at ambient temperature or an elevated temperature.

Scheme 6

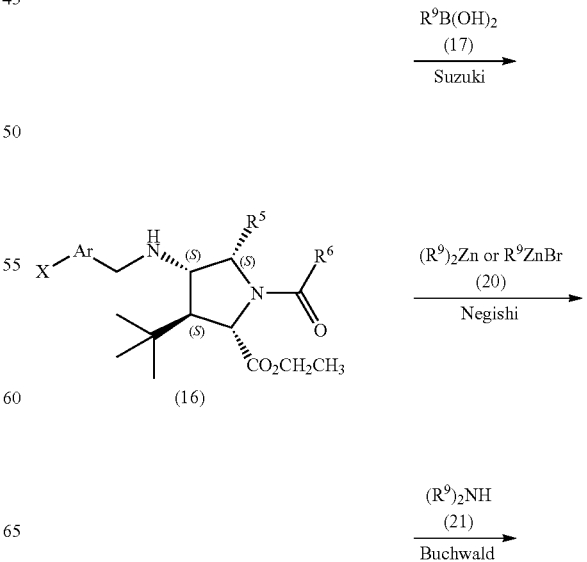

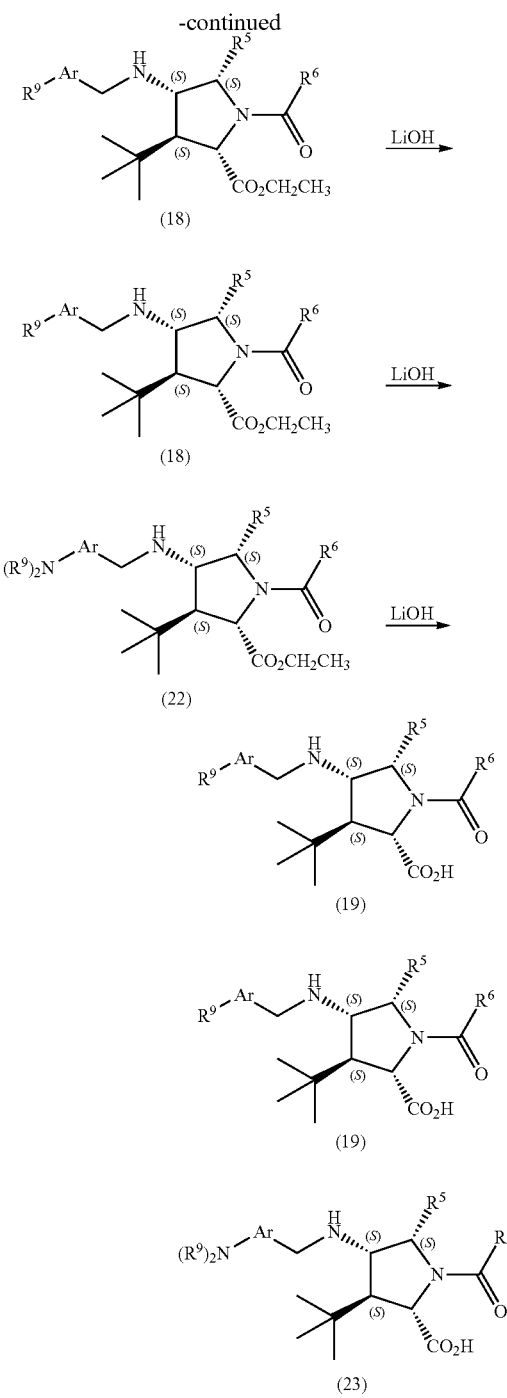

Scheme 6 depicts examples of ways to diversify the substituents on an aromatic ring (Ar) of the $R^4$ group. Compounds of formula (16), wherein X is I, Br, Cl or triflate and Ar is aryl or heteroaryl, can be prepared as described in Schemes 3 or 4. Compounds of formula (18) can be prepared by reacting compounds of formula (16) wherein X is I, Br, Cl or triflate with boronic acid compounds of formula (17), wherein $R^9$ is as described herein (or the boronic ester equivalents), under Suzuki coupling conditions known to those skilled in the art and widely available in the literature. The reaction typically requires the use of a base and a catalyst. Examples of bases include, but are not limited to, potassium carbonate, potassium t-butoxide, sodium carbonate, cesium carbonate, and cesium fluoride. Examples of catalysts include, but are not limited to, tetrakis(triphenylphosphine)palladium(0), [1,1'-bis(diphenylphosphino)ferrocene]dichloropalladium(II) dichloromethane, bis(triphenylphosphine)palladium(II) dichloride, and tris(dibenzylideneacetone)dipalladium(0). The reaction may be conducted in a solvent such as, but not limited to, water, dioxane, 1,2-dimethoxyethane, N,N-dimethylformamide, toluene, ethanol, tetrahydrofuran and the like or mixtures thereof. The reaction may be conducted at ambient or elevated temperatures, and optionally in a microwave oven. Esters of formula (18) can be hydrolyzed in an aqueous hydroxide solution to provide compounds of formula (19) which are representative of formula (I). The reaction is typically performed in a solvent such as, but not limited to, methanol, tetrahydrofuran, or mixtures thereof, and may be performed at ambient temperature or an elevated temperature. Compounds of formula (18) can be prepared by reacting compounds of formula (16) wherein X is I, Br, Cl or triflate with organozinc compounds of formula (20), wherein $R^9$ is as described herein, under Negishi coupling conditions known to those skilled in the art and widely available in the literature. The reaction typically requires the use of a palladium or nickel catalyst. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven. Esters of formula (18) can be hydrolyzed in an aqueous hydroxide solution to provide compounds of formula (19) which are representative of Formula (I). The reaction is typically performed in a solvent such as, but not limited to, methanol, tetrahydrofuran, or mixtures thereof, and may be performed at ambient temperature or an elevated temperature. Compounds of formula (22) can be prepared by reacting compounds of formula (16) wherein X is I, Br, Cl or triflate with amines compounds of formula (22), wherein $R^9$ is H or is as described herein, under Buchwald-Hartwig amination conditions known to those skilled in the art and widely available in the literature. The reaction typically requires the use of a base, catalyst, and optionally, a ligand. Examples of bases include, but are not limited to, potassium carbonate, potassium t-butoxide, sodium t-butoxide, sodium carbonate, cesium carbonate, and cesium fluoride. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), chloro-(2-dicyclohexylphosphino-2',6'-diisopropoxy-1,1'-biphenyl)[2-(2-aminoethyl)phenyl]palladium(II)-methyl-t-butyl ether adduct (RuPhos palladacycle), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. Examples of optional ligands include, but are not limited to, BINAP (2,2'-bis(diphenylphosphino)-1,1'-binaphthyl), DPPF (1,1'-bis(diphenylphosphino)ferrocene), and Xantphos (4,5-bis(diphenylphos-phino)-9,9-dimethylxanthene). The reaction may be conducted in a solvent such as, but not limited to, water, dioxane, 1-methyl-2-pyrrolidinone, N,N-dimethylacet-amide, dimethoxyethane, N,N-dimethylformamide, toluene, ethanol, tetrahydrofuran, and the like or mixtures thereof. The reaction may be conducted at ambient or elevated temperatures, and optionally in a microwave oven. Esters of formula (22) can be hydrolyzed in an aqueous hydroxide solution to provide compounds of formula (23) which are representative of Formula (I). The reaction is typically performed in a solvent such as, but not limited to, methanol, tetrahydrofuran, or mixtures thereof, and may be performed at ambient temperature or an elevated temperature.

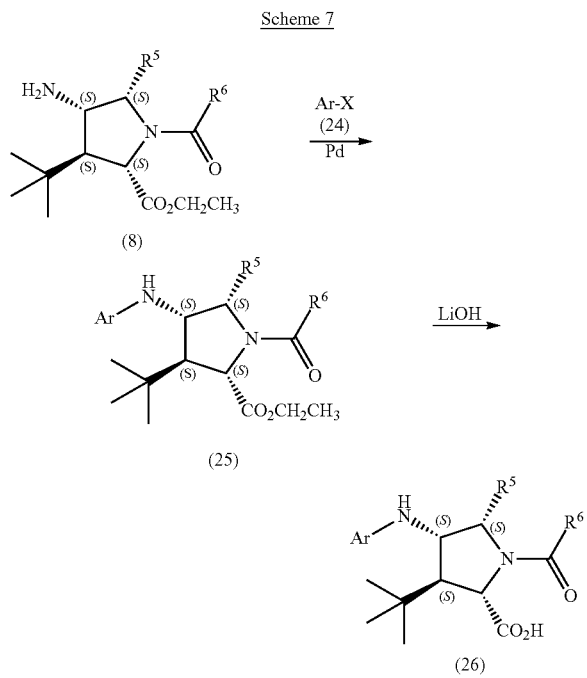

Scheme 7

Scheme 7 shows the preparation of compounds of formula (26) from compounds of formula (8). Compounds of formula (25) can be prepared by reacting compounds of formula (24) wherein X is I, Br, Cl or triflate, and Ar is aryl or heteroaryl, with amines of formula (8), under Buchwald-Hartwig amination conditions known to those skilled in the art and widely available in the literature. The reaction typically requires the use of a base, catalyst, and optionally, a ligand. Examples of bases include, but are not limited to, potassium carbonate, potassium t-butoxide, sodium t-butoxide, sodium carbonate, cesium carbonate, and cesium fluoride. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IP-entCl), chloro-(2-dicyclohexylphosphino-2',6'-diisopropoxy-1,1'-biphenyl)[2-(2-aminoethyl)phenyl]palladium (II)-methyl-t-butyl ether adduct (RuPhos palladacycle), tetrakis(triphenylphosphine)nickel(0), tetrakis(triphenylphosphine)palladium(0), bis(triphenylphosphine)palladium (II) dichloride, [1,1'-bis(diphenylphosphino)ferrocene]dichloropalladium(II) dichloromethane, tris (dibenzylideneacetone)dipalladium(0), and palladium(II) acetate. Examples of optional ligands include, but are not limited to, BINAP (2,2'-bis(diphenylphosphino)-1,1'-bi-naphthyl), DPPF (1,1'-bis(diphenylphosphino)ferrocene), and Xantphos (4,5-bis(diphenylphosphino)-9,9-dimethylxanthene). The reaction may be conducted in a solvent such as, but not limited to, water, dioxane, 1-methyl-2-pyrrolidinone, N,N-dimethylacetamide, dimethoxyethane, N,N-dimethylformamide, toluene, ethanol, tetrahydrofuran, and the like or mixtures thereof. The reaction may be conducted at ambient or elevated temperatures, and optionally in a microwave oven.

Esters of formula (25) can be hydrolyzed in an aqueous hydroxide solution to provide compounds of formula (26) which are representative of Formula (I). The reaction is typically performed in a solvent such as, but not limited to, methanol, tetrahydrofuran, or mixtures thereof, and may be performed at ambient temperature or an elevated temperature.

EXAMPLES

Catalyst and Intermediate Synthesis

Catalyst 1

(2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron The procedure for preparation of the chiral ligand was modified from Yan, X.-X., Peng, Q., Zhang, Y., Zhang, K., Hong, W., Hou, X.-L. and Wu, Y.-D., Angew. Chem., Int. Ed. 2006, 45 1979-1983.

Cyclopenta-2,4-dien-1-yl(3-((S)-4-isopropyl-4,5-dihydrooxazol-2-yl)cyclopenta-2,4-dien-1-yl)iron (515 mg, 1.733 mmol) was dissolved in 2-methyltetrahydrofuran (17 mL). The resulting solution was cooled to −78° C. in an acetone-dry ice bath, and tetramethylethylenediamine (0.340 mL, 2.253 mmol) was added, followed by dropwise addition of sec-butyllithium (1.485 mL, 2.080 mmol), maintaining an internal temperature <−70° C. After stirring for 30 minutes, the reaction mixture was treated with bis(3,5-bis(trifluoromethyl)phenyl)chlorophosphine (1110 mg, 2.253 mmol) in one portion. After stirring at −78° C. for 1 hour, the reaction flask was removed from the bath and warmed to ambient temperature before diluting with 20 mL of methyl tert-butyl ether and quenching with 10 mL of saturated aqueous ammonium chloride. The layers were separated, and the organic layer was washed with 10 mL of saturated aqueous ammonium chloride and 10 mL of brine, dried over sodium sulfate, filtered and concentrated. The crude material was purified via chromatography, eluting with isocratic 93:7 heptanes:methyl tert-butyl ether on an 80 g silica gel column for 20 minutes to provide 920 mg of the title compound. $^1$H NMR (300 MHz, CDCl$_3$) δ ppm 0.86 (d, J=6.6 Hz, 3H), 0.92 (d, J=6.3 Hz, 3H), 1.69-1.77 (m, 1H), 3.49-3.50 (m, 1H), 3.73-3.81 (m, 1H), 3.96 (t, J=7.8 Hz, 1H), 4.21-4.27 (m, 6H), 4.46-4.48 (m, 1H), 5.00-5.01 (m, 1H), 7.65 (d, J=6.3 Hz, 2H), 7.80 (s, 1H), 7.89 (d, J=6.0 Hz, 2H), 7.93 (s, 1H); MS (ESI+) m/z 754.0 (M+H)$^+$.

Intermediate 1

(E)-3,3-dimethyl-1-nitrobut-1-ene

Intermediate 1A 3,3-dimethyl-1-nitrobutan-2-ol

To a slurry of lithium aluminum hydride (0.881 g, 23.22 mmol) in dry tetrahydrofuran (140 mL), which had been stirred for 30 minutes at 0° C., was added dropwise nitromethane (70.9 g, 1161 mmol). After 30 minutes, pivaldehyde (20 g, 232 mmol) was added dropwise. The mixture was stirred at 0° C. for 5 hours, and quenched with 1 N aqueous HCl. The reaction mixture was poured into water, extracted with $CH_2Cl_2$ (2×250 mL), washed with brine (2×200 mL), dried over $Na_2SO_4$, filtered, and concentrated to provide the title compound (17 g, 107 mmol, 46.3% yield). LC-MS (ESI−) m/z=146.7 (M−H)$^-$.

Intermediate 1B (E)-3,3-dimethyl-1-nitrobut-1-ene

A solution of 3,3-dimethyl-1-nitrobutan-2-ol (10 g, 67.9 mmol) in dichloromethane (100 mL) was cooled to −10° C. under $N_2$, treated with 2,2,2-trifluoroacetic anhydride (15.70 g, 74.7 mmol), stirred at −15° C. for 5 minutes, and treated dropwise with triethylamine (20.84 mL, 149 mmol) keeping the bath at −15° C. during the addition. The mixture was stirred at 0° C. for 3 hours, treated with saturated aqueous $NH_4Cl$ solution (300 mL), and stirred for 5 minutes. The $CH_2Cl_2$ layer was isolated and the aqueous layer was extracted with $CH_2Cl_2$ (2×150 mL). The combined $CH_2Cl_2$ layers were dried ($Na_2SO_4$), filtered, and concentrated. The crude material was purified by column chromatography (ethyl acetate/petroleum ether=1/200) to provide the title compound (6.8 g, 48.4 mmol, 71.3% yield). $^1$H NMR (400 MHz, $CDCl_3$) δ ppm 7.19 (d, J=13.2 Hz, 1H), 6.83 (d, J=13.6 Hz, 1H), 1.09 (s, 9H).

Intermediate 2

2-(3-formyl-4-methoxyphenyl)-2-methylpropanenitrile

Intermediate 2A ((5-bromo-2-methoxybenzyl)oxy)(tert-butyl)dimethylsilane (5-Bromo-2-methoxyphenyl)methanol (1.89 g, 8.71 mmol) was dissolved in 25 mL of dichloromethane. Imidazole (0.711 g, 10.45 mmol) was added, followed by addition of tert-butyldimethylsilyl chloride (1.378 g, 9.14 mmol). After stirring at room temperature for 15 minutes, the reaction was complete by thin layer chromatography. $CH_3OH$ (1 mL) was added and the reaction mixture was stirred for 5 minutes and was washed with 1 M aqueous HCl (3×15 mL) and brine (15 mL), and was dried over sodium sulfate. After filtration, the filtrate was concentrated to provide the title compound, which was used without additional purification. $^1$H NMR (400 MHz, Chloroform-d) δ ppm 7.60 (dd, J=2.5, 1.2 Hz, 1H), 7.33 (dd, J=8.7, 2.6 Hz, 1H), 6.71 (d, J=8.6 Hz, 1H), 4.74 (d, J=1.0 Hz, 2H), 3.82 (d, J=1.1 Hz, 3H), 0.99 (s, 9H), 0.15 (s, 6H); MS (ESI+) m/z=329.8 (M+H)$^+$.

Intermediate 2B 2-(3-(((tert-butyldimethylsilyl)oxy)methyl)-4-methoxyphenyl)-2-methylpropanenitrile A 250-mL round-bottomed flask was charged with Intermediate 2A (2.7 g, 8.15 mmol), 2,2'-bis(diphenylphosphino)-1,1'-binaphthyl (BINAP, 0.507 g, 0.815 mmol), and diacetoxypalladium (0.183 g, 0.815 mmol). Toluene (20 mL) was added, and the suspension was sparged with a stream of $N_2$ for 15 minutes. A separate 100-mL flask was charged with the solution of sodium bis(trimethylsilyl)amide (NaHMDS, 0.6M in toluene, 20.37 mL, 12.22 mmol) and isobutyronitrile (0.841 mL, 9.37 mmol) was added dropwise. After stirring for 10 minutes, the HMDS solution was transferred via syringe to the 250-mL reaction flask. The resulting suspension was heated to 100° C. for 30 minutes, at which point it was cooled to ambient temperature, diluted with 30 mL of saturated aqueous ammonium chloride, and extracted with methyl tert-butyl ether (3×20 mL). The combined organic extracts were concentrated and purified via flash chromatography, eluting with 0:100 to 20:80 ethyl acetate:heptanes over 20 minutes on a 40 g silica gel column to provide 2.0 g of the title compound. $^1$H NMR (400 MHz, Chloroform-d) δ ppm 7.50 (dd, J=2.6, 1.4 Hz, 1H), 7.28 (dd, J=8.5, 2.7 Hz, 1H), 6.74 (d, J=8.5 Hz, 1H), 4.69 (s, 1H), 3.75 (s, 1H), 1.64 (s, 7H), 0.90 (s, 1H), 0.05 (s, 1H); MS (ESI+) m/z=188.0 (M-OTBS)$^+$.

Intermediate 2C 2-(3-(hydroxymethyl)-4-methoxyphenyl)-2-methylpropanenitrile

Intermediate 2B (2 g, 6.26 mmol) was dissolved in $CH_3OH$ (10 mL) and HCl (3 M in cyclopentyl methyl ether, 0.209 mL, 0.626 mmol) was added at ambient temperature. The solution turned very light yellow, and stirring was continued for 10 minutes, at which point complete deprotection had occurred as determined by thin layer chromatography analysis. The reaction mixture was concentrated in vacuo to provide 1.15 g of the title compound that was used directly in the subsequent oxidation reaction.

Intermediate 2D 2-(3-formyl-4-methoxyphenyl)-2-methylpropanenitrile

Intermediate 2C (600 mg, 2.92 mmol) was dissolved in dichloromethane (14.6 mL) and Dess-Martin Periodinane (1.49 g, 3.51 mmol) was added. The reaction mixture was stirred for 1 hour at ambient temperature, at which point it was complete by thin layer chromatography analysis. The reaction was diluted with methyl tert-butyl ether (30 mL) and quenched with saturated aqueous sodium thiosulfate and saturated aqueous sodium bicarbonate (15 mL each) then stirred for 15 minutes at room temperature. The organic material was extracted into methyl tert-butyl ether (2×30 mL) and the combined extracts were washed with brine (20 mL) and dried over sodium sulfate, filtered, concentrated, and used without additional purification to provide the title compound (570 mg). $^1$H NMR (400 MHz, Chloroform-d) δ ppm 10.47 (s, 1H), 7.86 (d, J=2.7 Hz, 1H), 7.75 (dd, J=8.8, 2.7 Hz, 1H), 7.03 (d, J=8.8 Hz), 3.96 (s, 3H), 1.72 (s, 6H); MS (ESI+) m/z=220.8 (M+NH$_4$)+.

Intermediate 3

2-methoxy-5-(1-(methoxymethyl)cyclopropyl)benzaldehyde

Intermediate 3A (1-(4-methoxyphenyl)cyclopropyl)methanol

Methyl 1-(4-methoxyphenyl)cyclopropanecarboxylate (2.2 g, 10.7 mmol) was dissolved in 50 mL of tetrahydrofuran. After cooling to <5° C. in an ice-water bath, LiAlH$_4$ (2 M in tetrahydrofuran, 5.33 mL, 10.7 mmol) was added slowly via syringe, maintaining an internal temperature <10° C. After the addition was complete, LC-MS showed complete consumption of the starting material. The reaction was quenched with 1 mL of CH$_3$OH then diluted with methyl tert-butyl ether and stirred with 1 M aqueous HCl (100 mL) for 5 minutes. The layers were separated and the organic layer was washed with brine (20 mL) then concentrated to a residue and the residue was loaded onto a 40 g silica gel column, eluting with 0:100 to 20:80 ethyl acetate:heptanes over 20 minutes to provide 1.6 g of (1-(4-methoxyphenyl)cyclopropyl)methanol. $^1$H NMR (400 MHz, Chloroform-d) δ ppm 7.29 (d, J=8.8 Hz, 2H), 6.85 (d, J=8.8 Hz, 2H), 3.79 (s, 3H), 3.62 (s, 2H), 0.82 (ddd, J=6.7, 2.2, 1.1 Hz, 4H); MS (ESI+) m/z=161.1 (M−OH)$^+$.

Intermediate 3B 1-methoxy-4-(1-(methoxymethyl)cyclopropyl)benzene

Intermediate 3A (1.45 g, 8.14 mmol) was dissolved in N,N-dimethylformamide (16.27 mL). After cooling to <5° C., sodium hydride (60% in oil, 0.423 g, 10.58 mmol) was added and the resulting solution was stirred for 15 minutes at ambient temperature before addition of iodomethane (1.017 mL, 16.27 mmol) in one portion. The reaction mixture was stirred at ambient temperature for 16 hours then was diluted with 50 mL of water and extracted with methyl tert-butyl ether (3×30 mL). The combined organic extracts were washed with water (4×20 mL) and brine (20 mL), then dried over sodium sulfate, filtered and concentrated to provide the title compound that was used without additional purification (1.66 g).

Intermediate 3C 2-bromo-1-methoxy-4-(1-(methoxymethyl)cyclopropyl)benzene

Intermediate 3B (1.66 g, 8.63 mmol) was dissolved in CH$_3$CN (21.59 mL) and N-bromosuccinimide (1.690 g, 9.50 mmol) was added in one portion. The reaction was stirred at ambient temperature for 1 hour, at which point it was complete by LC-MS. The reaction contents were concentrated in vacuo to approximately 5 mL and then diluted with 50 mL of methyl tert-butyl ether. The resulting suspension was washed with water (3×20 mL) and brine (20 mL) then dried over sodium sulfate, filtered, and concentrated to provide the title compound that was used without additional purification.

Intermediate 3D 2-methoxy-5-(1-(methoxymethyl)cyclopropyl)benzaldehyde

Intermediate 3C (2.25 g, 8.30 mmol) was dissolved in 40 mL of tetrahydrofuran and the solution was cooled to <−70° C. in a dry ice-acetone bath. n-Butyllithium (1.51 M in heptanes, 3.65 mL, 9.13 mmol) was added dropwise via syringe, maintaining an internal temperature <−65° C. After stirring for 10 minutes at the same temperature, N,N-dimethylformamide (1.928 mL, 24.89 mmol) was added in one portion, and the reaction mixture was allowed to warm to ambient temperature. Thin layer chromatography and LC-MS showed complete conversion of the starting aryl bromide. The reaction mixture was diluted with methyl tert-butyl ether (10 mL) and quenched with saturated aqueous ammonium chloride (20 mL). The layers were separated, and the organic layer was concentrated in vacuo then purified via flash chromatography, eluting with 0:100 to 15:85 ethyl acetate:heptanes over 20 minutes on an 80 g silica gel column to provide 720 mg of the title compound. $^1$H NMR (400 MHz, Chloroform-d) δ ppm 10.44 (s, 1H), 7.77 (d, J=2.5 Hz, 1H), 7.57 (dd, J=8.6, 2.5 Hz, 1H), 6.92 (d, J=8.6 Hz, 1H), 3.91 (s, 3H), 3.44 (s, 2H), 3.30 (s, 3H), 0.85 (br s, 4H). MS (ESI+) m/z=221.0 (M+H)$^+$.

Intermediate 4

3-(bromomethyl)-5-cyclobutyl-2-methoxypyridine

Intermediate 4A methyl 5-cyclobutyl-2-methoxynicotinate

Methyl 5-bromo-2-methoxynicotinate (8 g, 32.5 mmol) and PdCl$_2$(dppf) ([1,1'-bis(diphenylphosphino)ferrocene]dichloropalladium(II)), 0.595 g, 0.813 mmol) were suspended in tetrahydrofuran (163 mL) that had been sparged with N$_2$ for 10 minutes in a 20-mL nitrogen-purged vial. A commercial solution of cyclobutylzinc(II) bromide (0.5 M in tetrahydrofuran, 85 mL, 42.3 mmol) was added dropwise and the reaction was allowed to stir at ambient temperature for 16 hours. The reaction mixture was quenched with saturated aqueous ammonium chloride (50 mL) and the layers were separated. The organic layer was washed with saturated aqueous ammonium chloride (2×25 mL) and brine (50 mL) then dried over sodium sulfate, filtered, concentrated and purified via flash chromatography, eluting with 0:100 to 10:90 ethyl acetate:heptanes on a 120 g silica gel column over 20 minutes to provide 6.15 g of the title compound. $^1$H NMR (400 MHz, Chloroform-d) δ ppm 8.20-8.11 (s, 1H), 8.06-7.98 (s, 1H), 4.02 (s, 3H), 3.91 (s, 3H), 3.57-3.41 (m, 1H), 2.43-2.26 (m, 2H), 2.21-1.97 (m, 3H), 1.89 (dddd, J=11.6, 8.9, 7.0, 1.4 Hz, 1H); MS (ESI+) m/z=222.2 (M+H)$^+$.

Intermediate 4B (5-cyclobutyl-2-methoxypyridin-3-yl)methanol

Intermediate 4A (6.15 g, 27.8 mmol) was dissolved in tetrahydrofuran (69.5 mL) and the solution was cooled to <5° C. LiAlH$_4$ (2 M in tetrahydrofuran, 9.73 mL, 19.46 mmol) solution was added dropwise over 5 minutes, maintaining an internal temperature <10° C. After the addition was complete, LC-MS showed complete conversion to the desired alcohol. Saturated Rochelle's salt (potassium sodium tartrate) was added (75 mL) slowly to quench the reaction, which was then diluted with methyl tert-butyl ether (150 mL). The mixture was stirred at ambient temperature for 60 minutes. The layers were separated, and the aqueous layer was extracted with methyl tert-butyl ether (3×25 mL). The combined organic extracts were washed with 1 M aqueous NaOH (50 mL) and brine (50 mL), dried over sodium sulfate, filtered, and concentrated in vacuo to provide the title compound, which was used without additional purification. $^1$H NMR (400 MHz, Chloroform-d) δ ppm 7.90 (d, J=2.4 Hz, 1H), 7.49 (dd, J=2.5, 0.9 Hz, 1H), 4.64 (d, J=4.7 Hz, 2H), 3.96 (d, J=1.0 Hz, 3H), 3.48 (p, J=8.6 Hz, 1H), 2.51 (s, 1H), 2.42-2.23 (m, 2H), 2.23-1.95 (m, 3H), 1.95-1.83 (m, 1H); MS (ESI+) m/z=194.0 (M+H)+.

Intermediate 4C 3-(bromomethyl)-5-cyclobutyl-2-methoxypyridine

Intermediate 4B (5.2 g, 26.9 mmol) was dissolved in dichloromethane (135 mL) and triphenylphosphine (8.82 g, 33.6 mmol) was added. The resulting solution was cooled in an ice-water bath to <5° C. and NBS (N-bromosuccinimide) (5.99 g, 33.6 mmol) was added portionwise over 3-5 minutes, maintaining an internal temperature <20° C. The reaction mixture was stirred in the same bath for 20 minutes, at which point LC-MS showed complete conversion. Silica gel (50 g) was added and the suspension was concentrated in vacuo. The crude material was poured into a disposable fritted funnel (500 mL) containing 3 inches of heptanes-packed silica, washing the flask with heptanes. The desired product was eluted with 20:80 methyl tert-butyl ether: heptanes to provide 4.88 g of the title compound. $^1$H NMR (501 MHz, Chloroform-d) δ ppm 7.94 (dd, J=2.3, 0.8 Hz, 1H), 7.49 (dd, J=2.4, 0.6 Hz, 1H), 4.49 (s, 2H), 3.99 (s, 3H), 3.47 (ddddd, J=9.2, 8.6, 7.9, 7.2, 0.7 Hz, 1H), 2.41-2.25 (m, 2H), 2.18-1.95 (m, 3H), 1.95-1.82 (m, 1H); MS (ESI+) m/z=255.9 (M+H)+.

Intermediate 5

2-methoxy-5-(1-methylcyclobutyl)benzaldehyde

Intermediate 5A 1-(4-methoxyphenyl)cyclobutanol (4-Methoxyphenyl)magnesium bromide (56.9 mL, 28.5 mmol, 0.5M in tetrahydrofuran) solution was cooled to −78° C. before dropwise addition of cyclobutanone (2.239 mL, 30.0 mmol) via syringe. After the addition was complete, the mixture was warmed to ambient temperature and quenched with saturated aqueous ammonium chloride (10 mL). The mixture was diluted with methyl tert-butyl ether (20 mL) and the layers were separated. The organic layer was washed with saturated aqueous ammonium chloride (20 mL) and brine (20 mL) then dried over sodium sulfate, filtered, and concentrated to provide the title compound that was used without additional purification (5.3 g). $^1$H NMR (400 MHz, Chloroform-d) δ ppm 7.45 (d, J=8.8 Hz, 2H), 6.93 (d, J=8.8 Hz, 2H), 3.84 (s, 3H), 2.57 (dddd, J=12.4, 6.5, 2.8, 1.7 Hz, 2H), 2.43-2.27 (m, 2H), 2.18-1.89 (m, 2H), 1.76-1.60 (m, 1H).

Intermediate 5B 1-methoxy-4-(1-methylcyclobutyl)benzene

Intermediate 5A (3 g, 16.83 mmol) was dissolved in dichloromethane (84 mL) and the resulting solution was cooled to −78° C. in a dry ice-acetone bath. Titanium(IV) chloride (neat, 3.69 mL, 33.7 mmol) was added via syringe and the solution was stirred for 1 hour at the same temperature before addition of dimethylzinc (50.5 mL, 50.5 mmol) solution slowly as a 1 M solution in heptanes. After the addition was complete, the reaction flask was warmed to ambient temperature before pouring into 300 mL of ice in a beaker while stirring vigorously. The resulting suspension was diluted with dichloromethane (100 mL) and stirred for 5 minutes before filtering through diatomaceous earth and washing the organic layer with brine (50 mL). The organic layer was dried over sodium sulfate, filtered, and concentrated to provide the title compound (2.97 g), which was used without additional purification. $^1$H NMR (500 MHz, Chloroform-d) δ ppm 7.14 (d, J=8.7 Hz, 2H), 6.90 (d, J=8.7 Hz, 2H), 3.84 (s, 3H), 2.40 (qd, J=9.4, 8.9, 2.1 Hz, 2H), 2.21-2.04 (m, 3H), 1.92-1.81 (m, 1H), 1.48 (s, 3H).

Intermediate 5C 2-methoxy-5-(1-methylcyclobutyl)benzaldehyde

Intermediate 5B (3 g, 17.02 mmol) was dissolved in 110 mL of dichloromethane, and the resulting solution was cooled to <0° C. in an ice-brine bath. After addition of dichloro(methoxy)methane (1.70 mL, 18.7 mmol), titanium tetrachloride (2.065 mL, 18.72 mmol) was added dropwise as a solution in 10 mL of dichloromethane over 2 minutes, maintaining an internal temperature <5° C. After 15 minutes at the same temperature, thin layer chromatography indicated complete conversion. The resulting mixture was quenched with 40 mL of water, the layers were separated, and the organic layer was concentrated and loaded onto an 80 g silica gel column, eluting with 0:100 to 15:85 ethyl acetate:heptanes over 20 minutes to provide 2.05 g of the title compound. $^1$H NMR (400 MHz, Chloroform-d) δ ppm 10.49 (d, J=1.0 Hz, 1H), 7.67 (dd, J=2.6, 0.9 Hz, 1H), 7.40 (ddd, J=8.6, 2.6, 1.0 Hz, 1H), 6.96 (d, J=8.6 Hz, 1H), 3.94 (d, J=0.9 Hz, 3H), 2.37 (td, J=10.3, 9.7, 7.2 Hz, 2H), 2.19-2.01 (m, 3H), 1.89-1.73 (m, 1H), 1.46 (s, 3H); MS (ESI+) m/z=205.1 (M+H)+.

Intermediate 6

5-(tert-butyl)-2-methoxynicotinaldehyde

Intermediate 6A (5-bromo-2-methoxypyridin-3-yl)methanol

5-Bromo-2-methoxynicotinaldehyde (2 g, 9.26 mmol) was suspended in CH$_3$OH (40 mL) and the mixture was cooled to 0° C. Sodium borohydride (0.350 g, 9.26 mmol) was added in one portion, causing bubbling. The reaction mixture stirred at 00 C for 15 minutes, then the flask was removed from the ice bath and allowed to stir at room temperature for 2 hours. The reaction mixture was then concentrated in vacuo, and the crude material was taken up in methyl tert-butyl ether and saturated aqueous NaHCO$_3$ solution. The phases were separated, and the organic layer was dried over Na$_2$SO$_4$, filtered, and concentrated in vacuo to provide the title compound, (1.876 g, 93% yield). $^1$H NMR (400 MHz, CDCl$_3$) δ ppm 8.15 (d, J=2.5 Hz, 1H), 7.75 (d, J=2.4 Hz, 1H), 4.66 (d, J=6.2 Hz, 2H), 3.99 (s, 3H), 2.15 (t, J=6.3 Hz, 1H); MS (DCI+) m/z 217.8 (M+H).

Intermediate 6B 5-bromo-3-(((tert-butyldimethylsilyl)oxy)methyl)-2-methoxypyridine (5-Bromo-2-methoxypyridin-3-yl)methanol (1.876 g, 8.60 mmol), tert-butyldimethylsilyl chloride (1.556 g, 10.32 mmol), and imidazole (0.879 g, 12.91 mmol) were stirred in CH$_2$Cl$_2$ (35 mL) overnight at room temperature. After this time, 5 mL of CH$_3$OH was added to quench the reaction, and the reaction mixture was stirred at room temperature for 10 minutes. The mixture was diluted with $CH_2Cl_2$ and washed twice with saturated aqueous $NaHCO_3$ solution and once with brine. The organic solution was dried over $Na_2SO_4$, filtered, and concentrated to afford the title compound, 5-bromo-3-(((tert-butyldimethylsilyl)oxy)methyl)-2-methoxypyridine (2.71 g, 95% yield). $^1$H NMR (400 MHz, $CDCl_3$) δ ppm 8.08 (dt, J=2.5, 0.9 Hz, 1H), 7.81 (dt, J=2.5, 1.2 Hz, 1H), 4.65 (m, 2H), 3.93 (s, 3H), 0.93 (s, 9H), 0.14 (s, 6H); MS (ESI$^+$) m/z 332.0 (M+H).

Intermediate 6C 5-(tert-butyl)-3-(((tert-butyldimethylsilyl)oxy)methyl)-2-methoxypyridine To a 50 mL 2-neck round bottom flask was added nickel chloride-dimethoxyethane adduct (0.033 g, 0.150 mmol) and 1,3-dicyclohexyl-1H-imidazol-3-ium tetrafluoroborate (0.048 g, 0.150 mmol), followed by a solution of 5-bromo-3-(((tert-butyldimethylsilyl)oxy)methyl)-2-methoxypyridine (Intermediate 6B, 0.500 g, 1.505 mmol) in tetrahydrofuran (6 mL). The system was evacuated and back-filled with nitrogen seven times, and the reaction was cooled to −10° C. tert-Butylmagnesium chloride (1 M in tetrahydrofuran) (3 mL, 3.00 mmol) was added dropwise, and the reaction was stirred at −10° C. for 100 minutes. After this time, the reaction was quenched with chips of ice and was allowed to warm to room temperature. The mixture was poured into saturated aqueous $NH_4Cl$ solution and extracted three times with ethyl acetate. The combined organic extracts were washed with brine, dried over $Na_2SO_4$, filtered, and concentrated in vacuo. Silica gel chromatography, eluting with 0 to 10% ethyl acetate-heptanes, afforded the title compound, 236 mg. The impure material was used in the next step without additional purification. $^1$H NMR (400 MHz, $CDCl_3$) δ ppm 8.06 (m, 1H), 7.82 (m, 1H), 4.72 (s, 2H), 3.96 (s, 3H), 1.34 (s, 9H), 1.00 (s, 9H), 0.14 (s, 6H); MS (ESI$^+$) m/z 310.2 (M+H)$^+$.

Intermediate 6D (5-(tert-butyl)-2-methoxypyridin-3-yl)methanol

The impure material from Intermediate 6C (236 mg) was dissolved in tetrahydrofuran (7.6 mL) and treated with tetrabutylammonium fluoride trihydrate (1.20 g, 3.81 mmol). The reaction was stirred at room temperature. After 4 hours, the reaction mixture was poured into a mixture of saturated aqueous $NH_4Cl$ solution and brine. The mixture was extracted three times with ethyl acetate. The combined organics were dried over $Na_2SO_4$, filtered, and concentrated in vacuo to provide the crude title compound, which was taken directly into the next reaction without further purification. MS (APCI$^+$) m/z 196.2 (M+H).

Intermediate 6E 5-(tert-butyl)-2-methoxynicotinaldehyde

The crude product from Intermediate 6D (0.762 mmol) was dissolved in $CH_2Cl_2$ (6 mL), and the solution was cooled to 0° C. Dess-Martin periodinane (0.388 g, 0.914 mmol) was added in 4 portions. The flask was removed from the ice bath and was allowed to stir at room temperature. After 3 hours, the reaction mixture was diluted with 50 mL methyl tert-butyl ether and was stirred vigorously with 50 mL of saturated aqueous $Na_2S_2O_3$ solution and 50 mL of saturated $NaHCO_3$ solution for 5 minutes. The mixture was transferred to a separatory funnel, the phases were separated, and the organic layer was washed with brine, dried over $Na_2SO_4$, filtered, and concentrated in vacuo. Silica gel chromatography, eluting with 0 to 20% ethyl acetate-heptanes, provided the title compound, 0.060 g (41% yield). $^1$H NMR (500 MHz, DMSO-$d_6$) δ ppm 10.24 (s, 1H), 8.53 (d, J=2.7 Hz, 1H), 8.06 (d, J=2.8 Hz, 1H), 3.99 (s, 3H), 1.31 (s, 9H); MS (ESI$^+$) m/z 194.0 (M+H)$^+$.

Intermediate 7

6-(tert-butyl)-3-methoxypicolinaldehyde

Intermediate 7A (6-bromo-3-methoxypyridin-2-yl)methanol

6-Bromo-3-methoxypicolinaldehyde (0.880 g, 4.07 mmol) was suspended in $CH_3OH$ (20 mL) and the mixture was cooled to 0° C. Sodium borohydride (0.154 g, 4.07 mmol) was added, causing bubbling. The reaction mixture was stirred at 0° C. for 15 minutes, then the flask was removed from the ice bath and allowed to stir at room temperature for 2 hours. The reaction mixture was then concentrated in vacuo, and the crude material was taken up in methyl tert-butyl ether and saturated aqueous $NaHCO_3$ solution. The phases were separated, and the organic layer was dried over $Na_2SO_4$, filtered, and concentrated in vacuo to provide the title compound, (0.718 g, 81% yield). $^1$H NMR (501 MHz, $CDCl_3$) δ ppm 8.15 (d, J=2.4 Hz, 1H), 7.75 (m 1H), 4.66 (dt, J=6.3, 0.7 Hz, 2H), 2.16 (t, J=6.3 Hz, 1H); MS (ESI$^+$) m/z 218.0 (M+H)$^+$.

Intermediate 7B 6-bromo-2-(((tert-butyldimethylsilyl)oxy)methyl)-3-methoxypyridine (6-Bromo-3-methoxypyridin-2-yl)methanol (0.718 g, 3.29 mmol), tert-butyldimethylsilyl chloride (0.596 g, 3.95 mmol), and imidazole (0.336 g, 4.94 mmol) were stirred in $CH_2Cl_2$ (13 mL) overnight at room temperature. The reaction was then quenched with 3 mL of $CH_3OH$, and the reaction mixture was stirred at room temperature for 10 minutes. The mixture was diluted with $CH_2Cl_2$ and washed twice with saturated aqueous $NaHCO_3$ solution and once with brine. The organic solution was dried over $Na_2SO_4$, filtered and concentrated in vacuo to provide the title compound, (0.997 g, 91% yield). $^1$H NMR (400 MHz, $CDCl_3$) δ ppm 7.34 (d, J=8.5 Hz, 1H), 7.05 (d, J=8.5 Hz, 1H), 4.80 (s, 2H), 3.84 (s, 3H), 0.92 (s, 9H), 0.12 (s, 6H).

Intermediate 7C 6-(tert-butyl)-2-(((tert-butyldimethylsilyl)oxy)methyl)-3-methoxypyridine To a 100 mL 2-neck round bottom flask was added nickel chloride-dimethoxyethane adduct (0.066 g, 0.300 mmol) and 1,3-dicyclohexyl-1H-imidazol-3-ium tetrafluoroborate (0.096 g, 0.300 mmol), followed by a solution of 6-bromo-2-(((tert-butyldimethylsilyl)oxy)methyl)-3-methoxypyridine (0.997 g, 3.00 mmol) in tetrahydrofuran (12 mL). The system was evacuated and back-filled with nitrogen seven times, then the reaction was cooled to −10° C., and tert-butylmagnesium chloride (1 M in tetrahydrofuran) (6.00 mL, 6.00 mmol) was added dropwise. The reaction mixture was stirred at −10° C. for 150 minutes. The reaction was then quenched with chips of ice and allowed to warm to room temperature. The mixture was poured into saturated aqueous NH$_4$Cl solution and was extracted three times with ethyl acetate. The combined organic extracts were washed with brine, dried over Na$_2$SO$_4$, filtered, and concentrated in vacuo. Silica gel chromatography, eluting with 0 to 40% ethyl acetate-heptanes, afforded the crude title compound, 0.356 g, 38% yield. $^1$H NMR (400 MHz, CDCl$_3$) δ ppm 7.18 (d, J=8.5 Hz, 1H), 7.06 (d, J=8.5 Hz, 1H), 4.86 (s, 2H), 3.82 (s, 3H), 1.35 (s, 9H), 0.92 (s, 9H), 0.10 (s, 6H); MS (ESI$^+$) m/z 310.1 (M+H)$^+$.

Intermediate 7D (6-(tert-butyl)-3-methoxypyridin-2-yl)methanol 6-(tert-Butyl)-2-(((tert-butyldimethylsilyl)oxy)methyl)-3-methoxypyridine (0.356 g, 1.150 mmol) in tetrahydrofuran (11 mL) was treated with tetrabutylammonium fluoride trihydrate (1.814 g, 5.75 mmol), and the reaction was stirred overnight at room temperature. The reaction mixture was poured into a mixture of saturated aqueous NH$_4$Cl and brine solution in a separatory funnel, and the mixture was extracted three times with ethyl acetate. The combined extracts were dried over Na$_2$SO$_4$, filtered, and concentrated in vacuo. The material was taken directly into the next step without further purification. MS (APCI$^+$) m/z 196.3 (M+H)$^+$.

Intermediate 7E 6-(tert-butyl)-3-methoxypicolinaldehyde (6-(tert-Butyl)-3-methoxypyridin-2-yl)methanol (0.225 g, 1.15 mmol) was dissolved in CH$_2$Cl$_2$ (12 mL) and cooled to 0° C. Dess-Martin periodinane (0.585 g, 1.380 mmol) was added in portions, the flask was removed from the ice bath, and the mixture was allowed to stir at room temperature. After 2 hours, the reaction mixture was diluted with 80 mL methyl tert-butyl ether and treated with 80 mL of saturated aqueous Na$_2$S$_2$O$_3$ solution and 80 mL of saturated aqueous NaHCO$_3$ solution. The mixture was stirred vigorously for 5 minutes, then the mixture was transferred to a separatory funnel and the phases were separated. The organic layer was washed with brine, dried over Na$_2$SO$_4$, filtered, and concentrated in vacuo. Silica gel chromatography, eluting with 0 to 50% ethyl acetate-heptanes, afforded the title compound, 0.118 g, 53% yield. $^1$H NMR (400 MHz, CDCl$_3$) δ ppm 10.23 (s, 1H), 7.53 (d, J=8.8 Hz, 1H), 7.33 (d, J=8.9 Hz, 1H), 3.95 (s, 3H), 1.39 (s, 9H); MS (ESI$^+$) m/z 194.1 (M+H)$^+$.

Intermediate 8

3-methoxy-6-(1-(trifluoromethyl)cyclopropyl)picolinaldehyde

3-Methoxypicolinaldehyde (0.117 g, 0.850 mmol) and sodium 1-(trifluoromethyl)cyclopropane-1-sulfinate (0.500 g, 2.55 mmol) were dissolved in diethylcarbonate (5.1 mL) and water (3.4 mL), and the mixture was cooled to 0° C. tert-Butyl hydroperoxide (70% aqueous, 0.547 g, 4.25 mmol) was then added dropwise. The reaction was stirred in the ice bath for 5 minutes and was then heated at 90° C. for 2 hours. After this time, the mixture was cooled to room temperature, quenched with saturated aqueous Na$_2$S$_2$O$_3$ solution (10 mL), and diluted with ethanol (20 mL). The mixture was concentrated in vacuo, and the resulting material was taken up in 20% CH$_3$OH-ethyl acetate and filtered through a pad of silica gel on a fritted glass funnel, eluting with 10% CH$_3$OH-ethyl acetate. The combined filtrates were concentrated in vacuo, and the residue was purified by silica gel chromatography, eluting with 40% ethyl acetate-heptanes to 100% ethyl acetate (gradient). The title compound was obtained, 0.0253 g, 12% yield. $^1$H NMR (400 MHz, CDCl$_3$) δ ppm 10.35 (s, 1H), 8.47 (s, 1H), 7.50 (s, 1H), 4.02 (s, 3H), 1.53 (m, 2H), 1.28 (m, 2H); MS (ESI$^+$) m/z 246.1 (M+H)$^+$.

Intermediate 9

3-methoxy-6-(trifluoromethyl)picolinaldehyde

3-Methoxypicolinaldehyde (0.150 g, 1.094 mmol) and sodium trifluoromethanesulfinate (0.500 g, 3.20 mmol) were dissolved in diethylcarbonate (6.6 mL) and water (4.4 mL), and the mixture was cooled to 0° C. tert-Butyl hydroperoxide (70% aqueous, 0.704 g, 5.47 mmol) was then added dropwise. The reaction was stirred in the ice bath for 5 minutes and was then heated at 90° C. for 90 minutes. After this time, the reaction was quenched with saturated aqueous Na$_2$S$_2$O$_3$ solution (10 mL) and then diluted with ethanol (20 mL). The reaction mixture was concentrated in vacuo, then the resulting material was taken up in 20% CH$_3$OH-ethyl acetate and filtered through a pad of silica gel on a fritted glass funnel, eluting with 10% CH$_3$OH-ethyl acetate. The combined filtrates were concentrated in vacuo. The residue was purified by silica gel chromatography, eluting with an eluent gradient of 40% ethyl acetate-heptanes to 100% ethyl acetate, to provide the title compound, 0.0245 g, 11% yield. $^1$H NMR (400 MHz, CDCl$_3$) δ ppm 10.28 (s, 1H), 7.89 (m, 1H), 7.56 (m, 1H), 4.07 (s, 3H); MS (ESI$^+$) m/z 206.1 (M+H)$^+$.

Intermediate 10

5-(2,2-difluoro-1-methylcyclopropyl)-2-methoxynicotinaldehyde

Intermediate 10A (5-bromo-2-methoxypyridin-3-yl)methanol

5-Bromo-2-methoxynicotinaldehyde (2 g, 9.26 mmol) was suspended in CH$_3$OH (40 mL) and the mixture was cooled to 0° C. Sodium borohydride (0.350 g, 9.26 mmol) was added in one portion, causing bubbling. The reaction mixture stirred at 0° C. for 15 minutes, then the flask was removed from the ice bath and allowed to stir at room temperature for 2 hours. The reaction mixture was then concentrated in vacuo, and the crude material was taken up in methyl tert-butyl ether and saturated aqueous NaHCO$_3$ solution. The phases were separated, and the organic layer was dried over Na$_2$SO$_4$, filtered, and concentrated in vacuo to provide the title compound, 1.876 g, 93% yield. $^1$H NMR (400 MHz, CDCl$_3$) δ ppm 8.15 (d, J=2.5 Hz, 1H), 7.75 (d, J=2.4 Hz, 1H), 4.66 (d, J=6.2 Hz, 2H), 3.99 (s, 3H), 2.15 (t, J=6.3 Hz, 1H); MS (DCI$^+$) m/z 217.8 (M+H)$^+$.

Intermediate 10B

5-bromo-3-(((tert-butyldimethylsilyl)oxy)methyl)-2-methoxypyridine (5-Bromo-2-methoxypyridin-3-yl)methanol (1.876 g, 8.60 mmol), tert-butyldimethylsilyl chloride (1.556 g, 10.32 mmol), and imidazole (0.879 g, 12.91 mmol) were stirred in $CH_2Cl_2$ (35 mL) overnight at room temperature. After this time, 5 mL of $CH_3OH$ was added to quench the reaction, and the reaction mixture was stirred at room temperature for 10 minutes. The mixture was diluted with $CH_2Cl_2$ and washed twice with saturated aqueous $NaHCO_3$ solution and once with brine. The organic solution was dried over $Na_2SO_4$, filtered, and concentrated to afford the title compound, 2.71 g, 95% yield. $^1H$ NMR (400 MHz, $CDCl_3$) δ ppm 8.08 (dt, J=2.5, 0.9 Hz, 1H), 7.81 (dt, J=2.5, 1.2 Hz, 1H), 4.65 (m, 2H), 3.93 (s, 3H), 0.93 (s, 9H), 0.14 (s, 6H); MS ($ESI^+$) m/z 332.0 $(M+H)^+$.

Intermediate 10C

3-(((tert-butyldimethylsilyl)oxy)methyl)-2-methoxy-5-(prop-1-en-2-yl)pyridine 5-Bromo-3-(((tert-butyldimethylsilyl)oxy)methyl)-2-methoxypyridine (0.500 g, 1.505 mmol), 4,4,5,5-tetramethyl-2-(prop-1-en-2-yl)-1,3,2-dioxaborolane (0.329 g, 1.956 mmol), and $Pd(PPh_3)_4$ (tetrakis(triphenylphosphine)palladium(0)), 0.174 g, 0.150 mmol) were treated with dioxane (12 mL) and a solution of potassium carbonate (0.416 g, 3.01 mmol) in water (3 mL), and the reaction mixture was heated overnight at 100° C. After this time, the reaction mixture was diluted with ethyl acetate and washed three times with water and once with brine. After drying over $Na_2SO_4$, filtering, and concentrating in vacuo, the crude material was chromatographed on silica gel, eluting with 0 to 10% ethyl acetate-heptanes, to provide the title compound, 3-(((tert-butyldimethylsilyl)oxy)methyl)-2-methoxy-5-(prop-1-en-2-yl)pyridine (0.376 g, 85% yield). $^1H$ NMR (500 MHz, $CDCl_3$) δ ppm 8.07 (m, 1H), 7.74 (m, 1H), 5.35 (m, 1H), 5.06 (m, 1H), 4.71 (m, 2H), 3.98 (s, 3H), 2.16 (s, 3H), 0.99 (s, 9H), 0.15 (s, 6H); MS ($ESI^+$) m/z 294.2 $(M+H)^+$.

Intermediate 10D

3-(((tert-butyldimethylsilyl)oxy)methyl)-5-(2,2-difluoro-1-methylcyclopropyl)-2-methoxypyridine 3-(((tert-Butyldimethylsilyl)oxy)methyl)-2-methoxy-5-(prop-1-en-2-yl)pyridine (0.050 g, 0.170 mmol) in tetrahydrofuran (1.5 mL) was treated with sodium iodide (5.1 mg, 0.034 mmol) and then (trifluoromethyl)trimethylsilane (2 M in tetrahydrofuran, 0.21 mL, 0.426 mmol). The reaction mixture was stirred vigorously at 65° C. for 3 hours. The reaction mixture was cooled to room temperature and treated carefully with saturated aqueous $NH_4Cl$ solution, and the mixture was extracted three times with methyl tert-butyl ether. The combined organics were washed with water and brine, dried over $Na_2SO_4$, filtered, and concentrated in vacuo to provide the title compound, (75 mg, quantitative), which was taken directly into the following reaction without further purification. $^1H$ NMR (400 MHz, $CDCl_3$) δ ppm 7.99 (d, J=2.4 Hz, 1H), 7.68 (m, 1H), 4.69 (m, 2H), 3.95 (s, 3H), 1.65 (m, 1H), 1.51 (s, 3H), 1.43 (m, 1H), 0.97 (s, 9H), 0.13 (s, 3H), 0.12 (s, 3H); MS ($ESI^+$) m/z 344.1 $(M+H)^+$.

Intermediate 10E

(5-(2,2-difluoro-1-methylcyclopropyl)-2-methoxypyridin-3-yl)methanol 3-(((tert-Butyldimethylsilyl)oxy)methyl)-5-(2,2-difluoro-1-methylcyclopropyl)-2-methoxypyridine (0.246 g, 0.715 mmol) and tetrabutylammonium fluoride trihydrate (1.128 g, 3.58 mmol) were stirred in tetrahydrofuran (7 mL) overnight at room temperature. After this time, the mixture was poured into a mixture of saturated aqueous $NH_4Cl$ solution and brine, and the mixture was extracted three times with ethyl acetate. The combined organics were dried over $Na_2SO_4$, filtered, and concentrated in vacuo to provide the title compound, which was taken directly into the next reaction without purification. MS ($ESI^+$) m/z 230.3 $(M+H)^+$.

Intermediate 10F

5-(2,2-difluoro-1-methylcyclopropyl)-2-methoxynicotinaldehyde (5-(2,2-Difluoro-1-methylcyclopropyl)-2-methoxypyridin-3-yl)methanol (Intermediate 10E, 0.164 g, 0.715 mmol) in $CH_2Cl_2$ (5 mL) was cooled to 0° C. and treated in portions with Dess-Martin periodinane (0.364 g, 0.858 mmol). After completion of the addition, the reaction was removed from the ice bath and was allowed to stir at room temperature for 1 hour. The reaction mixture was then diluted with 85 mL of methyl tert-butyl ether, 85 mL of saturated aqueous $Na_2S_2O_3$ solution, and 85 mL of saturated aqueous $NaHCO_3$ solution. The mixture was stirred vigorously for 5 minutes. The mixture was transferred to a separatory funnel, the phases were separated, and the organic layer was washed with brine, dried over $Na_2SO_4$, filtered, and concentrated in vacuo. The resulting crude residue was purified by silica gel chromatography, eluting with 0 to 50% ethyl acetate-heptanes. The title compound was obtained, 0.097 g, 60% yield over three steps. $^1H$ NMR (400 MHz, $CDCl_3$) δ ppm 10.37 (s, 1H), 8.35 (dd, J=2.6, 0.8 Hz, 1H), 8.07 (d, J=2.6 Hz, 1H), 4.09 (s, 3H), 1.67 (m, 1H), 1.53 (m, 3H), 1.49 (m, 1H); MS ($APCI^+$) m/z 228.2 $(M+H)^+$.

Intermediate 11

2-(tert-butyl)-5-methoxyisonicotinaldehyde

Intermediate 11A

2-bromo-4-(((tert-butyldimethylsilyl)oxy)methyl)-5-methoxypyridine (2-Bromo-5-methoxypyridin-4-yl)methanol (Anichem; 0.500 g, 2.293 mmol), tert-butyldimethylsilyl chloride (TBDMS-Cl, 0.415 g, 2.75 mmol), and imidazole (0.234 g, 3.44 mmol) were stirred in $CH_2Cl_2$ (10 mL) for 3 days at room temperature. After this time, the mixture was diluted with $CH_2Cl_2$ and washed with water and brine. The organic layer was dried over $Na_2SO_4$, filtered, and concentrated in vacuo to provide the title compound, 2-bromo-4-(((tert-butyldimethylsilyl)oxy)methyl)-5-methoxypyridine (0.660 g, 87% yield). $^1H$ NMR (501 MHz, $CDCl_3$) δ ppm 7.92 (s, 1H), 7.58

(s, 1H), 4.72 (d, J=1.2 Hz, 2H), 3.91 (s, 3H), 0.89 (s, 9H), 0.16 (s, 6H); MS (ESI+) m/z 332.1 (M+H)+.

Intermediate 11B 2-(tert-butyl)-4-(((tert-butyldimethylsilyl)oxy)methyl)-5-methoxypyridine To a 100 mL 2-neck round bottom flask was added nickel chloride dimethoxyethane adduct (0.044 g, 0.199 mmol) and 1,3-dicyclohexyl-1H-imidazol-3-ium tetrafluoroborate (0.064 g, 0.199 mmol), followed by a solution of 2-bromo-4-(((tert-butyldimethylsilyl)oxy)methyl)-5-methoxypyridine (0.660 g, 1.986 mmol) in tetrahydrofuran (8 mL). The system was evacuated and back-filled with nitrogen seven times, and the reaction was cooled to −10° C. tert-Butylmagnesium chloride (1 M in tetrahydrofuran) (4 mL, 4 mmol) was added dropwise, and the reaction was stirred at −10° C. for 100 minutes. After this time, the reaction was quenched with chips of ice and was allowed to warm to room temperature. The mixture was poured into saturated aqueous NH$_4$Cl solution and was extracted three times with ethyl acetate. The combined organic extracts were washed with brine, dried over Na$_2$SO$_4$, filtered, and concentrated in vacuo. Silica gel chromatography, eluting with 5 to 50% ethyl acetate-heptane, afforded the title compound, 2-(tert-butyl)-4-(((tert-butyldimethylsilyl)oxy)methyl)-5-methoxypyridine (0.178 g, 29% yield). $^1$H NMR (501 MHz, CDCl$_3$) δ ppm 8.14 (s, 1H), 7.55 (s, 1H), 4.76 (d, J=1.1 Hz, 2H), 3.91 (s, 3H), 1.38 (s, 9H), 1.00 (s, 9H), 0.15 (s, 6H); MS (ESI+) m/z 310.3 (M+H)+.

Intermediate 11C (2-(tert-butyl)-5-methoxypyridin-4-yl)methanol 2-(tert-Butyl)-4-(((tert-butyldimethylsilyl)oxy)methyl)-5-methoxypyridine (0.178 g, 0.575 mmol) and tetrabutylammonium fluoride trihydrate (0.907 g, 2.88 mmol) were stirred in tetrahydrofuran (5 mL) overnight at room temperature. After this time, the reaction mixture was poured into a mixture of saturated aqueous NH$_4$Cl and brine in a separatory funnel, and was extracted three times with ethyl acetate. The combined organics were dried over Na$_2$SO$_4$, filtered, and concentrated in vacuo to provide the crude title compound, 328 mg, which was taken directly into the next reaction without further purification. $^1$H NMR (501 MHz, CDCl$_3$) δ ppm 8.22 (s, 1H), 7.37 (s, 1H), 4.74 (s, 2H), 3.95 (s, 3H), 1.38 (s, 9H); MS (ESI+) m/z 196.2 (M+H)+.

Intermediate 11D 2-(tert-butyl)-5-methoxyisonicotinaldehyde (2-(tert-Butyl)-5-methoxypyridin-4-yl)methanol (0.112 g, 0.575 mmol) in CH$_2$Cl$_2$ (5 mL) was cooled in an ice bath, then treated in three portions with Dess-Martin periodinane (0.293 g, 0.690 mmol). The mixture was stirred in the ice bath for 30 minutes, then the flask was removed from the ice bath, and stirring was continued at room temperature overnight. After this time, the reaction mixture was treated with 70 mL each of methyl tert-butyl ether, saturated aqueous Na$_2$S$_2$O$_3$ solution, and saturated aqueous NaHCO$_3$ solution. The mixture was stirred vigorously for 10 minutes. The mixture was transferred to a separatory funnel, the phases were separated, and the organic layer was washed with brine, dried over Na$_2$SO$_4$, filtered, and concentrated in vacuo. Silica gel chromatography, eluting with 0 to 50% ethyl acetate-heptanes, afforded the title compound, 2-(tert-butyl)-5-methoxyisonicotinaldehyde (0.040 g, 36% yield); MS (APCI+) m/z 194.2 (M+H)+.

Intermediate 12

2-methoxy-5-(1,1,1-trifluoro-2-methylpropan-2-yl)benzaldehyde

Intermediate 12A 4-(1,1,1-trifluoro-2-methylpropan-2-yl)phenol 4,4,5,5-Tetramethyl-2-(4-(1,1,1-trifluoro-2-methylpropan-2-yl)phenyl)-1,3,2-dioxaborolane (0.500 g, 1.592 mmol) in tetrahydrofuran (16 mL) was cooled in an ice bath to about 3° C. (internal temperature). Sodium hydroxide (1 M aqueous) (2.6 mL, 2.60 mmol) was added dropwise to keep the reaction temperature at 4° C. or lower. Hydrogen peroxide (30% aqueous) (0.2 mL, 1.958 mmol) was added dropwise, causing the reaction temperature to rise to 13° C. The mixture was stirred cold for 20 minutes, and was warmed to room temperature and stirred for 2 days. After this time, the mixture was treated with a 5 mL of saturated aqueous Na$_2$S$_2$O$_3$ solution and was stirred vigorously for 30 minutes. HCl (1 N, aqueous) was then added to pH 4, and the mixture was extracted three times with ethyl acetate. The combined extracts were washed with brine, and the combined aqueous washes were extracted once with ethyl acetate. The combined organics were dried over Na$_2$SO$_4$, filtered and concentrated in vacuo to provide the crude title compound, 4-(1,1,1-trifluoro-2-methylpropan-2-yl)phenol, 698 mg, which was taken into the next reaction without additional purification. $^1$H NMR (501 MHz, CDCl$_3$) δ ppm 7.38 (m, 2H), 6.85 (m, 2H), 5.53 (s, 1H), 1.57 (s, 6H).

Intermediate 12B 2-hydroxy-5-(1,1,1-trifluoro-2-methylpropan-2-yl)benzaldehyde 4-(1,1,1-Trifluoro-2-methylpropan-2-yl)phenol (Intermediate 12A, 1.592 mmol) in acetonitrile (8 mL) was treated with paraformaldehyde (0.416 g, 13.85 mmol), magnesium chloride (0.243 g, 2.55 mmol), and triethylamine (1.4 mL, 10.04 mmol). The reaction was heated at 80° C. with vigorous stirring for 18 hours. After this time, the reaction mixture was cooled to room temperature and treated with 50 mL of 1 M aqueous HCl. The mixture was extracted twice with CH$_2$Cl$_2$ (50 mL each). The combined organics were dried over Na$_2$SO$_4$, filtered, and concentrated in vacuo to provide the crude title compound, 391 mg, which was taken directly into the next reaction without additional purification. $^1$H NMR (400 MHz, CDCl$_3$) δ ppm 11.01 (s, 1H), 9.95 (s, 1H), 7.71-7.67 (m, 2H), 7.03 (d, J=8.7 Hz, 1H), 1.27 (s, 6H).

Intermediate 12C 2-methoxy-5-(1,1,1-trifluoro-2-methylpropan-2-yl)benzaldehyde

2-Hydroxy-5-(1,1,1-trifluoro-2-methylpropan-2-yl)benzaldehyde (Intermediate 12B, 1.592 mmol) in N,N-dimethylformamide (5.3 mL) was treated with potassium carbonate (0.330 g, 2.388 mmol) and iodomethane (0.15 mL, 2.399 mmol), and the mixture was stirred vigorously overnight at room temperature. The mixture was treated with 50 mL of 1 N aqueous NaOH, and was extracted (2×50 mL) with methyl tert-butyl ether. The combined organics were washed with water and brine, dried over $Na_2SO_4$, filtered, and concentrated in vacuo. Silica gel chromatography, eluting with 0 to 25% ethyl acetate-heptanes, yielded the title compound, 2-methoxy-5-(1,1,1-trifluoro-2-methylpropan-2-yl)benzaldehyde (0.209 g, 53% yield over three steps). $^1$H NMR (400 MHz, $CDCl_3$) δ ppm 10.48 (s, 1H), 7.96 (d, J=2.7 Hz, 1H), 7.71 (ddq, J=8.8, 2.7, 0.9 Hz, 1H), 7.01 (d, J=8.8 Hz, 1H), 3.96 (s, 3H), 1.59 (s, 3H), 1.58 (s, 3H).

Intermediate 13

6-cyclobutyl-2-methoxynicotinaldehyde

Intermediate 13A 6-bromo-3-(((tert-butyldimethylsilyl)oxy)methyl)-2-methoxypyridine (6-Bromo-2-methoxypyridin-3-yl)methanol (1.0 g, 4.59 mmol) in $CH_2Cl_2$ (20 mL) was treated with tert-butyldimethylsilyl chloride (TBDMS-Cl, 0.829 g, 5.50 mmol) and imidazole (0.468 g, 6.88 mmol), and the reaction mixture was stirred overnight at room temperature. The mixture was then treated with a 5 mL $CH_3OH$ and stirred for a few minutes to quench leftover TBDMS-Cl. The mixture was diluted with $CH_2Cl_2$ and washed twice with saturated aqueous $NaHCO_3$ solution and once with brine. The organic layer was dried over $Na_2SO_4$, filtered, and concentrated in vacuo to provide the title compound, 6-bromo-3-(((tert-butyldimethylsilyl)oxy)methyl)-2-methoxypyridine (1.453 g, 95% yield).

Intermediate 13B 3-(((tert-butyldimethylsilyl)oxy)methyl)-6-cyclobutyl-2-methoxypyridine 6-Bromo-3-(((tert-butyldimethylsilyl)oxy)methyl)-2-methoxypyridine (0.500 g, 1.505 mmol), dried azeotropically with toluene, was dissolved in tetrahydrofuran (15 mL) and treated with dichloro[1,3-bis(2,6-di-3-pentylphenyl)imidazol-2-ylidene](3-chloropyridyl)palladium(II) (PEPPSI IPentCl, 0.129 g, 0.150 mmol), followed by dropwise addition over a few minutes of cyclobutylzinc(II) bromide (0.5 M in tetrahydrofuran) (6.0 mL, 3.0 mmol) via syringe at room temperature. After 30 minutes, the reaction mixture had darkened to a clear medium green-brown-yellow. The mixture was poured into saturated aqueous $NH_4Cl$ solution and was extracted three times with ethyl acetate. The combined organics were dried over $Na_2SO_4$, filtered, and concentrated in vacuo, and the crude residue was purified by silica gel chromatography, eluting with 0 to 5% ethyl acetate-heptanes over 15 minutes. The still-impure title compound, 3-(((tert-butyldimethylsilyl)oxy)methyl)-6-cyclobutyl-2-methoxypyridine, 473 mg was used in the next reaction without further purification. $^1$H NMR (400 MHz, $CDCl_3$) δ ppm 7.59 (m, 1H), 6.73 (m, 1H), 4.68 (s, 2H), 3.98 (s, 3H), 3.55 (p, J=8.6 Hz, 1H), 2.42-2.22 (m, 4H), 2.07-1.93 (m, 1H), 1.96-1.85 (m, 1H), 0.96 (m, 9H), 0.12 (s, 6H); MS ($ESI^+$) m/z 308.2 $(M+H)^+$.

Intermediate 13C (6-cyclobutyl-2-methoxypyridin-3-yl)methanol

Crude 3-(((tert-Butyldimethylsilyl)oxy)methyl)-6-cyclobutyl-2-methoxypyridine (Intermediate 13B, 1.505 mmol) in tetrahydrofuran (15 mL) was treated with tetrabutylammonium fluoride trihydrate (2.374 g, 7.53 mmol), and the reaction mixture was stirred overnight at room temperature. The reaction mixture was then poured into a mixture of saturated $NH_4Cl$ and saturated $NaHCO_3$ aqueous solutions, and the mixture was extracted three times with ethyl acetate. The combined organics were dried over $Na_2SO_4$, filtered, and concentrated in vacuo, and the crude material was purified by silica gel chromatography, eluting with 0 to 20% ethyl acetate-heptanes. The title compound was obtained, (6-cyclobutyl-2-methoxypyridin-3-yl)methanol (0.102 g, 35% yield over two steps). $^1$H NMR (501 MHz, $CDCl_3$) δ ppm 7.46 (dt, J=7.2, 0.7 Hz, 1H), 6.72 (d, J=7.3 Hz, 1H), 4.64 (d, J=6.4 Hz, 2H), 4.05 (s, 3H), 3.57 (p, J=8.4 Hz, 1H), 2.42-2.23 (m, 5H), 2.11-1.97 (m, 1H), 1.98-1.87 (m, 1H); MS ($ESI^+$) m/z 194.1 $(M+H)^+$.

Intermediate 13D 6-cyclobutyl-2-methoxynicotinaldehyde (6-Cyclobutyl-2-methoxypyridin-3-yl)methanol (0.102 g, 0.528 mmol) in $CH_2Cl_2$ (3.5 mL) was cooled to 0° C. and treated in portions with Dess-Martin periodinane (0.269 g, 0.633 mmol). After completion of the addition, the reaction was removed from the ice bath and allowed to stir at room temperature for 1 hour. The mixture was then diluted with 30 mL of methyl tert-butyl ether, 30 mL of saturated aqueous $Na_2S_2O_3$ solution, and 30 mL of saturated aqueous $NaHCO_3$ solution, and the mixture was stirred vigorously for 15 minutes. The mixture was transferred to a separatory funnel, the phases were separated, and the organic layer was washed with brine, dried over $Na_2SO_4$, filtered, and concentrated in vacuo. Silica gel chromatography, eluting with 0 to 20% ethyl acetate-heptanes, afforded the title compound, 6-cyclobutyl-2-methoxynicotinaldehyde (0.081 g, 80% yield). $^1$H NMR (501 MHz, $CDCl_3$) δ ppm 10.34 (s, 1H), 8.03 (d, J=7.7 Hz, 1H), 6.84 (dt, J=7.8, 0.7 Hz, 1H), 4.12 (s, 3H), 3.69-3.58 (m, 1H), 2.46-2.29 (m, 4H), 2.15-2.01 (m, 1H), 2.02-1.91 (m, 1H); MS ($ESI^+$) m/z 192.1 $(M+H)^+$.

Intermediate 14

6-tert-butyl-2-methoxy-pyridine-3-carbaldehyde

Intermediate 14A 6-(tert-butyl)-2-methoxynicotinonitrile

To a stirred solution of 6-tert-butyl-2-chloro-pyridine-3-carbonitrile (CAS#4138-20-9, 3.30 g, 16.95 mmol, 1.0 eq) in methanol (25 mL) was added a sodium methoxide 25 weight % solution in methanol (CAS#124-41-4, 5.43 mL, 23.73 mmol, 1.4 eq). The reaction mixture was refluxed for 2 hours. A saturated aqueous $NH_4Cl$ solution was added and the reaction mixture was extracted twice with ethyl acetate. The combined organic layers were dried over $Na_2SO_4$, filtered and concentrated in vacuo. The crude mixture was purified by flash chromatography on silica gel (heptane/ethyl acetate 100/0 to 90/10) to afford the title compound. $^1$H NMR (400 MHz, Chloroform-d) δ ppm 7.79 (d, J=7.9 Hz, 1H), 6.98 (d, J=7.9 Hz, 1H), 4.05 (s, 3H), 1.34 (s, 9H); LC/MS (ESI+) m/z 191.3 (M+H)+.

Intermediate 14B 6-tert-butyl-2-methoxy-pyridine-3-carboxylic acid

Potassium hydroxide (CAS#1310-58-3, 5.14 g, 91.74 mmol, 6.0 eq) was added to a stirred solution of Intermediate 14A (2.91 g, 15.29 mmol, 1.0 eq) in methanol (80 mL) and water (20 mL). The reaction mixture was refluxed for 72 hours and was concentrated in vacuo. The crude material was acidified with a 2 N aqueous HCl solution (CAS#7607-01-0, 58 mL) and the resulting material was filtered, washed with water and dried in vacuo to afford the title compound. LC/MS (ESI+) m/z 210.2 (M+H)+.

Intermediate 14C methyl 6-tert-butyl-2-methoxy-pyridine-3-carboxylate

Sulfuric acid (CAS#7664-93-9, 700 µL, 13.06 mmol, 0.85 eq) was added to a stirred solution of the previously prepared 6-tert-butyl-2-methoxy-pyridine-3-carboxylic acid (3.20 g, 15.29 mmol, 1.0 eq) in methanol (50 mL). The reaction mixture was refluxed overnight. More sulfuric acid (CAS#7664-93-9, 700 µL, 13.06 mmol, 0.85 eq) was added and the reaction mixture was refluxed for 3 hours. A saturated aqueous NaHCO$_3$ solution was added and the reaction mixture was extracted twice with ethyl acetate. The combined organic layers were dried over Na$_2$SO$_4$, filtered and concentrated in vacuo. The crude mixture was purified by flash chromatography on silica gel (dichloromethane) to afford the title compound. $^1$H NMR (300 MHz, Chloroform-d) δ ppm 8.10 (d, J=7.9 Hz, 1H), 6.94 (d, J=7.9 Hz, 1H), 4.05 (s, 3H), 3.89 (s, 3H), 1.35 (s, 9H); LC/MS (ESI+) m/z 224.6 (M+H)+.

Intermediate 14D (6-tert-butyl-2-methoxy-3-pyridyl)methanol

Lithium aluminium hydride (1.0 M solution in tetrahydrofuran, CAS#16853-85-3, 34.47 mL, 34.47 mmol, 1.5 eq) was added to a solution of previously cooled (0° C.) methyl 6-tert-butyl-2-methoxy-pyridine-3-carboxylate (5.13 g, 22.98 mmol, 1.0 eq) in tetrahydrofuran (70 mL). The reaction mixture was stirred for 1 hour at 0° C. and at room temperature for 1 hour. The following work up was used in order to remove lithium salts. The reaction mixture was cooled to 0° C. and 1.3 mL of water was added dropwise followed by addition of 1.3 mL of a 15% aqueous NaOH solution and 3.25 mL of water. The mixture was stirred at room temperature for 10 minutes and then filtered over diatomaceous earth. The filtrate was dried over Na$_2$SO$_4$, filtered and concentrated in vacuo to afford the title compound. LC/MS (ESI+) m/z 196.3 (M+H)+.

Intermediate 14E 6-tert-butyl-2-methoxy-pyridine-3-carbaldehyde

Dess-Martin periodinane (CAS#87413-09-0, 10.68 g, 25.18 mmol, 1.1 eq) was added to a solution of (6-tert-butyl-2-methoxy-3-pyridyl)methanol (4.47 g, 22.89 mmol, 1.0 eq) in dichloromethane (100 mL) at 0° C. The reaction mixture was stirred for 1 hour at 0° C. and was allowed to warm to room temperature. A saturated aqueous NaHCO$_3$ solution was added and the organic layer was separated, dried over Na$_2$SO$_4$, filtered and concentrated in vacuo. The crude mixture was purified by flash chromatography on silica gel (dichloromethane) to afford the title compound. $^1$H NMR (400 MHz, Chloroform-d) δ ppm 10.33 (s, 1H), 8.05 (d, J=7.9 Hz, 1H), 7.03 (d, J=7.9 Hz, 1H), 4.07 (s, 3H), 1.37 (s, 9H); LC/MS (ESI+) m/z 194.2 (M+H)+.

Intermediate 15

2-methoxy-5-trimethylsilanyl-pyridine-3-carbaldehyde

Intermediate 15A 5-bromo-3-[1,3]dioxolan-2-yl-2-methoxy-pyridine

Ethylene glycol (CAS#107-21-1, 0.51 mL, 9.2 mmol, 2.0 eq) and a spatula of p-toluenesulfonic acid (PTSA, CAS#104-15-4) were added to a solution of 5-bromo-2-methoxynicotinaldehyde (CAS#25016-01-7, 1.0 g, 4.6 mmol, 1.0 eq) in toluene (20 mL). The reaction mixture was heated to reflux overnight. The reaction mixture was cooled to room temperature and diluted with ethyl acetate. The organic phase was washed with a saturated aqueous NaHCO$_3$ solution, dried on Na$_2$SO$_4$, filtered and concentrated in vacuo. The residue was purified by flash chromatography on silica gel (heptane/dichloromethane 90/10 to 20/80) to give the title compound (795 mg, 83%). LC/MS (ESI+) m/z 260.2 (M+H)+.

Intermediate 15B

3-[1,3]dioxolan-2-yl-2-methoxy-5-trimethylsilanyl-pyridine n-Butyllithium (2.5 M in hexanes, 1.25 mL, 3.2 mmol, 1.1 eq) was added at −78° C. to a solution of 5-bromo-3-[1,3]dioxolan-2-yl-2-methoxy-pyridine (746 mg, 2.9 mmol, 1.0 eq) in tetrahydrofuran (10 mL). The reaction mixture was stirred at −78° C. for 15 minutes and then trimethylchlorosilane (CAS#75-77-4, 0.40 mL, 3.2 mmol, 1.1 eq) was added dropwise. The resulting mixture was allowed to warm to room temperature. After 1 hour, the reaction mixture was quenched with water, concentrated in vacuo and extracted with dichloromethane. The combined organic phases were dried on Na$_2$SO$_4$, filtered and concentrated in vacuo. The crude product was used in next step without further purification.

Intermediate 15C 2-methoxy-5-trimethylsilyl-benzaldehyde

Intermediate 15B (1.0 eq) was dissolved in acetone (20 mL). A spatula of p-toluenesulfonic acid (PTSA) was added and the reaction mixture was refluxed for 1 hour. The mixture was concentrated in vacuo. The residue was purified by flash chromatography on silica gel (heptane/dichloromethane 90/10 to 0/100) to give the title compound (292 mg, 49% over two steps). $^1$H NMR (400 MHz, Chloroform-d) δ ppm 10.40 (s, 1H), 8.45 (d, J=2.0 Hz, 1H), 8.20 (d, J=2.0 Hz, 1H), 4.08 (s, 3H), 0.30 (s, 9H); LC/MS (ESI+) m/z 210.3 (M+H)+.

Intermediate 16

2-methoxy-5-trimethylsilanyl-benzaldehyde

Intermediate 16A 2-(5-bromo-2-methoxy-phenyl)-[1,3]dioxolane

Ethylene glycol (CAS#107-21-1, 1.11 mL, 20 mmol, 2.0 eq) and a spatula of p-toluenesulfonic acid (PTSA, CAS#104-15-4) were added to a solution of 5-bromo-2-methoxybenzaldehyde (CAS#25016-01-7, 2.15 g, 10 mmol, 1.0 eq) in toluene (40 mL). The reaction mixture was heated to reflux overnight. The reaction mixture was cooled to room temperature and was diluted with ethyl acetate. The organic phase was washed with a saturated aqueous NaHCO$_3$ solution, dried over Na$_2$SO$_4$, filtered and concentrated in vacuo. The residue was purified by flash chromatography on silica gel (heptane/dichloromethane 90/10 to 20/80) to give the title compound (2.55 g, 98%). $^1$H NMR (400 MHz, Chloroform-d) δ ppm 7.64 (d, J=2.6 Hz, 1H), 7.42 (dd, J=8.9, 2.6 Hz, 1H), 6.79 (d, J=8.9 Hz, 1H), 6.11 (s, 1H), 4.18-3.99 (m, 4H), 3.85 (s, 3H).

Intermediate 16B (3-[1,3]dioxolan-2-yl-4-methoxy-phenyl)-trimethylsilane n-Butyllithium (2.5 M in hexanes, 1.6 mL, 4.0 mmol, 1.1 eq) was added at −78° C. to a solution of 2-(5-bromo-2-methoxy-phenyl)-[1,3]dioxolane (964 mg, 3.7 mmol, 1.0 eq) in tetrahydrofuran (10 mL). The reaction mixture was stirred at −78° C. for 15 minutes and trimethylchlorosilane (CAS#75-77-4, 0.51 mL, 4.0 mmol, 1.1 eq) was added dropwise. The resulting mixture was allowed to warm to room temperature. After 1 hour, the reaction solution was quenched with water, concentrated in vacuo and extracted with dichloromethane. The combined organic phases were dried on Na$_2$SO$_4$, filtered and concentrated in vacuo. The crude product was used in next step without further purification. LC/MS (ESI+) m/z 253.3 (M+H)$^+$.

Intermediate 16C 2-methoxy-5-trimethylsilanyl-benzaldehyde

Intermediate 16B (1.0 eq) was dissolved in acetone (20 mL). A spatula of p-toluenesulfonic acid (PTSA) was added and the reaction mixture was refluxed for 1 hour. The mixture was concentrated in vacuo. The residue was purified by flash chromatography on silica gel (heptane/dichloromethane 90/10 to 50/50) to give the title compound (549 mg, 71% over two steps). LC/MS (ESI+) m/z 209.3 (M+H)$^+$.

Intermediate 17

1-(3-formyl-4-methoxy-phenyl)-cyclobutanecarbonitrile

Intermediate 17A 1-(3-[1,3]dioxolan-2-yl-4-methoxy-phenyl)-cyclobutanecarbonitrile Tris(dibenzylideneacetone)dipalladium(0) (Pd$_2$(dba)$_3$, CAS#51364-51-3, 46 mg, 0.05 mmol, 0.05 eq) and 2,2'-bis(diphenylphosphino)-1,1'-binaphthyl (BINAP, CAS#98327-87-8, 62 mg, 0.1 mmol, 0.1 eq) were loaded in a round bottom flask. Dry tetrahydrofuran (2.0 mL) was added and the reaction mixture was degassed with N$_2$. The mixture was stirred for 20 minutes at room temperature and was added to a vial containing a degassed solution of 2-(5-bromo-2-methoxy-phenyl)-[1,3]dioxolane (Intermediate 16A, 259 mg, 1.0 mmol, 1.0 eq) and cyclobutanecarbonitrile (CAS#4426-11-3, 140 µL, 1.5 mmol, 1.5 eq) in tetrahydrofuran (1.0 mL). Lithium bis(trimethylsilyl)amide (1 M in tetrahydrofuran, CAS#4039-32-1, 1.5 mL, 1.5 mmol, 1.5 eq) was slowly added to the reaction mixture. The vial was sealed and the reaction mixture was stirred at 80° C. for 3 hours. The mixture was partitioned between a saturated aqueous NH$_4$Cl solution and ethyl acetate. The organic layer was separated, dried on Na$_2$SO$_4$, filtered and concentrated in vacuo. The residue was purified by flash chromatography on silica gel (dichloromethane/ethyl acetate 100/0 to 95/5) to give the title compound (134 mg, 52%). $^1$H NMR (400 MHz, Chloroform-d) δ ppm 7.58 (d, J=2.6 Hz, 1H), 7.37 (dd, J=8.5, 2.6 Hz, 1H), 6.91 (d, J=8.5 Hz, 1H), 6.12 (s, 1H), 4.21-3.98 (m, 4H), 3.87 (s, 3H), 2.86-2.72 (m, 2H), 2.67-2.51 (m, 2H), 2.47-2.31 (m, 1H), 2.11-1.97 (m, 1H); LC/MS (ESI+) m/z 260.4 (M+H)$^+$.

Intermediate 17B 1-(3-formyl-4-methoxy-phenyl)-cyclobutanecarbonitrile 1-(3-[1,3]Dioxolan-2-yl-4-methoxy-phenyl)-cyclobutanecarbonitrile (134 mg, 0.52 mmol, 1.0 eq) was dissolved in acetone (15 mL). A spatula of p-toluenesulfonic acid (PTSA) (CAS#104-15-4) was added and the reaction mixture was stirred at room temperature for 72 hours. The mixture was concentrated in vacuo and the residue was purified by flash chromatography on silica gel (heptane/dichloromethane 50/50 to 0/100) to give the title compound (51 mg, 46%). LC/MS (ESI+) m/z 216.2 (M+H)$^+$.

Intermediate 18

1-(3-formyl-4-methoxy-phenyl)-cyclopropanecarbonitrile

Intermediate 18A 1-(3-[1,3]dioxolan-2-yl-4-methoxy-phenyl)-cyclopropanecarbonitrile Tris(dibenzylideneacetone)dipalladium(0) (Pd$_2$(dba)$_3$, CAS#51364-51-3, 229 mg, 0.25 mmol, 0.05 eq) and 2,2'-bis(diphenylphosphino)-1,1'-binaphthyl (BINAP, CAS#98327-87-8, 311 mg, 0.5 mmol, 0.1 eq) were loaded in a round bottom flask. Dry tetrahydrofuran (5.0 mL) was added and the reaction mixture was degassed with N$_2$. The mixture was stirred for 20 minutes at room temperature and was added to a vial containing a degassed solution of 2-(5-bromo-2-methoxy-phenyl)-[1,3]dioxolane (Intermediate 16A, 1.3 g, 5.0 mmol, 1.0 eq) and cyclopropanecarbonitrile (CAS#5500-21-0, 552 µL, 7.5 mmol, 1.5 eq) in cyclopentyl methyl ether (10 mL). Lithium bis(trimethylsilyl)amide (LiHMDS 1 M in tetrahydrofuran, CAS#4039-32-1, 7.5 mL, 7.5 mmol, 1.5 eq) was slowly added to the reaction mixture. The vial was sealed and the reaction mixture was stirred at 80° C. overnight. The mixture was partitioned between a saturated aqueous NH$_4$Cl solution and ethyl acetate. The organic layer was separated, washed with brine, dried on Na$_2$SO$_4$, filtered and concentrated in vacuo. The residue was purified by flash chromatography on silica gel (dichloromethane/ethyl acetate 100/0 to 95/5) to give the title compound (886 mg, 72%). $^1$H NMR (400 MHz, Chloroform-d) δ ppm 7.44 (d, J=2.6 Hz, 1H), 7.35 (dd, J=8.5, 2.6 Hz, 1H), 6.89 (d, J=8.5 Hz, 1H), 6.11 (s, 1H), 4.20-4.00 (m, 4H), 3.87 (s, 3H), 1.70-1.62 (m, 2H), 1.40-1.32 (m, 2H); LC/MS (ESI+) m/z 246.3 (M+H)$^+$.

Intermediate 18B

1-(3-formyl-4-methoxy-phenyl)-cyclopropanecarbonitrile 1-(3-[1,3]Dioxolan-2-yl-4-methoxy-phenyl)-cyclopropanecarbonitrile (245 mg, 1.0 mmol, 1.0 eq) was dissolved in acetone (20 mL). A spatula of p-toluenesulfonic acid (PTSA) (CAS#104-15-4) was added and the reaction mixture was refluxed for 1.5 hours. The mixture was concentrated in vacuo and the residue was purified by flash chromatography on silica gel (heptane/dichloromethane 50/50 to 0/100) to give the title compound (157 mg, 78%). LC/MS (ESI+) m/z 202.3 (M+H)$^+$.

Intermediate 19

2-tert-butyl-4-methoxy-pyrimidine-5-carbaldehyde

Dess-Martin periodinane (CAS#87413-09-0, 603 mg, 1.46 mmol, 1.5 eq) was added to a solution of [2-(tert-butyl)-4-methoxypyrimidin-5-yl]methanol (191 mg, 0.976 mmol, 1.0 eq) in dichloromethane (7 mL) at 0° C. The reaction mixture was stirred for 1 hour at 0° C. and filtered over diatomaceous earth. The residue was washed with dichloromethane and the filtrate was concentrated in vacuo. The crude mixture was purified by flash chromatography on silica gel (heptane/ethyl acetate 90/10 to 85/15) to afford the title compound (117 mg, 62%). LC/MS (ESI+) m/z 213.1 (M+H$_2$O+H)$^+$.

Intermediate 20

6-cyclobutyl-3-methoxy-pyridazine-4-carbaldehyde

Intermediate 20A

6-cyclobutyl-3-methoxy-pyridazine-4-carboxylic acid methyl ester

In a sealed tube charged with methyl 6-chloro-3-methoxy-pyridazine-4-carboxylate (53 mg, 0.26 mmol, 1.0 eq) and Pd(PPh$_3$)$_4$ (tetrakis(triphenylphosphine)palladium(0), CAS#14221-01-3, 30 mg, 0.026 mmol, 0.1 eq) in tetrahydrofuran (3 mL), a cyclobutyl zinc bromide solution 0.5 M in tetrahydrofuran (CAS#38256-93-8, 2.1 mL, 1.04 mmol, 4.0 eq) was added. The resulting mixture was flushed with N$_2$, and the vial was sealed and heated to 70° C. until reaction completion. The reaction mixture was quenched by addition of a saturated aqueous NH$_4$Cl solution and was extracted with ethyl acetate. The organic phase was separated, washed with brine, dried on MgSO$_4$, filtered and concentrated in vacuo. The residue was purified by flash chromatography on silica gel (ethyl acetate/heptane 0/100 to 20/80) to afford the title compound (30 mg, 52%). LC/MS (ESI+) m/z 223.3 (M+H)$^+$.

Intermediate 20B

(6-cyclobutyl-3-methoxy-pyridazin-4-yl)-methanol

Diisobutylaluminum hydride (DIBAL-H 1.0 M solution in tetrahydrofuran, CAS#1191-15-7, 1.25 mL, 1.25 mmol, 2.0 eq) was added to a previously cooled (−78° C.) solution of 6-cyclobutyl-3-methoxy-pyridazine-4-carboxylic acid methyl ester (137 mg, 0.62 mmol, 1.0 eq) in toluene (5 mL). The reaction mixture was warmed to 0° C. and was stirred for 15 minutes. Total completion was obtained. The reaction mixture was poured into a mixture of ethyl acetate and a saturated aqueous solution of potassium sodium tartrate tetrahydrate (Rochelle salt). The mixture was stirred vigorously for 30 minutes until a clear solution was obtained. The organic phase was separated, washed with brine, dried on MgSO$_4$, filtered and concentrated in vacuo. The residue was purified by flash chromatography on silica gel (heptane/ethyl acetate 80/20 to 50/50) to give the title compound (65 mg, 54%). LC/MS (ESI+) m/z 195.3 (M+H)$^+$.

Intermediate 20C

6-cyclobutyl-3-methoxy-pyridazine-4-carbaldehyde

Dess-Martin periodinane (CAS#87413-09-0, 213 mg, 0.50 mmol, 1.5 eq) was added to a solution of (6-cyclobutyl-3-methoxy-pyridazin-4-yl)-methanol (65 mg, 0.33 mmol, 1.0 eq) in dichloromethane (5 mL) at 0° C. The reaction mixture was stirred for 1 hour at room temperature and was filtered over diatomaceous earth. The residue was washed with dichloromethane and the filtrate was concentrated in vacuo. The crude mixture was purified by flash chromatography on silica gel (heptane/ethyl acetate 100/0 to 80/20) to afford the title compound (56 mg, 87%). LC/MS (ESI+) m/z 211.3 (M+H$_2$O+H)$^+$.

Intermediate 21

(R)-2-methoxy-3-phenyl-propionic acid

To a stirred solution of NaH (60% suspension in oil, 289 mg, 7.2 mmol, 2.5 eq) in tetrahydrofuran (15 mL) at 0° C. under N$_2$ was added (R)-3-phenyllactic acid (CAS#7326-19-4, 500 mg, 3.0 mmol, 1.0 eq). The resulting mixture was warmed to room temperature and stirred for 15 minutes before methyl iodide (CAS#74-88-4, 0.375 mL, 6.02 mmol, 2.0 eq) was added. The reaction mixture was stirred at room temperature for 16 hours, then 1 N aqueous HCl was added and the resulting mixture was concentrated in vacuo. HCl (1 N aqueous) was added to the residue and the mixture was extracted with diethyl ether. The combined organic layers were washed with brine, dried over MgSO$_4$, filtered, and concentrated in vacuo. The crude residue was purified by flash chromatography on silica gel (ethyl acetate/heptane/acetic acid 20/80/1) to give the title compound (223 mg, 41%). $^1$H NMR (400 MHz, Chloroform-d) δ ppm 7.37-7.23 (m, 5H), 4.05 (dd, J=7.9, 4.3 Hz, 1H), 3.41 (s, 3H), 3.17 (dd, J=15.9, 4.3 Hz, 1H), 3.04 (dd, J=15.9, 7.9 Hz, 1H); LC/MS (ESI−) m/z 179.1 (M−H)$^-$.

Intermediate 22

(3,4-difluoro-phenyl)-methoxy-acetic acid

To a solution of 3,4-difluorobenzaldehyde (CAS#34036-07-2, 522 µL, 5.0 mmol, 1.0 eq) and bromoform (CAS#75-

25-2, 555 µL, 6.35 mmol, 1.27 eq) in dioxane (5 mL) under argon at 0° C. was added dropwise a solution of KOH (281 mg, 5.0 mmol, 1.0 eq) in methanol (10 mL). The resulting mixture was stirred at room temperature overnight, diluted with 10 mL of water, and the methanol was evaporated. The aqueous layer was acidified by addition of an aqueous HCl solution until pH=3-4 and extracted several times with ethyl acetate. The combined organic phases were washed with brine, dried over MgSO$_4$, filtered, and concentrated in vacuo. The crude residue was purified by flash chromatography on silica gel (ethyl acetate/heptane/acetic acid 30/70/2) to afford the title compound (392 mg, 39%). LC/MS (ESI−) m/z 201.2 (M−H)−.

Intermediate 23

(3-chloro-phenyl)-methoxy-acetic acid

To a solution of 3-chlorobenzaldehyde (CAS#587-04-2, 569 µL, 5.0 mmol, 1.0 eq) and bromoform (CAS#75-25-2, 525 µL, 6.0 mmol, 1.2 eq) in methanol (5 mL) under argon at 0° C. was added dropwise a solution of KOH (1.4 g, 25.0 mmol, 5.0 eq) in methanol (10 mL). The resulting mixture was stirred at room temperature overnight then diluted with 10 mL of water and extracted with dichloromethane. The organic layer was separated. The aqueous layer was acidified by addition of an aqueous HCl solution until pH=3-4 and extracted several times with dichloromethane. The combined organic phases were washed with brine, dried over MgSO$_4$, filtered, and concentrated in vacuo. The crude residue was purified by flash chromatography on silica gel (ethyl acetate/heptane/acetic acid 20/80/1) to afford the title compound (636 mg, 63%). $^1$H NMR (400 MHz, Chloroform-d) δ ppm 7.50-7.44 (m, 1H), 7.38-7.30 (m, 3H), 4.77 (s, 1H), 3.45 (s, 3H); LC/MS (ESI−) m/z 199.1 (M−H)−.

Intermediate 24

2-methoxy-3,3-dimethyl-butyric acid

Intermediate 24A 2-hydroxy-3,3-dimethyl-butyric acid benzyl ester

Benzyl bromide (CAS#100-39-0, 0.65 mL, 5.5 mmol, 1.5 eq) was added to a solution of 2-hydroxy-3,3-dimethylbutyric acid (472 mg, 3.6 mmol, 1.0 eq) and triethylamine (0.76 mL, 5.5 mmol, 1.5 eq) in N,N-dimethylformamide (5 mL). The reaction mixture was stirred at room temperature overnight then partitioned between water and ethyl acetate. The organic layer was washed with brine, dried on Na$_2$SO$_4$, filtered and concentrated in vacuo. The residue was purified by flash chromatography on silica gel (heptane/dichloromethane 100/0 to 0/100) to provide the title compound (595 mg, 75%). $^1$H NMR (400 MHz, Chloroform-d) δ ppm 7.41-7.34 (m, 5H), 5.27-5.19 (m, 2H), 3.86 (d, J=7.7 Hz, 1H), 2.78 (d, J=7.7 Hz, 1H), 0.96 (s, 9H); LC/MS (ESI+) m/z 245.3 (M+Na)+.

Intermediate 24B 2-methoxy-3,3-dimethyl-butyric acid benzyl ester

To a solution of 2-hydroxy-3,3-dimethyl-butyric acid benzyl ester (430 mg, 1.93 mmol, 1.0 eq) in N,N-dimethylformamide (5 mL) at 0° C. was added NaH (60% suspension in oil, 93 mg, 2.32 mmol, 1.2 eq). After 15 minutes stirring, methyl iodide (CAS#74-88-4, 0.36 mL, 5.8 mmol, 3.0 eq) was added. The reaction mixture was stirred at room temperature for 48 hours, quenched by addition of a saturated aqueous NH$_4$Cl solution, and extracted with ethyl acetate. The organic layer was separated, washed with brine, dried over Na$_2$SO$_4$, filtered and concentrated in vacuo. The residue was purified by flash chromatography on silica gel (heptane/dichloromethane 90/10 to 20/80) to give the title compound (275 mg, 60%). $^1$H NMR (400 MHz, Chloroform-d) δ ppm 7.45-7.30 (m, 5H), 5.26-5.16 (m, 2H), 3.45 (s, 1H), 3.36-3.31 (m, 3H), 1.01-0.92 (m, 9H).

Intermediate 24C 2-methoxy-3,3-dimethyl-butyric acid

To a solution of 2-methoxy-3,3-dimethyl-butyric acid benzyl ester (375 mg, 1.59 mmol, 1.0 eq) in a mixture of ethyl acetate (5 mL) and methanol (5 mL) under N$_2$ was added palladium on charcoal 5% (38 mg, 10% w/w) and ammonium formate (CAS#540-69-2, 1.22 g, 15.9 mmol, 10 eq). The reaction mixture was heated to reflux for 18 hours. The reaction mixture was then concentrated in vacuo and diluted in ethyl acetate. The suspension was filtered over diatomaceous earth. The filtrate was washed with a 1 M aqueous HCl solution, dried on Na$_2$SO$_4$, filtered and concentrated in vacuo to deliver the title compound (150 mg, 65%) which was used directly in the next step without further purification. $^1$H NMR (400 MHz, Chloroform-d) δ ppm 3.44 (s, 3H), 3.42 (s, 1H), 1.02 (s, 9H).

Intermediate 25 rac-(S)-2-((R)-tetrahydro-2H-pyran-2-yl)propanoic acid

Intermediate 25A (tetrahydro-pyran-2-yl)-acetic acid benzyl ester

Benzyl bromide (CAS#100-39-0, 1.07 mL, 9.0 mmol, 1.3 eq) was added to a solution of 2-tetrahydropyran-2-ylacetic acid (1.0 g, 6.93 mmol, 1.0 eq) and triethylamine (1.54 mL, 11.1 mmol, 1.6 eq) in tetrahydrofuran (20 mL). The reaction mixture was stirred at 50° C. for 2 hours and was diluted with a saturated NH$_4$Cl aqueous solution and extracted twice with ethyl acetate. The combined organic layers were dried over Na$_2$SO$_4$, filtered and concentrated in vacuo. The residue was purified by flash chromatography on silica gel (heptane/ethyl acetate 100/0 to 80/20) to deliver the title compound (330 mg, 20%). $^1$H NMR (400 MHz, Chloroform-d) δ ppm 7.43-7.29 (m, 5H), 5.17 (d, J=12.1 Hz, 1H), 5.12 (d, J=12.1 Hz, 1H), 4.02-3.93 (m, 1H), 3.83-3.72 (m, 1H), 3.52-3.40-(m, 1H), 2.58 (dd, J=15.0, 8.5 Hz, 1H), 2.45 (dd, J=15.0, 4.8 Hz, 1H), 1.91-1.76 (m, 1H), 1.70-1.43 (m, 4H), 1.41-1.23 (m, 1H); LC/MS (ESI+) m/z 235.2 (M+H)+.

Intermediate 25B rac-(S)—(R)-2-(tetrahydro-pyran-2-yl)-propionic acid benzyl ester To a solution of (tetrahydro-pyran-2-yl)-acetic acid benzyl ester (322 mg, 1.37 mmol, 1.0 eq) in tetrahydrofuran (15 mL) at −78° C. under argon was added 1,3-dimethyl-3,4,5,6-tetrahydro-2(1H)-pyrimidinone, (DMPU, CAS#7226-23-5, 4.14 mL, 34.3 mmol, 25 eq). Lithium diisopropylamide solution, 2.0 M in tetrahydrofuran/heptane/ethylbenzene (1.03 mL, 2.06 mmol, 1.5 eq) was introduced dropwise. After 1 hour stirring at −78° C., methyl iodide (CAS#74-88-4, 428 µL, 6.87 mmol, 5.0 eq) was added. The resulting mixture was warmed slowly to room temperature over 2 hours and was stirred at room temperature overnight. The reaction mixture was then quenched by addition of a saturated aqueous NH$_4$Cl solution and was extracted with ethyl acetate. The organic phase was separated, washed with brine, dried on Na$_2$SO$_4$, filtered and concentrated in vacuo. The residue was purified by flash chromatography on silica gel (heptane/ethyl acetate 100/0 to 80/20) to separate diastereomers and afford the title compound (34 mg, 10%, second diastereomer to elute). $^1$H NMR (400 MHz, Chloroform-d) δ ppm 7.41-7.28 (m, 5H), 5.22 (d, J=12.5 Hz, 1H), 5.13 (d, J=12.5 Hz, 1H), 4.02-3.88 (m, 1H), 3.55-3.35 (m, 2H), 2.66-2.52 (m, 1H), 1.93-1.76 (m, 1H), 1.73-1.38 (m, 4H), 1.33-1.20 (m, 1H), 1.13 (d, J=7.2 Hz, 3H).

Intermediate 25C rac-(S)—(R)-2-(tetrahydro-pyran-2-yl)-propionic acid

To a solution of rac-(S)—(R)-2-(tetrahydro-pyran-2-yl)-propionic acid benzyl ester (34 mg, 0.14 mmol, 1.0 eq) in methanol (5 mL) under N$_2$ was added palladium on charcoal 10% (14 mg, 0.0137 mmol, 0.1 eq). The solution was then degassed, flushed with H$_2$ and stirred at room temperature for 2 hours. The reaction mixture was then filtered on diatomaceous earth and the filtrate was concentrated in vacuo to deliver the title compound (22 mg, quantitative) which was used directly in the next step without further purification.

Intermediate 26 rac-(S)-2-((S)-tetrahydro-2H-pyran-2-yl)propanoic acid

Intermediate 26A rac-(S)—(S)-2-(tetrahydro-pyran-2-yl)-propionic acid benzyl ester The title compound (39 mg, 11%, first diastereomer to elute) was obtained in the reaction described in Intermediate 25B. $^1$H NMR (400 MHz, Chloroform-d) δ ppm 7.42-7.28 (m, 5H), 5.19 (d, J=12.5 Hz, 1H), 5.11 (d, J=12.5 Hz, 1H), 4.04-3.94 (m, 1H), 3.57-3.47 (m, 1H), 3.46-3.35 (m, 1H), 2.56 (quin, J=6.9 Hz, 1H), 1.89-1.76 (m, 1H), 1.59-1.29 (m, 5H), 1.23 (d, J=6.9 Hz, 3H).

Intermediate 26B rac-(S)-2-((S)-tetrahydro-2H-pyran-2-yl)propanoic acid

To a solution of rac-(S)—(S)-2-(tetrahydro-pyran-2-yl)-propionic acid benzyl ester (39 mg, 0.16 mmol, 1.0 eq) in methanol (5 mL) under N$_2$ was added palladium on charcoal 10% (17 mg, 0.016 mmol, 0.1 eq). The solution was degassed, flushed with H$_2$ and stirred at room temperature for 2 hours. The reaction mixture was then filtered on diatomaceous earth and the filtrate was concentrated in vacuo to provide the title compound (24 mg, 97%) which was used directly in the next step without further purification.

Cores

Core 1 rac-(2R,3S,4R,5R)-tert-butyl 3-(tert-butyl)-4-nitro-5-phenylpyrrolidine-2-carboxylate Core 1A (E)-tert-butyl 2-(benzylideneamino)acetate A mixture of glycine tert-butyl ester hydrochloride (6.95 g, 41.5 mmol) and magnesium sulfate (5.67 g, 47.1 mmol) in CH$_2$Cl$_2$ (60 mL) was treated with triethylamine (5.78 mL, 41.5 mmol), stirred for 15 minutes, treated with benzaldehyde (3.82 mL, 37.7 mmol) and stirred at room temperature overnight. The mixture was filtered to remove the solids and the solids were washed with CH$_2$Cl$_2$. The combined filtrates were washed with water (20 mL). The layers were separated and the aqueous layer was extracted with CH$_2$Cl$_2$ (~15 mL). The combined CH$_2$Cl$_2$ layers were dried (MgSO$_4$), filtered and concentrated (room temperature water bath) to provide the title compound. $^1$H NMR (400 MHz, CDCl$_3$) δ ppm 8.27 (s, 1H), 7.80-7.76 (m, 2H), 7.47-7.37 (m, 3H), 4.31 (s, 2H), 1.50 (s, 9H); MS (ESI+) m/z 220 (M+H)$^+$.

Core 1B rac-(2R,3S,4R,5R)-tert-butyl 3-(tert-butyl)-4-nitro-5-phenylpyrrolidine-2-carboxylate A solution of (E)-tert-butyl 2-(benzylideneamino)acetate (3.23 g, 14.75 mmol) in tetrahydrofuran (30 mL) under N$_2$ was cooled to −78° C., treated with 1.5 M lithium bromide in tetrahydrofuran (14.75 mL, 22.12 mmol), treated with a solution of (E)-3,3-dimethyl-1-nitrobut-1-ene (2 g, 15.49 mmol) in tetrahydrofuran (20 mL), treated dropwise with 1,8-diazabicyclo[5.4.0]undec-7-ene (3.11 mL, 20.65 mmol), and stirred overnight, allowing the mixture to slowly warm to room temperature. The mixture was diluted with methyl tert-butyl ether (~150 mL) and washed with 10% aqueous KH$_2$PO$_4$ solution (30 mL). A solid present in the mixture was isolated by filtration and discarded. The methyl tert-butyl ether layer was isolated, washed with more 10% aqueous KH$_2$PO$_4$ solution, washed with brine, dried (MgSO$_4$), filtered and concentrated. The residue was treated with heptanes. The resulting solid was collected by filtration. The solid was treated with methyl tert-butyl ether (~30 mL) and heptanes (30 mL) and was heated to dissolve the majority of solid and boil off the methyl tert-butyl ether. The heptane solution was allowed to stand at room temperature for 30 minutes. The material was collected by filtration, washed with heptanes, and dried under vacuum with heating (70° C.) for 30 minutes to provide the desired product (1.09 g). The two filtrates from above were combined, concentrated, dissolved in CH$_2$Cl$_2$, treated with silica gel (8 g) and concentrated to dryness. The silica gel suspension was chromatographed on silica gel eluting with a gradient of 10 to 30% ethyl acetate in heptane to provide additional desired product (0.67 g). Total yield of desired product was 1.76 g. $^1$H NMR (400 MHz, DMSO-d$_6$) δ ppm 7.42-7.37 (m, 2H), 7.35-7.24 (m, 3H), 5.43 (dd, J=6.4, 2.9 Hz, 1H), 4.46 (dd, J=10.5, 6.5 Hz, 1H), 3.66-3.61 (m, 1H), 3.38 (t, J=9.8 Hz, 1H), 2.81 (dd, J=7.4, 2.9 Hz, 1H), 1.48 (s, 9H), 0.98 (s, 9H); MS (ESI+) m/z 349 (M+H)+.

Core 2 rac-(2R,3S,4R,5R)-ethyl 3-(tert-butyl)-4-nitro-5-phenylpyrrolidine-2-carboxylate Core 2A (E)-ethyl 2-(benzylideneamino)acetate To a mixture of glycine ethyl ester hydrochloride (7.23 g, 51.8 mmol) and magnesium sulfate (7.09 g, 58.9 mmol) in dichloromethane (80 mL) was added triethylamine (7.22 mL, 51.8 mmol). The mixture was stirred at ambient temperature for 20 minutes, and benzaldehyde (4.79 mL, 47.1 mmol) was added dropwise. The mixture was stirred overnight. The reaction mixture was filtered and the solid was washed with dichloromethane (20 mL×2). The combined organic layers were washed with brine, dried over MgSO$_4$, filtered and concentrated to provide (E)-ethyl 2-(benzylideneamino)acetate 8.2 g, (91% yield). $^1$H NMR (400 MHz, CDCl$_3$) δ ppm 8.30 (s, 1H), 7.83-7.71 (m, 2H), 7.48-7.37 (m, 2H), 4.40 (d, J=J=1.4 Hz, 2H), 4.24 (q, J=J=7.1 Hz, 2H), 1.30 (t, J=J=7.1 Hz, 3H); MS (ESI+) m/z 292.1 (M+H)+.

Core 2B rac-(2R,3S,4R,5R)-ethyl 3-(tert-butyl)-4-nitro-5-phenylpyrrolidine-2-carboxylate To a solution of Core 2A (1.0 g, 5.23 mmol) and (E)-3,3-dimethyl-1-nitrobut-1-ene (0.810 g, 6.28 mmol) in toluene (30 mL) cooled in an ice-bath was added acetyl(oxo)silver (1.309 g, 7.84 mmol) and 3A molecular sieves. Triethylamine (1.458 mL, 10.46 mmol) was added slowly to the well stirred reaction mixture. After stirring at 0° C. for 10 minutes, the reaction mixture was allowed to warm to ambient temperature and was stirred for another 4 hours. Saturated aqueous ammonium chloride was added, the precipitate was filtered off and the residue was extracted with ether. The combined organic fractions were dried over MgSO$_4$, filtered, concentrated, and purified by chromatography on 40 g silica gel cartridge, eluting with ethyl acetate in heptane, 0-40% gradient to provide the title compound (1.6 g, 95% yield). $^1$H NMR (400 MHz, CDCl$_3$) δ ppm 7.39-7.26 (m, 5H), 5.12 (dd, J=J=6.0, 2.5 Hz, 1H), 4.44 (d, J=J=5.7 Hz, 1H), 4.31 (q, J=J=7.2 Hz, 2H), 3.81 (d, J=J=7.1 Hz, 1H), 3.30 (s, 1H), 2.95 (dd, J=J=7.1, 2.5 Hz, 1H), 1.34 (t, J=J=7.2 Hz, 3H), 1.06 (s, 9H); MS (ESI+) m/z 321 (M+H)+.

Core 3 rac-(2R,3S,4R,5R)-ethyl 3-(tert-butyl)-5-(2-methoxyphenyl)-4-nitropyrrolidine-2-carboxylate Core 3A (E)-ethyl 2-((2-methoxybenzylidene)amino)acetate To a mixture of ethyl 2-aminoacetate hydrochloride (10.76 g, 77.12 mmol) and magnesium sulfate (10.61 g, 88.2 mmol) in dichloromethane (100 mL) was added triethylamine (11.2 mL, 80.8 mmol). The mixture was stirred at room temperature for 20 minutes and 2-methoxybenzaldehyde (10.0 g, 73.45 mmol) was added dropwise. The resulting mixture was stirred at room temperature overnight. The solid was filtered off and washed with dichloromethane (300 mL). The combined filtrate was washed with water (150 mL) and brine (150 mL), dried over magnesium sulfate, filtered and concentrated to provide the title compound (E)-ethyl 2-((2-methoxybenzylidene)amino)acetate (16 g, 50.60 mmol, 68.9% yield). $^1$H NMR (400 MHz, CDCl$_3$) δ ppm 8.73 (s, 1H), 8.01 (d, J=8.0 Hz, 1H), 7.37-7.44 (m, 1H), 6.89-7.00 (m, 2H), 4.40 (s, 2H), 4.20-4.26 (m, 2H), 3.85 (s, 3H), 1.28-1.31 (m, 3H).

Core 3B rac-(2R,3S,4R,5R)-ethyl 3-(tert-butyl)-5-(2-methoxyphenyl)-4-nitropyrrolidine-2-carboxylate To a solution of (E)-ethyl 2-((2-methoxybenzylidene)amino)acetate (26.72 g, 120.94 mmol) and lithium bromide (13.90 g, 131.02 mmol) in tetrahydrofuran (220 mL) at −78° C. was added (E)-3,3-dimethyl-1-nitrobut-1-ene (13.0 g, 110.78 mmol) in tetrahydrofuran (20 mL) and DBU (1,8-diazabicyclo[5.4.0]undec-7-ene, 22.6 mL, 151.18 mmol) dropwise. The mixture was stirred at −78° C. for 2.5 hours and quenched with saturated aqueous ammonium chloride (100 mL), extracted with ethyl acetate (2×150 mL), washed with brine (2×150 mL), dried over sodium sulfate, filtered and concentrated. The residue was triturated with petroleum ether (100 mL). The solid was collected by filtration and dried in vacuo to provide the title compound rac-(2R,3S,4R,5R)-ethyl 3-(tert-butyl)-5-(2-methoxyphenyl)-4-nitropyrrolidine-2-carboxylate (10.3 g, 29.43 mmol, 28.3% yield). $^1$H NMR (400 MHz, CDCl$_3$) δ ppm 7.22-7.28 (m, 2H), 6.86-6.95 (m, 2H), 5.33-5.35 (m, 1H), 4.56 (s, 1H), 4.30-4.32 (m, 2H), 3.89 (s, 3H), 3.77 (d, J=8.0 Hz, 1H), 3.36 (d, J=7.2 Hz, 1H), 2.88-2.90 (m, 1H), 1.34 (d, J=7.2 Hz, 3H), 1.05 (s, 9H); LC-MS (ESI+) m/z 351 (M+H)+.

Core 4 rac-(2R,3S,4R,5R)-benzyl 3-(tert-butyl)-4-nitro-5-phenylpyrrolidine-2-carboxylate Core 4A (E)-benzyl 2-(benzylideneamino)acetate To a mixture of benzyl 2-aminoacetate hydrochloride (CAS#2462-31-9) (5 g, 21.00 mmol) and magnesium sulfate (3.16 g, 26.2 mmol) in dichloromethane (80 mL) was added triethylamine (3.22 mL, 23.10 mmol). The mixture was stirred for 20 minutes, benzaldehyde (2.348 mL, 23.10 mmol) was added dropwise, and the mixture was stirred at ambient temperature overnight. The mixture was filtered and the solid was washed with dichloromethane. The combined organic layers were washed with brine, dried over MgSO$_4$, filtered, and concentrated to yield (E)-benzyl 2-(benzylideneamino)acetate (5.3 g, 100% yield). $^1$H NMR (400 MHz, CDCl$_3$) δ ppm 8.28 (s, 1H), 7.84-7.70 (m, 2H), 7.48-7.26 (m, 8H), 5.21 (s, 2H), 4.44 (d, J=J=1.3 Hz, 2H); MS (ESI+) m/z 254 (M+H)+.

Core 4B rac-(2R,3S,4R,5R)-benzyl 3-(tert-butyl)-4-nitro-5-phenylpyrrolidine-2-carboxylate The title compound was synthesized with the same procedure as Core 1B using Core 4A as starting material. LC/MS (ESI+) m/z 378.37 (M+H)+.

Core 5 rac-(2R,3S,4R,5R)-ethyl 3-(tert-butyl)-5-(2-(dimethylamino)pyridin-3-yl)-4-nitropyrrolidine-2-carboxylate

Core 5A

2-(dimethylamino)nicotinaldehyde

Dimethylamine (aqueous solution, 10 mL, 79 mmol) was diluted with 10 mL of methanol and 2-chloronicotinaldehyde (5.0 g, 35.3 mmol) was added all at once. The reaction mixture was heated to 55° C. for 24 hours and another 10 mL of dimethylamine solution was added. After an additional 24 hours, the starting material had been consumed. The reaction mixture was cooled to room temperature, diluted with saturated aqueous ammonium chloride and extracted with dichloromethane. The combined extracts were concentrated and purified via flash chromatography, eluting with 0-20% ethyl acetate/heptanes over 20 minutes on an 80 g silica gel column. The desired product was obtained (3.9988 g, 75%). $^1$H NMR (501 MHz, CDCl$_3$) δ ppm 9.96 (s, 1H), 8.31 (dd, J=J=4.6, 2.0 Hz, 1H), 7.94 (dd, J=J=7.6, 2.0 Hz, 1H), 6.77 (dd, J=J=7.6, 4.6 Hz, 1H), 3.13 (s, 6H); LC-MS (ESI+) m/z 151.1 (M+H)+.

Core 5B

(E)-ethyl 2-(((2-(dimethylamino)pyridin-3-yl)methylene)amino)acetate

Ethyl 2-aminoacetate hydrochloride (3.72 g, 26.6 mmol) and magnesium sulfate (6.41 g, 53.3 mmol) were suspended in dichloromethane (44.4 mL). The suspension was treated with 2-(dimethylamino)nicotinaldehyde (4 g, 26.6 mmol) and triethylamine (3.71 mL, 26.6 mmol) and the mixture was stirred at room temperature for 16 hours. The solid material was removed via filtration and the filtrate was washed with water, dried over sodium sulfate, filtered and concentrated to provide the crude imine (5.76 g, 92%), which was used without additional purification. $^1$H NMR (400 MHz, CDCl$_3$) δ ppm 8.42-8.37 (m, 1H), 8.26 (dd, J=4.8, 2.0 Hz, 1H), 8.06 (dd, J=7.6, 1.9 Hz, 1H), 6.84 (ddd, J=7.6, 4.8, 0.6 Hz, 1H), 4.40 (d, J=1.3 Hz, 2H), 4.23 (q, J=7.1 Hz, 2H), 2.97 (s, 6H), 1.29 (t, J=7.1 Hz, 3H).

Core 5C rac-(2R,3S,4R,5R)-ethyl 3-(tert-butyl)-5-(2-(dimethylamino)pyridin-3-yl)-4-nitropyrrolidine-2-carboxylate (E)-Ethyl 2-(((2-(dimethylamino)pyridin-3-yl)methylene)amino)acetate (3.31 g, 14.07 mmol) was dissolved in 60 mL of tetrahydrofuran. The resulting solution was cooled in an acetone-dry ice bath to −78° C. before adding (E)-3,3-dimethyl-1-nitrobut-1-ene (1.58 g, 12.23 mmol), and lithium bromide (10.60 mL, 15.90 mmol). 2,3,4,6,7,8,9,10-Octahydropyrimido[1,2-a]azepine (2.104 mL, 14.07 mmol) was added dropwise via syringe, and the resulting yellow mixture was stirred at −78° C. for 2 hours then warmed to ambient temperature before quenching with saturated aqueous ammonium chloride (30 mL). The mixture was extracted with 3×15 mL of methyl tert-butyl ether and concentrated in vacuo to provide a crude residue, which was purified via flash chromatography, eluting with 0:100 to 30:70 ethyl acetate:heptanes over 20 minutes on an 80 g silica gel column to provide 2.20 g of the title compound. $^1$H NMR (501 MHz, CDCl$_3$) δ ppm 8.30 (dd, J=4.8, 1.8 Hz, 1H), 7.62 (ddd, J=7.6, 1.8, 0.8 Hz, 1H), 6.99 (dd, J=7.7, 4.8 Hz, 1H), 5.48 (dd, J=5.7, 2.4 Hz, 1H), 4.62 (dd, J=12.3, 5.7 Hz, 1H), 4.31 (qd, J=7.2, 1.6 Hz, 2H), 3.80 (dd, J=9.7, 7.1 Hz, 1H), 3.18 (t, J=11.2 Hz, 1H), 2.94-2.90 (m, 1H), 2.79 (s, 6H), 1.34 (t, J=7.1 Hz, 3H), 1.07 (s, 10H); MS (ESI+) m/z 365.2 (M+H)+.

Core 6

(2S,3R,4S,5S)-tert-butyl 3-(tert-butyl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.583 g, 0.774 mmol)) and copper (I) triflate dimer, benzene complex (0.127 g, 0.252 mmol)) were dissolved in tetrahydrofuran (60 mL) that had been sparged with a nitrogen stream for 0.5 hour. The resulting mixture was stirred for 1 hour at 25° C. (continued nitrogen sparge), and (E)-tert-butyl 2-(benzylideneamino)acetate (Core 1A, 16.98 g, 77 mmol) was added as a solution in 4 mL of tetrahydrofuran and the resulting solution was cooled to <5° C. in an ice-water bath. Potassium 2-methylpropan-2-olate (0.134 g, 1.20 mmol) was added dropwise, followed by addition of (E)-3,3-dimethyl-1-nitrobut-1-ene (5 g, 38.7 mmol) over 10 minutes, maintaining a temperature less than 7° C. The reaction mixture was stirred for 45 minutes at 0° C. The reaction was quenched with 150 mL of saturated aqueous ammonium chloride, 20 mL of ethyl ether was added and the mixture was warmed to 15° C. The ether layer was separated, washed with saturated aqueous ammonium chloride (2×150 mL) and brine (200 mL), dried over Na$_2$SO$_4$ (45 g), filtered, and then concentrated to provide (2S,3R,4S,5S)-tert-butyl 3-(tert-butyl)-4-nitro-5-phenylpyrrolidine-2-carboxylate. The material was diluted with n-heptane (150 mL) at 15° C. for 10 hour, then filtered and the filter cake was dried to provide (2S,3R,4S,5S)-tert-butyl 3-(tert-butyl)-4-nitro-5-phenylpyrrolidine-2-carboxylate (9 g, 25.8 mmol, 71.1% yield). $^1$H NMR (400 MHz, CDCl$_3$) δ ppm 7.36-7.30 (m, 5H), 5.13 (dd, J=2.2, 5.7 Hz, 1H), 4.44 (d, J=5.3 Hz, 1H), 3.72 (d, J=6.6 Hz, 1H), 3.43-3.23 (m, 1H), 2.88 (dd, J=2.2, 7.1 Hz, 1H), 1.55 (s, 9H), 1.07 (s, 9H).

Core 7

(2S,3R,4S,5S)-ethyl 3-(tert-butyl)-4-nitro-5-phenylpyrrolidine-2-carboxylate

Core 7A

(E)-ethyl 2-(benzylideneamino)acetate

Ethyl 2-aminoacetate hydrochloride (30 g, 215 mmol) and magnesium sulfate (51.7 g, 430 mmol) were stirred in dichloromethane (358 mL) at ambient temperature, and triethylamine (30.0 mL, 215 mmol) was added. The resulting suspension was stirred for 5 minutes and benzaldehyde (21.78 mL, 215 mmol) was added dropwise via syringe. The mixture was then stirred at ambient temperature for 16 hours. The solid material was removed via filtration through a fritted funnel, and the filter cake was washed with 20 mL of dichloromethane. The filtrate was washed with 2×20 mL of water, dried over sodium sulfate, filtered, and concentrated to provide the title compound. $^1$H NMR (501 MHz, CDCl$_3$) δ ppm 8.30 (d, J=1.4 Hz, 1H), 7.82-7.74 (m, 2H), 7.50-7.36 (m, 3H), 4.40 (d, J=1.3 Hz, 2H), 4.24 (q, J=7.2 Hz, 2H), 1.30 (t, J=7.2 Hz, 3H).

Core 7B (2S,3R,4S,5S)-ethyl 3-(tert-butyl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (2.98 g, 3.96 mmol) and copper (I) triflate dimer, benzene complex (0.859 g, 1.707 mmol; 90% technical grade, Aldrich) were dissolved in tetrahydrofuran (697 mL) that had been sparged with a nitrogen stream for 2 hours. The resulting mixture was stirred for 90 minutes at ambient temperature, at which point the flask was cooled to an internal temperature below 5° C. (E)-ethyl 2-(benzylideneamino)acetate (73.3 g, 383 mmol) was added in one portion via syringe. Potassium 2-methylpropan-2-olate (2.73 mL, 2.73 mmol, 1 M solution in tetrahydrofuran) was added dropwise, followed by addition of (E)-3,3-dimethyl-1-nitrobut-1-ene (45 g, 348 mmol) neat over 25 minutes via syringe, maintaining an internal temperature <10° C. After the addition was complete, the reaction was stirred for an additional 5 minutes at the same temperature, at which point LC-MS showed complete conversion of the starting nitroalkene. The reaction mixture was diluted with 300 mL of methyl tert-butyl ether and stirred with 300 mL of saturated aqueous ammonium chloride at ambient temperature for 15 minutes. The layers were separated, and the organic layer was washed with saturated aqueous ammonium chloride and brine and dried over sodium sulfate. After filtration, the organic extracts were concentrated in vacuo to provide a crude residue (140 g), which was precipitated from 800 mL of heptanes. The resulting solid was removed via filtration using a fritted funnel, washed with 200 mL of cold heptanes, and dried to constant weight in a vacuum oven to provide 72.5 g of the title compound. $^1$H NMR (400 MHz, CDCl$_3$) δ ppm 7.37-7.18 (m, 5H), 5.13 (dd, J=6.0, 2.5 Hz, 1H), 4.45 (dd, J=12.4, 6.0 Hz, 1H), 4.32 (qd, J=7.2, 1.2 Hz, 2H), 3.82 (dd, J=9.7, 7.1 Hz, 1H), 3.30 (dd, J=12.3, 9.8 Hz, 1H), 2.96 (dd, J=7.2, 2.5 Hz, 1H), 1.35 (t, J=7.1 Hz, 3H), 1.06 (s, 9H); MS (ESI+) m/z 321.1 (M+H)$^+$; [α]$^{24.8}$=+16.1° (c=1, methanol).

Core 8

(2S,3R,4S,5S)-ethyl 3-(tert-butyl)-5-(2-isopropylphenyl)-4-nitropyrrolidine-2-carboxylate Core 8A (E)-ethyl 2-((2-isopropylbenzylidene)amino)acetate Ethyl 2-aminoacetate hydrochloride (5.02 g, 36.0 mmol) and magnesium sulfate (5.20 g, 43.2 mmol) were suspended in dichloromethane (45 mL) and treated with triethylamine (9.9 mL, 71.0 mmol). The heterogeneous white mixture was stirred for 20 minutes and was treated dropwise with 2-isopropylbenzaldehyde (5 g, 33.7 mmol), forming a yellow heterogeneous mixture. The reaction mixture was stirred at room temperature for 3 days. The mixture was filtered (fritted glass funnel), and the filter pad was washed with copious amount of CH$_2$Cl$_2$. The filtrates were washed twice with water and once with brine, dried over Na$_2$SO$_4$, filtered, and concentrated in vacuo to yield the title compound, 7.066 g (90% yield). $^1$H NMR (400 MHz, CDCl$_3$) δ ppm 8.73 (m, 1H), 7.94 (dd, J=J=7.9, 1.5 Hz, 1H), 7.42 (m, 1H), 7.35 (dd, J=J=7.9, 1.4 Hz, 1H), 7.24 (m, 1H), 4.44 (d, J=J=1.4 Hz, 2H), 4.26 (q, J=J=7.1 Hz, 2H), 3.53 (hept, J=J=6.8 Hz, 1H), 1.34-1.29 (m, 9H); MS (ESI$^+$) m/z 234.1 (M+H)$^+$.

Core 8B (2S,3R,4S,5S)-ethyl 3-(tert-butyl)-5-(2-isopropylphenyl)-4-nitropyrrolidine-2-carboxylate Tetrahydrofuran (30 mL) was sparged with nitrogen for 75 minutes, and copper(I) triflate dimer, benzene complex (0.033 g, 0.065 mmol) and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl) iron (0.098 g, 0.129 mmol) were added. The mixture turned medium brown-orange and was stirred at room temperature for 1 hour. It was then cooled to <5° C. and treated dropwise with a solution of (E)-ethyl 2-((2-isopropylbenzylidene) amino)acetate (4.15 g, 17.80 mmol) in 8 mL tetrahydrofuran, followed by dropwise addition of potassium 2-methylpropan-2-olate (1 M in tetrahydrofuran; 0.1 mL, 0.100 mmol), keeping the temperature <5° C. Neat (E)-3,3-dimethyl-1-nitrobut-1-ene (2.09 g, 16.18 mmol) was added dropwise over about 10 minutes to keep the temperature <10° C. After completion of the addition, the reaction continued to stir in the ice bath for 25 minutes. The reaction mixture was then quenched with 25 mL of saturated aqueous NH$_4$Cl solution and warmed up to room temperature. It was diluted with methyl tert-butyl ether and washed twice with saturated aqueous NH$_4$Cl solution and once with brine. The organic layer was dried over Na$_2$SO$_4$, filtered, and concentrated in vacuo. Silica gel chromatography, eluting with 10 to 50% ethyl acetate-heptanes, afforded the title compound, 1.902 g, (32% yield). $^1$H NMR (400 MHz, DMSO-d$_6$) δ ppm 7.42-7.34 (m, 1H), 7.30-7.17 (m, 2H), 7.08 (ddd, J=J=7.5, 6.9, 1.7 Hz, 1H), 5.08 (dd, J=J=6.9, 3.6 Hz, 1H), 4.77 (d, J=J=6.9 Hz, 1H), 4.23 (q, J=J=7.1 Hz, 2H), 3.77 (d, J=J=7.6 Hz, 1H), 3.25 (br s, 1H), 3.21-3.06 (m, 2H), 1.33-1.14 (m, 9H), 0.98 (s, 9H); MS (ESI$^+$) m/z 363.1 (M+H)$^+$.

Core 9

(2S,3R,4S,5S)-tert-butyl 3-(tert-butyl)-5-(2-isopropylphenyl)-4-nitropyrrolidine-2-carboxylate Core 9A (E)-tert-butyl 2-((2-isopropylbenzylidene)amino)acetate To a stirred suspension of tert-butyl 2-aminoacetate hydrochloride (2.55 g, 14.74 mmol) and magnesium sulfate (3.55 g, 29.5 mmol) in anhydrous CH$_2$Cl$_2$ (50 mL) at room temperature was slowly added triethylamine (2.158 mL, 15.48 mmol). The mixture was stirred for 15 minutes, treated with 2-isopropylbenzaldehyde (2.3 g, 14.74 mmol), and stirred overnight. The solid material was removed via filtration and the filtrate was washed with water (quick wash twice) and brine, then dried over sodium sulfate, filtered and concentrated to provide (E)-tert-butyl 2-((2-isopropylbenzylidene)amino)acetate (3.85 g, 14.74 mmol, 100% yield). $^1$H NMR (400 MHz, DMSO-$d_6$) δ ppm 8.68 (s, 1H), 7.75 (dd, J=7.8, 1.4 Hz, 1H), 7.44-7.32 (m, 2H), 7.21 (ddd, J=8.1, 7.0, 1.7 Hz, 1H), 4.30 (d, J=1.2 Hz, 2H), 3.58 (hept, J=6.8 Hz, 1H), 1.40 (s, 9H), 1.24-1.15 (m, 6H); MS (DCI+) m/z 262.1 (M+H)$^+$.

Core 9B (2S,3R,4S,5S)-tert-butyl 3-(tert-butyl)-5-(2-isopropylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.075 g, 0.100 mmol) and copper (I) triflate dimer, benzene complex (0.019 g, 0.038 mmol) were dissolved in tetrahydrofuran (11.83 mL) that had been sparged with an nitrogen stream for 2 hours. The resulting mixture was stirred for 1.5 hour at room temperature, and (E)-tert-butyl 2-((2-isopropylbenzylidene) amino)acetate (2.01 g, 7.69 mmol) neat was added after cooling to <5° C. in an ice-water bath. Potassium 2-methylpropan-2-olate (1 M in tetrahydrofuran, 0.077 mL, 0.077 mmol) was added drop wise, followed by addition of (E)-3,3-dimethyl-1-nitrobut-1-ene (0.993 g, 7.69 mmol) neat over 25 minutes, maintaining an internal temperature <10° C. After the addition was complete, the reaction mixture was stirred for 15 minutes at the same temperature. The reaction mixture was diluted with methyl tert-butyl ether (60 mL) and stirred with 40 mL of saturated aqueous ammonium chloride at room temperature for 15 minutes. The organic layer was separated and washed with saturated aqueous sodium bicarbonate and brine, dried over sodium sulfate, filtered, and concentrated. The residue was purified by flash chromatography (0 to 30% ethyl acetate in heptane) to provide (2S,3R,4S,5S)-tert-butyl 3-(tert-butyl)-5-(2-isopropylphenyl)-4-nitropyrrolidine-2-carboxylate (2.48 g, 6.35 mmol, 83% yield). $^1$H NMR (501 MHz, DMSO-$d_6$) δ ppm 7.35 (dd, J=7.9, 1.4 Hz, 1H), 7.31-7.18 (m, 2H), 7.10 (ddd, J=8.5, 7.3, 1.5 Hz, 1H), 5.08 (dd, J=7.0, 3.6 Hz, 1H), 4.70 (dd, J=8.5, 6.9 Hz, 1H), 3.61 (t, J=7.7 Hz, 1H), 3.40 (t, J=8.1 Hz, 1H), 3.10 (hept, J=6.8 Hz, 1H), 3.00 (dd, J=7.8, 3.5 Hz, 1H), 1.47 (s, 9H), 1.28 (d, J=6.8 Hz, 3H), 1.16 (d, J=6.7 Hz, 3H), 0.95 (s, 9H); MS (ESI$^+$)m/z 390.9 (M+H)$^+$.

Core 10

(2S,3R,4S,5S)-ethyl 3-(tert-butyl)-4-nitro-5-(o-tolyl) pyrrolidine-2-carboxylate Core 10A (E)-ethyl 2-((2-methylbenzylidene)amino)acetate Ethyl 2-aminoacetate hydrochloride (3.97 g, 28.5 mmol) and magnesium sulfate (3.43 g, 28.5 mmol) were stirred in dichloromethane (43.1 mL) at ambient temperature, and triethylamine (3.97 mL, 28.5 mmol) was added. The mixture was stirred for 5 minutes and 2-methylbenzaldehyde (2.97 mL, 25.9 mmol) was added dropwise. The mixture was stirred at ambient temperature for 16 hours. The solid material was filtered through a disposable plastic frit and washed with dichloromethane. The organic layer was washed with 30 mL of water, dried over sodium sulfate, filtered, and concentrated. $^1$H NMR (500 MHz, CDCl$_3$) δ ppm 8.63 (d, J=J=1.4 Hz, 1H), 7.96 (dd, J=J=7.7, 1.4 Hz, 1H), 7.35 (td, J=J=7.5, 1.5 Hz, 1H), 7.32-7.25 (m, 1H), 7.25-7.18 (m, 1H), 4.45 (d, J=J=1.4 Hz, 2H), 4.28 (q, J=J=7.2 Hz, 2H), 2.55 (s, 3H), 1.34 (t, J=J=7.1 Hz, 3H); MS (ESI+) m/z 206 (M+H)$^+$.

Core 10B (2S,3R,4S,5S)-ethyl 3-(tert-butyl)-4-nitro-5-(o-tolyl) pyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.222 g, 0.294 mmol) and copper (I) triflate dimer, benzene complex (0.064 g, 0.127 mmol) were dissolved in tetrahydrofuran (51.7 mL) that had been sparged with a stream of nitrogen for 4 hours. The resulting mixture was stirred for 1.5 hours at ambient temperature, and (E)-ethyl 2-((2-methylbenzylidene)amino) acetate (5.31 g, 25.9 mmol) was added after cooling to <5° C. in an ice-water bath. Potassium 2-methylpropan-2-olate (1 M in THF, 0.203 mL, 0.203 mmol) was added dropwise, followed by addition of (E)-3,3-dimethyl-1-nitrobut-1-ene (3.51 g, 27.2 mmol) neat over 25 minutes, maintaining an internal temperature <10° C. After the addition was complete, the reaction was stirred for 90 minutes at the same temperature. The reaction mixture was diluted with methyl tert-butyl ether (100 mL) and stirred with 50 mL of saturated aqueous ammonium chloride at ambient temperature for 15 minutes. The organic layer was washed with saturated aqueous sodium bicarbonate and brine, dried over sodium sulfate, and filtered. The filtrate was concentrated to provide a crude residue, which was diluted with 80 mL of heptanes and the solvent was reduced in volume until a solid precipitated out. The mixture was cooled in an ice bath to <5° C. for 15 minutes, and the resulting solid was filtered, washed with 20 mL of heptanes, and dried to constant weight in a vacuum oven to provide (2S,3R,4S,5S)-ethyl 3-(tert-butyl)-4-nitro-5-(o-tolyl)pyrrolidine-2-carboxylate (4.85 g, 14.50 mmol, 56% yield). $^1$H NMR (501 MHz, CDCl$_3$) δ ppm 7.34-7.27 (m, 1H), 7.27-7.16 (m, 3H), 5.18 (dd, J=6.1, 2.6 Hz, 1H), 4.55 (dd, J=J=10.1, 5.9 Hz, 1H), 4.35 (qd, J=J=7.2, 1.2 Hz, 2H), 3.81 (t, J=J=7.1 Hz, 1H), 3.31 (s, 1H), 3.07 (dd, J=J=7.3, 2.6 Hz, 1H), 2.41 (s, 3H), 1.38 (t, J=J=7.1 Hz, 3H), 1.08 (s, 9H). MS (APCI+) m/z 335 (M+H)$^+$.

Core 11

(2S,3R,4S,5S)-ethyl 3-(tert-butyl)-5-(2-(dimethylamino)pyridin-3-yl)-4-nitropyrrolidine-2-carboxylate Core 11A (E)-ethyl 2-(((2-(dimethylamino)pyridin-3-yl)methylene)amino)acetate Ethyl 2-aminoacetate hydrochloride (6.08 g, 43.6 mmol) and magnesium sulfate (9.99 g, 83 mmol) were suspended in dichloromethane (69.1 mL) and the suspension was treated with 2-(dimethylamino)nicotinaldehyde (6.23 g, 41.5 mmol) and triethylamine (5.78 mL, 41.5 mmol). The mixture was stirred at ambient temperature for 16 hours. The solid material was removed via filtration and the filtrate was washed with water (2×20 mL), dried over sodium sulfate, filtered and concentrated to provide the title compound, which was used without additional purification. ¹H NMR (400 MHz, Chloroform-d) δ ppm 8.42-8.37 (m, 1H), 8.26 (dd, J=4.8, 2.0 Hz, 1H), 8.06 (dd, J=7.6, 1.9 Hz, 1H), 6.84 (ddd, J=7.6, 4.8, 0.6 Hz, 1H), 4.40 (d, J=1.3 Hz, 2H), 4.23 (q, J=7.1 Hz, 2H), 2.97 (s, 6H), 1.29 (t, J=7.1 Hz, 3H).

Core 11B (2S,3R,4S,5S)-ethyl 3-(tert-butyl)-5-(2-(dimethyl-amino)pyridin-3-yl)-4-nitropyrrolidine-2-carboxylate (2-(Bis(3,5-bis(trifluoromethyl)phenyl)phosphine)-3-((S)-4-isopropyl-4,5-dihydrooxazol-2-yl)cyclopenta-2,4-dien-1-yl)(cyclopenta-2,4-dien-1-yl)iron (0.317 g, 0.421 mmol) and copper (I) triflate dimer, benzene complex (0.091 g, 0.181 mmol) were dissolved in tetrahydrofuran (43.0 mL) that had been sparged with a stream of $N_2$ for 1 hour. The resulting mixture was stirred for 1 hour at ambient temperature. Core 11A (5.47 g, 23.23 mmol) was added in one portion as a solution in 3 mL of tetrahydrofuran and the flask was cooled to <5° C. in an ice-water bath. Potassium 2-methylpropan-2-olate (1 M in tetrahydrofuran, 0.290 mL, 0.290 mmol) was added dropwise, followed by addition of (E)-3,3-dimethyl-1-nitrobut-1-ene (2.5 g, 19.36 mmol) as a solution in 2 mL of tetrahydrofuran over 10 minutes, maintaining a temperature less than 7° C. The reaction mixture was assayed by LC/MS immediately after the addition of the nitroalkene, which showed complete conversion. The reaction was quenched with 5 mL of saturated aqueous ammonium chloride, warmed to ambient temperature, diluted with methyl tert-butyl ether (50 mL) and washed with saturated aqueous ammonium chloride (2×20 mL) then brine (20 mL) and dried over sodium sulfate. After filtration, the filtrate was concentrated in vacuo to provide a crude residue, which was chromatographed on a 120 g silica gel column with 10:90 to 100:0 methyl tert-butyl ether:heptanes over 20 minutes to provide 5.97 g of the title compound. ¹H NMR (501 MHz, Chloroform-d) δ ppm 8.30 (dd, J=4.8, 1.8 Hz, 1H), 7.62 (ddd, J=7.6, 1.8, 0.8 Hz, 1H), 6.99 (dd, J=7.7, 4.8 Hz, 1H), 5.48 (dd, J=5.7, 2.4 Hz, 1H), 4.62 (dd, J=12.3, 5.7 Hz, 1H), 4.31 (qd, J=7.2, 1.6 Hz, 2H), 3.80 (dd, J=9.7, 7.1 Hz, 1H), 3.18 (t, J=11.2 Hz, 1H), 2.94-2.90 (m, 1H), 2.79 (s, 6H), 1.34 (t, J=7.1 Hz, 3H), 1.07 (s, 10H); MS (ESI+) m/z 365.2 (M+H)⁺.

Core 12

(2S,3R,4S,5S)-ethyl 3-(tert-butyl)-5-(2-methoxy-pyridin-3-yl)-4-nitropyrrolidine-2-carboxylate Core 12A (E)-ethyl 2-(((2-methoxypyridin-3-yl)methylene)amino)acetate Ethyl 2-aminoacetate hydrochloride (14.50 g, 104 mmol) and magnesium sulfate (20.01 g, 166 mmol) were suspended in 130 mL of dichloromethane. A solution of 2-methoxynicotinaldehyde (11.4 g, 83 mmol) in 9 mL of dichloromethane was added to the stirring mixture, followed by addition of triethylamine (14.48 mL, 104 mmol) and the reaction mixture was stirred for 16 hours at ambient temperature. The solid material was removed via filtration and the filtrate was washed quickly with cold water (2×10 mL) and brine (10 mL), dried over sodium sulfate, filtered and concentrated to provide the crude imine, which was used without additional purification. ¹H NMR (500 MHz, DMSO-d₆) δ ppm 8.58 (d, J=1.6 Hz, 1H), 8.31 (dd, J=4.9, 2.0 Hz, 1H), 8.19 (dd, J=7.4, 2.0 Hz, 1H), 7.09 (ddd, J=7.4, 4.9, 0.7 Hz, 1H), 4.45 (d, J=1.4 Hz, 2H), 4.14 (q, J=7.2 Hz, 2H), 3.96 (s, 3H), 1.22 (t, J=7.1 Hz, 3H).

Core 12B (2S,3R,4S,5S)-ethyl 3-(tert-butyl)-5-(2-methoxy-pyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.642 g, 0.853 mmol) and copper (I) triflate dimer, benzene complex (0.185 g, 0.367 mmol) were dissolved in tetrahydrofuran (150 mL) that had been sparged with an $N_2$ stream for 4 hours. The resulting mixture was stirred for 1.5 hours ambient temperature, and (E)-ethyl 2-(((2-methoxypyridin-3-yl)methylene)amino)acetate (17.50 g, 79 mmol) was then added via syringe after cooling the flask to an internal temperature of <5° C. in an ice-water bath. Potassium 2-methylpropan-2-olate (1 M in tetrahydrofuran, 0.588 mL, 0.588 mmol) was added dropwise via syringe, followed by addition of (E)-3,3-dimethyl-1-nitrobut-1-ene (9.69 g, 75.0 mmol) neat via syringe over 25 minutes, maintaining an internal temperature <10° C. The reaction mixture was stirred for an additional 20 minutes at the same temperature, at which point LC-MS indicated complete consumption of the nitroalkene. The reaction mixture was diluted with methyl tert-butyl ether (300 mL) and stirred with 300 mL of saturated aqueous ammonium chloride at ambient temperature for 15 minutes. The layers were separated and the organic layer was washed with saturated aqueous sodium bicarbonate and brine, dried over sodium sulfate, filtered and concentrated to provide a crude residue, which was purified via silica gel chromatography, eluting with 0:100 to 50:50 ethyl acetate:heptanes over 30 minutes on a 330 g column to provide 17.5 g of the title compound. ¹H NMR (400 MHz, CDCl₃) δ ppm 8.13 (dd, J=5.0, 1.5 Hz, 1H), 7.62-7.34 (m, 1H), 6.96-6.71 (m, 1H), 5.36 (dt, J=5.7, 1.8 Hz, 1H), 4.54-4.38 (m, 1H), 4.41-4.25 (m, 2H), 4.04 (s, 3H), 3.82-3.65 (m, 1H), 3.28 (s, 1H), 2.93 (dt, J=7.3, 1.8 Hz, 1H), 1.37 (td, J=7.2, 1.2 Hz, 3H), 1.08 (s, 9H); MS (ESI+) m/z 352.1 (M+H)⁺.

Core 13

(2S,3R,4S,5S)-ethyl 3-(tert-butyl)-5-(2-isopropoxy-pyridin-3-yl)-4-nitropyrrolidine-2-carboxylate Core 13A (E)-ethyl 2-(((2-isopropoxypyridin-3-yl)methylene)amino)acetate Ethyl 2-aminoacetate hydrochloride (4.97 g, 35.6 mmol) and magnesium sulfate (6.86 g, 57.0 mmol) were suspended in dichloromethane (47.5 mL) and the suspension was treated with 2-isopropoxynicotinaldehyde (4.8 g, 28.5 mmol) and triethylamine (4.96 mL, 35.6 mmol). The mixture was stirred for 16 hours at room temperature. The solid material was removed via filtration and the filtrate was washed with water (twice) and brine, dried over sodium sulfate, filtered and concentrated to provide the crude (E)-ethyl 2-(((2-isopropoxypyridin-3-yl)methylene)amino)acetate (7.14 g, 28.5 mmol, 100% yield), which was used without additional purification. ¹H NMR (400 MHz, DMSO-d$_6$) δ ppm 8.51 (s, 1H), 8.25 (dd, J=4.9, 2.0 Hz, 1H), 8.13 (dd, J=7.5, 2.1 Hz, 1H), 7.00 (ddd, J=7.5, 4.9, 0.7 Hz, 1H), 5.34 (hept, J=6.2 Hz, 1H), 4.41 (d, J=1.3 Hz, 2H), 4.15-3.99 (m, 2H), 1.30 (d, J=6.2 Hz, 6H), 1.18 (t, J=7.1 Hz, 3H); MS (DCI+) m/z 251.0 (M+H)$^+$.

Core 13B (2S,3R,4S,5S)-ethyl 3-(tert-butyl)-5-(2-isopropoxypyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.141 g, 0.187 mmol) and copper (I) triflate dimer, benzene complex (0.036 g, 0.072 mmol) were dissolved in tetrahydrofuran (22.13 mL) that had been sparged with a nitrogen stream for 2 hours. The resulting mixture was stirred for 1.5 hours at room temperature, and neat (E)-ethyl 2-(((2-isopropoxypyridin-3-yl)methylene)amino)acetate (3.6 g, 14.38 mmol) was added after cooling to <5° C. in an ice-water bath. Potassium 2-methylpropan-2-olate (1 M in tetrahydrofuran, 0.144 mL, 0.144 mmol) was added drop wise, followed by addition of neat (E)-3,3-dimethyl-1-nitrobut-1-ene (1.858 g, 14.38 mmol) over 25 minutes, maintaining an internal temperature <10° C. After the addition was complete, the reaction mixture was stirred for 15 minutes at the same temperature. The reaction mixture was diluted with methyl tert-butyl ether (100 mL) and stirred with 75 mL of saturated aqueous ammonium chloride at room temperature for 15 minutes. The organic layer was separated and washed with saturated aqueous sodium bicarbonate solution and brine, dried over sodium sulfate, filtered, and concentrated. The residue was purified by flash chromatography (0 to 20% ethyl acetate in heptane) to provide title compound (2S,3R,4S,5S)-ethyl 3-(tert-butyl)-5-(2-isopropoxypyridin-3-yl)-4-nitropyrrolidine-2-carboxylate carboxylate (4.51 g, 11.89 mmol, 83% yield). $^1$H NMR (400 MHz, DMSO-d$_6$) δ ppm 8.04 (dd, J=5.0, 1.8 Hz, 1H), 7.64 (dt, J=7.4, 1.4 Hz, 1H), 6.90 (dd, J=7.3, 5.0 Hz, 1H), 5.33-5.19 (m, 2H), 4.41 (dd, J=9.5, 6.1 Hz, 1H), 4.19 (qd, J=7.1, 5.3 Hz, 2H), 3.77 (dd, J=8.4, 7.3 Hz, 1H), 3.55 (t, J=8.9 Hz, 1H), 2.92 (dd, J=7.3, 2.6 Hz, 1H), 1.32 (dd, J=13.6, 6.1 Hz, 6H), 1.23 (t, J=7.1 Hz, 3H), 0.95 (s, 9H); MS (ESI$^+$) m/z 380.0 (M+H)$^+$.

Core 14

(2S,3R,4S,5S)-ethyl 3-(tert-butyl)-5-(2-cyclopropylphenyl)-4-nitropyrrolidine-2-carboxylate Core 14A (E)-ethyl 2-((2-cyclopropylbenzylidene)amino)acetate Ethyl 2-aminoacetate hydrochloride (4.50 g, 32.2 mmol) and magnesium sulfate (6.21 g, 51.6 mmol) were suspended in dichloromethane (43.0 mL) and the suspension was treated with triethylamine (4.49 mL, 32.2 mmol). After 1 hour, 2-cyclopropylbenzaldehyde (3.77 g, 25.8 mmol) in 5 mL of dichloromethane was added and the reaction was stirred at room temperature for 16 hours. The solid material was removed via filtration and the filtrate was washed with water and brine, dried over sodium sulfate, filtered, and concentrated to provide (E)-ethyl 2-((2-cyclopropylbenzylidene)amino)acetate (5.68 g, 24.56 mmol, 95% yield), which was used in the next step without further purification.

$^1$H NMR (400 MHz, DMSO-d$_6$) δ ppm 8.92 (d, J=1.5 Hz, 1H), 7.81 (dd, J=7.8, 1.5 Hz, 1H), 7.35 (td, J=7.6, 1.5 Hz, 1H), 7.22 (td, J=7.6, 1.2 Hz, 1H), 7.05 (dd, J=7.8, 1.2 Hz, 1H), 4.45 (d, J=1.3 Hz, 2H), 4.13 (q, J=7.1 Hz, 2H), 2.33 (tt, J=8.5, 5.3 Hz, 1H), 1.21 (t, J=7.1 Hz, 3H), 1.03-0.90 (m, 2H), 0.75-0.63 (m, 2H); MS (ESI$^+$) m/z 232.1 (M+H)$^+$.

Core 14B (2S,3R,4S,5S)-ethyl 3-(tert-butyl)-5-(2-cyclopropylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.241 g, 0.319 mmol) and copper (I) triflate dimer, benzene complex (0.062 g, 0.123 mmol) were dissolved in tetrahydrofuran (63.0 mL) that had been sparged with an nitrogen stream for 2 hours. The resulting mixture was stirred for 1.5 hour at room temperature, and (E)-ethyl 2-((2-cyclopropylbenzylidene)amino)acetate (5.68 g, 24.56 mmol) in tetrahydrofuran (8 mL) was added after cooling to <5° C. in an ice-water bath. Potassium 2-methylpropan-2-olate (1 M in tetrahydrofuran, 0.246 mL, 0.246 mmol) was added drop wise, followed by addition of (E)-3,3-dimethyl-1-nitrobut-1-ene (3.17 g, 24.56 mmol) neat over 25 minutes, maintaining an internal temperature <10° C. After the addition was complete, the reaction was stirred for 15 minutes at the same temperature, diluted with methyl tert-butyl ether (100 mL) and stirred with 75 mL of saturated aqueous ammonium chloride at room temperature for 15 minutes. The organic layer was separated, washed with saturated aqueous sodium bicarbonate and brine, dried over sodium sulfate, and filtered. The filtrate was concentrated and purified by flash chromatography (0 to 30% ethyl acetate in heptane) to provide (2S,3R,4S,5S)-ethyl 3-(tert-butyl)-5-(2-cyclopropylphenyl)-4-nitropyrrolidine-2-carboxylate (6.85 g, 19.00 mmol, 77% yield). ee >97%. $^1$H NMR (501 MHz, DMSO-d$_6$) δ ppm 7.34 (dd, J=7.6, 1.5 Hz, 1H), 7.15 (dtd, J=25.3, 7.5, 1.6 Hz, 2H), 7.07-7.01 (m, 1H), 5.31 (dd, J=6.7, 3.1 Hz, 1H), 4.92 (dd, J=8.4, 6.6 Hz, 1H), 4.27-4.12 (m, 2H), 3.75 (t, J=7.7 Hz, 1H), 3.51 (t, J=8.1 Hz, 1H), 3.04 (dd, J=7.6, 3.1 Hz, 1H), 2.06 (tt, J=8.5, 5.4 Hz, 1H), 1.24 (t, J=7.1 Hz, 3H), 0.95 (s, 9H), 1.00-0.78 (m, 2H), 0.81-0.68 (m, 1H), 0.64-0.55 (m, 1H); MS (ESI$^+$) m/z 361.2 (M+H)$^+$.

Core 15

(2S,3R,4S,5S)-ethyl 3-(tert-butyl)-5-(2-(difluoromethoxy)phenyl)-4-nitropyrrolidine-2-carboxylate Core 15A (E)-ethyl 2-((2-(difluoromethoxy)benzylidene)amino)acetate Ethyl 2-aminoacetate hydrochloride (2.5 g, 17.91 mmol) and magnesium sulfate (2.156 g, 17.91 mmol) were suspended in dichloromethane (23 mL). Triethylamine (2.496 mL, 17.91 mmol) was added, and the reaction mixture was stirred for 1 hour at ambient temperature before addition of 2-(difluoromethoxy)benzaldehyde (2.57 g, 14.93 mmol). The reaction was stirred overnight at ambient temperature. The solid material was removed via filtration using a fritted funnel, and the filter cake was washed with dichloromethane (10 mL). The filtrate was quickly washed with 2×10 mL of water then 10 mL of brine and dried over sodium sulfate, filtered and concentrated to provide the title compound (3.07 g), which was used without additional purification. $^1$H NMR (501 MHz, Chloroform-d) δ ppm 8.64 (s, 1H), 8.12 (dd, J=7.8, 1.8 Hz, 1H), 7.45 (ddd, J=8.2, 7.4, 1.8 Hz, 1H), 7.34-7.23 (m, 1H), 7.15 (dq, J=8.2, 1.1 Hz, 1H), 6.58 (t, J=73.5 Hz, 1H), 4.43 (d, J=1.3 Hz, 2H), 4.27 (q, J=7.1 Hz, 2H), 1.31 (t, J=7.2 Hz, 3H).

Core 15B (2S,3R,4S,5S)-ethyl 3-(tert-butyl)-5-(2-(difluoromethoxy)phenyl)-4-nitropyrrolidine-2-carboxylate (2-(Bis(3,5-bis(trifluoromethyl)phenyl)phosphine)-3-((S)-4-isopropyl-4,5-dihydrooxazol-2-yl)cyclopenta-2,4-dien-1-yl)(cyclopenta-2,4-dien-1-yl)iron (0.126 g, 0.168 mmol) and copper (I) triflate dimer, benzene complex (0.037 g, 0.073 mmol) were dissolved in tetrahydrofuran (21.60 mL) that had been sparged with an $N_2$ stream for 20 minutes. The resulting solution was stirred for 1 hour at ambient temperature, and 4 Å molecular sieves (3 g, 9.72 mmol) were added, followed by addition of the (E)-ethyl 2-((2-(difluoromethoxy)benzylidene)amino)acetate (3 g, 11.66 mmol) as a solution in 3 mL of tetrahydrofuran and the resulting suspension was cooled to <5° C. in an ice-water bath. Potassium 2-methylpropan-2-olate (1 M in tetrahydrofuran, 0.117 mL, 0.117 mmol) was added dropwise, followed by addition of (E)-3,3-dimethyl-1-nitrobut-1-ene (1.255 g, 9.72 mmol) as a solution in 2 mL of tetrahydrofuran over 5 minutes, maintaining a temperature less than 8° C. The reaction mixture was assayed by LC-MS immediately after the addition of the nitroalkene, which showed complete consumption of the reagent. The reaction mixture was quenched with 5 mL of saturated aqueous ammonium chloride and 5 mL of water then stirred for 5 minutes at room temperature. The solids were removed via filtration through diatomaceous earth and the filtrate was diluted with methyl tert-butyl ether (30 mL). The layers were separated and the organic layer was washed with saturated aqueous ammonium chloride (2×20 mL) and brine (20 mL), and dried over sodium sulfate, filtered, and concentrated. Heptanes (30 mL) were added, and the resulting suspension was stirred vigorously at ambient temperature for 1 hour. The resulting solid was removed via filtration using a fritted funnel and dried to constant weight in a vacuum oven at 40° C. to provide 2.94 g of the title compound. $^1$H NMR (400 MHz, Chloroform-d) δ ppm 7.42-7.27 (m, 2H), 7.21 (td, J=7.6, 1.1 Hz, 1H), 7.07 (dd, J=8.1, 1.4 Hz, 1H), 6.57 (dd, J=76.4, 70.9 Hz, 1H), 5.30 (dd, J=5.8, 2.3 Hz, 1H), 4.61 (dd, J=12.6, 5.8 Hz, 1H), 4.32 (qd, J=7.2, 1.5 Hz, 2H), 3.80 (dd, J=9.8, 7.1 Hz, 1H), 3.27 (dd, J=12.6, 10.0 Hz, 1H), 2.95 (dd, J=7.1, 2.3 Hz, 1H), 1.35 (t, J=7.2 Hz, 3H), 1.05 (s, 9H); MS (ESI+) m/z 387.1 (M+H)$^+$.

Core 16

(2S,3R,4S,5S)-ethyl 3-(tert-butyl)-5-(2-(difluoromethoxy)pyridin-3-yl)-4-nitropyrrolidine-2-carboxylate Core 16A 3-bromo-2-(difluoromethoxy)pyridine 3-Bromopyridin-2-ol (13 g, 72.5 mmol) was dissolved in acetonitrile (362 mL). 2,2-Difluoro-2-(fluorosulfonyl)acetic acid (15.49 g, 87 mmol) and sodium sulfate (11.32 g, 80 mmol) were added. The mixture was stirred at room temperature for 16 hours, diluted with ethyl acetate, and the layers were separated. The aqueous layer was extracted with ethyl acetate and the combined extracts were washed with saturated aqueous sodium bicarbonate, water, and brine. The organics were dried over sodium sulfate, filtered, and concentrated to provide ~20 g crude product which was purified via flash column chromatography, eluting on a 120 g silica gel column with 0-15% methyl tert-butyl ether/heptane to provide the title compound, 3-bromo-2-(difluoromethoxy)pyridine (13.21 g, 59.0 mmol, 81% yield). $^1$H NMR (400 MHz, DMSO-$d_6$) δ ppm 8.36-8.13 (m, 2H), 7.71 (td, J=72.2, 1.2 Hz, 1H), 7.22 (ddd, J=7.8, 4.8, 1.1 Hz, 1H); MS (DCI+) m/z 225.8 (M+H)$^+$.

Core 16B methyl 2-(difluoromethoxy)nicotinate

To 3-bromo-2-(difluoromethoxy)pyridine (17.51 g, 78 mmol), Pd-dppf (Heraeus) (0.572 g, 0.782 mmol) in a 180 mL SS reactor was added methanol (50 mL) and triethylamine (20 mL, 143 mmol). The reactor was degassed with argon several times, filled with carbon monoxide and heated to 132° C. for 10 minutes at 119 psi CO. The heat was turned off and the pressure gauge setting was lowered. The reaction mixture was stirred overnight under CO gas while cooling down. HPLC indicated starting material was consumed. The mixture was concentrated and partitioned between water and ethyl acetate. The combined extracts were washed with brine, dried over sodium sulfate, filtered, and concentrated to provide the crude product methyl 2-(difluoromethoxy)nicotinate (15.3 g, 75.3 mmol, 96% yield) which was used without additional purification. $^1$H NMR (500 MHz, DMSO-$d_6$) δ ppm 8.45 (dd, J=4.9, 1.9 Hz, 1H), 8.31 (dd, J=7.6, 2.0 Hz, 1H), 7.93-7.55 (m, 1H), 7.39 (dd, J=7.6, 4.9 Hz, 1H), 3.85 (s, 3H).

Core 16C (2-(difluoromethoxy)pyridin-3-yl)methanol

Methyl 2-(difluoromethoxy)nicotinate (4.72 g, 23.23 mmol) was dissolved in 100 mL of tetrahydrofuran. After cooling to <5° C., a solution of lithium aluminum hydride (18.82 mL, 18.82 mmol) in tetrahydrofuran was added over 10 minutes, maintaining an internal temperature <10° C. HPLC and LC-MS showed complete conversion after 30 minutes. The reaction mixture was cooled to 0° C. and the reaction was quenched by the addition of 3 mL of acetone then diluted with ethyl acetate (100 mL) and stirred for 1 hour with 80 mL of saturated aqueous potassium sodium tartrate (Rochelle's salt) to provide two clear layers. The mixture was diluted with ethyl acetate and the layers were separated. The organic layer was washed with brine, dried over sodium sulfate, filtered, and concentrated to provide (2-(difluoromethoxy)pyridin-3-yl)methanol (4.07 g, 23.24 mmol, 100% yield). $^1$H NMR (501 MHz, DMSO-$d_6$) δ ppm 8.15-8.05 (m, 1H), 7.91 (ddt, J=7.3, 1.9, 1.0 Hz, 1H), 7.69 (t, J=73.0 Hz, 1H), 7.26 (dd, J=7.4, 4.9 Hz, 1H), 5.37 (t, J=5.6 Hz, 1H), 4.53-4.36 (m, 2H); MS (ESI$^+$) m/z 175.9 (M+H)$^+$.

Core 16D 2-(difluoromethoxy)nicotinaldehyde (2-(Difluoromethoxy)pyridin-3-yl)methanol (4.07 g, 23.24 mmol) was dissolved in dichloromethane (93 mL).

After cooling to <5° C. in an ice-water bath, Dess-Martin periodinane (11.83 g, 27.9 mmol) was added in portions, maintaining an internal temperature <20° C. After the addition was complete, the flask was warmed to room temperature for 15 minutes, at which point the reaction was complete. The mixture was diluted with 250 mL of methyl tert-butyl ether and stirred with saturated aqueous sodium bicarbonate (80 mL) and saturated sodium thiosulfate (80 mL) for 15 minutes at room temperature. The layers were separated and the aqueous layer was extracted with methyl tert-butyl ether (2×150 mL). The combined organic layer was washed with brine then concentrated and purified via flash column (0 to 20% ethyl acetate in heptanes) to provide the title compound, 2-(difluoromethoxy)nicotinaldehyde (2.38 g, 13.75 mmol, 59.2% yield). $^1$H NMR (501 MHz, DMSO-$d_6$) δ ppm 10.20 (s, 1H), 8.53 (dd, J=4.9, 2.0 Hz, 1H), 8.27 (dd, J=7.6, 2.0 Hz, 1H), 7.83 (t, J=73.0 Hz, 1H), 7.45 (ddd, J=7.6, 4.9, 0.8 Hz, 1H); MS (DCI+) m/z 190.9 (M+NH$^4$)$^+$.

Core 16E (E)-ethyl 2-(((2-(difluoromethoxy)pyridin-3-yl) methylene)amino)acetate Ethyl 2-aminoacetate hydrochloride (2.399 g, 17.18 mmol) and magnesium sulfate (3.31 g, 27.5 mmol) were suspended in dichloromethane (22.91 mL) and the suspension was treated with triethylamine (2.395 mL, 17.18 mmol). The mixture was stirred at room temperature for 1 hour, and 2-(difluoromethoxy)nicotinaldehyde (2.38 g, 13.75 mmol) in 5 mL of dichloromethane was added. The mixture was stirred at room temperature for 16 hours. Thin layer chromatography (30% ethyl acetate in heptane with 5% triethylamine), showed the reaction was complete. The solid material was removed via filtration and the filtrate was washed with water (quick wash twice) and brine, dried over sodium sulfate, filtered, and concentrated to provide (E)-ethyl 2-(((2-(difluoromethoxy)pyridin-3-yl)methylene) amino)acetate (3.5 g, 13.55 mmol, 99% yield). $^1$H NMR (501 MHz, DMSO-$d_6$) δ ppm 8.55 (dt, J=1.5, 0.9 Hz, 1H), 8.40-8.31 (m, 2H), 7.93-7.64 (m, 1H), 7.36 (ddd, J=7.6, 4.8, 0.7 Hz, 1H), 4.50 (d, J=1.4 Hz, 2H), 4.13 (q, J=7.1 Hz, 2H), 1.24-1.12 (t, J=7.1 Hz, 3H); MS (DCI+) m/z 259.0 (M+H)$^+$.

Core 16F (2S,3R,4S,5S)-ethyl 3-(tert-butyl)-5-(2-(difluoromethoxy)pyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.133 g, 0.176 mmol) and copper (I) triflate dimer, benzene complex (0.034 g, 0.068 mmol) were dissolved in tetrahydrofuran (tetrahydrofuran) (30 mL) that had been sparged with an N$_2$ stream for 4 hours. The resulting mixture was stirred for 1.5 hours at room temperature, and (E)-ethyl 2-(((2-(difluoromethoxy) pyridin-3-yl)methylene)amino)acetate (3.5 g, 13.55 mmol) in tetrahydrofuran (8 mL) was added after cooling to <5° C. in an ice-water bath. Potassium 2-methylpropan-2-olate (1 M in tetrahydrofuran, 0.136 mL, 0.136 mmol) was added dropwise, followed by addition of (E)-3,3-dimethyl-1-nitrobut-1-ene (1.751 g, 13.55 mmol) neat over 25 minutes, maintaining an internal temperature <10° C. After the addition was complete, the reaction mixture was stirred for 15 minutes at the same temperature, and LC-MS showed reaction was done. The mixture was diluted with methyl tert-butyl ether (100 mL) and stirred with 75 mL of saturated aqueous ammonium chloride at room temperature for 15 minutes. The layers were separated and organic layer was washed with saturated aqueous sodium bicarbonate and brine and dried over sodium sulfate. After filtration, the filtrate was concentrated and purified by flash column chromatography (0 to 30% ethyl acetate in heptane) to provide (2S,3R,4S,5S)-ethyl 3-(tert-butyl)-5-(2-(difluoromethoxy) pyridin-3-yl)-4-nitropyrrolidine-2-carboxylate, (3.95 g, 10.20 mmol, 75% yield). $^1$H NMR (400 MHz, DMSO-$d_6$) δ ppm 8.17 (dd, J=5.0, 1.8 Hz, 1H), 7.95-7.88 (m, 1H), 7.25 (dd, J=7.6, 4.9 Hz, 1H), 5.15 (dd, J=6.6, 3.0 Hz, 1H), 4.59 (t, J=7.2 Hz, 1H), 4.19 (qd, J=7.1, 3.8 Hz, 2H), 3.80 (t, J=7.4 Hz, 1H), 3.71 (t, J=7.7 Hz, 1H), 3.04 (dd, J=7.4, 3.1 Hz, 1H), 1.24 (t, J=7.1 Hz, 3H), 0.94 (s, 9H); MS (ESI$^+$) m/z 388.1 (M+H)$^+$.

Core 17

(2S,3R,4S,5S)-ethyl 5-(2-(azetidin-1-yl)pyridin-3-yl)-3-(tert-butyl)-4-nitropyrrolidine-2-carboxylate Core 17A 2-(azetidin-1-yl)nicotinaldehyde Into a 40 mL vial was added azetidine hydrochloride (0.412 g, 4.40 mmol), 2-chloronicotinaldehyde (0.53 g, 3.67 mmol), K$_2$CO$_3$ (1.268 g, 9.17 mmol) and dimethyl sulfoxide (DMSO) (7.34 mL). The mixture was stirred at 110° C. for 20 hours. Saturated ammonium chloride was added, and the mixture was extracted with ethyl acetate. The combined organic layer was washed with brine, dried over Na$_2$SO$_4$, filtered, concentrated and purified by flash column chromatography (0 to 30% ethyl acetate in heptane) to provide 2-(azetidin-1-yl)nicotinaldehyde (0.52 g, 3.21 mmol, 87% yield). $^1$H NMR (400 MHz, DMSO-$d_6$) δ ppm 9.86 (s, 1H), 8.29 (dd, J=4.6, 1.9 Hz, 1H), 7.96 (dd, J=7.6, 1.9 Hz, 1H), 6.75 (dd, J=7.6, 4.6 Hz, 1H), 4.09 (d, J=15.2 Hz, 3H), 3.29 (s, 2H), 2.37-2.24 (m, 3H); MS (ESI$^+$) m/z 163.0 (M+H)$^+$.

Core 17B (E)-ethyl 2-(((2-(azetidin-1-yl)pyridin-3-yl)methylene)amino)acetate

Ethyl 2-aminoacetate hydrochloride (3.68 g, 26.4 mmol) and magnesium sulfate (5.08 g, 42.2 mmol) were suspended in dichloromethane (35.1 mL) and the suspension was treated with triethylamine (3.67 mL, 26.4 mmol). The mixture was stirred at room temperature for 1 hour, then 2-(azetidin-1-yl)nicotinaldehyde (3.42 g, 21.09 mmol) was added in 20 mL of dichloromethane. The mixture was stirred at room temperature overnight. Thin layer chromatography (30% ethyl acetate in heptane with 5% triethylamine in it), showed the reaction was complete. The solid material was removed via filtration and the filtrate was washed with water (quick wash twice) and brine, dried over sodium sulfate, filtered, and concentrated to provide (E)-ethyl 2-(((2-(azetidin-1-yl)pyridin-3-yl)methylene)amino)acetate, (5.13 g, 20.74 mmol, 98% yield). $^1$H NMR (400 MHz, DMSO-$d_6$) δ ppm 8.37 (s, 1H), 8.17 (dd, J=4.7, 1.9 Hz, 1H), 7.89 (dd, J=7.6, 1.9 Hz, 1H), 6.74 (dd, J=7.5, 4.7 Hz, 1H), 4.38 (d, J=1.2 Hz, 2H), 4.16-4.02 (m, 6H), 2.28 (dq, J=8.2, 7.3 Hz, 2H), 1.19 (t, J=7.1 Hz, 3H); MS (ESI$^+$) m/z 248.0 (M+H)$^+$.

Core 17C (2S,3R,4S,5S)-ethyl 5-(2-(azetidin-1-yl)pyridin-3-yl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.099 g, 0.131 mmol) and copper (I) triflate dimer, benzene complex (0.025 g, 0.051 mmol) were dissolved in tetrahydrofuran (25.9 mL) that had been sparged with an N$_2$ stream for 4 hours. The resulting mixture was stirred for 1.5 hours at room temperature, and Core 17B in tetrahydrofuran (8 mL) was added after cooling to <5° C. in an ice-water bath. Potassium 2-methylpropan-2-olate (1 M in tetrahydrofuran, 0.101 mL, 0.101 mmol) was added dropwise, followed by addition of (E)-3,3-dimethyl-1-nitrobut-1-ene (1.306 g, 10.11 mmol) neat over 25 minutes, maintaining an internal temperature <10° C. After the addition was complete, the reaction was stirred for 15 minutes at the same temperature. The mixture was diluted with methyl tert-butyl ether (50 mL) and stirred with 25 mL of saturated aqueous ammonium chloride at room temperature for 15 minutes. The organic layer was separated and washed with saturated aqueous sodium bicarbonate and brine, dried over sodium sulfate, filtered, and concentrated. The residue was purified by flash column chromatography (0 to 30% ethyl acetate in heptane) to provide (2S,3R,4S,5S)-ethyl 5-(2-(azetidin-1-yl)pyridin-3-yl)-3-(tert-butyl)-4-nitropyrrolidine-2-carboxylate (3.04 g, 8.08 mmol, 80% yield). $^1$H NMR (500 MHz, DMSO-d$_6$) δ ppm 8.03 (dd, J=4.7, 1.8 Hz, 1H), 7.60 (dd, J=7.6, 1.8 Hz, 1H), 6.67 (dd, J=7.6, 4.8 Hz, 1H), 5.08 (dd, J=7.1, 3.7 Hz, 1H), 4.46 (t, J=7.0 Hz, 1H), 4.25-4.06 (m, 4H), 4.03 (dq, J=9.6, 7.3 Hz, 2H), 3.70 (dd, J=8.1, 6.9 Hz, 1H), 3.49 (t, J=6.9 Hz, 1H), 3.13 (dd, J=8.1, 3.7 Hz, 1H), 2.29 (p, J=7.5 Hz, 2H), 1.24 (d, J=7.1 Hz, 3H), 0.93 (s, 9H); MS (ESI$^+$) m/z 377.2 (M+H)$^+$.

Core 18

(2S,3R,4S,5S)-ethyl 3-(tert-butyl)-4-nitro-5-(2-(trifluoromethyl)pyridin-3-yl)pyrrolidine-2-carboxylate Core 18A (E)-ethyl 2-(((2-(trifluoromethyl)pyridin-3-yl)methylene)amino)acetate Ethyl 2-aminoacetate hydrochloride (3.49 g, 24.98 mmol) and magnesium sulfate (4.81 g, 40.0 mmol) were suspended in dichloromethane (33.3 mL) and the suspension was treated with triethylamine (3.48 mL, 24.98 mmol). After 1 hour, 2-(trifluoromethyl)nicotinaldehyde (3.5 g, 19.99 mmol) in dichloromethane (5 mL) was added and the reaction mixture was stirred at room temperature for 16 hours. The solid material was removed via filtration and the filtrate was washed with water and brine, dried over sodium sulfate, filtered, and concentrated to provide (E)-ethyl 2-(((2-(trifluoromethyl)pyridin-3-yl)methylene)amino)acetate (5.08 g, 19.52 mmol, 98% yield), which was used without further purification. $^1$H NMR (400 MHz, DMSO-d$_6$) δ ppm 8.80 (dd, J=4.6, 1.6 Hz, 1H), 8.68 (td, J=2.5, 1.4 Hz, 1H), 8.62-8.45 (m, 1H), 7.87-7.62 (m, 1H), 4.56 (d, J=1.3 Hz, 2H), 4.13 (m, 2H), 1.19 (m, 3H); MS (ESI$^+$) m/z 261.0 (M+H)$^+$.

Core 18B (2S,3R,4S,5S)-ethyl 3-(tert-butyl)-4-nitro-5-(2-(trifluoromethyl)pyridin-3-yl)pyrrolidine-2-carboxylate To a 250 mL flask was added tetrahydrofuran (50 mL). It was sparged with a nitrogen stream for 2 hours, and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.191 g, 0.254 mmol), and copper (I) triflate dimer, benzene complex (0.049 g, 0.098 mmol) were added. The reaction mixture was sparged with a nitrogen stream for 90 minutes at room temperature, and (E)-ethyl 2-(((2-(trifluoromethyl)pyridin-3-yl)methylene)amino)acetate (5.08 g, 19.52 mmol) in tetrahydrofuran (8 mL) was added after cooling to <5° C. in an ice-water bath. Potassium 2-methylpropan-2-olate (1 M in tetrahydrofuran, 0.195 mL, 0.195 mmol) was added drop wise, followed by addition of (E)-3,3-dimethyl-1-nitrobut-1-ene (2.52 g, 19.52 mmol) neat over 25 minutes, maintaining an internal temperature <10° C. After the addition was complete, the reaction mixture was stirred for 15 minutes, diluted with methyl tert-butyl ether (100 mL), and stirred with 75 mL of saturated aqueous ammonium chloride at room temperature for 15 minutes. The organic layer was separated and washed with saturated aqueous sodium bicarbonate and brine, then dried over sodium sulfate. The mixture was filtered, concentrated and purified by flash chromatography (0 to 30% ethyl acetate in heptane) to provide (2S,3R,4S,5S)-ethyl 3-(tert-butyl)-4-nitro-5-(2-(trifluoromethyl)pyridin-3-yl)pyrrolidine-2-carboxylate, (4.56 g, 11.71 mmol, 60.0% yield). ee=95.4%. $^1$H NMR (501 MHz, DMSO-d$_6$) δ ppm 8.65 (m, 1H), 8.27 (dd, J=8.1, 1.5 Hz, 1H), 7.72 (ddd, J=19.7, 8.0, 4.6 Hz, 1H), 5.02 (dd, J=7.1, 3.3 Hz, 1H), 4.84 (t, J=6.5 Hz, 1H), 4.20 (qq, J=7.0, 3.7 Hz, 2H), 3.94 (t, J=5.9 Hz, 1H), 3.83 (dd, J=7.3, 6.3 Hz, 1H), 3.19 (dd, J=7.4, 3.3 Hz, 1H), 1.25 (t, J=7.1 Hz, 3H), 0.93 (s, 9H); MS (ESI$^+$) m/z 390.1 (M+H)$^+$.

Core 19

(2S,3R,4S,5S)-ethyl 3-(tert-butyl)-5-(2-cyclopropylpyridin-3-yl)-4-nitropyrrolidine-2-carboxylate Core 19A 2-cyclopropylnicotinaldehyde A 40 mL vial was charged with 6 mL of 1,4-dioxane and a stir bar. The mixture was degassed with nitrogen for 5 minutes. The vial was charged with 2-bromonicotinaldehyde (240 mg, 1.290 mmol), cyclopropylboronic acid (222 mg, 2.58 mmol), and cesium fluoride (588 mg, 3.87 mmol). The vial was degassed again with nitrogen. PdCl$_2$dppf (53.1 mg, 0.065 mmol) was added and the reaction mixture was heated to 100° C. under nitrogen. Upon reaction completion, the mixture was cooled to room temperature. Ethyl acetate (30 mL) was added, and the mixture was stirred for 5 minutes, filtered over a pad of silica gel with ethyl acetate, concentrated, and purified via flash column chromatography (0 to 20% ethyl acetate in heptanes) to provide 2-cyclopropylnicotinaldehyde (170 mg, 1.155 mmol, 90% yield). $^1$H NMR (501 MHz, DMSO-d$_6$) δ ppm 10.40 (s, 1H), 8.61 (dd, J=4.7, 1.8 Hz, 1H), 8.10 (dd, J=7.8, 1.9 Hz, 1H), 7.33 (dd, J=7.9, 4.8 Hz, 1H), 3.08 (tt, J=8.0, 4.7 Hz, 1H), 1.18-0.90 (m, 4H); MS (ESI$^+$) m/z 148.0 (M+H)$^+$.

Core 19B

(E)-ethyl 2-(((2-cyclopropylpyridin-3-yl)methylene) amino)acetate

Ethyl 2-aminoacetate hydrochloride (1.707 g, 12.23 mmol) and magnesium sulfate (2.355 g, 19.57 mmol) were suspended in dichloromethane (16.31 mL) and the suspension was treated with triethylamine (1.705 mL, 12.23 mmol). The reaction was stirred for 1 hour before 2-cyclopropylnicotinaldehyde (1.44 g, 9.78 mmol) in of dichloromethane (5 mL) was added. The mixture was stirred at room temperature for 16 hours. The solid material was removed via filtration and the filtrate was washed with water (quick wash twice) and brine, dried over sodium sulfate, filtered and concentrated to provide 3.5 g of (E)-ethyl 2-(((2-cyclopropylpyridin-3-yl)methylene)amino)acetate (2.06 g, 8.87 mmol, 91% yield). $^1$H NMR (500 MHz, DMSO-d$_6$) δ ppm 8.90 (s, 1H), 8.49 (dd, J=4.7, 1.8 Hz, 1H), 8.08 (dd, J=7.8, 1.9 Hz, 1H), 7.21 (dd, J=7.8, 4.7 Hz, 1H), 4.50 (d, J=1.3 Hz, 2H), 4.15 (q, J=7.1 Hz, 2H), 2.71 (tt, J=8.0, 4.7 Hz, 1H), 1.22 (t, J=7.1 Hz, 3H), 1.05 (tt, J=5.4, 2.7 Hz, 2H), 1.04-0.93 (m, 2H); MS (ESI$^+$) m/z 233.1 (M+H)$^+$.

Core 19C

(2S,3R,4S,5S)-ethyl 3-(tert-butyl)-5-(2-cyclopropylpyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.087 g, 0.115 mmol) and copper (I) triflate dimer, benzene complex (0.022 g, 0.044 mmol) were dissolved in tetrahydrofuran (22.74 mL) that had been sparged with an N$_2$ stream for 4 hours. The resulting mixture was stirred for 1.5 hours at room temperature, and (E)-ethyl 2-(((2-cyclopropylpyridin-3-yl)methylene)amino)acetate (2.06 g, 8.87 mmol) in tetrahydrofuran (8 mL) was added after cooling to <5° C. in an ice-water bath. Potassium 2-methylpropan-2-olate (1 M in tetrahydrofuran, 0.089 mL, 0.089 mmol) was added dropwise, followed by addition of (E)-3,3-dimethyl-1-nitrobut-1-ene (1.145 g, 8.87 mmol) neat over 25 minutes, maintaining an internal temperature <10° C. After the addition was complete, the mixture was stirred for 15 minutes at the same temperature, and LC-MS showed reaction was done. The mixture was diluted with methyl tert-butyl ether (50 mL) and stirred with 25 mL of saturated aqueous ammonium chloride at room temperature for 15 minutes. The organic layer was separated, washed with saturated aqueous sodium bicarbonate and brine, dried over sodium sulfate, filtered, and concentrated. The residue was purified by flash column chromatography (0 to 30% ethyl acetate in heptane) to provide (2S,3R,4S,5S)-ethyl 3-(tert-butyl)-5-(2-cyclopropylpyridin-3-yl)-4-nitropyrrolidine-2-carboxylate (2.6 g, 7.19 mmol, 81% yield). $^1$H NMR (400 MHz, DMSO-d$_6$) δ ppm 8.26 (dd, J=4.7, 1.7 Hz, 1H), 7.73 (dd, J=7.8, 1.7 Hz, 1H), 7.05 (dd, J=7.8, 4.7 Hz, 1H), 5.33 (dd, J=7.1, 3.7 Hz, 1H), 4.89 (t, J=7.2 Hz, 1H), 4.18 (qd, J=7.1, 2.9 Hz, 2H), 3.84-3.70 (m, 1H), 3.62 (t, J=7.1 Hz, 1H), 3.08 (dd, J=7.8, 3.7 Hz, 1H), 2.20 (tt, J=8.1, 4.9 Hz, 1H), 1.22 (t, J=7.1 Hz, 3H), 1.07-0.86 (m, 4H), 0.93 (s, 9H); MS (ESI$^+$) m/z 362.1 (M+H)$^+$.

Core 20

(2S,3R,4S,5S)-ethyl 3-(tert-butyl)-1-(cyclohexanecarbonyl)-5-(2-methylpyridin-3-yl)-4-nitropyrrolidine-2-carboxylate

Core 20A

(E)-ethyl 2-(((2-chloropyridin-3-yl)methylene) amino)acetate

Ethyl 2-aminoacetate hydrochloride (3.71 g, 26.6 mmol) and magnesium sulfate (6.39 g, 53.1 mmol) were suspended in dichloromethane (44.3 mL) and the suspension was treated with triethylamine (3.70 mL, 26.6 mmol) and 2-chloronicotinaldehyde (3.76 g, 26.6 mmol). The mixture was stirred for 16 hours at room temperature. The solid material was removed via filtration. The filtrate was washed with water (50 mL), and the organics were dried over sodium sulfate, filtered, and concentrated to provide the crude imine, which was used without additional purification. $^1$H NMR (400 MHz, Chloroform-d) δ ppm 8.67 (t, J=J=1.1 Hz, 1H), 8.49-8.40 (m, 2H), 7.32 (ddd, J=J=7.7, 4.7, 0.8 Hz, 1H), 4.48 (d, J=1.4 Hz, 2H), 4.26 (q, J=J=7.1 Hz, 2H), 1.32 (dd, J=J=7.5, 6.9 Hz, 3H); MS (ESI+) m/z 227 (M+H)$^+$.

Core 20B

(2S,3R,4S,5S)-ethyl 3-(tert-butyl)-5-(2-chloropyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.310 g, 0.412 mmol) and copper(I) triflate dimer, benzene complex (0.106 g, 0.211 mmol) were dissolved in tetrahydrofuran (48.0 mL) that had been sparged with a nitrogen stream for 1 hour. The resulting mixture was stirred for 1 hour at room temperature (continued nitrogen sparge), and 4 Å molecular sieves (6.00 g, 22.07 mmol) were added, followed by addition of Core 20A (6.00 g, 26.5 mmol) as a solution in 10 mL of tetrahydrofuran and the resulting suspension was cooled to <5° C. in an ice-water bath. Potassium 2-methylpropan-2-olate (1 M in tetrahydrofuran, 0.331 mL, 0.331 mmol) was added dropwise, followed by addition of (E)-3,3-dimethyl-1-nitrobut-1-ene (2.85 g, 22.07 mmol) over 10 minutes, maintaining a temperature less than 7° C. After 20 minutes, 150 mg additional (E)-3,3-dimethyl-1-nitrobut-1-ene was added. The mixture was quenched with 5 mL of saturated aqueous ammonium chloride and warmed to room temperature then filtered through a pad of diatomaceous earth to remove molecular sieves. The filtrate was diluted with methyl tert-butyl ether and washed with saturated aqueous ammonium chloride (2×50 mL) and brine and filtered through a pad of silica gel. The mixture was concentrated and was diluted with n-hexane. The solvent was reduced in volume and the crude material was triturated until a clumpy solid formed. The solvent was decanted and the resulting solid was precipitated from 100 mL of hot n-hexane to provide (2S,3R,4S,5S)-ethyl 3-(tert-butyl)-5-(2-chloropyridin-3-yl)-4-nitropyrrolidine-2-carboxylate (5.892 g, 16.56 mmol, 75% yield). $^1$H NMR (501 MHz, Chloroform-d) δ ppm 8.37 (dd, J=J=4.7, 1.9 Hz, 1H), 7.81 (ddd, J=J=7.7, 1.9, 0.8 Hz, 1H), 7.31-7.25 (m, 1H), 5.42 (dd, J=J=6.0, 2.4 Hz, 1H), 4.71 (dd, J=J=9.5, 5.9 Hz, 1H), 4.34 (qd, J=J=7.1, 2.3 Hz, 2H), 3.86 (t, J=J=6.9 Hz, 1H), 3.16-3.09 (m, 1H), 3.07 (dd, J=J=6.9, 2.3 Hz, 1H), 1.37 (t, J=J=7.2 Hz, 3H), 1.10 (s, 9H); MS (APCI+) m/z 356 (M+H)+. Absolute stereochemistry confirmed by X-ray analysis.

Core 20C (2S,3R,4S,5S)-ethyl 3-(tert-butyl)-5-(2-chloropyridin-3-yl)-1-(cyclohexanecarbonyl)-4-nitropyrrolidine-2-carboxylate Core 20B (1.034 g, 2.91 mmol) was dissolved in dichloromethane (5 mL) and N-ethyl-N-isopropylpropan-2-amine (1.269 mL, 7.26 mmol) was added, followed by dropwise addition of cyclohexanecarbonyl chloride (0.447 g, 3.05 mmol) as a solution in dichloromethane (5 mL). The reaction was stirred at room temperature for 4 hours. The reaction was then diluted with water, and extracted with dichloromethane. The combined extracts were dried over sodium sulfate, filtered, concentrated, and purified using an 80 g silica gel cartridge with a gradient of 5-100% ethyl acetate/heptanes over 20 minutes to provide (2S,3R,4S,5S)-ethyl 3-(tert-butyl)-5-(2-chloropyridin-3-yl)-1-(cyclohexanecarbonyl)-4-nitropyrrolidine-2-carboxylate (0.675 g, 1.449 mmol, 49.8% yield). $^1$H NMR (400 MHz, DMSO-$d_6$, 120° C.) δ ppm 8.29 (dd, J=J=4.7, 1.9 Hz, 1H), 8.25-8.12 (m, 1H), 7.35 (dd, J=7.8, 4.7 Hz, 1H), 5.76 (d, J=J=8.2 Hz, 1H), 5.60 (d, J=J=9.4 Hz, 1H), 4.77 (d, J=J=3.2 Hz, 1H), 4.28 (qd, J=J=7.1, 2.8 Hz, 2H), 3.10 (t, J=J=2.9 Hz, 1H), 2.38-2.12 (m, 1H), 1.80-1.73 (m, 1H), 1.73-1.64 (m, 1H), 1.58 (t, J=J=11.1 Hz, 2H), 1.48-1.36 (m, 1H), 1.33-1.23 (m, 5H), 1.20-1.07 (m, 2H), 1.03 (s, 9H), 0.90-0.79 (m, 1H); MS (ESI+) m/z 466 (M+H)+.

Core 20D (2S,3R,4S,5S)-ethyl 3-(tert-butyl)-1-(cyclohexanecarbonyl)-5-(2-methylpyridin-3-yl)-4-nitropyrrolidine-2-carboxylate Core 20C (238 mg, 0.511 mmol) was dissolved in dioxane (5108 μL) and PdCl$_2$(dppf) ([1,1'-bis(diphenylphosphino)ferrocene]dichloropalladium(II)), 18.69 mg, 0.026 mmol) was added. The resulting suspension was sparged with nitrogen for 15 minutes before addition of dimethylzinc, 1 M in heptanes (1.02 mL, 1.022 mmol). The resulting clear pale yellow solution was heated to 85° C. for 30 minutes. The mixture was cooled to room temperature and then <5° C. in an ice bath, and quenched by slow addition of saturated aqueous ammonium chloride (1.0 mL). The solvent was reduced under a stream of nitrogen. The crude material was purified using a 24 g silica gel cartridge with a gradient of 5-100% ethyl acetate/heptanes over 20 minutes to provide (2S,3R,4S,5S)-ethyl 3-(tert-butyl)-1-(cyclohexanecarbonyl)-5-(2-methylpyridin-3-yl)-4-nitropyrrolidine-2-carboxylate (165 mg, 0.370 mmol, 72.5% yield). $^1$H NMR (400 MHz, DMSO-$d_6$) δ ppm 8.30 (dd, J=J=4.8, 1.7 Hz, 1H), 8.12 (s, 1H), 7.10 (dd, J=J=8.0, 4.8 Hz, 1H), 5.75-5.61 (m, 2H), 4.72 (d, J=J=3.5 Hz, 1H), 4.27 (qd, J=J=7.1, 1.6 Hz, 2H), 3.09 (t, J=3.1 Hz, 1H), 2.59 (s, 3H), 2.12 (s, 1H), 1.78-1.61 (m, 2H), 1.53 (s, 2H), 1.38-1.20 (m, 6H), 1.12 (q, J=11.2, 10.1 Hz, 1H), 1.03 (s, 9H), 0.91-0.78 (m, 2H); MS (ESI+) m/z 446 (M+H)+.

Core 21

(2S,3R,4S,5S)-ethyl 3-(tert-butyl)-5-(2-isopropoxyphenyl)-4-nitropyrrolidine-2-carboxylate Core 21A (E)-ethyl 2-((2-isopropoxybenzylidene)amino)acetate To ethyl 2-aminoacetate, hydrochloric acid (CAS#623-33-6) (4.68 g, 33.5 mmol) and magnesium sulfate (4.03 g, 33.5 mmol) in dichloromethane (80 mL) was added triethylamine (4.67 mL, 33.5 mmol). The mixture was stirred at ambient temperature for 5 minutes, and then 2-isopropoxybenzaldehyde [CAS#22921-58-0] (5 g, 30.5 mmol) was added dropwise. The mixture was stirred overnight. The mixture was filtered and washed with dichloromethane (10 mL×2). The combined organic layers were washed with brine, dried over MgSO$_4$, filtered and concentrated to provide the title compound, 7.28 g (96% yield). $^1$H NMR (501 MHz, Chloroform-d) δ ppm 8.74 (d, J=1.5 Hz, 1H), 8.04 (dd, J=7.8, 1.8 Hz, 1H), 7.38 (ddd, J=8.4, 7.3, 1.8 Hz, 1H), 7.00-6.95 (m, 1H), 6.95-6.91 (m, 1H), 4.66-4.60 (m, 1H), 4.42 (d, J=1.4 Hz, 2H), 4.26 (q, J=7.1 Hz, 2H), 1.38 (d, J=6.1 Hz, 6H), 1.32 (t, J=7.1 Hz, 3H).

Core 21B (2S,3R,4S,5S)-ethyl 3-(tert-butyl)-5-(2-isopropoxyphenyl)-4-nitropyrrolidine-2-carboxylate A mixture of (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.109 g, 0.144 mmol) and copper(I) triflate dimer, benzene complex (0.030 g, 0.060 mmol) in tetrahydrofuran (40 mL) cooled in an ice-bath was sparged with N$_2$ for 1 hour. Core 21A (7. g, 28.1 mmol) in 10 mL tetrahydrofuran was added, followed by potassium 2-methylpropan-2-olate (10.80 mg, 0.096 mmol), and (E)-3,3-dimethyl-1-nitrobut-1-ene (1.632 g, 12.64 mmol) dropwise, maintaining an internal temperature <10° C. The mixture was stirred at the same temperature for 2 hours, and diluted with ethyl acetate (50 mL) and saturated aqueous ammonium chloride (50 mL). The organic layer was washed with saturated aqueous NaHCO$_3$, and brine and dried over Na$_2$SO$_4$, filtered, and concentrated. Purification via chromatography on a 80 g silica gel cartridge, eluting with ethyl acetate in heptane at 0-40% gradient provided the title compound, 2.84 g (62.4% yield). $^1$H NMR (501 MHz, Chloroform-d) δ ppm 7.29-7.22 (m, 2H), 6.93 (td, J=7.6, 1.1 Hz, 1H), 6.87 (dt, J=8.3, 0.7 Hz, 1H), 5.44 (dd, J=5.5, 2.2 Hz, 1H), 4.69 (dtd, J=12.1, 6.0, 0.7 Hz, 1H), 4.54 (s, 1H), 4.34 (qd, J=7.1, 2.0 Hz, 2H), 3.81 (s, 1H), 3.45 (s, 1H), 2.87 (dd, J=7.1, 2.2 Hz, 1H), 1.48 (d, J=6.0 Hz, 3H), 1.41-1.34 (m, 6H), 1.09 (s, 9H); MS (ESI+) m/z 379.1 (M+H)+.

Core 22

(2S,3R,4S,5S)-ethyl 3-(tert-butyl)-5-(2-methoxyphenyl)-4-nitropyrrolidine-2-carboxylate Core 22A (E)-ethyl 2-(benzylideneamino)acetate Ethyl 2-aminoacetate hydrochloride (30 g, 215 mmol) and magnesium sulfate (51.7 g, 430 mmol) were stirred in dichloromethane (358 mL) at ambient temperature, and triethylamine (30.0 mL, 215 mmol) was added to the suspension. After stirring for 5 minutes, benzaldehyde (21.78 mL, 215 mmol) was added dropwise and the suspension was stirred at ambient temperature for an additional 16 hours. The solid material was removed via filtration through a fritted funnel and the filter cake was washed with dichloromethane (15 mL). The filtrate was washed with 2×20 mL of water, dried over sodium sulfate, filtered, and concentrated to provide the title compound, which was used without additional purification. $^1$H NMR (501 MHz, Chloroform-d) δ ppm 8.29 (s, 1H), 7.78 (dd, J=7.9, 1.7 Hz, 2H), 7.47-7.36 (m, 3H), 4.39 (d, J=1.3 Hz, 2H), 4.24 (q, J=7.1 Hz, 2H), 1.30 (t, J=7.2 Hz, 3H).

Core 22B (2S,3R,4S,5S)-ethyl 3-(tert-butyl)-5-(2-methoxyphenyl)-4-nitropyrrolidine-2-carboxylate (2-(Bis(3,5-bis(trifluoromethyl)phenyl)phosphine)-3-((S)-4-isopropyl-4,5-dihydrooxazol-2-yl)cyclopenta-2,4-dien-1-yl)(cyclopenta-2,4-dien-1-yl)iron (0.261 g, 0.347 mmol) and copper (I) triflate dimer, benzene complex (0.076 g, 0.151 mmol) were dissolved in tetrahydrofuran (67.0 mL) that had been sparged with a stream of N$_2$ for 1 hour. The resulting mixture was stirred for 1 hour at ambient temperature, and 4 Å molecular sieves (8 g, 30.1 mmol) were added, followed by addition of (E)-ethyl 2-((2-methoxybenzylidene)amino)acetate (8 g, 36.2 mmol) as a solution in 3 mL of tetrahydrofuran. The resulting suspension was cooled to <5° C. in an ice-water bath. Potassium 2-methylpropan-2-olate (1 M in tetrahydrofuran, 0.241 mL, 0.241 mmol) was added dropwise, followed by addition of (E)-3,3-dimethyl-1-nitrobut-1-ene (3.89 g, 30.1 mmol) as a solution in 2 mL of tetrahydrofuran over 10 minutes, maintaining an internal temperature less than 6° C. After stirring for an additional 20 minutes in the ice bath, the reaction mixture was diluted with methyl tert-butyl ether (30 mL), stirred with saturated aqueous ammonium chloride (20 mL) for 5 minutes then filtered through diatomaceous earth. The layers were separated, and the organic layer was washed with saturated aqueous ammonium chloride (2×10 mL), brine (10 mL) and dried over sodium sulfate. After filtration, the filtrate was concentrated in vacuo to provide a crude residue, which was purified via flash chromatography, eluting with 0:100 to 60:40 methyl tert-butyl ether:heptanes over 25 minutes on an 80 g silica gel column to provide 2.30 g of the title compound. $^1$H NMR (400 MHz, Chloroform-d) δ ppm 7.37-7.14 (m, 2H), 6.99-6.90 (m, 1H), 6.88 (dd, J=8.2, 1.1 Hz, 1H), 5.35 (ddd, J=5.8, 2.5, 0.9 Hz, 1H), 4.56 (dd, J=13.0, 5.7 Hz, 1H), 4.40-4.22 (m, 2H), 3.90 (s, 3H), 3.81-3.72 (m, 1H), 3.37 (t, J=11.6 Hz, 1H), 2.90 (ddd, J=7.3, 2.5, 0.9 Hz, 1H), 1.39-1.30 (m, 3H), 1.07 (s, 9H); MS (ESI+) m/z 351.1 (M+H)$^+$.

Core 23

(2S,3R,4S,5S)-ethyl 3-(tert-butyl)-5-(2-fluorophenyl)-4-nitropyrrolidine-2-carboxylate Core 23A (E)-ethyl 2-((2-fluorobenzylidene)amino)acetate To a mixture of ethyl 2-aminoacetate hydrochloride (11.8 g, 84.7 mmol) and magnesium sulfate (11.7 g, 96.7 mmol) in dichloromethane (100 mL) was added triethylamine (12.5 mL, 88.7 mmol). The mixture was stirred for 20 minutes and 2-fluorobenzaldehyde (10.0 g, 80.6 mmol) was added dropwise. The resulting mixture was stirred at room temperature overnight. The solid was filtered off and washed with dichloromethane (200 mL). The filtrate was washed with water (100 mL) and brine (100 mL), dried over MgSO$_4$, filtered and concentrated to provide the title compound (E)-ethyl 2-((2-fluorobenzylidene)amino)acetate (16.0 g, 76.6 mmol, 95% yield). $^1$H NMR (400 MHz, CDCl$_3$) δ ppm 8.60 (s, 1H), 8.07-8.03 (m, 1H), 7.45-7.39 (m, 1H), 7.20-7.11 (m, 1H), 7.08-7.06 (m, 1H), 4.43 (s, 2H), 4.27, 4.24 (dd, J=7.2 Hz, 14.4 Hz, 2H), 1.36-1.32 (m, 3H), 1.33-1.26 (m, 3H); LC-MS (ESI+) m/z 210 (M+H)$^+$.

Core 23B (2S,3R,4S,5S)-ethyl 3-(tert-butyl)-5-(2-fluorophenyl)-4-nitropyrrolidine-2-carboxylate To a flame-dried Schlenk tube charged with activated 4 Å molecular sieves and a stirring bar was added copper (I) triflate dimer, benzene complex (417.8 mg, 0.83 mmol) and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (1.45 g, 1.93 mmol) in freshly distilled anhydrous tetrahydrofuran (160 mL) under an inert atmosphere. The mixture was stirred for 15 minutes and cooled to 0° C. (E)-Ethyl 2-((2-fluorobenzylidene)amino) acetate (16.0 g, 76.6 mmol) was added, followed by addition of potassium tert-butoxide (1.33 mL, 1.33 mmol) and (E)-3, 3-dimethyl-1-nitrobut-1-ene (8.56 g, 66.36 mmol). The reaction mixture was stirred at 0° C. for 2 hours, and then filtered through a short plug of silica gel. The filtrate was concentrated. The residue was purified by silica gel column chromatography (eluted with 10% petroleum ether/ethyl acetate) to provide the title compound (13.55 g, 40.09 mmol, 58.6% yield, ee=95.3%). $^1$H NMR (400 MHz, CDCl$_3$) δ ppm 7.33-7.30 (m, 2H), 7.17-7.15 (m, 1H), 7.07 (t, J=8.4 Hz, 1H), 5.24-5.22 (m, 1H), 4.60 (t, J=6.0 Hz, 1H), 4.35-4.29 (m, 2H), 3.80 (t, J=3.6 Hz, 1H), 3.33 (t, J=11.2 Hz, 1H), 2.96-2.93 (m, 1H), 1.35 (t, J=7.2 Hz, 3H), 1.06 (s, 9H); LC-MS (ESI+) m/z 339 (M+H)$^+$.

Core 24

(2S,3R,4S,5S)-ethyl 3-(tert-butyl)-5-(2-chlorophenyl)-4-nitropyrrolidine-2-carboxylate Core 24A (E)-ethyl 2-((2-chlorobenzylidene)amino)acetate A mixture of ethyl 2-aminoacetate hydrochloride (1.85 g, 13.25 mmol) and magnesium sulfate (3.19 g, 26.5 mmol) in dichloromethane (22.09 mL) was treated with triethylamine (1.847 mL, 13.25 mmol), stirred for 30 minutes and treated with 2-chlorobenzaldehyde (1.863 g, 13.25 mmol) as a solution in 3 mL of dichloromethane. The reaction was stirred at ambient temperature overnight. The solid material was filtered, the filtrate was concentrated, toluene (5 mL) was added, and the mixture was filtered again. The filtrate was concentrated to provide (E)-ethyl 2-((2-chlorobenzylidene)amino)acetate (2.76 g, 12.23 mmol, 92% yield). $^1$H NMR (400 MHz, Chloroform-d) δ ppm 8.77 (d, J=1.5 Hz, 1H), 8.19-8.04 (m, 1H), 7.45-7.39 (m, 2H), 7.34 (ddd, J=8.3, 6.0, 2.6 Hz, 1H), 4.48 (d, J=1.5 Hz, 2H), 4.28 (q, J=7.2 Hz, 2H), 1.34 (t, J=7.1 Hz, 3H).

Core 24B

(2S,3R,4S,5S)-ethyl 3-(tert-butyl)-5-(2-chlorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.175 g, 0.232 mmol) and copper (I) triflate dimer, benzene complex (0.047 g, 0.093 mmol) were dissolved in tetrahydrofuran (19.36 mL mL) that had been sparged with an nitrogen stream for 1 hour. The resulting mixture was stirred for 1 hour at ambient temperature (continued nitrogen sparge), and (E)-ethyl 2-((2-chlorobenzylidene)amino)acetate (2.75 g, 12.19 mmol) was added as a solution in 2 mL of tetrahydrofuran. The resulting solution was cooled to <5° C. in an ice-water bath. Potassium 2-methylpropan-2-olate in tetrahydrofuran (1 M in tetrahydrofuran, 0.209 mL, 0.209 mmol) was added dropwise, followed by addition of neat (E)-3,3-dimethyl-1-nitrobut-1-ene (1.5 g, 11.61 mmol) over 20 minutes, maintaining a temperature less than 7° C. The reaction mixture was stirred for 1 hour at 0° C. The mixture was quenched with 60 mL of saturated aqueous ammonium chloride. Ethyl acetate (100 mL) was added and the mixture was warmed to ambient temperature. The organic layer was separated and washed twice with saturated aqueous ammonium chloride and brine and filtered through a pad of silica gel. The filtrate was concentrated. Heptane (70 mL) was added and the precipitate (2.5 g) was filtered. The filtrate was purified by chromatography using a 12 g silica gel cartridge eluting with a gradient of 0-60% heptanes/ethyl acetate over a period of 20 minutes to provide (2S,3R,4S,5S)-ethyl 3-(tert-butyl)-5-(2-chlorophenyl)-4-nitropyrrolidine-2-carboxylate (2.85 g, 8.03 mmol, 69.2% yield). $^1$H NMR (400 MHz, DMSO-d$_6$) δ ppm 7.56-7.48 (m, 1H), 7.45-7.38 (m, 1H), 7.35-7.24 (m, 2H), 5.25 (dd, J=6.7, 3.0 Hz, 1H), 4.71 (t, J=7.0 Hz, 1H), 4.19 (qq, J=7.3, 3.7 Hz, 2H), 3.78 (t, J=7.3 Hz, 1H), 3.68 (t, J=7.3 Hz, 1H), 3.07 (dd, J=7.4, 3.0 Hz, 1H), 1.24 (t, J=7.1 Hz, 3H), 0.94 (s, 9H), 0.96 (s, 9H); MS (APCI+) m/z 355 (M+H+).

Core 25

(2S,3R,4S,5S)-ethyl 5-(2-bromophenyl)-3-(tert-butyl)-4-nitropyrrolidine-2-carboxylate

Core 25A

(E)-ethyl 2-((2-bromobenzylidene)amino)acetate

Ethyl 2-aminoacetate hydrochloride (2.63 g, 18.85 mmol) and magnesium sulfate (2.269 g, 18.85 mmol) were stirred in dichloromethane (28.6 mL) at ambient temperature, and triethylamine (2.63 mL, 18.85 mmol) was added. The mixture was stirred for 5 minutes, 2-bromobenzaldehyde (2.0 mL, 17.13 mmol) was added dropwise, and the mixture was stirred at ambient temperature for 16 hours. The solid material was filtered through a disposable plastic frit and washed with dichloromethane. The organic layer was washed with 30 mL of water then dried over sodium sulfate, filtered, and concentrated to provide (E)-ethyl 2-((2-bromobenzylidene)amino)acetate (4.6 g, 17.03 mmol, 99% yield). $^1$H NMR (400 MHz, CDCl$_3$) δ ppm 8.70 (d, J=1.6 Hz, 1H), 8.12 (dd, J=7.7, 1.9 Hz, 1H), 7.60 (dd, J=7.8, 1.3 Hz, 1H), 7.38 (tt, J=7.6, 1.1 Hz, 1H), 7.35-7.27 (m, 1H), 4.48 (d, J=1.4 Hz, 2H), 4.28 (q, J=7.1 Hz, 2H), 1.34 (t, J=7.1 Hz, 3H); MS (ESI+) m/z 270 (M+H)+.

Core 25B

(2S,3R,4S,5S)-ethyl 5-(2-bromophenyl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.147 g, 0.195 mmol) and copper (I) triflate dimer, benzene complex (0.042 g, 0.084 mmol) were dissolved in tetrahydrofuran (34.3 mL) that had been sparged with stream of nitrogen for 1 hour. The resulting mixture was stirred for 1.5 hours at ambient temperature, and (E)-ethyl 2-((2-bromobenzylidene)amino) acetate (4.63 g, 17.14 mmol) was added after cooling to <5° C. in an ice-water bath. Potassium 2-methylpropan-2-olate (1 M in tetrahydrofuran, 0.134 mL, 0.134 mmol) was added dropwise, followed by addition of (E)-3,3-dimethyl-1-nitrobut-1-ene (2.324 g, 18.00 mmol) neat over 25 minutes, maintaining an internal temperature <10° C. After the addition was complete and the reaction was stirred for 90 minutes, LC-MS showed complete conversion. The mixture was diluted with methyl tert-butyl ether (150 mL) and stirred with 50 mL of saturated aqueous ammonium chloride at ambient temperature for 15 minutes. The layers were separated and the organic layer was washed with saturated aqueous sodium bicarbonate and brine. The organic layer was dried over sodium sulfate, filtered, and concentrated to provide a crude solid, which was precipitated from 50 mL of heptane. The mixture was cooled in an ice bath to <5° C. for 15 minutes, and the resulting material was filtered and washed with 20 mL of heptanes to provide (2S,3R,4S,5S)-ethyl 5-(2-bromophenyl)-3-(tert-butyl)-4-nitropyrrolidine-2-carboxylate (4.303 g, 10.78 mmol, 62.9% yield). $^1$H NMR (400 MHz, CDCl$_3$) δ ppm 7.58 (dd, J=8.0, 1.2 Hz, 1H), 7.41-7.29 (m, 2H), 7.24-7.14 (m, 1H), 5.43 (dd, J=5.9, 2.3 Hz, 1H), 4.70 (dd, J=10.7, 5.9 Hz, 1H), 4.33 (qd, J=7.1, 1.2 Hz, 2H), 3.82 (t, J=7.5 Hz, 1H), 3.22 (t, J=9.8 Hz, 1H), 3.03 (dd, J=7.0, 2.3 Hz, 1H), 1.36 (t, J=7.1 Hz, 3H), 1.08 (s, 9H); MS (APCI+) m/z 399 (M+H)+.

Core 26

(2S,3R,4S,5S)-ethyl 3-(tert-butyl)-4-nitro-5-(2-(trifluoromethyl)phenyl)pyrrolidine-2-carboxylate

Core 26A

(E)-ethyl 2-((2-(trifluoromethyl)benzylidene)amino)acetate

A slurry of ethyl 2-aminoacetate hydrochloride (6.01 g, 43.1 mmol) and magnesium sulfate (5.88 g, 48.8 mmol) in dichloromethane (100 mL) was stirred at 0° C. Triethylamine (6.00 mL, 43.1 mmol) was added drop wise and the mixture was stirred at room temperature for 1 hour. 2-(Trifluoromethyl)benzaldehyde (5 g, 28.7 mmol) was added. After 15 hours, the solid was filtered and washed with dichloromethane (3×200 mL). The dichloromethane layer was washed with water (2×100 mL), dried (Na$_2$SO$_4$), filtered, and concentrated, to provide (E)-ethyl 2-((2-(trifluoromethyl)benzylidene)amino)acetate (7.2 g, 25.8 mmol, 90% yield). $^1$H NMR (400 MHz, CDCl$_3$) δ ppm 8.64 (s, 1H), 8.28 (d, J=7.6 Hz, 1H), 7.61-7.51 (m, 2H), 7.69-7.67 (m, 1H), 4.45 (s, 2H), 4.24 (q, J=6.8 Hz, 2H), 1.30 (t, J=7.0 Hz, 3H).

Core 26B

(2S,3R,4S,5S)-ethyl 3-(tert-butyl)-4-nitro-5-(2-(trifluoromethyl)phenyl)pyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.169 g, 0.225 mmol) and copper (I) triflate dimer, benzene complex (0.048 g, 0.095 mmol) were added under argon atmosphere to a flame-dried flask, containing activated 4 Å molecular sieves and a stirring bar. Freshly distilled anhydrous tetrahydrofuran (20 mL) was added. After stirring for 15 minutes, the solution was cooled to 0° C. before (E)-ethyl 2-((2-(trifluoromethyl)benzylidene)amino)acetate (2.408 g, 9.29 mmol) was added, followed by potassium tert-butoxide (0.155 mL, 0.155 mmol). (E)-3,3-Dimethyl-1-nitrobut-1-ene (1 g, 7.74 mmol) was added slowly. The reaction mixture was stirred at 0° C. for 5 hours, and water (80 mL) was added to the flask. The aqueous layer was extracted with ethyl acetate (2×100 mL). The organic layers were combined, washed with brine (2×80 mL), dried over $Na_2SO_4$, filtered, and concentrated. The crude material was purified by chromatography on silica gel (ethyl acetate/petroleum mixtures, 1:40) to provide the title compound (2 g, 5.10 mmol, 65.8% yield). $^1$H NMR (400 MHz, $CDCl_3$) δ ppm 7.69-7.41 (m, 4H), 5.07-5.06 (m, 1H), 4.81-4.78 (m, 1H), 4.32 (q, 2H), 3.82 (t, J=7.2 Hz, 1H), 3.15-3.13 (m, 1H), 3.01 (t, J=8.6 Hz, 1H), 1.34 (t, J=7.2 Hz, 3H), 1.03 (s, 9H).

Core 27

(2S,3R,4S,5S)-ethyl 3-(tert-butyl)-5-(2-(difluoromethyl)phenyl)-4-nitropyrrolidine-2-carboxylate

Core 27A

(E)-ethyl 2-((2-(difluoromethyl)benzylidene)amino)acetate

A mixture of ethyl 2-aminoacetate hydrochloride (1.788 g, 12.81 mmol) and magnesium sulfate (3.08 g, 25.6 mmol) in dichloromethane (21.35 mL) (anhydrous) was treated with triethylamine (1.785 mL, 12.81 mmol), stirred for 10 minutes, and treated with 2-(difluoromethyl)benzaldehyde (2.00 g, 12.81 mmol) as a solution in 4 mL of dichloromethane. The mixture was stirred at ambient temperature overnight. The solid material was filtered, the filtrate was concentrated, toluene (25 mL) was added, and the mixture was filtered again. The mixture was concentrated to provide (E)-ethyl 2-((2-(difluoromethyl)benzylidene)amino)acetate (3.0 g, 12.44 mmol, 97% yield) which was used directly on to the next step. $^1$H NMR (400 MHz, $CDCl_3$) δ ppm 8.59 (t, J=1.4 Hz, 1H), 8.00-7.87 (m, 1H), 7.70 (dd, J=6.6, 2.3 Hz, 1H), 7.63-7.52 (m, 2H), 7.35 (t, J=55.1 Hz, 1H), 4.47 (d, J=1.3 Hz, 2H), 4.28 (q, J=7.1 Hz, 2H), 1.34 (t, J=7.1 Hz, 3H).

Core 27B

(2S,3R,4S,5S)-ethyl 3-(tert-butyl)-5-(2-(difluoromethyl)phenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.187 g, 0.249 mmol) and copper (I) triflate dimer, benzene complex (0.050 g, 0.099 mmol) were dissolved in tetrahydrofuran (12.9 mL) that had been sparged with a $N_2$ stream for 1 hour. The resulting mixture was stirred for 1 hour at ambient temperature (continue nitrogen sparge), and (E)-ethyl 2-((2-(difluoromethyl)benzylidene)amino)acetate (3.0 g, 12.44 mmol) was added as a solution in 1.5 mL of tetrahydrofuran. The resulting solution was cooled to <5° C. in an ice-water bath. Potassium 2-methylpropan-2-olate in tetrahydrofuran (0.224 mL, 0.224 mmol) was added dropwise, followed by the addition of neat (E)-3,3-dimethyl-1-nitrobut-1-ene (1.606 g, 12.44 mmol) over 2 minutes, maintaining a temperature less than 7° C. The reaction mixture was stirred for 3 hours at 0° C. The mixture was quenched with 10 mL of saturated aqueous ammonium chloride, 30 mL of ethyl acetate was added, and it was warmed to ambient temperature. The organic layer was separated and washed with saturated aqueous ammonium chloride (2×20 mL) and brine and filtered through a pad of silica gel. The filtrate was concentrated. The residue was triturated with heptane, decanted, precipitated from hot heptane, and filtered to provide (2S,3R,4S,5S)-ethyl 3-(tert-butyl)-5-(2-(difluoromethyl)phenyl)-4-nitropyrrolidine-2-carboxylate (2.48 g, 6.70 mmol, 53.8% yield). $^1$H NMR (400 MHz, DMSO-$d_6$) δ ppm 7.64 (d, J=7.7 Hz, 1H), 7.57-7.53 (m, 1H), 7.48 (t, J=7.4 Hz, 1H), 7.45-7.39 (m, 1H), 7.38 (t, J=54.4 Hz, 1H), 5.19 (dd, J=7.0, 3.4 Hz, 1H), 4.79 (t, J=6.5 Hz, 1H), 4.19 (qd, J=7.1, 2.4 Hz, 2H), 3.83-3.61 (m, 2H), 3.11 (dd, J=6.9, 3.5 Hz, 1H), 1.24 (t, J=7.1 Hz, 3H), 0.93 (s, 9H); MS (ESI+) m/z 371 (M+H)$^+$.

Core 28

(2S,3R,4S,5S)-ethyl 3-(tert-butyl)-5-(2-ethylphenyl)-4-nitropyrrolidine-2-carboxylate

Core 28A

(E)-ethyl 2-((2-ethylbenzylidene)amino)acetate

A mixture of ethyl 2-aminoacetate hydrochloride (1.85 g, 13.25 mmol) and magnesium sulfate (3.19 g, 26.5 mmol) in dichloromethane (22 mL) was treated with triethylamine (1.847 mL, 13.25 mmol), stirred for 10 minutes and treated with 2-ethylbenzaldehyde (1.778 g, 13.25 mmol) as a solution in 1 mL of dichloromethane. The reaction was stirred at ambient temperature overnight. The solid material was filtered, the filtrate was washed with water, and the organic fraction was separated. The organic fraction was dried with $Na_2SO_4$, filtered, and concentrated to provide (E)-ethyl 2-((2-ethylbenzylidene)amino)acetate (2.65 g, 12.09 mmol, 91% yield). $^1$H NMR (400 MHz, Chloroform-d) δ ppm 8.63 (s, 1H), 7.96 (dd, J=7.8, 1.5 Hz, 1H), 7.37 (td, J=7.5, 1.5 Hz, 1H), 7.26 (d, J=6.1 Hz, 1H), 7.25-7.19 (m, 1H), 4.43 (d, J=1.4 Hz, 2H), 4.26 (q, J=7.1 Hz, 2H), 2.89 (q, J=7.5 Hz, 2H), 1.32 (t, J=7.1 Hz, 3H), 1.26 (t, J=7.6 Hz, 3H).

Core 28B

(2S,3R,4S,5S)-ethyl 3-(tert-butyl)-5-(2-ethylphenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.182 g, 0.242 mmol) and copper (I) triflate dimer, benzene complex (0.049 g, 0.097 mmol) were dissolved in tetrahydrofuran (18 mL)

that had been sparged with a nitrogen stream for 1 hour. The resulting mixture was stirred for 1 hour at ambient temperature (continued nitrogen sparge), and (E)-ethyl 2-((2-ethylbenzylidene)amino)acetate (Core 28A, 2.65 g, 12.09 mmol) in 1 mL tetrahydrofuran was added and the resulting solution was cooled to <5° C. in an ice-water bath. Potassium 2-methylpropan-2-olate in tetrahydrofuran (0.218 mL, 0.218 mmol) was added dropwise, followed by addition of (E)-3,3-dimethyl-1-nitrobut-1-ene (1.561 g, 12.09 mmol) in 1 mL tetrahydrofuran over 2 minutes, maintaining a temperature less than 7° C. The reaction mixture was stirred for 1.5 hours at 0° C. The mixture was quenched with 20 mL of saturated aqueous ammonium chloride and 50 mL of ethyl acetate and warmed to ambient temperature. The organic layer was separated and washed twice with saturated aqueous ammonium chloride, then brine and filtered through a pad of silica gel. The filtrate was concentrated and was purified by chromatography using a 40 g silica gel cartridge eluting with a gradient of 0-60% heptanes/ethyl acetate over a period of 20 minutes. The crude material was triturated with heptane and the precipitate was filtered to provide (2S,3R,4S,5S)-ethyl 3-(tert-butyl)-5-(2-ethylphenyl)-4-nitropyrrolidine-2-carboxylate (2.11 g, 6.06 mmol, 50.1% yield). $^1$H NMR (501 MHz, DMSO-d$_6$) δ ppm 7.40-7.29 (m, 1H), 7.25-7.15 (m, 2H), 7.11 (td, J=7.4, 1.8 Hz, 1H), 5.17 (dd, J=7.0, 3.5 Hz, 1H), 4.64 (t, J=7.4 Hz, 1H), 4.19 (qd, J=7.1, 3.8 Hz, 2H), 3.72 (t, J=7.6 Hz, 1H), 3.47 (t, J=7.5 Hz, 1H), 3.07 (dd, J=7.9, 3.5 Hz, 1H), 2.72 (dt, J=15.0, 7.5 Hz, 1H), 2.63 (dt, J=15.0, 7.5 Hz, 1H), 1.22 (dt, J=16.4, 7.3 Hz, 6H), 0.93 (s, 9H); MS (APCI+) m/z 349 (M+H+).

Core 29

(2S,3R,4S,5S)-ethyl 3-(tert-butyl)-5-(3-chlorophenyl)-4-nitropyrrolidine-2-carboxylate Core 29A (E)-ethyl 2-((3-chlorobenzylidene)amino)acetate Ethyl 2-aminoacetate hydrochloride (5.96 g, 42.7 mmol) and magnesium sulfate (5.14 g, 42.7 mmol) were suspended in dichloromethane (50.8 mL). Triethylamine (5.95 mL, 42.7 mmol) was added, and the reaction mixture was stirred for 1 hour at ambient temperature before addition of 3-chlorobenzaldehyde (4.03 mL, 35.6 mmol) via syringe. The reaction mixture was stirred overnight at ambient temperature. The solids were removed via filtration using a fritted funnel and the filter cake was washed with dichloromethane (10 mL). The filtrate was quickly washed twice with 10 mL of water and 10 mL of brine and dried over sodium sulfate, filtered and concentrated in vacuo to provide the title compound, which was used without additional purification. $^1$H NMR (400 MHz, CDCl$_3$) δ ppm 8.24 (d, J=1.3 Hz, 1H), 7.81 (t, J=1.8 Hz, 1H), 7.62 (dt, J=7.6, 1.4 Hz, 1H), 7.48-7.29 (m, 2H), 4.40 (d, J=1.3 Hz, 2H), 4.24 (q, J=7.1 Hz, 2H), 1.31 (t, J=7.1 Hz, 3H).

Core 29B (2S,3R,4S,5S)-ethyl 3-(tert-butyl)-5-(3-chlorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.192 g, 0.255 mmol) and copper (I) triflate dimer, benzene complex (0.056 g, 0.111 mmol) were dissolved in tetrahydrofuran (50 mL) that had been sparged with an N$_2$ stream for 1 hour. The resulting solution was stirred for 1 hour at ambient temperature, and 4 Å molecular sieves (6 g, 22.16 mmol) were added, followed by addition of the (E)-ethyl 2-((3-chlorobenzylidene)amino)acetate (6.0 g, 26.6 mmol) as a solution in 3 mL of tetrahydrofuran. The resulting suspension was cooled to <5° C. in an ice-water bath. Potassium 2-methylpropan-2-olate (1 M in tetrahydrofuran, 0.177 mL, 0.177 mmol) was added dropwise, followed by addition of (E)-3,3-dimethyl-1-nitrobut-1-ene (2.86 g, 22.16 mmol) as a solution in 2 mL of tetrahydrofuran over 10 minutes, maintaining a temperature less than 10° C. The reaction was complete after 10 minutes at the same temperature as determined by LC-MS. The reaction was quenched with 5 mL of saturated aqueous ammonium chloride and filtered through diatomaceous earth after diluting with methyl tert-butyl ether (50 mL). The filtrate was stirred at ambient temperature with saturated aqueous ammonium chloride (20 mL) for 15 minutes and the layers were separated. The organic layer was washed with saturated aqueous ammonium chloride and brine, dried over sodium sulfate, filtered, and concentrated in vacuo to provide a crude residue. The crude material was loaded onto a 120 g silica gel column and was eluted with 0:100 to 30:70 methyl tert-butyl ether: heptanes over 20 minutes to provide 5.83 g of the title compound. $^1$H NMR (501 MHz, CDCl$_3$) δ ppm 7.33 (dq, J=1.7, 1.0 Hz, 1H), 7.30-7.24 (m, 2H), 7.22-7.16 (m, 1H), 5.11 (dd, J=6.0, 2.5 Hz, 1H), 4.40 (dd, J=12.0, 6.0 Hz, 1H), 4.31 (qd, J=7.1, 1.1 Hz, 2H), 3.79 (dd, J=9.6, 7.1 Hz, 1H), 3.21 (dd, J=11.9, 9.7 Hz, 1H), 2.96 (dd, J=7.2, 2.6 Hz, 1H), 1.34 (t, J=7.1 Hz, 3H), 1.05 (s, 9H); MS (ESI+) m/z 355.1 (M+H)$^+$.

Core 30

(2S,3R,4S,5S)-ethyl 5-(3-bromophenyl)-3-(tert-butyl)-4-nitropyrrolidine-2-carboxylate Core 30A (E)-ethyl 2-((3-bromobenzylidene)amino)acetate Ethyl 2-aminoacetate hydrochloride (2.490 g, 17.84 mmol) and magnesium sulfate (2.147 g, 17.84 mmol) were stirred in dichloromethane (24.13 mL) at ambient temperature, and triethylamine (2.486 mL, 17.84 mmol) was added. The mixture was stirred for 5 minutes and 3-bromobenzaldehyde (1.890 mL, 16.21 mmol) was added dropwise. The mixture was stirred at ambient temperature for 16 hours. The solid material was filtered through a disposable plastic frit and washed with dichloromethane. The organic layer was washed with 30 mL of water, dried over sodium sulfate, filtered, and concentrated to provide (E)-ethyl 2-((3-bromobenzylidene)amino)acetate (4.38 g, 16.21 mmol, 100% yield). $^1$H NMR (500 MHz, CDCl$_3$) δ ppm 8.27 (d, J=1.4 Hz, 1H), 8.01 (t, J=1.8 Hz, 1H), 7.70 (dt, J=7.7, 1.3 Hz, 1H), 7.61 (ddd, J=8.0, 2.0, 1.0 Hz, 1H), 7.33 (t, J=7.8 Hz, 1H), 4.44 (d, J=1.3 Hz, 2H), 4.28 (q, J=7.1 Hz, 2H), 1.35 (t, J=7.1 Hz, 3H); MS (ESI+) m/z 224 (M+H)$^+$.

Core 30B (2S,3R,4S,5S)-ethyl 5-(3-bromophenyl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4- dien-1-yl)(cyclopenta-2,4-dien-1-yl)iron (0.139 g, 0.184 mmol) and copper (I) triflate dimer, benzene complex (0.040 g, 0.079 mmol) were dissolved in tetrahydrofuran (32.4 mL) that had been sparged with a nitrogen stream for 1 hour. The resulting mixture was stirred for 1.5 hours at ambient temperature, and (E)-ethyl 2-((3-bromobenzylidene)amino) acetate (4.38 g, 16.21 mmol) was added after cooling to <5° C. in an ice-water bath. Potassium 2-methylpropan-2-olate (1 M in tetrahydrofuran, 0.127 mL, 0.127 mmol) was added dropwise, followed by addition of (E)-3,3-dimethyl-1-nitrobut-1-ene (2.199 g, 17.03 mmol) neat over 25 minutes, maintaining an internal temperature <10° C. After the addition was complete, the mixture was stirred for 2 hours. Additional potassium 2-methylpropan-2-olate (1 M in tetrahydrofuran, 0.127 mL, 0.127 mmol) was added. After 30 minutes, the reaction mixture was diluted with methyl tert-butyl ether (150 mL) and stirred with 50 mL of saturated aqueous ammonium chloride at ambient temperature for 15 minutes. The layers were separated. The organic layer was washed with saturated aqueous sodium bicarbonate and brine, dried over sodium sulfate, filtered, and concentrated to provide a crude residue, which was triturated with 3×5 mL of heptanes. The heptane insolubles were chromatographed using an 80 g silica gel cartridge with a gradient of 5-50% ethyl acetate/heptanes over 40 minutes to provide (2S,3R,4S,5S)-ethyl 5-(3-bromophenyl)-3-(tert-butyl)-4-nitropyrrolidine-2-carboxylate (2.76 g, 6.91 mmol, 42.6% yield). n-Hexane (about 1 mL) was added to about 50 mg of the residue, and the mixture was warmed to 45° C., and then allowed to cool. $^1$H NMR (501 MHz, CDCl$_3$) δ ppm 7.50 (d, J=1.9 Hz, 1H), 7.45 (dt, J=7.5, 1.7 Hz, 1H), 7.29-7.19 (m, 2H), 5.13 (dd, J=6.0, 2.6 Hz, 1H), 4.41 (dd, J=11.9, 6.0 Hz, 1H), 4.33 (qd, J=7.1, 1.1 Hz, 2H), 3.81 (dd, J=9.5, 7.2 Hz, 1H), 3.27-3.17 (m, 1H), 2.98 (dd, J=7.2, 2.5 Hz, 1H), 1.37 (t, J=7.2 Hz, 3H), 1.07 (s, 9H); MS (APCI+) m/z 399 (M+H)$^+$. Relative and absolute stereochemistry were confirmed by X-ray analysis.

Core 31

(2S,3R,4S,5S)-ethyl 3-(tert-butyl)-5-(3-(tert-butyl) phenyl)-4-nitropyrrolidine-2-carboxylate Core 31A (E)-ethyl 2-((3-(tert-butyl)benzylidene)amino)acetate To ethyl 2-aminoacetate, hydrochloric acid (CAS#623-33-6, 776 mg, 5.56 mmol) and magnesium sulfate (669 mg, 5.56 mmol) in CH$_2$Cl$_2$ (10 mL) was added triethylamine (0.775 mL, 5.56 mmol). The mixture was stirred at ambient temperature for 5 minutes, 3-(tert-butyl)benzaldehyde (820 mg, 5.05 mmol) was added dropwise, and the mixture was stirred overnight. The mixture was filtered and the solid was washed with CH$_2$Cl$_2$ (10 mL×2). The combined organics were washed with water and brine, dried over MgSO$_4$, filtered, and concentrated to provide (E)-ethyl 2-((3-(tert-butyl)benzylidene)amino)acetate (1.08 g, 86% yield). $^1$H NMR (400 MHz, CDCl$_3$) δ ppm 8.31 (s, 1H), 7.81 (t, J=1.9 Hz, 1H), 7.60 (dt, J=7.5, 1.4 Hz, 1H), 7.50 (ddd, J=7.8, 2.1, 1.2 Hz, 1H), 7.37 (t, J=7.7 Hz, 1H), 4.41 (d, J=1.2 Hz, 2H), 4.25 (q, J=7.1 Hz, 2H), 1.36 (s, 9H), 1.32 (t, J=7.1 Hz, 3H).

Core 31B (2S,3R,4S,5S)-ethyl 3-(tert-butyl)-5-(3-(tert-butyl) phenyl)-4-nitropyrrolidine-2-carboxylate A mixture of (2-(bis(3,5-bis(trifluoromethyl)phenyl) phosphino)-3-((S)-4-isopropyl-4,5-dihydrooxazol-2-yl)cy-clopenta-2,4-dien-1-yl)(cyclopenta-2,4-dien-1-yl)iron (37 mg, 0.049 mmol) and copper(I) triflate dimer, benzene complex (CAS#42152-46-5, 10.18 mg, 0.020 mmol) in tetrahydrofuran (10 mL) was sparged with N$_2$ for one hour. Core 31A (1 g, 4.04 mmol) in tetrahydrofuran (5 mL) was added at 0° C., followed by addition of potassium 2-methylpropan-2-olate (3.63 mg, 0.032 mmol) dropwise, and finally (E)-3,3-dimethyl-1-nitrobut-1-ene (548 mg, 4.25 mmol) maintaining an internal temperature <10° C. The mixture was stirred at the same temperature for one hour, diluted with ethyl acetate (20 mL) and saturated aqueous ammonium chloride (20 mL) and stirred at ambient temperature for 30 minutes. The organic layer was washed with NaHCO$_3$ and brine, dried over Na$_2$SO$_4$, filtered, and concentrated to provide title compound which was used in next step without further purification. LC/MS (APCI+) m/z 377 (M+1)$^+$.

Core 32

(2S,3R,4S,5R)-ethyl 3-(tert-butyl)-5-(1-isopropyl-1H-pyrazol-5-yl)-4-nitropyrrolidine-2-carboxylate Core 32A (E)-ethyl 2-(((1-isopropyl-1H-pyrazol-5-yl)methylene)amino)acetate Ethyl 2-aminoacetate hydrochloride (2.223 g, 15.92 mmol) and magnesium sulfate (1.917 g, 15.92 mmol) were stirred in dichloromethane (24.13 mL) at ambient temperature, and triethylamine (2.185 mL, 15.67 mmol) was added. The mixture was stirred for 5 minutes and 1-isopropyl-1H-pyrazole-5-carbaldehyde (2.0 g, 14.48 mmol) was added dropwise. The mixture was stirred at ambient temperature for 16 hours. The solid material was filtered through a disposable plastic frit and was washed with dichloromethane. The organic layer was washed with 30 mL of water, dried over sodium sulfate, filtered, and concentrated to provide (E)-ethyl 2-(((1-isopropyl-1H-pyrazol-5-yl)methylene)amino)acetate (3.23 g, 14.47 mmol, 100% yield). $^1$H NMR (400 MHz, CDCl$_3$) δ ppm 8.29 (t, J=1.3 Hz, 1H), 7.52 (d, J=1.9 Hz, 1H), 6.58 (d, J=2.0 Hz, 1H), 5.48 (p, J=6.6 Hz, 1H), 4.38 (d, J=1.3 Hz, 2H), 4.24 (q, J=7.2 Hz, 2H), 1.50 (d, J=6.6 Hz, 6H), 1.31 (t, J=7.1 Hz, 3H); MS (ESI+) m/z 224 (M+H)$^+$.

Core 32B (2S,3R,4S,5R)-ethyl 3-(tert-butyl)-5-(1-isopropyl-1H-pyrazol-5-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.124 g, 0.164 mmol) and copper (I) triflate dimer, benzene complex (0.036 g, 0.071 mmol) were dissolved in tetrahydrofuran (28.9 mL) that had been sparged with a nitrogen stream for 1 hour. The resulting mixture was stirred for 1.5 hours at ambient temperature, and (E)-ethyl 2-(((1-isopropyl-1H-pyrazol-5-yl)methylene)amino)acetate (3.23 g, 14.47 mmol) was added after cooling to <5° C. in an ice-water bath. Potassium 2-methylpropan-2-olate (1 M in tetrahydrofuran, 0.113 mL, 0.113 mmol) was added dropwise, followed by addition of (E)-3,3-dimethyl-1-nitrobut-1-ene (1.962 g, 15.19 mmol) neat over 25 minutes, maintaining an internal temperature <10° C. After the addition was complete the reaction was stirred for 2 hours. The mixture was diluted with methyl tert-butyl ether (150 mL) and stirred with 50 mL of saturated aqueous ammonium chloride at ambient temperature for 15 minutes. The layers were separated, and the organic layer was washed with saturated aqueous sodium bicarbonate and brine, and dried over sodium sulfate. After filtration, the combined organic layers were concentrated and triturated with 3×5 mL of heptanes and left in dry ice overnight in heptanes. The solvent was removed and the resulting material was concentrated. n-Hexane was added and the mixture was triturated and stirred at ambient temperature for an hour. The mixture was filtered to provide a solid which was washed with 10 mL of heptanes to provide (2S,3R,4S,5R)-ethyl 3-(tert-butyl)-5-(1-isopropyl-1H-pyrazol-5-yl)-4-nitropyrrolidine-2-carboxylate (2.556 g, 7.25 mmol, 50.1% yield). $^1$H NMR (500 MHz, CDCl$_3$) δ ppm 7.50 (d, J=1.9 Hz, 1H), 6.21 (d, J=1.9 Hz, 1H), 5.04 (dd, J=5.9, 2.3 Hz, 1H), 4.47 (ddd, J=21.6, 12.9, 6.2 Hz, 2H), 4.35 (qd, J=7.2, 1.8 Hz, 2H), 3.82 (dd, J=9.4, 6.6 Hz, 1H), 3.30 (dd, J=12.3, 9.5 Hz, 1H), 3.02 (dd, J=6.7, 2.3 Hz, 1H), 1.60 (d, J=6.6 Hz, 3H), 1.56 (d, J=6.5 Hz, 3H), 1.37 (t, J=7.1 Hz, 3H), 1.10 (s, 9H); MS (APCI+) m/z 353 (M+H)$^+$. Absolute chemistry confirmed by X-ray diffraction analysis.

Core 33

(2S,3R,4S,5S)-ethyl 3-(tert-butyl)-5-(4-fluorophenyl)-4-nitropyrrolidine-2-carboxylate Core 33A (E)-ethyl 2-((4-fluorobenzylidene)amino)acetate To a mixture of ethyl 2-aminoacetate hydrochloride (33.7 g, 242 mmol) and magnesium sulfate (33.0 g, 274 mmol) in dichloromethane (320 mL) was added triethylamine (33.7 mL, 242 mmol). The mixture was stirred at room temperature for 20 minutes and then 4-fluorobenzaldehyde (20.00 g, 161 mmol) was added dropwise. The resulting mixture was stirred at 25° C. for 20 hours. LC/MS indicated the completion of the reaction. The solid was filtered off and washed with dichloromethane (200 mL). The combined filtrates were washed with water (150 mL) and brine (150 mL), dried over Na$_2$SO$_4$, filtered and concentrated to provide (E)-ethyl 2-((4-fluorobenzylidene)amino)acetate (30 g, 129 mmol, 80% yield). $^1$H NMR (400 MHz, CDCl$_3$) δ ppm 8.20 (s, 1H), 7.70-7.72 (m, 2H), 7.01-7.05 (m, 2H), 4.31 (s, 2H), 4.16 (q, J=8 Hz, 2H), 1.23 (t, J=8 Hz, 3H); LC/MS (ESI+) m/z 210.1 (M+H)$^+$.

Core 33B (2S,3R,4S,5S)-ethyl 3-(tert-butyl)-5-(4-fluorophenyl)-4-nitropyrrolidine-2-carboxylate To a flame-dried Schlenk tube containing activated 4 Å molecular sieves and a stirring bar was added copper (I) triflate dimer, benzene complex (145.1 mg, 0.28 mmol) and (2-(bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.423 g, 0.561 mmol) and freshly distilled anhydrous tetrahydrofuran (50 mL) under an argon atmosphere. The mixture was stirred at room temperature for 15 minutes and then cooled to 0° C. To the mixture was added (E)-ethyl 2-((4-fluorobenzylidene) amino)acetate (4.86 g, 23.23 mmol), potassium tert-butoxide (0.387 mL, 0.387 mmol) and (E)-3, 3-dimethyl-1-nitrobut-1-ene (2.50 g, 19.36 mmol). The mixture was stirred at 0° C. for 6 hours. The solid was filtered off through a short plug of silica gel. The filtrate was concentrated. The residue was purified by silica gel column chromatography (eluted with 10% petroleum ether/ethyl acetate) to provide the title compound, ((2S, 3R, 4S, 5S)-ethyl 3-(tert-butyl)-5-(4-fluorophenyl)-4-nitropyrrolidine-2-carboxylate (3.0 g, 8.87 mmol, 45.8% yield). $^1$H NMR (400 MHz, CDCl$_3$) δ ppm 7.28-7.33 (m, 2H), 7.05-7.07 (m, 2H), 5.11 (dd, J=4 Hz, 8 Hz, 1H), 4.44 (d, J=8 Hz, 1H), 4.33 (q, J=8 Hz, 2H), 3.82 (d, J=8 Hz, 1H), 2.99 (dd, J=4 Hz, 8 Hz, 1H), 1.36 (t, J=8 Hz, 3H), 1.06 (s, 9H); LC/MS (ESI+) m/z 339.2 (M+H)$^+$.

Core 34

(2S,3R,4S,5S)-ethyl 3-(tert-butyl)-5-(2, 6-difluorophenyl)-4-nitropyrrolidine-2-carboxylate Core 34A (E)-ethyl 2-((2,6-difluorobenzylidene)amino)acetate A mixture of ethyl 2-aminoacetate hydrochloride (1.85 g, 13.25 mmol) and magnesium sulfate (3.19 g, 26.5 mmol) in CH$_2$Cl$_2$ (22.09 mL) (anhydrous) was treated with triethylamine (1.847 mL, 13.25 mmol), stirred for 10 minutes and treated with the 2,6-difluorobenzaldehyde (1.883 g, 13.25 mmol) as a solution in CH$_2$Cl$_2$ (~3 mL). The vial was capped and stirred at room temperature overnight. The solid material was filtered and the filtrate was concentrated. Toluene (5 mL) was added and the mixture was filtered again. The filtrate was concentrated to provide (E)-ethyl 2-((2,6-difluorobenzylidene)amino)acetate (2.9 g, 12.76 mmol, 96% yield) which was used directly in the next step. $^1$H NMR (400 MHz, Chloroform-d) δ ppm 8.54 (d, J=1.3 Hz, 1H), 7.13-6.81 (m, 3H), 4.49 (s, 2H), 4.28 (q, J=7.1 Hz, 2H), 1.34 (t, J=7.1 Hz, 3H).

Core 34B (2S,3R,4S,5S)-ethyl 3-(tert-butyl)-5-(2, 6-difluorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.175 g, 0.232 mmol) and copper (I) triflate dimer, benzene complex (0.047 g, 0.093 mmol) were dissolved in tetrahydrofuran (19 mL) that had been sparged with an nitrogen stream for 1 hour. The resulting mixture was stirred for 1 hour at ambient temperature (continued nitrogen sparge). (E)-Ethyl 2-((2,6-difluorobenzylidene)amino)acetate (2.9 g, 12.76 mmol) in 2 mL tetrahydrofuran was added and the resulting solution was cooled to <5° C. in an ice-water bath. Potassium 2-methylpropan-2-olate in tetrahydrofuran (1 M in tetrahydrofuran, 0.244 mL, 0.244 mmol) was added dropwise, followed by addition of (E)-3,3-dimethyl-1-nitrobut-1-ene (1.5 g, 11.61 mmol) in 2 mL tetrahydrofuran over 2 minutes, maintaining a temperature less than 7° C. The reaction mixture was stirred for 1.5 hours at 0° C. The mixture was quenched with 20 mL of saturated aqueous ammonium chloride and 50 mL of ethyl acetate and warmed to ambient temperature. The organic layer was separated and washed twice with saturated aqueous ammonium chloride and brine and filtered through a pad of silica gel. The filtrate was concentrated. Heptane (60 mL) was added, the precipitate (1.5 g) was filtered, and the filtrate was purified by chromatography using a 40 g silica gel cartridge eluting with a gradient of 0-60% heptanes/ethyl acetate over a period of 20 minutes to provide a crude residue. The crude material was triturated with heptane and the precipitate was filtered to provide a combined yield of (2S,3R,4S,5S)-ethyl 3-(tert-butyl)-5-(2-ethylphenyl)-4-nitropyrrolidine-2-carboxylate (1.9 g, 5.33 mmol, 45.9% yield). $^1$H NMR (400 MHz, DMSO-d$_6$) δ ppm 7.64 (d, J=7.7 Hz, 1H), 7.57-7.53 (m, 1H), 7.48 (t, J=7.4 Hz, 1H), 7.45-7.39 (m, 1H), 7.38 (t, J=54.4 Hz, 1H), 5.19 (dd, J=7.0, 3.4 Hz, 1H), 4.79 (t, J=6.5 Hz, 1H), 4.19 (qd, J=7.1, 2.4 Hz, 2H), 3.83-3.61 (m, 2H), 3.11 (dd, J=6.9, 3.5 Hz, 1H), 1.24 (t, J=7.1 Hz, 3H), 0.93 (s, 9H); MS (ESI+) m/z 371 (M+H)$^+$.

Core 35 rac-(2S,3R,4S,5S)-tert-butyl 3-(tert-butyl)-5-(1-methyl-2-oxo-1,2-dihydropyridin-3-yl)-4-nitropyrrolidine-2-carboxylate Core 35A (E)-tert-butyl 2-(((1-methyl-2-oxo-1,2-dihydropyridin-3-yl)methylene)amino)acetate To a stirred suspension of tert-butyl 2-aminoacetate hydrochloride (503 mg, 3.00 mmol), 1-methyl-2-oxo-1,2-dihydropyridine-3-carbaldehyde (412 mg, 3.00 mmol) and magnesium sulfate (723 mg, 6.01 mmol) in anhydrous CH$_2$Cl$_2$ (5 mL) at room temperature was added triethylamine (420 µL, 3.01 mmol). The reaction mixture was stirred overnight and filtered with a 1:1 CH$_2$Cl$_2$/toluene rinse, then the filtrate was concentrated. The residue was added to toluene and the mixture was filtered through diatomaceous earth with a toluene rinse. The resulting filtrate was filtered through a filter disc, again with a toluene rinse, concentrated and reconcentrated from acetonitrile to provide 716 mg of a mixture of the imine and its dimers. The compound was used in the next step without further purification.

Core 35B rac-(2S,3R,4S,5S)-tert-butyl 3-(tert-butyl)-5-(1-methyl-2-oxo-1,2-dihydropyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (49 mg, 65 µmol) and copper(I) triflate benzene complex (13 mg, 26 µmol) were placed under nitrogen and dissolved into anhydrous tetrahydrofuran (2 mL) which had been sparged with nitrogen for 45 minutes. The resulting solution was stirred for 100 minutes at room temperature, cooled with a −10° C. bath, and treated dropwise with a solution of the Core 35A (0.71 g, <3 mmol) in tetrahydrofuran (6 mL). Potassium tert-butoxide (1 M in tetrahydrofuran, 60 µL, 60 mol) was added, and several minutes later (E)-3,3-dimethyl-1-nitrobut-1-ene (326 µL, 2.50 mmol) was added over 30 minutes. The −10° C. solution was permitted to warm to 15° C. over 90 minutes, removed from the cold bath and stirred at room temperature for one week. The reaction mixture was quenched with 1 M pH 7 potassium phosphate buffer (300 µL), stirred a couple of minutes, treated with concentrated aqueous NH$_4$OH (50 µL) and partitioned by the addition of methyl tert-butyl ether (8 mL) and heptane (1 mL). The organic phase was placed directly on silica, followed by methyl tert-butyl ether extracts of the wet residue, for quick chromatography (0 to 20% CH$_3$CN/methyl tert-butyl ether) to provide the crude product, which was further purified by a second chromatography on silica (20 to 100% ethyl acetate in 1:1 CH$_2$Cl$_2$/heptane) to provide 48 mg of a chirally enriched material (5% for two steps). $^1$H NMR (400 MHz, CDCl$_3$) δ ppm 7.35-7.32 (m, 1H), 7.28-7.25 (m, 1H), 6.18 (dd, J=7.0, 6.8 Hz, 1H), 5.56 (dd, J=5.5, 2.2 Hz, 1H), 4.47-4.41 (m, 1H), 3.69-3.65 (m, 1H), 3.57 (s, 3H), 3.21-3.14 (m, 1H), 2.80 (dd, J=6.9, 2.2 Hz, 1H), 1.53 (s, 9H), 1.06 (s, 9H); MS (ESI) m/z 138 (M+H)$^+$.

Core 36 rac-(2R,3S,4R,5R)-tert-butyl 3-(2-methoxypropan-2-yl)-4-nitro-5-phenylpyrrolidine-2-carboxylate Core 36A 2-methoxy-2-methylpropan-1-ol 2,2-Dimethyloxirane (25 g, 347 mmol) was dissolved in 100 mL of CH$_3$OH. The resulting solution was added dropwise to a solution of sulfuric acid (10 mg, 0.102 mmol) in methanol (2.0 mL) in a 250-mL 2-neck round bottomed flask open to the air over 30 minutes via addition funnel. The flask was placed into a room temperature water bath during the addition due to a large exotherm. The internal temperature was maintained <35° C. during the addition. Once the addition was complete, the solution was refluxed for 4 hours. The mixture was cooled to ambient temperature and neutralized to pH 7-7.5 with a solution of KOH in CH$_3$OH (used a pH meter to monitor). CH$_3$OH was removed in vacuo at 35° C. bath temperature to provide 2-methoxy-2-methylpropan-1-ol (36 g, 346 mmol). $^1$H NMR (400 MHz, Chloroform-d) δ ppm 3.41 (d, J=5.7 Hz, 2H), 3.21 (d, J=0.7 Hz, 3H), 2.20 (t, J=6.1 Hz, 1H), 1.14 (s, 6H).

Core 36B 2-methoxy-2-methylpropanal

Core 36A (26.77 g, 257 mmol) was dissolved in a mixture of dichloromethane (402 mL) and saturated aqueous sodium bicarbonate (268 mL). The resulting biphasic mixture was cooled to <5° C. in an ice-water bath. Potassium bromide (30.6 g, 257 mmol) and TEMPO (2,2,6,6-tetramethylpiperidin-1-yl)oxyl oroxidanyl, 0.803 g, 5.14 mmol) were added, followed by addition of 25-mL portions of sodium hypochlorite, 10-15% (225 mL, 3645 mmol). The mixture was extracted with dichloromethane and the combined extracts were washed with brine, dried over sodium sulfate, filtered, and concentrated in vacuo, maintaining a bath temperature <20° C. The residual residue was distilled at atmospheric pressure. The title compound had a boiling point of ~100° C. The fractions containing the desired product were combined to provide 2-methoxy-2-methylpropanal (6.8 g, 66.6 mmol). $^1$H NMR (501 MHz, Chloroform-d) δ ppm 9.59 (s, 1H), 3.31 (s, 3H), 1.28 (s, 6H).

Core 36C 3-methoxy-3-methyl-1-nitrobutan-2-ol

Core 36B (4 g, 39.2 mmol) and nitromethane (3.17 mL, 58.7 mmol) were dissolved in tetrahydrofuran (10 mL) and tert-butanol (6 mL). After cooling to <5° C. in an ice bath, 1 M potassium tert-butoxide (3.92 mL, 3.92 mmol) in tetrahydrofuran was added dropwise with caution to avoid any exotherm. The mixture was poured into 20 mL of water and extracted with 3×20 mL of methyl tert-butyl ether. The combined extracts were washed with brine, dried over sodium sulfate, filtered, and concentrated to provide 3-methoxy-3-methyl-1-nitrobutan-2-ol (4.82 g, 25 mmol). $^1$H NMR (501 MHz, Chloroform-d) δ ppm 4.63 (dd, J=12.9, 2.4 Hz, 1H), 4.45 (dd, J=12.9, 9.8 Hz, 1H), 4.21 (ddd, J=9.8, 6.2, 2.4 Hz, 1H), 3.26 (s, 3H), 2.83 (d, J=6.3 Hz, 1H), 1.24 (d, J=1.6 Hz, 6H). MS (DCI+) m/z 181 (M+NH$_4$)$^+$.

Core 36D (E)-3-methoxy-3-methyl-1-nitrobut-1-ene

Core 36C (4.6 g, 28.2 mmol) was dissolved in 40 mL of dry dichloromethane and the solution was cooled to −78° C. Triethylamine (9.82 mL, 70.5 mmol) was added, followed by dropwise addition of mesyl chloride (2.64 mL, 33.8 mmol). The reaction mixture was stirred for 2 hours at the same temperature then allowed to warm to ambient temperature. The mixture was washed with saturated aqueous sodium bicarbonate and brine, dried over sodium sulfate, filtered, concentrated in vacuo, and purified via flash column chromatography, eluting with 0-20% ethyl acetate/heptanes over 20 minutes on a 40 g silica gel column to provide 2.66 g of the desired product. $^1$H NMR (400 MHz, Chloroform-d) δ ppm 7.20 (d, J=13.4 Hz, 1H), 7.08 (d, J=13.4 Hz, 1H), 3.27 (d, J=0.7 Hz, 3H), 1.40 (s, 6H); MS (ESI+) m/z 163 (M+NH$_4$)$^+$.

Core 36E rac-(2R,3S,4R,5R)-tert-butyl 3-(2-methoxypropan-2-yl)-4-nitro-5-phenylpyrrolidine-2-carboxylate A 1.5 M solution of lithium bromide (14.25 mL, 21.38 mmol) was added to a solution of (E)-tert-butyl 2-(benzylideneamino)acetate (Core 1A, 3.0 g, 12.72 mmol) in anhydrous tetrahydrofuran (46 mL), and the resulting mixture was cooled with a dry ice/acetone bath. A solution of Core 36D (1.847 g, 12.72 mmol) in tetrahydrofuran (4.9 mL) was added slowly, followed by dropwise addition of 2,3,4,6,7,8,9,10-octahydropyrimido[1,2-a]azepine (2.56 mL, 16.99 mmol). After the reaction mixture had stirred an hour at about −78° C., the dry ice was removed from the bath and the bath was permitted to warm to −15° C. over 60 minutes, and 0° C. over another 60 minutes. The cold bath was removed, the reaction mixture was stirred at room temperature for 15 minutes, and saturated aqueous NH$_4$Cl (50 mL) was added with a methyl tert-butyl ether (50 mL) rinse. The biphasic mixture was stirred thoroughly and then diluted with brine (50 mL). The aqueous phase was separated and extracted twice with methyl tert-butyl ether, and the combined organic phases were washed with brine, dried (Na$_2$SO$_4$), filtered, and concentrated to a residue which was triturated with 40 mL heptane and stored 16 hours at ambient temperature. The resulting solid was filtered. The filtrate was concentrated and loaded on a 12 g column eluting with a gradient of 0-60% ethyl acetate/heptanes over a period of 20 minutes and combined with the filtered solid to provide rac-(2R,3S,4R,5R)-tert-butyl 3-(2-methoxypropan-2-yl)-4-nitro-5-phenylpyrrolidine-2-carboxylate, 1975 (2.45 g, 6.72 mmol, 52.8% yield). $^1$H NMR (501 MHz, Chloroform-d) δ ppm 7.40-7.29 (m, 5H), 5.36 (dd, J=6.0, 2.2 Hz, 1H), 4.58 (s, 1H), 3.96 (d, J=6.6 Hz, 1H), 3.27 (s, 3H), 3.04 (dd, J=6.7, 2.2 Hz, 1H), 1.57 (s, 9H), 1.35 (s, 3H), 1.31 (s, 3H); MS (ESI+) m/z 365 (M+H)$^+$.

Core 37

(2S,3R,4S,5S)-tert-butyl 3-(2-methoxypropan-2-yl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.169 g, 0.224 mmol) and copper (I) triflate dimer, benzene complex (0.056 g, 0.112 mmol) were dissolved in tetrahydrofuran (28 mL) that had been sparged with an nitrogen stream for 1 hour. The resulting mixture was stirred for 1 hour at ambient temperature (continued nitrogen sparge), and (E)-tert-butyl 2-(benzylideneamino)acetate (4.15 g, 18.95 mmol) was added as a solution in 5 mL of tetrahydrofuran and the resulting solution was cooled to <5° C. in an ice-water bath. Potassium 2-methylpropan-2-olate in tetrahydrofuran (1 M in tetrahydrofuran, 0.177 mL, 0.177 mmol) was added dropwise, followed by addition of (E)-3-methoxy-3-methyl-1-nitrobut-1-ene from Core 36D (2.5 g, 17.22 mmol) over 10 minutes, maintaining a temperature less than 7° C. The reaction mixture was stirred for 45 minutes at 0° C. The mixture was quenched with 50 mL of saturated aqueous ammonium chloride and 75 mL of ethyl ether and warmed to ambient temperature. The ether layer was separated and washed twice with saturated aqueous ammonium chloride then brine and filtered through a pad of silica gel. The mixture was concentrated to provide crude material, which was diluted with n-heptane (50 mL) and chromatographed using a 40 g silica gel cartridge eluting with a gradient of 0-50% heptanes/ethyl acetate over a period of 20 minutes to provide a crude product which was precipitated in 100 mL heptane to provide (2S,3R,4S,5S)-tert-butyl 3-(2-methoxypropan-2-yl)-4-nitro-5-phenylpyrrolidine-2-carboxylate (3.33 g, 9.14 mmol, 53.1% yield). $^1$H NMR (400 MHz, Chloroform-d) δ ppm 7.41-7.23 (m, 5H), 5.36 (dd, J=5.9, 2.2 Hz, 1H), 4.62-4.52 (m, 1H), 4.00-3.91 (m, 1H), 3.27 (s, 3H), 3.04 (dd, J=6.7, 2.2 Hz, 1H), 1.57 (s, 9H), 1.34 (s, 3H), 1.31 (s, 3H).; MS (APCI+) m/z 365 (M+H+). Absolute stereochemistry confirmed by X-ray diffraction analysis.

Core 38

(2S,3R,4S,5S)-tert-butyl 5-(2-(dimethylamino)pyridin-3-yl)-3-(2-methoxypropan-2-yl)-4-nitropyrrolidine-2-carboxylate Core 38A (E)-tert-butyl 2-(((2-(dimethylamino)pyridin-3-yl)methylene)amino)acetate tert-Butyl 2-aminoacetate, hydrochloric acid (2.411 g, 14.38 mmol) and magnesium sulfate (3.46 g, 28.8 mmol) were suspended in dichloromethane (23.97 mL) and the suspension was treated with 2-(dimethylamino)nicotinaldehyde (2.16 g, 14.38 mmol) and triethylamine (2.005 mL, 14.38 mmol). The mixture was stirred at ambient temperature for 16 hours. The solid material was filtered and the filtrate was washed with water. The organics ware removed and dried with Na$_2$SO$_4$ and filtered again, then concentrated to provide (E)-tert-butyl 2-(((2-(dimethylamino)pyridin-3-yl)methylene)amino)acetate (4.06 g, 15.42 mmol, 107% yield). ¹H NMR (400 MHz, Chloroform-d) δ ppm 8.38 (s, 1H), 8.29 (dd, J=4.8, 2.0 Hz, 1H), 8.10 (dd, J=7.6, 2.0 Hz, 1H), 6.87 (dd, J=7.5, 4.8 Hz, 1H), 4.34 (d, J=1.2 Hz, 2H), 3.01 (s, 6H), 1.52 (s, 9H); MS (ESI+) m/z 264 (M+H)⁺.

Core 38B (2S,3R,4S,5S)-tert-butyl 5-(2-(dimethylamino)pyridin-3-yl)-3-(2-methoxypropan-2-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.034 g, 0.045 mmol) and copper (I) triflate dimer, benzene complex (0.011 g, 0.022 mmol) were dissolved in tetrahydrofuran (5 mL) that had been sparged with a nitrogen stream for 1 hour. The resulting mixture was stirred for 1 hour at ambient temperature (continued nitrogen sparge), and (E)-tert-butyl 2-(((2-(dimethylamino)pyridin-3-yl)methylene)amino)acetate (0.998 g, 3.79 mmol) was added as a solution in 0.574 mL of tetrahydrofuran. The resulting solution was cooled to <5° C. in an ice-water bath. Potassium 2-methylpropan-2-olate in tetrahydrofuran (0.09 mL, 0.090 mmol) was added dropwise, followed by addition of (E)-3-methoxy-3-methyl-1-nitrobut-1-ene (0.5 g, 3.44 mmol) over 10 minutes, maintaining a temperature less than 7° C. The reaction mixture was stirred for 45 minutes at 0° C. The mixture was quenched with 3 mL of saturated aqueous ammonium chloride and 10 mL of ethyl ether and warmed to ambient temperature. The ether layer was separated and washed twice with saturated aqueous ammonium chloride then brine and filtered through a pad of silica gel. The filtrate was concentrated and was purified by chromatography using a 40 g silica gel cartridge eluting with a gradient of 0-50% heptanes/ethyl acetate over a period of 20 minutes to provide (2S,3R,4S,5S)-tert-butyl 5-(2-(dimethylamino)pyridin-3-yl)-3-(2-methoxypropan-2-yl)-4-nitropyrrolidine-2-carboxylate (0.98 g, 2.399 mmol, 69.6% yield). ¹H NMR (501 MHz, Chloroform-d) δ ppm 8.28 (dd, J=4.8, 1.8 Hz, 1H), 7.62 (ddd, J=7.6, 1.8, 0.9 Hz, 1H), 6.96 (dd, J=7.6, 4.8 Hz, 1H), 5.69 (dd, J=5.7, 2.2 Hz, 1H), 4.76 (s, 1H), 3.94 (d, J=6.6 Hz, 1H), 3.28 (s, 3H), 3.14 (s, 1H), 3.02 (dd, J=6.7, 2.1 Hz, 1H), 2.84 (s, 6H), 1.56 (s, 9H), 1.36 (s, 3H), 1.31 (s, 3H); MS (APCI+) m/z 409 (M+H+).

Core 39

(2S,3R,4S,5S)-tert-butyl 3-(2-methoxypropan-2-yl)-5-(2-methoxypyridin-3-yl)-4-nitropyrrolidine-2-carboxylate Core 39A (E)-tert-butyl 2-(((2-methoxypyridin-3-yl)methylene)amino)acetate A mixture of glycine tert-butyl ester hydrochloride (1.350 g, 8.05 mmol) and magnesium sulfate (1.494 g, 12.41 mmol) in dichloromethane (12.0 mL) was treated with triethylamine (1.122 mL, 8.05 mmol), stirred for 30 minutes and treated with the 2-methoxynicotinaldehyde (0.92 g, 6.71 mmol) as a solution in 3 mL of dichloromethane. The reaction was stirred at room temperature overnight. The mixture was transferred with dichloromethane and filtered to remove the solids. The solids were washed with dichloromethane. The combined filtrates were washed with water (5 mL). The layers were separated and the aqueous layer was extracted with 5 mL of dichloromethane. The combined dichloromethane layers were dried over sodium sulfate, filtered, and concentrated to provide (E)-tert-butyl 2-(((2-methoxypyridin-3-yl)methylene)amino)acetate (1.52 g, 6.07 mmol, 91% yield). ¹H NMR (501 MHz, Chloroform-d) δ ppm 8.73 (s, 1H), 8.05 (dd, J=7.7, 1.8 Hz, 1H), 7.42 (ddd, J=8.3, 7.3, 1.8 Hz, 1H), 7.06-6.96 (m, 1H), 6.93 (dd, J=8.4, 0.9 Hz, 1H), 4.34 (d, J=1.3 Hz, 2H), 3.90 (s, 3H), 1.52 (s, 9H).

Core 39B (2S,3R,4S,5S)-tert-butyl 3-(2-methoxypropan-2-yl)-5-(2-methoxypyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.034 g, 0.045 mmol) and copper (I) triflate dimer, benzene complex (0.011 g, 0.022 mmol) were dissolved in tetrahydrofuran (5 mL) that had been sparged with a nitrogen stream for 1 hour. The resulting mixture was stirred for 1 hour at ambient temperature (continued nitrogen sparge), and (E)-tert-butyl 2-(((2-methoxypyridin-3-yl)methylene)amino)acetate (0.948 g, 3.79 mmol) was added as a solution in 0.574 mL of tetrahydrofuran. The resulting solution was cooled to <5° C. in an ice-water bath. Potassium 2-methylpropan-2-olate in tetrahydrofuran (0.09 mL, 0.090 mmol) was added dropwise, followed by addition of Core 36D (0.5 g, 3.44 mmol) over 10 minutes, maintaining a temperature less than 7° C. The reaction mixture was stirred for 45 minutes at 0° C. The reaction was quenched with 3 mL of saturated aqueous ammonium chloride and 10 mL of diethyl ether and warmed to ambient temperature. The ether layer was separated and washed twice with saturated aqueous ammonium chloride then brine. The organic layer was concentrated to provide a crude residue and was purified by chromatography using a 12 g silica gel cartridge eluting with a gradient of 0-50% heptanes/ethyl acetate over a period of 20 minutes to provide (2S,3R,4S,5S)-tert-butyl 3-(2-methoxypropan-2-yl)-5-(2-methoxypyridin-3-yl)-4-nitropyrrolidine-2-carboxylate (0.77 g, 1.947 mmol, 56.5% yield). ¹H NMR (400 MHz, Chloroform-d) δ ppm 8.11 (ddd, J=5.0, 1.8, 0.6 Hz, 1H), 7.56 (ddd, J=7.3, 1.8, 1.0 Hz, 1H), 6.88 (dd, J=7.4, 5.0 Hz, 1H), 5.54 (dd, J=5.8, 2.3 Hz, 1H), 4.58 (s, 1H), 4.02 (s, 3H), 3.87 (d, J=6.9 Hz, 1H), 3.27 (s, 3H), 3.20 (s, 1H), 3.04 (dd, J=7.0, 2.3 Hz, 1H), 1.55 (s, 9H), 1.33 (s, 3H), 1.28 (s, 3H); MS (APCI+) m/z 396 (M+H+).

Core 40

(2S,3R,4S,5S)-tert-butyl 5-(2-methoxyphenyl)-3-(2-methoxypropan-2-yl)-4-nitropyrrolidine-2-carboxylate Core 40A (E)-tert-butyl 2-((2-methoxybenzylidene)amino)acetate A mixture of glycine tert-butyl ester hydrochloride (1.35 g, 8.05 mmol) and magnesium sulfate (1.494 g, 12.42 mmol) in CH₂Cl₂ (12.0 mL) (anhydrous) was treated with triethylamine (1.122 mL, 8.05 mmol), stirred for 15 minutes and treated with 2-methoxybenzaldehyde as a solution in CH₂Cl₂ (~3 mL). The vial was capped and the mixture was stirred at room temperature overnight. The mixture was transferred with CH₂Cl₂ and filtered to remove the solids. The solids were washed with CH₂Cl₂. The combined filtrates were washed with water (5 mL). The layers were separated and the aqueous layer was extracted with CH₂Cl₂ (~5 mL). The combined CH₂Cl₂ layers were dried over sodium sulfate, filtered, concentrated, and taken directly on to the next step. ¹H NMR (501 MHz, Chloroform-d) δ ppm 8.73 (s, 1H), 8.05 (dd, J=7.7, 1.8 Hz, 1H), 7.42 (ddd, J=8.3, 7.3, 1.8 Hz, 1H), 7.06-6.96 (m, 1H), 6.93 (dd, J=8.4, 0.9 Hz, 1H), 4.34 (d, J=1.3 Hz, 2H), 3.90 (s, 3H), 1.52 (s, 9H).

Core 40B (2S,3R,4S,5S)-tert-butyl 5-(2-methoxyphenyl)-3-(2-methoxypropan-2-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.034 g, 0.045 mmol) and copper(II) triflate (0.011 g, 0.022 mmol) were dissolved in tetrahydrofuran (5 mL) that had been sparged with an N₂ stream for 1 hour. The resulting mixture was stirred for 1 hour at room temperature (continued nitrogen sparge), and (E)-tert-butyl 2-((2-methoxybenzylidene)amino)acetate (0.945 g, 3.79 mmol) was added as a solution in 0.574 mL of tetrahydrofuran and the resulting solution was cooled to <5° C. in an ice-water bath. Potassium 2-methylpropan-2-olate in tetrahydrofuran (0.177 mL, 0.177 mmol) was added dropwise, followed by addition of (E)-3-methoxy-3-methyl-1-nitrobut-1-ene (0.5 g, 3.44 mmol) over 10 minutes, maintaining a temperature less than 7° C. The reaction mixture was stirred for 45 minutes at 0° C. The mixture was quenched with 3 mL of saturated aqueous ammonium chloride and 10 mL of ethyl ether and warmed to room temperature. The ether layer was separated and washed twice with saturated aqueous ammonium chloride then brine and filtered through a pad of silica gel. The filtrate was concentrated to give a crude residue and was purified by chromatography using a 40 g silica gel cartridge eluting with a gradient of 0-50% heptanes/ethyl acetate over a period of 20 minutes to give (2S,3R,4S,5S)-tert-butyl 5-(2-methoxyphenyl)-3-(2-methoxypropan-2-yl)-4-nitropyrrolidine-2-carboxylate (0.71 g, 1.800 mmol, 52.3% yield). ¹H NMR (400 MHz, Chloroform-d) δ ppm 7.32-7.29 (m, 1H), 7.28-7.23 (m, 1H), 6.96 (t, J=7.5 Hz, 1H), 6.89 (d, J=8.2 Hz, 1H), 5.55 (dd, J=5.8, 2.4 Hz, 1H), 4.68 (d, J=5.8 Hz, 1H), 3.91 (s, 3H), 3.86 (d, J=7.1 Hz, 1H), 3.32 (bs, 1H), 3.27 (s, 3H), 3.07 (dd, J=7.1, 2.5 Hz, 1H), 1.57 (s, 9H), 1.33 (s, 3H), 1.29 (s, 3H); MS (APCI+) m/z 395 (M+H)⁺.

Core 41

(2S,3R,4S,5S)-ethyl 4-nitro-5-phenyl-3-(1-(trifluoromethyl)cyclopropyl)pyrrolidine-2-carboxylate Core 41A N-methoxy-N-methyl-1-(trifluoromethyl)cyclopropanecarboxamide To a solution of 1-(trifluoromethyl)cyclopropanecarboxylic acid (29.5 g, 191.56 mmol) in dichloromethane (580 mL) at 10° C. was added 1, 1'-carbonyldiimidazole (40.96 g, 252.86 mmol) in portions over 1 hour, maintaining the reaction temperature below 20° C. The addition of 1, 1'-carbonyldiimidazole was slightly exothermic and CO₂ gas was evolved. The reaction was stirred at room temperature for 30 minutes and then triethylamine (37.1 mL, 268.19 mmol) was added followed by N,O-dimethylhydroxylamine hydrochloride (26.16 g, 268.19 mmol). The resulting mixture was stirred for 15 hours and then reverse quenched into a cooled (5° C.) 3 N aqueous HCl solution (200 mL). The organic layer was washed sequentially with saturated aqueous sodium bicarbonate (200 mL) and water (200 mL), and concentrated under reduced pressure to give the title compound N-methoxy-N-methyl-1-(trifluoromethyl)cyclopropanecarboxamide (31.32 g, 158.98 mmol, 83% yield) which was sufficiently pure for use without further purification. ¹H NMR (400 MHz, CDCl₃) δ ppm 3.75 (s, 3H), 3.29 (s, 3H), 1.24-1.33 (m, 4H).

Core 41B 1-(trifluoromethyl)cyclopropanecarbaldehyde

To a solution of powdered lithium aluminum hydride (6.36 g, 167.5 mmol) in anhydrous diethyl ether (165 mL) at 0° C. under inert atmosphere was added N-methoxy-N-methyl-1-(trifluoromethyl)cyclopropanecarboxamide (33 g, 167.5 mmol) in diethyl ether (50 mL) dropwise over 3 minutes with vigorous stirring. The reaction was stirred at the same temperature for 1 hour and was quenched carefully with water (14.85 mL), 15% aqueous NaOH (14.85 mL) dropwise, followed by additional water (14.85 mL). The slurry was filtered through a pad of diatomaceous earth and washed with diethyl ether (2×150 mL). The volatile solvent was carefully removed under reduced pressure at 0° C. to give the title compound 1-(trifluoromethyl)cyclopropanecarbaldehyde (12.7 g, 92.13 mmol, 55.0% yield) which was used in the next step without further purification due to its volatility. ¹H NMR (400 MHz, CDCl₃) δ ppm 9.69 (s, 1H), 1.20-1.46 (m, 4H).

Core 41C 2-nitro-1-(1-(trifluoromethyl)cyclopropyl)ethanol

To a slurry of lithium aluminum hydride (641 mg, 16.89 mmol) in dry tetrahydrofuran (200 mL) at 0° C. was added nitromethane (45.6 mL, 844.2 mmol) dropwise. The mixture was stirred at 0° C. for 30 minutes and 1-(trifluoromethyl)cyclopropanecarbaldehyde (23.3 g, 168.84 mmol) was added dropwise. The mixture was stirred at 0° C. for 2 hours and was quenched with 1 N aqueous HCl (100 mL), poured into water (150 mL), and extracted with dichloromethane (2×150 mL). The combined organic layers were washed with brine (2×100 mL), dried over sodium sulfate, filtered and concentrated to give the title compound 2-nitro-1-(1-(trifluoromethyl)cyclopropyl)ethanol (21.17 g, 106.38 mmol, 63.0% yield). ¹H NMR (400 MHz, CDCl₃) δ ppm 4.33-4.68 (m, 4H), 0.92-1.08 (m, 4H).

Core 41D (E)-1-(2-nitrovinyl)-1-(trifluoromethyl)cyclopropane

To a solution of 2-nitro-1-(1-(trifluoromethyl)cyclopropyl)ethanol (21.0 g, 106.4 mmol)) in dichloromethane (200 mL) at −10° C. under an inert atmosphere was added trifluoroacetic anhydride (16.52 mL, 117.2 mmol). The mixture was stirred at −15° C. for 5 minutes and then triethylamine (32.61 mL, 234.08 mmol) was added while keeping the bath temperature at −15° C. during the addition. The stirring was continued at −10° C. for 45 minutes. The reaction was monitored by TLC (stained with iodine and UV) and quenched with saturated aqueous ammonium chloride solution (150 mL). The mixture was diluted with dichloromethane (150 mL) and stirred for 5 minutes. The aqueous layer was extracted with dichloromethane (100 mL×2). The combined organic layers were dried over magnesium sulfate, filtered and concentrated. The residue was purified by silica gel column chromatography (eluted with 1/300 ethyl acetate/petroleum ether) to give the title compound (E)-1-(2-nitrovinyl)-1-(trifluoromethyl)cyclopropane (11.2 g, 61.88 mmol, 58.1% yield). $^1$H NMR (400 MHz, CDCl$_3$) δ ppm 7.14 (d, J=13.6 Hz, 1H), 7.02 (d, J=14.0 Hz, 1H), 1.58-1.62 (m, 2H), 1.20-1.22 (m, 2H).

Core 41E (2S,3R,4S,5S)-ethyl 4-nitro-5-phenyl-3-(1-(trifluoromethyl)cyclopropyl)pyrrolidine-2-carboxylate To a flame-dried Schlenk tube containing activated 4 Å MS and a stirring bar was added copper (I) triflate dimer, benzene complex (193 mg, 0.384 mmol), the Catalyst 1 (274 mg, 0.364 mmol) and freshly distilled anhydrous tetrahydrofuran (40 mL) under an inert atmosphere. The mixture was stirred at room temperature for 15 minutes and cooled to 0° C. To the mixture was added (E)-ethyl 2-(benzylideneamino)acetate (Core 22A, 4.12 g, 21.54 mmol), potassium tert-butoxide (37.18 mg, 0.332 mmol) and (E)-1-(2-nitrovinyl)-1-(trifluoromethyl)cyclopropane (3.0 g, 16.56 mmol). The mixture was stirred at 0° C. for 2 hours and was filtered through a short plug of silica gel. The filtrate was concentrated under reduced pressure. The residue was purified by silica gel column chromatography (eluted with 1/10 petroleum ether/ethyl acetate) to give the title compound (2S,3R,4S,5S)-ethyl 4-nitro-5-phenyl-3-(1-(trifluoromethyl)cyclopropyl)pyrrolidine-2-carboxylate (3.45 g, 9.28 mmol, 68% yield). $^1$H NMR (400 MHz, CDCl$_3$) δ ppm 7.29-7.38 (m, 5H), 5.43-5.45 (m, 1H), 4.60-4.64 (m, 1H), 4.31-4.37 (m, 2H), 3.88 (t, J=8.4 Hz, 1H), 3.12 (t, J=9.6 Hz, 1H), 2.99-3.02 (m, 1H), 1.37 (t, J=6.8 Hz, 3H), 1.15-1.22 (m, 2H), 0.87-0.95 (m, 2H); LC-MS (ESI+) m/z 373 (M+H)$^+$.

Core 42

(2S,3R,4S,5S)-tert-butyl 3-(bicyclo[1.1.1]pentan-1-yl)-4-nitro-5-phenylpyrrolidine-2-carboxylate Core 42A bicyclo[1.1.1]pentan-1-ylmethanol To a solution of bicyclo[1.1.1]pentane-1-carboxylic acid (4.0 g, 35.7 mmol) in tetrahydrofuran (89 mL) at 0° C. was added lithium aluminum hydride (1.801 g, 47.4 mmol) in portions and the reaction bubbled vigorously. The reaction was warmed to 24° C. and was stirred for 16 hours. The reaction was cooled in an ice bath and 4 g of sodium sulfate decahydrate was added in portions and the reaction was stirred for 1 hour. Aqueous NaOH solution (15%, 2 mL) was added, the reaction mixture was stirred for 0.5 hours, water (2 mL) was added, the ice-bath was removed and the mixture was stirred for 2 hours. The mixture was dried with 40 g anhydrous sodium sulfate. The suspension was filtered and the filtrate was washed with ether. The solvent was removed in vacuo to provide crude bicyclo[1.1.1]pentan-1-ylmethanol (3.2 g, 32.6 mmol, 91% yield). $^1$H NMR (501 MHz, Chloroform-d) δ ppm 3.56 (s, 2H), 2.57 (s, 1H), 1.77 (s, 6H).

Core 42B bicyclo[1.1.1]pentane-1-carbaldehyde

In a 250-mL round bottom flask was charged with oxalyl chloride (4.57 mL, 52.2 mmol) in 55 mL of dichloromethane and the flask was cooled to <−70° C. in an acetone-dry ice bath. Dimethyl sulfoxide (7.40 mL, 104 mmol) was added dropwise over 20 minutes, maintaining a temperature <−60° C. After the addition was complete, the resulting solution was stirred for 15 minutes at the same temperature before addition of bicyclo[1.1.1]pentan-1-ylmethanol (Core 42A, 3.2 g, 32.6 mmol) as a solution in dichloromethane (5 mL) over 30 minutes, maintaining a temperature of <−65° C. After the addition was complete, the reaction mixture (suspension) was stirred at the same temperature for 1 hour (allowed to warm no further than −60° C.), at which point neat triethylamine (22.72 mL, 163 mmol) was added at −78° C. over 10 minutes. A very thick slurry resulted. The flask was removed from the ice bath. After reaching ambient temperature, the reaction mixture was quenched by the addition of 200 mL of 1 M aqueous HCl. The layers were separated and the organic layer washed twice with 1 M aqueous HCl (30 mL) and brine then dried over sodium sulfate, filtered, and concentrated in vacuo (rotovap bath at 10° C.) to provide bicyclo[1.1.1]pentane-1-carbaldehyde (2.6 g, 27.0 mmol, 83% yield). $^1$H NMR (501 MHz, Chloroform-d) δ ppm 9.52 (d, J=0.7 Hz, 1H), 2.57 (d, J=0.8 Hz, 1H), 2.11 (s, 6H).

Core 42C 1-(bicyclo[1.1.1]pentan-1-yl)-2-nitroethanol

Core 42B (2.6 g, 27.0 mmol) and nitromethane (2.188 mL, 40.6 mmol) were dissolved in tetrahydrofuran (10 mL) and tert-butanol (3 mL). After cooling to <5° C. in an ice bath, potassium tert-butoxide (5.41 mL, 5.41 mmol) solution was added dropwise. After 1 hour, the ice-bath was removed and the mixture was stirred for 30 minutes. The mixture was poured into 40 mL of water and extracted with 3×30 mL of ether. The combined extracts were washed with brine, dried over sodium sulfate, filtered, and concentrated. Purification via flash column chromatography, eluting with 0-60% ethyl acetate/heptanes over 20 minutes on a 40 g silica gel column afforded the desired product 1-(bicyclo[1.1.1]pentan-1-yl)-2-nitroethanol (2.22 g, 14.13 mmol, 52.2% yield). $^1$H NMR (500 MHz, Chloroform-d) δ ppm 4.49-4.38 (m, 1H), 4.36-4.27 (m, 2H), 2.61 (s, 1H), 2.32-2.29 (m, 1H), 1.85-1.78 (m, 6H); MS (DCI+) m/z 175 (M+NH$_4$+).

Core 42D (E)-1-(2-nitrovinyl)bicyclo[1.1.1]pentane

Core 42C (2.22 g, 14.13 mmol) was dissolved in 18.8 mL of dry dichloromethane and the solution was cooled to −78° C. Triethylamine (4.92 mL, 35.3 mmol) was added, followed by dropwise addition of mesyl chloride (1.321 mL, 16.95 mmol). The reaction mixture was stirred for 1 hour at the same temperature, the dry ice bath was removed and the mixture was stirred for 1 hour. The mixture was washed with saturated aqueous sodium bicarbonate and brine then dried over sodium sulfate, filtered, concentrated in vacuo, and purified via flash column chromatography, eluting with 0-40% ethyl acetate/heptanes over 20 minutes on a 24 g silica gel column to provide the desired product (E)-1-(2-nitrovinyl)bicyclo[1.1.1]pentane (1.63 g, 11.71 mmol, 83% yield). $^1$H NMR (501 MHz, Chloroform-d) δ ppm 7.20 (d, J=13.4 Hz, 1H), 6.88 (d, J=13.4 Hz, 1H), 2.62 (s, 1H), 2.04 (s, 6H).

Core 42E (2S,3R,4S,5S)-tert-butyl 3-(bicyclo[1.1.1]pentan-1-yl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.065 g, 0.086 mmol) and copper (I) triflate dimer, benzene complex (0.017 g, 0.034 mmol) were dissolved in tetrahydrofuran (9.5 mL) that had been sparged with a nitrogen stream for 1 hour. The resulting mixture was stirred for 1 hour at ambient temperature (continued nitrogen sparge), and Core 1A (1.040 g, 4.74 mmol) was added as a solution in 1 mL of tetrahydrofuran and the resulting solution was cooled to <5° C. in an ice-water bath. Potassium 2-methylpropan-2-olate in tetrahydrofuran (0.177 mL, 0.177 mmol) was added dropwise, followed by addition of Core 42D (0.6 g, 4.31 mmol) over 3 minutes, maintaining a temperature less than 7° C. The reaction mixture was stirred for 45 minutes at 0° C. The mixture was quenched with 6 mL of saturated aqueous ammonium chloride and 20 mL of ethyl ether and warmed to ambient temperature. The ether layer was separated and washed twice with saturated aqueous ammonium chloride then brine and filtered through a pad of silica gel. The filtrate was concentrated to provide a residue, which was diluted with n-heptane (50 mL), and let stand over 2 hours. The mixture was filtered and precipitated in 50 mL hot heptane to provide (2S,3R,4S,5S)-tert-butyl 3-(bicyclo[1.1.1]pentan-1-yl)-4-nitro-5-phenylpyrrolidine-2-carboxylate (0.73 g, 2.037 mmol, 47.2% yield). $^1$H NMR (400 MHz, Chloroform-d) δ ppm 7.44-7.30 (m, 5H), 5.01 (dd, J=5.7, 2.0 Hz, 1H), 4.47 (d, J=5.5 Hz, 1H), 3.74 (d, J=6.0 Hz, 1H), 3.40 (bs, 1H), 3.02-2.92 (m, 1H), 2.69 (s, 1H), 1.96-1.79 (m, 6H), 1.57 (s, 9H); MS (ESI+) m/z 359 (M+H+).

Core 43

(2S,3R,4S,5S)-tert-butyl 3-(bicyclo[1.1.1]pentan-1-yl)-5-(2-(dimethylamino)pyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.036 g, 0.047 mmol) and copper (I) triflate dimer, benzene complex (9.55 mg, 0.019 mmol) were dissolved in tetrahydrofuran (4.2 mL mL) that had been sparged with a nitrogen stream for 1 hour. The resulting mixture was stirred for 1 hour at ambient temperature (continued nitrogen sparge), and Core 38A (0.72 g, 2.73 mmol) was added as a solution in 1 mL of tetrahydrofuran and the resulting solution was cooled to <5° C. in an ice-water bath. Potassium 2-methylpropan-2-olate in tetrahydrofuran (0.050 mL, 0.050 mmol) was added dropwise, followed by addition of Core 42D (0.33 g, 2.372 mmol) in 1 mL tetrahydrofuran over 2 minutes, maintaining a temperature less than 7° C. The reaction mixture was stirred for 1 hour at 0° C. The mixture was quenched with 4 mL of saturated aqueous ammonium chloride and 10 mL of diethyl ether and warmed to ambient temperature. The ether layer was separated and washed twice with saturated aqueous ammonium chloride then brine and filtered through a pad of silica gel. The mixture was concentrated and was purified by chromatography using a 24 g silica gel cartridge eluting with a gradient of 0-70% heptanes/ethyl acetate over a period of 20 minutes to provide (2S,3R,4S,5S)-tert-butyl 3-(bicyclo[1.1.1]pentan-1-yl)-5-(2-(dimethylamino)pyridin-3-yl)-4-nitropyrrolidine-2-carboxylate (0.73 g, 1.814 mmol, 76% yield). $^1$H NMR (501 MHz, Chloroform-d) δ ppm 8.33 (dd, J=4.9, 1.8 Hz, 1H), 7.61 (ddd, J=7.8, 2.0, 0.9 Hz, 1H), 7.02 (dd, J=7.6, 4.8 Hz, 1H), 5.37 (dd, J=5.3, 1.6 Hz, 1H), 4.64 (d, J=11.3 Hz, 1H), 3.72 (s, 1H), 3.24 (s, 1H), 2.94 (dd, J=6.2, 1.3 Hz, 1H), 2.82 (s, 6H), 2.70 (s, 1H), 1.97-1.80 (m, 6H), 1.56 (s, 9H); MS (ESI+) m/z 403 (M+H+).

Core 44

(2S,3R,4S,5S)-tert-butyl 3-(bicyclo[1.1.1]pentan-1-yl)-5-(2-methoxypyridin-3-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.045 g, 0.060 mmol) and copper (I) triflate dimer, benzene complex (0.012 g, 0.024 mmol) were dissolved in tetrahydrofuran (5.0 mL mL) that had been sparged with an nitrogen stream for 1 hour. The resulting mixture was stirred for 1 hour at ambient temperature (continued nitrogen sparge), and (E)-tert-butyl 2-(((2-methoxypyridin-3-yl)methylene)amino)acetate (0.923 g, 3.32 mmol) was added as a solution in 1 mL of tetrahydrofuran and the resulting solution was cooled to <5° C. in an ice-water bath. Potassium 2-methylpropan-2-olate in tetrahydrofuran (0.063 mL, 0.063 mmol) was added dropwise, followed by addition of Core 42D (0.42 g, 3.02 mmol) in 1 mL tetrahydrofuran over 2 minutes, maintaining a temperature less than 7° C. The reaction mixture was stirred for 1 hour at 0° C. The mixture was quenched with 4 mL of saturated aqueous ammonium chloride and 10 mL of diethyl ether and warmed to ambient temperature. The ether layer was separated and washed twice with saturated aqueous ammonium chloride then brine and filtered through a pad of silica gel. The mixture was concentrated to provide a crude residue and was purified by chromatography using a 24 g silica gel cartridge eluting with a gradient of 0-60% heptanes/ethyl acetate over a period of 20 minutes to provide (2S,3R,4S,5S)-tert-butyl 3-(bicyclo[1.1.1]pentan-1-yl)-5-(2-methoxypyridin-3-yl)-4-nitropyrrolidine-2-carboxylate (0.71 g, 1.823 mmol, 60.4% yield). $^1$H NMR (400 MHz, Chloroform-d) δ ppm 8.13 (dd, J=5.0, 1.8 Hz, 1H), 7.55 (ddd, J=7.5, 1.9, 1.0 Hz, 1H), 6.90 (dd, J=7.4, 5.0 Hz, 1H), 5.23 (dd, J=5.3, 1.7 Hz, 1H), 4.46 (s, 1H), 4.03 (s, 3H), 3.68 (d, J=6.0 Hz, 1H), 3.30 (s, 1H), 2.92 (dd, J=6.2, 1.7 Hz, 1H), 2.68 (s, 1H), 1.94-1.79 (m, 6H), 1.55 (s, 9H); MS (APCI+) m/z 390 (M+H+).

Core 45 rac-methyl (2R,3S,4R,5R)-3-cyclopropyl-4-nitro-5-phenylpyrrolidine-2-carboxylate Core 45A methyl (E)-2-(benzylideneamino)acetate Glycine methyl ester hydrochloride (H-Gly-OMe-HCl) (689.1 g, 5.49 mmol) and magnesium sulfate (751.6 mg, 6.24 mmol) were suspended in dichloromethane (10 mL), then triethylamine (760 µL, 5.45 mmol) was added, and the mixture was stirred at room temperature for 20 minutes. Benzaldehyde (500 µL, 4.93 mmol) was then added dropwise, and the reaction was allowed to stir for 17 hours at ambient temperature. After this time, the mixture was filtered, and the filter pad was washed with $CH_2Cl_2$. The combined filtrates were washed twice with water and once with brine, dried over $Na_2SO_4$, filtered, and concentrated to provide (E)-methyl 2-(benzylideneamino)acetate (1.284 g, 7.25 mmol, 91% yield). $^1$H NMR (400 MHz, Chloroform-d) δ ppm 8.31 (d, J=1.4 Hz, 1H), 7.79 (dd, J=7.7, 1.9 Hz, 2H), 7.49-7.38 (m, 3H), 4.43 (d, J=1.2 Hz, 2H), 3.79 (s, 3H); MS (ESI+) m/z 178 (M+H)$^+$.

Core 45B 1-cyclopropyl-2-nitroethanol

Tetrahydrofuran (10 mL) and tert-butanol (10.00 mL) were cooled to 0° C., and treated with cyclopropanecarboxaldehyde (1.1 mL, 14.60 mmol) and nitromethane (1.18 mL, 21.88 mmol). Potassium tert-butoxide (1 M in tetrahydrofuran) (2.92 mL, 2.92 mmol) was added dropwise, and the reaction was allowed to warm to room temperature and was stirred overnight. The mixture was diluted with saturated aqueous $NH_4Cl$ solution and extracted three times with $CH_2Cl_2$. The combined organics were dried over $Na_2SO_4$, filtered, and concentrated (no heat) to provide the title compound (2.669 g, 20.35 mmol, 139% yield) containing some tert-butanol. $^1$H NMR (400 MHz, $CDCl_3$) δ ppm 4.62-4.50 (m, 2H), 3.71 (m, 1H), 2.44 (d, J=4.1 Hz, 1H), 0.98 (qt, J=8.2, 4.9 Hz, 1H), 0.66 (m, 2H), 0.50 (m, 1H), 0.38 (m, 1H).

Core 45C (E)-(2-nitrovinyl)cyclopropane

1-Cyclopropyl-2-nitroethanol (Core 45B, 2.87 g, 21.88 mmol) in dichloromethane (30 mL) was cooled to 0° C. and treated slowly with trifluoroacetic acid anhydride (3.40 mL, 24.07 mmol). The mixture was then treated slowly with triethylamine (6.71 mL, 48.1 mmol), and the reaction stirred in the ice bath for 1.5 hours and at room temperature for another 1.5 hours. The mixture was then filtered through a pad of silica gel, washing with additional $CH_2Cl_2$. The combined organic filtrates were concentrated without heat, and the resulting residue was taken up in 20% ether-hexane and filtered through a pad of silica gel, washing with additional 20% ether-hexane. The combined filtrates were concentrated without heat. $^1$H NMR (400 MHz, $CDCl_3$) δ ppm 7.15 (d, J=13.1 Hz, 1H), 6.80 (dd, J=13.2, 10.8 Hz, 1H), 1.69-1.60 (m, 1H), 1.18-1.13 (m, 2H), 0.84-0.80 (m, 2H); MS (DCI+) m/z 131 (M+NH$_4$)$^+$.

Core 45D rac-methyl (2R,3S,4R,5R)-3-cyclopropyl-4-nitro-5-phenylpyrrolidine-2-carboxylate To a solution Core 45A (441.2 mg, 2.490 mmol) and (E)-(2-nitrovinyl)cyclopropane (Core 45C, 257.0 mg, 2.272 mmol) in toluene (5 mL) and tetrahydrofuran (5 mL) was added silver acetate (379 mg, 2.272 mmol) and 3 Å molecular sieves. The reaction mixture was cooled to 0° C. and triethylamine (0.63 mL, 4.52 mmol) was added slowly to the well stirred reaction mixture. After 10 minutes at 0° C., the reaction was allowed to warm to ambient temperature for 4 hours. The mixture was filtered and the solids were washed with ethyl acetate. To the combined mixture, saturated aqueous ammonium chloride (30 mL) was added, the precipitate was filtered off and the filtrate was extracted with ethyl acetate (2×35 mL). The combined organic fractions were dried over $MgSO_4$, filtered, and concentrated to provide 680 mg of crude material. The crude product was triturated from heptane (15 mL) and washed with additional heptane (2×15 mL) to provide the title compound (391.2 mg, 59%). $^1$H NMR (400 MHz, DMSO-d$_6$) δ ppm 7.41-7.17 (m, 5H), 5.28 (dd, J=6.8, 3.8 Hz, 1H), 4.78 (dd, J=9.5, 6.8 Hz, 1H), 3.76 (dd, J=8.2, 7.1 Hz, 1H), 3.71 (s, 3H), 3.52-3.43 (m, 1H), 2.37-2.27 (m, 1H), 1.11-0.98 (m, 1H), 0.58-0.38 (m, 2H), 0.31-0.17 (m, 2H). MS (ESI+) m/z 291 (M+H)$^+$.

Core 46 rac-(2R,3S,4R,5R)-tert-butyl 3-cyclopropyl-4-nitro-5-phenylpyrrolidine-2-carboxylate (E)-(2-Nitrovinyl)cyclopropane (Core 45C, 0.575 g, 5.08 mmol), (E)-tert-butyl 2-(benzylideneamino)acetate (Core 1A, 0.929 g, 4.24 mmol), silver acetate (1.061 g, 6.35 mmol), and powdered activated 3 Å sieves in toluene (8 mL) and tetrahydrofuran (8.00 mL) were cooled to 0° C. and treated dropwise with triethylamine (1.5 mL, 10.76 mmol). The mixture stirred from 0° C. to room temperature overnight. The reaction mixture was then filtered through diatomaceous earth, and the filter pad was washed with ethyl acetate. The combined filtrates were treated with 40 mL saturated aqueous $NH_4Cl$ solution, and the mixture was transferred to a separatory funnel. The mixture was extracted twice with ethyl acetate, and the combined organics were dried over $Na_2SO_4$, filtered, and concentrated in vacuo. The crude product was purified by silica gel chromatography, eluting with 0 to 40% ethyl acetate-heptanes, to provide the title compound, 0.615 g (44% yield). $^1$H NMR (400 MHz, DMSO-d$_6$) δ ppm 7.35-7.23 (m, 5H), 5.30 (dd, J=6.5, 3.3 Hz, 1H), 4.78 (dd, J=10.9, 6.4 Hz, 1H), 3.65 (dd, J=8.9, 6.8 Hz, 1H), 3.38-3.28 (m, 1H), 2.22 (m, 1H), 1.47 (s, 9H), 1.07 (m, 1H), 0.60-0.45 (m, 2H), 0.29 (m, 2H); MS (ESI$^+$) m/z 332.9 (M+H)$^+$.

Core 47 rac-(2R,3S,4R,5R)-4-nitro-3-tert-butyl-5-(2-dimethylamino-phenyl)-pyrrolidine-2-carboxylic acid methyl ester Glycine methyl ester hydrochloride (925 mg, 7.37 mmol, 1.1 eq) was added to a solution of triethylamine (1.07 mL, 8.04 mmol, 1.2 eq) in toluene (20 mL). The reaction mixture was stirred for 30 minutes on 3 Å molecular sieves. 2-Dimethylamino-benzaldehyde (1.00 g, 6.70 mmol, 1.0 eq) was added and the reaction mixture was stirred at room temperature overnight. The reaction mixture was filtered, diluted with toluene and cooled to 0° C. AgCO$_2$CH$_3$ (783 mg, 4.69 mmol, 0.7 eq) was added, followed by (E)-3,3-dimethyl-1-nitrobut-1-ene (606 mg, 4.69 mmol, 0.7 eq) and triethylamine (0.623 mL). The reaction was stirred at 0° C. for 1 hour, warmed to room temperature, stirred for 5 hours, and quenched with a saturated aqueous $NH_4Cl$ solution. Dichloromethane and water were added. The aqueous phase was separated and extracted with dichloromethane. The combined organic phases were dried with $Na_2SO_4$, filtered and concentrated to dryness. The crude material was purified by flash chromatography (cyclohexane/ethyl acetate 100/0 to 60/40) to provide the title compound (489 mg, 21% over two steps). LC/MS (ESI+) m/z 350.35 (M+H)+.

Core 48 rac-(2R,3S,4R,5S)-4-nitro-3-tert-butyl-5-(6-methoxy-pyridin-2-yl)-pyrrolidine-2-carboxylic acid methyl ester

Core 48A (E)-methyl 2-(((6-methoxypyridin-2-yl)methylene)amino)acetate

Glycine methyl ester hydrochloride (925 mg, 7.37 mmol, 1.1 eq) was added to a solution of triethylamine (1.07 mL, 8.04 mmol, 1.2 eq) in toluene (20 mL). The reaction mixture was stirred for 30 minutes on 3 Å molecular sieves. Then 6-methoxy-2-pyridinecarboxaldehyde (0.92 g, 6.70 mmol, 1.0 eq) was added and the reaction mixture was stirred at room temperature overnight. The reaction mixture was filtered, diluted with toluene and cooled to 0° C., and used in the next step without further purification.

Core 48B rac-(2R,3S,4R,5S)-4-nitro-3-tert-butyl-5-(6-methoxy-pyridin-2-yl)-pyrrolidine-2-carboxylic acid methyl ester To the solution of Core 48A, $AgCO_2CH_3$ (783 mg, 4.69 mmol, 0.7 eq) was added, followed by (E)-3,3-dimethyl-1-nitrobut-1-ene (606 mg, 4.69 mmol, 0.7 eq) and triethylamine (0.623 mL). The reaction was stirred at 0° C. for 1 hour and afterwards the temperature was raised to room temperature. The reaction was stirred for 5 hours, and quenched with a saturated aqueous $NH_4Cl$ solution. Dichloromethane and water were added. The aqueous phase was separated and extracted with dichloromethane. The combined organic phases were dried, filtered and concentrated to dryness. The crude material was purified by flash chromatography (cyclohexane/ethyl acetate 100/0 to 60/40) to provide the title compound (987 mg, 40% over two steps). LC/MS (ESI+) m/z 338.22 (M+H)+.

Core 49 rac-(2R,3S,4R,5S)-4-nitro-3-tert-butyl-5-pyridin-2-yl-pyrrolidine-2-carboxylic acid tert-butyl ester

Core 49A (E)-tert-butyl 2-((pyridin-2-ylmethylene)amino)acetate

The title compound was prepared according to the procedure described in Core 48A, substituting 6-methoxypicolinaldehyde for picolinaldehyde, and glycine tert-butyl ester hydrochloride for glycine methyl ester hydrochloride.

Core 49B rac-(2R,3S,4R,5S)-4-nitro-3-tert-butyl-5-pyridin-2-yl-pyrrolidine-2-carboxylic acid tert-butyl Silver acetate ($AgCO_2CH_3$, 194 mg, 1.16 mmol, 1.5 eq) was added to a solution of Core 49A (256 mg, 1.16 mmol, 1.5 eq) in toluene (0.5 mL) at 0° C. The reaction mixture was stirred for 10 minutes. A solution of (E)-3,3-dimethyl-1-nitrobut-1-ene (100.0 mg, 0.774 mmol, 1.0 eq) in toluene (0.5 mL) was slowly added, followed by dropwise addition of 1,8-diazabicyclo[5.4.0]undec-7-ene (174 µL, 1.16 mmol, 1.5 eq) in toluene (0.5 mL). The reaction mixture was stirred overnight at room temperature, and quenched with a saturated aqueous solution of $NH_4Cl$. Dichloromethane and water were added. The aqueous phase was extracted and the combined organic phases were dried, filtered and concentrated. The crude material was purified by flash chromatography (hexane/ethyl acetate 100/0 to 50/50) to provide the title compound (271 mg, 100%). LC/MS (ESI+) m/z 350.23 (M+H)+.

Core 50 rac-(2S,3R,4S,5R)-4-nitro-3-tert-butyl-5-(3-methoxy-pyridin-2-yl)-pyrrolidine-2-carboxylic acid methyl ester Methyl 2-aminoacetate hydrochloride (1.1 g, 8.75 mmol, 1.2 eq) was suspended in dry toluene (25 mL) and triethylamine (2.24 mL, 16.04 mmol, 2.2 eq) was added. The mixture was stirred for 10 minutes. 3-Methoxypyridine-2-carbaldehyde (1 g, 7.29 mmol, 1.00 eq) was added and the mixture was stirred at room temperature for 2 hours. The resulting mixture was filtered and the filtrate was cooled to 0° C. in an ice bath. Triethylamine (1017.7 µL, 1 eq) was added. (E)-3,3-Dimethyl-1-nitrobut-1-ene (706 mg, 5.47 mmol, 0.75 eq) was added followed by silver acetate ($AgCO_2CH_3$, 1.22 g, 7.29 mmol, 1.00 eq). After 2 hours, the reaction was quenched with aqueous ammonium chloride solution. The reaction mixture was extracted with dichloromethane. The organic layers were combined, passed through a hydrophobic frit, and concentrated in vacuo. The crude material was purified by flash chromatography (cyclohexane/ethyl acetate 100/0 to 40/60) to provide the title compound (625 mg, 25% over 2 steps). LC/MS (ESI+) m/z 338.24 (M+H)+.

Core 51 tert-butyl (2S,3S,4R,5S)-3-tert-butyl-4-nitro-5-phenyl-pyrrolidine-2-carboxylate To a previously degassed solution of ligand (S)-1-(diphenylphosphino)-2-[(S)-4-isopropyloxazolin-2-yl]ferrocene (CAS#163169-29-7, 20.5 mg, 0.04 mmol, 0.011 eq) in tetrahydrofuran (6 mL) under $N_2$ was added copper triflate complex (CAS#42152-46-5, 10 mg, 0.019 mmol, 0.005 eq). The reaction mixture was sparged with $N_2$ for 5 minutes. The solution was then stirred at room temperature for 45 minutes under $N_2$. The mixture was then cooled to 0° C.-5° C. (internal temperature) and (E)-tert-butyl 2-(benzylideneamino)acetate (Core 1A, 1.096 g, 5.0 mmol, 1.3 eq) in tetrahydrofuran (1 mL) was added maintaining the internal temperature below 5° C. A solution of potassium tert-butoxide (1 M in tetrahydrofuran, 310 µL, 0.31 mmol, 0.08 eq) was slowly added followed by (E)-3,3-dimethyl-1-nitrobut-1-ene (500 mg, 3.87 mmol, 1.0 eq) in tetrahydrofuran (1 mL). The resulting suspension was stirred at 0-5° C. for 20 minutes. The reaction mixture was quenched after 30 minutes by addition of a saturated aqueous $NH_4Cl$ solution and diluted in ethyl acetate. The organic layer was separated, washed with water and brine, dried over $MgSO_4$, filtered and concentrated in vacuo. The crude mixture was purified by flash chromatography on silica gel (heptane/ethyl acetate 98/2 to 80/20) to provide the title compound (940 mg, 70%). LC/MS (ESI+) m/z 349.4 (M+H)+.

Core 52 rac-(2R,3S,4R,5S)-methyl 3-(tert-butyl)-5-(3-chloro-pyridin-2-yl)-4-nitropyrrolidine-2-carboxylate Methyl 2-aminoacetate hydrochloride (1.06 g, 8.48 mmol, 1.2 eq) was suspended in dry toluene (25 mL) and triethylamine (2.17 mL, 15.5 mmol, 2.2 eq) was added and the reaction mixture was stirred for 10 minutes. Then 3-chloropyridine-2-carbaldehyde (1 g, 7.06 mmol, 1.00 eq) was added and the mixture was stirred at room temperature for 2 hours. The resulting mixture was filtered and filtrate was cooled to 0° C. in an ice bath. Triethylamine (986 µL, 7.1 mmol, 1 eq) was added. (E)-3,3-Dimethyl-1-nitrobut-1-ene (684.3 mg, 5.30 mmol, 0.75 eq) was added followed by silver acetate (AgCO$_2$CH$_3$, 1.18 g, 7.06 mmol, 1.00 eq). After 2 hours, the reaction was quenched with aqueous ammonium chloride solution. The reaction mixture was extracted with dichloromethane. The organic layer was passed through phase separator and concentrated in vacuo. The crude material was purified by flash chromatography (cyclohexane/ethyl acetate 100/0 to 40/60) to provide the title compound (900 mg, 37% over 2 steps). LC/MS (ESI+) m/z 342.21 (M+H)+.

Core 53 rac-(4R,6R,7R)-7-amino-5-cyclohexanecarbonyl-6-phenyl-5-aza-spiro[2.4]heptane-4-carboxylic acid methyl ester Core 53A (2-(benzyloxy)-2-oxoethyl)triphenylphosphonium bromide A mixture of benzyl 2-bromoacetate (6.6 mL, 42.1 mmol) and triphenylphosphine (11.58 g, 44.2 mmol) in toluene (200 mL) was stirred at room temperature for 3 days. The precipitate was collected by filtration and washed with diethyl ether to provide the title compound (2-(benzyloxy)-2-oxoethyl)triphenylphosphonium bromide (20 g, 40.3 mmol, 96% yield). LC/MS (ESI+) m/z 411 (M+H)+.

Core 53B benzyl 2-(triphenylphosphoranylidene)acetate

A solution of (2-(benzyloxy)-2-oxoethyl)triphenylphosphonium bromide (2.00 g, 4.07 mmol) and NaOH (0.081 g, 2.035 mmol) in CH$_2$Cl$_2$ (20 mL) was stirred at 25° C. for 1 hour. The mixture was diluted with CH$_2$Cl$_2$ (50 mL), and washed with water (30 mL). The organic layer was separated and concentrated to provide benzyl 2-(triphenylphosphoranylidene)acetate (1.5 g, 3.25 mmol, 80% yield). $^1$H NMR (400 MHz, CDCl$_3$) δ ppm 7.60-7.65 (m, 6H), 7.51-7.54 (m, 4H), 7.42-7.46 (m, 6H), 7.20 (s, 4H), 5.00 (s, 2H), 2.96 (s, 1H); LC-MS(ESI) m/z 411.1 (M+H)+.

Core 53C 1-ethoxycyclopropanol

A solution of (1-ethoxycyclopropoxy)trimethylsilane (1.499 mL, 7.46 mmol) and a drop of hydrogen chloride (7.16 mg, 0.075 mmol) in CH$_3$OH (6 mL) was stirred at 25° C. for 16 hours. The mixture was concentrated to provide the title compound 1-ethoxycyclopropanol (0.5 g, 4.90 mmol, 65.6% yield). $^1$H NMR (400 MHz, CDCl$_3$) δ ppm 3.76 (q, J=8 Hz, 2H), 1.22 (t, J=8 Hz, 4H), 0.93-0.95 (m, 4H).

Core 53D benzyl 2-cyclopropylideneacetate

To a solution of benzyl 2-(triphenylphosphoranylidene)acetate (5 g, 11.57 mmol) and benzoic acid (0.601 g, 4.92 mmol) in toluene (50 mL) at 80° C. was added 1-ethoxycyclopropanol (1.391 g, 11.57 mmol). The mixture was stirred at 80° C. for 5 hours and was concentrated. The residue was purified by column chromatography (on silica gel, eluted with 5% ethyl acetate/hexane) to provide the title compound benzyl 2-cyclopropylideneacetate (1.3 g, 5.66 mmol, 48.9% yield). LC/MS (ESI+) m/z 189.2 (M+H)+.

Core 53E rac-(4R,6S,7R)-7-benzyl 4-tert-butyl 6-phenyl-5-azaspiro[2.4]heptane-4,7-dicarboxylate To a mixture of (E)-tert-butyl 2-(benzylideneamino)acetate (Core 1A, 1.966 g, 7.17 mmol) and lithium bromide (0.747 g, 8.61 mmol) in tetrahydrofuran (20 mL) at −70° C. were added benzyl 2-cyclopropylideneacetate (1.8 g, 7.17 mmol) and 1,8-diazabicyclo[5.4.0]undec-7-ene (1.62 mL, 10.76 mmol). After the mixture was stirred for 30 minutes at −78° C., the mixture was warmed to 0° C. for 45 minutes and then at 25° C. for 2 hours. The reaction was quenched with saturated aqueous NH$_4$Cl (10 mL) and water (10 mL). The mixture was extracted with CH$_2$Cl$_2$ (30 mL). The organic layer was dried over Na$_2$SO$_4$, filtered and concentrated. The residue was purified by preparative HPLC (Instrument: Gilson 281; Column: Xbridge™ 21.2*250 mm c18, 10 um; Mobile Phase: A: water (10 mmol/L NH$_4$HCO$_3$) B: acetonitrile; gradient: 55-65% B in 10 minutes, stop at 15 minutes; flow rate (mL/minute) 25.00; detective wavelength (nm) 214) to provide the title compound (251 mg, 0.616 mmol, 8.59% yield). $^1$H NMR (400 MHz, CDCl$_3$) δ ppm 7.23-7.34 (m, 8H), 6.98-7.01 (m, 2H), 4.67-4.79 (m, 3H), 3.68 (s, 1H), 2.91 (d, J=8 Hz, 1H), 1.49 (s, 9H), 1.05-1.08 (m, 1H), 0.92-0.95 (m, 1H), 0.77-0.79 (m, 1H), 0.60-0.63 (m, 1H); LC-MS (ESI+) m/z 408.2 (M+H)+.

Core 53F rac-(4R,6R,7R)-5-cyclohexanecarbonyl-6-phenyl-5-aza-spiro[2.4]heptane-4,7-dicarboxylic acid 7-benzyl ester 4-tert-butyl ester Core 53E (408 mg, 1 mmol, 1.0 eq) was dissolved in dichloromethane (10 mL) and the reaction mixture was cooled to 0° C. Diisopropylethylamine (261 µL, 1.4 mmol, 1.5 eq) and cyclohexyl acyl chloride (161 µL, 1.2 mmol, 1.2 eq) were added. After 15 minutes at room temperature, the reaction mixture was quenched with aqueous ammonium chloride solution. The two phases were separated and the organic phase was concentrated in vacuo. The crude material was purified by flash chromatography (heptane/ethyl acetate 95/5 to 70/30) to provide the title compound (445 mg, 86%). LC/MS (ESI+) m/z 518.50 (M+H)+.

Core 53G rac-(4R,6R,7R)-5-cyclohexanecarbonyl-6-phenyl-5-aza-spiro[2.4]heptane-4,7-dicarboxylic acid 4-tert-butyl ester Core 53F (443 mg, 0.86 mmol, 1 eq) was dissolved in 20 mL of methanol. Pd/C 5% was added and the reaction mixture was stirred at room temperature for 2 hours, then filtered on diatomaceous earth. The filtrate was concentrated in vacuo. The resulting solid was suspended in dichloromethane and filtered. The material was dried under vacuum to provide the title compound (275 mg, 75%) which was used in the next step without further purification.

Core 53H rac-(4R,6R,7R)-7-benzyloxycarbonylamino-5-cyclohexanecarbonyl-6-phenyl-5-aza-spiro[2.4]heptane-4-carboxylic acid tert-butyl ester To a stirred solution of Core 53G (275 mg, 0.643 mmol, 1.0 eq) and triethylamine (108 µL, 0.772 mmol, 1.2 eq) in toluene (10 mL) was added diphenyl phosphoryl azide (CAS#26386-88-9, 152 L, 0.708 mmol, 1.1 eq). After stirring at room temperature for 10 minutes, the mixture was refluxed for 1 hour. To the refluxing mixture was added benzyl alcohol (133 µL, 1.29 mmol, 2.0 eq) and the reflux was continued for 2 hours. The resulting mixture was poured into 1 N aqueous NaOH and extracted with diethyl ether. The organic phase was washed with brine, dried over MgSO$_4$, filtered, and concentrated under reduced pressure. The residue was purified by flash chromatography (heptane/ethyl acetate 90/10 to 60/40) to provide the title compound (182 mg, 54%). LC/MS (ESI+) m/z 533.3 (M+H)$^+$.

Core 53I rac-(4R,6R,7R)-7-amino-5-cyclohexanecarbonyl-6-phenyl-5-aza-spiro[2.4]heptane-4-carboxylic acid tert-butyl ester To a solution of Core 53H (181 mg, 0.34 mmol, 1 eq) in methanol (5 mL) was added Pd/C 5% (72 mg, 0.03 mmol, 0.1 eq). The reaction mixture was stirred for 1 hour at room temperature then filtrated on diatomaceous earth. The filtrate was concentrated to dryness to provide the title compound (142 mg, quantitative) which was used in the next step without further purification.

Core 54 ethyl (2S,3S,4R,5S)-3-tert-butyl-4-nitro-5-phenyl-pyrrolidine-2-carboxylate

The filtrate from the preparation of Core 7 was concentrated and purified by chromatography on silica gel (heptane/ethyl acetate 80/20) to provide title compound (second diastereomer to elute). LC/MS (ESI+) m/z 321.5 (M+H)$^+$.

Core 55 rac-(2R,3R,4R,5R)-3-tert-butyl-2-methyl-4-nitro-5-phenyl-pyrrolidine-2-carboxylic acid tert-butyl ester

Core 55A (S)-2-{[1-phenyl-meth-(E)-ylidene]-amino}-propionic acid tert-butyl ester (L)-Alanine tert butyl ester hydrochloride (CAS#13404-22-3, 3.63 g, 20 mmol, 1.0 eq) and benzaldehyde (2.03 mL, 20 mmol, 1 eq) were suspended in dichloromethane. Molecular sieves (8 g) and triethylamine (2.78 mL, 20 mmol, 1 eq) were added and the reaction mixture was left without stirring for 4 hours. The reaction mixture was filtered and the cake was washed with dichloromethane. The organic layer was washed with water, dried on sodium sulfate, filtered and concentrated to provide the title compound (4.56 g, 98%).

Core 55B rac-(2S,3S,4S,5S)-3-tert-butyl-2-methyl-4-nitro-5-phenyl-pyrrolidine-2-carboxylic acid tert-butyl ester Silver acetate (CAS#563-63-3, 172 mg, 1.0 mmol, 0.15 eq) was added to a solution of (S)-2-{[1-phenyl-meth-(E)-ylidene]-amino}-propionic acid tert-butyl ester (1.6 g, 6.9 mmol, 1.0 eq) and (E)-3,3-dimethyl-1-nitrobut-1-ene (890 mg, 6.9 mmol, 1.0 eq) in acetonitrile under nitrogen atmosphere. Triethylamine (960 µL, 6.9 mmol, 1.0 eq) was added and the reaction mixture was stirred for 18 hours at room temperature. The solvent was evaporated, and the residue was dissolved in dichloromethane and filtered on diatomaceous earth. The filtrate was washed with water, and the combined organic layers were dried over sodium sulfate, filtered and concentrated in vacuo. The crude mixture was purified by flash chromatography on silica gel (heptane/ethyl acetate 100/0 to 80/20) to provide the title compound (350 mg, 14%). LC/MS (ESI+) m/z 363.4 (M+H)$^+$.

Core 56 rac-(2R,3S,4R,5R)-tert-butyl 3-(2-methoxypropan-2-yl)-4-nitro-5-phenylpyrrolidine-2-carboxylate A 1.5 M solution of lithium bromide (14.25 mL, 21.38 mmol) was added to a solution of the (E)-tert-butyl 2-(benzylideneamino)acetate (Core 1A, 3.0 g, 12.72 mmol) in anhydrous tetrahydrofuran (46 mL), and the resulting mixture was cooled with a dry ice/acetone bath. Then a solution of (E)-3-methoxy-3-methyl-1-nitrobut-1-ene (Core 36D, 1.847 g, 12.72 mmol) in tetrahydrofuran (4.9 mL) was added slowly, followed by dropwise addition of 2,3,4,6,7,8,9,10-octahydropyrimido[1,2-a]azepine (2.56 mL, 16.99 mmol). After the reaction mixture had stirred for an hour near −78° C., the dry ice was removed from the bath and the bath was permitted to warm to −15° C. over 60 minutes and then on to 0° C. over another 60 minutes. The cold bath was removed, the reaction mixture was stirred at room temperature for 15 minutes. Saturated aqueous NH$_4$Cl (50 mL) was added, with a methyl tert-butyl ether (50 mL) rinse. The biphasic mixture was stirred thoroughly and then diluted with brine (50 mL). The aqueous phase was separated and extracted twice with methyl tert-butyl ether, and the combined organic phases were washed with brine, dried (Na$_2$SO$_4$), and concentrated to a residue which was triturated with 40 mL heptane and stored 16 hours at ambient temperature. The resulting solid was filtered. The filtrate was concentrated and loaded on a 12 g column eluting with a gradient of 0-60% ethyl acetate/heptanes over a period of 20 minutes and combined with the filtered solid to give rac-(2R,3S,4R,5R)-tert-butyl 3-(2-methoxypropan-2-yl)-4-nitro-5-phenylpyrrolidine-2-carboxylate, (2.45 g, 6.72 mmol, 52.8% yield). $^1$H NMR (501 MHz, Chloroform-d) δ ppm 7.40-7.29 (m, 5H), 5.36 (dd, J=6.0, 2.2 Hz, 1H), 4.58 (s, 1H), 3.96 (d, J=6.6 Hz, 1H), 3.27 (s, 3H), 3.04 (dd, J=6.7, 2.2 Hz, 1H), 1.57 (s, 9H), 1.35 (s, 3H), 1.31 (s, 3H); MS (ESI+) m/z 365 (M+H)+.

Core 57

(2S,3R,4S,5S)-ethyl 3-(tert-butyl)-5-(2,2-dimethyl-2,3-dihydrobenzofuran-7-yl)-4-nitropyrrolidine-2-carboxylate Core 57A (E)-ethyl 2-(((2,2-dimethyl-2,3-dihydrobenzofuran-7-yl)methylene)amino)acetate Ethyl 2-aminoacetate hydrochloride [CAS#623-33-6] (4.95 g, 35.5 mmol) and magnesium sulfate (6.83 g, 56.7 mmol) were suspended in dichloromethane (47 mL) and were treated with triethylamine (4.94 mL, 35.5 mmol). The mixture was stirred at room temperature for 1 hour, 2,2-dimethyl-2,3-dihydrobenzofuran-7-carbaldehyde [CAS#38002-88-9] (5 g, 28.4 mmol) was added, and the mixture was stirred at room temperature overnight. The solid material was removed via filtration and the filtrate was washed with water and brine, dried over sodium sulfate, filtered, and concentrated to give the title compound which was used directly in the next step. $^1$H NMR (400 MHz, Chloroform-d) δ ppm 8.53 (d, J=1.5 Hz, 1H), 7.78 (dd, J=8.0, 1.2 Hz, 1H), 7.19 (dq, J=7.2, 1.3 Hz, 1H), 6.84 (t, J=7.4 Hz, 1H), 4.39 (d, J=1.3 Hz, 2H), 4.23 (q, J=7.1 Hz, 2H), 3.01 (t, J=1.1 Hz, 2H), 1.50 (s, 6H), 1.30 (t, J=7.1 Hz, 3H); MS (DCI+) m/z 262 (M+H)+.

Core 57B (2S,3R,4S,5S)-ethyl 3-(tert-butyl)-5-(2,2-dimethyl-2,3-dihydrobenzofuran-7-yl)-4-nitropyrrolidine-2-carboxylate (2S,3R,4S,5S)-Ethyl 3-(tert-butyl)-5-(2,2-dimethyl-2,3-dihydrobenzofuran-7-yl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.278 g, 0.369 mmol) and copper (I) triflate dimer benzene complex (0.071 g, 0.142 mmol) were dissolved in tetrahydrofuran (73 mL). The mixture was sparged with an N$_2$ stream for 4 hours. The resulting mixture was stirred for 1.5 hours at room temperature, and cooled to <5° C. in an ice-water bath. Example 57A (7.41 g, 28.4 mmol) in tetrahydrofuran (5 mL) was added. Potassium 2-methylpropan-2-olate (0.284 mL, 0.284 mmol) was added dropwise, and neat (E)-3,3-dimethyl-1-nitrobut-1-ene (3.66 g, 28.4 mmol) was added over 25 minutes, maintaining an internal temperature <10° C. After the addition was complete, the mixture was stirred for 15 minutes at the same temperature. The reaction mixture was diluted with methyl tert-butyl ether (200 mL) and saturated aqueous ammonium chloride (100 mL), and stirred at room temperature for 15 minutes. The organic layer was washed with saturated aqueous sodium bicarbonate and brine, dried over sodium sulfate, filtered, and concentrated. The crude material was purified via chromatography, eluting with 0-25% ethyl acetate in heptane on a 220 g silica gel column to give the title compound. $^1$H NMR (501 MHz, Chloroform-d) δ ppm 7.07 (ddt, J=16.1, 7.7, 1.1 Hz, 2H), 6.82 (t, J=7.6 Hz, 1H), 5.31 (dd, J=5.7, 2.4 Hz, 1H), 4.44 (dd, J=13.4, 5.7 Hz, 1H), 4.33 (qd, J=7.1, 1.6 Hz, 2H), 3.81 (dd, J=10.3, 7.2 Hz, 1H), 3.51 (dd, J=13.4, 10.5 Hz, 1H), 3.02 (q, J=1.1 Hz, 2H), 2.89 (dd, J=7.2, 2.3 Hz, 1H), 1.51 (d, J=2.7 Hz, 6H), 1.37 (t, J=7.2 Hz, 3H), 1.08 (s, 9H); MS (ESI+) m/z 391 (M+H)+.

Core 58

(2S,3R,4S,5S)-ethyl 5-(benzofuran-7-yl)-3-(tert-butyl)-4-nitropyrrolidine-2-carboxylate Core 58A (E)-ethyl 2-((benzofuran-7-ylmethylene)amino)acetate Ethyl 2-aminoacetate hydrochloride (1.089 g, 7.80 mmol) and magnesium sulfate (1.502 g, 12.48 mmol) were suspended in dichloromethane (10.40 mL) and the suspension was treated with triethylamine (1.087 mL, 7.80 mmol). The mixture was stirred at room temperature for 1 hour. Benzofuran-7-carbaldehyde (0.94 g, 6.24 mmol) in 1 mL of dichloromethane was added and the mixture was stirred at room temperature for 20 hours. The solid material was removed via filtration and the filtrate was washed with water (quick wash twice) and brine, dried over sodium sulfate, filtered and concentrated to provide the title compound. $^1$H NMR (400 MHz, DMSO-d$_6$) δ ppm 8.80 (d, J=1.5 Hz, 1H), 8.08 (d, J=2.2 Hz, 1H), 7.77 (ddd, J=12.1, 7.6, 1.2 Hz, 2H), 7.33 (t, J=7.6 Hz, 1H), 7.03 (d, J=2.2 Hz, 1H), 4.50 (d, J=1.3 Hz, 2H), 4.13 (q, J=7.1 Hz, 2H), 1.21 (t, J=7.1 Hz, 3H); MS (ESI+) m/z 232.2 (M+H)+.

Core 58B (2S,3R,4S,5S)-ethyl 5-(benzofuran-7-yl)-3-(tert-butyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.061 g, 0.081 mmol) and copper (I) triflate dimer, benzene complex (0.016 g, 0.031 mmol) were dissolved in tetrahydrofuran (15.97 mL) that had been sparged with an N$_2$ stream for 4 hours. The resulting mixture was stirred for 1.5 hours at room temperature, and (E)-ethyl 2-((benzofuran-7-ylmethylene)amino)acetate (1.44 g, 6.23 mmol) in tetrahydrofuran (1 mL) was added after cooling to <5° C. in an ice-water bath. Potassium 2-methylpropan-2-olate (0.062 mL, 0.062 mmol) was added dropwise, followed by addition of (E)-3,3-dimethyl-1-nitrobut-1-ene (0.804 g, 6.23 mmol) neat over 25 minutes, maintaining an internal temperature of <10° C. After the addition was complete, the mixture was stirred for 15 minutes at the same temperature. The mixture was diluted with methyl tert-butyl ether (30 mL) and stirred with 30 mL of saturated aqueous ammonium chloride at room temperature for 15 minutes. The organic layer was washed with saturated aqueous sodium bicarbonate and brine, dried over sodium sulfate, and filtered. The filtrate was concentrated and the residue was purified by flash chromatography (0 to 30% ethyl acetate in heptane) to give the title compound. $^1$H NMR (400 MHz, Chloroform-d) δ ppm 7.68 (d, J=2.2 Hz, 1H), 7.58 (dd, J=7.0, 1.9 Hz, 1H), 7.27 (dd, J=9.4, 7.1 Hz, 2H), 6.82 (d, J=2.2 Hz, 1H), 5.46 (dd, J=5.7, 2.3 Hz, 1H), 4.90 (dd, J=12.0, 5.7 Hz, 1H), 4.36 (qd, J=7.2, 1.3 Hz, 2H), 3.91 (t, J=7.8 Hz, 1H), 3.64 (dd, J=11.1 Hz, 1H), 2.98 (dd, J=7.0, 2.3 Hz, 1H), 1.38 (t, J=7.1 Hz, 3H), 1.14 (s, 9H); MS (ESI+) m/z 361.1 (M+H)+.

Example 1 rac-(2R,3R,4R,5R)-3-tert-butyl-1-(cyclohexanecarbonyl)-4-{[6-methyl-4-(trifluoromethyl)pyridin-2-yl]amino}-5-phenylpyrrolidine-2-carboxylic acid

Example 1A rac-(2R,3S,4R,5R)-tert-butyl 3-(tert-butyl)-1-(cyclohexanecarbonyl)-4-nitro-5-phenylpyrrolidine-2-carboxylate A solution of rac-(2R,3S,4R,5R)-tert-butyl 3-(tert-butyl)-4-nitro-5-phenylpyrrolidine-2-carboxylate (Core 1, 2.0 g, 5.74 mmol) and triethylamine (1.203 mL, 8.61 mmol) in $CH_2Cl_2$ (20 mL) at 0° C. was treated with cyclohexanecarbonyl chloride (0.998 mL, 7.46 mmol), stirred at 0° C. for 30 minutes, and stirred at room temperature for 1 hour. $CH_2Cl_2$ (20 mL) was added. The mixture was washed with saturated aqueous $NaHCO_3$ and brine, dried over $MgSO_4$, filtered, concentrated and chromatographed on a 25 g silica gel cartridge eluting with 0-60% ethyl acetate in heptane to provide title compound (1.6 g, 3.49 mmol, 60.8% yield), which was used without further purification. LC/MS (APCI+) m/z 403.3 $(M+H)^+$.

Example 1B rac-(2R,3R,4R,5R)-tert-butyl 4-amino-3-(tert-butyl)-1-(cyclohexanecarbonyl)-5-phenylpyrrolidine-2-carboxylate A solution of rac-(2R,3S,4R,5R)-tert-butyl 3-(tert-butyl)-1-(cyclohexanecarbonyl)-4-nitro-5-phenylpyrrolidine-2-carboxylate (Example 1A, 1.04 g, 2.268 mmol) in acetic acid (11.68 mL, 204 mmol) and ethyl acetate (66.6 mL, 680 mmol) was treated with zinc (2.224 g, 34.0 mmol) and stirred at 55° C. for 1 hour, cooled, diluted with ethyl acetate and filtered to remove the solids. The filtrate was concentrated to dryness. The residue was partitioned between ethyl acetate and saturated aqueous $NaHCO_3$. The ethyl acetate layer was washed with brine, dried over $MgSO_4$, filtered and concentrated. Purification via flash chromatography on a 24 g silica gel cartridge, eluting with ethyl acetate/methanol (9:1) in heptane provided the title compound, 0.95 g (98% yield). $^1H$ NMR (400 MHz, Chloroform-d) δ ppm 7.65-7.54 (m, 2H), 7.40 (q, J=7.1 Hz, 2H), 7.33-7.29 (m, 1H), 4.99 (d, J=6.6 Hz, 1H), 4.44 (d, J=3.3 Hz, 1H), 3.57 (dd, J=6.7, 2.4 Hz, 1H), 2.09-1.99 (m, 2H), 1.51 (s, 9H), 1.56-1.51 (m, 2H), 1.50-1.41 (m, 3H), 1.23-1.13 (m, 3H), 1.09 (dt, J=12.8, 3.4 Hz, 2H), 1.04 (s, 9H), 0.98 (dt, J=12.8, 3.3 Hz, 1H), 0.54 (qt, J=12.8, 4.1 Hz, 1H); MS (ESI+) m/z 429.0 $(M+H)^+$.

Example 1C rac-(2R,3R,4R,5R)-3-(tert-butyl)-1-(cyclohexanecarbonyl)-4-((6-methyl-4-(trifluoromethyl)pyridin-2-yl)amino)-5-phenylpyrrolidine-2-carboxylic acid A mixture of 2-chloro-6-methyl-4-(trifluoromethyl)pyridine (CAS#52334-81-3, 183 mg, 0.933 mmol), Example 1A (200 mg, 0.467 mmol) and potassium carbonate (193 mg, 1.400 mmol) in N,N-dimethylformamide (0.5 mL) was sealed in a microwave vial and stirred at 140° C. for 2 hours. The mixture was cooled, filtered, and the solids were washed with methanol. The filtrate was concentrated, dissolved in trifluoroacetic acid (0.5 mL) and stirred at ambient temperature overnight. The reaction mixture was directly purified via HPLC with trifluoroacetic acid method to provide the title compound, 78 mg (31.4% yield). $^1H$ NMR (400 MHz, Chloroform-d) δ ppm 7.17 (d, J=4.5 Hz, 6H), 6.48 (s, 1H), 6.20 (s, 1H), 5.45 (d, J=7.4 Hz, 1H), 5.17 (s, 1H), 4.76 (d, J=4.0 Hz, 1H), 2.76 (s, 1H), 2.43 (s, 3H), 2.23 (t, J=10.9 Hz, 1H), 1.76 (d, J=10.3 Hz, 2H), 1.46 (d, J=12.7 Hz, 2H), 1.12 (d, J=13.2 Hz, 4H), 1.07 (s, 9H), 0.96 (d, J=13.1 Hz, 1H), 0.68 (d, J=13.0 Hz, 1H); MS (ESI-) m/z 530 $(M-H)^-$.

Example 2 rac-(2R,3R,4R,5R)-3-tert-butyl-1-(cyclohexanecarbonyl)-4-{[6-methoxy-4-(trifluoromethyl)pyridin-2-yl]amino}-5-phenylpyrrolidine-2-carboxylic acid

Example 2A rac-(2R,3S,4R,5R)-ethyl 3-(tert-butyl)-1-(cyclohexanecarbonyl)-4-nitro-5-phenylpyrrolidine-2-carboxylate Core 1 (4.3666 g, 13.63 mmol) was dissolved in dichloromethane (34.1 mL) and triethylamine (3.80 mL, 27.3 mmol) was added, followed by the addition of cyclohexanecarbonyl chloride (1.668 mL, 13.77 mmol) at 0° C. while cooling in an ice-water bath. The reaction mixture was stirred at the same temperature for 15 minutes then warmed to room temperature, at which point it was complete by LC-MS. The reaction mixture was diluted with dichloromethane (30 mL) and washed with 3×50 mL of 1 M aqueous HCl and brine (30 mL). The organic layer was dried over sodium sulfate, filtered, and concentrated. The residue was triturated with heptanes (40 mL) to give 5.66 g of the title compound. $^1H$ NMR 400 MHz, dimethyl sulfoxide-$d_6$) δ ppm 7.58 (d, J=7.1 Hz, 2H), 7.27 (qd, J=7.6, 6.3, 3.6 Hz, 3H), 5.76-5.53 (m, 2H), 4.70 (d, J=3.7 Hz, 1H), 4.24 (q, J=7.0 Hz, 2H), 3.01 (t, J=3.4 Hz, 1H), 2.19 (s, 1H), 1.69 (d, J=14.7 Hz, 2H), 1.50 (d, J=9.8 Hz, 2H), 1.28 (t, J=7.1 Hz, 3H), 1.26-1.06 (m, 6H), 1.01 (s, 9H); MS (ESI+) m/z 431.2 $(M+H)^+$.

Example 2B rac-(2R,3R,4R,5R)-ethyl 4-amino-3-(tert-butyl)-1-(cyclohexanecarbonyl)-5-phenylpyrrolidine-2-carboxylate Example 2A (10.71 g, 24.88 mmol) was dissolved in a mixture of ethyl acetate (731 mL, 7463 mmol) and acetic acid (128 mL, 2239 mmol). Zinc (24.40 g, 373 mmol) was added, and the resulting suspension was heated to 55° C. for 90 minutes. The flask was cooled to ambient temperature, the solid material was removed via filtration through a fritted funnel, and the filtrate was concentrated in vacuo. The resulting residue was partitioned between saturated aqueous sodium bicarbonate and ethyl acetate. The organic extracts were dried over sodium sulfate, filtered, and concentrated in vacuo to give a crude solid, which was purified via flash chromatography, eluting on a 120 g silica gel column with 20:80 to 100:0 ethyl acetate:heptanes over 20 minutes to give 9.31 g of the title compound. $^1H$ NMR (400 MHz, dimethyl sulfoxide-$d_6$) δ ppm 7.75-7.49 (m, 2H), 7.29 (dt, J=36.0, 7.4 Hz, 3H), 5.05 (d, J=7.1 Hz, 1H), 4.39 (d, J=4.2 Hz, 1H), 4.24-4.09 (m, 2H), 3.67 (dd, J=7.2, 4.0 Hz, 1H), 2.16 (s, 1H), 2.03 (t, J=4.0 Hz, 1H), 1.74-1.54 (m, 2H), 1.46

Example 2C rac-(2R,3R,4R,5R)-ethyl 3-(tert-butyl)-1-(cyclohexanecarbonyl)-4-((6-methoxy-4-(trifluoromethyl)pyridin-2-yl)amino)-5-phenylpyrrolidine-2-carboxylate Example 2B (300 mg, 0.686 mmol), cesium carbonate (671 mg, 2.059 mmol), 4,5-bis(diphenylphosphino)-9,9-dimethylxanthene (Xantphos) (79 mg, 0.137 mmol), and Pd$_2$dba$_3$ (tris(dibenzylideneacetone)dipalladium(0), 62.9 mg, 0.069 mmol) were weighed into a microwave vial. Xylene (1961 µL) was added, followed by 2-chloro-6-methoxy-4-(trifluoromethyl)pyridine (290 mg, 1.373 mmol) and the resulting suspension was sparged with N$_2$ for 5 minutes. The vial was sealed and heated to 140° C. in a heating block for 16 hours. The mixture was cooled to ambient temperature, diluted with methyl tert-butyl ether (10 mL) and filtered through a syringe filter. The filtrate was concentrated and purified via flash chromatography, eluting with 0:100 to 20:80 ethyl acetate:heptanes over 20 minutes on a 40 g silica gel column to give 190 mg of the title compound. $^1$H NMR (400 MHz, Chloroform-d) δ ppm 7.58-7.46 (m, 2H), 7.35-7.20 (m, 4H), 6.12 (s, 1H), 5.72 (s, 1H), 5.22-5.13 (m, 2H), 4.45 (d, J=6.6 Hz, 1H), 4.37 (s, 1H), 4.29 (q, J=7.1 Hz, 2H), 3.89 (s, 2H), 2.23 (t, J=6.4 Hz, 1H), 2.07 (ddd, J=11.6, 8.4, 3.3 Hz, 1H), 1.79-1.55 (m, 5H), 1.52-1.37 (m, 5H), 1.35 (t, J=7.2 Hz, 3H), 1.06 (s, 9H); MS (ESI+) m/z 576.4 (M+H)$^+$.

Example 2D rac-(2R,3R,4R,5R)-3-tert-butyl-1-(cyclohexanecarbonyl)-4-{[6-methoxy-4-(trifluoromethyl)pyridin-2-yl]amino}-5-phenylpyrrolidine-2-carboxylic acid Example 2C (32 mg, 0.056 mmol) was dissolved in tetrahydrofuran (278 µL) and aqueous lithium hydroxide (1 M, 167 µl, 0.167 mmol) was added. The resulting mixture was stirred vigorously for 48 hours, at which point it was acidified to pH=3 by the addition of 1 M aqueous HCl. The entire mixture was loaded onto a 4 g silica gel column and was eluted with 0:100 to 50:50 ethyl acetate:heptanes over 15 minutes to give 18 mg of the title compound. $^1$H NMR (400 MHz, dimethyl sulfoxide-d$_6$) δ ppm 7.44 (d, J=6.8 Hz, 2H), 7.22-7.07 (m, 3H), 6.04 (d, J=9.4 Hz, 1H), 5.98 (d, J=6.6 Hz, 2H), 5.33 (d, J=8.2 Hz, 1H), 4.99 (dt, J=9.4, 8.0 Hz, 1H), 4.38 (d, J=6.1 Hz, 1H), 3.87 (s, 3H), 2.41 (t, J=6.7 Hz, 1H), 2.23 (s, 1H), 1.68 (d, J=14.1 Hz, 2H), 1.47 (s, 2H), 1.35-1.04 (m, 6H), 1.02 (s, 9H); MS (ESI+) m/z 548.2 (M+H)$^+$.

Example 3

(2R,3R,4R,5R)-3-tert-butyl-1-(cyclohexanecarbonyl)-4-{[6-methyl-4-(trifluoromethyl)pyridin-2-yl]amino}-5-phenylpyrrolidine-2-carboxylic acid

Example 3A rac-(2R,3R,4R,5R)-ethyl 3-(tert-butyl)-1-(cyclohexanecarbonyl)-4-((6-methyl-4-(trifluoromethyl)pyridin-2-yl)amino)-5-phenylpyrrolidine-2-carboxylate Example 2B (240 mg, 0.429 mmol), 4,5-bis(diphenylphosphino)-9,9-dimethylxanthene (Xantphos) (0.144 g, 0.250 mmol), cesium carbonate (2.440 g, 7.49 mmol) and palladium (II) acetate (0.028 g, 0.125 mmol) were weighed into a 50-mL round bottomed flask The flask was purged with a stream of N$_2$ and toluene (25 mL) that had been sparged for 1 hour with a nitrogen stream was added, followed by 2-chloro-6-methyl-4-(trifluoromethyl)pyridine (0.523 mL, 3.74 mmol). The resulting suspension was stirred at ambient temperature for 5 minutes. The flask was heated to 100° C. internal temperature in a heating mantle, and heating was continued for 16 hours at the same temperature. The flask was cooled to ambient temperature, and the solid material was removed via filtration using a fritted funnel. The filtrate was concentrated and purified via flash chromatography on a 40 g silica gel column, eluting with 0:100 to 30:70 ethyl acetate:heptanes over 15 minutes, then 30:70 to 100:0 ethyl acetate:heptanes over 5 minutes to give 260 mg of the title compound. $^1$H NMR (400 MHz, dimethyl sulfoxide-d$_6$) δ ppm 7.45 (d, J=7.3 Hz, 2H), 7.29-7.08 (m, 3H), 6.50 (s, 1H), 6.26 (s, 1H), 5.85 (s, 1H), 5.33 (d, J=8.3 Hz, 1H), 4.99 (q, J=8.4 Hz, 1H), 4.37 (d, J=6.8 Hz, 1H), 4.18 (q, J=7.0 Hz, 2H), 2.39 (t, J=7.4 Hz, 1H), 2.35 (s, 3H), 2.19 (s, 1H), 1.67 (d, J=12.1 Hz, 2H), 1.45 (t, J=14.4 Hz, 2H), 1.31 (d, J=12.1 Hz, 1H), 1.24 (t, J=7.0 Hz, 3H), 1.17-1.03 (m, 4H), 1.00 (s, 9H); MS (ESI+) m/z 560.4 (M+H)$^+$.

Example 3B (2S,3S,4S,5S)-ethyl 3-(tert-butyl)-1-(cyclohexanecarbonyl)-4-((6-methyl-4-(trifluoromethyl)pyridin-2-yl)amino)-5-phenylpyrrolidine-2-carboxylate and

Example 3C (2R,3R,4R,5R)-ethyl 3-(tert-butyl)-1-(cyclohexanecarbonyl)-4-((6-methyl-4-(trifluoromethyl)pyridin-2-yl)amino)-5-phenylpyrrolidine-2-carboxylate Example 3A (3.67 g) was separated via preparative chiral SFC chromatography using column WHELK-O S.S with a column size: 21×250 mm, 5 micron, serial number: 780103, CO$_2$ flow rate of 68 g/minute and a concentration of 52.8 mg/mL in methanol with co-solvent isopropyl alcohol to give 615 mg Example 3B (room temperature=8.4 minutes) and 760 mg of Example 3C (room temperature=6.4 minutes). Analytical data ($^1$H NMR and MS) are identical to those reported for Example 3A.

Example 3D (2R,3R,4R,5R)-3-(tert-butyl)-1-(cyclohexanecarbonyl)-4-((6-methyl-4-(trifluoromethyl)pyridin-2-yl)amino)-5-phenylpyrrolidine-2-carboxylic acid Example 3C (615 mg, 1.099 mmol) was dissolved in 6.5 mL of tetrahydrofuran, 3.3 mL of water, and 1.1 mL of methanol. Lithium hydroxide hydrate (461 mg, 10.99 mmol) was added, and the reaction mixture was stirred vigorously at ambient temperature for 2 hours. The reaction mixture was acidified to pH=3 with 1 M aqueous HCl, and the mixture was extracted with 3×10 mL of dichloromethane. The combined organic extracts were washed with brine (10 mL), dried over sodium sulfate, filtered, and concentrated to give the title compound (446 mg). $^1$H NMR (400 MHz, dimethyl sulfoxide-d$_6$) δ ppm 7.44 (d, J=7.4 Hz, 2H), 7.14 (dt, J=13.9, 6.8 Hz, 3H), 6.49 (s, 1H), 6.22 (s, 1H), 5.84 (d, J=9.0 Hz, 1H), 5.34 (d, J=8.2 Hz, 1H), 4.98 (q, J=8.0 Hz, 1H), 4.39 (d, J=5.9 Hz, 1H), 2.40 (t, J=6.4 Hz, 1H), 2.34 (s, 3H), 2.24 (s, 2H), 1.69 (d, J=13.1 Hz, 2H), 1.48 (d, J=8.4 Hz, 2H), 1.28 (d, J=16.8 Hz, 2H), 1.26-1.12 (m, 4H), 1.02 (s, 9H); MS (ESI+) m/z 532.4 (M+H)+; optical rotation data: $[\alpha]_D^{23}$=+97.2 (c=1, methanol).

Example 4

(2S,3S,4S,5S)-3-tert-butyl-1-(cyclohexanecarbonyl)-4-{[6-methyl-4-(trifluoromethyl)pyridin-2-yl]amino}-5-phenylpyrrolidine-2-carboxylic acid Example 3B (760 mg, 1.358 mmol) was dissolved in 8.1 mL of tetrahydrofuran, 4.1 mL of water, and 1.3 mL of methanol. Lithium hydroxide hydrate (570 mg, 13.58 mmol) was added, and the reaction mixture was stirred vigorously at ambient temperature for 3 hours. The mixture was acidified with 1 M aqueous HCl to pH=3 and was extracted with 3×15 mL of dichloromethane. The combined extracts were washed with brine (10 mL), dried over sodium sulfate, filtered, and concentrated to give 556 mg of the title compound. $^1$H NMR (400 MHz, dimethyl sulfoxide-$d_6$) δ ppm 7.44 (d, J=7.4 Hz, 2H), 7.14 (dt, J=13.9, 6.8 Hz, 3H), 6.49 (s, 1H), 6.22 (s, 1H), 5.84 (d, J=9.0 Hz, 1H), 5.34 (d, J=8.2 Hz, 1H), 4.98 (q, J=8.0 Hz, 1H), 4.39 (d, J=5.9 Hz, 1H), 2.40 (t, J=6.4 Hz, 1H), 2.34 (s, 3H), 2.24 (s, 2H), 1.69 (d, J=13.1 Hz, 2H), 1.48 (d, J=8.4 Hz, 2H), 1.28 (d, J=16.8 Hz, 2H), 1.26-1.12 (m, 4H), 1.02 (s, 9H); MS (ESI+) m/z 532.4 (M+H)+; optical rotation data. $[\alpha]_D^{23}$=−93.8 (c=1, methanol).

Example 5 rac-(2R,3R,4R,5R)-1-(cyclohexanecarbonyl)-3-(2-methoxypropan-2-yl)-4-{[6-methyl-4-(trifluoromethyl)pyridin-2-yl]amino}-5-phenylpyrrolidine-2-carboxylic acid Example 5A rac-(2R,3S,4R,5R)-tert-butyl 1-(cyclohexanecarbonyl)-3-(2-methoxypropan-2-yl)-4-nitro-5-phenylpyrrolidine-2-carboxylate A solution of Core 56 (1.7 g, 4.66 mmol) and triethylamine (1.300 mL, 9.33 mmol) in dichloromethane (21.20 mL) at 25° C. was treated with cyclohexanecarbonyl chloride (0.780 mL, 5.83 mmol) dropwise, stirred for 2 hours, diluted with methyl tert-butyl ether (20 mL), washed with saturated aqueous NaHCO$_3$ (5 mL) and with 1 N aqueous NH$_4$OH (1 mL) solution, dried over sodium sulfate, filtered, and concentrated to give a residue. The mixture was triturated with 100 mL heptane and stood for 16 hours at ambient temperature. The mixture was filtered to give a crude precipitate (2.01 g). The crude material was dissolved in 3 mL dichloromethane and loaded on a 40 g column eluting with a gradient of 0-70% ethyl acetate/heptanes over a period of 20 minutes to provide the desired product, rac-(2R,3S,4R,5R)-tert-butyl 1-(cyclohexanecarbonyl)-3-(2-methoxypropan-2-yl)-4-nitro-5-phenylpyrrolidine-2-carboxylate, 1980-2 (1.56 g, 3.29 mmol, 70.5% yield). $^1$H NMR (400 MHz, dimethyl sulfoxide-$d_6$) δ ppm 7.55 (d, J=6.9 Hz, 2H), 7.31-7.17 (m, 3H), 5.61 (d, J=3.0 Hz, 1H), 4.62 (d, J=3.9 Hz, 1H), 3.26 (dd, J=4.0, 2.6 Hz, 1H), 3.15 (s, 3H), 2.16 (s, 1H), 1.67 (s, 2H), 1.51 (s, 10H), 1.22 (d, J=6.0 Hz, 10H), 1.08 (t, J=10.0 Hz, 2H), 0.84 (d, J=7.6 Hz, 1H); MS (ESI+) m/z 475 (M+H)+.

Example 5B rac-(2R,3R,4R,5R)-tert-butyl 4-amino-1-(cyclohexanecarbonyl)-3-(2-methoxypropan-2-yl)-5-phenylpyrrolidine-2-carboxylate Example 5A (1.56 g, 3.29 mmol) and tetrahydrofuran (47.0 mL) were added to Raney®-Nickel 2800, water slurry (4 g, 30.7 mmol) in a 250 mL SS pressure bottle and the mixture was shaken for 16 hours at 50 psi and ambient temperature. The reaction was filtered and the solvent removed in vacuo to give rac-(2R,3R,4R,5R)-tert-butyl 4-amino-1-(cyclohexanecarbonyl)-3-(2-methoxypropan-2-yl)-5-phenylpyrrolidine-2-carboxylate (1.45 g, 3.26 mmol, 99% yield). $^1$H NMR (400 MHz, dimethyl sulfoxide-$d_6$) δ ppm 7.56 (bs, 2H), 7.31 (t, J=7.5 Hz, 2H), 7.22 (t, J=7.4 Hz, 1H), 5.02 (d, J=7.3 Hz, 1H), 4.33 (d, J=4.7 Hz, 1H), 3.65 (dd, J=7.3, 4.6 Hz, 1H), 3.13 (s, 3H), 2.32 (s, 1H), 2.15 (d, J=12.9 Hz, 1H), 1.62 (d, J=10.2 Hz, 2H), 1.46 (s, 10H), 1.30-1.10 (m, 2H), 1.21 (s, 3H), 1.19 (s, 3H), 1.05 (m, 2H), 0.82 (bs, 2H); MS (ESI+) m/z 445 (M+H)+.

Example 5C rac-(2R,3R,4R,5R)-1-(cyclohexanecarbonyl)-3-(2-methoxypropan-2-yl)-4-((6-methyl-4-(trifluoromethyl)pyridin-2-yl)amino)-5-phenylpyrrolidine-2-carboxylic acid A 4 mL vial was charged with Example 5B (100 mg, 0.225 mmol), Pd$_2$(dba)$_3$ (tris(dibenzylideneacetone)dipalladium(0)), 4.12 mg, 0.00450 mmol), 4-(di-tert-butylphosphino)-N,N-dimethylaniline (2.77 mg, 0.00990 mmol), and cesium carbonate (147 mg, 0.450 mmol). The mixture was purged with nitrogen for 15 minutes, and to the vial was added a solution of 2-chloro-6-methyl-4-(trifluoromethyl)pyridine (48.4 mg, 0.247 mmol) in anhydrous dioxane (0.9 mL) that had been purged with nitrogen for 15 minutes. The reaction mixture was heated at 80° C. for 16 hours. The mixture was filtered, and the filtrate was concentrated. The crude material was purified by flash chromatography (12 g cartridge, a gradient of 0%-70% ethyl acetate/heptanes over 20 minutes) to provide the crude t-butyl ester (43 mg) which was treated with trifluoroacetic acid (0.4 mL) for 2 hours at ambient temperature. The mixture was concentrated, and the residue was purified by reverse phase chromatography using the trifluoroacetic acid method to obtain (2R,3R,4R,5R)-1-(cyclohexanecarbonyl)-3-(2-methoxypropan-2-yl)-4-((6-methyl-4-(trifluoromethyl)pyridin-2-yl)amino)-5-phenylpyrrolidine-2-carboxylic acid, trifluoroacetic acid salt (31 mg, 0.047 mmol, 20.83% yield). $^1$H NMR (400 MHz, dimethyl sulfoxide-$d_6$) δ ppm 7.42 (d, J=7.3 Hz, 2H), 7.14 (dt, J=12.4, 6.7 Hz, 2H), 6.51 (s, 1H), 6.27 (s, 1H), 5.84 (s, 1H), 5.36 (d, J=8.2 Hz, 1H), 4.95 (d, J=7.8 Hz, 1H), 4.49 (d, J=6.2 Hz, 1H), 3.13 (s, 3H), 2.68 (t, J=6.7 Hz, 1H), 2.34 (s, 3H), 2.22 (s, 1H), 1.68 (d, J=13.5 Hz, 2H), 1.47 (bs, 2H), 1.30 (t, J=11.1 Hz, 1H), 1.22 (d, J=1.3 Hz, 6H), 1.12 (d, J=22.9 Hz, 3H), 0.73 (bs, 1H); MS (ESI+) m/z 548 (M+H)+.

Example 6 rac-(2R,3R,4R,5R)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid To a solution of 2-methoxy-5-(trifluoromethyl)benzaldehyde (38.6 mg, 0.189 mmol), Example 5B (70 mg, 0.157 mmol) and zinc(II) chloride (21.46 mg, 0.157 mmol) in sodium acetate/acetic acid buffer in methanol (pH=4, 1 mL) was added sodium cyanoborohydride (14.8 mg, 0.236 mmol) and the reaction was stirred at ambient temperature for 2 hours. The solvent was removed and the resulting residue was chromatographed using a 12 g silica gel cartridge eluting with a gradient of 0-80% ethyl acetate/heptanes over a period of 20 minutes to give a residue (76 mg) which was dissolved in trifluoroacetic acid (0.5 mL). The solvent was removed and the crude material was purified by reverse phase chromatography using the trifluoroacetic acid method to obtain rac-(2R,3R,4R,5R)-1-(cyclohexanecarbonyl)-4-((2-methoxy-5-(trifluoromethyl)benzyl)amino)-3-(2-methoxypropan-2-yl)-5-phenylpyrrolidine-2-carboxylic acid, trifluoroacetic acid salt (64 mg, 0.093 mmol, 58.9% yield). $^1$H NMR (400 MHz, dimethyl sulfoxide-$d_6$) δ ppm 7.57 (s, 2H), 7.52 (dd, J=9.1, 2.3 Hz, 1H), 7.37-7.24 (m, 4H), 7.05 (d, J=8.6 Hz, 1H), 5.28 (d, J=7.2 Hz, 1H), 4.50 (d, J=3.6 Hz, 1H), 3.69 (m, 4H), 3.65 (bs, 2H), 3.52 (d, J=14.0 Hz, 1H), 2.70 (s, 1H), 2.28 (m, 1H), 1.65 (d, J=9.3 Hz, 2H), 1.50 (m, 2H), 1.30-1.15 (m, 4H), 1.19 (d, J=6.1 Hz, 6H), 1.08 (m, 2H), 0.79 (bs, 1H); MS (ESI+) m/z 577 (M+H)$^+$.

Example 7

(2S,3S,4S,5S)-3-tert-butyl-4-{[(5-tert-butyl-2-methoxyphenyl)methyl]amino}-1-(cyclohexanecarbonyl)-5-phenylpyrrolidine-2-carboxylic acid

Example 7A ethyl (2S,3R,4S,5S)-3-(tert-butyl)-1-(cyclohexanecarbonyl)-4-nitro-5-phenylpyrrolidine-2-carboxylate Ethyl (2S,3R,4S,5S)-3-(tert-butyl)-4-nitro-5-phenylpyrrolidine-2-carboxylate (Core 7, 2.00 g, 6.24 mmol) was dissolved in dichloromethane (25 mL) and triethylamine (1.75 mL, 12.56 mmol) was added, followed by cyclohexanecarbonyl chloride (1.01 g, 6.89 mmol). The reaction was stirred at ambient temperature for 14 hours. The reaction was diluted with dichloromethane (50 mL) and washed with 1 M aqueous HCl (2×50 mL) and brine. The organic layer was dried over sodium sulfate, filtered, and concentrated to provide the title compound (2.68 g, 100%). $^1$H NMR (400 MHz, dimethyl sulfoxide-$d_6$, 120° C.) δ ppm 7.57 (d, J=7.1 Hz, 2H), 7.31-7.19 (m, 3H), 5.71-5.57 (m, 2H), 4.69 (d, J=3.7 Hz, 1H), 4.23 (q, J=7.1 Hz, 2H), 3.00 (t, J=3.4 Hz, 1H), 2.26-2.09 (m, 1H), 1.74-1.59 (m, 2H), 1.49 (d, J=8.7 Hz, 2H), 1.32-1.14 (m, 7H), 1.07 (t, J=9.5 Hz, 2H), 1.00 (s, 9H); MS (ESI+) m/z 431 (M+H)$^+$.

Example 7B (2S,3S,4S,5S)-ethyl 4-amino-3-(tert-butyl)-1-(cyclohexanecarbonyl)-5-phenylpyrrolidine-2-carboxylate Example 7A (1.23 g, 2.86 mmol) and tetrahydrofuran (30 mL) were added to Raney®-Nickel 2800, water slurry (2.54 g, 21.64 mmol) in a 250 mL stainless steel pressure bottle. The mixture was shaken for 16 hours at 50 psi and ambient temperature. HPLC monitoring indicated both starting material and product. Additional Raney®-Nickel 2800, water slurry (2.5 g, 19.17 mmol) was added and the reaction was shaken for 16 hours at 50 psi and ambient temperature at which point HPLC indicated the starting material had been consumed. The reaction was filtered and the filtrate was concentrated to provide the title compound (1.13 g, 99%). $^1$H NMR (400 MHz, dimethyl sulfoxide-$d_6$, 120° C.) δ ppm 7.58 (d, J=7.4 Hz, 2H), 7.33 (t, J=7.5 Hz, 2H), 7.24 (dd, J=8.2, 6.3 Hz, 1H), 5.04 (d, J=7.2 Hz, 1H), 4.38 (d, J=4.2 Hz, 1H), 4.15 (qd, J=7.1, 1.2 Hz, 2H), 3.66 (dd, J=7.2, 4.0 Hz, 1H), 2.16 (d, J=11.7 Hz, 1H), 2.03 (d, J=4.4 Hz, 1H), 1.67-1.56 (m, 2H), 1.46 (d, J=9.0 Hz, 2H), 1.23 (t, J=7.1 Hz, 3H), 1.20-1.11 (m, 4H), 1.05 (t, J=10.7 Hz, 2H), 0.99 (s, 9H); MS (ESI+) m/z 401 (M+H)$^+$.

Example 7C ethyl (2S,3S,4S,5S)-4-amino-3-(tert-butyl)-1-(cyclohexanecarbonyl)-5-phenylpyrrolidine-2-carboxylate Example 7B (54.4 mg, 0.136 mmol) and 5-(tert-butyl)-2-methoxybenzenecarbaldehyde (39.8 mg, 0.207 mmol) were dissolved in methanol (1 mL) and stirred at ambient temperature for 1 hour. Sodium cyanoborohydride (43.6 mg, 0.694 mmol) was added and the reaction was stirred at ambient temperature for an additional 16 hours. The reaction was diluted with dimethyl sulfoxide (1 mL), filtered and purified by reverse phase using the ammonium acetate method to provide the title compound (50.8 mg, 65%). $^1$H NMR (400 MHz, dimethyl sulfoxide-$d_6$, 120° C.) δ ppm 7.64-7.50 (m, 2H), 7.30 (t, J=7.4 Hz, 2H), 7.23 (t, J=7.3 Hz, 1H), 7.10 (dd, J=8.5, 2.6 Hz, 1H), 6.90 (d, J=2.6 Hz, 1H), 6.71 (d, J=8.5 Hz, 1H), 5.18 (d, J=6.8 Hz, 1H), 4.50 (d, J=2.9 Hz, 1H), 4.09 (qd, J=7.1, 2.9 Hz, 2H), 3.52 (s, 3H), 3.50-3.41 (m, 2H), 3.30 (d, J=13.5 Hz, 1H), 2.33 (s, 1H), 2.18 (s, 1H), 1.68-1.58 (m, 2H), 1.54-1.40 (m, 2H), 1.18 (d, J=8.4 Hz, 17H), 0.98 (s, 9H); MS (ESI+) m/z 577 (M+H)$^+$.

Example 7D (2S,3S,4S,5S)-3-tert-butyl-4-{[(5-tert-butyl-2-methoxyphenyl)methyl]amino}-1-(cyclohexanecarbonyl)-5-phenylpyrrolidine-2-carboxylic acid Example 7C (47.8 mg, 0.136 mmol) was dissolved in methanol (1 mL). LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase chromatography using the trifluoroacetic acid method to provide the title compound (45.7 mg, 83%) as the trifluoroacetic acid salt. $^1$H NMR (400 MHz, dimethyl sulfoxide-$d_6$, 120° C.) δ ppm 7.59-7.50 (m, 2H), 7.37 (t, J=7.5 Hz, 2H), 7.29 (t, J=7.3 Hz, 1H), 7.21 (dd, J=8.6, 2.6 Hz, 1H), 7.02 (d, J=2.5 Hz, 1H), 6.79 (d, J=8.6 Hz, 1H), 5.31 (d, J=7.0 Hz, 1H), 4.51 (d, J=2.1 Hz, 1H), 3.77-3.69 (m, 3H), 3.56 (s, 3H), 3.43 (d, J=13.6 Hz, 1H), 2.49 (s, 1H), 2.28 (s, 1H), 1.63 (d, J=10.0 Hz, 2H), 1.51 (s, 2H), 1.21 (d, J=0.6 Hz, 14H), 0.99 (s, 9H); MS (ESI+) m/z 549 (M+H)$^+$.

Example 8

(2S,3S,4S,5S)-3-tert-butyl-1-(cyclohexanecarbonyl)-4-({[2-methoxy-4-(trifluoromethyl)phenyl]methyl}amino)-5-phenylpyrrolidine-2-carboxylic acid Example 7B (82.0 mg, 0.205 mmol) and 2-methoxy-4-(trifluoromethyl)benzaldehyde (80.4 mg, 0.394 mmol) were dissolved in methanol (1 mL) and the mixture was stirred at 25° C. for 3 hours. Sodium cyanoborohydride (52.8 mg, 0.840 mmol) was added and the reaction was stirred at ambient temperature for an additional 3 hours. The mixture was poured into water (10 mL) and extracted with dichloromethane (3×5 mL). The combined organics were concentrated. The residue was dissolved in methanol and LiOH (1 M, 1.0 mL, 1.0 mmol) was added and the reaction was heated to 50° C. for 16 hours. The reaction was quenched by the addition of trifluoroacetic acid (0.2 mL), diluted with dimethyl sulfoxide (1 mL), filtered and purified by reverse phase using the trifluoroacetic acid method to provide the title compound (63.5 mg, 46%) as the trifluoroacetic acid salt. $^1$H NMR (400 MHz, dimethyl sulfoxide-$d_6$, 120° C.) δ ppm 7.61-7.46 (m, 2H), 7.32 (t, J=7.4 Hz, 2H), 7.25 (t, J=7.3 Hz, 1H), 7.16-7.09 (m, 2H), 7.06 (s, 1H), 5.22 (d, J=6.9 Hz, 1H), 4.48 (d, J=2.4 Hz, 1H), 3.64 (s, 3H), 3.60-3.48 (m, 2H), 3.39 (d, J=14.2 Hz, 1H), 2.36 (s, 1H), 2.31-2.15 (m, 1H), 1.63 (d, J=9.5 Hz, 2H), 1.49 (s, 2H), 1.32-1.03 (m, 6H), 0.97 (s, 9H); MS (ESI+) m/z 561 (M+H)$^+$.

Example 9

(2S,3S,4S,5S)-3-tert-butyl-1-(cyclohexanecarbonyl)-4-({[2-methoxy-5-(trifluoromethyl)phenyl]methyl}amino)-5-phenylpyrrolidine-2-carboxylic acid Example 9A ethyl (2S,3S,4S,5S)-3-(tert-butyl)-1-(cyclohexanecarbonyl)-4-((2-methoxy-5-(trifluoromethyl)benzyl)amino)-5-phenylpyrrolidine-2-carboxylate Example 7B (50.2 mg, 0.125 mmol) and 2-methoxy-5-(trifluoromethyl)benzaldehyde (34.7 mg, 0.170 mmol) were dissolved in methanol (1 mL) and the mixture was stirred at ambient temperature for 3 hours. Sodium cyanoborohydride (44.5 mg, 0.708 mmol) was added and the reaction was stirred at ambient temperature for an additional 16 hours. The reaction was diluted with dimethyl sulfoxide (1 mL), filtered and purified by reverse phase using the ammonium acetate method to provide the title compound (42.9 mg, 58%). $^1$H NMR (400 MHz, dimethyl sulfoxide-$d_6$, 120° C.) δ ppm 7.62-7.51 (m, 2H), 7.44 (dd, J=8.6, 2.4 Hz, 1H), 7.30 (t, J=7.4 Hz, 2H), 7.24 (d, J=7.2 Hz, 1H), 7.19 (d, J=2.4 Hz, 1H), 6.98 (d, J=8.6 Hz, 1H), 5.19 (d, J=6.9 Hz, 1H), 4.51 (d, J=2.8 Hz, 1H), 4.10 (q, J=7.0 Hz, 2H), 3.64 (s, 3H), 3.51-3.41 (m, 2H), 3.35 (d, J=14.4 Hz, 1H), 2.31 (s, 1H), 2.17 (d, J=10.6 Hz, 1H), 1.63 (d, J=9.7 Hz, 2H), 1.47 (s, 2H), 1.17 (t, J=7.0 Hz, 9H), 0.97 (s, 9H); MS (ESI+) m/z 589 (M+H)$^+$.

Example 9B (2S,3S,4S,5S)-3-tert-butyl-1-(cyclohexanecarbonyl)-4-({[2-methoxy-5-(trifluoromethyl)phenyl]methyl}amino)-5-phenylpyrrolidine-2-carboxylic acid Example 9A (39.9 mg, 0.068 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (32.3 mg, 71%) as the trifluoroacetic acid salt. $^1$H NMR (400 MHz, dimethyl sulfoxide-$d_6$, 120° C.) δ ppm 7.60-7.53 (m, 2H), 7.50 (dd, J=8.7, 2.3 Hz, 1H), 7.34 (t, J=7.4 Hz, 2H), 7.30-7.23 (m, 2H), 7.03 (d, J=8.6 Hz, 1H), 5.27 (d, J=7.0 Hz, 1H), 4.49 (d, J=2.3 Hz, 1H), 3.65 (d, J=18.6 Hz, 5H), 3.40 (d, J=14.2 Hz, 1H), 2.42 (s, 1H), 2.25 (s, 1H), 1.63 (d, J=10.1 Hz, 2H), 1.49 (s, 2H), 1.30-1.02 (m, 6H), 0.98 (d, J=0.9 Hz, 9H); MS (ESI+) m/z 561 (M+H)$^+$.

Example 10

(2S,3S,4S,5S)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid Example 10A rac-(2R,3S,4R,5R)-ethyl 3-(tert-butyl)-4-nitro-5-phenyl-1-((S)-tetrahydro-2H-pyran-2-carbonyl)pyrrolidine-2-carboxylate and Example 10B rac-(2R,3S,4R,5SR)-ethyl 3-(tert-butyl)-4-nitro-5-phenyl-1-((R)-tetrahydro-2H-pyran-2-carbonyl)pyrrolidine-2-carboxylate To the mixture of tetrahydro-2H-pyran-2-carboxylic acid (800 mg, 6.15 mmol) and a few drops of N,N-dimethylformamide in dichloromethane (10 mL) was added oxalyl chloride (5 mL, 2 M in dichloromethane) dropwise. The mixture was stirred at ambient temperature for 1 hour, the solvent was evaporated, fresh dichloromethane (5 mL) was added and the solvent was evaporated again. The residue was dissolved in dichloromethane (2 mL) and added dropwise to a mixture of rac-(2R,3S,4R,5R)-ethyl 3-(tert-butyl)-4-nitro-5-phenylpyrrolidine-2-carboxylate (Core 2, 1.9 g, 6.15 mmol) and triethylamine (1.285 mL, 9.22 mmol) in dichloromethane (10 mL) cooled in an ice-bath. After the addition, the reaction mixture was allowed to warm to ambient temperature. Dichloromethane (20 mL) was added and the mixture was washed with brine, dried over MgSO$_4$, filtered, and concentrated. Purification via chromatography on a 40 g silica gel cartridge, eluting with ethyl acetate in heptane provided a racemic compound of Example 10A (1.02 g, 38.36% yield) as the first compound to elute (structure was confirmed by X-ray); LC/MS (ESI+) m/z 432.90 (M+H)$^+$. Also obtained was racemic compound Example 10B (1.0 g, 37.6% yield) as the second compound to elute. LC/MS (ESI+) 433.31 (M+H)$^+$.

Example 10C rac-(2R,3R,4R,5R)-ethyl 4-amino-3-(tert-butyl)-5-phenyl-1-((R)-tetrahydro-2H-pyran-2-carbonyl)pyrrolidine-2-carboxylate A mixture of Example 10B (400 mg, 0.925 mmol), tetrahydrofuran (10 mL), and Raney®-Nickel 2800 in a water slurry (860 mg, 6.59 mmol) in a pressure bottle (50 mL) was shaken with 50 psi hydrogen at ambient temperature for 16 hours. The mixture was filtered and the solid was washed with methanol. The combined organic layer was concentrated to provide the title compound (345 mg, 93% yields). LC/MS (ESI+) m/z 403 (M+H)$^+$.

Example 10D (2S,3S,4S,5S)-3-tert-butyl-4-[[2-methoxy-4-(trifluoromethyl)phenyl]methylamino]-5-phenyl-1-[(2S)-tetrahydropyran-2-carbonyl]pyrrolidine-2-carboxylic acid A mixture of 2-methoxy-4-(trifluoromethyl)benzaldehyde (51.7 mg, 0.253 mmol), Example 10C (85 mg, 0.211 mmol) and zinc(II) chloride (2.8 mg, 0.02 mmol) in an acetic acid/sodium acetate buffer in methanol (pH=4, 2 mL) was stirred at ambient temperature for 10 minutes. Sodium cyanotrihydroborate (19.90 mg, 0.317 mmol) added, and the mixture was stirred for another 2 hours. The mixture was diluted with dichloromethane (20 mL) and washed with brine, dried over $MgSO_4$, filtered, and concentrated. Purification via chromatography on a 12 g silica gel cartridge, eluting with ethyl acetate/methanol (10:1) in heptane at 0-50% gradient provided a racemic ester (65 mg, 54.7% yield). The ester was dissolved in methanol (2 mL) and 4 M aqueous LiOH (0.5 mL) and stirred at 50° C. for 3 hours. The pH of the mixture was adjusted to 1~2 by adding 2 M aqueous HCl. The two enantiomers were separated via chiral SFC (Instrument: Aurora-1, Column: ChiralPak® IC, 5-30% methanol:$CO_2$, 10 minute @ 3 mL/minute, 150 bar. The first compound to elute was (2R,3R,4R,5R)-3-(tert-butyl)-4-((2-methoxy-4-(trifluoromethyl)benzyl)amino)-5-phenyl-1-((R)-tetrahydro-2H-pyran-2-carbonyl)pyrrolidine-2-carboxylic acid, 25.5 mg (42.5% yield). $^1$H NMR (400 MHz, dimethyl sulfoxide-$d_6$) δ ppm 7.57 (d, J=7.4 Hz, 2H), 7.32 (t, J=7.4 Hz, 2H), 7.25 (t, J=7.2 Hz, 1H), 7.09 (d, J=2.0 Hz, 2H), 7.05 (s, 1H), 5.36 (s, 1H), 4.50 (d, J=2.5 Hz, 1H), 3.77 (d, J=11.3 Hz, 1H), 3.64 (s, 3H), 3.49-3.31 (m, 5H), 2.64 (d, 5H), 2.28 (t, J=2.5 Hz, J=2.4 Hz, 1H), 1.58 (dd, J=65.2, 12.2 Hz, 6H), 0.96 (s, 9H); MS (ESI+) m/z 563.3 (M+H)$^+$. The second compound to elute was the title compound (2S,3S, 4S,5S)-3-(tert-butyl)-4-((2-methoxy-4-(trifluoromethyl)benzyl)amino)-5-phenyl-1-((S)-tetrahydro-2H-pyran-2-carbonyl)pyrrolidine-2-carboxylic acid, 26 mg (43.3% yield). $^1$H NMR (400 MHz, dimethyl sulfoxide-$d_6$) δ ppm 7.57 (d, J=7.4 Hz, 2H), 7.32 (t, J=7.4 Hz, 2H), 7.25 (t, J=7.2 Hz, 1H), 7.10 (t, J=1.3 Hz, 2H), 7.05 (s, 1H), 5.36 (s, 1H), 4.50 (d, J=2.5 Hz, 1H), 3.77 (d, J=11.5 Hz, 1H), 3.64 (s, 3H), 3.52-3.30 (m, 5H), 2.28 (d, J=2.7 Hz, 1H), 1.66 (d, J=12.6 Hz, 1H), 1.55-1.31 (m, 4H), 0.96 (s, 9H); MS (ESI+) m/z 563.2 (M+H)$^+$.

Example 11

(2S,3S,4S,5S)-3-tert-butyl-4-({[2-methoxy-4-(trifluoromethyl)phenyl]methyl}amino)-5-phenyl-1-[(2R*)-2-phenylpropanoyl]pyrrolidine-2-carboxylic acid

Example 11A rac-(2R,3S,4R,5R)-ethyl 3-(tert-butyl)-4-nitro-5-phenyl-1-((S)-2-phenylpropanoyl)pyrrolidine-2-carboxylate and

Example 11B rac-(2R,3S,4R,5R)-ethyl 3-(tert-butyl)-4-nitro-5-phenyl-1-((R)-2-phenylpropanoyl)pyrrolidine-2-carboxylate To 2-phenylpropanoic acid (1 g, 6.66 mmol) and one drop of N,N-dimethylformamide in dichloromethane (4 mL) was added oxalyl chloride (4 mL, 2 M in dichloromethane) dropwise. The mixture was stirred at ambient temperature for 1 hour, the solvent was removed, fresh dichloromethane (2 mL) was added, and the mixture was concentrated. The residue was dissolved in dichloromethane (2 mL) and added dropwise to the mixture of rac-(2R,3S,4R,5R)-ethyl 3-(tert-butyl)-4-nitro-5-phenylpyrrolidine-2-carboxylate (Core 2, 1.687 mL, 12.11 mmol) in dichloromethane (10 mL) in an ice bath. The mixture was stirred in the ice bath for 20 minutes and allowed to warm to ambient temperature. Dichloromethane (20 mL) was added and the mixture was washed with brine, dried over $MgSO_4$, filtered, and concentrated. The residue was purified via chromatography on a 40 g silica gel cartridge, eluting with ethyl acetate in heptane at 0-40% gradient. The first compound to elute was Example 11A (610 mg, 22.27% yield). LC/MS (APCI+) m/z 453.26 (M+H)$^+$. The second compound to elute was Example 11B (1006 mg, 36.7% yield). LC/MS (APCI+) m/z 453.29 (M+H)$^+$.

Example 11C rac-(2R,3R,4R,5R)-ethyl 4-amino-3-(tert-butyl)-5-phenyl-1-((S)-2-phenylpropanoyl)pyrrolidine-2-carboxylate Example 11A (600 mg, 1.326 mmol) in tetrahydrofuran (320 mL) was added to a Raney®-Nickel 2800, water slurry (1.23 mg, 9.43 μmol) in a 50 mL pressure bottle. The mixture was shaken at ambient temperature for 16 hours with 50 psi hydrogen, and filtered. The solids were washed with methanol. The combined solvents were removed to provide the title racemic compound, rac-(2R,3R,4R,5R)-ethyl 4-amino-3-(tert-butyl)-5-phenyl-1-((S)-2-phenylpropanoyl)pyrrolidine-2-carboxylate (558 mg, 100% yield) which was pure enough to be used in next step. LC/MS (ESI+) m/z 223 (M+H)$^+$.

Example 11D rac-(2R,3R,4R,5R)-ethyl 3-(tert-butyl)-4-((2-methoxy-4-(trifluoromethyl)benzyl)amino)-5-phenyl-1-((S)-2-phenylpropanoyl)pyrrolidine-2-carboxylate To 2-methoxy-4-(trifluoromethyl)benzaldehyde (53.1 mg, 0.260 mmol), Example 11C (100 mg, 0.237 mmol) and zinc(II) chloride (32.3 mg, 0.237 mmol) in a sodium acetate/acetic acid buffer in methanol (pH=4, 2 mL) was added sodium cyanotrihydroborate (10.20 mg, 0.162 mmol) and the reaction mixture was stirred at ambient temperature for 3 hours. The solvent was removed under $N_2$ and the residue was diluted with dichloromethane (10 mL), washed with brine, dried over $MgSO_4$, filtered, and concentrated. Purification via chromatography on a 12 g silica gel cartridge, eluting with ethyl acetate/methanol (10:1) in heptane at 0-50% gradient provided a racemic ester, rac-(2R,3R,4R, 5R)-ethyl 3-(tert-butyl)-4-((2-methoxy-4-(trifluoromethyl)benzyl)amino)-5-phenyl-1-((S)-2-phenylpropanoyl)pyrrolidine-2-carboxylate (140 mg, 97%). LC/MS (APCI+) m/z 611.2 (M+H)$^+$.

Example 11E (2S,3S,4S,5S)-3-tert-butyl-4-({[2-methoxy-4-(trifluoromethyl)phenyl]methyl}amino)-5-phenyl-1-[(2R*)-2-phenylpropanoyl]pyrrolidine-2-carboxylic acid A mixture of Example 11D (80 mg, 0.164 mmol) in methanol (1.5 mL) and 6 M aqueous LiOH (0.5 mL) was stirred at 50° C. for 3 hours. The pH was adjusted to 1 by adding 4 M HCl in dioxane. The mixture was concentrated to dryness. Dichloromethane (2 mL) was added, and the mixture was filtered through a syringe filter. The crude material was purified via chromatography, eluting with ethyl acetate/methanol (10:1) in heptane 0-60% to yield a racemic acid, (2R,3R,4R,5R)-3-(tert-butyl)-4-((2-methoxy-4-(trifluoromethyl)benzyl)amino)-5-phenyl-1-((R)-2-phenylpropanoyl)pyrrolidine-2-carboxylic acid which was isolated as two enantiomers via chiral SFC [Instrument: Aurora-1, Column: ChiralPak® IC, 5-30% methanol:$CO_2$, 10 minute @ 3 mL/minute, 150 bar. The first compound to elute was (2R,3R,4R,5R)-3-(tert-butyl)-4-((2-methoxy-4-(trifluoromethyl)benzyl)amino)-5-phenyl-1-((S)-2-phenylpropanoyl) pyrrolidine-2-carboxylic acid (26 mg, 40.6%); room temperature, retention time=4.701 minutes. $^1$H NMR (400 MHz, dimethyl sulfoxide-$d_6$) δ ppm 7.62 (b, 3H), 7.34 (db, J=28.4 Hz, 3H), 7.23 (t, J=7.3 Hz, 2H), 7.20-6.98 (m, 5H), 5.00 (s, 1H), 4.46 (s, 1H), 3.63 (s, 3H), 3.49-3.25 (m, 4H), 2.44-2.39 (m, 1H), 2.23 (s, 1H), 1.05 (s, 3H), 0.77 (s, 9H); MS (ESI+) m/z 583.2 (M+H)$^+$. The second compound to elute was the title compound (27 mg, 42.2%); room temperature, retention time=5.519 minute. $^1$H NMR (400 MHz, dimethyl sulfoxide-$d_6$) δ ppm 7.61 (s, 3H), 7.37 (s, 3H), 7.23 (t, J=7.3 Hz, 2H), 7.08 (t, J=22.6 Hz, 5H), 4.99 (s, 1H), 4.46 (s, 1H), 3.62 (s, 3H), 3.46-3.25 (m, 4H), 2.44-2.39 (m, 1H), 2.22 (s, 1H), 1.03 (s, 3H), 0.74 (s, 9H); MS (ESI+) m/z 583.2 (M+H)$^+$.

Example 12

(2S,3S,4S,5S)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid (2S,3S,4S,5S)-Ethyl 4-amino-3-(tert-butyl)-1-(cyclohexanecarbonyl)-5-phenylpyrrolidine-2-carboxylate (Example 7B, 20 mg, 0.05 mmol, 1.0 eq) dissolved in sodium acetate/acetic acid buffer in methanol (pH=4). 2-Methoxy-5-(trifluoromethyl)nicotinaldehyde (0.4 M in methanol, 187 μL, 0.075 mmol, 1.5 eq) was added to the vial. NaBH$_3$CN (0.22 M in acetate buffer, 300 μL, 0.065 mmol, 1.2 eq) was added and reaction was stirred at room temperature for 1 hour. The reaction was dried down under a stream of nitrogen and was carried on to the next step without purification. The residue was dissolved in 3:2 tetrahydrofuran/methanol (500 μL). LiOH monohydrate (20 mg, 0.5 mmol, 10 eq) in H$_2$O (100 μL) was added and the reaction was stirred at 45° C. for 3 hours (complete by LC/MS). The solvent was removed under a stream of nitrogen. The residue was acidified with 800 μL 1 M aqueous HCl and was diluted with 500 μL CH$_3$CN. The reaction mixture was loaded directly into an injection loop and purified using prep LC method trifluoroacetic acid 8 to provide the title compound (22.5 mg, 67% yield). $^1$H NMR (400 MHz, 120° C., dimethyl sulfoxide-$d_6$:D$_2$O=9:1 (v/v)) δ ppm 8.31 (s, 1H), 7.54 (s, 3H), 7.40-7.19 (m, 3H), 5.22 (d, J=7.0 Hz, 1H), 4.49 (d, J=2.4 Hz, 1H), 3.79 (s, 3H), 3.64-3.46 (m, 2H), 3.33 (d, J=14.9 Hz, 1H), 2.38-2.09 (m, 2H), 1.55 (d, J=63.9 Hz, 4H), 1.13 (d, J=60.8 Hz, 5H), 0.96 (s, 9H), 0.89-0.49 (m, 1H); MS (APCI+) m/z 561.9 (M+H)$^+$.

Example 13

(2S,3S,4S,5S)-3-tert-butyl-4-{[(5-tert-butyl-2-methoxyphenyl)methyl]amino}-5-(2-methoxyphenyl)-1-{[(propan-2-yl)oxy]carbonyl}pyrrolidine-2-carboxylic acid Example 13A (2S,3R,4S,5S)-2-ethyl 1-isopropyl 3-(tert-butyl)-5-(2-methoxyphenyl)-4-nitropyrrolidine-1,2-dicarboxylate (2S,3R,4S,5S)-Ethyl 3-(tert-butyl)-5-(2-methoxyphenyl)-4-nitropyrrolidine-2-carboxylate (Core 22, 0.349 g, 0.996 mmol) was dissolved in dichloromethane (3 mL) and triethylamine (0.450 mL, 3.23 mmol) was added, followed by dropwise addition of 1 M isopropyl carbonochloridate in toluene (2.00 mL, 2.000 mmol). The reaction was stirred at ambient temperature for 4 hours, then concentrated and purified using a 24 g silica gel cartridge with a gradient of 5-80% ethyl acetate/heptanes over 30 minutes to give (2S,3R,4S,5S)-2-ethyl 1-isopropyl 3-(tert-butyl)-5-(2-methoxyphenyl)-4-nitropyrrolidine-1,2-dicarboxylate (350 mg, 0.802 mmol, 81% yield). $^1$H NMR (400 MHz, dimethyl sulfoxide-$d_6$) δ ppm 7.68-7.59 (m, 1H), 7.19 (ddd, J=8.8, 7.5, 1.7 Hz, 1H), 6.91 (dd, J=8.3, 1.0 Hz, 1H), 6.84 (td, J=7.5, 1.0 Hz, 1H), 5.54 (d, J=8.3 Hz, 1H), 5.45 (dd, J=8.4, 2.6 Hz, 1H), 4.64 (s, 1H), 4.48 (d, J=3.2 Hz, 1H), 4.19 (q, J=7.1 Hz, 2H), 3.77 (s, 3H), 3.28 (s, 6H), 2.90 (t, J=2.9 Hz, 1H), 1.23 (t, J=7.1 Hz, 3H), 0.96 (s, 9H); MS (ESI+) m/z 437 (M+H)$^+$.

Example 13B (2S,3S,4S,5S)-2-ethyl 1-isopropyl 4-amino-3-(tert-butyl)-5-(2-methoxyphenyl)pyrrolidine-1,2-dicarboxylate Example 13A (0.35 g, 0.802 mmol) and tetrahydrofuran (20 mL) were added to Raney®-Nickel 2800, water slurry (0.9 g, 6.90 mmol) in a 50 mL pressure bottle. The mixture was stirred for 6 hours at 50 psi of hydrogen and 50° C., and for 10 hours at ambient temperature. The reaction was filtered and the solvent removed in vacuo to give (2S,3S,4S,5S)-2-ethyl 1-isopropyl 4-amino-3-(tert-butyl)-5-(2-methoxyphenyl)pyrrolidine-1,2-dicarboxylate (0.340 g, 0.84 mmol). $^1$H NMR (400 MHz, dimethyl sulfoxide-$d_6$) δ ppm 7.67 (dd, J=7.6, 1.8 Hz, 1H), 7.18 (td, J=7.8, 1.7 Hz, 1H), 6.94 (dd, J=8.2, 1.0 Hz, 1H), 6.89 (td, J=7.4, 1.1 Hz, 1H), 5.18 (d, J=6.9 Hz, 1H), 4.63 (p, J=6.2 Hz, 1H), 4.29 (d, J=3.3 Hz, 1H), 4.19-4.11 (m, 2H), 3.80 (s, 3H), 3.65 (dd, J=6.9, 2.7 Hz, 1H), 2.01 (t, J=3.1 Hz, 1H), 1.23 (t, J=7.0 Hz, 3H), 1.04 (d, J=6.2 Hz, 3H), 0.98 (s, 9H), 0.91 (d, J=6.2 Hz, 3H); MS (ESI+) m/z 407 (M+H)$^+$.

Example 13C (2S,3S,4S,5S)-3-(tert-butyl)-4-((5-(tert-butyl)-2-methoxybenzyl)amino)-1-(isopropoxycarbonyl)-5-(2-methoxyphenyl)pyrrolidine-2-carboxylic acid To a solution of 5-(tert-butyl)-2-methoxybenzaldehyde (37.5 mg, 0.195 mmol), Example 13B (66 mg, 0.162 mmol) and zinc(II) chloride (22.13 mg, 0.162 mmol) in sodium acetate/acetic acid buffer in methanol (pH=4, 1 mL) was added sodium cyanoborohydride (15.30 mg, 0.244 mmol)

and the reaction was stirred at ambient temperature for 5 hours. The solvent was removed under nitrogen. The residue was diluted with dichloromethane and water. The aqueous phase was extracted with dichloromethane (3×1 mL). The solvent was removed and the resulting residue was dissolved in 2 mL of methanol and 0.5 mL of water with lithium hydroxide (19.44 mg, 0.812 mmol). The mixture was stirred at 45° C. for 4 hours. The solvent was removed, the crude material was acidified with 2 N aqueous HCl (450 μL), taken up in dichloromethane, and purified using a 3:1:4 ethyl acetate/ethanol/heptanes solvent system with a 12 g silica gel cartridge to yield (2S,3S,4S,5S)-3-(tert-butyl)-4-((5-(tert-butyl)-2-methoxybenzyl)amino)-1-(isopropoxycarbonyl)-5-(2-methoxyphenyl)pyrrolidine-2-carboxylic acid, hydrochloric acid (71 mg, 0.120 mmol, 74.0% yield). $^1$H NMR (400 MHz, dimethyl sulfoxide-$d_6$) δ ppm 7.56 (dd, J=7.7, 1.7 Hz, 1H), 7.20 (ddd, J=8.2, 7.3, 1.8 Hz, 1H), 7.14 (dd, J=8.5, 2.6 Hz, 1H), 6.97 (d, J=2.6 Hz, 1H), 6.94-6.85 (m, 2H), 6.72 (d, J=8.5 Hz, 1H), 5.24 (d, J=6.3 Hz, 1H), 4.63 (p, J=6.2 Hz, 1H), 4.36 (d, J=1.8 Hz, 1H), 3.62 (s, 3H), 3.59 (d, J=13.7 Hz, 1H), 3.45 (s, 3H), 3.31 (d, J=13.7 Hz, 1H), 2.32 (dt, J=1.7, 0.8 Hz, 1H), 1.20 (s, 9H), 1.04 (d, J=6.2 Hz, 3H), 0.98 (s, 9H), 0.90 (d, J=6.3 Hz, 3H); MS (ESI+) m/z 555 (M+H)$^+$.

Example 14

(2S,3S,4S,5S)-3-tert-butyl-1-(cyclohexanecarbonyl)-5-[2-(difluoromethoxy)phenyl]-4-({[2-methoxy-5-(trifluoromethyl)pyridin-3-yl]methyl}amino)pyrrolidine-2-carboxylic acid Example 14A (2S,3R,4S,5S)-ethyl 3-(tert-butyl)-1-(cyclohexanecarbonyl)-5-(2-(difluoromethoxy)phenyl)-4-nitropyrrolidine-2-carboxylate To (2S,3R,4S,5S)-ethyl 3-(tert-butyl)-5-(2-(difluoromethoxy)phenyl)-4-nitropyrrolidine-2-carboxylate (Core 15, 1.0 g, 2.59 mmol) and one drop of N,N-dimethylformamide in dichloromethane (10 mL) in an ice-bath was added cyclohexanecarbonyl chloride (0.415 mL, 3.11 mmol) dropwise. The mixture was stirred for 2 hours. As the temperature was warmed to ambient temperature, dichloromethane (20 mL) was added, and the mixture was washed with brine, dried over MgSO$_4$, filtered, and concentrated. The residue was purified via chromatography on a 12 g silica gel cartridge, eluting with ethyl acetate in heptane at 0-40% gradient to provide the title compound, 1.28 g (100% yield). LC/MS (ESI+) m/z 497.24 (M+H)$^+$.

Example 14B (2S,3S,4S,5S)-ethyl 4-amino-3-(tert-butyl)-1-(cyclohexanecarbonyl)-5-(2-(difluoromethoxy)phenyl) pyrrolidine-2-carboxylate A mixture of Example 14A (300 mg, 0.604 mmol), tetrahydrofuran (20 mL) and Raney®-Nickel 2800, water slurry (2.5 g, 19.17 mmol) in a 50 mL pressure bottle was shaken at ambient temperature for 20 hours, filtered, and concentrated. The crude residue was dissolved in dichloromethane (20 mL), washed with brine, dried over MgSO$_4$, filtered, and concentrated to provide the title compound (300 mg, 100%) which used in next step without further purification. LC/MS (APCI+) m/z 467 (M+H)$^+$.

Example 14C (2S,3S,4S,5S)-3-(tert-butyl)-1-(cyclohexanecarbonyl)-5-(2-(difluoromethoxy)phenyl)-4-(((2-methoxy-5-(trifluoromethyl)pyridin-3-yl)methyl)amino)pyrrolidine-2-carboxylic acid A mixture of 2-methoxy-5-(trifluoromethyl)nicotinaldehyde (29.0 mg, 0.141 mmol), Example 14B (60 mg, 0.129 mmol), and zinc(II) chloride (3.51 mg, 0.026 mmol) in sodium acetate/acetic acid buffer in methanol (pH=4, 2 mL) was stirred at ambient temperature for 10 minutes. Sodium cyanoborohydride (12.1 mg, 0.193 mmol) was added, the mixture was stirred for another 3 hours, and the solvent was removed under pressure. The residue was dissolved in ethyl acetate (10 mL), washed with brine, dried over MgSO$_4$, filtered, and concentrated. Purification via chromatography, eluting with ethyl acetate/methanol (10:1) in heptane 0-40% provided the intermediate ester, (2S,3S,4S,5S)-ethyl 3-(tert-butyl)-1-(cyclohexanecarbonyl)-5-(2-(difluoromethoxy)phenyl)-4-(((2-methoxy-5-(trifluoromethyl)pyridin-3-yl)methyl)amino)pyrrolidine-2-carboxylate. The ester was dissolved in methanol (1.5 mL) and 6 M aqueous LiOH (0.5 mL). The mixture was stirred at 50° C. for 3 hours, and adjusted to pH 1~2 by adding 4 M HCl in dioxane. The solvent was removed and the residue was purified via HPLC using the ammonium acetate method to provide the title compound (64 mg, 79.2% yield). $^1$H NMR (400 MHz, dimethyl sulfoxide-$d_6$) δ ppm 8.25 (s, 1H), 8.09 (s, 1H), 7.42 (s, 1H), 7.15 (d, J=48.9 Hz, 3H), 5.37 (s, 1H), 3.84 (s, 3H), 3.59-3.15 (m, 5H), 2.64 (s, 1H), 2.35 (s, 1H), 1.76-1.06 (m, 10H), 0.94 (s, 9H); MS (ESI+) m/z 628.2 (M+H)$^+$.

Example 15

(2S,3S,4S,5S)-1-(benzenesulfonyl)-3-tert-butyl-4-{[(5-tert-butyl-2-methoxyphenyl)methyl]amino}-5-phenylpyrrolidine-2-carboxylic acid Example 15A (2S,3R,4S,5S)-4-nitro-1-benzenesulfonyl-3-tert-butyl-5-phenyl-pyrrolidine-2-carboxylic acid ethyl ester Triethylamine (CAS#121-44-8, 112 μL, 0.81 mmol, 1.3 eq) and benzenesulfonyl chloride (CAS#98-09-9, 95 μL, 0.74 mmol, 1.2 eq) were added to a stirred solution of Core 7 (200 mg, 0.62 mmol, 1.0 eq) in anhydrous dichloromethane (3 mL). The reaction mixture was stirred overnight at room temperature, and at 45° C. for 4 hours. The reaction mixture was washed with water and the organic layer was separated and concentrated in vacuo. The crude mixture was purified by flash chromatography on silica gel (heptane/ethyl acetate 100/0 to 80/20) to provide the title compound (230 mg, 80%). LC/MS (ESI+) m/z 461.4 (M+H)$^+$.

Example 15B (2S,3S,4S,5S)-4-amino-1-benzenesulfonyl-3-tert-butyl-5-phenyl-pyrrolidine-2-carboxylic acid ethyl ester Zinc dust (490 mg, 7.50 mmol, 15.0 eq) was added to a solution of (2S,3R,4S,5S)-4-nitro-1-benzenesulfonyl-3-tertbutyl-5-phenyl-pyrrolidine-2-carboxylic acid (230 mg, 0.50 mmol, 1.0 eq) in ethyl acetate (3 mL) and acetic acid (1 mL) at room temperature. The reaction was heated to 60° C. for 1 hour. The reaction was filtered on diatomaceous earth, washed with ethyl acetate and dichloromethane, concentrated to dryness, and partitioned between NaHCO$_3$ saturated aqueous solution and dichloromethane. The organic layer was concentrated to provide the title compound (208 mg, 96%) that was used in the next step without further purification. LC/MS (ESI+) m/z 431.6 (M+H)$^+$.

Example 15C (2S,3S,4S,5S)-1-benzenesulfonyl-3-tert-butyl-4-(5-tert-butyl-2-methoxy-benzylamino)-5-phenyl-pyrrolidine-2-carboxylic acid ethyl ester NaBH$_3$CN (20 mg, 0.31 mmol, 1.3 eq) was added to a solution of (2S,3S,4S,5S)-4-amino-1-benzenesulfonyl-3-tert-butyl-5-phenyl-pyrrolidine-2-carboxylic acid ethyl ester (104 mg, 0.24 mmol, 1.0 eq) and 5-tert-butyl-2-methoxybenzaldehyde (CAS#85943-26-6, 52 mg, 0.28 mmol, 1.2 eq) in acetic acid/sodium acetate buffer in methanol (96 mg acetic acid, 61 mg sodium acetate, 2 mL methanol). The reaction mixture was stirred at room temperature for 1 hour. The solvent was removed under vacuum. The residue was partitioned between dichloromethane and water. The organic phase was concentrated to dryness and the residue was purified by flash chromatography on silica gel (heptane/ethyl acetate 100/0 to 90/10) to give the title compound (97 mg, 66%). LC/MS (ESI+) m/z 608.1 (M+H)$^+$.

Example 15D (2S,3S,4S,5S)-1-benzenesulfonyl-3-tert-butyl-4-(5-tert-butyl-2-methoxy-benzylamino)-5-phenyl-pyrrolidine-2-carboxylic acid A solution of (2S,3S,4S,5S)-1-benzenesulfonyl-3-tert-butyl-4-(5-tert-butyl-2-methoxy-benzylamino)-5-phenyl-pyrrolidine-2-carboxylic acid ethyl ester (97 mg, 0.16 mmol, 1.0 eq) in methanol (2 mL) was treated with LiOH (1.0 M in water, 480 µL, 0.48 mmol, 3 eq) at room temperature and stirred overnight at 45° C. After completion of the reaction, the solvent was removed under vacuum and water was added. The resulting solution was acidified to pH=6 with 1 N aqueous HCl 1 N and extracted with dichloromethane. The organic phase was concentrated to dryness and the residue was purified by flash chromatography on silica gel (dichloromethane/methanol 100/0 to 94/$_6$) to provide the title compound (52 mg, 56%). $^1$H NMR (400 MHz, CDCl$_3$-d) δ ppm 7.54 (dd, J=8.4, 1.2 Hz, 2H), 7.44-7.51 (m, 1H), 7.32-7.39 (m, 2H), 7.28-7.31 (m, 1H), 7.15-7.25 (m, 3H), 6.96-7.09 (m, 3H), 6.57 (d, J=8.7 Hz, 1H), 5.25-5.35 (m, 2H), 5.01 (s, 1H), 3.99 (d, J=13.8 Hz, 1H), 3.28 (d, J=5.8 Hz, 1H), 3.12 (s, 3H), 2.37 (s, 1H), 1.22-1.29 (m, 9H), 1.05-1.15 (m, 9H); LC/MS (ESI+) m/z 579.7 (M+H)$^+$.

Example 16

(2S,3S,4S,5S)-3-tert-butyl-4-{[(5-cyclobutyl-2-methoxypyridin-3-yl)methyl]amino}-1-(cyclohexanecarbonyl)-5-phenylpyrrolidine-2-carboxylic acid In a 4 mL vial, (2S,3S,4S,5S)-tert-butyl 4-(((5-bromo-2-methoxypyridin-3-yl)methyl)amino)-3-(tert-butyl)-1-(cyclohexanecarbonyl)-5-phenylpyrrolidine-2-carboxylate (Example 25C, 20.0 mg, 0.032 mmol, 1.0 eq) and dichloro[4,5-dichloro-1,3-bis(2,6-di-3-pentylphenyl)imidazol-2-ylidene](3-chloropyridyl)palladium(II) (PEPPSI-IPentCl, 2.7 mg, 0.0032 mmol, 0.1 eq) were dissolved in tetrahydrofuran (0.5 mL), flushed with nitrogen and stirred at room temperature. Cyclobutylzinc bromide (0.5 M, 127 µL, 0.64 mmol, 2.0 eq) was added and the reaction was stirred at room temperature for 30 minutes. The solvent was removed under a stream of nitrogen. The residue was dissolved in neat trifluoroacetic acid (1 mL) and stirred at room temperature for 2 hours. The solvent was removed under a stream of nitrogen. The residue was reconstituted in dimethyl sulfoxide/acetonitrile. The reaction was loaded directly into an injection loop and purified using prep LC method trifluoroacetic acid 8 to provide the title compound (15.6 mg, 74.0% yield). $^1$H NMR (400 MHz, 120° C., dimethyl sulfoxide-d$_6$:D$_2$O=9:1 (v/v)) δ ppm 7.83-7.78 (m, 1H), 7.60-7.46 (m, 2H), 7.40-7.26 (m, 3H), 7.20 (s, 1H), 5.23 (d, J=6.9 Hz, 1H), 4.50 (d, J=2.1 Hz, 1H), 3.65 (s, 3H), 3.56 (d, J=8.3 Hz, 2H), 3.44-3.32 (m, 2H), 2.42-2.19 (m, 4H), 2.07-1.76 (m, 4H), 1.72-1.40 (m, 4H), 1.32-1.01 (m, 5H), 1.01-0.91 (m, 10H); MS (APCI+) m/z 548.1 (M+H)$^+$.

Example 17

(2S,3S,4S,5S)-3-tert-butyl-4-{[(5-tert-butyl-2-methoxyphenyl)methyl]amino}-1-(cyclohexanecarbonyl)-5-(2-methoxypyridin-3-yl)pyrrolidine-2-carboxylic acid Example 17A (2S,3R,4S,5S)-ethyl 3-(tert-butyl)-1-(cyclohexanecarbonyl)-5-(2-methoxypyridin-3-yl)-4-nitropyrrolidine-2-carboxylate To cyclohexanecarbonyl chloride (0.228 mL, 1.707 mmol) and one drop of N,N-dimethylformamide in dichloromethane (4 mL) was added oxalyl chloride (4 mL, 2 M in dioxane) dropwise at ambient temperature. The mixture was stirred for 30 minutes, the solvent was removed, fresh dichloromethane (2 mL) was added, and the mixture was concentrated again. The residue in dichloromethane (2 mL) was added dropwise to the mixture of (2S,3R,4S,5S)-ethyl 3-(tert-butyl)-5-(2-methoxypyridin-3-yl)-4-nitropyrrolidine-2-carboxylate (Core 12, 500 mg, 1.423 mmol) and triethylamine (0.297 mL, 2.134 mmol) in dichloromethane (10 mL) in an ice bath, keeping the temperature below 0° C. during the addition. The reaction mixture was stirred for 2 hours, and dichloromethane (20 mL) and water (10 mL) were added. The organic layer was washed with brine, dried over Na$_2$SO$_4$, filtered, and concentrated. The residue was purified via chromatography on a 24 g silica gel cartridge, eluting with ethyl acetate in heptane at 0-40% gradient to yield the title compound, 650 mg (99% yield). LC/MS (APCI+) m/z 462 (M+H)$^+$.

Example 17B (2S,3S,4S,5S)-ethyl 4-amino-3-(tert-butyl)-1-(cyclohexanecarbonyl)-5-(2-methoxypyridin-3-yl)pyrrolidine-2-carboxylate Example 17A (600 mg, 1.300 mmol) in tetrahydrofuran (20 mL) was added to Raney®-Nickel 2800, water slurry (2.2 g, 16.87 mmol) in a 250 mL pressure bottle. The mixture was shaken with 50 psi hydrogen at ambient temperature for 23 hours, filtered and concentrated to provide the title compound (560 mg, 100% yield) which used in next step without further purification. LC/MS (APCI+) m/z 432.35 (M+H)+.

Example 17C (2S,3S,4S,5S)-3-tert-butyl-4-{[(5-tert-butyl-2-methoxyphenyl)methyl]amino}-1-(cyclohexanecarbonyl)-5-(2-methoxypyridin-3-yl)pyrrolidine-2-carboxylic acid A mixture of 5-(tert-butyl)-2-methoxybenzaldehyde (CAS#: 85943-26-6) (39.2 mg, 0.204 mmol), (2S,3S,4S,5S)-ethyl 4-amino-3-(tert-butyl)-1-(cyclohexanecarbonyl)-5-(2-methoxypyridin-3-yl)pyrrolidine-2-carboxylate (80 mg, 0.185 mmol) and zinc(II) chloride (5.05 mg, 0.037 mmol) in sodium acetate/acetic acid buffer in methanol (pH=4, 2 mL) was stirred at ambient temperature for 10 minutes. Sodium cyanoborohydride (17.47 mg, 0.278 mmol) was added. The reaction mixture was stirred for 1 hour, and the solvent was removed under $N_2$. The residue was diluted with ethyl acetate (10 mL) and water (10 mL). The organic layer was washed with brine, dried over $Na_2SO_4$, filtered, and concentrated. Purification via chromatography on a 10 g silica gel cartridge, eluting with ethyl acetate/methanol (10:1) in heptane 0-40% provided the ester (2S,3S,4S,5S)-ethyl 3-(tert-butyl)-4-((5-(tert-butyl)-2-methoxybenzyl)amino)-1-(cyclohexanecarbonyl)-5-(2-methoxypyridin-3-yl)pyrrolidine-2-carboxylate, which was dissolved in methanol (1.5 mL) and 6 M aqueous LiOH (0.5 mL). The mixture was stirred at 50° C. for 3 hours. The solvent was removed, water (1 mL) was added, and the pH was adjusted to ~4 by adding 2 M aqueous HCl. The precipitate was filtered, washed with water and dried in an oven to provide the title compound, 75 mg (69.8% yield). $^1$H NMR (400 MHz, dimethyl sulfoxide-$d_6$) δ ppm 8.05 (d, J=4.6 Hz, 1H), 7.95 (s, 1H), 7.15 (dd, J=8.6, 2.6 Hz, 1H), 6.98 (d, J=2.5 Hz, 1H), 6.91 (t, J=6.2 Hz, 1H), 6.75 (d, J=8.5 Hz, 1H), 5.27 (s, 1H), 4.48 (s, 1H), 3.81 (s, 3H), 3.58 (d, J=13.3 Hz, 1H), 3.51 (s, 3H), 3.49 (s, 1H), 3.33 (d, J=13.6 Hz, 2H), 3.2 (s, 1H), 2.38 (s, 1H), 1.71-1.26 (m, 7H), 1.21 (s, 9H), 1.17-1.02 (m, 3H), 0.97 (s, 9H); MS (ESI+) m/z 580.2 (M+H)+.

Example 18

(2S,3S,4S,5S)-3-tert-butyl-4-{[(5-tert-butyl-2-methoxyphenyl)methyl]amino}-5-[2-(dimethylamino)pyridin-3-yl]-1-[(2S)-oxane-2-carbonyl]pyrrolidine-2-carboxylic acid Example 18A (2S,3R,4S,5S)-ethyl 3-(tert-butyl)-5-(2-(dimethylamino)pyridin-3-yl)-4-nitro-1-((R)-tetrahydro-2H-pyran-2-carbonyl)pyrrolidine-2-carboxylate and Example 18B (2S,3R,4S,5S)-ethyl 3-(tert-butyl)-5-(2-(dimethylamino)pyridin-3-yl)-4-nitro-1-((S)-tetrahydro-2H-pyran-2-carbonyl)pyrrolidine-2-carboxylate To a mixture of (2S,3R,4S,5S)-ethyl 3-(tert-butyl)-5-(2-(dimethylamino)pyridin-3-yl)-4-nitropyrrolidine-2-carboxylate (Core 11, 740 mg, 2.031 mmol) and triethylamine (0.849 mL, 6.09 mmol) in dichloromethane (20 mL) cooled in an ice-bath was added tetrahydro-2H-pyran-2-carboxylic acid (CAS#51673-83-7) (396 mg, 3.05 mmol) dropwise. The mixture was stirred for 1 hour while the temperature was warmed to ambient temperature. Dichloromethane (20 mL) added and the mixture was washed with brine, dried over $MgSO_4$, filtered, and concentrated. The residue was purified via chromatography on a 40 g silica gel cartridge, eluting with ethyl acetate in heptane. The first compound to elute was Example 18A, (2S,3R,4S,5S)-ethyl 3-(tert-butyl)-5-(2-(dimethylamino)pyridin-3-yl)-4-nitro-1-((R)-tetrahydro-2H-pyran-2-carbonyl)pyrrolidine-2-carboxylate, 360 mg (37.2% yield). LC/MS (APCI+) m/z 477.35 (M+H)+. The second compound to elute was Example 18B, (2S,3R,4S,5S)-ethyl 3-(tert-butyl)-5-(2-(dimethylamino)pyridin-3-yl)-4-nitro-1-((S)-tetrahydro-2H-pyran-2-carbonyl)pyrrolidine-2-carboxylate, 340 mg (35.1% yield). LC/MS (APCI+) m/z 477.35 (M+H)+.

Example 18C (2S,3S,4S,5S)-ethyl 4-amino-3-(tert-butyl)-5-(2-(dimethylamino)pyridin-3-yl)-1-((S)-tetrahydro-2H-pyran-2-carbonyl)pyrrolidine-2-carboxylate Example 18B (360 mg, 0.755 mmol) in tetrahydrofuran (20 mL) was added to Raney®-Nickel 2800, water slurry (998 mg, 7.65 mmol) in a 50 mL pressure bottle. The mixture was shaken with 50 psi hydrogen at ambient temperature for 16 hours, filtered and concentrated to provide the title compound (330 mg, 98% yield) which used in next step without further purification. LC/MS (APCI+) m/z 447 (M+H)+.

Example 18D (2S,3S,4S,5S)-3-tert-butyl-4-{[(5-tert-butyl-2-methoxyphenyl)methyl]amino}-5-[2-(dimethylamino)pyridin-3-yl]-1-[(2S)-oxane-2-carbonyl]pyrrolidine-2-carboxylic acid The mixture of 5-(tert-butyl)-2-methoxybenzaldehyde (25.8 mg, 0.134 mmol), Example 18C (60 mg, 0.134 mmol) and zinc(II) chloride (3.66 mg, 0.027 mmol) in a sodium acetate/acetic acid buffer in methanol (pH=4, 2 mL) was stirred at ambient temperature for 10 minutes to give a colorless solution. Sodium cyanoborohydride (12.66 mg, 0.202 mmol) was added and the mixture was stirred for 30 minutes. The solvent was removed under $N_2$ and the residue was purified via chromatography on a 4 g silica gel cartridge, eluting with ethyl acetate/methanol (10:1) in heptane at 0-40% gradient to provide the ester of (2S,3S,4S,5S)-ethyl 3-(tert-butyl)-4-((5-(tert-butyl)-2-methoxybenzyl)amino)-5-(2-(dimethylamino)pyridin-3-yl)-1-((R)-tetrahydro-2H-pyran-2-carbonyl)pyrrolidine-2-carboxylate, which dissolved in methanol (1.5 mL) and 6 M aqueous LiOH (0.5 mL). The mixture was stirred at 50° C. for 3 hours, the pH was adjusted to 4~5 by adding 4 M HCl in dioxane, and the mixture was concentrated to dryness. The residue was added to dichloromethane (2 mL) and filtered, and purified via chromatography, eluting with methanol in dichloromethane at 0-20% gradient to provide the title compound (52 mg, 65.1% yield). $^1$H NMR (400 MHz, dimethyl sulfoxide-$d_6$) δ ppm 8.23-8.13 (m, 2H), 7.17-7.10 (m, 1H), 6.98 (d, J=2.6 Hz, 1H), 6.95 (dd, J=7.5, 4.8 Hz, 1H), 6.72 (d, J=8.5 Hz, 1H), 5.61 (s, 1H), 5.55 (s, 1H), 4.60 (s, 1H), 3.76 (d, J=11.5 Hz, 1H), 3.63 (d, J=13.6 Hz, 1H), 3.54 (d, J=6.7 Hz, 1H), 3.47 (s, 3H), 3.27 (d, J=13.7 Hz, 1H), 3.20 (s, 1H), 2.65 (d, J=0.9 Hz, 6H), 2.61 (s, 1H), 2.39-2.34 (m, 1H), 1.66 (s, 2H), 1.42 (d, J=37.5 Hz, 4H), 1.19 (s, 9H), 1.00 (s, 9H); MS (ESI+) m/z 595.3 (M+H)$^+$.

Example 19

(2S,3S,4S,5S)-3-tert-butyl-4-{[(5-tert-butyl-2-methoxyphenyl)methyl]amino}-5-[2-(dimethylamino)pyridin-3-yl]-1-[(2R)-oxane-2-carbonyl]pyrrolidine-2-carboxylic acid Example 19A (2S,3S,4S,5S)-ethyl 4-amino-3-(tert-butyl)-5-(2-(dimethylamino)pyridin-3-yl)-1-((R)-tetrahydro-2H-pyran-2-carbonyl)pyrrolidine-2-carboxylate The title compound was prepared according to the procedure described in Example 10C, substituting Example 18A for Example 10B. LC/MS (APCI+) m/z 447.3 (M+H)$^+$.

Example 19B (2S,3S,4S,5S)-3-(tert-butyl)-4-((5-(tert-butyl)-2-methoxybenzyl)amino)-5-(2-(dimethylamino)pyridin-3-yl)-1-((R)-tetrahydro-2H-pyran-2-carbonyl)pyrrolidine-2-carboxylic acid The title compound was prepared according to the procedure described in Example 18D, substituting Example 19A for Example 18C. $^1$H NMR (400 MHz, dimethyl sulfoxide-d$_6$) δ ppm 8.17 (d, J=5.4 Hz, 1H), 7.91 (s, 1H), 7.13 (ddd, J=8.3, 5.6, 2.6 Hz, 1H), 6.98 (d, J=2.8 Hz, 1H), 6.94 (d, J=4.7 Hz, 1H), 6.72 (d, J=8.5 Hz, 1H), 5.61 (d, J=0.9 Hz, 1H), 5.40 (d, J=6.5 Hz, 1H), 4.84 (s, 1H), 4.6 (d, J=3.2 Hz, 1H), 3.65 (s, 1H), 3.53 (s, 1H), 3.49 (s, 1H), 3.46 (d, J=9.0 Hz, 3H), 3.30 (d, J=12.0 Hz, 1H), 3.25 (s, 1H), 2.63 (d, J=16.5 Hz, 6H), 2.36 (s, 1H), 1.79 (s, 2H), 1.45 (d, J=10.8 Hz, 4H), 1.19 (d, J=3.8 Hz, 9H), 1.00 (d, J=3.5 Hz, 9H); MS (ESI+) m/z 595.3 (M+H)$^+$.

Example 20

(2S,3S,4S,5S)-3-tert-butyl-4-{[(5-tert-butyl-2-methoxyphenyl)methyl]amino}-1-[(oxan-2-yl)acetyl]-5-phenylpyrrolidine-2-carboxylic acid 2-(Tetrahydro-2H-pyran-2-yl)acetic acid (0.4 M in dichloromethane, 139 μL, 0.056 mmol, 1.3 eq) was added to a 4 mL vial. Ghosez reagent (1-chloro-N,N,2-trimethyl-1-propenylamine, 17 μL, 0.13 mmol, 3.0 eq) was added neat and the reaction was stirred at room temperature for 10 minutes. (2S,3S,4S,5S)-Ethyl 3-(tert-butyl)-4-((5-(tert-butyl)-2-methoxybenzyl)amino)-5-phenylpyrrolidine-2-carboxylate (Example 34D, 20 mg, 0.043 mmol, 1.0 eq) in 1:1 tetrahydrofuran/pyridine (500 μL) was added and the reaction mixture was stirred for 1 hour at room temperature. The solvent was removed under a stream of nitrogen and the residue was dissolved in 3:2 tetrahydrofuran/methanol (0.5 mL). LiOH monohydrate (16 mg, 0.4 mmol, 7.1 eq) in H$_2$O (100 μL) was added and the reaction was stirred at 45° C. overnight. The solvent was removed under a stream of nitrogen. The residue was acidified with 800 μL 1 M aqueous HCl and was diluted with 400 μL CH$_3$CN. Purification was carried out using preparative reverse phase HPLC MS method trifluoroacetic acid 8 (15.7 mg, 54% yield). $^1$H NMR (400 MHz, 120° C., dimethyl sulfoxide-d$_6$:D$_2$O=9:1 (v/v)) δ ppm 7.61-7.30 (m, 5H), 7.24 (dd, J=8.6, 2.5 Hz, 1H), 7.06-6.99 (m, 1H), 6.81 (d, J=8.7 Hz, 1H), 5.34 (dd, J=22.5, 7.1 Hz, 1H), 4.72-4.55 (m, 1H), 3.89-3.67 (m, 3H), 3.60-3.53 (m, 4H), 3.53-3.41 (m, 1H), 3.30-3.19 (m, 1H), 2.36-2.12 (m, 2H), 1.79-1.27 (m, 6H), 1.21 (s, 9H), 0.99 (s, 10H); MS (APCI+) m/z 565.1 (M+H)$^+$.

Example 21

(2S,3S,4S,5S)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid Example 21A rac-(2R,3R,4R,5R)-3-(tert-butyl)-4-(((2-methoxy-5-(trifluoromethyl)pyridin-3-yl)methyl)amino)-5-phenyl-1-((S)-tetrahydro-2H-pyran-2-carbonyl)pyrrolidine-2-carboxylic acid A mixture of 2-chloro-5-(trifluoromethyl)nicotinaldehyde (132 mg, 0.629 mmol), Example 10C (230 mg, 0.571 mmol) and zinc(II) chloride in a sodium acetate/acetic acid buffer in methanol (pH=4, 2 mL) was stirred at ambient temperature for 10 minutes to give a colorless solution. Sodium cyanoborohydride (23.53 mg, 0.374 mmol) was added and the mixture was stirred for 30 minutes. The solvent was removed under N$_2$ and residue was diluted with ethyl acetate (20 mL) and water (10 mL). The organic layer was washed with brine, dried over MgSO$_4$, filtered, and concentrated. The residue was purified via chromatography on a 12 g silica gel cartridge, eluting with ethyl acetate/methanol (10:1) in heptane at 0-40% gradient to provide the ester of rac-(2R, 3R,4R,5R)-ethyl 3-(tert-butyl)-4-(((2-methoxy-5-(trifluoromethyl)pyridin-3-yl)methyl)amino)-5-phenyl-1-((R)-tetrahydro-2H-pyran-2-carbonyl)pyrrolidine-2-carboxylate, which was dissolved in methanol (1.5 mL) and 4 M aqueous LiOH (0.5 mL). The mixture was stirred at 50° C. for 3 hours and adjusted pH to 4~5 by adding 4 M HCl in dioxane and purified via chromatography, eluting with methanol in dichloromethane using a 0-20% gradient to provide the title compound (136 mg, 42% yield). $^1$H NMR (400 MHz, dimethyl sulfoxide-d$_6$) δ ppm 8.30 (s, 1H), 7.59 (d, J=7.5 Hz, 2H), 7.51 (d, J=2.4 Hz, 1H), 7.31 (t, J=7.3 Hz, 2H), 7.25 (d, J=7.1 Hz, 1H), 5.38 (s, 1H), 4.51 (s, 1H), 3.81 (s, 3H), 3.48-3.41 (m, 2H), 3.30 (s, 1H), 2.28 (s, 1H), 1.74-1.27 (m, 6H), 0.97 (s, 9H); MS (ESI+) m/z 564.2 (M+H)$^+$.

Example 21B (2R,3R,4R,5R)-3-(tert-butyl)-4-(((2-methoxy-5-(trifluoromethyl)pyridin-3-yl)methyl)amino)-5-phenyl-1-((R)-tetrahydro-2H-pyran-2-carbonyl)pyrrolidine-2-carboxylic acid and Example 21C (2S,3S,4S,5S)-3-(tert-butyl)-4-(((2-methoxy-5-(trifluoromethyl)pyridin-3-yl)methyl)amino)-5-phenyl-1-((S)-tetrahydro-2H-pyran-2-carbonyl)pyrrolidine-2-carboxylic acid The racemic compound of Example 21A was separated via SFC chiral column, 5-50% methanol:CO$_2$, 10 minutes @ 2 mL/minute, 150 bar; Column: Chiralpak® IC. The first compound to elute was Example 21B (25 mg, 19.23% yield). ¹H NMR (400 MHz, dimethyl sulfoxide-d₆) δ ppm 8.29 (t, J=1.5 Hz, 1H), 7.60 (d, J=7.4 Hz, 2H), 7.51 (d, J=2.4 Hz, 1H), 7.31 (t, J=7.3 Hz, 2H), 7.25 (d, J=7.3 Hz, 1H), 5.37 (s, 1H), 4.49 (s, 1H), 3.81 (d, J=1.1 Hz, 3H), 3.77 (d, J=11.4 Hz, 1H), 3.64-3.58 (m, 1H), 3.47 (s, 1H), 3.40 (s, 1H), 3.29 (s, 1H), 3.20 (s, 1H), 2.67-2.59 (m, 1H), 2.27 (s, 1H), 1.73-1.25 (m, 6H), 0.96 (d, J=0.9 Hz, 9H); MS (ESI+) m/z 564.2 (M+H)⁺. The second compound to elute was Example 21C (45 mg, 34.6% yield). ¹H NMR (400 MHz, dimethyl sulfoxide-d₆) δ ppm 8.29 (dd, J=2.5, 1.2 Hz, 1H), 7.59 (d, J=7.4 Hz, 2H), 7.51 (d, J=2.5 Hz, 1H), 7.31 (t, J=7.4 Hz, 2H), 7.25 (d, J=7.2 Hz, 1H), 5.37 (s, 1H), 4.50 (s, 1H), 3.80 (s, 3H), 3.76 (s, 1H), 3.49-3.41 (m, 2H), 3.27 (d, J=15.2 Hz, 3H), 2.67-2.59 (m, 1H), 2.27 (s, 1H), 1.73-1.28 (m, 6H), 0.97 (s, 9H); MS (ESI+) m/z 564.2 (M+H)⁺.

Example 22

(2S,3S,4S,5S)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid Example 22A (2S,3S,4R,5S)-tert-butyl 1-(cyclohexanecarbonyl)-3-(2-methoxypropan-2-yl)-4-nitro-5-phenylpyrrolidine-2-carboxylate A solution of Core 37 (1.2 g, 3.29 mmol) and triethylamine (0.918 mL, 6.59 mmol) in dichloromethane (14.97 mL) at 25° C. was treated with cyclohexanecarbonyl chloride (0.551 mL, 4.12 mmol) dropwise, stirred for 2 hours, washed with saturated aqueous NaHCO₃ (5 mL) and with 1 N aqueous NH₄OH (1 mL) solution, and concentrated to give a residue. The crude material was triturated with 10 mL heptane. After 0.5 hours at ambient temperature, the precipitate (1.5 g) was collected. The crude material was dissolved in 3 mL dichloromethane and loaded on a 12 g column eluting with a gradient of 0-70% ethyl acetate/heptanes over a period of 20 minutes to provide the desired product, (2S,3R,4S,5S)-tert-butyl 1-(cyclohexanecarbonyl)-3-(2-methoxypropan-2-yl)-4-nitro-5-phenylpyrrolidine-2-carboxylate (1.405 g, 2.96 mmol, 90% yield). ¹H NMR (400 MHz, dimethyl sulfoxide-d₆) δ ppm 7.55 (d, J=6.9 Hz, 2H), 7.31-7.17 (m, 3H), 5.61 (d, J=3.0 Hz, 2H), 4.62 (d, J=3.9 Hz, 1H), 3.26 (dd, J=4.0, 2.6 Hz, 1H), 3.15 (s, 3H), 2.16 (s, 1H), 1.67 (s, 2H), 1.51 (s, 10H), 1.22 (d, J=6.0 Hz, 10H), 1.08 (t, J=10.0 Hz, 2H), 0.84 (d, J=7.6 Hz, 1H); MS (ESI+) m/z 475 (M+H)⁺.

Example 22B (2S,3S,4S,5S)-tert-butyl 4-amino-1-(cyclohexanecarbonyl)-3-(2-methoxypropan-2-yl)-5-phenylpyrrolidine-2-carboxylate A 250 mL Parr shaker was charged with a Raney®-Nickel:2800, water slurry (3.6 g, 61.3 mmol) which had been washed with water followed by tetrahydrofuran several times. To the mixture was added Example 22A (1.405 g, 2.96 mmol) and tetrahydrofuran (45.0 mL), and the mixture was purged with argon followed by hydrogen. The reaction was stirred at ambient temperature under 50 psig of hydrogen for 16 hours. The material was filtered and the solvent was removed in vacuo to provide (2S,3S,4S,5S)-tert-butyl 4-amino-1-(cyclohexanecarbonyl)-3-(2-methoxypropan-2-yl)-5-phenylpyrrolidine-2-carboxylate (1.3 g, 2.92 mmol, 99% yield). ¹H NMR (400 MHz, dimethyl sulfoxide-d₆) δ ppm 7.56 (bs, 2H), 7.31 (t, J=7.5 Hz, 2H), 7.22 (t, J=7.4 Hz, 1H), 5.02 (d, J=7.3 Hz, 1H), 4.33 (d, J=4.7 Hz, 1H), 3.65 (dd, J=7.3, 4.6 Hz, 1H), 3.13 (s, 3H), 2.32 (s, 1H), 2.15 (d, J=12.9 Hz, 1H), 1.62 (d, J=10.2 Hz, 2H), 1.46 (s, 10H), 1.30-1.10 (m, 2H), 1.21 (s, 3H), 1.19 (s, 3H), 1.05 (m, 2H), 0.82 (bs, 2H); MS (ESI+) m/z 445 (M+H)⁺.

Example 22C (2S,3S,4S,5S)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid To a solution of 2-methoxy-5-(trifluoromethyl)nicotinaldehyde (33.2 mg, 0.162 mmol), Example 22B (60 mg, 0.135 mmol) and zinc(II) chloride (18.39 mg, 0.135 mmol) in sodium acetate/acetic acid buffer in methanol (pH=4, 1 mL) was added sodium cyanoborohydride (12.72 mg, 0.202 mmol) and the reaction was stirred at ambient temperature for 2 hours. The solvent was removed under nitrogen. The residue was diluted with dichloromethane and H₂O and the aqueous phase was extracted with dichloromethane (3×1 mL). The solvent was removed and the resulting residue was chromatographed using a 12 g silica gel cartridge eluting with a gradient of 0-80% ethyl acetate/heptanes over a period of 20 minutes to give a residue (90 mg) which was dissolved in trifluoroacetic acid (0.5 mL) and stirred for 2 hours at ambient temperature. The trifluoroacetic acid was removed and the crude material was purified by reverse phase using the trifluoroacetic acid method to obtain (2S,3S,4S,5S)-1-(cyclohexanecarbonyl)-4-(((2-methoxy-5-(trifluoromethyl)pyridin-3-yl)methyl)amino)-3-(2-methoxypropan-2-yl)-5-phenylpyrrolidine-2-carboxylic acid, trifluoroacetic acid (66 mg, 0.095 mmol, 70.7% yield). ¹H NMR (400 MHz, dimethyl sulfoxide-d₆) δ ppm 8.33 (s, 1H), 7.58 (m, 3H), 7.31 (t, J=7.4 Hz, 2H), 7.24 (t, J=7.3 Hz, 1H), 5.24 (d, J=7.2 Hz, 1H), 4.52 (d, J=3.5 Hz, 1H), 3.81 (s, 3H), 3.58 (d, J=14.9 Hz, 2H), 3.42 (d, J=14.9 Hz, 1H), 3.14 (s, 3H), 2.65 (s, 1H), 2.23 (s, 1H), 1.64 (d, J=9.8 Hz, 2H), 1.49 (s, 2H), 1.24 (m, 1H), 1.19 (s, 3H), 1.18 (s, 3H), 1.16 (m, 1H), 1.07 (bs, 3H), 0.77 (bs, 1H); MS (ESI+) m/z 578 (M+H)⁺.

Example 23

(2S,3S,4S,5S)-3-tert-butyl-4-{[(5-tert-butyl-2-methoxyphenyl)methyl]amino}-5-phenyl-1-[(2S*,3S*)-3-(propan-2-yl)oxolane-2-carbonyl]pyrrolidine-2-carboxylic acid Example 23A (2S,3R,4S,5S)-4-nitro-3-tert-butyl-1-((2R*,3R*)-3-isopropyl-tetrahydro-furan-2-carbonyl)-5-phenylpyrrolidine-2-carboxylic acid ethyl ester and Example 23B (2S,3R,4S,5S)-4-nitro-3-tert-butyl-1-((2S*,3S*)-3-isopropyl-tetrahydro-furan-2-carbonyl)-5-phenylpyrrolidine-2-carboxylic acid ethyl ester To a stirred solution of racemic cis 3-(propan-2-yl)oxolane-2-carboxylic acid (CAS#1808432-51-0, 122 mg, 0.77 mmol, 1.3 eq) in dichloromethane (5 mL) at 0° C. was added Ghosez's reagent (1-chloro-N,N,2-trimethyl-1-propenylamine, 237 µL, 1.77 mmol, 3.0 eq). The reaction mixture was stirred at 0° C. for 5 minutes and a solution of Core 7 (190 mg, 0.59 mmol, 1.0 eq) and diisopropylethylamine (411 µL, 2.36 mmol, 4.0 eq) in dichloromethane was added. The reaction mixture was stirred at 0° C. for 10 minutes and at room temperature for 1.5 hours. The reaction mixture was washed with water and the organic phase was concentrated to dryness. The residue was purified on silica gel (heptane/ethyl acetate 100/0 to 85/15) to give the title compounds (mixture of diastereomers, 190 mg, 70%).

Example 23C (2S,3S,4S,5S)-4-amino-3-tert-butyl-1-((2R*,3R*)-3-isopropyl-tetrahydro-furan-2-carbonyl)-5-phenyl-pyrrolidine-2-carboxylic acid ethyl ester and Example 23D (2S,3S,4S,5S)-4-amino-3-tert-butyl-1-((2S*,3S*)-3-isopropyl-tetrahydro-furan-2-carbonyl)-5-phenyl-pyrrolidine-2-carboxylic acid ethyl ester Zinc dust (490 mg, 7.50 mmol, 15.0 eq) was added to a solution of (2S,3R,4S,5S)-4-nitro-3-tert-butyl-1-((2R,3R)-3-isopropyl-tetrahydro-furan-2-carbonyl)-5-phenyl-pyrrolidine-2-carboxylic acid ethyl ester and (2S,3R,4S,5S)-4-nitro-3-tert-butyl-1-((2S,3S)-3-isopropyl-tetrahydro-furan-2-carbonyl)-5-phenyl-pyrrolidine-2-carboxylic acid ethyl ester (230 mg, 0.50 mmol, 1.0 eq) in ethyl acetate (3 mL) and acetic acid (1 mL) at room temperature. The reaction was heated to 60° C. for 2 hours. The reaction was filtered on diatomaceous earth, washed with ethyl acetate and concentrated to dryness. The crude product was partitioned between saturated aqueous $NaHCO_3$ solution and dichloromethane. The organic phase was concentrated. The residue was purified on silica gel (dichloromethane/methanol 100/0 to 99/1) to provide the title compounds (mixture of diastereomers, 170 mg, 96%). LC/MS (ESI+) m/z 431.6 (M+H)$^+$.

Example 23E (2S,3S,4S,5S)-3-tert-butyl-4-(5-tert-butyl-2-methoxy-benzylamino)-1-((2R*,3R*)-3-isopropyl-tetrahydro-furan-2-carbonyl)-5-phenyl-pyrrolidine-2-carboxylic acid ethyl ester and Example 23F (2S,3S,4S,5S)-3-tert-butyl-4-(5-tert-butyl-2-methoxy-benzylamino)-1-((2S*,3S*)-3-isopropyl-tetrahydro-furan-2-carbonyl)-5-phenyl-pyrrolidine-2-carboxylic acid ethyl ester $NaBH_3CN$ (23 mg, 0.36 mmol, 1.3 eq) was added to a solution of (2S,3S,4S,5S)-4-amino-3-tert-butyl-1-((2R,3R)-3-isopropyl-tetrahydro-furan-2-carbonyl)-5-phenyl-pyrrolidine-2-carboxylic acid ethyl ester and (2S,3S,4S,5S)-4-amino-3-tert-butyl-1-((2S,3S)-3-isopropyl-tetrahydro-furan-2-carbonyl)-5-phenyl-pyrrolidine-2-carboxylic acid ethyl ester (85 mg, 0.20 mmol, 1.0 eq) and 5-tert-butyl-2-methoxy-benzaldehyde (CAS#85943-26-6, 45 mg, 0.24 mmol, 1.2 eq) in acetic acid/sodium acetate buffer in methanol (96 mg acetic acid, 61 mg sodium acetate, 2 mL methanol). The reaction was stirred at room temperature for 1 hour. The solvent was removed under vacuum. The residue was partitioned between dichloromethane and water. The organic phase was concentrated to dryness and the residue was purified by flash chromatography on silica gel (dichloromethane/methanol 100/0 to 98/2) to give the title compounds (mixture of diastereomers, 96 mg, 79%). LC/MS (ESI+) m/z 607.7 (M+H)$^+$.

Example 23G (2S,3S,4S,5S)-3-tert-butyl-4-{[(5-tert-butyl-2-methoxyphenyl)methyl]amino}-5-phenyl-1-[(2S*, 3S*)-3-(propan-2-yl)oxolane-2-carbonyl]pyrrolidine-2-carboxylic acid A solution of Example 23E and Example 23F (96 mg, 0.15 mmol, 1.0 eq) in methanol (2 mL) was treated with LiOH 1.0 M in water (450 µL, 0.45 mmol, 3.0 eq) at room temperature and stirred overnight at 45° C. The solvent was removed under vacuum, water was added and the resulting solution was extracted with ethyl acetate. The organic phase was concentrated to dryness. The residue was purified on silica gel (dichloromethane/methanol 100/0 to 97/3) to provide the title compound (34 mg, 39%, second diastereomer to elute). Stereochemistry was arbitrarily assigned. $^1$H NMR (400 MHz, DMSO-$d_6$, 100° C.) δ ppm 7.67 (br. s., 2H), 7.26-7.47 (m, 3H), 7.18 (d, J=7.3 Hz, 1H), 7.00 (br. s., 1H), 6.78 (d, J=8.6 Hz, 1H), 5.39 (br. s., 1H), 4.57 (br. s., 1H), 4.14 (br. s., 1H), 3.68-3.84 (m, 2H), 3.56 (br. s., 3H), 3.49-3.61 (m, 2H), 3.40 (d, J=13.2 Hz, 1H), 2.37 (br. s., 1H), 1.78-2.11 (m, 3H), 1.48 (br. s., 1H), 1.25 (s, 9H), 1.05 (s, 9H), 0.83 (br. s., 3H), 0.47 (br. s., 3H). LC/MS (ESI+) m/z 579.90 (M+H)$^+$. Note Example I-104 (2S,3S,4S,5S)-3-tert-butyl-4-{[(5-tert-butyl-2-methoxyphenyl)methyl]amino}-5-phenyl-1-[(2R*,3R*)-3-(propan-2-yl)oxolane-2-carbonyl]pyrrolidine-2-carboxylic acid, was also isolated from the chromatography as first diastereomer to elute (30 mg, 34%). LC/MS (ESI+) m/z 579.90 (M+H)$^+$.

Example 24

(2S,3S,4S,5S)-3-tert-butyl-4-{[(5-tert-butyl-2-methoxyphenyl)methyl]amino}-1-(cyclohexanecarbonyl)-5-(2-fluorophenyl)pyrrolidine-2-carboxylic acid Example 24A ethyl (2S,3R,4S,5S)-3-(tert-butyl)-1-(cyclohexanecarbonyl)-5-(2-fluorophenyl)-4-nitropyrrolidine-2-carboxylate To a solution of (2S,3R,4S,5S)-ethyl 3-(tert-butyl)-5-(2-fluorophenyl)-4-nitropyrrolidine-2-carboxylate (Core 23, 10.5 g, 31.06 mmol) and triethylamine (10.0 mL, 71.44 mmol) in dichloromethane (100 mL) at 0° C. was added cyclohexanecarbonyl chloride (5.4 mL, 40.38 mmol). The mixture was stirred at 0° C. for 30 minutes and then at 25° C. for 1 hour. LC/MS indicated complete conversion to the desired product. The mixture was diluted with dichloromethane (20 mL), washed with saturated aqueous sodium bicarbonate (50 mL) and brine (100 mL), dried over $MgSO_4$, filtered and concentrated. The residue was purified by silica column chromatography (eluted with 50% petroleum ether/ethyl acetate) to give the title compound (2S, 3R, 4S, 5S)-ethyl 3-(tert-butyl)-1-(cyclohexanecarbonyl)-5-(2-fluorophenyl)-4-nitropyrrolidine-2-carboxylate (8.33 g, 18.6 mmol, 59.9% yield). LC-MS (ESI+) m/z 449 (M+H)$^+$.

Example 24B ethyl (2S,3S,4S,5S)-4-amino-3-(tert-butyl)-1-(cyclohexanecarbonyl)-5-(2-fluorophenyl)pyrrolidine-2-carboxylate To a solution of (2S,3R,4S,5S)-ethyl-3-(tert-butyl)-1-(cyclohexanecarbonyl)-5-(2-fluorophenyl)-4-nitropyrrolidine-2-carboxylate (Example 24A, 6.0 g, 13.39 mmol) in acetic acid (69.5 mL, 1208.7 mmol) and ethyl acetate (394.5 mL, 4029 mmol) was added zinc (13.0 g, 201.45 mmol) under an inert atmosphere. The resulting mixture was stirred at 55° C. for 1 hour and then cooled to room temperature, diluted with ethyl acetate (150 mL) and filtered to remove the solids. The filtrate was concentrated to dryness. The residue was partitioned between ethyl acetate (150 mL) and saturated aqueous sodium bicarbonate solution (100 mL). The organic layer was washed with brine (100 mL), dried over MgSO$_4$, filtered and concentrated. The residue was purified by prep-HPLC (ammonium carbonate method) to provide the title compound, (2S,3S,4S,5S)-ethyl 4-amino-3-(tert-butyl)-1-(cyclohexanecarbonyl)-5-(2-fluorophenyl)pyrrolidine-2-carboxylate (3.67 g, 8.77 mmol, 65.5% yield). $^1$H NMR (400 MHz, CDCl$_3$) δ ppm 8.11 (t, J=7.6 Hz, 1H), 7.22-7.32 (m, 2H), 6.99-7.12 (m, 1H), 5.38 (d, J=6.8 Hz, 1H), 4.56 (d, J=3.6 Hz, 1H), 4.22-4.31 (m, 2H), 3.75-3.77 (m, 1H), 1.96-2.07 (m, 2H), 1.62-1.83 (m, 3H), 1.20-1.51 (m, 12H), 0.89 (s, 9H), 0.55-0.75 (m, 2H); LC-MS (ESI+) m/z 419 (M+H)$^+$.

Example 24C ethyl (2S,3S,4S,5S)-3-(tert-butyl)-4-((5-(tert-butyl)-2-methoxybenzyl)amino)-1-(cyclohexanecarbonyl)-5-(2-fluorophenyl)pyrrolidine-2-carboxylate Example 24B (A-1671634.0, CP, 60.9 mg, 0.146 mmol) and 5-(tert-butyl)-2-methoxybenzenecarbaldehyde (40.7 mg, 0.212 mmol) were dissolved in methanol (1 mL) and stirred at ambient temperature for 1 hour. Sodium cyanoborohydride (34.0 mg, 0.541 mmol) was added and the reaction was stirred at ambient temperature for an additional 16 hours. The reaction was diluted with dimethyl sulfoxide (1 mL), filtered and purified by reverse phase using the ammonium acetate method to provide the title compound (47.4 mg, 45%). $^1$H NMR (400 MHz, dimethyl sulfoxide-d$_6$, 120° C.) δ ppm 7.85 (s, 1H), 7.29 (s, 1H), 7.19-7.03 (m, 3H), 6.92 (d, J=2.6 Hz, 1H), 6.73 (d, J=8.5 Hz, 1H), 5.40 (s, 1H), 4.54 (d, J=2.4 Hz, 1H), 4.12 (ddq, J=10.7, 7.4, 3.8 Hz, 2H), 3.53 (s, 3H), 3.48 (d, J=14.1 Hz, 2H), 3.32 (d, J=13.7 Hz, 1H), 2.43-2.11 (m, 2H), 1.67 (s, 2H), 1.53 (s, 2H), 1.19 (d, J=3.4 Hz, 18H), 0.97 (s, 9H); MS (ESI+) m/z 595 (M+H)$^+$.

Example 24D (2S,3S,4S,5S)-3-tert-butyl-4-{[(5-tert-butyl-2-methoxyphenyl)methyl]amino}-1-(cyclohexanecarbonyl)-5-(2-fluorophenyl)pyrrolidine-2-carboxylic acid Example 24C (44.4 mg, 0.075 mmol) was dissolved in methanol (1 mL). LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (39.6 mg, 78%) as the trifluoroacetic acid salt. $^1$H NMR (400 MHz, dimethyl sulfoxide-d$_6$, 120° C.) δ ppm 7.75 (s, 1H), 7.33 (q, J=7.0 Hz, 1H), 7.22-7.10 (m, 3H), 7.02 (d, J=2.5 Hz, 1H), 6.79 (d, J=8.5 Hz, 1H), 5.44 (d, J=6.9 Hz, 1H), 4.53 (d, J=1.9 Hz, 1H), 3.70 (d, J=13.7 Hz, 1H), 3.66 (d, J=7.0 Hz, 1H), 3.58 (s, 3H), 3.45 (d, J=13.7 Hz, 1H), 2.50 (s, 1H), 2.31 (s, 1H), 1.72-1.49 (m, 4H), 1.34-1.04 (m, 15H), 0.98 (s, 9H); MS (ESI+) m/z 567 (M+H)$^+$.

Example 25

(2S,3S,4S,5S)-3-tert-butyl-1-(cyclohexanecarbonyl)-4-{[(2-methoxy-5-phenylpyridin-3-yl)methyl]amino}-5-phenylpyrrolidine-2-carboxylic acid Example 25A (2S,3R,4S,5S)-tert-butyl 3-(tert-butyl)-1-(cyclohexanecarbonyl)-4-nitro-5-phenylpyrrolidine-2-carboxylate The title compound was prepared according to the procedure described in Example 7A, substituting Core 6 for Core 2. $^1$H NMR (400 MHz, dimethyl sulfoxide-d$_6$, 120° C.) δ ppm 7.61-7.55 (m, 2H), 7.30-7.21 (m, 3H), 5.66-5.55 (m, 2H), 4.58 (d, J=3.6 Hz, 1H), 2.96 (t, J=3.2 Hz, 1H), 2.24-2.12 (m, 1H), 1.84-1.61 (m, 4H), 1.51 (s, 9H), 1.44-1.04 (m, 6H), 1.00 (s, 9H); MS (ESI+) m/z 459 (M+H)$^+$.

Example 25B (2S,3S,4S,5S)-tert-butyl 4-amino-3-(tert-butyl)-1-(cyclohexanecarbonyl)-5-phenylpyrrolidine-2-carboxylate The title compound was prepared according to the procedure described in Example 7B, substituting Example 25A for Example 7A. $^1$H NMR (400 MHz, dimethyl sulfoxide-d$_6$, 120° C.) δ ppm 7.56 (d, J=7.3 Hz, 2H), 7.32 (t, J=7.5 Hz, 2H), 7.23 (t, J=7.3 Hz, 1H), 5.02 (d, J=7.1 Hz, 1H), 4.29 (d, J=4.0 Hz, 1H), 3.63 (dd, J=7.2, 3.6 Hz, 1H), 2.17 (d, J=0.8 Hz, 1H), 2.01 (d, J=4.1 Hz, 1H), 1.62 (d, J=8.2 Hz, 2H), 1.46 (d, J=0.8 Hz, 11H), 1.33-1.01 (m, 6H), 0.98 (d, J=0.7 Hz, 9H); MS (ESI+) m/z 429 (M+H)$^+$.

Example 25C (2S,3S,4S,5S)-tert-butyl 4-(((5-bromo-2-methoxypyridin-3-yl)methyl)amino)-3-(tert-butyl)-1-(cyclohexanecarbonyl)-5-phenylpyrrolidine-2-carboxylate 5-Bromo-2-methoxynicotinaldehyde (0.529 g, 2.450 mmol) and (2S,3S,4S,5S)-tert-butyl 4-amino-3-(tert-butyl)-1-(cyclohexanecarbonyl)-5-phenylpyrrolidine-2-carboxylate (Example 25B, 1 g, 2.333 mmol) were mixed in methanol (12 mL), and the reaction was stirred at room temperature for 1 hour. Sodium cyanoborohydride (0.740 g, 11.78 mmol) was then added in one portion, and the reaction continued to stir at room temperature for 1.5 days. After this time, the solvent was removed in vacuo, and the residue was taken up in 100 mL water and 100 mL CH$_2$Cl$_2$ and transferred to a separatory funnel. The separatory funnel was shaken, the phases were separated, and the aqueous layer was extracted twice more with CH$_2$Cl$_2$ (100 mL each time).

287

The combined organics were dried over Na$_2$SO$_4$, filtered, and concentrated in vacuo. Silica gel chromatography, eluting with 5 to 30% ethyl acetate-heptanes, provided the impure title compound, 1.02 g. The material was taken directly into the next reaction without additional purification. $^1$H NMR (400 MHz, dimethyl sulfoxide-d$_6$) δ ppm 8.00 (m, 1H), 7.59 (m, 2H), 7.40-7.19 (m, 4H), 5.17 (d, J=6.9 Hz, 1H), 4.40 (d, J=2.7 Hz, 1H), 3.68 (s, 3H), 3.41-3.21 (m, 3H), 2.26 (m, 1H), 2.19 (m, 1H), 1.68-1.02 (m, 10H), 1.43 (s, 9H), 0.98 (s, 9H); MS (ESI+) m/z 628.0 (M+H)$^+$.

Example 25D (2S,3S,4S,5S)-tert-butyl 3-(tert-butyl)-1-(cyclohexanecarbonyl)-4-(((2-methoxy-5-phenylpyridin-3-yl)methyl)amino)-5-phenylpyrrolidine-2-carboxylate The impure product from Example 25C (0.257 g, 0.409 mmol), phenylboronic acid (0.065 g, 0.531 mmol), and Pd(PPh$_3$)$_4$ (tetrakis(triphenylphosphine)palladium(0), 0.047 g, 0.041 mmol) were treated with dioxane (5 mL) and a solution of potassium carbonate (0.113 g, 0.818 mmol) in water (1.25 mL), and the reaction mixture was heated overnight at 100° C. After this time, the mixture was diluted with ethyl acetate and washed with water and brine. The organic layer was dried over Na$_2$SO$_4$, filtered, and concentrated in vacuo. Silica gel chromatography, eluting with 5 to 40% ethyl acetate-heptanes, provided the title compound (0.074 g, 29% yield). $^1$H NMR (400 MHz, dimethyl sulfoxide-d$_6$) δ ppm 8.21 (m, 1H), 7.59-7.21 (m, 9H), 5.20 (m, 1H), 4.42 (m, 1H), 3.74 (s, 3H), 3.51-3.32 (m, 3H), 2.29 (m, 1H), 2.16 (m, 1H), 1.67-0.97 (m, 9H), 1.40 (s, 9H), 0.99 (s, 9H), 0.84 (m, 1H); MS (ESI+) m/z 626.1 (M+H)$^+$.

Example 25E (2S,3S,4S,5S)-3-tert-butyl-1-(cyclohexanecarbonyl)-4-{[(2-methoxy-5-phenylpyridin-3-yl)methyl]amino}-5-phenylpyrrolidine-2-carboxylic acid Example 25D (0.074 g, 0.118 mmol) in dichloromethane (1.7 mL) was treated with trifluoroacetic acid (0.82 mL, 10.64 mmol), and the reaction was stirred overnight at room temperature. The mixture was then concentrated in vacuo, and the crude material thus obtained was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to provide the title compound (0.0345 g, 51% yield). $^1$H NMR (400 MHz, dimethyl sulfoxide-d$_6$) δ ppm 8.27 (d, J=2.5 Hz, 1H), 7.82-7.21 (m, 11H), 5.29 (d, J=7.0 Hz, 1H), 4.52 (d, J=2.3 Hz, 1H), 3.77 (s, 3H), 3.62 (m, 3H), 3.43 (d, J=14.3 Hz, 1H), 2.45 (m, 1H), 2.26 (m, 1H), 1.70-1.03 (m, 9H), 1.00 (s, 9H), 0.77 (m, 1H); MS (ESI+) m/z 570.2 (M+H)$^+$.

288

Example 26

(2S,3S,4S,5S)-3-tert-butyl-1-(cyclohexanecarbonyl)-5-(4-fluorophenyl)-4-({[2-methoxy-5-(trifluoromethyl)pyridin-3-yl]methyl}amino)pyrrolidine-2-carboxylic acid Example 26A (2S,3R,4S,5S)-ethyl 3-(tert-butyl)-1-(cyclohexanecarbonyl)-5-(4-fluorophenyl)-4-nitropyrrolidine-2-carboxylate A solution of (2S,3R,4S,5S)-ethyl 3-(tert-butyl)-5-(4-fluorophenyl)-4-nitropyrrolidine-2-carboxylate (Core 33, 1.90 g, 5.62 mmol)) and triethylamine (1.565 mL, 11.23 mmol) in dichloromethane (30 mL) at 0° C. was treated with cyclohexanecarbonyl chloride (0.906 g, 6.18 mmol). The mixture was stirred at 0° C. for 30 minutes and then at room temperature for 1 hour. LC/MS indicated complete conversion to the desired product. The mixture was diluted with dichloromethane (100 mL), washed with saturated aqueous NaHCO$_3$ (30 mL) and brine (30 mL), dried over magnesium sulfate, filtered and concentrated. The residue was purified by silica gel column chromatography (eluted with 0-60% ethyl acetate in heptanes) to provide the title compound, (2S,3R,4S,5S)-ethyl 3-(tert-butyl)-1-(cyclohexanecarbonyl)-5-(4-fluorophenyl)-4-nitropyrrolidine-2-carboxylate, (2 g, 4.46 mmol, 79% yield, ee=98.8%). $^1$H NMR (400 MHz, CDCl$_3$). δ ppm 7.36-7.68 (m, 2H), 6.98-7.08 (m, 2H), δ ppm 5.41-5.53 (m, 1H), 5.20-5.34 (m, 1H), 4.76 (d, J=8 Hz, 1H), 4.32 (q, J=8 Hz, 2H), 3.09-3.12 (m, 1H), 2.31-2.36 (m, 1H), 1.38-2.06 (m, 7H), 1.37 (t, J=8 Hz, 3H), 1.08-1.33 (m, 3H), 1.03 (s, 9H); LC/MS (ESI+) m/z 449.2 (M+H)$^+$.

Example 26B (2S,3S,4S,5S)-ethyl 4-amino-3-(tert-butyl)-1-(cyclohexanecarbonyl)-5-(4-fluorophenyl)pyrrolidine-2-carboxylate To a solution of Example 26A (2.0 g, 4.46 mmol)) in ethyl acetate (10 mL) and acetic acid (10 mL) was added zinc (5.83 g, 89 mmol). The mixture was stirred at 60° C. for 1 hour. Most of the solvent was evaporated. The residue was diluted with dichloromethane (100 mL), washed with saturated aqueous sodium bicarbonate solution (30 mL) and brine (30 mL), dried over Na$_2$SO$_4$, filtered and concentrated under reduced pressure. The residue was triturated with petroleum ether (5×2 mL) to give the title compound, (2S,3S,4S,5S)-ethyl 4-amino-3-(tert-butyl)-1-(cyclohexanecarbonyl)-5-(4-fluorophenyl)pyrrolidine-2-carboxylate (1.49 g, 3.56 mmol, 80% yield). $^1$H NMR (400 MHz, CDCl$_3$) δ ppm 7.35-7.64 (m, 2H), 6.97-7.12 (m, 2H), 5.00 (d, J=4 Hz, 1H), 4.51 (d, J=4 Hz, 1H), 4.24 (q, J=8 Hz, 2H), 3.58-3.64 (m, 1H), 1.99-2.05 (m, 2H), 1.31-1.70 (m, 8H), 1.30 (t, J=8 Hz, 3H), 1.23-1.27 (m, 1H), 1.04-1.14 (m, 2H), 1.03 (s, 9H), 0.55-0.65 (m, 1H); LC/MS (ESI+) m/z 419.3 (M+H)$^+$.

Example 26C (2S,3S,4S,5S)-3-tert-butyl-1-(cyclohexanecarbonyl)-5-(4-fluorophenyl)-4-({[2-methoxy-5-(trifluoromethyl)pyridin-3-yl]methyl}amino)pyrrolidine-2-carboxylic acid A mixture of 2-chloro-5-(trifluoromethyl)nicotinaldehyde (33.0 mg, 0.158 mmol), Example 26B (60 mg, 0.143 mmol)

and zinc(II) chloride in a sodium acetate/acetic acid buffer in methanol (pH=4, 2 mL) was stirred at ambient temperature for 10 minutes. Sodium cyanoborohydride (23.53 mg, 0.374 mmol) was added and the mixture was stirred for 1 hour until complete as monitored by LC/MS. The solvent was removed and residue was dissolved in dichloromethane (10 mL) and washed with brine, dried over MgSO$_4$, filtered, and concentrated. Purification via chromatography, eluting with ethyl acetate/methanol (10:1) in heptane at a 0-40% gradient provided the intermediate (2S,3S,4S,5S)-ethyl 3-(tert-butyl)-1-(cyclohexanecarbonyl)-5-(4-fluorophenyl)-4-(((2-methoxy-5-(trifluoromethyl)pyridin-3-yl)methyl)amino) pyrrolidine-2-carboxylate, which was dissolved in methanol (1.5 mL) and 4 M aqueous LiOH (0.5 mL). The mixture was stirred at 50° C. for 3 hours and the pH was adjusted to 4~5 by adding 4 M HCl in dioxane. The resulting mixture was purified via HTP with the trifluoroacetic acid method to provide the title compound (2S,3S,4S,5S)-3-(tert-butyl)-1-(cyclohexanecarbonyl)-5-(4-fluorophenyl)-4-(((2-methoxy-5-(trifluoromethyl)pyridin-3-yl)methyl)amino)pyrrolidine-2-carboxylic acid as trifluoroacetic acid salt. (44 mg, 44.3% yield). $^1$H NMR (400 MHz, dimethyl sulfoxide-d$_6$) δ ppm 8.32 (s, 1H), 7.62 (s, 2H), 7.56 (d, J=2.4 Hz, 1H), 7.08 (t, J=8.7 Hz, 2H), 5.23 (d, J=7.0 Hz, 1H), 4.47 (d, J=2.5 Hz, 1H), 3.83 (s, 3H), 3.58-3.47 (m, 4H), 2.34 (s, 1H), 2.22 (s, 1H), 1.70-1.04 (m, 10H), 0.97 (s, 9H); MS (ESI+) m/z 580.2 (M+H)$^+$.

Example 27

(2S,3S,4S,5S)-3-tert-butyl-4-{[(5-tert-butyl-2-methoxypyridin-3-yl)methyl]amino}-1-(cyclohexanecarbonyl)-5-phenylpyrrolidine-2-carboxylic acid Example 27A (2S,3S,4S,5S)-ethyl 3-(tert-butyl)-4-(((5-(tert-butyl)-2-methoxypyridin-3-yl)methyl)amino)-1-(cyclohexanecarbonyl)-5-phenylpyrrolidine-2-carboxylate (2S,3S,4S,5S)-Ethyl 4-amino-3-(tert-butyl)-1-(cyclohexanecarbonyl)-5-phenylpyrrolidine-2-carboxylate (Example 7B, 1.393 g) and 5-(tert-butyl)-2-methoxynicotinaldehyde (0.068 g, 0.352 mmol) were stirred in methanol (3.5 mL) at room temperature for 1 hour. Sodium cyanoborohydride (0.111 g, 1.759 mmol) was then added in one portion, and the reaction was stirred overnight at room temperature. The reaction mixture was then concentrated in vacuo, and then the remaining residue was taken up in CH$_2$Cl$_2$ and water. The phases were separated, and the aqueous layer was extracted twice more with CH$_2$Cl$_2$. The combined organic extracts were dried over Na$_2$SO$_4$, filtered, and concentrated in vacuo, and the resulting crude residue was purified by silica gel chromatography, eluting with 0 to 20% ethyl acetate-heptanes to provide the title compound, 0.127 g, (63% yield). $^1$H NMR (400 MHz, dimethyl sulfoxide-d$_6$) δ ppm 7.93 (d, J=2.7 Hz, 1H), 7.59 (m, 2H), 7.33-7.22 (m, 4H), 5.20 (d, J=6.9 Hz, 1H), 4.51 (d, J=2.8 Hz, 1H), 4.10 (m, 2H), 3.66 (s, 3H), 3.44 (m, 2H), 3.30 (m, 1H), 2.32 (m, 1H), 2.19 (m, 1H), 1.65-1.06 (m, 9H), 1.22 (s, 9H), 1.18 (t, J=7.0 Hz, 3H), 0.98 (s, 9H), 0.83 (m, 1H); MS (ESI+) m/z 578.3 (M+H)$^+$.

Example 27B (2S,3S,4S,5S)-3-tert-butyl-4-{[(5-tert-butyl-2-methoxypyridin-3-yl)methyl]amino}-1-(cyclohexanecarbonyl)-5-phenylpyrrolidine-2-carboxylic acid Example 27A (0.127 g, 0.220 mmol) was stirred with 1 M aqueous lithium hydroxide solution (1.8 mL, 1.800 mmol) in tetrahydrofuran (1.8 mL) and methanol (1.800 mL) at 45° C. After 3 hours, the mixture was concentrated in vacuo, and the excess water was removed azeotropically with acetonitrile. The resulting solid was treated with 0.25 mL trifluoroacetic acid and was taken up in ethyl acetate and applied to a silica gel column, eluting with 4:3:1 heptanes-ethyl acetate-ethanol (isocratic), to provide the crude title compound (trifluoroacetic acid salt), which was then further dried under vacuum at 80° C. to provide the title compound (0.164 g, 96% yield). $^1$H NMR (400 MHz, dimethyl sulfoxide-d$_6$) δ ppm 7.96 (m, 1H), 7.54 (m, 2H), 7.34-7.23 (m, 4H), 5.20 (d, J=6.8 Hz, 1H), 4.48 (d, J=2.5 Hz, 1H), 3.65 (s, 3H), 3.54-3.45 (m, 3H), 3.34 (m, 1H), 2.36-2.26 (m, 2H), 1.66-1.04 (m, 9H), 1.23 (s, 9H), 0.98 (s, 9H), 0.83 (m, 1H); MS (ESI+) m/z 550.3 (M+H)$^+$.

Example 28

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-phenylpyrrolidine-2-carboxylic acid Example 28A (2S,3R,4S,5S)-3-tert-butyl-1-(2,3-dihydro-benzofuran-2-carbonyl)-4-nitro-5-phenyl-pyrrolidine-2-carboxylic acid ethyl ester To a stirred solution of racemic 2,3-dihydro-2-benzofurancarboxylic acid (CAS#1914-60-9, 200 mg, 1.22 mmol, 2.1 eq) in dichloromethane (3 mL) at 0° C. was added Ghosez's reagent (1-chloro-N,N,2-trimethyl-1-propenylamine, 250 µL, 1.86 mmol, 1.9 eq). The reaction mixture was stirred at 0° C. for 5 minutes and a solution of Core 7 (190 mg, 0.59 mmol, 1.0 eq) and diisopropylethylamine (430 µL, 2.46 mmol, 4.2 eq) in dichloromethane was added. The reaction mixture was stirred at room temperature for 1 hour. The reaction mixture was quenched with ammonium chloride aqueous solution, diluted with ethyl acetate and the organic layer was washed with water and brine. The combined organic layers were dried over magnesium sulfate, filtered and concentrated to dryness. The residue was purified on silica gel (heptane/ethyl acetate 95/5 to 70/30) to give the title compound (mixture of diastereomers, 170 mg, 62%). LC/MS (ESI+) m/z 467.6 (M+H)$^+$.

Example 28B (2S,3S,4S,5S)-4-amino-3-tert-butyl-1-(2,3-dihydro-benzofuran-2-carbonyl)-5-phenyl-pyrrolidine-2-carboxylic acid ethyl ester Zinc dust (475 mg, 7.30 mmol, 20.0 eq) was added to a solution of (2S,3R,4S,5S)-3-tert-butyl-1-(2,3-dihydro-benzofuran-2-carbonyl)-4-nitro-5-phenyl-pyrrolidine-2-carboxylic acid ethyl ester (170 mg, 0.37 mmol, 1.0 eq) in ethyl acetate (7 mL) and acetic acid (2 mL) at room temperature. The reaction was heated to 100° C. for 2 hours. The reaction was filtered on diatomaceous earth, washed with ethyl acetate and dichloromethane, and concentrated to dryness. The crude product was partitioned between saturated aqueous NaHCO$_3$ solution and ethyl acetate. The organic layer was washed with water and brine. The combined organic layers were dried over magnesium sulfate, filtered and concentrated to dryness. The title compound was obtained as a mixture of diastereomers, (170 mg, 100%) which was used in the next step without further purification. LC/MS (ESI+) m/z 437.6 (M+H)$^+$.

Example 28C (2S,3S,4S,5S)-3-tert-butyl-4-(5-tert-butyl-2-methoxy-benzylamino)-1-(2,3-dihydro-benzofuran-2-carbonyl)-5-phenyl-pyrrolidine-2-carboxylic acid ethyl ester NaBH$_3$CN (15 mg, 0.24 mmol, 1.3 eq) was added to a solution of (2S,3S,4S,5S)-4-amino-3-tert-butyl-1-(2,3-dihydro-benzofuran-2-carbonyl)-5-phenyl-pyrrolidine-2-carboxylic acid ethyl ester (81 mg, 0.18 mmol, 1.0 eq) and 5-tert-butyl-2-methoxy-benzaldehyde (CAS#85943-26-6, 42 mg, 0.22 mmol, 1.2 eq) in acetic acid/sodium acetate buffer in methanol (96 mg acetic acid, 61 mg sodium acetate, 2 mL methanol). The reaction was stirred at room temperature for 1.5 hours. The solvent was removed under vacuum. The residue was partitioned between dichloromethane and water. The organic phase was concentrated to dryness and the residue was purified by flash chromatography on silica gel (heptane/ethyl acetate 95/5 to 70/30) to give the title compound (mixture of diastereomers, 72 mg, 63% over 2 steps). LC/MS (ESI+) m/z 613.9 (M+H)$^+$.

Example 28D (2S,3S,4S,5S)-3-tert-butyl-4-(5-tert-butyl-2-methoxy-benzylamino)-1-((S*)-2,3-dihydro-benzofuran-2-carbonyl)-5-phenyl-pyrrolidine-2-carboxylic acid A solution of (2S,3S,4S,5S)-3-tert-butyl-4-(5-tert-butyl-2-methoxy-benzylamino)-1-(2,3-dihydro-benzofuran-2-carbonyl)-5-phenyl-pyrrolidine-2-carboxylic acid ethyl ester (72 mg, 0.12 mmol, 1.0 eq) in methanol (1 mL) was treated with LiOH 1.0 M in water (240 µL, 0.24 mmol, 2.0 eq) at room temperature and stirred overnight at 40° C. The reaction mixture was diluted with dichloromethane and acidified with acetic acid. The organic layer was washed with water and brine, then dried over magnesium sulfate, filtered and concentrated in vacuo. The residue was purified by chromatography on silica gel (dichloromethane/methanol 100/0 to 90/10) to provide the title compound (11 mg, 16%, second to elute) and a diastereomer (3 mg, 4%, first to elute). LC/MS (ESI+) m/z 585.80 (M+H)$^+$.

Example 29

(2S,3S,4S,5S)-3-tert-butyl-4-{[(6-tert-butyl-2-methoxypyridin-3-yl)methyl]amino}-1-(cyclohexanecarbonyl)-5-phenylpyrrolidine-2-carboxylic acid Example 29A (2S,3S,4S,5S)-3-tert-butyl-4-[(6-tert-butyl-2-methoxy-pyridin-3-ylmethyl)-amino]-1-cyclohexanecarbonyl-5-phenyl-pyrrolidine-2-carboxylic acid ethyl ester NaBH$_3$CN (16 mg, 0.26 mmol, 1.3 eq) was added to a solution of (2S,3S,4S,5S)-4-amino-3-tert-butyl-1-cyclohexanecarbonyl-5-phenyl-pyrrolidine-2-carboxylic acid ethyl ester (Example 7B, 86 mg, 0.20 mmol, 1.0 eq) and 6-tert-butyl-2-methoxy-pyridine-3-carbaldehyde (47 mg, 0.24 mmol, 1.2 eq) in acetic acid/sodium acetate buffer in methanol (96 mg acetic acid, 61 mg sodium acetate, 2 mL methanol). The reaction was stirred at room temperature for 1 hour. The solvent was removed under vacuum. The residue was partitioned between dichloromethane and water. The organic phase was concentrated to dryness and the residue was purified (dichloromethane/methanol 100/0 to 98/2) to give the title compound (104 mg, 90%). LC/MS (ESI+) m/z 579.0 (M+H)$^+$.

Example 29B (2S,3S,4S,5S)-3-tert-butyl-4-[(6-tert-butyl-2-methoxy-pyridin-3-ylmethyl)-amino]-1-cyclohexanecarbonyl-5-phenyl-pyrrolidine-2-carboxylic acid A solution of (2S,3S,4S,5S)-3-tert-butyl-4-[(6-tert-butyl-2-methoxy-pyridin-3-yl-methyl)-amino]-1-cyclohexanecarbonyl-5-phenyl-pyrrolidine-2-carboxylic acid ethyl ester (104 mg, 0.18 mmol, 1.0 eq) in methanol (2 mL) was treated with aqueous LiOH 1.0 M (540 µL, 0.54 mmol, 3.0 eq) at room temperature and the mixture was stirred overnight at 45° C. After reaction completion, the solvent was removed under vacuum, water was added and the resulting solution was extracted with ethyl acetate. The organic phase was concentrated to dryness. The residue was purified on silica gel (dichloromethane/methanol 100/0 to 97/3) to provide the title compound (63 mg, 64%). $^1$H NMR (400 MHz, CDCl$_3$) δ ppm 7.31-7.44 (m, 4H), 7.17 (br. s., 2H), 6.82 (d, J=7.5 Hz, 1H), 5.20-5.34 (m, 1H), 4.68 (s, 1H), 3.86 (d, J=13.7 Hz, 1H), 3.49 (d, J=13.7 Hz, 1H), 3.44 (s, 3H), 3.39 (d, J=6.1 Hz, 1H), 2.89-3.07 (m, 1H), 2.40 (s, 1H), 2.06 (s, 1H), 1.84 (d, J=11.8 Hz, 1H), 1.69-1.80 (m, 4H), 1.35-1.52 (m, 4H), 1.29-1.34 (m, 9H), 1.08 (s, 9H); LC/MS (ESI+) m/z 550.9 (M+H)$^+$.

Example 30

(2S,3S,4S,5S)-3-tert-butyl-4-{[(5-tert-butyl-2-methoxyphenyl)methyl]amino}-1-[(1S)-3,3-difluoro-cyclohexane-1-carbonyl]-5-phenylpyrrolidine-2-carboxylic acid Example 30A (2S,3R,4S,5S)-4-nitro-3-tert-butyl-1-((S)-3,3-difluoro-cyclohexanecarbonyl)-5-phenyl-pyrrolidine-2-carboxylic acid ethyl ester Ghosez's reagent (1-chloro-N,N,2-trimethyl-1-propenylamine, CAS#26189-59-3, 0.55 mL, 4.2 mmol, 1.2 eq) was added at 0° C. to a solution of 3,3-difluorocyclohexane-1-carboxylic acid (629 mg, 3.8 mmol, 1.1 eq) in dry dichloromethane (10 mL). The reaction mixture was stirred at 0° C. for 30 minutes. Core 7 (1.11 g, 3.5 mmol, 1.0 eq) and diisopropylethylamine (1.82 mL, 10.4 mmol, 3.0 eq) were added and the reaction mixture was allowed to warm up to room temperature and stirred for 2 hours. The reaction mixture was quenched with water and the aqueous phase was extracted with dichloromethane. The combined organic phases were dried on sodium sulfate, filtered and concentrated. The residue was purified on silica gel (heptane/ethyl acetate 100/0 to 70/30) to give the title compound (525 mg, 32%) as the second diastereomer to elute. LC/MS (ESI+) m/z 467.4 (M+H)$^+$.

Example 30B

(2S,3S,4S,5S)-4-amino-3-tert-butyl-1-((S)-3,3-difluoro-cyclohexanecarbonyl)-5-phenyl-pyrrolidine-2-carboxylic acid ethyl ester Zinc dust (197 mg, 3.0 mmol, 15.0 eq) was added to a solution of (2S,3R,4S,5S)-4-nitro-3-tert-butyl-1-((S)-3,3-difluoro-cyclohexanecarbonyl)-5-phenyl-pyrrolidine-2-carboxylic acid ethyl ester (95 mg, 0.2 mmol, 1.0 eq) in ethyl acetate/acetic acid 10 mL/1.0 mL. The reaction mixture was stirred at 60° C. for 2 hours. A spatula of zinc was added and the reaction mixture was stirred at room temperature overnight. The reaction mixture was filtered and concentrated in vacuo. The residue was purified on silica gel (10 g, dichloromethane/ethyl acetate 100/0 to 50/50) to give the title compound (57 mg, 64% yield). LC/MS (ESI+) m/z 437.9 $(M+H)^+$.

Example 30C

(2S,3S,4S,5S)-3-tert-butyl-4-(5-tert-butyl-2-methoxy-benzylamino)-1-((S)-3,3-difluoro-cyclohexanecarbonyl)-5-phenyl-pyrrolidine-2-carboxylic acid ethyl ester $NaBH_3CN$ (5 mg, 0.12 mmol, 1.3 eq) was added to a solution of (2S,3S,4S,5S)-4-amino-3-tert-butyl-1-((S)-3,3-difluoro-cyclohexanecarbonyl)-5-phenyl-pyrrolidine-2-carboxylic acid ethyl ester (28 mg, 64 mmol, 1.0 eq) and 5-tert-butyl-2-methoxy-phenylcarbaldehyde (15 mg, 77 mmol, 1.2 eq) in buffer acetic acid/sodium acetate/methanol (2 mL). The reaction mixture was stirred at room temperature for 45 minutes. The reaction mixture was concentrated and the residue was partitioned between dichloromethane and aqueous $NaHCO_3$. The organic phase was concentrated and the residue was purified on silica gel (dichloromethane/ethyl acetate 100/0 to 95/5) to give the title compound (32 mg, 82% yield). LC/MS (ESI+) m/z 613.9 $(M+H)^+$.

Example 30D

(2S,3S,4S,5S)-3-tert-butyl-4-(5-tert-butyl-2-methoxy-benzylamino)-1-((S)-3,3-difluoro-cyclohexanecarbonyl)-5-phenyl-pyrrolidine-2-carboxylic acid LiOH (11 mg, 0.27 mmol, 5.0 eq) was added to a solution of (2S,3S,4S,5S)-3-tert-butyl-4-(5-tert-butyl-2-methoxy-benzylamino)-1-((S)-3,3-difluoro-cyclohexanecarbonyl)-5-phenyl-pyrrolidine-2-carboxylic acid ethyl ester (32 mg, 0.052 mmol, 1.0 eq) in tetrahydrofuran/methanol/water (1.5/1.5/1). The reaction mixture was stirred at 45-50° C. overnight. The reaction mixture was acidified with aqueous HCl 1 M (1 eq/LiOH). The mixture was concentrated and extracted with dichloromethane. The organic phase was concentrated. The residue was purified on silica gel (dichloromethane/methanol 100/0 to 95/5) to give the title compound (29 mg, 95% yield). $^1H$ NMR (400 MHz, DMSO-$d_6$, 100° C.) δ ppm 7.48-7.74 (m, 2H), 7.25-7.43 (m, 3H), 7.10-7.23 (m, 1H), 6.92-7.07 (m, 1H), 6.69-6.83 (m, 1H), 5.15-5.34 (m, 1H), 4.47 (br. s, 1H), 3.27-3.77 (m, 6H), 2.96 (br. s, 1H under peak of water), 2.27-2.46 (m, 1H), 1.47-2.12 (m, 8H), 1.23 (s, 9H), 1.01 (s, 9H). LC/MS (ESI+) m/z 585.7 $(M+H)^+$.

Example 31

(2S,3S,4S,5S)-3-tert-butyl-4-{[(5-tert-butyl-2-methoxyphenyl)methyl]amino}-1-[(1R)-3,3-difluorocyclohexane-1-carbonyl]-5-phenylpyrrolidine-2-carboxylic acid

Example 31A

(2S,3R,4S,5S)-4-nitro-3-tert-butyl-1-((R)-3,3-difluoro-cyclohexanecarbonyl)-5-phenyl-pyrrolidine-2-carboxylic acid ethyl ester The title compound was prepared as described in Example 30A as the first diastereomer to elute, (550 mg, 34%). LC/MS (ESI+) m/z 467.4 $(M+H)^+$.

Example 31B

(2S,3S,4S,5S)-4-amino-3-tert-butyl-1-((R)-3,3-difluoro-cyclohexanecarbonyl)-5-phenyl-pyrrolidine-2-carboxylic acid ethyl ester Zinc dust (11.6 g, 177 mmol, 15.0 eq) was added to a solution of (2S,3R,4S,5S)-4-nitro-3-tert-butyl-1-((R)-3,3-difluoro-cyclohexanecarbonyl)-5-phenyl-pyrrolidine-2-carboxylic acid ethyl ester (5.50 g, 11.8 mmol, 1.0 eq) in ethyl acetate/acetic acid (50 mL/12.8 mL). The reaction mixture was stirred at 60° C. for 45 minutes then filtered. The filtrate was concentrated to dryness. The residue was dissolved in dichloromethane and neutralized with a saturated aqueous solution of $NaHCO_3$. The aqueous phase was extracted with dichloromethane. The combined organic phases were dried on $Na_2SO_4$, filtered and concentrated to give the title compound which was used in the next step without further purification (5.03 g, 98%). LC/MS (ESI+) m/z 437.5 $(M+H)^+$.

Example 31C

(2S,3S,4S,5S)-3-tert-butyl-4-(5-tert-butyl-2-methoxy-benzylamino)-1-((R)-3,3-difluoro-cyclohexanecarbonyl)-5-phenyl-pyrrolidine-2-carboxylic acid ethyl ester $NaBH_3CN$ (372 mg, 5.92 mmol, 1.2 eq) was added to a solution of (2S,3S,4S,5S)-4-amino-3-tert-butyl-1-((R)-3,3-difluoro-cyclohexanecarbonyl)-5-phenyl-pyrrolidine-2-carboxylic acid ethyl ester (2.16 g, 4.94 mmol, 1.0 eq) and 5-tert-butyl-2-methoxy-benzaldehyde (CAS#85943-26-6, 1.04 g, 5.43 mmol, 1.1 eq) in acetic acid/sodium acetate buffer in methanol (96 mg acetic acid, 61 mg sodium acetate, 2 mL methanol). The reaction was stirred at room temperature for 1 hour. The solvent was removed under vacuum. The residue was partitioned between dichloromethane and water. The organic phase was concentrated to dryness and the residue was purified by chromatography on silica gel (heptane/ethyl acetate 100/0 to 70/30) to give the title compound (2.60 g, 85%). LC/MS (ESI+) m/z 613.9 $(M+H)^+$.

Example 31D

(2S,3S,4S,5S)-3-tert-butyl-4-(5-tert-butyl-2-methoxy-benzylamino)-1-((R)-3,3-difluoro-cyclohexanecarbonyl)-5-phenyl-pyrrolidine-2-carboxylic acid A solution of (2S,3S,4S,5S)-3-tert-butyl-4-(5-tert-butyl-2-methoxy-benzylamino)-1-((R)-3,3-difluoro-cyclohexanecarbonyl)-5-phenyl-pyrrolidine-2-carboxylic acid ethyl ester (2.60 g, 4.31 mmol, 1.0 eq) in methanol (40 mL) was treated with LiOH 1.0 M in water (12.93 mL, 12.93 mmol, 3.0 eq) at room temperature and stirred overnight at 45° C. After the reaction was complete, the solvent was removed under vacuum, and water and aqueous 2 N HCl were added followed by dichloromethane. The organic layer was separated and concentrated to dryness. The residue was purified on silica gel (dichloromethane/methanol 100/0 to 96/4) to provide the title compound (1.66 g, 66%). $^1$H NMR (400 MHz, Chloroform-d) δ ppm 7.29-7.49 (m, 5H), 7.18 (br. s., 1H), 7.07 (d, J=2.2 Hz, 1H), 6.65 (d, J=8.7 Hz, 1H), 5.24 (d, J=6.1 Hz, 1H), 4.67 (s, 1H), 4.11 (d, J=13.8 Hz, 1H), 3.55 (d, J=13.8 Hz, 1H), 3.37-3.50 (m, 1H), 3.33 (d, J=6.3 Hz, 1H), 3.25 (s, 3H), 2.48 (s, 1H), 2.01-2.26 (m, 2H), 1.41-1.95 (m, 6H), 1.27 (s, 9H), 1.09 (s, 9H); LC/MS (ESI+) m/z 585.8 (M+H)$^+$.

Example 32

(2S,3S,4S,5S)-3-tert-butyl-4-{[(5-tert-butyl-2-methoxyphenyl)methyl]amino}-1-[(2R)-2-methoxy-3-phenylpropanoyl]-5-phenylpyrrolidine-2-carboxylic acid Example 32A (2S,3R,4S,5S)-4-nitro-3-tert-butyl-1-((R)-2-methoxy-3-phenyl-propionyl)-5-phenyl-pyrrolidine-2-carboxylic acid ethyl ester Ghosez reagent (1-chloro-N,N,2-trimethyl-1-propenylamine, CAS#26189-59-3, 245 µL, 1.85 mmol, 3 eq) was added at 0° C. to a solution of (R)-2-methoxy-3-phenyl-propionic acid (223 mg, 1.24 mmol, 2.0 eq) in dry dichloromethane (10 mL). The reaction mixture was stirred at 0° C. for 30 minutes. Core 7 (198 mg, 0.62 mmol, 1.0 eq) and diisopropylethylamine (539 µL, 3.09 mmol, 5.0 eq) were successively added and the reaction mixture was allowed to warm to room temperature and stirred for 1 hour. The reaction mixture was partitioned between dichloromethane and a saturated aqueous solution of NH$_4$Cl. The organic phase was dried on Na$_2$SO$_4$, filtered and concentrated. The residue was purified on silica gel (heptane/ethyl acetate 95/5 to 70/30) to give the title compound as a single enantiomer (263 mg). LC/MS (ESI+) m/z 483.6 (M+H)$^+$.

Example 32B (2S,3S,4S,5S)-4-amino-3-tert-butyl-1-((R)-2-methoxy-3-phenyl-propionyl)-5-phenyl-pyrrolidine-2-carboxylic acid ethyl ester Zinc dust (534 mg, 8.175 mmol, 15.0 eq) was added to a solution of (2S,3R,4S,5S)-4-nitro-3-tert-butyl-1-((R)-2-methoxy-3-phenyl-propionyl)-5-phenyl-pyrrolidine-2-carboxylic acid ethyl ester (263 mg, 0.545 mmol, 1.0 eq) in ethyl acetate/acetic acid 20 mL/2.81 mL. The reaction mixture was stirred at 60° C. for 2 hours. A spatula of zinc was added and the reaction mixture was stirred at 60° C. for additional 1 hour. The reaction mixture was diluted in dichloromethane, and neutralized with aqueous NaHCO$_3$. The organic phase was concentrated under vacuum. The residue was purified on silica gel (heptane/ethyl acetate 70/30 to 30/70) to give the title compound (214 mg, 87% yield). LC/MS (ESI+) m/z 453.6 (M+H)$^+$.

Example 32C (2S,3S,4S,5S)-3-tert-butyl-4-(5-tert-butyl-2-methoxy-benzylamino)-1-((R)-2-methoxy-3-phenyl-propionyl)-5-phenyl-pyrrolidine-2-carboxylic acid ethyl ester NaBH$_3$CN (18 mg, 0.287 mmol, 1.3 eq) was added to a solution of (2S,3S,4S,5S)-4-amino-3-tert-butyl-1-((R)-2-methoxy-3-phenyl-propionyl)-5-phenyl-pyrrolidine-2-carboxylic acid ethyl ester (110 mg, 0.221 mmol, 1.0 eq) and 5-tert-butyl-2-methoxy-phenylcarbaldehyde (50 mg, 0.265 mmol, 1.2 eq) in acetic acid/sodium acetate/methanol buffer (2 mL). The reaction mixture was stirred at room temperature for 1 hour. The reaction mixture was concentrated and the residue was partitioned between dichloromethane and aqueous NaHCO$_3$. The organic phase was concentrated and the residue was purified on silica gel (heptane/ethyl acetate 99/1 to 80/20) to give the title compound (116 mg, 83% yield). LC/MS (ESI+) m/z 629.8 (M+H)$^+$.

Example 32D (2S,3S,4S,5S)-3-tert-butyl-4-{[(5-tert-butyl-2-methoxyphenyl)methyl]amino}-1-[(2R)-2-methoxy-3-phenylpropanoyl]-5-phenylpyrrolidine-2-carboxylic acid LiOH (77.5 mg, 1.38 mmol, 10.0 eq) was added to a solution of (2S,3S,4S,5S)-3-tert-butyl-4-(5-tert-butyl-2-methoxy-benzylamino)-1-((R)-2-methoxy-3-phenyl-propionyl)-5-phenyl-pyrrolidine-2-carboxylic acid ethyl ester (116 mg, 0.138 mmol, 1.0 eq) in tetrahydrofuran/methanol/water (5/5/3). The reaction mixture was stirred at 50° C. for 30 minutes then at room temperature overnight. The reaction mixture was quenched with water and ethyl acetate. The two layers were separated. The organic phase was concentrated to dryness. The residue was purified by flash chromatography on silica gel (dichloromethane/methanol 100/0 to 96/4) to provide the title compound (80 mg, 72%). $^1$H NMR (400 MHz, Chloroform-d) δ ppm 7.17-7.36 (m, 11H), 7.07 (d, J=2.4 Hz, 1H), 6.65 (d, J=8.7 Hz, 1H), 5.25-5.33 (m, 1H), 4.84-4.93 (m, 2H), 4.06 (d, J=13.8 Hz, 1H), 3.54 (d, J=13.8 Hz, 1H), 3.44 (s, 3H), 3.34 (d, J=6.1 Hz, 1H), 3.25 (s, 3H), 3.05 (dd, J=13.7, 6.8 Hz, 1H), 2.97 (dd, J=13.7, 7.5 Hz, 1H), 2.45 (s, 1H), 1.26 (s, 9H), 1.09 (s, 9H); LC/MS (ESI+) m/z 601.8 (M+H)$^+$.

Example 33

(2S,3S,4S,5S)-3-tert-butyl-1-(cyclohexanecarbonyl)-4-[({2-methoxy-5-[1-(trifluoromethyl)cyclopropyl]phenyl}methyl)amino]-5-phenylpyrrolidine-2-carboxylic acid Example 33A 4,4,5,5-tetramethyl-2-(4-(1-(trifluoromethyl)cyclopropyl)phenyl)-1,3,2-dioxaborolane To a solution of 1-bromo-4-(1-(trifluoromethyl)cyclopropyl)benzene (2.2 g, 8.30 mmol) in dioxane (6 mL) was added 4,4,4',4',5,5,5',5'-octamethyl-2,2'-bi(1,3,2-dioxaborolane) (2.64 g, 10.40 mmol), potassium acetate (2.42 g, 24.66 mmol), and dicyclohexyl(4'-ethyl-2',6'-diisopropyl-[1,1'-biphenyl]-2-yl)phosphine (220 mg, 0.475 mmol) under nitrogen. The mixture was stirred at 100° C. for 6 hours, then cooled down to 25° C. and diluted with ethyl acetate (50 mL). The insoluble matter was separated by filtration and the filtrate was concentrated under reduced pressure. The mixture was purified by preparative TLC (petroleum ether:ethyl acetate=15:1) to provide 4,4,5,5-tetramethyl-2-(4-(1-(trifluoromethyl)cyclopropyl)phenyl)-1,3,2-dioxaborolane (1.8 g, 4.61 mmol, 55.6% yield). $^1$H NMR (400 MHz, CDCl$_3$) δ ppm 1.04 (br. s., 2H), 1.30-1.40 (m, 14H), 7.48 (d, J=7.94 Hz, 2H), 7.80 (d, J=7.94 Hz, 2H).

Example 33B 4-(1-(trifluoromethyl)cyclopropyl)phenol

To a solution of 4,4,5,5-tetramethyl-2-(4-(1-(trifluoromethyl)cyclopropyl)phenyl)-1,3,2-dioxaborolane (1.8 g, 5.77 mmol) in tetrahydrofuran (30 mL), cooled with ice, was added dropwise a solution of aqueous sodium hydroxide (3 mL, 3 M), and the mixture was stirred at 0° C. for 0.5 hours. Hydrogen peroxide (30 weight %, 3 mL, 29.4 mmol) was added over a period of 5 minutes. The reaction was allowed to warm to 25° C. and stirring was continued for 12 hours. The reaction mixture was quenched by the addition of saturated aqueous NaHSO$_3$. Water was added. The mixture was extracted with diethyl ether (100 mL), and the organic layer was washed with saturated brine, dried over anhydrous magnesium sulfate, and filtered. The solvent was distilled off under reduced pressure to give the title compound, 4-(1-(trifluoromethyl)cyclopropyl)phenol (1.16 g, 100% yield). $^1$H NMR (400 MHz, CDCl$_3$) δ ppm 0.98 (br. s., 2H), 1.27-1.35 (m, 2H), 4.84 (s, 1H), 6.80 (d, J=8.38 Hz, 2H), 7.34 (d, J=7.94 Hz, 2H).

Example 33C 2-hydroxy-5-(1-(trifluoromethyl)cyclopropyl)benzaldehyde

Example 33B (507.3 mg, 2.509 mmol), magnesium chloride (367.5 mg, 3.86 mmol) and paraformaldehyde (537.6 mg, 17.90 mmol) were suspended in acetonitrile (8 mL) and triethylamine (1.4 mL, 10.04 mmol) was added. The resulting suspension was stirred vigorously and heated to 80° C. for 14 hours, at which point LC/MS showed complete conversion to the desired product. 1 M aqueous HCl (50 mL) was added and the reaction was extracted with dichloromethane (2×50 mL). The combined organic layers were dried over MgSO$_4$, filtered, and concentrated to provide the title compound (541.6 mg, 94%). $^1$H NMR (400 MHz, dimethyl sulfoxide-d$_6$) δ ppm 10.90 (s, 1H), 10.24 (s, 1H), 7.69 (d, J=2.4 Hz, 1H), 7.57 (dd, J=8.6, 2.4 Hz, 1H), 7.00 (d, J=8.5 Hz, 1H), 1.33-1.26 (m, 2H), 1.09-1.03 (m, 2H).

Example 33D 2-methoxy-5-(1-(trifluoromethyl)cyclopropyl)benzaldehyde

Example 33C (546.5 mg, 2.374 mmol), was dissolved in N,N-dimethylformamide (5 mL) and potassium carbonate (501.3 mg, 3.63 mmol) was added. The resulting suspension was stirred vigorously and methyl iodide (532.4 mg, 3.75 mmol) was added all at once. The suspension was stirred at room temperature for 20 hours. 1 M aqueous NaOH (50 mL) was added and the reaction was extracted with methyl tert-butyl ether (2×50 mL). The combined extracts were washed with water (50 mL) and brine (50 mL) then dried over magnesium sulfate, filtered, and concentrated to provide the title compound (505.7 mg, 87%). $^1$H NMR (400 MHz, dimethyl sulfoxide-d$_6$) δ ppm 10.32 (s, 1H), 7.72 (dq, J=4.5, 2.5 Hz, 2H), 7.24 (d, J=9.3 Hz, 1H), 3.91 (s, 3H), 1.35-1.29 (m, 2H), 1.12-1.05 (m, 2H); MS (ESI+) m/z 177 (M+H)$^+$.

Example 33E tert-butyl (2S,3R,4S,5S)-3-(tert-butyl)-1-(cyclohexanecarbonyl)-4-nitro-5-phenylpyrrolidine-2-carboxylate tert-Butyl (2S,3R,4S,5S)-3-(tert-butyl)-4-nitro-5-phenylpyrrolidine-2-carboxylate (Core 6, 2.02 g, 5.80 mmol) was dissolved in dichloromethane (25 mL) and triethylamine (1.2 mL, 8.61 mmol) was added, followed by cyclohexanecarbonyl chloride (1.07 g, 7.30 mmol). The reaction was stirred at ambient temperature for 17 hours. The reaction was diluted with dichloromethane (50 mL) and washed with 1 M aqueous HCl (2×50 mL) and brine. The organic layer was dried over sodium sulfate, filtered, then concentrated to provide the title compound (2.66 g, 100%). $^1$H NMR (400 MHz, dimethyl sulfoxide-d$_6$, 120° C.) δ ppm 7.61-7.55 (m, 2H), 7.30-7.21 (m, 3H), 5.66-5.55 (m, 2H), 4.58 (d, J=3.6 Hz, 1H), 2.96 (t, J=3.2 Hz, 1H), 2.24-2.12 (m, 1H), 1.84-1.61 (m, 4H), 1.51 (s, 9H), 1.44-1.04 (m, 6H), 1.00 (s, 9H); MS (ESI+) m/z 459 (M+H)$^+$.

Example 33F tert-butyl (2S,3S,4S,5S)-4-amino-3-(tert-butyl)-1-(cyclohexanecarbonyl)-5-phenylpyrrolidine-2-carboxylate Example 33E (2.66 g, 5.80 mmol) and tetrahydrofuran (65 mL) were added to Raney®-Nickel 2800, water slurry (10.8 g, 31.7 mmol) in a 120 mL Parr shaker and the mixture was shaken for 16 hours at 50 psi H$_2$ and ambient temperature. HPLC indicated the starting material had been consumed. The reaction was filtered and concentrated to provide the title compound (2.48 g, 100%). $^1$H NMR (400 MHz, dimethyl sulfoxide-d$_6$, 120° C.) δ ppm 7.56 (d, J=7.3 Hz, 2H), 7.32 (t, J=7.5 Hz, 2H), 7.23 (t, J=7.3 Hz, 1H), 5.02 (d, J=7.1 Hz, 1H), 4.29 (d, J=4.0 Hz, 1H), 3.63 (dd, J=7.2, 3.6 Hz, 1H), 2.17 (d, J=0.8 Hz, 1H), 2.01 (d, J=4.1 Hz, 1H), 1.62 (d, J=8.2 Hz, 2H), 1.46 (d, J=0.8 Hz, 11H), 1.33-1.01 (m, 6H), 0.98 (d, J=0.7 Hz, 9H); MS (ESI+) m/z 429 (M+H)$^+$.

Example 33G tert-butyl (2S,3S,4S,5S)-3-(tert-butyl)-1-(cyclohexanecarbonyl)-4-((2-methoxy-5-(1-(trifluoromethyl)cyclopropyl)benzyl)amino)-5-phenylpyrrolidine-2-carboxylate Example 33F (52.8 mg, 0.123 mmol) and Example 33D (40.9 mg, 0.167 mmol) were dissolved in methanol (1 mL) and stirred at ambient temperature for 1 hour. Sodium cyanoborohydride (43.3 mg, 0.689 mmol) was added and the reaction was stirred at ambient temperature for an additional 16 hours. The reaction was diluted with dimethyl sulfoxide (1 mL), filtered and purified by reverse phase chromatography using the ammonium acetate method to provide the title compound (51.1 mg, 63%). $^1$H NMR (400 MHz, dimethyl sulfoxide-d$_6$, 120° C.) δ ppm 7.63-7.51 (m, 2H), 7.35-7.22 (m, 3H), 7.19 (dd, J=8.4, 2.4 Hz, 1H), 6.95

(d, J=2.3 Hz, 1H), 6.79 (d, J=8.4 Hz, 1H), 5.16 (d, J=6.9 Hz, 1H), 4.40 (d, J=2.7 Hz, 1H), 3.56 (s, 3H), 3.46 (d, J=14.4 Hz, 2H), 3.29 (d, J=13.9 Hz, 1H), 2.34-2.14 (m, 2H), 1.71-1.44 (m, 4H), 1.41 (s, 9H), 1.33-0.89 (m, 19H); MS (ESI+) m/z 657 (M+H)$^+$.

Example 33H (2S,3S,4S,5S)-3-tert-butyl-1-(cyclohexanecarbonyl)-4-[({2-methoxy-5-[1-(trifluoromethyl)cyclopropyl]phenyl}methyl)amino)-5-phenylpyrrolidine-2-carboxylic acid Example 33G (49.9 mg, 0.076 mmol) was dissolved in dichloromethane (1 mL). Trifluoroacetic acid (0.5 mL, 6.49 mmol) was added and the reaction was stirred at ambient temperature for 16 hours. The reaction was concentrated to provide the title compound (54.2 mg, 100%) as the trifluoroacetic acid salt. $^1$H NMR (400 MHz, dimethyl sulfoxide-d$_6$, 120° C.) δ ppm 7.59 (d, J=7.4 Hz, 2H), 7.39 (t, J=7.5 Hz, 2H), 7.35-7.28 (m, 2H), 7.09 (d, J=2.3 Hz, 1H), 6.89 (d, J=8.5 Hz, 1H), 5.35 (d, J=7.1 Hz, 1H), 4.53 (d, J=2.1 Hz, 1H), 3.85-3.78 (m, 1H), 3.74 (d, J=13.8 Hz, 1H), 3.63 (s, 3H), 3.42 (d, J=13.8 Hz, 1H), 2.51 (s, 1H), 2.25 (s, 1H), 1.71-1.59 (m, 2H), 1.56-1.45 (m, 2H), 1.32-0.93 (m, 19H); MS (ESI+) m/z 601 (M+H)$^+$.

Example 34

(2S,3S,4S,5S)-3-tert-butyl-4-{[(5-tert-butyl-2-methoxyphenyl)methyl]amino}-1-[(2S)-oxolane-2-carbonyl]-5-phenylpyrrolidine-2-carboxylic acid Example 34A (2S,3R,4S,5S)-1-tert-butyl 2-ethyl 3-(tert-butyl)-4-nitro-5-phenylpyrrolidine-1,2-dicarboxylate Core 7 (5.00 g, 15.61 mmol) was dissolved in tetrahydrofuran (32 mL). Di-tert-butyl dicarbonate (5.10 g, 23.37 mmol) was added and the reaction was stirred at 55° C. for 16 hours. The reaction was cooled to ambient temperature. Imidazole (1.08 g, 15.86 mmol) was added to quench any excess di-tert-butyl dicarbonate. The reaction was diluted with methyl tert-butyl ether (250 mL) and washed with 2×100 mL of 1 M aqueous HCl then brine (50 mL). The organics were dried over sodium sulfate, filtered, and concentrated to provide the title compound (6.40 g, 98%). $^1$H NMR (400 MHz, dimethyl sulfoxide-d$_6$, 120° C.) δ ppm 7.55-7.48 (m, 2H), 7.28-7.17 (m, 3H), 5.58 (dd, J=8.8, 3.2 Hz, 1H), 5.39 (d, J=8.8 Hz, 1H), 4.47 (d, J=3.8 Hz, 1H), 4.25 (qd, J=7.1, 0.9 Hz, 2H), 2.96 (t, J=3.5 Hz, 1H), 1.29 (t, J=7.1 Hz, 3H), 1.19 (d, J=0.7 Hz, 9H), 1.02 (s, 9H); MS (ESI+) m/z 420 (M+H)$^+$.

Example 34B (2S,3S,4S,5S)-1-tert-butyl 2-ethyl 4-amino-3-(tert-butyl)-5-phenylpyrrolidine-1,2-dicarboxylate Example 34A (6.40 g, 15.22 mmol) and tetrahydrofuran (120 mL) were added to Raney®-Nickel 2800, water slurry (19 g, 146 mmol) in a 250 mL Parr shaker and the mixture was shaken for 16 hours at 50 psi H$_2$ and ambient temperature. HPLC indicated the starting material had been consumed. The reaction was filtered and concentrated to provide the title compound (5.94 g, 97%). $^1$H NMR (400 MHz, dimethyl sulfoxide-d$_6$, 120° C.) δ ppm 7.51-7.46 (m, 2H), 7.28 (t, J=7.6 Hz, 2H), 7.23-7.16 (m, 1H), 4.83 (d, J=7.0 Hz, 1H), 4.23 (d, J=3.8 Hz, 1H), 4.17 (qd, J=7.1, 4.8 Hz, 2H), 3.59 (dd, J=7.0, 3.4 Hz, 1H), 2.01 (t, J=3.6 Hz, 1H), 1.25 (t, J=7.1 Hz, 3H), 1.17 (s, 9H), 1.00 (s, 9H); MS (ESI+) m/z 391 (M+H)$^+$.

Example 34C (2S,3S,4S,5S)-1-tert-butyl 2-ethyl 3-(tert-butyl)-4-((5-(tert-butyl)-2-methoxybenzyl)amino)-5-phenylpyrrolidine-1,2-dicarboxylate Example 34B (4.92 g, 12.60 mmol) and 5-(tert-butyl)-2-methoxybenzenecarbaldehyde (2.65 g, 13.78 mmol) were dissolved in dichloroethane (50 mL). Sodium triaceotoxyborohydride (4.02 g, 18.97 mmol) was added and the reaction was stirred at ambient temperature for 1 hour. The reaction was diluted with dichloromethane (200 mL) and quenched with saturated aqueous sodium bicarbonate (50 mL). The mixture was stirred for 30 minutes. The organic layer was isolated and the aqueous layer was extracted with dichloromethane (2×50 mL). The combined organic layers were dried over Na$_2$SO$_4$, filtered and concentrated. The residue was dissolved in heptane (35 mL) and HCl was added (3 M in cyclopentylmethyl ether, 8.4 mL) dropwise. The resulting solid was removed via filtration and dried to provide the title compound (7.38 g, 97%) as the HCl salt. $^1$H NMR (400 MHz, dimethyl sulfoxide-d$_6$, 120° C.) δ ppm 7.59 (d, J=7.5 Hz, 2H), 7.36 (t, J=7.5 Hz, 2H), 7.28 (t, J=7.4 Hz, 1H), 7.22 (d, J=8.7 Hz, 1H), 7.04 (s, 1H), 6.81 (d, J=8.6 Hz, 1H), 5.12 (d, J=6.9 Hz, 1H), 4.36 (d, J=2.3 Hz, 1H), 4.19 (q, J=7.0 Hz, 2H), 3.86-3.77 (m, 1H), 3.68 (d, J=13.6 Hz, 1H), 3.61 (s, 3H), 3.40 (d, J=13.5 Hz, 1H), 2.58 (s, 1H), 1.28-1.20 (m, 12H), 1.16 (s, 9H), 1.01 (s, 9H); MS (ESI+) m/z 567 (M+H)$^+$.

Example 34D (2S,3S,4S,5S)-ethyl 3-(tert-butyl)-4-((5-(tert-butyl)-2-methoxybenzyl)amino)-5-phenylpyrrolidine-2-carboxylate Example 34C (7.38 g, 12.23 mmol) was dissolved in dichloromethane (40 mL). Trifluoroacetic acid (20 mL, 260 mmol) was added and the reaction was stirred at ambient temperature for 3 hours. The reaction was concentrated and diluted with dichloromethane (250 mL). The organic layer was washed with 1 M aqueous NaOH (2×100 mL) and brine (100 mL), dried over Na$_2$SO$_4$, filtered and concentrated to provide the title compound (5.71 g, 100%). $^1$H NMR (500 MHz, dimethyl sulfoxide-d$_6$) δ ppm 7.39 (d, J=7.1 Hz, 2H), 7.31 (t, J=7.6 Hz, 2H), 7.26-7.21 (m, 1H), 7.09 (dd, J=8.5, 2.6 Hz, 1H), 6.88 (d, J=2.5 Hz, 1H), 6.71 (d, J=8.5 Hz, 1H), 4.17-4.04 (m, 3H), 3.58 (d, J=5.9 Hz, 1H), 3.52 (s, 3H), 3.35-3.27 (m, 1H), 3.12-3.05 (m, 2H), 2.09 (d, J=5.8 Hz, 1H), 1.17 (d, J=7.2 Hz, 12H), 0.91 (s, 9H); MS (ESI+) m/z 467 (M+H)$^+$.

Example 34E (2S,3S,4S,5S)-3-tert-butyl-4-{[(5-tert-butyl-2-methoxyphenyl)methyl]amino}-1-[(2S)-oxolane-2-carbonyl]-5-phenylpyrrolidine-2-carboxylic acid (S)-Tetrahydrofuran-2-carboxylic acid (9.95 mg, 0.086 mmol, 2.0 eq) in dichloromethane (500 L) was added to a 4 mL vial. Ghosez reagent (1-chloro-N,N,2-trimethyl-1-propenylamine, 17 µL, 0.13 mmol, 3.0 eq) was added neat and reaction was stirred at room temperature for 10 minutes. (2S,3S,4S,5S)-Ethyl 3-(tert-butyl)-4-((5-(tert-butyl)-2-methoxybenzyl)amino)-5-phenylpyrrolidine-2-carboxylate (Example 34D, 20 mg, 0.043 mmol, 1.0 eq) in 1:1 tetrahydrofuran/pyridine (500 µL) was added and the reaction was stirred for 1 hour at room temperature. The solvent was removed under a stream of nitrogen and the residue was dissolved in 3:2 tetrahydrofuran/methanol (0.5 mL). LiOH monohydrate (20 mg, 0.5 mmol, 11.6 eq) in H$_2$O (100 µL) was added and the reaction was stirred at 45° C. overnight. The solvent was removed under a stream of nitrogen. The residue was acidified with 800 µL 1 M aqueous HCl and diluted with 400 µL CH$_3$CN. Purification was carried out using preparative reverse phase HPLC MS method trifluoroacetic acid 10 (15.7 mg, 54% yield). $^1$H NMR (400 MHz, 120° C., dimethyl sulfoxide-d$_6$:D$_2$O=9:1 (v/v)) δ ppm 7.60 (d, J=7.4 Hz, 2H), 7.41 (d, J=7.3 Hz, 2H), 7.41-7.29 (m, 2H), 7.26 (dd, J=8.6, 2.5 Hz, 1H), 7.03 (d, J=2.5 Hz, 1H), 6.82 (d, J=8.6 Hz, 1H), 5.50 (d, J=6.9 Hz, 1H), 4.61 (d, J=1.9 Hz, 1H), 4.23 (s, 1H), 3.92-3.85 (m, 1H), 3.82-3.63 (m, 2H), 3.60 (s, 3H), 3.42 (d, J=13.6 Hz, 1H), 2.55 (s, 1H), 1.89 (d, J=5.5 Hz, 1H), 1.78 (dq, J=13.7, 7.1, 6.6 Hz, 1H), 1.68 (s, 2H), 1.21 (s, 9H), 0.99 (s, 9H); MS (APCI+) m/z 537.1 (M+H)$^+$.

Example 35

(2S,3S,4S,5S)-3-tert-butyl-4-{[(5-tert-butyl-2-methoxyphenyl)methyl]amino}-1-(cis-4-hydroxy-4-propylcyclohexane-1-carbonyl)-5-phenylpyrrolidine-2-carboxylic acid (1r,4s)-4-Hydroxy-4-propylcyclohexanecarboxylic acid (11.9 mg, 0.064 mmol, 1.5 eq) in dichloromethane (500 µL) was added to a 4 mL vial. Ghosez reagent (1-chloro-N,N, 2-trimethyl-1-propenylamine, 17 µL, 0.13 mmol, 3.0 eq) was added neat and reaction was stirred at room temperature for 10 minutes. (2S,3S,4S,5S)-Ethyl 3-(tert-butyl)-4-((5-(tert-butyl)-2-methoxybenzyl)amino)-5-phenylpyrrolidine-2-carboxylate (Example 34D, 20 mg, 0.043 mmol, 1.0 eq) in 1:1 tetrahydrofuran/pyridine (500 µL) was added and the reaction was stirred for 1 hour at room temperature. The solvent was removed under a stream of nitrogen and the residue was dissolved in 3:2 tetrahydrofuran/methanol (0.5 mL). LiOH monohydrate (20 mg, 0.5 mmol, 11.6 eq) in H$_2$O (100 µL) was added and the reaction was stirred at 45° C. overnight. The solvent was removed under a stream of nitrogen. The residue was acidified with 800 µL 1 M aqueous HCl and diluted with 400 µL CH$_3$CN. Purification was carried out using preparative reverse phase HPLC MS method trifluoroacetic acid 10 (14.9 mg, 48% yield). $^1$H NMR (400 MHz, 120° C., dimethyl sulfoxide-d$_6$:D$_2$O=9:1 (v/v)) δ ppm 7.58 (s, 2H), 7.47-7.24 (m, 4H), 7.06 (d, J=2.6 Hz, 1H), 6.84 (d, J=8.6 Hz, 1H), 5.40 (d, J=7.2 Hz, 1H), 4.56 (d, J=2.0 Hz, 1H), 3.94 (d, J=7.0 Hz, 1H), 3.85 (d, J=13.6 Hz, 1H), 3.60 (s, 3H), 3.50 (d, J=13.5 Hz, 1H), 2.57 (s, 1H), 2.17 (s, 1H), 1.62 (td, J=12.4, 3.8 Hz, 2H), 1.50 (d, J=13.8 Hz, 1H), 1.39 (d, J=12.2 Hz, 2H), 1.21 (s, 14H), 1.11-0.90 (m, 11H), 0.82 (t, J=6.2 Hz, 3H); MS (APCI+) m/z 607.2 (M+H)$^+$.

Example 36

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-[2-(dimethylamino)pyridin-3-yl]pyrrolidine-2-carboxylic acid Example 36A (2S,3R,4S,5S)-ethyl 3-(tert-butyl)-1-((R*)-2,3-dihydrobenzofuran-2-carbonyl)-5-(2-(dimethylamino) pyridin-3-yl)-4-nitropyrrolidine-2-carboxylate and Example 36B (2S,3R,4S,5S)-ethyl 3-(tert-butyl)-1-((S*)-2,3-dihydrobenzofuran-2-carbonyl)-5-(2-(dimethylamino) pyridin-3-yl)-4-nitropyrrolidine-2-carboxylate To the mixture of (2S,3R,4S,5S)-ethyl 3-(tert-butyl)-5-(2-(dimethylamino)pyridin-3-yl)-4-nitropyrrolidine-2-carboxylate (Core 1, 920 mg, 2.5 mmol) and triethylamine (1.391 mL, 9.98 mmol) in dichloromethane (30 mL) was added 2,3-dihydrobenzofuran-2-carbonyl chloride (0.501 g, 2.74 mmol) cooling in an ice bath. The mixture was stirred in an ice bath for 30 minutes and allowed to warm to ambient temperature. Dichloromethane (10 mL) was added and the mixture was washed with brine, dried over MgSO$_4$, filtered, and concentrated. The residue was purified via chromatography on a 24 g silica gel cartridge, eluting with ethyl acetate in heptane at 0-25% gradient to provide (2S,3R,4S,5S)-ethyl 3-(tert-butyl)-1-((R)-2,3-dihydrobenzofuran-2-carbonyl)-5-(2-(dimethylamino)pyridin-3-yl)-4-nitropyrrolidine-2-carboxylate 435 mg (34.2% yield) as the first compound to elute. MS (ESI+) m/z 511.2 (M+H)$^+$. The second compound to elute was the title compound (2S,3R,4S,5S)-ethyl 3-(tert-butyl)-1-((S)-2,3-dihydrobenzofuran-2-carbonyl)-5-(2-(dimethylamino)pyridin-3-yl)-4-nitropyrrolidine-2-carboxylate (460 mg, 36.1% yield). MS (ESI+) m/z 511.2 (M+H)$^+$.

Example 36C (2S,3S,4S,5S)-ethyl 4-amino-3-(tert-butyl)-1-((S*)-2,3-dihydrobenzofuran-2-carbonyl)-5-(2-(dimethylamino)pyridin-3-yl)pyrrolidine-2-carboxylate Example 36B (450 mg, 0.881 mmol) in tetrahydrofuran (20 mL) was added to Raney®-Nickel 2800, water slurry (950 mg, 7.93 mmol) in a 250 mL pressure bottle. The mixture was flushed with argon 4 times and then flushed with hydrogen (50 psi) and shaken for 16 hours at 50° C. The mixture was filtered and concentrated to dryness to give 375 mg (89% yield) of title compound which used in next step without further purification. LC/MS (APCI+) 481 (M+H)$^+$.

Example 36D (2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-[2-(dimethylamino)pyridin-3-yl]pyrrolidine-2-carboxylic acid A mixture of 5-(tert-butyl)-2-methoxybenzaldehyde (28.8 mg, 0.150 mmol), Example 36C (60 mg, 0.125 mmol) and zinc(II) chloride (3.40 mg, 0.025 mmol) in a sodium acetate/acetic acid buffer in methanol (pH=4, 2 mL) was stirred at ambient temperature for 10 minutes. Sodium cyanoborohydride (11.77 mg, 0.187 mmol) was added and the mixture was stirred for 1 hour, and the solvent was removed under pressure. The residue was purified via chromatography on a 12 g silica gel cartridge, eluting with ethyl acetate/methanol (10:1) in heptane at 0-40% gradient to yield the ester, (2S,3S,4S,5S)-ethyl 3-(tert-butyl)-4-((5-(tert-butyl)-2-methoxybenzyl)amino)-1-((S)-2,3-dihydrobenzofuran-2-carbonyl)-5-(2-(dimethylamino)pyridin-3-yl)pyrrolidine-2-carboxylate. The ester was dissolved in methanol (0.5 mL) and 4 M aqueous LiOH (0.5 mL). The mixture was stirred at 50° C. overnight and was adjusted pH to 4~5 by adding 4 M HCl in dioxane. The mixture was concentrated and dissolved in dichloromethane (2 mL) and filtered. The filtrate was purified via chromatography on a 4 g silica gel cartridge, eluting with methanol in dichloromethane at 0-20% gradient yield 40 mg (51.0% yield). $^1$H NMR (400 MHz, dimethyl sulfoxide-$d_6$) δ ppm 8.20 (s, 2H), 7.18-7.12 (m, 1H), 7.09 (d, J=7.1 Hz, 1H), 7.04 (d, J=7.2 Hz, 1H), 7.02-6.94 (m, 2H), 6.78 (dd, J=7.5, 1.1 Hz, 1H), 6.73 (d, J=8.6 Hz, 1H), 6.66 (d, J=8.0 Hz, 1H), 5.65 (s, 1H), 4.61 (s, 1H), 3.63 (d, J=13.8 Hz, 1H), 3.57 (d, J=6.4 Hz, 1H), 3.47 (d, J=0.9 Hz, 3H), 3.28 (d, J=13.7 Hz, 1H), 3.18 (d, J=19.3 Hz, 3H), 2.88 (s, 2H), 2.66-2.62 (m, 6H), 2.60 (s, 1H), 1.20 (s, 9H), 1.04 (s, 9H); MS (ESI+) m/z 629.3 (M+H)$^+$.

Example 37

(2S,3S,4S,5S)-3-tert-butyl-1-[(2R*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid Example 37A (2S,3S,4S,5S)-ethyl 4-amino-3-(tert-butyl)-1-((R*)-2,3-dihydrobenzofuran-2-carbonyl)-5-(2-(dimethylamino)pyridin-3-yl)pyrrolidine-2-carboxylate The title compound was prepared according to the procedure described in Example 36C, substituting Example 36A for Example 36B. LC/MS (APCI+) m/z 481 (M+H)$^+$.

Example 37B (2S,3S,4S,5S)-3-tert-butyl-1-[(2R*)-2,3-dihydrobenzofuran-2-carbonyl]-5-[2-(dimethylamino)-3-pyridyl]-4-[[2-methoxy-5-[1-(trifluoromethyl)cyclopropyl]phenyl]methylamino]pyrrolidine-2-carboxylic acid A mixture of 2-methoxy-5-(1-(trifluoromethyl)cyclopropyl)benzaldehyde (30.5 mg, 0.125 mmol), (2S,3S,4S,5S)-ethyl 4-amino-3-(tert-butyl)-1-((R*)-2,3-dihydrobenzofuran-2-carbonyl)-5-(2-(dimethylamino)pyridin-3-yl)pyrrolidine-2-carboxylate (60 mg, 0.125 mmol) and zinc(II) chloride (3.40 mg, 0.025 mmol) in a sodium acetate/acetic acid buffer in methanol (pH=4, 2 mL) was stirred at room temperature for 10 minutes to give a colorless solution. Sodium cyanoborohydride (11.77 mg, 0.187 mmol) was added neat and the mixture was stirred at room temperature for 1 hour. The solvent was removed under $N_2$. The residue was purified by chromatography, eluting with ethyl acetate/methanol (10:1) in heptane 0-40% to yield the ester. The ester was dissolved in methanol (2 mL) with 4 M aqueous LiOH (0.5 mL). The mixture was stirred at 40° C. overnight. The solvent was removed and water (1 mL) was added. The pH was adjusted to 4-5. Purification by chromatography, eluting with methanol in $CH_2Cl_2$ at 0-20% gradient provided the title compound 54 mg (63.5% yield). $^1$H NMR (400 MHz, dimethyl sulfoxide-$d_6$) δ ppm 8.17 (d, J=4.5 Hz, 1H), 8.00 (s, 1H), 7.23 (dd, J=8.4, 2.4 Hz, 1H), 7.14 (d, J=7.5 Hz, 1H), 7.05 (d, J=2.0 Hz, 2H), 6.96 (d, J=5.8 Hz, 1H), 6.81 (dd, J=7.9, 3.1 Hz, 2H), 6.67 (d, J=8.1 Hz, 1H), 5.46 (d, J=6.4 Hz, 1H), 4.91 (s, 1H), 3.61 (s, 1H), 3.51 (s, 1H), 3.50 (s, 3H), 3.35-3.25 (m, 4H), 3.20 (s, 1H), 2.60 (s, 6H), 2.55 (s, 1H), 1.30-1.24 (m, 2H), 1.05 (s, 9H), 0.95 (dd, J=5.0, 3.3 Hz, 2H); MS (ESI+) m/z 681.2 (M+H)$^+$.

Example 38

(2S,3S,4S,5S)-3-tert-butyl-4-{[(6-tert-butyl-2-methoxypyridin-3-yl)methyl]amino}-1-[(2S)-oxane-2-carbonyl]-5-phenylpyrrolidine-2-carboxylic acid Example 38A (2S,3S,4S,5S)-3-tert-butyl-4-[(6-tert-butyl-2-methoxy-pyridin-3-ylmethyl)-amino]-5-phenyl-pyrrolidine-1,2-dicarboxylic acid 1-tert-butyl ester 2-ethyl ester $NaBH_3CN$ (209 mg, 3.32 mmol, 1.3 eq) was added to a solution of Example 34B (1.00 g, 2.56 mmol, 1.0 eq) and 6-tert-butyl-2-methoxy-pyridine-3-carbaldehyde (593 mg, 3.07 mmol, 1.2 eq) in acetic acid/sodium acetate/methanol buffer (1.2 g acetic acid, 763 mg sodium acetate, 25 mL methanol). The reaction mixture was stirred at room temperature for 1 hour. The solvent was removed under vacuum. The residue was partitioned between dichloromethane and water. The organic phase was concentrated to dryness and the residue was purified on silica gel (heptane/ethyl acetate, 100/0 to 80/20) to give the title compound (785 mg, 54% yield). LC/MS (ESI+) m/z 568.9 (M+H)$^+$.

Example 38B (2S,3S,4S,5S)-3-tert-butyl-4-[(6-tert-butyl-2-methoxy-pyridin-3-ylmethyl)-amino]-5-phenyl-pyrrolidine-2-carboxylic acid ethyl ester Trifluoroacetic acid (2 mL) was added to a solution of (2S,3S,4S,5S)-3-tert-butyl-4-[(6-tert-butyl-2-methoxy-pyridin-3-ylmethyl)-amino]-5-phenyl-pyrrolidine-1,2-dicarboxylic acid 1-tert-butyl ester 2-ethyl ester (785 mg, 1.38 mmol, 1.0 eq) in dichloromethane (12 mL). The reaction was stirred at room temperature for 72 hours. The solvent was removed under vacuum. The residue was partitioned between dichloromethane and saturated aqueous $NaHCO_3$ solution. The organic phase was concentrated to dryness and the residue was purified by flash chromatography on silica gel (dichloromethane/methanol 100/0 to 98/2) to provide the title compound (520 mg, 80%). LC/MS (ESI+) m/z 468.8 (M+H)$^+$.

Example 38C (2S,3S,4S,5S)-3-tert-butyl-4-[(6-tert-butyl-2-methoxy-pyridin-3-ylmethyl)-amino]-5-phenyl-1-((S)-tetrahydro-pyran-2-carbonyl)-pyrrolidine-2-carboxylic acid ethyl ester and

Example 38D (2S,3S,4S,5S)-3-tert-butyl-4-[(6-tert-butyl-2-methoxy-pyridin-3-ylmethyl)-amino]-5-phenyl-1-((R)-tetrahydro-pyran-2-carbonyl)-pyrrolidine-2-carboxylic acid ethyl ester To a stirred solution of tetrahydro-pyran-2-carboxylic acid (23 mg, 0.18 mmol, 1.3 eq) in dichloromethane (2 mL) at 0° C. was added Ghosez's reagent (1-chloro-N,N,2-trimethyl-1-propenylamine, 55 µL, 0.42 mmol, 3.0 eq). The reaction mixture was stirred at 0° C. for 5 minutes and a solution of amine Core 7 (65 mg, 0.14 mmol, 1.0 eq) and diisopropylethylamine (97 µL, 0.56 mmol, 4.0 eq) in dichloromethane was added. The reaction mixture was stirred at 0° C. for 10 minutes and at room temperature for 1.5 hours. The reaction mixture was washed with water and the organic phase was concentrated to dryness. The residue was purified on silica gel (heptane/ethyl acetate 100/0 to 85/15) to give the two diastereomers Example 38C (23 mg, 28%, first to elute) and Example 38D (23 mg, 28%, second to elute). LC/MS (ESI+) m/z 580.8 (M+H)$^+$.

Example 38E (2S,3S,4S,5S)-3-tert-butyl-4-{[(6-tert-butyl-2-methoxypyridin-3-yl)methyl]amino}-1-[(2S)-oxane-2-carbonyl]-5-phenylpyrrolidine-2-carboxylic acid A solution of (2S,3S,4S,5S)-3-tert-butyl-4-[(6-tert-butyl-2-methoxy-pyridin-3-ylmethyl)-amino]-5-phenyl-1-((S)-tetrahydro-pyran-2-carbonyl)-pyrrolidine-2-carboxylic acid ethyl ester (Example 38C, 23 mg, 0.04 mmol, 1.0 eq) in methanol (1 mL) was treated with LiOH 1.0 M in water (120 µL, 0.12 mmol, 3.0 eq) at room temperature and the mixture was stirred overnight at 45° C. After the reaction was complete, 1 N aqueous HCl was added, and the solvent was removed under vacuum. The residue was purified on silica gel (dichloromethane/methanol 100/0 to 95/5). The product fractions were combined and concentrated to dryness to provide the title compound (14 mg, 63%). $^1$H NMR (400 MHz, CDCl$_3$-d) δ ppm 7.30-7.52 (m, 4H), 7.12-7.26 (m, 2H), 6.80 (d, J=7.3 Hz, 1H), 5.30 (m, 1H), 4.62 (br. s., 1H), 4.28 (br. s., 1H), 3.99 (d, J=10.8 Hz, 1H), 3.68-3.85 (m, 1H), 3.56 (t, J=10.2 Hz, 1H), 3.51-3.49 (m, 1H), 3.41-3.49 (m, 3H), 3.38 (d, J=5.8 Hz, 1H), 2.26-2.43 (m, 1H), 1.89 (br. s., 1H), 1.42-1.78 (m, 5H), 1.24-1.37 (m, 9H), 1.00-1.15 (m, 9H); LC/MS (ESI+) m/z 552.8 (M+H)$^+$.

Example 39

(2S,3S,4S,5S)-3-tert-butyl-4-{[(6-tert-butyl-2-methoxypyridin-3-yl)methyl]amino}-1-[(2R)-oxane-2-carbonyl]-5-phenylpyrrolidine-2-carboxylic acid A solution of (2S,3S,4S,5S)-3-tert-butyl-4-[(6-tert-butyl-2-methoxy-pyridin-3-ylmethyl)-amino]-5-phenyl-1-((S)-tetrahydro-pyran-2-carbonyl)-pyrrolidine-2-carboxylic acid ethyl ester Example 38D (23 mg, 0.04 mmol, 1.0 eq) in methanol (1 mL) was treated with LiOH 1.0 M in water (120 µL, 0.12 mmol, 3.0 eq) at room temperature and the mixture was stirred overnight at 45° C. After the reaction was complete, 1 N aqueous HCl was added and solvent was removed under vacuum. The residue was purified on silica gel (dichloromethane/methanol 100/0 to 95/5). The product fractions were combined and concentrated to dryness to provide the title compound (12 mg, 54%). $^1$H NMR (400 MHz, CDCl$_3$-d) δ ppm 7.29-7.43 (m, 4H), 7.17 (d, J=7.2 Hz, 2H), 6.83 (d, J=7.3 Hz, 1H), 5.17 (s, 1H), 4.59 (dd, J=10.6, 2.0 Hz, 1H), 4.07 (dd, J=10.2, 2.7 Hz, 1H), 3.87 (d, J=13.7 Hz, 1H), 3.74 (td, J=11.2, 2.3 Hz, 1H), 3.50 (s, 1H), 3.33-3.47 (m, 4H), 2.39 (s, 1H), 1.45-1.94 (m, 7H), 1.24-1.35 (m, 9H), 1.01-1.14 (m, 9H); LC/MS (ESI+) m/z 552.8 (M+H)$^+$.

Example 40

(2S,3S,4S,5S)-4-{[(5-tert-butyl-2-methoxyphenyl)methyl]amino}-1-(cyclohexanecarbonyl)-3-(2-methoxypropan-2-yl)-5-(2-methoxypyridin-3-yl)pyrrolidine-2-carboxylic acid

Example 40A (2S,3R,4S,5S)-tert-butyl 1-(cyclohexanecarbonyl)-3-(2-methoxypropan-2-yl)-5-(2-methoxypyridin-3-yl)-4-nitropyrrolidine-2-carboxylate A solution of Core 39 (0.55 g, 1.391 mmol) and triethylamine (0.388 mL, 2.78 mmol) in dichloromethane (6.32 mL) at 25° C. was treated with cyclohexanecarbonyl chloride (0.233 mL, 1.739 mmol) dropwise. The mixture was stirred for 2 hours, and washed with saturated aqueous NaHCO$_3$ (3 mL) and 1 N aqueous NH$_4$OH (1 mL) solution. The mixture was concentrated. The crude material was dissolved in 1 mL dichloromethane and was loaded on a 12 g column eluting with a gradient of 0-70% ethyl acetate/heptanes over a period of 20 minutes to provide the title compound, (2S,3R,4S,5S)-tert-butyl 1-(cyclohexanecarbonyl)-3-(2-methoxypropan-2-yl)-5-(2-methoxypyridin-3-yl)-4-nitropyrrolidine-2-carboxylate (609 mg, 1.205 mmol, 87% yield). $^1$H NMR (400 MHz, dimethyl sulfoxide-d$_6$) δ ppm 8.05 (d, J=5.0 Hz, 1H), 7.99 (s, 1H), 6.90 (d, J=6.2 Hz, 1H), 5.64 (s, 1H), 5.58-5.49 (m, 1H), 4.67 (d, J=3.3 Hz, 1H), 3.93 (s, 3H), 3.23 (t, J=2.9 Hz, 1H), 3.16 (s, 3H), 2.18 (bs, 1H), 1.69 (d, J=16.3 Hz, 2H), 1.51 (s, 11H), 1.25 (d, J=14.5 Hz, 8H), 1.20-1.06 (m, 3H), 0.91-0.78 (m, 1H); MS (APCI+) m/z 506 (M+H)$^+$.

Example 40B (2S,3S,4S,5S)-tert-butyl 4-amino-1-(cyclohexanecarbonyl)-3-(2-methoxypropan-2-yl)-5-(2-methoxypyridin-3-yl)pyrrolidine-2-carboxylate To a solution of Example 40A (400 mg, 0.791 mmol) in tetrahydrofuran (12.000 mL) was added to Raney®-Nickel 2800, water slurry (555 mg, 4.26 mmol) under argon in a 250 mL SS pressure bottle and the mixture was shaken under 50 psi of hydrogen and heated at 50° C. for 16 hours. The reaction was filtered and the solvent was removed in vacuo and loaded on a 12 g column eluting with a gradient of 0-9% methanol/dichloromethane over a period of 20 minutes to provide the title compound, (2S,3S,4S,5S)-tert-butyl 4-amino-1-(cyclohexanecarbonyl)-3-(2-methoxypropan-2-yl)-5-(2-methoxypyridin-3-yl)pyrrolidine-2-carboxylate (330 mg, 0.694 mmol, 88% yield). $^1$H NMR (400 MHz, dimethyl sulfoxide-d$_6$) δ ppm 8.03 (bs, 2H), 6.92 (s, 1H), 5.22 (s, 1H), 4.39 (s, 1H), 3.93 (s, 3H), 3.75 (dd, J=7.4, 3.6 Hz, 1H), 3.14 (s, 3H), 2.35 (s, 1H), 2.08 (bs, 1H), 1.65 (m, 2H), 1.53 (bs, 2H), 1.46 (s, 9H), 1.38-1.24 (m, 2H), 1.20 (s, 3H), 1.17 (s, 3H), 1.12 (m, 2H), 0.90 (bs, 2H); MS (ESI+) m/z 476 (M+H)$^+$.

Example 40C (2S,3S,4S,5S)-4-{[(5-tert-butyl-2-methoxyphenyl) methyl]amino}-1-(cyclohexanecarbonyl)-3-(2-methoxypropan-2-yl)-5-(2-methoxypyridin-3-yl) pyrrolidine-2-carboxylic acid To a solution of 5-(tert-butyl)-2-methoxybenzaldehyde (30.6 mg, 0.151 mmol), Example 40B (60 mg, 0.126 mmol) and zinc(II) chloride (17.19 mg, 0.126 mmol) in sodium acetate/acetic acid buffer in methanol (pH=4, 1 mL) was added sodium cyanoborohydride (11.89 mg, 0.189 mmol) and the reaction was stirred at ambient temperature for 2 hours. The solvent was removed and the residue was chromatographed using a 12 g silica gel cartridge eluting with a gradient of 0-100% ethyl acetate/heptanes over a period of 20 minutes to give material (56 mg, 0.086 mmol, 68.1%) which was dissolved in trifluoroacetic acid (0.5 mL) and stirred at ambient temperature for 24 hours. The solvent was removed and the crude material was purified by reverse phase using the trifluoroacetic acid method to obtain (2S,3S,4S,5S)-4-((5-(tert-butyl)-2-methoxybenzyl)amino)-1-(cyclohexanecarbonyl)-3-(2-methoxypropan-2-yl)-5-(2-methoxypyridin-3-yl)pyrrolidine-2-carboxylic acid, trifluoroacetic acid salt, (36 mg, 0.051 mmol, 40.2% yield). $^1$H NMR (400 MHz, dimethyl sulfoxide-d$_6$) δ ppm 8.10 (d, J=4.9 Hz, 2H), 7.23 (dd, J=8.6, 2.5 Hz, 1H), 7.04 (d, J=2.6 Hz, 1H), 6.97 (d, J=6.4 Hz, 1H), 6.82 (d, J=8.6 Hz, 1H), 5.43 (s, 1H), 4.50 (s, 1H), 3.87 (s, 3H), 3.78 (d, J=13.7 Hz, 2H), 3.59 (s, 3H), 3.54 (d, J=13.4 Hz, 1H), 3.14 (s, 3H), 2.75 (m, 1H), 2.23 (bs, 1H), 1.74-1.47 (m, 5H), 1.23 (d, J=0.7 Hz, 9H), 1.22-1.17 (m, 7H), 1.11 (m, 3H), 0.86 (bs, 1H); MS (ESI+) m/z 596 (M+H)$^+$.

Example 41

(2S,3S,4S,5S)-4-{[(5-tert-butyl-2-methoxyphenyl) methyl]amino}-1-(cyclohexanecarbonyl)-5-[2-(dimethylamino)pyridin-3-yl]-3-(2-methoxypropan-2-yl) pyrrolidine-2-carboxylic acid

Example 41A (2S,3R,4S,5S)-tert-butyl 1-(cyclohexanecarbonyl)-5-(2-(dimethylamino)pyridin-3-yl)-3-(2-methoxypropan-2-yl)-4-nitropyrrolidine-2-carboxylate A solution of Core 38 (0.55 g, 1.346 mmol) and triethylamine (0.375 mL, 2.69 mmol) in dichloromethane (6.12 mL) at 25° C. was treated with cyclohexanecarbonyl chloride (0.225 mL, 1.683 mmol) dropwise, stirred for 2 hours, washed with saturated aqueous NaHCO$_3$ (3 mL) and with 1 N NH$_4$OH (1 mL) aqueous solution and concentrated to give a residue. The crude material was dissolved in 1 mL dichloromethane and loaded on a 12 g silica gel cartridge eluting with a gradient of 0-70% ethyl acetate/heptanes over a period of 20 minutes to provide the desired product, (2S,3R,4S,5S)-tert-butyl 1-(cyclohexanecarbonyl)-5-(2-(dimethylamino)pyridin-3-yl)-3-(2-methoxypropan-2-yl)-4-nitropyrrolidine-2-carboxylate (656 mg, 1.265 mmol, 94% yield). $^1$H NMR (400 MHz, dimethyl sulfoxide-d$_6$) δ ppm 8.24-8.14 (m, 1H), 8.01 (s, 1H), 6.94 (dd, J=7.7, 4.8 Hz, 1H), 5.78 (d, J=8.5 Hz, 1H), 5.58 (d, J=8.6 Hz, 1H), 4.68 (d, J=3.0 Hz, 1H), 3.25 (t, J=2.6 Hz, 1H), 3.17 (s, 3H), 2.80 (s, 6H), 2.12 (bs, 1H), 1.69 (m, 2H), 1.52 (s, 9H), 1.49 (bs, 2H), 1.29 (s, 3H), 1.27 (m, 1H), 1.24 (s, 3H), 1.20 (d, J=4.8 Hz, 2H), 1.12 (m, 2H), 0.90-0.82 (m, 1H); MS (APCI+) m/z 519 (M+H)$^+$.

Example 41B (2S,3S,4S,5S)-tert-butyl 4-amino-1-(cyclohexanecarbonyl)-5-(2-(dimethylamino)pyridin-3-yl)-3-(2-methoxypropan-2-yl)pyrrolidine-2-carboxylate To a solution of Example 41A (400 mg, 0.771 mmol) in tetrahydrofuran (11.700 mL) was added to Raney®-Nickel 2800, water slurry (550 mg, 4.59 mmol) in a 250 mL SS pressure bottle, flushed with argon 4 times, flushed with hydrogen (4.66 mg, 2.314 mmol) and shaken under 50 psi of hydrogen at room temperature overnight. The reaction mixture was filtered and the solvent was removed in vacuo. The crude material was purified using a 12 g silica gel cartridge eluting with a gradient of 0-9% methanol/dichloromethane over a period of 20 minutes to provide the title compound, (2S,3S,4S,5S)-tert-butyl 4-amino-1-(cyclohexanecarbonyl)-5-(2-(dimethylamino)pyridin-3-yl)-3-(2-methoxypropan-2-yl)pyrrolidine-2-carboxylate (334 mg, 0.683 mmol, 89% yield). $^1$H NMR (400 MHz, dimethyl sulfoxide-d$_6$) δ ppm 8.16 (d, J=4.6 Hz, 2H), 6.95 (dd, J=7.7, 4.8 Hz, 1H), 5.36 (d, J=7.1 Hz, 1H), 4.37 (d, J=3.8 Hz, 1H), 3.84 (s, 1H), 3.16 (s, 3H), 2.81 (s, 6H), 2.38 (t, J=3.6 Hz, 1H), 1.95 (bs, 1H), 1.66 (m, 1H), 1.58 (m, 1H), 1.46 (bs, 12H), 1.31 (m, 1H), 1.21 (s, 3H), 1.20 (s, 3H), 1.06 (bs, 4H); MS (ESI+) m/z 489 (M+H)$^+$.

Example 41C (2S,3S,4S,5S)-4-{[(5-tert-butyl-2-methoxyphenyl) methyl]amino}-1-(cyclohexanecarbonyl)-5-[2-(dimethylamino)pyridin-3-yl]-3-(2-methoxypropan-2-yl) pyrrolidine-2-carboxylic acid To a solution of 5-(tert-butyl)-2-methoxybenzaldehyde (29.8 mg, 0.147 mmol), Example 41B (60 mg, 0.123 mmol) and zinc(II) chloride (16.73 mg, 0.123 mmol) in sodium acetate/acetic acid buffer in methanol (pH=4, 1 mL) was added sodium cyanoborohydride (11.57 mg, 0.184 mmol) and the reaction was stirred at ambient temperature for 2 hours. The solvent was removed and the resulting crude material was chromatographed using a 12 g silica gel cartridge eluting with a gradient of 0-70% ethyl acetate/heptanes over a period of 20 minutes to give a residue (74 mg, 0.111 mmol, 91%) which was dissolved in trifluoroacetic acid (0.5 mL) and stirred at ambient temperature for 24 hours. The solvent was removed and the crude material was purified by reverse phase chromatography using the trifluoroacetic acid method to give (2S,3S,4S,5S)-4-((5-(tert-butyl)-2-methoxybenzyl)amino)-1-(cyclohexanecarbonyl)-5-(2-(dimethylamino)pyridin-3-yl)-3-(2-methoxypropan-2-yl)pyrrolidine-2-carboxylic acid, 2 trifluoroacetic acid salt, (69 mg, 0.082 mmol, 67.2% yield). $^1$H NMR (400 MHz, dimethyl sulfoxide-d$_6$) δ ppm 8.20 (dd, J=4.8, 1.8 Hz, 1H), 8.10 (s, 1H), 7.20 (dd, J=8.5, 2.6 Hz, 1H), 7.06 (d, J=2.5 Hz, 1H), 7.00 (dd, J=7.7, 4.8 Hz, 1H), 6.78 (d, J=8.6 Hz, 1H), 5.48 (d, J=6.6 Hz, 1H), 4.62 (d, J=1.9 Hz, 1H), 3.81 (d, J=13.6 Hz, 1H), 3.73 (d, J=6.7 Hz, 1H), 3.52 (s, 3H), 3.46

(d, J=13.7 Hz, 1H), 3.17 (d, J=1.0 Hz, 3H), 2.74 (s, 1H), 2.69 (d, J=1.0 Hz, 6H), 2.10 (bs, 1H), 1.70-1.43 (m, 4H), 1.25 (s, 3H), 1.21 (d, J=0.9 Hz, 13H), 1.06 (d, J=11.7 Hz, 3H), 0.85 (bs, 1H); MS (ESI+) m/z 609 (M+H)$^+$.

Example 42

(2S,3S,4S,5S)-3-tert-butyl-4-{[(5-tert-butyl-2-methoxyphenyl)methyl]amino}-1-[(1R*)-3,3-difluorocyclohexane-1-carbonyl]-5-[2-(dimethylamino)pyridin-3-yl]pyrrolidine-2-carboxylic acid Example 42A (2S,3R,4S,5S)-ethyl 3-(tert-butyl)-1-(3,3-difluorocyclohexanecarbonyl)-5-(2-(dimethylamino)pyridin-3-yl)-4-nitropyrrolidine-2-carboxylate To 3,3-difluorocyclohexanecarboxylic acid [CAS#849669-20-1] (393 mg, 2.395 mmol) and a few drops of N,N-dimethylformamide in dichloromethane (8 mL) was added oxalyl dichloride (760 mg, 5.99 mmol, 3 mL, 2 M in dichloromethane). The mixture was stirred at ambient temperature for 30 minutes, the solvent removed under pressure, and fresh dichloromethane (5 mL) was added and removed again. The residue was dissolved in dichloromethane (2 mL) and added dropwise to the solution of (2S,3R,4S,5S)-ethyl 3-(tert-butyl)-5-(2-(dimethylamino)pyridin-3-yl)-4-nitropyrrolidine-2-carboxylate (Core 11, 728 mg, 2.0 mmol) in dichloromethane (10 mL) cooling in an ice bath. The mixture was stirred for 1 hour at ambient temperature, was washed with brine and dried over MgSO$_4$. After filtration, the solvent was removed and the residue was purified via chromatography on a 40 g silica gel cartridge, eluting with ethyl acetate in heptane at 0-40% gradient to provide (2S,3R,4S,5S)-ethyl 3-(tert-butyl)-1-(3,3-difluorocyclohexanecarbonyl)-5-(2-(dimethylamino)pyridin-3-yl)-4-nitropyrrolidine-2-carboxylate 655 mg (64.3% yield), which was used in next step directly. LC/MS (APCI+) m/z 511 (M+H)$^+$.

Example 42B (2S,3S,4S,5S)-ethyl 4-amino-3-(tert-butyl)-1-(3,3-difluorocyclohexanecarbonyl)-5-(2-(dimethylamino)pyridin-3-yl)pyrrolidine-2-carboxylate The title compound was prepared according to the procedure described in Example 10C, substituting Example 42A for Example 10B. LC/MS (APCI+) m/z 447.3 (M+H)$^+$.

Example 42C (2S,3S,4S,5S)-methyl 3-(tert-butyl)-4-((5-(tert-butyl)-2-methoxybenzyl)amino)-1-((S)-3,3-difluorocyclohexanecarbonyl)-5-(2-(dimethylamino)pyridin-3-yl)pyrrolidine-2-carboxylate and Example 42D (2S,3S,4S,5S)-methyl 3-(tert-butyl)-4-((5-(tert-butyl)-2-methoxybenzyl)amino)-1-((R)-3,3-difluorocyclohexanecarbonyl)-5-(2-(dimethylamino)pyridin-3-yl)pyrrolidine-2-carboxylate A mixture of 5-(tert-butyl)-2-methoxybenzaldehyde [CAS# PH011292] (80 mg, 0.416 mmol), Example 42B (200 mg, 0.416 mmol) and zinc(II) chloride (11.34 mg, 0.083 mmol) in sodium acetate/acetic acid buffer in methanol (pH=4, 2 mL) was stirred at ambient temperature for 10 minutes before sodium cyanoborohydride (39.2 mg, 0.624 mmol) was added. The mixture was stirred for 1 hour and the solvent was removed under pressure. The residue was purified via chromatography on a 40 g silica gel cartridge, eluting with ethyl acetate/methanol (10:1) in heptane 0-40% to yield the first compound to elute as Example 42C (105 mg, 38.4% yield). LC/MS (APCI+) m/z 657.62 (M+H)$^+$. The second compound to elute was Example 42D 110 mg (40.2% yield). LC/MS (APCI+) m/z 657.67 (M+H)$^+$.

Example 42E (2S,3S,4S,5S)-3-(tert-butyl)-4-(5-(tert-butyl)-2-methoxybenzamido)-1-((R)-3,3-difluorocyclohexanecarbonyl)-5-(2-(dimethylamino)pyridin-3-yl)pyrrolidine-2-carboxylic acid A mixture of Example 42D (105 mg, 0.163 mmol) and 6 M LiOH (0.5 mL) in methanol (2 mL) was stirred at 50° C. for 3 hours. The pH was adjusted to 4-5 with 4 M HCl in dioxane. The solvent was removed under pressure and the residue was purified via chromatography on a 12 g silica gel cartridge, eluting with methanol in dichloromethane at 0-20% gradient to provide the title compound 93 mg (91% yield). $^1$H NMR (400 MHz, dimethyl sulfoxide-d$_6$) δ ppm 8.19 (s, 2H), 7.12 (dd, J=8.5, 2.6 Hz, 1H), 6.99 (t, J=2.8 Hz, 2H), 6.71 (dd, J=8.5, 1.5 Hz, 1H), 5.40 (t, J=5.9 Hz, 1H), 4.55 (s, 1H), 3.70-3.62 (m, 1H), 3.52 (d, J=5.5 Hz, 1H), 3.43 (d, J=1.3 Hz, 3H), 3.29 (d, J=13.8 Hz, 1H), 3.19 (s, 1H), 2.64 (s, 1H), 2.60 (s, 6H), 2.43 (s, 1H), 1.54 (s, 6H), 1.25 (s, 2H), 1.19 (s, 9H), 1.01 (s, 9H); MS (ESI+) m/z 629.2 (M+H)$^+$.

Example 43

(2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-[2-(dimethylamino)pyridin-3-yl]pyrrolidine-2-carboxylic acid Example 43A (2S,3R,4S,5S)-ethyl 3-(tert-butyl)-1-(chroman-2-carbonyl)-5-(2-(dimethylamino)pyridin-3-yl)-4-nitropyrrolidine-2-carboxylate A mixture of chroman-2-carboxylic acid (0.587 g, 3.29 mmol) and 1-chloro-N,N,2-trimethylprop-1-en-1-amine (Ghosez reagent, 0.726 mL, 5.49 mmol) in dichloromethane (20 mL) was stirred at ambient temperature for 10 minutes. (2S,3R,4S,5S)-Ethyl 3-(tert-butyl)-5-(2-(dimethylamino)pyridin-3-yl)-4-nitropyrrolidine-2-carboxylate (Core 11, 1 g, 2.74 mmol) in pyridine was added. The mixture was stirred for 1 hour at ambient temperature. Dichloromethane (10 mL) was added and the organic layer was washed with brine and dried over MgSO$_4$, filtered, and concentrated. The residue was purified via chromatography on a 24 g silica gel cartridge, eluting with ethyl acetate in heptane at 0-40% gradient to provide the title compound, 961 mg (67% yield). LC/MS (APCI+) m/z 525 (M+H)$^+$.

Example 43B (2S,3S,4S,5S)-ethyl 4-amino-3-(tert-butyl)-1-(chroman-2-carbonyl)-5-(2-(dimethylamino)pyridin-3-yl)pyrrolidine-2-carboxylate Example 43A (960 mg, 1.830 mmol) in tetrahydrofuran (30 mL) was added to a Raney®-Nickel 2800, water slurry (3 g, 23.00 mmol) in a 50 mL pressure bottle. The mixture was stirred for 16 hours at 50° C. flushing with 50 psi hydrogen, and then filtered and concentrated to provide the title compound 900 mg (99% yield). LC/MS (APCI+) m/z 495.35 (M+H)+.

Example 43C (2S,3S,4S,5S)-ethyl 4-amino-3-(tert-butyl)-1-((S)-chroman-2-carbonyl)-5-(2-(dimethylamino)pyridin-3-yl)pyrrolidine-2-carboxylate and

Example 43D (2S,3S,4S,5S)-ethyl 4-amino-3-(tert-butyl)-1-((R*)-chroman-2-carbonyl)-5-(2-(dimethylamino)pyridin-3-yl)pyrrolidine-2-carboxylate The diastereomers of Example 43B (960 mg, 1.94 mmol) were isolated via HPLC [Method: 10_29_100_CH₃CN_trifluoroacetic acid_120 mL_11 minute; Injection Vol: 1500 μL; Mobile Phase: CAN/trifluoroacetic acid; Column: Waters Sunfire™ Prep C8 OBD 10 um 50×150 mm] to yield the first compound to elute, Example 43C 340 mg (35.4% yield). Collection time: 6.66~7.35 minutes. LC/MS (APCI+) m/z 459.3 (M+H)+. The second compound to elute was Example 43D (350 mg (36.5% yield). Collection time: 7.41~8.32 minutes. LC/MS (APCI+) m/z 459.3 (M+H)+.

Example 43E (2S,3S,4S,5S)-3-tert-butyl-4-[(5-tert-butyl-2-methoxy-phenyl)methylamino]-1-[(2S*)-chromane-2-carbonyl]-5-[2-(dimethylamino)-3-pyridyl]pyrrolidine-2-carboxylic acid A mixture of 5-(tert-butyl)-2-methoxybenzaldehyde (23.32 mg, 0.121 mmol), Example 43C (60 mg, 0.121 mmol) and zinc (II) chloride (3.31 mg, 0.024 mmol) in sodium acetate/acetic acid buffer in methanol (pH=4, 2 mL) was stirred at ambient temperature for 10 minutes to give a colorless solution. Sodium cyanoborohydride (11.43 mg, 0.182 mmol) was added and the mixture was stirred for 1 hour. The solvent was removed under pressure, dichloromethane (10 mL) was added, and the mixture was filtered on a 10 g silica gel column, and concentrated. The residue was dissolved in methanol (1.5 mL) and 4 M aqueous LiOH (0.5 mL). The mixture was stirred at 50° C. for 3 hours, the pH was adjusted to 4~5 by adding 4 M HCl in dioxane, and the mixture was concentrated. The residue was dissolved in dichloromethane (1 mL), filtered through a syringe, and purified via chromatography on a 4 g silica gel cartridge, eluting with methanol in dichloromethane at 0-20% gradient to yield the title compound 39 mg (50.0% yield). ¹H NMR (400 MHz, dimethyl sulfoxide-d₆) δ ppm 8.17 (d, J=4.6 Hz, 1H), 7.12 (dd, J=8.5, 2.5 Hz, 1H), 7.06-6.92 (m, 5H), 6.79-6.67 (m, 3H), 5.64 (s, 1H), 4.64 (s, 1H), 3.64 (d, J=13.7 Hz, 1H), 3.56 (d, J=6.7 Hz, 1H), 3.46 (s, 3H), 3.28 (d, J=13.7 Hz, 1H), 3.19 (s, 1H), 2.64 (d, J=14.7 Hz, 3H), 2.55 (s, 6H), 2.44 (s, 1H), 1.81 (s, 2H), 1.19 (s, 9H), 1.02 (s, 9H); MS (ESI+) m/z 643.2 (M+H)+.

Example 44

(2S,3S,4S,5S)-3-tert-butyl-4-{[(5-tert-butyl-2-methoxyphenyl)methyl]amino}-1-[(1S*)-3,3-difluorocyclohexane-1-carbonyl]-5-[2-(dimethylamino)pyridin-3-yl]pyrrolidine-2-carboxylic acid The title compound was prepared according to the procedure described in Example 42E, substituting Example 42C for Example 42D. ¹H NMR (400 MHz, dimethyl sulfoxide-d₆) δ ppm 8.20 (d, J=5.4 Hz, 2H), 7.13 (dt, J=8.6, 2.5 Hz, 1H), 6.99 (t, J=3.1 Hz, 2H), 6.73-6.68 (m, 1H), 5.40 (t, J=5.9 Hz, 1H), 4.53 (d, J=14.8 Hz, 1H), 3.65 (dd, J=13.8, 7.1 Hz, 2H), 3.53 (d, J=6.0 Hz, 1H), 3.44 (d, J=1.0 Hz, 3H), 3.30 (dd, J=13.8, 4.7 Hz, 2H), 2.64 (s, 1H), 2.60 (d, J=1.1 Hz, 6H), 2.43 (s, 1H), 1.85-1.46 (m, 6H), 1.25 (s, 2H), 1.19 (s, 9H), 1.01 (s, 9H); MS (ESI+) m/z 629.2 (M+H)+.

Example 45

(2S,3S,4S,5S)-3-tert-butyl-4-{[(5-tert-butyl-2-methoxyphenyl)methyl]amino}-5-[2-(difluoromethoxy)phenyl]-1-[(2R)-oxane-2-carbonyl]pyrrolidine-2-carboxylic acid

Example 45A (2S,3R,4S,5S)-ethyl 3-(tert-butyl)-5-(2-(difluoromethoxy)phenyl)-4-nitro-1-((S)-tetrahydro-2H-pyran-2-carbonyl)pyrrolidine-2-carboxylate and

Example 45B (2S,3R,4S,5S)-ethyl 3-(tert-butyl)-5-(2-(difluoromethoxy)phenyl)-4-nitro-1-((R)-tetrahydro-2H-pyran-2-carbonyl)pyrrolidine-2-carboxylate A mixture of tetrahydro-2H-pyran-2-carboxylic acid [CAS#51673-83-7] (323 mg, 2.485 mmol) and 1-chloro-N,N,2-trimethylprop-1-en-1-amine (Ghosez reagent, 0.548 mL, 4.14 mmol) in dichloromethane (30 mL) was stirred at ambient temperature for 10 minutes. Core 15 (800 mg, 2.07 mmol) in pyridine/tetrahydrofuran (1:1, 4 mL) was added, and the mixture was stirred for 1 hour. The mixture was washed with brine, dried over MgSO₄, filtered, and concentrated. The residue was purified via chromatography on an 80 g silica gel cartridge, eluting with ethyl acetate in heptane at 0-40% gradient to yield Example 45A (520 mg, 50.4% yield) as the first compound to elute. LC/MS (APCI+) m/z 499.42 (M+H)+. Example 45B (350 mg, 33.9% yield) was obtained as the second compound to elute. LC/MS (APCI+) m/z 499.29 (M+H)+.

Example 45C (2S,3S,4S,5S)-ethyl 4-amino-3-(tert-butyl)-5-(2-(difluoromethoxy)phenyl)-1-((R)-tetrahydro-2H-pyran-2-carbonyl)pyrrolidine-2-carboxylate The title compound was prepared according to the procedure described in Example 36C, substituting Example 45B for Example 36B. MS (ESI+) m/z 469.1 (M+H)+.

Example 45D (2S,3S,4S,5S)-3-tert-butyl-4-[(5-tert-butyl-2-methoxy-phenyl)methylamino]-5-[2-(difluoromethoxy)phenyl]-1-[(2R)-tetrahydropyran-2-carbonyl]pyrrolidine-2-carboxylic acid A mixture of 5-(tert-butyl)-2-methoxybenzaldehyde (24.62 mg, 0.128 mmol), Example 45C (60 mg, 0.128 mmol) and zinc (II) chloride (3.49 mg, 0.026 mmol) in sodium acetate/acetic acid buffer in methanol (pH=4, 2 mL) was stirred at ambient temperature for 10 minutes. Sodium cyanoborohydride (12.07 mg, 0.192 mmol) was added, the mixture was stirred for another 1 hour, and dichloromethane (10 mL) added. The organic layer was washed with brine, dried over MgSO$_4$, filtered and concentrated. The residue was purified via chromatography on 12 g silica gel cartridge, eluting with ethyl acetate/methanol (10:1) in heptane at 0-40% gradient to yield (2S,3S,4S,5S)-ethyl 3-(tert-butyl)-4-((5-(tert-butyl)-2-methoxybenzyl)amino)-5-(2-(difluoromethoxy)phenyl)-1-((R)-tetrahydro-2H-pyran-2-carbonyl)pyrrolidine-2-carboxylate, which was dissolved in methanol (1.5 mL) and 4 M aqueous LiOH (0.5 mL). The mixture was stirred at 50° C. for 3 hours, the pH was adjusted to 4-5, and the mixture was concentrated. The residue was dissolved in dichloromethane (2 mL) and filtered through a syringe filter. The crude material was purified via chromatography on a 4 g silica gel cartridge, eluting with methanol in dichloromethane at 0-20% gradient to provide the title compound, 44 mg (55.7% yield). $^1$H NMR (400 MHz, dimethyl sulfoxide-d$_6$) δ ppm 7.69 (s, 1H), 7.35 (m, 1H), 7.24-7.10 (m, 3H), 7.03 (m, 1H), 6.8 (m, 1H), 5.41 (s, 1H), 4.91 (s, 1H), 4.14 (s, 1H), 3.90 (s, 1H), 3.64 (s, 2H), 3.54 (d, J=25.9 Hz, 3H), 3.48 (m, 2H), 3.37 (m, 1H), 2.46 (q, J=2.0 Hz, 1H), 1.68-1.42 (m, 6H), 1.26 (s, 9H), 1.05 (s, 9H); MS (ESI+) m/z 617.2 (M+H)$^+$.

Example 46

(2S,3S,4S,5S)-1-(bicyclo[3.1.0]hexane-6-carbonyl)-3-tert-butyl-4-{[(5-tert-butyl-2-methoxyphenyl)methyl]amino}-5-phenylpyrrolidine-2-carboxylic acid Example 46A (2S,3S,4S,5S)-1-(bicyclo[3.1.0]hexane-6-carbonyl)-3-tert-butyl-4-(5-tert-butyl-2-methoxy-benzylamino)-5-phenyl-pyrrolidine-2-carboxylic acid ethyl ester To a stirred solution of bicyclo[3.1.0]hexane-6-carboxylic acid (28 mg, 0.22 mmol, 1.3 eq) at 0° C. in dichloromethane (1 mL) was added Ghosez's reagent (1-chloro-N,N,2-trimethyl-1-propenylamine, 67 µL, 0.51 mmol, 3.0 eq). The reaction mixture was stirred at 0° C. for 5 minutes and a solution of (2S,3S,4S,5S)-3-tert-butyl-4-(5-tert-butyl-2-methoxy-benzylamino)-5-phenyl-pyrrolidine-2-carboxylic acid ethyl ester (Example 34D, 80 mg, 0.17 mmol, 1.0 eq) and diisopropylethylamine (118 µL, 0.68 mmol, 4.0 eq) in dichloromethane (1 mL) was added. The reaction mixture was stirred at 0° C. for 10 minutes and at room temperature for 72 hours. The reaction mixture was washed with water and the organic phase was concentrated to dryness. The residue was purified by flash chromatography (heptane/ethyl acetate 100/0 to 85/15) to provide the title compound (60 mg, 61%). LC/MS (ESI+) m/z 575.9 (M+H)$^+$.

Example 46B (2S,3S,4S,5S)-1-(bicyclo[3.1.0]hexane-6-carbonyl)-3-tert-butyl-4-(5-tert-butyl-2-methoxy-benzylamino)-5-phenyl-pyrrolidine-2-carboxylic acid A solution of (2S,3S,4S,5S)-1-(bicyclo[3.1.0]hexane-6-carbonyl)-3-tert-butyl-4-(5-tert-butyl-2-methoxy-benzylamino)-5-phenyl-pyrrolidine-2-carboxylic acid ethyl ester (60 mg, 0.10 mmol, 1.0 eq) in methanol (2 mL) was treated with LiOH 1.0 M in water (300 µL, 0.30 mmol, 3.0 eq) at room temperature and was stirred overnight at 45° C. Aqueous 1 N HCl was added and the solvent was removed under vacuum. The residue was purified by flash chromatography on silica gel (dichloromethane/methanol 100/0 to 92/8) to provide the title compound (38 mg, 70%). $^1$H NMR (400 MHz, CDCl$_3$) δ ppm 7.26-7.47 (m, 5H), 7.08 (d, J=2.2 Hz, 2H), 6.58-6.71 (m, 1H), 5.21 (d, J=6.1 Hz, 1H), 4.80 (s, 1H), 4.01-4.15 (m, 1H), 3.55 (d, J=14.0 Hz, 1H), 3.51 (s, 1H), 3.32 (d, J=6.3 Hz, 1H), 3.19-3.29 (m, 4H), 2.44 (s, 1H), 2.21 (t, J=2.9 Hz, 1H), 1.84-2.06 (m, 2H), 1.62-1.82 (m, 3H), 1.33-1.46 (m, 1H), 1.19-1.31 (m, 9H), 0.97-1.09 (m, 9H); LC/MS (ESI+) m/z 547.8 (M+H)$^+$.

Example 47

(2S,3S,4S,5S)-3-tert-butyl-1-(cyclohexanecarbonyl)-4-({[2-methoxy-5-(trimethylsilyl)pyridin-3-yl]methyl}amino)-5-phenylpyrrolidine-2-carboxylic acid Example 47A (2S,3S,4S,5S)-3-tert-butyl-1-cyclohexanecarbonyl-4-[(2-methoxy-5-trimethylsilanyl-pyridin-3-ylmethyl)-amino]-5-phenyl-pyrrolidine-2-carboxylic acid ethyl ester NaBH$_3$CN (10 mg, 0.15 mmol, 1.3 eq) was added to a solution of Example 7B (50 mg, 0.12 mmol, 1.0 eq) and 2-methoxy-5-trimethylsilanyl-pyridine-3-carbaldehyde (31 mg, 0.14 mmol, 1.2 eq) in acetic acid/sodium acetate/methanol buffer (2 mL). The reaction mixture was stirred at room temperature for 30 minutes. The reaction mixture was concentrated and the residue was partitioned between dichloromethane and aqueous NaHCO$_3$. The organic phase was dried on Na$_2$SO$_4$, filtered and concentrated. The residue was purified on silica gel (dichloromethane/ethyl acetate 100/0 to 95/5) to give the title compound (55 mg, 74% yield). LC/MS (ESI+) m/z 594.0 (M+H)$^+$.

Example 47D (2S,3S,4S,5S)-3-tert-butyl-1-cyclohexanecarbonyl-4-[(2-methoxy-5-trimethylsilanyl-pyridin-3-ylmethyl)-amino]-5-phenyl-pyrrolidine-2-carboxylic acid LiOH (19 mg, 0.45 mmol, 5.0 eq) was added to a solution of (2S,3S,4S,5S)-3-tert-butyl-1-cyclohexanecarbonyl-4-[(2-methoxy-5-trimethylsilanyl-pyridin-3-ylmethyl)-amino]-5-phenyl-pyrrolidine-2-carboxylic acid ethyl ester (55 mg, 0.09 mmol, 1.0 eq) in tetrahydrofuran/methanol/water (1.5/1.5/1). The reaction mixture was stirred at 45° C. overnight. The reaction mixture was acidified with aqueous HCl 1 M (1 eq/LiOH). The mixture was concentrated and extracted with dichloromethane. The organic phase was concentrated. The residue was purified on silica gel (dichloromethane/methanol 100/0 to 95/5) to give the title compound (50 mg, 96% yield). $^1$H NMR (400 MHz, CDCl$_3$) δ ppm 8.18 (d, J=1.5 Hz, 1H), 7.27-7.52 (m, 4H), 7.17 (d, J=5.5 Hz, 2H), 5.26 (d, J=6.1 Hz, 1H), 4.67 (s, 1H), 3.94 (d, J=14.0 Hz, 1H), 3.52 (d, J=14.0 Hz, 1H), 3.46 (s, 3H), 3.29 (d, J=6.1 Hz, 1H), 2.85-3.04 (m, 1H), 2.39 (s, 1H), 1.59-1.90 (m, 6H), 1.10-1.55 (m, 4H), 0.88-1.10 (m, 9H), 0.07-0.28 (m, 9H); LC/MS (ESI+) m/z 566.5 (M+H)$^+$.

Example 48

(2S,3S,4S,5S)-3-tert-butyl-4-{[(2-tert-butyl-5-methoxypyridin-4-yl)methyl]amino}-1-(cyclohexanecarbonyl)-5-phenylpyrrolidine-2-carboxylic acid

Example 48A (2S,3S,4S,5S)-ethyl 3-(tert-butyl)-4-(((2-(tert-butyl)-5-methoxypyridin-4-yl)methyl)amino)-1-(cyclohexanecarbonyl)-5-phenylpyrrolidine-2-carboxylate 2-(tert-Butyl)-5-methoxyisonicotinaldehyde (0.040 g, 0.207 mmol) and (2S,3S,4S,5S)-ethyl 4-amino-3-(tert-butyl)-1-(cyclohexanecarbonyl)-5-phenylpyrrolidine-2-carboxylate (Example 7B, 0.083 g, 0.207 mmol) were mixed in methanol (2 mL), and the reaction was stirred at room temperature for 1 hour. Sodium cyanoborohydride (0.065 g, 1.035 mmol) was then added in one portion, and the reaction continued to stir at room temperature overnight. After this time, the methanol was evaporated in vacuo, and the residue was taken up in $CH_2Cl_2$ and water and transferred to a separatory funnel. The phases were separated, and the aqueous layer was extracted twice more with $CH_2Cl_2$. The combined organics were dried over $Na_2SO_4$ filtered, and concentrated in vacuo. The crude title compound was taken into the next reaction without further purification. MS (APCI+) m/z 578.6 $(M+H)^+$.

Example 48B (2S,3S,4S,5S)-3-tert-butyl-4-{[(2-tert-butyl-5-methoxypyridin-4-yl)methyl]amino}-1-(cyclohexanecarbonyl)-5-phenylpyrrolidine-2-carboxylic acid Example 48A (0.120 g, 0.207 mmol) and lithium hydroxide (1 M aqueous) (1.7 mL, 1.7 mmol) were stirred in tetrahydrofuran (1.7 mL) and methanol (1.7 mL) at 45° C. for 2 hours. The mixture was cooled to room temperature and acidified to pH 1 with 1 N aqueous HCl. The mixture was concentrated in vacuo, and the crude product was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to provide the title compound (0.0356 g, 31% yield). $^1H$ NMR (400 MHz, dimethyl sulfoxide-$d_6$) δ ppm 8.08 (s, 1H), 7.59 (m, 2H), 7.35-7.24 (m, 3H), 7.06 (s, 1H), 5.25 (m, 1H), 4.49 (d, J=2.4 Hz, 1H), 3.71 (s, 3H), 3.65-3.54 (m, 2H), 3.38 (m, 1H), 2.38 (m, 1H), 2.24 (m, 1H), 1.65-1.02 (m, 9H), 1.25 (s, 9H), 0.98 (s, 9H), 0.77 (m, 1H); MS (ESI+) m/z 550.3 $(M+H)^+$.

Example 49

(2S,3S,4S,5S)-3-tert-butyl-1-[(1R)-3,3-difluorocyclohexane-1-carbonyl]-4-({[2-methoxy-5-(trifluoromethyl)pyridin-3-yl]methyl}amino)-5-phenylpyrrolidine-2-carboxylic acid

Example 49A (2S,3S,4S,5S)-3-tert-butyl-1-((R)-3,3-difluoro-cyclohexanecarbonyl)-4-[(2-methoxy-5-trifluoromethyl-pyridin-3-ylmethyl)-amino]-5-phenyl-pyrrolidine-2-carboxylic acid ethyl ester $NaBH_3CN$ (6 mg, 0.12 mmol, 1.3 eq) was added to a solution of (2S,3S,4S,5S)-4-amino-3-tert-butyl-1-((R)-3,3-difluoro-cyclohexanecarbonyl)-5-phenyl-pyrrolidine-2-carboxylic acid ethyl ester (Example 31B, 31 mg, 0.07 mmol, 1.0 eq) and 2-methoxy-5-(trifluoromethyl)nicotinaldehyde (17 mg, 0.085 mmol, 1.2 eq) in acetic acid/sodium acetate/methanol buffer (2 mL). The solution was stirred at room temperature for 30 minutes. The reaction mixture was concentrated and the residue was partitioned between dichloromethane and water. The organic phase was dried on $Na_2SO_4$, filtered and concentrated. The residue was purified by chromatography on silica gel (dichloromethane/ethyl acetate 100/0 to 95/5) to give the title compound which was used in the next step. LC/MS (ESI+) m/z 626.5 $(M+H)^+$.

Example 49B (2S,3S,4S,5S)-3-tert-butyl-1-((R)-3,3-difluoro-cyclohexanecarbonyl)-4-[(2-methoxy-5-trifluoromethyl-pyridin-3-ylmethyl)-amino]-5-phenyl-pyrrolidine-2-carboxylic acid LiOH (15 mg, 0.35 mmol, 5.0 eq) was added to a solution of (2S,3S,4S,5S)-3-tert-butyl-1-((R)-3,3-difluoro-cyclohexanecarbonyl)-4-[(2-methoxy-5-trifluoromethyl-pyridin-3-ylmethyl)-amino]-5-phenyl-pyrrolidine-2-carboxylic acid ethyl ester (31 mg, 0.07 mmol, 1.0 eq) in methanol/tetrahydrofuran/water (1.5/1.5/1). The reaction mixture was stirred at 45° C. overnight. The reaction mixture was acidified with aqueous HCl 1 M (1 eq/LiOH). The mixture was concentrated and extracted with dichloromethane. The organic phase was concentrated. The residue was purified by chromatography on silica gel (dichloromethane/methanol 100/0 to 95/5) to give the title compound (29 mg, 66% yield over 2 steps). $^1H$ NMR (300 MHz, $CDCl_3$) δ ppm 8.28-8.45 (m, 1H), 7.59 (br. s., 1H), 7.34-7.52 (m, 3H), 7.19 (d, J=6.5 Hz, 2H), 5.31 (d, J=5.9 Hz, 2H), 4.62-4.75 (m, 1H), 3.92 (d, J=14.1 Hz, 1H), 3.69-3.81 (m, 3H), 3.60-3.65 (m, 3H), 3.35 (d, J=5.9 Hz, 2H), 2.35-2.60 (m, 1H), 2.05-2.28 (m, 1H), 1.20-2.01 (m, 4H), 0.97-1.17 (m, 9H); LC/MS (ESI+) m/z 598.5 $(M+H)^+$.

Example 50

(2S,3S,4S,5S)-3-tert-butyl-4-{[(5-tert-butyl-2-methoxyphenyl)methyl]amino}-5-(2-fluorophenyl)-1-[(2R)-oxane-2-carbonyl]pyrrolidine-2-carboxylic acid

Example 50A ethyl (2S,3R,4S,5S)-3-(tert-butyl)-5-(2-fluorophenyl)-4-nitro-1-((R)-tetrahydro-2H-pyran-2-carbonyl)pyrrolidine-2-carboxylate Tetrahydropyran-2-carboxylic acid (318.1 mg, 2.444 mmol) was dissolved in dichloromethane (10 mL). Oxalyl chloride (436.5 mg, 3.44 mmol) was added followed by N,N-dimethylformamide (25 μL). The reaction was stirred at room temperature for 3 hours, at which point it was concentrated, redissolved in dichloromethane (1 mL), and concentrated again. The residue was taken up in dichloromethane (3×1 mL) and added to a solution of Core 23 (540.8 mg, 1.598 mmol) and triethylamine (500 μL, 3.59 mmol) in dichloromethane (10 mL). The reaction was stirred at ambient temperature for 17 hours. After this time, the mixture was diluted with $CH_2Cl_2$ (100 mL) and washed twice with saturated aqueous $NaHCO_3$ and once with brine. The organic layer was dried over $Na_2SO_4$, filtered, and concentrated. The residue was purified by silica gel chromatography (5% to 40% ethyl acetate in heptanes). The title compound was the second eluting diastereomer (212.8 mg, 30%). $^1$H NMR (400 MHz, dimethyl sulfoxide-$d_6$, 120° C.) δ ppm 7.73-7.61 (m, 1H), 7.31-7.22 (m, 1H), 7.06 (dd, J=10.1, 8.2 Hz, 2H), 5.81 (s, 1H), 5.51 (dd, J=8.8, 2.5 Hz, 1H), 5.11 (s, 1H), 4.29 (q, J=7.1 Hz, 2H), 3.79 (s, 1H), 3.33 (s, 1H), 1.95 (s, 1H), 1.78 (s, 1H), 1.50 (d, J=52.5 Hz, 4H), 1.29 (t, J=3.8 Hz, 3H), 1.26 (d, J=2.4 Hz, 2H), 1.02 (s, 9H); MS (ESI+) m/z 451 (M+H)$^+$.

Example 50B ethyl (2S,3S,4S,5S)-4-amino-3-(tert-butyl)-5-(2-fluorophenyl)-1-((R)-tetrahydro-2H-pyran-2-carbonyl)pyrrolidine-2-carboxylate Example 50A (212.8 mg, 0.472 mmol) and tetrahydrofuran (4 mL) were added to Raney®-Nickel 2800, water slurry (475 mg, 3.64 mmol) in a 20 mL pressure bottle and the mixture was shaken for 16 hours at 50 psi H$_2$ and ambient temperature. The reaction was filtered and concentrated to provide the title compound (196 mg, 99%). $^1$H NMR (400 MHz, dimethyl sulfoxide-$d_6$, 120° C.) δ ppm 7.77-7.65 (m, 1H), 7.30-7.19 (m, 1H), 7.14-7.01 (m, 2H), 5.30 (d, J=6.9 Hz, 1H), 4.20 (q, J=7.1 Hz, 2H), 3.83 (d, J=47.7 Hz, 2H), 3.72-3.64 (m, 1H), 2.13 (s, 1H), 1.83-1.71 (m, 2H), 1.37 (s, 6H), 1.25 (t, J=7.1 Hz, 3H), 0.99 (d, J=1.7 Hz, 9H); MS (ESI+) m/z 421 (M+H)$^+$.

Example 50C ethyl (2S,3S,4S,5S)-3-(tert-butyl)-4-((5-(tert-butyl)-2-methoxybenzyl)amino)-5-(2-fluorophenyl)-1-((R)-tetrahydro-2H-pyran-2-carbonyl)pyrrolidine-2-carboxylate Example 50B (51.0 mg, 0.121 mmol) and 5-(tert-butyl)-2-methoxybenzenecarbaldehyde (54.7 mg, 0.285 mmol) were dissolved in methanol (1 mL) and stirred at ambient temperature for 1 hour. Sodium cyanoborohydride (54.7 mg, 0.870 mmol) was added and the reaction was stirred at ambient temperature for an additional 16 hours. The reaction was diluted with dimethyl sulfoxide (1 mL), filtered and purified by reverse phase chromatography using the ammonium acetate method to provide the title compound (47.2 mg, 65%). $^1$H NMR (400 MHz, dimethyl sulfoxide-$d_6$, 120° C.) δ ppm 7.67 (s, 1H), 7.24 (d, J=8.5 Hz, 1H), 7.11 (dd, J=8.5, 2.6 Hz, 1H), 7.05 (t, J=9.7 Hz, 2H), 6.91 (d, J=2.6 Hz, 1H), 6.72 (d, J=8.5 Hz, 1H), 5.36 (s, 1H), 4.89 (s, 1H), 4.14 (qd, J=7.1, 1.8 Hz, 2H), 3.88 (d, J=50.1 Hz, 2H), 3.51 (s, 3H), 3.49-3.39 (m, 3H), 3.32 (d, J=13.5 Hz, 1H), 2.46-2.46 (m, 1H), 1.79 (s, 1H), 1.67-1.36 (m, 5H), 1.19 (s, 12H), 0.98 (s, 9H); MS (ESI+) m/z 597 (M+H)$^+$.

Example 50D (2S,3S,4S,5S)-3-tert-butyl-4-{[(5-tert-butyl-2-methoxyphenyl)methyl]amino}-5-(2-fluorophenyl)-1-[(2R)-oxane-2-carbonyl]pyrrolidine-2-carboxylic acid Example 50C (44.2 mg, 0.074 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (40.0 mg, 79%) as the trifluoroacetic acid salt. $^1$H NMR (400 MHz, dimethyl sulfoxide-$d_6$, 120° C.) δ ppm 7.65 (s, 1H), 7.34-7.23 (m, 1H), 7.20 (dd, J=8.6, 2.6 Hz, 1H), 7.12 (q, J=8.6, 8.0 Hz, 2H), 7.02 (d, J=2.5 Hz, 1H), 6.79 (d, J=8.6 Hz, 1H), 5.43 (d, J=6.9 Hz, 1H), 4.87 (s, 1H), 4.03 (s, 1H), 3.84 (s, 2H), 3.73 (d, J=13.7 Hz, 1H), 3.64 (d, J=7.0 Hz, 1H), 3.57 (s, 3H), 3.49-3.41 (m, 1H), 2.56 (s, 1H), 1.79 (s, 1H), 1.61-1.39 (m, 5H), 1.21 (s, 9H), 0.98 (s, 9H); MS (ESI+) m/z 569 (M+H)$^+$.

Example 51

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2S)-oxane-2-carbonyl]pyrrolidine-2-carboxylic acid Example 51A 5-(bicyclo[1.1.1]pentan-1-yl)-2-hydroxybenzaldehyde 4-(Bicyclo[1.1.1]pentan-1-yl)phenol (266.4 mg, 1.663 mmol), magnesium chloride (252.6 mg, 2.65 mmol) and paraformaldehyde (435.5 mg, 14.50 mmol) were suspended in acetonitrile (8 mL) and triethylamine (1.4 mL, 10.04 mmol) was added. The resulting suspension was stirred vigorously and heated to 80° C. for 18 hours, at which point LC/MS showed complete conversion to the desired product. Aqueous HCl (1 M, 50 mL) was added and the reaction was extracted with dichloromethane (2×50 mL). The combined organic layers were dried over MgSO$_4$, filtered, and concentrated to provide the title compound (313.1 mg, 100%). $^1$H NMR (500 MHz, dimethyl sulfoxide-$d_6$) δ ppm 10.61 (s, 1H), 10.22 (s, 1H), 7.42 (d, J=2.3 Hz, 1H), 7.35 (dd, J=8.4, 2.3 Hz, 1H), 6.92 (d, J=8.4 Hz, 1H), 2.50 (s, 1H), 2.00 (s, 6H); MS (ESI+) m/z 187 (M+H)$^+$.

Example 51B 5-(bicyclo[1.1.1]pentan-1-yl)-2-methoxybenzaldehyde

Example 51A (310.3 mg, 1.649 mmol), was dissolved in N,N-dimethylformamide (5 mL) and potassium carbonate (347.2 mg, 2.51 mmol) was added. The resulting suspension was stirred vigorously and methyl iodide (365.0 mg, 2.57 mmol) was added. The suspension was stirred at ambient temperature for 20 hours. Aqueous NaOH (1 M, 50 mL) was added and the reaction was extracted with methyl tert-butyl ether (2×50 mL). The combined extracts were washed with water (50 mL) and brine (50 mL) then dried over magnesium sulfate, filtered, and concentrated to give the title compound (300.5 mg, 90%). $^1$H NMR (500 MHz, dimethyl sulfoxide-$d_6$) δ ppm 10.32 (s, 1H), 7.51-7.44 (m, 2H), 7.18-7.13 (m, 1H), 3.88 (s, 3H), 2.52 (s, 1H), 2.02 (s, 6H); MS (ESI+) m/z 203 (M+H)$^+$.

Example 51C (2S,3S,4S,5S)-ethyl 4-amino-3-(tert-butyl)-5-(2-(dimethylamino)pyridin-3-yl)-1-(tetrahydro-2H-pyran-2-carbonyl)pyrrolidine-2-carboxylate The title compound was prepared according to the procedure described in Example 50B, substituting mixture of Example 18A and 18B for Example 50A.

Example 51D ethyl (2S,3S,4S,5S)-4-((5-(bicyclo[1.1.1]pentan-1-yl)-2-methoxybenzyl)amino)-3-(tert-butyl)-5-(2-(dimethylamino)pyridin-3-yl)-1-((S)-tetrahydro-2H-pyran-2-carbonyl)pyrrolidine-2-carboxylate Example 51C (92.3 mg, 0.207 mmol) and Example 51B (41.3 mg, 0.204 mmol) were dissolved in methanol (1 mL) and stirred at ambient temperature for 1 hour. Sodium cyanoborohydride (69.3 mg, 1.103 mmol) was added and the reaction was stirred at ambient temperature for an additional 16 hours. The reaction was diluted with dimethyl sulfoxide (1 mL), filtered and purified by reverse phase using the trifluoroacetic acid method. The title compound was the first eluting diastereomer (43.6 mg, 25%) isolated as the bis trifluoroacetic acid salt. $^1$H NMR (400 MHz, dimethyl sulfoxide-$d_6$, 120° C.) δ ppm 8.26 (dd, J=7.5, 1.8 Hz, 1H), 8.19 (dd, J=4.9, 1.8 Hz, 1H), 7.05 (dd, J=7.6, 4.9 Hz, 1H), 7.00 (dd, J=8.4, 2.2 Hz, 1H), 6.82 (d, J=2.2 Hz, 1H), 6.78 (d, J=8.3 Hz, 1H), 5.59 (d, J=6.7 Hz, 1H), 4.65 (d, J=1.6 Hz, 1H), 4.15 (qq, J=7.4, 3.7 Hz, 2H), 3.77-3.70 (m, 3H), 3.67 (d, J=13.6 Hz, 1H), 3.59 (s, 3H), 3.29 (d, J=13.5 Hz, 1H), 2.80 (s, 6H), 2.50 (d, J=3.3 Hz, 1H), 2.43 (s, 1H), 1.95 (s, 6H), 1.68 (s, 1H), 1.41 (s, 6H), 1.22 (t, J=7.1 Hz, 3H), 1.01 (s, 9H); MS (ESI+) m/z 633 (M+H)$^+$.

Example 51E (2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2S)-oxane-2-carbonyl]pyrrolidine-2-carboxylic acid Example 51D (43.6 mg, 0.051 mmol) was dissolved in methanol (1 mL). Aqueous LiOH (1 M, 0.5 mL, 0.5 mmol) was added and the reaction was heated to 50° C. for 16 hours. The reaction mixture was quenched by the addition of 1 M aqueous HCl (0.5 mL), diluted with dimethyl sulfoxide (1 mL), filtered and purified by reverse phase using the trifluoroacetic acid method to provide the title compound (33.1 mg, 78%) isolated as the first compound to elute as the bis trifluoroacetic acid salt. $^1$H NMR (400 MHz, dimethyl sulfoxide-$d_6$, 120° C.) δ ppm 8.20 (d, J=5.4 Hz, 2H), 7.08-6.98 (m, 2H), 6.86 (d, J=2.1 Hz, 1H), 6.80 (d, J=8.3 Hz, 1H), 5.61 (d, J=6.7 Hz, 1H), 4.59 (d, J=1.4 Hz, 1H), 3.81-3.72 (m, 3H), 3.59 (s, 3H), 3.31 (d, J=13.5 Hz, 1H), 2.79 (s, 6H), 2.53-2.48 (m, 4H), 1.95 (s, 6H), 1.74-1.63 (m, 1H), 1.41 (s, 5H), 1.01 (s, 9H); MS (ESI+) m/z 605 (M+H)$^+$.

Example 52

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2R)-oxane-2-carbonyl]pyrrolidine-2-carboxylic acid

Example 52A ethyl (2S,3S,4S,5S)-4-((5-(bicyclo[1.1.1]pentan-1-yl)-2-methoxybenzyl)amino)-3-(tert-butyl)-5-(2-(dimethylamino)pyridin-3-yl)-1-((R)-tetrahydro-2H-pyran-2-carbonyl)pyrrolidine-2-carboxylate The title compound was the second eluting diastereomer (49.2 mg, 28%) in Example 51D, and was isolated as the bistrifluoroacetic acid salt. $^1$H NMR (400 MHz, dimethyl sulfoxide-$d_6$, 120° C.) δ ppm 8.17 (dd, J=5.0, 1.8 Hz, 1H), 8.12 (d, J=7.6 Hz, 1H), 7.21 (dd, J=2.1, 1.0 Hz, 1H), 7.06-6.93 (m, 3H), 5.44 (d, J=6.6 Hz, 1H), 4.47 (d, J=0.7 Hz, 2H), 4.18 (q, J=7.0 Hz, 2H), 3.74 (s, 3H), 3.63-3.55 (m, 2H), 3.53 (s, 3H), 3.28 (d, J=13.6 Hz, 1H), 2.76 (s, 6H), 2.50 (d, J=3.4 Hz, 3H), 2.00 (s, 6H), 1.95 (s, 6H), 1.80 (s, 1H), 1.47 (d, J=28.9 Hz, 6H), 1.22 (t, J=7.1 Hz, 3H), 1.02 (s, 9H); MS (ESI+) m/z 633 (M+H)$^+$.

Example 52B (2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2R)-oxane-2-carbonyl]pyrrolidine-2-carboxylic acid Example 52A (49.2 mg, 0.057 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (25.4 mg, 53%), isolated as the bis trifluoroacetic acid salt. $^1$H NMR (400 MHz, dimethyl sulfoxide-$d_6$, 120° C.) δ ppm 8.19 (dd, J=4.9, 1.8 Hz, 1H), 8.08-7.99 (m, 1H), 7.04-6.96 (m, 2H), 6.83 (d, J=2.2 Hz, 1H), 6.77 (d, J=8.3 Hz, 1H), 5.45 (d, J=6.6 Hz, 1H), 4.91-4.84 (m, 1H), 3.69 (d, J=13.8 Hz, 1H), 3.63 (d, J=6.7 Hz, 1H), 3.54 (s, 3H), 3.32 (d, J=13.6 Hz, 1H), 2.86 (s, 1H), 2.74 (s, 6H), 2.59-2.48 (m, 4H), 1.95 (s, 6H), 1.83-1.74 (m, 1H), 1.47 (d, J=19.2 Hz, 5H), 1.01 (s, 9H); MS (ESI+) m/z 605 (M+H)$^+$.

Example 53

(2S,3S,4S,5S)-3-tert-butyl-4-{[(6-tert-butyl-2-methoxypyridin-3-yl)methyl]amino}-1-[(1R*)-3,3-difluorocyclohexane-1-carbonyl]-5-phenylpyrrolidine-2-carboxylic acid

Example 53A (2S,3S,4S,5S)-3-tert-butyl-4-[(6-tert-butyl-2-methoxy-pyridin-3-ylmethyl)-amino]-1-((R)-3,3-difluoro-cyclohexanecarbonyl)-5-phenyl-pyrrolidine-2-carboxylic acid ethyl ester NaBH$_3$CN (8 mg, 0.12 mmol, 1.2 eq) was added to a solution of (2S,3S,4S,5S)-4-amino-3-tert-butyl-1-((R)-3,3-difluoro-cyclohexanecarbonyl)-5-phenyl-pyrrolidine-2-carboxylic acid ethyl ester (Example 31B, 40 mg, 0.09 mmol, 1.0 eq) and 6-tert-butyl-2-methoxy-pyridine-3-carbaldehyde (19 mg, 0.1 mmol, 1.1 eq) in acetic acid/sodium acetate/methanol buffer (2 mL). The reaction mixture was stirred at room temperature for 30 minutes. The mixture was concentrated and the residue was partitioned between dichloromethane and water. The organic phase was dried on $Na_2SO_4$, filtered and concentrated. The residue was purified on silica gel (dichloromethane/ethyl acetate 100/0 to 97/3) to provide the title compound. LC/MS (ESI+) m/z 614.8 $(M+H)^+$.

Example 53B (2S,3S,4S,5S)-3-tert-butyl-4-{[(6-tert-butyl-2-methoxypyridin-3-yl)methyl]amino}-1-[(1R*)-3,3-difluorocyclohexane-1-carbonyl]-5-phenylpyrrolidine-2-carboxylic acid Example 53A was dissolved in methanol/tetrahydrofuran/water (1.5/1.5/1) and LiOH (19 mg, 0.45 mmol, 5.0 eq) was added to the reaction mixture. The solution was stirred at 45° C. overnight. The reaction mixture was acidified with aqueous HCl 1 M (1 eq/LiOH). The mixture was concentrated and extracted with dichloromethane. The organic phase was concentrated. The residue was purified by chromatography on silica gel (dichloromethane/methanol 100/0 to 95/5) to give the title compound (30 mg, 57% yield over 2 steps). $^1$H NMR (400 MHz, DMSO-$d_6$, 100° C.) δ ppm 7.61 (br. s., 2H), 7.26-7.41 (m, 3H), 7.22 (d, J=7.5 Hz, 1H), 6.81 (d, J=7.5 Hz, 1H), 5.21 (d, J=6.2 Hz, 1H), 4.50 (br. s, 1H), 3.68 (br. s., 3H), 3.37-3.57 (m, 2H), 3.24-3.36 (m, 1H), 2.95 (br. s., 1H under peak of water), 2.33 (br. s., 1H), 1.38-2.12 (m, 8H), 1.28 (s, 9H), 1.00 (s, 9H); LC/MS (ESI+) m/z 586.5 $(M+H)^+$.

Example 54

(2S,3S,4S,5S)-3-tert-butyl-4-{[(5-tert-butyl-2-methoxyphenyl)methyl]amino}-5-phenyl-1-(2,2,6,6-tetramethyloxane-4-carbonyl)pyrrolidine-2-carboxylic acid Example 54A 2,2,6,6-tetramethyltetrahydro-2H-pyran-4-carbonitrile 2,2,6,6-Tetramethyldihydro-2H-pyran-4(3H)-one (3 g, 19.20 mmol) and toluenesulfonylmethyl isocyanide (4.87 g, 24.96 mmol) were dissolved in dimethoxyethane (20 mL). After cooling to −10° C. in an acetone-ice bath, potassium tert-butoxide (2.80 g, 24.96 mmol) was added in portions over 40 minutes, maintaining a temperature <5° C. The reaction mixture was stirred at 0° C. for 1 hour then ambient temperature for 2 hours. The mixture was diluted with diethyl ether (30 mL) and the solids were removed via filtration through a fritted funnel. The filtrate was concentrated and the product was partitioned between diethyl ether and water. The combined organic extracts were concentrated and purified via flash chromatography, eluting on a 120 g silica gel column with 0:100 to 7:93 ethyl acetate:heptanes over 20 minutes to give 885 mg of the title compound. $^1$H NMR (500 MHz, Chloroform-d) δ ppm 2.95 (tt, J=12.7, 3.5 Hz, 1H), 1.96-1.85 (m, 2H), 1.67-1.52 (m, 2H), 1.27 (s, 6H), 1.26 (s, 6H); MS (DCI+) m/z 185.4 $(M+NH_4)^+$.

Example 54B 2,2,6,6-tetramethyltetrahydro-2H-pyran-4-carboxylic acid

Example 54A (700 mg, 4.19 mmol) was dissolved in ethanol (14 mL). A solution of sodium hydroxide (3 M, 13.95 mL, 41.9 mmol) in water was added dropwise, and the resulting mixture was heated to 80° C. for 7 hours. LC-MS showed complete conversion. The reaction was cooled to <10° C., diluted with 30 mL of methyl tert-butyl ether and acidified with 6 M aqueous HCl (10 mL). The desired product was extracted from the aqueous layer using additional methyl tert-butyl ether (20 mL). The combined organic extracts were washed with brine (20 mL) and dried over sodium sulfate, filtered, then concentrated to give the title compound (741 mg). $^1$H NMR (501 MHz, Chloroform-d) δ ppm 2.84 (tt, J=12.8, 3.4 Hz, 1H), 1.85 (dd, J=13.4, 3.4 Hz, 2H), 1.53-1.40 (m, 2H), 1.27 (s, 6H), 1.24 (s, 6H); MS (ESI+) m/z 187.0 $(M+H)^+$.

Example 54C (2S,3S,4S,5S)-ethyl 3-(tert-butyl)-4-((5-(tert-butyl)-2-methoxybenzyl)amino)-5-phenyl-1-(2,2,6,6-tetramethyltetrahydro-2H-pyran-4-carbonyl)pyrrolidine-2-carboxylate Example 54B (80 mg, 0.430 mmol) was dissolved in 2 mL of dichloromethane and oxalyl chloride (113 μl, 1.289 mmol) was added, followed by 1 drop of N,N-dimethylformamide. The resulting solution was stirred at ambient temperature for 2 hours then concentrated and redissolved in 0.5 mL of dichloromethane to give a solution of 2,2,6,6-tetramethyltetrahydro-2H-pyran-4-carbonyl chloride. The solution of freshly-prepared 2,2,6,6-tetramethyltetrahydro-2H-pyran-4-carbonyl chloride (32.9 mg, 0.161 mmol) in 0.5 mL of dichloromethane was added dropwise to a stirred solution of Example 34D (75 mg, 0.161 mmol) and triethylamine (44.8 μl, 0.321 mmol) in 1 mL of dichloromethane at 0° C. After 5 minutes, the reaction was complete by LC-MS. The reaction was quenched with 1 M aqueous HCl (5 mL), the layers were separated, and the organic layer was concentrated in vacuo, and the residue was purified via flash chromatography using 0:100 to 20:80 ethyl acetate:heptanes to give 89 mg of the title compound. $^1$H NMR (400 MHz, dimethyl sulfoxide-$d_6$) δ ppm 7.65 (s, 2H), 7.34 (t, J=7.5 Hz, 2H), 7.25 (t, J=7.4 Hz, 1H), 7.11 (dd, J=8.5, 2.6 Hz, 1H), 6.91 (d, J=2.6 Hz, 1H), 6.72 (d, J=8.5 Hz, 1H), 5.22 (d, J=6.8 Hz, 1H), 4.55 (d, J=2.9 Hz, 1H), 4.11 (q, J=7.0 Hz, 2H), 3.52 (s, 3H), 3.49 (d, J=13.6 Hz, 1H), 3.32 (d, J=13.6 Hz, 1H), 2.65 (d, J=12.5 Hz, 1H), 2.33 (s, 1H), 1.46 (d, J=13.0 Hz, 1H), 1.30-1.22 (m, 4H), 1.20 (s, 9H), 1.19 (t, J=6.5 Hz, 3H), 1.05 (s, 6H), 1.01 (br s, 3H), 1.00 (s, 9H), 0.95 (br s, 3H); MS (ESI+) m/z 635.5 $(M+H)^+$.

Example 54D (2S,3S,4S,5S)-3-(tert-butyl)-4-((5-(tert-butyl)-2-methoxybenzyl)amino)-5-phenyl-1-(2,2,6,6-tetramethyltetrahydro-2H-pyran-4-carbonyl)pyrrolidine-2-carboxylic acid Example 54C (89 mg, 0.140 mmol) was dissolved in a mixture of methanol (0.5 mL), tetrahydrofuran (1.0 mL), and water (1.000 mL). After addition of lithium hydroxide hydrate (58.8 mg, 1.402 mmol), the reaction was heated to 40° C. for 16 hours, at which point it was complete by LC-MS. The mixture was cooled to ambient temperature and acidified with 1 M aqueous HCl to pH=3. The mixture was extracted with dichloromethane (3×10 mL) and the combined extracts were dried over sodium sulfate, filtered, and concentrated to give 55 mg of the title compound. $^1$H NMR (400 MHz, dimethyl sulfoxide-$d_6$) δ ppm 7.57 (s, 2H), 7.35 (t, J=7.5 Hz, 2H), 7.26 (t, J=7.4 Hz, 1H), 7.14 (dd, J=8.5, 2.5 Hz, 1H), 6.97 (s, 1H), 6.73 (d, J=8.5 Hz, 1H), 5.22 (d, J=6.7 Hz, 1H), 4.52 (d, J=2.3 Hz, 1H), 3.58 (d, J=10.4 Hz, 1H), 3.54 (dd, J=6.6, 1.8 Hz, 1H), 3.50 (s, 3H), 3.38 (d, J=13.7 Hz, 1H), 2.70 (br s, 1H), 2.37 (br s, 1H), 1.45 (d, J=13.1 Hz, 1H), 1.28 (s, 3H), 1.27-1.20 (m, 3H), 1.20 (s, 9H), 1.04 (s, 6H), 0.98 (s, 12H; overlapping singlets of 3H and 9H); MS (ESI+) m/z 607.3 (M+H)$^+$.

Example 55

(2S,3S,4S,5S)-3-tert-butyl-4-[(5-tert-butyl-2-methoxypyridin-3-yl)amino]-1-(cyclohexanecarbonyl)-5-phenylpyrrolidine-2-carboxylic acid A nitrogen sparged solution of (2S,3S,4S,5S)-ethyl 4-amino-3-(tert-butyl)-1-(cyclohexanecarbonyl)-5-phenylpyrrolidine-2-carboxylate (Example 7B, 56 mg, 0.140 mmol) and 3-bromo-5-(tert-butyl)-2-methoxypyridine (68.3 mg, 0.280 mmol) was added to a nitrogen sparged suspension of 2,2'-bis(diphenylphosphino)-1,1'-binaphthalene (9.58 mg, 0.015 mmol), tris(dibenzylideneacetone)dipalladium(0) (6.40 mg, 6.99 μmol) and cesium carbonate (137 mg, 0.419 mmol) in toluene (0.3 mL). The reaction was heated at 110° C. in an aluminum block for 16 hours. The crude material was concentrated and loaded onto a 12 g silica gel column and eluted with 0-30% ethyl acetate/heptanes over 40 minutes to give (2S,3S,4S,5S)-ethyl 3-(tert-butyl)-4-((5-(tert-butyl)-2-methoxypyridin-3-yl)amino)-1-(cyclohexanecarbonyl)-5-phenylpyrrolidine-2-carboxylate (16 mg, 0.028 mmol, 20.30% yield). MS (APCI+) m/z 610 (M+H)$^+$. The material was taken up in methanol (1 mL) and to the resulting solution was added a 1 M solution of lithium hydroxide (0.284 mL, 0.284 mmol) in water. The reaction was warmed at 45° C. for 4 hours. The solvent was removed under a stream of nitrogen and the reaction was neutralized with 1 N aqueous HCl. The crude material was taken up in dichloromethane and purified using a 12 g silica gel cartridge with an ethyl acetate/ethanol/heptanes solvent system and then purified again using reverse phase HPLC with an acetonitrile/water/trifluoroacetic acid method to give (2S,3S,4S,5S)-3-(tert-butyl)-4-((5-(tert-butyl)-2-methoxypyridin-3-yl)amino)-1-(cyclohexanecarbonyl)-5-phenylpyrrolidine-2-carboxylic acid (4.8 mg, 8.96 μmol, 31.6% yield). $^1$H NMR (400 MHz, 120° C., dimethyl sulfoxide-$d_6$) δ ppm 7.49 (d, J=7.5 Hz, 2H), 7.21 (d, J=2.1 Hz, 1H), 7.17-7.03 (m, 3H), 6.77 (d, J=2.2 Hz, 1H), 5.32 (d, J=7.2 Hz, 1H), 4.44 (d, J=4.1 Hz, 1H), 4.32 (s, 1H), 3.62 (s, 3H), 2.25 (t, J=3.9 Hz, 1H), 2.18 (s, 1H), 1.72-1.59 (m, 3H), 1.44 (dd, J=14.8, 6.2 Hz, 4H), 1.33-1.23 (m, 1H), 1.23 (s, 9H), 1.21-1.12 (m, 1H), 1.04 (s, 9H), 1.05-0.93 (m, 1H); MS (APCI+) m/z 536 (M+H)$^+$.

Example 56

(2S,3S,4S,5S)-3-(bicyclo[1.1.1]pentan-1-yl)-1-(cyclohexanecarbonyl)-4-({[2-hydroxy-5-(trifluoromethyl)phenyl]methyl}amino)-5-phenylpyrrolidine-2-carboxylic acid Example 56A bicyclo[1.1.1]pentan-1-ylmethanol To a solution of bicyclo[1.1.1]pentane-1-carboxylic acid (4.0 g, 35.7 mmol) in tetrahydrofuran (89 mL) at 0° C. was added lithium aluminum hydride (1.801 g, 47.4 mmol) in portions and the reaction bubbled vigorously. The reaction was warmed to 24° C. and was stirred for 16 hours. The reaction was cooled in an ice bath and 4 g of sodium sulfate decahydrate was added in portions and the reaction was stirred for 1 hour. Then 15% aqueous NaOH solution (2 mL) was added. The mixture was stirred for 0.5 hour, 2 mL water was added, and ice-bath was removed. The mixture was stirred for 2 hours, and dried with 40 g anhydrous sodium sulfate. The suspension was filtered and the filtrate was washed with ether. The solvent was removed in vacuo to give crude bicyclo[1.1.1]pentan-1-ylmethanol (3.2 g, 32.6 mmol, 91% yield). $^1$H NMR (501 MHz, Chloroform-d) δ ppm 3.56 (s, 2H), 2.57 (s, 1H), 1.77 (s, 6H).

Example 56B bicyclo[1.1.1]pentane-1-carbaldehyde

Example 56A (3.2 g, 32.6 mmol) was dissolved in 5 mL of dichloromethane. A separate 250-mL round bottom flask was charged with oxalyl chloride (4.57 mL, 52.2 mmol) in 55 mL of dichloromethane and the flask was cooled to <–70° C. in an acetone-dry ice bath. Dimethyl sulfoxide (7.40 mL, 104 mmol) was added dropwise over 20 minutes, maintaining a temperature <–60° C. After the addition was complete, the resulting solution was stirred for 15 minutes at the same temperature before addition of bicyclo[1.1.1]pentan-1-ylmethanol (3.2 g, 32.6 mmol) as a solution in dichloromethane (5 mL) over 30 minutes, maintaining a temperature <–65° C. After the addition was complete, the reaction mixture was stirred at the same temperature for 1 hour (allowed to warm no further than –60° C.), at which point neat triethylamine (22.72 mL, 163 mmol) was added at –78° C. over 10 minutes. A very thick slurry resulted. The flask was removed from the ice bath. After reaching ambient temperature, the reaction mixture was quenched by the addition of 200 mL of 1 M aqueous HCl. The layers were separated and the organic layer was washed twice with 1 M aqueous HCl (30 mL) and brine then dried over sodium sulfate, filtered, and concentrated in vacuo (rotovap bath at 10° C.) to give bicyclo[1.1.1]pentane-1-carbaldehyde (2.6 g, 27.0 mmol, 83% yield). $^1$H NMR (501 MHz, Chloroform-d) δ ppm 9.52 (d, J=0.7 Hz, 1H), 2.57 (d, J=0.8 Hz, 1H), 2.11 (s, 6H).

Example 56C 1-(bicyclo[1.1.1]pentan-1-yl)-2-nitroethanol

Example 56B (2.6 g, 27.0 mmol) and nitromethane (2.188 mL, 40.6 mmol) were dissolved in tetrahydrofuran (10 mL) and tert-butanol (3 mL). After cooling to <5° C. in an ice bath, potassium tert-butoxide (5.41 mL, 5.41 mmol) solution was added dropwise. After 1 hour, the ice-bath was removed and the mixture was stirred for 30 minutes. The mixture was poured into 40 mL of water and extracted with 3×30 mL of ether. The combined extracts were washed with brine and dried over sodium sulfate, filtered, then concentrated to give a crude residue. The crude material was purified via flash column chromatography, eluting with 0-60% ethyl acetate/heptanes over 20 minutes on a 40 g silica gel column to provide the desired product, 1-(bicyclo[1.1.1]pentan-1-yl)-2-nitroethanol (2.22 g, 14.13 mmol, 52.2% yield). $^1$H NMR (500 MHz, Chloroform-d) δ ppm 4.49-4.38 (m, 1H), 4.36-4.27 (m, 2H), 2.61 (s, 1H), 2.32-2.29 (m, 1H), 1.85-1.78 (m, 6H); MS (DCI+) m/z 175 (M+NH$_4$+).

Example 56D (E)-1-(2-nitrovinyl)bicyclo[1.1.1]pentane

Example 56C (2.22 g, 14.13 mmol) was dissolved in 18.8 mL of dry dichloromethane and the solution was cooled to −78° C. Triethylamine (4.92 mL, 35.3 mmol) was added, followed by dropwise addition of mesyl chloride (1.321 mL, 16.95 mmol). The reaction mixture was stirred for 1 hour at the same temperature, removed from the dry ice bath and stirred for 1 hour. The mixture was washed with saturated aqueous sodium bicarbonate and brine then dried over sodium sulfate, filtered, concentrated in vacuo. The crude residue was purified via flash chromatography, eluting with 0-40% ethyl acetate/heptanes over 20 minutes on a 24 g silica gel column to provide the desired product, (E)-1-(2-nitrovinyl)bicyclo[1.1.1]pentane (1.63 g, 11.71 mmol, 83% yield). $^1$H NMR (501 MHz, Chloroform-d) δ ppm 7.20 (d, J=13.4 Hz, 1H), 6.88 (d, J=13.4 Hz, 1H), 2.62 (s, 1H), 2.04 (s, 6H).

Example 56E (2S,3R,4S,5S)-tert-butyl 3-(bicyclo[1.1.1]pentan-1-yl)-4-nitro-5-phenylpyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.065 g, 0.086 mmol) and copper (II) triflate (0.017 g, 0.034 mmol) were dissolved in tetrahydrofuran (9.5 mL) that had been sparged with an nitrogen stream for 1 hour. The resulting mixture was stirred for 1 hour at ambient temperature (continued nitrogen sparge), and (E)-tert-butyl 2-(benzylideneamino)acetate (1.040 g, 4.74 mmol) was added as a solution in 1 mL of tetrahydrofuran and the resulting solution was cooled to <5° C. in an ice-water bath. Potassium 2-methylpropan-2-olate in tetrahydrofuran (0.177 mL, 0.177 mmol) was added dropwise, followed by addition of Example 56D (0.6 g, 4.31 mmol) over 3 minutes, maintaining a temperature less than 7° C. The reaction mixture was stirred for 45 minutes at 0° C. The mixture was quenched with 6 mL of saturated aqueous ammonium chloride and 20 mL of diethyl ether and warmed to ambient temperature. The ether layer was separated and washed twice with saturated ammonium chloride then brine, filtered through a pad of silica gel, and concentrated to give a crude residue, which was diluted with n-heptane (50 mL), and let stand to precipitate over 2 hours. The mixture was filtered and precipitated in 50 mL hot heptane to give (2S,3R,4S,5S)-tert-butyl 3-(bicyclo[1.1.1]pentan-1-yl)-4-nitro-5-phenylpyrrolidine-2-carboxylate (0.73 g, 2.037 mmol, 47.2% yield). $^1$H NMR (400 MHz, Chloroform-d) δ ppm 7.44-7.30 (m, 5H), 5.01 (dd, J=5.7, 2.0 Hz, 1H), 4.47 (d, J=5.5 Hz, 1H), 3.74 (d, J=6.0 Hz, 1H), 3.40 (bs, 1H), 3.02-2.92 (m, 1H), 2.69 (s, 1H), 1.96-1.79 (m, 6H), 1.57 (s, 9H); MS (ESI+) m/z 359 (M+H)+.

Example 56F (2S,3R,4S,5S)-tert-butyl 3-(bicyclo[1.1.1]pentan-1-yl)-1-(cyclohexanecarbonyl)-4-nitro-5-phenylpyrrolidine-2-carboxylate A solution of Example 56E (0.5 g, 1.395 mmol) and triethylamine (0.389 mL, 2.79 mmol) in dichloromethane (6.34 mL) at 25° C. was treated with cyclohexanecarbonyl chloride (0.233 mL, 1.744 mmol) dropwise. The mixture was stirred for 2 hours, washed with saturated aqueous NaHCO$_3$ (5 mL) and with 1 N NH$_4$OH (1 mL) aqueous solution and concentrated. The mixture was triturated with 10 mL heptane and let stand for 0.5 hour at ambient temperature and the crude precipitate (1.5 g) was collected. The precipitate was dissolved in 3 mL dichloromethane and loaded on a 12 g column eluting with a gradient of 0-70% ethyl acetate/heptanes over a period of 20 minutes to provide the desired product, (2S,3R,4S,5S)-tert-butyl 3-(bicyclo[1.1.1]pentan-1-yl)-1-(cyclohexanecarbonyl)-4-nitro-5-phenylpyrrolidine-2-carboxylate (0.52 g, 1.110 mmol, 80% yield). $^1$H NMR (501 MHz, Chloroform-d) δ ppm 7.76-7.64 (m, 2H), 7.45-7.32 (m, 3H), 5.44 (d, J=8.9 Hz, 1H), 5.09 (dd, J=11.1, 8.9 Hz, 1H), 4.12 (d, J=10.1 Hz, 1H), 3.33 (t, J=10.6 Hz, 1H), 2.55 (s, 1H), 2.11-1.98 (m, 1H), 1.85 (dd, J=9.6, 2.0 Hz, 3H), 1.77 (dd, J=9.6, 2.0 Hz, 3H), 1.72 (d, J=15.0 Hz, 1H), 1.65 (s, 1H), 1.59 (s, 9H), 1.56-1.42 (m, 3H), 1.33-1.20 (m, 1H), 1.18-1.04 (m, 3H), 0.70-0.59 (m, 1H); MS (ESI−) m/z 467 (M−H)−.

Example 56G (2S,3S,4S,5S)-tert-butyl 4-amino-3-(bicyclo[1.1.1]pentan-1-yl)-1-(cyclohexanecarbonyl)-5-phenylpyrrolidine-2-carboxylate To a solution of Example 56F (0.52 g, 1.110 mmol) and tetrahydrofuran (20 mL) was added to RaNi:2800, water slurry (3 g, 23.00 mmol) in a 50 mL pressure bottle. The reaction was stirred for 16 hours at 50 psi hydrogen and ambient temperature. The reaction was filtered and the solvent removed in vacuo and loaded on a 12 g column eluting with a gradient of 0-9% methanol/dichloromethane over a period of 20 minutes to give (2S,3S,4S,5S)-tert-butyl 4-amino-3-(bicyclo[1.1.1]pentan-1-yl)-1-(cyclohexanecarbonyl)-5-phenylpyrrolidine-2-carboxylate (0.432 g, 0.985 mmol, 89% yield). $^1$H NMR (501 MHz, Chloroform-d) δ ppm 7.76-7.69 (m, 2H), 7.43 (td, J=7.4, 6.8, 0.9 Hz, 2H), 7.37-7.31 (m, 1H), 4.95 (d, J=8.2 Hz, 1H), 4.03 (d, J=9.7 Hz, 1H), 3.80-3.74 (m, 1H), 3.47 (dd, J=10.3, 8.1 Hz, 1H), 2.56 (s, 1H), 2.16-2.06 (m, 2H), 1.92-1.82 (m, 6H), 1.72 (t, J=12.5 Hz, 2H), 1.60 (s, 1H), 1.57 (s, 9H), 1.46 (m, 3H), 1.34-1.22 (m, 1H), 1.12 (tt, J=12.4, 6.3 Hz, 3H), 0.72-0.59 (m, 1H); MS (ESI+) m/z 439 (M+H)+.

Example 56H (2S,3S,4S,5S)-3-(bicyclo[1.1.1]pentan-1-yl)-1-(cyclohexanecarbonyl)-4-({[2-hydroxy-5-(trifluoromethyl)phenyl]methyl}amino)-5-phenylpyrrolidine-2-carboxylic acid To a solution of 2-methoxy-5-(trifluoromethyl)benzaldehyde (30.7 mg, 0.150 mmol), Example 56G (60 mg, 0.137 mmol) and zinc(II) chloride (18.64 mg, 0.137 mmol) in sodium acetate/acetic acid buffer in methanol (pH=4, 1 mL) was added sodium cyanoborohydride (12.89 mg, 0.205 mmol) and the reaction was stirred at ambient temperature for 2 hours. The solvent was removed and the resulting residue was chromatographed using a 12 g silica gel cartridge eluting with a gradient of 0-60% ethyl acetate/heptanes over a period of 20 minutes to give the crude material (84 mg, 0.134 mmol, 98% yield). The crude material was dissolved in 2,2,2-trifluoroacetic acid (0.5 mL, 6.49 mmol), and stirred for 3 hours. The solvent was removed and the crude material was purified by reverse phase using the trifluoroacetic acid method to give (2S,3S,4S,5S)-3-(bicyclo[1.1.1]pentan-1-yl)-1-(cyclohexanecarbonyl)-4-((2-methoxy-5-(trifluoromethyl)benzyl)amino)-5-phenylpyrrolidine-2-carboxylic acid, trifluoroacetic acid, (42 mg, 0.061 mmol, 44.8% yield). $^1$H NMR (400 MHz, dimethyl sulfoxide-$d_6$) δ ppm 7.62-7.45 (m, 3H), 7.39-7.18 (m, 4H), 7.06 (d, J=8.7 Hz, 1H), 5.15 (d, J=7.4 Hz, 1H), 4.12 (s, 1H), 3.73 (s, 3H), 3.61 (d, J=2.7 Hz, 2H), 3.32 (t, J=7.3 Hz, 1H), 2.50 (s, 1H), 2.44 (s, 1H), 2.31-2.12 (m, 1H), 1.76-1.69 (m, 6H), 1.67 (s, 1H), 1.49 (m, 2H), 1.27 (q, J=12.1 Hz, 1H), 1.10 (m, 4H), 0.77 (bs, 1H); MS (ESI+) m/z 571 (M+H)$^+$.

Example 57

(2S,3S,4S,5S)-3-(bicyclo[1.1.1]pentan-1-yl)-1-(cyclohexanecarbonyl)-4-({[2-methoxy-5-(trifluoromethyl)pyridin-3-yl]methyl}amino)-5-phenylpyrrolidine-2-carboxylic acid To a solution of 2-methoxy-5-(trifluoromethyl)nicotinaldehyde (30.9 mg, 0.150 mmol), Example 56G (60 mg, 0.137 mmol) and zinc(II) chloride (18.64 mg, 0.137 mmol) in sodium acetate/acetic acid buffer in methanol (pH=4, 1 mL) was added sodium cyanoborohydride (12.89 mg, 0.205 mmol) and the reaction was stirred at ambient temperature for 2 hours. The solvent was removed and the resulting residue was chromatographed using a 12 g silica gel cartridge eluting with a gradient of 0-60% ethyl acetate/heptanes over a period of 20 minutes to give a solid (80 mg, 0.127 mmol, 93%). The solid was dissolved in 2,2,2-trifluoroacetic acid (0.5 mL, 6.49 mmol), and stirred for 3 hours at ambient temperature. The solvent was removed and the crude material was purified by reverse phase using the trifluoroacetic acid method to give (2S,3S,4S,5S)-3-(bicyclo[1.1.1]pentan-1-yl)-1-(cyclohexanecarbonyl)-4-(((2-methoxy-5-(trifluoromethyl)pyridin-3-yl)methyl)amino)-5-phenylpyrrolidine-2-carboxylic acid, trifluoroacetic acid salt, (45 mg, 0.066 mmol, 48.0% yield). $^1$H NMR (400 MHz, dimethyl sulfoxide-$d_6$) δ ppm 8.34 (d, J=2.1 Hz, 1H), 7.67 (d, J=2.4 Hz, 1H), 7.57 (s, 2H), 7.37-7.15 (m, 3H), 5.15 (d, J=7.4 Hz, 1H), 4.10 (s, 1H), 3.86 (s, 3H), 3.57 (s, 2H), 3.29 (t, J=7.8 Hz, 1H), 2.44 (s, 1H), 2.39 (bs, 1H), 2.21 (bs, 1H), 1.78-1.68 (m, 6H), 1.66 (m, 2H), 1.49 (m, 2H), 1.35-1.20 (m, 1H), 1.09 (m, 4H), 0.73 (bs, 1H); MS (ESI+) m/z 572.0 (M+H)$^+$.

Example 58

(2S,3S,4S,5S)-3-tert-butyl-4-{[(5-tert-butyl-2-methoxyphenyl)methyl]amino}-1-(cyclohexanecarbonyl)-N-(methanesulfonyl)-5-phenylpyrrolidine-2-carboxamide Example 58A rac-(2R,3S,4R,5R)-3-(tert-butyl)-4-nitro-5-phenylpyrrolidine-2-carboxylic acid hydrochloride A solution of rac-(2R,3S,4R,5R)-ethyl 3-(tert-butyl)-4-nitro-5-phenylpyrrolidine-2-carboxylate (Core 2, 2.0 g, 6.24 mmol) in 38% concentrated hydrochloric acid (12 mL, 20.84 mmol) and 1,4-dioxane (4 mL) was irradiated at 100° C. for 1 hour in a microwave reactor (Biotage® Initiator). The precipitate was collected by filtration and washed with ethyl acetate (5 mL) to give the title compound as a hydrochloride salt (2.04 g, 5.77 mmol, 92% yield). LC/MS (ESI+) m/z 293.1 (M+H)$^+$.

Example 58B rac-(2R,3S,4R,5R)-3-(tert-butyl)-1-(cyclohexanecarbonyl)-4-nitro-5-phenylpyrrolidine-2-carboxylic acid To a solution of Example 58A (8.0 g, 24.33 mmol) and triethylamine (6.78 mL, 48.7 mmol) in dichloromethane (50 mL) at 0° C. was added cyclohexanecarbonyl chloride (2.497 g, 17.03 mmol). The mixture was stirred at 0° C. for 2 hours and then diluted with dichloromethane (100 mL), washed with saturated aqueous NaHCO$_3$ (25 mL) and brine (25 mL), dried over MgSO$_4$, filtered and concentrated to give the title compound (9.5 g, 22.19 mmol, 91% yield). LC/MS (ESI+) m/z 403.2 (M+H)$^+$.

Example 58C rac-(2R,3S,4R,5R)-3-(tert-butyl)-1-(cyclohexanecarbonyl)-N-(methylsulfonyl)-4-nitro-5-phenylpyrrolidine-2-carboxamide A solution of Example 58B (8.00 g, 19.88 mmol) and 1,1'-carbonyldiimidazole (9.67 g, 59.6 mmol) in 1,2-dichloroethane (100 mL) was stirred at 42° C. for 5 minutes. To the mixture was added methanesulfonamide (9.45 g, 99 mmol) and 1,8-diazabicyclo[5.4.0]undec-7-ene (DBU, 8.99 mL, 59.6 mmol) (DBU was dried with 4 Å molecular sieves prior to usage). The mixture was stirred at 42° C. for 2 hours and then diluted with ethyl acetate (200 mL), washed with 1 N aqueous HCl solution (30 mL) and brine (30 mL), dried over Na$_2$SO$_4$, filtered and concentrated to give the title compound (8.8 g, 12.48 mmol, 62.8% yield). LC/MS (ESI+) m/z 480.2 (M+H)$^+$.

Example 58D rac-(2R,3R,4R,5R)-4-amino-3-(tert-butyl)-1-(cyclohexanecarbonyl)-N-(methylsulfonyl)-5-phenylpyrrolidine-2-carboxamide To a solution of Example 58C (5.00 g, 10.43 mmol) in 38% concentrated hydrochloric acid (10 mL, 10.43 mmol) and ethanol (50 mL) was added zinc power (13.63 g, 209 mmol). The mixture was stirred at 60° C. for 2 hours. The solid was filtered and washed with ethyl acetate (5 mL) to give the crude product which was further purified by Combi-Flash column chromatography (Mobile phase: H$_2$O (5 mmol NH$_4$HCO$_3$) (A)/CH$_3$OH(B)) to give the title compound (2R,3R,4R,5R)-4-amino-3-(tert-butyl)-1-(cyclohexanecarbonyl)-N-(methylsulfonyl)-5-phenylpyrrolidine-2-carboxamide (845 mg, 1.748 mmol, 17% yield). $^1$H NMR (400 MHz, CDCl$_3$) δ ppm 7.60 (d, J=8 Hz, 2H), 7.39 (t, J=8 Hz, 2H), 7.31 (t, J=8 Hz, 1H), 4.71 (s, 1H), 4.55 (d, J=12 Hz, 1H), 3.64 (d, J=4 Hz, 1H), 3.29 (s, 3H), 2.50 (dd, J=4 Hz, 8 Hz, 1H), 2.05-2.08 (m, 1H), 1.73-1.82 (m, 2H), 1.09-1.52 (m, 7H), 1.09 (s, 9H), 0.73-0.74 (m, 1H); LC/MS (ESI+) m/z 450.3 (M+H)$^+$.

Example 58E (2S,3S,4S,5S)-3-tert-butyl-4-{[(5-tert-butyl-2-methoxyphenyl)methyl]amino}-1-(cyclohexanecarbonyl)-N-(methanesulfonyl)-5-phenylpyrrolidine-2-carboxamide A mixture of 5-(tert-butyl)-2-methoxybenzaldehyde (61.6 mg, 0.320 mmol), rac-(2R,3R,4R,5R)-4-amino-3-(tert-butyl)-1-(cyclohexanecarbonyl)-N-(methylsulfonyl)-5-phenylpyrrolidine-2-carboxamide (120 mg, 0.267 mmol) and zinc(II) chloride (7.27 mg, 0.053 mmol) in sodium acetate/acetic acid buffer in methanol (pH=4, 2 mL) was stirred at ambient temperature for 10 minutes to give a colorless solution. Sodium cyanoborohydride (25.2 mg, 0.400 mmol) was added, the mixture was stirred for 1 hour, and dichloromethane (10 mL) was added. The organic layer was washed with brine, dried over MgSO$_4$, filtered, and concentrated. The residue was purified via chromatography on a 12 g silica gel cartridge, eluting with methanol in dichloromethane at 0-20% gradient to yield a racemic product which isolated via chiral SFC [Instrument: Aurora-2, Column: Whelk-O 1 (S,S), 5-50% methanol:CO$_2$, 10 minute @ 3 mL/minute, 150 bar]. The first compound to elute was (2R,3R,4R,5R)-3-(tert-butyl)-4-((5-(tert-butyl)-2-methoxybenzyl)amino)-1-(cyclohexanecarbonyl)-N-(methylsulfonyl)-5-phenylpyrrolidine-2-carboxamide (45 mg, 26.9% yield). $^1$H NMR (400 MHz, dimethyl sulfoxide-d$_6$) δ ppm 11.5 (s, 1H), 7.63-7.52 (m, 2H), 7.36 (d, J=2.6 Hz, 1H), 7.35-7.27 (m, 2H), 7.24 (d, J=2.4 Hz, 1H), 7.22 (d, J=2.6 Hz, 1H), 6.89 (d, J=8.6 Hz, 1H), 4.89 (s, 1H), 4.41 (d, J=11.0 Hz, 1H), 3.97 (d, J=13.5 Hz, 1H), 3.84 (d, J=13.6 Hz, 1H), 3.77 (s, 3H), 3.17 (s, 4H), 2.21 (dd, J=11.0, 4.7 Hz, 1H), 2.02 (s, 1H), 1.82 (s, 1H), 1.66 (d, J=10.1 Hz, 2H), 1.48 (d, J=10.7 Hz, 2H), 1.26 (s, 9H), 1.20 (s, 2H), 1.11 (d, J=4.9 Hz, 2H), 0.95 (s, 9H), 0.73 (s, 1H); MS (ESI+) m/z 626.1 (M+H)$^+$. The second compound to elute was the title compound of (2S,3S,4S,5S)-3-(tert-butyl)-4-((5-(tert-butyl)-2-methoxybenzyl)amino)-1-(cyclohexanecarbonyl)-N-(methylsulfonyl)-5-phenylpyrrolidine-2-carboxamide (58.0 mg, 34.7% yield). $^1$H NMR (400 MHz, dimethyl sulfoxide-d$_6$) δ ppm 11.49 (s, 1H), 7.62-7.53 (m, 2H), 7.36 (d, J=2.6 Hz, 1H), 7.31 (t, J=7.5 Hz, 2H), 7.23 (dd, J=8.6, 2.5 Hz, 2H), 4.89 (s, 1H), 4.41 (d, J=11.0 Hz, 1H), 3.97 (d, J=13.5 Hz, 1H), 3.4 (d, J=13.5 Hz, 1H), 3.77 (s, 3H), 3.16 (s, 4H), 2.21 (dd, J=11.0, 4.7 Hz, 1H), 2.02 (s, 1H), 1.82 (s, 1H), 1.66 (d, J=10.1 Hz, 2H), 1.48 (d, J=10.8 Hz, 2H), 1.26 (s, 9H), 1.18-1.10 (m, 4H), 0.94 (s, 9H), 0.73 (s, 1H); MS (ESI+) m/z 626.1 (M+H)$^+$.

Example 59

(2S,3S,4S,5S)-3-tert-butyl-4-{[(5-tert-butyl-2-methoxyphenyl)methyl]amino}-5-[2-(difluoromethoxy)phenyl]-1-[(2S)-oxane-2-carbonyl]pyrrolidine-2-carboxylic acid Example 59A (2S,3S,4S,5S)-ethyl 4-amino-3-(tert-butyl)-5-(2-(difluoromethoxy)phenyl)-1-((S)-tetrahydro-2H-pyran-2-carbonyl)pyrrolidine-2-carboxylate The title compound was prepared according to the procedure described in Example 36C, substituting Example 45A for Example 36B.

Example 59B (2S,3S,4S,5S)-3-tert-butyl-4-{[(5-tert-butyl-2-methoxyphenyl)methyl]amino}-5-[2-(difluoromethoxy)phenyl]-1-[(2S)-oxane-2-carbonyl]pyrrolidine-2-carboxylic acid The title compound was prepared according to the procedure described in Example 45D, substituting Example 59A for Example 45C. $^1$H NMR (400 MHz, dimethyl sulfoxide-d$_6$) δ ppm 7.87 (s, 1H), 7.31 (t, J=7.9 Hz, 1H), 7.19 (t, J=7.6 Hz, 1H), 7.16-7.10 (m, 2H), 6.97 (s, 1H), 6.93 (d, J=2.5 Hz, 1H), 6.72 (d, J=8.5 Hz, 1H), 5.6 (s, 1H), 4.59 (d, J=1.7 Hz, 1H), 3.74 (d, J=11.4 Hz, 2H), 3.55 (d, J=13.6 Hz, 1H), 3.51 (s, 3H), 3.46 (d, J=6.8 Hz, 1H), 3.26 (d, J=13.8 Hz, 2H), 2.37-2.31 (m, 1H), 1.89 (s, 1H), 1.74-1.30 (m, 6H), 1.18 (s, 9H), 0.97 (s, 9H); MS (ESI+) m/z 617.2 (M+H)$^+$.

Example 60

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2S)-oxane-2-carbonyl]pyrrolidine-2-carboxylic acid Example 60A (2S,3R,4S,5S)-1-tert-butyl 2-ethyl 3-(tert-butyl)-5-(2-(dimethylamino)pyridin-3-yl)-4-nitropyrrolidine-1,2-dicarboxylate Core 11 (18.2 g, 50 mmol) was dissolved in 100 mL of tetrahydrofuran, and di-tert-butyl dicarbonate (16.37 g, 75 mmol) was added. The reaction mixture was heated to 50° C. for 3 hours, at which point complete conversion had occurred, as indicated by LC-MS. The flask was cooled to ambient temperature and imidazole (3.4 g, 50 mmol) was added. The reaction mixture was stirred for 5 minutes at ambient temperature then diluted with methyl tert-butyl ether (100 mL). The suspension was washed with 1 M aqueous HCl (3×50 mL) then saturated aqueous sodium bicarbonate (50 mL) and brine (50 mL) and dried over sodium sulfate, filtered, and concentrated in vacuo to give 23 g of the title compound. $^1$H NMR (400 MHz, dimethyl sulfoxide-d$_6$) δ ppm 8.18 (dd, J=4.8, 1.7 Hz, 1H), 8.06 (dd, J=7.7, 1.8 Hz, 1H), 6.97 (ddd, J=7.7, 4.7, 0.9 Hz, 1H), 5.63 (d, J=8.3 Hz, 1H), 5.48 (ddd, J=8.3, 2.5, 1.0 Hz, 1H), 4.50 (d, J=3.2 Hz, 1H), 4.24 (q, J=7.1 Hz, 2H), 2.92 (t, J=2.9 Hz, 1H), 2.75 (s, 6H), 1.95 (s, 1H), 1.28 (td, J=7.1, 0.9 Hz, 3H), 1.20 (s, 9H), 1.03 (s, 9H); MS (ESI+) m/z 465.3 (M+H)+.

Example 60B (2S,3S,4S,5S)-1-tert-butyl 2-ethyl 4-amino-3-(tert-butyl)-5-(2-(dimethylamino)pyridin-3-yl)pyrrolidine-1,2-dicarboxylate Example 60A (20.6 g, 44.3 mmol) and tetrahydrofuran (200 mL) were added to Raney®-Nickel 2800, water slurry (81 g, 621 mmol) in a 50 mL Hast C reactor and the mixture was stirred for 22 hours at 60 psi hydrogen and 60° C., and 16 hours at 25° C. The reaction mixture was filtered through a fritted funnel and the filter cake was washed with 50 mL of tetrahydrofuran. The filtrate was concentrated in vacuo to give the title compound (18.9 g), which was used without additional purification. $^1$H NMR (400 MHz, dimethyl sulfoxide-$d_6$) δ ppm 8.32-8.00 (m, 2H), 6.97 (dd, J=7.5, 4.8 Hz, 1H), 5.19 (d, J=6.7 Hz, 1H), 4.27 (d, J=3.0 Hz, 1H), 4.18 (qq, J=7.0, 3.8 Hz, 2H), 3.75 (dd, J=6.7, 2.2 Hz, 1H), 2.75 (s, 6H), 2.01 (t, J=2.6 Hz, 1H), 1.25 (t, J=7.1 Hz, 3H), 1.15 (s, 9H), 1.00 (s, 9H); MS (ESI+) m/z 435.1 (M+H)+.

Example 60C (2S,3S,4S,5S)-1-tert-butyl 2-ethyl 3-(tert-butyl)-5-(2-(dimethylamino)pyridin-3-yl)-4-((2-methoxy-5-(1-methylcyclobutyl)benzyl)amino)pyrrolidine-1,2-dicarboxylate Example 60B (130 mg, 0.299 mmol) and 2-methoxy-5-(1-methylcyclobutyl)benzaldehyde (Intermediate 5, 73.3 mg, 0.359 mmol) were dissolved in dichloroethane (1496 µL). Sodium triacetoxyborohydride (89 mg, 0.419 mmol) was added in one portion, and the reaction was stirred at ambient temperature for 0.5 hours, at which point it was complete by LC-MS. The solution was diluted with dichloromethane (5 mL), and 1 mL of saturated aqueous sodium bicarbonate was added. The mixture was stirred for 10 minutes then extracted with 3×5 mL of dichloromethane and the combined organic extracts were dried over sodium sulfate, filtered, and concentrated in vacuo. The material was dissolved in cyclopentyl methyl ether (5 mL). HCl in cyclopentyl methyl ether (3 M, 0.2 mL, 0.6 mmol) was added. The solution was diluted with heptanes (10 mL) and the resulting solid material was removed via filtration through a fritted funnel to give the title compound (197 mg). $^1$H NMR (400 MHz, dimethyl sulfoxide-$d_6$) δ ppm 8.28 (d, J=7.8 Hz, 1H), 8.19 (d, J=5.1 Hz, 1H), 7.08 (s, 1H), 7.00 (d, J=8.6 Hz, 1H), 6.84 (s, 1H), 6.78 (d, J=8.1 Hz, 1H), 5.28 (d, J=6.4 Hz, 1H), 4.38 (d, J=1.7 Hz, 1H), 4.17 (q, J=7.1 Hz, 2H), 3.74-3.58 (m, 4H), 3.55 (s, 3H), 2.76 (br s, 6H), 2.20 (m, 2H), 2.08-1.91 (m, 3H), 1.77-1.70 (m, 1H), 1.33 (s, 3H), 1.22 (t, J=7.1 Hz, 3H), 1.16 (s, 9H), 1.02 (s, 9H); MS (ESI+) m/z 623.1 (M+H)+.

Example 60D (2S,3S,4S,5S)-ethyl 3-(tert-butyl)-5-(2-(dimethylamino)pyridin-3-yl)-4-((2-methoxy-5-(1-methylcyclobutyl)benzyl)amino)pyrrolidine-2-carboxylate Example 60C (200 mg, 0.303 mmol) was dissolved in 2 mL of dichloromethane and 0.5 mL of trifluoroacetic acid was added. After 2 hour at ambient temperature, the reaction mixture was concentrated in vacuo and partitioned between 1 M aqueous NaOH and dichloromethane. The organic extracts were dried over sodium sulfate, filtered, and concentrated to give the crude product, which was used without additional purification (160 mg). $^1$H NMR (400 MHz, dimethyl sulfoxide-$d_6$) δ ppm 8.13 (dd, J=4.6, 1.9 Hz, 1H), 7.98 (dd, J=7.6, 2.0 Hz, 1H), 6.99-6.85 (m, 2H), 6.85-6.65 (m, 2H), 4.42 (s, 1H), 4.13 (qt, J=7.1, 3.5 Hz, 2H), 3.59 (br s, 4H), 3.43-3.22 (m, 2H), 3.08 (br s, 1H), 2.82 (br s, 1H), 2.72 (s, 6H), 2.20 (ddd, J=10.6, 6.2, 4.0 Hz, 2H), 2.12 (dd, J=5.9, 1.9 Hz, 1H), 2.07-1.89 (m, 3H), 1.75 (tdd, J=9.2, 7.2, 4.2 Hz, 1H), 1.33 (s, 3H), 1.20 (t, J=7.1 Hz, 3H), 0.96 (s, 9H); MS (ESI+) m/z 523.2 (M+H)+.

Example 60E (2S,3S,4S,5S)-ethyl 3-(tert-butyl)-5-(2-(dimethylamino)pyridin-3-yl)-4-((2-methoxy-5-(1-methylcyclobutyl)benzyl)amino)-1-((S)-tetrahydro-2H-pyran-2-carbonyl)pyrrolidine-2-carboxylate Example 60D (160 mg, 0.306 mmol) was dissolved in 2 mL of dichloromethane and the solution was cooled in an ice bath before addition of triethylamine (0.171 mL, 1.224 mmol) and a solution of tetrahydro-2H-pyran-2-carbonyl chloride (59.1 mg, 0.398 mmol) in dichloromethane (0.5 mL). After 5 minutes, the reaction mixture was diluted with methyl tert-butyl ether (30 mL), stirred with saturated aqueous sodium bicarbonate (15 mL) for 15 minutes then extracted with methyl tert-butyl ether (3×10 mL). The combined extracts were concentrated to give a crude residue, which was purified via flash chromatography, eluting on a 40 g silica gel column with 0:100 to 60:40 methyl tert-butyl ether:heptanes over 5 minutes and isocratic 60:40 methyl tert-butyl ether:heptanes to give two diastereomeric products. The first eluting peak, (57 mg), was the title compound. $^1$H NMR (400 MHz, dimethyl sulfoxide-$d_6$) δ ppm 8.17 (s, 2H), 6.93 (dd, J=8.4, 2.5 Hz, 2H), 6.83-6.62 (m, 2H), 5.56 (s, 1H), 4.67 (s, 1H), 4.21-4.01 (m, 3H), 3.75 (d, J=11.4 Hz, 1H), 3.55 (br s, 2H), 3.48 (s, 3H), 3.24 (s, 2H), 2.69 (s, 6H), 2.19 (t, J=9.3 Hz, 2H), 2.10-1.88 (m, 3H), 1.80-1.60 (m, 2H), 1.43 (d, J=42.0 Hz, 3H), 1.32 (s, 5H), 1.19 (t, J=7.0 Hz, 4H), 1.01 (s, 9H); MS (ESI+) m/z 635.6 (M+H)+.

Example 60F (2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2S)-oxane-2-carbonyl]pyrrolidine-2-carboxylic acid Example 60E (54 mg, 0.085 mmol) was dissolved in 0.2 mL of tetrahydrofuran and water (0.200 mL) and methanol (0.100 mL) mixture. Lithium hydroxide hydrate (17.85 mg, 0.425 mmol) was added, and the suspension was heated to 50° C. for 1 hour, at which point LC-MS indicated complete conversion. The vial was cooled to ambient temperature, diluted with dichloromethane (20 mL), and acidified to pH 3-4 with 1 M aqueous HCl. The layers were separated. The organic layer was dried over sodium sulfate, filtered, and concentrated under a stream of $N_2$ at 50° C. to give 49 mg of the title compound. $^1$H NMR (400 MHz, dimethyl sulfoxide-$d_6$) δ ppm 8.19 (dd, J=4.8, 1.6 Hz, 2H), 7.05-6.92 (m, 2H), 6.83-6.72 (m, 2H), 5.57 (d, J=6.6 Hz, 1H), 4.60 (s, 1H), 3.81-3.58 (m, 6H), 3.52 (s, 3H), 3.29 (d, J=13.7 Hz, 1H), 2.71 (s, 6H), 2.66 (br s, 1H), 2.44 (s, 1H), 2.25-2.14 (m, 2H), 2.10-1.88 (m, 3H), 1.81-1.62 (m, 3H), 1.51-1.36 (m, 3H), 1.33 (s, 3H), 1.00 (s, 9H); MS (ESI+) m/z 607.3 (M+H)$^+$.

Example 61

(2S,3S,4S,5S)-3-tert-butyl-4-{[(5-tert-butyl-2-methoxyphenyl)methyl]amino}-1-{[(propan-2-yl)oxy]carbonyl}-5-[2-(propan-2-yl)phenyl]pyrrolidine-2-carboxylic acid Example 61A (2S,3R,4S,5S)-3-tert-butyl-5-(2-isopropyl-phenyl)-4-nitro-pyrrolidine-1,2-dicarboxylic acid 1-tert-butyl ester 2-ethyl ester To a solution of (2S,3R,4S,5S)-ethyl 3-(tert-butyl)-5-(2-isopropylphenyl)-4-nitropyrrolidine-2-carboxylate (Core 8, 3.15 g, 8.69 mmol, 1.0 eq) in tetrahydrofuran (25 mL) was added di-tert-butyl dicarbonate (2.84 g, 13 mmol, 1.5 eq). The reaction mixture was stirred overnight at 55° C., then quenched with imidazole (591 mg, 8.69 mmol, 1 eq) and diluted with ethyl acetate. The resulting solution was washed with 1 N aqueous HCl solution, water and brine. The combined organic layers were dried over magnesium sulfate, filtered and concentrated in vacuo. The title compound (4.2 g, quantitative yield) was used in the next step without further purification. LC/MS (ESI+) m/z 463.4 (M+H)$^+$.

Example 61B (2S,3S,4S,5S)-4-amino-3-tert-butyl-5-(2-isopropyl-phenyl)-pyrrolidine-1,2-dicarboxylic acid 1-tert-butyl ester 2-ethyl ester Zinc dust (12.2 g, 187 mmol, 21 eq) was added to a solution of Example 61A (8.69 mmol, 1 eq) in acetic acid (30 mL) and ethyl acetate (100 mL). The resulting mixture was stirred at 60° C. for 1 hour. The reaction mixture was filtered on diatomaceous earth, washed with ethyl acetate, concentrated and then quenched with saturated aqueous NaHCO$_3$ solution. The crude mixture was diluted with ethyl acetate, and washed with water and brine. The combined organic layers were dried over MgSO$_4$, filtered and concentrated in vacuo. The title compound (4.5 g, quantitative) was used in the next steps without further purification. LC/MS (ESI+) m/z 433.5 (M+H)$^+$.

Example 61C (2S,3S,4S,5S)-3-tert-butyl-4-(5-tert-butyl-2-methoxy-benzylamino)-5-(2-isopropyl-phenyl)-pyrrolidine-1,2-dicarboxylic acid 1-tert-butyl ester 2-ethyl ester NaBH$_3$CN (8 mg, 0.12 mmol, 1.2 eq) was added to a solution of Example 61B (40 mg, 0.09 mmol, 1.0 eq) and 5-tert-butyl-2-methoxy-benzaldehyde (19 mg, 0.1 mmol, 1.1 eq) in acetic acid/sodium acetate/methanol buffer (2 mL). The reaction mixture was stirred at room temperature for 1 hour. The mixture was concentrated and the residue was partitioned between dichloromethane and water. The organic phase was concentrated to dryness and the residue was purified on silica gel (heptane/ethyl acetate 100/0 to 70/30) to give the title compound (350 mg, 57%). LC/MS (ESI+) m/z 609.6 (M+H)$^+$.

Example 61D (2S,3S,4S,5S)-3-tert-butyl-4-(5-tert-butyl-2-methoxy-benzylamino)-5-(2-isopropyl-phenyl)-pyrrolidine-2-carboxylic acid ethyl ester Trifluoroacetic acid (CAS#76-05-1, 350 µL) was added to a solution of protected (2S,3S,4S,5S)-3-tert-butyl-4-(5-tert-butyl-2-methoxy-benzylamino)-5-(2-isopropyl-phenyl)-pyrrolidine-1,2-dicarboxylic acid 1-tert-butyl ester 2-ethyl ester (145 mg, 0.25 mmol, 1.0 eq) in dichloromethane. The reaction was stirred at room temperature overnight, then the solvent was removed under vacuum. The residue was partitioned between dichloromethane and NaHCO$_3$ saturated aqueous solution. The organic phase was concentrated to dryness and the residue was purified by flash chromatography on silica gel (dichloromethane/methanol 100/0 to 97/3) to provide the title compound (90 mg, 70%). LC/MS (ESI+) m/z 509.8 (M+H)$^+$.

Example 61E (2S,3S,4S,5S)-3-tert-butyl-4-(5-tert-butyl-2-methoxy-benzylamino)-5-(2-isopropyl-phenyl)-pyrrolidine-1,2-dicarboxylic acid 2-ethyl ester 1-isopropyl ester To a stirred solution of (2S,3S,4S,5S)-3-tert-butyl-4-(5-tert-butyl-2-methoxy-benzylamino)-5-(2-isopropyl-phenyl)-pyrrolidine-2-carboxylic acid ethyl ester (45 mg, 0.08 mmol, 1.0 eq) and triethylamine (22 µL, 0.16 mmol, 2.0 eq) in dichloromethane (2 mL) was added at room temperature isopropyl chloroformate (CAS#108-23-6, 90 µL, 0.09 mmol, 1.1 eq). The reaction mixture was stirred for 1 hour, then washed with water and the organic phase was concentrated to dryness. The residue was purified by flash chromatography (heptane/ethyl acetate 100/0 to 85/15) to give the title compound (52 mg, 100%); LC/MS (ESI+) m/z 596.0 (M+H)$^+$.

Example 61F (2S,3S,4S,5S)-3-tert-butyl-4-(5-tert-butyl-2-methoxy-benzylamino)-5-(2-isopropyl-phenyl)-pyrrolidine-1,2-dicarboxylic acid 1-isopropyl ester A solution of (2S,3S,4S,5S)-3-tert-butyl-4-(5-tert-butyl-2-methoxy-benzylamino)-5-(2-isopropyl-phenyl)-pyrrolidine-1,2-dicarboxylic acid ethyl ester 1-isopropyl ester (52 mg, 0.08 mmol, 1.0 eq) in methanol (1 mL) was treated with LiOH 1.0 M in water (240 µL, 0.24 mmol, 3.0 eq) at room temperature and the mixture was stirred for 96 hours at 45° C. After the reaction was completed, 2 N aqueous HCl was added and the solvent was removed under vacuum. The residue was purified by chromatography on silica gel (dichloromethane/methanol 100/0 to 95/5). The product fractions were combined and concentrated to dryness to provide the title compound (33 mg, 72%). LC/MS (ESI+) m/z 567.7 (M+H)$^+$.

Example 62

(2S,3S,4S,5S)-3-tert-butyl-4-{[(5-tert-butyl-2-methoxyphenyl)methyl]amino}-1-[(2S*)-oxane-2-carbonyl]-5-[2-(propan-2-yl)phenyl]pyrrolidine-2-carboxylic acid

Example 62A (2S,3S,4S,5S)-3-tert-butyl-4-(5-tert-butyl-2-methoxy-benzylamino)-5-(2-isopropyl-phenyl)-1-(tetrahydro-pyran-2-carbonyl)-pyrrolidine-2-carboxylic acid ethyl ester To a stirred solution of tetrahydro-pyran-2-carboxylic acid (CAS#51673-83-7, 13 mg, 0.10 mmol, 1.3 eq) in dichloromethane (1 mL) was added Ghosez's reagent (1-chloro-N,N,2-trimethyl-1-propenylamine, CAS#26189-59-3, 32 µL, 0.24 mmol, 3.0 eq). The reaction mixture was stirred at 0° C. for 5 minutes and Example 61D (45 mg, 0.08 mmol, 1.0 eq) and diethylamine (56 µL, 0.32 mmol, 4.0 eq) in dichloromethane (1 mL) were added. The reaction mixture was stirred at 0° C. for 10 minutes and at room temperature for 1.5 hours. Water was added, the two phases were separated and the organic phase was concentrated to dryness. The residue was purified by chromatography on silica gel (heptane/ethyl acetate 100/0 to 85/15) to give the title compound as a mixture of diastereomers (54 mg, 100%). LC/MS (ESI+) m/z 621.6 (M+H)+.

Example 62B (2S,3S,4S,5S)-3-tert-butyl-4-(5-tert-butyl-2-methoxy-benzylamino)-5-(2-isopropyl-phenyl)-1-((5)-tetrahydro-pyran-2-carbonyl)-pyrrolidine-2-carboxylic acid A solution of (2S,3S,4S,5S)-3-tert-butyl-4-(5-tert-butyl-2-methoxy-benzylamino)-5-(2-isopropyl-phenyl)-1-(tetrahydro-pyran-2-carbonyl)-pyrrolidine-2-carboxylic acid ethyl ester (54 mg, 0.08 mmol, 1.0 eq) in methanol (2 mL) was treated with LiOH 1.0 M in water (240 µL, 0.24 mmol, 3.0 eq) at room temperature and the mixture was stirred for 96 hours at 45° C. After the reaction was complete, 2 N aqueous HCl was added, and the solvent was removed under vacuum. The residue was purified on silica gel (dichloromethane/methanol 100/0 to 95/5). The product fractions were combined and concentrated to dryness to provide the title compound, Example 62B (8 mg, 17%, second diastereomer to elute). LC/MS (ESI+) m/z 593.8 (M+H)+. Example I-217 (9 mg, 17%) was also obtained as first diastereomer to elute.

Example 63

(2S,3S,4S,5S)-3-tert-butyl-4-({[4-(3-chlorophenyl)oxan-4-yl]methyl}amino)-1-(cyclohexanecarbonyl)-5-phenylpyrrolidine-2-carboxylic acid A 4 mL vial was charged with a stir bar to which was added (2S,3S,4S,5S)-ethyl 4-amino-3-(tert-butyl)-1-(cyclohexanecarbonyl)-5-phenylpyrrolidine-2-carboxylate (Example 7B, 25 mg, 0.063 mmol) in 800 µL of sodium acetate/acetic acid buffer in methanol (pH=4). To this was added a solution of 4-(3-chlorophenyl)tetrahydro-2H-pyran-4-carbaldehyde (13 mg, 0.07 mmol) in methanol (200 µL) followed by sodium cyanoborohydride (5 mg, 0.081 mmol). The reaction mixture was allowed to stir at room temperature overnight. Upon completion of the first step, the crude material was dried, and to the residue was added 3:2 mixture of tetrahydrofuran and methanol and 300 µL of 5 M aqueous lithium hydroxide and was further allowed to be stirred at 45° C. overnight. The residues were dissolved in dimethyl sulfoxide and purified by reverse phase HPLC (trifluoroacetic acid method). The samples were purified by preparative HPLC on a Phenomenex® Luna® C8(2) 5 um 100 Å AXIA column (30 mm×150 mm). A gradient of ACN (A) and 0.1% trifluoroacetic acid in water (B) was used, at a flow rate of 50 mL/minute (0-0.5 minute 5% A, 0.5-8.5 minute linear gradient 5-100% A, 8.7-10.7 minute 100% A, 10.7-11.0 minute linear gradient 100-5% A) to obtain the desired compound. $^1$H NMR (400 MHz, dimethyl sulfoxide-$d_6$) δ ppm 7.35 (s, 2H), 7.17 (t, J=5.9 Hz, 2H), 7.15-7.06 (m, 3H), 6.93 (t, J=2.0 Hz, 1H), 6.87 (dt, J=7.5, 1.7 Hz, 1H), 5.08 (d, J=7.0 Hz, 1H), 4.41 (d, J=2.6 Hz, 1H), 3.56-3.41 (m, 2H), 3.37 (ddd, J=11.5, 7.5, 3.5 Hz, 1H), 3.30-3.23 (m, 2H), 2.64 (d, J=12.0 Hz, 1H), 2.26 (d, J=11.8 Hz, 1H), 2.15 (s, 2H), 1.83-1.74 (m, 1H), 1.66-1.37 (m, 7H), 1.18 (t, J=12.6 Hz, 3H), 1.06 (d, J=19.8 Hz, 2H), 0.93 (s, 9H); MS (APCI) m/z 581.1 (M+H)+.

Example 64

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-{[(propan-2-yl)oxy]carbonyl}pyrrolidine-2-carboxylic acid

Example 64A 2-ethyl 1-isopropyl (2S,3S,4S,5S)-4-((5-(bicyclo[1.1.1]pentan-1-yl)-2-methoxybenzyl)amino)-3-(tert-butyl)-5-(2-(dimethylamino)pyridin-3-yl)pyrrolidine-1,2-dicarboxylate (2S,3S,4S,5S)-2-Ethyl 1-isopropyl 4-amino-3-(tert-butyl)-5-(2-(dimethylamino)pyridin-3-yl)pyrrolidine-1,2-dicarboxylate (Example 66B, 84.9 mg, 0.202 mmol) and Example 51B (61.9 mg, 0.284 mmol) were dissolved in dichloroethane (2 mL). Sodium triacetoxyborohydride (69.0 mg, 0.326 mmol) was added and the reaction was stirred at ambient temperature for 1 hour. The reaction was diluted with dichloromethane (25 mL) and quenched with saturated aqueous sodium bicarbonate (25 mL) and stirred for 30 minutes. The organic layer was isolated and the aqueous layer was extracted with dichloromethane (25 mL). The combined organic layers were dried over $Na_2SO_4$, filtered and concentrated. The residue was dissolved in heptane and HCl was added (3 M in cyclopentyl methyl ether, 2 mL) dropwise. The resulting solid was removed via filtration and dried to give the product as the HCl salt (126.4 mg, 97%). $^1$H NMR (400 MHz, dimethyl sulfoxide-$d_6$, 120° C.) δ ppm 8.26 (d, J=8.1 Hz, 1H), 8.19 (d, J=5.0 Hz, 1H), 7.10-7.03 (m, 1H), 6.97 (d, J=8.3 Hz, 1H), 6.81 (s, 1H), 6.76 (d, J=8.1 Hz, 1H), 5.33 (d, J=6.5 Hz, 1H), 4.63 (p, J=6.2 Hz, 1H), 4.40 (d, J=1.7 Hz, 1H), 4.17 (q, J=7.1 Hz, 2H), 3.68-3.52 (m, 5H), 3.30 (d, J=14.2 Hz, 1H), 3.14 (s, 1H), 2.77 (t, J=2.4 Hz, 6H), 2.45 (s, 1H), 1.95 (s, 6H), 1.22 (t, J=7.1 Hz, 3H), 1.05-0.98 (m, 12H), 0.86 (d, J=6.2 Hz, 3H); MS (ESI+) m/z 607 (M+H)+.

Example 64B (2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-{[(propan-2-yl)oxy]carbonyl}pyrrolidine-2-carboxylic acid Example 64A (126.4 mg, 0.197 mmol) was dissolved in methanol (1 mL). Aqueous LiOH (1 M, 1.0 mL, 1.0 mmol) was added and the reaction was heated to 50° C. for 16 hours. The reaction was acidified to pH=5 by the addition of 1 M aqueous HCl (1 mL), then concentrated. The residue was purified by silica gel chromatography (10% ethanol in ethyl acetate) to provide the title compound (58.2 mg, 51%). $^1$H NMR (400 MHz, dimethyl sulfoxide-$d_6$, 120° C.) δ ppm 8.21-8.12 (m, 2H), 6.98-6.89 (m, 2H), 6.77 (d, J=2.2 Hz, 1H), 6.71 (d, J=8.3 Hz, 1H), 5.29 (d, J=6.4 Hz, 1H), 4.60 (p, J=6.2 Hz, 1H), 4.33 (d, J=1.6 Hz, 1H), 3.53 (d, J=13.8 Hz, 1H), 3.46 (d, J=5.7 Hz, 4H), 3.22 (d, J=13.8 Hz, 1H), 2.62 (d, J=0.9 Hz, 6H), 2.49 (s, 1H), 2.33 (d, J=1.6 Hz, 1H), 1.94 (s, 6H), 1.04-0.96 (m, 12H), 0.81 (d, J=6.2 Hz, 3H); MS (ESI+) m/z 579 (M+H)$^+$.

Example 65

(2S,3S,4S,5S)-1-(bicyclo[3.1.0]hexane-6-carbonyl)-3-tert-butyl-4-({[2-methoxy-4-(trifluoromethyl)phenyl]methyl}amino)-5-phenylpyrrolidine-2-carboxylic acid

Example 65A (2S,3S,4S,5S)-1-tert-butyl 2-ethyl 3-(tert-butyl)-4-((2-methoxy-4-(trifluoromethyl)benzyl)amino)-5-phenylpyrrolidine-1,2-dicarboxylate (2S,3S,4S,5S)-1-tert-Butyl 2-ethyl 4-amino-3-(tert-butyl)-5-phenylpyrrolidine-1,2-dicarboxylate (Example 34B, 1.3 g, 3.33 mmol) and 2-methoxy-4-(trifluoromethyl)benzaldehyde (0.680 g, 3.33 mmol) were dissolved in dichloroethane (11.10 mL). Sodium triacetoxyborohydride (0.882 g, 4.16 mmol) was added, and the reaction mixture was stirred at ambient temperature for 15 minutes, at which point the reaction was complete by LC-MS. The resulting suspension was diluted with methyl tert-butyl ether (30 mL) and stirred with saturated aqueous sodium bicarbonate (20 mL) for 15 minutes. The layers were separated and the organic layer was concentrated in vacuo to give a crude residue, which was loaded onto a 40 g silica gel column and was eluted with 0:100 to 15:85 ethyl acetate:heptanes over 20 minutes to give 1.45 g of the title compound. $^1$H NMR (400 MHz, dimethyl sulfoxide-$d_6$) δ ppm 7.59-7.40 (m, 2H), 7.35-7.14 (m, 3H), 7.13-7.01 (m, 3H), 4.96 (d, J=6.8 Hz, 1H), 4.31 (d, J=2.7 Hz, 1H), 4.12 (q, J=7.1 Hz, 2H), 3.64 (s, 3H), 3.49-3.27 (m, 2H), 2.27 (t, J=2.5 Hz, 1H), 1.20 (d, J=7.1 Hz, 3H), 1.18 (d, J=3.3 Hz, 9H), 0.99 (s, 9H); MS (ESI+) m/z 579.1 (M+H)$^+$.

Example 65B (2S,3S,4S,5S)-ethyl 3-(tert-butyl)-4-((2-methoxy-4-(trifluoromethyl)benzyl)amino)-5-phenylpyrrolidine-2-carboxylate Example 65A (1.25 g) was dissolved in a mixture of dichloromethane (10 mL) and trifluoroacetic acid (5 mL) and the solution was stirred for 1 hour at ambient temperature then concentrated in vacuo and azeotroped twice with 10 mL of dichloromethane. The residue was dissolved in ethyl acetate (20 mL) and washed with 1 M aqueous NaOH (3×10 mL) and brine (10 mL) before drying over sodium sulfate, filtering, and concentrating in vacuo to give the title compound (1.0 g) that was used without additional purification. $^1$H NMR (400 MHz, Chloroform-d) δ ppm 7.39-7.31 (m, 4H), 7.30-7.24 (m, 1H), 7.13-7.01 (m, 2H), 6.90 (d, J=1.5 Hz, 1H), 4.29-4.17 (m, 3H), 3.74 (d, J=5.7 Hz, 1H), 3.63 (s, 3H), 3.42 (s, 1H), 3.32 (d, J=14.4 Hz, 1H), 3.12 (dd, J=4.7, 1.3 Hz, 1H), 2.15 (dd, J=5.8, 1.3 Hz, 1H), 1.76 (br s, 2H), 1.28 (t, J=7.2 Hz, 3H), 1.00 (s, 9H); MS (ESI+) m/z 479.5 (M+H)$^+$.

Example 65C ethyl (2S,3S,4S,5S)-1-(bicyclo[3.1.0]hexane-6-carbonyl)-3-(tert-butyl)-4-((2-methoxy-4-(trifluoromethyl)benzyl)amino)-5-phenylpyrrolidine-2-carboxylate Bicyclo[3.1.0]hexane-6-carboxylic acid (29.4 mg, 0.233 mmol) was dissolved in dichloromethane (1 mL). Oxalyl chloride (40 μL, 0.457 mmol) was added followed by N,N-dimethylformamide (10 μL). The reaction was stirred at room temperature for 3 hours, at which point it was concentrated, redissolved in dichloromethane (1 mL), and concentrated again. The residue was taken up in dichloromethane (2×1 mL) and added to (2S,3S,4S,5S)-ethyl 3-(tert-butyl)-4-((2-methoxy-4-(trifluoromethyl)benzyl)amino)-5-phenylpyrrolidine-2-carboxylate (Example 65B) (54.7 mg, 0.114 mmol) and triethylamine (50 μL, 0.359 mmol) in dichloromethane (1 mL). The reaction was stirred at ambient temperature for 17 hours. The reaction was concentrated and the crude residue was purified by reverse phase using the ammonium acetate method to provide the title compound (64.9 mg, 97%). $^1$H NMR (400 MHz, dimethyl sulfoxide-$d_6$, 120° C.) δ ppm 7.58 (d, J=7.5 Hz, 2H), 7.32 (t, J=7.5 Hz, 2H), 7.28-7.22 (m, 1H), 7.11-7.02 (m, 3H), 5.24 (d, J=6.8 Hz, 1H), 4.52 (d, J=2.7 Hz, 1H), 4.10 (q, J=7.1 Hz, 2H), 3.64 (s, 3H), 3.51-3.31 (m, 4H), 2.28 (d, J=2.7 Hz, 1H), 1.69-1.53 (m, 3H), 1.49-1.30 (m, 3H), 1.18 (t, J=7.1 Hz, 3H), 1.13 (s, 1H), 0.98 (s, 9H), 0.65 (s, 1H); MS (ESI+) m/z 587 (M+H)$^+$.

Example 65D (2S,3S,4S,5S)-1-(bicyclo[3.1.0]hexane-6-carbonyl)-3-tert-butyl-4-({[2-methoxy-4-(trifluoromethyl)phenyl]methyl}amino)-5-phenylpyrrolidine-2-carboxylic acid Example 65C (64.9 mg, 0.111 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (52.5 mg, 71%) as the trifluoroacetic acid salt. $^1$H NMR (400 MHz, dimethyl sulfoxide-$d_6$, 120° C.) δ ppm 7.61-7.54 (m, 2H), 7.36 (t, J=7.6 Hz, 2H), 7.32-7.25 (m, 1H), 7.20-7.07 (m, 3H), 5.32 (d, J=6.9 Hz, 1H), 4.53 (d, J=2.2 Hz, 1H), 3.71-3.67 (m, 4H), 3.64 (d, J=14.2 Hz, 1H), 3.40 (d, J=14.2 Hz, 1H), 2.44-2.37 (m, 2H), 1.81-1.03 (m, 7H), 1.00 (s, 9H), 0.79-0.60 (m, 1H); MS (ESI+) m/z 559 (M+H)$^+$.

Example 66

(2S,3S,4S,5S)-3-tert-butyl-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid

Example 66A (2S,3R,4S,5S)-2-ethyl 1-isopropyl 3-(tert-butyl)-5-(2-(dimethylamino)pyridin-3-yl)-4-nitropyrrolidine-1,2-dicarboxylate (2S,3R,4S,5S)-Ethyl 3-(tert-butyl)-5-(2-(dimethylamino)pyridin-3-yl)-4-nitropyrrolidine-2-carboxylate hydrochloride (Core 11, 1 g, 2.494 mmol) in $CH_2Cl_2$ (8.3 mL) was treated with triethylamine (1.1 mL, 7.89 mmol) and then isopropyl chloroformate (1 M solution in toluene) (4.6 mL, 4.60 mmol) at room temperature. The reaction was stirred at room temperature overnight. The volatiles were removed in vacuo, and the crude material was purified by silica gel chromatography, eluting with 5 to 80% ethyl acetate-heptanes. The title compound was obtained, 0.548 g (49% yield). $^1$H NMR (501 MHz, dimethyl sulfoxide-$d_6$) δ ppm 8.20 (dd, J=4.8, 1.9 Hz, 1H), 8.05 (dd, J=7.7, 1.9 Hz, 1H), 7.03 (dd, J=7.7, 4.8 Hz, 1H), 5.64 (m, 1H), 5.52 (dd, J=8.5, 3.0 Hz, 1H), 4.64 (m, 1H), 4.47 (m, 1H), 4.23 (qd, J=7.2, 1.4 Hz, 2H), 2.97 (m, 1H), 2.71 (s, 6H), 1.26 (t, J=7.1 Hz, 3H), 1.14-0.85 (m, 6H), 0.98 (s, 9H); MS (ESI+) m/z 451.1 (M+H)$^+$.

Example 66B (2S,3S,4S,5S)-2-ethyl 1-isopropyl 4-amino-3-(tert-butyl)-5-(2-(dimethylamino)pyridin-3-yl)pyrrolidine-1,2-dicarboxylate Example 66A (0.548 g, 1.216 mmol) in tetrahydrofuran (20 mL) was added to Raney®-Nickel 2800, water slurry, solvent washed after weighing (1.59 g, 12.19 mmol) in a 250 mL SS pressure bottle, flushed with argon 3 times, flushed with hydrogen and shaken under 50 psi of hydrogen at 60° C. for 17 hours. The mixture was then filtered through a polypropylene membrane, and the filtrate was concentrated in vacuo to provide the title compound, 0.474 g (93% yield). $^1$H NMR (400 MHz, dimethyl sulfoxide-$d_6$) δ ppm 8.23-8.11 (m, 2H), 7.00 (dd, J=7.6, 4.8 Hz, 1H), 5.15 (d, J=6.5 Hz, 1H), 4.50 (m, 1H), 4.24-4.10 (m, 3H), 3.73 (m, 1H), 2.72 (s, 6H), 2.03 (m, 1H), 1.22 (t, J=7.1 Hz, 3H), 1.16-0.89 (m, 6H), 0.96 (s, 9H); MS (ESI+) m/z 421.1 (M+H)$^+$.

Example 66C (2S,3S,4S,5S)-2-ethyl 1-isopropyl 3-(tert-butyl)-4-((5-(tert-butyl)-2-methoxybenzyl)amino)-5-(2-(dimethylamino)pyridin-3-yl)pyrrolidine-1,2-dicarboxylate 5-(tert-Butyl)-2-methoxybenzaldehyde (0.022 g, 0.113 mmol) and Example 66B (0.050 g, 0.119 mmol) in dichloroethane (0.5 mL) were treated with sodium triacetoxyborohydride (0.034 g, 0.159 mmol), and the reaction was stirred at room temperature. After 130 minutes, the mixture was treated with 0.5 mL of saturated aqueous $NaHCO_3$ solution, and the mixture was stirred vigorously for 30 minutes. The phases were separated, and the aqueous layer was extracted three times with $CH_2Cl_2$. The combined organics were dried over $Na_2SO_4$, filtered, and concentrated in vacuo to provide the crude title compound, which was taken into the next reaction without further purification. MS (APCI+) m/z 597.7 (M+H)$^+$.

Example 66D (2S,3S,4S,5S)-3-tert-butyl-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid Example 66C (0.067 g, 0.113 mmol) in tetrahydrofuran (0.9 mL) and methanol (0.9 mL) was treated with lithium hydroxide (1 M aqueous) (0.9 mL, 0.900 mmol), and the reaction mixture was stirred overnight at 45° C. After this time, the reaction mixture was acidified to pH 1 with 1 N aqueous HCl, and the mixture was concentrated in vacuo. Excess moisture was removed azeotropically with acetonitrile, then the crude product was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound (0.0232 g, 36% yield). $^1$H NMR (400 MHz, dimethyl sulfoxide-$d_6$) δ ppm 8.23-8.12 (m, 2H), 7.18 (dd, J=8.5, 2.6 Hz, 1H), 7.03 (m, 2H), 6.77 (d, J=8.6 Hz, 1H), 5.34 (d, J=6.4 Hz, 1H), 4.62 (m, 1H), 4.37 (d, J=1.5 Hz, 1H), 3.75-3.60 (m, 2H), 3.53 (s, 3H), 3.34 (d, J=13.6 Hz, 1H), 2.68 (s, 6H), 2.44 (m, 1H), 1.20 (s, 9H), 1.02 (m, 12H), 0.84 (d, J=6.2 Hz, 3H); MS (ESI+) m/z 569.2 (M+H)$^+$.

Example 67

(2S,3S,4S,5S)-4-({[5-(bicyclo[1.1.1]pentan-1-yl)-2-methoxyphenyl]methyl}amino)-3-tert-butyl-1-[(1R)-3,3-difluorocyclohexane-1-carbonyl]-5-phenylpyrrolidine-2-carboxylic acid

Example 67A ethyl (2S,3S,4S,5S)-4-((5-(bicyclo[1.1.1]pentan-1-yl)-2-methoxybenzyl)amino)-3-(tert-butyl)-1-((R)-3,3-difluorocyclohexane-1-carbonyl)-5-phenylpyrrolidine-2-carboxylate Example 69D (28.3 mg, 0.065 mmol) and Example 51B (15.0 mg, 0.074 mmol) were dissolved in methanol (1 mL) and stirred at ambient temperature for 3 hours. Sodium cyanoborohydride (25.2 mg, 0.401 mmol) was added and the reaction was stirred at ambient temperature for an additional 16 hours. The reaction mixture was diluted with dimethyl sulfoxide (1 mL), filtered and purified by reverse phase using the ammonium acetate method to provide the title compound (23.9 mg, 59%). $^1$H NMR (400 MHz, dimethyl sulfoxide-$d_6$, 120° C.) δ ppm 7.57 (s, 2H), 7.29 (d, J=24.7 Hz, 3H), 6.92 (dd, J=8.3, 2.2 Hz, 1H), 6.74-6.68 (m, 2H), 5.18 (d, J=6.9 Hz, 1H), 4.52 (d, J=3.0 Hz, 1H), 4.11 (qd, J=7.1, 1.3 Hz, 2H), 3.51 (s, 3H), 3.44 (d, J=13.4 Hz, 3H), 3.29 (d, J=13.7 Hz, 1H), 2.49 (s, 1H), 2.36 (s, 1H), 1.94 (s, 6H), 1.90-1.41 (m, 6H), 1.23-1.16 (m, 5H), 0.99 (s, 9H); MS (ESI+) m/z 623 (M+H)$^+$.

Example 67B (2S,3S,4S,5S)-4-({[5-(bicyclo[1.1.1]pentan-1-yl)-2-methoxyphenyl]methyl}amino)-3-tert-butyl-1-[(1R)-3,3-difluorocyclohexane-1-carbonyl]-5-phenylpyrrolidine-2-carboxylic acid Example 67A (21.6 mg, 0.035 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (18.5 mg, 75%) as the trifluoroacetic acid salt. $^1$H NMR (400 MHz, dimethyl sulfoxide-$d_6$, 120° C.) δ ppm 7.54 (s, 2H), 7.36 (t, J=7.4 Hz, 2H), 7.28 (t, J=7.3 Hz, 1H), 6.98 (dd, J=8.3, 2.3 Hz, 1H), 6.81-6.73 (m, 2H), 5.26 (d, J=7.0 Hz, 1H), 4.51 (d, J=2.3 Hz, 1H), 3.67-3.57 (m, 3H), 3.53 (s, 3H), 3.36 (d, J=13.6 Hz, 1H), 2.50 (s, 1H), 1.99 (s, 1H), 1.96 (s, 6H), 1.93-1.10 (m, 8H), 0.99 (s, 9H); MS (ESI+) m/z 595 (M+H)$^+$.

Example 68

(2S,3S,4S,5S)-3-tert-butyl-4-{[(5-cyclobutyl-2-methoxypyridin-3-yl)methyl]amino}-1-{[(propan-2-yl)oxy]carbonyl}-5-[2-(propan-2-yl)phenyl]pyrrolidine-2-carboxylic acid

Example 68A (2S,3S,4S,5S)-1-tert-butyl 2-ethyl 3-(tert-butyl)-4-(((5-cyclobutyl-2-methoxypyridin-3-yl)methyl)amino)-5-(2-isopropylphenyl)pyrrolidine-1,2-dicarboxylate 5-Cyclobutyl-2-methoxynicotinaldehyde (0.084 g, 0.440 mmol) and (2S,3S,4S,5S)-1-tert-butyl 2-ethyl 4-amino-3-(tert-butyl)-5-(2-isopropylphenyl)pyrrolidine-1,2-dicarboxylate (Example 61B; 0.200 g, 0.462 mmol) were dissolved in dichloroethane (2.2 mL), then treated with sodium triacetoxyborohydride (0.131 g, 0.616 mmol). The reaction was stirred at room temperature for 30 minutes. The mixture was then treated with 2.2 mL of saturated aqueous NaHCO$_3$ solution, and the mixture was stirred vigorously at room temperature for 15 minutes. The phases were then separated, and the aqueous layer was extracted three times with CH$_2$Cl$_2$. The combined organics were dried over Na$_2$SO$_4$, filtered, and concentrated in vacuo. Silica gel chromatography, eluting with 10 to 50% ethyl acetate-heptanes, provided the title compound, 0.225 g (84% yield). $^1$H NMR (400 MHz, dimethyl sulfoxide-$d_6$) δ ppm 7.86 (m, 1H), 7.72 (m, 1H), 7.23 (m, 3H), 7.12 (m, 1H), 5.13 (m, 1H), 4.33 (d, J=1.1 Hz, 1H), 4.07 (m, 2H), 3.44 (m, 1H), 3.37 (s, 3H), 3.37-3.28 (m, 1H), 3.19 (m, 2H), 2.85 (m, 1H), 2.34 (m, 1H), 2.22-2.12 (m, 2H), 2.00-1.84 (m, 3H), 1.76 (m, 1H), 1.37-0.87 (m, 27H); MS (ESI+) m/z 608.2 (M+H)$^+$.

Example 68B (2S,3S,4S,5S)-ethyl 3-(tert-butyl)-4-(((5-cyclobutyl-2-methoxypyridin-3-yl)methyl)amino)-5-(2-isopropylphenyl)pyrrolidine-2-carboxylate Example 68A (0.224 g, 0.369 mmol) in CH$_2$Cl$_2$ (1.8 mL) was treated with trifluoroacetic acid (0.71 mL, 9.21 mmol), and the reaction was stirred at room temperature. After 2 hours, the mixture was concentrated in vacuo, and the residue was taken up in CH$_2$Cl$_2$ and washed twice with 1 N aqueous NaOH and once with brine. The organic layer was dried over Na$_2$SO$_4$, filtered, and concentrated in vacuo to provide the title compound, 0.131 g (70% yield). $^1$H NMR (400 MHz, dimethyl sulfoxide-$d_6$) δ ppm 7.73 (d, J=2.4 Hz, 1H), 7.64 (d, J=7.7 Hz, 1H), 7.28-7.07 (m, 5H), 4.43 (d, J=4.9 Hz, 1H), 4.14 (qd, J=7.0, 2.2 Hz, 2H), 3.66 (s, 1H), 3.63 (d, J=5.8 Hz, 1H), 3.41-3.24 (m, 2H), 3.21-3.05 (m, 2H), 3.01 (m, 1H), 2.29-2.15 (m, 3H), 2.04-1.87 (m, 3H), 1.82 (m, 1H), 1.26-1.13 (m, 9H), 0.98 (m, 9H); MS (ESI+) m/z 508.2 (M+H)$^+$.

Example 68C (2S,3S,4S,5S)-2-ethyl 1-isopropyl 3-(tert-butyl)-4-(((5-cyclobutyl-2-methoxypyridin-3-yl)methyl)amino)-5-(2-isopropylphenyl)pyrrolidine-1,2-dicarboxylate Example 68B (0.025 g, 0.049 mmol) in dichloroethane (0.2 mL) was treated with triethylamine (0.02 mL, 0.143 mmol) and isopropyl chloroformate (1 M in toluene) (0.09 mL, 0.090 mmol), and the mixture was stirred at 45° C. overnight. After this time, the mixture was cooled to room temperature, then diluted with ethyl acetate and washed twice with water and once with brine. The organic layer was dried over Na$_2$SO$_4$, filtered, and concentrated in vacuo. Silica gel chromatography, eluting with 5 to 25% ethyl acetate-heptanes, provided the title compound, 0.030 g (quantitative). $^1$H NMR (400 MHz, dimethyl sulfoxide-$d_6$) δ ppm 7.87 (m, 1H), 7.73 (m, 1H), 7.21 (m, 2H), 7.10 (m, 2H), 5.26 (d, J=6.3 Hz, 1H), 4.62 (m, 1H), 4.42 (d, J=1.6 Hz, 1H), 4.12 (q, J=7.1 Hz, 2H), 3.56 (s, 3H), 3.47-3.35 (m, 3H), 3.17 (m, 1H), 3.04 (m, 1H), 2.37 (m, 1H), 2.26 (m, 2H), 1.98-1.83 (m, 4H), 1.19 (m, 6H), 1.07 (d, J=6.8 Hz, 3H), 1.02 (s, 9H), 1.00 (d, J=6.1 Hz, 3H), 0.81 (d, J=6.1, 3H); MS (ESI+) m/z 594.3 (M+H)$^+$.

Example 68D (2S,3S,4S,5S)-3-tert-butyl-4-{[(5-cyclobutyl-2-methoxypyridin-3-yl)methyl]amino}-1-{[(propan-2-yl)oxy]carbonyl}-5-[2-(propan-2-yl)phenyl]pyrrolidine-2-carboxylic acid Example 68C (0.029 g, 0.049 mmol) in tetrahydrofuran (0.4 mL) and methanol (0.4 mL) was treated with lithium hydroxide (1 M aqueous) (0.4 mL, 0.400 mmol), and the reaction was stirred at 45° C. for 5 hours. After this time, the mixture was cooled to room temperature and treated with 0.5 mL of 1 N aqueous HCl, then was concentrated in vacuo. Excess moisture was removed azeotropically with acetonitrile, and the residue was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound (0.0076 g, 27% yield). $^1$H NMR (400 MHz, dimethyl sulfoxide-$d_6$) δ ppm 7.85-7.75 (m, 2H), 7.29-7.07 (m, 4H), 5.28 (d, J=6.4 Hz, 1H), 4.61 (p, J=6.2 Hz, 1H), 4.39 (d, J=1.6 Hz, 1H), 3.54 (d, J=14.1 Hz, 1H), 3.57 (s, 3H), 3.54 (m, 1H), 3.42-3.36 (m, 2H), 3.23 (d, J=14.2 Hz, 1H), 3.04 (t, J=6.7 Hz, 1H), 2.41 (m, 1H), 2.30-2.20 (m, 2H), 2.05-1.88 (m, 3H), 1.82 (m, 1H), 1.20 (d, J=6.7 Hz, 3H), 1.08 (d, J=6.8 Hz, 3H), 1.02 (s, 9H), 1.00 (d, J=6.2 Hz, 3H), 0.80 (d, J=6.2 Hz, 3H); MS (ESI+) m/z 566.3 (M+H)+.

Example 69

(2S,3S,4S,5S)-3-tert-butyl-4-{[(5-cyclobutyl-2-methoxypyridin-3-yl)methyl]amino}-1-[(1R)-3,3-difluorocyclohexane-1-carbonyl]-5-phenylpyrrolidine-2-carboxylic acid Example 69A (2S,3R,4S,5S)-ethyl 3-(tert-butyl)-4-nitro-1-((R)-3-oxocyclohexanecarbonyl)-5-phenylpyrrolidine-2-carboxylate and Example 69B (2S,3R,4S,5S)-ethyl 3-(tert-butyl)-4-nitro-1-((S)-3-oxocyclohexanecarbonyl)-5-phenylpyrrolidine-2-carboxylate (2S,3R,4S,5S)-Ethyl 3-(tert-butyl)-4-nitro-5-phenylpyrrolidine-2-carboxylate (Core 7, 0.995 g, 2.79 mmol) was dissolved in dichloromethane (10 mL) and triethylamine (0.972 mL, 6.97 mmol) was added. The reaction was cooled in an ice bath, and 3-oxocyclohexanecarbonyl chloride (0.537 g, 3.35 mmol) was added dropwise as a solution in 5 mL of dichloromethane. After 5 minutes, the ice bath was removed and saturated aqueous ammonium chloride (30 mL) and 200 mL of isopropyl acetate with 3 mL of ethanol were added. The organics were removed, dried over sodium sulfate, filtered then concentrated to give a residue, which was purified using a 80 g silica gel cartridge with 5-100% ethyl acetate/heptanes over 40 minutes to give (2S,3R,4S,5S)-ethyl 3-(tert-butyl)-4-nitro-1-((R)-3-oxocyclohexanecarbonyl)-5-phenylpyrrolidine-2-carboxylate (0.554 g, 1.246 mmol, 44.7% yield). 1H NMR (400 MHz, dimethyl sulfoxide-d6) δ ppm 7.54 (s, 2H), 7.26 (q, J=7.5, 7.0 Hz, 3H), 5.71 (d, J=9.0 Hz, 1H), 5.62 (dd, J=8.8, 3.6 Hz, 1H), 4.72 (d, J=3.8 Hz, 1H), 4.25 (q, J=7.1 Hz, 2H), 3.06 (t, J=3.7 Hz, 1H), 2.85-2.76 (m, 3H), 2.42-2.31 (m, 1H), 2.29-2.14 (m, 2H), 2.08 (d, J=15.1 Hz, 1H), 1.79 (s, 1H), 1.45 (d, J=9.8 Hz, 1H), 1.28 (td, J=7.1, 0.9 Hz, 3H), 1.01 (s, 9H); MS (APCI+) m/z 445 (M+H)+. The other isomer was (2S,3R,4S,5S)-ethyl 3-(tert-butyl)-4-nitro-1-((S)-3-oxocyclohexanecarbonyl)-5-phenylpyrrolidine-2-carboxylate (0.414 g, 0.931 mmol, 33.4% yield). 1H NMR (400 MHz, dimethyl sulfoxide-d6) δ ppm 7.54 (d, J=7.1 Hz, 2H), 7.26 (q, J=7.8 Hz, 3H), 5.70 (d, J=8.9 Hz, 1H), 5.64 (dd, J=8.8, 2.9 Hz, 1H), 4.75 (d, J=3.4 Hz, 1H), 4.24 (q, J=7.1 Hz, 2H), 3.01 (t, J=3.2 Hz, 1H), 2.91-2.76 (m, 1H), 2.33-2.16 (m, 2H), 2.10 (d, J=14.7 Hz, 1H), 1.99-1.78 (m, 3H), 1.68 (tdd, J=12.8, 8.7, 4.6 Hz, 1H), 1.61-1.45 (m, 1H), 1.28 (t, J=7.1 Hz, 3H), 1.01 (s, 9H); MS (APCI+) m/z 445 (M+H)+. Absolute stereochemistry was determined by X-ray diffraction analysis on the first eluting compound (R) about the cyclohexyl amide.

Example 69C (2S,3R,4S,5S)-ethyl 3-(tert-butyl)-1-((R)-3,3-difluorocyclohexanecarbonyl)-4-nitro-5-phenylpyrrolidine-2-carboxylate To a solution of diethylaminosulfur trifluoride (DAST, 282 μl, 2.133 mmol) in dichloromethane (1.8 mL) was added a solution of Example 69A (158 mg, 0.355 mmol) in dichloromethane (1.8 mL). The reaction mixture was stirred at room temperature for 4 hours. The reaction was quenched with 20 mL of saturated aqueous sodium bicarbonate over 10 minutes and diluted with 75 mL of dichloromethane. The layers were separated, the aqueous layer extracted with 50 mL more dichloromethane and the organic layer was purified using a 12 g silica gel cartridge, eluting with 5-100% ethyl acetate/heptanes to give the (2S,3R,4S,5S)-ethyl 3-(tert-butyl)-1-((R)-3,3-difluorocyclohexanecarbonyl)-4-nitro-5-phenylpyrrolidine-2-carboxylate (114 mg, 0.244 mmol, 68.7% yield). 1H NMR (400 MHz, dimethyl sulfoxide-d6) δ ppm 7.55 (s, 2H), 7.27 (d, J=7.9 Hz, 3H), 5.77-5.53 (m, 2H), 4.72 (s, 1H), 4.25 (q, J=7.1 Hz, 2H), 3.05 (t, J=3.5 Hz, 1H), 2.05 (s, 1H), 1.94-1.44 (m, 4H), 1.39-1.10 (m, 5H), 1.01 (d, J=1.8 Hz, 10H), 0.91-0.79 (m, 1H); MS (APCI+) m/z 467 (M+H)+.

Example 69D (2S,3S,4S,5S)-ethyl 4-amino-3-(tert-butyl)-1-((R)-3,3-difluorocyclohexanecarbonyl)-5-phenylpyrrolidine-2-carboxylate Example 69C (114 mg, 0.244 mmol) in tetrahydrofuran (3.5 mL) was added to Raney®-Nickel 2800, water slurry, solvent washed after weighing (344 mg, 2.64 mmol) in a 8 mL pressure bottle. The mixture was flushed with argon 4 times, flushed with hydrogen and shaken under 60 psi of hydrogen at ambient temperature overnight. The mixture was filtered through a polypropylene membrane and the solvent was removed in vacuo to give (2S,3R,4S,5S)-ethyl 3-(tert-butyl)-1-((R)-3,3-difluorocyclohexanecarbonyl)-4-nitro-5-phenylpyrrolidine-2-carboxylate. 1H NMR (400 MHz, dimethyl sulfoxide-d6) δ ppm 7.58 (s, 2H), 7.33 (t, J=7.5 Hz, 2H), 7.25 (t, J=7.2 Hz, 1H), 5.04 (d, J=7.2 Hz, 1H), 4.39 (dd, J=7.9, 4.6 Hz, 1H), 4.16 (q, J=7.1 Hz, 2H), 3.70 (dd, J=7.3, 4.3 Hz, 1H), 2.07 (s, 1H), 2.02-1.89 (m, 1H), 1.91-1.59 (m, 2H), 1.60-1.46 (m, 1H), 1.37 (s, 1H), 1.27-1.21 (m, 3H), 1.22-1.04 (m, 1H), 1.00 (s, 9H), 0.89-0.71 (m, 3H); MS (APCI+) m/z 467 (M+H)+.

Example 69E (2S,3S,4S,5S)-ethyl 3-(tert-butyl)-4-(((5-cyclobutyl-2-methoxypyridin-3-yl)methyl)amino)-1-((R)-3,3-difluorocyclohexanecarbonyl)-5-phenylpyrrolidine-2-carboxylate 5-Cyclobutyl-2-methoxynicotinaldehyde (0.021 g, 0.109 mmol) and Example 69D (0.050 g, 0.115 mmol) were dissolved in dichloroethane (0.6 mL), and treated with sodium triacetoxyborohydride (0.032 g, 0.153 mmol). The reaction was stirred at room temperature for 30 minutes. The mixture was then treated with 0.6 mL of saturated aqueous NaHCO3 solution, and the mixture was stirred vigorously at room temperature for 15 minutes. The phases were then separated, and the aqueous layer was extracted three times with dichloromethane. The combined organics were dried over Na2SO4, filtered, and concentrated in vacuo. The title compound thus obtained was taken into the next reaction without additional purification. MS (APCI+) m/z 612.6 (M+H)+.

Example 69F (2S,3S,4S,5S)-3-(tert-butyl)-4-(((5-cyclobutyl-2-methoxypyridin-3-yl)methyl)amino)-1-((R)-3,3-difluorocyclohexanecarbonyl)-5-phenylpyrrolidine-2-carboxylic acid Example 69E (0.067 g, 0.109 mmol) in tetrahydrofuran (0.9 mL) and methanol (0.9 mL) was treated with lithium hydroxide (1 M aqueous) (0.9 mL, 0.900 mmol), and the reaction was stirred at 45° C. overnight. After this time, the reaction mixture was concentrated in vacuo, then further dried azeotropically with acetonitrile. The residue was then treated with 0.13 mL of trifluoroacetic acid and 0.7 mL of ethyl acetate, and the solution was applied to a silica gel column, eluting with 4:3:1 heptanes-ethyl acetate-ethanol (isocratic). The partially-purified product thus obtained was further purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A). to obtain the title compound (0.0165 g, 26% yield). $^1$H NMR (400 MHz, dimethyl sulfoxide-$d_6$) δ ppm 7.81 (d, J=2.5 Hz, 1H), 7.58 (m, 2H), 7.32 (dt, J=28.9, 7.2 Hz, 3H), 7.19 (d, J=2.4 Hz, 1H), 5.29 (m, 1H), 4.54-4.46 (m, 1H), 3.67 (s, 3H), 3.65-3.52 (m, 2H), 3.36 (m, 2H), 2.44 (m, 1H), 2.33-2.21 (m, 2H), 2.07-1.52 (m, 11H), 1.21 (m, 2H), 0.99 (s, 9H); MS (ESI+) m/z 584.2 (M+H)$^+$.

Example 70

(2S,3S,4S,5S)-3-(bicyclo[1.1.1]pentan-1-yl)-4-{[(6-tert-butyl-2-methoxypyridin-3-yl)methyl]amino}-5-phenyl-1-{[(propan-2-yl)oxy]carbonyl}pyrrolidine-2-carboxylic acid

Example 70A (2S,3R,4S,5S)-2-tert-butyl 1-isopropyl 3-(bicyclo[1.1.1]pentan-1-yl)-4-nitro-5-phenylpyrrolidine-1,2-dicarboxylate A solution of Example 56E (0.1 g, 0.279 mmol) and triethylamine (0.1 mL, 0.717 mmol) in toluene (0.1 mL) at ambient temperature was treated with isopropyl carbonochloridate in toluene (0.446 mL, 0.446 mmol) dropwise, stirred for 3 hours at 45° C., washed with 1 N aqueous NH$_4$OH (1 mL) solution, and concentrated to give a residue. The crude material was dissolved in 1 mL dichloromethane and loaded on a 12 g cartridge eluting with a gradient of 0-40% ethyl acetate/heptanes over a period of 20 minutes to provide the title compound, (2S,3R,4S,5S)-2-tert-butyl 1-isopropyl 3-(bicyclo[1.1.1]pentan-1-yl)-4-nitro-5-phenylpyrrolidine-1,2-dicarboxylate (91 mg, 0.205 mmol, 73.4% yield). $^1$H NMR (400 MHz, Chloroform-d) δ ppm 7.58 (d, J=7.0 Hz, 2H), 7.38-7.28 (m, 3H), 5.39 (d, J=41.2 Hz, 1H), 5.05 (t, J=9.2 Hz, 1H), 4.97-4.69 (m, 1H), 4.08 (s, 1H), 3.35 (t, J=9.1 Hz, 1H), 2.56 (s, 1H), 1.84 (dd, J=9.6, 1.9 Hz, 3H), 1.76 (dd, J=9.5, 2.0 Hz, 3H), 1.60 (s, 9H), 1.55 (s, 6H); MS (DCI+) m/z 445 (M+H)$^+$.

Example 70B (2S,3S,4S,5S)-3-(bicyclo[1.1.1]pentan-1-yl)-4-(((6-(tert-butyl)-2-methoxypyridin-3-yl)methyl)amino)-1-(isopropoxycarbonyl)-5-phenylpyrrolidine-2-carboxylic acid Example 70A (90 mg, 0.202 mmol) in tetrahydrofuran (3 mL) was added to Raney®-Nickel 2800, water slurry (334 mg, 2.56 mmol) in a 8 mL pressure bottle, flushed with argon 4 times, flushed with hydrogen and shaken under 50 psi of hydrogen overnight. The reaction was filtered and the solvent was removed in vacuo to provide the desired product (2S,3S,4S,5S)-2-tert-butyl 1-isopropyl 4-amino-3-(bicyclo[1.1.1]pentan-1-yl)-5-phenylpyrrolidine-1,2-dicarboxylate (75 mg, 0.181 mmol, 35.9% yield). $^1$H NMR (400 MHz, Chloroform-d) δ ppm 7.61 (d, J=7.4 Hz, 2H), 7.35 (t, J=7.5 Hz, 2H), 7.27 (m, 1H), 4.86 (t, J=44.0 Hz, 2H), 3.98 (bs, 1H), 3.41 (t, J=8.4 Hz, 1H), 2.55 (s, 1H), 2.17 (t, J=8.5 Hz, 1H), 1.84 (qd, J=9.7, 1.7 Hz, 6H), 1.57 (s, 9H), 1.20 (bs, 3H), 1.10 (bs, 3H); MS (ESI+) m/z 415 (M+H)$^+$.

Example 70C (2S,3S,4S,5S)-3-(bicyclo[1.1.1]pentan-1-yl)-4-{[(6-tert-butyl-2-methoxypyridin-3-yl)methyl]amino}-5-phenyl-1-{[(propan-2-yl)oxy]carbonyl}pyrrolidine-2-carboxylic acid To a solution of 6-(tert-butyl)-2-methoxynicotinaldehyde (15.85 mg, 0.082 mmol), Example 70B (34 mg, 0.082 mmol) and zinc(II) chloride (11.18 mg, 0.082 mmol) in sodium acetate/acetic acid buffer in methanol (pH=4, 1 mL) was added sodium cyanoborohydride (7.73 mg, 0.123 mmol) and the reaction was stirred at ambient temperature for 2 hours. The solvent was removed and the resulting residue was chromatographed using a 12 g silica gel cartridge eluting with a gradient of 0-60% ethyl acetate/heptanes over a period of 20 minutes (48 mg, 0.080 mmol, 92%). The mixture was dissolved in 2,2,2-trifluoroacetic acid (0.5 mL, 6.49 mmol) and stirred for 5 hours at ambient temperature. The solvent was removed and the crude material was taken up in 0.5 mL water and adjusted to pH 7 with 1 N aqueous NaHCO$_3$ then extracted with 2 mL diethyl ether. The crude residue, after solvent evaporation, was purified by chromatography using a 4 g silica gel cartridge eluting with a gradient of 0-10% methanol/dichloromethane over a period of 15 minutes to give (2S,3S,4S,5S)-3-(bicyclo[1.1.1]pentan-1-yl)-4-(((6-(tert-butyl)-2-methoxypyridin-3-yl)methyl)amino)-1-(isopropoxycarbonyl)-5-phenylpyrrolidine-2-carboxylic acid (34 mg, 0.063 mmol, 77% yield). $^1$H NMR (400 MHz, dimethyl sulfoxide-$d_6$) δ ppm 7.55-7.41 (m, 2H), 7.26 (ddd, J=7.6, 5.8, 2.2 Hz, 3H), 7.23-7.16 (m, 1H), 6.80 (d, J=7.5 Hz, 1H), 4.92 (d, J=7.3 Hz, 1H), 4.62 (p, J=6.2 Hz, 1H), 4.01 (d, J=6.1 Hz, 1H), 3.74 (d, J=0.9 Hz, 3H), 3.43 (s, 2H), 3.22 (t, J=7.0 Hz, 1H), 2.44 (s, 1H), 2.37 (t, J=6.4 Hz, 1H), 1.71 (d, J=2.4 Hz, 6H), 1.26 (d, J=0.7 Hz, 9H), 1.07 (d, J=6.3 Hz, 3H), 0.93 (d, J=6.2 Hz, 3H); MS (ESI+) m/z 536 (M+H)$^+$.

Example 71

(2S,3S,4S,5S)-3-(bicyclo[1.1.1]pentan-1-yl)-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid

Example 71A (2S,3R,4S,5S)-2-tert-butyl 1-isopropyl 3-(bicyclo[1.1.1]pentan-1-yl)-5-(2-(dimethylamino)pyridin-3-yl)-4-nitropyrrolidine-1,2-dicarboxylate (2S,3R,4S,5S)-tert-Butyl 3-(bicyclo[1.1.1]pentan-1-yl)-5-(2-(dimethylamino)pyridin-3-yl)-4-nitropyrrolidine-2-carboxylate (Core 43, 200 mg, 0.497 mmol) was dissolved in toluene (0.745 mL) and triethylamine (0.173 mL, 1.242 mmol) was added, followed by slow addition of isopropyl carbonochloridate (0.298 mL, 0.596 mmol) solution after cooling in an ice-water bath to ~10° C. The addition was at such a rate that the temperature was maintained at or below ambient temperature during the addition (2 minutes). After the addition was complete, the reaction was removed from the water bath and stirred at ambient temperature for 1 hour. The mixture was diluted with diethyl ether and stirred with saturated aqueous sodium bicarbonate for 20 minutes before separating the layers, washing the organics three times with 1 M aqueous HCl and brine, drying over sodium sulfate, filtering, and concentrating to give a crude material. The mixture was dissolved in 1 mL heptanes and loaded on a 12 g cartridge eluting with a gradient of 0-60% ethyl acetate/heptanes over a period of 20 minutes to provide the desired (2S,3R,4S,5S)-2-tert-butyl 1-isopropyl 3-(bicyclo[1.1.1]pentan-1-yl)-5-(2-(dimethylamino)pyridin-3-yl)-4-nitropyrrolidine-1,2-dicarboxylate (225 mg, 0.461 mmol, 93% yield). $^1$H NMR (400 MHz, Chloroform-d) δ ppm 8.30 (d, J=5.0 Hz, 2H), 7.04 (t, J=6.4 Hz, 1H), 5.82 (s, 1H), 5.24 (dd, J=8.1, 5.7 Hz, 1H), 4.88 (s, 1H), 4.30 (s, 1H), 3.17 (t, J=5.6 Hz, 1H), 2.78 (s, 7H), 2.62 (s, 1H), 1.94-1.73 (m, 6H), 1.59 (d, J=2.9 Hz, 12H), 1.28 (s, 4H), 1.00 (d, J=105.5 Hz, 4H); MS (ESI+) m/z 489 (M+H)$^+$.

Example 71B (2S,3S,4S,5S)-2-tert-butyl 1-isopropyl 4-amino-3-(bicyclo[1.1.1]pentan-1-yl)-5-(2-(dimethylamino)pyridin-3-yl)pyrrolidine-1,2-dicarboxylate Example 71A (224 mg, 0.458 mmol) and tetrahydrofuran (10 mL) were added to Raney®-Nickel 2800, water slurry (630 mg, 4.83 mmol) in a 50 mL pressure bottle and shaken for 16 hours at 50 psi hydrogen and ambient temperature. The reaction was filtered and the solvent was removed in vacuo to provide the desired product (2S,3S,4S,5S)-2-tert-butyl 1-isopropyl 4-amino-3-(bicyclo[1.1.1]pentan-1-yl)-5-(2-(dimethylamino)pyridin-3-yl)pyrrolidine-1,2-dicarboxylate (205 mg, 0.447 mmol, 98% yield). The material was dissolved in 1 mL dichloromethane and loaded on a 12 g cartridge eluting with a gradient of 0-7% methanol/dichloromethane over a period of 20 minutes to provide the desired (2S,3S,4S,5S)-2-tert-butyl 1-isopropyl 4-amino-3-(bicyclo[1.1.1]pentan-1-yl)-5-(2-(dimethylamino)pyridin-3-yl)pyrrolidine-1,2-dicarboxylate (205 mg, 0.447 mmol, 98% yield). $^1$H NMR (500 MHz, Chloroform-d) δ ppm 8.50 (d, J=7.6 Hz, 1H), 8.28 (s, 1H), 7.08 (d, J=6.5 Hz, 1H), 5.46 (dd, 1H), 5.01-4.74 (m, 1H), 4.00 (dd, 1H), 3.59 (t, J=8.6 Hz, 1H), 2.86 (d, J=14.5 Hz, 6H), 2.56 (s, 1H), 2.08 (t, J=8.9 Hz, 1H), 1.92-1.79 (m, 6H), 1.59 (s, 9H), 1.36-1.20 (m, 3H), 1.02 (dd, 3H); MS (ESI+) m/z 459 (M+H)$^+$.

Example 71C (2S,3S,4S,5S)-3-(bicyclo[1.1.1]pentan-1-yl)-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid To a solution of 5-(tert-butyl)-2-methoxybenzaldehyde (21 mg, 0.104 mmol), Example 71B (47.6 mg, 0.104 mmol) and zinc(II) chloride (14.14 mg, 0.104 mmol) in sodium acetate/acetic acid buffer in methanol (pH=4, 1 mL) was added sodium cyanoborohydride (9.78 mg, 0.156 mmol) and the reaction was stirred at ambient temperature for 2 hours. The solvent was removed and the resulting residue was chromatographed using a 12 g silica gel cartridge eluting with a gradient of 0-70% ethyl acetate/heptanes over a period of 20 minutes to give an intermediate (35 mg, 0.055 mmol, 53.1% yield). The mixture was dissolved in 2,2,2-trifluoroacetic acid (0.5 mL, 6.49 mmol), and stirred for 5 hours. The solvent was removed and the crude material was taken up in 0.5 mL water and the solution was adjusted to pH 7 with 1 N aqueous NaHCO$_3$ and extracted with 2 mL ethyl ether. The crude residue, after solvent evaporation, was purified by chromatography using a 4 g silica gel cartridge eluting with a gradient of 0-10% methanol/dichloromethane over a period of 15 minutes to give (2S,3S,4S,5S)-3-(bicyclo[1.1.1]pentan-1-yl)-4-((5-(tert-butyl)-2-methoxybenzyl)amino)-5-(2-(dimethylamino)pyridin-3-yl)-1-(isopropoxycarbonyl)pyrrolidine-2-carboxylic acid, (20 mg, 0.035 mmol, 33.3% yield). $^1$H NMR (400 MHz, dimethyl sulfoxide-d$_6$) δ ppm 8.20-8.10 (m, 2H), 7.12 (dd, J=8.5, 2.6 Hz, 1H), 6.97 (d, J=2.6 Hz, 1H), 6.94 (dd, J=7.6, 4.7 Hz, 1H), 6.73 (d, J=8.6 Hz, 1H), 5.28 (d, J=6.2 Hz, 1H), 4.63 (p, J=6.2 Hz, 1H), 4.16 (d, J=2.6 Hz, 1H), 3.56 (d, J=13.7 Hz, 1H), 3.50 (s, 3H), 3.33 (d, J=13.8 Hz, 1H), 3.31-3.27 (m, 1H), 2.62 (s, 6H), 2.56 (t, J=2.7 Hz, 1H), 2.49 (s, 1H), 1.70 (t, J=1.4 Hz, 6H), 1.20 (s, 9H), 1.03 (d, J=6.2 Hz, 3H), 0.87 (d, J=6.2 Hz, 3H); MS (ESI+) m/z 579 (M+H)$^+$.

Example 72

(2S,3S,4S,5S)-3-tert-butyl-4-{[(5-cyclobutyl-2-methoxypyridin-3-yl)methyl]amino}-1-[(2R)-oxane-2-carbonyl]-5-[2-(propan-2-yl)phenyl]pyrrolidine-2-carboxylic acid

Example 72A (2S,3S,4S,5S)-ethyl 3-(tert-butyl)-4-(((5-cyclobutyl-2-methoxypyridin-3-yl)methyl)amino)-5-(2-isopropylphenyl)-1-(tetrahydro-2H-pyran-2-carbonyl)pyrrolidine-2-carboxylate Tetrahydro-2H-pyran-2-carboxylic acid (0.022 g, 0.171 mmol) was refluxed in thionyl chloride (0.33 mL, 4.52 mmol) for 1 hour. The mixture was cooled to room temperature and then concentrated in vacuo, and excess leftover thionyl chloride was chased three times with CH$_2$Cl$_2$. The residue was then treated with a solution of Example 68B (0.087 g, 0.171 mmol) in CH$_2$Cl$_2$ (0.34 mL) and pyridine (0.17 mL, 2.102 mmol). The reaction was stirred overnight at room temperature. After this time, the reaction mixture was diluted with ethyl acetate and washed three times with water and once with brine. The organic layer was dried over Na$_2$SO$_4$, filtered, and concentrated in vacuo, then the resulting residue was purified by silica gel chromatography, eluting with 0 to 40% ethyl acetate-heptanes. The title compound was obtained impurely, 0.085 g (80% yield), and was not purified further but was taken directly into the next reaction. MS (ESI+) m/z 620.3 (M+H)$^+$.

Example 72B (2S,3S,4S,5S)-3-tert-butyl-4-{[(5-cyclobutyl-2-methoxypyridin-3-yl)methyl]amino}-1-[(2R)-oxane-2-carbonyl]-5-[2-(propan-2-yl)phenyl]pyrrolidine-2-carboxylic acid Example 72A (0.085 g, 0.137 mmol) and lithium hydroxide (1 M aqueous) (1.1 mL, 1.100 mmol) in tetrahydrofuran (1.1 mL) and methanol (1.1 mL) was stirred at 45° C. overnight. After this time, the reaction mixture was acidified with 1.2 mL 1 N aqueous HCl, then concentrated in vacuo. Excess moisture was removed azeotropically with acetonitrile, and the residue thus obtained was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A). The title compound, the second of the main peaks to elute, was obtained, 0.0167 g (21% yield). $^1$H NMR (400 MHz, dimethyl sulfoxide-d$_6$) δ ppm 7.78 (d, J=2.4 Hz, 1H), 7.65 (m, 1H), 7.30-7.15 (m, 3H), 7.07 (m, 1H), 5.40 (d, J=6.5 Hz, 1H), 4.87 (m, 1H), 4.02 (m, 1H), 3.84 (m, 1H), 3.59 (m, 1H), 3.56 (s, 3H), 3.44-3.26 (m, 3H), 3.06 (m, 2H), 2.51 (m, 1H), 2.31-2.21 (m, 2H), 1.96 (m, 3H), 1.84-1.77 (m, 2H), 1.60-1.41 (m, 5H), 1.22 (d, J=6.7 Hz, 3H), 1.07 (d, J=6.8 Hz, 3H), 1.03 (s, 9H); MS (ESI+) m/z 592.3 (M+H)$^+$.

Example 73

(2S,3S,4S,5S)-3-tert-butyl-4-{[(5-cyclobutyl-2-methoxypyridin-3-yl)methyl]amino}-1-[(2S)-oxane-2-carbonyl]-5-[2-(propan-2-yl)phenyl]pyrrolidine-2-carboxylic acid The title compound was obtained (first of the main peaks to elute) from the reverse-phase HPLC purification of the reaction mixture described in Example 72B (0.0166 g, 21% yield). $^1$H NMR (400 MHz, dimethyl sulfoxide-d$_6$) δ ppm 7.86 (d, J=7.9 Hz, 1H), 7.78 (d, J=2.4 Hz, 1H), 7.35-7.21 (m, 2H), 7.17-7.13 (m, 2H), 5.62 (m, 1H), 4.63 (d, J=1.5 Hz, 1H), 3.74 (m, 1H), 3.61 (s, 3H), 3.65-3.50 (m, 2H), 3.43-3.33 (m, 1H), 3.19 (m, 2H), 3.10 (m, 2H), 2.43 (m, 1H), 2.31-2.20 (m, 2H), 2.02-1.90 (m, 3H), 1.83 (m, 1H), 1.68 (m, 1H), 1.53 (m, 1H), 1.43-1.33 (m, 4H), 1.27 (d, J=6.7 Hz, 3H), 1.08 (d, J=6.8 Hz, 3H), 1.02 (s, 9H); MS (ESI+) m/z 592.2 (M+H)$^+$.

Example 74

(2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-[2-(propan-2-yl)phenyl]pyrrolidine-2-carboxylic acid

Example 74A (2S,3S,4S,5S)-1-tert-butyl 2-ethyl 3-(tert-butyl)-4-((5-(tert-butyl)-2-methoxybenzyl)amino)-5-(2-isopropylphenyl)pyrrolidine-1,2-dicarboxylate A suspension of Example 61B, 5-(tert-butyl)-2-methoxybenzaldehyde (309 mg, 1.607 mmol), and zinc(II) chloride (159 mg, 1.165 mmol) in methanol/acetic acid/sodium acetate buffer (8 mL) was stirred with gentle heating followed by addition of 3 mL of tetrahydrofuran. The solution was stirred for 30 minutes, followed by addition of sodium cyanoborohydride (110 mg, 1.748 mmol) and the reaction was stirred at room temperature for 30 minutes. The solvent was removed under nitrogen. The residue was diluted with aqueous bicarbonate and the crude material was taken up in 200 mL of dichloromethane. The organics were separated, filtered through diatomaceous earth, concentrated and purified using a ethyl acetate/heptane solvent system with a 40 g silica gel cartridge to yield (2S,3S,4S,5S)-1-tert-butyl 2-ethyl 3-(tert-butyl)-4-((5-(tert-butyl)-2-methoxybenzyl)amino)-5-(2-isopropylphenyl)pyrrolidine-1,2-dicarboxylate (0.542 g, 0.890 mmol, 76% yield). $^1$H NMR (400 MHz, dimethyl sulfoxide-d$_6$) δ ppm 7.88 (dd, J=7.9, 1.4 Hz, 1H), 7.23-7.13 (m, 2H), 7.08 (ddd, J=8.4, 5.6, 2.2 Hz, 2H), 6.88 (d, J=2.6 Hz, 1H), 6.66 (d, J=8.5 Hz, 1H), 5.21 (d, J=6.2 Hz, 1H), 4.40 (d, J=1.5 Hz, 1H), 4.11 (qd, J=7.1, 1.9 Hz, 2H), 3.49 (dd, J=13.5, 6.5 Hz, 1H), 3.41 (s, 3H), 3.38 (d, J=6.3 Hz, 1H), 3.18 (dd, J=13.5, 6.2 Hz, 1H), 3.02 (p, J=6.8 Hz, 1H), 2.37 (d, J=1.4 Hz, 1H), 1.20 (d, J=0.9 Hz, 3H), 1.18 (d, J=2.2 Hz, 12H), 1.13 (s, 9H), 1.02 (d, J=8.3 Hz, 13H); MS (ESI+) m/z 609 (M+H)$^+$.

Example 74B (2S,3S,4S,5S)-ethyl 3-(tert-butyl)-4-((5-(tert-butyl)-2-methoxybenzyl)amino)-5-(2-isopropylphenyl)pyrrolidine-2-carboxylate (2S,3S,4S,5S)-1-tert-Butyl 2-ethyl 3-(tert-butyl)-4-((5-(tert-butyl)-2-methoxybenzyl)amino)-5-(2-isopropylphenyl)pyrrolidine-1,2-dicarboxylate (0.455 g, 0.70 mmol) was dissolved in dichloromethane (2.88 mL). Trifluoroacetic acid (1.358 mL, 17.63 mmol) was added and the reaction was stirred at room temperature for 4 hours. The reaction was concentrated and diluted with dichloromethane (200 mL). The organic layer was washed with 1 M aqueous NaOH (2×50 mL), brine (50 mL), dried over Na$_2$SO$_4$, filtered and concentrated to give (2S,3S,4S,5S)-ethyl 3-(tert-butyl)-4-((5-(tert-butyl)-2-methoxybenzyl)amino)-5-(2-isopropylphenyl)pyrrolidine-2-carboxylate (0.366 g, 0.719 mmol, 102% yield). $^1$H NMR (501 MHz, Chloroform-d) δ ppm 7.60 (d, J=7.5 Hz, 1H), 7.31-7.26 (m, 2H), 7.24 (dt, J=7.5, 4.3 Hz, 1H), 7.13 (dd, J=8.5, 2.6 Hz, 1H), 6.96 (d, J=2.5 Hz, 1H), 6.61 (d, J=8.5 Hz, 1H), 4.43 (d, J=4.4 Hz, 1H), 4.31-4.20 (m, 2H), 3.72 (d, J=6.1 Hz, 1H), 3.51 (d, J=13.2 Hz, 1H), 3.46 (s, 3H), 3.14 (dd, J=4.5, 1.3 Hz, 1H), 3.07 (dt, J=13.7, 3.7 Hz, 2H), 2.21 (dd, J=6.0, 1.3 Hz, 1H), 1.32 (t, J=7.1 Hz, 3H), 1.26 (s, 9H), 1.23 (d, J=6.8 Hz, 3H), 1.11 (d, J=6.9 Hz, 3H), 1.07 (s, 9H); MS (ESI+) m/z 508 (M+H)$^+$.

Example 74C (2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-[2-(propan-2-yl)phenyl]pyrrolidine-2-carboxylic acid To (1S,2R,4R)-7-oxabicyclo[2.2.1]heptane-2-carboxylic acid [catalog # EN300-77440] (58.1 mg, 0.409 mmol) and a few drops of N,N-dimethylformamide in dichloromethane (10 mL) was added oxalyl dichloride (100 mg, 0.786 mmol, 0.4 mL, 2 M in dichloromethane). The mixture was stirred at ambient temperature for 30 minutes, the solvent was removed under pressure and fresh dichloromethane (5 mL) was added and removed again. The residue was dissolved in dichloromethane (2 mL) and added dropwise to the solution of Example 74B (160 mg, 0.315 mmol) and triethylamine (0.175 mL, 1.258 mmol) in dichloromethane (10 mL) cooled in an ice bath. The mixture was stirred in the ice bath for 1 hour and allowed to warm to ambient temperature. Dichloromethane (10 mL) was added. The mixture was washed with brine, dried over MgSO$_4$, filtered, and concentrated. The residue was purified via chromatography on a 12 g silica gel cartridge, eluting with ethyl acetate in heptane at 0-40% gradient to provide the title compound, 28 mg (15% yield). $^1$H NMR (400 MHz, dimethyl sulfoxide-d$_6$) δ ppm 7.77-7.69 (m, 1H), 7.29-7.21 (m, 2H), 7.15-7.10 (m, 2H), 6.95 (d, J=2.5 Hz, 1H), 6.68 (d, J=8.5 Hz, 1H), 5.39 (d, J=6.4 Hz, 1H), 4.56 (d, J=3.0 Hz, 1H), 4.41 (t, J=5.0 Hz, 1H), 4.25 (s, 1H), 3.65 (d, J=13.6 Hz, 1H), 3.45-3.37 (m, 2H), 3.39 (s, 3H), 3.29 (d, J=13.6 Hz, 1H), 3.03 (q, J=6.8 Hz, 1H), 2.54 (q, J=6.8 Hz, 1H), 2.44 (s, 1H), 1.73-1.39 (m, 4H), 1.20 (d, J=6.8 Hz, 3H), 1.18 (s, 9H), 1.02 (s, 9H), 0.99-0.97 (m, 3H); MS (ESI+) m/z 605.3 (M+H)$^+$.

Example 75

(2S,3S,4S,5S)-3-tert-butyl-1-[(1R)-3,3-difluorocyclohexane-1-carbonyl]-4-({[2-methoxy-4-(trifluoromethyl)phenyl]methyl}amino)-5-phenylpyrrolidine-2-carboxylic acid Example 75A (2S,3S,4S,5S)-ethyl 3-(tert-butyl)-4-((2-methoxy-4-(trifluoromethyl)benzyl)amino)-1-((R)-3-oxocyclohexanecarbonyl)-5-phenylpyrrolidine-2-carboxylate To a solution of (R)-3-oxocyclohexanecarboxylic acid (223 mg, 1.567 mmol) in dichloromethane (10 mL) and 2 drops of N,N-dimethylformamide was added oxalyl dichloride (1.567 mL, 3.13 mmol) (2 M in dichloromethane) and the mixture was stirred at ambient temperature for 30 minutes. The solvent was removed under reduced pressure and fresh dichloromethane was added and removed again. The residue was dissolved in dichloromethane (3 mL) and added dropwise to a cooled (ice bath) solution of (2S,3S,4S,5S)-ethyl 3-(tert-butyl)-4-((2-methoxy-4-(trifluoromethyl)benzyl)amino)-5-phenylpyrrolidine-2-carboxylate (Example 65B, 500 mg, 1.045 mmol) and triethylamine (0.583 mL, 4.18 mmol) in dichloromethane. The mixture was stirred for 1 hour at ambient temperature. The reaction was diluted with dichloromethane and a small amount of ethanol, washed with brine and dried over sodium sulfate. After filtration, the solvent was removed and the crude material was purified using a 40 g silica gel cartridge, eluting with ethyl acetate/heptane with a 5-100% gradient over 40 minutes to give (2S,3S,4S,5S)-ethyl 3-(tert-butyl)-4-((2-methoxy-4-(trifluoromethyl)benzyl)amino)-1-((R)-3-oxocyclohexanecarbonyl)-5-phenylpyrrolidine-2-carboxylate (0.471 g, 0.782 mmol, 74.8% yield). $^1$H NMR (400 MHz, dimethyl sulfoxide-d$_6$) δ ppm 7.58 (s, 2H), 7.28 (dt, J=27.6, 7.5 Hz, 3H), 7.15-6.97 (m, 3H), 5.23 (d, J=6.9 Hz, 1H), 4.51 (d, J=3.1 Hz, 1H), 4.11 (q, J=7.1 Hz, 2H), 3.64 (s, 3H), 3.47 (d, J=14.1 Hz, 2H), 3.38 (d, J=14.3 Hz, 1H), 2.81-2.64 (m, 1H), 2.33 (ddd, J=14.6, 10.1, 1.1 Hz, 2H), 2.26-2.11 (m, 2H), 2.08 (s, 1H), 1.77 (s, 1H), 1.57-1.30 (m, 1H), 1.19 (t, J=7.1 Hz, 3H), 1.18-1.06 (m, 1H), 0.98 (s, 9H), 0.90-0.75 (m, 1H); MS (APCI+) m/z 603 (M+H)$^+$.

Example 75B (2S,3S,4S,5S)-ethyl 3-(tert-butyl)-1-((R)-3,3-difluorocyclohexanecarbonyl)-4-((2-methoxy-4-(trifluoromethyl)benzyl)amino)-5-phenylpyrrolidine-2-carboxylate To a solution of diethylaminosulfur trifluoride (DAST, 0.146 mL, 1.105 mmol) in dichloromethane (1 mL) was added a solution of Example 75A (111 mg, 0.184 mmol) in 2 mL of dichloromethane. The reaction was stirred at room temperature overnight. The reaction was concentrated by 25%, then carefully quenched with saturated aqueous sodium bicarbonate. The crude material was chromatographed using a 24 g silica gel cartridge, eluting with 5-100% methyl tert-butyl ether/heptanes to give (2S,3S,4S,5S)-ethyl 3-(tert-butyl)-1-((R)-3,3-difluorocyclohexanecarbonyl)-4-((2-methoxy-4-(trifluoromethyl)benzyl)amino)-5-phenylpyrrolidine-2-carboxylate (62 mg, 0.099 mmol, 53.9% yield). $^1$H NMR (400 MHz, dimethyl sulfoxide-d$_6$) δ ppm 7.57 (s, 2H), 7.38-7.20 (m, 3H), 7.14-6.98 (m, 3H), 5.20 (d, J=6.9 Hz, 1H), 4.51 (d, J=3.1 Hz, 1H), 4.12 (q, J=7.1 Hz, 2H), 3.64 (s, 3H), 3.47 (d, J=14.1 Hz, 2H), 3.38 (d, J=14.2 Hz, 1H), 2.62-2.50 (m, 1H), 2.33 (s, 1H), 2.07-1.91 (m, 1H), 1.93-1.44 (m, 3H), 1.32-1.21 (m, 2H), 1.19 (t, J=7.1 Hz, 3H), 1.16-1.07 (m, 1H), 1.02-0.96 (m, 9H), 0.89-0.80 (m, 1H); MS (APCI+) m/z 625 (M+H)$^+$.

Example 75C (2S,3S,4S,5S)-3-tert-butyl-1-[(1R)-3,3-difluorocyclohexane-1-carbonyl]-4-({[2-methoxy-4-(trifluoromethyl)phenyl]methyl}amino)-5-phenylpyrrolidine-2-carboxylic acid To a solution of Example 75B (69 mg, 0.110 mmol) in methanol (1 mL) and tetrahydrofuran (1.0 mL) was added a solution of lithium hydroxide (33 mg, 1.378 mmol) in 1 mL of water. The reaction was warmed at 45° C. for 3 hours. The solvent was removed under a stream of nitrogen and the crude reaction was neutralized with 1.4 mL of 1 N aqueous HCl. The crude product was chromatographed using an ethyl acetate/ethanol/heptanes solvent system with a 12 g silica gel cartridge to give (2S,3S,4S,5S)-3-(tert-butyl)-1-((R)-3,3-difluorocyclohexanecarbonyl)-4-((2-methoxy-4-(trifluoromethyl)benzyl)amino)-5-phenylpyrrolidine-2-carboxylic acid, hydrochloric acid (45 mg, 0.071 mmol, 64.4% yield). $^1$H NMR (400 MHz, dimethyl sulfoxide-d$_6$) δ ppm 7.68 (s, 2H), 7.31-7.12 (m, 3H), 7.11-6.96 (m, 3H), 5.11 (d, J=7.3 Hz, 1H), 4.33 (s, 1H), 3.69 (s, 3H), 3.42 (d, J=15.1 Hz, 1H), 3.35 (s, 1H), 3.27 (d, J=15.1 Hz, 1H), 2.40 (s, 1H), 1.93-1.84 (m, 1H), 1.83-1.64 (m, 2H), 1.64-1.42 (m, 2H), 1.36-1.20 (m, 2H), 0.95 (s, 9H), 0.90-0.79 (m, 2H); MS (APCI+) m/z 597 (M+H)$^+$.

Example 76

(2S,3S,4S,5S)-3-(bicyclo[1.1.1]pentan-1-yl)-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid

Example 76A (2S,3R,4S,5S)-2-tert-butyl 1-isopropyl 3-(bicyclo[1.1.1]pentan-1-yl)-5-(2-methoxypyridin-3-yl)-4-nitropyrrolidine-1,2-dicarboxylate Core 44 (250 mg, 0.642 mmol) was dissolved in toluene (1.2 mL) and triethylamine (0.224 mL, 1.605 mmol) was added, followed by slow addition of isopropyl carbonochloridate (0.385 mL, 0.770 mmol) solution after cooling in an ice-water bath to −10° C. The addition was at such a rate that the temperature was maintained at or below ambient temperature during the addition (2-3 minutes). After the addition was complete, the reaction was removed from the water bath and was stirred at ambient temperature for 1 hour. Diethyl ether was added and the mixture was stirred with saturated aqueous sodium bicarbonate for 20 minutes before separating the layers, washing the organic three times with 1 M aqueous HCl and brine then drying over sodium sulfate, filtering, and concentrating to give a crude residue. The mixture was dissolved in 1 mL heptanes and loaded on a 12 g cartridge eluting with a gradient of 0-50% ethyl acetate/heptanes over a period of 20 minutes to provide the desired product (2S,3R,4S,5S)-2-tert-butyl 1-isopropyl 3-(bicyclo[1.1.1]pentan-1-yl)-5-(2-methoxypyridin-3-yl)-4-nitropyrrolidine-1,2-dicarboxylate (251 mg, 0.528 mmol, 82% yield). $^1$H NMR (400 MHz, Chloroform-d) δ ppm 8.25 (s, 1H), 8.13-8.04 (m, 1H), 6.92 (dd, J=7.2, 5.2 Hz, 1H), 5.65 (s, 1H), 5.29-5.10 (m, 1H), 4.92 (s, 1H), 4.28 (s, 1H), 3.95 (d, J=1.0 Hz, 3H), 3.18 (t, J=5.8 Hz, 1H), 2.62 (s, 1H), 1.93-1.72 (m, 6H), 1.59 (s, 9H), 1.29 (s, 3H), 1.16-0.84 (m, 3H); MS (ESI+) m/z 476 (M+H)$^+$.

Example 76B (2S,3S,4S,5S)-2-tert-butyl 1-isopropyl 4-amino-3-(bicyclo[1.1.1]pentan-1-yl)-5-(2-methoxypyridin-3-yl)pyrrolidine-1,2-dicarboxylate Example 76A (250 mg, 0.526 mmol) and tetrahydrofuran (15 mL) were added to Raney®-Nickel 2800, water slurry (700 mg, 5.37 mmol) in a 50 mL pressure bottle and shaken for 16 hours at 50 psi hydrogen and ambient temperature. The reaction was filtered and the solvent was removed in vacuo to provide the desired product. The crude material was dissolved in 1 mL dichloromethane and loaded on a 12 g cartridge eluting with a gradient of 0-5% methanol/dichloromethane over a period of 20 minutes to provide the desired (2S,3S,4S,5S)-2-tert-butyl 1-isopropyl 4-amino-3-(bicyclo[1.1.1]pentan-1-yl)-5-(2-methoxypyridin-3-yl)pyrrolidine-1,2-dicarboxylate (187 mg, 0.420 mmol, 80% yield). $^1$H NMR (400 MHz, Chloroform-d) δ ppm 8.37 (s, 1H), 8.07 (dd, J=4.9, 1.9 Hz, 1H), 6.95 (dd, J=7.3, 5.0 Hz, 1H), 5.31 (d, 1H), 4.88 (d, 1H), 3.98 (m, 4H), 3.55 (t, J=8.2 Hz, 1H), 2.53 (s, 1H), 2.12 (t, J=8.3 Hz, 1H), 1.83 (qd, J=9.6, 1.7 Hz, 6H), 1.55 (s, 9H), 1.24 (m, 3H), 0.96 (d, J=112.6 Hz, 3H); MS (ESI+) m/z 446 (M+H)$^+$.

Example 76C (2S,3S,4S,5S)-3-(bicyclo[1.1.1]pentan-1-yl)-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid To a solution of 5-(tert-butyl)-2-methoxybenzaldehyde (15.19 mg, 0.079 mmol), Example 76B (32 mg, 0.072 mmol) and zinc(II) chloride (9.79 mg, 0.072 mmol) in sodium acetate/acetic acid buffer in methanol (pH=4, 1 mL) was added sodium cyanoborohydride (6.77 mg, 0.108 mmol) and the reaction was stirred at ambient temperature for 2 hours. The solvent was removed and the resulting residue was chromatographed using a 12 g silica gel cartridge eluting with a gradient of 0-60% ethyl acetate/heptanes over a period of 20 minutes (42 mg, 0.068 mmol, 94%). The crude material was dissolved in 2,2,2-trifluoroacetic acid (0.5 mL, 6.49 mmol), and stirred for 16 hours. The solvent was removed and the crude material was diluted with 0.5 mL water. The pH was adjusted to pH 7 with 1 N aqueous NaHCO$_3$ and extracted with 2 mL diethyl ether. The crude material, after solvent evaporation, was purified by chromatography using a 4 g silica gel cartridge eluting with a gradient of 0-10% methanol/dichloromethane over a period of 15 minutes to give (2S,3S,4S,5S)-3-(bicyclo[1.1.1]pentan-1-yl)-4-((5-(tert-butyl)-2-methoxybenzyl)amino)-1-(isopropoxycarbonyl)-5-(2-methoxypyridin-3-yl)pyrrolidine-2-carboxylic acid, (32 mg, 0.057 mmol, 79% yield). $^1$H NMR (400 MHz, dimethyl sulfoxide-d$_6$) δ ppm 8.13-7.93 (m, 2H), 7.14 (dd, J=8.5, 2.6 Hz, 1H), 6.98 (d, J=2.5 Hz, 1H), 6.94 (dd, J=7.1, 5.2 Hz, 1H), 6.75 (d, J=8.6 Hz, 1H), 5.06 (s, 1H), 4.59 (d, J=29.3 Hz, 1H), 4.06 (d, J=3.8 Hz, 1H), 3.69 (s, 3H), 3.53 (d, J=13.6 Hz, 1H), 3.46 (s, 3H), 3.38-3.32 (d, 1H), 3.19 (dd, J=6.6, 4.2 Hz, 1H), 2.44 (s, 1H), 1.72-1.54 (m, 6H), 1.19 (s, 9H), 1.15-1.01 (m, 3H), 0.82 (d, J=117.4 Hz, 3H); MS (ESI+) m/z 566 (M+H)$^+$.

Example 77

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-[2-(propan-2-yl)phenyl]pyrrolidine-2-carboxylic acid

Example 77A 1-(tert-butyl) 2-ethyl (2S,3S,4S,5S)-3-(tert-butyl)-5-(2-isopropylphenyl)-4-(((2-methoxy-5-(trifluoromethyl)pyridin-3-yl)methyl)amino)pyrrolidine-1,2-dicarboxylate Example 61B (106.9 mg, 0.247 mmol) and 2-methoxy-5-(trifluoromethyl)nicotinaldehyde (93.1 mg, 0.454 mmol) were dissolved in methanol (1 mL) and stirred at ambient temperature for 1 hour. Sodium cyanoborohydride (82.5 mg, 1.313 mmol) was added and the reaction was stirred at ambient temperature for an additional 16 hours. The reaction was diluted with dimethyl sulfoxide (1 mL), filtered and purified by reverse phase using the ammonium acetate method to provide the title compound (105.7 mg, 69%). $^1$H NMR (400 MHz, dimethyl sulfoxide-d$_6$, 120° C.) δ ppm 8.29-8.24 (m, 1H), 7.90-7.84 (m, 1H), 7.49 (d, J=2.4 Hz, 1H), 7.25-7.15 (m, 2H), 7.12-7.05 (m, 1H), 5.23 (d, J=6.3 Hz, 1H), 4.39 (d, J=1.6 Hz, 1H), 4.12 (q, J=7.1 Hz, 2H), 3.71 (s, 3H), 3.45 (dd, J=14.9, 5.6 Hz, 1H), 3.37 (d, J=6.4 Hz, 1H), 3.24 (dd, J=15.1, 5.2 Hz, 1H), 3.06 (p, J=6.8 Hz, 1H), 2.32 (d, J=1.5 Hz, 1H), 1.23-1.16 (m, 6H), 1.13 (s, 9H), 1.09 (d, J=6.8 Hz, 3H), 1.02 (s, 9H); MS (ESI+) m/z 622 (M+H)+.

Example 77B ethyl (2S,3S,4S,5S)-3-(tert-butyl)-5-(2-isopropylphenyl)-4-(((2-methoxy-5-(trifluromethyl)pyridin-3-yl)methyl)amino)pyrrolidine-2-carboxylate Example 77A (102.5 mg, 0.165 mmol) was dissolved in dichloromethane (1 mL). Trifluoroacetic acid (0.5 mL, 6.49 mmol) was added and the reaction was stirred at ambient temperature for 16 hours. The reaction mixture was concentrated to provide the title compound (124 mg, 100%) as the bistrifluoroacetic acid salt. $^1$H NMR (400 MHz, dimethyl sulfoxide-$d_6$, 120° C.) δ ppm 8.47-8.41 (m, 1H), 7.85 (d, J=2.5 Hz, 1H), 7.66 (d, J=7.8 Hz, 1H), 7.43-7.33 (m, 2H), 7.23 (ddd, J=8.4, 6.9, 1.9 Hz, 1H), 4.57 (d, J=4.2 Hz, 1H), 4.27-4.13 (m, 2H), 4.09 (s, 1H), 3.69 (s, 3H), 3.59 (d, J=14.4 Hz, 1H), 3.44 (d, J=4.3 Hz, 1H), 3.09 (d, J=14.5 Hz, 1H), 2.95 (p, J=6.8 Hz, 1H), 2.60 (d, J=7.2 Hz, 1H), 1.23 (t, J=7.1 Hz, 3H), 1.21-1.11 (m, 6H), 0.97 (s, 9H); MS (ESI+) m/z 522 (M+H)+.

Example 77C 2-ethyl 1-isopropyl (2S,3S,4S,5S)-3-(tert-butyl)-5-(2-isopropylphenyl)-4-(((2-methoxy-5-(trifluoromethyl)pyridin-3-yl)methyl)amino)pyrrolidine-1,2-dicarboxylate Example 77B (102.5 mg, 0.165 mmol) was dissolved in dichloromethane (1.5 mL) and triethylamine (0.10 mL, 0.717 mmol) was added, followed by isopropyl chloroformate (0.10 mL, 2 M, 0.20 mmol). The reaction was stirred at ambient temperature for 14 hours. The reaction was diluted with ethyl acetate (35 mL) and washed with 1 M aqueous HCl (35 mL) then brine (35 mL) and dried over sodium sulfate, filtered and concentrated to give the title compound (47.9 mg, 95%). $^1$H NMR (400 MHz, dimethyl sulfoxide-$d_6$, 120° C.) δ ppm 8.28 (d, J=2.1 Hz, 1H), 7.86 (dd, J=7.8, 1.4 Hz, 1H), 7.50 (d, J=2.4 Hz, 1H), 7.27-7.13 (m, 2H), 7.08 (td, J=7.5, 1.5 Hz, 1H), 5.27 (d, J=6.4 Hz, 1H), 4.62 (hept, J=6.2 Hz, 1H), 4.41 (d, J=1.7 Hz, 1H), 4.13 (q, J=7.0 Hz, 2H), 3.71 (s, 3H), 3.45 (d, J=15.0 Hz, 1H), 3.38 (dd, J=6.4, 0.9 Hz, 1H), 3.24 (d, J=15.0 Hz, 1H), 3.14-3.03 (m, 1H), 2.38-2.31 (m, 1H), 1.23-1.16 (m, 6H), 1.11 (d, J=6.8 Hz, 3H), 1.04-0.97 (m, 12H), 0.81 (d, J=6.2 Hz, 3H); MS (ESI+) m/z 608 (M+H)+.

Example 77D (2S,3S,4S,5S)-3-tert-butyl-4-({[2-methoxy-5-(trifluoromethyl)phenyl]methyl}amino)-1-{[(propan-2-yl)oxy]carbonyl}-5-[2-(propan-2-yl)phenyl]pyrrolidine-2-carboxylic acid Example 77C (21.6 mg, 0.035 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the ammonium acetate method to provide the title compound (27.7 mg, 61%). $^1$H NMR (400 MHz, dimethyl sulfoxide-$d_6$, 120° C.) δ ppm 8.32-8.23 (m, 1H), 7.87 (dd, J=7.8, 1.4 Hz, 1H), 7.52 (d, J=2.5 Hz, 1H), 7.26-7.14 (m, 2H), 7.08 (ddd, J=8.5, 7.0, 1.6 Hz, 1H), 5.25 (d, J=6.5 Hz, 1H), 4.61 (hept, J=6.2 Hz, 1H), 4.36 (d, J=1.8 Hz, 1H), 3.70 (s, 3H), 3.48 (d, J=15.0 Hz, 1H), 3.35 (d, J=6.5 Hz, 1H), 3.23 (d, J=15.0 Hz, 1H), 3.06 (p, J=6.8 Hz, 1H), 2.36 (t, J=1.1 Hz, 1H), 1.20 (d, J=6.8 Hz, 3H), 1.09 (d, J=6.8 Hz, 3H), 1.04-0.97 (m, 12H), 0.80 (d, J=6.2 Hz, 3H); MS (ESI+) m/z 580 (M+H)+.

Example 78

(2S,3S,4S,5S)-3-tert-butyl-4-({[2-methoxy-5-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid Example 78A (2S,3R,4S,5S)-2-ethyl 1-isopropyl 3-(tert-butyl)-5-(2-isopropoxypyridin-3-yl)-4-nitropyrrolidine-1,2-dicarboxylate To (2S,3R,4S,5S)-ethyl 3-(tert-butyl)-5-(2-isopropoxypyridin-3-yl)-4-nitropyrrolidine-2-carboxylate (Core 13, 2.00 g, 5.27 mmol) and triethylamine (5.88 mL, 42.2 mmol) in dichloromethane (10 mL) was added isopropyl carbonochloridate (3.88 g, 31.6 mmol) dropwise at ambient temperature. The mixture was stirred at ambient temperature overnight, and dichloromethane (20 mL) and water (10 mL) were added. The organic layer was washed with brine, dried over MgSO$_4$, filtered, and concentrated. Purification via chromatography on an 80 g silica gel cartridge, eluting with ethyl acetate in heptane at 0-40% gradient provided the title compound, 2.26 g (92% yield). $^1$H NMR (501 MHz, Chloroform-d) δ ppm 8.06 (dd, J=5.0, 1.8 Hz, 2H), 6.84 (dd, J=7.4, 5.0 Hz, 1H), 5.52 (d, J=7.9 Hz, 1H), 5.39 (dd, J=14.6, 7.8 Hz, 2H), 4.90 (s, 1H), 4.72 (s, 1H), 4.36 (tq, J=7.1, 3.4 Hz, 2H), 2.96 (t, J=1.9 Hz, 1H), 1.43 (d, J=6.1 Hz, 3H), 1.41 (d, J=6.2 Hz, 3H), 1.38 (t, J=7.1 Hz, 3H), 1.32-1.13 (m, 3H), 1.10 (s, 9H), 0.98 (m, 3H); MS (ESI+) m/z 466 (M+H)+.

Example 78B (2S,3S,4S,5S)-2-ethyl 1-isopropyl 4-amino-3-(tert-butyl)-5-(2-isopropoxypyridin-3-yl)pyrrolidine-1,2-dicarboxylate The title compound was prepared according to the procedure described in Example 10C, substituting Example 78A for Example 10B. LC/MS (ESI+) m/z 436.62 (M+H)+.

Example 78C (2S,3S,4S,5S)-3-tert-butyl-4-({[2-methoxy-5-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid A mixture of 2-methoxy-5-(trifluoromethyl)benzaldehyde [CAS#146539-83-5] (30.9 mg, 0.152 mmol), Example 78B (60 mg, 0.138 mmol) and zinc(II) chloride (1.9 mg, 0.014 mmol) in sodium acetate/acetic acid buffer in methanol (pH=4, 2 mL) was stirred at ambient temperature for 10 minutes to give a colorless solution. Sodium cyanoborohydride (13.13 mg, 0.209 mmol) was added and the mixture was stirred for 1 hour. Dichloromethane (10 mL) and water (10 mL) were added. The organic layer was washed with brine, dried over MgSO$_4$, filtered, and concentrated. The residue was purified via chromatography on a 12 g silica gel cartridge, eluting with ethyl acetate/methanol (10:1) in heptane 0-40% to yield (2S,3S,4S,5S)-2-ethyl 1-isopropyl 3-(tert-butyl)-5-(2-isopropoxypyridin-3-yl)-4-((2-methoxy-5-(trifluoromethyl)benzyl)amino)pyrrolidine-1,2-dicarboxylate, which was dissolved in methanol (1.5 mL) and 6 M aqueous LiOH (0.5 mL). The mixture was stirred at 50° C. for 4 hours, the pH was adjusted to 4~5 by adding 4 M HCl in dioxane, and the mixture was concentrated. The residue was dissolved in dichloromethane (2 mL) and filtered. The mixture was purified via chromatography on a 4 g silica gel cartridge, eluting with methanol in dichloromethane at 0-20% gradient to provide the title compound, 74 mg (90% yield). $^1$H NMR (400 MHz, dimethyl sulfoxide-$d_6$) δ ppm 8.01-7.94 (m, 2H), 7.46 (dd, J=8.6, 2.3 Hz, 1H), 7.23 (d, J=2.3 Hz, 1H), 6.99 (d, J=8.6 Hz, 1H), 6.85 (dd, J=7.4, 4.9 Hz, 1H), 5.23-5.15 (m, 1H), 5.13 (d, J=6.4 Hz, 1H), 4.71-4.60 (m, 1H), 4.35 (d, J=1.8 Hz, 1H), 3.61 (d, J=1.0 Hz, 3H), 3.55 (d, J=14.4 Hz, 1H), 3.42 (d, J=6.5 Hz, 1H), 3.31 (d, J=14.4 Hz, 1H), 2.64 (s, 1H), 2.32 (s, 1H), 1.28-1.23 (m, 3H), 1.13 (dd, J=6.1, 1.1 Hz, 3H), 1.03 (d, J=6.2 Hz, 3H), 0.97 (d, J=1.0 Hz, 9H), 0.91 (d, J=6.2 Hz, 3H); MS (ESI+) m/z 596.2 (M+H)$^+$.

Example 79

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 78C, substituting 2-methoxy-5-(trifluoromethyl)nicotinaldehyde [CAS#124432-66-2] for 2-methoxy-5-(trifluoromethyl)benzaldehyde. $^1$H NMR (400 MHz, dimethyl sulfoxide-$d_6$) δ ppm 8.30 (s, 1H), 8.01-7.96 (m, 2H), 7.53 (d, J=2.4 Hz, 1H), 6.88-6.83 (m, 1H), 5.21 (p, J=6.1 Hz, 1H), 5.14 (d, J=6.6 Hz, 1H), 4.65 (hept, J=6.2 Hz, 1H), 4.35 (d, J=1.9 Hz, 1H), 3.77 (s, 3H), 3.52 (d, J=15.1 Hz, 1H), 3.42 (dd, J=6.6, 1.2 Hz, 1H), 3.30 (d, J=15.1 Hz, 1H), 2.64 (m, 1H), 2.31 (s, 1H), 1.26 (d, J=5.9 Hz, 3H), 1.15 (d, J=6.1 Hz, 3H), 1.03 (d, J=6.2 Hz, 3H), 0.98 (s, 9H), 0.91 (d, J=6.2 Hz, 3H); MS (ESI+) m/z 597.2 (M+H)$^+$.

Example 80

(2S,3S,4S,5S)-3-tert-butyl-5-[2-(dimethylamino)pyridin-3-yl]-4-({[2-methoxy-5-(1-methylcyclobutyl)phenyl]methyl}amino)-1-{[(propan-2-yl)oxy]carbonyl}pyrrolidine-2-carboxylic acid

Example 80A 2-ethyl 1-isopropyl (2S,3S,4S,5S)-3-(tert-butyl)-5-(2-(dimethylamino)pyridin-3-yl)-4-((2-methoxy-5-(1-methylcyclobutyl)benzyl)amino)pyrrolidine-1,2-dicarboxylate Example 66B (62.0 mg, 0.147 mmol) and 2-methoxy-5-(1-methylcyclobutyl)benzaldehyde (Intermediate 5, 35.1 mg, 0.172 mmol) were dissolved in methanol (1 mL) and stirred at ambient temperature for 3 hours. Sodium cyanoborohydride (42.9 mg, 0.683 mmol) was added and the reaction was stirred at ambient temperature for an additional 16 hours. The reaction mixture was diluted with dimethyl sulfoxide (1 mL), filtered and purified by reverse phase using the ammonium acetate method to provide the title compound (51.1 mg, 57%). $^1$H NMR (400 MHz, dimethyl sulfoxide-$d_6$, 120° C.) δ ppm 8.19-8.12 (m, 2H), 6.98-6.89 (m, 2H), 6.75 (d, J=2.5 Hz, 1H), 6.70 (d, J=8.4 Hz, 1H), 5.30 (d, J=6.3 Hz, 1H), 4.61 (hept, J=6.2 Hz, 1H), 4.39 (d, J=1.6 Hz, 1H), 4.13 (qd, J=7.1, 2.7 Hz, 2H), 3.53-3.41 (m, 5H), 3.22 (d, J=13.6 Hz, 1H), 2.62 (s, 6H), 2.37-2.28 (m, 1H), 2.26-2.14 (m, 2H), 2.07-1.88 (m, 3H), 1.80-1.66 (m, 1H), 1.32 (s, 3H), 1.19 (t, J=7.1 Hz, 3H), 1.02-0.97 (m, 12H), 0.83 (d, J=6.2 Hz, 3H); MS (ESI+) m/z 609 (M+H)$^+$.

Example 80B (2S,3S,4S,5S)-3-tert-butyl-5-[2-(dimethylamino)pyridin-3-yl]-4-({[2-methoxy-5-(1-methylcyclobutyl)phenyl]methyl}amino)-1-{[(propan-2-yl)oxy]carbonyl}pyrrolidine-2-carboxylic acid Example 80A (48.1 mg, 0.079 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the ammonium acetate method to provide the title compound (27.7 mg, 61%). $^1$H NMR (400 MHz, dimethyl sulfoxide-$d_6$, 120° C.) δ ppm 8.21-8.11 (m, 2H), 6.97-6.91 (m, 2H), 6.79 (d, J=2.5 Hz, 1H), 6.71 (d, J=8.4 Hz, 1H), 5.29 (d, J=6.4 Hz, 1H), 4.66-4.52 (m, 1H), 4.32 (d, J=1.5 Hz, 1H), 3.56 (d, J=13.8 Hz, 1H), 3.46 (s, 4H), 3.23 (d, J=13.8 Hz, 1H), 2.61 (d, J=1.0 Hz, 6H), 2.37-2.30 (m, 1H), 2.26-2.13 (m, 2H), 2.08-1.89 (m, 3H), 1.79-1.66 (m, 1H), 1.32 (s, 3H), 1.00 (d, J=5.8 Hz, 12H), 0.81 (d, J=6.2 Hz, 3H); MS (ESI+) m/z 581 (M+H)$^+$.

Example 81

(2S,3S,4S,5S)-3-tert-butyl-4-({[2-methoxy-4-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 78C, substituting 2-methoxy-4-(trifluoromethyl)benzaldehyde for 2-methoxy-5-(trifluoromethyl)benzaldehyde. $^1$H NMR (400 MHz, dimethyl sulfoxide-$d_6$) δ ppm 8.00 (dd, J=4.9, 1.9 Hz, 1H), 7.96 (dd, J=7.3, 1.9 Hz, 1H), 7.11 (t, J=6.1 Hz, 2H), 7.05 (s, 1H), 6.87 (dd, J=7.4, 4.9 Hz, 1H), 5.19 (hept, J=6.1 Hz, 1H), 5.12 (d, J=6.5 Hz, 1H), 4.65 (hept, J=6.2 Hz, 1H), 4.36 (d, J=1.7 Hz, 1H), 3.61 (s, 3H), 3.54 (d, J=14.5 Hz, 1H), 3.43 (d, J=6.4 Hz, 1H), 3.37 (d, J=14.5 Hz, 1H), 2.64 (m, 1H), 2.32 (s, 1H), 1.26 (d, J=6.1 Hz, 3H), 1.14 (d, J=6.2 Hz, 3H), 1.03 (d, J=6.2 Hz, 3H), 0.97 (s, 9H), 0.91 (d, J=6.2 Hz, 3H); MS (ESI+) m/z 596.2 (M+H)$^+$.

Example 82

(2S,3S,4S,5S)-3-tert-butyl-4-{[6-methyl-4-(trifluoromethyl)pyridin-2-yl]amino}-1-{[(propan-2-yl)oxy]carbonyl}-5-[2-(propan-2-yl)phenyl]pyrrolidine-2-carboxylic acid

Example 82A (2S,3R,4S,5S)-2-tert-butyl 1-isopropyl 3-(tert-butyl)-5-(2-isopropylphenyl)-4-nitropyrrolidine-1,2-dicarboxylate (2S,3R,4S,5S)-tert-Butyl 3-(tert-butyl)-5-(2-isopropylphenyl)-4-nitropyrrolidine-2-carboxylate (Core 9, 1.5 g, 3.84 mmol) was dissolved in toluene (4.52 mL) and triethylamine (1.338 mL, 9.60 mmol) was added, followed by slow addition of isopropyl carbonochloridate (2.305 mL, 4.61 mmol) solution after cooling in an ice-water bath to ~10° C. The addition was at such a rate that the temperature was maintained at or below room temperature during the addition (2-3 min). When the addition was complete, the reaction mixture was removed from the water bath, stirred at room temperature for 1 hour, diluted with diethyl ether and stirred with saturated aqueous sodium bicarbonate for 20 minutes before separating the layers. The organic layer was washed three times with 1 M aqueous HCl and brine then dried over sodium sulfate, filtered, and concentrated. The crude material was triturated with 20 mL hot heptanes, filtered and the filtrate was concentrated. The residue was loaded onto a 24 g cartridge, eluting with a gradient of 0-50% ethyl acetate/heptanes over a period of 20 minutes to provide desired product (2S,3R,4S,5S)-2-tert-butyl 1-isopropyl 3-(tert-butyl)-5-(2-isopropylphenyl)-4-nitropyrrolidine-1,2-dicarboxylate (1.55 g, 3.25 mmol, 85% yield). $^1$H NMR (400 MHz, Chloroform-d) δ ppm 7.93 (d, J=7.9 Hz, 1H), 7.25 (d, J=3.3 Hz, 2H), 7.15 (ddd, J=8.4, 5.3, 3.3 Hz, 1H), 5.61 (s, 1H), 5.26 (dd, J=8.5, 1.5 Hz, 1H), 4.83 (s, 1H), 4.60 (s, 1H), 3.12-2.98 (m, 2H), 1.63 (s, 9H), 1.40 (d, J=6.8 Hz, 3H), 1.30 (d, J=6.8 Hz, 3H), 1.11 (bs, 12H), 0.74 (s, 3H); MS (ESI+) m/z 477 (M+H)$^+$.

Example 82B ethyl (2S,3S,4S,5S)-3-(tert-butyl)-4-((5-(tert-butyl)-2-methoxybenzyl)amino)-1-(cyclohexanecarbonyl)-5-phenylpyrrolidine-2-carboxylate Example 82A (513.3 mg, 1.075 mmol) and tetrahydrofuran (8 mL) were added to Raney®-Nickel 2800, water slurry (140 mg, 1.075 mmol) in a 20 mL stainless steel pressure bottle and flushed with argon 3 times, flushed with hydrogen and shaken under 50 psi of hydrogen for 14.6 hours at ambient temperature. The reaction was filtered and concentrated to provide the title compound (478 mg, 100%). $^1$H NMR (400 MHz, dimethyl sulfoxide-d$_6$, 120° C.) δ ppm 7.84 (dd, J=7.8, 1.6 Hz, 1H), 7.24 (dd, J=7.8, 1.5 Hz, 1H), 7.17 (td, J=7.5, 1.6 Hz, 1H), 7.08 (td, J=7.5, 1.6 Hz, 1H), 5.16 (d, J=6.7 Hz, 1H), 4.61 (p, J=6.2 Hz, 1H), 4.19 (d, J=3.2 Hz, 1H), 3.60 (dd, J=6.8, 2.3 Hz, 1H), 3.14 (p, J=6.7 Hz, 1H), 2.02 (t, J=2.7 Hz, 1H), 1.48 (s, 9H), 1.27-1.17 (m, 6H), 1.04-0.97 (m, 12H), 0.83 (d, J=6.2 Hz, 3H); MS (ESI+) m/z 447 (M+H)$^+$.

Example 82C (2S,3S,4S,5S)-3-tert-butyl-4-{[6-methyl-4-(trifluoromethyl)pyridin-2-yl]amino}-1-{[(propan-2-yl)oxy]carbonyl}-5-[2-(propan-2-yl)phenyl]pyrrolidine-2-carboxylic acid Example 82B (48.9 mg, 0.109 mmol) and 2-chloro-6-methyl-4-(trifluoromethyl)pyridine (55.7 mg, 0.285 mmol) were dissolved in dimethyl sulfoxide (1 mL). Potassium carbonate (106.3 mg, 0.5 mmol) was added and the reaction was heated to 150° C. for 15 hours. The reaction was cooled to room temperature, diluted with methanol (1 mL), filtered and purified by reverse phase using the trifluoroacetic acid method to provide the title compound (27.8 mg, 38%) as the trifluoroacetic acid salt. $^1$H NMR (400 MHz, dimethyl sulfoxide-d$_6$, 120° C.) δ ppm 8.03-7.95 (m, 1H), 7.14-7.02 (m, 3H), 6.47 (s, 1H), 6.17 (s, 1H), 5.54 (d, J=9.6 Hz, 1H), 5.39 (d, J=8.2 Hz, 1H), 5.23-5.11 (m, 1H), 4.64 (hept, J=6.2 Hz, 1H), 4.26 (d, J=5.7 Hz, 1H), 3.08 (hept, J=6.8 Hz, 1H), 2.34 (t, J=5.9 Hz, 1H), 2.30 (s, 3H), 1.13 (d, J=6.8 Hz, 3H), 1.04 (d, J=6.3 Hz, 3H), 1.02 (d, J=0.7 Hz, 9H), 0.84 (d, J=6.3 Hz, 3H), 0.80 (dd, J=6.7, 0.9 Hz, 3H); MS (ESI+) m/z 550 (M+H)$^+$.

Example 83

(2S,3S,4S,5S)-3-tert-butyl-4-({[2-methoxy-5-(trifluoromethyl)phenyl]methyl}amino)-1-{[(propan-2-yl)oxy]carbonyl}-5-[2-(propan-2-yl)phenyl]pyrrolidine-2-carboxylic acid Example 83A 2-(tert-butyl) 1-isopropyl (2S,3S,4S,5S)-3-(tert-butyl)-5-(2-isopropylphenyl)-4-((2-methoxy-5-(trifluoromethyl)benzyl)amino)pyrrolidine-1,2-dicarboxylate Example 82B (48.2 mg, 0.108 mmol) and 2-methoxy-5-(trifluoromethyl)benzaldehyde (40.6 mg, 0.199 mmol) were dissolved in methanol (1 mL) and stirred at ambient temperature for 1 hour. Sodium cyanoborohydride (33.2 mg, 0.528 mmol) was added and the reaction was stirred at ambient temperature for an additional 16 hours. The reaction was diluted with dimethyl sulfoxide (1 mL), filtered and purified by reverse phase using the ammonium acetate method to provide the title compound (40.6 mg, 59%). $^1$H NMR (400 MHz, dimethyl sulfoxide-d$_6$, 120° C.) δ ppm 7.88 (dd, J=7.9, 1.4 Hz, 1H), 7.45-7.38 (m, 1H), 7.26-7.15 (m, 3H), 7.06 (td, J=7.4, 1.6 Hz, 1H), 6.94 (d, J=8.6 Hz, 1H), 5.24 (d, J=6.3 Hz, 1H), 4.62 (hept, J=6.2 Hz, 1H), 4.30 (d, J=1.7 Hz, 1H), 3.54 (d, J=0.9 Hz, 3H), 3.47 (dd, J=14.1, 7.4 Hz, 1H), 3.34 (dd, J=6.6, 3.0 Hz, 1H), 3.24 (dd, J=14.1, 6.7 Hz, 1H), 3.06 (h, J=6.9 Hz, 1H), 2.33 (d, J=1.6 Hz, 1H), 1.41 (d, J=0.8 Hz, 9H), 1.20 (d, J=6.7 Hz, 3H), 1.10 (d, J=6.8 Hz, 3H), 1.00 (d, J=2.4 Hz, 12H), 0.83 (d, J=6.2 Hz, 3H); MS (ESI+) m/z 635 (M+H)$^+$.

Example 83B (2S,3S,4S,5S)-3-tert-butyl-4-({[2-methoxy-5-(trifluoromethyl)phenyl]methyl}amino)-1-{[(propan-2-yl)oxy]carbonyl}-5-[2-(propan-2-yl)phenyl]pyrrolidine-2-carboxylic acid Example 83A (37.6 mg, 0.059 mmol) was dissolved in dichloromethane (1 mL). Trifluoroacetic acid (0.5 mL, 6.49 mmol) was added and the reaction was stirred at ambient temperature for 16 hours. The reaction was concentrated to provide the title compound (41.0 mg, 100%) as the trifluoroacetic acid salt. $^1$H NMR (400 MHz, dimethyl sulfoxide-d$_6$, 120° C.) δ ppm 7.82 (dd, J=7.8, 1.4 Hz, 1H), 7.51 (dd, J=8.7, 2.3 Hz, 1H), 7.31-7.20 (m, 3H), 7.15 (td, J=7.4, 1.8 Hz, 1H), 7.01 (d, J=8.6 Hz, 1H), 5.29 (d, J=6.4 Hz, 1H), 4.60 (hept, J=6.2 Hz, 1H), 4.37 (d, J=1.7 Hz, 1H), 3.69 (d, J=13.9 Hz, 1H), 3.59-3.53 (m, 4H), 3.26 (d, J=14.0 Hz, 1H), 3.04 (h, J=6.8 Hz, 1H), 2.46 (s, 1H), 1.19 (d, J=6.7 Hz, 3H), 1.10 (d, J=6.8 Hz, 3H), 1.01 (s, 9H), 0.99 (d, J=6.3 Hz, 3H), 0.77 (d, J=6.2 Hz, 3H); MS (ESI+) m/z 579 (M+H)$^+$.

Example 84

(2S,3S,4S,5S)-3-tert-butyl-4-({[2-methoxy-5-(trifluoromethyl)pyridin-3-yl]methyl}amino)-1-[(2S)-oxane-2-carbonyl]-5-[2-(propan-2-yl)phenyl]pyrrolidine-2-carboxylic acid

Example 84A ethyl (2S,3S,4S,5S)-3-(tert-butyl)-5-(2-isopropylphenyl)-4-(((2-methoxy-5-(trifluromethyl)pyridin-3-yl)methyl)amino)-1-((S)-tetrahydro-2H-pyran-2-carbonyl)pyrrolidine-2-carboxylate Tetrahydropyran-2-carboxylic acid (21.7 mg, 0.167 mmol) was dissolved in dichloromethane (1 mL). Oxalyl chloride (35.2 mg, 0.277 mmol) was added followed by N,N-dimethylformamide (10 µL). The reaction was stirred at room temperature for 3 hours, at which point it was concentrated, redissolved in dichloromethane (1 mL), and concentrated again. The residue was taken up in dichloromethane (2×1 mL) and added to a solution of Example 77B (97.0 mg, 0.129 mmol) and triethylamine (150 µL, 1.076 mmol) in dichloromethane (1 mL). The reaction was stirred at ambient temperature for 18 hours. After this time, the mixture was concentrated and dissolved in dimethyl sulfoxide/methanol (1:1, 2 mL) and purified by reverse phase using the ammonium acetate method. The title compound was the first eluting diastereomer (27.1 mg, 33%). $^1$H NMR (400 MHz, dimethyl sulfoxide-$d_6$, 120° C.) δ ppm 8.29 (s, 1H), 7.89 (d, J=7.9 Hz, 1H), 7.50 (d, J=2.4 Hz, 1H), 7.30 (d, J=7.7 Hz, 1H), 7.23 (t, J=7.4 Hz, 1H), 7.11 (t, J=7.5 Hz, 1H), 5.60 (s, 1H), 4.62 (d, J=1.5 Hz, 1H), 3.74 (s, 3H), 3.54 (d, J=14.9 Hz, 1H), 3.45 (d, J=6.7 Hz, 1H), 3.22 (d, 1H), 3.15-3.08 (m, 4H), 2.37 (s, 1H), 1.72-1.32 (m, 6H), 1.27 (d, J=6.7 Hz, 3H), 1.08 (d, J=6.7 Hz, 3H), 1.01 (s, 9H); MS (ESI+) m/z 634 (M+H)$^+$.

Example 84B (2S,3S,4S,5S)-3-tert-butyl-4-({[2-methoxy-5-(trifluoromethyl)pyridin-3-yl]methyl}amino)-1-[(2S)-oxane-2-carbonyl]-5-[2-(propan-2-yl)phenyl]pyrrolidine-2-carboxylic acid Example 84A (24.1 mg, 0.038 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (19.5 mg, 62%) as the bis trifluoroacetic acid salt. $^1$H NMR (400 MHz, dimethyl sulfoxide-$d_6$, 120° C.) δ ppm 8.29 (s, 1H), 7.89 (d, J=7.9 Hz, 1H), 7.50 (d, J=2.4 Hz, 1H), 7.30 (d, J=7.7 Hz, 1H), 7.23 (t, J=7.4 Hz, 1H), 7.11 (t, J=7.5 Hz, 1H), 5.60 (s, 1H), 4.62 (d, J=1.5 Hz, 1H), 3.74 (s, 3H), 3.54 (d, J=14.9 Hz, 1H), 3.45 (d, J=6.7 Hz, 1H), 3.22 (d, 1H), 3.15-3.08 (m, 4H), 2.37 (s, 1H), 1.72-1.32 (m, 6H), 1.27 (d, J=6.7 Hz, 3H), 1.08 (d, J=6.7 Hz, 3H), 1.01 (s, 9H); MS (ESI+) m/z 606 (M+H)$^+$.

Example 85

(2S,3S,4S,5S)-3-tert-butyl-4-({[2-methoxy-5-(trifluoromethyl)pyridin-3-yl]methyl}amino)-1-[(2R)-oxane-2-carbonyl]-5-[2-(propan-2-yl)phenyl]pyrrolidine-2-carboxylic acid

Example 85A ethyl (2S,3S,4S,5S)-3-(tert-butyl)-5-(2-isopropylphenyl)-4-(((2-methoxy-5-(trifluromethyl)pyridin-3-yl)methyl)amino)-1-((R)-tetrahydro-2H-pyran-2-carbonyl)pyrrolidine-2-carboxylate Tetrahydropyran-2-carboxylic acid (21.7 mg, 0.167 mmol) was dissolved in dichloromethane (1 mL). Oxalyl chloride (35.2 mg, 0.277 mmol) was added followed by N,N-dimethylformamide (10 µL). The reaction was stirred at room temperature for 3 hours, at which point it was concentrated, redissolved in dichloromethane (1 mL), and concentrated again. The residue was taken up in dichloromethane (2×1 mL) and added to a solution of Example 77B (97.0 mg, 0.129 mmol) and triethylamine (150 µL, 1.076 mmol) in dichloromethane (1 mL). The reaction was stirred at ambient temperature for 18 hours. After this time, the mixture was concentrated and dissolved in dimethyl sulfoxide/methanol (1:1, 2 mL) and purified by reverse phase using the ammonium acetate method. The title compound was the second eluting diastereomer (12.0 mg, 15%). $^1$H NMR (400 MHz, dimethyl sulfoxide-$d_6$, 120° C.) δ ppm 8.28 (d, J=2.2 Hz, 1H), 7.74 (s, 1H), 7.49 (d, J=2.5 Hz, 1H), 7.25 (d, J=7.7 Hz, 1H), 7.18 (t, J=7.5 Hz, 1H), 7.04 (t, J=7.5 Hz, 1H), 5.39 (d, J=6.4 Hz, 1H), 4.91 (s, 1H), 4.15 (q, J=7.1 Hz, 2H), 3.96-3.76 (m, 2H), 3.70 (s, 3H), 3.49 (d, J=14.8 Hz, 1H), 3.38 (d, J=6.5 Hz, 1H), 3.27 (d, J=14.9 Hz, 1H), 3.09 (p, J=6.8 Hz, 1H), 2.50 (s, 1H), 1.79 (s, 1H), 1.63-1.32 (m, 6H), 1.23 (d, J=6.8 Hz, 3H), 1.19 (t, J=7.1 Hz, 3H), 1.10 (d, J=6.8 Hz, 3H), 1.02 (s, 9H); MS (ESI+) m/z 634 (M+H)$^+$.

Example 85B (2S,3S,4S,5S)-3-tert-butyl-4-({[2-methoxy-5-(trifluoromethyl)pyridin-3-yl]methyl}amino)-1-[(2R)-oxane-2-carbonyl]-5-[2-(propan-2-yl)phenyl]pyrrolidine-2-carboxylic acid Example 85A (9.0 mg, 0.014 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (8.1 mg, 68%) as the bis trifluoroacetic acid salt. $^1$H NMR (400 MHz, dimethyl sulfoxide-$d_6$, 120° C.) δ ppm 8.29 (d, J=2.3 Hz, 1H), 7.71 (s, 1H), 7.53 (d, J=2.4 Hz, 1H), 7.25 (d, J=7.7 Hz, 1H), 7.18 (t, J=7.4 Hz, 1H), 7.05 (t, J=7.5 Hz, 1H), 5.39 (d, J=6.6 Hz, 1H), 4.86 (s, 1H), 4.04-3.77 (m, 3H), 3.70 (d, J=1.2 Hz, 3H), 3.55 (d, J=14.8 Hz, 1H), 3.38 (d, J=6.6 Hz, 1H), 3.28 (d, J=14.8 Hz, 1H), 3.08 (p, J=6.8 Hz, 1H), 2.47 (s, 1H), 1.78 (s, 1H), 1.61-1.35 (m, 5H), 1.22 (d, J=6.7 Hz, 3H), 1.08 (dd, J=6.8, 1.1 Hz, 3H), 1.01 (s, 9H); MS (ESI+) m/z 606 (M+H)$^+$.

Example 86

(2S,3S,4S,5S)-3-tert-butyl-4-{[(5-tert-butyl-2-methoxyphenyl)methyl]amino}-5-(3-chlorophenyl)-1-{[(propan-2-yl)oxy]carbonyl}pyrrolidine-2-carboxylic acid

Example 86A (2S,3R,4S,5S)-2-ethyl 1-isopropyl 3-(tert-butyl)-5-(3-chlorophenyl)-4-nitropyrrolidine-1,2-dicarboxylate (2S,3R,4S,5S)-Ethyl 3-(tert-butyl)-5-(3-chlorophenyl)-4-nitropyrrolidine-2-carboxylate (Core 29, 2.003 g, 5.64 mmol) was dissolved in toluene (6.64 mL) and triethylamine (1.967 mL, 14.11 mmol) was added, followed by slow addition of isopropyl carbonochloridate (3.39 mL, 6.77 mmol) solution after cooling in an ice-water bath to ~10° C. The addition was at such a rate that the temperature was maintained at or below ambient temperature during the addition (2-3 minutes). After the addition was complete, the reaction was removed from the water bath and stirred at ambient temperature for 1 hour. Isopropyl chloroformate (0.4 mL) was added, and the reaction was stirred at ambient temperature for 30 more minutes. The mixture was diluted with diethyl ether and stirred with saturated aqueous sodium bicarbonate for 20 minutes before separating the layers, washing the organic layer twice with 1 M aqueous HCl and brine then drying over sodium sulfate, filtering, and concentrating to give a crude residue, which was loaded onto a 40 g silica gel cartridge eluting with a gradient of 5-100% ethyl acetate/heptanes over a period of 40 minutes to provide impure product. The product was precipitated from hexanes to give (2S,3R,4S,5S)-2-ethyl 1-isopropyl 3-(tert-butyl)-5-(3-chlorophenyl)-4-nitropyrrolidine-1,2-dicarboxylate (2.086 g, 4.73 mmol, 84% yield). $^1$H NMR (400 MHz, dimethyl sulfoxide-$d_6$) δ ppm 7.63 (t, J=1.5 Hz, 1H), 7.48-7.41 (m, 1H), 7.29-7.20 (m, 2H), 5.64 (dd, J=8.7, 3.0 Hz, 1H), 5.44 (d, J=8.7 Hz, 1H), 4.70 (p, J=6.2 Hz, 1H), 4.51 (d, J=3.6 Hz, 1H), 4.25 (q, J=7.1 Hz, 2H), 2.96 (t, J=3.3 Hz, 1H), 1.30 (t, J=7.1 Hz, 3H), 1.08 (d, J=6.2 Hz, 3H), 1.01 (s, 9H), 0.95 (d, J=6.2 Hz, 3H); MS (ESI+) m/z 441 (M+H)$^+$.

Example 86B (2S,3S,4S,5S)-2-ethyl 1-isopropyl 4-amino-3-(tert-butyl)-5-(3-chlorophenyl)pyrrolidine-1,2-dicarboxylate Example 86A (119 mg, 0.270 mmol) was dissolved in tetrahydrofuran (1349 µL) and zinc (200 mg, 3.06 mmol) was added, followed by addition of acetic acid (100 µl, 1.747 mmol). The mixture was warmed to 40° C. for 3 hours and stirred at ambient temperature for 73 hours. The reaction was filtered and the solvent was removed to give (2S,3S,4S,5S)-2-ethyl 1-isopropyl 4-amino-3-(tert-butyl)-5-(3-chlorophenyl)pyrrolidine-1,2-dicarboxylate (110 mg, 0.268 mmol, 99% yield). MS (ESI+) m/z 411 (M+H)$^+$.

Example 86C (2S,3S,4S,5S)-2-ethyl 1-isopropyl 3-(tert-butyl)-4-((5-(tert-butyl)-2-methoxybenzyl)amino)-5-(3-chlorophenyl)pyrrolidine-1,2-dicarboxylate Example 86B (55 mg, 0.134 mmol), zinc(II) chloride (12 mg, 0.088 mmol) and 5-(tert-butyl)-2-methoxybenzaldehyde (33.5 mg, 0.174 mmol) were dissolved in sodium acetate/acetic acid buffer in methanol (pH=4, 669 µL) and stirred at ambient temperature for 25 minutes. Sodium cyanotrihydroborate (12.62 mg, 0.201 mmol) was added and the reaction was stirred at ambient temperature for 90 minutes. The solvent was removed under nitrogen. The residue was diluted with saturated aqueous sodium bicarbonate and the crude material was taken up in dichloromethane and purified using a ethyl acetate/heptane solvent system with a 12 g silica gel cartridge to yield (2S,3S,4S,5S)-2-ethyl 1-isopropyl 3-(tert-butyl)-4-((5-(tert-butyl)-2-methoxybenzyl)amino)-5-(3-chlorophenyl)pyrrolidine-1,2-dicarboxylate (36 mg, 0.043 mmol, 32.1% yield). MS (ESI+) m/z 588 (M+H)$^+$.

Example 86D (2S,3S,4S,5S)-3-tert-butyl-4-{[(5-tert-butyl-2-methoxyphenyl)methyl]amino}-5-(3-chlorophenyl)-1-{[(propan-2-yl)oxy]carbonyl}pyrrolidine-2-carboxylic acid Example 86C (36 mg, 0.061 mmol), and lithium hydroxide (0.2 mL, 0.400 mmol) were dissolved in methanol (0.2 mL), tetrahydrofuran (0.200 mL) and water (0.200 mL). The reaction was warmed at 45° C. overnight. The solvent was removed under nitrogen. The residue was diluted with 1 N aqueous HCl and the crude material was taken up in dichloromethane and purified using a ethyl acetate/ethanol/heptane solvent system with a 4 g silica gel cartridge to yield (2S,3S,4S,5S)-3-(tert-butyl)-4-((5-(tert-butyl)-2-methoxybenzyl)amino)-5-(3-chlorophenyl)-1-(isopropoxycarbonyl)pyrrolidine-2-carboxylic acid (19 mg, 0.034 mmol, 55.4% yield). $^1$H NMR (400 MHz, dimethyl sulfoxide-$d_6$) δ ppm 7.59 (t, J=1.8 Hz, 1H), 7.42 (dt, J=7.6, 1.6 Hz, 1H), 7.28 (t, J=7.7 Hz, 1H), 7.23 (ddd, J=7.9, 2.1, 1.3 Hz, 1H), 7.13 (dd, J=8.5, 2.6 Hz, 1H), 6.94 (d, J=2.6 Hz, 1H), 6.74 (d, J=8.5 Hz, 1H), 4.98 (d, J=6.8 Hz, 1H), 4.64 (p, J=6.2 Hz, 1H), 4.30 (d, J=2.4 Hz, 1H), 3.58-3.48 (m, 4H), 3.44 (dd, J=6.8, 1.9 Hz, 1H), 3.30 (d, J=13.8 Hz, 1H), 2.31 (t, J=2.3 Hz, 1H), 1.99-1.84 (m, 1H), 1.20 (s, 9H), 1.05 (d, J=6.2 Hz, 3H), 0.96 (s, 9H), 0.90 (d, J=6.2 Hz, 3H); MS (ESI+) m/z 559 (M+H)$^+$.

Example 87

(2S,3S,4S,5S)-3-tert-butyl-4-{[(5-cyclobutyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid The title compound was prepared according to the procedure described in Example 78C, substituting 5-cyclobutyl-2-methoxynicotinaldehyde for 2-methoxy-5-(trifluoromethyl)benzaldehyde. $^1$H NMR (400 MHz, dimethyl sulfoxide-$d_6$) δ ppm 8.00 (dd, J=4.9, 1.9 Hz, 1H), 7.95 (dd, J=7.3, 1.9 Hz, 1H), 7.77 (d, J=2.4 Hz, 1H), 7.15 (d, J=2.3 Hz, 1H), 6.87 (dd, J=7.4, 4.9 Hz, 1H), 5.24-5.16 (m, 1H), 5.13 (d, J=6.4 Hz, 1H), 4.66 (dq, J=12.3, 6.1 Hz, 1H), 4.36 (d, J=1.6 Hz, 1H), 3.62 (d, J=0.9 Hz, 3H), 3.50 (d, J=14.3 Hz, 1H), 3.43 (d, J=6.5 Hz, 1H), 3.38 (q, J=8.5 Hz, 1H), 3.26 (d, J=14.3 Hz, 1H), 2.64 (m, 1H), 2.33 (s, 1H), 2.31-2.21 (m, 2H), 1.97 (dq, J=5.9, 3.9, 3.3 Hz, 4H), 1.26 (d, J=6.0 Hz, 3H), 1.13 (dd, J=6.2, 1.0 Hz, 3H), 1.04 (d, J=6.2 Hz, 3H), 0.98 (s, 9H), 0.91 (d, J=6.2 Hz, 3H); MS (ESI+) m/z 583.3 (M+H)$^+$.

Example 88

(2S,3S,4S,5S)-3-tert-butyl-1-(cyclohexanecarbonyl)-4-({[2-methoxy-4-(trifluoromethyl)phenyl]methyl}amino)-5-(2-methylphenyl)pyrrolidine-2-carboxylic acid

Example 88A ethyl (2S,3R,4S,5S)-3-(tert-butyl)-1-(cyclohexanecarbonyl)-4-nitro-5-(o-tolyl)pyrrolidine-2-carboxylate Ethyl (2S,3R,4S,5S)-3-(tert-butyl)-4-nitro-5-(o-tolyl)pyrrolidine-2-carboxylate (Core 10, 1.03 g, 3.08 mmol) was dissolved in dichloromethane (10 mL) and triethylamine (0.80 mL, 5.74 mmol) was added, followed by cyclohexanecarbonyl chloride (489.6 mg, 3.34 mmol). The reaction was stirred at ambient temperature for 16 hours. The reaction was diluted with dichloromethane (50 mL) and washed with 1 M aqueous HCl (2×50 mL) and brine. The organic layer was dried over sodium sulfate, filtered, and concentrated to provide the title compound (1.37 g, 100%). $^1$H NMR (400 MHz, dimethyl sulfoxide-$d_6$, 120° C.) δ ppm 7.83 (s, 1H), 7.17-7.05 (m, 3H), 5.71 (d, J=8.9 Hz, 1H), 5.59 (dd, J=9.0, 3.3 Hz, 1H), 4.69 (d, J=3.8 Hz, 1H), 4.26 (q, J=7.1 Hz, 2H), 3.08 (t, J=3.5 Hz, 1H), 2.41 (s, 3H), 2.05 (s, 1H), 1.83-1.43 (m, 4H), 1.34-1.05 (m, 9H), 1.02 (s, 9H); MS (ESI+) m/z 445 (M+H)$^+$.

Example 88B (2S,3S,4S,5S)-ethyl 4-amino-3-(tert-butyl)-1-(cyclohexanecarbonyl)-5-(o-tolyl)pyrrolidine-2-carboxylate Example 88A (1.37 g, 3.08 mmol) and tetrahydrofuran (50 mL) were added to a Raney®-Nickel 2800, water slurry (3.1 g, 23.77 mmol) in a 250 mL stainless steel pressure bottle and the mixture was shaken for 16 hours at 50 psi hydrogen and ambient temperature. The reaction was filtered and concentrated to provide the title compound (1.28 g, 100%). $^1$H NMR (400 MHz, dimethyl sulfoxide-$d_6$, 120° C.) δ ppm 7.87 (s, 1H), 7.20-7.07 (m, 3H), 5.20 (d, J=7.0 Hz, 1H), 4.43 (d, J=3.5 Hz, 1H), 4.17 (qd, J=7.1, 0.9 Hz, 2H), 3.74 (dd, J=7.1, 3.0 Hz, 1H), 2.34 (s, 3H), 2.10-1.93 (m, 2H), 1.70-1.58 (m, 2H), 1.47 (d, J=10.2 Hz, 2H), 1.29-1.01 (m, 9H), 0.99 (s, 9H); MS (ESI+) m/z 415 (M+H)$^+$.

Example 88C ethyl (2S,3S,4S,5S)-3-(tert-butyl)-1-(cyclohexanecarbonyl)-4-((2-methoxy-4-(trifluoromethyl)benzyl)amino)-5-(o-tolyl)pyrrolidine-2-carboxylate Example 88B (55.3 mg, 0.133 mmol) and 2-methoxy-4-(trifluoromethyl)benzaldehyde (43.7 mg, 0.214 mmol) were dissolved in methanol (1 mL) and the mixture was stirred at ambient temperature for 1 hour. Sodium cyanoborohydride (41.6 mg, 0.662 mmol) was added and the reaction was stirred at ambient temperature for an additional 16 hours. The reaction was diluted with dimethyl sulfoxide (1 mL), filtered and purified by reverse phase using the ammonium acetate method to provide the title compound (39.2 mg, 49%). $^1$H NMR (400 MHz, dimethyl sulfoxide-$d_6$, 120° C.) δ ppm 7.85 (s, 1H), 7.17-7.00 (m, 6H), 5.23 (d, J=6.6 Hz, 1H), 4.59 (d, J=1.8 Hz, 1H), 4.12 (q, J=7.1 Hz, 2H), 3.59 (d, J=1.1 Hz, 3H), 3.54-3.41 (m, 2H), 3.32 (d, J=14.4 Hz, 1H), 2.38-2.31 (m, 2H), 2.17 (s, 3H), 1.69-1.41 (m, 4H), 1.31-1.02 (m, 9H), 0.99 (s, 9H); MS (ESI+) m/z 603 (M+H)$^+$.

Example 88D (2S,3S,4S,5S)-3-tert-butyl-1-(cyclohexanecarbonyl)-4-({[2-methoxy-4-(trifluoromethyl)phenyl]methyl}amino)-5-(2-methylphenyl)pyrrolidine-2-carboxylic acid Example 88C (36.2 mg, 0.060 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (37.3 mg, 90%) as the trifluoroacetic acid salt. $^1$H NMR (400 MHz, dimethyl sulfoxide-$d_6$, 120° C.) δ ppm 7.76 (s, 1H), 7.19-7.10 (m, 5H), 7.07 (s, 1H), 5.27 (d, J=6.7 Hz, 1H), 4.56 (d, J=1.6 Hz, 1H), 3.67-3.59 (m, 4H), 3.57 (d, J=6.7 Hz, 1H), 3.37 (d, J=14.2 Hz, 1H), 2.43 (s, 1H), 2.29 (s, 1H), 2.21 (s, 3H), 1.69-1.44 (m, 4H), 1.32-1.02 (m, 6H), 1.00 (s, 9H); MS (ESI+) m/z 575 (M+H)$^+$.

Example 89

(2S,3S,4S,5S)-3-tert-butyl-4-{[(5-cyclobutyl-2-methoxypyridin-3-yl)methyl]amino}-1-[(2S)-oxolane-2-carbonyl]-5-[2-(propan-2-yl)phenyl]pyrrolidine-2-carboxylic acid

Example 89A (2S,3S,4S,5S)-ethyl 3-(tert-butyl)-4-(((5-cyclobutyl-2-methoxypyridin-3-yl)methyl)amino)-5-(2-isopropylphenyl)-1-((S)-tetrahydrofuran-2-carbonyl)pyrrolidine-2-carboxylate (2S,3S,4S,5S)-Ethyl 4-amino-3-(tert-butyl)-5-(2-isopropylphenyl)-1-((S)-tetrahydrofuran-2-carbonyl)pyrrolidine-2-carboxylate (0.240 g, 0.557 mmol) and 5-cyclobutyl-2-methoxynicotinaldehyde (0.107 g, 0.557 mmol) in dichloroethane (2.7 mL) was treated with sodium triacetoxyborohydride (0.165 g, 0.780 mmol), and the reaction was stirred at room temperature for 45 minutes. The mixture was treated with 2.7 mL of saturated aqueous NaHCO$_3$ solution, and the mixture was stirred vigorously for 30 minutes. The phases were separated, and the organic layer was extracted three times with CH$_2$Cl$_2$. The combined organics were dried over Na$_2$SO$_4$, filtered, and concentrated in vacuo, and the crude residue was purified by silica gel chromatography, eluting with 5 to 30% ethyl acetate-CH$_2$Cl$_2$ to obtain the title compound, 0.156 g (46% yield). $^1$H NMR (400 MHz, dimethyl sulfoxide-$d_6$) δ ppm 7.90 (m, 1H), 7.73 (m, 1H), 7.25 (m, 2H), 7.16-7.02 (m, 2H), 5.61 (m, 1H), 4.72 (m, 1H), 4.22-4.03 (m, 3H), 3.85-3.57 (m, 5H), 3.40 (m, 3H), 3.14 (m, 2H), 2.39 (m, 1H), 2.35-2.14 (m, 2H), 2.08-1.71 (m, 7H), 1.61 (m, 1H), 1.24-1.14 (m, 6H), 1.06 (d, J=6.8 Hz, 3H), 1.02 (s, 9H); MS (ESI+) m/z 606.4 (M+H)$^+$.

Example 89B (2S,3S,4S,5S)-3-tert-butyl-4-{[(5-cyclobutyl-2-methoxypyridin-3-yl)methyl]amino}-1-[(2S)-oxolane-2-carbonyl]-5-[2-(propan-2-yl)phenyl]pyrrolidine-2-carboxylic acid Example 89A (0.156 g, 0.258 mmol) in tetrahydrofuran (2.6 mL) and methanol (2.6 mL) was treated with lithium hydroxide (1 M aqueous) (2.6 mL, 2.60 mmol), and the reaction was stirred at 45° C. for 1 hour. The reaction mixture was then diluted with 3 mL water and acidified to pH 2 with 1 N aqueous HCl. The aqueous mixture was then extracted 4 times with CH$_2$Cl$_2$, and the combined organics were dried over Na$_2$SO$_4$, filtered, and concentrated in vacuo. The crude product was purified by silica gel chromatography, eluting with 0 to 5% methanol-ethyl acetate, then was further purified with additional silica gel chromatography, eluting with 0 to 2% methanol-ethyl acetate to obtain the title compound, 0.0393 g (26% yield). $^1$H NMR (400 MHz, dimethyl sulfoxide-d$_6$) δ ppm 7.86 (d, J=7.9 Hz, 1H), 7.75 (m, 1H), 7.31-7.18 (m, 2H), 7.15-7.07 (m, 2H), 5.62 (m, 1H), 4.64 (m, 1H), 4.11 (m, 1H), 3.63 (m, 2H), 3.57 (s, 3H), 3.50 (m, 1H), 3.38 (m, 2H), 3.22 (d, J=14.3 Hz, 1H), 3.09 (m, 1H), 2.41 (m, 1H), 2.25 (m, 2H), 2.04-1.88 (m, 4H), 1.85-1.75 (m, 2H), 1.64 (m, 2H), 1.19 (d, J=6.9 Hz, 3H), 1.05 (dd, J=6.9 Hz, 3H), 1.02 (s, 9H); MS (APCI+) m/z 578.7 (M+H)$^+$.

Example 90

(2S,3S,4S,5S)-3-tert-butyl-4-{[(6-methoxy-2,3-dihydro-1H-inden-5-yl)methyl]amino}-5-(2-methylphenyl)-1-{[(propan-2-yl)oxy]carbonyl}pyrrolidine-2-carboxylic acid Example 90A 2-ethyl 1-isopropyl (2S,3R,4S,5S)-3-(tert-butyl)-4-nitro-5-(o-tolyl)pyrrolidine-1,2-dicarboxylate Ethyl (2S,3R,4S,5S)-3-(tert-butyl)-4-nitro-5-(o-tolyl)pyrrolidine-2-carboxylate (Core 10, 1.86 g, 5.56 mmol) was dissolved in dichloromethane (10 mL) and triethylamine (2.326 mL, 16.69 mmol) was added, followed by isopropyl chloroformate (3.34 mL, 2 M, 6.68 mmol). The reaction was stirred at ambient temperature for 16 hours. The reaction was diluted with dichloromethane (50 mL) and washed with 1 M aqueous HCl (2×50 mL) and brine. The organic layer was dried over sodium sulfate, filtered, then concentrated. The residue was purified by silica gel chromatography (5% to 50% methyl tert-butyl ether in heptanes) to provide the title compound (1.44 g, 62%). $^1$H NMR (400 MHz, dimethyl sulfoxide-d$_6$, 120° C.) δ ppm 7.78 (dd, J=7.9, 1.8 Hz, 1H), 7.14-7.02 (m, 3H), 5.54 (d, J=2.7 Hz, 2H), 4.64 (p, J=6.2 Hz, 1H), 4.49 (d, J=4.0 Hz, 1H), 4.26 (q, J=7.1 Hz, 2H), 3.07 (dd, J=4.1, 2.4 Hz, 1H), 2.36 (s, 3H), 1.30 (t, J=7.1 Hz, 3H), 1.05 (d, J=6.2 Hz, 3H), 1.02 (s, 9H), 0.88 (d, J=6.2 Hz, 3H); MS (ESI+) m/z 421 (M+H)$^+$.

Example 90B (2S,3S,4S,5S)-2-ethyl 1-isopropyl 4-amino-3-(tert-butyl)-5-(o-tolyl)pyrrolidine-1,2-dicarboxylate Example 90A (469 mg, 1.115 mmol) and tetrahydrofuran (8 mL) were added to a Raney®-Nickel 2800, water slurry (986.7 mg, 7.56 mmol) in a 20 mL stainless steel pressure bottle and shaken for 18 hours at 60 psi hydrogen and ambient temperature. The reaction was filtered and concentrated to provide the title compound (405.7 mg, 93%). $^1$H NMR (400 MHz, dimethyl sulfoxide-d$_6$, 120° C.) δ ppm 7.79 (dd, J=7.9, 2.0 Hz, 1H), 7.15-7.03 (m, 3H), 5.05 (d, J=7.0 Hz, 1H), 4.67-4.56 (m, 1H), 4.29 (d, J=3.4 Hz, 1H), 4.18 (q, J=7.1 Hz, 2H), 3.68 (dd, J=6.9, 2.8 Hz, 1H), 2.29 (s, 3H), 2.07 (t, J=3.1 Hz, 1H), 1.25 (td, J=7.1, 0.7 Hz, 3H), 1.03 (d, J=6.2 Hz, 3H), 1.00 (d, J=0.7 Hz, 9H), 0.87 (d, J=6.2 Hz, 3H); MS (ESI+) m/z 391 (M+H)$^+$.

Example 90C 2-ethyl 1-isopropyl (2S,3S,4S,5S)-3-(tert-butyl)-4-(((6-methoxy-2,3-dihydro-1H-inden-5-yl)methyl)amino)-5-(o-tolyl)pyrrolidine-1,2-dicarboxylate Example 90B (51.4 mg, 0.132 mmol) and 6-methoxy-5-indanecarbaldehyde (39.6 mg, 0.225 mmol) were dissolved in methanol (1 mL) and the mixture was stirred at ambient temperature for 1 hour. Sodium cyanoborohydride (43.7 mg, 0.695 mmol) was added and the reaction was stirred at ambient temperature for an additional 16 hours. The reaction was diluted with dimethyl sulfoxide (1 mL), filtered and purified by reverse phase using the ammonium acetate method to provide the title compound (54.6 mg, 75%). $^1$H NMR (400 MHz, dimethyl sulfoxide-d$_6$, 120° C.) δ ppm 7.80 (dq, J=4.3, 2.5 Hz, 1H), 7.09 (d, J=3.4 Hz, 3H), 6.66 (s, 1H), 6.63 (s, 1H), 5.09 (d, J=6.5 Hz, 1H), 4.62 (hept, J=6.2 Hz, 1H), 4.40 (d, J=1.7 Hz, 1H), 4.13 (q, J=7.1 Hz, 2H), 3.46 (s, 3H), 3.41 (dd, J=6.6, 1.1 Hz, 1H), 3.37 (d, J=13.5 Hz, 1H), 3.23 (d, J=13.6 Hz, 1H), 2.77 (t, J=7.5 Hz, 2H), 2.68 (t, J=7.4 Hz, 2H), 2.35 (d, J=1.7 Hz, 1H), 2.13 (s, 3H), 2.02-1.93 (m, 2H), 1.21 (t, J=7.1 Hz, 3H), 1.03 (d, J=6.2 Hz, 3H), 0.99 (s, 9H), 0.87 (d, J=6.2 Hz, 3H); MS (ESI+) m/z 551 (M+H)$^+$.

Example 90D (2S,3S,4S,5S)-3-tert-butyl-4-{[(6-methoxy-2,3-dihydro-1H-inden-5-yl)methyl]amino}-5-(2-methylphenyl)-1-{[(propan-2-yl)oxy]carbonyl}pyrrolidine-2-carboxylic acid Example 90C (51.4 mg, 0.094 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (56.3 mg, 94%) as the trifluoroacetic acid salt. $^1$H NMR (400 MHz, dimethyl sulfoxide-d$_6$, 120° C.) δ ppm 7.74-7.67 (m, 1H), 7.22-7.14 (m, 3H), 6.78 (s, 1H), 6.74 (s, 1H), 5.18 (d, J=6.6 Hz, 1H), 4.61 (pd, J=6.2, 1.0 Hz, 1H), 4.40 (d, J=1.5 Hz, 1H), 3.75-3.64 (m, 2H), 3.52 (d, J=0.9 Hz, 3H), 3.34 (d, J=13.3 Hz, 1H), 2.80 (t, J=7.4 Hz, 2H), 2.71 (t, J=7.4 Hz, 2H), 2.50 (s, 1H), 2.22 (s, 3H), 1.98 (p, J=7.4 Hz, 2H), 1.05-1.02 (m, 3H), 1.01 (d, J=0.9 Hz, 9H), 0.84 (d, J=6.2 Hz, 3H); MS (ESI+) m/z 523 (M+H)$^+$.

Example 91

(2S,3S,4S,5S)-3-tert-butyl-5-(2-cyclopropylphenyl)-4-({[2-methoxy-5-(trifluoromethyl)pyridin-3-yl]methyl}amino)-1-{[(propan-2-yl)oxy]carbonyl}pyrrolidine-2-carboxylic acid Example 91A 2-ethyl 1-isopropyl (2S,3R,4S,5S)-3-(tert-butyl)-5-(2-cyclopropylphenyl)-4-nitropyrrolidine-1,2-dicarboxylate Ethyl (2S,3R,4S,5S)-3-(tert-butyl)-5-(2-cyclopropylphenyl)-4-nitropyrrolidine-2-carboxylate (Core 14, 1.32 g, 3.66 mmol) was dissolved in dichloromethane (10 mL) and triethylamine (2.0 mL, 14.35 mmol) was added, followed by isopropyl chloroformate (7.0 mL, 2 M, 14.00 mmol). The reaction was stirred at ambient temperature for 16 hour. The reaction was diluted with dichloromethane (50 mL) and washed with 1 M aqueous HCl (2×50 mL) and brine. The organic layer was dried over sodium sulfate, filtered, and concentrated. The residue was purified by silica gel chromatography (5% ethyl acetate in dichloromethane) to provide the title compound (1.30 g, 79%). $^1$H NMR (400 MHz, dimethyl sulfoxide-$d_6$, 120° C.) δ ppm 7.74 (dd, J=7.5, 1.7 Hz, 1H), 7.16-7.04 (m, 2H), 6.98 (dd, J=7.4, 1.6 Hz, 1H), 5.88 (d, J=8.5 Hz, 1H), 5.62 (dd, J=8.5, 2.1 Hz, 1H), 4.72 (hept, J=6.2 Hz, 0H), 4.51 (d, J=3.0 Hz, 1H), 4.23 (q, J=7.1 Hz, 2H), 2.98 (t, J=2.6 Hz, 1H), 2.10 (ddd, J=13.6, 8.3, 5.5 Hz, 1H), 1.26 (t, J=7.1 Hz, 3H), 1.14 (d, J=6.2 Hz, 4H), 1.04-0.79 (m, 16H); MS (ESI+) m/z 447 (M+H)$^+$.

Example 91B (2S,3S,4S,5S)-2-ethyl 1-isopropyl 4-amino-3-(tert-butyl)-5-(2-cyclopropylphenyl)pyrrolidine-1,2-dicarboxylate Example 91A (482.8 mg, 1.081 mmol) and tetrahydrofuran (9 mL) were added to a Raney®-Nickel 2800, water slurry (1.83 g, 14.03 mmol) in a 20 mL stainless steel pressure bottle and shaken for 18 hours at 50 psi hydrogen and ambient temperature. The reaction was filtered and concentrated to provide the title compound (410.3 mg, 91%). $^1$H NMR (400 MHz, dimethyl sulfoxide-$d_6$, 120° C.) δ ppm 7.83-7.77 (m, 1H), 7.16-7.08 (m, 2H), 7.05-7.00 (m, 1H), 5.50 (d, J=6.7 Hz, 1H), 4.61 (hept, J=6.2 Hz, 1H), 4.33 (d, J=2.9 Hz, 1H), 4.20 (q, J=7.1 Hz, 2H), 3.78 (dd, J=6.7, 2.1 Hz, 1H), 2.10 (t, J=2.5 Hz, 1H), 1.94 (tt, J=8.4, 5.4 Hz, 1H), 1.26 (t, J=7.0 Hz, 3H), 1.05-0.99 (m, 12H), 0.91 (dddd, J=14.3, 12.7, 8.0, 3.6 Hz, 2H), 0.83 (d, J=6.2 Hz, 3H), 0.70 (dtd, J=9.2, 5.2, 3.4 Hz, 1H), 0.59 (dtd, J=8.5, 5.3, 3.2 Hz, 1H); MS (ESI+) m/z 417 (M+H)$^+$.

Example 91C 2-ethyl 1-isopropyl (2S,3S,4S,5S)-3-(tert-butyl)-5-(2-cyclopropylphenyl)-4-(((2-methoxy-5-(trifluoromethyl)pyridin-3-yl)methyl)amino)pyrrolidine-1,2-dicarboxylate Example 91B (42.4 mg, 0.102 mmol) and 2-methoxy-5-(trifluoromethyl)nicotinaldehyde (42.4 mg, 0.207 mmol) were dissolved in methanol (1 mL) and stirred at ambient temperature for 1 hour. Sodium cyanoborohydride (34.2 mg, 0.544 mmol) was added and the reaction was stirred at ambient temperature for an additional 16 hours. The reaction was diluted with dimethyl sulfoxide (1 mL), filtered and purified by reverse phase using the ammonium acetate method to provide the title compound (40.9 mg, 66%). $^1$H NMR (400 MHz, dimethyl sulfoxide-$d_6$, 120° C.) δ ppm 8.28 (t, J=1.6 Hz, 1H), 7.87-7.81 (m, 1H), 7.49 (d, J=2.4 Hz, 1H), 7.16-7.07 (m, 2H), 7.03-6.97 (m, 1H), 5.55 (d, J=6.4 Hz, 1H), 4.62 (hept, J=6.2 Hz, 1H), 4.43 (d, J=1.7 Hz, 1H), 4.13 (q, J=7.1 Hz, 2H), 3.72 (s, 3H), 3.46 (dd, J=15.1, 6.2 Hz, 2H), 3.29 (dd, J=15.0, 6.0 Hz, 1H), 2.37-2.32 (m, 1H), 1.77 (tt, J=8.3, 5.4 Hz, 1H), 1.19 (t, J=7.1 Hz, 3H), 1.03-0.99 (m, 12H), 0.93-0.75 (m, 5H), 0.60-0.46 (m, 2H); MS (ESI+) m/z 606 (M+H)$^+$.

Example 91D (2S,3S,4S,5S)-3-tert-butyl-5-(2-cyclopropylphenyl)-4-({[2-methoxy-5-(trifluoromethyl)pyridin-3-yl]methyl}amino)-1-{[(propan-2-yl)oxy]carbonyl}pyrrolidine-2-carboxylic acid Example 91C (38.8 mg, 0.064 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (22.9 mg, 44%) as the bis trifluoroacetic acid salt. $^1$H NMR (400 MHz, dimethyl sulfoxide-$d_6$, 120° C.) δ ppm 8.30 (d, J=2.3 Hz, 1H), 7.86-7.77 (m, 1H), 7.54 (d, J=2.4 Hz, 1H), 7.12 (hept, J=5.1 Hz, 2H), 7.05-6.97 (m, 1H), 5.57 (d, J=6.5 Hz, 1H), 4.61 (hept, J=6.2 Hz, 1H), 4.39 (d, J=1.6 Hz, 1H), 3.73 (s, 3H), 3.57-3.46 (m, 2H), 3.31 (d, J=14.9 Hz, 1H), 2.39 (s, 1H), 1.77 (ddd, J=13.8, 8.4, 5.3 Hz, 1H), 1.04-0.98 (m, 12H), 0.90 (td, J=8.9, 2.7 Hz, 1H), 0.86-0.72 (m, 4H), 0.60-0.49 (m, 2H); MS (ESI+) m/z 578 (M+H)$^+$.

Example 92

(2S,3S,4S,5S)-3-tert-butyl-4-{[(5-cyclobutyl-2-methoxypyridin-3-yl)methyl]amino}-1-(cyclohexanecarbonyl)-5-(2-methylphenyl)pyrrolidine-2-carboxylic acid Example 92A (2S,3S,4S,5S)-ethyl 3-(tert-butyl)-4-(((5-cyclobutyl-2-methoxypyridin-3-yl)methyl)amino)-1-(cyclohexanecarbonyl)-5-(o-tolyl)pyrrolidine-2-carboxylate (2S,3S,4S,5S)-Ethyl 4-amino-3-(tert-butyl)-1-(cyclohexanecarbonyl)-5-(o-tolyl)pyrrolidine-2-carboxylate (Example 88B, 0.050 g, 0.121 mmol), 5-cyclobutyl-2-methoxynicotinaldehyde (0.021 g, 0.110 mmol), and sodium triacetoxyhydroborate (0.033 g, 0.153 mmol) were stirred in dichloroethane (0.6 mL) overnight at room temperature. After this time, the mixture was treated with 0.6 mL of saturated aqueous NaHCO$_3$ solution, and the mixture was stirred vigorously for 30 minutes. The phases were separated, and the aqueous layer was extracted three times with dichloromethane. The combined organics were dried over Na$_2$SO$_4$, filtered, and concentrated in vacuo to provide the crude title compound, which was taken directly into the next reaction without further purification. MS (APCI+) m/z 590.4 (M+H)$^+$.

Example 92B (2S,3S,4S,5S)-3-tert-butyl-4-{[(5-cyclobutyl-2-methoxypyridin-3-yl)methyl]amino}-1-(cyclohexanecarbonyl)-5-(2-methylphenyl)pyrrolidine-2-carboxylic acid Example 92A (0.065 g, 0.110 mmol) and lithium hydroxide (1 M aqueous) (0.9 mL, 0.9 mmol) were stirred in tetrahydrofuran (0.9 mL) and methanol (0.9 mL) overnight at 45° C. The reaction mixture was concentrated in vacuo, then treated with 1 mL of 1 N aqueous HCl and concentrated in vacuo again. The residue was further dried azeotropically with acetonitrile, then it was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound, 0.0238 g (39% yield). $^1$H NMR (400 MHz, dimethyl sulfoxide-$d_6$) δ ppm 7.82 (d, J=2.4 Hz, 1H), 7.75 (m, 1H), 7.21-7.12 (m, 4H), 5.28 (d, J=6.8 Hz, 1H), 4.59-4.53 (m, 1H), 3.67 (m, 1H), 3.64 (s, 3H), 3.57 (m, 1H), 3.45-3.28 (m, 2H), 2.45 (m, 1H), 2.31-2.22 (m, 3H), 2.22 (s, 3H), 2.06-1.91 (m, 3H), 1.89-1.80 (m, 1H), 1.65 (m, 2H), 1.51 (m, 2H), 1.26-1.04 (m, 5H), 1.00 (s, 9H), 0.84 (m, 1H); MS (ESI+) m/z 562.3 (M+H)$^+$.

Example 93

(2S,3S,4S,5S)-3-tert-butyl-4-{[(5-cyclobutyl-2-methoxypyridin-3-yl)methyl]amino}-5-(2-cyclopropylphenyl)-1-{[(propan-2-yl)oxy]carbonyl}pyrrolidine-2-carboxylic acid Example 93A (2S,3S,4S,5S)-2-ethyl 1-isopropyl 3-(tert-butyl)-4-(((5-cyclobutyl-2-methoxypyridin-3-yl)methyl)amino)-5-(2-cyclopropylphenyl)pyrrolidine-1,2-dicarboxylate 5-Cyclobutyl-2-methoxynicotinaldehyde (0.025 g, 0.130 mmol), (2S,3S,4S,5S)-2-ethyl 1-isopropyl 4-amino-3-(tert-butyl)-5-(2-cyclopropylphenyl)pyrrolidine-1,2-dicarboxylate (Example 91B, 0.0542 g, 0.130 mmol), and sodium triacetoxyborohydride (0.039 g, 0.182 mmol) were stirred in dichloroethane (0.6 mL) overnight at room temperature. The mixture was treated with 0.6 mL of saturated aqueous NaHCO$_3$ solution and stirred vigorously for 30 minutes. The phases were separated, and the aqueous phase was extracted three times more with CH$_2$Cl$_2$. The combined organics were dried over Na$_2$SO$_4$, filtered, and concentrated in vacuo to provide the crude title compound, which was taken directly into the next reaction without further purification. MS (APCI+) m/z 592.7 (M+H)$^+$.

Example 93B (2S,3S,4S,5S)-3-tert-butyl-4-{[(5-cyclobutyl-2-methoxypyridin-3-yl)methyl]amino}-5-(2-cyclopropylphenyl)-1-{[(propan-2-yl)oxy]carbonyl}pyrrolidine-2-carboxylic acid Example 93A (0.077 g, 0.130 mmol) and lithium hydroxide (1 M aqueous) (1.0 mL, 1.0 mmol) were stirred at 45° C. in tetrahydrofuran (1.0 mL) and methanol (1.0 mL) overnight. The mixture was acidified with 1.2 mL of 1 N aqueous HCl and concentrated in vacuo. Excess moisture was removed azeotropically with acetonitrile. The residue was then purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound, 0.0146 g (20% yield). $^1$H NMR (400 MHz, dimethyl sulfoxide-$d_6$) δ ppm 7.83-7.74 (m, 2H), 7.21-7.11 (m, 3H), 7.08-7.01 (m, 1H), 5.58 (d, J=6.4 Hz, 1H), 4.61 (hept, J=6.2 Hz, 1H), 4.41 (d, J=1.5 Hz, 1H), 3.59 (s, 3H), 3.63-3.53 (m, 2H), 3.44-3.35 (m, 1H), 3.30 (d, J=14.3 Hz, 1H), 2.43 (d, J=1.4 Hz, 1H), 2.31-2.20 (m, 2H), 2.03-1.91 (m, 3H), 1.85 (m, 1H), 1.75 (m, 1H), 1.03-1.00 (m, 12H), 0.95-0.72 (m, 5H), 0.54 (dq, J=4.6, 2.6 Hz, 2H); MS (ESI+) m/z 564.3 (M+H)$^+$.

Example 94

(2S,3S,4S,5S)-3-tert-butyl-4-{[(5-cyclobutyl-2-methoxypyridin-3-yl)methyl]amino}-5-(2-methylphenyl)-1-{[(propan-2-yl)oxy]carbonyl}pyrrolidine-2-carboxylic acid Example 94A (2S,3S,4S,5S)-2-ethyl 1-isopropyl 3-(tert-butyl)-4-(((5-cyclobutyl-2-methoxypyridin-3-yl)methyl)amino)-5-(o-tolyl)pyrrolidine-1,2-dicarboxylate 5-Cyclobutyl-2-methoxynicotinaldehyde (0.025 g, 0.131 mmol), (2S,3S,4S,5S)-2-ethyl 1-isopropyl 4-amino-3-(tert-butyl)-5-(o-tolyl)pyrrolidine-1,2-dicarboxylate (Example 90B, 0.0512 g, 0.131 mmol), and sodium triacetoxyborohydride (0.039 g, 0.184 mmol) were stirred in dichloroethane (0.6 mL) overnight at room temperature. After this time, the mixture was treated with 0.6 mL of saturated aqueous NaHCO$_3$ solution and stirred vigorously for 30 minutes. The phases were separated, and the aqueous phase was extracted three times more with CH$_2$Cl$_2$. The combined organics were dried over Na$_2$SO$_4$, filtered, and concentrated in vacuo to provide the crude title compound, which was taken directly into the next reaction without further purification. MS (APCI+) m/z 566.7 (M+H)$^+$.

Example 94B (2S,3S,4S,5S)-3-tert-butyl-4-{[(5-cyclobutyl-2-methoxypyridin-3-yl)methyl]amino}-5-(2-methylphenyl)-1-{[(propan-2-yl)oxy]carbonyl}pyrrolidine-2-carboxylic acid Example 94A (0.074 g, 0.131 mmol) and lithium hydroxide (1 M aqueous) (1.1 mL, 1.1 mmol) were stirred in tetrahydrofuran (1.1 mL) and methanol (1.1 mL) overnight at 45° C. After this time, the mixture was acidified with 1.2 mL of 1 N aqueous HCl and concentrated in vacuo. Excess moisture was removed azeotropically with acetonitrile. The residue was then purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound, 0.0178 g (25% yield). $^1$H NMR (400 MHz, dimethyl sulfoxide-$d_6$) δ ppm 7.84-7.74 (m, 2H), 7.21-7.10 (m, 4H), 5.14 (d, J=6.6 Hz, 1H), 4.61 (h, J=6.2 Hz, 1H), 4.39 (d, J=1.8 Hz, 1H), 3.64 (s, 3H), 3.62-3.50 (m, 3H), 3.47-3.33 (m, 1H), 2.43 (m, 1H), 2.33-2.21 (m, 2H), 2.18 (s, 3H), 2.06-1.88 (m, 3H), 1.84 (m, 1H), 1.03 (d, J=6.2 Hz, 3H), 1.00 (s, 9H), 0.85 (d, J=6.2 Hz, 3H); MS (ESI+) m/z 538.2 (M+H)$^+$.

Example 95

(2S,3S,4S,5S)-3-tert-butyl-4-({[2-methoxy-5-(trifluoromethyl)pyridin-3-yl]methyl}amino)-1-[(2S)-oxolane-2-carbonyl]-5-[2-(propan-2-yl)phenyl]pyrrolidine-2-carboxylic acid

Example 95A ethyl (2S,3R,4S,5S)-3-(tert-butyl)-5-(2-isopropylphenyl)-4-nitro-1-((S)-tetrahydrofuran-2-carbonyl)pyrrolidine-2-carboxylate (S)-Tetrahydrofuran-2-carboxylic acid (248.1 mg, 2.137 mmol) was dissolved in dichloromethane (10 mL). Oxalyl chloride (436.5 mg, 3.44 mmol) was added followed by N,N-dimethylformamide (25 µL). The reaction was stirred at ambient temperature for 3 hours, at which point it was concentrated, redissolved in dichloromethane (1 mL), and concentrated again. The residue was taken up in dichloromethane (3×1 mL) and added to a solution of Core 8 (502.5 mg, 1.386 mmol) and triethylamine (500 µL, 3.59 mmol) and in dichloromethane (10 mL). The reaction was stirred at ambient temperature for 17 hours. After this time, the mixture was diluted with $CH_2Cl_2$ (100 mL) and washed twice with saturated aqueous $NaHCO_3$ and once with brine. The organic layer was dried over $Na_2SO_4$, filtered, and concentrated to provide the title compound (535.0 mg, 84%). $^1$H NMR (400 MHz, dimethyl sulfoxide-$d_6$, 120° C.) δ ppm 7.91 (d, J=7.9 Hz, 1H), 7.29-7.17 (m, 2H), 7.07 (t, J=7.3 Hz, 1H), 6.07 (s, 1H), 5.54 (dd, J=9.0, 2.7 Hz, 1H), 4.81 (s, 1H), 4.26 (q, J=7.1 Hz, 2H), 3.75-3.55 (m, 2H), 3.26 (hept, J=7.0 Hz, 1H), 3.03 (t, J=3.2 Hz, 1H), 2.91 (s, 1H), 2.01-1.89 (m, 2H), 1.86-1.57 (m, 2H), 1.36-1.14 (m, 9H), 1.03 (s, 9H); MS (ESI+) m/z 461 (M+H)$^+$.

Example 95B ethyl (2S,3S,4S,5S)-4-amino-3-(tert-butyl)-5-(2-isopropylphenyl)-1-((S)-tetrahydrofuran-2-carbonyl)pyrrolidine-2-carboxylate Example 95A (535.0 mg, 1.162 mmol) and tetrahydrofuran (10 mL) were added to a Raney®-Nickel 2800, water slurry (1.71 g, 13.11 mmol) in a 50 mL stainless steel pressure bottle and the mixture was shaken for 26 hours at 50 psi hydrogen and 50° C. The reaction was filtered and concentrated to provide the title compound (404.3 mg, 81%). $^1$H NMR (400 MHz, dimethyl sulfoxide-$d_6$, 120° C.) δ ppm 7.90 (d, J=7.8 Hz, 1H), 7.29 (dd, J=7.8, 1.4 Hz, 1H), 7.21 (t, J=7.4 Hz, 1H), 7.13 (t, J=7.5 Hz, 1H), 5.57 (s, 1H), 4.53 (s, 1H), 4.18 (t, J=7.1 Hz, 2H), 4.13-3.97 (m, 1H), 3.73-3.63 (m, 2H), 3.63-3.53 (m, 1H), 3.20 (p, J=6.7 Hz, 1H), 2.06 (t, J=2.9 Hz, 1H), 1.83-1.70 (m, 1H), 1.62 (s, 1H), 1.32-1.14 (m, 11H), 1.00 (s, 9H); MS (ESI+) m/z 431 (M+H)$^+$.

Example 95C ethyl (2S,3S,4S,5S)-3-(tert-butyl)-5-(2-cyclopropylphenyl)-4-(((2-methoxy-5-(trifluoromethyl)pyridin-3-yl)methyl)amino)-1-((S)-tetrahydrofuran-2-carbonyl)pyrrolidine-2-carboxylate Example 95B (211.6 mg, 0.491 mmol) and 2-methoxy-5-(trifluoromethyl)nicotinaldehyde (158.3 mg, 0.771 mmol) were dissolved in methanol (4.5 mL). Sodium cyanoborohydride (107.1 mg, 1.704 mmol) was added and the reaction was stirred at ambient temperature for 17 hours. The reaction was diluted with dichloromethane (50 mL), quenched with saturated aqueous sodium bicarbonate (50 mL), and stirred for 30 minutes. The organic layer was isolated and the aqueous layer was extracted with dichloromethane (2×50 mL). The combined organic layers were dried over $Na_2SO_4$, filtered and concentrated. The residue was purified by reverse phase using the ammonium acetate method to provide the title compound (119.2 mg, 39%). $^1$H NMR (400 MHz, dimethyl sulfoxide-$d_6$, 120° C.) δ ppm 8.27 (t, J=1.6 Hz, 1H), 7.90 (d, J=7.8 Hz, 1H), 7.49 (d, J=2.4 Hz, 1H), 7.25 (dd, J=19.8, 7.5 Hz, 2H), 7.10 (t, J=7.4 Hz, 1H), 5.64 (s, 1H), 4.71 (s, 1H), 4.11 (q, J=7.1 Hz, 2H), 3.71 (d, J=1.3 Hz, 3H), 3.67 (q, J=7.1, 6.6 Hz, 1H), 3.60 (s, 1H), 3.52-3.38 (m, 2H), 3.24 (dd, J=14.9, 7.0 Hz, 1H), 3.12 (p, J=6.9 Hz, 1H), 2.36 (s, 1H), 2.05-1.93 (m, 2H), 1.84-1.55 (m, 2H), 1.22 (dd, J=6.9, 1.1 Hz, 3H), 1.18 (td, J=7.1, 0.9 Hz, 3H), 1.09 (dd, J=6.9, 1.3 Hz, 3H), 1.03-0.99 (m, 9H); MS (ESI+) m/z 620 (M+H)$^+$.

Example 95D (2S,3S,4S,5S)-3-tert-butyl-4-({[2-methoxy-5-(trifluoromethyl)pyridin-3-yl]methyl}amino)-1-[(2S)-oxolane-2-carbonyl]-5-[2-(propan-2-yl)phenyl]pyrrolidine-2-carboxylic acid Example 95C (116.2 mg, 0.188 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the ammonium acetate method to provide the title compound (61.7 mg, 56%). $^1$H NMR (400 MHz, dimethyl sulfoxide-$d_6$, 120° C.) δ ppm 8.26 (s, 1H), 7.98 (d, J=7.8 Hz, 1H), 7.47 (d, J=2.4 Hz, 1H), 7.24 (d, J=7.8 Hz, 1H), 7.19 (t, J=7.5 Hz, 1H), 7.07 (t, J=7.5 Hz, 1H), 5.59 (s, 1H), 4.55 (s, 1H), 3.74 (s, 3H), 3.69 (t, J=7.0 Hz, 1H), 3.63-3.55 (m, 2H), 3.47 (d, J=15.2 Hz, 1H), 3.38 (d, J=6.8 Hz, 1H), 3.22-3.07 (m, 2H), 2.39 (s, 1H), 1.95 (dt, J=8.4, 5.4 Hz, 1H), 1.79 (dt, J=14.1, 6.7 Hz, 1H), 1.73-1.55 (m, 2H), 1.22 (d, J=6.7 Hz, 3H), 1.09 (d, J=6.8 Hz, 3H), 1.00 (s, 9H); MS (ESI+) m/z 592 (M+H)$^+$.

Example 96

(2S,3S,4S,5S)-3-tert-butyl-4-{[(5-tert-butyl-2-methoxyphenyl)methyl]amino}-5-(2-cyclopropylpyridin-3-yl)-1-[(2S)-oxolane-2-carbonyl]pyrrolidine-2-carboxylic acid

Example 96A (2S,3R,4S,5S)-ethyl 3-(tert-butyl)-5-(2-cyclopropylpyridin-3-yl)-4-nitro-1-((S)-tetrahydrofuran-2-carbonyl)pyrrolidine-2-carboxylate To (S)-tetrahydrofuran-2-carboxylic acid (321 mg, 2.77 mmol) and a few drops of N,N-dimethylformamide in dichloromethane (10 mL) at ambient was added oxalyl dichloride (527 mg, 4.15 mmol, 2.2 mL, 2 M in dichloromethane). The mixture was stirred for 30 minutes, the solvent was removed under pressure, and fresh dichloromethane (5 mL) added and removed again. The residue was dissolved in dichloromethane (3 mL) and added dropwise to the solution of (2S,3R,4S,5S)-ethyl 3-(tert-butyl)-5-

(2-cyclopropylpyridin-3-yl)-4-nitropyrrolidine-2-carboxylate (Core 19, 500 mg, 1.383 mmol) and triethylamine (0.771 mL, 5.53 mmol) in dichloromethane (10 mL) in an ice bath. The mixture was stirred in ice bath for 30 minutes, and then allowed to warm to room temperature. Dichloromethane (10 mL) and saturated aqueous NH$_4$Cl (10 mL) was added and the organic layer was washed with brine, dried over MgSO$_4$, filtered, and concentrated to provide the title compound, 620 mg (98%), which used in next step without further purification. LC/MS (APCI+) m/z 460.23 (M+H)$^+$.

Example 96B (2S,3S,4S,5S)-ethyl 4-amino-3-(tert-butyl)-5-(2-cyclopropylpyridin-3-yl)-1-((S)-tetrahydrofuran-2-carbonyl)pyrrolidine-2-carboxylate The title compound (489 mg, 87% yield) was prepared according to the procedure described in Example 10C, substituting Example 96A (600 mg, 1.306 mmol) for Example 10B. LC/MS (APCI+) m/z 430.23 (M+H)$^+$.

Example 96C (2S,3S,4S,5S)-3-(tert-butyl)-4-((5-(tert-butyl)-2-methoxybenzyl)amino)-5-(2-cyclopropylpyridin-3-yl)-1-((S)-tetrahydrofuran-2-carbonyl)pyrrolidine-2-carboxylic acid 5-(tert-Butyl)-2-methoxybenzaldehyde (29.5 mg, 0.154 mmol), Example 96B (60 mg, 0.140 mmol) and zinc(II) chloride (1.9 mg, 0.014 mmol) sodium acetate/acetic acid buffer in methanol (pH=4, 2 mL) was stirred at ambient temperature for 10 minutes to give a colorless solution, and then sodium cyanoborohydride (8.78 mg, 0.140 mmol) was added and the mixture was stirred for 1 hour. The solvent was removed under pressure and the residue was purified via chromatography on a 10 g silica gel cartridge, eluting with ethyl acetate/methanol (10:1) in heptane 0-40% to yield the ester of (2S,3S,4S,5S)-ethyl 3-(tert-butyl)-4-((5-(tert-butyl)-2-methoxybenzyl)amino)-5-(2-cyclopropylpyridin-3-yl)-1-((S)-tetrahydrofuran-2-carbonyl)pyrrolidine-2-carboxylate, which was dissolved in methanol (1.5 mL) and 6 M aqueous LiOH (0.5 mL). The mixture was stirred at 50° C. for 4 hours, adjusted pH to 4-5, and then concentrated. The residue was dissolved in dichloromethane (1 mL) and filtered through a syringe filter. The filtrate was purified via chromatography on a 4 g silica gel cartridge, eluting with methanol in dichloromethane at 0-20% gradient to provide the title compound, 61 mg (76% yield). $^1$H NMR (400 MHz, dimethyl sulfoxide-d$_6$) δ ppm 8.32 (dd, J=4.9, 1.6 Hz, 1H), 8.22 (d, J=7.9 Hz, 1H), 7.18 (td, J=8.3, 3.8 Hz, 2H), 6.97 (d, J=2.5 Hz, 1H), 6.76 (d, J=8.6 Hz, 1H), 5.77 (s, 1H), 4.69 (d, J=1.5 Hz, 1H), 3.76 (d, J=7.0 Hz, 1H), 3.74-3.62 (m, 4H), 3.53 (s, 3H), 3.31 (d, J=7.3 Hz, 1H), 3.07 (q, J=7.3 Hz, 1H), 2.53 (s, 1H), 2.12-2.07 (m, 1H), 1.99-1.91 (m, 1H), 1.81-1.71 (m, 2H), 1.22 (d, J=7.3 Hz, 1H), 1.19 (s, 9H), 1.09-1.04 (m, 1H), 1.03 (s, 9H), 0.98-0.93 (m, 2H), 0.91-0.81 (m, 2H); MS (ESI+) m/z 578.2 (M+H)$^+$.

Example 97

(2S,3S,4S,5S)-3-tert-butyl-1-(ethoxycarbonyl)-4-({[2-methoxy-5-(trifluoromethyl)pyridin-3-yl]methyl}amino)-5-[2-(propan-2-yl)phenyl]pyrrolidine-2-carboxylic acid Example 77B (38 mg, 0.073 mmol, 1.0 eq) and triethylamine (31 μL, 0.29 mmol, 3.0 eq) were dissolved in dichloromethane (0.5 mL). Ethyl chloroformate (11.9 mg, 0.11 mmol, 1.5 eq) was added neat. The reaction was stirred for 2 hours at room temperature. The reaction was concentrated and the residue was dissolved in 3:2 tetrahydrofuran/methanol (1 mL). Aqueous LiOH monohydrate (5 M, 300 L) was added and the reaction was stirred at 45° C. overnight. The solvent was removed under a stream of nitrogen. The residue was acidified with 2 M aqueous HCl and diluted with CH$_3$CN. Purification was carried out using preparative reverse phase HPLC MS method AA7 (29.3 mg, 59% yield). $^1$H NMR (400 MHz, 120° C., dimethyl sulfoxide-d$_6$: D$_2$O=9:1 (v/v)) δ ppm 8.26 (s, 1H), 7.89-7.82 (m, 1H), 7.48 (d, J=2.4 Hz, 1H), 7.25-7.13 (m, 2H), 7.11-7.02 (m, 1H), 5.26 (d, J=6.5 Hz, 1H), 4.36 (d, J=1.6 Hz, 1H), 3.85 (q, J=7.0 Hz, 2H), 3.70 (s, 3H), 3.46 (d, J=15.1 Hz, 1H), 3.31 (d, J=6.5 Hz, 1H), 3.20 (d, J=15.1 Hz, 1H), 3.08-3.00 (m, 1H), 2.35 (d, J=1.6 Hz, 1H), 1.18 (d, J=6.8 Hz, 3H), 1.07 (d, J=6.8 Hz, 3H), 0.99 (s, 9H), 0.90 (t, J=7.0 Hz, 3H); MS (APCI+) m/z 566.1 (M+H)$^+$.

Example 98

(2S,3S,4S,5S)-3-tert-butyl-1-(cyclopentanecarbonyl)-4-({[2-methoxy-5-(trifluoromethyl)pyridin-3-yl]methyl}amino)-5-[2-(propan-2-yl)phenyl]pyrrolidine-2-carboxylic acid Cyclopentanecarboxylic acid (12.5 mg, 0.11 mmol, 1.5 eq) in dichloromethane (500 μL) was added to a 4 mL vial. Ghosez reagent (1-chloro-N,N,2-trimethyl-1-propenylamine, 20 μL, 0.14 mmol, 2.0 eq) was added neat and the reaction was stirred at room temperature for 10 minutes. Example 77B (38 mg, 0.072 mmol, 1.0 eq) in 1:1 tetrahydrofuran/pyridine (500 μL) was added and the reaction was stirred for 2 hours at room temperature. The reaction was concentrated and the residue was dissolved in 3:2 tetrahydrofuran/methanol (1 mL). Aqueous LiOH monohydrate (5 M, 300 μL) was added and the reaction was stirred at 45° C. overnight. The solvent was removed under a stream of nitrogen. The residue acidified with 2 M aqueous HCl and diluted with CH$_3$CN. Purification was carried out using preparative reverse phase HPLC MS method AA8 (31.9 mg, 62% yield). $^1$H NMR (400 MHz, 120° C., dimethyl sulfoxide-d$_6$:D$_2$O=9:1 (v/v)) δ ppm 8.26 (d, J=2.2 Hz, 1H), 7.82 (s, 1H), 7.49 (d, J=2.5 Hz, 1H), 7.29-7.17 (m, 2H), 7.09 (t, J=7.3 Hz, 1H), 5.40 (d, J=6.6 Hz, 1H), 4.56 (s, 1H), 3.70 (s, 3H), 3.50 (d, J=15.0 Hz, 1H), 3.38 (d, J=6.5 Hz, 1H), 3.23 (d, J=15.0 Hz, 1H), 3.12-2.97 (m, 2H), 2.39 (s, 1H), 1.79-1.23 (m, 8H), 1.18 (t, J=6.7 Hz, 3H), 1.06 (d, J=6.8 Hz, 3H), 0.99 (s, 9H); MS (APCI+) m/z 590.1 (M+H)$^+$.

Example 99

(2S,3S,4S,5S)-5-[2-(azetidin-1-yl)pyridin-3-yl]-3-tert-butyl-4-{[(5-tert-butyl-2-methoxyphenyl)methyl]amino}-1-{[(propan-2-yl)oxy]carbonyl}pyrrolidine-2-carboxylic acid

Example 99A (2S,3R,4S,5S)-2-ethyl 1-isopropyl 5-(2-(azetidin-1-yl)pyridin-3-yl)-3-(tert-butyl)-4-nitropyrrolidine-1,2-dicarboxylate The title compound was prepared according to the procedure described in Example 78A, substituting Core 17 for Core 16. LC/MS (APCI+) m/z 463.34 (M+H)$^+$.

Example 99B (2S,3S,4S,5S)-2-ethyl 1-isopropyl 4-amino-5-(2-(azetidin-1-yl)pyridin-3-yl)-3-(tert-butyl)pyrrolidine-1,2-dicarboxylate The title compound was prepared according to the procedure described in Example 78B, substituting Example 99A for Example 78A. LC/MS (APCI+) m/z 433.44 (M+H)+.

Example 99C (2S,3S,4S,5S)-5-[2-(azetidin-1-yl)pyridin-3-yl]-3-tert-butyl-4-{[(5-tert-butyl-2-methoxyphenyl)methyl]amino}-1-{[(propan-2-yl)oxy]carbonyl}pyrrolidine-2-carboxylic acid Example 99B (44.2 mg, 0.10 mmol, 1.0 eq) and 2-methoxy-4-t-butylbenzaldehyde (23.6 mg, 0.12, 1.2 eq) was dissolved in sodium acetate/acetic acid buffer in methanol (pH=4, 1 mL). Sodium cyanoborohydride (12.84 mg, 0.24 mmol, 2.0 eq) was dissolved in methanol and added to the reaction. The reaction was stirred at room temperature for 20 minutes. The solvent was removed under a stream of nitrogen. The residue was dissolved in dichloromethane/$H_2O$, and the aqueous phase was extracted with dichloromethane (2×1 mL). The organic layer was concentrated. The residue was dissolved in 3:2 tetrahydrofuran/methanol (1 mL). Aqueous LiOH monohydrate (5 M, 300 µL) was added and reaction was stirred at 45° C. overnight. The solvent was removed under a stream of nitrogen. The residue was acidified with 2 M aqueous HCl and diluted with $CH_3CN$. Purification was carried out using preparative reverse phase HPLC MS method trifluoroacetic acid 6 (34.7 mg, 49% yield). $^1$H NMR (400 MHz, 120° C., dimethyl sulfoxide-$d_6$:$D_2O$=9:1 (v/v)) δ ppm 8.04 (d, J=7.5 Hz, 1H), 7.99 (d, J=4.8 Hz, 1H), 7.17 (dd, J=8.4, 2.5 Hz, 1H), 7.01 (d, J=2.5 Hz, 1H), 6.76 (d, J=8.5 Hz, 1H), 6.67 (dd, J=7.5, 4.8 Hz, 1H), 4.89 (d, J=6.4 Hz, 1H), 4.65-4.54 (m, 1H), 4.31 (s, 1H), 3.90 (q, J=7.4 Hz, 2H), 3.81-3.72 (m, 2H), 3.61 (d, J=14.0 Hz, 1H), 3.44 (s, 3H), 3.33-3.24 (m, 2H), 2.32 (s, 1H), 2.10 (p, J=7.4 Hz, 2H), 1.20 (d, J=0.8 Hz, 9H), 1.03 (d, J=6.3 Hz, 3H), 0.96 (s, 9H), 0.86 (d, J=6.2 Hz, 3H); MS (APCI+) m/z 581.2 (M+H)+.

Example 100

(2S,3S,4S,5S)-3-tert-butyl-4-{[(2-methoxyquinolin-3-yl)methyl]amino}-1-[(2S)-oxolane-2-carbonyl]-5-[2-(propan-2-yl)phenyl]pyrrolidine-2-carboxylic acid

Example 100A (2S,3R,4S,5S)-ethyl 3-(tert-butyl)-5-(2-isopropylphenyl)-4-nitro-1-((S)-tetrahydrofuran-2-carbonyl)pyrrolidine-2-carboxylate (S)-Tetrahydrofuran-2-carboxylic acid (3.64 g, 31.3 mmol) was refluxed in thionyl chloride (30 mL, 411 mmol) for 1 hour. The reaction mixture was cooled to room temperature, and the mixture was concentrated in vacuo. Excess thionyl chloride was chased three times with $CH_2Cl_2$, and the resulting crude acid chloride was treated with a solution of (2S,3R,4S,5S)-ethyl 3-(tert-butyl)-5-(2-isopropylphenyl)-4-nitropyrrolidine-2-carboxylate (Core 8, 5.30 g, 14.62 mmol) in $CH_2Cl_2$ (78 mL) and with pyridine (15.2 mL, 188 mmol). The reaction was stirred at room temperature. After 2 hours, the reaction mixture was diluted with ethyl acetate and washed three times with water and once with brine. The organic layer was dried over $Na_2SO_4$, filtered, and concentrated in vacuo to provide the crude title compound, which was taken directly into the next reaction without purification. MS (APCI+) m/z 461.4 (M+H)+.

Example 100B (2S,3S,4S,5S)-ethyl 4-amino-3-(tert-butyl)-5-(2-isopropylphenyl)-1-((S)-tetrahydrofuran-2-carbonyl)pyrrolidine-2-carboxylate Example 100A (6.202 g, 13.47 mmol) in tetrahydrofuran (60 mL) was added to Raney®-Nickel 2800, (water slurry, solvent washed after weighing, 15.4 g, 118 mmol) in a 250 mL SS pressure bottle, flushed with argon 3 times, flushed with hydrogen, and shaken under 50 psi of hydrogen. After 15.7 hours, the mixture was filtered through a polypropylene membrane, and the cloudy filtrate was stirred with magnesium sulfate for 20 minutes. The clear solution was filtered through diatomaceous earth and concentrated in vacuo to provide the title compound, 5.25 g (91%). $^1$H NMR (400 MHz, dimethyl sulfoxide-$d_6$) δ ppm 7.90 (d, J=7.8 Hz, 1H), 7.30 (m 1H), 7.21 (m, 1H), 7.13 (m, 1H), 5.57 (m, 1H), 4.56-4.50 (m, 1H), 4.17 (q, J=7.1 Hz, 2H), 4.07 (m, 1H), 3.64 (m, 2H), 3.20 (m, 1H), 2.06 (m, 1H), 1.94 (m, 1H), 1.62 (m, 1H), 1.47 (m, 2H), 1.31-1.19 (m, 9H), 1.00 (s, 9H); MS (ESI+) m/z 431.3 (M+H)+.

Example 100C (2S,3S,4S,5S)-ethyl 3-(tert-butyl)-5-(2-isopropylphenyl)-4-(((2-methoxyquinolin-3-yl)methyl)amino)-1-((S)-tetrahydrofuran-2-carbonyl)pyrrolidine-2-carboxylate Example 100B (0.150 g, 0.348 mmol) and 2-methoxyquinoline-3-carbaldehyde (0.065 g, 0.348 mmol) in dichloroethane (1.7 mL) were treated with sodium triacetoxyborohydride (0.103 g, 0.488 mmol), and the reaction was stirred at room temperature. After 30 minutes, the reaction mixture was treated with 1.7 mL of saturated aqueous $NaHCO_3$ solution and was stirred vigorously for 30 minutes. The phases were separated, and the aqueous layer was extracted three times with $CH_2Cl_2$. The combined organics were dried over $Na_2SO_4$, filtered, and concentrated in vacuo, and the crude residue was purified by silica gel chromatography, eluting with 0 to 20% ethyl acetate-heptanes to obtain the title compound, 0.169 g (81% yield). $^1$H NMR (400 MHz, dimethyl sulfoxide-$d_6$) δ ppm 7.94 (d, J=7.9 Hz, 1H), 7.69-7.59 (m, 3H), 7.53 (ddd, J=8.3, 7.0, 1.4 Hz, 1H), 7.38-7.20 (m, 3H), 7.14 (t, J=7.4 Hz, 1H), 5.64 (m, 1H), 4.73 (m, 1H), 4.12 (m, 3H), 3.73 (s, 3H), 3.71-3.53 (m, 3H), 3.45 (m, 1H), 3.35 (m, 1H), 3.09 (m, 1H), 2.42 (m, 1H), 2.04-1.93 (m, 1H), 1.79 (dq, J=14.0, 6.9 Hz, 1H), 1.64 (m, 2H), 1.23-1.13 (m, 6H), 1.03 (s, 9H), 1.09-0.98 (m, 3H); MS (ESI+) m/z 602.4 (M+H)+.

Example 100D (2S,3S,4S,5S)-3-tert-butyl-4-{[(2-methoxyquinolin-3-yl)methyl]amino}-1-[(2S)-oxolane-2-carbonyl]-5-[2-(propan-2-yl)phenyl]pyrrolidine-2-carboxylic acid Example 100C (0.169 g, 0.281 mmol) and lithium hydroxide (1 M aqueous) (2.8 mL, 2.80 mmol) were stirred in tetrahydrofuran (2.8 mL) and methanol (2.8 mL) overnight at 45° C. After this time, the reaction mixture was cooled to room temperature and was acidified to pH 2 with 1 N aqueous HCl. The mixture was diluted with 5 mL water and extracted three times with $CH_2Cl_2$. The combined organics were dried over $Na_2SO_4$, filtered, and concentrated in vacuo, and the resulting residue was purified by silica gel chromatography, eluting with 0 to 2% methanol-ethyl acetate to obtain the title compound, 0.097 g (60% yield). $^1$H NMR (400 MHz, dimethyl sulfoxide-$d_6$) δ ppm 7.94 (d, J=7.8 Hz, 1H), 7.65 (m, 3H), 7.54 (t, J=7.7 Hz, 1H), 7.38-7.20 (m, 3H), 7.12 (m, 1H), 5.62 (m, 1H), 4.62 (m, 1H), 4.11 (m, 1H), 3.74 (s, 3H), 3.69 (d, J=7.1 Hz, 1H), 3.59 (m, 2H), 3.44 (d, J=6.7 Hz, 1H), 3.35 (d, J=14.8 Hz, 1H), 3.07 (m, 1H), 2.44 (m, 1H), 1.95 (m, 1H), 1.84-1.75 (m, 1H), 1.64 (m, 2H), 1.18 (d, J=6.9 Hz, 3H), 1.02 (m, 12H); MS (ESI+) m/z 574.3 (M+H)$^+$.

Example 101

(2S,3S,4S,5S)-3-tert-butyl-4-{[(5-cyclopropyl-2-methoxypyridin-3-yl)methyl]amino}-1-[(2S)-oxolane-2-carbonyl]-5-[2-(propan-2-yl)phenyl]pyrrolidine-2-carboxylic acid Example 101A ethyl (2S,3S,4S,5S)-3-(tert-butyl)-4-(((5-cyclopropyl-2-methoxypyridin-3-yl)methyl)amino)-5-(2-cyclopropylphenyl)-1-((S)-tetrahydrofuran-2-carbonyl)pyrrolidine-2-carboxylate Example 95B (116.3 mg, 0.270 mmol) and 5-cyclopropyl-2-methoxynicotinaldehyde (47.9 mg, 0.270 mmol) were dissolved in dichloroethane (4 mL). Sodium triacetoxyborohydride (78.1 mg, 0.368 mmol) was added and the reaction was stirred at ambient temperature for 1 hour. The reaction was diluted with dichloromethane (35 mL) and quenched with saturated aqueous sodium bicarbonate (35 mL) and stirred for 30 minutes. The organic layer was isolated and the aqueous layer was extracted with dichloromethane (35 mL). The combined organic layers were dried over $Na_2SO_4$, filtered and concentrated. The residue was purified by silica gel chromatography (10% ethyl acetate in dichloromethane) to provide the title compound (70.1 mg, 44%). $^1$H NMR (400 MHz, dimethyl sulfoxide-$d_6$, 120° C.) δ ppm 7.89 (d, J=7.8 Hz, 1H), 7.73 (d, J=2.4 Hz, 1H), 7.25 (dd, J=15.8, 7.4 Hz, 2H), 7.11 (t, J=7.5 Hz, 1H), 6.86 (d, J=2.4 Hz, 1H), 5.69-5.55 (m, 2H), 4.71 (s, 1H), 4.11 (qd, J=7.0, 0.9 Hz, 2H), 3.67 (q, J=7.2 Hz, 1H), 3.62-3.51 (m, 5H), 3.40 (dd, J=14.0, 6.4 Hz, 3H), 3.13 (ddd, J=33.9, 13.9, 6.5 Hz, 2H), 2.37 (s, 1H), 2.05-1.91 (m, 1H), 1.84-1.55 (m, 3H), 1.25-1.14 (m, 6H), 1.07 (dd, J=6.8, 1.2 Hz, 3H), 1.02 (d, J=0.9 Hz, 9H), 0.88-0.79 (m, 2H), 0.50-0.41 (m, 2H); MS (ESI+) m/z 592 (M+H)$^+$.

Example 101B (2S,3S,4S,5S)-3-tert-butyl-4-{[(5-cyclopropyl-2-methoxypyridin-3-yl)methyl]amino}-1-[(2S)-oxolane-2-carbonyl]-5-[2-(propan-2-yl)phenyl]pyrrolidine-2-carboxylic acid Example 101A (67.0 mg, 0.113 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (73.4 mg, 82%) as the bis trifluoroacetic acid salt. $^1$H NMR (400 MHz, dimethyl sulfoxide-$d_6$, 120° C.) δ ppm 7.86 (d, J=7.8 Hz, 1H), 7.76 (d, J=2.4 Hz, 1H), 7.30 (dd, J=7.8, 1.5 Hz, 1H), 7.25 (t, J=7.4 Hz, 1H), 7.14 (t, J=7.6 Hz, 1H), 6.94 (d, J=2.4 Hz, 1H), 5.65 (s, 1H), 4.65 (d, J=1.5 Hz, 1H), 4.12 (s, 1H), 3.68 (q, J=7.2 Hz, 1H), 3.59 (s, 3H), 3.57-3.49 (m, 4H), 3.19 (d, J=14.1 Hz, 1H), 3.10 (h, J=6.8 Hz, 1H), 2.45 (s, 1H), 2.04-1.92 (m, 1H), 1.84-1.56 (m, 3H), 1.22 (d, J=6.7 Hz, 3H), 1.09 (d, J=6.8 Hz, 3H), 1.02 (s, 8H), 0.88-0.80 (m, 2H), 0.53-0.43 (m, 2H); MS (ESI+) m/z 564 (M+H)$^+$.

Example 102

(2S,3S,4S,5S)-5-[2-(azetidin-1-yl)pyridin-3-yl]-3-tert-butyl-4-{[(5-tert-butyl-2-methoxyphenyl)methyl]amino}-1-(cyclobutanecarbonyl)pyrrolidine-2-carboxylic acid Example 102A (2S,3R,4S,5S)-ethyl 5-(2-(azetidin-1-yl)pyridin-3-yl)-3-(tert-butyl)-1-(cyclobutanecarbonyl)-4-nitropyrrolidine-2-carboxylate To cyclobutanecarboxylic acid (50.0 mg, 0.5 mmol) and a drop of N,N-dimethylformamide in dichloromethane (5 mL) was added oxalyl dichloride (127 mg, 1.0 mmol, 0.5 mL, 2 M in dichloromethane). The mixture was stirred at ambient temperature for 30 minutes. The solvent was removed under pressure and fresh dichloromethane (5 mL) was added and removed again. The residue was dissolved in dichloromethane (1 mL) and added dropwise to a solution of (2S,3R,4S,5S)-ethyl 5-(2-(azetidin-1-yl)pyridin-3-yl)-3-(tert-butyl)-4-nitropyrrolidine-2-carboxylate (Core 17, 94 mg, 0.250 mmol) and triethylamine (0.139 mL, 0.999 mmol) in dichloromethane (6 mL) cooling in an ice-bath. The mixture was stirred in an ice bath for 30 minutes and allowed to warm to ambient temperature. Dichloromethane (10 mL) and saturated aqueous $NH_4Cl$ (10 mL) were added and the organic layer was washed with brine, dried over $MgSO_4$, filtered, and concentrated. The residue was purified via chromatography on a 12 g silica gel cartridge, eluting with ethyl acetate in heptane at 0-40% gradient to yield (2S,3R,4S,5S)-ethyl 5-(2-(azetidin-1-yl)pyridin-3-yl)-3-(tert-butyl)-1-(cyclobutanecarbonyl)-4-nitropyrrolidine-2-carboxylate 110 mg (96% yield). LC/MS (APCI+) m/z 459.32 (M+H)$^+$.

Example 102B (2S,3S,4S,5S)-ethyl 4-amino-5-(2-(azetidin-1-yl)pyridin-3-yl)-3-(tert-butyl)-1-(cyclobutanecarbonyl)pyrrolidine-2-carboxylate The title compound was prepared according to the procedure described in Example 10C, substituting Example 102A for Example 10B. LC/MS (APCI+) m/z 429.37 (M+H)$^+$.

Example 102C (2S,3S,4S,5S)-5-[2-(azetidin-1-yl)pyridin-3-yl]-3-tert-butyl-4-{[(5-tert-butyl-2-methoxyphenyl)methyl]amino}-1-(cyclobutanecarbonyl)pyrrolidine-2-carboxylic acid 5-(tert-Butyl)-2-methoxybenzaldehyde (24.67 mg, 0.128 mmol), (2S,3S,4S,5S)-ethyl 4-amino-5-(2-(azetidin-1-yl)

pyridin-3-yl)-3-(tert-butyl)-1-(cyclobutanecarbonyl)pyrrolidine-2-carboxylate (Example 102B, 50 mg, 0.117 mmol) and zinc (II) chloride (15.90 mg, 0.117 mmol) in sodium acetate/acetic acid buffer in methanol (pH=4, 2 mL) was stirred at room temperature for 10 minutes to give a colorless solution. Sodium cyanoborohydride (11.00 mg, 0.175 mmol) was added neat and the mixture was stirred at room temperature for 1 hour. The solvent was removed under $N_2$. The residue was purified by chromatography, eluting with ethyl acetate/methanol (10:1) in heptane 0-40% to yield the ester which was more polar than S-form. The ester was dissolved in methanol (2 mL) with 4 M aqueous LiOH (0.5 mL). The mixture was stirred at 40° C. for 4 hours. The solvent was removed, water (1 mL) was added, and the pH was adjusted to 4~5. Purification by chromatography, eluting with methanol in $CH_2Cl_2$ 0-20% provided (2S,3S,4S,5S)-5-(2-(azetidin-1-yl)pyridin-3-yl)-3-(tert-butyl)-4-((5-(tert-butyl)-2-methoxybenzyl)amino)-1-(cyclobutanecarbonyl)pyrrolidine-2-carboxylic acid (18 mg, 0.031 mmol, 26.7% yield). $^1$H NMR (400 MHz, dimethyl sulfoxide-$d_6$) δ ppm 8.03 (dd, J=4.8, 1.7 Hz, 1H), 7.22-7.12 (m, 1H), 7.01 (dd, J=19.8, 2.6 Hz, 1H), 6.77 (d, J=8.5 Hz, 2H), 6.74-6.63 (m, 1H), 4.96 (d, J=6.4 Hz, 1H), 4.45 (s, 1H), 4.25 (s, 2H), 3.95 (q, J=7.5 Hz, 2H), 3.79-3.69 (m, 2H), 3.64 (s, 1H), 3.44 (s, 3H), 3.38-3.28 (m, 2H), 2.39 (s, 1H), 2.10 (td, J=13.5, 12.4, 6.1 Hz, 4H), 2.00 (s, 2H), 1.73 (s, 2H), 1.21 (d, J=2.5 Hz, 9H), 0.96 (d, J=8.5 Hz, 9H); MS (ESI+) m/z 577.4 (M+H)$^+$.

Example 103

(2S,3S,4S,5S)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid Example 103A (2S,3R,4S,5S)-ethyl 3-(tert-butyl)-5-(2-chlorophenyl)-4-nitropyrrolidine-2-carboxylate (2-(Bis(3,5-bis(trifluoromethyl)phenyl)phosphino)-3-((S)-4-isopropyl-4,5-dihydrooxazol-2-yl)cyclopenta-2,4-dien-1-yl)(cyclopenta-2,4-dien-1-yl)iron (0.175 g, 0.232 mmol) and copper(II) triflate (0.047 g, 0.093 mmol) were dissolved in tetrahydrofuran (19.36 mL mL) that had been sparged with a nitrogen stream for 1 hour. The resulting mixture was stirred for 1 hour at ambient temperature (continue nitrogen sparge), and (E)-ethyl 2-((2-chlorobenzylidene)amino)acetate (2.75 g, 12.19 mmol) was added as a solution in 2 mL of tetrahydrofuran and the resulting solution was cooled to <5° C. in an ice-water bath. Potassium 2-methylpropan-2-olate in tetrahydrofuran (0.209 mL, 0.209 mmol) was added dropwise, followed by addition of neat (E)-3,3-dimethyl-1-nitrobut-1-ene (1.5 g, 11.61 mmol) over 20 minutes, maintaining a temperature less than 7° C. The reaction mixture was stirred for 1 hour at 0° C. The mixture was quenched with 60 mL of saturated aqueous ammonium chloride and 100 mL of ethyl acetate and warmed to ambient temperature. The organic layer was separated and washed twice with saturated aqueous ammonium chloride, then brine and filtered through a pad of silica gel. The organics were concentrated. Heptane (70 mL) was added, and the mixture was filtered to provide a precipitate (2.5 g). The filtrate was purified by chromatography using a 12 g silica gel cartridge eluting with a gradient of 0-60% heptanes/ethyl acetate over a period of 20 minutes to provide (2S,3R,4S,5S)-ethyl 3-(tert-butyl)-5-(2-chlorophenyl)-4-nitropyrrolidine-2-carboxylate (2.85 g, 8.03 mmol, 69.2% yield). $^1$H NMR (400 MHz, dimethyl sulfoxide-$d_6$) δ ppm 7.56-7.48 (m, 1H), 7.45-7.38 (m, 1H), 7.35-7.24 (m, 2H), 5.25 (dd, J=6.7, 3.0 Hz, 1H), 4.71 (t, J=7.0 Hz, 1H), 4.19 (qq, J=7.3, 3.7 Hz, 2H), 3.78 (t, J=7.3 Hz, 1H), 3.68 (t, J=7.3 Hz, 1H), 3.07 (dd, J=7.4, 3.0 Hz, 1H), 1.24 (t, J=7.1 Hz, 3H), 0.94 (s, 9H), 0.96 (s, 9H); MS (APCI+) m/z 355 (M+H)$^+$.

Example 103B (2S,3R,4S,5S)-1-allyl 2-ethyl 3-(tert-butyl)-5-(2-chlorophenyl)-4-nitropyrrolidine-1,2-dicarboxylate To Example 103A (2.85 g, 8.03 mmol) in toluene (9.34 mL) and saturated aqueous $NaHCO_3$ (9.34 mL) was added allyl carbonochloridate (0.880 mL, 8.03 mmol) dropwise at ambient temperature. The mixture was stirred at ambient temperature overnight. Dichloromethane (60 mL) and water (30 mL) were added and the organic layer was washed with brine and concentrated. The crude material was triturated with 50 mL heptane, and filtered to provide a precipitate (2.03 g). The filtrate was purified on a 12 g cartridge eluting with a gradient of 0-80% ethyl acetate/heptanes over a period of 12 minutes to provide (2S,3R,4S,5S)-1-allyl 2-ethyl 3-(tert-butyl)-5-(2-chlorophenyl)-4-nitropyrrolidine-1,2-dicarboxylate (3.52 g, 8.02 mmol, 100% yield). $^1$H NMR (400 MHz, dimethyl sulfoxide-$d_6$) δ ppm 7.90 (s, 1H), 7.44-7.36 (m, 1H), 7.36-7.24 (m, 2H), 5.82 (bs, 1H), 5.68 (s, 1H), 5.60-5.52 (m, 1H), 5.05 (d, J=91.9 Hz, 2H), 4.59 (d, J=3.3 Hz, 1H), 4.46 (bs, 2H), 4.24 (q, J=7.1 Hz, 2H), 3.05 (t, J=3.0 Hz, 1H), 1.26 (t, J=7.1 Hz, 3H), 1.00 (s, 9H); MS (APCI+) m/z 439 (M+H)$^+$.

Example 103C (2S,3S,4S,5S)-1-allyl 2-ethyl 4-amino-3-(tert-butyl)-5-(2-chlorophenyl)pyrrolidine-1,2-dicarboxylate Example 103B (240 mg, 0.547 mmol) was dissolved in tetrahydrofuran (2734 µL) and zinc (358 mg, 5.47 mmol) was added, followed by addition of acetic acid (203 µl, 3.55 mmol). The reaction was stirred at 40° C. overnight. Acetic acid (50 µL) was added and the mixture was stirred at ambient temperature for two hours more. The mixture was filtered, and the filtrate was concentrated. The crude residue was purified using a gradient of 5-100% ethyl acetate/heptanes to give (2S,3S,4S,5S)-1-allyl 2-ethyl 4-amino-3-(tert-butyl)-5-(2-chlorophenyl)pyrrolidine-1,2-dicarboxylate (175 mg, 0.428 mmol, 78% yield). $^1$H NMR (400 MHz, dimethyl sulfoxide-$d_6$) δ ppm 7.89 (dd, J=7.7, 1.9 Hz, 1H), 7.36 (dd, J=7.7, 1.5 Hz, 1H), 7.32-7.18 (m, 2H), 5.77-5.63 (m, 1H), 5.26 (d, J=6.8 Hz, 1H), 5.04 (d, J=1.6 Hz, 1H), 5.03-4.97 (m, 1H), 4.42-4.37 (m, 3H), 4.19 (q, J=7.0 Hz, 2H), 3.81 (dd, J=6.8, 2.3 Hz, 1H), 2.09 (t, J=2.7 Hz, 1H), 1.25 (t, J=7.1 Hz, 3H), 1.00 (s, 9H), 0.87-0.74 (m, 2H); MS (ESI+) m/z 409 (M+H)$^+$.

Example 103D (2S,3S,4S,5S)-1-allyl 2-ethyl 3-(tert-butyl)-5-(2-chlorophenyl)-4-(((5-cyclobutyl-2-methoxypyridin-3-yl)methyl)amino)pyrrolidine-1,2-dicarboxylate Example 103C (95 mg, 0.232 mmol), zinc(II) chloride (41 mg, 0.301 mmol) and 5-cyclobutyl-2-methoxynicotinaldehyde (59 mg, 0.309 mmol) were dissolved in sodium acetate/acetic acid buffer in methanol (pH=4, 669 μL). The mixture was stirred at ambient temperature for 25 minutes. Sodium cyanotrihydroborate (24 mg, 0.382 mmol) was added and the reaction was stirred at ambient temperature for 90 minutes. The solvent was removed under nitrogen. The residue was diluted with aqueous sodium bicarbonate and the crude material was taken up in dichloromethane and purified using a ethyl acetate/heptane solvent system with a 10 g silica gel cartridge to yield (2S,3S,4S,5S)-1-allyl 2-ethyl 3-(tert-butyl)-5-(2-chlorophenyl)-4-(((5-cyclobutyl-2-methoxypyridin-3-yl)methyl)amino)pyrrolidine-1,2-dicarboxylate (89 mg, 0.152 mmol, 65.6% yield). $^1$H NMR (400 MHz, dimethyl sulfoxide-$d_6$) δ ppm 7.91 (dd, J=7.1, 2.4 Hz, 1H), 7.77 (d, J=2.4 Hz, 1H), 7.35 (dd, J=7.1, 2.1 Hz, 1H), 7.30-7.18 (m, 2H), 7.12 (d, J=2.4 Hz, 1H), 5.70 (ddt, J=17.7, 10.2, 5.1 Hz, 1H), 5.32 (d, J=6.5 Hz, 1H), 5.04 (s, 1H), 5.03-4.97 (m, 1H), 4.48 (d, J=1.6 Hz, 1H), 4.43-4.37 (m, 2H), 4.14 (q, J=7.1 Hz, 2H), 3.64 (s, 3H), 3.56 (dd, J=6.7, 2.9 Hz, 1H), 3.47-3.34 (m, 2H), 3.26 (dd, J=14.3, 6.7 Hz, 1H), 2.37 (s, 1H), 2.26 (tdt, J=6.7, 4.5, 2.0 Hz, 2H), 2.05-1.90 (m, 3H), 1.85 (tt, J=7.4, 3.4 Hz, 1H), 1.19 (t, J=7.2 Hz, 3H), 0.99 (s, 9H); MS (ESI+) m/z 584 (M+H)$^+$.

Example 103E (2S,3S,4S,5S)-ethyl 3-(tert-butyl)-5-(2-chlorophenyl)-4-(((5-cyclobutyl-2-methoxypyridin-3-yl)methyl)amino)pyrrolidine-2-carboxylate Example 103D (89 mg, 0.152 mmol) was dissolved in ethyl acetate (5 mL) and dichloromethane (5 mL), degassed with a stream of nitrogen bubbling through, and treated with 1,3-dimethylpyrimidine-2,4,6(1H,3H,5H)-trione (47.6 mg, 0.305 mmol) and tetrakis(triphenylphosphine)palladium(0) (1.1 mg, 0.914 μmol). The reaction was stirred at ambient temperature. After 10 minutes, the reaction mixture was quenched with 2 mL of saturated aqueous NaHCO$_3$ and put through an aqueous/organic separator tube. The solvent was removed and the crude organics were purified using a 12 g silica gel cartridge with a gradient of 5-100% ethyl acetate/heptanes over 20 minutes to give (2S,3S,4S,5S)-ethyl 3-(tert-butyl)-5-(2-chlorophenyl)-4-(((5-cyclobutyl-2-methoxypyridin-3-yl)methyl)amino)pyrrolidine-2-carboxylate (71 mg, 0.142 mmol, 93% yield). $^1$H NMR (400 MHz, Chloroform-d) δ ppm 7.80-7.76 (m, 1H), 7.69 (dd, J=7.6, 1.8 Hz, 1H), 7.39 (dd, J=7.8, 1.5 Hz, 1H), 7.32 (td, J=7.5, 1.5 Hz, 1H), 7.28-7.23 (m, 1H), 7.08 (d, J=2.4 Hz, 1H), 4.45 (d, J=4.4 Hz, 1H), 4.25 (qd, J=7.1, 2.2 Hz, 2H), 3.76 (s, 3H), 3.69 (d, J=6.1 Hz, 1H), 3.42 (d, J=8.9 Hz, 1H), 3.38 (dd, J=4.5, 1.3 Hz, 1H), 3.22 (s, 2H), 2.35-2.19 (m, 2H), 2.11 (dd, J=6.1, 1.3 Hz, 1H), 2.08-1.96 (m, 3H), 1.87 (dtt, J=4.8, 3.9, 2.3 Hz, 1H), 1.31 (t, J=7.1 Hz, 3H), 0.97 (s, 9H); (APCI+) m/z 500 (M+H)$^+$.

Example 103F (2S,3S,4S,5S)-ethyl 3-(tert-butyl)-5-(2-chlorophenyl)-4-(((5-cyclobutyl-2-methoxypyridin-3-yl)methyl)amino)-1-((S)-tetrahydrofuran-2-carbonyl)pyrrolidine-2-carboxylate Example 103E (70 mg, 0.140 mmol) was dissolved in dichloromethane (1 mL), cooled in an iced bath, and treated with triethylamine (0.078 mL, 0.560 mmol) and (S)-tetrahydrofuran-2-carbonyl chloride (37.7 mg, 0.280 mmol) as a solution in 1 mL of dichloromethane. The reaction was stirred at ambient temperature for 20 minutes. The reaction mixture was quenched with 2 mL of saturated aqueous NaHCO$_3$, the phases were separated and the organics were concentrated. The crude organics were purified using a 12 g silica gel cartridge with a gradient of 5-60% ethyl acetate/heptanes over 20 minutes to give 68 mg of crude product and the mixture was further purified using reverse phase HPLC using the trifluoroacetic acid method to give (2S,3S,4S,5S)-ethyl 3-(tert-butyl)-5-(2-chlorophenyl)-4-(((5-cyclobutyl-2-methoxypyridin-3-yl)methyl)amino)-1-((S)-tetrahydrofuran-2-carbonyl)pyrrolidine-2-carboxylate (45 mg, 0.075 mmol, 53.7% yield). $^1$H NMR (400 MHz, dimethyl sulfoxide-$d_6$) δ ppm 7.93 (s, 1H), 7.77 (d, J=2.4 Hz, 1H), 7.38 (dd, J=6.1, 3.0 Hz, 1H), 7.27 (dt, J=5.9, 2.8 Hz, 2H), 7.14 (d, J=2.4 Hz, 1H), 5.59 (s, 1H), 4.73 (s, 1H), 4.14 (q, J=7.1 Hz, 2H), 3.67 (d, J=8.5 Hz, 4H), 3.59 (d, J=7.1 Hz, 1H), 3.47 (d, J=14.2 Hz, 1H), 3.43-3.35 (m, 1H), 3.27 (d, J=14.3 Hz, 1H), 2.37 (s, 1H), 2.26 (dddd, J=13.3, 7.0, 3.9, 1.8 Hz, 2H), 2.05-1.92 (m, 6H), 1.87-1.61 (m, 4H), 1.20 (t, J=7.1 Hz, 3H), 0.98 (d, J=2.1 Hz, 9H).

Example 103G (2S,3S,4S,5S)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid Example 103F (45 mg, 0.075 mmol) was dissolved in methanol (1 mL) and tetrahydrofuran (1.0 mL) and treated with lithium hydroxide (18.02 mg, 0.752 mmol) as a solution in water (0.5 mL). The reaction was warmed in a 45° C. heating block for 3 hours. The reaction was concentrated and then brought to pH 6 using 2 N aqueous HCl (300 μL). The crude organics were purified using a 10 g silica gel cartridge with an ethyl acetate/ethanol/heptanes solvent system to give (2S,3S,4S,5S)-3-(tert-butyl)-5-(2-chlorophenyl)-4-(((5-cyclobutyl-2-methoxypyridin-3-yl)methyl)amino)-1-((S)-tetrahydrofuran-2-carbonyl)pyrrolidine-2-carboxylic acid (41 mg, 0.072 mmol, 96% yield). $^1$H NMR (400 MHz, dimethyl sulfoxide-$d_6$) δ ppm 8.04 (s, 1H), 7.76 (d, J=2.4 Hz, 1H), 7.35 (d, J=7.0 Hz, 1H), 7.29-7.16 (m, 2H), 7.12 (d, J=2.4 Hz, 1H), 5.55 (s, 1H), 4.55 (s, 1H), 3.78-3.68 (m, 1H), 3.68 (s, 3H), 3.69-3.57 (m, 1H), 3.52 (d, J=7.1 Hz, 1H), 3.46 (d, J=14.8 Hz, 1H), 3.41-3.34 (m, 1H), 3.25 (d, J=14.8 Hz, 1H), 2.67-2.60 (m, 1H), 2.38 (s, 1H), 2.26 (dddt, J=13.1, 8.5, 5.4, 2.7 Hz, 2H), 2.04-1.87 (m, 5H), 1.89-1.76 (m, 2H), 1.70 (s, 1H), 0.96 (s, 9H); (APCI+) m/z 570 (M+H)$^+$.

Example 104

(2S,3S,4S,5S)-3-tert-butyl-4-{[(5-tert-butyl-2-methoxyphenyl)methyl]amino}-1-[(2S)-oxolane-2-carbonyl]-5-[2-(propan-2-yl)phenyl]pyrrolidine-2-carboxylic acid Example 104A (2S,3S,4S,5S)-ethyl 3-(tert-butyl)-4-((5-(tert-butyl)-2-methoxybenzyl)amino)-5-(2-isopropylphenyl)-1-((S)-tetrahydrofuran-2-carbonyl)pyrrolidine-2-carboxylate A solution of Example 100B (0.150 g, 0.348 mmol) and 5-(tert-butyl)-2-methoxybenzaldehyde (0.067 g, 0.348 mmol) in dichloroethane (1.7 mL) was treated with sodium triacetoxyborohydride (0.103 g, 0.488 mmol), and the reaction was stirred at room temperature. After 30 minutes, the reaction mixture was treated with 1.7 mL of saturated aqueous NaHCO$_3$ solution and was stirred vigorously for 30 minutes. The phases were separated, and the aqueous layer was extracted three times with CH$_2$Cl$_2$. The combined organics were dried over Na$_2$SO$_4$, filtered, and concentrated in vacuo, and the crude material was purified by silica gel chromatography, eluting with 0 to 30% ethyl acetate-heptanes over 15 minutes to obtain the title compound, 0.180 g (85% yield). $^1$H NMR (400 MHz, dimethyl sulfoxide-d$_6$) δ ppm 7.89 (d, J=7.7 Hz, 1H), 7.23 (m, 2H), 7.08 (m, 2H), 6.88 (d, J=2.6 Hz, 1H), 6.66 (d, J=8.5 Hz, 1H), 5.62 (m, 1H), 4.72 (m, 1H), 4.10 (m, 3H), 3.67 (m, 2H), 3.51 (m, 1H), 3.41 (m, 4H), 3.18 (m, 1H), 3.07 (m, 1H), 2.41 (m, 1H), 1.97 (m, 1H), 1.78-1.63 (m, 3H), 1.23-1.13 (m, 15H), 1.03 (m, 12H); MS (ESI+) m/z 607.4 (M+H)$^+$.

Example 104B (2S,3S,4S,5S)-3-tert-butyl-4-{[(5-tert-butyl-2-methoxyphenyl)methyl]amino}-1-[(2S)-oxolane-2-carbonyl]-5-[2-(propan-2-yl)phenyl]pyrrolidine-2-carboxylic acid Example 104A (0.180 g, 0.297 mmol) and lithium hydroxide (1 M aqueous) (3 mL, 3.00 mmol) were stirred in tetrahydrofuran (3 mL) and methanol (3 mL) overnight at 45° C. After this time, the mixture was acidified to pH 2 with 1 N aqueous HCl, and concentrated in vacuo. Excess moisture was removed azeotropically with acetonitrile, and the crude material was purified by reverse-phase HPLC on a Phenomenex® Luna® C8(2) 5 um 100 Å AXIA column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A) to obtain the title compound, 0.066 g (38% yield). $^1$H NMR (400 MHz, dimethyl sulfoxide-d$_6$) δ ppm 7.82 (d, J=7.8 Hz, 1H), 7.35-7.13 (m, 4H), 6.98 (d, J=2.6 Hz, 1H), 6.75 (d, J=8.5 Hz, 1H), 5.67 (m, 1H), 4.64 (d, J=1.4 Hz, 1H), 4.16 (m, 1H), 3.76 (d, J=13.5 Hz, 1H), 3.67 (m, 3H), 3.50 (s, 3H), 3.34 (m, 1H), 3.24 (d, J=13.4 Hz, 1H), 2.53 (d, J=18.3 Hz, 1H), 1.98 (m, 1H), 1.77 (dt, J=14.2, 6.8 Hz, 1H), 1.66 (m, 2H), 1.22 (d, J=6.8 Hz, 3H), 1.19 (s, 9H), 1.12-1.02 (m, 3H), 1.04 (s, 9H); MS (ESI+) m/z 579.4 (M+H)$^+$.

Example 105

(2S,3S,4S,5S)-3-tert-butyl-1-(cyclohexanecarbonyl)-4-{[(5-cyclopropyl-2-methoxypyridin-3-yl)methyl]amino}-5-(2-methylphenyl)pyrrolidine-2-carboxylic acid Example 105A ethyl (2S,3S,4S,5S)-3-(tert-butyl)-1-(cyclohexanecarbonyl)-4-(((5-cyclopropyl-2-methoxypyridin-3-yl)methyl)amino)-5-(o-tolyl)pyrrolidine-2-carboxylate Example 88B (101.3 mg, 0.244 mmol) and 5-cyclopropyl-2-methoxynicotinaldehyde (67.2 mg, 0.379 mmol) were dissolved in methanol (1 mL). Sodium cyanoborohydride (69.9 mg, 1.112 mmol) was added and the reaction was stirred at ambient temperature for 17 hours. The reaction was diluted with dichloromethane (35 mL), quenched with saturated aqueous sodium bicarbonate (35 mL), and stirred for 30 minutes. The organic layer was isolated and the aqueous layer was extracted with dichloromethane (2×35 mL). The combined organic layers were dried over Na$_2$SO$_4$, filtered and concentrated. The residue was purified by reverse phase using the ammonium acetate method to provide the title compound (59.4 mg, 42%). $^1$H NMR (400 MHz, dimethyl sulfoxide-d$_6$, 120° C.) δ ppm 7.85 (s, 1H), 7.75 (d, J=2.4 Hz, 1H), 7.15 (s, 3H), 6.87 (d, J=2.4 Hz, 1H), 5.24 (d, J=6.6 Hz, 1H), 4.60 (s, 1H), 4.19-4.06 (m, 2H), 3.60 (d, J=1.0 Hz, 3H), 3.49-3.33 (m, 2H), 3.27-3.17 (m, 1H), 2.35 (s, 1H), 2.19 (s, 3H), 2.10-1.93 (m, 1H), 1.76 (tt, J=8.4, 5.1 Hz, 1H), 1.64 (d, J=11.0 Hz, 2H), 1.48 (s, 2H), 1.19 (t, J=7.1 Hz, 5H), 0.99 (s, 13H), 0.89-0.79 (m, 2H), 0.52-0.43 (m, 2H); MS (ESI+) m/z 592 (M+H)$^+$.

Example 105B (2S,3S,4S,5S)-3-tert-butyl-1-(cyclohexanecarbonyl)-4-{[(5-cyclopropyl-2-methoxypyridin-3-yl)methyl]amino}-5-(2-methylphenyl)pyrrolidine-2-carboxylic acid Example 105A (56.4 mg, 0.098 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (48.2 mg, 63%) as the bis trifluoroacetic acid salt. $^1$H NMR (400 MHz, dimethyl sulfoxide-d$_6$, 120° C.) δ ppm 7.81 (d, J=2.4 Hz, 1H), 7.75 (s, 1H), 7.18 (d, J=2.8 Hz, 3H), 6.99 (d, J=2.4 Hz, 1H), 5.30 (d, J=6.8 Hz, 1H), 4.56 (d, J=1.6 Hz, 1H), 3.69-3.56 (m, 5H), 3.30 (d, J=14.1 Hz, 1H), 2.47 (s, 1H), 2.25 (s, 3H), 2.21-2.04 (m, 1H), 1.79 (tt, J=8.4, 5.2 Hz, 1H), 1.71-1.42 (m, 4H), 1.00 (s, 15H), 0.92-0.81 (m, 2H), 0.57-0.45 (m, 2H); MS (ESI+) m/z 548 (M+H)$^+$.

Example 106

(2S,3S,4S,5S)-5-(2-bromophenyl)-3-tert-butyl-4-{[(5-cyclobutyl-2-methoxypyridin-3-yl)methyl]amino}-1-[(2S)-oxolane-2-carbonyl]pyrrolidine-2-carboxylic acid Example 106A ethyl (2S,3R,4S,5S)-5-(2-bromophenyl)-3-(tert-butyl)-4-nitro-1-((S)-tetrahydrofuran-2-carbonyl)pyrrolidine-2-carboxylate (S)-Tetrahydrofuran-2-carboxylic acid (428.8 mg, 3.69 mmol) was dissolved in dichloromethane (10 mL). Oxalyl chloride (1.8 mL, 2 M, 3.60 mmol) was added followed by N,N-dimethylformamide (25 µL). The reaction was stirred at ambient temperature for 3 hours, at which point it was concentrated, redissolved in dichloromethane (2 mL), and concentrated again. The residue was taken up in dichloromethane (3×2 mL) and added to a solution of Core 25 (1.38 g, 3.46 mmol) and triethylamine (1.5 mL, 10.76 mmol) and in dichloromethane (10 mL). The reaction was stirred at ambient temperature for 17 hours. After this time, the mixture was diluted with CH$_2$Cl$_2$ (100 mL) and washed twice with saturated aqueous NaHCO$_3$ and once with brine. The organic layer was dried over Na$_2$SO$_4$, filtered, and concentrated to provide the title compound (1.58 g, 92%). $^1$H NMR (400 MHz, dimethyl sulfoxide-d$_6$, 120° C.) δ ppm 7.94 (d, J=7.8 Hz, 1H), 7.59-7.50 (m, 1H), 7.31 (td, J=7.7, 3.6 Hz, 1H), 7.24-7.14 (m, 1H), 6.02 (s, 1H), 5.57-5.48 (m, 1H), 4.90 (s, 1H), 4.30-4.22 (m, 2H), 3.70 (dq, J=11.4, 6.8, 6.3 Hz, 2H), 3.46 (s, 1H), 3.03 (t, J=2.5 Hz, 1H), 2.04-1.89 (m, 1H), 1.78 (ddd, J=23.2, 14.8, 8.4 Hz, 3H), 1.29 (td, J=7.1, 0.9 Hz, 3H), 1.03 (d, J=1.0 Hz, 9H); MS (ESI+) m/z 497 & 499 (M+H)$^+$.

Example 106B ethyl (2S,3S,4S,5S)-4-amino-5-(2-bromophenyl)-3-(tert-butyl)-1-((S)-tetrahydrofuran-2-carbonyl)pyrrolidine-2-carboxylate Example 106A (300 mg, 0.603 mmol) was dissolved in tetrahydrofuran (3 mL) and zinc (394 mg, 6.03 mmol) was added, followed by addition of acetic acid (0.224 mL, 3.92 mmol). The reaction was heated to 65° C. for 2 hours. The reaction was filtered and concentrated, then purified using a gradient of 50-100% ethyl acetate in dichloromethane to give the title compound (105.9 mg, 0.227 mmol, 37.6% yield). $^1$H NMR (400 MHz, dimethyl sulfoxide-d$_6$, 120° C.) δ ppm 7.93 (s, 1H), 7.56 (d, J=7.9 Hz, 1H), 7.33 (t, J=7.6 Hz, 1H), 7.17 (t, J=7.6 Hz, 1H), 5.50 (s, 1H), 4.60 (s, 1H), 4.18 (q, J=7.1 Hz, 2H), 3.85 (dd, J=6.7, 2.1 Hz, 1H), 3.67 (dd, J=13.4, 6.5 Hz, 3H), 2.07 (t, J=2.5 Hz, 1H), 2.01-1.90 (m, 1H), 1.85-1.57 (m, 3H), 1.25 (t, J=7.1 Hz, 3H), 1.00 (s, 9H); MS (ESI+) m/z 467 & 469 (M+H)$^+$.

Example 106C ethyl (2S,3S,4S,5S)-5-(2-bromophenyl)-3-(tert-butyl)-4-(((5-cyclobutyl-2-methoxypyridin-3-yl)methyl)amino)-1-((S)-tetrahydrofuran-2-carbonyl)pyrrolidine-2-carboxylate Example 106B (89.0 mg, 0.190 mmol) and 5-cyclobutyl-2-methoxynicotinaldehyde (60.0 mg, 0.314 mmol) were dissolved in dichloroethane (3 mL). Sodium triacetoxyborohydride (83.8 mg, 0.395 mmol) was added and the reaction was stirred at ambient temperature for 1 hour. The reaction was diluted with dichloromethane (35 mL) and quenched with saturated aqueous sodium bicarbonate (35 mL) and stirred for 30 minutes. The organic layer was isolated and the aqueous layer was extracted with dichloromethane (2×35 mL). The combined organic layers were dried over Na$_2$SO$_4$, filtered and concentrated. The residue was purified by silica gel chromatography (10% to 20% ethyl acetate in dichloromethane) to provide the title compound (120.3 mg, 98%). $^1$H NMR (400 MHz, dimethyl sulfoxide-d$_6$, 120° C.) δ ppm 7.96 (s, 1H), 7.87 (d, J=2.4 Hz, 1H), 7.80 (d, J=2.4 Hz, 1H), 7.63 (d, J=2.4 Hz, 1H), 7.58 (d, J=8.0 Hz, 1H), 7.35 (s, 1H), 7.27-7.12 (m, 2H), 5.73-5.33 (m, 1H), 4.77 (s, 1H), 4.63 (dd, J=5.8, 3.6 Hz, 1H), 4.25-4.10 (m, 2H), 3.88 (d, J=1.5 Hz, 3H), 3.77-3.60 (m, 6H), 3.58-3.36 (m, 3H), 3.29 (dd, J=14.3, 7.5 Hz, 1H), 2.41-2.23 (m, 4H), 2.17-1.65 (m, 10H), 1.27-1.19 (m, 3H), 1.02 (d, J=1.6 Hz, 9H); MS (ESI+) m/z 642 & 644 (M+H)$^+$.

Example 106D (2S,3S,4S,5S)-5-(2-bromophenyl)-3-tert-butyl-4-{[(5-cyclobutyl-2-methoxypyridin-3-yl)methyl]amino}-1-[(2S)-oxolane-2-carbonyl]pyrrolidine-2-carboxylic acid Example 106C (120.3 mg, 0.187 mmol) was dissolved in methanol (1 mL). Aqueous LiOH (1 M, 1.0 mL, 1.0 mmol) was added and the reaction was heated to 50° C. for 16 hours. The reaction was quenched by the addition of 1 M aqueous HCl (1 mL), diluted with dimethyl sulfoxide (1 mL), filtered and purified by reverse phase using the trifluoroacetic acid method to provide the title compound (85.9 mg, 55%) as the bis trifluoroacetic acid salt. $^1$H NMR (400 MHz, dimethyl sulfoxide-d$_6$, 120° C.) δ ppm 7.93 (d, J=7.6 Hz, 1H), 7.79 (d, J=2.4 Hz, 1H), 7.56 (dd, J=7.9, 1.3 Hz, 1H), 7.33 (t, J=7.5 Hz, 1H), 7.23-7.15 (m, 2H), 5.56 (s, 1H), 4.67 (d, J=1.6 Hz, 1H), 4.17 (s, 1H), 3.73-3.61 (m, 6H), 3.52 (d, J=14.4 Hz, 1H), 3.45-3.34 (m, 1H), 3.28 (d, J=14.4 Hz, 1H), 2.41 (s, 1H), 2.33-2.18 (m, 2H), 2.05-1.62 (m, 8H), 0.98 (s, 9H); MS (ESI+) m/z 614 & 616 (M+H)$^+$.

Example 107

(2S,3S,4S,5S)-3-tert-butyl-4-{[(5-cyclobutyl-2-methoxypyridin-3-yl)methyl]amino}-5-(2-cyclopropylphenyl)-1-[(2S)-oxolane-2-carbonyl]pyrrolidine-2-carboxylic acid Example 107A ethyl (2S,3R,4S,5S)-3-(tert-butyl)-5-(2-cyclopropylphenyl)-4-nitro-1-((S)-tetrahydrofuran-2-carbonyl)pyrrolidine-2-carboxylate (S)-Tetrahydrofuran-2-carboxylic acid (408.2 mg, 3.03 mmol) was dissolved in dichloromethane (10 mL). Oxalyl chloride (1.5 mL, 2 M, 3.00 mmol) was added followed by N,N-dimethylformamide (25 µL). The reaction was stirred at ambient temperature for 3 hours, at which point it was concentrated, redissolved in dichloromethane (2 mL), and concentrated again. The residue was taken up in dichloromethane (3×2 mL) and added to a solution of Core 14 (905.0 mg, 2.51 mmol) and triethylamine (1.0 mL, 7.17 mmol) and in dichloromethane (10 mL). The reaction was stirred at ambient temperature for 17 hours. After this time, the mixture was diluted with CH$_2$Cl$_2$ (100 mL) and washed twice with saturated aqueous NaHCO$_3$ and once with brine. The organic layer was dried over Na$_2$SO$_4$, filtered, and concentrated to provide the title compound (1158 g, 100%). $^1$H NMR (400 MHz, dimethyl sulfoxide-d$_6$, 120° C.) δ ppm 7.84 (d, J=7.7 Hz, 1H), 7.19-7.07 (m, 2H), 7.03-6.98 (m, 1H), 6.31 (d, J=8.6 Hz, 1H), 5.66-5.54 (m, 1H), 4.86 (d, J=2.8 Hz, 1H), 4.26 (qd, J=7.1, 1.2 Hz, 2H), 4.07 (s, 1H), 3.66 (dq, J=24.9, 7.5 Hz, 2H), 3.02 (t, J=2.5 Hz, 1H), 2.11 (tt, J=8.4, 5.4 Hz, 1H), 1.99-1.58 (m, 4H), 1.30 (dd, J=7.5, 6.7 Hz, 3H), 1.04 (s, 9H), 0.97 (pt, J=8.8, 2.6 Hz, 2H), 0.81 (ddd, J=9.4, 6.3, 3.4 Hz, 1H), 0.67-0.52 (m, 1H); MS (ESI+) m/z 459 (M+H)$^+$.

Example 107B ethyl (2S,3S,4S,5S)-4-amino-3-(tert-butyl)-5-(2-cyclopropylphenyl)-1-((S)-tetrahydrofuran-2-carbonyl)pyrrolidine-2-carboxylate Example 107A (1.13 g, 2.464 mmol) and tetrahydrofuran (25 mL) were added to a Raney®-Nickel 2800, water slurry (5.00 g, 38.3 mmol) in a 50 mL stainless steel pressure bottle and shaken for 16 hours at 50 psi hydrogen and 50° C. The reaction was filtered and concentrated to provide the title compound (1.05 g, 99%). $^1$H NMR (400 MHz, dimethyl sulfoxide-d$_6$, 120° C.) δ ppm 7.87 (s, 1H), 7.14 (dt, J=7.0, 3.9 Hz, 2H), 7.04 (dt, J=4.7, 3.3 Hz, 1H), 5.81 (s, 1H), 4.56 (s, 1H), 4.17 (q, J=7.1 Hz, 2H), 4.07 (s, 1H), 3.83 (dd, J=6.9, 2.2 Hz, 1H), 3.68 (q, J=7.3 Hz, 1H), 3.60 (dddd, J=6.6, 4.1, 2.7, 1.4 Hz, 2H), 2.07 (t, J=2.6 Hz, 1H), 1.92 (s, 1H), 1.84-1.53 (m, 3H), 1.25 (t, J=7.1 Hz, 3H), 1.01 (s, 9H), 0.97-0.81 (m, 2H), 0.67 (dddd, J=12.0, 10.6, 5.8, 3.2 Hz, 2H); MS (ESI+) m/z 429 (M+H)+.

Example 107C ethyl (2S,3S,4S,5S)-3-(tert-butyl)-4-(((5-cyclobutyl-2-methoxypyridin-3-yl)methyl)amino)-5-(2-cyclopropylphenyl)-1-((S)-tetrahydrofuran-2-carbonyl)pyrrolidine-2-carboxylate Example 107B (210.5 mg, 0.491 mmol) and 5-cyclobutyl-2-methoxynicotinaldehyde (133.3 mg, 0.697 mmol) were dissolved in dichloroethane (6 mL). Sodium triacetoxyborohydride (207.9 mg, 0.981 mmol) was added and the reaction was stirred at ambient temperature for 1 hour. The reaction was diluted with dichloromethane (35 mL) and quenched with saturated aqueous sodium bicarbonate (35 mL) and stirred for 30 minutes. The organic layer was isolated and the aqueous layer was extracted with dichloromethane (2×35 mL). The combined organic layers were dried over $Na_2SO_4$, filtered and concentrated. The residue was purified by silica gel chromatography (10% to 25% ethyl acetate in dichloromethane) to provide the title compound (165.9 mg, 56%). $^1$H NMR (400 MHz, dimethyl sulfoxide-$d_6$, 120° C.) δ ppm 7.88 (s, 1H), 7.75 (d, J=2.5 Hz, 1H), 7.15 (s, 2H), 7.10 (d, J=2.4 Hz, 1H), 7.08-6.97 (m, 1H), 5.87 (s, 1H), 4.73 (s, 1H), 4.11 (q, J=7.1 Hz, 2H), 3.72-3.30 (m, 10H), 3.24 (dd, J=14.3, 7.3 Hz, 1H), 2.39 (s, 1H), 2.33-2.18 (m, 2H), 2.11-1.53 (m, 8H), 1.18 (t, J=7.1 Hz, 3H), 1.02 (s, 9H), 0.87 (tdd, J=9.4, 5.8, 4.0 Hz, 1H), 0.76 (tt, J=8.6, 4.7 Hz, 1H), 0.61 (dtd, J=9.5, 5.6, 4.0 Hz, 1H), 0.50-0.40 (m, 1H); MS (ESI+) m/z 604 (M+H)+.

Example 107D (2S,3S,4S,5S)-3-tert-butyl-4-{[(5-cyclobutyl-2-methoxypyridin-3-yl)methyl]amino}-5-(2-cyclopropylphenyl)-1-[(2S)-oxolane-2-carbonyl]pyrrolidine-2-carboxylic acid Example 107C (161.9 mg, 0.268 mmol) was dissolved in methanol (1 mL). Aqueous LiOH (1 M, 1.0 mL, 1.0 mmol) was added and the reaction was heated to 50° C. for 16 hours. The reaction was quenched by the addition of 1 M aqueous HCl (1 mL), diluted with dimethyl sulfoxide (1 mL), filtered and purified by reverse phase using the trifluoroacetic acid method to provide the title compound (130.7 mg, 61%) as the bis trifluoroacetic acid salt. $^1$H NMR (400 MHz, dimethyl sulfoxide-$d_6$, 120° C.) δ ppm 7.82 (dd, J=14.5, 4.2 Hz, 2H), 7.18 (td, J=3.8, 2.2 Hz, 3H), 7.07 (dt, J=6.2, 3.4 Hz, 1H), 5.91 (d, J=6.6 Hz, 1H), 4.67 (d, J=1.4 Hz, 1H), 4.12 (s, 2H), 3.73-3.54 (m, 7H), 3.46-3.33 (m, 1H), 3.28 (d, J=14.2 Hz, 1H), 2.48 (s, 1H), 2.34-2.18 (m, 2H), 2.05-1.41 (m, 8H), 1.03 (s, 9H), 0.95-0.84 (m, 1H), 0.83-0.73 (m, 1H), 0.62 (dtd, J=9.3, 5.5, 3.9 Hz, 1H), 0.52 (dtd, J=9.5, 5.6, 3.9 Hz, 1H); MS (ESI+) m/z 576 (M+H)+.

Example 108

(2S,3S,4S,5S)-3-tert-butyl-4-{[(5-tert-butyl-2-methoxyphenyl)methyl]amino}-5-(2-cyclopropyphenyl)-1-[(2S)-oxolane-2-carbonyl]pyrrolidine-2-carboxylic acid Example 107B (103.2 mg, 0.241 mmol) and 5-(tert-butyl)-2-methoxybenzaldehyde (84.9 mg, 0.442 mmol) were dissolved in methanol (2 mL). Sodium cyanoborohydride (74.5 mg, 1.186 mmol) was added and the reaction was stirred at ambient temperature for 17 hours. Aqueous LiOH (1 M, 1.0 mL, 1.0 mmol) was added and the reaction was heated to 50° C. for 16 hours. The reaction was quenched by the addition of trifluoroacetic acid (0.2 mL), diluted with dimethyl sulfoxide (1 mL), filtered and purified by reverse phase using the trifluoroacetic acid method to provide the title compound (108.2 mg, 56%) as the trifluoroacetic acid salt. $^1$H NMR (400 MHz, dimethyl sulfoxide-$d_6$, 120° C.) δ ppm 7.79 (s, 1H), 7.22 (dt, J=8.4, 3.3 Hz, 3H), 7.13-7.07 (m, 1H), 7.02 (d, J=2.6 Hz, 1H), 6.77 (d, J=8.6 Hz, 1H), 5.94 (s, 1H), 4.67 (d, J=1.3 Hz, 1H), 4.15 (s, 1H), 3.85-3.57 (m, 4H), 3.49 (s, 3H), 3.36-3.29 (m, 1H), 2.57 (s, 1H), 1.97 (dt, J=8.5, 5.6 Hz, 1H), 1.78 (ddt, J=11.8, 8.5, 5.0 Hz, 2H), 1.67 (s, 2H), 1.21 (d, J=0.8 Hz, 9H), 1.04 (s, 9H), 0.89 (dddd, J=12.9, 9.2, 6.2, 3.2 Hz, 1H), 0.77 (tdd, J=9.1, 5.7, 4.0 Hz, 1H), 0.61 (dtd, J=9.5, 5.6, 4.0 Hz, 1H), 0.50 (dtd, J=9.5, 5.6, 4.0 Hz, 1H); MS (ESI+) m/z 577 (M+H)+.

Example 109

(2S,3S,4S,5S)-3-tert-butyl-4-({[2-methoxy-5-(1-methylcyclobutyl)phenyl]methyl}amino)-5-(2-methylphenyl)-1-[(2S)-oxane-2-carbonyl]pyrrolidine-2-carboxylic acid Example 109A ethyl (2S,3R,4S,5S)-3-(tert-butyl)-4-nitro-1-((S)-tetrahydro-2H-pyran-2-carbonyl)-5-(o-tolyl)pyrrolidine-2-carboxylate (S)-Tetrahydropyran-2-carboxylic acid (389 mg, 2.99 mmol) was dissolved in dichloromethane (10 mL). Oxalyl chloride (1.5 mL, 2 M, 3.00 mmol) was added followed by N,N-dimethylformamide (25 μL). The reaction was stirred at ambient temperature for 3 hours, at which point it was concentrated, redissolved in dichloromethane (2 mL), and concentrated again. The residue was taken up in dichloromethane (3×2 mL) and added to a solution of Core 10 (1.00 g, 2.99 mmol) and triethylamine (1.0 mL, 7.17 mmol) in dichloromethane (10 mL). The reaction was stirred at ambient temperature for 17 hours. After this time, the mixture was diluted with $CH_2Cl_2$ (100 mL) and washed twice with saturated aqueous $NaHCO_3$ and once with brine. The organic layer was dried over $Na_2SO_4$, filtered, and concentrated to provide the title compound (1.33 g, 100%). $^1$H NMR (400 MHz, dimethyl sulfoxide-$d_6$, 120° C.) δ ppm $^1$H NMR (400 MHz, dimethyl sulfoxide-$d_6$) δ ppm 7.90 (d, J=7.6 Hz, 1H), 7.19-7.09 (m, 3H), 6.01 (m, 1H), 5.56 (d, J=9.1 Hz, 1H), 4.77 (m, 1H), 4.24 (q, J=7.0 Hz, 2H), 3.79 (m, 1H), 2.99 (t, J=3.1 Hz, 1H), 2.40 (s, 3H), 1.71-1.62 (m, 1H), 1.51 (m, 1H), 1.45-1.26 (m, 8H), 1.02 (s, 9H), 0.83 (m, 1H); MS (ESI+) m/z 447 (M+H)+.

Example 109B ethyl (2S,3S,4S,5S)-4-amino-3-(tert-butyl)-1-((S)-tetrahydro-2H-pyran-2-carbonyl)-5-(o-tolyl)pyrrolidine-2-carboxylate The title compound was prepared according to the procedure described in Example 107B, substituting Example 109A for Example 107A. $^1$H NMR (400 MHz, DMSO-$d_6$) δ ppm 7.87 (m, 1H), 7.15 (m, 3H), 5.46 (m, 1H), 4.47 (m, 1H), 4.16 (m, 2H), 3.80-3.68 (m, 2H), 2.32 (s, 3H), 2.01 (t, J=2.8

Hz, 1H), 1.66 (m, 1H), 1.54-1.30 (m, 5H), 1.27-1.19 (m, 3H), 0.99 (s, 9H), 0.80 (m, 2H); MS (ESI+) m/z 417 (M+H)⁺.

Example 109C ethyl (2S,3S,4S,5S)-3-(tert-butyl)-4-((2-methoxy-5-(1-methylcyclobutyl)benzyl)amino)-1-((S)-tetrahydro-2H-pyran-2-carbonyl)-5-(o-tolyl)pyrrolidine-2-carboxylate Example 109B (69.1 mg, 0.166 mmol) and 2-methoxy-5-(1-methylcyclobutyl)benzaldehyde (Intermediate 5, 52.6 mg, 0.258 mmol) were dissolved in methanol (1 mL) and stirred at ambient temperature for 3 hours. Sodium cyanoborohydride (64.2 mg, 1.022 mmol) was added and the reaction was stirred at ambient temperature for an additional 16 hours. The reaction was diluted with dimethyl sulfoxide (1 mL), filtered and purified by reverse phase using the ammonium acetate method to provide the title compound (62.9 mg, 63%). ¹H NMR (400 MHz, dimethyl sulfoxide-d₆, 120° C.) δ ppm 7.93 (s, 1H), 7.17 (s, 3H), 6.96 (dd, J=8.4, 2.5 Hz, 1H), 6.78-6.70 (m, 2H), 5.61 (s, 1H), 4.69 (s, 1H), 4.13 (qq, J=7.4, 3.9 Hz, 2H), 3.71 (d, J=49.1 Hz, 1H), 3.55-3.42 (m, 5H), 3.23 (dd, J=13.8, 7.1 Hz, 1H), 2.35 (s, 1H), 2.22 (t, J=9.8 Hz, 2H), 2.16 (s, 3H), 2.09-1.91 (m, 4H), 1.82-1.72 (m, 2H), 1.72-1.25 (m, 9H), 1.21 (t, J=7.1 Hz, 3H), 1.02 (s, 9H); MS (ESI+) m/z 605 (M+H)⁺.

Example 109D (2S,3S,4S,5S)-3-tert-butyl-4-({[2-methoxy-5-(1-methylcyclobutyl)phenyl]methyl}amino)-5-(2-methylphenyl)-1-[(2S)-oxane-2-carbonyl]pyrrolidine-2-carboxylic acid Example 109C (59.9 mg, 0.099 mmol) was dissolved in methanol (1 mL). Aqueous LiOH (1 M, 0.5 mL, 0.5 mmol) was added and the reaction was heated to 50° C. for 16 hours. The reaction was quenched by the addition of 1 M aqueous HCl (0.5 mL), diluted with dimethyl sulfoxide (1 mL), filtered and purified by reverse phase using the trifluoroacetic acid method to provide the title compound (58.8 mg, 86%) as the trifluoroacetic acid salt. ¹H NMR (400 MHz, dimethyl sulfoxide-d₆, 120° C.) δ ppm 7.83 (s, 1H), 7.22 (s, 3H), 7.06 (dd, J=8.5, 2.5 Hz, 1H), 6.87-6.78 (m, 2H), 5.58 (s, 1H), 4.60 (s, 1H), 3.84-3.69 (m, 3H), 3.57 (s, 3H), 3.31-3.26 (m, 1H), 2.53 (s, 1H), 2.23 (d, J=10.4 Hz, 6H), 2.09-1.93 (m, 3H), 1.80-1.63 (m, 2H), 1.35 (s, 8H), 1.02 (s, 10H); MS (ESI+) m/z 577 (M+H)⁺.

Example 110

(2S,3S,4S,5S)-3-tert-butyl-4-{[(5-tert-butyl-2-methoxyphenyl)methyl]amino}-5-(2-methylphenyl)-1-[(2S)-oxane-2-carbonyl]pyrrolidine-2-carboxylic acid Example 110A ethyl (2S,3S,4S,5S)-3-(tert-butyl)-4-((5-(tert-butyl)-2-methoxybenzyl)amino)-1-((S)-tetrahydro-2H-pyran-2-carbonyl)-5-(o-tolyl)pyrrolidine-2-carboxylate Example 109B (69.1 mg, 0.266 mmol) and 5-(tert-butyl)-2-methoxybenzaldehyde (46.2 mg, 0.240 mmol) were dis-solved in methanol (1 mL). Sodium cyanoborohydride (49.9 mg, 0794 mmol) was added and the reaction was stirred at ambient temperature for 17 hours. The reaction was diluted with dimethyl sulfoxide (1 mL), filtered and purified by reverse phase using the ammonium acetate method to provide the title compound (67.1 mg, 68%). ¹H NMR (400 MHz, dimethyl sulfoxide-d₆, 120° C.) δ ppm 7.94 (s, 1H), 7.17 (s, 3H), 7.14 (dd, J=8.5, 2.6 Hz, 1H), 6.92 (d, J=2.6 Hz, 1H), 6.72 (d, J=8.5 Hz, 1H), 5.61 (s, 1H), 4.70 (s, 1H), 4.14 (qt, J=7.1, 3.7 Hz, 2H), 3.76 (d, J=11.1 Hz, 1H), 3.56-3.43 (m, 5H), 3.38-3.25 (m, 2H), 3.23 (d, J=13.7 Hz, 1H), 2.35 (s, 1H), 2.15 (s, 3H), 1.73-1.27 (m, 6H), 1.21 (d, J=4.2 Hz, 12H), 1.02 (s, 9H); MS (ESI+) m/z 593 (M+H)⁺.

Example 110B (2S,3S,4S,5S)-3-tert-butyl-4-{[(5-tert-butyl-2-methoxyphenyl)methyl]amino}-5-(2-methylphenyl)-1-[(2S)-oxane-2-carbonyl]pyrrolidine-2-carboxylic acid Example 110A (64.1 mg, 0.108 mmol) was dissolved in methanol (1 mL). Aqueous LiOH (1 M, 1.0 mL, 1.0 mmol) was added and the reaction was heated to 50° C. for 16 hours. The reaction was quenched by the addition of 1 M aqueous HCl (1 mL), diluted with dimethyl sulfoxide (1 mL), filtered and purified by reverse phase using the trifluoroacetic acid method to provide the title compound (49.7 mg, 68%) as the trifluoroacetic acid salt. ¹H NMR (400 MHz, dimethyl sulfoxide-d₆, 120° C.) δ ppm 7.86 (d, J=6.9 Hz, 1H), 7.29-7.22 (m, 4H), 7.05 (d, J=2.5 Hz, 1H), 6.83 (d, J=8.7 Hz, 1H), 5.61 (s, 1H), 4.62 (s, 1H), 3.91-3.74 (m, 4H), 3.60 (s, 3H), 3.52 (s, 1H), 3.33-3.26 (m, 1H), 2.57 (s, 1H), 2.27 (s, 3H), 1.70 (d, J=12.4 Hz, 1H), 1.56-1.31 (m, 5H), 1.24 (s, 9H), 1.04 (s, 9H); MS (ESI+) m/z 565 (M+H)⁺.

Example 111

(2S,3S,4S,5S)-3-tert-butyl-4-{[(5-cyclobutyl-2-methoxypyridin-3-yl)methyl]amino}-5-(2-ethylphenyl)-1-[(2S)-oxolane-2-carbonyl]pyrrolidine-2-carboxylic acid Example 111A (2S,3R,4S,5S)-ethyl 3-(tert-butyl)-5-(2-ethylphenyl)-4-nitro-1-((S)-tetrahydrofuran-2-carbonyl)pyrrolidine-2-carboxylate To a solution of Core 28 (0.5 g, 1.435 mmol) in dichloromethane (5.0 mL) at ambient temperature was added triethylamine (1.100 mL, 7.89 mmol) followed by dropwise addition of (S)-tetrahydrofuran-2-carbonyl chloride (0.367 g, 2.73 mmol) as a solution in 2 mL dichloromethane. The reaction was stirred at room temperature for 20 minutes, then quenched with 10 mL of saturated aqueous sodium bicarbonate and the crude residue was chromatographed using a 24 g silica gel cartridge with a gradient of 0-80% ethyl acetate/heptanes over a period of 20 minutes to give (2S,3R,4S,5S)-ethyl 3-(tert-butyl)-5-(2-ethylphenyl)-4-nitro-1-((S)-tetrahydrofuran-2-carbonyl)pyrrolidine-2-carboxylate (0.603 g, 1.350 mmol, 94% yield). ¹H NMR (500 MHz, dimethyl sulfoxide-d₆) δ ppm 7.91 (d, J=7.9 Hz, 1H), 7.21 (dt, J=13.9, 7.4 Hz, 2H), 7.12 (t, J=7.5 Hz, 1H), 6.02 (s, 1H), 5.58 (d, J=8.2 Hz, 1H), 4.83 (s, 1H), 4.32-4.24 (m, 2H), 4.07 (bs, 1H), 3.71 (q, J=7.2 Hz, 1H), 3.66 (t, J=6.9 Hz, 1H), 3.06 (t, J=3.0 Hz, 1H), 2.84 (q, J=15.4, 1H), 2.71 (dq, J=15.4, 7.7 Hz, 1H), 2.00-1.91 (m, 1H), 1.81 (ddd, J=15.1, 7.4, 5.6 Hz, 1H), 1.68 (s, 1H), 1.32 (t, J=7.1 Hz, 3H), 1.28 (t, J=7.5 Hz, 3H), 1.05 (s, 9H); MS (APCI+) m/z 447 (M+H)+.

Example 111B (2S,3S,4S,5S)-ethyl 4-amino-3-(tert-butyl)-5-(2-ethylphenyl)-1-((S)-tetrahydrofuran-2-carbonyl)pyrrolidine-2-carboxylate Example 111A (602 mg, 1.348 mmol) and tetrahydrofuran (9.5 mL) were added to Raney®-Nickel 2800, water slurry (1641 mg, 12.58 mmol) in a 50 mL pressure bottle and the mixture was shaken for 16 hours at 50 psi of hydrogen. The reaction was filtered and the solvent was removed in vacuo. The crude material was dissolved in 1 mL dichloromethane and loaded onto a 24 g cartridge eluting with a gradient of 0-100% ethyl acetate/heptanes over a period of 15 minutes to provide (2S,3S,4S,5S)-ethyl 4-amino-3-(tert-butyl)-5-(2-ethylphenyl)-1-((S)-tetrahydrofuran-2-carbonyl)pyrrolidine-2-carboxylate (481 mg, 1.155 mmol, 86% yield). $^1$H NMR (500 MHz, dimethyl sulfoxide-$d_6$) δ ppm 7.92 (d, J=7.4 Hz, 1H), 7.27-7.14 (m, 3H), 5.50 (s, 1H), 4.55 (s, 1H), 4.20 (q, J=7.1 Hz, 2H), 4.07 (bs, 1H), 3.73 (d, J=6.7 Hz, 1H), 3.69 (q, J=7.3 Hz, 1H), 3.62 (d, J=7.6 Hz, 1H), 2.74 (dt, J=14.9, 7.4 Hz, 1H), 2.66 (dt, J=14.9, 7.6 Hz, 1H), 2.08 (s, 1H), 1.95 (s, 1H), 1.79 (tt, J=13.7, 6.5 Hz, 1H), 1.65 (s, 1H), 1.26 (dt, J=12.4, 7.3 Hz, 6H), 1.02 (s, 9H), 0.78 (s, 2H); MS (APCI+) m/z 417 (M+H)+.

Example 111C (2S,3S,4S,5S)-ethyl 3-(tert-butyl)-4-(((5-cyclobutyl-2-methoxypyridin-3-yl)methyl)amino)-5-(2-ethylphenyl)-1-((S)-tetrahydrofuran-2-carbonyl)pyrrolidine-2-carboxylate To a solution of 5-cyclobutyl-2-methoxynicotinaldehyde (60.6 mg, 0.317 mmol), Example 111B (120 mg, 0.288 mmol) and zinc(II) chloride (39.3 mg, 0.288 mmol) in sodium acetate/acetic acid buffer in methanol (pH=4, 2 mL) was added sodium cyanoborohydride (27.2 mg, 0.432 mmol) and the reaction was stirred at ambient temperature for 2 hours. The solvent was removed and the resulting residue was chromatographed using a 24 g silica gel cartridge eluting with a gradient of 0-60% ethyl acetate/heptanes over a period of 20 minutes to give (2S,3S,4S,5S)-ethyl 3-(tert-butyl)-4-(((5-cyclobutyl-2-methoxypyridin-3-yl)methyl)amino)-5-(2-ethylphenyl)-1-((S)-tetrahydrofuran-2-carbonyl)pyrrolidine-2-carboxylate (149 mg, 0.252 mmol, 87% yield). $^1$H NMR (500 MHz, dimethyl sulfoxide-$d_6$) δ ppm 7.93 (s, 1H), 7.78 (s, 1H), 7.20 (m, 3H), 7.12 (s, 1H), 5.56 (s, 1H), 4.73 (s, 1H), 4.14 (q, J=7.1 Hz, 2H), 3.69 (d, J=7.4 Hz, 1H), 3.60 (s, 3H), 3.43 (ddd, J=17.5, 14.8, 7.6 Hz, 3H), 3.24 (dd, J=14.3, 6.3 Hz, 1H), 2.61 (dt, J=14.9, 7.4 Hz, 1H), 2.49-2.43 (m, 1H), 2.40 (s, 1H), 2.28 (ddt, J=8.8, 5.9, 3.7 Hz, 2H), 2.12-1.92 (m, 4H), 1.90-1.74 (m, 2H), 1.66 (s, 1H), 1.21 (t, J=7.1 Hz, 3H), 1.15 (t, J=7.5 Hz, 3H), 1.03 (s, 9H); MS (ESI+) m/z 593 (M+H)+.

Example 111D (2S,3S,4S,5S)-3-tert-butyl-4-{[(5-cyclobutyl-2-methoxypyridin-3-yl)methyl]amino}-5-(2-ethylphenyl)-1-[(2S)-oxolane-2-carbonyl]pyrrolidine-2-carboxylic acid To a solution of Example 111C (148 mg, 0.250 mmol) in tetrahydrofuran (0.760 mL), methanol (0.760 mL) and water (0.760 mL) was added lithium hydroxide, H$_2$O (73.5 mg, 1.751 mmol) and the reaction was heated at 45° C. for 16 hours. The solvent was removed under a stream of nitrogen. Water (0.5 mL) was added to the crude material, and the mixture was acidified with 1 M aqueous HCl (1.63 mL) to pH-6, extracted with dichloromethane, and he solvent was evaporated in vacuo. The resulting crude residue was chromatographed using a 4 g silica gel cartridge with a gradient of 0-10% methanol/dichloromethane over a period of 10 minutes to give (2S,3S,4S,5S)-3-(tert-butyl)-4-(((5-cyclobutyl-2-methoxypyridin-3-yl)methyl)amino)-5-(2-ethylphenyl)-1-((S)-tetrahydrofuran-2-carbonyl)pyrrolidine-2-carboxylic acid (57 mg, 0.101 mmol, 40.4% yield). $^1$H NMR (400 MHz, dimethyl sulfoxide-$d_6$) δ ppm 7.88 (d, J=7.7 Hz, 1H), 7.76 (d, J=2.4 Hz, 1H), 7.23-7.08 (m, 4H), 5.51 (s, 1H), 4.65-4.57 (m, 1H), 4.10 (s, 1H), 3.68 (t, J=7.0 Hz, 1H), 3.59 (s, 3H), 3.48 (d, J=14.5 Hz, 1H), 3.44-3.32 (m, 2H), 3.23 (d, J=14.4 Hz, 1H), 2.60 (dq, J=15.0, 7.5 Hz, 2H), 2.42 (d, J=7.4 Hz, 1H), 2.40-2.35 (m, 1H), 2.31-2.19 (m, 2H), 2.02-1.89 (m, 4H), 1.88-1.74 (m, 2H), 1.64 (s, 1H), 1.12 (t, J=7.5 Hz, 3H), 0.99 (s, 9H); MS (APCI+) m/z 565 (M+H)+.

Example 112

(2S,3S,4S,5S)-3-tert-butyl-5-(2-cyclopropylphenyl)-4-({[2-methoxy-5-(1-methylcyclobutyl)phenyl]methyl}amino)-1-[(2S)-oxolane-2-carbonyl]pyrrolidine-2-carboxylic acid Example 107B (101.2 mg, 0.236 mmol) and the 2-methoxy-5-(1-methylcyclobutyl)benzaldehyde (Intermediate 5, 75.2 mg, 0.368 mmol) were dissolved in methanol (2 mL). Sodium cyanoborohydride (47.4 mg, 0.754 mmol) was added and the reaction was stirred at ambient temperature for 17 hours. Aqueous LiOH (1 M, 1.0 mL, 1.0 mmol) was added and the reaction was heated to 50° C. for 16 hours. The reaction was quenched by the addition of trifluoroacetic acid (0.2 mL), diluted with dimethyl sulfoxide (1 mL), filtered and purified by reverse phase using the trifluoroacetic acid method to provide the title compound (101.9 mg, 61%) as the trifluoroacetic acid salt. $^1$H NMR (400 MHz, dimethyl sulfoxide-$d_6$, 120° C.) δ ppm 7.79 (t, J=4.6 Hz, 1H), 7.25-7.17 (m, 2H), 7.13-7.07 (m, 1H), 7.04 (dd, J=8.4, 2.4 Hz, 1H), 6.84 (d, J=2.4 Hz, 1H), 6.78 (d, J=8.5 Hz, 1H), 5.94 (d, J=6.5 Hz, 1H), 4.67 (d, J=1.3 Hz, 1H), 4.15 (s, 1H), 3.84-3.59 (m, 4H), 3.50 (s, 3H), 3.32 (d, J=13.6 Hz, 1H), 2.56 (s, 1H), 2.28-2.16 (m, 2H), 2.10-1.90 (m, 4H), 1.85-1.59 (m, 5H), 1.34 (s, 3H), 1.04 (s, 9H), 0.95-0.83 (m, 1H), 0.83-0.73 (m, 1H), 0.61 (dtd, J=9.3, 5.6, 3.9 Hz, 1H), 0.51 (dtd, J=9.4, 5.6, 3.9 Hz, 1H); MS (ESI+) m/z 589 (M+H)+.

Example 113

(2S,3S,4S,5S)-5-(2-bromophenyl)-3-tert-butyl-4-{[(5-tert-butyl-2-methoxyphenyl)methyl]amino}-1-[(2S)-oxane-2-carbonyl]pyrrolidine-2-carboxylic acid Example 113A ethyl (2S,3R,4S,5S)-5-(2-bromophenyl)-3-(tert-butyl)-4-nitro-1-((S)-tetrahydro-2H-pyran-2-carbonyl)pyrrolidine-2-carboxylate (S)-Tetrahydropyran-2-carboxylic acid (425 mg, 3.27 mmol) was dissolved in dichloromethane (10 mL). Oxalyl chloride (1.7 mL, 2 M, 3.40 mmol) was added followed by N,N-dimethylformamide (25 µL). The reaction was stirred at ambient temperature for 3 hours. The mixture was concentrated, redissolved in dichloromethane (2 mL), and concentrated again. The residue was taken up in dichloromethane (3×2 mL) and added to a solution of Core 25 (1.30 g, 3.26 mmol) and triethylamine (1.5 mL, 10.76 mmol) and in dichloromethane (10 mL). The reaction was stirred at ambient temperature for 17 hours. After this time, the mixture was diluted with CH$_2$Cl$_2$ (100 mL) and washed twice with saturated aqueous NaHCO$_3$ and once with brine. The organic layer was dried over Na$_2$SO$_4$, filtered, and concentrated to provide the title compound (1.66 g, 100%). $^1$H NMR (400 MHz, dimethyl sulfoxide-d$_6$, 120° C.) δ ppm 7.99 (dd, J=7.8, 1.7 Hz, 1H), 7.59 (d, J=8.0 Hz, 1H), 7.34 (t, J=7.5 Hz, 1H), 7.28-7.19 (m, 1H), 6.14 (s, 1H), 5.51 (dd, J=8.7, 2.1 Hz, 1H), 4.86 (s, 1H), 4.26 (q, J=7.1 Hz, 2H), 3.81 (dtd, J=11.4, 4.2, 3.7, 1.5 Hz, 1H), 3.61-3.26 (m, 2H), 2.99 (t, J=2.6 Hz, 1H), 1.75-1.34 (m, 6H), 1.30 (t, J=7.1 Hz, 3H), 1.03 (s, 9H); MS (ESI+) m/z 511 & 513 (M+H)$^+$.

Example 113B ethyl (2S,3S,4S,5S)-4-amino-5-(2-bromophenyl)-3-(tert-butyl)-1-((S)-tetrahydro-2H-pyran-2-carbonyl) pyrrolidine-2-carboxylate Example 113A (1.66 g, 3.25 mmol) was dissolved in tetrahydrofuran (15 mL) and zinc (2.122 g, 32.5 mmol) was added, followed by addition of acetic acid (1.858 mL, 32.5 mmol). The reaction was heated to 65° C. for 2 hours. The reaction was filtered and concentrated, then purified using a gradient of 50-100% ethyl acetate in dichloromethane to give the title compound (901.2 mg, 58% yield). $^1$H NMR (400 MHz, dimethyl sulfoxide-d$_6$, 120° C.) δ ppm 7.95 (s, 1H), 7.59 (d, J=8.0 Hz, 1H), 7.35 (t, J=7.3 Hz, 1H), 7.18 (t, J=7.7 Hz, 1H), 5.58 (s, 1H), 4.53 (s, 1H), 4.18 (qd, J=7.0, 2.6 Hz, 2H), 3.86-3.72 (m, 2H), 3.44-3.15 (m, 2H), 2.03 (t, J=2.4 Hz, 1H), 1.69 (d, J=12.3 Hz, 1H), 1.62-1.30 (m, 5H), 1.25 (t, J=7.0 Hz, 3H), 1.00 (s, 9H); MS (ESI+) m/z 481 & 483 (M+H)$^+$.

Example 113C (2S,3S,4S,5S)-5-(2-bromophenyl)-3-tert-butyl-4-{[(5-tert-butyl-2-methoxyphenyl)methyl]amino}-1-[(2S)-oxane-2-carbonyl]pyrrolidine-2-carboxylic acid Example 113B (118.9 mg, 0.247 mmol) and 5-(tert-butyl)-2-methoxybenzaldehyde (70.9 mg, 0.369 mmol) were dissolved in methanol (2 mL). Sodium cyanoborohydride (37.8 mg, 0.602 mmol) was added and the reaction was stirred at ambient temperature for 17 hours. Aqueous LiOH (1 M, 1.0 mL, 1.0 mmol) was added and the reaction was heated to 50° C. for 16 hours. The reaction was quenched by the addition of trifluoroacetic acid (0.2 mL), diluted with dimethyl sulfoxide (1 mL), filtered and purified by reverse phase using the trifluoroacetic acid method to provide the title compound (110.4 mg, 60%) as the trifluoroacetic acid salt. $^1$H NMR (400 MHz, dimethyl sulfoxide-d$_6$, 120° C.) δ ppm 7.94 (d, J=7.7 Hz, 1H), 7.63-7.56 (m, 1H), 7.38 (t, J=7.5 Hz, 1H), 7.25-7.20 (m, 1H), 7.18 (dd, J=8.6, 2.6 Hz, 1H), 7.01 (d, J=2.6 Hz, 1H), 6.77 (d, J=8.6 Hz, 1H), 5.67 (s, 1H), 4.62 (d, J=1.5 Hz, 1H), 3.85-3.63 (m, 4H), 3.57 (s, 3H), 3.53-3.50 (m, 1H), 3.31 (d, J=13.6 Hz, 1H), 2.44 (s, 1H), 1.69 (d, J=12.1 Hz, 1H), 1.56-1.33 (m, 5H), 1.21 (s, 9H), 1.00 (s, 9H); MS (ESI+) m/z 629 & 631 (M+H)$^+$.

Example 114

(2S,3S,4S,5S)-3-tert-butyl-1-(cyclohexanecarbonyl)-4-{[2-methoxy-5-(trifluoromethyl)pyridin-3-yl]amino}-5-phenylpyrrolidine-2-carboxylic acid Example 114A (2S,3R,4S,5S)-ethyl 3-(tert-butyl)-1-(cyclohexanecarbonyl)-4-nitro-5-phenylpyrrolidine-2-carboxylate To the mixture of (2S,3R,4S,5S)-ethyl 3-(tert-butyl)-4-nitro-5-phenylpyrrolidine-2-carboxylate (Core 7, 500 mg, 1.561 mmol) and triethylamine (0.653 mL, 4.68 mmol) in dichloromethane (10 mL) cooling in an ice bath was added cyclohexanecarbonyl chloride (0.251 mL, 1.873 mmol) dropwise. The mixture was stirred in ice bath for 30 minutes and allowed to warm to room temperature. Dichloromethane (10 mL) was added. The mixture was washed with brine, dried over MgSO$_4$, filtered, and concentrated to provide the title compound (490 mg, 72.9% yield), which used in the next step without further purification. LC/MS (APCI+) m/z 431 (M+H)$^+$.

Example 114B (2S,3S,4S,5S)-ethyl 4-amino-3-(tert-butyl)-1-(cyclohexanecarbonyl)-5-phenylpyrrolidine-2-carboxylate Example 114A (300 mg, 0.697 mmol) in tetrahydrofuran (10 mL) was added to Raney®-Nickel 2800, water slurry (2.2 g, 16.87 mmol) in a 50 mL pressure bottle. The mixture was shaken with 50 psi hydrogen at ambient temperature for 20 hours, filtered and concentrated to provide the title compound (280 mg, 100% yield). LC/MS (APCI+) m/z 400.93 (M+H)$^+$.

Example 114C (2S,3S,4S,5S)-3-(tert-butyl)-1-(cyclohexanecarbonyl)-4-((2-methoxy-5-(trifluoromethyl)pyridin-3-yl)amino)-5-phenylpyrrolidine-2-carboxylic acid The mixture of (2S,3S,4S,5S)-ethyl 4-amino-3-(tert-butyl)-1-(cyclohexanecarbonyl)-5-phenylpyrrolidine-2-carboxylate (Example 114B, 100 mg, 0.250 mmol), 3-bromo-2-methoxy-5-(trifluoromethyl)pyridine (70.3 mg, 0.275 mmol), 4-(di-tert-butylphosphino)-N,N-dimethylaniline (6.63 mg, 0.025 mmol), cesium carbonate (96 mg, 0.499 mmol) and 1,4-dioxane (2 mL) in a vial was purged with N$_2$ for ~30 minutes when Pd$_2$(dba)$_3$ (tris(dibenzylideneacetone)dipalladium(0), 11.43 mg, 0.012 mmol) was added. The reaction mixture was purged with N$_2$ again for 10 minutes, and then heated at 40° C. for 16 hours. The mixture was filtered, and washed with ethyl acetate. The combined organic layer was concentrated. The residue was purified by chromatography, eluting with ethyl acetate in heptanes 0-40% to provide (2S,3S,4S,5S)-ethyl 3-(tert-butyl)-1-(cyclohexanecarbonyl)-4-((2-methoxy-5-(trifluoromethyl)pyridin-3-yl)amino)-5-phenylpyrrolidine-2-carboxylate, which was dissolved in methanol (4 mL) and aqueous 4 M aqueous HCl (1 mL). The mixture was stirred at 40° C. overnight. The solvent was removed and the residue was adjusted with 1 N HCl aqueous to pH~5. Purification of the resulting mixture using reverse phase HPLC with trifluoroacetic acid method provided (2S,3S,4S,5S)-3-(tert-butyl)-1-(cyclohexanecarbonyl)-4-((2-methoxy-5-(trifluoromethyl)pyridin-3-yl)amino)-5-phenylpyrrolidine-2-carboxylic acid (46 mg, 0.084 mmol, 33.6% yield) as trifluoroacetic acid salt. $^1$H NMR (400 MHz, dimethyl sulfoxide-d$_6$) δ ppm 7.54-7.44 (m, 3H), 7.09 (dd, J=8.1, 6.5 Hz, 2H), 7.03 (t, J=7.2 Hz, 1H), 6.97 (d, J=2.1 Hz, 1H), 5.35 (d, J=7.2 Hz, 1H), 4.85 (d, J=10.5 Hz, 1H), 4.54 (s, 1H), 4.45 (d, J=3.7 Hz, 1H), 3.74 (s, 3H), 2.26 (t, J=3.7 Hz, 1H), 2.17 (s, 1H), 1.64 (s, 2H), 1.45 (s, 2H), 1.29-1.07 (m, 4H), 1.04 (s, 9H), 1.02 (s, 2H); MS (ESI+) m/z 548.2 (M+H)$^+$.

Example 115

(2S,3S,4S,5S)-3-tert-butyl-4-{[(5-cyclopropyl-2-methoxypyridin-3-yl)methyl]amino}-1-[(2S)-oxane-2-carbonyl]-5-[2-(propan-2-yl)phenyl]pyrrolidine-2-carboxylic acid Example 115A (2S,3S,4S,5S)-ethyl 3-(tert-butyl)-4-(((5-cyclopropyl-2-methoxypyridin-3-yl)methyl)amino)-5-(2-isopropylphenyl)pyrrolidine-2-carboxylate Example 61B (0.300 g, 0.693 mmol), 5-cyclopropyl-2-methoxynicotinaldehyde (0.123 g, 0.693 mmol), and sodium triacetoxyhydroborate (0.220 g, 1.040 mmol) were stirred in 1,2-dichloroethane (3.5 mL) overnight at room temperature. The mixture was then stirred vigorously with 3.5 mL of saturated aqueous sodium bicarbonate solution for 30 minutes. The mixture was extracted three times with dichloromethane. The combined organic extracts were dried over Na$_2$SO$_4$, filtered and concentrated in vacuo to afford the crude intermediate, (2S,3S,4S,5S)-1-tert-butyl 2-ethyl 3-(tert-butyl)-4-(((5-cyclopropyl-2-methoxypyridin-3-yl)methyl)amino)-5-(2-isopropylphenyl)pyrrolidine-1,2-dicarboxylate. MS (APCI$^+$) m/z 594.7 (M+H). The crude material was dissolved in dichloromethane (2.7 mL) and stirred with trifluoroacetic acid (1.3 mL, 17.3 mmol) at room temperature for 4 hours. The mixture was concentrated in vacuo, and the residue was taken up in dichloromethane and washed twice with 1 N aqueous LiOH solution and once with brine. The organic layer was dried over Na$_2$SO$_4$, filtered and concentrated in vacuo to afford the title compound. $^1$H NMR (400 MHz, DMSO-d$_6$) δ ppm 7.70 (m, 1H), 7.62 (m, 1H), 7.31-7.15 (m, 2H), 7.12 (m, 1H), 6.88 (d, J=2.5 Hz, 1H), 4.41 (d, J=4.9 Hz, 1H), 4.14 (q, J=7.0 Hz, 2H), 3.64 (s, 3H), 3.62 (m, 1H), 3.25 (d, J=14.3 Hz, 1H), 3.14 (m, 1H), 3.06 (dd, J=5.0, 1.7 Hz, 1H), 2.98 (d, J=14.3 Hz, 1H), 2.17 (dd, J=5.8, 1.6 Hz, 1H), 1.74 (m, 1H), 1.27-1.11 (m, 9H), 0.97 (s, 9H), 0.82 (m, 2H), 0.46 (m, 2H); MS (ESI$^+$) m/z 494.2 (M+H)$^+$.

Example 115B (2S,3S,4S,5S)-ethyl 3-(tert-butyl)-4-(((5-cyclopropyl-2-methoxypyridin-3-yl)methyl)amino)-5-(2-isopropylphenyl)-1-((S)-tetrahydro-2H-pyran-2-carbonyl)pyrrolidine-2-carboxylate Tetrahydro-2H-pyran-2-carboxylic acid (0.149 g, 1.146 mmol) was refluxed in thionyl chloride (1.088 mL, 14.90 mmol) for 1 hour. The mixture was cooled to room temperature and concentrated in vacuo. Excess thionyl chloride was chased three times with dichloromethane, and the residue was treated with a solution of Example 115A (0.283 g, 0.573 mmol) in 3 mL dichloromethane and pyridine (0.556 mL, 6.88 mmol). The reaction stirred overnight at room temperature. The mixture was diluted with ethyl acetate and washed three times with water and once with brine. The organic layer was concentrated in vacuo, and the residue was purified by silica gel chromatography, eluting with 0 to 20% ethyl acetate-dichloromethane, to afford the title compound. $^1$H NMR (400 MHz, DMSO-d$_6$) δ ppm 7.90 (d, J=7.7 Hz, 1H), 7.72 (d, J=2.6 Hz, 1H), 7.26 (m, 2H), 7.11 (m, 1H), 6.85 (d, J=2.5 Hz, 1H), 5.61 (m, 1H), 4.69 (d, J=1.4 Hz, 1H), 4.10 (q, J=7.1 Hz, 2H), 3.73 (m, 1H), 3.57 (s, 3H), 3.40 (m, 3H), 3.12 (m, 2H), 2.32 (m, 1H), 1.77-1.31 (m, 4H), 1.26 (d, J=6.7 Hz, 3H), 1.22-1.15 (m, 6H), 1.05 (m, 2H), 1.02 (s, 9H), 0.94 (m, 2H), 0.84 (m, 2H), 0.46 (m, 2H); MS (ESI$^+$) m/z 606.4 (M+H).

Example 115C (2S,3S,4S,5S)-3-tert-butyl-4-{[(5-cyclopropyl-2-methoxypyridin-3-yl)methyl]amino}-1-[(2S)-oxane-2-carbonyl]-5-[2-(propan-2-yl)phenyl]pyrrolidine-2-carboxylic acid Example 115B (0.054 g, 0.089 mmol) and lithium hydroxide (1 M aqueous) (1 mL, 1 mmol) were stirred in tetrahydrofuran (1 mL) and methanol (1 mL) at 45° C. overnight. The reaction mixture was diluted with water and adjusted to pH 2 with 1 N aqueous hydrochloric acid. The mixture was extracted three times with dichloromethane. The combined extracts were dried over Na$_2$SO$_4$, filtered, and concentrated in vacuo, and the residue was purified by silica gel chromatography, eluting with 0 to 5% methanol-ethyl acetate, to afford the title compound. $^1$H NMR (400 MHz, DMSO-d$_6$) δ ppm 7.84 (d, J=7.9 Hz, 1H), 7.77-7.70 (m, 1H), 7.27 (m, 2H), 7.11 (t, J=7.5 Hz, 1H), 6.89 (m, 1H), 5.59 (m, 1H), 4.62 (d, J=1.4 Hz, 1H), 3.73 (m, 1H), 3.56 (s, 3H), 3.53-3.43 (m, 2H), 3.39 (d, J=6.5 Hz, 1H), 3.23-3.01 (m, 4H), 2.36 (m, 1H), 1.81-1.31 (m, 6H), 1.26 (d, J=6.8 Hz, 3H), 1.04 (d, J=6.9 Hz, 3H), 1.01 (s, 9H), 0.89-0.79 (m, 2H), 0.51-0.43 (m, 2H); MS (ESI$^+$) m/z 578.3 (M+H)$^+$.

Example 116

(2S,3S,4S,5S)-3-tert-butyl-5-(2-cyclopropylphenyl)-4-({[2-methoxy-5-(trifluoromethyl)pyridin-3-yl]methyl}amino)-1-[(2S)-oxane-2-carbonyl]pyrrolidine-2-carboxylic acid Example 116A ethyl (2S,3R,4S,5S)-3-(tert-butyl)-5-(2-cyclopropylphenyl)-4-nitro-1-((S)-tetrahydro-2H-pyran-2-carbonyl)pyrrolidine-2-carboxylate (S)-Tetrahydropyran-2-carboxylic acid (161.3 mg, 1.24 mmol) was dissolved in dichloromethane (5 mL). Oxalyl chloride (2 M, 0.63 mL, 1.26 mmol) was added followed by N,N-dimethylformamide (25 μL). The reaction was stirred at ambient temperature for 1 hour, at which point it was concentrated, redissolved in dichloromethane (1 mL), and concentrated again. The residue was taken up in dichloromethane (3×1 mL) and was added to a solution of Core 14 (374.7 mg, 1.04 mmol) and triethylamine (500 μL, 3.59 mmol) in dichloromethane (10 mL). The reaction was stirred at ambient temperature for 2 hours. The mixture was diluted with CH$_2$Cl$_2$ (50 mL) and washed twice with saturated aqueous NaHCO$_3$ and once with brine. The organic layer was dried over Na$_2$SO$_4$, filtered, and concentrated to provide the title compound. $^1$H NMR (400 MHz, dimethyl sulfoxide-d$_6$, 120° C.) δ ppm 7.87 (dd, J=7.8, 1.4 Hz, 1H), 7.21-7.13 (m, 1H), 7.13-7.06 (m, 1H), 6.99 (dd, J=7.7, 1.4 Hz, 1H), 6.29 (d, J=8.6 Hz, 1H), 5.56 (dd, J=8.6, 2.1 Hz, 1H), 4.85 (s, 1H), 4.32-4.18 (m, 2H), 3.81-3.70 (m, 1H), 3.66-3.44 (m, 1H), 3.13-3.01 (m, 1H), 2.98 (t, J=2.5 Hz, 1H), 2.09 (tt, J=8.3, 5.3 Hz, 1H), 1.71-1.33 (m, 6H), 1.29 (t, J=7.1 Hz, 3H), 1.08-0.96 (m, 11H), 0.78 (ddt, J=10.0, 4.9, 2.1 Hz, 1H), 0.73-0.63 (m, 1H); MS (ESI+) m/z 473 (M+H)$^+$.

Example 116B ethyl (2S,3S,4S,5S)-4-amino-3-(tert-butyl)-5-(2-cyclopropylphenyl)-1-((S)-tetrahydro-2H-pyran-2-carbonyl)pyrrolidine-2-carboxylate Example 116A (394.8 mg, 1.162 mmol) and tetrahydrofuran (7.5 mL) were added to a Raney®-Nickel 2800, water slurry (719.3 mg, 5.52 mmol) in a 50 mL stainless steel pressure bottle and the mixture was shaken for 26 hours at 50 psi hydrogen and 50° C. The reaction was filtered and concentrated to provide the title compound. $^1$H NMR (400 MHz, dimethyl sulfoxide-d$_6$, 120° C.) δ ppm 7.85 (s, 1H), 7.15 (t, J=4.6 Hz, 2H), 7.06-7.00 (m, 1H), 5.78 (s, 1H), 4.52 (d, J=2.7 Hz, 1H), 4.17 (qd, J=7.0, 2.1 Hz, 2H), 3.86-3.67 (m, 2H), 3.65-3.36 (m, 2H), 3.19 (d, J=2.7 Hz, 1H), 2.02 (t, J=2.4 Hz, 1H), 1.71-1.29 (m, 6H), 1.24 (t, J=7.1 Hz, 3H), 1.00 (s, 9H), 0.96-0.85 (m, 2H), 0.76-0.57 (m, 2H); MS (ESI+) m/z 443 (M+H)$^+$.

Example 116C

(2S,3S,4S,5S)-3-tert-butyl-5-(2-cyclopropylphenyl)-4-({[2-methoxy-5-(trifluoromethyl)pyridin-3-yl]methyl}amino)-1-[(2S)-oxane-2-carbonyl]pyrrolidine-2-carboxylic acid Example 116B (72.2 mg, 0.163 mmol) and 2-methoxy-5-(trifluoromethyl)nicotinaldehyde (51.3 mg, 0.250 mmol) were dissolved in methanol (1 mL). Sodium cyanoborohydride (24.9 mg, 0.396 mmol) was added and the reaction was stirred at ambient temperature for 3 hours. Aqueous LiOH (1 M, 0.5 mL, 0.5 mmol) was added to the reaction. The reaction was then heated to 50° C. for 16 hours. The reaction was quenched with 1 M aqueous HCl (0.5 mL), diluted with dimethyl sulfoxide (1 mL), and filtered. The resulting residue was purified by reverse phase HPLC using the trifluoroacetic acid method to provide the title compound as the trifluoroacetic acid salt. $^1$H NMR (400 MHz, dimethyl sulfoxide-d$_6$, 120° C.) δ ppm 8.31 (d, J=2.0 Hz, 1H), 7.92-7.81 (m, 1H), 7.54 (d, J=2.5 Hz, 1H), 7.16 (qt, J=7.3, 4.0 Hz, 2H), 7.03 (dd, J=7.0, 2.1 Hz, 1H), 5.88 (d, J=6.4 Hz, 1H), 4.61 (d, J=1.5 Hz, 1H), 3.75 (s, 4H), 3.64-3.51 (m, 4H), 3.27 (d, J=14.9 Hz, 1H), 2.38 (s, 1H), 1.85 (tt, J=8.6, 5.5 Hz, 1H), 1.71-1.62 (m, 1H), 1.59-1.06 (m, 5H), 1.00 (s, 9H), 0.95-0.86 (m, 1H), 0.86-0.74 (m, 1H), 0.68 (dtd, J=9.5, 5.6, 4.0 Hz, 1H), 0.49 (dt, J=10.2, 5.1 Hz, 1H); MS (ESI+) m/z 604 (M+H)$^+$.

Example 117

(2S,3S,4S,5S)-3-tert-butyl-4-{[(5-cyclobutyl-2-methoxypyridin-3-yl)methyl]amino}-1-(cyclohexanecarbonyl)-5-[2-(propan-2-yl)phenyl]pyrrolidine-2-carboxylic acid

Example 117A ethyl (2S,3S,4S,5S)-3-(tert-butyl)-4-(((5-cyclobutyl-2-methoxypyridin-3-yl)methyl)amino)-1-(cyclohexanecarbonyl)-5-(2-isopropylphenyl)pyrrolidine-2-carboxylate Example 68B (101.2 mg, 0.199 mmol) was dissolved in dichloromethane (2 mL). Triethylamine (0.1 mL, 0.717 mmol) was added followed by cyclohexanecarbonyl chloride (67.5 mg, 0.460 mmol). The reaction was concentrated and purified by reverse phase using the ammonium acetate method to provide the title compound. $^1$H NMR (400 MHz, dimethyl sulfoxide-d$_6$, 120° C.) δ ppm 7.89 (s, 1H), 7.73 (d, J=2.4 Hz, 1H), 7.26 (dd, J=18.5, 7.4 Hz, 2H), 7.15-7.07 (m, 2H), 5.40 (d, J=6.4 Hz, 1H), 4.63 (s, 1H), 4.11 (qd, J=7.0, 1.1 Hz, 2H), 3.56 (s, 3H), 3.48-3.31 (m, 3H), 3.20 (dd, J=14.2, 6.2 Hz, 1H), 3.09 (hept, J=6.7 Hz, 1H), 2.39 (s, 1H), 2.30-2.18 (m, 2H), 2.02-1.77 (m, 4H), 1.66-1.40 (m, 4H), 1.23 (d, J=6.8 Hz, 6H), 1.18 (t, J=7.1 Hz, 3H), 1.07 (d, J=6.8 Hz, 3H), 1.02 (s, 9H); MS (ESI+) m/z 618 (M+H)$^+$.

Example 117B

(2S,3S,4S,5S)-3-tert-butyl-4-{[(5-cyclobutyl-2-methoxypyridin-3-yl)methyl]amino}-1-(cyclohexanecarbonyl)-5-[2-(propan-2-yl)phenyl]pyrrolidine-2-carboxylic acid Example 117A (92.9 mg, 0.150 mmol) and lithium hydroxide (1 M aqueous) (1.0 mL, 1.0 mmol) in tetrahydrofuran (1 mL) and methanol (1 mL) was stirred at 50° C. for 16 hours. The reaction mixture was acidified with 1.2 mL 1 N aqueous HCl, and concentrated in vacuo. The residue was purified by reverse phase chromatography using the trifluoroacetic acid method to provide the title compound as the bistrifluoroacetic acid salt. $^1$H NMR (400 MHz, dimethyl sulfoxide-d$_6$) δ ppm 7.81-7.72 (m, 2H), 7.30 (dd, J=7.9, 1.5 Hz, 1H), 7.24 (td, J=7.5, 1.4 Hz, 1H), 7.16 (d, J=2.4 Hz, 1H), 7.15-7.08 (m, 1H), 5.41 (d, J=6.5 Hz, 1H), 4.78-4.42 (m, 1H), 3.56 (s, 5H), 3.46 (d, J=6.5 Hz, 1H), 3.43-3.32 (m, 1H), 3.25 (d, J=14.2 Hz, 1H), 3.08 (p, J=6.8 Hz, 1H), 2.43 (s, 1H), 2.25 (dddd, J=10.6, 8.6, 4.5, 2.1 Hz, 2H), 2.04-1.89 (m, 3H), 1.89-1.76 (m, 1H), 1.71-1.42 (m, 4H), 1.23 (d, J=6.7 Hz, 9H), 1.07 (d, J=6.8 Hz, 3H), 1.02 (s, 9H); MS (ESI+) m/z 590 (M+H)$^+$.

Example 118

(2S,3S,4S,5S)-3-tert-butyl-1-(cyclohexanecarbonyl)-5-(2,2-dimethyl-2,3-dihydro-1-benzofuran-7-yl)-4-({[2-methoxy-5-(trifluoromethyl)pyridin-3-yl]methyl}amino)pyrrolidine-2-carboxylic acid

Example 118A

(2S,3R,4S,5S)-ethyl 3-(tert-butyl)-1-(cyclohexanecarbonyl)-5-(2,2-dimethyl-2,3-dihydrobenzofuran-7-yl)-4-nitropyrrolidine-2-carboxylate To the solution of (2S,3R,4S,5S)-ethyl 3-(tert-butyl)-5-(2,2-dimethyl-2,3-dihydrobenzofuran-7-yl)-4-nitropyrrolidine-2-carboxylate (core 57, 2.0 g, 5.12 mmol) and triethylamine (2.142 mL, 15.37 mmol) in dichloromethane (10 mL) was added cyclohexanecarbonyl chloride (0.754 mL, 5.63 mmol) in an ice bath. The mixture was stirred at 0° C. for 30 minutes. Dichloromethane (50 mL) and saturated aqueous NH$_4$Cl (20 mL) were added and the organic layer was separated and washed with brine. The organic layer was concentrated and the residue was purified via chromatography on a 40 g silica gel cartridge, eluting with ethyl acetate in hexane at 0-60% gradient to provide the title compound. MS (APCI+) m/z 501.5 (M+H)$^+$.

Example 118B (2S,3S,4S,5S)-ethyl 4-amino-3-(tert-butyl)-1-(cyclohexanecarbonyl)-5-(2,2-dimethyl-2,3-dihydrobenzofuran-7-yl)pyrrolidine-2-carboxylate To Raney®-Nickel 2800, water slurry (1.5 g, 11.50 mmol) in a 50 mL pressure bottle were added Example 118A (500 mg, 0.999 mmol) and tetrahydrofuran (10 mL). The mixture was shaken at 60 psi hydrogen and room temperature for 16 hours. The mixture was filtered. The filter cake was washed with methanol. The filtrate was concentrated under pressure to provide the title compound. MS (APCI+) m/z 471 (M+H)$^+$.

Example 118C (2S,3S,4S,5S)-3-tert-butyl-1-(cyclohexanecarbonyl)-5-(2,2-dimethyl-2,3-dihydro-1-benzofuran-7-yl)-4-({[2-methoxy-5-(trifluoromethyl)pyridin-3-yl]methyl}amino)pyrrolidine-2-carboxylic acid A mixture of 2-methoxy-5-(trifluoromethyl)nicotinaldehyde [CAS#58002-88-9] (28.8 mg, 0.140 mmol), Example 118B (60 mg, 0.127 mmol) and zinc(II) chloride (17.37 mg, 0.127 mmol) were combined in a buffer solution of 4 M acetic acid/sodium acetate in methanol (2 mL). The mixture was stirred at room temperature for 10 minutes. Sodium cyanoborohydride (13.13 mg, 0.209 mmol) was added neat and the mixture was stirred at room temperature for 1 hour. The solvent was removed under pressure and the residue was purified via chromatography, eluting with ethyl acetate/methanol (10:1) in heptane at 0-40% gradient to yield (2S,3S,4S,5S)-ethyl 3-(tert-butyl)-4-(((5-cyclobutyl-2-methoxypyridin-3-yl)methyl)amino)-1-(cyclohexanecarbonyl)-5-(2,2-dimethyl-2,3-dihydrobenzofuran-7-yl)pyrrolidine-2-carboxylate, which was concentrated. The resulting ester was dissolved in methanol (2 mL) with 6 M aqueous LiOH solution (0.5 mL), and stirred at 45° C. for 4 hours. The solvent was removed and water (0.5 mL) was added. The pH was adjusted to ~4-5 with 1 M aqueous HCl. Purification via reverse phase HPLC using the trifluoroacetic acid method provided the title compound as the trifluoroacetic acid salt. $^1$H NMR (400 MHz, DMSO-d$_6$) δ ppm 8.30 (d, J=2.4 Hz, 1H), 7.58 (s, 1H), 7.55 (s, 1H), 7.07 (d, J=7.2 Hz, 1H), 6.77 (t, J=7.5 Hz, 1H), 5.29 (d, J=7.2 Hz, 1H), 4.42 (d, J=3.2 Hz, 1H), 3.80 (s, 3H), 3.56 (s, 1H), 3.46 (dd, J=7.2, 3.2 Hz, 2H), 3.35 (s, 1H), 2.35 (t, J=3.2 Hz, 1H), 2.20 (s, 1H), 1.65 (d, J=9.4 Hz, 1H), 1.59 (s, 1H), 1.49 (d, J=9.8 Hz, 2H), 1.41 (s, 3H), 1.36 (s, 3H), 1.27-1.04 (m, 7H), 0.96 (s, 9H); MS (ESI+) m/z 632 (M+H)$^+$.

Example 119

(2S,3S,4S,5S)-3-tert-butyl-4-{[(5-cyclobutyl-2-methoxypyridin-3-yl)methyl](methyl)amino}-1-[(2S)-oxane-2-carbonyl]-5-[2-(propan-2-yl)phenyl]pyrrolidine-2-carboxylic acid Example 73 (50 mg, 84 mol), 37% aqueous formaldehyde (40 μL, 0.54 mmol [contains ~10% methanol]), triethylamine (60 μL, 0.43 mmol) and sodium triacetoxyborohydride (54 mg, 0.25 mmol) were placed into N,N-dimethylformamide (300 μL). The mixture was stirred at room temperature for over six hours. Additional sodium triacetoxyborohydride (18 mg, 0.08 mmol) and N,N-dimethylformamide (100 μL) were added and the mixture was stirred overnight. The mixture was diluted with methanol and purified by reverse-phase HPLC [Waters XBridge™ C18 5 μm OBD column, 30×100 mm, flow rate 40 mL/minute, 20 to 80% gradient of acetonitrile in 0.1% aqueous trifluoroacetic acid] to provide the title compound. $^1$H NMR (400 MHz, DMSO-d$_6$, 120° C.) δ ppm 7.94 (d, J=7.8 Hz, 1H), 7.66 (d, J=2.4 Hz, 1H), 7.36 (d, J=7.8 Hz, 1H), 7.17 (dd, J=7.8, 7.3 Hz, 1H), 6.94 (dd, J=7.8, 7.3 Hz, 1H), 6.17-6.14 (m, 1H), 5.68 (d, J=9.7 Hz, 1H), 4.72 (d, J=2.4 Hz, 1H), 3.94-3.90 (m, 1H), 3.77 (s, 3H), 3.76-3.71 (m, 1H), 3.68-3.58 (m, 1H), 3.35-3.13 (m, 6H), 2.54-2.51 (m, 1H), 2.24-2.14 (m, 2H), 2.00-1.79 (m, 7H), 1.73-1.55 (m, 2H), 1.45-1.25 (m, 9H), 1.04 (s, 9H); MS (ESI+) m/z 606 (M+H)$^+$.

Example I-121

(2S,3S,4S,5S)-3-(tert-butyl)-1-(cyclohexanecarbonyl)-4-((2-methoxy-5-(pyrrolidin-1-yl)benzyl)amino)-5-phenylpyrrolidine-2-carboxylic acid Example I-121-A (2S,3S,4S,5S)-4-((5-bromo-2-methoxybenzyl)amino)-3-(tert-butyl)-1-(cyclohexanecarbonyl)-5-phenylpyrrolidine-2-carboxylic acid The title compound was prepared according to the procedure described in Example 7C, substituting 5-bromo-2-methoxybenzaldehyde for 5-(tert-butyl)-2-methoxybenzenecarbaldehyde. $^1$H NMR (400 MHz, dimethyl sulfoxide-d$_6$, 120° C.) δ ppm 7.62-7.53 (m, 2H), 7.32 (t, J=7.4 Hz, 2H), 7.28-7.20 (m, 2H), 7.00 (d, J=2.6 Hz, 1H), 6.77 (d, J=8.7 Hz, 1H), 5.18 (d, J=6.9 Hz, 1H), 4.50 (d, J=2.8 Hz, 1H), 4.12 (q, J=7.1 Hz, 2H), 3.56 (s, 3H), 3.46-3.41 (m, 1H), 3.38 (d, J=14.3 Hz, 1H), 3.29 (d, J=14.3 Hz, 1H), 2.33-2.11 (m, 2H), 1.63 (d, J=9.6 Hz, 2H), 1.47 (s, 2H), 1.20 (t, J=7.1 Hz, 9H), 0.97 (s, 9H); MS (ESI+) m/z 599.2 and 601.2 (M+H)$^+$.

Example I-121-B (2S,3S,4S,5S)-3-(tert-butyl)-1-(cyclohexanecarbonyl)-4-((2-methoxy-5-(pyrrolidin-1-yl)benzyl)amino)-5-phenylpyrrolidine-2-carboxylic acid A 4 mL vial was charged with potassium tert-butoxide (9.36 mg, 2.5 eq, 0.08 mmol), dichloro[4,5-dichloro-1,3-bis(2,6-di-3-pentylphenyl)imidazol-2-ylidene](3-chloropyridyl)palladium(II) (PEPPSI-IPentCl, 2.87 mg, 10 mol %, 0.003 mmol), and a stir bar. The vial was capped with a septa cap and flushed under a N$_2$ flow. Via syringe, a 170 μL of a 0.6 mmol pre-weighed vial containing pyrrolidine in 1 mL solution of dimethoxyethane (71.1 mg, 1.5 eq, 0.05 mmol)

was added. A 500 µL of a solution of (2S,3S,4S,5S)-ethyl 4-((5-bromo-2-methoxybenzyl)amino)-3-(tert-butyl)-1-(cyclohexanecarbonyl)-5-phenylpyrrolidine-2-carboxylate (Example I-121-A, 20 mg, 0.03 mmol) was added to the vial containing the Pd complex. The vial was placed to heat/stir at 90° C. overnight. Upon completion, the crude material was concentrated to dryness. To the dried crude material, 250 µL of tetrahydrofuran and 1500 µL of a 1 M aqueous solution of LiOH in 75% methanol were added. The vial was capped once more and placed to stir with heat (60° C.) for 1 hour. Upon complete hydrolysis, the crude material was passed through a filter cartridge filled with 300 mg of diatomaceous earth. The cartridge was washed twice with 500 µL of methanol. The material was then dried under $N_2$ once more. The dried crude material was re-dissolved in 1400 µL of dimethyl sulfoxide/$CH_3CN$ solution (1:1 v/v) and purified using reverse phase HPLC to obtain (2S,3S,4S,5S)-3-(tert-butyl)-1-(cyclohexanecarbonyl)-4-((2-methoxy-5-(pyrrolidin-1-yl)benzyl)amino)-5-phenylpyrrolidine-2-carboxylic acid. (3.8 mg, 16.1% isolated yield). $^1$H NMR (400 MHz, dimethyl sulfoxide-$d_6$) δ ppm 7.58-7.52 (m, 2H), 7.44-7.37 (m, 2H), 7.36-7.32 (m, 1H), 6.78-6.75 (m, 1H), 6.49-6.45 (m, 1H), 6.32-6.30 (m, 1H), 5.37-5.34 (m, 1H), 4.54 (d, J=1.8 Hz, 1H), 3.89-3.86 (m, 1H), 3.76 (d, J=13.2 Hz, 1H), 3.49 (s, 3H), 3.13-3.10 (m, 5H) 1.94-1.90 (m, 3H), 1.66-1.59 (m, 2H), 1.55-1.47 (m, 2H), 1.27-1.18 (m, 2H), 1.18-1.15 (m, 1H), 1.12-1.04 (m, 1H), 1.02 (s, 1H), 1.01 (s, 9H), 0.99-0.97 (m, 3H); MS (APCI+) m/z 590.6 (M+H)$^+$.

Example I-244

(2S,3S,4S,5S)-3-tert-butyl-4-{[(5-tert-butyl-2-methoxyphenyl)methyl]amino}-1-{[(oxetan-3-yl)oxy]carbonyl}-5-phenylpyrrolidine-2-carboxylic acid Example I-244-A (2S,3S,4S,5S)-2-ethyl 1-oxetan-3-yl 3-(tert-butyl)-4-((5-(tert-butyl)-2-methoxybenzyl)amino)-5-phenylpyrrolidine-1,2-dicarboxylate Phosgene (15 wt. % in toluene) (677 mg, 1.026 mmol), was cooled to 0° C., treated with a solution of oxetan-3-ol (38 mg, 0.513 mmol) in $CH_2Cl_2$ (~0.5 mL), treated with triethylamine (71.5 µl, 0.513 mmol), stirred at room temperature for 30 minutes, diluted with methyl tert-butyl ether, stirred for 5 minutes and filtered to remove the solids. The filtrate was concentrated. The residue was diluted with $CH_2Cl_2$ (1 mL), thus making a theoretical solution of 0.5 M oxetan-3-yl carbonochloridate in $CH_2Cl_2$. A portion of this 0.5 M solution (0.1 mL, 0.05 mmol) was added to a solution of (2S,3S,4S,5S)-ethyl 3-(tert-butyl)-4-((5-(tert-butyl)-2-methoxybenzyl)amino)-5-phenylpyrrolidine-2-carboxylate (Example 34D, 31 mg, 0.066 mmol) in $CH_2Cl_2$ (0.2 mL). The mixture was stirred at room temperature for 30 minutes, treated with more 0.5 M oxetan-3-yl carbonochloridate in $CH_2Cl_2$ (0.1 mL, 0.05 mmol), stirred for 30 minutes and partitioned between ethyl acetate (30 mL) and saturated aqueous $NaHCO_3$ solution (5 mL). The ethyl acetate layer was washed with brine, dried ($MgSO_4$), filtered, concentrated and chromatographed on silica gel eluting with a gradient of 50% to 100% (9:1 $CH_2Cl_2$:ethyl acetate) in heptanes to provide the title compound (29 mg, 0.051 mmol, 77% yield). $^1$H NMR (400 MHz, dimethyl sulfoxide-$d_6$) δ ppm 7.55 (d, J=7.2 Hz, 2H), 7.32 (t, J=7.4 Hz, 2H), 7.24 (t, J=7.2 Hz, 1H), 7.14 (dd, J=8.5, 2.5 Hz, 1H), 6.93 (d, J=2.5 Hz, 1H), 6.74 (d, J=8.5 Hz, 1H), 5.23 (p, J=6.2, 5.8 Hz, 1H), 5.09 (d, J=6.8 Hz, 1H), 4.65 (t, J=6.8 Hz, 1H), 4.61 (t, J=6.6 Hz, 1H), 4.41 (d, J=2.7 Hz, 1H), 4.25-4.22 (m, 1H), 4.19-4.11 (m, 3H), 3.54 (s, 3H), 3.52-3.44 (m, 2H), 3.35-3.29 (m, 1H), 2.40 (t, J=2.6 Hz, 1H), 1.24-1.19 (m, 12H), 1.03 (s, 9H); LC/MS (ESI+) m/z 568 (M+H)$^+$.

Example I-244-B (2S,3S,4S,5S)-3-tert-butyl-4-{[(5-tert-butyl-2-methoxyphenyl)methyl]amino}-1-{[(oxetan-3-yl)oxy]carbonyl}-5-phenylpyrrolidine-2-carboxylic acid A solution of Example I-244-A (28 mg, 0.049 mmol) in tetrahydrofuran (~1 mL) was diluted with methanol (~1 mL), treated with 1 M aqueous NaOH (~20 drops) and heated to 55° C. for 3 hours. The mixture was cooled, treated with 1 M aqueous HCl (2 mL) and extracted with ethyl acetate (30 mL). The ethyl acetate layer was washed with brine, dried ($MgSO_4$), filtered, concentrated and chromatographed on silica gel eluting with a gradient of 0% to 100% (200:1:1 ethyl acetate:HCOOH:$H_2O$) in (10:1:1 ethyl acetate:HCOOH:$H_2O$) to provide the title compound (19 mg, 0.035 mmol, 71.4% yield). $^1$H NMR (400 MHz, dimethyl sulfoxide-$d_6$) δ ppm 7.54 (d, J=7.4 Hz, 2H), 7.35 (t, J=7.5 Hz, 2H), 7.28 (t, J=7.3 Hz, 1H), 7.19 (dd, J=8.5, 2.5 Hz, 1H), 7.00 (d, J=2.4 Hz, 1H), 6.78 (d, J=8.6 Hz, 1H), 5.26-5.20 (m, 1H), 5.14 (d, J=6.7 Hz, 1H), 4.65 (t, J=6.8 Hz, 1H), 4.60 (t, J=6.8 Hz, 1H), 4.40 (d, J=2.3 Hz, 1H), 4.26-4.22 (m, 1H), 4.17-4.13 (m, 1H), 3.63 (d, J=13.6 Hz, 1H), 3.60-3.57 (m, 1H), 3.55 (s, 3H), 3.39 (d, J=13.7 Hz, 1H), 2.46 (bs, 1H), 1.24 (s, 9H), 1.03 (s, 9H); LC/MS (ESI+) m/z 539.4 (M+H)$^+$.

Example I-246

(2S,3S,4S,5S)-3-tert-butyl-4-{[(5-tert-butyl-2-methoxyphenyl)methyl]amino}-5-phenyl-1-[(3R)-1-{[(propan-2-yl)oxy]carbonyl}piperidine-3-carbonyl]pyrrolidine-2-carboxylic acid Example I-246-A (R)-tert-butyl 3-((2S,3R,4S,5S)-3-(tert-butyl)-2-(ethoxycarbonyl)-4-nitro-5-phenylpyrrolidine-1-carbonyl)piperidine-1-carboxylate A solution of (R)—N-boc-piperidine-3-carboxylic acid (CAS#163438-09-3, 0.859 g, 3.75 mmol) in $CH_2Cl_2$ (15 mL) was treated with 1-chloro-N,N,2-trimethylpropenylamine (CAS #26189-59-3, 0.826 mL, 6.24 mmol), stirred at room temperature for 10 minutes, treated with a solution of (2S,3R,4S,5S)-ethyl 3-(tert-butyl)-4-nitro-5-phenylpyrrolidine-2-carboxylate (Core 7, 1 g, 3.12 mmol) in 1:1 pyridine/tetrahydrofuran (2 mL). The mixture was stirred for 2 hours. The mixture was concentrated to remove the $CH_2Cl_2$. The residue was partitioned between ethyl acetate (~100 mL) and 10% citric acid solution (~25 mL). The layers were separated and the ethyl acetate layer was washed with 10% citric acid solution (~10 mL), washed with saturated aqueous $NaHCO_3$ solution, washed with brine, dried ($MgSO_4$), filtered, concentrated and chromatographed on silica gel eluting with a gradient of 10 to 50% ethyl acetate in heptane to provide the title compound (1.76 g, 3.31 mmol, 106% yield). $^1$H NMR (400 MHz, dimethyl sulfoxide-$d_6$) δ ppm 7.63-7.55 (m, 2H), 7.29 (d, J=5.8 Hz, 3H), 5.78-5.72 (m, 1H), 5.67 (d, J=8.7 Hz, 1H), 4.73 (d, J=3.2 Hz, 1H), 4.28 (q, J=7.0 Hz, 2H), 4.01-3.89 (m, 1H), 3.82-3.71 (m, 1H), 3.06 (t, J=3.4 Hz, 1H), 2.75-2.60 (m, 2H), 1.49-1.38 (m, 13H), 1.32 (t, J=7.1 Hz, 3H), 1.05 (s, 9H); MS (ESI–) m/z 530 (M–H)⁻.

Example I-246-B (R)-tert-butyl 3-((2S,3S,4S,5S)-3-amino-4-(tert-butyl)-5-(ethoxycarbonyl)-2-phenylpyrrolidine-1-carbonyl)piperidine-1-carboxylate A solution of Example I-246-A (1.648 g, 3.1 mmol) in acetic acid (15.97 mL, 279 mmol) and ethyl acetate (91 mL, 930 mmol) was treated with zinc (3.04 g, 46.5 mmol), stirred at 55° C. for 1 hour, heated at 55° C. for 2 hours and was allowed to stir at room temperature overnight. The mixture was diluted with ethyl acetate and filtered to remove the solids. The filtrate was concentrated to dryness. The residue was partitioned between ethyl acetate and saturated aqueous NaHCO₃ solution. The ethyl acetate layer was washed with brine, dried (MgSO₄), filtered, concentrated and chromatographed on silica gel eluting with a gradient of 25 to 100% ethyl acetate in heptane to provide the title compound (1.59 g, 3.17 mmol, 102% yield). ¹H NMR (400 MHz, dimethyl sulfoxide-d₆) δ ppm 7.64-7.56 (m, 2H), 7.36 (t, J=7.4 Hz, 2H), 7.28 (t, J=7.2 Hz, 1H), 5.09 (d, J=7.1 Hz, 1H), 4.44 (d, J=4.1 Hz, 1H), 4.20 (q, J=7.0 Hz, 2H), 3.89 (d, J=11.4 Hz, 1H), 3.79-3.71 (m, 2H), 2.72-2.56 (m, 2H), 2.27 (bs, 1H), 2.08 (bs, 1H), 1.50-1.35 (m, 13H), 1.27 (t, J=7.1 Hz, 3H), 1.04 (s, 9H); LC/MS (ESI+) m/z 502.4 (M+H)⁺.

Example I-246-C (R)-tert-butyl 3-((2S,3S,4S,5S)-3-(tert-butyl)-4-((5-(tert-butyl)-2-methoxybenzyl)amino)-2-(ethoxycarbonyl)-5-phenylpyrrolidine-1-carbonyl)piperidine-1-carboxylate A 100 mL graduated cylinder containing sodium acetate trihydrate (3.6 g, 26.5 mmol) and acetic acid (4.58 mL, 80 mmol) was dissolved in methanol (50 mL) and then further diluted with methanol to bring the total volume to 100 mL. To 10 mL of this solution was added Example I-246-B (0.522 g, 1.040 mmol) and 5-(tert-butyl)-2-methoxybenzaldehyde (CAS #85943-26-6, 0.26 g, 1.352 mmol). The resulting solution was treated with zinc chloride (0.142 g, 1.040 mmol), treated with sodium cyanoborohydride (0.098 g, 1.560 mmol) and stirred at room temperature for 2 hours. The mixture was diluted with ethyl acetate (100 mL) and washed with saturated aqueous NaHCO₃ solution (30 mL). The layers were separated and the aqueous layer was extracted with ethyl acetate (25 mL). The combined ethyl acetate layers were washed with brine, dried (MgSO₄), filtered, concentrated, and chromatographed on silica gel eluting with a gradient of 15 to 50% ethyl acetate in heptane to provide 330 mg of the pure title compound. ¹H NMR (400 MHz, dimethyl sulfoxide-d₆) δ ppm 7.65-7.54 (m, 2H), 7.34 (s, 3H), 7.14 (dd, J=8.6, 2.5 Hz, 1H), 6.94 (d, J=2.3 Hz, 1H), 6.75 (d, J=8.6 Hz, 1H), 5.22 (d, J=6.5 Hz, 1H), 4.56 (d, J=2.7 Hz, 1H), 4.14 (q, J=7.0 Hz, 2H), 3.96-3.70 (m, 1H), 3.55 (s, 3H), 3.49 (d, J=13.6 Hz, 1H), 3.34 (d, J=13.6 Hz, 1H), 2.71-2.56 (m, 2H), 2.44-2.28 (m, 1H), 1.43 (s, 9H), 1.32-1.18 (m, 16H), 1.02 (s, 9H); LC/MS (ESI+) m/z 678.4 (M+H)⁺.

Example I-246-D (2S,3S,4S,5S)-ethyl 3-(tert-butyl)-4-((5-(tert-butyl)-2-methoxybenzyl)amino)-5-phenyl-1-((R)-piperidine-3-carbonyl)pyrrolidine-2-carboxylate A solution of Example I-246-C in trifluoroacetic acid (2 mL) was heated to 60° C. for 1 minute and concentrated. The residue was partitioned between methyl tert-butyl ether (60 mL) and saturated aqueous NaHCO₃ solution (30 mL). The layers were separated and the aqueous layer was extracted with methyl tert-butyl ether (30 mL). The combined methyl tert-butyl ether layers were washed with brine, dried (MgSO₄), filtered and concentrated to provide the title compound (44 mg, 0.076 mmol). ¹H NMR (400 MHz, dimethyl sulfoxide-d₆) δ ppm 7.71-7.24 (m, 5H), 7.14 (dd, J=8.5, 2.6 Hz, 1H), 6.93 (d, J=2.4 Hz, 1H), 6.75 (d, J=8.6 Hz, 1H), 5.30-5.22 (m, 1H), 4.53 (d, J=3.0 Hz, 1H), 4.14 (qd, J=7.1, 2.5 Hz, 2H), 3.59-3.46 (m, 5H), 3.36 (d, J=13.5 Hz, 1H), 3.15-2.67 (m, 10H), 1.26-1.18 (m, 12H), 1.02 (s, 9H); LC/MS (ESI+) m/z 578.4 (M+H)⁺.

Example I-246-E (R)-isopropyl 3-((2S,3S,4S,5S)-3-(tert-butyl)-4-((5-(tert-butyl)-2-methoxybenzyl)amino)-2-(ethoxycarbonyl)-5-phenylpyrrolidine-1-carbonyl)piperidine-1-carboxylate A solution of Example I-246-D (44 mg, 0.076 mmol) and triethylamine (21.23 μl, 0.152 mmol) in CH₂Cl₂ (~0.5 mL) was cooled to 0° C., treated with 2 M isopropyl chloroformate in toluene (49.5 μl, 0.099 mmol), stirred at room temperature for 20 minutes, treated with 37% aqueous NH₄OH solution (~0.5 mL), stirred at room temperature for 5 minutes and partitioned between methyl tert-butyl ether (~30 mL) and saturated aqueous NaHCO₃ solution (~5 mL). The methyl tert-butyl ether layer was washed with brine, dried (MgSO₄), filtered, concentrated and chromatographed on silica gel eluting with a gradient of 15 to 50% ethyl acetate in heptane to provide the title compound (43 mg, 0.065 mmol, 85% yield). ¹H NMR (400 MHz, dimethyl sulfoxide-d₆) δ ppm 7.68-7.53 (m, 2H), 7.38-7.25 (m, 3H), 7.14 (dd, J=8.5, 2.5 Hz, 1H), 6.94 (d, J=2.2 Hz, 1H), 6.75 (d, J=8.5 Hz, 1H), 5.80 (bs, 1H), 5.22 (d, J=6.1 Hz, 1H), 4.77 (dp, J=21.9, 6.2 Hz, 2H), 4.55 (d, J=2.7 Hz, 1H), 4.14 (q, J=7.0 Hz, 2H), 4.01-3.72 (m, 1H), 3.57-3.46 (m, 5H), 3.34 (d, J=13.3 Hz, 1H), 1.48-1.35 (m, 2H), 1.31-1.13 (m, 23H), 1.03 (s, 9H); LC/MS (ESI+) m/z 664.4 (M+H)⁺.

Example I-246-F (2S,3S,4S,5S)-3-tert-butyl-4-{[(5-tert-butyl-2-methoxyphenyl)methyl]amino}-5-phenyl-1-[(3R)-1-{[(propan-2-yl)oxy]carbonyl}piperidine-3-carbonyl]pyrrolidine-2-carboxylic acid A solution of Example I-246-E (43 mg, 0.065 mmol) in tetrahydrofuran (1 mL) was diluted with methanol (~1 mL), treated with 1 M aqueous NaOH (~0.5 mL), heated to 55° C. for 4 hours, cooled and partitioned between 1 M aqueous HCl (3 mL) and ethyl acetate (30 mL). The ethyl acetate layer was washed with brine, dried (MgSO₄), filtered and concentrated to provide the title compound (33 mg, 0.052 mmol, 80% yield). ¹H NMR (400 MHz, dimethyl sulfoxide-d₆) δ ppm 7.65 (d, J=5.7 Hz, 2H), 7.43 (t, J=7.5 Hz, 2H), 7.35 (t, J=7.1 Hz, 1H), 7.26 (dd, J=8.6, 2.3 Hz, 1H), 7.09 (d, J=2.1 Hz, 1H), 6.84 (d, J=8.6 Hz, 1H), 5.64-5.63 (m, 1H), 5.40 (d, J=7.0 Hz, 1H), 4.80 (hept, J=6.2 Hz, 1H), 4.57 (d, J=1.8 Hz, 1H), 3.98 (d, J=6.3 Hz, 1H), 3.92-3.86 (m, 1H), 3.81-3.75 (m, 2H), 3.64 (s, 3H), 3.45 (d, J=13.6 Hz, 1H), 2.76-2.65 (m, 3H), 1.52-1.38 (m, 2H), 1.32-1.15 (m, 17H), 1.04 (s, 9H); LC/MS (ESI+) m/z 636.4 (M+H)$^+$.

Example II-341

(2S,3S,4S,5S)-3-(tert-butyl)-1-(cyclohexanecarbonyl)-4-(((2-methoxy-5-(3-methoxyphenyl)pyridin-3-yl)methyl)amino)-5-phenylpyrrolidine-2-carboxylic acid A 0.5-2.0 mL conical vial from Biotage containing a conical stir bar, was charged with [1,1'-bis(diphenylphosphino)ferrocene]dichloropalladium(II) (PdCl$_2$(dppf)), 4.7 mg, 10 mol %, 0.006 mmol). To this, 1000 µL of (2S,3S, 4S,5S)-tert-butyl 4-(((5-bromo-2-methoxypyridin-3-yl)methyl)amino)-3-(tert-butyl)-1-(cyclohexanecarbonyl)-5-phenylpyrrolidine-2-carboxylate (Example 25C, 36.0 mg, 0.06 mmol) in anhydrous 1,4-dioxane, 115 µL of a 0.6 mmol pre-weighed vial containing a solution of 2-(3-methoxyphenyl)-4,4,5,5-tetramethyl-1,3,2-dioxaborolane in 1000 µL of anhydrous 1,4-dioxane (16.1 mg, 1.2 eq, 0.07 mmol), and 172 µL of a 1 M aqueous solution of Cs$_2$CO$_3$ (55.97 mg, 3 eq, 0.17 mmol) were added. The vial was capped and placed to heat in the Biotage optimizer at 120° C. for 30 minutes. Upon completion, the crude mixture was dried under N$_2$ and 1000 µL of trifluoroacetic acid was added. The vial was capped once more and placed to shake at room temperature for 1 hour. Upon completion, the material was passed through a filter cartridge containing 300 mg of diatomaceous earth. The material was washed twice with acetonitrile. The compound was dried under N$_2$ in a 4 mL vial. The crude material was dissolved in 1400 µL of dimethyl sulfoxide/acetonitrile and purified by reverse phase HPLC purification to yield (2S,3S,4S,5S)-3-(tert-butyl)-1-(cyclohexanecarbonyl)-4-(((2-methoxy-5-(3-methoxyphenyl)pyridin-3-yl)methyl)amino)-5-phenylpyrrolidine-2-carboxylic acid (21.9 mg, 49.0% isolated yield). $^1$H NMR (400 MHz, dimethyl sulfoxide-d$_6$) δ ppm 8.26 (d, J=2.4 Hz, 1H), 7.60-7.55 (m, 2H), 7.36 (td, J=7.8, 2.1 Hz, 3H), 7.31-7.26 (m, 1H), 7.08 (d, J=7.7 Hz, 1H), 7.04 (t, J=2.1 Hz, 1H), 6.93 (dd, J=8.2, 2.5 Hz, 1H), 5.30 (d, J=7.0 Hz, 1H), 4.53 (d, J=2.1 Hz, 1H), 3.82 (s, 3H), 3.76 (s, 3H), 3.71 (d, J=7.8 Hz, 1H), 3.44 (d, J=14.3 Hz, 1H), 2.47-2.44 (m, 1H), 1.64 (s, 2H), 1.49 (s, 2H), 1.22 (d, J=12.3 Hz, 3H), 1.11-1.03 (m, 3H), 1.02 (s, 1H), 1.00 (s, 9H); MS (APCI+) m/z 600.1 (M+H)$^+$.

Example III-228 rac-(2S,3S,4S,5S)-3-tert-butyl-4-{[(5-tert-butyl-2-methoxyphenyl)methyl]amino}-1-(cyclohexanecarbonyl)-5-(1-methyl-2-oxo-1,2-dihydropyridin-3-yl)pyrrolidine-2-carboxylic acid Example III-228-A rac-(2S,3R,4S,5S)-tert-butyl 3-(tert-butyl)-1-(cyclohexanecarbonyl)-5-(1-methyl-2-oxo-1,2-dihydropyridin-3-yl)-4-nitropyrrolidine-2-carboxylate rac-(2S,3R,4S,5S)-tert-Butyl 3-(tert-butyl)-5-(1-methyl-2-oxo-1,2-dihydropyridin-3-yl)-4-nitropyrrolidine-2-carboxylate (Core 35, chirally enriched, low ee) pyrrolidine (42 mg, 0.11 mmol) and triethylamine (35 µL, 0.25 mmol) were dissolved into anhydrous dichloromethane (1.0 mL) and treated slowly dropwise with cyclohexanecarbonyl chloride (19.5 µL, 0.15 mmol). The reaction mixture was stirred one hour at room temperature and then placed directly onto silica for chromatography (100% methyl tert-butyl ether) to give the title compound, 45 mg (83%). MS (ESI+) m/z 512 (M+Na)$^+$.

Example III-228-B rac-(2S,3S,4S,5S)-tert-butyl 4-amino-3-(tert-butyl)-1-(cyclohexanecarbonyl)-5-(1-methyl-2-oxo-1,2-dihydropyridin-3-yl)pyrrolidine-2-carboxylate Example III-228-A (44 mg, 90 µmol) and zinc dust (60 mg, 920 µmol) were stirred in acetic acid (200 µL) and ethyl acetate (700 µL) overnight. More zinc dust (20 mg, 310 µmol) was added and the suspension was stirred first at room temperature, then at 40° C. for about 24 hours. The reaction mixture was brought to room temperature, diluted with methyl tert-butyl ether and filtered through diatomaceous earth with a thorough methyl tert-butyl ether rinse. The filtrate was placed on a short column of silica for chromatography (0 to 1% concentrated NH$_4$OH/CH$_3$CN) to give title compound (22 mg, 53%). $^1$H NMR (400 MHz, dimethyl sulfoxide-d$_6$, 120° C.) δ ppm 7.88-7.67 (m, 1H), 7.56-7.49 (m, 1H), 6.22-6.16 (m, 1H), 5.19-5.12 (m, 1H), 4.30 (d, J=3.4 Hz, 1H), 3.73 (dd, J=7.1, 3.0 Hz, 1H), 3.48 (s, 3H), 2.24-2.05 (m, 1H), 2.01-1.95 (m, 1H), 1.45 (s, 9H), 1.71-1.04 (m, 10H), 0.97 (s, 9H); MS (ESI) m/z 460 (M+H)$^+$.

Example III-228-C rac-(2S,3S,4S,5S)-tert-butyl 3-(tert-butyl)-4-((5-(tert-butyl)-2-methoxybenzyl)amino)-1-(cyclohexanecarbonyl)-5-(1-methyl-2-oxo-1,2-dihydropyridin-3-yl)pyrrolidine-2-carboxylate Example III-228-B (21 mg, 46 µmol), 5-(tert-butyl)-2-methoxybenzaldehyde (12 mg, 62 µmol) and zinc chloride (7 mg, 0.05 mmol) were dissolved into sodium acetate/acetic acid buffer in methanol (pH=4, 100 µL) and treated with NaBH$_3$CN (4 mg, <0.07 mmol), then stirred at room temperature one hour. The reaction mixture was concentrated, treated with drops of concentrated aqueous NH$_4$OH, extracted with CH$_2$Cl$_2$/ethyl acetate/heptane and placed directly on silica for chromatography (20 to 100% ethyl acetate/heptane then 5% methanol/ethyl acetate) to give 22 mg (76%) of the title compound. $^1$H NMR (400 MHz, dimethyl sulfoxide-d$_6$, 120° C.) δ ppm 7.93-7.66 (m, 1H), 7.58-7.49 (m, 1H), 7.11 (dd, J=8.5, 2.6 Hz, 1H), 7.01 (d, J=2.6 Hz, 1H), 6.74 (d, J=8.5 Hz, 1H), 6.22-6.11 (m, 1H), 5.35-5.21 (m, 1H), 4.42-4.37 (m, 1H), 3.59 (s, 3H), 3.54-3.42 (m, 5H), 3.38-3.32 (m, 1H), 2.33-2.05 (m, 2H), 1.73-1.50 (m, 4H), 1.39 (s, 9H), 1.21 (s, 9H), 1.34-1.04 (m, 6H), 0.95 (s, 9H); MS (ESI+) m/z 636 (M+H)$^+$.

Example III-228-D rac-(2S,3S,4S,5S)-3-tert-butyl-4-{[(5-tert-butyl-2-methoxyphenyl)methyl]amino}-1-(cyclohexanecarbonyl)-5-(1-methyl-2-oxo-1,2-dihydropyridin-3-yl)pyrrolidine-2-carboxylic acid Example III-228-C (20 mg, 31 µmol) was dissolved into trifluoroacetic acid (150 µL) and stirred at room temperature two hours, concentrated and reconcentrated from methyl tert-butyl ether, then placed under prolonged vacuum to give 28 mg of the title compound as a di-trifluoroacetic acid salt. $^1$H NMR (400 MHz, dimethyl sulfoxide-d$_6$, 120° C.) δ ppm 7.73-7.60 (m, 2H), 7.25 (dd, J=8.6, 2.6 Hz, 1H), 7.16 (d, J=2.6 Hz, 1H), 6.84 (d, J=8.6 Hz, 1H), 6.29-6.24 (m, 1H), 5.37 (d, J=7.1 Hz, 1H), 4.51 (d, J=2.0 Hz, 1H), 3.89-3.83 (m, 1H), 3.82-3.78 (m, 1H), 3.70-3.65 (m, 4H), 3.49 (s, 3H), 2.57-2.52 (m, 1H), 2.30 (m, 1H), 1.71-1.52 (m, 4H), 1.48-1.08 (m, "6H"), 1.24 (s, 9H), 0.96 (s, 9H); MS (ESI) m/z 580 (M+H)$^+$.

Example III-49 rac-(2R,3R,4R,5R)-3-(tert-butyl)-1-(cyclohexanecarbonyl)-N-((2-methoxyethyl)sulfonyl)-4-((6-methyl-4-(trifluoromethyl)pyridin-2-yl)amino)-5-phenylpyrrolidine-2-carboxamide A 4 mL vial was charged with a stir bar, a solution of rac-(2R,3R,4R,5R)-3-(tert-butyl)-1-(cyclohexanecarbonyl)-4-((6-methyl-4-(trifluoromethyl)pyridin-2-yl)amino)-5-phenylpyrrolidine-2-carboxylic acid (20.0 mg, 0.04 mmol) in dichloroethane and a solution of 1,1'-carbonyldiimidazole (CDI, 13.5 mg, 2.22 eq, 0.08 mmol) in dichloroethane. The vial was capped and placed to stir at 42° C. for 4 hours. To the mixture a solution of 2-methoxyethanesulfonamide (15.7 mg, 3 eq, 0.112 mmol) in dichloroethane and 1,8-diazabicyclo[5.4.0]undec-7-ene (DBU, 17.0 μL, 3 eq, 0.112 mmol) was added and the vial was capped. The vial was placed to stir at 50° C. for another 2 hours. Upon completion the compound was concentrated to dryness and redissolved in 1400 μL of dimethyl sulfoxide/methanol (1:1 v/v). The mixture was purified using reverse phase HPLC to obtain rac-(2R,3R,4R,5R)-3-(tert-butyl)-1-(cyclohexanecarbonyl)-N-((2-methoxyethyl)sulfonyl)-4-((6-methyl-4-(trifluoromethyl)pyridin-2-yl)amino)-5-phenylpyrrolidine-2-carboxamide (8.3 mg, 33.8% isolated yield). $^1$H NMR (400 MHz, dimethyl sulfoxide-d$_6$) δ ppm 7.38-7.32 (m, 2H), 7.18 (m, 3H), 6.53 (s, 1H), 6.29 (s, 1H), 5.35 (d, J=8.3 Hz, 1H), 5.00 (t, J=8.6 Hz, 1H), 4.44 (d, J=7.2 Hz, 1H), 3.80 (t, J=6.3 Hz, 2H), 3.63 (dt, J=6.1, 2.7 Hz, 2H), 3.26 (s, 3H), 2.56-2.53 (m, 1H) 2.37 (s, 3H), 2.28-2.18 (m, 1H), 1.79-1.66 (m, 2H), 1.50-1.41 (m, 2H), 1.20-1.06 (m, 4H), 1.00 (s, 10H), 0.75-0.65 (m, 1H); MS (APCI+) m/z 653.0 (M+H)$^+$.

TABLE 1

| Example | | |
|---|---|---|
| Example I-1 | rac-(2R,3R,4R,5R)-3-tert-butyl-1-(cyclohexanecarbonyl)-4-[(4,6-dimethoxypyrimidin-2-yl)amino]-5-phenylpyrrolidine-2-carboxylic acid | $^1$HNMR (400 MHz, dimethyl sulfoxide-d$_6$) δ ppm 7.47 (d, J = 7.5 Hz, 2H), 7.20 (t, J = 7.4 Hz, 2H), 7.13 (t, J = 7.3 Hz, 1H), 5.55 (d, J = 9.6 Hz, 1H), 5.31 (d, J = 8.0 Hz, 1H), 5.25 (s, 1H), 5.08-4.97 (m, 1H), 4.41 (d, J = 4.9 Hz, 1H), 3.72 (s, 6H), 2.35 (t, J = 5.2 Hz, 1H), 2.20 (s, 1H), 1.70-1.06 (m, 10H), 1.02 (s, 9H); MS (ESI+) m/z 511.2 (M + H)$^+$. |
| Example I-2 | rac-(2R,3R,4R,5R)-3-tert-butyl-4-[(4-chloro-6-methoxypyrimidin-2-yl)amino]-1-(cyclohexanecarbonyl)-5-phenylpyrrolidine-2-carboxylic acid | $^1$HNMR (501 MHz, dimethyl sulfoxide-d$_6$) δ ppm 7.54 (d, J = 8.2 Hz, 2H), 7.34-7.24 (m, 2H), 7.24-7.18 (m, 1H), 6.07 (s, 1H), 5.32 (d, J = 8.3 Hz, 1H), 4.91 (q, J = 8.6 Hz, 1H), 4.23 (s, 1H), 3.94 (s, 3H), 3.65 (s, 1H), 2.47-2.42 (m, 1H), 2.07 (d, J = 2.5 Hz, 1H), 1.74-1.13 (m, 6H), 1.02 (s, 2H), 0.98 (s, 9H), 0.83 (d, J = 12.3 Hz, 1H), 0.48 (d, J = 13.6 Hz, 1H); MS (ESI+) m/z 515.1 (M + H)$^+$. |
| Example I-3 | rac-(2R,3R,4R,5R)-3-tert-butyl-1-(cyclohexanecarbonyl)-4-{[1-(2,2-difluoro-2H-1,3-benzodioxol-5-yl)ethyl]amino}-5-phenylpyrrolidine-2-carboxylic acid | $^1$HNMR (400 MHz, dimethyl sulfoxide-d$_6$) δ ppm 7.87 (d, J = 7.6 Hz, 2H), 7.45 (t, J = 7.4 Hz, 2H), 7.38-7.32 (m, 1H), 7.28-7.19 (m, 1H), 7.11 (d, J = 4.7 Hz, 2H), 5.27 (d, J = 6.9 Hz, 2H), 4.26 (d, J = 2.9 Hz, 2H), 3.72-3.63 (m, 1H), 3.49-3.42 (m, 1H), 3.34-3.21 (m, 1H), 3.00 (p, J = 6.9 Hz, 1H), 2.10 (s, 1H), 2.05 (t, J = 6.7 Hz, 1H), 1.74-1.31 (m, 5H), 1.17 (d, J = 39.7 Hz, 3H), 1.04-0.83 (m, 4H), 0.73 (s, 9H), 0.43 (d, J = 12.3 Hz, 1H); MS (ESI+) m/z 557.2 (M + H)$^+$. |
| Example I-4 | rac-(2R,3R,4R,5R)-3-tert-butyl-1-(cyclohexanecarbonyl)-4-{[(5-methoxy-1,3-dimethyl-1H-pyrazol-4-yl)methyl]amino}-5-phenylpyrrolidine-2-carboxylic acid | $^1$HNMR (400 MHz, 120° C., dimethyl sulfoxide-d$_6$: D$_2$O = 9:1 (v/v)) δ ppm 7.56 (s, 2H), 7.29-7.16 (m, 3H), 5.16 (d, J = 7.2 Hz, 1H), 4.41 (s, 1H), 3.59 (s, 3H), 3.47 (s, 1H), 3.36 (s, 3H), 3.21 (d, J = 12.9 Hz, 1H), 2.95 (d, J = 12.8 Hz, 1H), 2.52 (s, 1H), 2.28 (s, 1H), 1.71 (s, 3H), 1.64-1.59 (m, 2H), 1.51-1.46 (m, 2H), 1.25-1.01 (m, 5H), 0.98 (s, 10H); MS (APCI+) m/z 511.2 (M + H)$^+$. |
| Example I-5 | rac-(2R,3R,4R,5R)-3-tert-butyl-1-(cyclohexanecarbonyl)-5-phenyl-4-{[4-(trifluoromethyl)pyrimidin-2-yl]amino}pyrrolidine-2-carboxylic acid | LC/MS (ESI+) m/z 519.5 (M + H)$^+$. |
| Example I-6 | rac-(2R,3R,4R,5R)-3-tert-butyl-1-(cyclohexanecarbonyl)-4-({[2-methoxy-5-(trifluoromethyl)phenyl]methyl}amino)-5-phenylpyrrolidine-2-carboxylic acid | $^1$HNMR (400 MHz, dimethyl sulfoxide-d$_6$) δ ppm 7.54 (s, 2H), 7.46 (dd, J = 8.6, 2.4 Hz, 1H), 7.31 (t, J = 7.4 Hz, 2H), 7.27-7.20 (m, 2H), 7.00 (d, J = 8.6 Hz, 1H), 5.19 (d, J = 6.9 Hz, 1H), 4.47 (d, J = 2.5 Hz, 1H), 3.64 (s, 3H), 3.54 (d, J = 14.3 Hz, 1H), 3.44 (d, J = 7.0 Hz, 1H), 3.38 (d, J = 14.3 Hz, 1H), 2.34 (s, 1H), 1.63 (d, J = 9.2 Hz, 2H), 1.49 (s, 2H), 1.22 (s, 2H), 1.10 (d, J = 20.0 Hz, 2H), 0.97 (s, 9H), 0.81 (s, 2H); MS (ESI+) m/z 561.2 (M + H)$^+$. |

TABLE 1-continued

| Example | | |
|---|---|---|
| Example I-7 | rac-(2R,3R,4R,5R)-1-(cyclohexanecarbonyl)-3-cyclopropyl-4-{[6-methyl-4-(trifluoromethyl)pyridin-2-yl]amino}-5-phenylpyrrolidine-2-carboxylic acid | $^1$HNMR (400 MHz, dimethyl sulfoxide-$d_6$, 120° C.) δ ppm 7.77 (d, J = 4.4 Hz, 2H), 7.31 (t, J = 7.6 Hz, 2H), 7.22 (t, J = 7.3 Hz, 1H), 7.08 (s, 1H), 6.70 (s, 1H), 6.60 (s, 1H), 4.95 (d, J = 3.4 Hz, 1H), 4.52 (d, J = 7.9 Hz, 1H), 4.46 (s, 1H), 2.38 (s, 3H), 2.06 (s, 1H), 1.84 (d, J = 7.8 Hz, 1H), 1.66-1.42 (m, 4H), 1.34-1.17 (m, 2H), 1.13-0.89 (m, 3H), 0.76 (s, 1H), 0.49 (tdd, J = 9.5, 6.9, 4.5 Hz, 1H), 0.39-0.26 (m, 1H), 0.10 (dq, J = 9.9, 5.0 Hz, 1H), −0.08 (dq, J = 9.9, 5.1 Hz, 1H); MS (ESI+) m/z 516 (M + H)$^+$. |
| Example I-8 | rac-(2R,3R,4R,5R)-3-tert-butyl-1-(cyclohexanecarbonyl)-4-({1-[2-methoxy-5-(trifluoromethyl)phenyl]ethyl}amino)-5-phenylpyrrolidine-2-carboxylic acid | $^1$HNMR (400 MHz, dimethyl sulfoxide-$d_6$) δ ppm 7.69 (s, 1H), 7.50 (d, J = 2.4 Hz, 1H), 7.45 (td, J = 8.3, 2.5 Hz, 2H), 7.38 (t, J = 7.5 Hz, 2H), 7.31 (t, J = 7.3 Hz, 1H), 7.06-7.02 (m, 1H), 5.14 (d, J = 6.9 Hz, 1H), 4.37 (d, J = 2.7 Hz, 1H), 3.77 (s, 3H), 3.64 (s, 1H), 3.48 (q, J = 6.6 Hz, 1H), 3.25 (dd, J = 6.9, 2.2 Hz, 1H), 2.38 (s, 1H), 2.19 (s, 1H), 1.63 (s, 2H), 1.49 (s, 2H), 1.27-1.16 (m, 3H), 1.03 (dd, J = 31.1, 8.3 Hz, 3H), 0.87 (s, 3H), 0.81 (s, 9H); MS (ESI+) m/z 575.2 (M + H)$^+$. |
| Example I-9 | rac-(2S,3S,4S,5S)-3-tert-butyl-1-(cyclohexanecarbonyl)-4-[(2,6-dimethoxypyrimidin-4-yl)amino]-5-phenylpyrrolidine-2-carboxylic acid | LC/MS (ESI+) m/z 511.5 (M + H)$^+$. |
| Example I-10 | rac-(2R,3R,4R,5R)-3-tert-butyl-4-{[6-methoxy-4-(trifluoromethyl)pyridin-2-yl]amino}-5-phenyl-1-{[(propan-2-yl)oxy]carbonyl}pyrrolidine-2-carboxylic acid | $^1$HNMR (400 MHz, dimethyl sulfoxide-$d_6$, 120° C.) δ ppm 7.41-7.33 (m, 2H), 7.16-7.02 (m, 3H), 6.00-5.89 (m, 3H), 5.13 (d, J = 8.3 Hz, 1H), 4.94 (ddd, J = 9.3, 8.2, 7.0 Hz, 1H), 4.69-4.59 (m, 1H), 4.24 (d, J = 6.0 Hz, 1H), 3.85 (s, 3H), 2.42-2.34 (m, 1H), 1.07 (d, J = 6.2 Hz, 3H), 1.01 (s, 9H), 0.91 (d, J = 6.2 Hz, 3H); MS (ESI+) m/z 524 (M + H)$^+$. |
| Example I-11 | rac-(2R,3R,4R,5S)-3-tert-butyl-1-(cyclohexanecarbonyl)-4-({[2-(difluoromethoxy)phenyl]methyl}amino)-5-(pyridin-2-yl)pyrrolidine-2-carboxylic acid | LC/MS (ESI+) m/z 530.3 (M + H)$^+$. |
| Example I-12 | rac-(2R,3R,4R,5R)-3-tert-butyl-4-{(5-chloro-2-methoxyphenyl)methyl]amino}-5-phenyl-1-{[(propan-2-yl)oxy]carbonyl}pyrrolidine-2-carboxylic acid | $^1$HNMR (400 MHz, dimethyl sulfoxide-$d_6$, 120° C.) δ ppm 7.55-7.47 (m, 2H), 7.31 (dd, J = 8.4, 6.7 Hz, 2H), 7.28-7.20 (m, 1H), 7.17 (dd, J = 8.7, 2.7 Hz, 1H), 6.96 (d, J = 2.7 Hz, 1H), 6.85 (d, J = 8.7 Hz, 1H), 5.06 (d, J = 6.9 Hz, 1H), 4.62 (hept, J = 6.2 Hz, 1H), 4.33 (d, J = 2.2 Hz, 1H), 3.61-3.50 (m, 5H), 2.39 (d, J = 2.1 Hz, 1H), 1.04 (d, J = 6.3 Hz, 3H), 0.99 (s, 9H), 0.87 (d, J = 6.2 Hz, 3H); MS (ESI+) m/z 503 (M + H)$^+$. |
| Example I-13 | rac-(2R,3R,4R,5R)-3-tert-butyl-4-{[4-methyl-6-(trifluoromethyl)pyrimidin-2-yl]amino}-5-phenyl-1-{[(propan-2-yl)oxy]carbonyl}pyrrolidine-2-carboxylic acid | $^1$HNMR (400 MHz, dimethyl sulfoxide-$d_6$, 120° C.) δ ppm 7.46-7.37 (m, 2H), 7.18-7.02 (m, 3H), 6.72 (s, 1H), 6.09 (d, J = 9.1 Hz, 1H), 5.13 (d, J = 7.8 Hz, 1H), 4.91 (td, J = 8.5, 4.6 Hz, 1H), 4.70-4.59 (m, 1H), 4.30 (dd, J = 4.4, 1.0 Hz, 1H), 2.51 (s, 1H), 2.39 (t, J = 4.6 Hz, 1H), 1.06 (d, J = 6.3 Hz, 3H), 1.03 (s, 9H), 0.90 (d, J = 6.2 Hz, 3H); MS (ESI+) m/z 509 (M + H)$^+$. |
| Example I-14 | rac-(2R,3R,4R,5R)-3-tert-butyl-1-(cyclohexanecarbonyl)-4-({[2-(difluoromethoxy)-5-methoxyphenyl]methyl}amino)-5-phenylpyrrolidine-2-carboxylic acid | $^1$HNMR (400 MHz, dimethyl sulfoxide-$d_6$) δ ppm 7.74 (d, J = 7.6 Hz, 1H), 7.52-7.35 (m, 2H), 7.36-7.12 (m, 2H), 6.99 (d, J = 8.8 Hz, 1H), 6.81 (s, 1H), 6.61 (dd, J = 18.7, 5.5 Hz, 1H), 5.37 (d, J = 6.8 Hz, 1H), 4.41 (d, J = 2.2 Hz, 1H), 3.65 (d, J = 3.0 Hz, 3H), 3.52 (s, 2H), 3.24 (d, J = 14.1 Hz, 2H), 2.52 (s, 1H), 2.31 (s, 1H), 2.06-1.03 (m, 9H), 0.93 (d, J = 10.2 Hz, 9H), 0.50-0.25 (m, 1H); MS (ESI+) m/z 559.2 (M + H)$^+$. |
| Example I-15 | rac-(2R,3R,4R,5R)-3-tert-butyl-1-(cyclohexanecarbonyl)-4-{[2,-methoxy-5-(trifluoromethyl)pyridin-3-yl]amino}-5-phenylpyrrolidine-2-carboxylic acid | $^1$HNMR (501 MHz, dimethyl sulfoxide-$d_6$) δ ppm 7.55-7.49 (m, 2H), 7.26-7.21 (m, 2H), 7.20-7.16 (m, 1H), 6.54 (s, 1H), 6.04 (d, J = 1.1 Hz, 1H), 6.00 (s, 1H), 5.30 (d, J = 8.5 Hz, 1H), 4.97 (d, J = 10.0 Hz, 1H), 4.19 (d, J = 8.3 Hz, 1H), 3.89 (s, 3H), 2.53 (s, 1H), 2.35 (dd, J = 9.7, 8.2 Hz, 1H), 2.08 (tt, J = 8.5, 3.6 Hz, 1H), 1.64 (dd, J = 30.3, 12.0 Hz, 2H), 1.46-1.15 (m, 6H), 1.06-1.01 (m, 1H), 0.97 (s, 9H), 0.83 (d, J = 12.6 Hz, 1H); MS (ESI+) m/z 548.2 (M + H)$^+$. |
| Example I-16 | rac-(2R,3R,4R,5S)-3-tert-butyl-1-(cyclohexanecarbonyl)-4-({[2-(difluoromethoxy)phenyl]methyl}amino)-5-(6-methoxypyridin-2-yl)pyrrolidine-2-carboxylic acid | LC/MS (ESI+) m/z 560.5 (M + H)$^+$. |

TABLE 1-continued

| Example | | |
|---|---|---|
| Example I-17 | rac-(4R,6R,7R)-5-(cyclohexanecarbonyl)-7-{[6-methyl-4-(trifluoromethyl)pyridin-2-yl]amino}-6-phenyl-5-azaspiro[2.4]heptane-4-carboxylic acid | ¹HNMR (400 MHz, DMSO-d₆, 100° C.) δ ppm 7.50 (br. s., 2H), 7.18 (br. s., 3H), 6.49 (br. s., 2H), 5.35 (d, J = 6.7 Hz, 1H), 4.84-5.17 (m, 1H), 4.16-4.53 (m, 1H), 2.85-3.11 (m, 1H under peak of water), 2.32 (br. s., 3H), 0.97-1.81 (m, 10H), 0.49-0.84 (m, 4H); LC/MS (ESI+) m/z 502.5 (M + H)⁺. |
| Example I-18 | rac-(2R,3R,4R,5S)-3-tert-butyl-4-({[2-(difluoromethoxy)phenyl]methyl}amino)-5-(6-methoxypyridin-2-yl)-1-(oxane-2-carbonyl)pyrrolidine-2-carboxylic acid | LC/MS (ESI+) m/z 562.6 (M + H)⁺. |
| Example I-19 | rac-(2R,3R,4R,5S)-3-tert-butyl-1-(cyclohexanecarbonyl)-5-(6-methoxypyridin-2-yl)-4-({[2-methoxy-5-(trifluoromethyl)phenyl]methyl}amino)pyrrolidine-2-carboxylic acid | LC/MS (ESI+) m/z 592.5 (M + H)⁺. |
| Example I-20 | (2S,3S,4S,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid | ¹HNMR (400 MHz, Chloroform-d) δ ppm 7.45-7.60 (m, 4H), 7.16-7.39 (m, 8H), 6.82 (d, J = 8.5 Hz, 1H), 5.28-5.33 (m, 2H), 4.89 (s, 1H), 3.90 (d, J = 13.8 Hz, 1H), 3.53 (d, J = 13.8 Hz, 1H), 3.47 (s, 3H), 3.46 (s, 3H), 3.33 (d, J = 6.3 Hz, 1H), 2.45 (s, 1H), 0.88 (s, 9H); LC/MS (ESI+) m/z 599.6 (M + H)⁺. |
| Example I-21 | rac-(2R,3R,4R,5R)-3-tert-butyl-1-(cyclohexanecarbonyl)-4-{[6-(difluoromethoxy)pyridin-2-yl]amino}-5-phenylpyrrolidine-2-carboxylic acid | LC/MS (ESI+) m/z 516.6 (M + H)⁺. |
| Example I-22 | rac-(2R,3R,4R,5R)-3-tert-butyl-1-(cyclohexanecarbonyl)-5-[2-(dimethylamino)phenyl]-4-({[2-methoxy-5-(trifluoromethyl)phenyl]methyl}amino)pyrrolidine-2-carboxylic acid | LC/MS (ESI+) m/z 604.8 (M + H)⁺. |
| Example I-23 | rac-(2R,3R,4R,5S)-3-tert-butyl-5-(6-methoxypyridin-2-yl)-4-({[2-methoxy-5-(trifluoromethyl)phenyl]methyl}amino)-1-[oxane-2-carbonyl]pyrrolidine-2-carboxylic acid | LC/MS (ESI+) m/z 594.6 (M + H)⁺. |
| Example I-24 | rac-(2R,3R,4R,5R)-3-tert-butyl-5-[2-(dimethylamino)phenyl]-4-({[2-methoxy-4-(trifluoromethyl)phenyl]methyl}amino)-1-(3-oxabicyclo[3.1.0]hexane-6-carbonyl)pyrrolidine-2-carboxylic acid | LC/MS (ESI+) m/z 604.7 (M + H)⁺. |
| Example I-25 | rac-(2R,3R,4R,5R)-3-tert-butyl-5-[2-(dimethylamino)phenyl]-4-({[2-methoxy-4-(trifluoromethyl)phenyl]methyl}amino)-1-[oxane-2-carbonyl]pyrrolidine-2-carboxylic acid | LC/MS (ESI+) m/z 606.8 (M + H)⁺. |
| Example I-26 | rac-(2R,3R,4R,5R)-3-tert-butyl-5-[2-(dimethylamino)phenyl]-1-[(2,2-dimethyloxane-4-carbonyl]-4-({[2-methoxy-4-(trifluoromethyl)phenyl]methyl}amino)pyrrolidine-2-carboxylic acid | LC/MS (ESI+) m/z 634.9 (M + H)⁺. |

TABLE 1-continued

| Example | | |
|---|---|---|
| Example I-27 | rac-(2R,3R,4R,5R)-3-tert-butyl-1-[(3R)-1-(methoxycarbonyl)piperidine-3-carbonyl]-4-{[6-methyl-4-(trifluoromethyl)pyridin-2-yl]amino}-5-phenylpyrrolidine-2-carboxylic acid | $^1$HNMR (400 MHz, dimethyl sulfoxide-d$_6$) δ ppm 7.42 (d, J = 7.3 Hz, 2H), 7.21-7.04 (m, 3H), 6.49 (d, J = 1.3 Hz, 1H), 6.25 (s, 1H), 5.90 (s, 1H), 5.35 (d, J = 8.3 Hz, 1H), 4.99 (d, J = 8.1 Hz, 1H), 4.37 (d, J = 6.4 Hz, 1H), 3.99-3.88 (m, 1H), 3.73 (d, J = 13.6 Hz, 2H), 2.79 (dd, J = 13.1, 10.5 Hz, 1H), 2.72-2.61 (m, 1H), 2.50 (s, 2H), 2.46 (p, J = 1.9 Hz, 4H), 2.43 (t, J = 7.1 Hz, 1H), 2.35 (s, 3H), 1.02 (s, 9H); MS (ESI+) m/z 591 (M + H)$^+$. |
| Example I-28 | rac-(2R,3R,4R,5R)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid | $^1$HNMR (400 MHz, dimethyl sulfoxide-d$_6$) δ ppm 8.19-8.13 (m, 2H), 7.16-7.07 (m, 2H), 7.04 (d, J = 1.5 Hz, 1H), 6.95 (dd, J = 7.3, 5.0 Hz, 1H), 5.30 (d, J = 6.4 Hz, 1H), 4.61 (pd, J = 6.2, 0.7 Hz, 1H), 4.35 (d, J = 1.6 Hz, 1H), 3.61 (d, J = 0.8 Hz, 3H), 3.53 (d, J = 14.4 Hz, 1H), 3.47 (d, J = 6.4 Hz, 1H), 3.33 (d, J = 14.3 Hz, 1H), 2.66 (d, J = 0.9 Hz, 6H), 2.35-2.30 (m, 1H), 1.01 (d, J = 6.2 Hz, 3H), 0.99 (s, 9H), 0.83 (d, J = 6.1 Hz, 3H); MS (APCI+) m/z 581 (M + H)$^+$. |
| Example I-29 | rac-(2R,3R,4R,5R)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid | $^1$HNMR (400 MHz, dimethyl sulfoxide-d$_6$) δ ppm 8.20-8.11 (m, 2H), 7.45 (dd, J = 8.6, 2.4 Hz, 1H), 7.25 (d, J = 2.4 Hz, 1H), 6.98 (d, J = 8.6 Hz, 1H), 6.94 (dd, J = 7.1, 5.2 Hz, 1H), 5.30 (d, J = 6.4 Hz, 1H), 4.61 (p, J = 6.2 Hz, 1H), 4.34 (d, J = 1.7 Hz, 1H), 3.60 (s, 3H), 3.54 (d, J = 14.3 Hz, 1H), 3.46 (d, J = 6.4 Hz, 1H), 3.29 (d, J = 14.3 Hz, 1H), 2.65 (s, 6H), 2.36-2.30 (m, 1H), 1.00 (d, J = 6.2 Hz, 3H), 0.98 (s, 9H), 0.84 (dd, J = 10.9, 6.0 Hz, 3H); MS (APCI+) m/z 581 (M + H)$^+$. |
| Example I-30 | rac-(2R,3R,4R,5R)-3-tert-butyl-1-(cyclohexanecarbonyl)-4-({[5-(methanesulfonyl)-2-methoxyphenyl]methyl}amino)-5-phenylpyrrolidine-2-carboxylic acid | $^1$HNMR (400 MHz, dimethyl sulfoxide-d$_6$) δ ppm 7.73 (dd, J = 8.7, 2.4 Hz, 1H), 7.57 (s, 2H), 7.54 (d, J = 2.4 Hz, 1H), 7.34 (t, J = 7.5 Hz, 2H), 7.27 (t, J = 7.2 Hz, 1H), 7.07 (d, J = 8.7 Hz, 1H), 5.26 (d, J = 7.0 Hz, 1H), 4.49 (d, J = 2.4 Hz, 1H), 3.69 (s, 3H), 3.64 (s, 1H), 3.60 (q, J = 2.3, 1.7 Hz, 2H), 3.38 (d, J = 2.8 Hz, 1H), 3.01 (s, 3H), 2.41 (s, 1H), 2.25 (s, 1H), 1.64 (m, J = 9.5 Hz, 2H), 1.49 (s, 2H), 1.21 (s, 3H), 1.14-1.01 (m, 3H), 0.98 (s, 9H); MS (ESI+) m/z 571.2 (M + H)$^+$. |
| Example I-31 | rac-(2R,3R,4R,5R)-3-tert-butyl-1-[(1R,3R)-3-methoxycyclohexane-l-carbonyl]-4-{[6-methyl-4-(trifluoromethyl)pyridin-2-yl]amino}-5-phenylpyrrolidine-2-carboxylic acid | $^1$HNMR (400 MHz, dimethyl sulfoxide-d$_6$, 120° C.) δ ppm 7.43 (d, J = 7.5 Hz, 2H), 7.19-6.99 (m, 3H), 6.44 (s, 1H), 6.16 (d, J = 11.8 Hz, 1H), 5.27 (d, J = 7.8 Hz, 1H), 4.96 (s, 1H), 4.34 (d, J = 5.1 Hz, 1H), 3.32 (s, 1H), 3.20 (s, 1H), 2.40-2.25 (m, 4H), 1.88 (s, 6H), 1.82 (d, J = 13.9 Hz, 1H), 1.69-1.53 (m, 2H), 1.50-1.18 (m, 3H), 1.00 (d, J = 2.3 Hz, 9H); MS (ESI+) m/z 562 (M + H)$^+$. |
| Example I-32 | rac-(2R,3R,4R,5R)-3-tert-butyl-4-({[2-methoxy-5-(trifluoromethyl)phenyl]methyl}amino)-1-[(2S*)-2-phenoxypropanoyl]-5-phenylpyrrolidine-2-carboxylic acid | LC/MS (ESI+) m/z 599.5 (M + H)$^+$. |
| Example I-33 | (2R*,3R*,4R*,5R*)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid | LC/MS (ESI+) m/z 570.6 (M + H)$^+$. |
| Example I-34 | (2S,3S,4S,5S)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid | $^1$HNMR (400 MHz, Chloroform-d) δ ppm 7.66-7.77 (m, 2H), 7.58 (d, J = 8.5 Hz, 1H), 7.32-7.47 (m, 5H), 7.16-7.31 (m, 4H), 6.81 (d, J = 8.7 Hz, 1H), 5.35 (s, 1H), 5.23 (d, J = 6.3 Hz, 1H), 4.59 (s, 1H), 4.01 (d, J = 14.0 Hz, 1H), 3.54 (d, J = 14.0 Hz, 1H), 3.40 (s, 3H), 3.31 (s, 3H), 3.21 (d, J = 6.3 Hz, 1H), 2.33 (s, 1H), 0.61 (s, 9H); LC/MS (ESI+) m/z 599.6 (M + H)$^+$. |
| Example I-35 | rac-(2R,3R,4R,5R)-3-tert-butyl-1-(cyclohexanecarbonyl)-5-phenyl-4-({[2-(propan-2-yl)phenyl]methyl}amino)pyrrolidine-2-carboxylic acid | LC/MS (ESI+) m/z 505.9 (M + H)$^+$. |
| Example I-36 | rac-(2R,3R,4R,5R)-3-tert-butyl-4-{[(5-chloro-2-methoxypyridin-3-yl)methyl]amino}-1-(cyclohexanecarbonyl)-5-phenylpyrrolidine-2-carboxylic acid | LC/MS (ESI+) m/z 528.5 (M + H)$^+$. |

TABLE 1-continued

| Example | | |
|---|---|---|
| Example I-37 | rac-(2R,3R,4R,5R)-3-tert-butyl-4-{[6-methyl-4-(trifluoromethyl)pyridin-2-yl]amino}-5-phenyl-1-(spiro[2.5]octane-6-carbonyl)pyrrolidine-2-carboxylic acid | LC/MS (ESI+) m/z 558.5 (M + H)+. |
| Example I-38 | rac-(2R,3R,4R,5R)-1-(cyclohexanecarbonyl)-3-(2-methoxypropan-2-yl)-4-{[6-methoxy-4-(trifluoromethyl)pyridin-2-yl]amino}-5-phenylpyrrolidine-2-carboxylic acid | $^1$HNMR (400 MHz, dimethyl sulfoxide-$d_6$) δ ppm 7.43 (d, J = 7.4 Hz, 2H), 7.24-7.09 (m, 3H), 6.00 (s, 2H), 5.35 (d, J = 8.2 Hz, 1H), 4.97 (q, J = 8.1 Hz, 1H), 4.48 (d, J = 6.3 Hz, 1H), 3.86 (s, 3H), 3.13 (s, 3H), 2.69 (t, J = 7.0 Hz, 1H), 2.22 (s, 1H), 1.67 (d, J = 13.0 Hz, 2H), 1.47 (s, 2H), 1.30 (d, J = 3.9 Hz, 1H), 1.21 (d, J = 2.4 Hz, 6H), 1.12 (d, J = 29.2 Hz, 3H), 0.73 (bs, 1H); MS (ESI+) m/z 564 (M + H)+. |
| Example I-39 | (2S,3S,4S,5S)-3-tert-butyl-1-(cyclohexanecarbonyl)-5-(2-methoxypyridin-3-yl)-4-({[2,-methoxy-4-(trifluoromethyl)phenyl]methyl}amino)pyrrolidine-2-carboxylic acid | $^1$HNMR (400 MHz, dimethyl sulfoxide-$d_6$) δ ppm 8.13-7.92 (m, 2H), 7.12 (d, J = 1.3 Hz, 2H), 7.07 (s, 1H), 6.90 (t, J = 6.2 Hz, 1H), 5.28 (s, 1H), 4.49 (d, J = 2.1 Hz, 1H), 3.85 (d, J = 9.3 Hz, 3H), 3.64 (s, 3H), 3.53 (d, J = 14.4 Hz, 1H), 3.48 (d, J = 6.9 Hz, 1H), 3.38 (d, J = 14.4 Hz, 1H), 3.19 (s, 1H), 2.34 (s, 1H), 1.60 (d, J = 48.7 Hz, 5H), 1.35-0.99 (m, 6H), 0.96 (s, 9H); MS (ESI+) m/z 592.3 (M + H)+. |
| Example I-40 | rac-(2S,3S,4S,5R)-3-tert-butyl-4-{[(5-chloro-2-methoxyphenyl)methyl]amino}-1-(cyclohexanecarbonyl)-5-(3-methoxypyridin-2-yl)pyrrolidine-2-carboxylic acid | LC/MS (ESI+) m/z 558.4 (M + H)+. |
| Example I-41 | rac-(2R,3R,4R,5R)-3-tert-butyl-1-(2-methoxy-2-methylpropanoyl)-4-({[2-methoxy-5-(trifluoromethyl)phenyl]methyl}amino)-5-phenylpyrrolidine-2-carboxylic acid | LC/MS (ESI+) m/z 551.9 (M + H)+. |
| Example I-42 | (2S,3S,4S,5S)-3-tert-butyl-1-(cyclohexanecarbonyl)-4-{[(3-methoxynaphthalen-2-yl)methyl]amino}-5-phenylpyrrolidine-2-carboxylic acid | $^1$HNMR (400 MHz, dimethyl sulfoxide-$d_6$, 120° C.) δ ppm 7.72 (d, J = 8.2 Hz, 1H), 7.67 (d, J = 8.1 Hz, 1H), 7.61-7.53 (m, 2H), 7.47 (s, 1H), 7.42-7.35 (m, 3H), 7.30 (ddd, J = 8.1, 6.9, 1.3 Hz, 2H), 7.17 (s, 1H), 5.30 (d, J = 7.0 Hz, 1H), 4.53 (d, J = 2.1 Hz, 1H), 3.81 (d, J = 13.9 Hz, 1H), 3.76 (d, J = 7.1 Hz, 1H), 3.69 (s, 3H), 3.56 (d, J = 13.8 Hz, 1H), 2.51 (s, 1H), 2.36-2.18 (m, 1H), 1.64 (d, J = 9.4 Hz, 2H), 1.50 (s, 2H), 1.30-1.03 (m, 6H), 1.00 (s, 9H); MS (ESI+) m/z 543 (M + H)+. |
| Example I-43 | (2S,3S,4S,5S)-3-tert-butyl-1-(cyclohexanecarbonyl)-5-[2-(difluoromethoxy)phenyl]-4-({[2-methoxy-4-(trifluoromethyl)phenyl]methyl}amino)pyrrolidine-2-carboxylic acid | $^1$HNMR (400 MHz, dimethyl sulfoxide-$d_6$) δ ppm 7.84 (s, 1H), 7.32 (t, J = 7.7 Hz, 1H), 7.19 (t, J = 8.1 Hz, 2H), 7.15-7.10 (m, 2H), 7.06 (s, 1H), 6.99 (s, 1H), 5.41 (d, J = 6.7 Hz, 1H), 4.53 (d, J = 1.8 Hz, 1H), 3.65 (s, 3H), 3.58 (d, J = 14.3 Hz, 1H), 3.51 (d, J = 6.8 Hz, 1H), 3.38 (d, J = 14.3 Hz, 2H), 2.40 (s, 1H), 2.12 (m, 1H), 1.58 (d, J = 48.9 Hz, 4H), 1.25 (s, 6H), 0.97 (s, 9H); MS (ESI+) m/z 627.2 (M + H)+. |
| Example I-44 | (2S,3S,4S,5S)-3-tert-butyl-1-(cyclohexanecarbonyl)-5-[2-(dimethylamino)pyridin-3-yl]-4-({[2-methoxy-4-(trifluoromethyl)phenyl]methyl}amino)pyrrolidine-2-carboxylic acid | $^1$HNMR (400 MHz, dimethyl sulfoxide-$d_6$) δ ppm 8.42-8.13 (m, 2H), 7.16 (d, J = 7.8 Hz, 1H), 7.13-7.08 (m, 1H), 7.05 (d, J = 1.6 Hz, 1H), 6.97-6.94 (m, 1H), 5.40 (d, J = 6.6 Hz, 1H), 4.52 (s, 1H), 3.61 (s, 3H), 3.58 (s, 1H), 3.52 (d, J = 6.6 Hz, 1H), 3.37 (d, J = 14.3 Hz, 1H), 3.18 (s, 1H), 2.38 (s, 1H), 2.31 (m, 1H), 1.57 (d, J = 52.3 Hz, 4H), 1.29-1.02 (m, 6H), 0.99 (s, 9H); MS (ESI+) m/z 605.3 (M + H)+. |
| Example I-45 | (2R,3R,4R,5R)-3-tert-butyl-4-({[2-methoxy-4-(trifluoromethyl)phenyl]methyl}amino)-5-phenyl-1-[(2R)-2-phenylpropanoyl]pyrrolidine-2-carboxylic acid | $^1$HNMR (400 MHz, dimethyl sulfoxide-$d_6$) δ ppm 7.62 (s, 2H), 7.37 (s, 2H), 7.30 (s, 1H), 7.23 (t, J = 7.3 Hz, 2H), 7.17 (d, J = 7.0 Hz, 1H), 7.13 (s, 2H), 7.05 (d, J = 13.6 Hz, 3H), 5.00 (s, 1H), 4.46 (s, 1H), 3.63 (s, 3H), 3.43 (d, J = 14.2 Hz, 2H), 3.38-3.24 (m, 3H), 2.23 (s, 1H), 1.05 (s, 3H), 0.77 (s, 9H); MS (ESI+) m/z 583.2 (M + H)+. |
| Example I-46 | (2S,3S,4S,5S)-4-{[(1-benzofuran-2-yl)methyl]amino}-3-tert-butyl-1- | $^1$HNMR (400 MHz, dimethyl sulfoxide-$d_6$, 120° C.) δ ppm 7.66-7.57 (m, 2H), 7.47 (dd, J = 7.4, 1.5 Hz, 1H), 7.34 (t, J = 7.6 Hz, 3H), 7.27 (t, J = 7.2 Hz, 1H), 7.16 (dtd, J = 19.0, 7.3, 1.3 Hz, 2H), 6.38 (d, J = 1.2 Hz, 1H), |

TABLE 1-continued

| | | |
|---|---|---|
| | (cyclohexanecarbonyl)-5-phenylpyrrolidine-2-carboxylic acid | 5.23 (d, J = 7.1 Hz, 1H), 4.46 (d, J = 2.7 Hz, 1H), 3.60 (dd, J = 7.1, 2.5 Hz, 1H), 3.55 (d, J = 15.2 Hz, 1H), 3.46 (d, J = 15.3 Hz, 1H), 2.34 (s, 1H), 2.22 (s, 1H), 1.64 (d, J = 9.5 Hz, 2H), 1.48 (s, 2H), 1.16 (ddd, J = 59.7, 21.0, 10.5 Hz, 6H), 0.97 (s, 9H); MS (ESI+) m/z 503 (M + H)+. |
| Example I-47 | (2S,3S,4S,5S)-3-tert-butyl-1-(cyclohexanecarbonyl)-4-{[(2,3-dihydro-1,4-benzodioxin-6-yl)methyl]amino}-5-phenylpyrrolidine-2-carboxylic acid | $^1$HNMR (400 MHz, 120° C., dimethyl sulfoxide-d$_6$: D$_2$O = 9:1 (v/v)) δ ppm 7.54 (s, 2H), 7.39 (q, J = 7.3 Hz, 3H), 6.70 (d, J = 8.3 Hz, 1H), 6.61-6.32 (m, 2H), 5.37 (d, J = 7.2 Hz, 1H), 4.50 (s, 1H), 4.14 (s, 5H), 3.95 (d, J = 6.8 Hz, 1H), 3.00 (s, 1H), 2.49 (d, J = 1.5 Hz, 1H), 2.03-1.98 (m, 1H), 1.52 (d, J = 49.7 Hz, 4H), 0.93 (s, 15H); MS (APCI+) m/z 521.1 (M + H)+. |
| Example I-48 | (2S,3S,4S,5S)-3-tert-butyl-1-(cyclohexanecarbonyl)-4-{[(4-methoxy[1,1'-biphenyl]-3-yl)methyl]amino}-5-phenylpyrrolidine-2-carboxylic acid | $^1$HNMR (400 MHz, dimethyl sulfoxide-d$_6$, 120° C.) δ ppm 7.59 (d, J = 7.4 Hz, 2H), 7.49 (ddd, J = 7.9, 2.9, 1.7 Hz, 3H), 7.39 (dt, J = 8.7, 7.3 Hz, 4H), 7.33-7.25 (m, 3H), 6.97 (d, J = 8.5 Hz, 1H), 5.35 (d, J = 7.0 Hz, 1H), 4.53 (d, J = 2.0 Hz, 1H), 3.83 (d, J = 7.0 Hz, 1H), 3.78 (d, J = 13.6 Hz, 1H), 3.65 (s, 3H), 3.50 (d, J = 13.7 Hz, 1H), 2.53 (s, 1H), 2.32-2.21 (m, 1H), 1.64 (d, J = 9.6 Hz, 2H), 1.50 (s, 2H), 1.30-1.03 (m, 6H), 1.00 (s, 9H); MS (ESI+) m/z 569 (M + H)+. |
| Example I-49 | (2S,3S,4S,5S)-3-tert-butyl-1-(cyclohexanecarbonyl)-4-{[(6-methoxy-2,3-dihydro-1H-inden-5-yl)methyl]amino}-5-phenylpyrrolidine-2-carboxylic acid | $^1$HNMR (400 MHz, 120° C., dimethyl sulfoxide-d$_6$: D$_2$O = 9:1 (v/v)) δ ppm 7.54(s, 2H), 7.38 (dt, J = 27.1, 7.4 Hz, 3H), 6.85 (s, 1H), 6.77 (s, 1H), 5.38 (d, J = 7.1 Hz, 1H), 4.54 (s, 1H), 3.98-3.91 (m, 1H), 3.75 (d, J = 13.4 Hz, 1H), 3.56 (s, 3H), 3.44 (d, J = 13.3 Hz, 1H), 2.80 (t, J = 7.4 Hz, 2H), 2.71 (t, J = 7.5 Hz, 2H), 2.55 (s, 1H), 2.25 (s, 1H), 1.97 (p, J = 7.4 Hz, 2H), 1.70-1.42 (m, 4H), 1.22 (s, 5H), 1.00 (s, 9H), 0.95-0.62 (m, 1H); MS (APCI+) m/z 533.1 (M + H)+. |
| Example I-50 | (2S,3S,4S,5S)-3-tert-butyl-1-(cyclohexanecarbonyl)-4-({[2-(cyclopropylmethoxy)-4-fluorophenyl]methyl}amino)-5-phenylpyrrolidine-2-carboxylic acid | $^1$HNMR (400 MHz, 120° C., dimethyl sulfoxide-d$_6$: D$_2$O = 9:1 (v/v)) δ ppm 7.60-7.48 (m, 2H), 7.42-7.22 (m, 3H), 6.95 (t, J = 7.6 Hz, 1H), 6.68 (dd, J = 11.3, 2.4 Hz, 1H), 6.58 (td, J = 8.5, 2.5 Hz, 1H), 5.28 (d, J = 7.0 Hz, 1H), 4.50 (d, J = 2.3 Hz, 1H), 3.77-3.69 (m, 3H), 3.59 (d, J = 14.0 Hz, 1H), 3.37 (d, J = 13.7 Hz, 1H), 2.43 (s, 1H), 2.24 (s, 1H), 1.70-1.39 (m, 4H), 1.33-1.02 (m, 6H), 0.97 (s, 9H), 0.82 (s, 1H), 0.59-0.48 (m, 2H), 0.25 (dt, J = 6.1, 4.4 Hz, 2H); MS (APCI+) m/z 551.1 (M + H)+. |
| Example I-51 | (2S,3S,4S,5S)-3-tert-butyl-4-{[(5-chloro-2-hydroxyphenyl)methyl]amino}-1-(cyclohexanecarbonyl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.56(s, 2H), 7.32 (dt, J = 25.2, 7.4 Hz, 3H), 7.03 (dd, J = 8.5, 2.6 Hz, 1H), 6.86 (s, 1H), 6.69 (d, J = 8.7 Hz, 1H), 5.30 (d, J = 7.2 Hz, 1H), 4.51 (d, J = 2.2 Hz, 1H), 3.70 (d, J = 7.1 Hz, 1H), 3.59 (d, J = 14.0 Hz, 1H), 3.38 (d, J = 14.0 Hz, 1H), 2.41 (s, 1H), 2.22 (s, 1H), 1.65-1.60 (m, 2H), 1.51-1.46 (m, 2H), 1.25-1.13 (m, 3H), 1.08-1.03 (m, 2H), 0.97 (s, 9H), 0.87-0.64 (m, 1H); MS (APCI+) m/z 513.0 (M + H)+. |
| Example I-52 | (2S,3S,4S,5S)-3-tert-butyl-4-{[(5-tert-butyl-2-methoxyphenyl)methyl]amino}-1-(cyclohexanecarbonyl)-5-[2-(dimethylamino)pyridin-3-yl]pyrrolidine-2-carboxylic acid | $^1$HNMR (400 MHz, dimethyl sulfoxide-d$_6$) δ ppm 8.18 (d, J = 4.7 Hz, 2H), 7.12 (dd, J = 8.6, 2.5 Hz, 1H), 6.99 (d, J = 2.6 Hz, 1H), 6.96 (s, 1H), 6.71 (d, J = 8.6 Hz, 1H), 5.39 (d, J = 6.6 Hz, 1H), 4.51 (s, 1H), 3.65 (d, J = 13.7 Hz, 2H), 3.52 (d, J = 6.5 Hz, 1H), 3.44 (s, 3H), 3.32 (s, 1H), 2.63 (s, 6H), 2.41 (s, 1H), 2.21 (s, 1H), 1.65-1.24 (m, 10H), 1.19 (s, 9H), 1.00 (s, 9H); MS (ESI+) m/z 593.4 (M + H)+. |
| Example I-53 | (2S,3S,4S,5S)-3-tert-butyl-1-(cyclohexanecarbonyl)-5-[2-(dimethylamino)pyridin-3-yl]-4-({[2-methoxy-5-(trifluoromethyl)phenyl]methyl}amino)pyrrolidine-2-carboxylic acid | $^1$HNMR (400 MHz, dimethyl sulfoxide-d$_6$) δ ppm 8.19 (d, J = 4.9 Hz, 2H), 7.52-7.46 (m, 1H), 7.30 (d, J = 2.3 Hz, 1H), 7.04-6.97 (m, 2H), 5.41 (d, J = 6.6 Hz, 1H), 4.53 (s, 1H), 3.66 (d, J = 14.2 Hz, 2H), 3.62 (s, 3H), 3.38 (d, J = 14.2 Hz, 2H), 2.74 (s, 6H), 2.43 (s, 1H), 2.15-2.05 (m, 1H), 1.54 (dd, J = 47.4, 24.3 Hz, 5H), 1.27-1.03 (m, 5H), 0.99 (s, 9H); MS (ESI+) m/z 605.3 (M + H)+. |
| Example I-54 | (2S,3S,4S,5S)-3-tert-butyl-1-(cyclohexanecarbonyl)-5-phenyl-4-{[6-(propan-2-yl)-4-(trifluoromethyl)pyridin-2-yl]amino}pyrrolidine-2-carboxylic acid | $^1$HNMR (400 MHz, 120° C., dimethyl sulfoxide-d$_6$: D$_2$O = 9:1 (v/v)) δ ppm 7.37 (d, J = 6.6 Hz, 2H), 7.18-7.03 (m, 3H), 6.47 (s, 1H), 6.18 (s, 1H), 5.32 (d, J = 8.1 Hz, 1H), 5.06 (t, J = 7.7 Hz, 1H), 4.38 (d, J = 6.0 Hz, 1H), 2.88 (p, J = 6.8 Hz, 1H), 2.43-2.37 (m, 1H), 2.20 (s, 1H), 1.67 (d, J = 7.8 Hz, 3H), 1.46 (s, 2H), 1.32-1.02 (m, 10H), 1.00 (s, 10H), 0.74 (d, J = 7.4 Hz, 1H); MS (APCI+) m/z 560.3 (M + H)+. |
| Example I-55 | (2S,3S,4S,5S)-3-tert-butyl-4-[(3-cyano-4-methoxyquinolin-2-yl)amino]-1-(cyclohexanecarbonyl)-5- | $^1$HNMR (400 MHz, dimethyl sulfoxide-d$_6$) δ ppm 7.87-7.82 (m, 1H), 7.63 (dd, J = 6.8, 1.6 Hz, 1H), 7.57-7.49 (m, 3H), 7.28-7.21 (m, 3H), 7.14 (dd, J = 9.7, 6.8 Hz, 2H), 5.45-5.38 (m, 2H), 4.53 (d, J = 3.6 Hz, 1H), 4.22 |

TABLE 1-continued

| | | |
|---|---|---|
| | phenylpyrrolidine-2-carboxylic acid | (s, 3H), 2.40-2.37 (m, 1H), 1.73-1.65 (m, 2H), 1.53-1.46 (m, 2H), 1.31-1.22 (m, 3H), 1.18 (s, 3H), 1.11 (s, 9H), 1.07 (d, J = 6.5 Hz, 1H); MS (APCI+) m/z 555.5 (M + H)+. |
| Example I-56 | (2S,3S,4S,5S)-3-tert-butyl-1-(cyclohexanecarbonyl)-5-phenyl-4-[3-(trifluoromethyl)anilino]pyrrolidine-2-carboxylic acid | ¹HNMR (400 MHz, dimethyl sulfoxide-d₆) δ ppm 7.48 (d, J = 7.3 Hz, 2H), 7.21-7.12 (m, 4H), 6.75 (d, J = 7.7 Hz, 1H), 6.70-6.66 (m, 1H), 6.62 (d, J = 2.0 Hz, 1H), 5.37 (d, J = 7.9 Hz, 1H), 4.44-4.38 (m, 2H), 2.37 (t, J = 6.1 Hz, 1H), 2.27-2.18 (m, 1H), 1.74-1.64 (m, 2H), 1.52-1.40 (m, 2H), 1.34-1.23 (m, 1H), 1.19-1.05 (m, 3H), 1.02 (s, 9H); MS (APCI+) m/z 517.4 (M + H)+. |
| Example I-57 | (2S,3S,4S,5S)-3-tert-butyl-4-{[(5-chloro-2-methoxyphenyl)methyl]amino}-1-(cyclohexanecarbonyl)-5-(2-methoxyphenyl)pyrrolidine-2-carboxylic acid | ¹HNMR (400 MHz, DMSO-d₆, 120° C.) δ ppm ¹HNMR (400 MHz, DMSO-d₆) δ ppm 7.64 (s, 1H), 7.27 (t, J = 7.6 Hz, 1H), 7.17 (dd, J = 8.7, 2.7 Hz, 1H), 7.01 (d, J = 8.3 Hz, 1H), 6.98-6.88 (m, 2H), 6.85 (d, J = 8.7 Hz, 1H), 5.46 (d, J = 6.8 Hz, 1H), 4.52 (d, J = 1.8 Hz, 1H), 3.78 (s, 3H), 3.59-3.52 (m, 5H), 3.37 (d, J = 14.1 Hz, 1H), 2.40 (s, 1H), 2.22 (s, 1H), 1.63 (t, J = 11.6 Hz, 2H), 1.51 (s, 2H), 1.32-1.00 (m, 6H), 0.97 (d, J = 0.9 Hz, 9H); MS (ESI+) m/z 557 (M + H)+. |
| Example I-58 | (2S,3S,4S,5S)-3-tert-butyl-4-{[(5-tert-butyl-2-methoxyphenyl)methyl]amino}-1-[(1S,3S)-3-methoxycyclohexane-1-carbonyl]-5-phenylpyrrolidine-2-carboxylic acid | ¹HNMR (400 MHz, dimethyl sulfoxide-d₆) δ ppm 7.47 (s, 2H), 7.31 (t, J = 7.5 Hz, 2H), 7.24 (td, J = 6.9, 3.2 Hz, 1H), 7.15 (dd, J = 8.5, 2.6 Hz, 1H), 6.97 (d, J = 2.6 Hz, 1H), 6.74 (d, J = 8.6 Hz, 1H), 5.21 (d, J = 6.8 Hz, 1H), 4.46 (d, J = 2.3 Hz, 1H), 3.62 (d, J = 13.7 Hz, 1H), 3.53 (dd, J = 6.9, 1.8 Hz, 1H), 3.50 (s, 3H), 3.40 (d, J = 13.7 Hz, 1H), 3.35 (s, 0H), 2.88 (s, 2H), 2.39 (s, 1H), 1.66-1.55 (m, 4H), 1.48-1.34 (m, 2H), 1.33-1.22 (m, 3H), 1.20 (s, 9H), 0.97 (s, 9H), 0.89-0.78 (m, 4H); MS (APCI+) m/z 579 (M + H)+. |
| Example I-59 | (2S,3S,4S,5S)-3-tert-butyl-1-[(1R,3R)-3-methoxycyclohexane-1-carbonyl]-4-({[2-methoxy-5-(trifluoromethyl)phenyl]methyl}amino)-5-phenylpyrrolidine-2-carboxylic acid | ¹HNMR (400 MHz, dimethyl sulfoxide-d₆) δ ppm 7.53 (s, 2H), 7.47 (dd, J = 8.7, 2.3 Hz, 1H), 7.31 (t, J = 7.4 Hz, 2H), 7.27-7.18 (m, 2H), 7.00 (d, J = 8.6 Hz, 1H), 5.15 (d, J = 7.0 Hz, 1H), 4.47 (d, J = 2.5 Hz, 1H), 3.65 (s, 3H), 3.54 (d, J = 14.3 Hz, 1H), 3.48 (d, J = 7.0 Hz, 1H), 3.42 (s, 1H), 3.37 (d, J = 14.3 Hz, 1H), 3.18 (s, 3H), 2.64 (s, 1H), 2.36 (s, 1H), 1.75 (d, J = 13.6 Hz, 1H), 1.61 (d, J = 12.6 Hz, 1H), 1.39 (ddd, J = 13.8, 11.1, 2.6 Hz, 1H), 1.30-1.20 (m, 3H), 0.98 (s, 9H), 0.89-0.79 (m, 2H); MS (APCI+) m/z 591 (M + H)+. |
| Example I-60 | (2S,3S,4S,5S)-3-tert-butyl-1-[(1S,3S)-3-methoxycyclohexane-1-carbonyl]-4-({[2-methoxy-5-(trifluoromethyl)phenyl]methyl}amino)-5-phenylpyrrolidine-2-carboxylic acid | ¹HNMR (400 MHz, dimethyl sulfoxide-d₆) δ ppm 7.52 (s, 2H), 7.47 (dd, J = 8.6, 2.4 Hz, 1H), 7.31 (t, J = 7.5 Hz, 2H), 7.26-7.18 (m, 2H), 7.00 (d, J = 8.6 Hz, 1H), 5.20 (d, J = 7.0 Hz, 1H), 4.46 (d, J = 2.5 Hz, 1H), 3.65 (s, 3H), 3.55 (d, J = 14.3 Hz, 1H), 3.46 (dd, J = 7.0, 2.1 Hz, 1H), 3.38 (d, J = 14.4 Hz, 1H), 3.34 (s, 1H), 2.85 (s, 3H), 2.65 (s, 0H), 2.35 (s, 1H), 1.67-1.55 (m, 2H), 1.47-1.35 (m, 2H), 1.31-1.22 (m, 2H), 0.97 (s, 9H), 0.89-0.78 (m, 3H); MS (APCI+) m/z 591 (M + H)+. |
| Example I-61 | (2S,3S,4S,5S)-4-{[(5-tert-butyl-2-methoxyphenyl)methyl]amino}-1-(cyclohexanecarbonyl)-3-(2-methoxypropan-2-yl)-5-phenylpyrrolidine-2-carboxylic acid | ¹HNMR (400 MHz, dimethyl sulfoxide-d₆) δ ppm 7.62 (s, 2H), 7.39 (t, J = 7.4 Hz, 2H), 7.33 (d, J = 7.2 Hz, 1H), 7.25 (dd, J = 8.7, 2.5 Hz, 1H), 7.06 (d, J = 2.5 Hz, 1H), 6.83 (d, J = 8.6 Hz, 1H), 5.36 (d, J = 7.3 Hz, 1H), 4.48 (d, J = 4.0 Hz, 1H), 3.82 (d, J = 12.6 Hz, 2H), 3.61 (m, 3H), 3.15 (s, 3H), 2.79 (m, 1H), 2.30 (m, 1H), 1.66 (d, J = 10.6 Hz, 2H), 1.52 (bs, 2H), 1.23 (d, J = 1.2 Hz, 12H), 1.21 (s, 3H), 1.18-1.04 (m, 5H), 0.83 (bs, 1H); MS (ESI+) m/z 565 (M + H)+. |
| Example I-62 | (2S,3S,4S,5S)-4-{[(4-tert-butyl-2-methoxyphenyl)methyl]amino}-1-(cyclohexanecarbonyl)-3-(2-methoxypropan-2-yl)-5-phenylpyrrolidine-2-carboxylic acid | ¹HNMR (400 MHz, dimethyl sulfoxide-d₆) δ ppm 7.61 (bs, 2H), 7.39 (t, J = 7.5 Hz, 2H), 7.32 (t, J = 7.3 Hz, 1H), 6.97 (d, J = 7.7 Hz, 1H), 6.91-6.85 (m, 2H), 5.37 (d, J = 7.4 Hz, 1H), 4.47 (d, J = 4.1 Hz, 1H), 3.86 (bs, 1H), 3.75 (d, J = 13.3 Hz, 1H), 3.65 (s, 3H), 3.56 (d, J = 13.4 Hz, 1H), 3.14 (s, 3H), 2.78 (d, J = 4.5 Hz, 1H), 2.30 (m, 1H), 1.66 (d, J = 10.6 Hz, 2H), 1.52 (bs, 2H), 1.26 (d, J = 0.7 Hz, 9H), 1.21 (d, J = 3.0 Hz, 6H), 1.19-1.01 (m, 5H), 0.82 (bs, 1H); MS (ESI+) m/z 565 (M + H)+. |
| Example I-63 | (2S,3S,4S,5S)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid | ¹HNMR (400 MHz, dimethyl sulfoxide-d₆) δ ppm 7.61-7.47 (m, 3H), 7.37-7.22 (m, 4H), 7.05 (d, J = 8.6 Hz, 1H), 5.28 (d, J = 7.2 Hz, 1H), 4.50 (d, J = 3.6 Hz, 1H), 3.69 (s, 3H), 3.52 (d, J = 14.0 Hz, 1H), 2.70 (d, J = 4.5 Hz, 1H), 2.35-2.13 (m, 1H), 1.65 (d, J = 9.3 Hz, 2H), 1.50 (bs, 2H), 1.19 (d, J = 6.2 Hz, 7H), 1.08 (m, 2H), 0.80 (bs, 1H); MS (ESI+) m/z 577 (M + H)+. |

TABLE 1-continued

| Example | Name | Data |
|---|---|---|
| Example I-64 | (2S,3S,4S,5S)-3-tert-butyl-4-{[(5-tert-butyl-2-methoxyphenyl)methyl]amino}-5-phenyl-1-(pyridine-3-carbonyl)pyrrolidine-2-carboxylic acid | LC/MS (ESI+) m/z 544.6 (M + H)+. |
| Example I-65 | (2S,3S,4S,5S)-1-benzoyl-3-tert-butyl-4-{[(5-tert-butyl-2-methoxyphenyl)methyl]amino}-5-phenylpyrrolidine-2-carboxylic acid | LC/MS (ESI+) m/z 543.6 (M + H)+. |
| Example I-66 | (2S,3S,4S,5S)-3-tert-butyl-4-{[(5-tert-butyl-2-methoxyphenyl)methyl]amino}-1-(1,1-dioxo-1$\lambda^6$-thiane-3-carbonyl)-5-phenylpyrrolidine-2-carboxylic acid | LC/MS (ESI+) m/z 599.8 (M + H)+. |
| Example I-67 | (2S,3S,4S,5S)-3-tert-butyl-4-{[(6-cyclobutyl-4-(trifluoromethyl)pyridin-2-yl]amino}-1-(cyclohexanecarbonyl)-5-phenylpyrrolidine-2-carboxylic acid | $^1$HNMR (400 MHz, 120° C., dimethyl sulfoxide-$d_6$: $D_2O$ = 9:1 (v/v)) δ ppm 7.39 (d, J = 7.3 Hz, 2H), 7.20-7.07 (m, 3H), 6.45 (d, J = 1.4 Hz, 1H), 6.20 (s, 1H), 5.36 (d, J = 8.2 Hz, 1H), 5.09 (t, J = 7.7 Hz, 1H), 4.39 (d, J = 6.1 Hz, 1H), 3.52 (q, J = 8.2 Hz, 1H), 2.45-2.38 (m, 1H), 2.37-2.12 (m, 5H), 2.08-1.82 (m, 2H), 1.76-1.60 (m, 2H), 1.55-1.42 (m, 2H), 1.40-0.56 (m, 15H); MS (APCI+) m/z 572.1 (M + H)+. |
| Example I-68 | (2S,3S,4S,5S)-3-tert-butyl-4-{[(5-cyclobutyl-2-methoxyphenyl)methyl]amino}-1-(cyclohexanecarbonyl)-5-phenylpyrrolidine-2-carboxylic acid | $^1$HNMR (400 MHz, 120° C., dimethyl sulfoxide-$d_6$: $D_2O$ = 9:1 (v/v)) δ ppm 7.54 (s, 2H), 7.39 (t, J = 7.4 Hz, 2H), 7.33 (d, J = 7.2 Hz, 1H), 7.14-7.06 (m, 1H), 6.93-6.86 (m, 1H), 6.81 (d, J = 8.4 Hz, 1H), 5.33 (d, J = 7.0 Hz, 1H), 4.53 (s, 1H), 3.81 (d, J = 7.0 Hz, 1H), 3.75 (d, J = 13.5 Hz, 1H), 3.56 (s, 3H), 3.47 (s, 1H), 3.45-3.36 (m, 1H), 2.35-2.23 (m, 3H), 2.06-1.86 (m, 3H), 1.86-1.74 (m, 1H), 1.72-1.44 (m, 4H), 1.37-1.05 (m, 5H), 1.05-0.72 (m, 11H); MS (APCI+) m/z 547.1 (M + H)+. |
| Example I-69 | (2S,3S,4S,5S)-4-{[(5-benzyl-2-methoxypyridin-3-yl)methyl]amino}-3-tert-butyl-1-(cyclohexanecarbonyl)-5-phenylpyrrolidine-2-carboxylic acid | $^1$HNMR (400 MHz, 120° C., dimethyl sulfoxide-$d_6$: $D_2O$ = 9:1 (v/v)) δ ppm 7.88 (d, J = 2.2 Hz, 1H), 7.53-7.48 (m, 2H), 7.38-7.22 (m, 5H), 7.22-7.11 (m, 4H), 5.24 (d, J = 7.0 Hz, 1H), 4.50 (d, J = 2.2 Hz, 1H), 3.80 (s, 2H), 3.68 (s, 3H), 3.64 (d, J = 7.1 Hz, 1H), 3.57 (d, J = 14.1 Hz, 1H), 3.32 (d, J = 14.1 Hz, 1H), 2.39 (s, 1H), 2.22 (s, 1H), 1.61 (d, J = 13.6 Hz, 2H), 1.52-1.47 (m, 2H), 1.25-1.14 (m, 3H), 1.09-1.04 (m, 2H), 0.94 (s, 9H), 0.86-0.65 (m, 1H); MS (APCI+) m/z 584.1 (M + H)+. |
| Example I-70 | (2S,3S,4S,5S)-4-({[5-(butan-2-yl)-2-methoxypyridin-3-yl)methyl]amino)-3-tert-butyl-1-(cyclohexanecarbonyl)-5-phenylpyrrolidine-2-carboxylic acid | $^1$HNMR (400 MHz, 120° C., dimethyl sulfoxide-$d_6$: $D_2O$ = 9:1 (v/v)) δ ppm 7.83 (d, J = 2.4 Hz, 1H), 7.57 (d, J = 7.1 Hz, 2H), 7.35 (dt, J = 27.3, 7.3 Hz, 3H), 7.20 (s, 1H), 5.32 (d, J = 7.1 Hz, 1H), 4.53 (d, J = 2.1 Hz, 1H), 3.77-3.73 (m, 1H), 3.72-3.63 (m, 4H), 3.43-3.34 (m, 1H), 2.55-2.44 (m, 2H), 2.23 (s, 1H), 1.62 (d, J = 12.8 Hz, 2H), 1.56-1.43 (m, 4H), 1.22 (d, J = 11.6 Hz, 3H), 1.16-1.04 (m, 5H), 0.98 (s, 9H), 0.80-0.71 (m, 4H); MS (APCI+) m/z 550.1 (M + H)+. |
| Example I-71 | (2S,3S,4S,5S)-3-tert-butyl-1-(cyclohexanecarbonyl)-4-({[5-(cyclohexylmethyl)-2-methoxypyridin-3-yl]methyl}amino)-5-phenylpyrrolidine-2-carboxylic acid | $^1$HNMR (400 MHz, 120° C., dimethyl sulfoxide-$d_6$: $D_2O$ = 9:1 (v/v)) δ ppm 7.76 (d, J = 2.3 Hz, 1H), 7.54 (s, 2H), 7.41-7.33 (m, 2H), 7.33-7.25 (m, 1H), 7.11 (s, 1H), 5.27 (d, J = 7.0 Hz, 1H), 4.51 (d, J = 2.2 Hz, 1H), 3.69-3.64 (m, 4H), 3.59 (d, J = 14.2 Hz, 1H), 3.36 (d, J = 14.2 Hz, 1H), 2.42 (s, 1H), 2.33 (d, J = 6.9 Hz, 2H), 2.29-2.20 (m, 1H), 1.71-1.35 (m, 10H), 1.28-1.02 (m, 8H), 0.97 (s, 9H), 0.97-0.68 (m, 3H); MS (APCI+) m/z 590.2 (M + H)+. |
| Example I-72 | (2S,3S,4S,5S)-3-tert-butyl-1-(cyclohexanecarbonyl)-4-{[(5-cyclohexyl-2-methoxypyridin-3-yl)methyl]amino}-5-phenylpyrrolidine-2-carboxylic acid | $^1$HNMR (400 MHz, 120° C., dimethyl sulfoxide-$d_6$: $D_2O$ = 9:1 (v/v)) δ ppm 7.85 (d, J = 2.4 Hz, 1H), 7.56 (d, J = 7.1 Hz, 2H), 7.42-7.35 (m, 2H), 7.35-7.27 (m, 1H), 7.20 (s, 1H), 5.31 (d, J = 6.9 Hz, 1H), 4.52 (d, J = 2.1 Hz, 1H), 3.72 (d, J = 7.1 Hz, 1H), 3.70-3.61 (m, 4H), 3.37 (d, J = 14.1 Hz, 1H), 2.47-2.36 (m, 2H), 2.26-2.21 (m, 1H), 1.82-1.56 (m, 7H), 1.50 (s, 2H), 1.44-1.14 (m, 6H), 1.07 (s, 4H), 0.98 (s, 9H), 0.90-0.69 (m, 1H); MS (APCI+) m/z 576.1 (M + H)+. |
| Example I-73 | (2S,3S,4S,5S)-3-tert-butyl-1-(cyclohexanecarbonyl)-4-{[(5-cyclopentyl-2-methoxypyridin-3-yl)methyl]amino}-5-phenylpyrrolidine-2-carboxylic acid | $^1$HNMR (400 MHz, 120° C., dimethyl sulfoxide-$d_6$: $D_2O$ = 9:1 (v/v)) δ ppm 7.87 (d, J = 2.3 Hz, 1H), 7.64-7.50 (m, 2H), 7.44-7.36 (m, 2H), 7.36-7.27 (m, 1H), 7.26-7.20 (m, 1H), 5.32 (d, J = 7.0 Hz, 1H), 4.53 (d, J = 2.1 Hz, 1H), 3.75 (d, J = 7.0 Hz, 1H), 3.72-3.61 (m, 4H), 3.38 (d, J = 14.0 Hz, 1H), 2.89 (p, J = 8.5 Hz, 1H), 2.46 (s, 1H), 2.31-2.13 (m, 1H), 1.95 (s, 2H), 1.85-1.56 (m, |

TABLE 1-continued

| | | |
|---|---|---|
| | | 6H), 1.46 (d, J = 24.6 Hz, 4H), 0.98 (s, 14H), 0.92-0.59 (m, 1H); MS (APCI+) m/z 561.9 (M + H)+. |
| Example I-74 | (2S,3S,4S,5S)-3-tert-butyl-1-(cyclohexanecarbonyl)-4-({[5-(2-ethylbutyl)-2-methoxypyridin-3-yl]methyl}amino)-5-phenylpyrrolidine-2-carboxylic acid | $^1$HNMR (400 MHz, 120° C., dimethyl sulfoxide-d$_6$: D$_2$O = 9:1 (v/v)) δ ppm 7.78 (d, J = 2.3 Hz, 1H), 7.60-7.47 (m, 2H), 7.42-7.33 (m, 2H), 7.33-7.25 (m, 1H), 7.16-7.09 (m, 1H), 5.28 (d, J = 7.0 Hz, 1H), 4.51 (d, J = 2.3 Hz,1H), 3.68 (s, 4H), 3.60 (d, J = 14.2 Hz, 1H), 3.36 (d, J = 14.0 Hz, 1H), 2.42 (s, 1H), 2.37 (d, J = 6.9 Hz, 2H), 2.32-2.14 (m, 1H), 1.73-1.32 (m, 5H), 1.29-1.01 (m, 9H), 0.98 (s, 9H), 0.88-0.67 (m, 7H); MS (APCI+) m/z 578.0 (M + H)+. |
| Example I-75 | (2S,3S,4S,5S)-3-tert-butyl-1-(cyclohexanecarbonyl)-4-({[2-methoxy-5-(1-phenylethyl)pyridin-3-yl]methyl}amino)-5-phenylpyrrolidine-2-carboxylic acid | $^1$HNMR (400 MHz, 120° C., dimethyl sulfoxide-d$_6$: D$_2$O = 9:1 (v/v)) δ ppm 7.95-7.86 (m, 1H), 7.60-7.47 (m, 2H), 7.34 (t, J = 7.3 Hz, 2H), 7.31-7.23 (m, 3H), 7.23-7.09 (m, 4H), 5.25 (d, J = 7.0 Hz, 1H), 4.50 (d, J = 2.1 Hz, 1H), 4.04 (d, J = 7.0 Hz, 1H), 3.68 (s, 5H), 3.33 (d, J = 14.3 Hz, 1H), 2.40 (s, 1H), 2.29-2.15 (m, 1H), 1.71-1.57 (m, 2H), 1.57-1.42 (m, 5H), 1.31-0.98 (m, 5H), 0.94 (d, J = 1.5 Hz, 9H), 0.85-0.63 (m, 1H); MS (APCI+) m/z 598.1 (M + H)+. |
| Example I-76 | (2S,3S,4S,5S)-3-tert-butyl-1-(cyclohexanecarbonyl)-4-({[2-methoxy-5-(2-methylpropyl)pyridin-3-yl]methyl}amino)-5-phenylpyrrolidine-2-carboxylic acid | $^1$HNMR (400 MHz, 120° C., dimethyl sulfoxide-d$_6$: D$_2$O = 9:1 (v/v)) δ ppm 7.79 (d, J = 2.3 Hz, 1H), 7.56 (s, 2H), 7.44-7.35 (m, 2H), 7.35-7.26 (m, 1H), 7.14 (s, 1H), 5.31 (d, J = 7.1 Hz, 1H), 4.52 (d, J = 2.1 Hz, 1H), 3.74 (d, J = 7.2 Hz, 1H), 3.69 (s, 3H), 3.64 (d, J = 14.1 Hz, 1H), 3.37 (d, J = 14.1 Hz, 1H), 2.45 (s, 1H), 2.32 (d, J = 7.0 Hz, 2H), 2.30-2.14 (m, 1H), 1.76 (dq, J = 13.4, 6.8 Hz, 1H), 1.71-1.41 (m, 4H), 1.30-1.00 (m, 5H), 0.98 (s, 9H), 0.92-0.66 (m, 7H); MS (APCI+) m/z 550.1 (M + H)+. |
| Example I-77 | (2S,3S,4S,5S)-3-tert-butyl-4-[({5-[(3-cyanophenyl)methyl]-2-methoxypyridin-3-yl}methyl)amino]-1-(cyclohexanecarbonyl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.97-7.88 (m, 1H), 7.66-7.47 (m, 6H), 7.40-7.32 (m, 2H), 7.32-7.24 (m, 1H), 7.22-7.13 (m, 1H), 5.25 (d, J = 6.9 Hz, 1H), 4.50 (d, J = 2.1 Hz, 1H), 3.88 (s, 2H), 3.69 (s, 3H), 3.65-3.54 (m, 2H), 3.33 (d, J = 14.3 Hz, 1H), 2.39 (s, 1H), 2.30-2.12 (m, 1H), 1.72-1.41 (m, 4H), 1.31-0.98 (m, 5H), 0.93 (s, 9H), 0.89-0.64 (m, 1H); MS (APCI+) m/z 609.0 (M + H)+. |
| Example I-78 | (2S,3S,4S,5S)-3-tert-butyl-4-{[(4-methoxy[1,1'-biphenyl]-3-yl)methyl]amino}-1-[(1R,3R)-3-methoxycyclohexane-1-carbonyl]-5-phenylpyrrolidine-2-carboxylic acid | $^1$HNMR (400 MHz, dimethyl sulfoxide-d$_6$) δ ppm 7.60 (d, J = 7.4 Hz, 2H), 7.54-7.46 (m, 3H), 7.45-7.34 (m, 4H), 7.33-7.25 (m, 3H), 6.98 (d, J = 8.5 Hz, 1H), 5.31 (d, J = 7.0 Hz, 1H), 4.53 (d, J = 2.1 Hz, 1H), 3.87 (d, J = 7.2 Hz, 1H), 3.77 (d, J = 13.7 Hz, 1H), 3.67 (s, 3H), 3.48 (d, J = 13.7 Hz, 2H), 3.44-3.39 (m, 2H), 3.18 (s, 3H), 2.68-2.57 (m, 1H), 2.54 (s, 1H), 1.75 (d, J = 13.8 Hz, 1H), 1.62 (d, J = 12.4 Hz, 1H), 1.44-1.32 (m, 1H), 1.33-1.18 (m, 3H), 1.01 (s, 9H); MS (APCI+) m/z 599 (M + H)+. |
| Example I-79 | (2S,3S,4S,5S)-3-tert-butyl-1-[(1R,3R)-3-methoxycyclohexane-1-carbonyl]-4-({[2-methoxy-5-(trifluoromethyl)pyridin-3-yl]methyl}amino)-5-phenylpyrrolidine-2-carboxylic acid | $^1$HNMR (400 MHz, dimethyl sulfoxide-d$_6$) δ ppm 8.33 (t, J = 1.6 Hz, 1H), 7.59 (t, J = 3.6 Hz, 3H), 7.33 (t, J = 7.5 Hz, 2H), 7.26 (t, J = 7.3 Hz, 1H), 5.22 (d, J = 7.1 Hz, 1H), 4.49 (d, J = 2.4 Hz, 1H), 3.82 (s, 3H), 3.64 (d, J = 7.0 Hz, 1H), 3.59 (d, J = 14.8 Hz, 1H), 3.41 (d, J = 3.5 Hz, 1H), 3.34 (d, J = 14.8 Hz, 1H), 3.18 (s, 3H), 2.60 (s, 1H), 2.41 (s, 1H), 1.75 (d, J = 13.7 Hz, 1H), 1.61 (d, J = 12.6 Hz, 1H), 1.45-1.34 (m, 1H), 1.31-1.16 (m, 4H), 1.16-1.05 (m, 1H), 0.99 (s, 9H); MS (APCI+) m/z 592 (M + H)+. |
| Example I-80 | (2S,3S,4S,5S)-3-tert-butyl-4-{[(5-tert-butyl-2-hydroxyphenyl)methyl]amino}-1-(cyclohexanecarbonyl)-5-phenylpyrrolidine-2-carboxylic acid | $^1$HNMR (400 MHz, DMSO-d$_6$, 120° C.) δ ppm 7.63-7.52 (m, 2H), 7.36 (t, J = 7.4 Hz, 2H), 7.29 (t, J = 7.3 Hz, 1H), 7.05 (dd, J = 8.4, 2.5 Hz, 1H), 6.88 (d, J = 2.5 Hz, 1H), 6.62 (d, J = 8.4 Hz, 1H), 5.33 (d, J = 7.1 Hz, 1H), 4.51 (d, J = 2.1 Hz, 1H), 3.75 (d, J = 7.2 Hz, 1H), 3.70 (d, J = 13.6 Hz, 1H), 3.43 (d, J = 13.6 Hz, 1H), 2.36-2.17 (m, 2H), 1.64 (d, J = 10.0 Hz, 2H), 1.51 (s, 2H), 1.19 (s, 15H), 0.98 (s, 9H); MS (ESI+) m/z 535 (M + H)+. |
| Example I-81 | (2S,3S,4S,5S)-3-tert-butyl-4-{[(5-tert-butyl-2-methoxyphenyl)methyl]amino}-5-phenyl-1-{[(propan-2-yl)oxy]carbonyl}pyrrolidine-2-carboxylic acid | $^1$HNMR (400 MHz, DMSO-d$_6$, 120° C.) δ ppm $^1$HNMR (400 MHz, DMSO-d$_6$) δ ppm 7.57-7.49 (m, 2H), 7.37-7.31 (m, 2H), 7.29-7.24 (m, 1H), 7.20 (dd, J = 8.6, 2.6 Hz, 1H), 7.01 (d, J = 2.5 Hz, 1H), 6.79 (d, J = 8.6 Hz, 1H), 5.11 (d, J = 6.8 Hz, 1H), 4.63 (hept, J = 6.2 Hz, 1H), 4.36 (d, J = 2.1 Hz, 1H), 3.69 (dd, J = 10.2, 3.3 Hz, 2H), 3.56 (s, 3H), 3.40 (d, J = 13.6 Hz, 1H), 2.32-2.23 (m, 1H), 1.21 (d, J = 0.5 Hz, 9H), 1.05 (d, J = 6.2 Hz, 3H), 1.00 (s, 9H), 0.87 (d, J = 6.2 Hz, 3H); MS (ESI+) m/z 525 (M + H)+. |
| Example I-82 | (2S,3S,4S,5S)-3-tert-butyl-4-(5-tert-butyl-2-methoxyanilino)-1- | $^1$HNMR (400 MHz, dimethyl sulfoxide-d$_6$) δ ppm 7.52 (d, J = 7.5 Hz, 2H), 7.15 (t, J = 7.4 Hz, 2H), 7.10 (d, J = 7.1 Hz, 1H), 6.59 (d, J = 2.2 Hz, 1H), 6.50 (d, J = 8.3 |

TABLE 1-continued

| | | |
|---|---|---|
| | (cyclohexanecarbonyl)-5-phenylpyrrolidine-2-carboxylic acid | Hz, 1H), 6.43 (dd, J = 8.3, 2.3 Hz, 1H), 5.32 (d, J = 7.3 Hz, 1H), 4.44 (d, J = 4.3 Hz, 1H), 4.40 (s, 1H), 3.45 (s, 3H), 2.95 (d, J = 4.5 Hz, 1H), 2.30 (d, J = 4.5 Hz, 1H), 2.22 (s, 1H), 1.74-1.25 (m, 8H), 1.23 (s, 9H), 1.19-1.07 (m, 2H), 1.04 (s, 9H); MS (ESI+) m/z 535.3 (M + H)+. |
| Example I-83 | (2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-phenylpyrrolidine-2-carboxylic acid | LC/MS (ESI+) m/z 599.9 (M + H)+. |
| Example I-84 | (2S,3S,4S,5S)-3-tert-butyl-4-({[2-methoxy-5-(trifluoromethyl)phenyl]methyl}amino)-1-[(oxan-2-yl)acetyl]-5-phenylpyrrolidine-2-carboxylic acid | LC/MS (ESI+) m/z 577.5 (M + H)+. |
| Example I-85 | (2S,3S,4S,5S)-3-tert-butyl-1-(cyclohexanecarbonyl)-4-[({5-[(dimethylamino)methyl]-2-methoxyphenyl}methy)amino]-5-phenylpyrrolidine-2-carboxylic acid | 1HNMR (400 MHz, dimethyl sulfoxide-d6) δ ppm 7.52 (s, 2H), 7.39-7.29 (m, 2H), 7.26 (d, J = 7.3 Hz, 1H), 7.13 (d, J = 8.2 Hz, 1H), 6.98 (s, 1H), 6.80 (dd, J = 8.3, 2.8 Hz, 1H), 5.19 (dd, J = 7.0, 2.6 Hz, 1H), 4.47, (s, 1H), 3.54 (d, J = 2.6 Hz, 3H), 3.52-3.35 (m, 5H), 2.34 (s, 1H), 2.26 (d, J = 3.0 Hz, 6H), 1.58 (d, J = 50.2 Hz, 4H), 1.31-1.03 (m, 6H), 0.97 (d, J = 2.8 Hz, 9H); MS (ESI+) m/z 550.3 (M + H)+. |
| Example I-86 | (2S,3S,4S,5S)-3-tert-butyl-1-(cyclohexanecarbonyl)-4-({[2-methoxy-5-(pentafluoro-λ6-sulfanyl)phenyl]methyl}amino)-5-phenylpyrrolidine-2-carboxylic acid | 1HNMR (400 MHz, dimethyl sulfoxide-d6, 120° C.) δ ppm 7.67 (dd, J = 9.1, 2.9 Hz, 1H), 7.61-7.54 (m, 2H), 7.48 (d, J = 2.9 Hz, 1H), 7.35 (t, J = 7.5 Hz, 2H), 7.27 (t, J = 7.3 Hz, 1H), 7.03 (d, J = 9.1 Hz, 1H), 5.28 (d, J = 7.0 Hz, 1H), 4.50 (d, J = 2.4 Hz, 1H), 3.73-3.66 (m, 4H), 3.63 (d, J = 7.5 Hz, 1H), 3.40 (d, J = 14.4 Hz, 1H), 2.42 (s, 1H), 2.32-2.16 (m, 1H), 1.67-1.59 (m, 2H), 1.56-1.44 (m, 2H), 1.30-1.03 (m, 6H), 0.98 (s, 9H); MS (ESI+) m/z 619 (M + H)+. |
| Example I-87 | (2S,3S,4S,5S)-1-(cyclohexanecarbonyl)-4-{[(4-methoxy[1,1'-biphenyl]-3-yl)methyl]amino}-3-(2-methoxypropan-2-yl)-5-phenylpyrrolidine-2-carboxylic acid | 1HNMR (400 MHz, dimethyl sulfoxide-d6) δ ppm 7.61 (s, 2H), 7.53-7.48 (m, 3H), 7.44-7.33 (m, 4H), 7.32-7.26 (m, 3H), 6.99 (d, J = 8.5 Hz, 1H), 5.35 (d, J = 7.3 Hz, 1H), 4.51 (d, J = 3.8 Hz, 1H), 3.82 (d, J = 13.2 Hz, 2H), 3.68 (s, 3H), 3.63 (d, J = 13.6 Hz, 1H), 3.14 (s, 3H), 2.78 (s, 1H), 2.28 (bs, 1H), 1.66 (d, J = 10.2 Hz, 2H), 1.51 (d, J = 10.0 Hz, 2H), 1.27 (m, 1H), 1.22 (d, J = 4.0 Hz, 6H), 1.13 (m, 4H), 0.83 (bs, 1H); MS (ESI+) m/z 585 (M + H)+. |
| Example I-88 | (2S,3S,4S,5S)-3-tert-butyl-4-({[5-(2-cyanopropan-2-yl)-2-methoxyphenyl]methyl}amino)-1-(cyclohexanecarbonyl)-5-phenylpyrrolidine-2-carboxylic acid | 1HNMR (400 MHz, dimethyl sulfoxide-d6) δ ppm 7.52 (d, J = 2.8 Hz, 2H), 7.38-7.18 (m, 4H), 7.07 (d, J = 2.6 Hz, 1H), 6.86 (d, J = 8.6 Hz, 1H), 5.19 (d, J = 6.9 Hz, 1H), 4.47 (d, J = 2.5 Hz, 1H), 3.65-3.57 (m, 1H), 3.55 (s, 3H), 3.48 (dd, J = 6.9, 2.1 Hz, 1H), 3.41 (s, 1H), 2.36 (s, 1H), 1.69-1.61 (m, 3H), 1.60 (s, 6H), 1.51 (s, 2H), 1.33-1.02 (m, 6H), 0.98 (s, 9H); MS (ESI+) m/z 560.2 (M + H)+. |
| Example I-89 | (2S,3S,4S,5S)-3-tert-butyl-1-(cyclohexanecarbonyl)-4-({[4-(2-hydroxypropan-2-yl)-2-methoxyphenyl]methyl}amino)-5-phenylpyrrolidine-2-carboxylic acid | 1HNMR (400 MHz, dimethyl sulfoxide-d6) δ ppm 7.48 (s, 2H), 7.33 (d, J = 7.3 Hz, 2H), 7.25 (t, J = 7.3 Hz, 1H), 6.96 (s, 1H), 6.86 (d, J = 1.5 Hz, 2H), 5.20 (d, J = 6.8 Hz, 1H), 4.47 (d, J = 2.3 Hz, 1H), 4.39 (s, 1H), 3.52 (d, J = 3.1 Hz, 5H), 3.37 (d, J = 13.4 Hz, 1H), 2.63 (s, 1H), 2.36 (s, 1H), 1.68-1.47 (m, 4H), 1.40 (s, 6H), 1.32-1.04 (m, 5H), 0.99 (s, 9H); MS (ESI+) m/z 551.2 (M + H)+. |
| Example I-90 | (2S,3S,4S,5S)-3-tert-butyl-4-{[(5-tert-butyl-2-methoxyphenyl)methyl]amino}-1-(5-cyano-2-methoxybenzoyl)-5-phenylpyrrolidine-2-carboxylic acid | 1HNMR (400 MHz, 120° C., dimethyl sulfoxide-d6: D2O = 9:1 (v/v)) δ ppm 7.75-6.88 (m, 10H), 6.80 (d, J = 8.6 Hz, 1H), 5.44-5.19 (m, 1H), 4.67-4.27 (m, 1H), 3.93-3.70 (m, 5H), 3.56 (s, 3H), 3.40 (d, J = 13.7 Hz, 1H), 2.54 (s, 1H), 1.19 (s, 9H), 1.04 (s, 9H); MS (APCI+) m/z 598.1 (M + H)+. |
| Example I-91 | (2S,3S,4S,5S)-3-tert-butyl-4-{[(5-tert-butyl-2-methoxyphenyl)methyl]amino}-1-[(1,3-dihydro-2H-isoindol-2-yl)acetyl]-5-phenylpyrrolidine-2-carboxylic acid | 1HNMR (400 MHz, 120° C., dimethyl sulfoxide-d6: D2O = 9:1 (v/v)) δ ppm 7.49 (s, 2H), 7.35 (d, J = 25.5 Hz, 7H), 7.24-7.17 (m, 1H), 7.05-6.97 (m, 1H), 6.77 (d, J = 8.6 Hz, 1H), 5.32 (d, J = 6.8 Hz, 1H), 4.69-4.46 (m, 5H), 4.39-4.24 (m, 1H), 3.77-3.61 (m, 2H), 3.57-3.40 (m, 5H), 2.57 (s, 1H), 1.20 (s, 9H), 1.01 (s, 9H); MS (APCI+) m/z 598.1 (M + H)+. |
| Example I-92 | (2S,3S,4S,5S)-3-tert-butyl-4-{[(5-tert-butyl-2-methoxyphenyl)methyl]amino}-5-phenyl-1-[(thiophen-3- | 1HNMR (400 MHz, 120° C., dimethyl sulfoxide-d6: D2O = 9:1 (v/v)) δ ppm 7.53 (s, 2H), 7.39 (t, J = 7.4 Hz, 2H), 7.36-7.29 (m, 2H), 7.23 (dd, J = 8.6, 2.5 Hz, 1H), 7.06-7.00 (m, 2H), 6.90-6.71 (m, 2H), 5.31 (d, J = 7.0 |

TABLE 1-continued

| | | |
|---|---|---|
| | yl)acetyl]pyrrolidine-2-carboxylic acid | Hz, 1H), 4.56 (s, 1H), 3.82-3.72 (m, 2H), 3.54 (s, 3H), 3.50-3.44 (m, 3H), 2.48 (s, 1H), 1.20 (s, 9H), 0.90 (s, 9H); MS (APCI+) m/z 563.0 (M + H)+. |
| Example I-93 | (2S,3S,4S,5S)-3-tert-butyl-4-{(5-tert-butyl-2-methoxyphenyl)methyl]amino}-1-(8-fluoroquinoline-2-carbonyl)-5-phenylpyrrolidine-2-carboxylic acid | ¹HNMR (400 MHz, 120° C., dimethyl sulfoxide-d₆: D₂O = 9:1 (v/v)) δ ppm 8.35-8.20 (m, 1H), 7.78-6.89 (m, 11H), 6.78 (d, J = 8.7 Hz, 1H), 5.90 (m, 1H), 5.10 (m, 1H), 3.85 (s, 1H), 3.70 (d, J = 13.7 Hz, 1H), 3.54 (s, 3H), 3.38 (d, J = 13.8 Hz, 1H), 2.60 (s, 1H), 1.19 (s, 9H), 1.10 (s, 9H); MS (APCI+) m/z 612.1 (M + H)+. |
| Example I-94 | (2S,3S,4S,5S)-3-tert-butyl-1-(cyclohexanecarbonyl)-4-({[2-methoxy-5-(2-methylpropyl)phenyl]methyl}amino)-5-phenylpyrrolidine-2-carboxylic acid | ¹HNMR (400 MHz, 120° C., dimethyl sulfoxide-d₆: D₂O = 9:1 (v/v)) δ ppm 7.66-7.48 (m, 2H), 7.44-7.35 (m, 2H), 7.35-7.28 (m, 1H), 7.01 (dd, J = 8.3, 2.2 Hz, 1H), 6.82-6.75 (m, 2H), 5.33 (d, J = 7.0 Hz, 1H), 4.52 (d, J = 1.9 Hz, 1H), 3.81 (d, J = 7.1 Hz, 1H), 3.73 (d, J = 13.5 Hz, 1H), 3.56 (s, 3H), 3.45 (d, J = 13.6 Hz, 1H), 2.48 (s, 1H), 2.37-2.22 (m, 3H), 1.82-1.69 (m, 1H), 1.69-1.43 (m, 4H), 1.34-1.03 (m, 5H), 0.99 (s, 9H), 0.92-0.69 (m, 7H); MS (APCI+) m/z 549.1 (M + H)+. |
| Example I-95 | (2S,3S,4S,5S)-3-tert-butyl-4-{{[(5-tert-butyl-2-methoxyphenyl)methyl]amino}-1-[(2R*)-2-cyclopropyl-2-methoxyacetyl]-5-phenylpyrrolidine-2-carboxylic acid | LC/MS (ESI+) m/z 551.6 (M + H)+. |
| Example I-96 | (2S,3S,4S,5S)-3-tert-butyl-4-{{[(5-tert-butyl-2-methoxyphenyl)methyl]amino}-1-[(2S*)-2-cyclopropyl-2-methoxyacetyl]-5-phenylpyrrolidine-2-carboxylic acid | ¹HNMR (400 MHz, Chloroform-d) δ ppm 7.29-7.44 (m, 4H), 7.21 (br. s., 2H), 7.08 (d, J = 2.4 Hz, 1H), 6.67 (d, J = 8.7 Hz, 1H), 5.32 (d, J = 6.3 Hz, 1H), 4.87 (s, 1H), 4.10 (d, J = 13.8 Hz, 1H), 3.90 (d, J = 9.0 Hz, 1H), 3.56 (d, J = 13.8 Hz, 1H), 3.52 (s, 3H), 3.36 (d, J = 6.3 Hz, 1H), 3.27 (s, 3H), 2.45 (s, 1H), 1.27 (s, 9H), 1.14-1.24 (m, 1H), 1.07 (s, 9H), 0.63-0.73 (m, 1H), 0.53-0.63 (m, 1H), 0.41-0.51 (m, 1H), 0.30-0.40 (m, 1H); LC/MS (ESI+) m/z 551.6 (M + H)+. |
| Example I-97 | (2S,3S,4S,5S)-3-tert-butyl-1-(cyclohexanecarbonyl)-4-[({2-methoxy-5-[(1S,3s)-tricyclo[3.3.1.1³,⁷]decan-1-yl]phenyl}methyl)amino]-5-phenylpyrrolidine-2-carboxylic acid | ¹HNMR (400 MHz, dimethyl sulfoxide-d₆, 120° C.) δ ppm 7.59 (d, J = 7.2 Hz, 2H), 7.40 (t, J = 7.5 Hz, 2H), 7.32 (t, J = 7.3 Hz, 1H), 7.21 (dd, J = 8.6, 2.5 Hz, 1H), 7.01 (d, J = 2.5 Hz, 1H), 6.83 (d, J = 8.6 Hz, 1H), 5.37 (d, J = 6.9 Hz, 1H), 4.53 (d, J = 2.0 Hz, 1H), 3.85 (d, J = 7.1 Hz, 1H), 3.79 (d, J = 13.5 Hz, 1H), 3.59 (s, 3H), 3.45 (d, J = 13.5 Hz, 1H), 2.54 (s, 1H), 2.35-2.17 (m, 1H), 2.05 (s, 3H), 1.83-1.71 (m, 12H), 1.71-1.58 (m, 2H), 1.51 (s, 2H), 1.30-1.04 (m, 6H), 1.00 (s, 9H); MS (ESI+) m/z 627 (M + H)+. |
| Example I-98 | (2S,3S,4S,5S)-3-tert-butyl-4-{(5-tert-butyl-2-methoxyphenyl)methyl]amino}-1{(1H-imidazol-4-yl)acetyl]-5-phenylpyrrolidine-2-carboxylic acid | ¹HNMR (400 MHz, 120° C., dimethyl sulfoxide-d₆: D₂O = 9:1 (v/v)) δ ppm 8.65 (s, 1H), 7.60-7.45 (m, 2H), 7.42-7.28 (m, 3H), 7.24-7.15 (m, 2H), 7.04-6.99 (m, 1H), 6.78 (d, J = 8.7 Hz, 1H), 5.37-5.30 (m, 2H), 4.57 (d, J = 2.0 Hz, 1H), 3.82-3.64 (m, 3H), 3.58-3.38 (m, 4H), 2.50 (s, 1H), 1.20 (s, 9H), 1.00 (s, 9H); MS (APCI+) m/z 547.1 (M + H)+. |
| Example I-99 | (2S,3S,4S,5S)-3-tert-butyl-4-{[(5-tert-butyl-2-methoxyphenyl)methyl]amino}-1-[(1-hydroxycyclopenty)acetyl]-5-phenylpyrrolidine-2-carboxylic acid | ¹HNMR (400 MHz, 120° C., dimethyl sulfoxide-d₆: D₂O = 9:1 (v/v)) δ ppm 7.55-7.50 (m, 2H), 7.38 (t, J = 7.5 Hz, 2H), 7.35-7.27 (m, 1H), 7.23 (dd, J = 8.6, 2.5 Hz, 1H), 7.02 (d, J = 2.5 Hz, 1H), 6.80 (d, J = 8.6 Hz, 1H), 5.36-5.33 (m, 1H), 4.60 (d, J = 2.0 Hz, 1H), 3.79-3.70 (m, 2H), 3.57-3.52 (m, 3H), 3.47 (d, J = 13.6 Hz, 1H), 2.51 (s, 1H), 2.43 (s, 2H), 1.68-1.32 (m, 8H), 1.20 (s, 9H), 1.00 (s, 9H); MS (APCI+) m/z 565.2 (M + H)+. |
| Example I-100 | (2S,3S,4S,5S)-1-[(azepan-1-yl)acetyl]-3-tert-butyl-4-{[(5-tert-butyl-2-methoxyphenyl)methyl]amino}-5-phenylpyrrolidine-2-carboxylic acid | ¹HNMR (400 MHz, 120° C., dimethyl sulfoxide-d₆: D₂O = 9:1 (v/v)) δ ppm 7.64-7.27 (m, 5H), 7.24-7.17 (m, 1H), 6.99 (m, 1H), 6.77 (d, J = 8.5 Hz, 1H), 5.30 (d, J = 6.8 Hz, 1H), 4.61-4.46 (m, 1H), 4.23-4.02 (m, 1H), 3.81-3.59 (m, 2H), 3.56-3.41 (m, 4H), 3.27-3.11 (m, 4H), 2.58 (s, 1H), 1.67 (d, J = 68.1 Hz, 9H), 1.20 (s, 9H), 1.00 (s, 9H); MS (APCI+) m/z 577.9 (M + H)+. |
| Example I-101 | (2S,3S,4S,5S)-3-tert-butyl-4-{[(5-tert-butyl-2-methoxyphenyl)methyl]amino}-1-(1-ethyl-4-oxo-1,4-dihydropyridine-3-carbonyl)-5-phenylpyrrolidine-2-carboxylic acid | ¹HNMR (400 MHz, 120° C., dimethyl sulfoxide-d₆: D₂O = 9:1 (v/v)) δ ppm 7.54-7.16 (m, 8H), 7.03 (d, J = 2.5 Hz, 1H), 6.83 (d, J = 8.6 Hz, 1H), 6.09 (d, J = 7.3 Hz, 1H), 5.69-5.59 (m, 1H), 4.59 (d, J = 2.0 Hz, 1H), 4.00-3.90 (m, 1H), 3.79 (d, J = 13.5 Hz, 1H), 3.75-3.62 (m, 2H), 3.60 (s, 3H), 3.40 (d, J = 13.4 Hz, 1H), 2.54 (s, 1H), 1.20 (s, 9H), 1.14 (t, J = 7.1 Hz, 3H), 1.06 (s, 9H); MS (APCI+) m/z 588.1 (M + H)+. |
| Example I-102 | (2S,3S,4S,5S)-3-tert-butyl-4-{[(5-tert-butyl-2-methoxyphenyl)methyl]amino}-1-(4-methyl-4H-furo[3,2-b]pyrrole-5-carbonyl)-5- | ¹HNMR (400 MHz, 120° C., dimethyl sulfoxide-d₆: D₂O = 9:1 (v/v)) δ ppm 7.59-7.51 (m, 3H), 7.36-7.29 (m, 2H), 7.29-7.18 (m, 2H), 7.08-7.03 (m, 1H), 6.82 (d, J = 8.6 Hz, 1H), 6.57 (d, J = 2.2 Hz, 1H), 6.45 (s, 1H), 5.63 (d, J = 6.9 Hz, 1H), 4.58 (s, 1H), 3.86 (d, J = 6.9 |

TABLE 1-continued

| | | |
|---|---|---|
| | phenylpyrrolidine-2-carboxylic acid | Hz, 1H), 3.79 (d, J = 13.6 Hz, 1H), 3.61-3.53 (m, 6H), 3.47 (d, J = 13.5 Hz, 1H), 2.57 (s, 1H), 1.21 (s, 9H), 0.99 (s, 9H); MS (APCI+) m/z 586.1 (M + H)+. |
| Example I-103 | (2S,3S,4S,5S)-3-tert-butyl-4-{[(5-tert-butyl-2-methoxyphenyl)methyl]amino}-1-2-(4-chloro-1H-pyrazol-1-yl)propanoyl]-5-phenylpyrrolidine-2-carboxylic acid | $^1$HNMR (400 MHz, 120° C., dimethyl sulfoxide-d$_6$: D$_2$O = 9:1 (v/v), asterisk denotes minor diastereomer peak) δ ppm 7.84-7.26 (m, 7H), 7.25-7.15 (m, 1H), 7.06-6.95 (m, 1H), 6.82-6.72 (m, 1H), 5.37 (d, J = 7.1 Hz, 1H), 5.28-5.19* (m, 1H), 4.87-4.69* (m, 1H), 4.53-4.40 (m, 1H), 3.87-3.58 (m, 2H), 3.58-3.32 (m, 4H), 2.63-2.53* (m, 1H), 1.51* (d, J = 6.8 Hz, 2H), 1.28-1.14 (m, 10H), 0.98-0.83 (m, 9H); MS (APCI+) m/z 595.0 (M + H)+. |
| Example I-104 | (2S,3S,4S,5S)-3-tert-butyl-4-{[(5-tert-butyl-2-methoxyphenyl)methyl]amino}-5-phenyl-1-[(2R*,3R*)-3-(propan-2-yl)oxolane-2-carbonyl]pyrrolidine-2-carboxylic acid | LC/MS (ESI+) m/z 579.9 (M + H)+. |
| Example I-105 | (2S,3S,4S,5S)-3-tert-butyl-4-({[2-methoxy-5-(trifluoromethyl)phenyl]methyl}amino)-5-phenyl-1-(2R*,3R*)-3-(propan-2-yl)oxolane-2-carbonyl]pyrrolidine-2-carboxylic acid | LC/MS (ESI+) m/z 591.7 (M + H)+. |
| Example I-106 | (2S,3S,4S,5S)-3-tert-butyl-4-({[2-methoxy-5-(trifluoromethyl)phenyl]methyl}amino)-5-phenyl-1-[(2S*,3S*)-3-(propan-2-yl)oxolane-2-carbonyl]pyrrolidine-2-carboxylic acid | LC/MS (ESI+) m/z 591.7 (M + H)+. |
| Example I-107 | (2S,3S,4S,5S)-3-tert-butyl-4-{[(5-tert-butyl-2-methoxyphenyl)methyl]amino}-1-[(3aR*,6aS*)-hexahydro-1H-cyclopenta[c]furan-1-carbonyl]-5-phenylpyrrolidine-2-carboxylic acid | LC/MS (ESI+) m/z 577.9 (M + H)+. |
| Example I-108 | (2S,3S,4S,5S)-3-tert-butyl-1-[(3aR*,6aS*)-hexahydro-1H-cyclopenta[c]furan-1-carbonyl]-4-({[2-methoxy-5-(trifluoromethyl)phenyl]methyl}amino)-5-phenylpyrrolidine-2-carboxylic acid | LC/MS (ESI+) m/z 589.5 (M + H)+. |
| Example I-109 | (2S,3S,4S,5S)-3-tert-butyl-1-(cyclohexanecarbonyl)-5-(4-fluorophenyl)-4-({[2-methoxy-5-(propan-2-yl)phenyl]methyl}amino)pyrrolidine-2-carboxylic acid | $^1$HNMR (400 MHz, dimethyl sulfoxide-d$_6$) δ ppm 7.55 (s, 2H), 7.09 (t, J = 8.7 Hz, 2H), 7.00 (dd, J = 8.4, 2.4 Hz, 1H), 6.80 (d, J = 2.3 Hz, 1H), 6.75 (d, J = 8.3 Hz, 1H), 5.20 (d, J = 6.9 Hz, 1H), 4.46 (d, J = 2.4 Hz, 1H), 3.54 (s, 3H), 3.50-3.43 (m, 2H), 3.39-3.32 (m, 1H), 2.64 (m, 1H), 2.79-2.71 (m, 1H), 2.35 (s, 1H), 2.10 (d, J = 2.8 Hz, 1H), 1.70-1.45 (m, 4H), 1.33-1.15 (m, 4H), 1.14 (d, J = 2.0 Hz, 3H), 1.12 (d, J = 2.0 Hz, 3H), 1.10-0.99 (m, 2H), 0.97 (s, 9H); MS (ESI+) m/z 553.2 (M + H)+. |
| Example I-110 | (2S,3S,4S,5S)-3-tert-butyl-1-(cyclohexanecarbonyl)-5-(2-fluorophenyl)-4-({2-methoxy-5-(trifluoromethyl)pyridin-3-yl]methyl}amino)pyrrolidine-2-carboxylic acid | $^1$HNMR (400 MHz, dimethyl sulfoxide-d$_6$, 120° C.) δ ppm 8.31 (s, 1H), 7.83 (s, 1H), 7.54 (d, J = 2.4 Hz, 1H), 7.28 (q, J = 7.1 Hz, 1H), 7.16-7.03 (m, 2H), 5.40 (d, J = 7.2 Hz, 1H), 4.51 (d, J = 2.3 Hz, 1H), 3.83 (s, 3H), 3.57 (d, J = 15.2 Hz, 1H), 3.50 (d, J = 7.1 Hz, 1H), 3.38 (d, J = 15.1 Hz, 1H), 2.38 (s, 1H), 2.32-2.15 (m, 1H), 1.67 (d, J = 9.1 Hz, 2H), 1.54 (s, 2H), 1.36-1.03 (m, 6H), 0.97 (d, J = 0.8 Hz, 9H); MS (ESI+) m/z 580 (M + H)+. |
| Example I-111 | (2S,3S,4S,5S)-3-tert-butyl-1-(cyclohexanecarbonyl)-5-(2-fluorophenyl)-4-({[2,-methoxy-5-(propan-2-yl)phenyl]methyl}amino)pyrrolidine-2-carboxylic acid | $^1$HNMR (400 MHz, dimethyl sulfoxide-d$_6$, 120° C.) δ ppm 7.75 (s, 1H), 7.32 (q, J = 7.0 Hz, 1H), 7.15 (q, J = 10.2, 8.6 Hz, 2H), 7.03 (dd, J = 8.5, 2.3 Hz, 1H), 6.84 (d, J = 2.3 Hz, 1H), 6.77 (d, J = 8.4 Hz, 1H), 5.43 (d, J = 6.9 Hz, 1H), 4.52 (d, J = 2.1 Hz, 1H), 3.70-3.60 (m, 2H), 3.56 (s, 3H), 3.43 (d, J = 13.6 Hz, 1H), 2.76 (hept, J = 6.9 Hz, 1H), 2.40-2.23 (m, 2H), 1.73-1.49 (m, 4H), 1.13 (dd, J = 6.9, 1.7 Hz, 12H), 0.97 (s, 9H); MS (ESI+) m/z 553 (M + H)+. |

TABLE 1-continued

| Example I-112 | (2S,3S,4S,5S)-3-tert-butyl-4-{[(5-tert-butyl-2-methoxyphenyl)methyl]amino}-1-(cyclohexanecarbonyl)-5-(4-fluorophenyl)pyrrolidine-2-carboxylic acid | $^1$HNMR (400 MHz, dimethyl sulfoxide-d$_6$) δ ppm 7.55 (s, 2H), 7.15 (dd, J = 8.5, 2.6 Hz, 1H), 7.09 (t, J = 8.8 Hz, 2H), 6.97 (d, J = 2.6 Hz, 1H), 6.75 (d, J = 8.6 Hz, 1H), 5.20 (d, J = 8.6 Hz, 1H), 4.46 (d, J = 2.5 Hz, 1H), 3.60 (s, 1H), 3.54 (s, 3H), 3.47 (dd, J = 6.9, 2.1 Hz, 2H), 3.37 (d, J = 13.7 Hz, 1H), 2.64 (s, 1H), 2.36 (s, 1H), 1.69-1.48 (m, 5H), 1.25 (s, 2H), 1.21 (s, 9H), 1.05 (s, 3H), 0.97 (s, 9H); MS (ESI+) m/z 567.3 (M + H)$^+$. |
| --- | --- | --- |
| Example I-113 | (2S,3S,4S,5S)-3-tert-butyl-1-(cyclohexanecarbonyl)-4-({[2-methoxy-5-(2-methoxypropan-2-yl)pyridin-3-yl]methyl}amino)-5-phenylpyrrolidine-2-carboxylic acid | $^1$HNMR (400 MHz, dimethyl sulfoxide-d$_6$) δ ppm 7.96 (d, J = 2.6 Hz, 1H), 7.54 (s, 2H), 7.36-7.28 (m, 3H), 7.24 (t, J = 7.3 Hz, 1H), 5.20 (d, J = 7.0 Hz, 1H), 4.47 (d, J = 2.5 Hz, 1H), 3.67 (s, 3H), 3.51 (d, J = 14.3 Hz, 1H), 3.47-3.43 (m, 2H), 3.34 (d, J = 14.4 Hz, 1H), 2.97 (s, 3H), 2.64 (s, 1H), 2.35 (s, 1H), 1.68-1.41 (m, 4H), 1.40 (s, 6H), 1.15 (d, J = 57.3 Hz, 6H), 0.97 (s, 9H); MS (ESI+) m/z 554.2 (M + H)$^+$. |
| Example I-114 | (2S,3S,4S,5S)-3-tert-butyl-1-(cyclohexanecarbonyl)-4-({[2-methoxy-5-(pyrimidin-5-yl)phenyl]methyl}amino)-5-phenylpyrrolidine-2-carboxylic acid | $^1$HNMR (400 MHz, dimethyl sulfoxide-d$_6$) δ ppm 8.90 (s, 2H), 7.56 (dd, J = 8.5, 2.5 Hz, 2H), 7.33-7.18 (m, 4H), 6.99 (d, J = 8.5 Hz, 1H), 5.22 (d, J = 6.9 Hz, 1H), 4.49 (d, J = 2.3 Hz, 1H), 3.63 (s, 3H), 3.61-3.43 (m, 3H), 3.20 (s, 1H 2.64 (s, 1H), 2.39 (s, 1H), 1.70-1.43 (m, 5H), 1.15 (d, J = 58.5 Hz, 5H), 0.99 (s, 9H); MS (ESI+) m/z 571.3 (M + H)$^+$. |
| Example I-115 | (2S,3S,4S,5S)-4-{[(5-cyclobutyl-2-methoxypyridin-3-yl)methyl]amino}-1-(cyclohexanecarbonyl)-3-(2-methoxypropan-2-yl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.89 (d, J = 2.4 Hz, 1H), 7.74-7.56 (m, 2H), 7.46-7.27 (m, 4H), 5.38 (d, J = 7.5 Hz, 1H), 4.48 (d, J = 4.1 Hz, 1H), 3.88 (s, 1H), 3.80 (d, J = 13.8 Hz, 1H), 3.74 (s, 3H), 3.59 (d, J = 13.9 Hz, 1H), 3.48-3.38 (m, 1H), 3.15 (s, 3H), 2.78 (t, J = 4.5 Hz, 1H), 2.37-2.14 (m, 3H), 2.11-1.79 (m, 4H), 1.74-1.41 (m, 4H), 1.32-0.97 (m, 11H), 0.78 (s, 1H); MS (APCI+) m/z 564.1 (M + H)$^+$. |
| Example I-116 | (2S,3S,4S,5S)-1-(cyclohexanecarbonyl)-4-{[(5-cyclopentyl-2-methoxypyridin-3-yl)methyl]amino}-3-(2-methoxypropan-2-yl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.91 (d, J = 2.4 Hz, 1H), 7.63 (s, 2H), 7.44-7.31 (m, 3H), 7.28 (s, 1H), 5.38 (d, J = 7.4 Hz, 1H), 4.48 (d, J = 4.3 Hz, 1H), 3.87 (s, 1H), 3.79 (d, J = 13.8 Hz, 1H), 3.74 (s, 3H), 3.59 (d, J = 13.8 Hz, 1H), 3.15 (s, 3H), 2.99-2.85 (m, 1H), 2.78 (t, J = 4.6 Hz, 1H), 2.25-2.20 (m, 1H), 2.04-1.91 (m, 2H), 1.79-1.59 (m, 6H), 1.55-1.38 (m, 4H), 1.33-1.03 (m, 11H), 0.80-0.75 (m, 1H); MS (APCI+) m/z 577.9 (M + H)$^+$. |
| Example I-117 | (2S,3S,4S,5S)-4-({[5-(bicyclo[2.2.1]heptan-2-yl)-2-methoxyphenyl]methyl}amino)-1-(cyclohexanecarbonyl)-3-(2-methoxypropan-2-yl)-5-phenylpyrrolidine-2-carboxylic acid | $^1$HNMR (400 MHz, 120° C., dimethyl sulfoxide-d$_6$: D$_2$O = 9:1 (v/v), asterisk denotes minor diastereomer peak) δ ppm 7.67-7.62 (m, 2H), 7.47-7.39 (m, 2H), 7.39-7.32 (m, 1H), 7.18-7.09 (m, 1H), 6.94-6.88 (m, 1H), 6.88-6.82 (m, 1H), 5.42 (d, J = 7.6 Hz, 1H), 4.44 (d, J = 4.7 Hz, 1H), 4.02-3.94 (m, 1H), 3.90 (d, J = 13.3 Hz, 1H), 3.75-3.61 (m, 4H), 3.15 (s, 3H), 2.84 (t, J = 5.0 Hz, 1H), 2.64-2.57* (m, 1H), 2.30 (d, J = 11.7 Hz, 3H), 1.95-1.84 (m, 1H), 1.66 (d, J = 9.6 Hz, 3H), 1.58-1.44 (m, 4H), 1.43-1.34 (m, 1H), 1.37-1.03 (m, 15H), 0.80 (s, 1H); MS (APCI+) m/z 603.1 (M + H)$^+$. |
| Example I-118 | (2S,3S,4S,5S)-1-(cyclohexanecarbonyl)-4-({[5-(cyclohexylmethyl)-2-methoxyphenyl]methyl}amino)-3-(2-methoxypropan-2-yl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.65 (s, 2H), 7.50-7.39 (m, 2H), 7.39-7.31 (m, 1H), 7.06 (dd, J = 8.4, 2.2 Hz, 1H), 6.90-6.82 (m, 2H), 5.42 (d, J = 7.6 Hz, 1H), 4.43 (d, J = 4.6 Hz, 1H), 4.00-3.93 (m, 1H), 3.88 (d, J = 13.4 Hz, 1H), 3.69 (d, J = 13.4 Hz, 1H), 3.64 (s, 3H), 3.14 (s, 3H), 2.83 (t, J = 5.1 Hz, 1H), 2.36 (d, J = 6.9 Hz, 2H), 2.31-2.17 (m, 1H), 1.74-1.36 (m, 10H), 1.33-0.99 (m, 14H), 0.99-0.63 (m, 3H); MS (APCI+) m/z 605.1 (M + H)$^+$. |
| Example I-119 | (2S,3S,4S,5S)-3-tert-butyl-4-{[(5-tert-butyl-2-methoxyphenyl)methyl]amino}-1-(cyclopentyloxy)carbonyl]-5-phenylpyrrolidine-2-carboxylic acid | $^1$HNMR (400 MHz, dimethyl sulfoxide-d$_6$, 120° C.) δ ppm 7.52 (dd, J = 7.4, 1.7 Hz, 2H), 7.34 (t, J = 7.4 Hz, 2H), 7.30-7.24 (m, 1H), 7.20 (dd, J = 8.6, 2.6 Hz, 1H), 7.01 (d, J = 2.6 Hz, 1H), 6.78 (d, J = 8.6 Hz, 1H), 5.08 (d, J = 6.8 Hz, 1H), 4.88 (tt, J = 5.2, 2.3 Hz, 1H), 4.35 (d, J = 2.2 Hz, 1H), 3.71-3.63 (m, 2H), 3.55 (s, 3H), 3.39 (d, J = 13.6 Hz, 1H), 2.45 (d, J = 2.1 Hz, 1H), 1.70-1.23 (m, 8H), 1.21 (s, 9H), 1.00 (s, 9H); MS (ESI+) m/z 551 (M + H)$^+$. |
| Example I-120 | (2S,3S,4S,5S)-3-tert-butyl-1-(cyclohexanecarbonyl)-5-[2-(dimethylamino)pyridin-3-yl]-4-({[2-methoxy-5-(trifluoromethyl)pyridin-3-yl]methyl}amino)pyrrolidine-2-carboxylic acid | $^1$HNMR (400 MHz, dimethyl sulfoxide-d$_6$) δ ppm 8.31 (d, J = 2.3 Hz, 1H), 8.19 (d, J = 4.6 Hz, 2H), 7.60 (d, J = 2.4 Hz, 1H), 7.01-6.92 (m, 1H), 5.42 (d, J = 6.7 Hz, 1H), 4.53 (s, 1H), 3.77 (s, 3H), 3.61-3.48 (m, 3H), 3.33 (d, J = 14.9 Hz, 1H), 2.72 (s, 6H), 2.39 (s, 1H), 2.07 (s, 1H), 1.68-1.44 (m, 4H), 1.32-1.02 (m, 6H), 1.00 (s, 9H); MS (ESI+) m/z 606.2 (M + H)$^+$. |
| Example I-121 | (2S,3S,4S,5S)-3-tert-butyl-1-(cyclohexanecarbonyl)-4-({[2-methoxy-5-(pyrrolidin- | $^1$HNMR (400 MHz, dimethyl sulfoxide-d$_6$) δ ppm 7.58-7.52 (m, 2H), 7.44-7.37 (m, 2H), 7.36-7.32 (m, 1H), 6.78-6.75 (m, 1H), 6.49-6.45 (m, 1H), 6.32-6.30 (m, |

TABLE 1-continued

| | | |
|---|---|---|
| | 1-yl)phenyl]methyl}amino)-5-phenylpyrrolidine-2-carboxylic acid | 1H), 5.37-5.34 (m, 1H), 4.54 (d, J = 1.8 Hz, 1H), 3.89-3.86 (m, 1H), 3.76 (d, J = 13.2 Hz, 1H), 3.49 (s, 3H), 3.13-3.10 (m, 5H)1.94-1.90 (m, 3H), 1.66-1.59 (m, 2H), 1.55-1.47 (m, 2H), 1.27-1.18 (m, 2H), 1.18-1.15 (m, 1H), 1.12-1.04 (m, 1H), 1.02 (s, 1H), 1.01 (s, 9H), 0.99-0.97 (m, 3H); MS (APCI+) m/z 590.6 (M + H)+. |
| Example I-123 | (2S,3S,4S,5S)-3-tert-butyl-1-(cyclohexanecarbonyl)-4-({[2-methoxy-5-(piperidin-1-yl)phenyl]methyl}amino)-5-phenylpyrrolidine-2-carboxylic acid | $^1$HNMR (400 MHz, dimethyl sulfoxide-d$_6$) δ ppm 7.59-7.54 (m, 3H), 7.39 (t, J = 7.5 Hz, 2H), 7.33 (d, J = 7.2 Hz, 1H), 7.02 (d, J = 8.7 Hz, 1H), 6.87-6.81 (m, 2H), 5.34 (d, J = 7.0 Hz, 1H), 4.53 (d, J = 2.0 Hz, 1H), 3.82-3.79 (m, 1H), 3.73-3.68 (m, 1H), 3.57 (s, 3H), 3.43 (d, J = 13.8 Hz, 1H), 3.12-3.09 (m, 5H), 1.75-1.68 (m, 4H), 1.67-1.62 (m, 2H), 1.61-1.54 (m, 2H), 1.52-1.47 (m, 2H), 1.26-1.16 (m, 4H), 1.07 (s, 2H), 1.02 (s, 1H), 1.00 (s, 9H), 0.99-0.97 (m, 1H); MS (APCI+) m/z 604.6 (M + H)+. |
| Example I-124 | (2S,3S,4S,5S)-3-tert-butyl-1-[(1R)-3,3-difluorocyclohexane-1-carbonyl]-4-({[2-methoxy-5-(trifluoromethyl)phenyl]methyl}amino)-5-phenylpyrrolidine-2-carboxylic acid | LC/MS (ESI+) m/z 597.5 (M + H)+. |
| Example I-125 | (2S,3S,4S,5S)-3-tert-butyl-1-(cyclohexanecarbonyl)-4-({[2-methoxy-5-(pyridazin-4-yl)phenyl]methyl}amino)-5-phenylpyrrolidine-2-carboxylic acid | $^1$HNMR (400 MHz, dimethyl sulfoxide-d$_6$) δ ppm 9.38 (d, J = 2.4 Hz, 1H), 9.16 (d, J = 5.5 Hz, 1H), 7.75-7.71 (m, 2H), 7.57-7.50 (m, 2H), 7.46-7.43 (m, 1H), 7.35 (t, J = 7.3 Hz, 2H), 7.29 (d, J = 7.5 Hz, 1H), 7.05 (d, J = 8.6 Hz, 1H), 5.27 (d, J = 6.9 Hz, 1H), 4.52 (d, J = 2.0 Hz, 1H), 3.73-3.68 (m, 0H), 3.66 (s, 3H), 3.50 (d, J = 13.8 Hz, 1H), 2.46-2.43 (m, 1H), 1.67-1.59 (m, 2H), 1.54-1.47 (m, 2H), 1.27-1.19 (m, 3H), 1.16 (s, 1H), 1.12-1.04 (m, 2H), 0.99 (s, 9H); MS (APCI+) m/z 571.4 (M + H)+. |
| Example I-126 | (2S,3S,4S,5S)-3-tert-butyl-1-(cyclohexanecarbonyl)-4-{[(2'-fluoro-4-methoxy[1,1'-biphenyl]-3-yl)methyl]amino}-5-phenylpyrrolidine-2-carboxylic acid | $^1$HNMR (400 MHz, dimethyl sulfoxide-d$_6$) δ ppm 7.54-7.48 (m, 3H), 7.41-7.31 (m, 4H), 7.30-7.22 (m, 2H), 7.21-7.14 (m, 1H), 6.97 (d, J = 2.8 Hz, 1H), 5.27 (d, J = 7.0 Hz, 1H), 4.52 (s, 1H), 3.73-3.65 (m, 2H), 3.62 (s, 3H), 3.49 (d, J = 13.5 Hz, 1H), 2.46-2.42 (m, 1H), 1.68-1.60 (m, 2H), 1.57-1.48 (m, 2H), 1.30-1.16 (m, 3H), 1.14-1.05 (m, 2H), 1.00 (s, 9H); MS (APCI+) m/z 587.4 (M + H)+. |
| Example I-127 | (2S,3S,4S,5S)-3-tert-butyl-1-(cyclohexanecarbonyl)-4-({[5-(2,4-dimethyl-1,3-thiazol-5-yl)-2-methoxyphenyl]methyl}amino)-5-phenylpyrrolidine-2-carboxylic acid | $^1$HNMR (400 MHz, dimethyl sulfoxide-d$_6$) δ ppm 7.59-7.52 (m, 2H), 7.37 (t, J = 7.5 Hz, 2H), 7.33-7.28 (m, 2H), 7.06 (d, J = 2.2 Hz, 1H), 6.97 (d, J = 8.5 Hz, 1H), 5.32 (d, J = 7.1 Hz, 1H), 4.53 (d, J = 2.1 Hz, 1H), 3.80-3.70 (m, 2H), 3.65 (s, 3H), 3.46 (d, J = 13.7 Hz, 1H), 2.59 (s, 3H), 2.48-2.46 (m, 1H), 2.28 (s, 3H), 1.68-1.60 (m, 2H), 1.56-1.48 (m, 1H), 1.29-1.17 (m, 3H), 1.13-1.05 (m, 2H), 1.00 (s, 9H); MS (APCI+) m/z 604.4 (M + H)+. |
| Example I-128 | (2S,3S,4S,5S)-3-tert-butyl-4-{[(2'-cyano-4-methoxy[1,1'-biphenyl]-3-yl)methyl]amino}-1-(cyclohexanecarbonyl)-5-phenylpyrrolidine-2-carboxylic acid | MS (APCI+) m/z 594.4 (M + H)+. |
| Example I-129 | (2S,3S,4S,5S)-3-tert-butyl-1-(cyclohexanecarbonyl)-4-({[5-(3,6-dihydro-2H-pyran-4-yl)-2-methoxyphenyl]methyl}amino)-5-phenylpyrrolidine-2-carboxylic acid | $^1$HNMR (400 MHz, 120° C., dimethyl sulfoxide-d$_6$: D$_2$O = 9:1 (v/v)) δ ppm 7.53 (s, 2H), 7.46-7.36 (m, 2H), 7.36-7.26 (m, 2H), 7.09-7.04 (m, 1H), 6.86 (d, J = 8.6 Hz, 1H), 6.06-5.94 (m, 1H), 5.33 (d, J = 7.1 Hz, 1H), 4.53 (d, J = 1.9 Hz, 1H), 4.18 (q, J = 2.8 Hz, 2H), 3.84-3.70 (m, 4H), 3.59 (s, 3H), 3.47 (d, J = 13.6 Hz, 1H), 2.51 (s, 2H), 2.38-2.28 (m, 2H), 1.73-1.41 (m, 4H), 1.35-1.03 (m, 5H), 0.99 (s, 9H), 0.85-0.60 (m, 1H); MS (APCI+) m/z 575.1 (M + H)+. |
| Example I-130 | (2S,3S,4S,5S)-3-tert-butyl-4-{[(5-tert-butyl-2-methoxypyridin-3-yl)methyl]amino}-1-(cyclohexanecarbonyl)-5-(4-fluorophenyl)pyrrolidine-2-carboxylic acid | $^1$HNMR (400 MHz, dimethyl sulfoxide-d$_6$) δ ppm 7.96 (s, 1H), 7.60 (s, 2H), 7.31 (d, J = 2.6 Hz, 1H), 7.09 (t, J = 8.7 Hz, 2H), 5.21 (d, J = 7.0 Hz, 1H), 4.46 (d, J = 2.5 Hz, 1H), 3.69 (s, 3H), 3.56-3.39 (m, 3H), 3.32 (d, J = 14.4 Hz, 1H), 2.34 (s, 2H), 1.74-1.42 (m, 5H), 1.23 (s, 9H), 1.25-1.09 (d, J = 9.6 Hz, 5H), 0.97 (s, 9H); MS (ESI+) m/z 568.2 (M + H)+. |
| Example I-131 | (2S,3S,4S,5S)-3-tert-butyl-4-{[(5-cyclobutyl-2-methoxypyridin-3-yl)methyl]amino}-1-(cyclohexanecarbonyl)-5-[2-(dimethylamino)pyridin-3- | $^1$HNMR (400 MHz, 120° C., dimethyl sulfoxide-d$_6$: D$_2$O = 9:1 (v/v)) δ ppm 8.29-8.15 (m, 2H), 7.81 (d, J = 2.5 Hz, 1H), 7.30-7.24 (m, 1H), 7.10-7.00 (m, 1H), 5.41 (d, J = 6.6 Hz, 1H), 4.55 (s, 1H), 3.70-3.55 (m, 5H), 3.47-3.31 (m, 2H), 2.76 (s, 6H), 2.45 (s, 1H), 2.36-2.20 (m, 2H), 2.05-1.76 (m, 4H), 1.58 (d, J = 49.8 Hz, |

TABLE 1-continued

| | | |
|---|---|---|
| | yl]pyrrolidine-2-carboxylic acid | 4H), 1.13 (d, J = 51.7 Hz, 5H), 1.03-0.97 (m, 10H), 0.89-0.81 (m, 1H); MS (APCI+) m/z 592.1 (M + H)+. |
| Example I-132 | (2S,3S,4S,5S)-3-tert-butyl-1-(cyclohexanecarbonyl)-4-{[(5-cyclopentyl-2-methoxypyridin-3-yl)methyl]amino}-5-[2-(dimethylamino)pyridin-3-yl]pyrrolidine-2-carboxylic acid | ¹HNMR (400 MHz, 120° C., dimethyl sulfoxide-d₆: D₂O = 9:1 (v/v)) δ ppm 8.20 (d, J = 5.0 Hz, 2H), 7.83 (d, J = 2.4 Hz, 1H), 7.22 (d, J = 2.2 Hz, 1H), 7.10-6.98 (m, 1H), 5.40 (d, J = 6.6 Hz, 1H), 4.55 (s, 1H), 3.66-3.51 (m, 5H), 3.33 (d, J = 14.2 Hz, 1H), 2.89 (p, J = 8.5 Hz, 1H), 2.73 (s, 6H), 2.43 (s, 1H), 2.05-1.87 (m, 2H), 1.81-1.34 (m, 11H), 1.32-0.95 (m, 15H); MS (APCI+) m/z 606.1 (M + H)+. |
| Example I-133 | (2S,3S,4S,5S)-4-({[5-(bicyclo[2.2.1]heptan-2-yl)-2-methoxypyridin-3-yl]methyl}amino)-3-tert-butyl-1-(cyclohexanecarbonyl)-5-[2-(dimethylamino)pyridin-3-yl]pyrrolidine-2-carboxylic acid | ¹HNMR (400 MHz, 120° C., dimethyl sulfoxide-d₆: D₂O = 9:1 (v/v)) δ ppm 8.28-8.11 (m, 2H), 7.84-7.77 (m, 1H), 7.20-7.16 (m, 1H), 7.04-6.98 (m, 1H), 5.40 (d, J = 6.8 Hz, 1H), 4.54 (s, 1H), 3.70-3.47 (m, 5H), 3.37-3.24 (m, 1H), 2.72-2.68 (m, 6H), 2.41 (s, 1H), 2.32 (s, 2H), 1.73-1.43 (m, 8H), 1.42-1.02 (m, 11H), 1.01-0.97 (m, 10H); MS (APCI+) m/z 632.3 (M + H)+. |
| Example I-134 | (2S,3S,4S,5S)-4-{[(6-bromo-3-methoxypyridin-2-yl)methyl]amino}-3-tert-butyl-1-(cyclohexanecarbonyl)-5-phenylpyrrolidine-2-carboxylic acid | ¹HNMR (400 MHz, dimethyl sulfoxide-d₆) δ ppm 7.55 (m, 2H), 7.38-7.23 (m, 5H), 5.25 (d, J = 7.0 Hz, 1H), 4.52 (d, J = 2.3 Hz, 2H), 3.74-3.66 (m, 5H), 3.51 (m, 1H), 2.42 (m, 1H), 2.26 (m, 1H), 1.67-1.04 (m, 9H), 0.98 (s, 9H), 0.82 (m, 1H); MS (ESI+); m/z 572.2 (M + H)+. |
| Example I-135 | (2S,3S,4S,5S)-3-tert-butyl-4-{[(5-tert-butyl-2-methoxypyridin-3-yl)methyl]amino}-1-(cyclohexanecarbonyl)-5-(2-methoxypyridin-3-yl)pyrrolidine-2-carboxylic acid | ¹HNMR (400 MHz, dimethyl sulfoxide-d₆) δ ppm 8.05 (d, J = 4.8 Hz, 2H), 7.96 (d, J = 2.6 Hz, 1H), 7.31 (d, J = 2.6 Hz, 1H), 6.96-6.86 (m, 1H), 5.29 (s, 1H), 4.49 (d, J = 2.1 Hz, 1H), 3.83 (d, J = 2.4 Hz, 2H), 3.66 (s, 3H), 3.59-3.42 (m, 2H), 3.29 (d, J = 14.3 Hz, 1H), 3.20 (s, 3H), 2.36 (s, 1H), 1.67-1.23 (d, J = 147.5 Hz, 10H), 1.23 (s, 9H), 0.97 (s, 9H); MS (ESI+) m/z 581.2 (M + H)+. |
| Example I-136 | (2S,3S,4S,5S)-1-(cyclohexanecarbonyl)-4-({[2-methoxy-5-(trifluoromethyl)phenyl]methyl}amino)-3-(1-methylcyclopropyl)-5-phenylpyrrolidine-2-carboxylic acid | ¹HNMR (400 MHz, dimethyl sulfoxide-d₆) δ ppm 7.65 (d, J = 7.2 Hz, 2H), 7.56 (s, 1H), 7.52 (d, J = 8.7 Hz, 1H), 7.41-7.29 (m, 2H), 7.29-7.21 (m, 1H), 7.09 (d, J = 8.5 Hz, 1H), 5.20 (d, J = 7.7 Hz, 1H), 4.17 (d, J = 8.9 Hz, 1H), 3.84 (d, J = 17.8 Hz, 4H), 3.77 (s, 1H), 3.56-3.47 (m, 1H), 2.19 (bs, 1H), 1.68 (d, J = 10.8 Hz, 3H), 1.49 (m, 2H), 1.35-1.21 (m, 1H), 1.09 (q, J = 12.3 Hz, 3H), 0.98 (s, 3H), 0.77 (bs, 1H), 0.49 (d, J = 8.0 Hz, 1H), 0.29 (d, J = 4.4 Hz, 3H); MS (APCI+) m/z 559 (M + H)+. |
| Example I-137 | (2S,3S,4S,5S)-3-tert-butyl-4-{[(5-tert-butyl-2-methoxyphenyl)methyl]amino}-1-[(2R)-2-phenoxypropanoyl]-5-phenylpyrrolidine-2-carboxylic acid | ¹HNMR (400 MHz, 120° C., dimethyl sulfoxide-d₆: D₂O = 9:1 (v/v)) δ ppm 7.56-7.51 (m, 2H), 7.41-7.13 (m, 7H), 7.03 (s, 1H), 6.92 (s, 1H), 6.84-6.60 (m, 2H), 5.33 (d, J = 7.0 Hz, 1H), 5.28-4.83 (m, 1H), 4.59 (s, 1H), 3.79-3.73 (m, 2H), 3.53 (s, 4H), 2.53 (s, 1H), 1.33 (d, J = 6.4 Hz, 3H), 1.20 (s, 9H), 0.94 (s, 9H); MS (APCI+) m/z 587.1 (M + H)+. |
| Example I-138 | (2S,3S,4S,5S)-3-tert-butyl-4-{[(5-tert-butyl-2-methoxyphenyl)methyl]amino}-1-[1-(methanesulfonyl)piperidine-2-carbonyl]-5-phenylpyrrolidine-2-carboxylic acid | ¹HNMR (400 MHz, 120° C., dimethyl sulfoxide-d₆: D₂O = 9:1 (v/v), asterisk denotes minor diastereomer peak) δ ppm 7.67-7.57 (m, 1H), 7.49-7.18 (m, 5H), 7.15-6.97 (m, 1H), 6.87-6.76 (m, 1H), 5.44 (d, J = 7.3 Hz, 1H), 5.32 (d, 0H), 4.63* (s, 1H), 4.55 (d, J = 2.8 Hz, 1H), 4.45-4.39 (m, 1H), 3.96-3.64 (m, 3H), 3.64-3.32 (m, 6H), 2.74 (s, 3H), 1.21 (d, J = 2.6 Hz, 16H), 1.00 (d, J = 9.9 Hz, 10H); MS (APCI+) m/z 628.1 (M + H)+. |
| Example I-139 | (2S,3S,4S,5S)-3-tert-butyl-4-{[(5-tert-butyl-2-methoxyphenyl)methyl]amino}-5-phenyl-1-{(trans)-2-(pyridin-3-yl)cyclopropane-1-carbonyl]pyrrolidine-2-carboxylic acid | ¹HNMR (400 MHz, 120° C., dimethyl sulfoxide-d₆: D₂O = 9:1 (v/v), asterisk denotes minor diastereomer peak) δ ppm 8.45* (d, J = 5.0 Hz, 1H), 8.37 (s, 1H), 8.12* (s, 1H), 7.54 (dd, J = 13.3, 7.6 Hz, 3H), 7.48-7.14 (m, 5H), 7.05 (dd, J = 10.3, 2.6 Hz, 1H), 6.90-6.74 (m, 1H), 5.59* (d, J = 6.7 Hz, 1H), 5.45 (d, J = 7.1 Hz, 1H), 4.76-4.70* (m, 1H), 4.59 (d, J = 1.8 Hz, 1H), 4.09-3.92 (m, 1H), 3.92-3.77 (m, 1H), 3.64-3.56 (m, 3H), 3.52* (d, J = 13.5 Hz, 1H), 3.43 (d, J = 13.6 Hz, 1H), 2.64* (s, 1H), 2.59 (s, 1H), 2.45-2.37* (m, 1H), 2.20-2.09 (m, 1H), 2.05-1.76 (m, 1H), 1.61-1.52 (m, 1H), 1.39-1.30* (m, 1H), 1.20 (d, J = 3.3 Hz, 9H), 1.01 (d, J = 5.8 Hz, 9H); MS (APCI+) m/z 584.1 (M + H)+. |
| Example I-140 | (2S,3S,4S,5S)-3-tert-butyl-1-(cyclohexanecarbonyl)-4-({[5-(2-fluorophenyl)-2-methoxypyridin-3-yl]methyl}amino)-5-phenylpyrrolidine-2-carboxylic acid | ¹HNMR (400 MHz, dimethyl sulfoxide-d₆) δ ppm 8.16 (d, J = 2.0 Hz, 1H), 7.59-7.53 (m, 2H), 7.51-7.48 (m, 1H), 7.43-7.40 (m, 1H), 7.40-7.37 (m, 1H), 7.35-7.29 (m, 3H), 7.29-7.21 (m, 2H), 5.27 (d, J = 7.0 Hz, 1H), 4.51 (d, J = 2.2 Hz, 1H), 3.76 (s, 3H), 3.67-3.60 (m, 2H), 3.41 (d, J = 14.3 Hz, 1H), 2.43-2.40 (m, 1H), 1.66-1.59 (m, 2H), 1.53-1.46 (m, 2H), 1.27-1.15 (m, 3H), 1.11-1.03 (m, 3H), 0.98 (s, 9H); MS (APCI+) m/z 588.1 (M + H)+. |

TABLE 1-continued

| | | |
|---|---|---|
| Example I-141 | (2S,3S,4S,5S)-3-tert-butyl-4-[({2-methoxy-5-[1-(trifluoromethyl)cyclopropyl]phenyl}methyl)amino]-5-phenyl-1-{[(propan-2-yl)oxy]carbonyl}pyrrolidine-2-carboxylic acid | $^1$HNMR (400 MHz, dimethyl sulfoxide-d$_6$, 120° C.) δ ppm 7.54-7.48 (m, 2H), 7.33 (t, J = 7.7 Hz, 2H), 7.30-7.23 (m, 2H), 7.04 (d, J = 2.2 Hz, 1H), 6.85 (d, J = 8.5 Hz, 1H), 5.08 (d, J = 6.8 Hz, 1H), 4.63 (hept, J = 6.2 Hz, 1H), 4.35 (d, J = 2.2 Hz, 1H), 3.66-3.57 (m, 5H), 3.37 (d, J = 13.8 Hz, 1H), 2.42 (d, J = 1.9 Hz, 1H), 1.31-1.24 (m, 2H), 1.05 (d, J = 6.2 Hz, 3H), 1.01-0.93 (m, 11H), 0.88 (d, J = 6.2 Hz, 3H); MS (ESI+) m/z 577 (M + H)$^+$. |
| Example I-142 | (2S,3S,4S,5S)-3-tert-butyl-4-{[(5-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid | $^1$HNMR (400 MHz, dimethyl sulfoxide-d$_6$) δ ppm 8.23 (s, 1H), 8.17 (d, J = 4.8 Hz, 1H), 7.93 (d, J = 2.7 Hz, 1H), 7.32 (d, J = 2.7 Hz, 1H), 6.94 (dd, J = 7.7, 4.8 Hz, 1H), 5.56 (s, 1H), 4.59 (d, J = 1.5 Hz, 1H), 3.76 (d, J = 11.6 Hz, 2H), 3.63 (s, 3H), 3.59 (d, J = 12.3 Hz, 1H), 3.53 (d, J = 8.9 Hz, 2H), 3.24 (d, J = 14.3 Hz, 2H), 2.68 (s, 6H), 2.64 (s, 1H), 2.37-2.31 (m, 1H), 1.71-1.33 (m, 6H), 1.21 (s, 9H), 1.00 (s, 9H); MS (ESI+) m/z 596.3 (M + H)$^+$. |
| Example I-143 | (2S,3S,4S,5S)-3-tert-butyl-4-{[(5-tert-butyl-2-methoxyphenyl)methyl]amino}-5-phenyl-1-(pyrazolo[1,5-a]pyridine-3-carbonyl)pyrrolidine-2-carboxylic acid | $^1$HNMR (400 MHz, 120° C., dimethyl sulfoxide-d$_6$: D$_2$O = 9:1 (v/v)) δ ppm 8.58 (d, J = 7.0 Hz, 1H), 8.25 (s, 1H), 7.96 (d, J = 8.9 Hz, 1H), 7.59 (d, J = 7.5 Hz, 2H), 7.43-7.19 (m, 5H), 7.09 (d, J = 2.6 Hz, 1H), 7.05-6.97 (m, 1H), 6.84 (d, J = 8.6 Hz, 1H), 5.73 (d, J = 7.0 Hz, 1H), 4.69 (d, J = 1.6 Hz, 1H), 3.93 (d, J = 7.0 Hz, 1H), 3.88 (d, J = 13.7 Hz, 1H), 3.58 (s, 3H), 3.54 (d, J = 13.6 Hz, 1H), 2.63 (s, 1H), 1.22 (s, 9H), 0.98 (s, 9H); MS (APCI+) m/z 583.1 (M + H)$^+$. |
| Example I-144 | (2S,3S,4S,5S)-3-tert-butyl-4-{[(5-tert-butyl-2-methoxyphenyl)methyl]amino}-1-[5-ethyl-1-(6-methoxypyridazin-3-yl)-1H-pyrazole-4-carbonyl]-5-phenylpyrrolidine-2-carboxylic acid | $^1$HNMR (400 MHz, 120° C., dimethyl sulfoxide-d$_6$: D$_2$O = 9:1 (v/v)) δ ppm 7.80 (d, J = 9.4 Hz, 1H), 7.72 (s, 1H), 7.58 (d, J = 8.0 Hz, 2H), 7.38-7.30 (m, 3H), 7.30-7.21 (m, 2H), 7.06 (d, J = 2.5 Hz, 1H), 6.83 (d, J = 8.6 Hz, 1H), 5.59 (d, J = 6.9 Hz, 1H), 4.58-4.52 (m, 1H), 4.09 (d, J = 0.9 Hz, 3H), 3.93 (d, J = 7.2 Hz, 1H), 3.81 (d, J = 13.5 Hz, 1H), 3.59 (s, 3H), 3.47 (d, J = 13.5 Hz, 1H), 3.05-2.79 (m, 2H), 2.61 (s, 1H), 1.21 (s, 9H), 1.05-0.97 (m, 12H); MS (APCI+) m/z 669.1 (M + H)$^+$. |
| Example I-145 | (2S,3S,4S,5S)-3-tert-butyl-4-{[(5-tert-butyl-2-methoxyphenyl)methyl]amino}-1-[1-tert-butyl-5-(propan-2-yl)-1H-pyrazole-4-carbonyl]-5-phenylpyrrolidine-2-carboxylic acid | $^1$HNMR (400 MHz, 120° C., dimethyl sulfoxide-d$_6$: D$_2$O = 9:1 (v/v)) δ ppm 7.54 (d, J = 7.8 Hz, 2H), 7.39-7.19 (m, 5H), 7.04 (d, J = 2.5 Hz, 1H), 6.83 (d, J = 8.6 Hz, 1H), 5.55 (d, J = 7.0 Hz, 1H), 4.46 (d, J = 2.3 Hz, 1H), 3.91 (d, J = 7.1 Hz, 1H), 3.78 (d, J = 13.4 Hz, 1H), 3.61 (s, 3H), 3.50-3.35 (m, 2H), 2.57 (s, 1H), 1.50 (s, 9H), 1.30 (d, J = 6.9 Hz, 3H), 1.21 (s, 9H), 1.08 (d, J = 7.0 Hz, 3H), 1.02 (s, 9H); MS (APCI+) m/z 631.2 (M + H)$^+$. |
| Example I-146 | (2S,3S,4S,5S)-3-tert-butyl-4-{[(5-tert-butyl-2-methoxyphenyl)methyl]amino}-1-[1-(2-fluorophenyl)-3,5-dimethyl-1H-pyrazole-4-carbonyl]-5-phenylpyrrolidine-2-carboxylic acid | $^1$HNMR (400 MHz, 120° C., dimethyl sulfoxide-d$_6$: D$_2$O = 9:1 (v/v)) δ ppm 7.52 (d, J = 7.6 Hz, 2H), 7.38-7.12 (m, 7H), 7.04-7.00 (m, 1H), 6.82 (d, J = 8.6 Hz, 1H), 5.33 (d, J = 7.1 Hz, 1H), 4.52 (d, J = 2.5 Hz, 1H), 3.90 (d, J = 7.1 Hz, 1H), 3.74 (d, J = 13.5 Hz, 1H), 3.59 (s, 3H), 3.38 (d, J = 13.5 Hz, 1H), 2.55 (s, 1H), 2.04 (s, 3H), 1.87 (s, 3H), 1.20 (s, 9H), 1.06 (s, 9H); MS (APCI+) m/z 655.1 (M + H)$^+$. |
| Example I-147 | (2S,3S,4S,5S)-3-tert-butyl-4-{[(5-tert-butyl-2-methoxyphenyl)methyl]amino}-1-(1,5-dimethyl-2,3-dihydro-1H-indene-1-carbonyl)-5-phenylpyrrolidine-2-carboxylic acid | $^1$HNMR (400 MHz, 120° C., dimethyl sulfoxide-d$_6$: D$_2$O = 9:1 (v/v)) δ ppm 7.48 (d, J = 7.5 Hz, 2H), 7.38-7.19 (m, 4H), 7.11 (d, J = 8.0 Hz, 1H), 6.98 (dd, J = 5.3, 2.5 Hz, 3H), 6.81 (d, J = 8.6 Hz, 1H), 5.22 (d, J = 7.4 Hz, 1H), 4.52 (d, J = 3.1 Hz, 1H), 3.61 (s, 5H), 3.35 (d, J = 13.4 Hz, 1H), 2.88-2.71 (m, 1H), 2.71-2.54 (m, 1H), 2.46-2.32 (m, 2H), 2.28 (s, 3H), 1.91-1.79 (m, 1H), 1.38 (s, 3H), 1.20 (s, 9H), 0.93 (s, 9H); MS (APCI+) m/z 611.1 (M + H)$^+$. |
| Example I-148 | (2S,3S,4S,5S)-3-tert-butyl-4-{[(5-tert-butyl-2-methoxyphenyl)methyl]amino}-1-[(1-hydroxycyclobutyl)acetyl]-5-phenylpyrrolidine-2-carboxylic acid | $^1$HNMR (400 MHz, 120° C., dimethyl sulfoxide-d$_6$: D$_2$O = 9:1 (v/v)) δ ppm 7.58-7.53 (m, 2H), 7.42 (d, J = 7.6 Hz, 2H), 7.42-7.30 (m, 1H), 7.26 (dd, J = 8.6, 2.6 Hz, 1H), 7.04 (d, J = 2.5 Hz, 1H), 6.83 (d, J = 8.6 Hz, 1H), 5.40 (d, J = 7.2 Hz, 1H), 4.69-4.64 (m, 1H), 3.87 (d, J = 7.1 Hz, 1H), 3.81 (d, J = 13.5 Hz, 1H), 3.58 (s, 3H), 3.48 (d, J = 13.6 Hz, 1H), 2.56 (s, 1H), 2.52-2.38 (m, 2H), 1.90 (q, J = 10.7, 9.3 Hz, 4H), 1.63-1.57 (m, 1H), 1.36 (s, 0H), 1.33 (s, 1H), 1.27 (s, 0H), 1.21 (s, 9H), 1.00 (s, 9H); MS (APCI+) m/z 551.2 (M + H)$^+$. |
| Example I-149 | (2S,3S,4S,5S)-1-[2-(azetidine-1-carbonyl)cyclohexane-1-carbonyl]-3-tert-butyl-4-{[(5-tert-butyl-2-methoxyphenyl)methyl]amino}-5-phenylpyrrolidine-2-carboxylic acid | $^1$HNMR (400 MHz, 120° C., dimethyl sulfoxide-d$_6$: D$_2$O = 9:1 (v/v), complex mixture of diastereomers, asterisk denotes diastereomer peak) δ ppm 7.69 (s, 1H), 7.48-7.24 (m, 5H), 7.13-7.01 (m, 1H), 6.92-6.76 (m, 1H), 5.28 (d, J = 6.8 Hz, 1H), 4.90 (s, 1H), 4.58* (s, 1H), 3.91 (dd, J = 32.6, 10.1 Hz, 6H), 3.70-3.38 (m, 5H), 2.59 (s, 1H), 2.39 (d, J = 13.9 Hz, 1H), 2.26-2.04 (m, 2H), 1.77-1.35 (m, 3H), 1.35-0.86 (m, 26H); MS (APCI+) m/z 632.2 (M + H)$^+$. |

TABLE 1-continued

| Example | Compound | Data |
|---|---|---|
| Example I-150 | (2S,3S,4S,5S)-3-tert-butyl-4-{[(5-tert-butyl-2-methoxyphenyl)methyl]amino}-1-[cis-4-hydroxy-4-(prop-2-en-1-yl)cyclohexane-1-carbonyl]-5-phenylpyrrolidine-2-carboxylic acid | $^1$HNMR (400 MHz, 120° C., dimethyl sulfoxide-$d_6$:D$_2$O = 9:1 (v/v)) δ ppm 7.58-7.53 (m, 2H), 7.41 (t, J = 7.4 Hz, 2H), 7.34 (t, J = 7.3 Hz, 1H), 7.27 (dd, J = 8.6, 2.5 Hz, 1H), 7.05 (d, J = 2.5 Hz, 1H), 6.83 (d, J = 8.7 Hz, 1H), 5.83-5.70 (m, 1H), 5.38 (d, J = 7.0 Hz, 1H), 5.01-4.89 (m, 2H), 4.55 (s, 1H), 3.92-3.78 (m, 2H), 3.58 (s, 3H), 2.55 (s, 1H), 2.19 (s, 1H), 2.02 (d, J = 7.1 Hz, 2H), 1.65 (s, 2H), 1.54-1.46 (m, 1H), 1.41-1.36 (m, 2H), 1.21 (s, 10H), 1.14 (d, J = 11.6 Hz, 1H), 1.02-0.77 (m, 11H); MS (APCI+) m/z 605.2 (M + H)$^+$. |
| Example I-151 | (2S,3S,4S,5S)-3-tert-butyl-4-{[(5-tert-butyl-2-methoxyphenyl)methyl]amino}-1-(cis-4-ethyl-4-hydroxycyclohexane-1-carbonyl)-5-phenylpyrrolidine-2-carboxylic acid | $^1$HNMR (400 MHz, 120° C., dimethyl sulfoxide-$d_6$:D$_2$O = 9:1 (v/v)) δ ppm 7.65-7.55 (m, 2H), 7.42 (t, J = 7.5 Hz, 2H), 7.39-7.33 (m, 1H), 7.28 (d, J = 8.8 Hz, 1H), 7.08-7.05 (m, 1H), 6.84 (d, J = 8.5 Hz, 1H), 5.40 (d, J = 7.1 Hz, 1H), 4.56 (d, J = 1.7 Hz, 1H), 3.94 (d, J = 7.2 Hz, 1H), 3.85 (d, J = 13.5 Hz, 1H), 3.60 (s, 3H), 3.50 (d, J = 13.5 Hz, 1H), 2.57 (s, 1H), 2.17 (s, 1H), 1.69-1.57 (m, 2H), 1.39 (t, J = 11.3 Hz, 3H), 1.31-1.22 (m, 3H), 1.21 (s, 9H), 1.09-1.04 (m, 1H), 1.00 (s, 10H), 0.75 (t, J = 7.4 Hz, 3H); MS (APCI+) m/z 593.1 (M + H)$^+$. |
| Example I-152 | (2S,3S,4S,5S)-3-tert-butyl-4-{[(5-tert-butyl-2-methoxyphenyl)methyl]amino}-1-[cis-4-hydroxy-4-(propan-2-yl)cyclohexane-1-carbonyl]-5-phenylpyrrolidine-2-carboxylic acid | $^1$HNMR (400 MHz, 120° C., dimethyl sulfoxide-$d_6$:D$_2$O = 9:1 (v/v)) δ ppm 7.57 (s, 2H), 7.42 (t, J = 7.4 Hz, 2H), 7.35 (t, J = 7.3 Hz, 1H), 7.27 (dd, J = 8.6, 2.5 Hz, 1H), 7.06 (d, J = 2.5 Hz, 1H), 6.84 (d, J = 8.7 Hz, 1H), 5.39 (d, J = 7.0 Hz, 1H), 4.56 (d, J = 1.8 Hz, 1H), 3.92 (d, J = 7.0 Hz, 1H), 3.84 (d, J = 13.5 Hz, 1H), 3.59 (s, 3H), 3.50 (d, J = 13.6 Hz, 1H), 2.56 (s, 1H), 2.41-1.90 (m, 1H), 1.80-1.27 (m, 7H), 1.21 (s, 9H), 1.14 (d, J = 16.0 Hz, 2H), 1.00 (s, 9H), 0.76 (d, J = 6.9 Hz, 6H); MS (APCI+) m/z 607.2 (M + H)$^+$. |
| Example I-153 | (2S,3S,4S,5S)-3-tert-butyl-4-{[(5-tert-butyl-2-methoxyphenyl)methyl]amino}-1-(phenoxycarbonyl)-5-phenylpyrrolidine-2-carboxylic acid | $^1$HNMR (400 MHz, dimethyl sulfoxide-$d_6$) δ ppm 7.61 (d, J = 7.6 Hz, 2H), 7.43-7.33 (m, 2H), 7.33-7.20 (m, 4H), 7.13 (t, J = 7.4 Hz, 1H), 7.03 (d, J = 2.5 Hz, 1H), 6.88-6.77 (m, 3H), 5.32 (d, J = 6.9 Hz, 1H), 4.53 (d, J = 2.1 Hz, 1H), 3.85-3.69 (m, 2H), 3.57 (s, 3H), 3.45 (d, J = 13.6 Hz, 1H), 1.21 (s, 9H), 1.06 (s, 9H); MS (APCI) m/z 559.1(M + H)$^+$. |
| Example I-154 | (2S,3S,4S,5S)-3-tert-butyl-4-{[(5-tert-butyl-2-methoxyphenyl)methyl]amino}-1-{[(2-chlorophenyl)methoxy]carbonyl}-5-phenylpyrrolidine-2-carboxylic acid | $^1$HNMR (400 MHz, dimethyl sulfoxide-$d_6$) δ ppm 7.53-7.48 (m, 2H), 7.37-7.30 (m, 3H), 7.30-7.15 (m, 3H), 7.07-6.98 (m, 2H), 6.79 (d, J = 8.6 Hz, 1H), 5.18 (d, J = 6.8 Hz, 1H), 5.07-5.00 (m, 2H), 4.45 (d, J = 2.0 Hz, 1H), 3.70 (s, 1H), 3.54 (s, 3H), 3.41 (d, J = 13.6 Hz, 1H), 1.20 (s, 9H), 0.97 (s, 9H); MS (APCI) m/z 607.1 (M + H)$^+$. |
| Example I-155 | (2S,3S,4S,5S)-3-tert-butyl-4-({[5-(1-cyanocyclobutyl)-2-methoxyphenyl]methyl}amino)-1-(cyclohexanecarbonyl)-5-phenylpyrrolidine-2-carboxylic acid | LC/MS (ESI+) m/z 572.9 (M + H)$^+$. |
| Example I-156 | (2S,3S,4S,5S)-3-tert-butyl-4-[(4-chloro-2,3-dihydro-1H-inden-2-yl)amino]-1-(cyclohexanecarbonyl)-5-phenylpyrrolidine-2-carboxylic acid | $^1$HNMR (400 MHz, Chloroform-d) δ ppm 7.27 (s, 4H), 7.03-7.20 (m, 3H), 6.93-7.02 (m, 1H), 5.34-5.45 (m, 1H), 4.69 (s, 1H), 3.56-3.71 (m, 2H), 3.11-3.36 (m, 2H), 2.96 (d, J = 3.6 Hz, 1H), 2.42-2.67 (m, 2H), 2.34 (d, J = 7.3 Hz, 1H), 1.17-1.87 (m, 10H), 1.10 (br. s., 9H); LC/MS (ESI+) m/z 524.4 (M + H)$^+$. |
| Example I-157 | (2S,3S,4S,5S)-3-tert-butyl-4-[(5-chloro-2,3-dihydro-1H-inden-2-yl)amino]-1-(cyclohexanecarbonyl)-5-phenylpyrrolidine-2-carboxylic acid | $^1$HNMR (400 MHz, Chloroform-d) δ ppm 6.95-7.40 (m, 8H), 5.37 (d, J = 6.3 Hz, 1H), 4.67 (s, 1H), 3.53-3.68 (m, 2H), 3.02-3.21 (m, 2H), 2.86-3.00 (m, 1H), 2.48-2.60 (m, 1H), 2.36-2.48 (m, 1H), 2.33 (s, 1H), 1.15-1.87 (m, 10H), 1.10 (s, 9H); LC/MS (ESI+) m/z 524.4 (M + H)$^+$. |
| Example I-158 | (2S,3S,4S,5S)-3-tert-butyl-4-[(5-chloro-2,3-dihydro-1H-inden-1-yl)amino]-1-(cyclohexanecarbonyl)-5-phenylpyrrolidine-2-carboxylic acid | LC/MS (ESI+) m/z 524.4 (M + H)$^+$. |
| Example I-159 | (2S,3S,4S,5S)-3-tert-butyl-4-{[(5-tert-butyl-2-methoxyphenyl)methyl]amino}-1-[(2R*)-2-(3,4-difluorophenyl)-2-methoxyacetyl]-5-phenylpyrrolidine-2-carboxylic acid | $^1$HNMR (400 MHz, Chloroform-d) δ ppm 7.26-7.38 (m, 6H), 7.20-7.26 (m, 1H), 6.99-7.16 (m, 3H), 6.65 (d, J = 8.7 Hz, 1H), 5.56 (s, 1H), 5.29 (d, J = 6.3 Hz, 1H), 5.00 (s, 1H), 4.12 (d, J = 13.8 Hz, 1H), 3.58 (d, J = 13.8 Hz, 1H), 3.45 (s, 3H), 3.34 (d, J = 6.3 Hz, 1H), 3.23 (s, 3H), 2.49 (s, 1H), 1.27 (s, 9H), 1.08 (s, 9H); LC/MS (ESI+) m/z 623.9 (M + H)$^+$. |

TABLE 1-continued

| Example I-160 | (2S,3S,4S,5S)-3-tert-butyl-4-{[(5-tert-butyl-2-methoxyphenyl)methyl]amino}-1-[cyclohexyl(methoxy)acetyl]-5-phenylpyrrolidine-2-carboxylic acid | LC/MS (ESI+) m/z 594.0 (M + H)+. |
|---|---|---|
| Example I-161 | (2S,3S,4S,5S)-1-(bicyclo[3.1.0]hexane-6-carbonyl)-3-tert-butyl-4-({[2-methoxy-5-(trifluoromethyl)phenyl]methyl}amino)-5-phenylpyrrolidine-2-carboxylic acid | LC/MS (ESI+) m/z 559.5 (M + H)+. |
| Example I-162 | (2S,3S,4S,5S)-1-(bicyclo[3.1.0]hexane-3-carbonyl)-3-tert-butyl-4-({[2-methoxy-5-(trifluoromethyl)phenyl]methyl}amino)-5-phenylpyrrolidine-2-carboxylic acid | LC/MS (ESI+) m/z 559.5 (M + H)+. |
| Example I-163 | (2S,3S,4S,5S)-3-tert-butyl-4-({[2-methoxy-5-(trifluoromethyl)phenyl]methyl}amino)-5-phenyl-1-[3-(trifluoromethyl)cyclopentane-l-carbonyl]pyrrolidine-2-carboxylic acid | LC/MS (ESI+) m/z 615.5 (M + H)+. |
| Example I-164 | (2S,3S,4S,5S)-3-tert-butyl-1-(5,5-dimethyloxane-2-carbonyl)-4-({[2-methoxy-5-(trifluoromethyl)phenyl]methyl}amino)-5-phenylpyrrolidine-2-carboxylic acid | LC/MS (ESI+) m/z 577.8 (M + H)+. |
| Example I-165 | (2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-(2-methoxypyridin-3-yl)pyrrolidine-2-carboxylic acid | $^1$HNMR (400 MHz, dimethyl sulfoxide-$d_6$) δ ppm 8.06 (s, 1H), 7.15 (dd, J = 8.5, 2.6 Hz, 2H), 7.11 (d, J = 6.9 Hz, 1H), 7.04 (t, J = 7.7 Hz, 1H), 6.97 (d, J = 2.6 Hz, 1H), 6.92 (s, 1H), 6.81-6.72 (m, 2H), 6.67 (d, J = 8.0 Hz, 1H), 5.61 (s, 1H), 5.50 (s, 1H), 4.62 (d, J = 1.8 Hz, 1H), 3.82 (s, 3H), 3.57 (d, J = 14.2 Hz, 2H), 3.53 (s, 3H), 3.33-3.23 (m, 4H), 2.42 (s, 1H), 1.22 (d, J = 1.0 Hz, 9H), 1.00 (s, 9H); MS (ESI+) m/z 616.2 (M + H)+. |
| Example I-166 | (2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-(2-methoxypyridin-3-yl)pyrrolidine-2-carboxylic acid | $^1$HNMR (400 MHz, dimethyl sulfoxide-$d_6$) δ ppm 8.03 (dd, J = 4.9, 1.8 Hz, 1H), 7.84 (s, 1H), 7.21-7.11 (m, 2H), 7.05 (t, J = 7.7 Hz, 1H), 6.99 (d, J = 2.5 Hz, 1H), 6.90 (t, J = 6.2 Hz, 1H), 6.81 (d, J = 7.3 Hz, 1H), 6.76 (d, J = 8.5 Hz, 1H), 6.67 (s, 1H), 5.29 (s, 1H), 4.91 (s, 1H), 3.77 (s, 3H), 3.62 (d, J = 13.9 Hz, 2H), 3.53 (s, 1H), 3.50 (s, 3H), 3.33 (dd, J = 20.2, 13.4 Hz, 4H), 2.53 (s, 1H), 1.22 (s, 9H), 1.03 (s, 9H); MS (ESI+) m/z 616.2 (M + H)+. |
| Example I-167 | (2S,3S,4S,5S)-3-tert-butyl-4-{[(5-tert-butyl-2-methoxyphenyl)methyl]amino}-1-[(2R)-2,3-dihydro-1,4-benzodioxine-2-carbonyl]-5-phenylpyrrolidine-2-carboxylic acid | $^1$HNMR (400 MHz, 120° C., dimethyl sulfoxide-$d_6$: D$_2$O = 9:1 (v/v)) δ ppm 7.67-7.53 (m, 2H), 7.44-7.17 (m, 4H), 7.10-6.88 (m, 3H), 6.84-6.66 (m, 3H), 5.48 (d, J = 6.9 Hz, 1H), 4.85 (s, 1H), 4.75 (d, J = 2.7 Hz, 1H), 4.14 (d, J = 2.5 Hz, 1H), 3.87-3.74 (m, 2H), 3.57-3.47 (m, 4H), 2.53 (s, 1H), 1.20 (d, J = 2.6 Hz, 9H), 0.99 (s, 9H); MS (APCI+) m/z 601.1 (M + H)+. |
| Example I-168 | (2S,3S,4S,5S)-3-tert-butyl-4-{[(2-cyclobutyl-5-methoxypyridin-4-yl)methyl]amino}-1-(cyclohexanecarbonyl)-5-phenylpyrrolidine-2-carboxylic acid | $^1$HNMR (400 MHz, 120° C., dimethyl sulfoxide-$d_6$: D$_2$O = 9:1 (v/v)) δ ppm 8.08 (s, 1H), 7.59 (s, 2H), 7.39-7.32 (m, 2H), 7.32-7.25 (m, 1H), 7.12 (s, 1H), 5.25 (d, J = 7.0 Hz, 1H), 4.51 (d, J = 2.3 Hz, 1H), 3.76 (s, 3H), 3.72-3.58 (m, 3H), 3.41 (d, J = 15.9 Hz, 1H), 2.45-2.11 (m, 6H), 2.08-1.99 (m, 1H), 1.95-1.84 (m, 1H), 1.72-1.58 (m, 2H), 1.58-1.45 (m, 2H), 1.33-1.14 (m, 3H), 1.13-1.03 (m, 2H), 0.98 (s, 9H), 0.83 (s, 1H); MS (APCI+) m/z 548.1 (M + H)+. |
| Example I-169 | (2S,3S,4S,5S)-3-tert-butyl-1-(cyclohexanecarbonyl)-4-{[(2-cyclopentyl-5-methoxypyridin-4-yl)methyl]amino]-5-phenylpyrrolidine-2-carboxylic acid | $^1$HNMR (400 MHz, 120° C., dimethyl sulfoxide-$d_6$: D$_2$O = 9:1 (v/v)) δ ppm 8.06 (s, 1H), 7.58 (s, 2H), 7.34 (t, J = 7.5 Hz, 2H), 7.31-7.22 (m, 1H), 7.08 (s, 1H), 5.24 (d, J = 7.1 Hz, 1H), 4.51 (d, J = 2.4 Hz, 1H), 3.75 (s, 3H), 3.67-3.51 (m, 2H), 3.40 (d, J = 15.8 Hz, 1H), 3.22-3.14 (m, 1H), 2.35 (s, 1H), 2.28-1.93 (m, 3H), 1.85-1.42 (m, 10H), 1.29-1.01 (m, 5H), 0.98 (s, 9H), 0.93-0.49 (m, 1H); MS (APCI+) m/z 652.0 (M + H)+. |
| Example I-170 | (2S,3S,4S,5S)-3-tert-butyl-1-(cyclohexanecarbonyl)-4-[({3-methoxy-6{1-(trifluoromethyl)cyclopropyl] | $^1$HNMR (400 MHz, dimethyl sulfoxide-$d_6$) δ ppm 8.01 (d, J = 1.6 Hz, 1H), 7.54 (m, 2H), 7.38-7.21 (m, 4H), 5.28 (d, J = 7.0 Hz, 1H), 4.52 (d, J = 2.2 Hz, 1H), 3.80 (m, 2H), 3.72 (s, 3H), 3.54 (m, 1H), 2.44 (m, 1H), 2.30 |

TABLE 1-continued

| | | |
|---|---|---|
| | pyridin-2-yl}methyl]amino]-5-phenylpyrrolidine-2-carboxylic acid | (m, 1H), 1.65-1.51 (m, 4H), 1.36 (m, 2H), 1.24-1.02 (m, 5H), 0.99 (s, 9H), 0.83 (m, 1H); MS (ESI+) m/z 602.2 (M + H)+. |
| Example I-171 | (2S,3S,4S,5S)-3-tert-butyl-1-(cyclohexanecarbonyl)-4-({[2-methoxy-5-(trimethylsilyl)phenyl]methyl}amino)-5-phenylpyrrolidine-2-carboxylic acid | 1HNMR (400 MHz, Chloroform-d) δ ppm 7.29-7.50 (m, 6H), 7.19 (s, 1H), 6.73 (d, J = 8.2 Hz, 1H), 5.23 (d, J = 6.1 Hz, 1H), 4.68 (s, 1H), 4.10 (d, J = 13.8 Hz, 1H), 3.56 (d, J = 13.8 Hz, 1H), 3.29-3.32 (m, 1H), 3.28 (s, 3H), 2.96-3.06 (m, 1H), 2.45 (s, 1H), 1.12-1.91 (m, 10H), 1.06 (s, 9H), 0.23 (s, 9H); LC/MS (ESI+) m/z 565.5 (M + H)+. |
| Example I-172 | (2S,3S,4S,5S)-3-tert-butyl-4-{[(5-tert-butyl-2-methoxyphenyl)methyl]amino}-1-(8-oxabicyclo[3.2.1]octane-3-carbonyl)-5-phenylpyrrolidine-2-carboxylic acid | LC/MS (ESI+) m/z 577.5 (M + H)+. |
| Example I-173 | (2R,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid | 1HNMR (400 MHz, Chloroform-d) δ ppm 7.29-7.41 (m, 2H), 7.15-7.28 (m, 3H), 7.02-7.06 (m, 1H), 6.94-7.00 (m, 1H), 6.84 (d, J = 8.7 Hz, 1H), 5.68 (br. s., 1H), 4.45-4.49 (m, 1H), 4.38 (d, J = 13.5 Hz, 1H), 4.17 (d, J = 13.5 Hz, 1H), 3.83 (s, 3H), 3.63 (br. s, 1H), 2.59-2.69 (m, 2H), 1.23 (s, 9H), 1.17-1.99 (m, 10H), 0.71 (s, 9H); LC/MS (ESI+) m/z 549.8 (M + H)+. |
| Example I-174 | (2S,3S,4S,5S)-3-(2-methoxypropan-2-yl)-4-({[2-methoxy-5-(trifluoromethyl)phenyl]methyl}amino)-5-phenyl-1-{[(propan-2-yl)oxy]carbonyl}pyrrolidine-2-carboxylic acid | 1HNMR (400 MHz, dimethyl sulfoxide-d6) δ ppm 7.56-7.49 (m, 3H), 7.35-7.28 (m, 3H), 7.28-7.21 (m, 1H), 7.05 (d, J = 8.6 Hz, 1H), 5.09 (d, J = 7.1 Hz, 1H), 4.63 (p, J = 6.2 Hz, 1H), 4.38 (d, J = 3.5 Hz, 1H), 3.69 (s, 3H), 3.67 (d, J = 14.1 Hz, 1H), 3.60 (dd, J = 7.1, 3.4 Hz, 1H), 3.48 (d, J = 14.1 Hz, 1H), 3.15 (s, 3H), 2.68 (t, J = 3.5 Hz, 1H), 1.20 (d, J = 9.1 Hz, 6H), 1.06 (d, J = 6.2 Hz, 3H), 0.89 (d, J = 6.2 Hz, 3H); MS (APCI+) m/z 553 (M + H)+. |
| Example I-175 | (2S,3S,4S,5S)-3-tert-butyl-1-[(2S*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid | 1HNMR (400 MHz, dimethyl sulfoxide-d6) δ ppm 8.20 (s, 2H), 7.22 (dd, J = 8.4, 2.4 Hz, 1H), 7.13-6.93 (m, 4H), 6.84-6.74 (m, 2H), 6.66 (d, J = 8.0 Hz, 1H), 5.66 (s, 1H), 4.62 (d, J = 1.3 Hz, 1H), 3.59 (d, J = 14.0 Hz, 2H), 3.52 (s, 3H), 3.27 (d, J = 14.0 Hz, 2H), 3.22-3.13 (m, 2H), 2.64 (s, 6H), 2.61 (s, 1H), 2.45 (s, 1H), 1.28-1.25 (m, 2H), 1.03 (s, 9H), 0.95 (tt, J = 3.5, 1.9 Hz, 2H); MS (ESI+) m/z 681.2 (M + H)+. |
| Example I-176 | (2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-[(2S)-oxane-2-carbonyl]pyrrolidine-2-carboxylic acid | 1HNMR (400 MHz, dimethyl sulfoxide-d6, 120° C.) δ ppm 1HNMR (400 MHz, dimethyl sulfoxide-d6) δ ppm 8.68 (d, J = 7.5 Hz, 1H), 8.09 (s, 1H), 7.14 (dd, J = 8.4, 2.4 Hz, 1H), 6.98 (d, J = 2.3 Hz, 1H), 6.85 (t, J = 6.1 Hz, 1H), 6.77 (d, J = 8.5 Hz, 1H), 5.51 (s, 1H), 4.29 (s, 1H), 3.79 (d, J = 11.2 Hz, 1H), 3.63 (s, 3H), 3.20 (s, 1H), 3.12 (s, 2H), 2.72 (s, 6H), 2.51 (s, 1H), 2.36 (s, 1H), 1.37 (s, 6H), 1.23-1.15 (m, 2H), 0.95 (s, 9H), 0.89-0.82 (m, 2H); MS (ESI+) m/z 647 (M + H)+. |
| Example I-177 | (2S,3S,4S,5S)-3-tert-butyl-4-{[(6-tert-butyl-2-methoxypyridin-3-yl)methyl]amino}-1-(oxane-2-carbonyl)-5-[2-(propan-2-yl)phenyl]pyrrolidine-2-carboxylic acid | LC/MS (ESI+) m/z 594.9 (M + H)+. |
| Example I-178 | (2S,3S,4S,5S)-3-tert-butyl-4-{[(5-tert-butyl-2-methoxyphenyl)methyl]amino}-5-phenyl-1-[(2R*,3R*)-3-phenyloxolane-2-carbonyl]pyrrolidine-2-carboxylic acid | LC/MS (ESI+) m/z 613.6 (M + H)+. |
| Example I-179 | (2S,3S,4S,5S)-3-tert-butyl-4-{[(5-tert-butyl-2-methoxyphenyl)methyl]amino}-5-phenyl-1-[(2S*,3S*)-3-phenyloxolane-2-carbonyl]pyrrolidine-2-carboxylic acid | LC/MS (ESI+) m/z 613.6 (M + H)+. |
| Example I-180 | (2S,3S,4S,5S)-3-tert-butyl-4-{[(6-tert-butyl-2-methoxypyridin-3-yl)methyl]amino}-1-(3,3-difluorocyclohexane-1-carbonyl)-5-phenylpyrrolidine-2-carboxylic acid | LC/MS (ESI+) m/z 586.8 (M + H)+. |

TABLE 1-continued

| | | |
|---|---|---|
| Example I-181 | (2S,3S,4S,5S)-3-tert-butyl-4-{[(6-tert-butyl-2-methoxypyridin-3-yl)methyl]amino}-1-[(2S*)-2,3-dihydro-1-benzofuran-2-carbonyl]-5-phenylpyrrolidine-2-carboxylic acid | LC/MS (ESI+) m/z 586.8 (M + H)+. |
| Example I-182 | (2S,3S,4S,5S)-3-tert-butyl-4-{[(6-tert-butyl-2-methoxypyridin-3-yl)methyl]amino}-5-phenyl-1-[(2R)-2-phenylpropanoyl]pyrrolidine-2-carboxylic acid | $^1$HNMR (400 MHz, Chloroform-d) δ ppm 7.44-7.58 (m, 2H), 7.13-7.41 (m, 7H), 7.06 (d, J = 6.8 Hz, 1H), 6.92 (br. s., 1H), 6.80 (d, J = 7.5 Hz, 1H), 5.35 (d, J = 6.0 Hz, 1H), 4.78-4.84 (m, 1H), 4.50 (d, J = 6.8 Hz, 1H), 3.86 (d, J = 13.7 Hz, 1H), 3.39 (s, 3H), 3.33-3.41 (m, 1H), 3.19-3.27 (m, 1H), 2.46 (s, 1H), 1.44 (d, J = 6.8 Hz, 3H), 1.28 (s, 9H), 1.11 (s, 9H); LC/MS (ESI+) m/z 572.9 (M + H)+. |
| Example I-183 | (2S,3S,4S,5S)-3-tert-butyl-1-(3,3-difluorocyclohexane-1-carbonyl)-4-({[2-methoxy-5-(trifluoromethyl)pyridin-3-yl]methyl}amino)-5-phenylpyrrolidine-2-carboxylic acid | LC/MS (ESI+) m/z 598.5 (M + H)+. |
| Example I-184 | (2S,3S,4S,5S)-3-tert-butyl-1-(cyclohexanecarbonyl)-4-[({2-methoxy-5-[(trifluoromethyl)sulfanyl]phenyl}methyl)amino]-5-phenylpyrrolidine-2-carboxylic acid | $^1$HNMR (400 MHz, dimethyl sulfoxide-d$_6$, 120° C.) δ ppm 7.55 (s, 2H), 7.49 (dd, J = 8.6, 2.4 Hz, 1H), 7.33 (t, J = 7.4 Hz, 2H), 7.30-7.22 (m, 2H), 6.99 (d, J = 8.5 Hz, 1H), 5.23 (d, J = 7.0 Hz, 1H), 4.48 (d, J = 2.4 Hz, 1H), 3.64 (s, 3H), 3.61-3.52 (m, 2H), 3.37 (d, J = 14.1 Hz, 1H), 2.38 (s, 1H), 2.33-2.17 (m, 1H), 1.63 (d, J = 9.9 Hz, 2H), 1.49 (s, 2H), 1.30-1.01 (m, 6H), 0.97 (s, 9H); MS (ESI+) m/z 593 (M + H)+. |
| Example I-185 | (2S,3S,4S,5S)-3-tert-butyl-4-{[(5-tert-butyl-2-methoxyphenyl)methyl]amino}-1-(cyclohexanecarbonyl)-5{2-(propan-2-yl)phenyl]pyrrolidine-2-carboxylic acid | LC/MS (ESI+) m/z 592.0 (M + H)+. |
| Example I-186 | (2S,3S,4S,5S)-1-(bicyclo[3.1.0]hexane-3-carbonyl)-3-tert-butyl-4-{[(5-tert-butyl-2-methoxyphenyl)methyl]amino}-5-phenylpyrrolidine-2-carboxylic acid | $^1$HNMR (400 MHz, Chloroform-d) δ ppm 7.21-7.48 (m, 6H), 7.04-7.11 (m, 1H), 6.65(d, J = 8.7 Hz, 1H), 5.20 (d, J = 6.1 Hz, 1H), 4.62 (s, 1H), 4.09 (d, J = 13.8 Hz, 1H), 3.72-3.83 (m, 1H), 3.54 (d, J = 13.8 Hz, 1H), 3.30 (d, J = 6.3 Hz, 1H), 3.25 (s, 3H), 2.42 (s, 1H), 2.26-2.38 (m, 2H), 1.83 (dt, J = 13.2, 4.5 Hz, 2H), 1.28 (s, 9H), 1.23-1.33 (m, 2H), 1.05 (s, 9H), 0.39-0.48 (m, 1H), 0.31-0.38 (m, 1H); LC/MS (ESI+) m/z 547.8 (M + H)+. |
| Example I-187 | (2S,3S,4S,5S)-3-tert-butyl-4-{[(6-tert-butyl-2-methoxypyridin-3-yl)methyl]amino}-1-(cyclohexanecarbonyl)-5-[2-(propan-2-yl)phenyl]pyrrolidine-2-carboxylic acid | $^1$HNMR (400 MHz, Chloroform-d) δ ppm 7.14-7.35 (m, 5H), 6.80 (d, J = 7.5 Hz, 1H), 5.53 (d, J = 6.0 Hz, 1H), 4.68 (s, 1H), 3.93 (d, J = 13.7 Hz, 1H), 3.36-3.46 (m, 1H), 3.38 (s, 3H), 3.30 (d, J = 6.0 Hz, 1H), 2.96-3.07 (m, 1H), 2.70-2.82 (m, 1H), 2.40 (s, 1H), 1.27 (s, 9H), 1.24 (d, J = 7.5 Hz, 3H), 1.13-1.89 (m, 10H), 1.09 (s, 9H), 0.81 (d, J = 6.8 Hz, 3H); LC/MS (ESI+) m/z 592.9 (M + H)+. |
| Example I-188 | (2S,3S,4S,5S)-3-tert-butyl-1-(cyclohexanecarbonyl)-4-{[(2-methoxynaphthalen-1-yl)methyl]amino}-5-phenylpyrrolidine-2-carboxylic acid | $^1$HNMR (400 MHz, dimethyl sulfoxide-d$_6$, 120° C.) δ ppm 7.81 (d, J = 9.0 Hz, 1H), 7.77 (d, J = 8.2 Hz, 1H), 7.60 (t, J = 7.0 Hz, 3H), 7.42-7.22 (m, 6H), 5.35 (d, J = 7.1 Hz, 1H), 4.50 (d, J = 2.5 Hz, 1H), 4.12 (d, J = 12.7 Hz, 1H), 3.94 (d, J = 7.2 Hz, 1H), 3.78 (s, 3H), 3.69 (d, J = 12.7 Hz, 1H), 2.52 (s, 1H), 2.27 (s, 1H), 1.58 (d, J = 58.0 Hz, 4H), 1.31-1.04 (m, 6H), 1.00 (s, 9H); MS (ESI+) m/z 543 (M + H)+. |
| Example I-189 | (2S,3S,4S,5S)-3-tert-butyl-1-[(1R)-3,3-difluorocyclohexane-1-carbonyl]-4-({[2-methoxy-5-(trimethylsilyl)pyridin-3-yl]methyl}amino)-5-phenylpyrrolidine-2-carboxylic acid | LC/MS (ESI+) m/z 602.6 (M + H)+. |
| Example I-190 | (2S,3S,4S,5S)-3-tert-butyl-1-[(1R)-3,3-difluorocyclohexane-1-carbonyl]-4-{[(6-methoxy-2,3-dihydro-1H-inden-5-yl)methyl]amino}-5-phenylpyrrolidine-2-carboxylic acid | LC/MS (ESI+) m/z 569.5 (M + H)+. |
| Example I-191 | (2S,3S,4S,5S)-3-tert-butyl-4-{[(5-tert-butyl-2-methoxyphenyl)methyl]amino}-1-[(3S*)-1- | LC/MS (ESI+) m/z 578.8 (M + H)+. |

TABLE 1-continued

| | | |
|---|---|---|
| Example I-192 | (2S,3S,4S,5S)-3-tert-butyl-4-{[(5-tert-butyl-2-methoxyphenyl)methyl]amino}-1-(1,1-dioxo-1λ⁶-thiolane-2-carbonyl)-5-phenylpyrrolidine-2-carboxylic acid | LC/MS (ESI+) m/z 586.0 (M + H)⁺. |
| Example I-193 | (2S,3S,4S,5S)-3-tert-butyl-4-{[(5-tert-butyl-2-methoxyphenyl)methyl]amino}-1-[(2S*)-oxane-2-carbonyl]-5-phenylpyrrolidine-2-carboxylic acid | ¹HNMR (400 MHz, dimethyl sulfoxide-d₆, 120° C.) δ ppm 7.66-7.59 (m, 2H), 7.40 (t, J = 7.5 Hz, 2H), 7.32 (t, J = 7.4 Hz, 1H), 7.23 (dd, J = 8.6, 2.5 Hz, 1H), 7.03 (d, J = 2.5 Hz, 1H), 6.81 (d, J = 8.6 Hz, 1H), 5.50 (d, J = 7.0 Hz, 1H), 4.54 (d, J = 1.9 Hz, 1H), 3.84 (d, J = 7.2 Hz, 2H), 3.75 (t, J = 12.9 Hz, 2H), 3.61 (s, 3H), 3.37 (d, J = 13.5 Hz, 1H), 3.14 (s, 1H), 2.54-2.49 (m, 1H), 1.68 (d, J = 13.4 Hz, 1H), 1.54-1.31 (m, 5H), 1.21 (d, J = 0.8 Hz, 9H), 0.99 (d, J = 0.8 Hz, 9H); MS (ESI+) m/z 551 (M + H)⁺. |
| Example I-194 | (2S,3S,4S,5S)-3-tert-butyl-4-{[(6-tert-butyl-2-methoxypyridin-3-yl)methyl]amino}-5-phenyl-1-{[(propan-2-yl)oxy]carbonyl}pyrrolidine-2-carboxylic acid | ¹HNMR (400 MHz, Chloroform-d) δ ppm 7.31-7.45 (m, 3H), 7.20-7.26 (m, 2H), 6.79 (d, J = 7.5 Hz, 1H), 5.12 (br. s., 1H), 4.84 (br. s, 1H), 4.64 (br. s., 1H), 3.79 (d, J = 13.7 Hz, 1H), 3.44 (s, 3H), 3.39-3.47 (m, 1H), 3.35 (d, J = 5.8 Hz, 1H), 2.29 (s, 1H), 1.29 (s, 9H), 1.07 (s, 9H); LC/MS (ESI+) m/z 526.8 (M + H)⁺. |
| Example I-195 | (2S,3S,4S,5S)-3-tert-butyl-4-{[(5-tert-butyl-2-methoxyphenyl)methyl]amino}-1-{(2S*)-2-[(2S*)-oxan-2-yl]propanoyl}-5-phenylpyrrolidine-2-carboxylic acid | LC/MS (ESI+) m/z 579.9 (M + H)⁺. |
| Example I-196 | (2S,3S,4S,5S)-3-tert-butyl-4-{[(5-tert-butyl-2-methoxyphenyl)methyl]amino}-1-{(2R*)-2-[(2R*)-oxan-2-yl]propanoyl}-5-phenylpyrrolidine-2-carboxylic acid | LC/MS (ESI+) m/z 579.9 (M + H)⁺. |
| Example I-197 | (2S,3S,4S,5S)-3-tert-butyl-4-{[(6-tert-butyl-2-methoxypyridin-3-yl)methyl]amino}-1-(3-methoxycyclohexane-l-carbonyl)-5-phenylpyrrolidine-2-carboxylic acid | LC/MS (ESI+) m/z 580.8 (M + H)⁺. |
| Example I-198 | (2S,3S,4S,5S)-3-tert-butyl-4-{[(6-tert-butyl-2-methoxypyridin-3-yl)methyl]amino}-1-[(1R*,3S*)-3-methoxycyclohexane-l-carbonyl]-5-phenylpyrrolidine-2-carboxylic acid | LC/MS (ESI+) m/z 580.8 (M + H)⁺. |
| Example I-199 | (2S,3S,4S,5S)-3-tert-butyl-4-{[(5-tert-butyl-2-methoxyphenyl)methyl]amino}-1-(2,3-dihydro-1,4-benzodioxine-6-carbonyl)-5-[2-(dimethylamino)pyridin-3-yl]pyrrolidine-2-carboxylic acid | ¹HNMR (400 MHz, dimethyl sulfoxide-d₆) δ ppm 8.33 (dd, J = 7.8, 1.8 Hz, 1H), 8.10 (dd, J = 4.9, 1.8 Hz, 1H), 7.21 (dd, J = 8.7, 2.6 Hz, 1H), 7.13-6.99 (m, 2H), 6.79 (d, J = 8.5 Hz, 1H), 6.75-6.65 (m, 2H), 5.58 (d, J = 6.7 Hz, 1H), 4.36 (s, 1H), 4.19 (dt, J = 8.7, 4.3 Hz, 4H), 3.85-3.70 (m, 2H), 3.55 (s, 3H), 3.43 (d, J = 13.5 Hz, 1H), 2.67 (s, 6H), 1.19 (s, 9H), 1.00 (s, 9H); MS (APCI) m/z 645.1 (M + H)⁺ |
| Example I-200 | (2S,3S,4S,5S)-3-tert-butyl-4-{[(5-tert-butyl-2-methoxyphenyl)methyl]amino}-1-[4-(cyclohexyloxy)benzoyl]-5-[2-(dimethylamino)pyridin-3-yl]pyrrolidine-2-carboxylic acid | ¹HNMR (400 MHz, dimethyl sulfoxide-d₆) δ ppm 8.31 (dd, J = 7.7, 1.8 Hz, 1H), 8.09 (dd, J = 4.9, 1.8 Hz, 1H), 7.91-7.82 (m, 2H), 7.21-7.12 (m, 2H), 7.08-7.00 (m, 1H), 7.00-6.89 (m, 3H), 6.78 (dd, J = 8.7, 2.1 Hz, 2H), 5.60 (d, J = 6.6 Hz, 1H), 4.47-4.31 (m, 2H), 4.28 (tt, J = 8.1, 3.6 Hz, 1H), 3.80 (d, J = 13.4 Hz, 1H), 3.75-3.66 (m, 1H), 3.53 (s, 3H), 3.41 (d, J = 13.6 Hz, 1H), 2.63 (s, 6H), 1.97-1.77 (m, 2H), 1.70 (tq, J = 9.3, 2.9 Hz, 2H), 1.55-1.26 (m, 8H), 1.19 (s, 9H), 1.00 (s, 9H); MS (APCI) m/z 685.2 (M + H)⁺. |
| Example I-201 | (2S,3S,4S,5S)-1-(bicyclo[3.1.0]hexane-6-carbonyl)-3-tert-butyl-4-{[(5-tert-butyl-2-methoxyphenyl)methyl]amino}-5-[2-(dimethylamino)pyridin-3-yl]pyrrolidine-2-carboxylic acid | ¹HNMR (400 MHz, dimethyl sulfoxide-d₆) δ ppm 8.23 (dd, J = 4.8, 1.8 Hz, 1H), 8.12 (d, J = 7.8 Hz, 1H), 7.22 (dd, J = 8.5, 2.6 Hz, 1H), 7.15-7.03 (m, 2H), 6.79 (d, J = 8.6 Hz, 1H), 5.46 (d, J = 6.6 Hz, 1H), 4.59 (d, J = 1.4 Hz, 1H), 3.84 (d, J = 13.8 Hz, 1H), 3.74 (s, 1H), 3.51 (d, J = 18.8 Hz, 3H), 3.45 (s, 1H), 2.70 (s, 6H), 1.71-1.57 (m, 2H), 1.44 (d, J = 39.0 Hz, 3H), 1.19 (s, 9H), 1.01 (s, 9H), 0.82 (s, 2H); MS (APCI) m/z 591.2 (M + H)⁺. |
| Example I-202 | (2S,3S,4S,5S)-3-(bicyclo[1.1.1]pentan-l-yl)-4-{[(5-tert-butyl-2-methoxyphenyl)methyl]amino}- | ¹HNMR (400 MHz, dimethyl sulfoxide-d₆) δ ppm 7.54 (s, 2H), 7.33 (t, J = 7.5 Hz, 2H), 7.27 (d, J = 7.3 Hz, 1H), 7.20 (dd, J = 8.6, 2.6 Hz, 1H), 7.06 (d, J = 2.6 Hz, 1H), 6.81 (d, J = 8.6 Hz, 1H), 5.18 (d, J = 7.2 Hz, 1H), |

TABLE 1-continued

| | | |
|---|---|---|
| | 1-(cyclohexanecarbonyl)-5-phenylpyrrolidine-2-carboxylic acid | 4.15 (s, 1H), 3.71-3.51 (m, 2H), 3.62 (s,3H), 3.40 (t, J = 6.9 Hz, 1H), 2.50 (s, 1H), 2.27 (bs, 1H), 1.79-1.69 (m, 6H), 1.67 (m, 2H), 1.49 (m, 2H), 1.27 (m, 1H), 1.23 (d, J = 0.7 Hz, 9H), 1.10 (m, 4H), 0.80 (bs, 1H); MS (ESI+) m/z 559 (M + H)+. |
| Example I-203 | (2R,3R,4R,5R)-3-tert-butyl-4-{(S-tert-butyl-2-methoxyphenyl)methyl]amino}-1-(cyclohexanecarbonyl)-N-(methanesulfonyl)-5-phenylpyrrolidine-2-carboxamide | 1HNMR (400 MHz, dimethyl sulfoxide-d6) δ ppm 7.65-7.50 (m, 2H), 7.36 (d, J = 2.6 Hz, 1H), 7.35-7.28 (m, 2H), 7.27-7.18 (m, 2H), 6.89 (d, J = 8.6 Hz, 1H), 4.89 (s, 1H), 4.41 (d, J = 11.0 Hz, 1H), 3.97 (d, J = 13.5 Hz, 1H), 3.89-3.80 (m, 1H), 3.77 (s, 3H), 3.17 (s, 4H), 2.21 (dd, J = 11.0, 4.7 Hz, 1H), 2.02 (s, 1H), 1.82 (s, 1H), 1.66 (d, J = 10.1 Hz, 2H), 1.48 (d, J = 10.7 Hz, 2H), 1.31 (d, J = 4.9 Hz, 4H), 1.26 (d, J = 4.9 Hz, 4H), 0.95 (s, 9H), 0.73 (s, 1H); MS (ESI+) m/z 626.1 (M + H)+. |
| Example I-204 | (2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3R*,4S*)-3-(trifluoromethyl)-7-oxabicyclo[2.2.1]heptane-2-carbonyl]pyrrolidine-2-carboxylic acid | 1HNMR (400 MHz, dimethyl sulfoxide-d6) δ ppm 8.21-8.16 (m, 2H), 7.18-7.10 (m, 1H), 7.00 (d, J = 3.3 Hz, 1H), 6.95 (dd, J = 7.6, 4.7 Hz, 1H), 6.72 (dd, J = 8.5, 3.2 Hz, 1H), 5.40 (s, 1H), 4.63 (s, 1H), 4.53 (d, J = 23.6 Hz, 2H), 3.76-3.60 (m, 2H), 3.44 (d, J = 1.0 Hz, 3H), 3.38-3.29 (m, 2H), 2.61 (t, J = 4.1 Hz, 6H), 1.76-1.42 (m, 4H), 1.19 (s, 9H), 1.06-0.94 (m, 9H), 0.99 (m, 2H); MS (ESI+) m/z 675.3 (M + H)+. |
| Example I-205 | (2S,3S,4S,5S)-3-tert-butyl-4-{[(5-cyclobutyl-2-methoxypyridin-3-yl)methyl]amino}-1-[(2S*)-2,3-dihydro-1,4-benzodioxine-2-carbonyl]-5-phenylpyrrolidine-2-carboxylic acid | 1HNMR (400 MHz, dimethyl sulfoxide-d6) δ ppm 7.80 (d, J = 2.4 Hz, 1H), 7.48 (s, 3H), 7.37-7.18 (m, 4H), 6.79 (s, 4H), 5.32 (d, 1H), 4.29 (d, J = 11.7 Hz, 1H), 4.11 (s, 1H), 3.63 (s, 3H), 3.57 (d, J = 6.8 Hz, 2H), 3.43-3.36 (m, 2H), 2.31-2.24 (m, 2H), 2.00-1.91 (m, 3H), 1.86-1.74 (m, 1H), 1.01 (s, 9H); MS (APCI) m/z 600.1 (M + H)+. |
| Example I-206 | (2S,3S,4S,5S)-3-tert-butyl-4-{[(5-cyclobutyl-2-methoxypyridin-3-yl)methyl]amino}-1-(3,4-dihydro-1H-2-benzopyran-3-carbonyl)-5-phenylpyrrolidine-2-carboxylic acid | 1HNMR (400 MHz, dimethyl sulfoxide-d6) δ ppm 7.81 (d, J = 2.6 Hz, 2H), 7.47 (m, 3H), 7.37-7.21 (m, 4H), 7.11 (d, J = 4.9 Hz, 3H), 5.31 (d, 1H), 4.6 (d, 1H), 3.64 (s, 3H), 3.61 (d, J = 6.9 Hz, 2H), 3.48-3.38 (m, 2H), 2.66 (d, J = 15.5 Hz, 2H), 2.27 (dd, J = 7.3, 4.2 Hz, 2H), 1.98 (ddd, J = 9.2, 7.6, 4.4 Hz, 3H), 1.85(m, 1H); 1.01 (d, J = 5.6 Hz, 9H); MS (APCI) m/z 598.1 (M + H)+. |
| Example I-207 | (2S,3S,4S,5S)-3-tert-butyl-4-{[(2-tert-butyl-4-methoxypyrimidin-5-yl)methyl]amino}-1-(cyclohexanecarbonyl)-5-phenylpyrrolidine-2-carboxylic acid | LC/MS (ESI+) m/z 551.8 (M + H)+. |
| Example I-208 | (2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxane-2-carbonyl]pyrrolidine-2-carboxylic acid | 1HNMR (400 MHz, dimethyl sulfoxide-d6, 120° C.) δ ppm 8.29 (s, 1H), 8.28-8.20 (m, 1H), 8.15 (d, J = 4.7 Hz, 1H), 7.54 (d, J = 2.3 Hz, 1H), 6.92 (dd, J = 7.6, 4.7 Hz, 1H), 5.56 (s, 1H), 4.57 (d, J = 1.5 Hz, 1H), 3.79 (s, 4H), 3.52 (d, J = 11.3 Hz, 2H), 3.40 (s, 2H), 3.26 (d, J = 15.1 Hz, 1H), 2.72 (s, 6H), 2.31 (d, J = 1.5 Hz, 1H), 1.66 (s, 1H), 1.43 (d, J = 38.9 Hz, 5H), 0.98 (s, 9H); MS (ESI+) m/z 608 (M + H)+. |
| Example I-209 | (2S,3S,4S,5S)-3-tert-butyl-4-{[(5-tert-butyl-2-methoxyphenyl)methyl]amino}-5-(2-methoxypyridin-3-yl)-1-[(2S)-oxane-2-carbonyl]pyrrolidine-2-carboxylic acid | 1HNMR (400 MHz, dimethyl sulfoxide-d6, 120° C.) δ ppm 8.09 (dd, J = 4.8, 1.6 Hz, 1H), 8.03 (s, 1H), 7.25-7.19 (m, 1H), 7.04 (d, J = 2.5 Hz, 1H), 6.98 (dd, J = 7.2, 4.8 Hz, 1H), 6.81 (d, J = 8.6 Hz, 1H), 5.57 (s, 1H), 4.65-4.53 (m, 1H), 3.89 (s, 3H), 3.83-3.68 (m, 4H), 3.60 (s, 3H), 3.41 (d, J = 13.5 Hz, 1H), 1.76-1.65 (m, 2H), 1.57-1.35 (m, 6H), 1.21 (s, 9H), 0.98 (s, 9H); MS (ESI+) m/z 582 (M + H)+. |
| Example I-210 | (2S,3S,4S,5S)-4-({[5-(bicyclo[1.1.1]pentan-1-yl)-2-methoxyphenyl]methyl}amino)-3-tert-butyl-5-phenyl-1-{(propan-2-yl)oxy]carbonyl}pyrrolidine-2-carboxylic acid | 1HNMR (400 MHz, dimethyl sulfoxide-d6, 120° C.) δ ppm 7.59-7.50 (m, 2H), 7.40-7.33 (m, 2H), 7.29 (dd, J = 8.1, 6.5 Hz, 1H), 7.04 (dd, J = 8.3, 2.1 Hz, 1H), 6.84 (d, J = 2.2 Hz, 1H), 6.81 (d, J = 8.3 Hz, 1H), 5.15 (d, J = 6.9 Hz, 1H), 4.63 (hept, J = 6.2 Hz, 1H), 4.37 (d, J = 2.0 Hz, 1H), 3.80 (d, J = 6.9 Hz, 1H), 3.73 (d, J = 13.5 Hz, 1H), 3.59 (s, 3H), 3.38 (d, J = 13.6 Hz, 1H), 2.52-2.49 (m, 2H), 1.96 (s, 6H), 1.04 (d, J = 6.2 Hz, 3H), 1.00 (s, 9H), 0.87 (d, J = 6.2 Hz, 3H); MS (ESI+) m/z 535 (M + H)+. |
| Example I-211 | rac-(2S,3S,4S,5S)-3-tert-butyl-4-{[(5-tert-butyl-2-methoxyphenyl)methyl]amino}-1-(cyclohexanecarbonyl)-2-methyl-5-phenylpyrrolidine-2-carboxylic acid | LC/MS (ESI+) m/z 563.8 (M + H)+. |
| Example I-212 | (2S,3S,4S,5S)-3-tert-butyl-1-(cyclohexanecarbonyl)-4- | 1HNMR (400 MHz, dimethyl sulfoxide-d6) δ ppm 7.61 (m, 2H), 7.39-7.19 (m, 4H), 6.45 (s, 1H), 5.23 (d, J = |

TABLE 1-continued

| | | |
|---|---|---|
| | ({[5-methoxy-2-(pyrrolidin-1-yl)pyridin-4-yl]methyl}amino)-5-phenylpyrrolidine-2-carboxylic acid | 6.9 Hz, 1H), 4.50 (d, J = 2.4 Hz, 1H), 3.63 (s, 3H), 3.57-3.09 (m, 7H), 2.33 (m, 1H), 2.22 (m, 1H), 2.05-1.95 (m, 4H), 1.65-1.02 (m, 9H), 1.00 (s, 9H), 0.76 (m, 1H); MS (ESI+) m/z 563.3 (M + H)+. |
| Example I-213 | (2S,3S,4S,5S)-3-tert-butyl-1-(cyclohexanecarbonyl)-4-({[2-methoxy-5-(1,1,1-trifluoro-2-methylpropan-2-yl)phenyl]methyl}amino)-5-phenylpyrrolidine-2-carboxylic acid | $^1$HNMR (400 MHz, dimethyl sulfoxide-d$_6$) δ ppm 7.56 (m, 2H), 7.41-7.25 (m, 4H), 7.14 (m, 1H), 6.88 (d, J = 8.8 Hz, 1H), 5.31 (m, 1H), 4.51 (d, J = 2.1 Hz, 1H), 3.77-3.71 (m, 2H), 3.61 (s, 3H), 3.43 (d, J = 13.8 Hz, 1H), 2.50 (m, 1H), 2.26 (m, 1H), 1.65-1.05 (m, 9H), 1.46 (s, 6H), 0.98 (s, 9H), 0.83 (m, 1H); MS (ESI+) m/z 603.2 (M + H)+. |
| Example I-214 | (2S,3S,4S,5S)-3-tert-butyl-4-{[(5-cyclobutyl-2-methoxypyridin-3-yl)methyl]amino}-5-phenyl-1-{[(propan-2-yl)oxy]carbonyl}pyrrolidine-2-carboxylic acid | $^1$HNMR (400 MHz, dimethyl sulfoxide-d$_6$) δ ppm 7.82 (d, J = 2.4 Hz, 1H), 7.56-7.49 (m, 2H), 7.36-7.17 (m, 5H), 5.07 (d, J = 6.8 Hz, 1H), 4.63 (hept, J = 6.3 Hz, 1H), 4.34 (d, J = 2.3 Hz, 1H), 3.67 (s, 3H), 3.58-3.31 (m, 4H), 2.40 (m, 1H), 2.31-1.83 (m, 6H), 1.04 (d, J = 6.2 Hz, 3H), 0.99 (s, 9H), 0.87 (d, J = 6.2 Hz, 3H); MS (ESI+) m/z 524.2 (M + H)+. |
| Example I-215 | (2S,3S,4S,5S)-3-tert-butyl-5-[2-(dimethylamino)pyridin-3-yl]-4-{[2-methoxy-5-(trifluoromethyl)pyridin-3-yl]amino}-1-[(2S)-oxane-2-carbonyl]pyrrolidine-2-carboxylic acid | $^1$HNMR (400 MHz, Pyridine-d5) δ ppm 8.78 (d, J = 7.6 Hz, 1H), 8.19 (s, 1H), 7.77 (s, 1H), 7.05 (d, J = 2.1 Hz, 1H), 6.98-6.85 (m, 1H), 6.20 (s, 1H), 5.79 (s, 1H), 5.12-5.03 (m, 1H), 4.81 (s, 1H), 3.79 (s, 3H), 3.39 (s, 1H), 2.89 (s, 6H), 2.65 (s, 1H), 1.92 (d, J = 12.4 Hz, 1H), 1.73 (s, 1H), 1.56-1.25 (m, 4H), 1.19 (s, 9H), 1.03-0.86 (m, 1H); MS (APCI+) m/z 594 (M + H)+. |
| Example I-216 | (2S,3S,4S,5S)-3-tert-butyl-4-{[(6-tert-butyl-2-methoxypyridin-3-yl)methyl]amino}-1-{[(propan-2-yl)oxy]carbonyl}-5-[2-(propan-2-yl)oxy]phenyl]pyrrolidine-2-carboxylic acid | LC/MS (ESI+) m/z 568.8 (M + H)+. |
| Example I-217 | (2S,3S,4S,5S)-3-tert-butyl-4-{[(5-tert-butyl-2-methoxyphenyl)methyl]amino}-1-[(2R*)-oxane-2-carbonyl]-5-[2-(propan-2-yl)phenyl]pyrrolidine-2-carboxylic acid | LC/MS (ESI+) m/z 593.7 (M + H)+. |
| Example I-218 | (2S,3S,4S,5S)-3-tert-butyl-4-{[(5-tert-butyl-2-methoxyphenyl)methyl]amino}-5-phenyl-1-[2-(propan-2-yl)oxolane-3-carbonyl]pyrrolidine-2-carboxylic acid | LC/MS (ESI+) m/z 579.5 (M + H)+. |
| Example I-219 | (2S,3S,4S,5S)-3-tert-butyl-4-({[4-(2-chlorophenyl)oxan-4-yl]methyl}amino)-1-(cyclohexanecarbonyl)-5-phenylpyrrolidine-2-carboxylic acid | $^1$HNMR (400 MHz, dimethyl sulfoxide-d$_6$) δ ppm 7.33 (s, 2H), 7.21-7.08 (m, 5H), 7.01-6.94 (m, 1H), 5.08 (d, J = 7.0 Hz, 1H), 4.40 (d, J = 2.6 Hz, 1H), 3.56 (ddd, J = 11.0, 7.2, 3.4 Hz, 1H),3.45 (tdd, J = 11.1, 7.4, 3.5 Hz, 2H), 3.34-3.27 (m, 2H), 2.88 (d, J = 12.0 Hz, 1H), 2.76 (d, J = 12.1 Hz, 1H), 2.24-1.97 (m, 4H), 1.77 (tdd, J = 10.2, 7.7, 3.8 Hz, 2H), 1.57 (d, J = 15.0 Hz, 2H), 1.45 (s, 2H), 1.17 (s, 2H), 1.03 (s, 2H), 0.91 (s, 9H); MS (APCI) m/z 581.1(M + H)+. |
| Example I-220 | (2S,3S,4S,5S)-4-{[(5-tert-butyl-2-methoxyphenyl)methyl]amino}-5-[2-(dimethylamino)pyridin-3-yl]-3-(2-methoxypropan-2-yl)-1-{[(propan-2-yl)oxy]carbonyl}pyrrolidine-2-carboxylic acid | $^1$HNMR (400 MHz, dimethyl sulfoxide-d$_6$) δ ppm 8.19 (dd, J = 6.2, 4.3 Hz, 2H), 7.22 (m, 3H), 8.7, 2.6 Hz, 1H), 7.09-6.98 (m, 2H), 6.80 (d, J = 8.5 Hz, 1H), 5.44 (d, J = 6.7 Hz, 1H), 4.63 (p, J = 6.2 Hz, 1H), 4.42 (d, J = 2.8 Hz, 1H), 3.78 (t, J = 11.4 Hz, 2H), 3.57 (s, 3H), 3.48 (d, J = 13.6 Hz, 1H), 3.16 (s, 3H), 2.70 (s, 7H), 2.50 (s, 1H), 1.26-1.19(m, 15H), 1.03 (d, J = 6.2 Hz, 3H), 0.87 (d, J = 6.2 Hz, 3H); MS (ESI+) m/z 585 (M + H)+. |
| Example I-221 | (2S,3S,4S,5S)-3-tert-butyl-4-{[(5-tert-butyl-2-methoxyphenyl)methyl]amino}-5-(2-fluorophenyl)-1-{[(propan-2-yl)oxy]carbonyl}pyrrolidine-2-carboxylic acid | $^1$HNMR (400 MHz, dimethyl sulfoxide-d$_6$, 120° C.) δ ppm 7.81 (td, J = 7.7, 1.8 Hz, 1H), 7.29 (tdd, J = 7.7, 5.3, 1.7 Hz, 1H), 7.20-7.05 (m, 3H), 6.99 (d, J = 2.6 Hz, 1H), 6.77 (d, J = 8.6 Hz, 1H), 5.27 (d, J = 6.8 Hz, 1H), 4.64 (hept, J = 6.3 Hz, 1H), 4.36 (d, J = 2.1 Hz, 1H), 3.64 (d, J = 13.7 Hz, 1H), 3.59 (d, J = 7.1 Hz, 1H), 3.57 (s, 3H), 3.40 (d, J = 13.7 Hz, 1H), 2.43 (d, J = 1.8 Hz, 1H), 1.20 (s, 9H), 1.05 (d, J = 6.2 Hz, 3H), 0.97 (s, 9H), 0.89 (d, J = 6.2 Hz, 3H); MS (ESI+) m/z 543 (M + H)+. |
| Example I-222 | (2S,3S,4S,5S)-1-(bicyclo[3.1.0]hexane-6-carbonyl)-3-tert-butyl-5{2-(dimethylamino)pyridin-3-yl]-4-{[6-methyl-4-(trifluoromethyl)pyridin-2-yl]amino}pyrrolidine-2-carboxylic acid | $^1$HNMR (400 MHz, dimethyl sulfoxide-d$_6$) δ ppm 8.29 (d, J = 7.7 Hz, 1H), 8.06 (dd, J = 4.8, 1.9 Hz, 1H), 6.94 (dd, J = 7.7, 4.8 Hz, 1H), 6.48 (s, 1H), 6.29 (s, 1H), 5.83 (s, 1H), 5.60 (d, J = 7.7 Hz, 1H), 5.30 (s, 1H), 4.43 (d, J = 4.4 Hz, 1H), 2.68 (s, 6H), 2.31 (t, J = 4.4 Hz, 1H), 2.27 (s, 3H), 1.75-1.57 (m, 3H), 1.54-1.33 (m, 3H), 1.15-1.04 (m, 2H), 1.02 (s, 8H), 0.83-0.69 (m, 1H); MS (ESI+) m/z 574 (M + H)+. |
| Example I-223 | (2S,3S,4S,5S)-3-tert-butyl-4-{[(5-tert-butyl-2-methoxyphenyl)methyl]amino}-5-[2- | $^1$HNMR (400 MHz, dimethyl sulfoxide-d$_6$) δ ppm 7.99 (s, 1H), 7.36 (d, J = 7.9 Hz, 1H), 7.22 (d, J = 8.4 Hz, 2H), 7.13 (dd, J = 8.6, 2.6 Hz, 1H), 6.94 (d, J = 2.5 Hz, |

TABLE 1-continued

| | | |
|---|---|---|
| | (difluoromethoxy)phenyl]-1-[(1S*,2S*,3S*,4R*)-3-(trifluoromethyl)-7-oxabicyclo[2.2.1]heptane-2-carbonyl]pyrrolidine-2-carboxylic acid | 1H), 7.08, 6.89,7.32 (t, 1H), 6.73 (d, J = 8.6 Hz, 1H), 5.44 (d, J = 6.6 Hz, 1H), 4.63 (s, 1H), 4.57 (s, 1H), 3.55 (s, 1H), 3.50 (s, 3H), 3.48 (s, 1H), 3.28 (d, J = 12.5 Hz, 3H), 2.64 (s, 1H), 2.41 (s, 1H), 1.74-1.35 (m, 4H), 1.19 (s, 9H), 0.95 (s, 9H); MS (ESI+) m/z 697.2 (M + H)+. |
| Example I-224 | (2S,3S,4S,5S)-4-({[5-(bicyclo[1.1.1]pentan-1-yl)-2-methoxyphenyl]methyl}amino)-3-tert-butyl-5-(2-methoxypyridin-3-yl)-1-{[(propan-2-yl)oxy]carbonyl}pyrrolidine-2-carboxylic acid | 1HNMR (400 MHz, dimethyl sulfoxide-d6, 120° C.) δ ppm 8.06 (dd, J = 5.0, 1.9 Hz, 1H), 7.96 (dd, J = 7.4, 1.9 Hz, 1H), 7.00 (dd, J = 8.3, 2.2 Hz, 1H), 6.95 (dd, J = 7.4, 4.9 Hz, 1H), 6.81 (d, J = 2.2 Hz, 1H), 6.78 (d, J = 8.3 Hz, 1H), 5.18 (d, J = 6.7 Hz, 1H), 4.65 (p, J = 6.2 Hz, 1H), 4.38 (d, J = 1.8 Hz, 1H), 3.83 (s, 3H), 3.71-3.59 (m, 2H), 3.55 (s, 3H), 3.35 (d, J = 13.6 Hz, 1H), 2.50 (s, 1H), 2.42 (s, 1H), 1.96 (s, 6H), 1.05 (d, J = 6.2 Hz, 3H), 0.98 (s, 9H), 0.92 (d, J = 6.2 Hz, 3H); MS (ESI+) m/z 566 (M + H)+. |
| Example I-225 | (2S,3S,4S,5S)-3-tert-butyl-4-{[(5-tert-butyl-2-methoxyphenyl)methyl]amino}-1-(cyclohexanecarbonyl)-5-[2-(difluoromethoxy)pyridin-3-yl]pyrrolidine-2-carboxylic acid | 1HNMR (400 MHz, dimethyl sulfoxide-d6) δ ppm 8.11 (d, J = 4.8 Hz, 2H), 7.66, 7.50, 7.32 (t, 1H), 7.19 (d, J = 6.2 Hz, 1H), 7.13 (dd, J = 8.6, 2.6 Hz, 1H), 6.94 (d, J = 2.6 Hz, 1H), 6.74 (dd, J = 8.5, 1H), 5.28 (s, 1H), 4.50 (d, J = 2.0 Hz, 1H), 3.53 (s, 3H), 3.50 (d, J = 6.3 Hz, 2H), 3.28 (d, J = 13.6 Hz, 2H), 2.38 (s, 1H), 1.61 (d, J = 44.9 Hz, 5H), 1.25 (s, 3H), 1.19 (s, 9H), 1.13 (d, J = 12.7 Hz, 3H), 0.96 (s, 9H); MS (ESI+) m/z 616.2 (M + H)+. |
| Example I-226 | (2S,3S,4S,5S)-3-(bicyclo[1.1.1]pentan-1-yl)-4-{[(5-tert-butyl-2-methoxyphenyl)methyl]amino}-5-phenyl-1-{[(propan-2-yl)oxy]carbonyl}pyrrolidine-2-carboxylic acid | 1HNMR (400 MHz, dimethyl sulfoxide-d6) δ ppm 7.52-7.47 (m, 2H), 7.30 (t, J = 7.3 Hz, 2H), 7.24 (d, J = 7.2 Hz, 1H), 7.19 (dd, J = 8.5, 2.6 Hz, 1H), 7.02 (d, J = 2.6 Hz, 1H), 6.80 (d, J = 8.5 Hz, 1H), 5.00 (d, J = 7.2 Hz, 1H), 4.63 (p, J = 6.2 Hz, 1H), 4.08 (d, J = 5.4 Hz, 1H), 3.61 (s, 3H), 3.60 (d, J = 13.3 Hz, 1H), 3.50 (d, J = 13.3 Hz, 1H), 3.38 (t, J = 6.6 Hz, 1H), 2.52 (t, J = 5.8 Hz, 1H), 2.00 (s, 1H), 1.74 (q, J = 1.3 Hz, 6H), 1.22 (s, 9H), 1.07 (d, J = 6.2 Hz, 3H), 0.92 (d, J = 6.2 Hz, 3H); MS (ESI+) m/z 535 (M + H)+. |
| Example I-227 | (2S,3S,4S,5S)-3-tert-butyl-4-{[(5-tert-butyl-2-methoxyphenyl)methyl]amino}-5-[2-(difluoromethoxy)pyridin-3-yl]-1-{[(propan-2-yl)oxy]carbonyl}pyrrolidine-2-carboxylic acid | 1HNMR (400 MHz, dimethyl sulfoxide-d6) δ ppm 8.26 (d, J = 7.6 Hz, 1H), 8.09 (dd, J = 4.9, 2.0 Hz, 1H), 7.66, 7.47, 7.29 (t, 1H, 7.19 (dd, J = 7.5, 4.8 Hz, 1H), 7.12 (dd, J = 8.5, 2.6 Hz, 1H), 6.92 (d, J = 2.6 Hz, 1H), 6.73 (d, J = 8.5 Hz, 1H), 5.14 (d, J = 6.8 Hz, 1H), 4.67 (s, 1H), 4.35 (t, J = 3.5 Hz, 1H), 3.54 (d, J = 0.9 Hz, 3H), 3.51-3.44 (m, 2H), 3.23 (d, J = 13.7 Hz, 2H), 2.30 (t, J = 1.7 Hz, 1H), 1.18 (s, 9H), 1.05 (d, J = 6.2 Hz, 3H), 0.96 (d, J = 5.7 Hz, 9H), 0.90 (d, J = 6.2 Hz, 3H); MS (ESI+) m/z 592.1 (M + H)+. |
| Example I-228 | (2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(difluoromethoxy)pyridin-3-yl]pyrrolidine-2-carboxylic acid | 1HNMR (400 MHz, dimethyl sulfoxide-d6) δ ppm 8.12 (d, J = 4.7 Hz, 2H), 7.20 (t, J = 6.1 Hz, 1H), 6.94 (dd, J = 8.2, 2.2 Hz, 1H), 6.74 (dd, J = 5.3, 3.0 Hz, 2H), 5.28 (d, J = 6.7 Hz, 1H), 4.50 (d, J = 2.0 Hz, 1H), 3.53 (s, 3H), 3.49 (d, J = 8.2 Hz, 2H), 3.28-3.18 (m, 2H), 2.49 (s, 1H), 2.37 (s, 1H), 1.94 (s, 6H), 1.89 (s, 1H), 1.61 (d, J = 45.5 Hz, 5H), 1.33-1.06 (m, 5H), 0.96 (s, 9H); MS (ESI+) m/z 626.2 (M + H)+. |
| Example I-229 | (2S,3S,4S,5S)-3-tert-butyl-4-{[(5-tert-butyl-2-methoxyphenyl)methyl]amino}-1-(cyclohexanecarbonyl)-5-[2-(difluoromethoxy)phenyl]pyrrolidine-2-carboxylic acid | 1HNMR (400 MHz, dimethyl sulfoxide-d6) δ ppm 7.78 (s, 1H), 7.31 (t, J = 7.8 Hz, 1H), 7.23-7.11 (m, 3H), 6.96 (d, J = 2.6 Hz, 1H), 7.01, 6.81,.6.63 (t, 1H), 6.73 (d, J = 8.5 Hz, 1H), 5.39 (d, J = 6.6 Hz, 1H), 4.52 (s, 1H), 3.58 (d, J = 13.8 Hz, 1H), 3.49 (s, 3H), 3.47 (s, 1H), 3.32 (d, J = 13.7 Hz, 2H), 2.40 (s, 1H), 1.58 (d, J = 43.9 Hz, 5H), 1.26 (t, J = 7.6 Hz, 3H), 1.19 (s, 9H), 1.11 (d, J = 12.1 Hz, 3H), 0.97 (s, 9H); MS (ESI+) m/z 615.2 (M + H)+. |
| Example I-230 | (2S,3S,4S,5S)-3-tert-butyl-4-{[(6-tert-butyl-2-methoxypyridin-3-yl)methyl]amino}-1-(cyclohexanecarbonyl)-5-(2-methoxypyridin-3-yl)pyrrolidine-2-carboxylic acid | 1HNMR (400 MHz, dimethyl sulfoxide-d6, 120° C.) δ ppm 8.08 (d, J = 5.0 Hz, 1H), 7.96 (s, 1H), 7.25 (d, J = 7.6 Hz, 1H), 6.98-6.90 (m, 1H), 6.82 (d, J = 7.5 Hz, 1H), 5.32 (d, J = 7.0 Hz, 1H), 4.52 (d, J = 1.8 Hz, 1H), 3.86 (s, 3H), 3.71 (s, 3H), 3.63-3.51 (m, 2H), 3.35 (d, J = 14.0 Hz, 1H), 2.42 (s, 1H), 2.29 (s, 1H), 1.74-1.47 (m, 4H), 1.38-1.04 (m, 15H), 0.97 (s, 9H); MS (ESI+) m/z 581 (M + H)+. |
| Example I-231 | (2S,3S,4S,5S)-3-tert-butyl-4-{[(6-tert-butyl-2-methoxypyridin-3-yl)methyl]amino}-5-(2-fluorophenyl)-1-[(2S)-oxane-2-carbonyl]pyrrolidine-2-carboxylic acid | 1HNMR (400 MHz, dimethyl sulfoxide-d6, 120° C.) δ ppm 7.88 (s, 1H), 7.31 (t, J = 7.0 Hz, 1H), 7.21 (d, J = 7.6 Hz, 1H), 7.19-7.07 (m, 2H), 6.79 (d, J = 7.5 Hz, 1H), 5.63 (s, 1H), 4.56 (s, 1H), 3.74 (s, 4H), 3.58 (d, J = 7.2 Hz, 1H), 3.52 (d, J = 14.0 Hz, 1H), 3.32-3.26 (m, 4H), 2.36 (s, 1H), 1.75-1.64 (m, 1H), 1.58-1.31 (m, 5H), 1.25 (s, 8H), 0.96 (s, 9H); MS (ESI+) m/z 570 (M + H)+. |
| Example I-232 | (2S,3S,4S,5S)-1-(tert-butoxycarbonyl)-3-tert-butyl-4-{[(5-tert-butyl-2- | 1HNMR (400 MHz, dimethyl sulfoxide-d6) δ ppm 8.11-8.02 (m, 1H), 7.89 (s, 1H),7.14 (dd, J = 8.5, 2.5 Hz, 1H), 6.99 (d, J = 2.6 Hz, 2H), 6.72 (d, J = 8.6 Hz, 1H), |

TABLE 1-continued

| | | |
|---|---|---|
| | methoxyphenyl)methyl]amino}-5-(2-methoxypyridin-3-yl)pyrrolidine-2-carboxylic acid | 4.96 (s, 1H), 4.25 (s, 1H), 3.63 (s, 2H), 3.57 (d, J = 14.0 Hz, 1H), 3.35 (s, 3H), 3.29 (s, 3H), 3.27 (s, 9H), 3.23 (s, 1H), 2.28 (s, 1H), 1.18 (s, 9H), 0.92 (s, 9H); MS (ESI+) m/z 570.1 (M + H)+. |
| Example I-233 | (2S,3S,4S,5S)-3-tert-butyl-4-{[(5-tert-butyl-2-methoxyphenyl)methyl]amino}-5-[2-(dimethylamino)pyridin-3-yl]-1-[(2R)-2-phenylpropanoyl]pyrrolidine-2-carboxylic acid | $^1$HNMR (400 MHz, dimethyl sulfoxide-$d_6$) δ ppm 8.22 (s, 2H), 7.21 (d, J = 5.8 Hz, 5H), 7.14 (td, J = 8.3, 2.8 Hz, 2H), 6.99 (d, J = 2.6 Hz, 1H), 6.72 (d, J = 8.6 Hz, 1H), 5.39, (s, 1H), 4.52 (s, 1H), 3.67 (d, J = 13.7 Hz, 2H), 3.50 (d, J = 6.6 Hz, 1H), 3.45 (s, 3H), 3.30 (d, J = 13.8 Hz, 2H), 2.66 (s, 6H), 2.37 (s, 1H), 1.18 (d, J = 1.0 Hz, 9H), 0.84 (m, 12H); MS (ESI+) m/z 615.3 (M + H)+. |
| Example I-234 | (2S,3S,4S,5S)-3-tert-butyl-4-{[(6-tert-butyl-2-methoxypyridin-3-yl)methyl]amino}-5-(2-methoxypyridin-3-yl)-1-{(propan-2-yl)oxy]carbonyl}pyrrolidine-2-carboxylic acid | $^1$HNMR (400 MHz, dimethyl sulfoxide-$d_6$) δ ppm 8.08-7.95 (m, 2H), 7.22 (d, J = 7.4 Hz, 1H), 6.93 (dd, J = 7.4, 4.9 Hz, 1H), 6.81 (d, J = 7.5 Hz, 1H), 5.13 (d, J = 6.7 Hz, 1H), 4.65 (p, J = 6.2 Hz, 1H), 4.37 (d, J = 1.9 Hz, 1H), 3.81 (s, 3H), 3.69 (s, 3H), 3.55-3.45 (m, 2H), 3.30 (d, J = 14.1 Hz, 1H), 2.34 (m, 1H), 1.26 (s, 9H), 1.05 (d, J = 6.2 Hz, 3H), 0.97 (s, 9H), 0.92 (d, J = 6.2 Hz, 3H); MS (ESI+) m/z 557.2 (M + H)+. |
| Example I-235 | (2S,3S,4S,5S)-3-tert-butyl-4-{[(6-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid | $^1$HNMR (400 MHz, dimethyl sulfoxide-$d_6$, 120° C.) δ ppm 8.24 (s, 1H), 8.17 (d, J = 4.3 Hz, 1H), 7.19 (d, J = 7.5 Hz, 1H), 6.94 (dd, J = 7.6, 4.7 Hz, 1H), 6.76 (d, J = 7.5 Hz, 1H), 5.53 (s, 1H), 4.57 (d, J = 1.5 Hz, 1H), 3.76 (d, J = 11.6 Hz, 1H), 3.64 (d, J = 1.4 Hz, 1H), 3.53-3.41 (m, 2H), 3.23 (d, J = 14.2 Hz, 1H), 2.68 (d, J = 1.3 Hz, 6H), 2.52-2.48 (m, 2H), 2.32 (s, 1H), 1.89 (s, 1H), 1.72-1.31 (m, 6H), 1.24 (d, J = 0.8 Hz, 9H), 0.98 (d, J = 0.9 Hz, 9H); MS (ESI+) m/z 596 (M + H)+. |
| Example I-236 | (2S,3S,4S,5S)-3-(bicyclo[1.1.1]pentan-1-yl)-4-{[(5-cyclobutyl-2-methoxypyridin-3-yl)methyl]amino}-5-phenyl-1-{[(propan-2-yl)oxylcarbonyl]pyrrolidine-2-carboxylic acid | $^1$HNMR (400 MHz, dimethyl sulfoxide-$d_6$) δ ppm 7.80 (d, J = 2.4 Hz, 1H), 7.49 (d, J = 7.5 Hz, 2H), 7.31-7.17 (m, 4H), 4.94 (d, J = 7.2 Hz, 1H), 4.63 (p, J = 6.2 Hz, 1H), 4.03 (d, J = 5.9 Hz, 1H), 3.72 (s, 3H), 3.52-3.36 (m, 3H), 3.22 (t, J = 6.9 Hz, 1H), 2.41 (t, J = 6.2 Hz, 1H), 2.34-2.22 (m, 3H), 2.08-1.94 (m, 3H), 1.86 (td, J = 8.4, 8.0, 2.5 Hz, 1H), 1.79-1.63 (m, 6H), 1.07 (d, J = 6.1 Hz, 3H), 0.93 (d, J = 6.2 Hz, 3H); MS (ESI+) m/z 534 (M + H)+. |
| Example I-237 | (2S,3S,4S,5S)-3-tert-butyl-4-{[(5-cyclobutyl-2-methoxypyridin-3-yl)methyl]amino}-1-(cyclohexanecarbonyl)-5-(2-methoxypyridin-3-yl)pyrrolidine-2-carboxylic acid | $^1$HNMR (400 MHz, dimethyl sulfoxide-$d_6$) δ ppm 8.06-7.92 (m, 2H), 7.81 (d, J = 2.5 Hz, 1H), 7.19 (s, 1H), 6.92 (m, 1H), 5.31 (m, 1H), 4.51 (d, J = 2.0 Hz, 1H), 3.85 (s, 3H), 3.67 (s, 3H), 3.56-3.52 (m, 2H), 3.46-3.28 (m, 2H), 2.39 (m, 1H), 2.34-2.23 (m, 2H), 2.05-1.91 (m, 3H), 1.85 (m, 1H), 1.67-1.10 (m, 10H), 0.97 (s, 9H), 0.85 (m, 1H); MS (ESI+) m/z 579.3 (M + H)+. |
| Example I-238 | (2S,3S,4S,5S)-3-tert-butyl-1-(cyclohexanecarbonyl)-4-({[2-methoxy-5-(1-methylcyclobutyl)phenyl]methyl}amino)-5-(2-methoxypyridin-3-yl)pyrrolidine-2-carboxylic acid | $^1$HNMR (400 MHz, dimethyl sulfoxide-$d_6$, 120° C.) δ ppm 8.11 (dd, J = 4.9, 1.8 Hz, 1H), 7.93 (s, 1H), 7.07 (dd, J = 8.4, 2.4 Hz, 1H), 6.98 (dd, J = 7.4, 5.0 Hz, 1H), 6.89 (d, J = 2.3 Hz, 1H), 6.84 (d, J = 8.4 Hz, 1H), 5.39 (d, J = 7.0 Hz, 1H), 4.55 (d, J = 1.8 Hz, 1H), 3.89 (s, 3H), 3.81 (dd, J = 15.0, 10.5 Hz, 2H), 3.59 (s, 3H), 3.49 (d, J = 13.6 Hz, 1H), 2.56 (s, 1H), 2.24 (td, J = 10.2, 9.4, 6.1 Hz, 2H), 2.10-1.90 (m, 3H), 1.84-1.48 (m, 6H), 1.36 (s, 3H), 1.33-1.04 (m, 6H), 0.99 (s, 9H); MS (ESI+) m/z 592 (M + H)+. |
| Example I-239 | (2S,3S,4S,5S)-3-tert-butyl-4-{[(5-tert-butyl-2-methoxyphenyl)methyl]amino}-5-(2-methoxypyridin-3-yl)-1-[(2R)-2-phenylpropanoyl]pyrrolidine-2-carboxylic acid | $^1$HNMR (400 MHz, dimethyl sulfoxide-$d_6$) δ ppm 8.10 (s, 1H), 7.26-7.21 (m, 3H), 7.19-7.11 (m, 4H), 6.92 (s, 1H), 6.73 (d, J = 8.5 Hz, 2H), 5.19 (d, J = 6.8 Hz, 1H), 4.53 (s, 1H), 3.85 (s, 3H), 3.50 (s, 3H), 3.40 (s, 2H), 3.29-3.19 (m, 2H), 3.04 (m, 2H), 1.23 (s, 9H), 1.19 (s, 9H), 0.75 (s, 3H); MS/ESI (+) m/z 602.2 (M + H)+. |
| Example I-240 | (2S,3S,4S,5S)-3-tert-butyl-5-(2-methoxypyridin-3-yl)-4-({[2-methoxy-5-(trifluoromethyl)pyridin-3-yl]methyl}amino)-1-[(2R)-2-phenylpropanoyl]pyrrolidine-2-carboxylic acid | $^1$HNMR (400 MHz, dimethyl sulfoxide-$d_6$) δ ppm 8.30 (s, 1H), 8.10 (s, 1H), 7.49 (s, 1H), 7.23 (t, J = 7.2 Hz, 2H), 7.20-7.13 (m, 1H), 7.09 (s, 2H), 6.97 (s, 1H), 5.20 (d, J = 7.0 Hz, 1H), 4.53 (s, 1H), 3.89 (s, 3H), 3.80 (s, 3H), 3.80 (m, 3H), 3.27 (d, J = 15.2 Hz, 2H), 2.25 (s, 1H), 1.11 (s, 3H), 0.75 (s, 9H); MS (ESI+) m/z 615.2 (M + H)+. |
| Example I-241 | (2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-phenylpyrrolidine-2-carboxylic acid | $^1$HNMR (400 MHz, dimethyl sulfoxide-$d_6$) δ ppm 7.54 (s, 2H), 7.33 (dt, J = 31.0, 7.5 Hz, 3H), 7.21 (dd, J = 8.6, 2.5 Hz, 1H), 7.03 (d, J = 2.6 Hz, 1H), 6.79 (d, J = 8.6 Hz, 1H), 5.29 (d, J = 7.0 Hz, 1H), 4.53 (d, J = 2.2 Hz, 1H), 4.42 (dd, J = 20.6, 4.6 Hz, 3H), 3.73 (d, J = 10.8 Hz, 4H), 3.46 (s, 1H), 2.50 (s, 2H), 1.82 (dd, J = 11.2, 5.6 Hz, 1H), 1.55-1.25 (m, 5H), 1.21 (s, 9H), 1.15 (s, 1H), 1.00 (s, 9H); MS (ESI+) m/z 563.2 (M + H)+. |
| Example I-242 | (2S,3S,4S,5S)-3-tert-butyl-4-{[(6-cyclobutyl-2-methoxypyridin-3-yl)methyl]amino}-1-(cyclohexanecarbonyl)-5- | $^1$HNMR (400 MHz, dimethyl sulfoxide-$d_6$) δ ppm 7.56 (m, 2H), 7.35 (t, J = 7.5 Hz, 2H), 7.25 (m, 2H), 6.66 (d, J = 7.3 Hz, 1H), 5.27 (d, J = 7.0 Hz, 1H), 4.50 (d, J = 2.3 Hz, 1H), 3.72 (s, 3H), 3.65 (d, J = 7.1 Hz, 1H), |

TABLE 1-continued

| | | |
|---|---|---|
| | phenylpyrrolidine-2-carboxylic acid | 3.58-3.44 (m, 2H), 3.32 (d, J = 13.9 Hz, 1H), 2.42 (s, 1H), 2.21 (m, 5H), 2.03-1.80 (m, 2H), 1.64 (m, 2H), 1.50 (m, 2H), 1.23 (m, 3H), 1.08 (m, 2H), 0.98 (s, 9H), 0.77 (m, 1H); MS (ESI+) m/z 548.2 (M + H)+. |
| Example I-243 | (2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-(2-methoxypyridin-3-yl)pyrrolidine-2-carboxylic acid | $^1$HNMR (400 MHz, dimethyl sulfoxide-d$_6$) δ ppm 8.10-8.00 (m, 2H), 7.81 (d, J = 2.4 Hz, 1H), 7.20 (s, 1H), 7.00-6.92 (m, 1H), 5.35 (m, 1H), 4.55 (m, 1H), 3.83 (s, 3H), 3.67 (s, 3H), 3.58-3.50 (m, 2H), 3.46-3.19 (m, 3H), 2.38 (s, 2H), 2.28 (m, 2H), 1.99 (s, 1H), 2.05-1.91 (m, 3H), 1.84 (m, 1H), 1.70 (m, 1H), 1.63 (m, 2H), 1.56-1.15 (m, 4H), 0.98 (s, 9H), 0.76 (m, 1H), MS (ESI+) m/z 577.3 (M + H)+. |
| Example I-244 | (2S,3S,4S,5S)-3-tert-butyl-4-{[(5-tert-butyl-2-methoxyphenyl)methyl]amino}-1-{[(oxetan-3-yl)oxy]carbonyl}-5-phenylpyrrolidine-2-carboxylic acid | $^1$HNMR (400 MHz, dimethyl sulfoxide) δ ppm 7.54 (d, J = 7.4 Hz, 2H), 7.35 (t, J = 7.5 Hz, 2H), 7.28 (t, J = 7.3 Hz, 1H), 7.19 (dd, J = 8.5, 2.5 Hz, 1H), 7.00 (d, J = 2.4 Hz, 1H), 6.78 (d, J = 8.6 Hz, 1H), 5.26-5.20 (m, 1H), 5.14 (d, J = 6.7 Hz, 1H), 4.65 (t, J = 6.8 Hz, 1H), 4.60 (t, J = 6.8 Hz, 1H), 4.40 (d, J = 2.3 Hz, 1H), 4.26-4.22 (m, 1H), 4.17-4.13 (m, 1H), 3.63 (d, J = 13.6 Hz, 1H), 3.60-3.57 (m, 1H), 3.55 (s, 3H), 3.39 (d, J = 13.7 Hz, 1H), 2.46 (bs, 1H), 1.24 (s, 9H), 1.03 (s, 9H); LC/MS (ESI+) m/z 539.4 (M + H)+. |
| Example I-245 | (2S,3S,4S,5S)-3-tert-butyl-5-[2-(dimethylamino)pyridin-3-yl]-4-({[2-methoxy-5-(pentafluoro-λ$^6$-sulfanyl)phenyl]methyl}amino)-1-{(propan-2-yl)oxy]carbonyl}pyrrolidine-2-carboxylic acid | $^1$HNMR (400 MHz, dimethyl sulfoxide-d$_6$) δ ppm 8.27 (dd, J = 7.7, 1.7 Hz, 1H), 8.16 (dd, J = 4.9, 1.9 Hz, 1H), 7.64 (dd, J = 9.1, 2.9 Hz, 1H), 7.46 (d, J = 2.9 Hz, 1H), 7.06-6.97 (m, 2H), 5.30 (d, J = 6.5 Hz, 1H), 4.63 (m, 1H), 4.35 (d, J = 1.8 Hz, 1H), 3.67 (s, 3H), 3.64-3.50 (m, 2H), 3.31 (d, J = 14.4 Hz, 1H), 2.75 (s, 6H), 2.36 (s, 1H), 1.02 (d, J = 6.2 Hz, 3H), 0.99 (s, 8H), 0.85 (d, J = 6.2 Hz, 3H); MS (ESI+) m/z 639.1 (M + H)+. |
| Example I-246 | (2S,3S,4S,5S)-3-tert-butyl-4-{[(5-tert-butyl-2-methoxyphenyl)methyl]amino}-5-phenyl-1-{(3R)-1-{[(propan-2-yl)oxy]carbonyl}piperidine-3-carbonyl]pyrrolidine-2-carboxylic acid | $^1$HNMR (400 MHz, dimethyl sulfoxide-d$_6$) δ ppm 7.65 (d, J = 5.7 Hz, 2H), 7.43 (t, J = 7.5 Hz, 2H), 7.35 (t, J = 7.1 Hz, 1H), 7.26 (dd, J = 8.6, 2.3 Hz, 1H), 7.09 (d, J = 2.1 Hz, 1H), 6.84 (d, J = 8.6 Hz, 1H), 5.64-5.63 (m, 1H), 5.40 (d, J = 7.0 Hz, 1H), 4.80 (hept, J = 6.2 Hz, 1H), 4.57 (d, J = 1.8 Hz, 1H), 3.98 (d, J = 6.3 Hz, 1H), 3.92-3.86 (m, 1H), 3.81-3.75 (m, 2H), 3.64 (s, 3H), 3.45 (d, J = 13.6 Hz, 1H), 2.76-2.65 (m, 3H), 1.52-1.38 (m, 2H), 1.32-1.15 (m, 17H), 1.04 (s, 9H); LC/MS (ESI+) m/z 636.4 (M + H)+. |
| Example I-247 | (2S,3S,4S,5S)-3-tert-butyl-4-{[(6-tert-butyl-2-chloropyridin-3-yl)methyl]amino}-1-[(1R)-3,3-difluorocyclohexane-1-carbonyl]-5-phenylpyrrolidine-2-carboxylic acid | $^1$HNMR (400 MHz, dimethyl sulfoxide-d$_6$) δ ppm 7.62 (s, 2H), 7.46-7.27 (m, 3H), 7.23 (d, J = 12.7, 7.5 Hz, 2H), 5.21 (d, J = 7.0 Hz, 1H), 4.46 (d, J = 2.9 Hz, 1H), 3.57-3.48 (m, 1H), 3.43 (d, J = 14.7 Hz, 1H), 3.30 (d, J = 14.6 Hz, 1H), 2.59-2.54 (m, 1H), 2.34 (s, 1H), 2.09 (d, J = 2.9 Hz, 1H), 2.06-1.48 (m, 6H), 1.24 (s, 9H), 1.19-1.06 (m, 2H), 0.98 (s, 9H); MS (ESI+) m/z 590.2 (M + H)+. |
| Example I-248 | (2S,3S,4S,5S)-3-tert-butyl-4-{[(5-tert-butyl-2-methoxyphenyl)methyl]amino}-5-(2-methoxypyridin-3-yl)-1-(1-phenylcyclopropane-1-carbonyl)pyrrolidine-2-carboxylic acid | $^1$HNMR (400 MHz, 120° C., dimethyl sulfoxide-d$_6$: D$_2$O = 9:1 (v/v)) δ ppm 8.08 (dd, J = 5.0, 1.9 Hz, 1H), 7.92-7.85 (m, 1H), 7.30-7.16 (m, 5H), 7.07 (s, 2H), 7.01-6.92 (m, 2H), 6.79 (d, J = 8.6 Hz, 1H), 4.54 (d, J = 1.7 Hz, 1H), 3.79 (s, 3H), 3.73 (d, J = 13.5 Hz, 1H), 3.62-3.55 (m, 1H), 3.55 (s, 3H), 3.36 (d, J = 13.6 Hz, 1H), 2.36 (s, 1H), 1.43 (s, 1H), 1.18 (s, 9H), 1.05-1.00 (m, 2H), 0.88-0.82 (m, 1H), 0.75 (s, 9H); MS (APCI+) m/z 614.2 (M + H)+. |
| Example I-249 | (2S,3S,4S,5S)-3-tert-butyl-4-{[(6-methoxy-2,3-dihydro-1H-inden-5-yl)methyl]amino}-1-{(propan-2-yl)oxylcarbonyl]-5-[2-(propan-2-yl)phenyl]pyrrolidine-2-carboxylic acid | $^1$HNMR (400 MHz, dimethyl sulfoxide-d$_6$, 120° C.) 7.76 (dd, J = 7.8, 1.3 Hz, 1H), 7.34-7.24 (m, 2H), 7.23-7.14 (m, 1H), 6.80 (s, 1H), 6.73 (s, 1H), 5.35 (d, J = 6.5 Hz, 1H), 4.62 (hept, J = 6.2 Hz, 1H), 4.41 (d, J = 1.5 Hz, 1H), 3.74 (d, J = 5.8 Hz, 1H), 3.69 (d, J = 13.3 Hz, 1H), 3.49 (s, 3H), 3.29 (d, J = 13.2 Hz, 1H), 3.10 (hept, J = 6.7 Hz, 1H), 2.78 (t, J = 7.4 Hz, 2H), 2.70 (t, J = 7.4 Hz, 2H), 2.54 (s, 1H), 1.96 (p, J = 7.4 Hz, 2H), 1.22 (d, J = 6.8 Hz, 3H), 1.17 (d, J = 6.8 Hz, 3H), 1.03 (s, 9H), 1.01 (d, J = 6.2 Hz, 3H), 0.79 (d, J = 6.1 Hz, 3H); MS (ESI+) m/z 592 (M + H)+. |
| Example I-250 | (2S,3S,4S,5S)-3-tert-butyl-4-{[(2-methoxyquinolin-3-yl)methyl]amino}-1-{(propan-2-yl)oxylcarbonyl]-5-[2-(propan-2-yl)phenyl]pyrrolidine-2-carboxylic acid | $^1$HNMR (400 MHz, dimethyl sulfoxide-d$_6$, 120° C.) δ ppm 7.91 (d, J = 7.8 Hz, 1H), 7.69-7.61 (m, 3H), 7.54 (ddd, J = 8.1, 6.8, 1.4 Hz, 1H), 7.34 (ddd, J = 8.1, 7.0, 1.1 Hz, 1H), 7.26-7.18 (m, 2H), 7.11 (ddd, J = 8.3, 6.7, 1.9 Hz, 1H), 5.26 (d, J = 6.4 Hz, 1H), 4.61 (hept, J = 6.1 Hz, 1H), 4.38 (d, J = 1.6 Hz, 1H), 3.73 (s, 3H), 3.62-3.53 (m, 1H), 3.40 (d, J = 6.4 Hz, 1H), 3.36 (d, J = 14.7 Hz, 1H), 3.03 (p, J = 6.8 Hz, 1H), 2.44-2.37 (m, 1H), 1.18 (d, J = 6.7 Hz, 3H), 1.05-0.98 (m, 15H), 0.80 (d, J = 6.2 Hz, 3H); MS (ESI+) m/z 562 (M + H)+. |
| Example I-251 | (2S,3S,4S,5S)-3-tert-butyl-5-[2-(dimethylamino)pyridin- | $^1$HNMR (400 MHz, dimethyl sulfoxide-d$_6$, 120° C.) δ ppm 8.20 (dd, J = 4.7, 1.9 Hz, 1H), 8.13 (dd, J = 7.6, 1.9 |

TABLE 1-continued

| | | |
|---|---|---|
| | 3-yl]-4-{[(3-methoxy-5,5,8,8-tetramethyl-5,6,7,8-tetrahydronaphthalen-2-yl)methyl]amino}-1-{[(propan-2-yl)oxy]carbonyl}pyrrolidine-2-carboxylic acid | Hz, 1H), 7.03 (dd, J = 7.6, 4.7 Hz, 1H), 6.90 (s, 1H), 6.68 (s, 1H), 5.32 (d, J = 6.4 Hz, 1H), 4.61 (p, J = 6.2 Hz, 1H), 4.37 (d, J = 1.6 Hz, 1H), 3.67 (d, J = 13.3 Hz, 1H), 3.59 (d, J = 6.4 Hz, 1H), 3.49 (s, 3H), 3.28 (d, J = 13.7 Hz, 1H), 2.63 (s, 6H), 2.41 (s, 1H), 1.64-1.55 (m, 4H), 1.19 (s, 6H), 1.14 (s, 3H), 1.14 (s, 3H), 1.03-0.98 (m, 12H), 0.83 (d, J = 6.2 Hz, 3H); MS (ESI+) m/z 623 (M + H)⁺. |
| Example I-252 | (2S,3S,4S,5S)-3-tert-butyl-5-(3-chlorophenyl)-4-({[2-methoxy-5-(trifluoromethyl)phenyl]methyl}amino)-1-{[(propan-2-yl)oxy]carbonyl}pyrrolidine-2-carboxylic acid | ¹HNMR (400 MHz, dimethyl sulfoxide-d₆) δ ppm 7.79 (d, J = 2.0 Hz, 1H), 7.54 (dt, J = 7.5, 1.4 Hz, 1H), 7.42 (dd, J = 8.7, 2.4 Hz, 1H), 7.31-7.13 (m, 3H), 6.99 (d, J = 8.6 Hz, 1H), 4.93 (d, J = 7.2 Hz, 1H), 4.61 (p, J = 6.2 Hz, 1H), 4.20 (d, J = 2.1 Hz, 1H), 3.71 (s, 3H), 3.46 (d, J = 15.2 Hz, 1H), 3.32 (dd, J = 7.2, 1.5 Hz, 1H), 3.26 (d, J = 15.2 Hz, 1H), 2.27 (t, J = 1.8 Hz, 1H), 1.29-1.22 (m, 1H), 1.03 (d, J = 6.2 Hz, 3H), 0.94 (s, 9H), 0.89-0.85 (m, 3H); MS (ESI+) m/z 571 (M + H)⁺. |
| Example I-253 | (2S,3S,4S,5S)-3-tert-butyl-4-{[(5-tert-butyl-2-methoxyphenyl)methyl]amino}-5-(2-methoxypyridin-3-yl)-1-[(2S)-2-phenylbutanoyl]pyrrolidine-2-carboxylic acid | ¹HNMR (400 MHz, 120° C., dimethyl sulfoxide-d₆: D₂O = 9:1 (v/v)) δ ppm 8.04 (s, 1H), 7.77 (d, J = 7.0 Hz, 1H), 7.28 (s, 4H), 7.23-7.14 (m, 2H), 6.98 (s, 1H), 6.91 (s, 1H), 6.75 (d, J = 8.5 Hz, 1H), 5.16 (s, 1H), 4.37 (s, 1H), 3.85-3.60 (m, 5H), 3.46 (s, 3H), 3.41-3.32 (m, 2H), 2.33 (s, 1H), 1.90 (s, 1H), 1.54 (tt, J = 13.4, 7.2 Hz, 1H), 1.19 (s, 9H), 0.80-0.67 (m, 3H), 0.56 (s, 9H); MS (APCI+) m/z 616.2 (M + H)⁺. |
| Example I-254 | (2S,3S,4S,5S)-3-tert-butyl-4-{[(5-tert-butyl-2-methoxyphenyl)methyl]amino}-1-[(7R)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid | ¹HNMR (400 MHz, 120° C., dimethyl sulfoxide-d₆: D₂O = 9:1 (v/v), complex mixture of rotamers) δ ppm 8.01-7.97 (m, 2H), 7.21 (s, 1H), 7.18-7.13 (m, 1H), 6.95 (d, J = 2.6 Hz, 1H), 6.89-6.80 (m, 2H), 6.77-6.72 (m, 1H), 5.33 (d, J = 6.9 Hz, 1H), 4.87-4.82 (m, 1H), 4.40-4.37 (m, 1H), 4.36-4.29 (m, 1H), 3.73 (s, 3H), 3.64-3.58 (m, 1H), 3.50 (s, 3H), 3.43 (d, J = 6.9 Hz, 1H), 3.31 (d, J = 13.8 Hz, 1H), 2.35 (s, 1H), 1.53 (s, 3H), 1.18 (s, 9H), 0.92 (s, 9H); MS (APCI+) m/z 710.2 (M + H)⁺. |
| Example I-255 | (2S,3S,4S,5S)-3-tert-butyl-1-[(1R,3R)-3-methoxycyclohexane-1-carbonyl]-4-({[2-methoxy-4-(trifluoromethyl)phenyl]methyl}amino)-5-phenylpyrrolidine-2-carboxylic acid | ¹HNMR (400 MHz, dimethyl sulfoxide-d₆, 120° C.) δ ppm 7.54 (s, 2H), 7.32 (t, J = 7.4 Hz, 2H), 7.24 (t, J = 7.3 Hz, 1H), 7.16-7.09 (m, 2H), 7.07 (s, 1H), 5.23 (d, J = 6.9 Hz, 1H), 4.46 (d, J = 2.3 Hz, 1H), 3.65 (s, 3H), 3.60-3.52 (m, 2H), 3.39 (d, J = 14.3 Hz, 1H), 3.34 (s, 1H), 2.37 (s, 1H), 1.60 (d, J = 12.6 Hz, 2H), 1.45-1.18 (m, 6H), 0.98 (s, 9H); MS (ESI+) m/z 591 (M + H)⁺. |
| Example I-256 | (2S,3S,4S,5S)-3-tert-butyl-1-difluorocyclohexane-1-carbonyl]-5-(2-methoxypyridin-3-yl)-4-({[2-methoxy-5-(trifluoromethyl)phenyl]methyl}amino)pyrrolidine-2-carboxylic acid | ¹HNMR (400 MHz, dimethyl sulfoxide-d₆) δ ppm 8.05 (d, J = 5.0 Hz, 1H), 7.83 (s, 1H), 7.48 (dd, J = 8.7, 2.2 Hz, 1H), 7.25 (d, J = 2.4 Hz, 1H), 7.02 (d, J = 8.6 Hz, 1H), 6.92 (t, J = 6.3 Hz, 1H), 5.33 (s, 1H), 4.51 (d, J = 2.3 Hz, 1H), 4.25 (s, 1H), 3.85 (s, 3H), 3.66 (s, 3H), 3.37 (d, J = 14.3 Hz, 1H), 3.53 (m, 2H), 2.42 (s, 1H), 2.02-1.17 (m, 8H), 0.97 (s, 9H); MS (ESI+) m/z 628.2 (M + H)⁺. |
| Example I-257 | (2S,3S,4S,5S)-3-tert-butyl-1-difluorocyclohexane-1-carbonyl]-5-(2-methoxypyridin-3-yl)-4-({[2-methoxy-4-(trifluoromethyl)phenyl]methyl}amino)pyrrolidine-2-carboxylic acid | ¹HNMR (400 MHz, dimethyl sulfoxide-d₆) δ ppm 8.06 (s, 2H), 7.13 (s, 2H), 7.08 (s, 1H), 6.93 (d, J = 6.5 Hz, 1H), 5.32 (s, 1H), 4.52 (d, J = 2.2 Hz, 1H), 3.84 (d, J = 5.0 Hz, 3H), 3.66 (s, 3H), 3.58-3.42 (m, 4H), 3.38 (s, 1H), 2.41 (s, 1H), 1.91 (s, 2H), 1.59 (s, 4H), 1.26 (s, 2H), 0.98 (s, 9H); MS (ESI+) m/z 628.2 (M + H)⁺. |
| Example I-258 | (2S,3S,4S,5S)-3-tert-butyl-1-(cyclohexanecarbonyl)-4-({[2-methoxy-5-(trifluoromethyl)pyridin-3-yl]methyl}amino)-5-(2-methylphenyl)pyrrolidine-2-carboxylic acid | ¹HNMR (400 MHz, dimethyl sulfoxide-d₆, 120° C.) 8.32 (s, 1H), 7.81 (s, 1H), 7.53 (s, 1H), 7.14 (q, J = 3.6 Hz, 3H), 5.27 (d, J = 6.8 Hz, 1H), 4.55 (d, J = 1.8 Hz, 1H), 3.77 (s, 3H), 3.59-3.49 (m, 2H), 3.32 (d, J = 14.9 Hz, 1H), 2.40 (s, 1H), 2.24 (s, 3H), 2.08 (s, 1H), 1.57 (d, J = 62.4 Hz, 4H), 1.30-1.02 (m, 6H), 0.99 (s, 9H); MS (ESI+) m/z 576 (M + H)⁺. |
| Example I-259 | (2S,3S,4S,5S)-3-tert-butyl-4-{[(5-cyclobutyl-2-methoxypyridin-3-yl)methyl]amino}-5-phenyl-1-[(1R*,3S*)-3-(trifluoromethyl)cyclohexane-1-carbonyl]pyrrolidine-2-carboxylic acid | ¹HNMR (400 MHz, dimethyl sulfoxide-d₆) δ ppm 7.77 (m, 1H), 7.58 (m, 2H), 7.39-7.17 (m, 3H), 7.15 (d, J = 2.4 Hz, 1H), 5.22 (m, 1H), 4.44 (m, 1H), 3.66 (s, 3H), 3.57-3.23 (m, 5H), 2.38 (m, 1H), 2.35-2.19 (m, 2H), 2.10 (m, 1H), 1.97 (m, 3H), 1.88-1.57 (m, 4H), 1.38-1.08 (m, 5H), 0.97 (s, 9H), 0.82 (m, 1H); MS (ESI+) m/z 616.2 (M + H)⁺. |
| Example I-260 | (2S,3S,4S,5S)-3-tert-butyl-4-{[(5-cyclobutyl-2-methoxypyridin-3-yl)methyl]amino}-5-phenyl-1-[(1S*,3R*)-3-(trifluoromethyl)cyclohexane-1-carbonyl]pyrrolidine-2-carboxylic acid | ¹HNMR (400 MHz, dimethyl sulfoxide-d₆) δ ppm 7.77 (d, J = 2.4 Hz, 1H), 7.59 (m, 2H), 7.31-7.25 (m, 2H), 7.15 (m, 1H), 5.21 (d, J = 7.0 Hz, 1H), 4.47 (d, J = 2.5 Hz, 1H), 3.65 (s, 3H), 3.45 (m,4H), 2.66 (m, 1H), 2.36 (m, 1H), 2.31-2.22 (m, 2H), 2.04-1.90 (m, 3H), 1.85 (m, 1H), 1.75 (m, 3H), 1.25-1.05 (m, 5H), 0.98 (s, 9H), 0.84 (m, 1H); MS (ESI+) m/z 616.2 (M + H)⁺. |
| Example I-261 | (2S,3S,4S,5S)-3-tert-butyl-4-{[(5-tert-butyl-2-methoxyphenyl)methyl]amino}-5-(2-methylphenyl)-1-[(2S)-oxolane- | ¹HNMR (400 MHz, dimethyl sulfoxide-d₆, 120° C.) δ ppm 7.80 (d, J = 6.3 Hz, 1H), 7.27-7.11 (m, 4H), 7.01 (d, J = 2.6 Hz, 1H), 6.79 (d, J = 8.6 Hz, 1H), 5.55 (s, 1H), 4.65 (d, J = 1.5 Hz, 1H), 3.80-3.60 (m, 4H), 3.54 |

TABLE 1-continued

| | | |
|---|---|---|
| | 2-carbonyl]pyrrolidine-2-carboxylic acid | (s, 3H), 3.30 (d, J = 13.6 Hz, 1H), 2.55 (s, 1H), 2.21 (s, 3H), 2.04-1.91 (m, 1H), 1.83-1.60 (m, 4H), 1.21 (s, 9H), 1.02 (s, 9H); MS (ESI+) m/z 551 (M + H)+. |
| Example I-262 | (2S,3S,4S,5S)-3-tert-butyl-4-({[2-methoxy-5-(trifluoromethyl)pyridin-3-yl]methyl}amino)-5-(2-methylphenyl)-1-[(2S)-oxolane-2-carbonyl]pyrrolidine-2-carboxylic acid | ¹HNMR (400 MHz, dimethyl sulfoxide-d₆, 120° C.) δ ppm 8.32 (s, 1H), 7.87 (s, 1H), 7.51 (d, J = 2.4 Hz, 1H), 7.14 (d, J = 3.1 Hz, 3H), 5.51 (s, 1H), 4.63 (d, J = 1.7 Hz, 1H), 3.78 (s, 3H), 3.74-3.56 (m, 2H), 3.58-3.47 (m, 2H), 3.30 (d, J = 14.9 Hz, 1H), 2.39 (s, 1H), 2.22 (s, 3H), 2.03-1.91 (m, 1H), 1.84-1.57 (m, 4H), 0.99 (s, 9H); MS (ESI+) m/z 564 (M + H)+. |
| Example I-263 | (2S,3S,4S,5S)-3-tert-butyl-5-phenyl-4-{(2-phenylethyl)amino]-1-{[(propan-2-yl)oxy]carbonyl}pyrrolidine-2-carboxylic acid | ¹HNMR (400 MHz, 120° C., dimethyl sulfoxide-d₆: D₂O = 9:1 (v/v)) δ ppm 7.52-7.45 (m, 2H), 7.36-7.04 (m, 6H), 6.93-6.86 (m, 2H), 5.13 (d, J = 7.1 Hz, 1H), 4.61 (dd, J = 6.7, 5.6 Hz, 1H), 4.39-4.31 (m, 1H), 3.89-3.82 (m, 1H), 2.84-2.72 (m, 1H), 2.62-2.51 (m, 1H), 2.50-2.39 (m, 3H), 1.07-0.98 (m, 12H), 0.85 (d, J = 6.1 Hz, 3H); MS (APCI+) m/z 453.1 (M + H)+. |
| Example I-264 | (2S,3S,4S,5S)-3-tert-butyl-4-[(2-methyl-2-phenylpropyl)amino]-5-phenyl-1-{[(propan-2-yl)oxy]carbonyl}pyrrolidine-2-carboxylic acid | ¹HNMR (400 MHz, 120° C., dimethyl sulfoxide-d₆: D₂O = 9:1 (v/v)) δ ppm 7.38-7.30 (m, 2H), 7.21-7.12 (m, 3H), 7.12-7.07 (m, 2H), 7.07-7.03 (m, 1H), 7.00-6.94 (m, 2H), 4.94 (d, J = 6.8 Hz, 1H), 4.65-4.54 (m, 1H), 4.27 (d, J = 2.6 Hz, 1H), 3.36-3.29 (m, 1H), 2.48 (s, 1H), 2.29 (d, J = 11.6 Hz, 1H), 2.18 (s, 1H), 1.02 (d, J = 6.2 Hz, 3H), 0.99 (d, J = 3.4 Hz, 6H), 0.95 (s, 9H), 0.85 (d, J = 6.1 Hz, 3H); MS (APCI+) m/z 481.1 (M + H)+. |
| Example I-265 | (2S,3S,4S,5S)-3-tert-butyl-4-{[(5-cyclobutyl-2-methoxypyridin-3-yl)methyl]amino}-5-(2-methylphenyl)-1-[(2S)-oxolane-2-carbonyl]pyrrolidine-2-carboxylic acid | ¹HNMR (400 MHz, dimethyl sulfoxide-d₆) δ ppm 7.83 (m, 2H), 7.21-7.14 (m, 4H), 5.54 (m, 1H), 4.65 (d, J = 1.6 Hz, 1H), 3.72-3.56 (m, 8H), 3.40 (m, 1H), 3.28 (d, J = 14.2 Hz, 1H), 2.50 (m, 1H), 2.34-2.22 (m, 2H), 2.23 (s, 3H), 2.07-1.91 (m, 3H), 1.89 (m, 1H), 1.72 (m, 2H), 1.65 (m, 2H), 1.01 (s, 9H); MS (ESI+) m/z 550.3 (M + H)+. |
| Example I-266 | (2S,3S,4S,5S)-3-tert-butyl-4-{[(5-cyclobutyl-2-methoxypyridin-3-yl)methyl]amino}-5-(2-methylphenyl)-1-[(2R)-oxane-2-carbonyl]pyrrolidine-2-carboxylic acid | ¹HNMR (400 MHz, dimethyl sulfoxide-d₆) δ ppm 7.82 (d, J = 2.4 Hz, 1H), 7.62 (m, 1H), 7.21-7.09 (m, 4H), 5.26 (d, J = 6.8 Hz, 1H), 4.87 (m, 1H), 4.02 (m, 1H), 3.83 (m, 2H), 3.69-3.55 (m, 4H), 3.50 (d, J = 6.7 Hz, 1H), 3.45-3.30 (m, 2H), 2.50 (m, 1H), 2.31-2.20 (m, 2H), 2.17 (s, 3H), 1.98 (m, 3H), 1.85 (m, 1H), 1.78 (m, 1H), 1.57-1.36 (m, 5H), 1.00 (s, 9H); MS (ESI+) m/z 564.3 (M + H)+. |
| Example I-267 | (2S,3S,4S,5S)-3-tert-butyl-4-({[4-(2-methoxyphenyl)oxan-4-yl]methyl}amino)-5-phenyl-1-{[(propan-2-yl)oxy]carbonyl}pyrrolidine-2-carboxylic acid | ¹HNMR (400 MHz, 120° C., dimethyl sulfoxide-d₆: D₂O = 9:1 (v/v)) δ ppm 7.26-7.19 (m, 2H), 7.23-7.06 (m, 4H), 6.86-6.73 (m, 3H), 4.98 (d, J = 6.8 Hz, 1H), 4.59 (q, J = 6.2 Hz, 1H), 4.31 (d, J = 2.2 Hz, 1H), 3.63 (s, 3H), 3.59-3.33 (m, 4H), 3.31-3.20 (m, 1H), 2.97 (dd, J = 11.8, 1.7 Hz, 1H), 2.76 (d, J = 11.8 Hz, 1H), 2.28-2.23 (m, 1H), 2.08-1.88 (m, 2H), 1.62 (ddt, J = 14.4, 7.3, 3.4 Hz, 2H), 1.01 (d, J = 6.1 Hz, 3H), 0.95 (s, 9H), 0.84 (d, J = 6.1 Hz, 3H); MS (APCI+) m/z 553.1 (M + H)+. |
| Example I-268 | (2S,3S,4S,5S)-3-tert-butyl-5-phenyl-1-{[(propan-2-yl)oxy]carbonyl}-4-[({1-[4-(trifluoromethyl)phenyl]piperidin-3-yl}methyl)amino]pyrrolidine-2-carboxylic acid | ¹HNMR (400 MHz, 120° C., dimethyl sulfoxide-d₆: D₂O = 9:1 (v/v)) δ ppm 7.58-7.51 (m, 2H), 7.41 (d, J = 8.6 Hz, 2H), 7.38-7.30 (m, 2H), 7.30-7.22 (m, 1H), 6.82 (dd, J = 11.5, 8.7 Hz, 2H), 5.12 (dd, J = 7.0, 1.8 Hz, 1H), 4.63 (h, J = 6.1 Hz, 1H), 4.36 (t, J = 2.4 Hz, 1H), 3.68 (t, J = 7.3 Hz, 1H), 3.57-3.48 (m, 1H), 3.46-3.25 (m, 1H), 2.83-2.69 (m, 1H), 2.49-2.26 (m, 4H), 2.18-2.08 (m, 1H), 1.65-1.35 (m, 4H), 1.04 (d, J = 6.2 Hz, 3H), 1.00 (s, 9H), 0.86 (d, J = 6.2 Hz, 3H); MS (APCI+) m/z 590.1 (M + H)+. |
| Example I-269 | (2S,3S,4S,5S)-3-tert-butyl-5-(2-cyclopropylpyridin-3-yl)-4-({[2-methoxy-5-(trifluoromethyl)phenyl]methyl}amino)-1-[(2S)-oxolane-2-carbonyl]pyrrolidine-2-carboxylic acid | ¹HNMR (400 MHz, 120° C., dimethyl sulfoxide-d₆: D₂O = 9:1 (v/v)) δ ppm 8.37 (d, J = 7.9 Hz, 1H), 8.35-8.30 (m, 1H), 7.49 (dd, J = 8.6, 2.4 Hz, 1H), 7.36-7.29 (m, 1H), 7.26-7.18 (m, 1H), 7.02 (d, J = 8.6 Hz, 1H), 5.87-5.64 (m, 1H), 4.70 (s, 1H), 4.27 (s, 1H), 3.79-3.58 (m, 7H), 3.41-3.25 (m, 1H), 2.45 (s, 1H), 2.21-2.08 (m, 1H), 2.04-1.64 (m, 4H), 1.15-0.89 (m, 13H); MS (APCI+) m/z 590.1 (M + H)+. |
| Example I-270 | (2S,3S,4S,5S)-3-tert-butyl-4-({[2-methoxy-5-(trifluoromethyl)pyridin-3-yl]methyl}amino)-1-[rel-(1R,2S,4S)-7-oxabicyclo[2.2.1]heptane-2-carbonyl]-5{2-(propan-2-yl)phenyl]pyrrolidine-2-carboxylic acid | ¹HNMR (400 MHz, 120° C., dimethyl sulfoxide-d₆: D₂O = 9:1 (v/v)) δ ppm 8.27 (s, 1H), 7.99-7.71 (m, 1H), 7.49 (s, 1H), 7.36-7.15 (m, 2H), 7.09 (q, J = 8.9, 7.4 Hz, 1H), 5.39 (d, J = 6.3 Hz, 1H), 4.55 (s, 1H), 4.49-4.38 (m, 2H), 3.69 (d, J = 1.9 Hz, 3H), 3.58-3.47 (m, 1H), 3.41-3.34 (m, 1H), 3.30-3.20 (m, 1H), 3.11-3.08 (m, 1H), 2.46-2.36 (m, 2H), 1.79-1.65 (m, 1H), 1.57-1.34 (m, 2H), 1.34-1.11 (m, 5H), 1.09-0.95 (m, 13H); MS (APCI+) m/z 618.1 (M + H)+. |
| Example I-271 | (2S,3S,4S,5S)-3-tert-butyl-1-(cyclopropanecarbonyl)-4- | ¹HNMR (400 MHz, 120° C., dimethyl sulfoxide-d₆: D₂O = 9:1 (v/v)) δ ppm 8.26 (s, 1H), 7.84 (d, J = 7.8 |

TABLE 1-continued

| | | |
|---|---|---|
| | ({[2-methoxy-5-(trifluoromethyl)pyridin-3-yl]methyl}amino)-5-[2-(propan-2-yl)phenyl]pyrrolidine-2-carboxylic acid | Hz, 1H), 7.49 (s, 1H), 7.28-7.15 (m, 2H), 7.09 (t, J = 7.4 Hz, 1H), 5.45 (d, J = 6.6 Hz, 1H), 4.65 (s, 1H), 3.70 (s, 3H), 3.52 (d, J = 14.9 Hz, 1H), 3.39 (d, J = 6.6 Hz, 1H), 3.25 (d, J = 15.0 Hz, 1H), 3.13-3.03 (m, 1H), 2.44 (s, 1H), 1.50-1.45 (m, 1H), 1.17 (d, J = 6.8 Hz, 3H), 1.06 (d, J = 6.8 Hz, 3H), 1.00 (s, 9H), 0.75-0.65 (m, 1H), 0.62-0.54 (m, 2H), 0.57-0.48 (m, 1H); MS (APCI+) m/z 561.9 (M + H)$^+$. |
| Example I-272 | (2S,3S,4S,5S)-1-(bicyclo[1.1.1]pentane-1-carbonyl)-3-tert-butyl-4-({[2-methoxy-5-(trifluoromethyl)pyridin-3-yl]methyl}amino)-5-[2-(propan-2-yl)phenyl]pyrrolidine-2-carboxylic acid | $^1$HNMR (400 MHz, 120° C., dimethyl sulfoxide-d$_6$: D$_2$O = 9:1 (v/v)) δ ppm 8.25 (s, 1H), 7.83 (d, J = 8.2 Hz, 1H), 7.45 (s, 1H), 7.19 (dt, J = 15.0, 7.7 Hz, 2H), 7.10-6.99 (m, 1H), 5.39 (d, J = 6.6 Hz, 1H), 4.62 (s, 1H), 3.70 (s, 3H), 3.51 (d, J = 14.9 Hz, 1H), 3.33 (d, J = 6.7 Hz, 1H), 3.24 (d, J = 15.0 Hz, 1H), 3.12-3.03 (m, 1H), 2.43 (s, 1H), 2.31 (s, 1H), 2.08-1.77 (m, 6H), 1.21 (d, J = 6.7 Hz, 3H), 1.03 (d, J = 6.8 Hz, 3H), 0.99 (s, 9H); MS (APCI+) m/z 588.1 (M + H)$^+$. |
| Example I-273 | (2S,3S,4S,5S)-3-tert-butyl-1-(cyclobutanecarbonyl)-4-({[2-methoxy-5-(trifluoromethyl)pyridin-3-yl]methyl}amino)-5-[2-(propan-2-yl)phenyl]pyrrolidine-2-carboxylic acid | $^1$HNMR (400 MHz, 120° C., dimethyl sulfoxide-d$_6$: D$_2$O = 9:1 (v/v)) δ ppm 8.26 (s, 1H), 7.75 (d, J = 7.8 Hz, 1H), 7.47 (s, 1H), 7.31-7.17 (m, 2H), 7.07 (t, J = 7.5 Hz, 1H), 5.33 (d, J = 6.6 Hz, 1H), 4.47 (s, 1H), 3.69 (s, 3H), 3.50 (d, J = 14.9 Hz, 1H), 3.35 (d, J = 6.6 Hz, 1H), 3.23 (d, J = 14.9 Hz, 1H), 3.14-3.02 (m, 2H), 2.39 (s, 1H), 2.12-1.99 (m, 2H), 1.94-1.87 (m, 2H), 1.71-1.66 (m, 2H), 1.24 (d, J = 6.8 Hz, 3H), 1.05 (d, J = 6.8 Hz, 3H), 0.98 (s, 9H); MS (APCI+) m/z 576.1 (M + H)$^+$. |
| Example I-274 | (2S,3S,4S,5S)-5-[2-(azetidin-1-yl)pyridin-3-yl]-4-{[(5-bromo-2-ethoxyphenyl)methyl]amino}-3-tert-butyl-1-{[(propan-2-yl)oxy]carbonyl}pyrrolidine-2-carboxylic acid | $^1$HNMR (400 MHz, 120° C., dimethyl sulfoxide-d$_6$: D$_2$O = 9:1 (v/v)) δ ppm 8.08-8.02 (m, 1H), 8.02-7.96 (m, 1H), 7.27 (dd, J = 8.7, 2.6 Hz, 1H), 7.10 (d, J = 2.6 Hz, 1H), 6.79 (d, J = 8.7 Hz, 1H), 6.66 (dd, J = 7.6, 4.8 Hz, 1H), 4.92 (d, J = 6.7 Hz, 1H), 4.66-4.53 (m, 1H), 4.32 (s, 1H), 4.01-3.72 (m, 6H), 3.47 (d, J = 14.4 Hz, 1H), 3.31-3.25 (m, 2H), 2.30 (s, 1H), 2.24-2.11 (m, 2H), 1.16-1.07 (m, 3H), 1.03 (d, J = 6.2 Hz, 3H), 0.95 (s, 9H), 0.87 (d, J = 6.1 Hz, 3H); MS (APCI+) m/z 619.1 (M + H)$^+$. |
| Example I-275 | (2S,3S,4S,5S)-5-[2-(azetidin-1-yl)pyridin-3-yl]-3-tert-butyl-4-({[2-methoxy-4-(trifluoromethyl)phenyl]methyl}amino)-1-{[(propan-2-yl)oxy]carbonyl}pyrrolidine-2-carboxylic acid | $^1$HNMR (400 MHz, 120° C., dimethyl sulfoxide-d$_6$: D$_2$O = 9:1 (v/v)) δ ppm 8.09 (d, J = 7.5 Hz, 1H), 7.99 (d, J = 4.9 Hz, 1H), 7.49 (dd, J = 8.5, 2.3 Hz, 1H), 7.29 (d, J = 2.3 Hz, 1H), 7.02 (d, J = 8.6 Hz, 1H), 6.66 (dd, J = 7.5, 4.8 Hz, 1H), 4.92 (d, J = 7.3 Hz, 1H), 4.68-4.55 (m, 1H), 4.30 (s, 1H), 3.97-3.83 (m, 4H), 3.61 (s, 3H), 3.55 (d, J = 14.5 Hz, 1H), 3.33 (d, J = 14.4 Hz, 1H), 3.26 (d, J = 6.3 Hz, 1H), 2.30 (s, 1H), 2.20-2.07 (m, 2H), 1.03 (d, J = 6.2 Hz, 3H), 0.94 (s, 9H), 0.87 (d, J = 6.2 Hz, 3H); MS (APCI+) m/z 593.0 (M + H)$^+$. |
| Example I-276 | (2S,3S,4S,5S)-3-tert-butyl-5-(2-cyclopropylphenyl)-4-({3{(2-methoxypyridin-3-yl)amino]cyclobutyl}amino)-1-{[(propan-2-yl)oxy]carbonyl}pyrrolidine-2-carboxylic acid | $^1$HNMR (400 MHz, 120° C., dimethyl sulfoxide-d$_6$: D$_2$O = 9:1 (v/v), asterisk denotes minor diastereomer peak) δ ppm 7.81-7.71 (m, 1H), 7.39-7.33 (m, 1H), 7.28-7.16 (m, 2H), 7.15-7.05 (m, 1H), 6.76-6.65 (m, 1H), 6.65-6.56 (m, 1H), 6.46-6.40* (m, 1H), 5.69 (d, J = 6.7 Hz, 1H), 4.68-4.50 (m, 1H), 4.40 (d, J = 1.7 Hz, 1H), 3.90-3.84 (m, 3H), 3.82-3.72 (m, 1H), 3.72-3.64* (m, 1H), 3.46 (p, J = 7.6 Hz, 1H), 3.24-3.15* (m, 1H), 2.85 (p, J = 7.9 Hz, 1H), 2.74-2.59 (m, 1H), 2.44-1.79 (m, 3H), 1.78-1.48 (m, 1H), 1.09-0.70 (m, 19H), 0.64-0.53 (m, 1H); MS (APCI+) m/z 565.3 (M + H)$^+$. |
| Example I-277 | (2S,3S,4S,5S)-3-tert-butyl-4-{[(5-tert-butyl-2-methoxyphenyl)methyl]amino}-1-(cyclobutanecarbonyl)-5-[2-(trifluoromethyl)phenyl]pyrrolidine-2-carboxylic acid | $^1$HNMR (400 MHz, 120° C., dimethyl sulfoxide-d$_6$: D$_2$O = 9:1 (v/v)) δ ppm 8.05 (d, J = 7.9 Hz, 1H), 7.72 (d, J = 7.8 Hz, 1H), 7.61 (t, J = 7.6 Hz, 1H), 7.49 (t, J = 7.7 Hz, 1H), 7.17 (dd, J = 8.6, 2.5 Hz, 1H), 6.96 (d, J = 2.4 Hz, 1H), 6.73 (d, J = 8.6 Hz, 1H), 5.36 (d, J = 6.5 Hz, 1H), 4.46 (s, 1H), 3.69-3.61 (m, 4H), 3.53-3.41 (m, 1H), 3.29 (d, J = 13.7 Hz, 1H), 3.12-3.05 (m, 1H), 2.50 (s, 1H), 2.16-1.90 (m, 3H), 1.86-1.67 (m, 3H), 1.18 (s, 9H), 0.95 (s, 9H); MS (APCI+) m/z 589.2 (M + H)$^+$. |
| Example I-278 | (2S,3S,4S,5S)-3-tert-butyl-1-(cyclobutanecarbonyl)-4-{[(5-cyclobutyl-2-methoxypyridin-3-yl)methyl]amino}-5-[2-(trifluoromethyl)phenyl]pyrrolidine-2-carboxylic acid | $^1$HNMR (400 MHz, 120° C., dimethyl sulfoxide-d$_6$: D$_2$O = 9:1 (v/v)) δ ppm 8.11 (d, J = 7.9 Hz, 1H), 7.78 (d, J = 2.4 Hz, 1H), 7.71 (d, J = 7.9 Hz, 1H), 7.59 (t, J = 7.6 Hz, 1H), 7.48 (t, J = 7.6 Hz, 1H), 7.14 (d, J = 2.4 Hz, 1H), 5.35 (d, J = 6.5 Hz, 1H), 4.48 (s, 1H), 3.60 (s, 3H), 3.49 (d, J = 14.4 Hz, 1H), 3.44-3.32 (m, 2H), 3.21 (d, J = 14.3 Hz, 1H), 3.10-3.04 (m, 1H), 2.43 (s, 1H), 2.30-2.19 (m, 2H), 2.17-1.64 (m, 10H), 0.95 (s, 9H); MS (APCI+) m/z 588.1 (M + H)$^+$. |
| Example I-279 | (2S,3S,4S,5S)-3-tert-butyl-1-(cyclobutanecarbonyl)-4-({[2-methoxy-5-(1-methylcyclobutyl)phenyl]methyl}amino)-5-[2- | $^1$HNMR (400 MHz, 120° C., dimethyl sulfoxide-d$_6$: D$_2$O = 9:1 (v/v)) δ ppm 8.05 (d, J = 7.4 Hz, 1H), 7.71 (d, J = 7.9 Hz, 1H), 7.60 (t, J = 7.6 Hz, 1H), 7.49 (t, J = 7.6 Hz, 1H), 7.00 (dd, J = 8.5, 2.4 Hz, 1H), 6.80-6.71 (m, 2H), 5.36 (d, J = 6.4 Hz, 1H), 4.46 (s, 1H), 3.62 (d, |

TABLE 1-continued

| | | |
|---|---|---|
| | (trifluoromethyl)phenyl] pyrrolidine-2-carboxylic acid | J = 13.8 Hz, 1H), 3.49-3.43 (m, 4H), 3.27 (d, J = 13.8 Hz, 1H), 3.14-3.06 (m, 1H), 2.47 (s, 1H), 2.24-1.88 (m, 8H), 1.81-1.67 (m, 4H), 1.31 (s, 3H), 0.95 (s, 9H); MS (APCI+) m/z 601.1 (M + H)+. |
| Example I-280 | (2S,3S,4S,5S)-3-tert-butyl-1-(cyclobutanecarbonyl)-4-({[2-methoxy-5-(trifluoromethyppyridin-3-yl]methyl}amino)-5-[2-(trifluoromethyl)phenyl] pyrrolidine-2-carboxylic acid | $^1$HNMR (400 MHz, 120° C., dimethyl sulfoxide-d$_6$: D$_2$O = 9:1 (v/v)) δ ppm 8.31-8.25 (m, 1H), 8.15 (d, J = 7.9 Hz, 1H), 7.68 (d, J = 7.8 Hz, 1H), 7.56 (t, J = 7.5 Hz, 1H), 7.49-7.41 (m, 2H), 5.32 (d, J = 6.6 Hz, 1H), 4.47 (s, 1H), 3.73 (s, 3H), 3.45 (d, J = 15.2 Hz, 1H), 3.32 (d, J = 6.6 Hz, 1H), 3.23 (d, J = 15.2 Hz, 1H), 3.01 (s, 1H), 2.37 (s, 1H), 2.17-1.62 (m, 6H), 0.93 (s, 9H); MS (APCI+) m/z 602.1 (M + H)+. |
| Example I-281 | (2S,3S,4S,5S)-3-tert-butyl-4-{[(5-cyclobutyl-2-methoxypyridin-3-yl)methyl amino}-5-[2-(dimethylamino) pyridin-3-yl]-1-[(2S)-oxolane-2-carbonyl]pyrrolidine-2-carboxylic acid | $^1$HNMR (400 MHz, dimethyl sulfoxide-d$_6$, 120° C.) δ ppm 8.25 (s, 1H), 8.16 (dd, J = 4.9, 1.9 Hz, 1H), 7.75 (d, J = 2.4 Hz, 1H), 7.15 (d, J = 2.4 Hz, 1H), 6.94 (dd, J = 7.6, 4.7 Hz, 1H), 5.54 (s, 1H), 4.55 (s, 1H), 4.22 (s, 1H), 3.77-3.65 (m, 2H), 3.63 (s, 3H), 3.53-3.45 (m, 2H), 3.44-3.31 (m, 1H), 3.21 (d, J = 14.5 Hz, 1H), 2.66 (s, 6H), 2.37 (s, 1H), 2.26 (dqt, J = 8.6, 5.5, 2.5 Hz, 2H), 2.05-1.53 (m, 8H), 0.99 (s, 9H); MS (ESI+) m/z 580 (M + H)+. |
| Example I-282 | (2S,3S,4S,5S)-3-tert-butyl-5-(2-chlorophenyl)-4-({[2-methoxy-5-(trifluoromethyl) pyridin-3-yl]methyl}amino)-1-[(2S)-oxolane-2-carbonyl]pyrrolidine-2-carboxylic acid | $^1$HNMR (500 MHz, dimethyl sulfoxide-d$_6$) δ ppm 8.28 (d, J = 2.3 Hz, 1H), 7.45 (d, J = 2.5 Hz, 1H), 7.30 (s, 1H), 7.19 (s, 3H), 3.89 (s, 3H), 3.80 (s, 1H), 3.71 (d, J = 25.1 Hz 1H), 3.51 (d, J = 16.2 Hz, 1H), 3.43 (s, 1H), 3.29 (d, J = 16.2 Hz, 1H), 2.38 (s, 1H), 1.87 (s, 2H), 1.72 (s, 1H), 0.97 (s, 9H), 0.91-0.82 (m, 4H); MS (APCI+) m/z 585 (M + H)+. |
| Example I-283 | (2S,3S,4S,5S)-3-tert-butyl-5-[2-(dimethylamino)pyridin-3-yl]-4-({[2-methoxy-5-(1-methylcyclobutyl)phenyl] methyl}amino)-1-[(2S)-oxolane-2-carbonyl] pyrrolidine-2-carboxylic acid | $^1$HNMR (400 MHz, dimethyl sulfoxide-d$_6$, 120° C.) δ ppm 8.27-8.19 (m, 2H), 7.07 (ddd, J = 10.7, 8.1, 3.7 Hz, 2H), 6.89 (d, J = 2.4 Hz, 1H), 6.83 (d, J = 8.5 Hz, 1H), 5.64 (s, 1H), 4.68 (d, J = 1.4 Hz, 1H), 4.30 (s, 1H), 3.83-3.63 (m, 4H), 3.60 (s, 3H), 3.35 (d, J = 13.5 Hz, 1H), 2.77 (s, 6H), 2.56 (s, 1H), 2.29-2.18 (m, 2H), 2.12-1.64 (m, 8H), 1.37 (s, 3H), 1.04 (s, 9H); MS (ESI+) m/z 593 (M + H)+. |
| Example I-284 | (2S,3S,4S,5S)-3-tert-butyl-4-{[(5-tert-butyl-2-methoxyphenyl)methyl] amino}-5-[2-(dimethylamino) pyridin-3-yl]-1-[(2S)-oxolane-2-carbonyl]pyrrolidine-2-carboxylic acid | $^1$HNMR (400 MHz, dimethyl sulfoxide-d$_6$, 120° C.) δ ppm 8.19 (dd, J = 5.6, 3.7 Hz, 2H), 7.20 (dd, J = 8.6, 2.6 Hz, 1H), 7.09-7.00 (m, 2H), 6.78 (d, J = 8.6 Hz, 1H), 5.61 (d, J = 6.7 Hz, 1H), 4.65 (s, 1H), 4.25 (s, 1H), 3.82-3.60 (m, 4H), 3.56 (s, 3H), 3.33 (d, J = 13.5 Hz, 1H), 2.74 (s, 6H), 2.52 (s, 1H), 1.95-1.60 (m, 4H), 1.20 (s, 9H), 1.01 (s, 9H); MS (ESI+) m/z 581 (M + H)+. |
| Example I-285 | (2S,3S,4S,5S)-3-tert-butyl-4-{[(5-tert-butyl-2-hydroxyphenyl) methyl]amino}-1-[(2S)-oxolane-2-carbonyl]-5{2-(propan-2-yl)phenyl] pyrrolidine-2-carboxylic acid | $^1$HNMR (400 MHz, dimethyl sulfoxide-d$_6$) δ ppm 7.96 (d, J = 7.8 Hz, 1H), 7.26 (d, J = 7.7 Hz, 1H), 7.19 (t, J = 7.5 Hz, 1H), 7.06 (t, J = 7.5 Hz, 1H), 6.96 (dd, J = 8.4, 2.6 Hz, 1H), 6.77 (d, J = 2.5 Hz, 1H), 6.47 (d, J = 8.4 Hz, 1H), 5.58 (s, 1H), 4.50 (s, 1H), 4.20 (bs, 1H), 3.70 (d, J = 7.4 Hz, 1H), 3.59 (d, J = 13.8 Hz, 2H), 3.44-3.39 (m, 1H), 3.28 (d, J = 13.9 Hz, 1H), 3.12 (p, J = 6.8 Hz, 1H), 2.39 (s, 1H), 1.91 (dt, J = 10.3, 5.4 Hz, 1H), 1.82 (dt, J = 13.2, 6.3 Hz, 1H), 1.64 (s, 1H), 1.23 (d, J = 6.7 Hz, 3H), 1.18 (d, J = 6.8 Hz, 3H), 1.15 (s, 9H), 0.98 (s, 9H); MS (APCI+) m/z 566 (M + H)+. |
| Example I-286 | (2S,3S,4S,5S)-3-tert-butyl-4-{[(5-cyclobutyl-2-methoxypyridin-3-yl)methyl] amino}-1-(2S)-oxolane-2-carbonyl]-5-[2-(trifluoromethyl) phenyl]pyrrolidine-2-carboxylic acid | $^1$HNMR (500 MHz, dimethyl sulfoxide-d$_6$) δ ppm 8.33 (d, J = 8.0 Hz, 1H), 7.78 (d, J = 2.4 Hz, 1H), 7.69 (d, J = 7.8 Hz, 1H), 7.60 (t, J = 7.7 Hz, 1H), 7.47 (t, J = 7.8 Hz, 1H), 7.12 (d, J = 2.4 Hz, 1H), 5.55 (s, 1H), 4.66 (s, 1H), 3.73 (q, J = 7.2 Hz, 1H), 3.63 (d, J = 2.0 Hz, 3H), 3.43 (d, J = 14.5 Hz, 1H), 3.38 (dd, J = 8.0, 4.3 Hz, 2H), 3.19 (d, J = 14.6 Hz, 1H), 2.41 (s, 1H), 2.33-2.20 (m, 3H), 2.05-1.89 (m, 4H), 1.86 (ddd, J = 12.2, 5.6, 3.0 Hz, 2H), 1.79 (qd, J = 8.5, 2.0 Hz, 2H), 1.75-1.64 (m, 2H), 0.99 (s, 9H); MS (APCI+) m/z 604 (M + H)+. |
| Example I-287 | (2S,3S,4S,5S)-4-{[(5-bromo-2-methoxypyridin-3-yl) methyl]amino}-3-tert-butyl-5-(2-methylphenyl)-1-[(2S)-oxane-2-carbonyl]pyrrolidine-2-carboxylic acid | $^1$HNMR (500 MHz, dimethyl sulfoxide-d$_6$) δ ppm 8.04 (d, J = 2.5 Hz, 1H), 7.92 (m, 1H), 7.35 (d, J = 2.5 Hz, 1H), 7.20 (m, 3H), 5.56 (m, 1H), 4.61 (m, 1H), 3.77 (d, J = 11.2 Hz, 1H), 3.70 (s, 3H), 3.46-3.39 (m, 2H), 3.25 (d, J = 15.1 Hz, 1H), 2.52 (m, 2H), 2.31 (m, 1H), 2.25 (s, 3H), 1.72-1.32 (m, 6H), 1.00 (s, 9H); MS (ESI+) m/z 588.2. |
| Example I-288 | (2S,3S,4S,5S)-5-(2-bromophenyl)-3-tert-butyl-4-({[2-methoxy-5-(trifluoromethyl)pyridin-3-yl]methyl}amino)-1-[(2S)-oxane-2-carbonyl] pyrrolidine-2-carboxylic acid | $^1$HNMR (500 MHz, dimethyl sulfoxide-d$_6$, 120° C.) δ ppm 8.31 (dd, J = 2.6, 1.2 Hz, 1H), 8.00 (s, 1H), 7.56 (d, J = 8.2 Hz, 1H), 7.52 (d, J = 2.5 Hz, 1H), 7.33 (t, J = 7.5 Hz, 1H), 7.19 (t, J = 7.6 Hz, 1H), 5.65 (s, 1H), 4.61 (d, J = 1.7 Hz, 1H), 3.86-3.73 (m, 5H), 3.60-3.48 (m, 3H), 3.30 (d, J = 15.3 Hz, 1H), 2.31 (s, 1H), 1.76-1.23 (m, 6H), 0.98 (s, 9H); MS (ESI+) m/z 642 & 644 (M + H)+. |

TABLE 1-continued

| Example I-289 | (2S,3S,4S,5S)-5-(2-bromophenyl)-3-tert-butyl-4-({[2-methoxy-4-(trifluoromethyl)phenyl]methyl}amino)-1-[(2S)oxane-2-carbonyl]pyrrolidine-2-carboxylic acid | $^1$HNMR (500 MHz, dimethyl sulfoxide-d$_6$, 120° C.) δ ppm 7.98 (s, 1H), 7.58 (d, J = 7.9 Hz, 1H), 7.34 (t, J = 7.6 Hz, 1H), 7.19 (t, J = 7.6 Hz, 1H), 7.14-7.03 (m, 3H), 5.64 (s, 1H), 4.61 (d, J = 1.7 Hz, 1H), 3.78 (dd, J = 9.6, 5.9 Hz, 1H), 3.66 (s, 3H), 3.60 (d, J = 6.8 Hz, 1H), 3.54 (d, J = 14.5 Hz, 1H), 3.33 (d, J = 14.4 Hz, 1H), 3.12 (s, 2H), 2.32 (s, 1H), 1.74-1.30 (m, 6H), 0.97 (s, 9H); MS (ESI+) m/z 641 & 643 (M + H)$^+$. |
|---|---|---|
| Example I-290 | (2S,3S,4S,5S)-5-(2-bromophenyl)-3-tert-butyl-4-({[2-methoxy-5-(trifluoromethyl)phenyl]methyl}amino)-1-[(2S)oxane-2-carbonyl]pyrrolidine-2-carboxylic acid | $^1$HNMR (500 MHz, dimethyl sulfoxide-d$_6$, 120° C.) δ ppm 7.97 (s, 1H), 7.57 (d, J = 8.0 Hz, 1H), 7.46 (dd, J = 8.7, 2.5 Hz, 1H), 7.33 (t, J = 7.5 Hz, 1H), 7.23 (d, J = 2.4 Hz, 1H), 7.19 (t, J = 7.7 Hz, 1H), 7.00 (d, J = 8.5 Hz, 1H), 5.64 (s, 1H), 4.61 (d, J = 1.8 Hz, 1H), 3.81-3.73 (m, 1H), 3.67 (s, 3H), 3.64-3.53 (m, 2H), 3.34-3.28 (m, 3H), 2.33 (s, 1H), 1.68 (d, J = 12.7 Hz, 1H), 1.59-1.28 (m, 5H), 0.97 (s, 9H); MS (ESI+) m/z 641 & 643 (M + H)$^+$. |
| Example I-291 | (2S,3S,4S,5S)-5-(2-bromophenyl)-3-tert-butyl-4-{[(5-cyclobutyl-2-methoxypyridin-3-yl)methyl]amino}-1-[(2S)-oxane-2-carbonyl]pyrrolidine-2-carboxylic acid | $^1$HNMR (500 MHz, DMSO-d$_6$, 120° C.) δ ppm 7.97 (d, J = 7.6 Hz, 1H), 7.79 (d, J = 2.3 Hz, 1H), 7.59 (d, J = 7.9 Hz, 1H), 7.35 (t, J = 7.5 Hz, 1H), 7.25-7.14 (m, 2H), 5.65 (s, 1H), 4.62 (d, J = 1.5 Hz, 1H), 3.78 (d, J = 11.4 Hz, 1H), 3.68 (s, 3H), 3.64-3.60 (m, 2H), 3.52 (d, J = 14.5 Hz, 1H), 3.45-3.34 (m, 2H), 3.27 (d, J = 14.4 Hz, 1H), 2.35 (s, 1H), 2.32-2.18 (m, 2H), 2.05-1.77 (m, 4H), 1.68 (d, J = 12.5 Hz, 1H), 1.43 (d, J = 47.3 Hz, 5H), 0.98 (s, 9H); MS (ESI+) m/z 628 (M + H)$^+$. |
| Example I-292 | (2S,3S,4S,5S)-5-(2-bromophenyl)-3-tert-butyl-4-({[2-methoxy-5-(trifluoromethyl)pyridin-3-yl]methyl]amino)-1-[(2S)-oxolane-2-carbonyl]pyrrolidine-2-carboxylic acid | $^1$HNMR (400 MHz, DMSO-d$_6$) δ ppm 8.30 (d, J = 2.4 Hz, 1H), 7.95 (m, 1H), 7.56-7.49 (m, 2H), 7.30 (t, J = 7.5 Hz, 1H), 7.16 (td, J = 7.6, 1.7 Hz, 1H), 5.54 (m, 1H), 4.66 (d, J = 1.5 Hz, 1H), 4.17 (m, 1H), 3.79 (s, 3H), 3.74-3.61 (m, 2H), 3.61-3.48 (m, 2H), 3.31 (d, J = 15.1 Hz, 1H), 2.36 (m, 1H), 1.96 (m, 1H), 1.78 (m, 1H), 1.69 (m, 2H), 0.98 (s, 9H); MS (ESI$^+$) m/z 628.2 (M + H)$^+$. |
| Example I-293 | (2S,3S,4S,5S)-5-(2-bromophenyl)-3-tert-butyl-4-{[(5-cyclopropyl-2-methoxypyridin-3-yl)methyl]amino}-1-[(2S)-oxolane-2-carbonyl]pyrrolidine-2-carboxylic acid | $^1$HNMR (400 MHz, DMSO-d$_6$) δ ppm 7.93 (d, J = 7.6 Hz, 1H), 7.76 (d, J = 2.5 Hz, 1H), 7.56 (dd, J = 8.0, 1.2 Hz, 1H), 7.32 (t, J = 7.5 Hz, 1H), 7.23-7.14 (m, 1H), 6.94 (d, J = 2.5 Hz, 1H), 5.55 (m, 1H), 4.66 (d, J = 1.5 Hz, 1H), 4.18 (m, 1H), 3.71 (m, 2H), 3.65 (s, 3H), 3.66-3.54 (m, 2H), 3.47 (d, J = 14.4 Hz, 1H), 3.25 (d, J = 14.4 Hz, 1H), 2.38 (m, 1H), 1.96 (m, 1H), 1.82-1.72 (m, 1H), 1.70 (m, 2H), 0.98 (s, 9H), 0.90-0.80 (m, 2H), 0.55-0.46 (m, 2H); MS (ESI$^+$) m/z 600.1 (M + H)$^+$. |
| Example I-294 | (2S,3S,4S,5S)-5-(2-bromophenyl)-3-tert-butyl-4-{[(5-tert-butyl-2-methoxyphenyl)methyl]amino}-1-[(2S)-oxolane-2-carbonyl]pyrrolidine-2-carboxylic acid | $^1$HNMR (400 MHz, DMSO-d$_6$) δ ppm 7.89 (d, J = 7.4 Hz, 1H), 7.56 (dd, J = 8.0, 1.2 Hz, 1H), 7.33 (t, J = 7.4 Hz, 1H), 7.18 (ddd, J = 17.3, 8.2, 2.2 Hz, 2H), 6.98 (d, J = 2.5 Hz, 1H), 6.75 (d, J = 8.6 Hz, 1H), 5.56 (m, 1H), 4.66 (d, J = 1.4 Hz, 1H), 4.22 (m, 1H), 3.75-3.58 (m, 4H), 3.54 (s, 3H), 3.30 (d, J = 13.6 Hz, 1H), 2.45 (m, 1H), 1.96 (m, 1H), 1.83-1.75 (m, 1H), 1.71 (m, 2H), 1.20 (s, 9H), 0.99 (s, 9H); MS (ESI$^+$) m/z 615.2 (M + H)$^+$. |
| Example I-295 | (2S,3S,4S,5S)-5-(2-bromophenyl)-3-tert-butyl-4-({[2-methoxy-5-(1-methylcyclobutyl)phenyl]methyl}amino)-1-[(2S)-oxolane-2-carbonyl]pyrrolidine-2-carboxylic acid | $^1$HNMR (400 MHz, DMSO-d$_6$) δ ppm 7.89 (d, J = 7.7 Hz, 1H), 7.56 (dd, J = 8.1, 1.2 Hz, 1H), 7.32 (t, J = 7.6 Hz, 1H), 7.18 (td, J = 7.6, 1.7 Hz, 1H), 6.98 (dd, J = 8.4, 2.5 Hz, 1H), 6.82-6.72 (m, 2H), 5.56 (m, 1H), 4.66 (d, J = 1.5 Hz, 1H), 4.20 (m, 1H), 3.76-3.56 (m, 4H), 3.54 (s, 3H), 3.30 (d, J = 13.7 Hz, 1H), 2.43 (m, 1H), 2.25-2.16 (m, 2H), 2.09-1.90 (m, 4H), 1.85-1.68 (m, 4H), 1.33 (s, 3H), 0.99 (s, 9H); MS (ESI$^+$) m/z 629.3 (M + H)$^+$. |
| Example I-296 | (2S,3S,4S,5S)-3-tert-butyl-4-{[(5-cyclobutyl-2-methoxypyridin-3-yl)methyl]amino}-5-(2-cyclopropylphenyl)-1-[(2S)-oxane-2-carbonyl]pyrrolidine-2-carboxylic acid | $^1$HNMR (400 MHz, DMSO-d$_6$, 120° C.) δ ppm 7.84 (q, J = 3.6 Hz, 2H), 7.26-7.19 (m, 3H), 7.11-7.06 (m, 1H), 5.94 (d, J = 6.6 Hz, 1H), 4.62 (d, J = 1.4 Hz, 1H), 3.80-3.58 (m, 7H), 3.47-3.37 (m, 1H), 3.26-3.23 (m, 3H), 2.50 (s, 1H), 2.33-2.20 (m, 2H), 2.05-1.78 (m, 4H), 1.73-1.62 (m, 1H), 1.59-1.15 (m, 5H), 1.03 (s, 9H), 0.93 (tdd, J = 9.1, 5.8, 3.9 Hz, 1H), 0.83 (tdt, J = 9.1, 5.7, 3.0 Hz, 1H), 0.70 (dtd, J = 9.4, 5.6, 4.0 Hz, 1H), 0.54 (s, 1H); MS (ESI+) m/z 590 (M + H)$^+$. |
| Example I-297 | (2S,3S,4S,5S)-3-tert-butyl-4-{[(5-cyclobutyl-2-methoxypyridin-3-yl)methyl]amino}-5-(2-ethylphenyl)-1-[(2S)-oxane-2-carbonyl]pyrrolidine-2-carboxylic acid | $^1$HNMR (400 MHz, DMSO-d$_6$) δ ppm 7.88 (d, J = 7.7 Hz, 1H), 7.76 (d, J = 2.4 Hz, 1H), 7.26-7.13 (m, 3H), 7.12 (d, J = 2.5 Hz, 1H), 5.53 (s, 1H), 4.60 (d, J = 1.5 Hz, 1H), 3.72 (d, J = 11.5 Hz, 1H), 3.59 (s, 3H), 3.48 (d, J = 14.4 Hz, 1H), 3.38 (dd, J = 11.4, 7.4 Hz, 2H), 3.22 (d, J = 14.4 Hz, 1H), 2.61 (dq, J = 15.1, 7.5 Hz, 1H), 2.47 (m, 1H), 2.34 (d, J = 1.5 Hz, 1H), |

TABLE 1-continued

| | | |
|---|---|---|
| | | 2.31-2.21 (m, 2H), 2.03-1.80 (m, 3H), 1.66 (d, J = 12.1 Hz, 1H), 1.50 (m, 2H), 1.35 (m, 3H), 1.12 (t, J = 7.5 Hz, 3H), 0.99 (s, 9H); MS (APCI+) m/z 578 (M + H)+. |
| Example I-298 | (2S,3S,4S,5S)-3-tert-butyl-5-(2,3-dihydro-1-benzofuran-7-yl)-4-({[2-methoxy-5-(trifluoromethyl)pyridin-3-yl]methyl}amino)-1-[(2S)-oxane-2-carbonyl]pyrrolidine-2-carboxylic acid | $^1$HNMR (400 MHz, DMSO-d$_6$) δ ppm 8.31 (dd, J = 2.4, 1.1 Hz, 1H), 7.56 (d, J = 2.4 Hz, 2H), 7.11 (d, J = 7.2 Hz, 1H), 6.78 (t, J = 7.5 Hz, 1H), 5.54 (s, 1H), 4.51-4.43 (m, 3H), 3.81 (s, 3H), 3.76 (dd, J = 9.7, 5.5 Hz, 1H), 3.52 (d, J = 15.2 Hz, 1H), 3.41 (dd, J = 7.2, 2.2 Hz, 1H), 3.32 (s, 1H), 3.19-3.12 (m, 3H), 2.29 (t, J = 2.3 Hz, 1H), 1.74-1.58 (m, 2H), 1.55-1.29 (m, 5H), 1.20-1.09 (m, 1H), 0.94 (s, 9H); MS (ESI+) m/z 606 (M + H)+. |
| Example I-299 | (2S,3S,4S,5S)-3-tert-butyl-5-(2,3-dihydro-1-benzofuran-7-yl)-4-({[2-methoxy-5-(trifluoromethyl)phenyl]methyl}amino)-1-[(2S)-oxane-2-carbonyl]pyrrolidine-2-carboxylic acid | $^1$HNMR (400 MHz, DMSO-d$_6$) δ ppm 7.50 (dd, J = 8.7, 2.7 Hz, 2H), 7.29 (d, J = 2.4 Hz, 1H), 7.14 (dd, J = 7.3, 1.4 Hz, 1H), 7.04 (d, J = 8.6 Hz, 1H), 6.81 (t, J = 7.5 Hz, 1H), 5.55 (s, 1H), 4.53-4.43 (m, 3H), 3.80-3.75 (m, 1H), 3.69 (s, 3H), 3.67-3.60 (m, 2H), 3.50 (dd, J = 7.0, 2.0 Hz, 1H), 3.41 (d, J = 14.3 Hz, 1H), 3.22-3.13 (m, 4H), 2.37 (d, J = 2.3 Hz, 1H), 1.72-1.65 (m, 1H), 1.54-1.32 (m, 4H), 1.27-1.09 (m, 2H), 0.95 (s, 9H); MS (ESI+) m/z 605 (M + H)+. |
| Example I-300 | (2S,3S,4S,5S)-3-tert-butyl-5-(2,3-dihydro-1-benzofuran-7-yl)-4-({[2-methoxy-4-(trifluoromethyl)phenyl]methyl}amino)-1-[(2S)-oxane-2-carbonyl]pyrrolidine-2-carboxylic acid | $^1$HNMR (400 MHz, DMSO-d$_6$) δ ppm 7.54 (s, 1H), 7.16-7.08 (m, 3H), 7.06 (d, J = 1.5 Hz, 1H), 6.78 (t, J = 7.5 Hz, 1H), 5.52 (s, 1H), 4.52-4.38 (m, 3H), 3.80-3.73 (m, 1H), 3.65 (s, 3H), 3.52 (d, J = 14.6 Hz, 1H), 3.42 (s, 1H), 3.40-3.35 (m, 2H), 3.17 (td, J = 8.6, 4.5 Hz, 3H), 2.28 (t, J = 2.2 Hz, 1H), 1.73-1.64 (m, 1H), 1.54-1.30 (m, 5H), 0.94 (s, 9H); MS (ESI) m/z 605 (M + H)+. |
| Example I-301 | (2S,3S,4S,5S)-3-tert-butyl-4-{[(5-cyclobutyl-2-methoxypyridin-3-yl)methyl]amino}-5-(2,3-dihydro-1-benzofuran-7-yl)-1-[(2S)-oxane-2-carbonyl]pyrrolidine-2-carboxylic acid | $^1$HNMR (400 MHz, DMSO-d$_6$) δ ppm 7.84 (d, J = 2.4 Hz, 1H), 7.50 (d, J = 7.8 Hz, 1H), 7.25 (d, J = 2.4 Hz, 1H), 7.16 (d, J = 7.3 Hz, 1H), 6.83 (t, J = 7.5 Hz, 1H), 5.57 (s, 1H), 4.53-4.45 (m, 3H), 3.76 (d, J = 11.3 Hz, 1H), 3.70 (s, 3H), 3.67-3.63 (m, 1H), 3.59 (d, J = 6.9 Hz, 1H), 3.42 (dd, J = 7.3, 2.4 Hz, 1H), 3.39 (d, J = 2.2 Hz, 1H), 3.18 (d, J = 6.3 Hz, 2H), 2.41 (s, 1H), 2.32-2.23 (m, 2H), 2.06-1.90 (m, 4H), 1.88-1.80 (m, 1H), 1.71-1.66 (m, 1H), 1.50-1.32 (m, 5H), 0.96 (s, 9H); MS (ESI) m/z 592 (M + H)+. |
| Example I-302 | (2S,3S,4S,5S)-3-tert-butyl-5-(2,3-dihydro-1-benzofuran-7-yl)-4-{[(3-methoxy-5,6,7,8-tetrahydronaphthalen-2-yl)methyl]amino}-1-[(2S)-oxane-2-carbonyl]pyrrolidine-2-carboxylic acid | $^1$HNMR (400 MHz, DMSO-d$_6$) δ ppm 7.44 (d, J = 7.7 Hz, 1H), 7.19 (dd, J = 7.3, 1.3 Hz, 1H), 6.85 (t, J = 7.5 Hz, 1H), 6.67 (s, 1H), 6.57 (s, 1H), 4.52 (dt, J = 9.3, 8.3 Hz, 3H), 3.74 (ddd, J = 15.7, 9.1, 2.7 Hz, 4H), 3.57 (s, 3H), 3.43 (s, 1H), 3.40 (s, 1H), 3.20 (dt, J = 8.9, 4.0 Hz, 4H), 2.65 (s, 2H), 2.55 (d, J = 5.7 Hz, 2H), 2.51 (s, 1H), 1.68 (dq, J = 6.7, 3.2 Hz, 4H), 1.32 (dd, J = 73.4, 20.9 Hz, 6H), 0.97 (s, 9H); MS (ESI+) m/z 591 (M + H)+. |
| Example I-303 | (2S,3S,4S,5S)-3-tert-butyl-4-{[(5-cyclobutyl-2-methoxypyridin-3-yl)methyl]amino}-1-(6-methoxypyridine-2-sulfonyl)-5-[2-(propan-2-yl)phenyl]pyrrolidine-2-carboxylic acid | $^1$HNMR (400 MHz, DMSO-d$_6$) δ ppm 7.81-7.70 (m, 2H), 7.66 (d, J = 7.7 Hz, 1H), 7.25-7.18 (m, 2H), 7.14 (td, J = 8.0, 7.5, 1.5 Hz, 2H), 7.09 (d, J = 2.5 Hz, 1H), 6.96 (dd, J = 8.3, 0.7 Hz, 1H), 6.86 (ddd, J = 8.4, 7.3, 1.4 Hz, 1H), 5.61 (d, J = 6.7 Hz, 1H), 4.54 (d, J = 2.9 Hz, 1H), 3.89 (s, 3H), 3.55 (s, 3H), 3.39 (d, J = 14.4 Hz, 1H), 3.37-3.29 (m, 2H), 3.17-3.06 (m, 2H), 2.36 (t, J = 2.4 Hz, 1H), 2.23 (ddd, J = 10.1, 8.2, 5.0 Hz, 2H), 2.00-1.87 (m, 3H), 1.87-1.78 (m, 1H), 1.25 (d, J = 6.8 Hz, 3H), 1.07 (d, J = 6.8 Hz, 3H), 0.95 (s, 9H), 0.84 (q, J = 6.5 Hz, 1H); MS (APCI+) m/z 651 (M + H)+. |
| Example I-304 | (2S,3S,4S,5S)-3-tert-butyl-4-({[2-methoxy-5-(1-methylcyclobutyl)phenyl]methyl}amino)-1-[(2S)-oxane-2-carbonyl]-5[2-(propan-2-yl)phenyl]pyrrolidine-2-carboxylic acid | $^1$HNMR (400 MHz, DMSO-d$_6$) δ ppm 7.83 (d, J = 7.7 Hz, 1H), 7.51-7.06 (m, 5H), 6.92-6.62 (m, 4H), 5.66 (d, J = 6.1 Hz, 1H), 5.31 (d, J = 6.2 Hz, 1H), 4.58 (s, 1H), 4.49 (s, 1H), 4.18 (dd, J = 9.6, 2.5 Hz, 1H), 3.80-3.65 (m, 2H), 3.26 (s 3H), 2.92 (dt, J = 18.2, 6.9 Hz, 2H), 2.74 (td, J = 11.1, 3.2 Hz, 1H), 2.37 (s, 1H), 2.25-1.85 (m, 5H), 1.71-1.33 (m, 5H), 1.32-1.14 (m, 5H), 0.99 (s, 9H), 0.95-0.78 (m, 2H), 0.73 (d, J = 6.7 Hz, 2H); MS (ESI) m/z 605.4 (M + H)+. |
| Example I-305 | (2S,3S,4S,5S)-3-tert-butyl-4-{[(2,2-dimethyl-2,3-dihydro-1-benzofuran-7-yl)methyl]amino}-1-[(2S)-oxolane-2-carbonyl]-5-[2-(propan-2-yl)phenyl]pyrrolidine-2-carboxylic acid | $^1$HNMR (400 MHz, DMSO-d$_6$) δ ppm 7.85 (d, J = 7.8 Hz, 1H), 7.28 (dd, J = 7.9, 1.5 Hz, 1H), 7.25-7.18 (m, 1H), 7.15-7.09 (m, 1H), 6.95 (dt, J = 7.2, 1.3 Hz, 1H), 6.68 (d, J = 7.6 Hz, 1H), 6.61 (t, J = 7.4 Hz, 1H), 5.64 (s, 1H), 4.65 (d, J = 1.5 Hz, 1H), 4.1 (m, 1H), 3.64 (tt, J = 13.5, 7.0 Hz, 2H), 3.50 (d, J = 13.6 Hz, 1H), 3.25 (d, J = 13.5 Hz, 1H), 3.20- |

TABLE 1-continued

| | | |
|---|---|---|
| | | 3.12 (m, 2H), 2.87 (s, 2H), 1.97 (m, 2H), 1.77 (m, 2H), 1.64 (s, 2H), 1.28 (s, 3H), 1.25-1.22 (m, 6H), 1.17 (d, J = 6.8 Hz, 3H), 1.01 (s, 9H); MS (ESI+) m/z 563.3 (M + H)+. |
| Example I-306 | (2S,3S,4S,5S)-3-tert-butyl-4-{[(2,2-dimethyl-2,3-dihydro-1-benzofuran-7-yl)methyl]amino}-1-[(2S)-oxane-2-carbonyl]-5-[2-(propan-2-yl)phenyl]pyrrolidine-2-carboxylic acid | $^1$HNMR (400 MHz, DMSO-d$_6$) δ ppm 7.85 (dd, J = 7.9, 1.4 Hz, 1H), 7.31 (dd, J = 7.8, 1.4 Hz, 1H), 7.23 (td, J = 7.5, 1.4 Hz, 1H), 7.13 (td, J = 7.5, 1.5 Hz, 1H), 6.70 (d, J = 7.6 Hz, 1H), 6.62 (t, J = 7.4 Hz, 1H), 5.61 (d, J = 6.6 Hz, 1H), 4.62 (d, J = 1.3 Hz, 1H), 3.77-3.67 (m, 2H), 3.56 (d, J = 13.5 Hz, 1H), 3.26 (s, 3H), 2.87 (s, 2H), 2.49 (s, 1H), 1.73-1.35 (m, 6H), 1.33-1.22 (m, 9H), 1.17 (d, J = 6.7 Hz, 3H); 1.01 (s, 9H); MS (ESI+) m/z 577.4 (M + H)+. |
| Example I-307 | (2S,3S,4S,5S)-3-tert-butyl-4-{[(5-cyclobutyl-2-methoxypyridin-3-yl)methyl]amino}-1-(cyclohexanecarbonyl)-5-(2,2-dimethyl-2,3-dihydro-1-benzofuran-7-yl)pyrrolidine-2-carboxylic acid | $^1$HNMR (400 MHz, DMSO-d$_6$) δ ppm 7.82 (d, J = 2.4 Hz, 1H), 7.48 (s, 1H), 7.23 (d, J = 2.3 Hz, 1H), 7.10 (dd, J = 7.2, 1.3 Hz, 1H), 6.80 (t, J = 7.5 Hz, 1H), 5.32 (d, J = 7.0 Hz, 1H), 4.46 (d, J = 2.8 Hz, 1H), 3.68 (s, 3H), 3.62 (d, J = 14.3 Hz, 1H), 3.56 (dd, J = 7.0, 2.6 Hz, 1H), 3.43-3.37 (m, 3H), 3.19 (s, 1H), 3.00 (d, J = 3.1 Hz, 2H), 2.43 (t, J = 2.7 Hz, 1H), 2.30-2.22 (m, 2H), 1.98 (dtt, J = 7.3, 5.8, 3.8 Hz, 3H), 1.84 (tdt, J = 8.3, 5.5, 2.8 Hz, 1H), 1.65 (dd, J = 12.4, 5.6 Hz, 2H), 1.59-1.43 (m, 3H), 1.41 (s, 3H), 1.37 (s, 3H), 1.31-1.03 (m, 6H), 0.98 (s, 9H); MS (ESI+) m/z 618 (M + H)+. |
| Example I-308 | (2S,3S,4S,5S)-3-tert-butyl-4-(4-chloro-7-methoxy-1,3-dihydro-2H-isoindol-2-yl)-1-[(2S)-oxane-2-carbonyl]-5-[2-(propan-2-yl)phenyl]pyrrolidine-2-carboxylic acid | $^1$HNMR (400 MHz, DMSO-d$_6$, 120° C.) δ ppm 8.16 (dd, J = 1.3, 7.9 Hz, 1H), 7.23-7.15 (m, 2H), 7.08-7.04 (m, 1H), 7.03 (d, J = 8.7 Hz, 1H), 6.71 (d, J = 8.6 Hz, 1H), 5.64 (d, J = 8.2 Hz, 1H), 4.64 (d, J = 3.5 Hz, 1H), 4.09-4.04 (m, 1H), 3.83-3.73 (m, 3H), 3.71-3.60 (m, 2H), 3.68 (s, 3H), 3.56 (dt, J = 2.8, 13.5 Hz, 1H), 3.27 (hept, J = 6.7 Hz, 1H), 3.22-3.15 (m, 1H), 2.62 (t, J = 3.5 Hz, 1H), 1.74-1.53 (m, 3H), 1.47-1.34 (m, 3H), 1.28 (d, J = 6.7 Hz, 3H), 1.19 (d, J = 6.7 Hz, 3H), 1.04 (s, 9H). |
| Example I-309 | (2S,3S,4S,5S)-3-tert-butyl-4-({2-[2-methoxy-5-(trifluoromethyl)phenoxy]ethyl}amino)-1-{[(propan-2-yl)oxy]carbonyl}-5-{2-[(propan-2-yl)oxy]pyridin-3-yl}pyrrolidine-2-carboxylic acid | $^1$HNMR (400 MHz, DMSO-d$_6$) δ ppm 7.98 (s, 1H), 7.97 (q, J = 2.0 Hz, 1H), 7.22 (dd, J = 8.6, 2.0 Hz, 1H), 7.07 (d, J = 8.6 Hz, 1H), 6.99 (d, J = 2.2 Hz, 1H), 6.85 (dd, J = 7.0, 5.3 Hz, 1H), 5.27 (dq, J = 12.3, 6.1 Hz, 1H), 5.18 (d, J = 6.7 Hz, 1H), 4.65 (dq, J = 12.4, 6.2 Hz, 1H), 4.36 (d, J = 2.0 Hz, 1H), 3.88 (ddd, J = 10.5, 5.9, 4.7 Hz, 1H), 3.84-3.78 (m, 1H), 3.77 (s, 3H), 3.63 (dd, J = 6.6, 1.3 Hz, 1H), 2.75 (ddd, J = 13.1, 5.9, 4.7 Hz, 1H), 2.62-2.55 (m, 1H), 2.32 (t, J = 1.6 Hz, 1H), 1.29 (d, J = 6.1 Hz, 3H), 1.26 (d, J = 6.1 Hz, 3H), 1.05 (d, J = 6.2 Hz, 3H), 1.01 (s, 9H), 0.91 (d, J = 6.2 Hz, 3H); MS (ESI+) m/z 626.2 (M + H)+. |
| Example I-310 | (2S,3S,4S,5S)-3-tert-butyl-4-{[(5-tert-butyl-2-methoxyphenyl)methyl]amino}-1-(cyclohexanecarbonyl)-5-(2-hydroxyphenyl)pyrrolidine-2-carboxylic acid | $^1$HNMR (400 MHz, DMSO-d$_6$, 120° C.) δ ppm 7.55-7.48 (m, 1H), 7.24 (dd, J = 2.5, 8.6 Hz, 1H), 7.15 (td, J = 1.7, 7.7 Hz, 1H), 7.09 (d, J = 2.5 Hz, 1H), 6.92 (dd, J = 1.2, 8.1 Hz, 1H), 6.87-6.80 (m, 2H), 5.58 (d, J = 6.9 Hz, 1H), 4.55 (d, J = 1.8 Hz, 2H), 3.90-3.80 (m, 2H), 3.59 (s, 3H), 3.56 (s, 1H), 2.59 (s, 1H), 2.32-2.18 (m, 1H), 1.69-1.48 (m, 4H), 1.28-1.22 (m, 3H), 1.21 (s, 9H), 1.21-1.17 (m, 1H), 1.13-1.05 (m, 3H), 0.99 (s, 9H). |

TABLE 2

| | | |
|---|---|---|
| Example II-1 | rac-(2R,3R,4R,5R)-3-tert-butyl-4-[(5-chloropyridin-2-yl)amino]-1-(cyclohexanecarbonyl)-5-phenylpyrrolidine-2-carboxylic acid | MS (ESI−) m/z 483 (M − H)−. |
| Example II-2 | rac-(2R,3R,4R,5R)-3-tert-butyl-4-{[6-chloro-4-(trifluoromethyl)pyridin-2-yl]amino}-1-(cyclohexanecarbonyl)-5-phenylpyrrolidine-2-carboxylic acid | MS (ESI−) m/z 516 (M − H)−. |
| Example II-3 | rac-(2R,3R,4R,5R)-3-tert-butyl-4-{[(3-chloro-2,4-dimethoxyphenyl)methyl]amino}-1-(cyclohexanecarbonyl)-5-phenylpyrrolidine-2-carboxylic acid | MS (APCI+) m/z 557.1 (M + H)+. |

TABLE 2-continued

| Example II-4 | rac-(2R,3R,4R,5R)-3-tert-butyl-1-(cyclohexanecarbonyl)-5-phenyl-4-[({2-[(propan-2-yl)oxy]phenyl}methyl)amino]pyrrolidine-2-carboxylic acid | MS (APCI+) m/z 521.2 (M + H)+. |
|---|---|---|
| Example II-5 | rac-(2R,3R,4R,5R)-3-tert-butyl-1-(cyclohexanecarbonyl)-4-({[2-(2-methylpropoxy)phenyl]methyl}amino)-5-phenylpyrrolidine-2-carboxylic acid | MS (APCI+) m/z 535.2 (M + H)+. |
| Example II-6 | rac-(2R,3R,4R,5R)-3-tert-butyl-1-(cyclohexanecarbonyl)-4-{[(2-methoxypyridin-3-yl)methyl]amino}-5-phenylpyrrolidine-2-carboxylic acid | MS (APCI+) m/z 494.1 (M + H)+. |
| Example II-7 | rac-(2R,3R,4R,5R)-3-tert-butyl-4-{[(3-chloro-2-methoxyphenyl)methyl]amino}-1-(cyclohexanecarbonyl)-5-phenylpyrrolidine-2-carboxylic acid | MS (APCI+) m/z 527.1 (M + H)+. |
| Example II-8 | rac-(2R,3R,4R,5R)-3-tert-butyl-4-({[5-chloro-2-(difluoromethoxy)phenyl]methyl}amino)-1-(cyclohexanecarbonyl)-5-phenylpyrrolidine-2-carboxylic acid | MS (APCI+) m/z 563.1 (M + H)+. |
| Example II-9 | rac-(2R,3R,4R,5R)-3-tert-butyl-4-{[(5-chloro-2-ethoxyphenyl)methyl]amino}-1-(cyclohexanecarbonyl)-5-phenylpyrrolidine-2-carboxylic acid | MS (APCI+) m/z 541.1 (M + H)+. |
| Example II-10 | rac-(2R,3R,4R,5R)-3-tert-butyl-4-{[(2-chloro-6-methoxyphenyl)methyl]amino}-1-(cyclohexanecarbonyl)-5-phenylpyrrolidine-2-carboxylic acid | MS (APCI+) m/z 527.1 (M + H)+. |
| Example II-11 | (2R,3R,4R,5R)-1-[di(propan-2-yl)carbamoyl]-3-methyl-4-{6-methyl-4-(trifluoromethyl)pyridin-2-yl]amino}-5-phenylpyrrolidine-2-carboxylic acid | MS (ESI+) m/z 507.1 (M + H) |
| Example II-12 | rac-(2R,3R,4R,5R)-4-{[(5-chloro-2-methoxyphenyl)methyl]amino}-1-(cyclohexanecarbonyl)-3-cyclopropyl-5-phenylpyrrolidine-2-carboxylic acid | MS (ESI+) m/z 511 (M + H)+. |
| Example II-13 | rac-(2R,3R,4R,5R)-3-tert-butyl-4-{[6-methyl-4-(trifluoromethyl)pyridin-2-yl]amino}-5-phenyl-1-{[(propan-2-yl)oxy]carbonyl}pyrrolidine-2-carboxylic acid | MS (ESI+) m/z 508 (M + H)+. |
| Example II-14 | rac-(2R,3R,4R,5R)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid | MS (ESI+) m/z 534 (M + H)+. |
| Example II-15 | rac-(2R,3R,4R,5R)-3-tert-butyl-4-({[2-chloro-5-(trifluoromethyl)pyridin-3-yl]methyl}amino)-1-(cyclohexanecarbonyl)-5-phenylpyrrolidine-2-carboxylic acid | MS (ESI+) m/z 566.2 (M + H)+. |
| Example II-16 | rac-(2R,3R,4R,5R)-3-tert-butyl-4-({[2-chloro-5-(trifluoromethyl)pyridin-3-yl]methyl}amino)-1-(cyclohexanecarbonyl)-5-(2-methoxyphenyl)pyrrolidine-2-carboxylic acid | MS (ESI+) m/z 596.1 (M + H)+. |
| Example II-17 | rac-(2R,3R,4R,5R)-3-tert-butyl-1-(cyclohexanecarbonyl)-5-(2-methoxyphenyl)-4-({[2- | MS (ESI+) m/z 591.2 (M + H)+. |

TABLE 2-continued

| | | |
|---|---|---|
| Example II-18 | methoxy-5-(trifluoromethyl) phenyl]methyl}amino) pyrrolidine-2-carboxylic acid rac-(2R,3R,4R,5R)-3-tert-butyl-1-(cyclohexanecarbonyl)-4-({[2-(difluoromethoxy)-4-methoxyphenyl]methyl} amino)-5-phenylpyrrolidine-2-carboxylic acid | MS (ESI+) m/z 573.2 (M + H)+. |
| Example II-19 | rac-(2R,3R,4R,5S)-3-tert-butyl-4-{[(5-chloro-2-methoxyphenyl) methyl]amino}-1-(cyclohexanecarbonyl)-5-(6-methoxypyridin-2-yl) pyrrolidine-2-carboxylic acid | LC/MS (ESI+) m/z 558.4 (M + H)+. |
| Example II-20 | rac-(2R,3R,4R,5R)-3-tert-butyl-5-[2-(dimethylamino)phenyl]-4-({[2-methoxy-5-(trifluoromethyl) phenyl]methyl}amino)-1-[oxane-2-carbonyl]pyrrolidine-2-carboxylic acid | LC/MS (ESI+) m/z 606.7 (M + H)+. |
| Example II-21 | rac-(2R,3R,4R,5R)-3-tert-butyl-5-[2-(dimethylamino)phenyl]-4-({[2-methoxy-5-(trifluoromethyl) phenyl]methyl}amino)-1-[oxane-3-carbonyl]pyrrolidine-2-carboxylic acid | LC/MS (ESI+) m/z 606.8 (M + H)+. |
| Example II-22 | rac-(2R,3R,4R,5R)-3-tert-butyl-5-[2-(dimethylamino)phenyl]-4-({[2-methoxy-4-(trifluoromethyl) phenyl]methyl}amino)-1-[oxane-3-carbonyl] pyrrolidine-2-carboxylic acid | LC/MS (ESI+) m/z 606.8 (M + H)+. |
| Example II-23 | rac-(2R,3R,4R,5R)-3-tert-butyl-4-{[(4-chloro-2-methoxyphenyl) methyl]amino}-5-[2-(dimethylamino)phenyl]-1-[oxane-3-carbonyl] pyrrolidine-2-carboxylic acid | LC/MS (ESI+) m/z 572.3 (M + H)+. |
| Example II-24 | rac-(2R,3R,4R,5R)-3-tert-butyl-5-{2-(dimethylamino)phenyl]-1-[2,2-dimethyloxane-4-carbonyl]-4-({[2-methoxy-5-(trifluoromethyl)phenyl] methyl]amino)pyrrolidine-2-carboxylic acid | LC/MS (ESI+) m/z 634.9 (M + H)+. |
| Example II-25 | rac-(2R,3R,4R,5R)-3-tert-butyl-4-{[(5-chloro-2-methoxyphenyl) methyl]amino}-5-[2-(dimethylamino)phenyl]-1-[2,2-dimethyloxane-4-carbonyl] pyrrolidine-2-carboxylic acid | LC/MS (ESI+) m/z 600.4 (M + H)+. |
| Example II-26 | rac-(2R,3R,4R,5R)-3-tert-butyl-4-{[(4-chloro-2-methoxyphenyl) methyl]amino}-5-[2-(dimethylamino)phenyl]-1-[2,2-dimethyloxane-4-carbonyl] pyrrolidine-2-carboxylic acid | LC/MS (ESI+) m/z 600.5 (M + H)+. |
| Example II-27 | rac-(2R,3R,4R,5R)-3-tert-butyl-1-[(3S)-1-(methoxycarbonyl) piperidine-3-carbonyl]-4-{[6-methyl-4-(trifluoromethyl) pyridin-2-yl]amino}-5-phenylpyrrolidine-2-carboxylic acid | 1HNMR (400 MHz, dimethyl sulfoxide-d6) δ ppm 7.42 (d, J = 7.2 Hz, 2H), 7.14 (p, J = 6.8 Hz, 3H), 6.49 (s, 1H), 6.24 (s, 1H), 5.83 (s, 1H), 5.33 (d, J = 8.2 Hz, 1H), 4.98 (d, J = 7.9 Hz, 1H), 4.39 (d, J = 6.0 Hz, 1H), 3.74 (s, 1H), 3.59 (s, 3H), 3.42-3.38 (m, 2H), 2.68 (dt, J = 23.2, 11.8 Hz, 2H), 2.33 (s, 3H), 1.85 (d, J = 13.3 Hz, 1H), 1.61 (dt, J = 13.1, 3.5 Hz, 1H), 1.56-1.41 (m, 1H), 1.31-1.15 (m, 1H), 1.01 (s, 9H); MS (ESI+) m/z 591 (M + H)+. |
| Example II-28 | rac-(2R,3R,4R,5R)-3-tert-butyl-4-{(5-chloro-2-methoxyphenyl) methyl]amino}-5-[2-(dimethylamino)pyridin-3-yl]-1-{[(propan-2-yl)oxy]carbonyl} pyrrolidine-2-carboxylic acid | 1HNMR (400 MHz, dimethyl sulfoxide-d6) δ ppm 8.20-8.12 (m, 2H), 7.12 (dd, J = 8.7, 2.8 Hz, 1H), 6.97-6.90 (m, 2H), 6.81 (d, J = 8.7 Hz, 1H), 5.31 (d, J = 6.4 Hz, 1H), 4.61 (pd, J = 6.2, 0.8 Hz, 1H), 4.34 (d, J = 1.6 Hz, 1H), 3.53 (d, J = 0.8 Hz, 3H), 3.48 (d, J = 2.7 Hz, 1H), 3.45 (d, J = 5.0 Hz, 1H), 3.25 (d, J = 14.2 Hz, 1H), 2.67 (d, J = 0.9 Hz, 6H), 2.35-2.30 (m, 1H), 1.01 (d, J = 6.3 Hz, 3H), 0.99 (s, 9H), 0.83 (d, J = 6.2 Hz, 3H); MS (APCI+) m/z 547 (M + H)+. |
| Example II-29 | rac-(2R,3R,4R,5R)-3-tert-butyl-4-{[(4-chloro-2-methoxyphenyl) methyl]amino}-5-[2-(dimethylamino)pyridin-3-yl]-1- | 1HNMR (400 MHz, dimethyl sulfoxide-d6) δ ppm 8.19-8.10 (m, 2H), 6.97-6.89 (m, 2H), 6.84 (d, J = 2.0 Hz, 1H), 6.79 (dd, J = 8.0, 2.0 Hz, 1H), 5.30 (d, J = 6.4 Hz, 1H), 4.61 (p, J = 6.2 Hz, 1H), 4.34 (d, J = 1.7 Hz, 1H), |

TABLE 2-continued

| | | |
|---|---|---|
| | {[(propan-2-yl)oxy]carbonyl} pyrrolidine-2-carboxylic acid | 3.54 (s, 3H), 3.49-3.43 (m, 2H), 3.25 (d, J = 14.0 Hz, 1H), 2.67 (s, 6H), 2.36-2.26 (m, 1H), 1.01 (d, J = 6.2 Hz, 3H), 0.98 (s, 9H), 0.83 (d, J = 6.2 Hz, 3H); MS (APCI+) m/z 547 (M + H)+. |
| Example II-30 | rac-(2R,3R,4R,5R)-3-tert-butyl-1-(cyclohexanecarbonyl)-4-{[(5-fluoro-2-methoxypyridin-3-yl)methyl]amino}-5-phenylpyrrolidine-2-carboxylic acid | MS (ESI+) m/z 512.3 (M + H)+. |
| Example II-31 | rac-(2R,3R,4R,5R)-3-tert-butyl-1-(cyclohexanecarbonyl)-5-phenyl-4-({[2-(trifluoromethyl)phenyl]methyl}amino) pyrrolidine-2-carboxylic acid | LC/MS (ESI+) m/z 531.7 (M + H)+. |
| Example II-32 | rac-(2R,3R,4R,5R)-3-tert-butyl-4-({[2-methoxy-5-(trifluoromethyl)phenyl]methyl}amino)-5-phenyl-1-(phenylacetyl)pyrrolidine-2-carboxylic acid | LC/MS (ESI+) m/z 569.5 (M + H)+. |
| Example II-33 | rac-(2S,3S,4S,5S)-3-tert-butyl-5-{2-(dimethylamino)pyridin-3-yl}-1-[(2R)-2-methoxy-2-phenylacetyl]-4-({[2-methoxy-5-(trifluoromethyl)phenyl]methyl]amino)pyrrolidine-2-carboxylic acid | $^1$HNMR (400 MHz, dimethyl sulfoxide-$d_6$) δ ppm 8.19 (s, 2H), 7.45 (dd, J = 8.7, 2.4 Hz, 1H), 7.36-7.22 (m, 6H), 6.99 (d, J = 8.6 Hz, 1H), 6.94 (s, 1H), 5.39 (s, 1H), 4.53 (s, 1H), 3.62 (s, 2H), 3.56 (s, 0H), 3.45 (d, J = 6.8 Hz, 1H), 3.35-3.26 (m, 1H), 2.71 (s, 6H), 2.33 (s, 1H), 1.25 (s, 3H), 0.84 (td, J = 6.3, 4.4 Hz, 3H), 0.80-0.66 (m, 9H); MS (ESI+) m/z 643 (M + H)+. |
| Example II-34 | rac-(2R,3R,4R,5R)-3-tert-butyl-4-({[2-methoxy-5-(trifluoromethyl)phenyl]methyl]amino)-1-[(2R,3R)-2-methyloxane-3-carbonyl]-5-phenylpyrrolidine-2-carboxylic acid | $^1$HNMR (400 MHz, dimethyl sulfoxide-$d_6$) δ ppm 7.56 (s, 2H), 7.49-7.43 (m, 1H), 7.29 (t, J = 7.4 Hz, 2H), 7.25-7.19 (m, 2H), 6.99 (d, J = 8.6 Hz, 1H), 5.16 (d, J = 7.1 Hz, 1H), 4.45 (s, 1H), 3.68-3.63 (m, 3H), 3.63-3.58 (m, 1H), 3.53 (d, J = 14.4 Hz, 1H), 3.46 (d, J = 7.0 Hz, 1H), 3.38 (d, J = 14.3 Hz, 1H), 3.32-3.22 (m, 1H), 3.18 (d, J = 6.3 Hz, 1H), 2.34 (s, 1H), 1.86 (t, J = 10.1 Hz, 1H), 1.71-1.58 (m, 1H), 1.53 (ddt, J = 13.2, 8.9, 4.5 Hz, 1H), 1.25 (s, 2H), 1.06 (t, J = 7.0 Hz, 2H), 0.97 (s, 9H), 0.86-0.80 (m, 1H); MS (APCI+) m/z 577 (M + H)+. |
| Example II-35 | rac-(2R,3R,4R,5R)-3-tert-butyl-4-({[2-methoxy-5-(trifluoromethyl)phenyl]methyl]amino)-1-[(2S,3S)-2-methyloxane-3-carbonyl]-5-phenylpyrrolidine-2-carboxylic acid | $^1$HNMR (400 MHz, dimethyl sulfoxide-$d_6$) δ ppm 7.54 (s, 2H), 7.46 (dd, J = 8.6, 2.3 Hz, 1H), 7.30 (t, J = 8.2, 6.5 Hz, 2H), 7.23 (dd, J = 9.0, 4.5 Hz, 2H), 6.99 (d, J = 8.6 Hz, 1H), 5.20 (d, J = 6.9 Hz, 1H), 4.43 (d, J = 2.5 Hz, 1H), 3.77 (s, 1H), 3.63 (s, 3H), 3.53 (d, J = 14.4 Hz, 1H), 3.48-3.40 (m, 1H), 3.36 (d, J = 14.2 Hz, 1H), 3.27 (s, 1H), 2.33 (s, 1H), 1.64 (tt, J = 8.9, 4.5 Hz, 2H), 1.59-1.43 (m, 1H), 1.25 (s, 1H), 1.04 (d, J = 6.6 Hz, 3H), 0.97 (s, 9H), 0.96-0.88 (m, 1H), 0.84 (tt, J = 7.4, 4.0 Hz, 1H); MS (ESI+) m/z 577 (M + H)+. |
| Example II-36 | rac-(2R,3R,4R,5R)-3-(tert-butyl)-4-((2-methoxy-5-(trifluoromethyl)benzyl) amino)-1-((1R,3R)-3-methoxycyclohexanecarbonyl)-5-phenylpyrrolidine-2-carboxylic acid | $^1$HNMR (400 MHz, dimethyl sulfoxide-$d_6$) δ ppm 7.52 (s, 2H), 7.46 (d, J = 8.7 Hz, 1H), 7.30 (t, J = 7.4 Hz, 2H), 7.27-7.19 (m, 2H), 7.00 (d, J = 8.6 Hz, 1H), 5.17 (dd, J = 18.9, 7.0 Hz, 1H), 4.46 (t, J = 2.6 Hz, 1H), 3.64 (s, 3H), 3.54 (dd, J = 14.4, 4.7 Hz, 1H), 3.50-3.44 (m, 1H), 3.45-3.32 (m, 2H), 3.17 (s, 3H), 2.63 (d, J = 2.0 Hz, 1H), 2.35 (s, 1H), 1.74 (s, 1H), 1.59 (s, 1H), 1.45-1.34 (m, 2H), 1.32-1.16 (m, 3H), 0.97 (d, J = 1.1 Hz, 9H), 0.89-0.80 (m, 1H); MS (APCI+) m/z 591 (M + H)+. |
| Example II-37 | rac-(2R,3R,4R,5R)-3-(tert-butyl)-4-((2-methoxy-4-(trifluoromethyl)benzyl) amino)-1-((1R,3R)-3-methoxycyclohexanecarbonyl)-5-phenylpyrrolidine-2-carboxylic acid | $^1$HNMR (400 MHz, dimethyl sulfoxide-$d_6$) δ ppm 7.53 (s, 2H), 7.31 (t, J = 7.5 Hz, 2H), 7.23 (dd, J = 8.4, 5.9 Hz, 1H), 7.16-7.08 (m, 2H), 7.06 (s, 1H), 5.18 (dd, J = 18.9, 6.9 Hz, 1H), 4.46 (t, J = 2.8 Hz, 1H), 3.64 (s, 3H), 3.59-3.48 (m, 2H), 3.38 (dd, J = 14.4, 5.0 Hz, 1H), 3.17 (s, 3H), 2.84 (s, 1H), 2.69-2.56 (m, 1H), 2.35 (s, 1H), 1.75 (d, J = 13.6 Hz, 1H), 1.60 (d, J = 12.6 Hz, 2H), 1.39 (d, J = 8.5 Hz, 2H), 1.33-1.18 (m, 3H), 0.98 (d, J = 1.1 Hz, 9H); MS (ESI+) m/z 581 (M + H)+. |
| Example II-38 | rac-(2R,3R,4R,5R)-3-(tert-butyl)-4-((4-chloro-2-methoxybenzyl)amino)-1-((1R,3R)-3-methoxycyclohexanecarbonyl)-5-phenylpyrrolidine-2-carboxylic acid | $^1$HNMR (400 MHz, dimethyl sulfoxide-$d_6$) δ ppm 7.49 (s, 2H), 7.30 (t, J = 7.4 Hz, 2H), 7.26-7.19 (m, 1H), 6.90 (dd, J = 8.0, 2.2 Hz, 1H), 6.84 (t, J = 1.5 Hz, 1H), 6.80 (ddd, J = 8.0, 2.0, 1.2 Hz, 1H), 5.15 (dd, J = 18.7, 6.9 Hz, 1H), 4.45 (t, J = 2.5 Hz, 1H), 3.56 (d, J = 1.2 Hz, 3H), 3.50-3.44 (m, 2H), 3.44-3.39 (m, 1H), 3.37 (d, J = 7.0 Hz, 1H), 3.31 (dd, J = 14.0, 7.2 Hz, 1H), 3.20-3.14 (m, 3H), 2.32 (s, 1H), 1.76 (d, J = 19.8 Hz, 1H), 1.66-1.54 (m, 2H), 1.39 (d, J = 9.1 Hz, 2H), 1.07 (dt, J = 7.7, 7.0 Hz, 3H), 0.97 (d, J = 0.8 Hz, 9H); MS (APCI+) m/z 557 (M + H)+. |

TABLE 2-continued

| Example II-39 | rac-(2R,3R,4R,5R)-3-tert-butyl-4-{[(4-fluoro-2-methoxyphenyl)methyl]amino}-5-phenyl-1-{[(propan-2-yl)oxy]carbonyl}pyrrolidine-2-carboxylic acid | MS (APCI) m/z 487.0 (M + H)+. |
|---|---|---|
| Example II-40 | rac-(2R,3R,4R,5R)-3-tert-butyl-4-{[(2-methoxy-5-methylphenyl)methyl]amino}-5-phenyl-1-{[(propan-2-yl)oxy]carbonyl}pyrrolidine-2-carboxylic acid | MS (APCI) m/z 483.0 (M + H)+. |
| Example II-41 | rac-(2R,3R,4R,5R)-3-tert-butyl-4-({[2-methoxy-4-(trifluoromethoxy)phenyl]methyl}amino)-5-phenyl-1-{[(propan-2-yl)oxy]carbonyl}pyrrolidine-2-carboxylic acid | MS (APCI) m/z 553.0 (M + H)+. |
| Example II-42 | rac-(2R,3R,4R,5R)-3-tert-butyl-4-{[(5-fluoro-2-methoxyphenyl)methyl]amino}-5-phenyl-1-{[(propan-2-yl)oxy]carbonyl}pyrrolidine-2-carboxylic acid | MS (APCI) m/z 487.1 (M + H)+. |
| Example II-43 | rac-(2R,3R,4R,5R)-3-tert-butyl-4-{[(5-tert-butyl-2-methoxyphenyl)methyl]amino}-5-phenyl-1-{[(propan-2-yl)oxy]carbonyl}pyrrolidine-2-carboxylic acid | MS (APCI) m/z 525.1 (M + H)+. |
| Example II-44 | rac-(2R,3R,4R,5R)-3-tert-butyl-4-({[2-methoxy-5-(propan-2-yl)phenyl]methyl}amino)-5-phenyl-1-{[(propan-2-yl)oxy]carbonyl}pyrrolidine-2-carboxylic acid | MS (APCI) m/z 511.1 (M + H)+. |
| Example II-45 | rac-(2R,3R,4R,5R)-3-tert-butyl-4-{[(4-chloro-2-methoxyphenyl)methyl]amino}-5-phenyl-1-{[(propan-2-yl)oxy]carbonyl}pyrrolidine-2-carboxylic acid | MS (APCI) m/z 503.0 (M + H)+. |
| Example II-46 | rac-(2R,3R,4R,5R)-3-tert-butyl-4-{[(2-methoxyphenyl)methyl]amino}-5-phenyl-1-{[(propan-2-yl)oxy]carbonyl}pyrrolidine-2-carboxylic acid | MS (APCI) m/z 469.1 (M + H)+. |
| Example II-47 | rac-(2S,3S,4S,5S)-3-tert-butyl-4-{[(4-chloro-2-methoxyphenyl)methyl]amino}-5-[2-(dimethylamino)pyridin-3-yl]-1-[(2R)-2-methoxy-2-phenylacetyl]pyrrolidine-2-carboxylic acid | $^1$HNMR (400 MHz, dimethyl sulfoxide-d$_6$) δ ppm 8.19 (s, 2H), 7.39-7.22 (m, 6H), 6.92 (d, J = 8.0 Hz, 1H), 6.84 (d, J = 1.9 Hz, 1H), 6.79 (dd, J = 8.0, 2.0 Hz, 1H), 5.39 (s, 1H), 4.59 (d, J = 35.1 Hz, 1H), 3.54 (s, 3H), 3.45 (dt, J = 6.9, 3.5 Hz, 1H), 3.25 (d, J = 13.9 Hz, 1H), 2.73 (s, 6H), 2.32 (s, 1H), 1.26 (d, J = 2.5 Hz, 2H), 0.85 (ddt, J = 7.4, 5.1, 2.8 Hz, 3H), 0.75 (d, J = 8.4 Hz, 9H); MS (APCI+) m/z 609 (M + H)+. |
| Example II-48 | rac-(2S,3S,4S,5S)-3-tert-butyl-5-{2-(dimethylamino)pyridin-3-yl]-1-[(2R)-2-methoxy-2-phenylacetyl]-4-({[2-methoxy-4-(trifluoromethyl)phenyl]methyl}amino)pyrrolidine-2-carboxylic acid | $^1$HNMR (400 MHz, dimethyl sulfoxide-d$_6$) δ ppm 8.19 (s, 2H), 7.39-7.25 (m, 6H), 7.20-7.06 (m, 3H), 7.00 (s, 1H), 5.40 (s, 1H), 4.57 (s, 1H), 3.66 (s, 3H), 3.64-3.57 (m, 2H), 3.38-3.28 (m, 1H), 2.79 (s, 6H), 2.50 (s, 3H), 2.35 (s, 1H), 0.75 (s, 9H); MS (APCI+) m/z 643 (M + H)+. |
| Example II-49 | rac-(2R,3R,4R,5R)-3-tert-butyl-4-({[2-methoxy-4-(trifluoromethyl)phenyl]methyl}amino)-1-((2S)-oxane-2-carbonyl)-5-phenylpyrrolidine-2-carboxylic acid | MS (ESI+) m/z 563.2 (M + H)+. |
| Example II-50 | rac-(2S,3S,4S,5S)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid | MS (ESI+) m/z 591.2 (M + H)+. |
| Example II-51 | rac-(2R,3R,4R,5R)-3-tert-butyl-1-(cyclohexanecarbonyl)-5-[2-(dimethylamino)pyridin-3-yl]-4-({[2-methoxy-4-(trifluoromethyl)phenyl]methyl}amino)pyrrolidine-2-carboxylic acid | MS (ESI+) m/z 605 (M + H)+. |

TABLE 2-continued

| Example | Name | MS Data |
|---|---|---|
| Example II-52 | rac-(2R,3R,4R,5R)-3-tert-butyl-1-(cyclohexanecarbonyl)-5-[2-(dimethylamino)pyridin-3-yl]-4-({[2-methoxy-5-(trifluoromethyl)pyridin-3-yl]methyl}amino)pyrrolidine-2-carboxylic acid | MS (ESI+) m/z 606 (M + H)+. |
| Example II-53 | rac-(2S,3S,4S,5R)-3-tert-butyl-1-(cyclohexanecarbonyl)-4-{[6-methyl-4-(trifluoromethyl)pyridin-2-yl]amino}-5-(pyridin-2-yl)pyrrolidine-2-carboxylic acid | LC/MS (ESI+) m/z 533.5 (M + H)+. |
| Example II-54 | (2S*,3S*,4S*,5S*)-3-tert-butyl-4-{[(4-chloro-2-methoxyphenyl)methyl]amino}-1-{(2R)-2-methoxy-2-phenylacetyl]-5-phenylpyrrolidine-2-carboxylic acid | LC/MS (ESI+) m/z 565.5 (M + H)+. |
| Example II-55 | rac-(2R,3R,4R,5R)-3-tert-butyl-4-{[6-methyl-4-(trifluoromethyl)pyridin-2-yl]amino}-5-phenyl-1-(phenylacetyl)pyrrolidine-2-carboxylic acid | LC/MS (ESI+) m/z 540.5 (M + H)+. |
| Example II-56 | rac-(2R,3R,4R,5R)-3-tert-butyl-5-[2-(dimethylamino)phenyl]-4-({[2-methoxy-5-(trifluoromethyl)phenyl]methyl}amino)-1-{[(propan-2-yl)oxy]carbonyl}pyrrolidine-2-carboxylic acid | LC/MS (ESI+) m/z 580.6 (M + H)+. |
| Example II-57 | rac-(2R,3R,4R,5R)-3-tert-butyl-5-[2-(dimethylamino)phenyl]-4-({[2-methoxy-4-(trifluoromethyl)phenyl]methyl}amino)-1-{[(propan-2-yl)oxy]carbonyl}pyrrolidine-2-carboxylic acid | LC/MS (ESI+) m/z 580.6 (M + H)+. |
| Example II-58 | rac-(2R,3R,4R,5R)-3-tert-butyl-4-({[2-methoxy-4-(trifluoromethyl)phenyl]methyl}amino)-1-[(2S*)-2-phenoxypropanoyl]-5-phenylpyrrolidine-2-carboxylic acid | LC/MS (ESI+) m/z 599.5 (M + H)+. |
| Example II-59 | rac-(2S,3S,4S,5S)-3-tert-butyl-4-({[2-methoxy-5-(trifluoromethyl)phenyl]methyl}amino)-1-(oxolane-2-carbonyl)-5-phenylpyrrolidine-2-carboxylic acid | LC/MS (ESI+) m/z 549.8 (M + H)+. |
| Example II-60 | rac-(2S,3S,4S,5S)-3-tert-butyl-4-({[2-methoxy-4-(trifluoromethyl)phenyl]methyl}amino)-1-(oxolane-2-carbonyl)-5-phenylpyrrolidine-2-carboxylic acid | LC/MS (ESI+) m/z 549.8 (M + H)+. |
| Example II-61 | rac-(2S,3S,4S,5S)-3-tert-butyl-4-{[(5-chloro-2-methoxyphenyl)methyl]amino}-1-(oxolane-2-carbonyl)-5-phenylpyrrolidine-2-carboxylic acid | LC/MS (ESI+) m/z 515.6 (M + H)+. |
| Example II-62 | (2S,3S,4S,5S)-3-tert-butyl-5-[2-(dimethylamino)phenyl]-1-[(2R)-2-methoxy-2-phenylacetyl]-4-({[2-methoxy-5-(trifluoromethyl)phenyl]methyl}amino)pyrrolidine-2-carboxylic acid | LC/MS (ESI+) m/z 642.9 (M + H)+. |
| Example II-63 | (2S,3S,4S,5S)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid | LC/MS (ESI+) m/z 608.4 (M + H)+. |

TABLE 2-continued

| Example II-64 | (2R,3R,4R,5R)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid | LC/MS (ESI+) m/z 599.5 (M + H)+. |
|---|---|---|
| Example II-65 | (2S,3S,4S,5S)-3-tert-butyl-1-[(2S)-2-methoxy-2-phenylacetyl]-4-({[2-methoxy-4-(trifluoromethyl)phenyl]methyl}amino)-5-phenylpyrrolidine-2-carboxylic acid | LC/MS (ESI+) m/z 599.5 (M + H)+. |
| Example II-66 | rac-(2R,3R,4R,5R)-3-tert-butyl-4-({[2-methoxy-5-(trifluoromethyl)phenyl]methyl}amino)-1-[(2R)-2-phenoxypropanoyl]-5-phenylpyrrolidine-2-carboxylic acid | LC/MS (ESI+) m/z 599.6 (M + H)+. |
| Example II-67 | rac-(2R,3R,4R,5R)-3-tert-butyl-4-({[2-methoxy-4-(trifluoromethyl)phenyl]methyl}amino)-1-[(2R*)-2-phenoxypropanoyl]-5-phenylpyrrolidine-2-carboxylic acid | LC/MS (ESI+) m/z 599.5 (M + H)+. |
| Example II-68 | rac-(2R,3R,4R,5R)-3-tert-butyl-1-(4,4-difluorocyclohexane-1-carbonyl)-4-({[2-methoxy-5-(trifluoromethyl)phenyl]methyl}amino)-5-phenylpyrrolidine-2-carboxylic acid | LC/MS (ESI+) m/z 597.8 (M + H)+. |
| Example II-69 | rac-(2R,3R,4R,5R)-3-tert-butyl-1-(4,4-difluorocyclohexane-1-carbonyl)-4-({[2-methoxy-4-(trifluoromethyl)phenyl]methyl}amino)-5-phenylpyrrolidine-2-carboxylic acid | LC/MS (ESI+) m/z 597.5 (M + H)+. |
| Example II-70 | rac-(2R,3R,4R,5R)-3-tert-butyl-4-({[2-methoxy-5-(trifluoromethyl)phenyl]methyl}amino)-5-phenyl-1-(spiro[2.5]octane-6-carbonyl)pyrrolidine-2-carboxylic acid | LC/MS (ESI+) m/z 587.5 (M + H)+. |
| Example II-71 | rac-(2R,3R,4R,5R)-3-tert-butyl-4-{[(5-cyano-2-methoxyphenyl)methyl]amino}-1-(cyclohexanecarbonyl)-5-phenylpyrrolidine-2-carboxylic acid | LC/MS (ESI+) m/z 5 1 8.8 (M + H)+. |
| Example II-72 | rac-(2R,3R,4R,5R)-3-tert-butyl-1-(cyclohexanecarbonyl)-4-({[2-methyl-5-(trifluoromethyl)phenyl]methyl}amino)-5-phenylpyrrolidine-2-carboxylic acid | LC/MS (ESI+) m/z 545.8 (M + H)+. |
| Example II-73 | rac-(2R,3R,4R,5R)-3-tert-butyl-1-(cyclohexanecarbonyl)-4-({[2-methoxy-5-(propan-2-yl)phenyl]methyl}amino)-5-phenylpyrrolidine-2-carboxylic acid | LC/MS (ESI+) m/z 535.9 (M + H)+. |
| Example II-74 | rac-(2R,3R,4R,5R)-3-tert-butyl-4-{[(4-cyano-2-methoxyphenyl)methyl]amino}-1-(cyclohexanecarbonyl)-5-phenylpyrrolidine-2-carboxylic acid | LC/MS (ESI+) m/z 518.8 (M + H)+. |
| Example II-75 | rac-(2R,3R,4R,5R)-3-tert-butyl-4-({[5-chloro-2-(trifluoromethoxy)phenyl]methyl}amino)-1-(cyclohexanecarbonyl)-5-phenylpyrrolidine-2-carboxylic acid | LC/MS (ESI+) m/z 581.3 (M + H)+. |
| Example II-76 | rac-(2R,3R,4R,5R)-3-tert-butyl-1-(cyclohexanecarbonyl)-5-phenyl-4-({[2- | LC/MS (ESI+) m/z 547.8 (M + H)+. |

TABLE 2-continued

| | | |
|---|---|---|
| Example II-77 | rac-(2R,3R,4R,5R)-3-tert-butyl-1-(cyclohexanecarbonyl)-4-({[2-methoxy-6-(trifluoromethyl)pyridin-3-yl]methyl}amino)-5-phenylpyrrolidine-2-carboxylic acid (trifluoromethoxy)phenyl]methyl}amino)pyrrolidine-2-carboxylic acid | LC/MS (ESI+) m/z 562.5 (M + H)+. |
| Example II-79 | rac-(2R,3R,4R,5R)-4-{[(5-chloro-2-methoxyphenyl)methyl]amino}-1-(cyclohexanecarbonyl)-3-(2-methoxypropan-2-yl)-5-phenylpyrrolidine-2-carboxylic acid | $^1$HNMR (400 MHz, dimethyl sulfoxide-d$_6$) δ ppm 7.57 (s, 2H), 7.35 (t, J = 7.4 Hz, 2H), 7.29 (d, J = 7.2 Hz, 1H), 7.20 (dd, J = 8.7, 2.7 Hz, 1H), 7.02 (d, J = 2.7 Hz, 1H), 6.88 (d, J = 8.7 Hz, 1H), 5.28 (d, J = 7.3 Hz, 1H), 4.50 (d, J = 3.6 Hz, 1H), 3.65 (d, J = 8.3 Hz, 1H), 3.61 (s, 3H), 3.46 (d, J = 13.9 Hz, 1H), 2.70 (d, J = 4.0 Hz, 1H), 2.27 (d, J = 18.2 Hz, 1H), 1.65 (d, J = 9.9 Hz, 2H), 1.49 (bs, 2H), 1.20 (s, 4H), 1.19 (s, 4H), 1.08 (m, 3H), 0.81 (bs, 1H); MS (ESI+) m/z 543 (M + H)+. |
| Example II-80 | rac-(2R,3R,4R,5R)-3-tert-butyl-4-({[2-methoxy-4-(trifluoromethyl)phenyl]methyl}amino)-5-phenyl-1-[(2S*)-2-phenylpropanoyl]pyrrolidine-2-carboxylic acid | MS (ESI+) m/z 583.2 (M + H)+. |
| Example II-81 | (2S,3S,4S,5S)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid | MS (ESI+) m/z 563.2 (M + H)+. |
| Example II-82 | (2R,3R,4R,5R)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid | MS (ESI+) m/z 563.2 (M + H)+. |
| Example II-83 | (2S,3S,4S,5S)-3-tert-butyl-1-[(2R)-2-methoxy-2-phenylacetyl]-4-({[2-methoxy-5-(trifluoromethyl)pyridin-3-yl]methyl}amino)-5-phenylpyrrolidine-2-carboxylic acid | MS (ESI+) m/z 600.2 (M + H)+. |
| Example II-84 | (2S,3S,4S,5S)-3-tert-butyl-1-[(2R)-2-methoxy-2-phenylacetyl]-5-(2-methoxypyridin-3-yl)-4-({[2-methoxy-4-(trifluoromethyl)phenyl]methyl}amino)pyrrolidine-2-carboxylic acid | MS (ESI+) m/z 630.2 (M + H)+. |
| Example II-85 | rac-(2R,3R,4R,5R)-3-tert-butyl-1-(1,4-dioxane-2-carbonyl)-4-({[2-methoxy-5-(trifluoromethyl)phenyl]methyl}amino)-5-phenylpyrrolidine-2-carboxylic acid | LC/MS (ESI+) m/z 565.5 (M + H)+. |
| Example II-86 | rac-(2R,3R,4R,5R)-3-tert-butyl-4-{[(5-chloro-2-methoxyphenyl)methyl]amino}-1-(1,4-dioxane-2-carbonyl)-5-phenylpyrrolidine-2-carboxylic acid | LC/MS (ESI+) m/z 531.4 (M + H)+. |
| Example II-87 | (2S,3S,4S,5S)-3-tert-butyl-5-[2-(dimethylamino)pyridin-3-yl]-1-[(2R)-2-methoxy-2-phenylacetyl]-4-({[2-methoxy-4-(trifluoromethyl)phenyl]methyl}amino)pyrrolidine-2-carboxylic acid | MS (ESI+) m/z 643.2 (M + H)+. |
| Example II-88 | rac-(2R,3R,4R,5R)-1-(cyclohexanecarbonyl)-3-(2-methoxypropan-2-yl)-4-({[2-methoxy-4-(trifluoromethyl)phenyl]methyl}amino)-5-phenylpyrrolidine-2-carboxylic acid | $^1$HNMR (400 MHz, dimethyl sulfoxide-d$_6$) δ ppm 7.57 (s, 2H), 7.34 (t, J = 7.4 Hz, 2H), 7.28 (d, J = 7.2 Hz, 1H), 7.20 (d, J = 7.8 Hz, 1H), 7.14 (d, J = 8.1 Hz, 1H), 7.11 (s, 1H), 5.28 (d, J = 7.2 Hz, 1H), 4.51 (d, J = 3.6 Hz, 1H), 3.67 (d, J = 15.0 Hz, 5H), 3.52 (d, J = 14.1 Hz, 1H), 3.14 (s, 3H), 2.69 (s, 1H), 2.27 (d, J = 20.4 Hz, 1H), 1.65 (d, J = 10.6 Hz, 2H), 1.49 (bs, 2H), 1.31-1.22 (m, 1H), 1.20 (s, 3H), 1.18 (s, 3H), 1.16 (bs, 1H), 1.08 (m, 3H), 0.79 (bs, 1H); MS (ESI+) m/z 577 (M + H)+. |
| Example II-89 | rac-(2R,3R,4R,5R)-1-(cyclohexanecarbonyl)-3-(2-methoxypropan-2-yl)-4-{[2-methoxy-5-(trifluoromethyl) | $^1$HNMR (400 MHz, dimethyl sulfoxide-d$_6$) δ ppm 7.54 (s, 1H), 7.49 (d, J = 7.5 Hz, 2H), 7.15 (dd, J = 8.2, 6.6 Hz, 2H), 7.08 (t, J = 7.3 Hz, 1H), 7.04 (d, J = 2.1 Hz, 1H), 5.38 (d, J = 7.4 Hz, 1H), 4.80 (d, J = 9.3 Hz, 1H), 4.52 (d, J = |

TABLE 2-continued

| | | |
|---|---|---|
| | pyridin-3-yl]amino}-5-phenylpyrrolidine-2-carboxylic acid | 4.1 Hz, 2H), 3.73 (s, 3H), 3.17 (s, 3H), 2.57 (t, J = 3.9 Hz, 1H), 2.19 (s, 1H), 1.67 (d, J = 13.7 Hz, 2H), 1.46 (s, 2H), 1.25 (s, 3H), 1.23 (s, 3H), 1.18 (d, J = 14.0 Hz, 2H), 1.07 (d, J = 10.6 Hz, 2H), 0.69 (bs, 1H); MS (ESI+) m/z 564 (M + H)⁺. |
| Example II-90 | rac-(2R,3R,4R,5R)-3-tert-butyl-4-{[(5-tert-butyl-2-methoxyphenyl)methyl]amino}-1-[(cyclobutyloxy)carbonyl]-5-phenylpyrrolidine-2-carboxylic acid | MS (ESI+) m/z 537 (M + H)⁺. |
| Example II-91 | (2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid | MS (ESI+) m/z 558.2 (M + H)⁺. |
| Example II-92 | (2S,3S,4S,5S)-3-tert-butyl-5-(2-methoxypyridin-3-yl)-4-({[2-methoxy-4-(trifluoromethyl)phenyl]methyl}amino)-1-[(2S)-oxane-2-carbonyl]pyrrolidine-2-carboxylic acid | MS (ESI+) m/z 594.2 (M + H)⁺. |
| Example II-93 | (2S,3S,4S,5S)-3-tert-butyl-1-(cyclohexanecarbonyl)-4-({[2-methoxy-5-(trifluoromethyl)phenyl]methyl}amino)-5-(2-methylpyridin-3-yl)pyrrolidine-2-carboxylic acid | ¹HNMR (400 MHz, dimethyl sulfoxide-d₆) δ ppm 8.27 (d, J = 4.6 Hz, 1H), 8.23-8.10 (m, 1H), 7.45 (dd, J = 8.7, 2.4 Hz, 1H), 7.18 (d, J = 2.3 Hz, 1H), 7.13-7.02 (m, 1H), 6.99 (d, J = 8.6 Hz, 1H), 5.19 (d, J = 7.0 Hz, 1H), 4.48 (s, 1H), 3.64 (s, 3H), 3.52 (d, J = 14.6 Hz, 1H), 3.47 (d, J = 7.2 Hz, 1H), 3.29 (d, J = 14.6 Hz, 1H), 3.17 (d, J = 6.2 Hz, 1H), 2.37 (s, 3H), 1.70-1.61 (m, 2H), 1.58-1.46 (m, 2H), 1.31-1.19 (m, 3H), 1.13-1.02 (m, 2H), 0.97 (s, 9H), 0.89-0.77 (m, 2H); MS (ESI+) m/z 576 (M + H)⁺. |
| Example II-94 | (2S,3S,4S,5S)-3-tert-butyl-1-(cyclohexanecarbonyl)-4-({[2-methoxy-4-(trifluoromethyl)phenyl]methyl}amino)-5-(2-methylpyridin-3-yl)pyrrolidine-2-carboxylic acid | ¹HNMR (400 MHz, dimethyl sulfoxide-d₆) δ ppm 8.35-8.26 (m, 1H), 8.20-8.00 (m, 1H), 7.16-7.08 (m, 3H), 7.05 (s, 1H), 5.20 (d, J = 6.8 Hz, 1H), 4.54 (s, 1H), 3.61 (s, 3H), 3.57-3.49 (m, 2H), 3.33 (d, J = 14.2 Hz, 1H), 2.37 (s, 3H), 1.72-1.60 (m, 2H), 1.59-1.45 (m, 2H), 1.33-1.20 (m, 3H), 1.14-1.05 (m, 2H), 0.99 (s, 9H), 0.89-0.78 (m, 3H); MS (ESI+) m/z 576 (M + H)⁺. |
| Example II-95 | (2S,3S,4S,5S)-3-tert-butyl-4-{[(5-chloro-2-methoxyphenyl)methyl]amino}-1-(cyclohexanecarbonyl)-5-(2-methylpyridin-3-yl)pyrrolidine-2-carboxylic acid | ¹HNMR (400 MHz, dimethyl sulfoxide-d₆) δ ppm 8.28 (s, 1H), 8.15 (s, 1H), 7.11 (dd, J = 8.7, 2.7 Hz, 1H), 7.08 (s, 1H), 6.86 (d, J = 2.3 Hz, 1H), 6.82 (d, J = 8.7 Hz, 1H), 5.18 (d, J = 7.0 Hz, 1H), 4.48 (s, 1H), 3.55 (s, 3H), 3.49-3.41 (m, 2H), 3.24 (d, J = 14.4 Hz, 1H), 3.17 (d, J = 6.3 Hz, 1H), 2.39 (s, 3H), 1.71-1.59 (m, 3H), 1.57-1.47 (m, 2H), 1.29-1.19 (m, 2H), 1.13-1.02 (m, 2H), 0.97 (s, 9H), 0.91-0.78 (m, 2H); MS (ESI+) m/z 542 (M + H)⁺. |
| Example II-96 | (2S,3S,4S,5S)-3-tert-butyl-4-{[(4-chloro-2-methoxyphenyl)methyl]amino}-1-(cyclohexanecarbonyl)-5-(2-methylpyridin-3-yl)pyrrolidine-2-carboxylic acid | ¹HNMR (400 MHz, dimethyl sulfoxide-d₆) δ ppm 8.27 (s, 1H), 8.22-8.08 (m, 1H), 7.11-7.02 (m, 1H), 6.87-6.82 (m, 2H), 6.78 (dd, J = 8.0, 1.9 Hz, 1H), 5.18 (d, J = 7.0 Hz, 1H), 4.52-4.43 (m, 1H), 3.57 (s, 3H), 3.48 (d, J = 7.0 Hz, 1H), 3.43 (d, J = 14.2 Hz, 1H), 3.23 (d, J = 14.1 Hz, 1H), 2.38 (s, 3H), 1.73-1.60 (m, 2H), 1.60-1.46 (m, 2H), 1.31-1.21 (m, 3H), 1.15-1.05 (m, 3H), 0.98 (s, 9H), 0.89-0.80 (m, 2H); MS (ESI+) m/z 542 (M + H)⁺. |
| Example II-97 | (2S,3S,4S,5S)-3-tert-butyl-4-{[(5-chloro-2-methoxyphenyl)methyl]amino}-1-(cyclohexanecarbonyl)-5-phenylpyrrolidine-2-carboxylic acid | MS (ESI+) m/z 527 (M + H)⁺. |
| Example II-98 | (2S,3S,4S,5S)-3-tert-butyl-5-(2-methoxypyridin-3-yl)-4-({[2-methoxy-4-(trifluoromethyl)phenyl]methyl}amino)-1-[(2R*)-oxane-2-carbonyl]pyrrolidine-2-carboxylic acid | MS (ESI+) m/z 594.2 (M + H)⁺. |
| Example II-99 | (2S,3S,4S,5S)-3-tert-butyl-4-{[(4-chloro-2-methoxyphenyl)methyl]amino}-1-(cyclohexanecarbonyl)-5-phenylpyrrolidine-2-carboxylic acid | MS (ESI+) m/z 527 (M + H)⁺. |

TABLE 2-continued

| Example | Compound | MS |
|---|---|---|
| Example II-100 | (2S,3S,4S,5S)-4-{[(1-benzofuran-3-yl)methyl]amino}-3-tert-butyl-1-(cyclohexanecarbonyl)-5-phenylpyrrolidine-2-carboxylic acid | MS (ESI+) m/z 503 (M + H)+. |
| Example II-101 | (2S,3S,4S,5S)-3-tert-butyl-4-{[(4-tert-butyl-2-methoxyphenyl)methyl]amino}-1-(cyclohexanecarbonyl)-5-(2-methoxypyridin-3-yl)pyrrolidine-2-carboxylic acid | MS (ESI+) m/z 580.3 (M + H)+. |
| Example II-102 | (2S,3S,4S,5S)-3-tert-butyl-4-{[(4-tert-butyl-2-methoxyphenyl)methyl]amino}-1-(cyclohexanecarbonyl)-5-[2-(dimethylamino)pyridin-3-yl]pyrrolidine-2-carboxylic acid | MS (ESI+) m/z 593.3 (M + H)+. |
| Example II-103 | (2S,3S,4S,5S)-3-tert-butyl-4-{[(4-tert-butyl-2-methoxyphenyl)methyl]amino}-1-(cyclohexanecarbonyl)-5-phenylpyrrolidine-2-carboxylic acid | MS (ESI+) m/z 549 (M + H)+. |
| Example II-104 | (2S,3S,4S,5S)-3-tert-butyl-4-{[(4-chloro-2-fluoro-5-methoxyphenyl)methyl]amino}-1-(cyclohexanecarbonyl)-5-phenylpyrrolidine-2-carboxylic acid | MS (APCI+) m/z 545.0 (M + H)+. |
| Example II-105 | (2S,3S,4S,5S)-3-tert-butyl-1-(cyclohexanecarbonyl)-4-{[(2,5-dichlorophenyl)methyl]amino}-5-phenylpyrrolidine-2-carboxylic acid | MS (APCI+) m/z 530.9 (M + H)+. |
| Example II-106 | (2S,3S,4S,5S)-3-tert-butyl-1-(cyclohexanecarbonyl)-4-{[(2-fluoro-5-methoxyphenyl)methyl]amino}-5-phenylpyrrolidine-2-carboxylic acid | MS (APCI+) m/z 511.1 (M + H)+. |
| Example II-107 | (2S,3S,4S,5S)-3-tert-butyl-4-({[5-chloro-2-(difluoromethoxy)phenyl]methyl}amino)-1-(cyclohexanecarbonyl)-5-phenylpyrrolidine-2-carboxylic acid | MS (APCI+) m/z 563.0 (M + H)+. |
| Example II-108 | (2S,3S,4S,5S)-4-({[3,5-bis(trifluoromethyl)phenyl]methyl}amino)-3-tert-butyl-1-(cyclohexanecarbonyl)-5-phenylpyrrolidine-2-carboxylic acid | MS (APCI+) m/z 599.0 (M + H)+. |
| Example II-109 | (2S,3S,4S,5S)-3-tert-butyl-1-(cyclohexanecarbonyl)-4-({[4-methoxy-2-(trifluoromethyl)phenyl]methyl}amino)-5-phenylpyrrolidine-2-carboxylic acid | MS (APCI+) m/z 561.0 (M + H)+. |
| Example II-110 | (2S,3S,4S,5S)-4-{[(2-bromo-5-methoxyphenyl)methyl]amino}-3-tert-butyl-1-(cyclohexanecarbonyl)-5-phenylpyrrolidine-2-carboxylic acid | MS (APCI+) m/z 573.0 (M + H)+. |
| Example II-111 | (2S,3S,4S,5S)-3-tert-butyl-1-(cyclohexanecarbonyl)-4-{[(3,5-dichlorophenyl)methyl]amino}-5-phenylpyrrolidine-2-carboxylic acid | MS (APCI+) m/z 531.0 (M + H)+. |
| Example II-112 | (2S,3S,4S,5S)-3-tert-butyl-1-(cyclohexanecarbonyl)-4-{[(4-fluoro-3-methoxyphenyl)methyl]amino}-5-phenylpyrrolidine-2-carboxylic acid | MS (APCI+) m/z 511.1 (M + H)+. |
| Example II-113 | (2S,3S,4S,5S)-3-tert-butyl-1-(cyclohexanecarbonyl)-4-{[(2,4-dichlorophenyl)methyl]amino}-5-phenylpyrrolidine-2-carboxylic acid | MS (APCI+) m/z 531.0 (M + H)+. |

TABLE 2-continued

| | | |
|---|---|---|
| Example II-114 | (2S,3S,4S,5S)-4-{[(2-bromo-4-fluoro-5-methoxyphenyl)methyl]amino}-3-tert-butyl-1-(cyclohexanecarbonyl)-5-phenylpyrrolidine-2-carboxylic acid | MS (APCI+) m/z 591.0 (M + H)+. |
| Example II-115 | (2S,3S,4S,5S)-3-tert-butyl-1-(cyclohexanecarbonyl)-4-{[(3,5-difluorophenyl)methyl]amino}-5-phenylpyrrolidine-2-carboxylic acid | MS (APCI+) m/z 499.0 (M + H)+. |
| Example II-116 | (2S,3S,4S,5S)-3-tert-butyl-1-(cyclohexanecarbonyl)-4-{[(6-methoxy-2H-1,3-benzodioxol-5-yl)methyl]amino}-5-phenylpyrrolidine-2-carboxylic acid | MS (APCI+) m/z 537.1 (M + H)+. |
| Example II-117 | (2S,3S,4S,5S)-3-tert-butyl-1-(cyclohexanecarbonyl)-4-{[(2,5-dimethylphenyl)methyl]amino}-5-phenylpyrrolidine-2-carboxylic acid | MS (APCI+) m/z 491.1 (M + H)+. |
| Example II-118 | (2S,3S,4S,5S)-3-tert-butyl-1-(cyclohexanecarbonyl)-4-{[(4-fluoro-2-methoxyphenyl)methyl]amino}-5-phenylpyrrolidine-2-carboxylic acid | MS (APCI+) m/z 511.1 (M + H)+. |
| Example II-119 | (2S,3S,4S,5S)-3-tert-butyl-1-(cyclohexanecarbonyl)-4-{[(4-ethoxy-2-methylphenyl)methyl]amino}-5-phenylpyrrolidine-2-carboxylic acid | MS (APCI+) m/z 521.1 (M + H)+. |
| Example II-120 | (2S,3S,4S,5S)-3-tert-butyl-1-[(2R)-2-methoxypropanoyl]-4-({[2-methoxy-5-(trifluoromethyl)phenyl]methyl}amino)-5-phenylpyrrolidine-2-carboxylic acid | LC/MS (ESI+) m/z 537.8 (M + H)+. |
| Example II-121 | (2S,3S,4S,5S)-3-tert-butyl-4-{[(3-tert-butylphenyl)methyl]amino}-1-(cyclohexanecarbonyl)-5-phenylpyrrolidine-2-carboxylic acid | MS (APCI+) m/z 519.1 (M + H)+. |
| Example II-122 | (2S,3S,4S,5S)-3-tert-butyl-1-(cyclohexanecarbonyl)-5-phenyl-4-({[3-(trifluoromethyl)phenyl]methyl}amino)pyrrolidine-2-carboxylic acid | MS (APCI+) m/z 531.1 (M + H)+. |
| Example II-123 | (2S,3S,4S,5S)-3-tert-butyl-4-{[(2-methoxy-4-methylphenyl)methyl]amino}-5-(2-methoxypyridin-3-yl)-1-[(2S)-oxane-2-carbonyl]pyrrolidine-2-carboxylic acid | MS (ESI+) m/z 540.3 (M + H)+. |
| Example II-124 | (2S,3S,4S,5S)-3-tert-butyl-4-{[(4-tert-butyl-2-methoxyphenyl)methyl]amino}-1-(cyclohexanecarbonyl)-5-[2-(difluoromethoxy)phenyl]pyrrolidine-2-carboxylic acid | MS (ESI+) m/z 615.3 (M + H)+. |
| Example II-125 | (2S,3S,4S,5S)-3-tert-butyl-1-(cyclohexanecarbonyl)-4-{[(3-methoxy-5,6,7,8-tetrahydronaphthalen-2-yl)methyl]amino}-5-phenylpyrrolidine-2-carboxylic acid | MS (APCI+) m/z 547.1 (M + H)+. |
| Example II-126 | (2S,3S,4S,5S)-4-{[(5-bromo-2-ethoxyphenyl)methyl]amino}-3-tert-butyl-1-(cyclohexanecarbonyl)-5-phenylpyrrolidine-2-carboxylic acid | MS (APCI+) m/z 587.0 (M + H)+. |
| Example II-127 | (2S,3S,4S,5S)-3-tert-butyl-1-(cyclohexanecarbonyl)-4-({[4-methoxy-3-(trifluoromethyl)phenyl]methyl}amino)-5-phenylpyrrolidine-2-carboxylic acid | MS (APCI+) m/z 561.0 (M + H)+. |

TABLE 2-continued

| Example | Compound | Data |
|---|---|---|
| Example II-128 | (2S,3S,4S,5S)-3-tert-butyl-1-(cyclohexanecarbonyl)-4-{[(4,5-difluoro-2-methoxyphenyl)methyl]amino}-5-phenylpyrrolidine-2-carboxylic acid | MS (APCI+) m/z 529.0 (M + H)+. |
| Example II-129 | (2S,3S,4S,5S)-3-tert-butyl-1-(cyclohexanecarbonyl)-4-{[(6-ethoxy-2,3-dihydro-1H-inden-5-yl)methyl]amino}-5-phenylpyrrolidine-2-carboxylic acid | MS (APCI+) m/z 547.1 (M + H)+. |
| Example II-130 | (2S,3S,4S,5S)-3-tert-butyl-1-(cyclohexanecarbonyl)-4-{[(4-fluoro-3-phenoxyphenyl)methyl]amino}-5-phenylpyrrolidine-2-carboxylic acid | MS (APCI+) m/z 573.1 (M + H)+. |
| Example II-131 | (2S,3S,4S,5S)-3-tert-butyl-1-(cyclohexanecarbonyl)-4-{[(2,4-dimethylphenyl)methyl]amino}-5-phenylpyrrolidine-2-carboxylic acid | MS (APCI+) m/z 491.1 (M + H)+. |
| Example II-132 | (2S,3S,4S,5S)-3-tert-butyl-1-(cyclohexanecarbonyl)-4-{[(3,5-dimethylphenyl)methyl]amino}-5-phenylpyrrolidine-2-carboxylic acid | MS (APCI+) m/z 491.1 (M + H)+. |
| Example II-133 | (2S,3S,4S,5S)-3-tert-butyl-1-(cyclohexanecarbonyl)-4-{[(3,5-di-tert-butylphenyl)methyl]amino}-5-phenylpyrrolidine-2-carboxylic acid | MS (APCI+) m/z 575.2 (M + H)+. |
| Example II-134 | (2S,3S,4S,5S)-3-tert-butyl-5-(2-methoxyphenyl)-4-({[2-methoxy-4-(trifluoromethyl)phenyl]methyl}amino)-1-{[(propan-2-yl)oxy]carbonyl}pyrrolidine-2-carboxylic acid | 1HNMR (400 MHz, dimethyl sulfoxide-d6) δ ppm 7.71 (dd, J = 7.6, 1.7 Hz, 1H), 7.19 (ddd, J = 8.8, 7.3, 1.6 Hz, 1H), 7.10 (d, J = 1.3 Hz, 2H), 7.05 (s, 1H), 6.92 (dd, J = 8.2, 1.2 Hz, 1H), 6.87 (td, J = 7.5, 1.1 Hz, 1H), 5.25 (d, J = 6.5 Hz, 1H), 4.63 (pd, J = 6.1, 1.0 Hz, 1H), 4.34 (d, J = 1.7 Hz, 1H), 3.69 (d, J = 1.1 Hz, 3H), 3.62 (d, J = 1.0 Hz, 3H), 3.52 (d, J = 14.5 Hz, 1H), 3.43-3.33 (m, 2H), 2.30 (d, J = 1.8 Hz, 1H), 1.04 (dd, J = 6.2, 1.1 Hz, 3H), 0.97 (d, J = 1.1 Hz, 9H), 0.90 (d, J = 6.2 Hz, 3H); MS (ESI+) m/z 567 (M + H)+. |
| Example II-135 | (2S,3S,4S,5S)-3-tert-butyl-4-{[(4-tert-butyl-2-methoxyphenyl)methyl]amino}-5-(2-methoxyphenyl)-1-{[(propan-2-yl)oxy]carbonyl}pyrrolidine-2-carboxylic acid | 1HNMR (400 MHz, dimethyl sulfoxide-d6) δ ppm 7.57 (dd, J = 7.6, 1.7 Hz, 1H), 7.25-7.17 (m, 1H), 6.93 (dd, J = 8.3, 1.0 Hz, 1H), 6.88 (td, J = 7.5, 1.0 Hz, 1H), 6.86-6.77 (m, 3H), 5.23 (d, J = 6.3 Hz, 1H), 4.64 (p, J = 6.2 Hz, 1H), 4.37 (d, J = 1.6 Hz, 1H), 3.65 (s, 3H), 3.55-3.48 (m, 4H), 3.46 (d, J = 6.4 Hz, 1H), 3.32 (d, J = 13.6 Hz, 1H), 2.34-2.27 (m, 1H), 1.24 (d, J = 0.7 Hz, 9H), 1.04 (d, J = 6.2 Hz, 3H), 0.98 (s, 9H), 0.91 (d, J = 6.2 Hz, 3H); MS (ESI+) m/z 555 (M + H)+. |
| Example II-136 | (2S,3S,4S,5S)-3-tert-butyl-5-(2-methoxyphenyl)-4-({[2-methoxy-5-(trifluoromethyl)phenyl]methyl}amino)-1-{[(propan-2-yl)oxy]carbonyl}pyrrolidine-2-carboxylic acid | 1HNMR (400 MHz, dimethyl sulfoxide-d6) δ ppm 7.68 (dd, J = 7.6, 1.7 Hz, 1H), 7.46 (dd, J = 8.6, 2.4 Hz, 1H), 7.23 (d, J = 2.4 Hz, 1H), 7.19 (ddd, J = 8.2, 7.3, 1.8 Hz, 1H), 6.99 (d, J = 8.6 Hz, 1H), 6.94-6.83 (m, 2H), 5.25 (d, J = 6.5 Hz, 1H), 4.63 (p, J = 6.2 Hz, 1H), 4.34 (d, J = 1.8 Hz, 1H), 3.67 (d, J = 1.0 Hz, 3H), 3.61 (s, 3H), 3.54 (d, J = 14.4 Hz, 1H), 3.42-3.37 (m, 1H), 3.34 (d, J = 14.4 Hz, 1H), 2.34-2.29 (m, 1H), 1.04 (d, J = 6.2 Hz, 3H), 0.96 (s, 9H), 0.89 (d, J = 6.2 Hz, 3H); MS (ESI+) m/z 567 (M + H)+. |
| Example II-137 | (2S,3S,4S,5S)-3-tert-butyl-4-{(5-chloro-2-methoxyphenyl)methyl]amino}-5-(2-methoxyphenyl)-1-{[(propan-2-yl)oxy]carbonyl}pyrrolidine-2-carboxylic acid | 1HNMR (400 MHz, dimethyl sulfoxide-d6) δ ppm 7.66 (dd, J = 7.6, 1.7 Hz, 1H), 7.24-7.17 (m, 1H), 7.12 (dd, J = 8.7, 2.7 Hz, 1H), 6.95-6.85 (m, 3H), 6.82 (d, J = 8.7 Hz, 1H), 5.25 (d, J = 6.5 Hz, 1H), 4.63 (p, J = 6.2 Hz, 1H), 4.35 (d, J = 1.8 Hz, 1H), 3.72 (s, 3H), 3.54 (s, 3H), 3.46 (d, J = 14.4 Hz, 1H), 3.41 (d, J = 6.5 Hz, 1H), 3.31 (d, J = 14.3 Hz, 1H), 2.30 (dd, J = 1.8, 0.9 Hz, 1H), 1.04 (d, J = 6.2 Hz, 3H), 0.97 (s, 9H), 0.90 (d, J = 6.2 Hz, 3H); MS (ESI+) m/z 533 (M + H)+. |
| Example II-138 | (2S,3S,4S,5S)-3-tert-butyl-1-(cyclohexanecarbonyl)-4-{[(2-methoxy-4-methylphenyl)methyl]amino}-5-(2-methoxypyridin-3-yl)pyrrolidine-2-carboxylic acid | MS (ESI+) m/z 538.2 (M + H)+. |

TABLE 2-continued

| Example | | |
|---|---|---|
| Example II-139 | (2S,3S,4S,5S)-3-tert-butyl-4-({[5-chloro-2-(cyclopropylmethoxy)phenyl]methyl}amino)-1-(cyclohexanecarbonyl)-5-phenylpyrrolidine-2-carboxylic acid | MS (ESI+) m/z 567 (M + H)+. |
| Example II-140 | (2S,3S,4S,5S)-3-tert-butyl-4-{[(5-tert-butyl-2-methoxyphenyl)methyl]amino}-1-(cyclohexanecarbonyl)-5-(2-methoxyphenyl)pyrrolidine-2-carboxylic acid | MS (ESI+) m/z 579 (M + H)+. |
| Example II-141 | (2S,3S,4S,5S)-3-tert-butyl-4-{[(4-tert-butyl-2-methoxyphenyl)methyl]amino}-1-(cyclohexanecarbonyl)-5-(2-methoxyphenyl)pyrrolidine-2-carboxylic acid | MS (ESI+) m/z 579 (M + H)+. |
| Example II-142 | rac-(2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid | LC/MS (ESI+) m/z 559.0 (M + H)+. |
| Example II-143 | rac-(2S,3S,4S,5S)-3-tert-butyl-4-{[(5-chloro-2-methoxyphenyl)methyl]amino}-1-(cyclohexanecarbonyl)-5-(2-methoxypyridin-3-yl)pyrrolidine-2-carboxylic acid | LC/MS (ESI+) m/z 559.0 (M + H)+. |
| Example II-144 | (2S,3S,4S,5S)-3-tert-butyl-4-[(2-chloro-6-fluoro-4-methylquinolin-3-yl)amino]-1-(cyclohexanecarbonyl)-5-phenylpyrrolidine-2-carboxylic acid | $^1$HNMR (400 MHz, dimethyl sulfoxide-$d_6$) δ ppm 7.61 (dd, J = 9.0, 5.6 Hz, 1H), 7.53 (d, J = 7.4 Hz, 2H), 7.47 (dd, J = 10.6, 2.8 Hz, 1H), 7.38 (td, J = 8.8, 2.9 Hz, 1H), 7.15 (dt, J = 15.4, 7.1 Hz, 3H), 5.43 (d, J = 7.6 Hz, 1H), 5.33-5.28 (m, 1H), 4.54 (d, J = 3.4 Hz, 1H), 2.46 (s, 3H), 2.40-2.36 (m, 1H), 1.74-1.64 (m, 2H), 1.53-1.44 (m, 2H), 1.32-1.20 (m, 2H), 1.11 (s, 9H), 1.10-1.05 (m, 2H); MS (APCI+) m/z 566.4 (M + H)+. |
| Example II-145 | (2S,3S,4S,5S)-3-tert-butyl-4-[(2-chloro-5-cyanopyridin-3-yl)amino]-1-(cyclohexanecarbonyl)-5-phenylpyrrolidine-2-carboxylic acid | $^1$HNMR (400 MHz, dimethyl sulfoxide-$d_6$) δ ppm 8.24 (d, J = 1.9 Hz, 1H), 7.72-7.70 (m, 1H), 7.48-7.44 (m, 3H), 7.22-7.12 (m, 2H), 5.37 (d, J = 7.8 Hz, 1H), 5.30-5.26 (m, 1H), 4.54-4.51 (m, 1H), 2.35-2.33 (m, 1H), 1.71-1.63 (m, 3H), 1.52-1.46 (m, 2H), 1.29-1.22 (m, 2H), 1.18 (s, 1H), 1.05 (s, 9H); MS (APCI+) m/z 509.4 (M + H)+. |
| Example II-146 | (2S,3S,4S,5S)-3-tert-butyl-4-[(3-cyano-6-methylpyridin-2-yl)amino]-1-(cyclohexanecarbonyl)-5-phenylpyrrolidine-2-carboxylic acid | $^1$HNMR (400 MHz, dimethyl sulfoxide-$d_6$) δ ppm 7.51-7.44 (m, 3H), 7.23-7.11 (m, 3H), 6.45 (d, J = 7.7 Hz, 1H), 5.36 (d, J = 7.7 Hz, 1H), 5.29-5.25 (m, 1H), 4.50 (d, J = 3.6 Hz, 1H), 2.33 (s, 3H), 2.32-2.31 (m, 1H), 2.25-2.19 (m, 1H), 1.71-1.64 (m, 2H), 1.52-1.46 (m, 2H), 1.30-1.17 (m, 5H), 1.11-1.07 (m, 2H), 1.06 (s, 9H); MS (APCI+) m/z 489.4 (M + H)+. |
| Example II-147 | (2S,3S,4S,5S)-3-tert-butyl-4-{[3-cyano-4-(methoxymethyl)-6-methylpyridin-2-yl]amino}-1-(cyclohexanecarbonyl)-5-phenylpyrrolidine-2-carboxylic acid | $^1$HNMR (400 MHz, dimethyl sulfoxide-$d_6$) δ ppm 7.49 (d, J = 7.5 Hz, 2H), 7.23-7.10 (m, 3H), 6.49 (s, 1H), 5.35 (d, J = 7.6 Hz, 1H), 5.30-5.25 (m, 1H), 4.50 (d, J = 3.5 Hz, 1H), 4.25 (d, J = 1.4 Hz, 2H), 3.27 (s, 3H), 2.33 (s, 3H), 2.32-2.30 (m, 1H), 2.27-2.17 (m, 1H), 1.71-1.63 (m, 2H), 1.52-1.45 (m, 2H), 1.32-1.16 (m, 2H), 1.11-1.08 (m, 1H), 1.06 (s, 9H); MS (APCI+) m/z 533.5 (M + H)+. |
| Example II-148 | (2S,3S,4S,5S)-4-[3,5-bis(trifluoromethyl)anilino]-3-tert-butyl-1-(cyclohexanecarbonyl)-5-phenylpyrrolidine-2-carboxylic acid | $^1$HNMR (400 MHz, dimethyl sulfoxide-$d_6$) δ ppm 7.47 (d, J = 7.3 Hz, 2H), 7.16-7.07 (m, 3H), 6.91 (d, J = 5.7 Hz, 3H), 5.40 (d, J = 7.9 Hz, 1H), 4.54-4.49 (m, 1H), 4.39 (d, J = 5.7 Hz, 1H), 2.39 (t, J = 5.9 Hz, 1H), 2.27-2.20 (m, 1H), 1.74-1.64 (m, 2H), 1.51-1.40 (m, 2H), 1.34-1.23 (m, 1H), 1.19-1.05 (m, 5H), 1.02 (s, 9H); MS (APCI+) m/z 585.4 (M + H)+. |
| Example II-149 | (2S,3S,4S,5S)-3-tert-butyl-4-{[(5-tert-butyl-2-methoxyphenyl)methyl]amino}-1-[(1R,3R)-3-methoxycyclohexane-1-carbonyl]-5-phenylpyrrolidine-2-carboxylic acid | $^1$HNMR (400 MHz, dimethyl sulfoxide-$d_6$) δ ppm 7.67 (d, J = 6.7 Hz, 2H), 7.48-7.36 (m, 5H), 7.33-7.23 (m, 1H), 7.19 (t, J = 7.3 Hz, 2H), 7.15-7.05 (m, 1H), 7.01 (d, J = 2.5 Hz, 1H), 6.92 (d, J = 8.5 Hz, 1H), 5.15 (d, J = 6.5 Hz, 1H), 4.44 (d, J = 3.1 Hz, 1H), 4.33 (d, J = 12.6 Hz, 1H), 4.30-4.23 (m, 1H), 4.03 (d, J = 12.6 Hz, 1H), 3.73 (s, 3H), 3.44 (s, 1H), 3.19 (s, 3H), 2.69-2.60 (m, 2H), 2.61-2.52 (m, 1H), 1.77 (d, J = 11.6 Hz, 1H), 1.67-1.57 (m, 2H), 1.42 (td, J = 13.4, 12.3, 2.7 Hz, 1H), 1.21-1.10 (m, 2H), 0.99 (s, 9H), 0.92-0.77 (m, 1H); MS (APCI+) m/z 600 (M + H)+. |
| Example II-150 | (2S,3S,4S,5S)-1-(cyclohexanecarbonyl)-3-(2-methoxypropan-2-yl)-4-({[2-methoxy-4-(trifluoromethyl) | $^1$HNMR (400 MHz, dimethyl sulfoxide-$d_6$) δ ppm 7.57 (s, 2H), 7.34 (t, J = 7.4 Hz, 2H), 7.28 (d, J = 7.2 Hz, 1H), 7.20 (d, J = 7.8 Hz, 1H), 7.14 (d, J = 8.1 Hz, 1H), 7.11 (s, 1H), 5.28 (d, J = 7.2 Hz, 1H), 4.51 (d, J = 3.6 Hz, 1H), |

TABLE 2-continued

| | | |
|---|---|---|
| | phenyl]methyl}amino)-5-phenylpyrrolidine-2-carboxylic acid | 3.67 (d, J = 15.0 Hz, 5H), 3.52 (d, J = 14.1 Hz, 1H), 3.14 (s, 3H), 2.69 (s, 1H), 2.27 (d, J = 20.4 Hz, 1H), 1.65 (d, J = 10.6 Hz, 2H), 1.49 (bs, 2H), 1.31-1.22 (m, 1H), 1.20 (s, 3H), 1.18 (s, 3H), 1.16 (bs, 1H), 1.08 (m, 3H), 0.79 (bs, 1H); MS (ESI+) m/z 577 (M + H)+. |
| Example II-151 | rac-(2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid | LC/MS (ESI+) m/z 593.0 (M + H)+. |
| Example II-152 | (2S,3S,4S,5S)-1-benzoyl-3-tert-butyl-4-({[2-methoxy-4-(trifluoromethyl)phenyl]methyl}amino)-5-phenylpyrrolidine-2-carboxylic acid | LC/MS (ESI+) m/z 555.7 (M + H)+. |
| Example II-153 | (2S,3S,4S,5S)-3-tert-butyl-4-{[(5-tert-butyl-2-methoxyphenyl)methyl]amino}-1-(1,1-dioxo-1λ6-thiane-2-carbonyl)-5-phenylpyrrolidine-2-carboxylic acid | LC/MS (ESI+) m/z 599.8 (M + H)+. |
| Example II-154 | (2S,3S,4S,5S)-3-tert-butyl-4-{[(5-tert-butyl-2-methoxyphenyl)methyl]amino}-1-(1-methyl-1H-pyrazole-3-sulfonyl)-5-phenylpyrrolidine-2-carboxylic acid | LC/MS (ESI+) m/z 583.8 (M + H)+. |
| Example II-155 | (2S,3S,4S,5S)-1-(benzenesulfonyl)-3-tert-butyl-4-({[2-methoxy-5-(trifluoromethyl)phenyl]methyl}amino)-5-phenylpyrrolidine-2-carboxylic acid | LC/MS (ESI+) m/z 591.7 (M + H)+. |
| Example II-156 | (2S,3S,4S,5S)-3-tert-butyl-1-(2,3-dihydro-1,4-benzodioxine-2-carbonyl)-4-({[2-methoxy-5-(trifluoromethyl)phenyl]methyl}amino)-5-phenylpyrrolidine-2-carboxylic acid | LC/MS (ESI+) m/z 613.5 (M + H)+. |
| Example II-157 | (2S,3S,4S,5S)-3-tert-butyl-1-(cyclohexanecarbonyl)-4-({[2-methoxy-5-(propan-2-yl)pyridin-3-yl]methyl}amino)-5-phenylpyrrolidine-2-carboxylic acid | MS (APCI+) m/z 536.1 (M + H)+. |
| Example II-158 | (2S,3S,4S,5S)-4-{[(5-bromo-2-methoxypyridin-3-yl)methyl]amino}-3-tert-butyl-1-(cyclohexanecarbonyl)-5-phenylpyrrolidine-2-carboxylic acid | MS (ESI+) m/z 572 & 574 (M + H)+. |
| Example II-159 | (2S,3S,4S,5S)-3-tert-butyl-1-(cyclohexanecarbonyl)-4-[({2-methoxy-5-[(2R)-3-methoxy-2-methyl-3-oxopropyl]pyridin-3-yl}methyl)amino]-5-phenylpyrrolidine-2-carboxylic acid | MS (APCI+) m/z 593.9 (M + H)+. |
| Example II-160 | (2S,3S,4S,5S)-3-tert-butyl-4-{[(4-methoxy[1,1'-biphenyl]-3-yl)methyl]amino}-5-phenyl-1-{[(propan-2-yl)oxy]carbonyl}pyrrolidine-2-carboxylic acid | MS (ESI+) m/z 545 (M + H)+. |
| Example II-161 | (2S,3S,4S,5S)-3-tert-butyl-4-({[2-methoxy-4-(trifluoromethyl)phenyl]methyl}amino)-1-[(2-methylpropoxy)carbonyl]-5-phenylpyrrolidine-2-carboxylic acid | MS (ESI+) m/z 551 (M + H)+. |
| Example II-162 | (2S,3S,4S,5S)-3-tert-butyl-4-{[(5-tert-butyl-2-methoxyphenyl)methyl]amino}-1-(oxan-4-yl)acetyl]-5-phenylpyrrolidine-2-carboxylic acid | MS (APCI+) m/z 565.1 (M + H)+. |
| Example II-163 | (2S,3S,4S,5S)-3-tert-butyl-1-(3,4-dihydro-2H-1-benzopyran-2-carbonyl)-4-({[2-methoxy-5-(trifluoromethyl)phenyl]methyl}amino)-5-phenylpyrrolidine-2-carboxylic acid | LC/MS (ESI+) m/z 611.5 (M + H)+. |

TABLE 2-continued

| | | |
|---|---|---|
| Example II-164 | (2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-phenylpyrrolidine-2-carboxylic acid | LC/MS (ESI+) m/z 599.9 (M + H)+. |
| Example II-165 | (2S,3S,4S,5S)-3-tert-butyl-4-{[(5-tert-butyl-2-methoxyphenyl)methyl]amino}-1-(3,4-dihydro-1H-2-benzopyran-1-carbonyl)-5-phenylpyrrolidine-2-carboxylic acid | LC/MS (ESI+) m/z 599.7 (M + H)+. |
| Example II-166 | (2S,3S,4S,5S)-3-tert-butyl-1-(cyclohexanecarbonyl)-5-phenyl-4-([{2-(propan-2-yl)phenyl]methyl}amino)pyrrolidine-2-carboxylic acid | LC/MS (ESI+) m/z 505.9 (M + H)+. |
| Example II-167 | (2S,3S,4S,5S)-3-tert-butyl-4-[(6-chloro-3,4-dihydro-2H-1-benzopyran-4-yl)amino]-1-(cyclohexanecarbonyl)-5-phenylpyrrolidine-2-carboxylic acid | LC/MS (ESI+) m/z 539.6 (M + H)+. |
| Example II-168 | (2S,3S,4S,5S)-3-tert-butyl-1-(cyclohexanecarbonyl)-4-({[2-methoxy-5-(propan-2-yl)phenyl]methyl}amino)-5-phenylpyrrolidine-2-carboxylic acid | MS (ESI+) m/z 535 (M + H)+. |
| Example II-169 | (2S,3S,4S,5S)-3-tert-butyl-4-({[2-methoxy-5-(propan-2-yl)phenyl]methyl}amino)-5-phenyl-1-{[(propan-2-yl)oxy]carbonyl}pyrrolidine-2-carboxylic acid | MS (ESI+) m/z 511 (M + H)+. |
| Example II-170 | (2S,3S,4S,5S)-4-{[(5-bromo-2-methoxypyridin-3-yl)methyl]amino}-3-tert-butyl-5-phenyl-1-{[(propan-2-yl)oxy]carbonyl}pyrrolidine-2-carboxylic acid | MS (ESI+) m/z 548 & 550 (M + H)+. |
| Example II-171 | (2S,3S,4S,5S)-4-{[(5-bromo-2-methoxyphenyl)methyl]amino}-3-tert-butyl-5-phenyl-1-{[(propan-2-yl)oxy]carbonyl}pyrrolidine-2-carboxylic acid | MS (ESI+) m/z 547 & 549 (M + H)+. |
| Example II-172 | (2S,3S,4S,5S)-3-tert-butyl-4-{[(5-tert-butyl-2-methoxyphenyl)methyl]amino}-1-[(1-ethyl-2-methyl-1H-indol-3-yl)acetyl]-5-phenylpyrrolidine-2-carboxylic acid | MS (APCI+) m/z 638.1 (M + H)+. |
| Example II-173 | (2S,3S,4S,5S)-3-tert-butyl-4-{[(5-tert-butyl-2-methoxyphenyl)methyl]amino}-1-[(1S,2R,4R)-4-(2-cyanoethyl)-2-methylcyclopentane-1-carbonyl]-5-phenylpyrrolidine-2-carboxylic acid | MS (APCI+) m/z 602.1 (M + H)+. |
| Example II-174 | (2S,3S,4S,5S)-3-tert-butyl-4-{[(5-tert-butyl-2-methoxyphenyl)methyl]amino}-1-(4-methyloxane-2-carbonyl)-5-phenylpyrrolidine-2-carboxylic acid | MS (APCI+) m/z 565.1 (M + H)+. |
| Example II-175 | (2S,3S,4S,5S)-3-tert-butyl-4-{[(5-tert-butyl-2-methoxyphenyl)methyl]amino}-1-(4-cyanocyclohexane-1-carbonyl)-5-phenylpyrrolidine-2-carboxylic acid | MS (APCI+) m/z 574.1 (M + H)+. |
| Example II-176 | (2S,3S,4S,5S)-3-tert-butyl-4-{[(5-tert-butyl-2-methoxyphenyl)methyl]amino}-1-[(6,6-dimethyloxan-3-yl)acetyl]-5-phenylpyrrolidine-2-carboxylic acid | MS (APCI+) m/z 593.1 (M + H)+. |

TABLE 2-continued

| | | |
|---|---|---|
| Example II-177 | (2S,3S,4S,5S)-1-[(bicyclo[1.1.1]pentan-1-yl)acetyl]-3-tert-butyl-4-{[(5-tert-butyl-2-methoxyphenyl)methyl]amino}-5-phenylpyrrolidine-2-carboxylic acid | MS (APCI+) m/z 547.1 (M + H)+. |
| Example II-178 | (2S,3S,4S,5S)-3-tert-butyl-4-{[(5-tert-butyl-2-methoxyphenyl)methyl]amino}-1-{[(1R)-3,4-dihydro-1H-2-benzopyran-1-yl]acetyl}-5-phenylpyrrolidine-2-carboxylic acid | MS (APCI+) m/z 613.1 (M + H)+. |
| Example II-179 | (2S,3S,4S,5S)-3-tert-butyl-4-{[(5-tert-butyl-2-methoxyphenyl)methyl]amino}-1-[(oxan-3-yl)acetyl]-5-phenylpyrrolidine-2-carboxylic acid | MS (APCI+) m/z 565.1 (M + H)+. |
| Example II-180 | (2S,3S,4S,5S)-3-tert-butyl-4-{[(5-tert-butyl-2-methoxyphenyl)methyl]amino}-5-phenyl-1-(phenylacetyl)pyrrolidine-2-carboxylic acid | MS (APCI+) m/z 557.1 (M + H)+. |
| Example II-181 | (2S,3S,4S,5S)-3-tert-butyl-4-{[(5-tert-butyl-2-methoxyphenyl)methyl]amino}-1-[(4-fluorophenyl)acetyl]-5-phenylpyrrolidine-2-carboxylic acid | MS (APCI+) m/z 575.1 (M + H)+. |
| Example II-182 | (2S,3S,4S,5S)-3-tert-butyl-4-{[(5-tert-butyl-2-methoxyphenyl)methyl]amino}-5-phenyl-1-[(thiophen-2-yl)acetyl]pyrrolidine-2-carboxylic acid | MS (APCI+) m/z 563.0 (M + H)+. |
| Example II-183 | (2S,3S,4S,5S)-3-tert-butyl-4-{[(5-tert-butyl-2-methoxyphenyl)methyl]amino}-1-[(2-chlorophenyl)acetyl]-5-phenylpyrrolidine-2-carboxylic acid | MS (APCI+) m/z 591.1 (M + H)+. |
| Example II-184 | (2S,3S,4S,5S)-3-tert-butyl-4-{[(5-tert-butyl-2-methoxyphenyl)methyl]amino}-5-phenyl-1-[(pyridin-3-yl)acetyl]pyrrolidine-2-carboxylic acid | MS (APCI+) m/z 558.1 (M + H)+. |
| Example II-185 | (2S,3S,4S,5S)-1-(1-benzofuran-3-carbonyl)-3-tert-butyl-4-{[(5-tert-butyl-2-methoxyphenyl)methyl]amino}-5-phenylpyrrolidine-2-carboxylic acid | MS (APCI+) m/z 583.1 (M + H)+. |
| Example II-186 | (2S,3S,4S,5S)-3-tert-butyl-4-{[(5-tert-butyl-2-methoxyphenyl)methyl]amino}-5-phenyl-1-[3-(trifluoromethyl)cyclohexane-l-carbonyl]pyrrolidine-2-carboxylic acid | MS (APCI+) m/z 617.1 (M + H)+. |
| Example II-187 | (2S,3S,4S,5S)-3-tert-butyl-4-{[(5-tert-butyl-2-methoxyphenyl)methyl]amino}-5-phenyl-1-[(pyrrolidin-1-yl)acetyl]pyrrolidine-2-carboxylic acid | MS (APCI+) m/z 550.1 (M + H)+. |
| Example II-188 | (2S,3S,4S,5S)-3-tert-butyl-4-{[(5-tert-butyl-2-methoxyphenyl)methyl]amino}-1-[(4,4-difluorocyclohexyl)acetyl]-5-phenylpyrrolidine-2-carboxylic acid | MS (APCI+) m/z 599.1 (M + H)+. |
| Example II-189 | (2S,3S,4S,5S)-3-tert-butyl-4-{[(5-tert-butyl-2-methoxyphenyl)methyl]amino}-5-phenyl-1-[1-(pyridin-2-yl)cyclopropane-1-carbonyl]pyrrolidine-2-carboxylic acid | MS (ESI+) m/z 584.2 (M + H)+. |
| Example II-190 | (2S,3S,4S,5S)-3-tert-butyl-1-(cyclohexanecarbonyl)-4-({[2-methoxy-5-(trifluoromethoxy)phenyl]methyl}amino)-5-phenylpyrrolidine-2-carboxylic acid | MS (ESI+) m/z 577 (M + H)+. |

TABLE 2-continued

| Example II-191 | (2S,3S,4S,5S)-4-{[(5-benzyl-2-methoxyphenyl)methyl]amino}-3-tert-butyl-1-(cyclohexanecarbonyl)-5-phenylpyrrolidine-2-carboxylic acid | MS (APCI+) m/z 583.1 (M + H)+. |
|---|---|---|
| Example II-192 | (2S,3S,4S,5S)-3-tert-butyl-1-(cyclohexanecarbonyl)-4-{[(5-cyclohexyl-2-methoxyphenyl)methyl]amino}-5-phenylpyrrolidine-2-carboxylic acid | MS (APCI+) m/z 575.1 (M + H)+. |
| Example II-193 | (2S,3S,4S,5S)-3-tert-butyl-1-(cyclohexanecarbonyl)-4-{[(5-cyclopentyl-2-methoxyphenyl)methyl]amino}-5-phenylpyrrolidine-2-carboxylic acid | MS (APCI+) m/z 561.0 (M + H)+. |
| Example II-194 | (2S,3S,4S,5S)-4-({[5-(bicyclo[2.2.1]heptan-2-yl]-2-methoxyphenyl]methyl}amino)-3-tert-butyl-1-(cyclohexanecarbonyl)-5-phenylpyrrolidine-2-carboxylic acid | MS (APCI+) m/z 587.2 (M + H)+. |
| Example II-195 | (2S,3S,4S,5S)-3-tert-butyl-4-{[(5-tert-butyl-2-methoxyphenyl)methyl]amino}-1-[(4-hydroxyphenyl)acetyl]-5-phenylpyrrolidine-2-carboxylic acid | MS (APCI+) m/z 573.1 (M + H)+. |
| Example II-196 | (2S,3S,4S,5S)-3-tert-butyl-4-{[(5-tert-butyl-2-methoxyphenyl)methyl]amino}-1-[(3-hydroxyphenyl)acetyl]-5-phenylpyrrolidine-2-carboxylic acid | MS (APCI+) m/z 573.1 (M + H)+. |
| Example II-197 | (2S,3S,4S,5S)-3-tert-butyl-4-{[(5-tert-butyl-2-methoxyphenyl)methyl]amino}-1-(2,6-dimethylpyridine-4-carbonyl)-5-phenylpyrrolidine-2-carboxylic acid | MS (APCI+) m/z 572.1 (M + H)+. |
| Example II-198 | (2S,3S,4S,5S)-3-tert-butyl-4-{[(5-tert-butyl-2-methoxyphenyl)methyl]amino}-1-(2-methylpyridine-3-carbonyl)-5-phenylpyrrolidine-2-carboxylic acid | MS (APCI+) m/z 558.1 (M + H)+. |
| Example II-199 | (2S,3S,4S,5S)-3-tert-butyl-4-{[(5-tert-butyl-2-methoxyphenyl)methyl]amino}-1-[(3-fluorophenyl)acetyl]-5-phenylpyrrolidine-2-carboxylic acid | MS (APCI+) m/z 575.1 (M + H)+. |
| Example II-200 | (2S,3S,4S,5S)-3-tert-butyl-4-{[(5-tert-butyl-2-methoxyphenyl)methyl]amino}-1-[(3,5-difluorophenyl)acetyl]-5-phenylpyrrolidine-2-carboxylic acid | MS (APCI+) m/z 593.0 (M + H)+. |
| Example II-201 | (2S,3S,4S,5S)-3-tert-butyl-4-{[(5-tert-butyl-2-methoxyphenyl)methyl]amino}-1-[(2,6-difluorophenyl)acetyl]-5-phenylpyrrolidine-2-carboxylic acid | MS (APCI+) m/z 593.0 (M + H)+. |
| Example II-202 | (2S,3S,4S,5S)-3-tert-butyl-4-{[(5-tert-butyl-2-methoxyphenyl)methyl]amino}-1-[(2,5-difluorophenyl)acetyl]-5-phenylpyrrolidine-2-carboxylic acid | MS (APCI+) m/z 593.0 (M + H)+. |
| Example II-203 | (2S,3S,4S,5S)-3-tert-butyl-4-{[(5-tert-butyl-2-methoxyphenyl)methyl]amino}-1-[(3-methylphenyl)acetyl]-5-phenylpyrrolidine-2-carboxylic acid | MS (APCI+) m/z 571.1 (M + H)+. |

TABLE 2-continued

| Example II-204 | (2S,3S,4S,5S)-3-tert-butyl-4-{[(5-tert-butyl-2-methoxyphenyl)methyl]amino}-1-[(4-methylphenyl)acetyl]-5-phenylpyrrolidine-2-carboxylic acid | MS (APCI+) m/z 571.1 (M + H)+. |
|---|---|---|
| Example II-205 | (2S,3S,4S,5S)-3-tert-butyl-4-{[(5-tert-butyl-2-methoxyphenyl)methyl]amino}-1-[(2-methylphenyl)acetyl]-5-phenylpyrrolidine-2-carboxylic acid | MS (APCI+) m/z 571.1 (M + H)+. |
| Example II-206 | (2S,3S,4S,5S)-3-tert-butyl-4-{[(5-tert-butyl-2-methoxyphenyl)methyl]amino}-1-[(2-fluorophenyl)acetyl]-5-phenylpyrrolidine-2-carboxylic acid | MS (APCI+) m/z 575.1 (M + H)+. |
| Example II-207 | (2S,3S,4S,5S)-3-tert-butyl-4-{[(5-tert-butyl-2-methoxyphenyl)methyl]amino}-1-(4-methoxy-1-methyl-1H-pyrazole-5-carbonyl)-5-phenylpyrrolidine-2-carboxylic acid | MS (APCI+) m/z 577.0 (M + H)+. |
| Example II-208 | (2S,3S,4S,5S)-3-tert-butyl-4-{[(5-tert-butyl-2-methoxyphenyl)methyl]amino}-1-[(2,5-dimethylthiophen-3-yl)acetyl]-5-phenylpyrrolidine-2-carboxylic acid | MS (APCI+) m/z 591.1 (M + H)+. |
| Example II-209 | (2S,3S,4S,5S)-3-tert-butyl-4-{[(5-tert-butyl-2-methoxyphenyl)methyl]amino}-1-[(morpholin-4-yl)acetyl]-5-phenylpyrrolidine-2-carboxylic acid | MS (APCI+) m/z 566.1 (M + H)+. |
| Example II-210 | (2S,3S,4S,5S)-3-tert-butyl-4-{[(5-tert-butyl-2-methoxyphenyl)methyl]amino}-1-[(1-hydroxycyclohexyl)acetyl]-5-phenylpyrrolidine-2-carboxylic acid | MS (APCI+) m/z 579.1 (M + H)+. |
| Example II-211 | (2S,3S,4S,5S)-1-(bicyclo[2.2.1]hept-5-ene-2-carbonyl)-3-tert-butyl-4-{[(5-tert-butyl-2-methoxyphenyl)methyl]amino}-5-phenylpyrrolidine-2-carboxylic acid | MS (APCI+) m/z 559.1 (M + H)+. |
| Example II-212 | (2S,3S,4S,5S)-3-tert-butyl-4-{[(5-tert-butyl-2-methoxyphenyl)methyl]amino}-1-[(cyclohex-2-en-1-yl)acetyl]-5-phenylpyrrolidine-2-carboxylic acid | MS (APCI+) m/z 561.0 (M + H)+. |
| Example II-213 | (2S,3S,4S,5S)-3-tert-butyl-4-{[(5-tert-butyl-2-methoxyphenyl)methyl]amino}-1-[(3,4-dihydro-2H-1-benzopyran-4-yl)acetyl]-5-phenylpyrrolidine-2-carboxylic acid | MS (APCI+) m/z 613.1 (M + H)+. |
| Example II-214 | (2S,3S,4S,5S)-3-tert-butyl-4-{[(5-tert-butyl-2-methoxyphenyl)methyl]amino}-1-(4-methoxycyclohexane-1-carbonyl)-5-phenylpyrrolidine-2-carboxylic acid | MS (APCI+) m/z 579.1 (M + H)+. |
| Example II-215 | (2S,3S,4S,5S)-3-tert-butyl-4-{[(5-tert-butyl-2-methoxyphenyl)methyl]amino}-5-phenyl-1-(2-phenylpropanoyl)pyrrolidine-2-carboxylic acid | MS (APCI+) m/z 571.1 (M + H)+. |
| Example II-216 | (2S,3S,4S,5S)-3-tert-butyl-4-{[(5-tert-butyl-2-methoxyphenyl)methyl]amino}-5-phenyl-1-[2-(propan-2-yl)-1,3-dioxane-5-carbonyl]pyrrolidine-2-carboxylic acid | MS (APCI+) m/z 595.1 (M + H)+. |

TABLE 2-continued

| Example | Compound | MS |
|---|---|---|
| Example II-217 | (2S,3S,4S,5S)-3-tert-butyl-4-{[(5-tert-butyl-2-methoxyphenyl)methyl]amino}-1-[(3-oxo-2,3-dihydro-1H-inden-1-yl)acetyl]-5-phenylpyrrolidine-2-carboxylic acid | MS (APCI+) m/z 611.1 (M + H)+. |
| Example II-218 | (2S,3S,4S,5S)-3-tert-butyl-4-{[(5-tert-butyl-2-methoxyphenyl)methyl]amino}-1-[(3,3-difluorocyclopentyl)acetyl]-5-phenylpyrrolidine-2-carboxylic acid | MS (APCI+) m/z 585.1 (M + H)+. |
| Example II-219 | (2S,3S,4S,5S)-3-tert-butyl-4-{[(5-tert-butyl-2-methoxyphenyl)methyl]amino}-1-[(2,2-difluorocyclopentyl)acetyl]-5-phenylpyrrolidine-2-carboxylic acid | MS (APCI+) m/z 585.1 (M + H)+. |
| Example II-220 | (2S,3S,4S,5S)-3-tert-butyl-4-{[(5-tert-butyl-2-methoxyphenyl)methyl]amino}-1-[(3,3-difluoro-1-methylcyclopentyl)acetyl]-5-phenylpyrrolidine-2-carboxylic acid | MS (APCI+) m/z 599.1 (M + H)+. |
| Example II-221 | (2S,3S,4S,5S)-3-tert-butyl-4-{[(5-tert-butyl-2-methoxyphenyl)methyl]amino}-1-[(3-methyl-4-oxo-3,4-dihydrophthalazin-1-yl)acetyl]-5-phenylpyrrolidine-2-carboxylic acid | MS (APCI+) m/z 639.1 (M + H)+. |
| Example II-222 | (2S,3S,4S,5S)-3-tert-butyl-4-{[(5-tert-butyl-2-methoxyphenyl)methyl]amino}-1-(2,3-dihydro-1-benzofuran-7-carbonyl)-5-phenylpyrrolidine-2-carboxylic acid | MS (APCI+) m/z 585.1 (M + H)+. |
| Example II-223 | (2S,3S,4S,5S)-3-tert-butyl-4-{[(5-tert-butyl-2-methoxyphenyl)methyl]amino}-1-[5-chloro-6-oxo-1-(propan-2-yl)-1,6-dihydropyridine-3-carbonyl]-5-phenylpyrrolidine-2-carboxylic acid | MS (APCI+) m/z 636.0 (M + H)+. |
| Example II-224 | (2S,3S,4S,5S)-3-tert-butyl-4-{[(5-tert-butyl-2-methoxyphenyl)methyl]amino}-5-phenyl-1-{4-[(pyridin-2-yl)oxy]benzoyl}pyrrolidine-2-carboxylic acid | MS (APCI+) m/z 636.1 (M + H)+. |
| Example II-225 | (2S,3S,4S,5S)-3-tert-butyl-4-{[(5-tert-butyl-2-methoxyphenyl)methyl]amino}-5-phenyl-1-{3-[(1H-1,2,4-triazol-1-yl)methyl]benzoyl}pyrrolidine-2-carboxylic acid | MS (APCI+) m/z 624.1 (M + H)+. |
| Example II-226 | (2S,3S,4S,5S)-3-tert-butyl-4-{[(5-tert-butyl-2-methoxyphenyl)methyl]amino}-1-(1-methyl-3-phenyl-1H-pyrazole-5-carbonyl)-5-phenylpyrrolidine-2-carboxylic acid | MS (APCI+) m/z 623.1 (M + H)+. |
| Example II-227 | (2S,3S,4S,5S)-3-tert-butyl-4-{[(5-tert-butyl-2-methoxyphenyl)methyl]amino}-1-(1-methyl-5-phenyl-1H-pyrazole-3-carbonyl)-5-phenylpyrrolidine-2-carboxylic acid | MS (APCI+) m/z 623.1 (M + H)+. |
| Example II-228 | (2S,3S,4S,5S)-3-tert-butyl-4-{[(5-tert-butyl-2-methoxyphenyl)methyl]amino}-1-[5-methyl-1-(2-methylphenyl)-1H-pyrazole-4-carbonyl]-5-phenylpyrrolidine-2-carboxylic acid | MS (APCI+) m/z 637.1 (M + H)+. |
| Example II-229 | (2S,3S,4S,5S)-3-tert-butyl-4-{[(5-tert-butyl-2-methoxyphenyl)methyl]amino}-1-(3,5-dimethyl-1-phenyl-1H-pyrazole-4-carbonyl)-5-phenylpyrrolidine-2-carboxylic acid | MS (APCI+) m/z 637.1 (M + H)+. |

TABLE 2-continued

| Example II-230 | (2S,3S,4S,5S)-3-tert-butyl-4-{[(5-tert-butyl-2-methoxyphenyl)methyl]amino}-1-(3,4-dihydro-2H-1,5-benzodioxepine-7-carbonyl)-5-phenylpyrrolidine-2-carboxylic acid | MS (APCI+) m/z 615.1 (M + H)+. |
|---|---|---|
| Example II-231 | (2S,3S,4S,5S)-1-(2,1-benzoxazole-3-carbonyl)-3-tert-butyl-4-{[(5-tert-butyl-2-methoxyphenyl)methyl]amino}-5-phenylpyrrolidine-2-carboxylic acid | MS (APCI+) m/z 584.1 (M + H)+. |
| Example II-232 | (2S,3S,4S,5S)-3-tert-butyl-4-{[(5-tert-butyl-2-methoxyphenyl)methyl]amino}-1-(3,4-dihydro-2H-1-benzopyran-3-carbonyl)-5-phenylpyrrolidine-2-carboxylic acid | MS (APCI+) m/z 599.1 (M + H)+. |
| Example II-233 | (2S,3S,4S,5S)-3-tert-butyl-4-{[(5-tert-butyl-2-methoxyphenyl)methyl]amino}-1-[(2,3-difluorophenyl)acetyl]-5-phenylpyrrolidine-2-carboxylic acid | MS (APCI+) m/z 593.0 (M + H)+. |
| Example II-234 | (2S,3S,4S,5S)-3-tert-butyl-4-{[(5-tert-butyl-2-methoxyphenyl)methyl]amino}-1-[(cyclopent-1-en-1-yl)acetyl]-5-phenylpyrrolidine-2-carboxylic acid | MS (APCI+) m/z 547.1 (M + H)+. |
| Example II-235 | (2S,3S,4S,5S)-3-tert-butyl-4-{[(5-tert-butyl-2-methoxyphenyl)methyl]amino}-1-[(oxolan-2-yl)acetyl]-5-phenylpyrrolidine-2-carboxylic acid | MS (APCI+) m/z 551.1 (M + H)+. |
| Example II-236 | (2S,3S,4S,5S)-3-tert-butyl-4-{[(5-tert-butyl-2-methoxyphenyl)methyl]amino}-1-[(5-chloro-3-fluoropyridin-2-yl)acetyl]-5-phenylpyrrolidine-2-carboxylic acid | MS (APCI+) m/z 609.8 (M + H)+. |
| Example II-237 | (2S,3S,4S,5S)-3-tert-butyl-4-{[(5-tert-butyl-2-methoxyphenyl)methyl]amino}-1-[(R*)-2-(4-chloro-3-methyl-1H-pyrazol-1-yl)propanoyl]-5-phenylpyrrolidine-2-carboxylic acid | MS (APCI+) m/z 609.0 (M + H)+. |
| Example II-238 | (2S,3S,4S,5S)-3-tert-butyl-4-{[(5-tert-butyl-2-methoxyphenyl)methyl]amino}-1-[5-oxo-1-(propan-2-yl)pyrrolidine-3-carbonyl]-5-phenylpyrrolidine-2-carboxylic acid | MS (APCI+) m/z 592.1 (M + H)+. |
| Example II-239 | (2S,3S,4S,5S)-3-tert-butyl-4-{[(5-tert-butyl-2-methoxyphenyl)methyl]amino}-1-(1-cyclopropyl-5-oxopyrrolidine-3-carbonyl)-5-phenylpyrrolidine-2-carboxylic acid | MS (APCI+) m/z 590.1 (M + H)+. |
| Example II-240 | (2S,3S,4S,5S)-3-tert-butyl-4-{[(5-tert-butyl-2-methoxyphenyl)methyl]amino}-1-[(3-cyanophenyl)acetyl]-5-phenylpyrrolidine-2-carboxylic acid | MS (APCI+) m/z 582.1 (M + H)+. |
| Example II-241 | (2S,3S,4S,5S)-3-tert-butyl-1-[(3aR,6aS)-hexahydro-1H-cyclopent[c]furan-1-carbonyl]-4-({[2-methoxy-4-(trifluoromethyl)phenyl]methyl}amino)-5-phenylpyrrolidine-2-carboxylic acid | LC/MS (ESI+) m/z 589.5 (M + H)+. |
| Example II-242 | (2S,3S,4S,5S)-3-tert-butyl-1-(cyclohexanecarbonyl)-4-({[2-methoxy-5-(methoxymethyl)phenyl]methyl}amino)-5-phenylpyrrolidine-2-carboxylic acid | MS (ESI+) m/z 537.2 (M + H)+. |

TABLE 2-continued

| | | |
|---|---|---|
| Example II-243 | (2S,3S,4S,5S)-3-tert-butyl-1-(cyclohexanecarbonyl)-5-(4-fluorophenyl)-4-[({2-methoxy-5-{(1S,3s)-tricyclo[3.3.1.1$^{3,7}$]decan-1-yl]phenyl}methyl)amino]pyrrolidine-2-carboxylic acid | MS (ESI+) m/z 645.3 (M + H)+. |
| Example II-244 | (2S,3S,4S,5S)-3-tert-butyl-1-(cyclohexanecarbonyl)-4-{[(2-methoxyquinolin-3-yl)methyl]amino}-5-phenylpyrrolidine-2-carboxylic acid | MS (ESI+) m/z 544 (M + H)+. |
| Example II-245 | (2S,3S,4S,5S)-3-tert-butyl-1-(cyclohexanecarbonyl)-5-(2-fluorophenyl)-4-{[(4-methoxy[1,1'-biphenyl]-3-yl)methyl]amino}pyrrolidine-2-carboxylic acid | MS (ESI+) m/z 587 (M + H)+. |
| Example II-246 | (2S,3S,4S,5S)-3-tert-butyl-1-(cyclohexanecarbonyl)-4-({[2-methoxy-5-(pyrrolidin-1-yl)pyridin-3-yl]methyl}amino)-5-phenylpyrrolidine-2-carboxylic acid | MS (ESI+) m/z 563.2 (M + H)+. |
| Example II-247 | (2S,3S,4S,5S)-4-{[(5-bromo-2-methoxypyridin-3-yl)methyl]amino}-1-(cyclohexanecarbonyl)-3-(2-methoxypropan-2-yl)-5-phenylpyrrolidine-2-carboxylic acid | $^1$HNMR (400 MHz, dimethyl sulfoxide-d$_6$) δ ppm 8.06 (d, J = 2.5 Hz, 1H), 7.57 (s, 2H), 7.46 (d, J = 2.4 Hz, 1H), 7.33 (t, J = 7.4 Hz, 2H), 7.27 (t, J = 7.3 Hz, 1H), 5.25 (d, J = 7.2 Hz, 1H), 4.53 (d, J = 3.3 Hz, 1H), 3.72 (d, J = 1.2 Hz, 3H), 3.57 (t, J = 5.4 Hz, 1H), 3.52 (d, J = 14.7 Hz, 1H), 3.37 (d, J = 14.7 Hz, 1H), 2.65 (s, 1H), 2.24 (bs, 1H), 1.65 (d, J = 10.0 Hz, 2H), 1.50 (d, J = 8.5 Hz, 2H), 1.20 (d, J = 5.5 Hz, 8H), 1.09 (m, 3H), 0.78 (bs, 1H); MS (ESI+) m/z 590 (M + H)+. |
| Example II-248 | (2S,3S,4S,5S)-4-{[(5-bromo-2-methoxyphenyl)methyl]amino}-1-(cyclohexanecarbonyl)-3-(2-methoxypropan-2-yl)-5-phenylpyrrolidine-2-carboxylic acid | $^1$HNMR (400 MHz, dimethyl sulfoxide-d$_6$) δ ppm 7.58 (s, 2H), 7.34 (dt, J = 18.8, 7.5 Hz, 4H), 7.16 (d, J = 2.5 Hz, 1H), 6.85 (d, J = 8.7 Hz, 1H), 5.29 (d, J = 7.3 Hz, 1H), 4.51 (d, J = 3.7 Hz, 1H), 3.71-3.68 (m, 1H), 3.65 (d, J = 14.4 Hz, 2H), 3.62 (s, 3H), 3.47 (d, J = 13.9 Hz, 1H), 3.15 (s, 3H), 2.71 (s, 1H), 2.28 (bs,1H), 1.66 (d, J = 9.7 Hz, 2H), 1.50 (bs, 2H), 1.20 (d, J = 2.9 Hz, 8H), 1.09 (s, 3H), 0.81 (bs, 1H); MS (ESI+) m/z 578 (M + H)+. |
| Example II-249 | (2S,3S,4S,5S)-3-tert-butyl-1-(cyclohexanecarbonyl)-4-{[(4-methoxy-4'-methyl[1,1'-biphenyl]-3-yl)methyl]amino}-5-phenylpyrrolidine-2-carboxylic acid | $^1$HNMR (400 MHz, dimethyl sulfoxide-d$_6$) δ ppm 7.58-7.51 (m, 3H), 7.47 (dd, J =8.5, 2.4 Hz, 1H), 7.42-7.29 (m, 5H), 7.27-7.20 (m, 3H), 6.95 (d, J =8.5 Hz, 1H), 5.31 (d, J = 6.9 Hz, 1H), 4.54 (s, 1H), 3.76 (d, J = 11.9 Hz, 2H), 3.61 (s, 3H), 3.55-3.49 (m, 1H), 2.33 (s, 3H), 1.67-1.61 (m, 2H), 1.56-1.48 (m, 2H), 1.29-1.17 (m, 2H), 1.13-1.04 (m, 2H), 1.01 (s, 9H); MS (APCI+) m/z 583.5 (M + H)+. |
| Example II-250 | (2S,3S,4S,5S)-3-tert-butyl-1-(cyclohexanecarbonyl)-4-({[2-methoxy-5-(2-methoxypyridin-3-yl)phenyl]methyl}amino)-5-phenylpyrrolidine-2-carboxylic acid | MS (APCI+) m/z 600.1 (M + H)+. |
| Example II-251 | (2S,3S,4S,5S)-4-({[5-(bicyclo[2.2.1]heptan-2-yl)-2-methoxypyridin-3-yl]methyl}amino)-1-(cyclohexanecarbonyl)-3-(2-methoxypropan-2-yl)-5-phenylpyrrolidine-2-carboxylic acid | MS (APCI+) m/z 604.1 (M + H)+. |
| Example II-252 | (2S,3S,4S,5S)-1-(cyclohexanecarbonyl)-4-{[(5-cyclohexyl-2-methoxypyridin-3-yl)methyl]amino}-3-(2-methoxypropan-2-yl)-5-phenylpyrrolidine-2-carboxylic acid | MS (APCI+) m/z 592.1 (M + H)+. |
| Example II-253 | (2S,3S,4S,5S)-1-(cyclohexanecarbonyl)-4-({[5-(cyclohexylmethyl)-2-methoxypyridin-3-yl]methyl}amino)-3-(2-methoxypropan-2-yl)-5-phenylpyrrolidine-2-carboxylic acid | MS (APCI+) m/z 606.1 (M + H)+. |

TABLE 2-continued

| | | |
|---|---|---|
| Example II-254 | (2S,3S,4S,5S)-1-(cyclohexanecarbonyl)-3-(2-methoxypropan-2-yl)-4-({[2-methoxy-5-(propan-2-yl)pyridin-3-yl]methyl}amino)-5-phenylpyrrolidine-2-carboxylic acid | MS (APCI+) m/z 552.1 (M + H)+. |
| Example II-255 | (2S,3S,4S,5S)-4-{[(5-cyclobutyl-2-methoxyphenyl)methyl]amino}-1-(cyclohexanecarbonyl)-3-(2-methoxypropan-2-yl)-5-phenylpyrrolidine-2-carboxylic acid | MS (APCI+) m/z 563.1 (M + H)+. |
| Example II-256 | (2S,3S,4S,5S)-1-(cyclohexanecarbonyl)-4-{[(5-cyclopentyl-2-methoxyphenyl)methyl]amino}-3-(2-methoxypropan-2-yl)-5-phenylpyrrolidine-2-carboxylic acid | MS (APCI+) m/z 577.0 (M + H)+. |
| Example II-257 | (2S,3S,4S,5S)-1-(cyclohexanecarbonyl)-4-{[(5-cyclohexyl-2-methoxyphenyl)methyl]amino}-3-(2-methoxypropan-2-yl)-5-phenylpyrrolidine-2-carboxylic acid | MS (APCI+) m/z 591.1 (M + H)+. |
| Example II-258 | (2S,3S,4S,5S)-1-(cyclohexanecarbonyl)-3-(2-methoxypropan-2-yl)-4-({[2-methoxy-5-(propan-2-yl)phenyl]methyl}amino)-5-phenylpyrrolidine-2-carboxylic acid | MS (APCI+) m/z 551.1 (M + H)+. |
| Example II-259 | (2S,3S,4S,5S)-3-tert-butyl-1-(cyclohexanecarbonyl)-4-{[(5-cyclopropyl-2-methoxypyridin-3-yl)methyl]amino}-5-phenylpyrrolidine-2-carboxylic acid | MS (ESI+) m/z 534 (M + H)+. |
| Example II-260 | (2S,3S,4S,5S)-3-tert-butyl-1-(cyclohexanecarbonyl)-5-(2-fluorophenyl)-4-({[2-methoxy-5-(trifluoromethyl)phenyl]methyl}amino)pyrrolidine-2-carboxylic acid | MS (ESI+) m/z 579.2 (M + H)+. |
| Example II-261 | (2S,3S,4S,5S)-3-tert-butyl-1-(cyclohexanecarbonyl)-5-(2-fluorophenyl)-4-({[2-methoxy-4-(trifluoromethyl)phenyl]methyl}amino)pyrrolidine-2-carboxylic acid | MS (ESI+) m/z 579.2 (M + H)+. |
| Example II-262 | (2S,3S,4S,5S)-4-{[(5-bromo-2-methoxyphenyl)methyl]amino}-3-tert-butyl-1-(cyclohexanecarbonyl)-5-(2-fluorophenyl)pyrrolidine-2-carboxylic acid | MS (ESI+) m/z 589.1/591.1 (M + H, 79 Br/81 Br). |
| Example II-263 | (2S,3S,4S,5S)-4-{[(5-bromo-2-methoxypyridin-3-yl)methyl]amino}-3-tert-butyl-1-(cyclohexanecarbonyl)-5-(2-fluorophenyl)pyrrolidine-2-carboxylic acid | MS (ESI+) m/z 590.1 (M + H)+. |
| Example II-264 | (2S,3S,4S,5S)-3-tert-butyl-4-{[(5-tert-butyl-2-methoxyphenyl)methyl]amino}-1-[(2-methylpropoxy)carbonyl]-5-phenylpyrrolidine-2-carboxylic acid | MS (ESI+) m/z 539 (M + H)+. |
| Example II-265 | (2S,3S,4S,5S)-3-tert-butyl-1-[(2R*)-2,3-dihydro-1-benzofuran-2-carbonyl]-4-({[2-methoxy-5-(trifluoromethyl)phenyl]methyl}amino)-5-phenylpyrrolidine-2-carboxylic acid | LC/MS (ESI+) m/z 597.7 (M + H)+. |

TABLE 2-continued

| Example | | |
|---|---|---|
| Example II-266 | (2S,3S,4S,5S)-3-tert-butyl-1-[(2S*)-2,3-dihydro-1-benzofuran-2-carbonyl]-4-({[2-methoxy-5-(trifluoromethyl)phenyl]methyl}amino)-5-phenylpyrrolidine-2-carboxylic acid | LC/MS (ESI+) m/z 597.7 (M + H)+. |
| Example II-267 | (2S,3S,4S,5S)-3-tert-butyl-4-{[(5-tert-butyl-2-methoxyphenyl)methyl]amino}-1-(2-methoxy-3-methylbutanoyl)-5-phenylpyrrolidine-2-carboxylic acid | LC/MS (ESI+) m/z 553.8 (M + H)+. |
| Example II-268 | (2S,3S,4S,5S)-3-tert-butyl-4-{[(5-tert-butyl-2-methoxyphenyl)methyl]amino}-1-[(2R*,3S*)-3-methyloxolane-2-carbonyl]-5-phenylpyrrolidine-2-carboxylic acid | LC/MS (ESI+) m/z 551.9 (M + H)+. |
| Example II-269 | (2S,3S,4S,5S)-3-tert-butyl-4-{[(5-tert-butyl-2-methoxyphenyl)methyl]amino}-1-[(2S*,3R*)-3-methyloxolane-2-carbonyl]-5-phenylpyrrolidine-2-carboxylic acid | LC/MS (ESI+) m/z 551.9 (M + H)+. |
| Example II-270 | (2S,3S,4S,5S)-3-tert-butyl-4-{[(5-tert-butyl-2-methoxyphenyl)methyl]amino}-1-[(2R*)-2-(3-chlorophenyl)-2-methoxyacetyl]-5-phenylpyrrolidine-2-carboxylic acid | LC/MS (ESI+) m/z 621.6 (M + H)+. |
| Example II-271 | (2S,3S,4S,5S)-3-tert-butyl-4-{[(5-tert-butyl-2-methoxyphenyl)methyl]amino}-1-[(2S*)-2-(3-chlorophenyl)-2-methoxyacetyl]-5-phenylpyrrolidine-2-carboxylic acid | LC/MS (ESI+) m/z 621.6 (M + H)+. |
| Example II-272 | (2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-phenylpyrrolidine-2-carboxylic acid | LC/MS (ESI+) m/z 585.8 (M + H)+. |
| Example II-273 | (2S,3S,4S,5S)-3-tert-butyl-1-(2-methoxy-3-methylbutanoyl)-4-({[2-methoxy-5-(trifluoromethyl)phenyl]methyl}amino)-5-phenylpyrrolidine-2-carboxylic acid | LC/MS (ESI+) m/z 565.7 (M + H)+. |
| Example II-274 | (2S,3S,4S,5S)-3-tert-butyl-4-({[2-methoxy-5-(trifluoromethyl)phenyl]methyl}amino)-1-[(2R*,3S*)-3-methyloxolane-2-carbonyl]-5-phenylpyrrolidine-2-carboxylic acid | LC/MS (ESI+) m/z 563.6 (M + H)+. |
| Example II-275 | (2S,3S,4S,5S)-3-tert-butyl-1-(cyclohexanecarbonyl)-4-({[2-methoxy-5-(thiophen-2-yl)phenyl]methyl}amino)-5-phenylpyrrolidine-2-carboxylic acid | MS (APCI+) m/z 575.1 (M + H)+. |
| Example II-276 | (2S,3S,4S,5S)-3-tert-butyl-1-(cyclohexanecarbonyl)-4-({[5-(furan-3-yl)-2-methoxyphenyl]methyl}amino)-5-phenylpyrrolidine-2-carboxylic acid | MS (APCI+) m/z 559.1 (M + H)+. |
| Example II-277 | (2S,3S,4S,5S)-3-tert-butyl-1-(cyclohexanecarbonyl)-4-{[(3',4'-dimethoxy[1,1'-biphenyl]-3-yl)methyl]amino}-5-phenylpyrrolidine-2-carboxylic acid | $^1$HNMR (400 MHz, dimethyl sulfoxide-$d_6$) δ ppm 7.58-7.52 (m, 4H), 7.50 (dd, J = 8.5, 2.3 Hz, 1H), 7.40-7.35 (m, 2H), 7.35-7.30 (m, 1H), 7.30-7.26 (m, 1H), 7.08 (d, J = 7.8 Hz, 1H), 7.05-7.03 (m, 1H), 6.97 (d, J = 8.5 Hz, 1H), 6.89 (dd, J = 8.3, 2.7 Hz, 1H),5.31 (d, J = 6.9 Hz, 1H), 4.55-4.53 (m, 1H), 3.83 (s, 3H), 3.79-3.73 (m, 2H), 3.63 (s, 3H), 3.53 (d, J = 14.0 Hz, 1H), 1.67-1.61 (m, 2H), 1.56-1.49 (m, 2H), 1.29-1.16 (m, 3H), 1.13-1.05 (m, 2H), 1.01 (s, 9H); MS (APCI+) m/z 599.5 (M + H)+. |

TABLE 2-continued

| Example II-278 | (2S,3S,4S,5S)-3-tert-butyl-1-(cyclohexanecarbonyl)-4-({[2-methoxy-5-(6-methylpyridin-3-yl)phenyl]methyl}amino)-5-phenylpyrrolidine-2-carboxylic acid | $^1$HNMR (400 MHz, dimethyl sulfoxide-$d_6$) δ ppm 8.62 (d, J = 2.4 Hz, 1H), 7.93 (d, J = 8.3 Hz, 1H), 7.56 (d, J = 8.2 Hz, 3H), 7.43 (d, J = 8.2 Hz, 1H), 7.38 (t, J = 7.3 Hz, 2H), 7.34-7.29 (m, 2H), 7.02 (d, J = 8.5 Hz, 1H), 5.33 (d, J = 6.9 Hz, 1H), 4.55 (d, J = 2.0 Hz, 1H), 3.80-3.74 (m, 2H), 3.66 (s, 3H), 3.52 (d, J = 13.9 Hz, 1H), 2.56 (s, 3H), 1.69-1.60 (m, 2H), 1.58-1.46 (m, 2H), 1.30-1.16 (m, 3H), 1.14-1.05 (m, 2H), 1.01 (s, 9H); MS (APCI+) m/z 584.5 (M + H)$^+$. |
|---|---|---|
| Example II-279 | (2S,3S,4S,5S)-3-tert-butyl-1-(cyclohexanecarbonyl)-4-{[(4-methoxy-2'-methyl[1,1'-biphenyl]-3-yl)methyl]amino}-5-phenylpyrrolidine-2-carboxylic acid | $^1$HNMR (400 MHz, dimethyl sulfoxide-$d_6$) δ ppm 7.55-7.50 (m, 2H), 7.33 (t, J = 7.4 Hz, 2H), 7.30-7.19 (m, 3H), 7.19-7.14 (m, 1H), 7.10-7.06 (m, 1H), 6.94 (d, J = 8.8 Hz, 2H), 5.29 (d, J = 6.8 Hz, 1H), 4.54-4.49 (m, 1H), 3.75-3.69 (m, 2H), 3.63 (s, 3H), 3.50 (d, J = 13.8 Hz, 1H), 2.46-2.43 (m, 1H), 2.16 (s, 3H), 1.67-1.61 (m, 2H), 1.56-1.48 (m, 2H), 1.29-1.17 (m, 3H), 1.13-1.04 (m, 2H), 0.99 (s, 9H); MS (APCI+) m/z 583.4 (M + H)$^+$. |
| Example II-280 | (2S,3S,4S,5S)-3-tert-butyl-1-(cyclohexanecarbonyl)-4-({[2-methoxy-5-(4-methylpyridin-3-yl)phenyl]methyl}amino)-5-phenylpyrrolidine-2-carboxylic acid | $^1$HNMR (400 MHz, dimethyl sulfoxide-$d_6$) δ ppm 8.42 (d, J = 5.2 Hz, 1H), 8.29 (s, 1H), 7.56-7.50 (m, 2H), 7.40 (d, J = 5.3 Hz, 1H), 7.33 (t, J = 7.4 Hz, 2H), 7.25 (dd, J = 15.4, 8.0 Hz, 2H), 7.00 (d, J = 8.5 Hz, 1H), 6.98-6.96 (m, 1H), 5.29 (d, J = 7.0 Hz, 1H), 4.52 (d, J = 2.1 Hz, 1H), 3.74-3.69 (m, 2H), 3.66 (s, 3H), 3.50 (d, J = 14.0 Hz, 1H), 2.46-2.43 (m, 1H), 2.24 (s, 3H), 1.68-1.61 (m, 2H), 1.55-1.48 (m, 2H), 1.29-1.17 (m, 5H), 1.14-1.05 (m, 3H), 0.99 (s, 9H); MS (APCI+) m/z 584.4 (M + H)$^+$. |
| Example II-281 | (2S,3S,4S,5S)-3-tert-butyl-4-{[(3'-cyano-4-methoxy[1,1'-biphenyl]-3-yl)methyl]amino}-1-(cyclohexanecarbonyl)-5-phenylpyrrolidine-2-carboxylic acid | $^1$HNMR (400 MHz, dimethyl sulfoxide-$d_6$) δ ppm 7.83 (d, J = 8.7 Hz, 2H), 7.72-7.60 (m, 2H), 7.56 (dd, J = 8.9, 2.7 Hz, 3H), 7.37 (t, J = 7.4 Hz, 2H), 7.35-7.27 (m, 2H), 7.01 (d, J = 8.6 Hz, 1H), 5.31 (d, J = 6.9 Hz, 1H), 4.57-4.51 (m, 1H), 3.78-3.70 (m, 2H), 3.65 (s, 3H), 3.53 (d, J = 13.7 Hz, 1H), 2.49-2.45 (m, 1H), 1.70-1.61 (m, 2H), 1.57-1.48 (m, 2H), 1.29-1.17 (m, 3H), 1.14-1.05 (m, 4H), 1.01 (s, 9H); MS (APCI+) m/z 594.4 (M + H)$^+$. |
| Example II-282 | (2S,3S,4S,5S)-3-tert-butyl-1-(cyclohexanecarbonyl)-4-{[(4'-fluoro-4-methoxy-2'-methyl[1,1'-biphenyl]-3-yl)methyl]amino}-5-phenylpyrrolidine-2-carboxylic acid | $^1$HNMR (400 MHz, dimethyl sulfoxide-$d_6$) δ ppm 7.54-7.49 (m, 2H), 7.36-7.24 (m, 3H), 7.16-6.96 (m, 5H), 6.95-6.89 (m, 2H), 5.29 (d, J = 6.9 Hz, 1H), 4.52 (d, J = 2.1 Hz, 1H), 3.71 (d, J = 9.0 Hz, 2H), 3.63 (s, 3H), 3.49 (d, J = 13.8 Hz, 1H), 2.47-2.43 (m, 1H), 2.15 (s, 3H), 1.68-1.60 (m, 2H), 1.56-1.48 (m, 2H), 1.29-1.17 (m, 3H), 1.15-1.05 (m, 2H), 0.99 (s, 10H); MS (APCI+) m/z 601.5 (M + H)$^+$. |
| Example II-283 | (2S,3S,4S,5S)-3-tert-butyl-1-(cyclohexanecarbonyl)-4-{[(2',4'-difluoro-4-methoxy[1,1'-biphenyl]-3-yl)methyl]amino}-5-phenylpyrrolidine-2-carboxylic acid | $^1$HNMR (400 MHz, dimethyl sulfoxide-$d_6$) δ ppm 7.56-7.47 (m, 2H), 7.34 (tt, J = 26.1, 8.0 Hz, 5H), 7.18-7.06 (m, 2H), 6.97 (d, J = 8.5 Hz, 1H), 5.28 (d, J = 7.1 Hz, 1H), 4.54-4.52 (m, 1H), 3.74-3.67 (m, 2H), 3.64-3.61 (m, 3H), 3.48 (d, J = 13.7 Hz, 1H), 2.47-2.43 (m, 1H), 1.68-1.61 (m, 2H), 1.57-1.48 (m, 1H), 1.31-1.17 (m, 2H), 1.15-1.05 (m, 3H), 1.00 (s, 9H); MS (APCI+) m/z 605.4 (M + H)$^+$. |
| Example II-284 | (2S,3S,4S,5S)-3-tert-butyl-1-(cyclohexanecarbonyl)-4-({[2-methoxy-5-(pyridin-3-yl)phenyl]methyl}amino)-5-phenylpyrrolidine-2-carboxylic acid | $^1$HNMR (400 MHz, dimethyl sulfoxide-$d_6$) δ ppm 8.75 (d, J = 2.4 Hz, 1H), 8.53 (dd, J = 4.9, 1.6 Hz, 1H), 7.98 (dd, J = 8.1, 2.1 Hz, 1H), 7.60 (dd, J = 9.9, 3.8 Hz, 3H), 7.52 (dd, J = 8.0, 4.9 Hz, 1H), 7.43-7.31 (m, 4H), 7.05 (d, J = 8.5 Hz, 1H), 5.37 (d, J = 7.1 Hz, 1H), 4.56 (d, J = 2.0 Hz, 1H), 3.91-3.79 (m, 2H), 3.68 (s, 3H), 3.54 (d, J = 13.8 Hz, 1H), 2.54-2.52 (m, 1H), 1.69-1.61 (m, 2H), 1.58-1.48 (m, 2H), 1.30-1.17 (m, 3H), 1.13-1.05 (m, 1H), 1.02 (s, 9H); MS (APCI+) m/z 570.4 (M + H)$^+$. |
| Example II-285 | (2S,3S,4S,5S)-3-tert-butyl-1-(cyclohexanecarbonyl)-4-({[5-(3,5-dimethyl-1,2-oxazol-4-yl)-2-methoxyphenyl]methyl}amino)-5-phenylpyrrolidine-2-carboxylic acid | $^1$HNMR (400 MHz, dimethyl sulfoxide-$d_6$) δ ppm 7.59-7.50 (m, 2H), 7.38-7.27 (m, 3H), 7.20-7.16 (m, 1H), 6.98 (d, J = 8.4 Hz, 1H), 6.96-6.93 (m, 1H), 5.31 (d, J = 7.0 Hz, 1H), 4.53 (d, J = 2.1 Hz, 1H), 3.77-3.69 (m, 2H), 3.64 (s, 3H), 3.48 (d, J = 13.6 Hz, 1H), 2.47-2.45 (m, 1H), 2.30 (s, 3H), 2.12 (s, 3H), 1.68-1.61 (m, 2H), 1.56-1.49 (m, 2H), 1.29-1.17 (m, 3H), 1.13-1.05 (m, 2H), 1.00 (s, 9H); MS (APCI+) m/z 588.5 (M + H)$^+$. |
| Example II-286 | (2S,3S,4S,5S)-3-tert-butyl-1-(cyclohexanecarbonyl)-4-{[(2',3'-difluoro-4-methoxy[1,1'-biphenyl]-3-yl)methyl]amino}-5-phenylpyrrolidine-2-carboxylic acid | $^1$HNMR (400 MHz, dimethyl sulfoxide-$d_6$) δ ppm 7.59-7.49 (m, 2H), 7.42 (d, J = 8.7 Hz, 2H), 7.38-7.22 (m, 4H), 7.20-7.15 (m, 2H), 7.00 (d, J = 8.5 Hz, 1H), 5.28 (d, J = 7.3 Hz, 1H), 4.52 (s, 1H), 3.75-3.66 (m, 2H), 3.64 (s, 3H), 3.49 (d, J = 13.2 Hz, 1H), 2.45-2.43 (m, 1H), 1.68-1.61 (m, 2H), 1.56-1.47 (m, 2H), 1.30-1.15 (m, 2H), 1.13-1.05 (m, 1H), 1.00 (s, 9H); MS (APCI+) m/z 605.4 (M + H)$^+$. |
| Example II-287 | (2S,3S,4S,5S)-3-tert-butyl-1-(cyclohexanecarbonyl)-4-({[5-(5-fluoropyridin-3-yl)-2-methoxyphenyl]methyl}amino)-5-phenylpyrrolidine-2-carboxylic acid | $^1$HNMR (400 MHz, dimethyl sulfoxide-$d_6$) δ ppm 8.61 (d, J = 1.9 Hz, 1H), 8.45 (d, J = 2.7 Hz, 1H), 7.74 (dd, J = 10.3, 2.2 Hz, 1H), 7.66-7.56 (m, 3H), 7.43-7.30 (m, 4H), 7.05 (d, J = 8.5 Hz, 1H), 5.36 (d, J = 7.1 Hz, 1H), 4.56 (d, J = 1.9 Hz, 1H), 3.88-3.78 (m, 2H), 3.69 (s, 3H), 3.54 (d, J = 13.8 Hz, 1H), 2.55-2.53 (m, 1H), 1.68-1.60 (m, 2H), 1.57-1.47 (m, 2H), 1.29-1.17 (m, 3H), 1.12-1.05 (m, 2H), 1.02 (s, 9H); MS (APCI+) m/z 588.5 (M + H)$^+$. |

TABLE 2-continued

| Example | Compound | Data |
|---|---|---|
| Example II-288 | (2S,3S,4S,5S)-3-tert-butyl-1-(cyclohexanecarbonyl)-4-({[2-methoxy-5-(2-methylpyridin-3-yl)phenyl]methyl}amino)-5-phenylpyrrolidine-2-carboxylic acid | $^1$HNMR (400 MHz, dimethyl sulfoxide-$d_6$) δ ppm 8.51 (dd, J = 5.2, 1.7 Hz, 1H), 7.77 (d, J = 8.0 Hz, 1H), 7.60-7.49 (m, 3H), 7.36 (t, J = 7.4 Hz, 2H), 7.32-7.27 (m, 2H), 7.03 (d, J = 8.2 Hz, 2H), 5.34 (d, J = 7.0 Hz, 1H), 4.54 (d, J = 2.1 Hz, 1H), 3.84-3.74 (m, 2H), 3.69 (s, 3H), 3.51 (d, J = 13.7 Hz, 1H), 2.46 (s, 3H), 1.68-1.60 (m, 2H), 1.56-1.48 (m, 2H), 1.29-1.17 (m, 2H), 1.13-1.05 (m, 2H), 1.00 (s, 9H); MS (APCI+) m/z 584.5 (M + H)$^+$. |
| Example II-289 | (2S,3S,4S,5S)-3-tert-butyl-4-{[(4'-cyano-4-methoxy[1,1'-biphenyl]-3-yl)methyl]amino}-1-(cyclohexanecarbonyl)-5-phenylpyrrolidine-2-carboxylic acid | $^1$HNMR (400 MHz, dimethyl sulfoxide-$d_6$) δ ppm 7.84-7.79 (m, 2H), 7.69 (d, J = 8.3 Hz, 2H), 7.62-7.52 (m, 3H), 7.41-7.29 (m, 4H), 7.02 (d, J = 8.6 Hz, 1H), 5.31 (d, J = 6.9 Hz, 1H), 4.54 (s, 1H), 3.77-3.72 (m, 2H), 3.66 (s, 3H), 3.51 (d, J = 13.8 Hz, 1H), 2.49-2.46 (m, 1H), 1.69-1.60 (m, 1H), 1.58-1.46 (m, 2H), 1.31-1.15 (m, 3H), 1.14-1.04 (m, 2H), 1.01 (s, 9H); MS (APCI+) m/z 594.5 (M + H)$^+$. |
| Example II-290 | (2S,3S,4S,5S)-3-tert-butyl-4-({[5-(1-cyclobutyl-1H-pyrazol-4-yl)-2-methoxyphenyl]methyl}amino)-1-(cyclohexanecarbonyl)-5-phenylpyrrolidine-2-carboxylic acid | $^1$HNMR (400 MHz, dimethyl sulfoxide-$d_6$) δ ppm 7.87 (s, 1H), 7.64 (s, 1H), 7.55 (s, 2H), 7.44-7.28 (m, 4H), 7.17 (d, J = 2.2 Hz, 1H), 6.89 (d, J = 8.5 Hz, 1H), 5.34 (d, J = 7.0 Hz, 1H), 4.87-4.74 (m, 1H), 4.55 (d, J = 1.9 Hz, 1H), 3.83-3.73 (m, 2H), 3.60 (s, 3H), 3.49 (d, J = 13.6 Hz, 1H), 2.49-2.42 (m, 3H), 1.86 (q, J = 8.9 Hz, 1H), 1.65 (s, 2H), 1.52 (s, 2H), 1.31-1.17 (m, 3H), 1.09 (s, 2H), 1.02 (s, 9H), 0.91 (d, J = 2.8 Hz, 1H); MS (APCI+) m/z 613.5 (M + H)$^+$. |
| Example II-291 | (2S,3S,4S,5S)-3-tert-butyl-1-(cyclohexanecarbonyl)-4-({[5-(furan-2-yl)-2-methoxyphenyl]methyl}amino)-5-phenylpyrrolidine-2-carboxylic acid | MS (APCI+) m/z 559.1 (M + H)$^+$. |
| Example II-292 | (2S,3S,4S,5S)-3-tert-butyl-1-(cyclohexanecarbonyl)-4-({[5-(difluoromethoxy)-2-methoxyphenyl]methyl}amino)-5-phenylpyrrolidine-2-carboxylic acid | MS (ESI+) m/z 559 (M + H)$^+$. |
| Example II-293 | (2S,3S,4S,5S)-3-tert-butyl-1-(cyclohexanecarbonyl)-4-({[5-(2,5-dihydrofuran-3-yl)-2-methoxyphenyl]methyl}amino)-5-phenylpyrrolidine-2-carboxylic acid | MS (ESI+) m/z 561.2 (M + H)$^+$. |
| Example II-294 | (2S,3S,4S,5S)-4-{[(5-tert-butyl-2-methoxyphenyl)methyl]amino}-1-(cyclohexanecarbonyl)-5-(2-methoxyphenyl)-3-(2-methoxypropan-2-yl)pyrrolidine-2-carboxylic acid | $^1$HNMR (400 MHz, dimethyl sulfoxide-$d_6$) δ ppm 7.66 (s, 1H), 7.31 (t, J = 7.8 Hz, 1H), 7.25 (dd, J = 8.6, 2.5 Hz, 1H), 7.12-7.01 (m, 2H), 6.97 (t, J = 7.5 Hz, 1H), 6.83 (d, J = 8.6 Hz, 1H), 5.59 (s, 1H), 4.52 (d, J = 3.5 Hz, 1H), 3.88-3.68 (m, 5H), 3.57 (d, J = 12.9 Hz, 4H), 3.16 (s, 3H), 2.79 (d, J = 3.5 Hz, 1H), 2.27 (m, 1H), 1.65 (d, J = 13.4 Hz, 3H), 1.53 (bs, 2H), 1.22 (m, 17H), 1.09 (m, 2H), 0.86 (bs, 1H); MS (APCI+) m/z 595 (M + H)$^+$. |
| Example II-295 | (2S,3S,4S,5S)-1-(cyclohexanecarbonyl)-5-(2-methoxyphenyl)-3-(2-methoxypropan-2-yl)-4-({[2-methoxy-5-(trifluoromethyl)phenyl]methyl}amino)pyrrolidine-2-carboxylic acid | $^1$HNMR (400 MHz, dimethyl sulfoxide-$d_6$) δ ppm 7.70 (s, 2H), 7.54 (d, J = 8.6 Hz, 1H), 7.32 (s, 1H), 7.28 (t, J = 7.9 Hz, 1H), 7.06 (d, J = 8.6 Hz, 1H), 7.01 (d, J = 8.2 Hz, 1H), 6.95 (d, J = 7.4 Hz, 1H), 5.53 (s, 1H), 4.55 (d, J = 3.0 Hz, 1H), 3.75 (s, 3H), 3.68 (m, 5H), 3.50 (d, J = 14.1 Hz, 1H), 3.15 (s, 3H), 2.72 (s, 1H), 2.20 (bs, 1H), 1.64 (m, 3H), 1.52 (bs, 2H), 1.19 (d, J = 5.6 Hz, 8H), 1.08 (bs, 2H), 0.83 (bs, 1H); MS (APCI+) m/z 607 (M + H)$^+$. |
| Example II-296 | (2S,3S,4S,5S)-3-tert-butyl-1-(cyclohexanecarbonyl)-4-{[(3-methoxy-6-phenylpyridin-2-yl)methyl]amino}-5-phenylpyrrolidine-2-carboxylic acid | MS (ESI+) m/z 570.2 (M + H)$^+$. |
| Example II-297 | (2S,3S,4S,5S)-3-tert-butyl-4-{[(5-tert-butyl-2-methoxyphenyl)methyl]amino}-1-[(2S*)-2-methoxy-3,3-dimethylbutanoyl]-5-phenylpyrrolidine-2-carboxylic acid | LC/MS (ESI+) m/z 567.8 (M + H)$^+$. |
| Example II-298 | (2S,3S,4S,5S)-3-tert-butyl-4-{[(5-tert-butyl-2-methoxyphenyl)methyl]amino}-1-[(2R*)-2-methoxy-3,3-dimethylbutanoyl]-5-phenylpyrrolidine-2-carboxylic acid | LC/MS (ESI+) m/z 567.8 (M + H)$^+$. |

TABLE 2-continued

| Example II-299 | (2S,3S,4S,5S)-3-tert-butyl-1-(3,4-dihydro-1H-2-benzopyran-3-carbonyl)-4-({[2-methoxy-5-(trifluoromethyl)phenyl]methyl}amino)-5-phenylpyrrolidine-2-carboxylic acid | LC/MS (ESI+) m/z 611.8 (M + H)+. |
|---|---|---|
| Example II-300 | (2S,3S,4S,5S)-3-tert-butyl-4-{[(5-tert-butyl-2-methoxyphenyl)methyl]amino}-1-(3,4-dihydro-1H-2-benzopyran-3-carbonyl)-5-phenylpyrrolidine-2-carboxylic acid | LC/MS (ESI+) m/z 599.9 (M + H)+. |
| Example II-301 | (2S,3S,4S,5S)-3-tert-butyl-4-{[(5-tert-butyl-2-methoxypyridin-3-yl)methyl]amino}-1-[(2,6-difluorophenyl)acetyl]-5-phenylpyrrolidine-2-carboxylic acid | MS (ESI+) m/z 594.2 (M + H)+. |
| Example II-302 | (2S,3S,4S,5S)-4-{[(5-tert-butyl-2-methoxyphenyl)methyl]amino}-1-(cyclohexanecarbonyl)-3-(1-methylcyclopropyl)-5-phenylpyrrolidine-2-carboxylic acid | $^1$HNMR (400 MHz, dimethyl sulfoxide-$d_6$) δ ppm 7.66 (d, J = 7.3 Hz, 2H), 7.34 (t, J = 7.4 Hz, 2H), 7.29 (d, J = 7.2 Hz, 1H), 7.26-7.17 (m, 2H), 6.86 (d, J = 8.5 Hz, 1H), 5.25 (d, J = 7.7 Hz, 1H), 4.22 (d, J = 8.5 Hz, 1H), 3.88 (d, J = 13.4 Hz, 1H), 3.80 (d, J = 13.6 Hz, 1H), 3.71 (s, 3H), 3.63 (t, J = 8.5 Hz, 1H), 2.19 (bs, 1H), 1.81 (bs, 1H), 1.68 (d, J = 11.4 Hz, 2H), 1.50 (m, 2H), 1.25 (d, J = 0.8 Hz, 10H), 1.21-1.03 (m, 3H), 1.00 (s, 3H), 0.75 (bs, 1H), 0.50 (d, J = 8.8 Hz, 1H), 0.32 (m, 3H); MS (APCI+) m/z 547 (M + H)+. |
| Example II-303 | (2S,3S,4S,5S)-1-(cyclohexanecarbonyl)-4-({[2-methoxy-4-(trifluoromethyl)phenyl]methyl}amino)-3-(1-methylcyclopropyl)-5-phenylpyrrolidine-2-carboxylic acid | $^1$HNMR (400 MHz, dimethyl sulfoxide-$d_6$) δ ppm 7.65 (d, J = 7.3 Hz, 2H), 7.40 (d, J = 7.8 Hz, 1H), 7.32 (t, J = 7.4 Hz, 2H), 7.26 (dd, J = 8.1, 6.1 Hz, 1H), 7.19 (d, J = 7.9 Hz, 1H), 7.16 (s, 1H), 5.21 (d, J = 7.8 Hz, 1H), 4.18 (d, J = 8.7 Hz, 1H), 3.81 (s, 5H), 3.53 (t, J = 8.7 Hz, 1H), 2.19 (bs, 1H), 1.68 (d, J = 12.5 Hz, 3H), 1.49 (m, 2H), 1.29 (q, J = 10.8, 10.0 Hz, 1H), 1.09 (q, J = 11.7 Hz, 3H), 0.98 (s, 3H), 0.77 (bs, 1H), 0.48 (d, J = 8.1 Hz, 1H), 0.34-0.24 (m, 3H); MS (APCI+) m/z 559 (M + H)+. |
| Example II-304 | (2S,3S,4S,5S)-3-tert-butyl-4-{[(5-tert-butyl-2-methoxyphenyl)methyl]amino}-5-phenyl-1-(4,4,4-trifluoro-2-methylbutanoyl)pyrrolidine-2-carboxylic acid | MS (APCI+) m/z 577.0 (M + H)+. |
| Example II-305 | (2S,3S,4S,5S)-3-tert-butyl-4-{[(5-tert-butyl-2-methoxyphenyl)methyl]amino}-1-[2-(3-fluorophenoxy)propanoyl]-5-phenylpyrrolidine-2-carboxylic acid | MS (APCI+) m/z 605.1 (M + H)+. |
| Example II-306 | (2S,3S,4S,5S)-3-tert-butyl-4-{[(5-tert-butyl-2-methoxyphenyl)methyl]amino}-1-(3-methylcyclobutane-1-carbonyl)-5-phenylpyrrolidine-2-carboxylic acid | MS (APCI+) m/z 535.1 (M + H)+. |
| Example II-307 | (2S,3S,4S,5S)-3-tert-butyl-4-{[(5-tert-butyl-2-methoxyphenyl)methyl]amino}-1-[2-(4-fluorophenyl)cyclopropane-1-carbonyl]-5-phenylpyrrolidine-2-carboxylic acid | MS (APCI+) m/z 601.1 (M + H)+. |
| Example II-308 | (2S,3S,4S,5S)-3-tert-butyl-4-{[(5-tert-butyl-2-methoxyphenyl)methyl]amino}-1-[(2S)-2-methoxypropanoyl]-5-phenylpyrrolidine-2-carboxylic acid | MS (APCI+) m/z 525.1 (M + H)+. |
| Example II-309 | (2S,3S,4S,5S)-3-tert-butyl-4-{[(5-tert-butyl-2-methoxyphenyl)methyl]amino}-1-(2,2-dimethylcyclopropane-1-carbonyl)-5-phenylpyrrolidine-2-carboxylic acid | MS (APCI+) m/z 535.1 (M + H)+. |
| Example II-310 | (2S,3S,4S,5S)-3-tert-butyl-4-{[(5-tert-butyl-2-methoxyphenyl)methyl]amino}-1-[2-(4-fluorophenoxy)propanoyl]-5-phenylpyrrolidine-2-carboxylic acid | MS (APCI+) m/z 605.1 (M + H)+. |

TABLE 2-continued

| | | |
|---|---|---|
| Example II-311 | (2S,3S,4S,5S)-3-tert-butyl-4-{[(5-tert-butyl-2-methoxyphenyl)methyl]amino}-1-[(2R)-2-methoxypropanoyl]-5-phenylpyrrolidine-2-carboxylic acid | MS (APCI+) m/z 525.1 (M + H)+. |
| Example II-312 | (2S,3S,4S,5S)-3-tert-butyl-4-{[(5-tert-butyl-2-methoxyphenyl)methyl]amino}-1-[2-(2-chlorophenoxy)propanoyl]-5-phenylpyrrolidine-2-carboxylic acid | MS (APCI+) m/z 621.1 (M + H)+. |
| Example II-313 | (2S,3S,4S,5S)-3-tert-butyl-4-{[(5-tert-butyl-2-methoxyphenyl)methyl]amino}-1-(cyclobutanecarbonyl)-5-phenylpyrrolidine-2-carboxylic acid | MS (APCI+) m/z 521.2 (M + H)+. |
| Example II-314 | (2S,3S,4S,5S)-3-tert-butyl-4-{[(5-tert-butyl-2-methoxyphenyl)methyl]amino}-1-(2,3-dihydro-1-benzothiophene-2-carbonyl)-5-phenylpyrrolidine-2-carboxylic acid | MS (APCI+) m/z 601.1 (M + H)+. |
| Example II-315 | (2S,3S,4S,5S)-3-tert-butyl-4-{[(5-tert-butyl-2-methoxyphenyl)methyl]amino}-5-phenyl-1-[(2R)-2-phenylpropanoyl]pyrrolidine-2-carboxylic acid | MS (APCI+) m/z 571.1 (M + H)+. |
| Example II-316 | (2S,3S,4S,5S)-3-tert-butyl-4-{[(5-tert-butyl-2-methoxyphenyl)methyl]amino}-1-[1-(cyclopropanecarbonyl)piperidine-4-carbonyl]-5-phenylpyrrolidine-2-carboxylic acid | MS (APCI+) m/z 618.1 (M + H)+. |
| Example II-317 | (2S,3S,4S,5S)-3-tert-butyl-4-{[(5-tert-butyl-2-methoxyphenyl)methyl]amino}-1-(8-methoxy-1,2,3,4-tetrahydronaphthalene-2-carbonyl)-5-phenylpyrrolidine-2-carboxylic acid | MS (APCI+) m/z 627.1 (M + H)+. |
| Example II-318 | (2S,3S,4S,5S)-3-tert-butyl-4-{[(5-tert-butyl-2-methoxyphenyl)methyl]amino}-1-(oxane-2-carbonyl)-5-phenylpyrrolidine-2-carboxylic acid | MS (APCI+) m/z 551.1 (M + H)+. |
| Example II-319 | (2S,3S,4S,5S)-3-tert-butyl-4-{[(5-tert-butyl-2-methoxyphenyl)methyl]amino}-1-[(2S)-2-phenoxypropanoyl]-5-phenylpyrrolidine-2-carboxylic acid | MS (APCI+) m/z 587.1 (M + H)+. |
| Example II-320 | (2S,3S,4S,5S)-3-tert-butyl-4-{[(5-tert-butyl-2-methoxyphenyl)methyl]amino}-1-(6-fluoro-3,4-dihydro-2H-1-benzopyran-2-carbonyl)-5-phenylpyrrolidine-2-carboxylic acid | MS (APCI+) m/z 617.1 (M + H)+. |
| Example II-321 | (2S,3S,4S,5S)-3-tert-butyl-4-{[(5-tert-butyl-2-methoxyphenyl)methyl]amino}-1-(cyclopent-3-ene-1-carbonyl)-5-phenylpyrrolidine-2-carboxylic acid | MS (APCI+) m/z 533.1 (M + H)+. |
| Example II-322 | (2S,3S,4S,5S)-3-tert-butyl-4-{[(5-tert-butyl-2-methoxyphenyl)methyl]amino}-1-[(2R)-oxolane-2-carbonyl]-5-phenylpyrrolidine-2-carboxylic acid | MS (APCI+) m/z 537.1 (M + H)+. |
| Example II-323 | (2S,3S,4S,5S)-3-tert-butyl-4-{[(5-tert-butyl-2-methoxyphenyl)methyl]amino}-1-[2-(2,3-dimethylphenoxy)propanoyl]-5-phenylpyrrolidine-2-carboxylic acid | MS (APCI+) m/z 615.1 (M + H)+. |

TABLE 2-continued

| | | |
|---|---|---|
| Example II-324 | (2S,3S,4S,5S)-3-tert-butyl-4-{[(5-tert-butyl-2-methoxyphenyl)methyl]amino}-1-[2-(2-fluorophenoxy)propanoyl]-5-phenylpyrrolidine-2-carboxylic acid | MS (APCI+) m/z 605.1 (M + H)+. |
| Example II-325 | (2S,3S,4S,5S)-3-tert-butyl-4-{[(5-tert-butyl-2-methoxyphenyl)methyl]amino}-5-phenyl-1-[2-(phenylsulfanyl)propanoyl]pyrrolidine-2-carboxylic acid | MS (APCI+) m/z 603.1 (M + H)+. |
| Example II-326 | (2S,3S,4S,5S)-3-tert-butyl-4-{[(5-tert-butyl-2-methoxyphenyl)methyl]amino}-5-phenyl-1-[(2S)-2-phenylpropanoyl]pyrrolidine-2-carboxylic acid | MS (APCI+) m/z 571.1 (M + H)+. |
| Example II-327 | (2S,3S,4S,5S)-3-tert-butyl-4-{[(5-tert-butyl-2-methoxyphenyl)methyl]amino}-1-(2,2-difluorocyclopropane-1-carbonyl)-5-phenylpyrrolidine-2-carboxylic acid | MS (APCI+) m/z 543.1 (M + H)+. |
| Example II-328 | (2S,3S,4S,5S)-3-tert-butyl-4-{[(5-tert-butyl-2-methoxyphenyl)methyl]amino}-1-(3,3-dimethylcyclobutane-1-carbonyl)-5-phenylpyrrolidine-2-carboxylic acid | MS (APCI+) m/z 549.1 (M + H)+. |
| Example II-329 | (2S,3S,4S,5S)-3-tert-butyl-4-{[(5-tert-butyl-2-methoxyphenyl)methyl]amino}-1-(2-ethylbutanoyl)-5-phenylpyrrolidine-2-carboxylic acid | MS (APCI+) m/z 537.2 (M + H)+. |
| Example II-330 | (2S,3S,4S,5S)-3-tert-butyl-4-{[(5-tert-butyl-2-methoxyphenyl)methyl]amino-1-[2-(3-chlorophenoxy)propanoyl]-5-phenylpyrrolidine-2-carboxylic acid | MS (APCI+) m/z 621.1 (M + H)+. |
| Example II-331 | (2S,3S,4S,5S)-3-tert-butyl-4-{[(5-tert-butyl-2-methoxyphenyl)methyl]amino}-5-phenyl-1-[2-(pyridin-4-yl)cyclopropane-1-carbonyl]pyrrolidine-2-carboxylic acid | MS (APCI+) m/z 584.1 (M + H)+. |
| Example II-332 | (2S,3S,4S,5S)-3-tert-butyl-4-{[(5-tert-butyl-2-methoxyphenyl)methyl]amino}-1-(cyclopentanecarbonyl)-5-phenylpyrrolidine-2-carboxylic acid | MS (APCI+) m/z 535.2 (M + H)+. |
| Example II-333 | (2S,3S,4S,5S)-3-tert-butyl-4-{[(5-tert-butyl-2-methoxyphenyl)methyl]amino}-1-(cyclopropanecarbonyl)-5-phenylpyrrolidine-2-carboxylic acid | MS (APCI+) m/z 507.1 (M + H)+. |
| Example II-334 | (2S,3S,4S,5S)-3-tert-butyl-4-{[(5-tert-butyl-2-methoxyphenyl)methyl]amino}-1-(3,3-difluorocyclopentane-1-carbonyl)-5-phenylpyrrolidine-2-carboxylic acid | MS (APCI+) m/z 571.1 (M + H)+. |
| Example II-335 | (2S,3S,4S,5S)-3-tert-butyl-4-{[(5-tert-butyl-2-methoxyphenyl)methyl]amino}-1-(3-fluorocyclobutane-1-carbonyl)-5-phenylpyrrolidine-2-carboxylic acid | MS (APCI+) m/z 539.1 (M + H)+. |
| Example II-336 | (2S,3S,4S,5S)-3-tert-butyl-4-{[(5-tert-butyl-2-methoxyphenyl)methyl]amino-1-[3,3-difluorocyclobutane-1-carbonyl)-5-phenylpyrrolidine-2-carboxylic acid | MS (APCI+) m/z 557.1 (M + H)+. |

TABLE 2-continued

| Example II-337 | (2S,3S,4S,5S)-3-tert-butyl-4-{[(5-tert-butyl-2-methoxyphenyl)methyl]amino}-1-(2,3-dihydro-1H-indene-1-carbonyl)-5-phenylpyrrolidine-2-carboxylic acid | MS (APCI+) m/z 583.1 (M + H)+. |
|---|---|---|
| Example II-339 | (2S,3S,4S,5S)-3-tert-butyl-4-{[(5-tert-butyl-2-methoxyphenyl)methyl]amino}-5-phenyl-1-[trans-2-phenylcyclopropane-1-carbonyl]pyrrolidine-2-carboxylic acid | MS (APCI+) m/z 583.1 (M + H)+. |
| Example II-340 | (2S,3S,4S,5S)-3-tert-butyl-1-(cyclohexanecarbonyl)-4-({[2-methoxy-5-(oxan-4-yl)phenyl]methyl}amino)-5-phenylpyrrolidine-2-carboxylic acid | MS (APCI+) m/z 577.0 (M + H)+. |
| Example II-341 | (2S,3S,4S,5S)-3-tert-butyl-1-(cyclohexanecarbonyl)-4-({[2-methoxy-5-(3-methoxyphenyl)pyridin-3-yl]methyl}amino)-5-phenylpyrrolidine-2-carboxylic acid | $^1$HNMR (400 MHz, dimethyl sulfoxide-d$_6$) δ ppm 8.26 (d, J = 2.4 Hz, 1H), 7.60-7.55 (m, 2H), 7.36 (td, J = 7.8, 2.1 Hz, 3H), 7.31-7.26 (m, 1H), 7.08 (d, J = 7.7 Hz, 1H), 7.04 (t, J = 2.1 Hz, 1H), 6.93 (dd, J = 8.2, 2.5 Hz, 1H), 5.30 (d, J = 7.0 Hz, 1H), 4.53 (d, J = 2.1 Hz, 1H), 3.82 (s, 3H), 3.76 (s, 3H), 3.71 (d, J = 7.8 Hz, 1H), 3.44 (d, J = 14.3 Hz, 1H), 2.47-2.44 (m, 1H), 1.64 (s, 2H), 1.49 (s, 2H), 1.22 (d, J = 12.3 Hz, 3H), 1.11-1.03 (m, 3H), 1.02 (s, 1H), 1.00 (s, 9H); MS (APCI+) m/z 600.1 (M + H)+. |
| Example II-342 | (2S,3S,4S,5S)-3-tert-butyl-1-(cyclohexanecarbonyl)-4-({[2-methoxy-5-(2-methylphenyl)pyridin-3-yl]methyl}amino)-5-phenylpyrrolidine-2-carboxylic acid | $^1$HNMR (400 MHz, dimethyl sulfoxide-d$_6$) δ ppm 7.92 (d, J = 2.1 Hz, 1H), 7.56-7.51 (m, 2H), 7.34-7.22 (m, 6H), 7.08 (dd, J = 7.1, 1.4 Hz, 1H), 5.26 (d, J = 7.0 Hz, 1H), 4.50 (d, J = 2.2 Hz, 1H), 3.76 (s, 3H), 3.67-3.58 (m, 2H), 3.40 (d, J = 14.3 Hz, 1H), 2.42-2.36 (m, 1H), 2.15 (s, 3H), 1.66-1.59 (m, 2H), 1.54-1.45 (m, 2H), 1.28-1.15 (m, 3H), 1.06 (s, 2H), 0.97 (s, 9H); MS (APCI+) m/z 584.1 (M + H)+. |
| Example II-343 | (2S,3S,4S,5S)-3-tert-butyl-1-(cyclohexanecarbonyl)-4-({[5-(4-fluoro-2-methylphenyl)-2-methoxypyridin-3-yl]methyl}amino)-5-phenylpyrrolidine-2-carboxylic acid | $^1$HNMR (400 MHz, dimethyl sulfoxide-d$_6$) δ ppm 7.89 (d, J = 2.3 Hz, 1H), 7.55-7.50 (m, 3H), 7.32-7.20 (m, 4H), 7.14-7.06 (m, 2H), 7.05-6.98 (m, 1H), 5.24 (m, 1H), 4.49 (d, J = 2.1 Hz, 1H), 3.74 (s, 3H), 3.61-3.55 (m, 2H), 3.39 (d, J = 14.3 Hz, 1H), 2.39-2.35 (m, 1H), 2.14 (s, 3H), 1.66-1.59 (m, 2H), 1.53-1.46 (m, 2H), 1.26-1.15 (m, 3H), 1.11-1.04 (m, 2H), 0.97 (s, 9H); MS (APCI+) m/z 602.1 (M + H)+. |
| Example II-344 | (2S,3S,4S,5S)-3-tert-butyl-1-(cyclohexanecarbonyl)-4-({[5-(2,4-difluorophenyl)-2-methoxypyridin-3-yl]methyl}amino)-5-phenylpyrrolidine-2-carboxylic acid | $^1$HNMR (400 MHz, dimethyl sulfoxide-d$_6$) δ ppm 8.15-8.08 (m, 1H), 7.59-7.51 (m, 2H), 7.46-7.39 (m, 2H), 7.31 (t, J = 2H), 7.28-7.23 (m, 2H), 7.22-7.09 (m, 2H), 5.22 (d, J = 7.0 Hz, 1H), 4.50 (d, J = 2.3 Hz, 1H), 3.74 (s, 3H), 3.61-3.54 (m, 2H), 3.39 (d, J = 14.4 Hz, 1H), 2.41-2.36 (m, 1H), 1.68-1.60 (m, 2H), 1.55-1.47 (m, 2H), 1.27-1.15 (m, 3H), 1.10-1.03 (m, 2H), 0.99 (s, 9H); MS (APCI+) m/z 606.1 (M + H)+. |
| Example II-345 | (2S,3S,4S,5S)-3-tert-butyl-1-(cyclohexanecarbonyl)-4-{[(6-methoxy[3,3'-bipyridin]-5-yl)methyl]amino}-5-phenylpyrrolidine-2-carboxylic acid | $^1$HNMR (400 MHz, dimethyl sulfoxide-d$_6$) δ ppm 8.76-8.71 (m, 1H), 8.56 (d, J = 5.2 Hz, 1H), 8.32 (d, J +32 2.4 Hz, 1H), 7.95 (d, J = 8.5 Hz, 1H), 7.63-7.58 (m, 1H), 7.59-7.55 (m, 2H), 7.51 (dd, J = 8.1, 4.9 Hz, 1H), 7.34 (t, J = 7.4 Hz, 2H), 7.28 (d, J = 7.2 Hz, 1H), 5.28 (d, J = 7.0 Hz, 1H), 4.52 (d, J = 2.1 Hz, 1H), 3.77 (s, 3H), 3.68-3.62 (m, 2H), 3.44 (d, J = 14.5 Hz, 1H), 2.44-2.41 (m, 1H), 1.66-1.59 (m, 2H), 1.53-1.46 (m, 2H), 1.29-1.16 (m, 3H), 1.09-1.04 (m, 2H), 0.99 (s, 9H); MS (APCI+) m/z 571.1 (M + H)+. |
| Example II-346 | (2S,3S,4S,5S)-3-tert-butyl-1-(cyclohexanecarbonyl)-4-({[5-(2,3-difluorophenyl)-2-methoxypyridin-3-yl]methyl}amino)-5-phenylpyrrolidine-2-carboxylic acid | $^1$HNMR (400 MHz, dimethyl sulfoxide-d$_6$) δ ppm 8.16 (d, J = 2.2 Hz, 1H), 7.60-7.50 (m, 3H), 7.46 (d, J = 1.9 Hz, 2H), 7.37-7.15 (m, 7H), 5.26-5.19 (m, 1H), 4.54-4.47 (m, 1H), 3.75 (s, 3H), 3.62-3.52 (m, 2H), 3.39 (d, J = 14.3 Hz, 1H), 2.41-2.35 (m, 1H), 1.66-1.60 (m, 3H), 1.55-1.45 (m, 2H), 1.29-1.14 (m, 3H), 1.05 (s, 3H), 0.98 (s, 9H); MS (APCI+) m/z 606.1 (M + H)+. |
| Example II-347 | (2S,3S,4S,5S)-3-tert-butyl-1-(cyclohexanecarbonyl)-4-({[2-methoxy-5-(4-methylphenyl)pyridin-3-yl]methyl}amino)-5-phenylpyrrolidine-2-carboxylic acid | $^1$HNMR (400 MHz, dimethyl sulfoxide-d$_6$) δ ppm 8.23 (d, J = 2.4 Hz, 1H), 7.60-7.54 (m, 3H), 7.43-7.33 (m, 4H), 7.29 (dd, J = 15.2, 7.6 Hz, 3H), 5.29 (d, J +32 6.9 Hz, 1H), 4.53 (d, J = 2.2 Hz, 1H), 3.75 (s, 3H), 3.69-3.62 (m, 2H), 3.44 (d, J = 14.3 Hz, 1H), 2.46-2.42 (m, 1H), 2.35 (s, 3H), 1.68-1.60 (m, 2H), 1.56-1.46 (m, 2H), 1.29-1.16 (m, 3H), 1.14-1.04 (m, 2H), 1.00 (s, 9H); MS (APCI+) m/z 584.1 (M + H)+. |
| Example II-348 | (2S,3S,4S,5S)-3-tert-butyl-1-(cyclohexanecarbonyl)-4-{[(6-methoxy-2'-methyl[3,3'-bipyridin]-5-yl)methyl]amino}- | $^1$HNMR (400 MHz, dimethyl sulfoxide-d$_6$) δ ppm 8.53 (dd, J = 5.1, 1.6 Hz, 1H), 8.03 (d, J = 2.4 Hz, 1H), 7.75 (d, J = 7.8 Hz, 1H), 7.56 (d, J = 7.1 Hz, 2H), 7.52-7.48 (m, 1H), 7.36-7.29 (m, 3H), 7.28-7.22 (m, 1H), |

TABLE 2-continued

| | | |
|---|---|---|
| | 5-phenylpyrrolidine-2-carboxylic acid | 5.29 (d, J = 7.0 Hz, 1H), 4.52 (d, J = 2.3 Hz, 1H), 3.80 (s, 3H), 3.69-3.61 (m, 2H), 3.43 (d, J = 14.4 Hz, 1H), 2.44 (s, 3H), 2.43-2.40 (m, 1H), 1.68-1.60 (m, 2H), 1.55-1.47 (m, 2H), 1.30-1.16 (m, 3H), 1.12-1.04 (m, 2H), 0.99 (s, 9H); MS (APCI+) m/z 585.1 (M + H)$^+$. |
| Example II-349 | (2S,3S,4S,5S)-3-tert-butyl-1-(cyclohexanecarbonyl)-4-({[5-(3,6-dihydro-2H-pyran-4-yl)-2-methoxypyridin-3-yl]methyl}amino)-5-phenylpyrrolidine-2-carboxylic acid | $^1$HNMR (400 MHz, dimethyl sulfoxide-d$_6$) δ ppm 8.04 (d, J = 2.5 Hz, 1H), 7.60-7.50 (m, 3H), 7.39-7.26 (m, 4H), 6.06-6.02 (m, 1H), 5.28 (d, J = 6.9 Hz, 1H), 4.53 (d, J = 2.1 Hz, 1H), 4.21 (q, J = 2.9 Hz, 2H), 3.83 (t, J = 5.5 Hz, 2H), 3.72 (s, 3H), 3.67-3.58 (m, 2H), 3.42-3.36 (m, 1H), 2.44-2.41 (m, 1H), 2.39-2.34 (m, 2H), 1.68-1.60 (m, 2H), 1.56-1.47 (m, 2H), 1.30-1.17 (m, 4H), 1.14-1.04 (m, 2H), 1.00 (s, 9H); MS (APCI+) m/z 576.1 (M + H)$^+$. |
| Example II-350 | (2S,3S,4S,5S)-3-tert-butyl-1-(cyclohexanecarbonyl)-4-({[5-(2,5-dihydrofuran-3-yl)-2-methoxypyridin-3-yl]methyl}amino)-5-phenylpyrrolidine-2-carboxylic acid | $^1$HNMR (400 MHz, dimethyl sulfoxide-d$_6$) δ ppm 7.99 (d, J = 2.4 Hz, 1H), 7.59-7.53 (m, 2H), 7.40-7.26 (m, 4H), 6.24-6.23 (m, 1H), 5.27 (d, J = 6.9 Hz, 1H), 4.80 (tt, J = 4.8, 2.1 Hz, 2H), 4.73-4.68 (m, 2H), 4.53 (d, J = 2.1 Hz, 1H), 3.72 (s, 3H), 3.64-3.56 (m, 2H), 3.37 (d, J = 14.4 Hz, 1H), 2.43-2.40 (m, 1H), 1.68-1.60 (m, 2H), 1.55-1.47 (m, 2H), 1.30-1.17 (m, 3H), 1.12-1.04 (m, 2H), 1.00 (s, 9H); MS (APCI+) m/z 562.0 (M + H)$^+$. |
| Example II-351 | (2S,3S,4S,5S)-3-tert-butyl-4-{[(5-tert-butyl-2-methoxypyridin-3-yl)methyl]amino}-1-(cyclohexanecarbonyl)-5-(2-fluorophenyl)pyrrolidine-2-carboxylic acid | MS (ESI+) m/z 568.3 (M + H)$^+$. |
| Example II-352 | (2S,3S,4S,5S)-3-tert-butyl-1-(cyclohexanecarbonyl)-4-{[(5-cyclopropyl-2-methoxyphenyl)methyl]amino}-5-phenylpyrrolidine-2-carboxylic acid | MS (ESI+) m/z 533 (M + H)$^+$. |
| Example II-353 | (2S,3S,4S,5S)-3-tert-butyl-1-(cyclohexanecarbonyl)-5-(2-fluorophenyl)-4-[({2-methoxy-5-{1-(trifluoromethyl)cyclopropyl]phenyl}methyl)amino]pyrrolidine-2-carboxylic acid | MS (ESI+) m/z 619 (M + H)$^+$. |
| Example II-354 | (2S,3S,4S,5S)-3-tert-butyl-4-{[(5-tert-butyl-2-methoxyphenyl)methyl]amino}-1-[1-(4-fluorophenyl)-5-methyl-1H-1-pyrazole-4-carbonyl]-5-phenylpyrrolidine-2-carboxylic acid | MS (APCI+) m/z 641.0 (M + H)$^+$. |
| Example II-355 | (2S,3S,4S,5S)-3-tert-butyl-1-(1-tert-butyl-5-cyano-1H-pyrazole-4-carbonyl)-4-{[(5-tert-butyl-2-methoxyphenyl)methyl]amino}-5-phenylpyrrolidine-2-carboxylic acid | MS (APCI+) m/z 614.1 (M + H)$^+$. |
| Example II-356 | (2S,3S,4S,5S)-3-tert-butyl-4-{[(5-tert-butyl-2-methoxyphenyl)methyl]amino-1-[1-(2,4-difluorophenyl)-5-methyl-1H-pyrazole-4-carbonyl]-5-phenylpyrrolidine-2-carboxylic acid | MS (APCI+) m/z 659.0 (M + H)$^+$. |
| Example II-357 | (2S,3S,4S,5S)-3-tert-butyl-4-{[(5-tert-butyl-2-methoxyphenyl)methyl]amino}-1-[1-(4-methoxyphenyl)-5-methyl-1H-pyrazole-4-carbonyl]-5-phenylpyrrolidine-2-carboxylic acid | MS (APCI+) m/z 653.1 (M + H)$^+$. |
| Example II-358 | (2S,3S,4S,5S)-3-tert-butyl-4-{[(5-tert-butyl-2-methoxyphenyl)methyl]amino}-1-(1-methyl-5-phenyl-1H-pyrazole-4-carbonyl)-5-phenylpyrrolidine-2-carboxylic acid | MS (APCI+) m/z 623.1 (M + H)$^+$. |

TABLE 2-continued

| Example II-359 | (2S,3S,4S,5S)-3-tert-butyl-4-{[(5-tert-butyl-2-methoxyphenyl)methyl]amino}-1-[5-ethyl-1-(4-fluorophenyl)-3-methyl-1H-pyrazole-4-carbonyl]-5-phenylpyrrolidine-2-carboxylic acid | MS (APCI+) m/z 669.1 (M + H)+. |
|---|---|---|
| Example II-360 | (2S,3S,4S,5S)-3-tert-butyl-4-{[(5-tert-butyl-2-methoxyphenyl)methyl]amino}-1-[1-tert-butyl-5-(trifluoromethyl)-1H-pyrazole-4-carbonyl]-5-phenylpyrrolidine-2-carboxylic acid | MS (APCI+) m/z 657.0 (M + H)+. |
| Example II-361 | (2S,3S,4S,5S)-3-tert-butyl-4-{[(5-tert-butyl-2-methoxyphenyl)methyl]amino}-1-(5-methyl-1-phenyl-1H-pyrazole-4-carbonyl)-5-phenylpyrrolidine-2-carboxylic acid | MS (APCI+) m/z 623.1 (M + H)+. |
| Example II-362 | (2S,3S,4S,5S)-3-tert-butyl-4-{[(5-tert-butyl-2-methoxyphenyl)methyl]amino}-1-(1-ethyl-3,5-dimethyl-1H-pyrazole-4-carbonyl)-5-phenylpyrrolidine-2-carboxylic acid | MS (APCI+) m/z 589.2 (M + H)+. |
| Example II-363 | (2S,3S,4S,5S)-3-tert-butyl-4-{[(5-tert-butyl-2-methoxyphenyl)methyl]amino}-1-(2-methyl-4,5,6,7-tetrahydropyrazolo[1,5-a]pyridine-3-carbonyl)-5-phenylpyrrolidine-2-carboxylic acid | MS (APCI+) m/z 601.1 (M + H)+. |
| Example II-364 | (2S,3S,4S,5S)-3-tert-butyl-4-{[(5-tert-butyl-2-methoxyphenyl)methyl]amino}-5-phenyl-1-(4,5,6,7-tetrahydropyrazolo[1,5-a]pyridine-3-carbonyl)pyrrolidine-2-carboxylic acid | MS (APCI+) m/z 587.1 (M + H)+. |
| Example II-365 | (2S,3S,4S,5S)-3-tert-butyl-4-{[(5-tert-butyl-2-methoxyphenyl)methyl]amino}-1-(5-methoxy-2,3-dihydro-1H-indene-1-carbonyl)-5-phenylpyrrolidine-2-carboxylic acid | MS (APCI+) m/z 613.1 (M + H)+. |
| Example II-366 | (2S,3S,4S,5S)-3-tert-butyl-4-{[(5-tert-butyl-2-methoxyphenyl)methyl]amino}-1-[(1R)-4-methoxy-1-methyl-2,3-dihydro-1H-indene-1-carbonyl]-5-phenylpyrrolidine-2-carboxylic acid | MS (APCI+) m/z 627.1 (M + H)+. |
| Example II-367 | (2S,3S,4S,5S)-3-tert-butyl-4-{[(5-tert-butyl-2-methoxyphenyl)methyl]amino}-1-(4-chloro-1-methyl-2,3-dihydro-1H-indene-1-carbonyl)-5-phenylpyrrolidine-2-carboxylic acid | MS (APCI+) m/z 631.1 (M + H)+. |
| Example II-368 | (2S,3S,4S,5S)-3-tert-butyl-4-{[(5-tert-butyl-2-methoxyphenyl)methyl]amino}-1-(1-methyl-2,3-dihydro-1H-indene-1-carbonyl)-5-phenylpyrrolidine-2-carboxylic acid | MS (APCI+) m/z 597.1 (M + H)+. |
| Example II-369 | (2S,3S,4S,5S)-3-tert-butyl-4-{[(5-tert-butyl-2-methoxyphenyl)methyl]amino}-1-(5-chloro-2,3-dihydro-1H-indene-1-carbonyl)-5-phenylpyrrolidine-2-carboxylic acid | MS (APCI+) m/z 617.1 (M + H)+. |
| Example II-370 | (2S,3S,4S,5S)-3-tert-butyl-4-{[(5-tert-butyl-2-methoxyphenyl)methyl]amino}-5-phenyl-1-(3-phenyl-2,3-dihydro-1-benzofuran-3-carbonyl)pyrrolidine-2-carboxylic acid | MS (APCI+) m/z 661.1 (M + H)+. |

TABLE 2-continued

| Example II-371 | (2S,3S,4S,5S)-3-tert-butyl-4-{[(5-tert-butyl-2-methoxyphenyl)methyl]amino}-1-(3-hydroxy-3-methylpentanoyl)-5-phenylpyrrolidine-2-carboxylic acid | MS (APCI+) m/z 553.2 (M + H)+. |
|---|---|---|
| Example II-372 | (2S,3S,4S,5S)-3-tert-butyl-4-{[(5-tert-butyl-2-methoxyphenyl)methyl]amino}-1-(3-hydroxy-3,4-dimethylpentanoyl)-5-phenylpyrrolidine-2-carboxylic acid | MS (APCI+) m/z 567.2 (M + H)+. |
| Example II-373 | (2S,3S,4S,5S)-3-tert-butyl-4-{[(6-tert-butyl-3-methoxypyridin-2-yl)methyl]amino}-1-(cyclohexanecarbonyl)-5-phenylpyrrolidine-2-carboxylic acid | MS (ESI+) m/z 550.3 (M + H)+. |
| Example II-374 | (2S,3S,4S,5S)-3-tert-butyl-4-{[(5-tert-butyl-2-methoxyphenyl)methyl]amino}-5-phenyl-1-[4-(trifluoromethyl)cyclohexane-l-carbonyl]pyrrolidine-2-carboxylic acid | MS (APCI+) m/z 617.1 (M + H)+. |
| Example II-375 | (2S,3S,4S,5S)-3-tert-butyl-4-{[(5-tert-butyl-2-methoxyphenyl)methyl]amino}-1-[(1s,3R,5S)-3,5-dimethylcyclohexane-1-carbonyl]-5-phenylpyrrolidine-2-carboxylic acid | MS (APCI+) m/z 577.1 (M + H)+. |
| Example II-376 | (2S,3S,4S,5S)-3-tert-butyl-4-{[(5-tert-butyl-2-methoxyphenyl)methyl]amino}-5-phenyl-1-(4,7,7-trimethylbicyclo[4.1.0]heptane-3-carbonyl)pyrrolidine-2-carboxylic acid | MS (APCI+) m/z 603.2 (M + H)+. |
| Example II-377 | (2S,3S,4S,5S)-3-tert-butyl-4-{[(5-tert-butyl-2-methoxyphenyl)methyl]amino}-1-(4,4-difluorocyclohexane-1-carbonyl)-5-phenylpyrrolidine-2-carboxylic acid | MS (APCI+) m/z 585.1 (M + H)+. |
| Example II-378 | (2S,3S,4S,5S)-3-tert-butyl-4-{[(5-tert-butyl-2-methoxyphenyl)methyl]amino}-5-phenyl-1-[2-(trifluoromethyl)cyclohexane-l-carbonyl]pyrrolidine-2-carboxylic acid | MS (APCI+) m/z 617.1 (M + H)+. |
| Example II-379 | (2S,3S,4S,5S)-3-tert-butyl-4-{[(5-tert-butyl-2-methoxyphenyl)methyl]amino}-1-[trans-4-hydroxy-4-(prop-2-en-1-yl)cyclohexane-1-carbonyl]-5-phenylpyrrolidine-2-carboxylic acid | MS (APCI+) m/z 605.2 (M + H)+. |
| Example II-380 | (2S,3S,4S,5S)-3-tert-butyl-4-{[(5-tert-butyl-2-methoxyphenyl)methyl]amino}-1-(trans-4-ethyl-4-hydroxycyclohexane-1-carbonyl)-5-phenylpyrrolidine-2-carboxylic acid | MS (APCI+) m/z 593.1 (M + H)+. |
| Example II-381 | (2S,3S,4S,5S)-3-tert-butyl-4-{[(5-tert-butyl-2-methoxyphenyl)methyl]amino}-1-[trans-4-hydroxy-4-(propan-2-yl)cyclohexane-1-carbonyl]-5-phenylpyrrolidine-2-carboxylic acid | MS (APCI+) m/z 607.2 (M + H)+. |
| Example II-382 | (2S,3S,4S,5S)-3-tert-butyl-4-{[(5-tert-butyl-2-methoxyphenyl)methyl]amino}-1-(trans-4-hydroxy-4-propylcyclohexane-1-carbonyl)-5-phenylpyrrolidine-2-carboxylic acid | MS (APCI+) m/z 607.2 (M + H)+. |
| Example II-383 | (2S,3S,4S,5S)-1-(butoxycarbonyl)-3-tert-butyl-4-{[(5-tert-butyl-2-methoxyphenyl)methyl]amino}-5-phenylpyrrolidine-2-carboxylic acid | MS (APCI) m/z 539.2 (M + H)+. |

TABLE 2-continued

| Example | Name | MS |
|---|---|---|
| Example II-384 | (2S,3S,4S,5S)-3-tert-butyl-4-{[(5-tert-butyl-2-methoxyphenyl)methyl]amino}-5-phenyl-1-{[(prop-2-yn-1-yl)oxy]carbonyl}pyrrolidine-2-carboxylic acid | MS (APCI) m/z 521.1 (M + H)+. |
| Example II-385 | (2S,3S,4S,5S)-3-tert-butyl-4-{[(5-tert-butyl-2-methoxyphenyl)methyl]amino}-1-[(pentyloxy)carbonyl]-5-phenylpyrrolidine-2-carboxylic acid | MS (APCI) m/z 553.2 (M + H)+. |
| Example II-386 | (2S,3S,4S,5S)-3-tert-butyl-4-{[(5-tert-butyl-2-methoxyphenyl)methyl]amino}-1-({[(1S,2R,5S)-5-methyl-2-(propan-2-yl)cyclohexyl]oxy}carbonyl)-5-phenylpyrrolidine-2-carboxylic acid | MS (APCI) m/z 621.2 (M + H)+. |
| Example II-387 | (2S,3S,4S,5S)-1-{[(but-3-en-1-yl)oxy]carbonyl}-3-tert-butyl-4-{[(5-tert-butyl-2-methoxyphenyl)methyl]amino}-5-phenylpyrrolidine-2-carboxylic acid | MS (APCI) m/z 537.1 (M + H)+. |
| Example II-388 | (2S,3S,4S,5S)-3-tert-butyl-4-{[(5-tert-butyl-2-methoxyphenyl)methyl]amino}-1-(methoxycarbonyl)-5-phenylpyrrolidine-2-carboxylic acid | MS (APCI) m/z 497.0 (M + H)+. |
| Example II-389 | (2S,3S,4S,5S)-3-tert-butyl-4-{[(5-tert-butyl-2-methoxyphenyl)methyl]amino}-1-{[(but-2-yn-1-yl)oxy]carbonyl}-5-phenylpyrrolidine-2-carboxylic acid | MS (APCI) m/z 535.1 (M + H)+. |
| Example II-390 | (2S,3S,4S,5S)-3-tert-butyl-4-{[(5-tert-butyl-2-methoxyphenyl)methyl]amino}-5-phenyl-1-(propoxycarbonyl)pyrrolidine-2-carboxylic acid | MS (APCI) m/z 525.1 (M + H)+. |
| Example II-391 | (2S,3S,4S,5S)-3-tert-butyl-4-{[(5-tert-butyl-2-methoxyphenyl)methyl]amino}-5-phenyl-1-{[(prop-2-en-1-yl)oxy]carbonyl}pyrrolidine-2-carboxylic acid | MS (APCI) m/z 523.1 (M + H)+. |
| Example II-392 | (2S,3S,4S,5S)-3-tert-butyl-4-{[(5-tert-butyl-2-methoxyphenyl)methyl]amino}-1-[(2,2-dimethylpropoxy)carbonyl]-5-phenylpyrrolidine-2-carboxylic acid | MS (APCI) m/z 553.2 (M + H)+. |
| Example II-393 | (2S,3R,4R,5S)-3-tert-butyl-4-{[(5-tert-butyl-2-methoxyphenyl)methyl]amino}-1-[(2R)-2-methoxy-2-phenylacetyl]-5-phenylpyrrolidine-2-carboxylic acid | LC/MS (ESI+) m/z 587.7 (M + H)+. |
| Example II-394 | (2S,3S,4S,5S)-3-tert-butyl-1-(cyclohexanecarbonyl)-4-{[(1-methoxycyclohexyl)methyl]amino}-5-phenylpyrrolidine-2-carboxylic acid | LC/MS (ESI+) m/z 499.8 (M + H)+. |
| Example II-395 | (2S,3R,4R,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid | LC/MS (ESI+) m/z 599.4 (M + H)+. |
| Example II-396 | (2S,3S,4S,5S)-3-tert-butyl-4-{[(5-tert-butyl-2-methoxyphenyl)methyl]amino}-1-[(2S)-2-(3,4-difluorophenyl)-2-methoxyacetyl]-5-phenylpyrrolidine-2-carboxylic acid | LC/MS (ESI+) m/z 623.9 (M + H)+. |

TABLE 2-continued

| | | |
|---|---|---|
| Example II-397 | (2S,3S,4S,5S)-3-tert-butyl-4-({[2-methoxy-5-(trifluoromethyl)phenyl]methyl}amino)-1-(6-methyl-3,4-dihydro-2H-1-benzopyran-2-carbonyl)-5-phenylpyrrolidine-2-carboxylic acid | LC/MS (ESI+) m/z 625.5 (M + H)+. |
| Example II-398 | (2S,3S,4S,5S)-3-tert-butyl-1-(7-fluoro-3,4-dihydro-2H-1-benzopyran-2-carbonyl)-4-({[2-methoxy-5-(trifluoromethyl)phenyl]methyl}amino)-5-phenylpyrrolidine-2-carboxylic acid | LC/MS (ESI+) m/z 629.5 (M + H)+. |
| Example II-399 | (2S,3S,4S,5S)-3-tert-butyl-1-[2-(4-chlorophenoxy)-3-methylbutanoyl]-4-({[2-methoxy-5-(trifluoromethyl)phenyl]methyl}amino)-5-phenylpyrrolidine-2-carboxylic acid | LC/MS (ESI+) m/z 661.5 (M + H)+. |
| Example II-400 | (2S,3S,4S,5S)-3-tert-butyl-4-({[5-(1-cyanocyclopropyl)-2-methoxyphenyl]methyl}amino)-1-(cyclohexanecarbonyl)-5-phenylpyrrolidine-2-carboxylic acid | LC/MS (ESI+) m/z 558.9 (M + H)+. |
| Example II-401 | (2S,3S,4S,5S)-3-tert-butyl-4-{[(5-tert-butyl-2-methoxyphenyl)methyl]amino}-1-(3,3-dimethylcyclopentane-1-carbonyl)-5-phenylpyrrolidine-2-carboxylic acid | LC/MS (ESI+) m/z 563.9 (M + H)+. |
| Example II-402 | (2S,3S,4S,5S)-3-tert-butyl-4-{[(5-tert-butyl-2-methoxyphenyl)methyl]amino}-1-(8-methoxy-3,4-dihydro-2H-1-benzopyran-3-carbonyl)-5-phenylpyrrolidine-2-carboxylic acid | MS (APCI+) m/z 629.3 (M + H)+. |
| Example II-403 | (2S,3S,4S,5S)-4-({[2-(bicyclo[2.2.1]heptan-2-yl)-5-methoxypyridin-4-yl]methyl}amino)-3-tert-butyl-1-(cyclohexanecarbonyl)-5-phenylpyrrolidine-2-carboxylic acid | MS (APCI+) m/z 588.2 (M + H)+. |
| Example II-404 | (2S,3S,4S,5S)-3-tert-butyl-1-(cyclohexanecarbonyl)-4-{[(2-cyclohexyl-5-methoxypyridin-4-yl)methyl]amino}-5-phenylpyrrolidine-2-carboxylic acid | MS (APCI+) m/z 576.2 (M + H)+. |
| Example II-405 | (2S,3S,4S,5S)-3-tert-butyl-1-(cyclohexanecarbonyl)-5-[2-(dimethylamino)pyridin-3-yl]-4-({[5-(2-fluorophenyl)-2-methoxypyridin-3-yl]methyl}amino)pyrrolidine-2-carboxylic acid | MS (APCI+) m/z 632.1 (M + H)+. |
| Example II-406 | (2S,3S,4S,5S)-3-tert-butyl-1-(cyclohexanecarbonyl)-4-({[5-(2,4-difluorophenyl)-2-methoxypyridin-3-yl]methyl}amino)-5-[2-(dimethylamino)pyridin-3-yl]pyrrolidine-2-carboxylic acid | MS (APCI+) m/z 650.1 (M + H)+. |
| Example II-407 | (2S,3S,4S,5S)-3-tert-butyl-1-(cyclohexanecarbonyl)-4-{[(2,6-dimethoxyphenyl)methyl]amino}-5-phenylpyrrolidine-2-carboxylic acid | MS (ESI+) m/z 523 (M + H)+. |
| Example II-408 | (2S,3S,4S,5S)-3-tert-butyl-1-(cyclohexanecarbonyl)-4-({[3-methoxy-6-(trifluoromethyl)pyridin-2-yl]methyl}amino)-5-phenylpyrrolidine-2-carboxylic acid | MS (ESI+) m/z 562.2 (M + H)+. |

TABLE 2-continued

| | | |
|---|---|---|
| Example II-409 | (2S,3S,4S,5S)-3-tert-butyl-1-(cyclohexanecarbonyl)-5-[2-(dimethylamino)pyridin-3-yl]-4-({[5-(4-fluoro-2-methylphenyl)-2-methoxypyridin-3-yl]methyl}amino)pyrrolidine-2-carboxylic acid | MS (APCI+) m/z 646.4 (M + H)+. |
| Example II-410 | (2S,3S,4S,5S)-3-tert-butyl-1-(cyclohexanecarbonyl)-5-[2-(dimethylamino)pyridin-3-yl]-4-({[2-methoxy-5-(4-methylphenyl)pyridin-3-yl]methyl}amino)pyrrolidine-2-carboxylic acid | MS (APCI+) m/z 628.3 (M + H)+. |
| Example II-411 | (2S,3S,4S,5S)-3-tert-butyl-4-{[(5-tert-butyl-2-methoxyphenyl)methyl]amino}-1-(2-fluorocyclohex-1-ene-1-carbonyl)-5-phenylpyrrolidine-2-carboxylic acid | LC/MS (ESI+) m/z 565.5 (M + H)+. |
| Example II-412 | (2S,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid | LC/MS (ESI+) m/z 549.8 (M + H)+. |
| Example II-413 | (2S,3R,4R,5S)-3-tert-butyl-1-(cyclohexanecarbonyl)-4-({[2-methoxy-5-(trifluoromethyl)phenyl]methyl}amino)-5-phenylpyrrolidine-2-carboxylic acid | LC/MS (ESI+) m/z 561.6 (M + H)+. |
| Example II-414 | (2S,3S,4S,5S)-3-tert-butyl-4-{[(5-tert-butyl-2-methoxyphenyl)methyl]amino}-1-(6-chloro-2,3-dihydro-1H-indene-1-carbonyl)-5-phenylpyrrolidine-2-carboxylic acid | LC/MS (ESI+) m/z 618.4 (M + H)+. |
| Example II-415 | (2S,3S,4S,5S)-3-tert-butyl-4-{[(5-tert-butyl-2-methoxyphenyl)methyl]amino}-1-[3-methyl-2-(2-methylphenoxy)butanoyl]-5-phenylpyrrolidine-2-carboxylic acid | LC/MS (ESI+) m/z 629.6 (M + H)+. |
| Example II-416 | (2S,3S,4S,5S)-3-tert-butyl-1-(cyclohexanecarbonyl)-4-({[2-(2-fluoro-4-methylphenyl)-5-methoxypyridin-4-yl]methyl}amino)-5-phenylpyrrolidine-2-carboxylic acid | MS (APCI+) m/z 602.1 (M + H)+. |
| Example II-417 | (2S,3S,4S,5S)-3-tert-butyl-1-(cyclohexanecarbonyl)-4-({[2-(2-fluorophenyl)-5-methoxypyridin-4-yl]methyl}amino)-5-phenylpyrrolidine-2-carboxylic acid | MS (APCI+) m/z 588.1 (M + H)+. |
| Example II-418 | (2S,3S,4S,5S)-3-tert-butyl-1-(cyclohexanecarbonyl)-4-({[5-methoxy-2-(3-methoxyphenyl)pyridin-4-yl]methyl}amino)-5-phenylpyrrolidine-2-carboxylic acid | MS (APCI+) m/z 600.1 (M + H)+. |
| Example II-419 | (2S,3S,4S,5S)-4-{[(5-tert-butyl-2-methoxyphenyl)methyl]amino}-3-(2-methoxypropan-2-yl)-5-phenyl-1-{[(propan-2-yl)oxy]carbonyl}pyrrolidine-2-carboxylic acid | $^1$HNMR (400 MHz, dimethyl sulfoxide-d$_6$) δ ppm 7.62 (d, J = 7.6 Hz, 2H), 7.38 (t, J = 7.5 Hz, 2H), 7.33 (d, J = 7.3 Hz, 1H), 7.29 (dd, J = 8.6, 2.4 Hz, 1H), 7.07 (d, J = 2.5 Hz, 1H), 6.86 (d, J = 8.6 Hz, 1H), 5.22 (d, J = 7.5 Hz, 1H), 4.68-4.58 (m, 1H), 4.34 (dd, J = 4.7, 1.5 Hz, 1H), 3.94 (d, J = 5.8 Hz, 1H), 3.87 (d, J = 13.3 Hz, 1H), 3.65 (s, 3H), 3.63 (d, J = 13.3 Hz, 1H), 3.16 (d, J = 0.8 Hz, 3H), 2.83 (t, J = 4.8 Hz, 1H), 1.23 (d, J = 2.9 Hz, 15H), 1.07 (d, J = 6.2 Hz, 3H), 0.90 (d, J = 6.2 Hz, 3H); MS (APCI+) m/z 541 (M + H)+. |
| Example II-420 | (2S,3S,4S,5S)-3-tert-butyl-1-(cyclohexanecarbonyl)-4-[({2-methoxy-5-[1-(methoxymethyl)cyclopropyl]phenyl}methyl)amino]-5-phenylpyrrolidine-2-carboxylic acid | $^1$HNMR (400 MHz, dimethyl sulfoxide-d$_6$) δ ppm 7.49 (s, 2H), 7.32 (t, J = 7.4 Hz, 2H), 7.25 (t, J = 7.2 Hz, 1H), 7.09 (dd, J = 8.4, 2.4 Hz, 1H), 6.87 (d, J = 2.4 Hz, 1H), 6.72 (d, J = 8.4 Hz, 1H), 5.18 (d, J = 6.8 Hz, 1H), 4.46 (s, 1H), 3.62-3.53 (m, 2H), 3.50 (s, 3H), 3.47 (d, J = 7.1 Hz, 1H), 3.40-3.35 (m, 3H), 3.19 (s, 3H), 2.36 |

TABLE 2-continued

| | | |
|---|---|---|
| | | (s, 1H), 1.71-1.39 (m, 4H), 1.38-1.03 (m, 6H), 0.98 (s, 9H), 0.77 (q, J = 3.7 Hz, 2H), 0.66 (t, J = 3.0 Hz, 2H); MS (ESI+) m/z 577.3 (M + H)+. |
| Example II-421 | (2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-[2-(dimethylamino)pyridin-3-yl]pyrrolidine-2-carboxylic acid | LC/MS (ESI+) m/z 629.15 (M + H)+. |
| Example II-422 | (2S,3S,4S,5S)-3-tert-butyl-1-(cyclohexanecarbonyl)-4-({[5-(2,2-difluoro-1-methylcyclopropyl)-2-methoxypyridin-3-yl]methyl}amino)-5-phenylpyrrolidine-2-carboxylic acid | MS (ESI+) m/z 584.2 (M + H)+. |
| Example II-423 | (2S,3S,4S,5S)-3-tert-butyl-1-(cyclohexanecarbonyl)-5-(2-fluorophenyl)-4-{[(2-methoxy-5-phenylpyridin-3-yl)methyl]amino}pyrrolidine-2-carboxylic acid | MS (ESI+) m/z 588.2 (M + H)+. |
| Example II-424 | (2S,3S,4S,5S)-3-tert-butyl-1-(cyclohexanecarbonyl)-5-(2-fluorophenyl)-4-({[5-(2-fluorophenyl)-2-methoxypyridin-3-yl]methyl}amino)pyrrolidine-2-carboxylic acid | MS (ESI+) m/z 606.2 (M + H)+. |
| Example II-425 | (2S,3S,4S,5S)-3-tert-butyl-4-({[2-methoxy-5-(trifluoromethyl)pyridin-3-yl]methyl}amino)-5-phenyl-1-{[(propan-2-yl)oxy]carbonyl}pyrrolidine-2-carboxylic acid | MS (ESI+) m/z 538 (M + H)+. |
| Example II-426 | (2S,3S,4S,5S)-3-tert-butyl-4-({[2-methoxy-5-(trifluoromethyl)pyridin-3-yl]methyl}amino)-5-phenyl-1-[(2R*,5S*)-5-phenyloxolane-2-carbonyl]pyrrolidine-2-carboxylic acid | LC/MS (ESI+) m/z 626.8 (M + H)+. |
| Example II-427 | (2S,3S,4S,5S)-3-tert-butyl-4-{[(6-tert-butyl-2-methoxypyridin-3-yl)methyl]amino}-1-[(2-methylphenyl)acetyl]-5-[2-(propan-2-yl)phenyl]pyrrolidine-2-carboxylic acid | LC/MS (ESI+) m/z 614.6 (M + H)+. |
| Example II-428 | (2S,3S,4S,5S)-3-tert-butyl-4-{[(6-tert-butyl-2-methoxypyridin-3-yl)methyl]amino}-1-(3,3-dimethylcyclopentane-1-carbonyl)-5-phenylpyrrolidine-2-carboxylic acid | LC/MS (ESI+) m/z 564.9 (M + H)+. |
| Example II-429 | (2S,3S,4S,5S)-3-tert-butyl-4-{[(6-tert-butyl-2-methoxypyridin-3-yl)methyl]amino}-1-[(2-methylphenyl)acetyl]-5-phenylpyrrolidine-2-carboxylic acid | LC/MS (ESI+) m/z 572.8 (M + H)+. |
| Example II-430 | (2S,3S,4S,5S)-3-tert-butyl-4-{[(6-tert-butyl-2-methoxypyridin-3-yl)methyl]amino}-1-[(2R*)-2,3-dihydro-1-benzofuran-2-carbonyl]-5-phenylpyrrolidine-2-carboxylic acid | LC/MS (ESI+) m/z 586.8 (M + H)+. |
| Example II-431 | (2S,3S,4S,5S)-3-tert-butyl-4-{[(6-tert-butyl-2-methoxypyridin-3-yl)methyl]amino}-1-[(1R*,3aR*,6aS*)-hexahydro-1H-cyclopenta[c]furan-1-carbonyl]-5-phenylpyrrolidine-2-carboxylic acid | LC/MS (ESI+) m/z 578.8 (M + H)+. |
| Example II-432 | (2S,3S,4S,5S)-3-tert-butyl-4-{[(6-tert-butyl-2-methoxypyridin-3-yl)methyl]amino}-1-[(1S*,3aS*,6aR*)-hexahydro-1H-cyclopenta[c]furan-1-carbonyl]-5-phenylpyrrolidine-2-carboxylic acid | LC/MS (ESI+) m/z 578.8 (M + H)+. |

TABLE 2-continued

| Example II-433 | (2S,3S,4S,5S)-3-tert-butyl-4-{[(6-tert-butyl-2-methoxypyridin-3-yl)methyl]amino}-1-[(2R)-2-methoxy-2-phenylacetyl]-5-phenylpyrrolidine-2-carboxylic acid | LC/MS (ESI+) m/z 588.9 (M + H)+. |
|---|---|---|
| Example II-434 | (2S,3S,4S,5S)-3-tert-butyl-1-(5,5-dimethyloxolane-2-carbonyl)-4-({[2-methoxy-5-(trifluoromethyl)pyridin-3-yl]methyl}amino)-5-phenylpyrrolidine-2-carboxylic acid | LC/MS (ESI+) m/z 578.8 (M + H)+. |
| Example II-435 | (2S,3S,4S,5S)-3-tert-butyl-1-(7-fluoro-3,4-dihydro-2H-1-benzopyran-2-carbonyl)-4-({[2-methoxy-5-(trifluoromethyl)pyridin-3-yl]methyl}amino)-5-phenylpyrrolidine-2-carboxylic acid | LC/MS (ESI+) m/z 630.8 (M + H)+. |
| Example II-436 | (2S,3S,4S,5S)-1-(cyclohexanecarbonyl)-3-(2-methoxypropan-2-yl)-5-(2-methoxypyridin-3-yl)-4-({[2-methoxy-5-(trifluoromethyl)phenyl]methyl}amino)pyrrolidine-2-carboxylic acid | 1HNMR (400 MHz, dimethyl sulfoxide-d6) δ ppm 8.06 (d, J = 4.9 Hz, 2H), 7.56-7.49 (m, 1H), 7.30 (d, J = 2.3 Hz, 1H), 7.05 (d, J = 8.6 Hz, 1H), 6.93 (d, J = 6.4 Hz, 1H), 5.36 (s, 1H), 4.54 (d, J = 3.0 Hz, 1H), 3.84 (s, 3H), 3.67 (d, J = 12.7 Hz, 4H), 3.61 (s, 1H), 3.46 (d, J = 14.3 Hz, 1H), 2.68 (s, 1H), 2.10 (bs,1H), 1.65 (d, J = 13.3 Hz, 2H), 1.54 (m, 3H), 1.26 (m, 2H), 1.18 (d, J = 9.4 Hz, 6H), 1.10 (m, 2H), 0.85 (bs,1H); MS (ESI+) m/z 608 (M + H)+. |
| Example II-437 | (2S,3S,4S,5S)-1-(cyclohexanecarbonyl)-5-[2-(dimethylamino)pyridin-3-yl]-3-(2-methoxypropan-2-yl)-4-({[2-methoxy-5-(trifluoromethyl)phenyl]methyl}amino)pyrrolidine-2-carboxylic acid | 1HNMR (400 MHz, dimethyl sulfoxide-d6) δ ppm 8.17 (d, J = 4.9 Hz, 2H), 7.56-7.45 (m, 1H), 7.32 (d, J = 2.3 Hz, 1H), 7.02 (d, J = 8.6 Hz, 1H), 6.98 (dd, J = 7.6, 4.9 Hz, 1H), 5.44 (d, J = 6.7 Hz, 1H), 4.62 (d, J = 1.8 Hz, 1H), 3.69 (d, J = 14.2 Hz, 1H), 3.64 (d, J = 1.0 Hz, 4H), 3.17 (d, J = 1.0 Hz, 3H), 2.72 (d, J = 1.0 Hz, 6H), 2.69 (s, 1H), 2.51 (s, 1H), 2.07 (bs, 1H), 1.70-1.45 (m, 4H), 1.21 (d, J = 10.9 Hz, 7H), 1.07 (m, 3H), 0.85 (bs, 1H); MS (ESI+) m/z 621 (M + H)+. |
| Example II-438 | (2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-[2-(dimethylamino)pyridin-3-yl]pyrrolidine-2-carboxylic acid | LC/MS (ESI+) m/z 643.4 (M + H)+. |
| Example II-439 | (2S,3S,4S,5S)-1-{(4E)-2-[(2E)-but-2-en-1-yl]hex-4-enoyl}-3-tert-butyl-4-{[(5-tert-butyl-2-methoxyphenyl)methyl]amino}-5-phenylpyrrolidine-2-carboxylic acid | LC/MS (ESI+) m/z 589.6 (M + H)+. |
| Example II-440 | (2S,3S,4S,5S)-3-tert-butyl-1-(cyclohexanecarbonyl)-4-({[2-methoxy-5-(1-methylcyclopropyl)pyridin-3-yl]methyl}amino)-5-phenylpyrrolidine-2-carboxylic acid | MS (ESI+) m/z 548.2 (M + H)+. |
| Example II-441 | (2S,3S,4S,5S)-3-tert-butyl-1-[(1S)-3,3-difluorocyclohexane-1-carbonyl]-4-({[2-methoxy-5-(trimethylsilyl)phenyl]methyl}amino)-5-phenylpyrrolidine-2-carboxylic acid | LC/MS (ESI+) m/z 601.5 (M + H)+. |
| Example II-442 | (2S,3S,4S,5S)-3-tert-butyl-4-{[(5-tert-butyl-2-methoxyphenyl)methyl]amino}-1-(6-oxaspiro[2.5]octane-1-carbonyl)-5-phenylpyrrolidine-2-carboxylic acid | LC/MS (ESI+) m/z 577.8 (M + H)+. |
| Example II-443 | (2S,3S,4S,5S)-3-tert-butyl-4-{[(5-tert-butyl-2-methoxyphenyl)methyl]amino}-1-(oxetane-2-carbonyl)-5-phenylpyrrolidine-2-carboxylic acid | LC/MS (ESI+) m/z 523.8 (M + H)+. |
| Example II-444 | (2S,3S,4S,5S)-3-tert-butyl-4-{[(5-tert-butyl-2-methoxyphenyl)methyl]amino}-1-[(3R*)-1-methyl-2-oxopiperidine-3-carbonyl]-5-phenylpyrrolidine-2-carboxylic acid | LC/MS (ESI+) m/z 578.9 (M + H)+. |

TABLE 2-continued

| | | |
|---|---|---|
| Example II-445 | (2S,3S,4S,5S)-3-tert-butyl-4-{[(5-tert-butyl-2-methoxyphenyl)methyl]amino}-1-(1,5-dimethyl-1H-pyrazole-3-carbonyl)-5-phenylpyrrolidine-2-carboxylic acid | LC/MS (ESI+) m/z 561.5 (M + H)+. |
| Example II-446 | (2S,3S,4S,5S)-3-tert-butyl-4-({[2-methoxy-5-(trifluoromethyl)pyridin-3-yl]methyl}amino)-1-(7-methyl-2,3-dihydro-1-benzofuran-2-carbonyl)-5-phenylpyrrolidine-2-carboxylic acid | LC/MS (ESI+) m/z 612.5 (M + H)+. |
| Example II-447 | (2S,3S,4S,5S)-3-tert-butyl-5-[2-(dimethylamino)pyridin-3-yl]-4-{[(4-methoxy[1,1'-biphenyl]-3-yl)methyl]amino}-1-[(2R)-oxane-2-carbonyl]pyrrolidine-2-carboxylic acid | MS (ESI+) m/z 615 (M + H)+. |
| Example II-448 | (2S,3S,4S,5S)-3-tert-butyl-4-{[(5-tert-butyl-2-methoxyphenyl)methyl]amino}-5-[2-(dimethylamino)pyridin-3-yl]-1-[(1S*,3S*)-3-methoxycyclohexane-1-carbonyl]pyrrolidine-2-carboxylic acid | $^1$HNMR (400 MHz, dimethyl sulfoxide-d$_6$) δ ppm 8.28-8.13 (m, 2H), 7.19 (dd, J = 8.5, 2.5 Hz, 1H), 7.06-6.99 (m, 2H), 6.78 (d, J = 8.6 Hz, 1H), 5.46 (d, J = 6.7 Hz, 1H), 4.54 (s, 1H), 3.79 (d, J = 13.7 Hz, 1H), 3.72 (d, J = 6.6 Hz, 1H), 3.54 (s, 3H), 3.44-3.34 (m, 2H), 3.15 (s, 3H), 2.73 (s, 6H), 2.52 (s, 1H), 1.67 (q, J = 12.2, 9.8 Hz, 4H), 1.44-1.32 (m, 2H), 1.32-1.20 (m, 3H), 1.20 (s, 9H), 1.02 (s, 9H); MS (APCI+) m/z 623 (M + H)+. |
| Example II-449 | (2S,3S,4S,5S)-3-tert-butyl-4-{[(5-tert-butyl-2-methoxyphenyl)methyl]amino}-5-[2-(dimethylamino)pyridin-3-yl]-1-[(1R*,3R*)-3-methoxycyclohexane-1-carbonyl]pyrrolidine-2-carboxylic acid | $^1$HNMR (400 MHz, dimethyl sulfoxide-d$_6$) δ ppm 8.24-8.19 (m, 1H), 8.16 (s, 1H), 7.18 (dd, J = 8.6, 2.6 Hz, 1H), 7.03 (dd, J = 9.2, 3.8 Hz, 2H), 6.76 (d, J = 8.5 Hz, 1H), 5.47 (d, J = 6.6 Hz, 1H), 4.52 (s, 1H), 3.75 (d, J = 13.6 Hz, 1H), 3.67 (d, J = 6.6 Hz, 1H), 3.52 (s, 3H), 3.36 (d, J = 13.7 Hz, 1H), 3.05-2.86 (m, 3H), 2.70 (s, 6H), 2.49 (s, 1H), 1.65 (d, J = 13.3 Hz, 1H), 1.56 (d, J = 12.3 Hz, 1H), 1.46-1.31 (m, 4H), 1.30-1.21 (m, 4H), 1.22-1.17 (m, 9H), 1.01 (s, 9H); MS (APCI+) m/z 623 (M + H)+. |
| Example II-450 | (2S,3S,4S,5S)-3-tert-butyl-5-[2-(dimethylamino)pyridin-3-yl]-4-{[(4-methoxy[1,1'-biphenyl]-3-yl)methyl]amino}-1-[(2S)-oxane-2-carbonyl]pyrrolidine-2-carboxylic acid | MS (ESI+) m/z 615 (M + H)+. |
| Example II-451 | (2S,3S,4S,5S)-3-tert-butyl-4-{[(5-tert-butyl-2-methoxyphenyl)methyl]amino}-1-[(2R)-oxane-2-carbonyl]-5-phenylpyrrolidine-2-carboxylic acid | MS (ESI+) m/z 551 (M + H)+. |
| Example II-452 | (2S,3S,4S,5S)-3-tert-butyl-4-{[(5-tert-butyl-2-methoxyphenyl)methyl]amino}-5-[2-(dimethylamino)pyridin-3-yl]-1-[(2S*)-7-fluoro-3,4-dihydro-2H-1-benzopyran-2-carbonyl]pyrrolidine-2-carboxylic acid | MS (ESI+) m/z 661.3 (M + H)+. |
| Example II-453 | (2S,3S,4S,5S)-3-tert-butyl-4-{[(5-tert-butyl-2-methoxyphenyl)methyl]amino-5-[2-(dimethylamino)pyridin-3-yl]-1-[(2R*)-7-fluoro-3,4-dihydro-2H-1-benzopyran-2-carbonyl]pyrrolidine-2-carboxylic acid | MS (ESI+) m/z 661.3 (M + H)+. |
| Example II-454 | (2S,3S,4S,5S)-3-tert-butyl-4-{[(5-tert-butyl-2-methoxyphenyl)methyl]amino}-1-{(2R*)-2-[(2S*)-oxan-2-yl]propanoyl}-5-phenylpyrrolidine-2-carboxylic acid | LC/MS (ESI+) m/z 579.9 (M + H)+. |
| Example II-455 | (2S,3S,4S,5S)-3-tert-butyl-4-{[(5-tert-butyl-2-methoxyphenyl)methyl]amino}-1-{(2S*)-2-[(2R*)-oxan-2-yl]propanoyl}-5-phenylpyrrolidine-2-carboxylic acid | LC/MS (ESI+) m/z 579.9 (M + H)+. |
| Example II-456 | (2S,3S,4S,5S)-3-tert-butyl-4-{[(6-tert-butyl-2-methoxypyridin-3-yl)methyl]amino}-1-(1S*,3R*)-3-methoxycyclohexane-1-carbonyl]-5-phenylpyrrolidine-2-carboxylic acid | LC/MS (ESI+) m/z 580.8 (M + H)+. |

TABLE 2-continued

| | | |
|---|---|---|
| Example II-457 | (2S,3S,4S,5S)-3-tert-butyl-4-{[(5-tert-butyl-2-methoxyphenyl)methyl]amino}-1-[2-(oxan-2-yl)propanoyl]-5-phenylpyrrolidine-2-carboxylic acid | LC/MS (ESI+) m/z 579.8 (M + H)+. |
| Example II-458 | (2S,3S,4S,5S)-3-tert-butyl-4-{[(5-tert-butyl-2-methoxyphenyl)methyl]amino}-1-{cis-4-hydroxy-4-(trifluoromethyl)cyclohexane-1-carbonyl]-5-phenylpyrrolidine-2-carboxylic acid | LC/MS (ESI+) m/z 633.2 (M + H)+. |
| Example II-459 | (2S,3S,4S,5S)-3-tert-butyl-4-{[(5-tert-butyl-2-methoxyphenyl)methyl]amino}-1-{trans-4-hydroxy-4-(trifluoromethyl)cyclohexane-1-carbonyl]-5-phenylpyrrolidine-2-carboxylic acid | LC/MS (ESI+) m/z 633.4 (M + H)+. |
| Example II-460 | (2S,3S,4S,5S)-3-tert-butyl-4-{[(5-tert-butyl-2-methoxyphenyl)methyl]amino}-5-(2-fluorophenyl)-1-[(2S)-oxane-2-carbonyl]pyrrolidine-2-carboxylic acid | |
| Example II-461 | (2S,3S,4S,5S)-3-tert-butyl-1-(cyclohexanecarbonyl)-5-[2-(dimethylamino)pyridin-3-yl]-4-{[2-methoxy-5-(trifluoromethyl)pyridin-3-yl]amino}pyrrolidine-2-carboxylic acid | |
| Example II-462 | (2S,3S,4S,5S)-3-tert-butyl-1-(cyclohexanecarbonyl)-4-({[2-methoxy-5-(1-methylcyclobutyl)phenyl]methyl}amino)-5-phenylpyrrolidine-2-carboxylic acid | $^1$HNMR (400 MHz, dimethyl sulfoxide-d$_6$) δ ppm 7.49 (s, 2H), 7.32 (t, J = 7.4 Hz, 2H), 7.25 (t, J = 7.3 Hz, 1H), 6.98 (dd, J = 8.4, 2.4 Hz, 1H), 6.85-6.67 (m, 2H), 5.21 (d, J = 6.9 Hz, 1H), 4.48 (d, J = 2.3 Hz, 1H), 3.60 (d, J = 2.3 Hz, 1H), 3.54 (dd, J = 6.9, 2.0 Hz, 1H), 3.51 (s, 3H), 3.40 (d, J = 13.7 Hz, 1H), 2.39 (s, 2H), 2.26-2.16 (m, 2H), 2.08-1.92 (m, 3H), 1.83-1.68 (m, 1H), 1.64 (d, J = 9.4 Hz, 2H), 1.50 (d, J = 6.9 Hz, 2H), 1.34 (s, 3H), 1.30-1.05 (m, 6H), 0.98 (s, 9H); MS (ESI+) m/z 561.3 (M + H)+. |
| Example II-463 | (2S,3S,4S,5S)-3-tert-butyl-4-{[(5-tert-butyl-2-methoxyphenyl)methyl]amino}-5-[2-(dimethylamino)pyridin-3-yl]-1-[4-hydroxy-4-(trifluoromethyl)cyclohexane-1-carbonyl]pyrrolidine-2-carboxylic acid | MS (APCI) m/z 677.2 (M + H)+. |
| Example II-464 | (2S,3S,4S,5S)-3-tert-butyl-4-{[(5-tert-butyl-2-methoxyphenyl)methyl]amino}-5-[2-(dimethylamino)pyridin-3-yl]-1-(4-phenoxybenzoyl)pyrrolidine-2-carboxylic acid | MS (APCI) m/z 679.2 (M + H)+. |
| Example II-465 | (2S,3S,4S,5S)-3-tert-butyl-4-{[(5-tert-butyl-2-methoxyphenyl)methyl]amino-5-[2-(dimethylamino)pyridin-3-yl]-1-{4-[(oxan-4-yl)oxy]benzoyl}pyrrolidine-2-carboxylic acid | MS (APCI) m/z 687.2 (M + H)+. |
| Example II-466 | (2S,3S,4S,5S)-3-tert-butyl-4-{[(5-tert-butyl-2-methoxyphenyl)methyl]amino-5-[2-(dimethylamino)pyridin-3-yl]-1-{4-[(pyridin-2-yl)oxy]benzoyl}pyrrolidine-2-carboxylic acid | MS (APCI) m/z 680.2 (M + H)+. |
| Example II-467 | (2S,3S,4S,5S)-3-tert-butyl-4-{[(5-tert-butyl-2-methoxyphenyl)methyl]amino-5-[2-(dimethylamino)pyridin-3-yl]-1-[4-(trifluoromethoxy)benzoyl]pyrrolidine-2-carboxylic acid | MS (APCI) m/z 671.1 (M + H)+. |
| Example II-468 | (2S,3S,4S,5S)-3-tert-butyl-4-{[(5-tert-butyl-2-methoxyphenyl)methyl]amino}-1-(4,4-difluorocyclohexane-1-carbonyl)-5-[2-(dimethylamino)pyridin-3-yl]pyrrolidine-2-carboxylic acid | MS (APCI) m/z 629.2 (M + H)+. |

TABLE 2-continued

| Example | Compound | Data |
|---|---|---|
| Example II-469 | (2S,3S,4S,5S)-3-tert-butyl-4-{[(5-tert-butyl-2-methoxyphenyl)methyl]amino}-5-[2-(dimethylamino)pyridin-3-yl]-1-(3,5-dimethylcyclohexane-1-carbonyl)pyrrolidine-2-carboxylic acid | MS (APCI) m/z 621.3 (M + H)+. |
| Example II-470 | (2S,3S,4S,5S)-3-(bicyclo[1.1.1]pentan-1-yl)-1-(cyclohexanecarbonyl)-4-({[2-methoxy-4-(trifluoromethyl)phenyl]methyl}amino)-5-phenylpyrrolidine-2-carboxylic acid | $^1$HNMR (400 MHz, dimethyl sulfoxide-$d_6$) δ ppm 7.56 (s, 2H), 7.31 (t, J = 7.4 Hz, 2H), 7.24 (dd, J = 9.5, 7.5 Hz, 2H), 7.18-7.08 (m, 2H), 5.16 (d, J = 7.3 Hz, 1H), 4.13 (d, J = 6.5 Hz, 1H), 3.73 (s, 3H), 3.61 (d, J = 2.6 Hz, 2H), 3.32 (t, J = 7.2 Hz, 1H), 2.50 (s, 1H), 2.44 (s, 1H), 2.41 (bs, 1H), 2.24 (bs, 1H), 1.77-1.69 (m, 6H), 1.67 (m, 2H), 1.49 (m, 2H), 1.34-1.21 (m, 1H), 1.21-1.00 (m, 4H), 0.78 (bs, 1H); MS (ESI+) m/z 571 (M + H)+. |
| Example II-471 | (2S,3S,4S,5S)-3-tert-butyl-4-{(5-tert-butyl-2-methoxyphenyl)methyl]amino}-1-[(2R*)-2,3-dihydro-1,4-benzodioxine-2-carbonyl]-5-[2-(dimethylamino)pyridin-3-yl]pyrrolidine-2-carboxylic acid | MS (ESI+) m/z 645.2 (M + H)+. |
| Example II-472 | (2S,3S,4S,5S)-3-tert-butyl-4-{[(5-tert-butyl-2-methoxyphenyl)methyl]amino}-1-[(2S*)-2,3-dihydro-1,4-benzodioxine-2-carbonyl]-5-[2-(dimethylamino)pyridin-3-yl]pyrrolidine-2-carboxylic acid | MS (ESI+) m/z 645.3 (M + H)+. |
| Example II-473 | (2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3S*,4S*)-3-(trifluoromethyl)-7-oxabicyclo[2.2.1]heptane-2-carbonyl]pyrrolidine-2-carboxylic acid | MS (ESI+) m/z 675.2 (M + H)+. |
| Example II-474 | (2S,3S,4S,5S)-3-tert-butyl-4-{[(5-cyclobutyl-2-methoxypyridin-3-yl)methyl]amino}-1-[(2R*)-2,3-dihydro-1,4-benzodioxine-2-carbonyl]-5-phenylpyrrolidine-2-carboxylic acid | MS (APCI) m/z 600.1 (M + H)+. |
| Example II-475 | (2S,3S,4S,5S)-3-tert-butyl-4-{[(5-cyclobutyl-2-methoxypyridin-3-yl)methyl]amino}-1-(2,3-dihydro-1,4-benzodioxine-6-carbonyl)-5-phenylpyrrolidine-2-carboxylic acid | MS (APCI) m/z 600.1 (M + H)+. |
| Example II-476 | (2S,3S,4S,5S)-3-tert-butyl-4-{[(5-cyclobutyl-2-methoxypyridin-3-yl)methyl]amino}-1-(6-fluoro-3,4-dihydro-2H-1-benzopyran-2-carbonyl)-5-phenylpyrrolidine-2-carboxylic acid | MS (APCI) m/z 616.1 (M + H)+. |
| Example II-477 | (2S,3S,4S,5S)-3-tert-butyl-4-{[(2-tert-butyl-4-methoxypyrimidin-5-yl)methyl]amino}-1-[(1R*)-3,3-difluorocyclohexane-1-carbonyl]-5-phenylpyrrolidine-2-carboxylic acid | LC/MS (ESI+) m/z 587.8 (M + H)+. |
| Example II-478 | (2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2R)-oxane-2-carbonyl]pyrrolidine-2-carboxylic acid | MS (ESI+) m/z 608 (M + H)+. |
| Example II-479 | (2S,3S,4S,5S)-4-({[5-(bicyclo[1.1.1]pentan-1-yl)-2-methoxyphenyl]methyl}amino)-3-tert-butyl-1-[(1R,3R)-3-methoxycyclohexane-1-carbonyl]-5-phenylpyrrolidine-2-carboxylic acid | MS (ESI+) m/z 589 (M + H)+. |

TABLE 2-continued

| Example | Compound | Data |
|---|---|---|
| Example II-480 | (2S,3S,4S,5S)-3-tert-butyl-4-{[(5-tert-butyl-2-methoxyphenyl)methyl]amino}-1-[(3R*)-3,4-dihydro-1H-2-benzopyran-3-carbonyl]-5-[2-(dimethylamino)pyridin-3-yl]pyrrolidine-2-carboxylic acid | MS (APCI) m/z 643.2 (M + H)+. |
| Example II-481 | (2S,3S,4S,5S)-3-tert-butyl-4-{[(5-tert-butyl-2-methoxyphenyl)methyl]amino}-1-[(3S*)-3,4-dihydro-1H-2-benzopyran-3-carbonyl]-5-[2-(dimethylamino)pyridin-3-yl]pyrrolidine-2-carboxylic acid | MS (APCI) m/z 643.2 (M + H)+. |
| Example II-482 | (2S,3S,4S,5S)-3-tert-butyl-4-{[(5-tert-butyl-2-methoxyphenyl)methyl]amino}-5-[2-(dimethylamino)pyridin-3-yl]-1-[(2S*)-6-fluoro-3,4-dihydro-2H-1-benzopyran-2-carbonyl]pyrrolidine-2-carboxylic acid | MS (APCI) m/z 661.3 (M + H)+. |
| Example II-483 | (2S,3S,4S,5S)-1-(bicyclo[3.1.0]hexane-6-carbonyl)-3-tert-butyl-5-[2-(dimethylamino)pyridin-3-yl]-4-{[2-methoxy-5-(trifluoromethyl)pyridin-3-yl]amino}pyrrolidine-2-carboxylic acid | $^1$HNMR (400 MHz, dimethyl sulfoxide-$d_6$) δ ppm 8.29 (d, J = 8.0 Hz, 1H), 7.95 (d, J = 4.7 Hz, 1H), 7.50 (dt, J = 2.4, 1.2 Hz, 1H), 6.91-6.80 (m, 1H), 6.73 (s, 1H), 5.56 (d, J = 6.9 Hz, 1H), 4.46 (d, J = 2.6 Hz, 1H), 3.78 (s, 3H), 2.62 (s, 6H), 2.23 (t, J = 2.3 Hz, 1H), 1.75-1.69 (m, 2H), 1.68-1.60 (m, 1H), 1.60-1.36 (m, 1H), 1.27 (d, J = 8.3 Hz, 3H), 1.04 (s, 9H), 0.92-0.77 (m, 4H); MS (ESI+) m/z 590 (M + H)+. |
| Example II-484 | (2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxyphenyl)pyrrolidine-2-carboxylic acid | MS (ESI+) m/z 589 (M + H)+. |
| Example II-485 | (2S,3S,4S,5S)-3-tert-butyl-5-[2-(dimethylamino)pyridin-3-yl]-4-{[2-methoxy-5-(trifluoromethyl)pyridin-3-yl]amino}-1-[(1R,2R)-2-(trifluoromethyl)cyclohexane-1-carbonyl]pyrrolidine-2-carboxylic acid | $^1$HNMR (400 MHz, dimethyl sulfoxide-$d_6$) δ ppm 8.53-8.24 (m, 1H), 8.05-7.82 (m, 1H), 7.61-7.35 (m, 1H), 6.83-6.70 (m, 2H), 6.70-6.56 (m, 1H), 5.65-5.50 (m, 1H), 4.44-4.34 (m, 2H), 4.33-4.18 (m, 1H), 3.79 (s, 3H), 2.67 (s, 6H), 2.37-2.12 (m, 2H), 1.71-1.55 (m, 3H), 1.55-1.40 (m, 1H), 1.33-1.22 (m, 3H), 1.02 (s, 9H), 0.96-0.74 (m, 1H); MS (APCI+) m/z 660 (M + H)+. |
| Example II-486 | (2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxypyridin-3-yl)pyrrolidine-2-carboxylic acid | MS (ESI+) m/z 590 (M + H)+. |
| Example II-487 | (2S,3S,4S,5S)-3-tert-butyl-4-({[2-methoxy-4-(trifluoromethyl)phenyl]methyl}amino)-5-phenyl-1-{[(propan-2-yl)oxy]carbonyl}pyrrolidine-2-carboxylic acid | MS (ESI+) m/z 537 (M + H)+. |
| Example II-488 | (2S,3S,4S,5S)-3-tert-butyl-1-(3,3-difluorocyclohexane-1-carbonyl)-5-{2-(dimethylamino)pyridin-3-yl}-4-{[2-methoxy-5-(trifluoromethyl)pyridin-3-yl]amino}pyrrolidine-2-carboxylic acid | $^1$HNMR (400 MHz, dimethyl sulfoxide-$d_6$) δ ppm 8.39 (s, 1H), 7.90 (s, 1H), 7.47 (s, 1H), 6.78 (s, 1H), 6.66 (s, 1H), 6.21-6.02 (m, 1H), 5.99-5.80 (m, 1H), 5.52 (dd, J = 7.1, 2.4 Hz, 1H), 4.54-4.22 (m, 2H), 3.77 (s, 3H), 2.64 (d, J = 2.1 Hz, 6H), 2.25 (d, J = 10.9 Hz, 1H), 2.09-1.45 (m, 4H), 1.33-1.13 (m, 3H), 1.03 (d, J = 2.2 Hz, 9H); MS (APCI+) m/z 628 (M + H)+. |
| Example II-489 | (2S,3S,4S,5S)-3-tert-butyl-4-{[(5-tert-butyl-2-methoxyphenyl)methyl]amino}-5-[2-(difluoromethoxy)pyridin-3-yl]-1-[(2R*)-oxane-2-carbonyl]pyrrolidine-2-carboxylic acid | MS (ESI+) m/z 618.2 (M + H)+. |
| Example II-490 | (2S,3S,4S,5S)-3-tert-butyl-4-{[(5-tert-butyl-2-methoxyphenyl)methyl]amino}-5-{2-(difluoromethoxy)pyridin-3-yl]-1-[(2S*)-oxane-2-carbonyl]pyrrolidine-2-carboxylic acid | MS (ESI+) m/z 618.2 (M + H)+. |

TABLE 2-continued

| Example II-491 | (2S,3S,4S,5S)-3-tert-butyl-4-{[(5-cyclobutyl-2-methoxypyridin-3-yl)methyl]amino}-5-[2-(dimethylamino)pyridin-3-yl]-1-(oxane-2-carbonyl)pyrrolidine-2-carboxylic acid | MS (ESI+) m/z 594.2 (M + H)+. |
|---|---|---|
| Example II-492 | (2S,3S,4S,5S)-3-tert-butyl-4-{[(5-cyclobutyl-2-methoxypyridin-3-yl)methyl]amino}-1-(3,3-difluorocyclohexane-1-carbonyl)-5-phenylpyrrolidine-2-carboxylic acid | MS (ESI+) m/z 584.2 (M + H)+. |
| Example II-493 | (2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2R)-oxane-2-carbonyl]pyrrolidine-2-carboxylic acid | $^1$HNMR (400 MHz, dimethyl sulfoxide-$d_6$) δ ppm 8.16 (d, J = 5.0 Hz, 1H), 7.90 (s, 1H), 7.02-6.84 (m, 2H), 6.80 (d, J = 2.4 Hz, 1H), 6.73 (d, J = 8.4 Hz, 1H), 5.40 (d, J = 6.4 Hz, 1H), 4.83 (s, 1H), 4.15-3.70 (m, 4H), 3.62 (d, J = 13.8 Hz, 2H), 3.50-3.45 (m, 1H), 3.46 (s, 3H), 3.29 (d, J = 13.7 Hz, 1H), 2.62 (d, J = 1.2 Hz, 6H), 2.30-2.13 (m, 2H), 2.13-1.88 (m, 3H), 1.75 (tq, J = 8.8, 3.6, 3.0 Hz, 2H), 1.63-1.45 (m, 5H), 1.33 (s, 3H), 1.00 (s, 9H); MS (ESI+) m/z 607.3 (M + H)+. |
| Example II-494 | (2S,3S,4S,5S)-3-tert-butyl-5-[2-(dimethylamino)pyridin-3-yl]-4-({[2-methoxy-4-(trifluoromethyl)phenyl]methyl}amino)-1-[(2R)-oxane-2-carbonyl]pyrrolidine-2-carboxylic acid | MS (ESI+) m/z 607 (M + H)+. |
| Example II-495 | (2S,3S,4S,5S)-3-tert-butyl-5-[2-(dimethylamino)pyridin-3-yl]-4-({[2-methoxy-4-(trifluoromethyl)phenyl]methyl}amino)-1-[(2S)-oxane-2-carbonyl]pyrrolidine-2-carboxylic acid | MS (ESI+) m/z 607 (M + H)+. |
| Example II-496 | (2S,3S,4S,5S)-3-tert-butyl-4-{[(6-cyclobutyl-3-methoxypyridazin-4-yl)methyl]amino}-1-(cyclohexanecarbonyl)-5-phenylpyrrolidine-2-carboxylic acid | LC/MS (ESI+) m/z 549.8 (M + H)+. |
| Example II-497 | (2S,3S,4S,5S)-3-tert-butyl-4-{[(5-tert-butyl-2-methoxyphenyl)methyl]amino}-1-[3-(3-chlorophenyl)oxetane-3-carbonyl]-5-phenylpyrrolidine-2-carboxylic acid | LC/MS (ESI+) m/z 633.5 (M + H)+. |
| Example II-498 | (2S,3S,4S,5S)-3-tert-butyl-4-{[(5-tert-butyl-2-methoxyphenyl)methyl]amino}-1-(3-fluorobicyclo[1.1.1]pentane-1-carbonyl)-5-phenylpyrrolidine-2-carboxylic acid | LC/MS (ESI+) m/z 551.5 (M + H)+. |
| Example II-499 | (2S,3S,4S,5S)-3-tert-butyl-1-(cyclohexanecarbonyl)-4-({[1-(2,2-difluoro-2H-1,3-benzodioxol-5-yl)cyclopropyl]methyl}amino)-5-phenylpyrrolidine-2-carboxylic acid | MS (APCI) m/z 583.1 (M + H)+. |
| Example II-500 | (2S,3S,4S,5S)-3-tert-butyl-4-{[2-(4-chlorophenyl)-2-methylpropyl]amino}-1-(cyclohexanecarbonyl)-5-phenylpyrrolidine-2-carboxylic acid | MS (APCI) m/z 538.3 (M + H)+. |
| Example II-501 | (2S,3S,4S,5S)-4-({[5-(bicyclo[1.1.1]pentan-1-yl)-2-methoxyphenyl]methyl}amino)-5-[2-(dimethylamino)pyridin-3-yl]-3-(2-methoxypropan-2-yl)-1-{(propan-2-yl)oxy]carbonyl}pyrrolidine-2-carboxylic acid | $^1$HNMR (400 MHz, dimethyl sulfoxide-$d_6$) δ ppm 8.25-8.13 (m, 2H), 7.08-6.95 (m, 2H), 6.85 (d, J = 2.2 Hz, 1H), 6.80 (d, J = 8.3 Hz, 1H), 5.43 (d, J = 6.7 Hz, 1H), 4.63 (p, J = 6.2 Hz, 1H), 4.43 (d, J = 2.7 Hz, 1H), 3.78-3.69 (m, 2H), 3.57 (s, 3H), 3.43 (d, J = 13.6 Hz, 1H), 3.17 (s, 3H), 2.71 (s, 6H), 2.68 (d, J = 2.6 Hz, 1H), 2.50 (s, 1H), 1.96 (s, 6H), 1.22 (d, J = 9.4 Hz, 6H), 1.03 (d, J = 6.2 Hz, 3H), 0.87 (d, J = 6.2 Hz, 3H); MS (ESI+) m/z 595 (M + H)+. |
| Example II-502 | (2S,3S,4S,5S)-3-tert-butyl-5-[2-(dimethylamino)pyridin-3-yl]-4-{[6-methyl-4-(trifluoromethyl)pyridin-2-yl]amino}-1-[2-(trifluoromethyl)cyclohexane- | $^1$HNMR (400 MHz, dimethyl sulfoxide-$d_6$) δ ppm 8.32 (d, J = 7.7 Hz, 1H), 8.09-8.01 (m, 1H), 6.92 (td, J = 7.8, 4.7 Hz, 1H), 6.45 (s, 1H), 6.38 (d, J = 20.1 Hz, 1H), 5.61 (dd, J = 24.9, 8.2 Hz, 1H), 5.31 (s, 1H), 4.32 (dd, J = 12.1, 5.3 Hz, 1H), 3.19 (s, 1H), 2.93-2.82 (m, 1H), |

TABLE 2-continued

| | | |
|---|---|---|
| | 1-carbonyl]pyrrolidine-2-carboxylic acid | 2.76 (s, 2H), 2.71 (s, 4H), 2.40 (t, J = 5.2 Hz, 1H), 2.25 (s, 3H), 2.24-2.12 (m, 1H), 1.92-1.79 (m, 1H), 1.72-1.52 (m, 1H), 1.54-1.43 (m, 1H), 1.38-1.23 (m, 1H), 1.24-1.06 (m, 3H), 0.99 (d, J = 3.6 Hz, 9H); MS (ESI+) m/z 644 (M + H)+. |
| Example II-503 | (2S,3S,4S,5S)-3-tert-butyl-1-(3,3-difluorocyclohexane-1-carbonyl)-5-[2-(dimethylamino)pyridin-3-yl]-4-{[6-methyl-4-(trifluoromethyl)pyridin-2-yl]amino}pyrrolidine-2-carboxylic acid | 1HNMR (400 MHz, dimethyl sulfoxide-d6) δ ppm 8.33 (s, 1H), 8.07 (d, J = 5.3 Hz, 1H), 7.01-6.87 (m, 1H), 6.49 (s, 1H), 6.35 (d, J = 6.3 Hz, 1H), 6.01 (s, 1H), 5.60 (dd, J = 8.0, 4.5 Hz, 1H), 5.30 (s, 1H), 4.40 (t, J = 4.8 Hz, 1H), 2.70 (s, 6H), 2.45-2.33 (m, 1H), 2.27 (d, J = 2.7 Hz, 3H), 2.05-1.92 (m, 1H), 1.95-1.80 (m, 1H), 1.82-1.69 (m, 1H), 1.70-1.48 (m, 2H), 1.39-1.19 (m, 2H), 1.02 (d, J = 0.9 Hz, 9H); MS (ESI+) m/z 612 (M + H)+. |
| Example II-504 | (2S,3S,4S,5S)-3-tert-butyl-5-[2-(dimethylamino)pyridin-3-yl]-4-{[6-methyl-4-(trifluoromethyl)pyridin-2-yl]amino}-1-[(2S*)-oxane-2-carbonyl]pyrrolidine-2-carboxylic acid | 1HNMR (400 MHz, dimethyl sulfoxide-d6) δ ppm 8.26 (d, J = 7.6 Hz, 1H), 8.03 (dd, J = 5.1, 1.9 Hz, 1H), 6.93 (dd, J = 7.6, 4.9 Hz, 1H), 6.49 (s, 1H), 6.22 (s, 1H), 5.86-5.73 (m, 1H), 5.71 (d, J = 7.7 Hz, 1H), 5.25 (s, 1H), 4.47 (d, J = 3.8 Hz, 1H), 3.84-3.77 (m, 1H), 3.30 (s, 2H), 2.73 (s, 6H), 2.27 (s, 3H), 1.73-1.58 (m, 1H), 1.55-1.36 (m, 4H), 1.36-1.17 (m, 1H), 1.02 (s, 9H); MS (ESII+30) m/z 578 (M + H)+. |
| Example II-505 | (2S,3S,4S,5S)-3-tert-butyl-4-{[(5-tert-butyl-2-methoxyphenyl)methyl]amino}-5-phenyl-1-[(1R*,2R*,3R*,4S*)-3-(trifluoromethyl)-7-oxabicyclo[2.2.1]heptane-2-carbonyl]pyrrolidine-2-carboxylic acid | MS (ESI+) m/z 631.2 (M + H)+. |
| Example II-506 | (2S,3S,4S,5S)-3-tert-butyl-4-{[(5-tert-butyl-2-methoxyphenyl)methyl]amino}-5-phenyl-1-[(1S*,2S*,3S*,4R*)-3-(trifluoromethyl)-7-oxabicyclo[2.2.1]heptane-2-carbonyl]pyrrolidine-2-carboxylic acid | MS (ESI+) m/z 631.2 (M + H)+. |
| Example II-507 | (2S,3S,4S,5S)-3-tert-butyl-4-{[(5-tert-butyl-2-methoxyphenyl)methyl]amino}-5-[2-(difluoromethoxy)phenyl]-1-[(1R*,2R*,3R*,4S*)-3-(trifluoromethyl)-7-oxabicyclo[2.2.1]heptane-2-carbonyl]pyrrolidine-2-carboxylic acid | MS (ESI+) m/z 697.2 (M + H)+. |
| Example II-508 | (2S,3S,4S,5S)-3-tert-butyl-1-(3,3-difluorocyclohexane-1-carbonyl)-4-({[2-methoxy-4-(trifluoromethyl)phenyl]methyl}amino)-5-phenylpyrrolidine-2-carboxylic acid | MS (ESI+) m/z 597 (M + H)+. |
| Example II-509 | (2S,3S,4S,5S)-4-({[5-(bicyclo[1.1.1]pentan-1-yl)-2-methoxyphenyl]methyl}amino)-3-tert-butyl-1-[(1S)-3,3-difluorocyclohexane-1-carbonyl]-5-phenylpyrrolidine-2-carboxylic acid | MS (ESI+) m/z 595 (M + H)+. |
| Example II-510 | (2S,3S,4S,5S)-3-tert-butyl-5-[2-(dimethylamino)pyridin-3-yl]-4-({[2-methoxy-5-(trifluoromethyl)pyridin-3-yl]methyl}amino)-1-{[(propan-2-yl)oxy]carbonyl}pyrrolidine-2-carboxylic acid | MS (ESI+) m/z 582.1 (M + H)+. |
| Example II-511 | (2S,3S,4S,5S)-3-tert-butyl-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid | MS (ESI+) m/z 556.2 (M + H)+. |
| Example II-512 | (2S,3S,4S,5S)-3-tert-butyl-5-(2-methoxypyridin-3-yl)-4-({[2-methoxy-5-(trifluoromethyl)pyridin-3-yl]methyl}amino)-1-{[(propan-2-yl)oxy]carbonyl}pyrrolidine-2-carboxylic acid | MS (APCI+) m/z 569.5 (M + H)+. |

TABLE 2-continued

| | | |
|---|---|---|
| Example II-513 | (2S,3S,4S,5S)-3-tert-butyl-5-(2-methoxypyridin-3-yl)-4-({[2-methoxy-4-(trifluoromethyl)phenyl]methyl}amino)-1-{[(propan-2-yl)oxy]carbonyl}pyrrolidine-2-carboxylic acid | MS (APCI+) m/z 568.6 (M + H)+. |
| Example II-514 | (2S,3S,4S,5S)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid | MS (ESI+) m/z 581.2 (M + H)+. |
| Example II-515 | (2S,3S,4S,5S)-3-tert-butyl-4-{[(5-tert-butyl-2-methoxyphenyl)methyl]amino}-1-[(1R,3S)-3-hydroxycyclohexane-1-carbonyl]-5-phenylpyrrolidine-2-carboxylic acid | $^1$HNMR (400 MHz, dimethyl sulfoxide-d$_6$) δ ppm 7.51 (s, 2H), 7.33 (t, J = 7.4 Hz, 2H), 7.27 (d, J = 7.2 Hz, 1H), 7.16 (dd, J = 8.6, 2.6 Hz, 1H), 6.98 (d, J = 2.7 Hz, 1H), 6.75 (d, J = 8.5 Hz, 1H), 5.23 (d, J = 6.7 Hz, 1H), 4.48 (d, J = 2.2 Hz, 1H), 3.63 (d, J = 13.8 Hz, 1H), 3.57 (dd, J = 6.9, 1.9 Hz, 1H), 3.51 (s, 3H), 3.40 (d, J = 13.8 Hz, 1H), 3.31-3.18 (m, 3H), 2.41 (s, 1H), 1.87-1.75 (m, 1H), 1.71 (dt, J = 14.3, 5.6 Hz, 1H), 1.62-1.39 (m, 2H), 1.30-1.24 (m, 1H), 1.20 (s, 9H), 1.17-1.03 (m, 2H), 0.98 (d, J = 1.9 Hz, 9H), 0.99-0.87 (m, 1H); MS (APCI+) m/z 565 (M + H)+. |
| Example II-516 | (2S,3S,4S,5S)-4-({[5-(bicyclo[1.1.1]pentan-1-yl)-2-methoxyphenyl]methyl}amino)-3-tert-butyl-1-[(1S,3S)-3-methoxycyclohexane-1-carbonyl]-5-phenylpyrrolidine-2-carboxylic acid | MS (ESI+) m/z 589 (M + H)+. |
| Example II-517 | (2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-fluorophenyl)pyrrolidine-2-carboxylic acid | MS (ESI+) m/z 577 (M + H)+. |
| Example II-518 | (2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-[2-(dimethylamino)pyridin-3-yl]pyrrolidine-2-carboxylic acid | MS (ESI+) m/z 590.3 (M + H)+. |
| Example II-519 | (2S,3S,4S,5S)-3-tert-butyl-4-{[(6-tert-butyl-2-methoxypyridin-3-yl)methyl]amino}-5-(2-fluorophenyl)-1-{[(propan-2-yl)oxy]carbonyl}pyrrolidine-2-carboxylic acid | MS (ESI+) m/z 544 (M + H)+. |
| Example II-520 | (2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(dimethylamino)pyridin-3-yl]pyrrolidine-2-carboxylic acid | MS (ESI+) m/z 603 (M + H)+. |
| Example II-521 | (2S,3S,4S,5S)-3-tert-butyl-4-{[(6-tert-butyl-2-methoxypyridin-3-yl)methyl]amino}-5-[2-(dimethylamino)pyridin-3-yl]-1-[(2R)-oxane-2-carbonyl]pyrrolidine-2-carboxylic acid | MS (ESI+) m/z 596 (M + H)+. |
| Example II-522 | (2S,3S,4S,5S)-3-tert-butyl-4-{[(5-tert-butyl-2-methoxyphenyl)methyl]amino}-5-(2-methoxypyridin-3-yl)-1-[(1S*,2R*,4R*)-7-oxabicyclo[2.2.1]heptane-2-carbonyl]pyrrolidine-2-carboxylic acid | MS (ESI+) m/z 594.2 (M + H)+. |
| Example II-523 | (2S,3S,4S,5S)-3-tert-butyl-4-({[2-methoxy-5-(trifluoromethoxy)phenyl]methyl}amino)-5-phenyl-1-{[(propan-2-yl)oxy]carbonyl}pyrrolidine-2-carboxylic acid | MS (ESI+) m/z 553 (M + H)+. |
| Example II-524 | (2S,3S,4S,5S)-3-tert-butyl-1-(cyclohexanecarbonyl)-5-(2-methoxypyridin-3-yl)-4-({[2- | MS (ESI+) m/z 608 (M + H)+. |

TABLE 2-continued

| | | |
|---|---|---|
| | methoxy-5-(trifluoromethoxy)phenyl]methyl}amino)pyrrolidine-2-carboxylic acid | |
| Example II-525 | (2S,3S,4S,5S)-3-tert-butyl-4-{[(6-tert-butyl-2-methoxypyridin-3-yl)methyl]amino}-1-(cyclohexanecarbonyl)-5-(2-fluorophenyl)pyrrolidine-2-carboxylic acid | MS (ESI+) m/z 568 (M + H)+. |
| Example II-526 | (2S,3S,4S,5S)-3-tert-butyl-4-{(5-tert-butyl-2-methoxyphenyl)methyl]amino}-1-{(1R,3S)-3-hydroxy-3-methylcyclohexane-1-carbonyl]-5-phenylpyrrolidine-2-carboxylic acid | 1HNMR (400 MHz, dimethyl sulfoxide-$d_6$) δ ppm 7.53 (s, 2H), 7.30 (t, J = 7.4 Hz, 2H), 7.24 (d, J = 7.2 Hz, 1H), 7.13 (dd, J = 8.5, 2.6 Hz, 1H), 6.96 (s, 1H), 6.73 (d, J = 8.6 Hz, 1H), 5.21 (d, J = 7.0 Hz, 1H), 4.45 (d, J = 2.6 Hz, 1H), 3.57 (d, J = 14.8 Hz, 2H), 3.52 (s, 3H), 3.47 (dd, J = 7.0, 2.3 Hz, 1H), 3.38 (d, J = 13.7 Hz, 1H), 3.18 (d, J = 6.3 Hz, 0H), 2.36 (s, 1H), 1.88 (s, 3H), 1.58-1.48 (m, 1H), 1.47-1.33 (m, 1H), 1.26 (d, J = 6.4 Hz, 2H), 1.20 (s, 9H), 1.14-0.99 (m, 4H), 0.97 (s, 8H), 0.90-0.78 (m, 2H); MS (APCI+) m/z 579 (M + H)+. |
| Example II-527 | (2S,3S,4S,5S)-3-tert-butyl-1-(cyclohexanecarbonyl)-5-(2-methoxypyridin-3-yl)-4-[({2-methoxy-5-[(trifluoromethyl)sulfanyl]phenyl}methyl)amino]pyrrolidine-2-carboxylic acid | MS (ESI+) m/z 624 (M + H)+. |
| Example II-528 | (2S,3S,4S,5S)-3-tert-butyl-4-{[(6-tert-butyl-2-methoxypyridin-3-yl)methyl]amino}-1-(cyclohexanecarbonyl)-5-[2-(difluoromethoxy)phenyl]pyrrolidine-2-carboxylic acid | MS (ESI+) m/z 616.3 (M + H)+. |
| Example II-529 | (2S,3S,4S,5S)-3-tert-butyl-4-[({2-methoxy-5-[(trifluoromethyl)sulfanyl]phenyl}methyl)amino}-5-phenyl-1-{[(propan-2-yl)oxy]carbonyl}pyrrolidine-2-carboxylic acid | MS (ESI+) m/z 593 (M + H)+. |
| Example II-530 | (2S,3S,4S,5S)-3-tert-butyl-1-(cyclohexanecarbonyl)-5-(2-methoxypyridin-3-yl)-4-({[2-methoxy-5-(trifluoromethyl)pyridin-3-yl]methyl}amino)pyrrolidine-2-carboxylic acid | MS (ESI+) m/z 569 (M + H)+. |
| Example II-531 | (2S,3S,4S,5S)-3-tert-butyl-4-{[(5-cyclobutyl-2-methoxypyridin-3-yl)methyl]amino}-5-(2-fluorophenyl)-1-[(2S)-oxane-2-carbonyl]pyrrolidine-2-carboxylic acid | MS (ESI+) m/z 568.2 (M + H)+. |
| Example II-532 | (2S,3S,4S,5S)-3-tert-butyl-4-{[(5-cyclobutyl-2-methoxypyridin-3-yl)methyl]amino}-1-[(1R,3R)-3-fluorocyclohexane-1-carbonyl]-5-phenylpyrrolidine-2-carboxylic acid | MS (ESI+) m/z 566.2 (M + H)+. |
| Example II-533 | (2S,3S,4S,5S)-3-tert-butyl-4-{[(5-tert-butyl-2-methoxyphenyl)methyl]amino}-1-[(1R,3R)-3-hydroxy-3-methylcyclohexane-1-carbonyl]-5-phenylpyrrolidine-2-carboxylic acid | 1HNMR (400 MHz, dimethyl sulfoxide-$d_6$) δ ppm 7.51 (s, 3H), 7.32 (t, J = 7.4 Hz, 2H), 7.26 (d, J = 7.1 Hz, 1H), 7.14 (dd, J = 8.6, 2.6 Hz, 1H), 6.97 (d, J = 2.4 Hz, 1H), 6.74 (d, J = 8.6 Hz, 1H), 5.18 (d, J = 6.8 Hz, 1H), 4.48 (d, J = 2.2 Hz, 1H), 3.63 (s, 1H), 3.58 (d, J = 7.1 Hz, 1H), 3.50 (s, 3H), 3.38 (d, J = 13.6 Hz, 1H), 2.42 (s, 1H), 1.57-1.46 (m, 1H), 1.46-1.34 (m, 1H), 1.34-1.21 (m, 6H), 1.19 (s, 9H), 1.06-0.99 (m, 1H), 0.97 (m, 11H); MS (APCI+) m/z 579 (M + H)+. |
| Example II-534 | (2S,3S,4S,5S)-3-tert-butyl-4-[({2-methoxy-5-[(1S,3s)-tricyclo[3.3.1.1³,⁷]decan-1-yl]phenyl}methyl)amino]-5-phenyl-1-{[(propan-2-yl)oxy]carbonyl}pyrrolidine-2-carboxylic acid | MS (ESI+) m/z 603 (M + H)+. |
| Example II-535 | (2S,3S,4S,5S)-3-tert-butyl-4-({[2-methoxy-5-(pentafluoro-$\lambda^6$-sulfanyl)phenyl]methyl}amino)-5-phenyl-1-{[(propan-2-yl)oxy]carbonyl}pyrrolidine-2-carboxylic acid | MS (ESI+) m/z 595 (M + H)+. |
| Example II-536 | (2S,3S,4S,5S)-3-tert-butyl-4-{[(5-tert-butyl-2-methoxyphenyl)methyl]amino}-1-[(1R,2S,4S)-7- | MS (ESI+) m/z 605.3 (M + H)+. |

TABLE 2-continued

| | | |
|---|---|---|
| | oxabicyclo[2.2.1]heptane-2-carbonyl]-5-[2-(propan-2-yl)phenyl]pyrrolidine-2-carboxylic acid | |
| Example II-537 | (2S,3S,4S,5S)-3-tert-butyl-4-({[2-methoxy-5-(1-methylcyclobutyl)phenyl]methyl}amino)-5-phenyl-1-{[(propan-2-yl)oxy]carbonyl}pyrrolidine-2-carboxylic acid | MS (ESI+) m/z 537 (M + H)⁺. |
| Example II-538 | (2S,3S,4S,5S)-3-tert-butyl-1-[(1R,3S)-3-hydroxycyclohexane-1-carbonyl]-4-({[2-methoxy-4-(trifluoromethyl)phenyl]methyl}amino)-5-phenylpyrrolidine-2-carboxylic acid | $^1$HNMR (400 MHz, dimethyl sulfoxide-d$_6$) δ ppm 7.75-7.54 (m, 2H), 7.32-7.13 (m, 3H), 7.12-6.92 (m, 3H), 5.20-5.09 (m, 1H), 4.32 (s, 1H), 4.07 (s, 1H), 3.69 (d, J = 3.6 Hz, 3H), 3.42 (d, J = 15.0 Hz, 1H), 3.38-3.30 (m, 3H), 3.28 (d, J = 15.0 Hz, 1H), 2.37 (d, J = 2.6 Hz, 1H), 1.92-1.75 (m, 1H), 1.77-1.62 (m, 1H), 1.60-1.33 (m, 1H), 1.31-1.20 (m, 1H), 1.19-1.00 (m, 2H), 1.01-0.96 (m, 1H), 0.93 (s, 9H); MS (APCI+) m/z 577 (M + H)⁺. |
| Example II-539 | (2S,3S,4S,5S)-3-tert-butyl-4-{[(5-tert-butyl-2-methoxyphenyl)methyl]amino}-5-(2-methoxypyridin-3-yl)-1-[(2S)-2-phenylpropanoyl]pyrrolidine-2-carboxylic acid | MS (ESI+) m/z 602.2 (M + H)⁺. |
| Example II-540 | (2S,3S,4S,5S)-3-tert-butyl-4-{[(5-tert-butyl-2-methoxyphenyl)methyl]amino}-5-(2-methoxypyridin-3-yl)-1-[(1R,3R)-3-(trifluoromethoxy)cyclohexane-1-carbonyl]pyrrolidine-2-carboxylic acid | MS (ESI+) m/z 664.2 (M + H)⁺. |
| Example II-541 | (2S,3S,4S,5S)-3-tert-butyl-5-(2-methoxypyridin-3-yl)-4-({[2-methoxy-5-(trifluoromethyl)phenyl]methyl}amino)-1-[(2R)-2-phenylpropanoyl]pyrrolidine-2-carboxylic acid | MS (ESI+) m/z 614.2 (M + H)⁺. |
| Example II-542 | (2S,3S,4S,5S)-3-tert-butyl-5-(2-methoxypyridin-3-yl)-4-({[2-methoxy-5-(trifluoromethoxy)phenyl]methyl}amino)-1-[(2R)-2-phenylpropanoyl]pyrrolidine-2-carboxylic acid | MS (ESI+) m/z 630.2 (M + H)⁺. |
| Example II-543 | (2S,3S,4S,5S)-3-tert-butyl-4-{[(5-tert-butyl-2-methoxyphenyl)methyl]amino}-1-[(1R,2S,4S)-7-oxabicyclo[2.2.1]heptane-2-carbonyl]-5-phenylpyrrolidine-2-carboxylic acid | MS (ESI+) m/z 563.3 (M + H)⁺. |
| Example II-544 | (2S,3S,4S,5S)-3-(bicyclo[1.1.1]pentan-1-yl)-5-(2-fluorophenyl)-4-({[2-methoxy-5-(trifluoromethyl)pyridin-3-yl]methyl}amino)-1-{[(propan-2-yl)oxy]carbonyl}pyrrolidine-2-carboxylic acid | $^1$HNMR (400 MHz, dimethyl sulfoxide-d$_6$) δ ppm 8.31 (s, 1H), 7.93 (dd, J = 8.6, 6.9 Hz, 1H), 7.60 (d, J = 2.4 Hz, 1H), 7.32-7.16 (m, 1H), 7.09 (t, J = 7.5 Hz, 1H), 6.98 (dd, J = 10.9, 8.2 Hz, 1H), 5.25 (d, J = 7.3 Hz, 1H), 4.64 (p, J = 6.1 Hz, 1H), 4.07 (d, J = 5.3 Hz, 1H), 3.85 (d, J = 0.8 Hz, 3H), 3.56 (d, J = 15.1 Hz, 1H), 3.46 (d, J = 15.1 Hz, 1H), 3.31 (t, J = 6.6 Hz, 1H), 1.81-1.62 (m, 6H), 1.25 (s, 1H), 1.07 (d, J = 6.2 Hz, 3H), 0.93 (d, J = 6.2 Hz, 3H); MS (ESI+) m/z 566 (M + H)⁺. |
| Example II-545 | (2S,3S,4S,5S)-3-tert-butyl-1-(cyclohexanecarbonyl)-4-({[2-methoxy-5-(trifluoromethyl)pyridin-3-yl]methyl}amino)-5-[2-(propan-2-yl)phenyl]pyrrolidine-2-carboxylic acid | MS (ESI+) m/z 604 (M + H)⁺. |
| Example II-546 | (2S,3S,4S,5S)-3-tert-butyl-5-(2-fluorophenyl)-4-({[2-methoxy-5-(1-methylcyclobutyl)phenyl]methyl}amino)-1-[(2S)-oxane-2-carbonyl]pyrrolidine-2-carboxylic acid | MS (ESI+) m/z 581 (M + H)⁺. |
| Example II-547 | (2S,3S,4S,5S)-3-tert-butyl-5-[2-(dimethylamino)pyridin-3-yl]-4-{(4-methoxy[1,1'-biphenyl]-3-yl)methyl]amino}-1-{[(propan-2-yl)oxy]carbonyl}pyrrolidine-2-carboxylic acid | MS (ESI+) m/z 589.2 (M + H)⁺. |
| Example II-548 | (2S,3S,4S,5S)-3-tert-butyl-4-{[(6-cyclobutyl-2-methoxypyridin-3-yl)methyl] | MS (ESI+) m/z 568.2 (M + H)⁺. |

TABLE 2-continued

| | | |
|---|---|---|
| | amino}-5-[2-(dimethylamino)pyridin-3-yl]-1-{[(propan-2-yl)oxy]carbonyl}pyrrolidine-2-carboxylic acid | |
| Example II-549 | (2S,3S,4S,5S)-3-tert-butyl-4-{[(5-cyclobutyl-2-methoxyphenyl)methyl]amino}-5-[2-(dimethylamino)pyridin-3-yl]-1-{[(propan-2-yl)oxy]carbonyl}pyrrolidine-2-carboxylic acid | MS (ESI+) m/z 568.2 (M + H)+. |
| Example II-550 | (2S,3S,4S,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid | MS (ESI+) m/z 519 (M + H)+. |
| Example II-551 | (2S,3S,4S,5S)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid | MS (ESI+) m/z 581 (M + H)+. |
| Example II-552 | (2S,3S,4S,5S)-3-tert-butyl-5-[2-(dimethylamino)pyridin-3-yl]-4-({[2-methoxy-5-(trifluoromethoxy)phenyl]methyl}amino)-1-{[(propan-2-yl)oxy]carbonyl}pyrrolidine-2-carboxylic acid | MS (ESI+) m/z 597 (M + H)+. |
| Example II-553 | (2S,3S,4S,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid | MS (ESI+) m/z 537 (M + H)+. |
| Example II-554 | (2S,3S,4R,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid | MS (ESI+) m/z 519 (M + H)+. |
| Example II-555 | (2S,3S,4R,5S)-3-tert-butyl-4-{[(6-methoxy-2,3-dihydro-1H-inden-5-yl)methyl]amino}-5-phenyl-1-{[(propan-2-yl)oxy]carbonyl}pyrrolidine-2-carboxylic acid | MS (ESI+) m/z 509 (M + H)+. |
| Example II-556 | (2S,3S,4R,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid | MS (ESI+) m/z 537 (M + H)+. |
| Example II-557 | (2S,3S,4S,5S)-3-tert-butyl-4-{[(6-tert-butyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid | MS (ESI+) m/z 585.2 (M + H)+. |
| Example II-558 | (2S,3S,4S,5S)-3-tert-butyl-4-({[2-methoxy-4-(trifluoromethyl)phenyl]methyl}amino)-1-(3-methylbutanoyl)-5-phenylpyrrolidine-2-carboxylic acid | MS (ESI+) m/z 535 (M + H)+. |
| Example II-559 | (2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-{[(propan-2-yl)oxy]carbonyl}pyrrolidine-2-carboxylic acid | MS (ESI+) m/z 621 (M + H)+. |
| Example II-560 | (2S,3S,4S,5S)-3-tert-butyl-4-({[2-methoxy-5-(trifluoromethoxy)phenyl]methyl}amino)-1-{[(propan-2-yl)oxy]carbonyl}-5-[2-(propan-2-yl)phenyl]pyrrolidine-2-carboxylic acid | MS (ESI+) m/z 595 (M + H)+. |

TABLE 2-continued

| | | |
|---|---|---|
| Example II-561 | (2S,3S,4S,5S)-3-tert-butyl-4-({[2-methoxy-4-(trifluoromethyl)phenyl]methyl}amino)-1-{(propan-2-yl)oxy]carbonyl}-5-[2-(propan-2-yl)phenyl]pyrrolidine-2-carboxylic acid | MS (ESI+) m/z 579 (M + H)+. |
| Example II-562 | (2S,3S,4S,5S)-3-tert-butyl-5-[2-(dimethylamino)pyridin-3-yl]-4-{(3-methoxynaphthalen-2-yl)methyl]amino}-1-{[(propan-2-yl)oxy]carbonyl}pyrrolidine-2-carboxylic acid | MS (ESI+) m/z 563 (M + H)+. |
| Example II-563 | (2S,3S,4S,5S)-3-tert-butyl-5-[2-(dimethylamino)pyridin-3-yl]-4-{[(6-methoxy-2,3-dihydro-1H-inden-5-yl)methyl]amino}-1-{[(propan-2-yl)oxy]carbonyl}pyrrolidine-2-carboxylic acid | MS (ESI+) m/z 553 (M + H)+. |
| Example II-564 | (2S,3S,4S,5S)-3-tert-butyl-4-{[(5-tert-butyl-2-methoxyphenyl)methyl]amino}-1-(3-methylbutanoyl)-5-phenylpyrrolidine-2-carboxylic acid | MS (ESI+) m/z 523 (M + H)+. |
| Example II-565 | (2S,3S,4S,5S)-3-tert-butyl-5-[2-(dimethylamino)pyridin-3-yl]-4-{[(3-methoxy-5,6,7,8-tetrahydronaphthalen-2-yl)methyl]amino}-1-{[(propan-2-yl)oxy]carbonyl}pyrrolidine-2-carboxylic acid | MS (ESI+) m/z 567 (M + H)+. |
| Example II-566 | (2S,3S,4S,5S)-3-tert-butyl-4-{[(5-cyclobutyl-2-methoxypyridin-3-yl)methyl]amino}-5-(2-fluorophenyl)-1-[(2R)-oxane-2-carbonyl]pyrrolidine-2-carboxylic acid | MS (ESI+) m/z 568.2 (M + H)+. |
| Example II-567 | (2S,3S,4S,5S)-3-tert-butyl-4-{[(5-chloro-2-methoxyphenyl)methyl]amino}-1-{[(propan-2-yl)oxy]carbonyl}-5-[2-(propan-2-yl)phenyl]pyrrolidine-2-carboxylic acid | MS (ESI+) m/z 545 (M + H)+. |
| Example II-568 | (2S,3S,4S,5S)-3-tert-butyl-4-{[(5-chloro-2-methoxyphenyl)methyl]amino}-5-[2-(dimethylamino)pyridin-3-yl]-1-{[(propan-2-yl)oxy]carbonyl}pyrrolidine-2-carboxylic acid | MS (ESI+) m/z 547 (M + H)+. |
| Example II-569 | (2S,3S,4S,5S)-3-tert-butyl-4-{[(5-tert-butyl-2-methoxyphenyl)methyl]amino}-1-[(1S)-6-methoxy-1-methyl-2,3-dihydro-1H-indene-1-carbonyl]-5-(2-methoxypyridin-3-yl)pyrrolidine-2-carboxylic acid | MS (APCI+) m/z 658.0 (M + H)+. |
| Example II-570 | (2S,3S,4S,5S)-3-tert-butyl-4-{[(5-tert-butyl-2-methoxyphenyl)methyl]amino}-1-[(1R)-6-methoxy-1-methyl-2,3-dihydro-1H-indene-1-carbonyl]-5-(2-methoxypyridin-3-yl)pyrrolidine-2-carboxylic acid | MS (APCI+) m/z 658.0 (M + H)+. |
| Example II-571 | (2S,3S,4S,5S)-3-tert-butyl-1-[(1S,3S)-3-methoxycyclohexane-1-carbonyl]-4-({[2-methoxy-4-(trifluoromethyl)phenyl]methyl}amino)-5-phenylpyrrolidine-2-carboxylic acid | MS (ESI+) m/z 591 (M + H)+. |
| Example II-572 | (2S,3S,4S,5S)-3-tert-butyl-1-[(1R)-3,3-difluorocyclohexane-1-carbonyl]-5-(2-methoxypyridin-3-yl)-4-({[2-methoxy-5-(trifluoromethyl)pyridin-3-yl]methyl}amino)pyrrolidine-2-carboxylic acid | MS (ESI+) m/z 629.2 (M + H)+. |

TABLE 2-continued

| | | |
|---|---|---|
| Example II-573 | (2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid | MS (ESI+) m/z 592 (M + H)+. |
| Example II-574 | (2S,3S,4S,5S)-3-tert-butyl-4-{[(6-methoxy-2,3-dihydro-1H-inden-5-yl)methyl]amino}-1-{[(propan-2-yl)oxy]carbonyl}-5-{2-[(propan-2-yl)oxy]pyridin-3-yl}pyrrolidine-2-carboxylic acid | MS (ESI+) m/z 568.2 (M + H)+. |
| Example II-575 | (2S,3S,4S,5S)-3-tert-butyl-1-(cyclohexanecarbonyl)-5-(2-methylphenyl)-4-{[6-methyl-4-(trifluoromethyl)pyridin-2-yl]amino}pyrrolidine-2-carboxylic acid | MS (ESI+) m/z 546 (M + H)+. |
| Example II-576 | (2S,3S,4S,5S)-3-tert-butyl-4-{[(5-tert-butyl-2-methoxyphenyl)methyl]amino}-1-(cyclohexanecarbonyl)-5-(2-methylphenyl)pyrrolidine-2-carboxylic acid | MS (ESI+) m/z 563 (M + H)+. |
| Example II-577 | (2S,3S,4S,5S)-3-tert-butyl-5-[2-(dimethylamino)pyridin-3-yl]-4-({[2-methoxy-5-(pyrrolidin-1-yl)pyridin-3-yl]methyl}amino)-1-{[(propan-2-yl)oxy]carbonyl}pyrrolidine-2-carboxylic acid | MS (ESI+) m/z 583.2 (M + H)+. |
| Example II-578 | (2S,3S,4S,5S)-3-tert-butyl-4-({[2-methoxy-5-(1-methylcyclobutyl)phenyl]methyl}amino)-5-(2-methylphenyl)-1-[(2S)-oxolane-2-carbonyl]pyrrolidine-2-carboxylic acid | MS (ESI+) m/z 563 (M + H)+. |
| Example II-579 | (2S,3S,4S,5S)-3-tert-butyl-4-{[(2-methoxyquinolin-3-yl)methyl]amino}-5-(2-methylphenyl)-1-{[(propan-2-yl)oxy]carbonyl}pyrrolidine-2-carboxylic acid | MS (ESI+) m/z 534 (M + H)+. |
| Example II-580 | (2S,3S,4S,5S)-3-tert-butyl-4-({[2-methoxy-5-(trifluoromethyl)pyridin-3-yl]methyl}amino)-5-(2-methylphenyl)-1-{[(propan-2-yl)oxy]carbonyl}pyrrolidine-2-carboxylic acid | MS (ESI+) m/z 552 (M + H)+. |
| Example II-581 | (2S,3S,4S,5S)-3-tert-butyl-4-({[2-methoxy-5-(trifluoromethyl)phenyl]methyl}amino)-5-(2-methylphenyl)-1-{[(propan-2-yl)oxy]carbonyl}pyrrolidine-2-carboxylic acid | MS (ESI+) m/z 551 (M + H)+. |
| Example II-582 | (2S,3S,4S,5S)-3-tert-butyl-4-{[(5-tert-butyl-2-methoxyphenyl)methyl]amino}-5-(2-methylphenyl)-1-{[(propan-2-yl)oxy]carbonyl}pyrrolidine-2-carboxylic acid | MS (ESI+) m/z 539 (M + H)+. |
| Example II-583 | (2S,3S,4S,5S)-4-[({1-[(benzyloxy)carbonyl]piperidin-3-yl}methyl)amino]-3-tert-butyl-5-phenyl-1-{[(propan-2-yl)oxy]carbonyl}pyrrolidine-2-carboxylic acid | MS (APCI+) m/z 580.2 (M + H)+. |
| Example II-584 | (2S,3S,4S,5S)-3-tert-butyl-5-phenyl-1-{[(propan-2-yl)oxy]carbonyl}-4-({[3-(trifluoromethyl)cyclohexyl]methyl}amino)pyrrolidine-2-carboxylic acid | MS (APCI+) m/z 513.0 (M + H)+. |
| Example II-585 | (2S,3S,4S,5S)-3-tert-butyl-4-{[(5-cyclobutyl-2-methoxypyridin-3-yl)methyl]amino}-5-(2-methylphenyl)-1-[(2S)-oxane-2-carbonyl]pyrrolidine-2-carboxylic acid | MS (ESI+) m/z 564.3 (M + H)+. |
| Example II-586 | (2S,3S,4S,5S)-3-tert-butyl-5-(2-cyclopropylpyridin-3-yl)-4-({[2-methoxy-5- | MS (APCI+) m/z 591.1 (M + H)+. |

TABLE 2-continued

| | | |
|---|---|---|
| | (trifluoromethyl)pyridin-3-yl]methyl}amino)-1-[(2S)-oxolane-2-carbonyl]pyrrolidine-2-carboxylic acid | |
| Example II-587 | (2S,3S,4S,5S)-3-tert-butyl-5-(2-cyclopropylpyridin-3-yl)-4-({[2-methoxy-4-(trifluoromethyl)phenyl]methyl}amino)-1-[(2S)-oxolane-2-carbonyl]pyrrolidine-2-carboxylic acid | MS (APCI+) m/z 590.1 (M + H)+. |
| Example II-588 | (2S,3S,4S,5S)-3-tert-butyl-4-{[(5-cyclobutyl-2-methoxypyridin-3-yl)methyl]amino}-5-(2-cyclopropylpyridin-3-yl)-1-[(2S)-oxolane-2-carbonyl]pyrrolidine-2-carboxylic acid | MS (APCI+) m/z 578.0 (M + H)+. |
| Example II-589 | (2S,3S,4S,5S)-3-tert-butyl-1-(3,3-difluorocyclopentane-1-carbonyl)-4-({[2-methoxy-5-(trifluoromethyl)pyridin-3-yl]methyl}amino)-5-[2-(propan-2-yl)phenyl]pyrrolidine-2-carboxylic acid | MS (APCI+) m/z 626.0 (M + H)+. |
| Example II-590 | (2S,3S,4S,5S)-3-tert-butyl-1-[(2S)-2-methoxypropanoyl]-4-({[2-methoxy-5-(trifluoromethyl)pyridin-3-yl]methyl}amino)-5-[2-(propan-2-yl)phenyl]pyrrolidine-2-carboxylic acid | MS (APCI+) m/z 580.1 (M + H)+. |
| Example II-591 | (2S,3S,4S,5S)-3-tert-butyl-4-({[2-methoxy-5-(trifluoromethyl)pyridin-3-yl]methyl}amino)-1-(oxane-4-carbonyl)-5-[2-(propan-2-yl)phenyl]pyrrolidine-2-carboxylic acid | MS (APCI+) m/z 606.1 (M + H)+. |
| Example II-592 | (2S,3S,4S,5S)-5-[2-(azetidin-1-yl)pyridin-3-yl]-3-tert-butyl-4-({[2-methoxy-5-(trifluoromethyl)pyridin-3-yl]methyl}amino)-1-{[(propan-2-yl)oxy]carbonyl}pyrrolidine-2-carboxylic acid | MS (APCI+) m/z 594.0 (M + H)+. |
| Example II-593 | (2S,3S,4S,5S)-3-tert-butyl-4-({[2-methoxy-5-(1-methylcyclobutyl)phenyl]methyl}amino)-1-[(2S)-oxolane-2-carbonyl]-5-[2-(propan-2-yl)phenyl]pyrrolidine-2-carboxylic acid | MS (ESI+) m/z 591.4 (M + H)+. |
| Example II-594 | (2S,3S,4S,5S)-4-{[(5-bromo-2-methoxypyridin-3-yl)methyl]amino}-3-tert-butyl-1-[(2S)-oxolane-2-carbonyl]-5-[2-(propan-2-yl)phenyl]pyrrolidine-2-carboxylic acid | MS (ESI+) m/z 602.2 (M + H)+. |
| Example II-595 | (2S,3S,4S,5S)-3-tert-butyl-4-({[2-methoxy-5-(trifluoromethyl)phenyl]methyl}amino)-1-[(2S)-oxolane-2-carbonyl]-5-[2-(propan-2-yl)phenyl]pyrrolidine-2-carboxylic acid | MS (ESI+) m/z 591 (M + H)+. |
| Example II-596 | (2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxolane-2-carbonyl]pyrrolidine-2-carboxylic acid | MS (ESI+) m/z 594 (M + H)+. |
| Example II-597 | (2S,3S,4S,5S)-3-tert-butyl-4-{[(5-cyclobutyl-2-methoxypyridin-3-yl)methyl]amino}-5-[2-(difluoromethyl)phenyl]-1-[(2S)-oxolane-2-carbonyl]pyrrolidine-2-carboxylic acid | 1HNMR (500 MHz, dimethyl sulfoxide-d6) δ ppm 8.21 (s, 1H), 7.77 (d, J = 2.4 Hz, 1H), 7.57 (d, J = 7.7 Hz, 1H), 7.48 (s, 1H), 7.41 (d, J = 7.6 Hz, 1H), 7.19 (d, J = 55.1 Hz, 1H), 7.09 (d, J = 2.3 Hz, 1H), 5.56 (s, 1H), 4.59 (s, 1H), 3.74 (d, J = 7.3 Hz, 1H), 3.66 (d, J = 1.3 Hz, 3H), 3.48-3.32 (m, 3H), 3.17 (d, J = 14.6 Hz, 1H), 2.40 (s, 1H), 2.26 (td, J = 9.6, 8.6, 4.9 Hz, 2H), 2.03-1.88 (m, 3H), 1.88-1.77 (m, 2H), 1.69 (s, 1H), 1.00 (d, J = 1.2 Hz, 9H).; MS (APCI+) m/z 586 (M + H)+. |

TABLE 2-continued

| | | |
|---|---|---|
| Example II-598 | (2S,3S,4S,5S)-3-tert-butyl-4-{[(2-methoxyquinolin-3-yl)methyl]amino}-1-(oxane-4-carbonyl)-5-[2-(propan-2-yl)phenyl]pyrrolidine-2-carboxylic acid | MS (ESI+) m/z 588.4 (M + H)+. |
| Example II-599 | (2S,3S,4S,5S)-3-tert-butyl-5-[2-(dimethylamino)pyridin-3-yl]-4-{[(2-methoxyquinolin-3-yl)methyl]amino}-1-[(2S)-oxolane-2-carbonyl]pyrrolidine-2-carboxylic acid | MS (ESI+) m/z 576.3 (M + H)+. |
| Example II-600 | (2S,3S,4S,5S)-3-tert-butyl-5-[2-(dimethylamino)pyridin-3-yl]-4-{[(2-methoxyquinolin-3-yl)methyl]amino}-1-(oxane-4-carbonyl)pyrrolidine-2-carboxylic acid | MS (ESI+) m/z 590.4 (M + H)+. |

TABLE 3

| | | |
|---|---|---|
| Example III-1 | rac-(2R,3R,4R,5R)-3-tert-butyl-4-{[2-chlorophenyl)methyl]amino}-1-(cyclopentylacetyl)-5-phenylpyrrolidine-2-carboxylic acid | MS (APCI+) m/z 497.4 (M + H)+. |
| Example III-2 | rac-(2R,3R,4R,5R)-3-tert-butyl-1-(cyclopentylacetyl)-4-{[(2-methylphenyl)methyl]amino 5-phenylpyrrolidine-2-}-carboxylic acid | MS (APCI+) m/z 477.5 (M + H)+. |
| Example III-3 | rac-(2R,3R,4R,5R)-3-tert-butyl-1-(cyclopentylacetyl)-4-{[(2,4-dichlorophenyl)methyl]amino}-5-phenylpyrrolidine-2-carboxylic acid | MS (APCI+) m/z 531.4 (M + H )+. |
| Example III-4 | rac-(2R,3R,4R,5R)-3-tert-butyl-1-(cyclohexanecarbonyl)-5-phenyl-4-{[4-(trifluoromethyl)pyridin-2-yl]amino}pyrrolidine-2-carboxylic acid | |
| Example III-5 | rac-(2R,3R,4R,5R)-3-tert-butyl-1-(cyclohexanecarbonyl)-5-phenyl-4-{[5-(trifluoromethyl)pyridin-2-yl]amino}pyrrolidine-2-carboxylic acid | |
| Example III-6 | rac-(2R,3R,4R,5R)-3-tert-butyl-4-[(4-chloropyridin-2-yl)amino]-1-(cyclohexanecarbonyl)-5-phenylpyrrolidine-2-carboxylic acid | MS (ESI+) m/z 484.2 (M + H)+. |
| Example III-7 | rac-(2R,3R,4R,5R)-3-tert-butyl-1-(cyclohexanecarbonyl)-4-({[2-(difluoromethoxy)phenyl]methyl}amino)-5-phenylpyrrolidine-2-carboxylic acid | MS (ESI+) m/z 529.2 (M + H)+. |
| Example III-8 | rac-(2R,3R,4R,5R)-3-tert-butyl-1-(cyclohexanecarbonyl)-4-[(6-methoxypyridin-2-yl)amino]-5-phenylpyrrolidine-2-carboxylic acid | MS (ESI+) m/z 480.2 (M + H)+. |
| Example III-9 | rac-(2R,3R,4R,5R)-3-tert-butyl-4-{[(3-chloro-2-hydroxyphenyl)methyl]amino}- | MS (APCI+) m/z 513.0 (M + H)+. |

TABLE 3-continued

| | | |
|---|---|---|
| | 1-(cyclohexanecarbonyl)-5-phenylpyrrolidine-2-carboxylic acid | |
| Example III-10 | rac-(2R,3R,4R,5R)-3-tert-butyl-1-(cyclohexanecarbonyl)-4-[({6-[(oxan-4-yl)oxy]pyridin-2-yl}methyl)amino]-5-phenylpyrrolidine-2-carboxylic acid | MS APCI+) m/z 564.2 (M + H)+. |
| Example III-11 | rac-(2R,3R,4R,5R)-3-tert-butyl-1-(cyclohexanecarbonyl)-4-{[(2,5-dimethoxyphenyl)methyl]amino}-5-phenylpyrrolidine-2-carboxylic acid | MS (APCI+) m/z 523.1 (M + H)+. |
| Example III-12 | rac-(2R,3R,4R,5R)-3-tert-butyl-1-(cyclohexanecarbonyl)-4-{[(2-methoxyphenyl)methyl]amino}-5-phenylpyrrolidine-2-carboxylic acid | MS (APCI+) m/z 493.1 (M + H)+. |
| Example III-13 | rac-(2R,3R,4R,5R)-3-tert-butyl-1-(cyclohexanecarbonyl)-4-{[(2,3-dimethoxyphenyl)methyl]amino}-5-phenylpyrrolidine-2-carboxylic acid | MS (APCI+) m/z 523.2 (M + H)+. |
| Example III-14 | rac-(2R,3R,4R,5R)-3-tert-butyl-1-(cyclohexanecarbonyl)-4-{[(3-methoxyphenyl)methyl]amino}-5-phenylpyrrolidine-2-carboxylic acid | MS (APCI+) m/z 493.1 (M + H)+. |
| Example III-15 | rac-(2R,3R,4R,5R)-3-tert-butyl-4-{[3-chloro-2,4-dimethoxyphenyl)methyl]-amino}-1-(cyclohexanecarbonyl)-5-phenylpyrrolidine-2-carboxylic acid | MS (APCI+) m/z 557.1 (M + H)+. |
| Example III-6 | rac-(2R,3R,4R,5R)-3-tert-butyl-1-(cyclohexanecarbonyl)-4-{R4-methoxypyridin-3-yl)methyl]amino}-5-phenylpyrrolidine-2-carboxylic acid | MS (APCI+) m/z 494.1 (M + H)+. |
| Example III-17 | rac-(2R,3R,4R,5R)-3-tert-butyl-1-(cyclohexanecarbonyl)-4-{[6-methoxy-4-(trifluoromethyl)pyridin-2-yl](methyl)amino}-5-phenylpyrrolidine-2-carboxylic acid | MS (ESI+) m/z 562.2 (M + H)+. |
| Example III-18 | rac-(2R,3R,4R,5R)-3-tert-butyl-1-(cyclohexanecarbonyl)-4-{[(2,2-difluoro-2H-1,3-benzodioxol-5-yl)amino]-5-phenylpyrrolidine-2-carboxylic acid | MS (ESI+) m/z 557.1 (M + H)+. |
| Example III-19 | rac-(2R,3R,4R,5R)-3-tert-butyl-1-(cyclohexanecarbonyl)-4-{[6-methoxypyridin-2-yl)methyl]amino}-5-phenylpyrrolidine-2-carboxylic acid | MS (APCI+) m/z 494.1 (M + H)+. |

TABLE 3-continued

| Example III-20 | rac-(2R,3R,4R,5R)-3-tert-butyl-4-{[5-chloro-2,4-dimethoxyphenyl)methyl]-amino}-1-(cyclohexanecarbonyl)-5-phenylpyrrolidine-2-carboxylic acid | MS (APCI+) m/z 557.1 (M + H)+. |
|---|---|---|
| Example III-21 | rac-(2R,3R,4R,5R)-3-tert-butyl-1-(cyclohexanecarbonyl)-4-{[(3-methoxypyridin-2-yl)methyl]amino}-5-phenylpyrrolidine-2-carboxylic acid | MS (APCI+) m/z 494.1 (M + H)+. |
| Example III-22 | rac-(2R,3R,4R,5R)-3-tert-butyl-1-(cyclohexanecarbonyl)-4-{[4-methoxypyrimidin-2-yl)methyl]amino}-5-phenylpyrrolidine-2-carboxylic acid | MS (APCI+) m/z 495.1 (M + H)+. |
| Example III-23 | rac-(2R,3R,4R,5R)-3-tert-butyl-1-(cyclohexanecarbonyl)-4-{[6-oxo-4-(trifluoromethyl)-1,6-dihydropyridin-2-yl]amino}-5-phenylpyrrolidine-2-carboxylic acid | MS (ESI+) m/z 534.1 (M + H)+. |
| Example III-24 | rac-(2R,3R,4R,5R)-3-tert-butyl-1-(cyclohexanecarbonyl)-4-({[1-(2-methoxyethyl)-1H-imidazol-2-yl]methyl}amino)-5-phenylpyrrolidine-2-carboxylic acid | MS (APCI+) m/z 511.2 (M + H)+. |
| Example III-25 | rac-(2R,3R,4R,5R)-3-tert-butyl-1-(cyclohexanecarbonyl)-4-{[(6-methoxypyridin-3-yl)methyl]amino}-5-phenylpyrrolidine-2-carboxylic acid | MS (APCI+) m/z 494.1 (M + H)+. |
| Example III-26 | rac-(2R,3R,4R,5R)-3-tert-butyl-4-{[(5-chloro-2,3-dimehoxyphenyl)mehyl]-amino}-1-(cyclohexanecarbonyl)-5-phenylpyrrolidine-2-carboxylic acid | MS (APCI+) m/z 525.1 (M + H)+. |
| Example III-27 | rac-(2R,3R,4R,5R)-3-tert-butyl-4-{[(5-chloro-2-methoxyphenyl)methyl]amino}-1-(cyclohexanecarbonyl)-5-phenylpyrrolidine-2-carboxylic acid | MS (APCI+) m/z 527.1 (M + H)+. |
| Example III-28 | rac-(2R,3R,4R,5R)-3-tert-butyl-1-(cyclohexanecarbonyl)-4-({[2-(morpholin-4-yl)pyridin-3-yl]methyl}amino)-5-phenylpyrrolidine-2-carboxylic acid | MS (APCI+) m/z 549.2 (M + H)+. |
| Example III-29 | rac-(2R,3R,4R,5R)-3-tert-butyl-1-(cyclohexanecarbonyl)-4-{[(2,4-dimethoxypyrimidin-5-yl)methyl]amino}-5-phenylpyrrolidine-2-carboxylic acid | MS (APCI+) m/z 525.1 (M + H)+. |
| Example III-30 | rac-(2R,3R,4R,5R)-3-tert-butyl-4-{[(4-chloro-2-methoxyphenyl)methyl]amino}-1-(cyclohexanecarbonyl)-5-phenylpyrrolidine-2-carboxylic acid | MS (APCI+) m/z 527.1 (M + H)+. |

TABLE 3-continued

| Example III-31 | rac-(2R,3R,4R,5R)-3-tert-butyl-1-(cyclohexanecarbonyl)-4-{[1-oxo-4-(trifluoromethyl)-1λ$^5$-pyridin-2-yl]amino}-5-phenylpyrrolidine-2-carboxylic acid | MS (ESI+) 534.4 (M + H)$^+$. |
|---|---|---|
| Example III-32 | rac-(2R3RAR.5R)-3-tert-butyl-1-(cyclohexanecarbonyl)-4-{[6-methyl-1-oxo-4-(trifluoromethyl)-1λ$^5$-pyridin-2-yl]amino}-5-phenylpyrrolidine-2-carboxylic acid | MS (ESI+) m/z 548.2 (M + H)$^+$. |
| Example III-33 | rac-(2R,3R,4R,5R)-1-(cyclohexanecarbonyl)-3-cyclopropyl-5-phenyl-4-{[4-(trifluoromethyl)pyridin-2-yl]amino}pyrrolidine-2-carboxylic acid | MS (ESI+) m/z 502.2 (M + H)$^+$. |
| Example III-34 | rac-(2R,3R,4R,5R)-4-({[2-(difluoromethoxy)phenyl]-methyl}amino)-1-[di(propan-2-yl)carbamoyl]-3-methyl-5-phenylpyrrolidine-2-carboxylic acid | MS (ESI+) m/z 526.2 (M + Na); m/z 5.2.3 (M − H)$^-$ |
| Example III-35 | rac-(2R,3R,4R,5R)-3-tert-butyl-1-(cyclohexanecarbonyl)-4-({[2-methoxy-4-(trifluoromethyl)phenyl]-methyl}amino)-5-phenylpyrrolidine-2-carboxylic acid | MS (ESI+) m/z 561.2 (M + H)$^+$. |
| Example III-36 | rac-(2R,3R,4R,5R)-3-tert-butyl-1-(cyclohexanecarbonyl)-4-({[2-(dimethylamino)-5-(trifluoromethyl)pyridin-3-yl]methyl}amino)-5-phenylpyrrolidine-2-carboxylic acid | MS (ESI+) m/z 573.3 (M − H)$^-$. |
| Example III-37 | rac-(2R,3R,4R,5R)-4-{[(5-chloro-2-methoxyphenyl)methyl]amino}-1-[di(propan-2-yl)carbamoyl]-3-methyl-5-phenylpyrrolidine-2-carboxylic acid | MS (ESI+) m/z 502.1 (M + H)$^+$. |
| Example III-38 | rac-(2R,3R,4R,5R)-3-tert-butyl-5-phenyl-1-{[(propan-2-yl)oxylcarbonyl]-4-{[4-(trifluoromethyppyridin-2-yl]amino}pyrrolidine-2-carboxylic acid | MS (ESI+) m/z494.1 (M + H)$^+$. |
| Example III-39 | rac-(2R,3R,4R,5R)-4-{[(4-chloro-2-methoxyphenyl)methyl]-amino}-1-[di(propan-2-yl)carbamoyl]-3-methyl-5-phenylpyrrolidine-2-carboxylic acid | MS (ESI+) m/z 502.1 (M + H)$^+$. |
| Example III-40 | rac-(2R,3R,4R,5R)-3-tert-butyl-1-(cyclohexanecarbonyl)-5-(2-methoxyphenyl)-4-({[2-methoxy-4-(trifluoromethyl)phenyl]methyl}-amino)pyrrolidine-2-carboxylic acid | MS (ESI+) m/z 591.2 (M + H)$^+$. |
| Example III-41 | rac-(2R,3R,4R,5R)-3-tert-butyl-1-(cyclohexanecarbonyl)-5-[2-(dimethylamino)pyridin-3-yl]-4-({[2-mcthoxy-5-(trifluoromethyl)phenyl]-methyl}amino)pyrrolidine-2-carboxylic acid | MS (ESI+) m/z 605.2 (M + H)$^+$. |
| Example III-42 | rac-(2R,3R,4,R5R)-3-tert-butyl-4-[(4-cyanopyridin-2-yl)amino]-1- | LC/MS (ESI+) m/z 475.5 (M + H)$^+$. |

TABLE 3-continued

| | | |
|---|---|---|
| | (cyclohexanecarbonyl)-5-phenylpyrrolidine-2-carboxylic acid | |
| Example III-44 | rac-(2R,3RAR,5R)-3-tert-butyl-5-phenyl-1-{[(propan-2-yl)oxy]carbonyl}-4-{[6-(trifluoromethyl)pyridin-2-yl]amino}pyrrolidine-2-carboxylic acid | MS (ESI+) m/z 494.1 (M + H)+. |
| Example III-45 | rac-(2R,3R,4R,5R)-3-tert-butyl-1-(cyclohexanecarbonyl)-4-{[(2,2-difluoro-2H-1,3-benzodioxol-4-yl)methyl]amino}-5-(2-methoxyphenyl)pyrrolidine-2-carboxylic acid | MS (ESI+) m/z 573.2 (M + H)+. |
| Example III-46 | rac-{2R,3R,4R,5R)-2-tert-butyl-1-(cyclohexanecarbonyl)-5-[2-(dimethylamino)pyridin-3-yl]-4-{[6-methyl-4-(trifluoromethyl)pyridin-2-yl]amino}pyrrolidine-2-carboxylic acid | MS (ESI+) m/z 576.2 (M + H)+. |
| Example III-47 | rac-(2R,3R,4R)-3-cyclopropyl-1-[di(propan-2-yl)carbamoyl]-4-{[6-methyl-4-(trifluoromethyl)pyridin-2-yl]amino}-5-phenylpyrrolidine-2-carboxylic acid | MS (ESI+) m/z 533.1 (M + H)+. |
| Example III-48 | rac-(2R,3R,4R,5R)-4-{[(5-chloro-2-methoxyphenyl)methyl]amino}-3-cyclopropyl-1-[di(propan-2-yl)carbamoyl]-5-phenylpyrrolidine-2-carboxylic acid | |
| Example III-49 | rac-(2R,3R,4R,5R)-3-tert-butyl-1-(cyclohexanecarbonyl)-N-(2-methoxyethanesulfonyl)-4-{[6-methyl-4-(trifluoromethyl)pyridin-2-yl]amino}-5-phenylpyrrolidine-2-carboxamide | 1HNMR (400 MHz, dimethyl sulfoxide-$d_6$) δ ppm 7.38-7.32. (m. 2H), 7.18 (m, 3H), 6.53 (s, 1H), 6.29 (s, 1H), 5.35 (d, J = 8.3 Hz, 1H), 5.00 (t, J = 8.6 Hz, 1H). 4.44 (d, J = 7.2 Hz, 1H), 3.80 (t, J = 6.3 Hz, 2H), 3.63 (dt, J = 6.1, 2.7 Hz, 2H), 3.26 (s, 3H), 2.56-2.53 (m, 1H) 2.37 (s, 3H), 2.28-2.18 (m, 1H), 1.79-1.66 (m, 2H), 1.50-1.41 (m, 2H), 1.20-1.06 (m, 4H), 1.00 (s, 10H), 0.75-0.65 (m, 1H); . MS (APCI+) m/z 653.0 (M + H)+ |
| Example II-50 | rac-(2R,3R,4R,5R)-3-tert-butyl-1-(cyclohexanecarbonyl)-N-(2-methylpropane-2-sulfonyl)-4-{[6-methyl-4-(trifluoromethyl)pyridin-2-yl]amino}-5-phenylpyrrolidine-2-carboxamide | 1HNMR (400 MHz, dimethyl sulfoxide-$d_6$) δ ppm 7.32-7.27 (m, 2H), 7.18-7.12 (m, 3H), 6.51 (s, 1H), 6.27 (s, 1H), 5.36 (d, J = 8.4 Hz, 1H), 4.96 (t, J = 8.6 Hz, 1H), 4.49 (d, J = 6.4 Hz, 1H), 2.58 (t, J = 7.6 Hz, 1H), 2.35 (s, 3H), 2.27-2.19 (m, 1H), 1.75-1.64 (m, 2H), 1.47 (m, 1H), 1.38 (s, 9H), 1.34 (m, 1H), 1.17-1.03 (m, 3H), 0.98 (s, 9H), 0.75-0.63 (m, 1H); MS (APCI+) m/z 651.0 (M + H)+. |
| Example III-51 | rac-(2R,3R,4R,5R)-3-tert-butyl-1-(cyclohexanecarbonyl)-N-(1-methylcyclopropane-1-sulfonyl)-4-{[6-methyl-4-(trifluoromethyl)pyridin-2-yl]amino}-5-phenylpyrrolidine-2-carboxamide | 1HNMR (400 MHz, dimethyl sulfoxide-$d_6$) δ ppm 7.30 (d, J = 7.0 Hz, 2H), 7.21-7.14 (m, 3H), 6.53 (s, 1H), 6.30 (s, IH), 5.40 (d, J = 8.4 Hz, 1H), 4.99 (t, J = 8.5 Hz, 1H), 4.52 (d, J = 6.8 Hz, IH), 2.65-2.59 (m, 1H), 2.38 (s, 3H), 2.31-2.22 (m, IH), 1.73 (t, J= 15.6 Hz, 2H), 1.59-1.53 (m, IH), 1.49 (s, 3H), 1.45 (d, J= 1.5 Hz, IH), 1.45-1.39 (m, IH), 1.36 (d, J= 12.1 Hz, IH), 1.12 (dd, J = 27.6, 14.9 Hz, 2H), 0.99 (s, 9H), 0.90 (q, J = 3.6 Hz, 2H), 0.78-0.66 (m, IH); MS (APCI+) m/z 649.0 (M + H)+. |
| Example III-52 | rac-(2R,3R,4R,5R)-3-tert-butyl-1-(cyclohexanecarbonyl)-N-(cyclopropanesulfonyl)-4-{[6-methyl-4-(trifluoromethyl)pyridin-2-yl]amino}-5-phenylpyrrolidine-2-carboxamide | 1HNMR (400 MHz, dimethyl sulfoxide-$d_6$) δ ppm 7.33 (d, J = 7.1 Hz, 2H), 7.18 (d, J = 7.1 Hz, 3H), 6.53 (d, J = 1.1 Hz, IH), 6,30 (s, IH), 5,37 (d, J = 8.4 Hz. IH), 5.00 (t, J = 8.7 Hz, Iff), 4.47 (d, J = 7.0 Hz, IH), 2.95-2.89 (m, IH), 2.63-2.56 (m, IH), 2.38 (s, 3H), 2.28-2.19 (m, IH), 1.79-1.64 (m, 2H), 1.53-1.39 (m, 2H), 1.34 (m, 2H), 1.22-1.04 (m, 8H), 1.00 (s, 9H), 0.73 (m, IH); MS (APCI+) m/z 649.0 (M + H)+. |
| Example III-53 | rac-(2R,3R,4R,5R)-3-tert-butyl-1-(cyclohexanecarbonyl)-N-(ethanesulfonyl)-4-{[6- | 1HNMR (400 MHz, dimethyl sulfoxide-$d_6$) δ ppm 7.35 (d, J = 7.2 Hz, 2H), 7.18 (d, J = 7.1 Hz, 3H), 6.53 (d, (d, = 7.2 Hz, 2H), 7.18 (d, J = 7.1 Hz, 3H), 6.53 (s, 1H), 6.29 (s, 1H), 5.35 (d, J = 8.5 Hz, 1H), 5.00 (t, J = |

TABLE 3-continued

| | | |
|---|---|---|
| | methyl-4-(trifluoromethyl)pyridin-2-yl]amino}-5-phenylpyrrolidine-2-carboxamide | 8.7 Hz, 1H), 4.46 (d, J= 7.2 Hz, 1H), 3.47-3.27 (m, 2H), 2.58-2.52 (m, 1H), 2.37 (s, 3H), 2.29-2.15 (m, 1H), 1,78-1.65 (m, 2H), 1.51-1.37(m, 2H), 1.30 (t, J = 7.4 Hz, 4H), 1.19-1.07 (m, 3H), 1.00 (s, 9H), 0.98-0.90 (m, 1H) 0.75-0.62 (m, 1H);<br>MS (APCI+) m/z 623.0 (M + H)+. |
| Example III-54 | rac-(2R,3R,4R,5R)-3-tert-butyl-1-(cyclohexanecarbonyl)-N-(dimethylsulfamoyl)-4-{[6-methyl-4-(trifluoromethyl)pyridin-2-yl]amino}-5-phenylpyrrolidine-2-carboxamide | $^1$HNMR (400 MHz, dimethyl sulfoxide-$d_6$) δ ppm 7.32 (d, J = 6.7 Hz, 2H), 7.20-7.15 (m, 3H), 6.53 (d, J = 1.3 Hz, 1H), 6.29 (s, 1H), 5.37 (d, J = 8.4 Hz, 1H), 4.99 (t, J = 8.6 Hz, 1H), 4.48 (d, J = 7.0 Hz, 1H), 2.87 (s, 6H), 2.63-2.56 (m, 1H), 2.37 (s, 3H), 2.25 (t, J = 11.2 Hz, 1H), 1.72 (t, J = 15.1 Hz, 2H), 1.52-1.40 (m, 2H), 1.35 (dd, J = 11.1, 2.8 Hz, 1H), 1.21-1.15 (m, 1H), 1.11 (dd, J = 12.5, 3.2 Hz, 2H), 0.99 (s, 10H), 0 79-0.65 (m, 1H); MS (APCI+) m/z 638.0 (M + H)+. |
| Example III-55 | rac-(2R,3R,4R,5R)-3-tert-butyl-1-(cyclohexanecarbonyl)-N-[ethyl(methyl)sulfamoyl]-4-{[6-methyl-4-(trifluoromethyl)pyridin-2-yl]amino}-5-phenylpyrrolidine-2-carboxamide | $^1$HNMR (400 MHz, dimethyl sulfoxide-$d_6$) δ ppm 7.31-7.25 (m, 2H), 7.20-7.11 (m, 3H), 6.51 (s, 1H), 6.27 (s, 1H), 5.35 (d, J = 8.5 Hz, 1H), 4.96 (t, J = 8.5 Hz, 1H), 4.45 (d, J = 6.9 Hz, 1H), 3.25 (dq, J = 17.0, 7.0 Hz, 2H), 2,84 (s, 3H), 2.56 (t, J = 7.8 Hz, 1H), 2.35 (s, 3H), 2.22 (t, 1H), 1.70 (t, J = 14.8 Hz, 2H), 1.51-1.36 (m, 2H), 1.32 (m, 1H), 1.18-1.06 (m, 6H), 0.96 (s, 11H), 0.80-0.64 (m, 1H);<br>MS (APCI+) m/z 652.1 (M + H)+. |
| Example III-56 | rac-(2R,3R,4R,5R)-3-tert-butyl-1-(cyclohexanecarbonyl)-N-(methanesulfonyl)-4-{[6-methyl-4-(trifluoromethyl)pyridin-2-yl]amino}-5-phenylpyrrolidine-2-carboxamide | $^1$HNMR (400 MHz, dimethyl sulfoxide-$d_6$) δ ppm 7.38 (d, J = 7.1 Hz, 2H), 7.19 (d, J = 7.0 Hz, 3H), 6.54 (s, 1H), 6.30 (s, 1H), 5.34 (d, J = 8.5 Hz, 1H), 5.01 (t, J = 8.8 Hz, 1H), 4.43 (d, J = 8.2 Hz, 1H), 3.22 (s, 3H), 2.59-2.53 (m, 1H), 2.38 (s, 3H), 2.24-2.13 (m, 1H), 1.71 (t, J = 16.0 Hz, 2H), 1.54-1.37 (m, 0H), 1.35-1.25 (m, 0H), 1.19-1.05 (m, 2H), 1.00 (s, 9H), 0.96-0.89 (m, 1H), 0.72-0.62 (m, 1H);<br>MS (APCI+) m/z 609.0 (M + H)+. |
| Example III-57 | rac-(4R,5R,7R)-5-(cyclohexanecarbonyl)-7-({[2-(difluoromethoxy)phenyl]methyl}amino)-6-phenyl-5-azaspiro[2.4]heptane-4-carboxylic acid | LC/MS (ESI+) m/z 499.6 (M + H)+. |
| Example III-58 | rac-(2R,3R,4R,5S)-3-tert-butyl-4-({[2-(difluoromethoxy)phenyl]methyl}amino)-5-(6-methoxypyridin-2-yl)-1-[(1R,5S,6S)-3-oxabicyclo[3.1.0]hexane-6-carbonyl]pyrrolidine-2-carboxylic acid | LC/MS (ESI+) m/z 560.5 (M + H)+. |
| Example III-59 | rac-(2R,3R,4R,5S)-3-tert-butyl-4-({[2-(difluoromethoxy)phenyl]methyl}amino)-1-[di(propan-2-yl)carbamoyl]-5-(6-methoxypyridin-2-yl)pyrrolidine-2-carboxylic acid | LC/MS (ESI+) m/z 577.5 (M + H)+. |
| Example III-60 | rac-(2R,3R,4R,5S)-3-tert-butyl-1-(cyclohexanecarbonyl)-4-({[2-methoxy-5-(trifluoromethyl)phenyl]methyl}amino)-5-(pyridin-2-yl)pyrrolidine-2-carboxylic acid | LC/MS (ESI+) m/z 562.4 (M + H)+. |
| Example III-61 | rac-(2R,3R,4R,5S)-3-tert-butyl-4-{[(5-chloro-2-methoxyphenyl)methyl]amino}-1-(cyclohexanecarbonyl)-5-(pyridin-2-yl)pyrrolidine-2-carboxylic acid | LC/MS (ESI+) m/z 528.3 (M + H)+. |
| Example III-62 | rac-(2R,3R,4R,5S)-3-tert-butyl-5-(6-methoxypyridin-2-yl)-4-{[6-methyl-4-(trifluoromethyl)pyridin-2-yl]amino}-1-(3-oxabicyclo[3.1.0]hexane-6-carbonyl)pyrrolidine-2-carboxylic acid | LC/MS (ESI+) m/z 563.5 (M + H)+. |

TABLE 3-continued

| Example III-63 | rac-(2R,3R,4R,5S)-3-tert-butyl-5-(6-methoxypyridin-2-yl)-4-{[6-methyl-4-(trifluoromethyl)pyridin-2-yl]amino}-1-(oxane-2-carbonyl)pyrrolidine-2-carboxylic acid | LC/MS (ESI+) m/z 565.5 (M + H)+. |
|---|---|---|
| Example III-64 | rac-(2R,3R,4R,5R)-3-tert-butyl-1-(cyclohexanecarbonyl)-4-({[2-(2-methoxyethoxy)-5-(trifluoromethyl)phenyl]methyl}amino)-5-phenylpyrrolidine-2-carboxylic acid | MS (ESI+) m/z 605.3 (M + H)+. |
| Example III-65 | rac-(2S,3S,4S,5S)-3-tert-butyl-1-(cyclohexanecarbonyl)-4-({[1-(2-methoxyethyl)-2-oxo-5-(trifluoromethyl)-1,2-dihydropyridin-3-yl]methyl}amino)-5-phenylpyrrolidine-2-carboxylic acid | MS (ESI+) m/z 606.3 (M + H)+. |
| Example III-66 | rac-(2R,3R,4R,5R)-3-tert-butyl-1-(cyclohexanecarbonyl)-4-({[2-(2-hydroxyethoxy)-5-(trifluoromethyl)phenyl]methyl}amino)-5-phenylpyrrolidine-2-carboxylic acid | MS (ESI+) m/z 591.2 (M + H)+. |
| Example III-67 | rac-(2R,3R,4R,5S)-3-tert-butyl-4-{[(4-chloro-2-methoxyphenyl)methyl]amino}-1-(cyclohexanecarbonyl)-5-(6-methoxypyridin-2-yl)pyrrolidine-2-carboxylic acid | LC/MS (ESI+) m/z 558.4 (M + H)+. |
| Example III-68 | (2R,3R,4R,5R)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid | LC/MS (ESI+) m/z 599.8 (M + H)+. |
| Example III-69 | (2R,3R,4R,5R)-3-tert-butyl-5-(6-methoxypyridin-2-yl)-4-({[2-methoxy-5-(trifluoromethyl)phenyl]methyl}-amino)-1-(oxane-3-carbonyl)pyrrolidine-2-carboxylic acid | LC/MS (ESI+) m/z 594.7 (M + H)+. |
| Example III-70 | rac-(2S,3S,4S,5R)-3-tert-butyl-5-(6-methoxypyridin-2-yl)-4-({[2-methoxy-5-(trifluoromethyl)phenyl]methyl}amino-1-[3R*)-3-methyloxane-3-carbonyl]pyrrolidine-2-carboxylic acid | LC/MS (ESI+) m/z 608.5 (M + H)+. |
| Example III-71 | rac-(2R,3R,4R,5R)-3-tert-butyl-5-[2-(dimethylamino)phenyl]-4-({[2-methoxy-5-(trifluoromethyl)phenyl]methyl}amino)-1-(3-oxabicyclo[3.1.0]hexane-6-carbonyl)pyrrolidine-2-carboxylic acid | LC/MS (ESI+) m/z 604.8 (M + H)+. |
| Example III-72 | rac-(2R,3R,4R,5R)-3-tert-butyl-4-({[2-chloro-5-(2-methoxyethoxy)pyridin-4-yl]methyl}amino)-1-(cyclohexanecarbonyl)-5-phenylpyrrolidine-2-carboxylic acid | MS (ESI+) m/z 572.3 (M + H)+. |

TABLE 3-continued

| Example III-73 | rac-(2R,3R,4R,5R)-3-tert-butyl-4-{[(2-chloro-5-hydroxypyridin-4-yl)methyl]amino}-1-(cyclohexanecarbonyl)-5-phenylpyrrolidine-2-carboxylic acid | MS (ESI+) m/z 514.2 (M + H)+. |
|---|---|---|
| Example III-74 | rac-(2R,3R,4R,5R)-4-({[2-amino-5-(trifluoromethyl)pyridin-3-yl]methyl}amino)-3-tert-butyl-1-(cyclohexanecarbonyl)-5-phenylpyrrolidine-2-carboxylic acid | MS (ESI+) m/z 547.1 (M + H)+. |
| Example III-75 | (2R,3R,4R,5R)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid | LC/MS (ESI+) m/z 570.8 (M + H)+. |
| Example III-76 | rac-(2S,3S,4S,5R)-3-tert-butyl-4-{[6-(difluoromethoxy)pyridin-2-yl]amino}-5-(6-methoxypyridin-2-yl)-1-(3-methyloxane-3-carbonyl)pyrrolidine-2-carboxylic acid | LC/MS (ESI+) m/z 563.4 (M + H)+. |
| Example III-77 | rac-(2S,3S,4S,5S)-3-tert-butyl-5-[2-(dimethylamino)phenyl]-4-({[2-methoxy-5-(trifluoromethyl)phenyl]-methyl}amino)-1-(3-methyloxane-3-carbonyl)pyrrolidine-2-carboxylic acid | LC/MS (ESI+) m/z 620.8 (M + H)+. |
| Example III-78 | (2S,3S,4S,5S)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid | LC/MS (ESI+) m/z 570.8 (M + H)+. |
| Example III-79 | rac-(2R,3R,4R,5R)-3-tert-butyl-1-(cyclohexanecarbonyl)-4-({[2-hydroxy-5-(methanesulfonyl)phenyl]-methyl}amino)-5-phenylpyrrolidine-2-carboxylic acid | MS (ESI+) m/z 557.2 (M + H)+. |
| Example III-80 | rac-(2R,3R,4R,5R)-3-tert-butyl-1-(cyclohexanecarbonyl)-4-({[2-(2-methoxyethoxy)-5-(trifluoromethyl)pyridin-3-yl]methyl}amino)-5-phenylpyrrolidine-2-carboxylic acid | MS (ESI+) m/z 606.3 (M + H)+. |
| Example III-81 | rac-(2R,3R,4R,5R)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid | MS (ESI+) m/z 562.2 (M + H)+. |
| Example III-82 | rac-(2R,3R,4R,5S)-3-tert-butyl-4-{[(4-chloro-2-methoxyphenyl)methyl]amino}-1-(cyclohexanecarbonyl)-5-(pyridin-2-yl)pyrrolidine-2-carboxylic acid | LC/MS (ESI+) m/z 528.3 (M + H)+. |

TABLE 3-continued

| Example III-83 | rac-(2R,3R,4R,5R)-3-tert-butyl-4-{[(2-cyanophenyl)methyl]amino}-1-(cyclohexanecarbonyl)-5-phenylpyrrolidine-2-carboxylic acid | LC/MS (ESI+) m/z 488.7 (M + H)+. |
|---|---|---|
| Example III-84 | rac-(2R,3R,4R,5R)-3-tert-butyl-1-(cyclohexanecarbonyl)-4-[({2-[3-(methanesulfonyl)propoxy]-5-(trifluoromethyl)phenyl}methyl)amino]-5-phenylpyrrolidine-2-carboxylic acid | MS (APCI+) m/z 677.0 (M + H)+. |
| Example III-85 | rac-(2R,3RAR,5R)-3-tert-butyl-1-(cyclohexanecarbonyl)-4-({[2-(3-fluoropropoxy)-5-(trifluoromethyl)phenyl]methyl}amino)-5-phenylpyrrolidine-2-carboxylic acid | MS (APCI+) m/z 607.1 (M + H)+. |
| Example III-86 | rac-(2R,3R,4R,5R)-3-tert-butyl-1-(cyclohexanecarbonyl)-5-phenyl-4-[({2-[2-(trifluoromethoxy)ethoxy]-5-(trifluoromethyl)phenyl}methyl)amino]pyrrolidine-2-carboxylic acid | MS (APCI+) m/z 659.0 (M + H)+. |
| Example III-87 | rac-(2R,3R,4R,5R)-3-tert-butyl-1-(cyclohexanecarbonyl)-4-({[2-(2-hydroxyethoxy)-5-(trifluoromethyl)pyridin-3-yl]methyl}amino)-5-phenylpyrrolidine-2-carboxylic acid | MS (ESI+) m/z 592.2 (M + H)+. |
| Example III-88 | rac-(2R,3R,4R,5R)-3-tert-butyl-5-[2-(dimethylamino)pyridin-3-yl]-1-[(2R*)-2-methoxy-2-phenylacetyl]-4-({[2-methoxy-5-(trifluoromethyl)phenyl]methyl}amino)pyrrolidine-2-carboxylic acid | MS (APCI+) m/z 643 (M + H)+. |
| Example III-89 | rac-(2R,3R,4R,5R)-3-tert-butyl-5-[2-(dimethylamino)pyridin-3-yl]-1-[(2R)-2-methoxy-2-phenylacetyl]-4-({[6-methyl-4-(trifluoromethyl)pyridin-2-yl]amino}pyrrolidine-2-carboxylic acid | MS (ESI+) m/z 614.1 (M + H)+. |
| Example III-89 | rac-(2R,3R,4R,5R)-3-tert-butyl-5-[2-(dimethylamino)pyridin-3-yl]-1-[(2S)-2-methoxy-2-phenylacetyl]-4-({[6-methyl-4-(trifluoromethyl)pyridin-2-yl]amino}pyrrolidine-2-carboxylic acid | MS (ESI+) m/z 614.1 (M + H)+. |
| Example III-91 | rac-(2R,3R,4R,5R)-3-tert-butyl-4-{[(2,4-dimethoxyphenyl)methyl]amino}-5-phenyl-1-{[(propan-2-yl)oxy]carbonyl}pyrrolidine-2-carboxvlic acid | MS (APCI+) m/z 499.0 (M + H)+. |
| Example III-92 | rac-(2R,3R,4R,5R)-3-tert-butyl-4-{[(3-methoxy[1,1'-biphenyl]-4-yl)methyl]amino}-5-phenyl-1-{[(propan-2-yl)oxy]carbonyl}pyrrolidine-2-carboxylic acid | MS (APCI+) m/z 545.0 (M + H)+. |

TABLE 3-continued

| Example III-93 | rac-(2R,3R,4R,5R)-3-tert-butyl-5-[2-(dimethylamino)pyridin-3-yl]-4-{[6-methyl-4-(trifluoromethyl)pyridin-2-yl]amino}-1-{[(propan-2-yl)oxy]carbonyl}pyrrolidine-2-carboxylic acid | MS (ESI+) m/z 552.2 (M + H)+. |
| --- | --- | --- |
| Example III-94 | rac-(2R,3R,4R,5R)-3-tert-butyl-4-{[(5-chloro-2-methoxyphenyl)methyl]amino}-1-(cyclohexanecarbonyl)-5-[2-(dimethylamino)pyridin-3-yl]pyrrolidine-2-carboxylic acid | MS (ESI+) m/z 571.2 (M + H)+. |
| Example III-95 | (2R,3R,4R,5R)-3-tert-butyl-1-(cyclohexanecarbonyl)-5-(2-methoxyphenyl)-4-({[2-methoxy-4-(trifluoromethyl)phenyl]methyl}-amino)pyrrolidine-2-carboxylic acid | MS (ESI+) m/z 591.2 (M + H)+. |
| Example III-96 | rac-(2R,3R,4R95R)-3-tert-butyl-4-{[(5-chloro-2-methoxyphenyl)methyl]amino}-1-[(cyclobutyloxy)carbonyl]-5-phenylpyrrolidine-2-carboxylic acid | LC/MS (ESI+) m/z 563.4 (M + H)+. |
| Example III-97 | rac-(2S,3S,4S,5R)-3-tert-butyl-1-(cyclohexanecarbonyl)-5-(6-methoxypyridin-2-yl)-4-{[6-methyl-4-(trifluoromethyl)pyridin-2-yl]amino}pyrrolidine-2-carboxylic acid | LC/MS (ESI+) m/z 563.4 (M + H)+. |
| Example III-98 | (2R93R,4R,5R)-3-tert-butyl-5-[2-(dimethylamino)phenyl]-1-[(2R)-2-methoxy-2-phenylacetyl]-4-({[2-methoxy-5-(trifluoromethyl)-phenyl]methyl}amino)pyrrolidine-2-carboxylic acid | LC/MS (ESI+) m/z 642.9 (M + H)+. |
| Example III-99 | (2R,3R,4R,5R)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid | LC/MS (ESI+) m/z 608.5 (M + H)+. |
| Example III-100 | (2S,3S,4S,5S)-3-tert-butyl-4-({[2-methoxy-5-(trifluoromethyl)phenyl]methyl}-amino)-5-phenyl-1-[(2R)-3,3,3-trifluoro-2-methoxy-2-phenylpropanoyl]pyrrolidine-2-carboxylic acid | LC/MS (ESI+) m/z 667.7 (M + H)+. |
| Example III-101 | (2R,3R,4R,5R)-3-tert-butyl-1-[(2S)-2-methoxy-2-phenylacetyl]-4-({[2-methoxy-4-(trifluoromethyl)phenyl]-methyl}amino)-5-phenylpyrrolidine-2-carboxylic acid | LC/MS (ESI+) m/z 599.5 (M + H)+. |
| Example III-102 | (2R,3RAR,5R)-3-tert-butyl-4-({[2-methoxy-5-(trifluoromethyl)phenyl]-methyl}amino)-5-phenyl-1-[(2R)-3,3,3-trifluoro-2-methoxy-2-phenylpropanoyl]pyrrolidine-2-carboxylic acid | LC/MS (ESI+) m/z 667.8 (M + H)+. |

TABLE 3-continued

| Example III-103 | (2S,3S,4S,5S)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid | LC/MS (ESI+) m/z 570.5 (M + H)+. |
|---|---|---|
| Example III-104 | rac-(2R,3R,4R,5R)-3-tert-butyl-1-(4,4-difluorocyclohexane-1-carbonyl)-4-{[6-methyl-4-(trifluoromethyl)pyridin-2-yl]amino}-5-phenylpyrrolidine-2-carboxylic acid | LC/MS (ESI+) m/z 568.5 (M + H)+. |
| Example III-105 | rac-(2R,3R,4R,5R)-3-tert-butyl-4-({[2-methoxy-4-(trifluoromethyl)phenyl]methyl}-amino)-5-phenyl-1-(spiro[2.5]octane-6-carbonyl)pyrrolidine-2-carboxylic acid | LC/MS (ESI+) m/z 587.5 (M + H)+. |
| Example III-106 | rac-(2R,3R,4R,5R)-3-tert-butyl-1-(cyclohexanecarbonyl)-4-({[5-methoxy-2-(trifluoromethyl)phenyl]-methyl}amino)-5-phenylpyrrolidine-2-carboxylic acid | LC/MS (ESI+) m/z 561.8 (M + H)+. |
| Example III-107 | rac-(2R,3R,4R,5R)-3-tert-butyl-4-{[(5-tert-butyl-2-methoxyphenyl)methyl]amino}-1-(cyclohexanecarbonyl)-5-phenylpyrrolidine-2-carboxylic acid | LC/MS (ESI+) m/z 549.9 (M + H)+. |
| Example III-108 | rac-(2R,3R,4R,5R)-3-tert-butyl-1-(cyclohexanecarbonyl)-4-({[5-fluoro-2-(methanesulfonyl)phenyl]-methyl}amino)-5-phenylpyrrolidine-2-carboxylic acid | LC/MS (ESI+) m/z 559.5 (M + H)+. |
| Example III-109 | rac-(2R,3R,4R,5R)-4-{[(5-bromo-2-cyanophenyl)methyl]-amino}-3-tert-butyl-1-(cyclohexanecarbonyl)-5-phenylpyrrolidine-2-carboxylic acid | LC/MS (ESI+) m/z 566.4 (M + H)+. |
| Example III-110 | rac-(2R,3R,4R,5R)-1-[(1R,2S,4S)-bicyclo[2.2.1]heptane-2-carbonyl]-3-tert-butyl-4-{[6-methyl-4-(trifluoromethyl)pyridin-2-yl]amino}-5-phenylpyrrolidine-2-carboxylic acid | MS (ESI+) m/z 544 (M + H)+. |
| Example III-111 | rac-(2R,3R94R,5R)-4-[(5-chloro-3-methoxypyridin-2-yl)amino]-1-(cyclohexanecarbonyl)-3-(2-methoxypropan-2-yl)-5-phenylpyrrolidine-2-carboxylic acid | MS (ESI+) m/z 530 (M + H)+. |
| Example III-112 | rac-(2R,3R,4R,5R)-3-tert-butyl-4-[[2-methoxy-4-(trifluoromethyl)phenyl]-methylamino]-5-phenyl-1-[(2R*)-2-phenylpropanoyl]pyrrolidine-2-carboxylic acid | MS (ESI+) m/z 583.2 (M + H)+. |
| Example III-113 | rac-(2R,3R,4R,5R)-3-tert-butyl-1-(1,4-dioxane-2-carbonyl)-4-({[2-methoxy-4-(trifluoromethyl)phenyl]methyl}-amino)-5-phenylpyrrolidine-2-carboxylic acid | LC/MS (ESI+) m/z 565.5 (M + H)+. |

TABLE 3-continued

| | | |
|---|---|---|
| Example III-114 | rac-(2R,3R,4R,5R)-3-tert-butyl-1-[(cyclobutyloxy)carbonyl]-4-({[2-methoxy-4-(trifluoromethyl)phenyl]methyl}amino)-5-phenylpyrrolidine-2-carboxylic acid | MS (ESI+) m/z 549.2 (M + H)+. |
| Example III-115 | rac-(2R,3R,4R,5R)-4-{[(4-chloro-2-methoxyphenyl)methyl]amino}-1-(cyclohexanecarbonyl)-3-(2-methoxypropan-2-yl)-5-phenylpyrrolidine-2-carboxylic acid | MS (ESI+) m/z 534 (M + H)+. |
| Example III-116 | rac-(2R,3R,4R,5R)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid | MS (ESI+) m/z 578 (M + H)+. |
| Example III-117 | (2R,3R,4R,5R)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid | MS (ESI+) m/z 563.3 (M + H)+. |
| Example III-118 | (2S,3S,4S,5S)-4-{[(5-bromo-2-methoxyphenyl)methyl]amino}-3-tert-butyl-1-(cyclohexanecarbonyl)-5-phenylpyrrolidine-2-carboxylic acid | |
| Example III-119 | (2S,3S,4S,5S)-3-tert-bxxtyl-1-(cyclohexanecarbonyl)-4-{[(3-methoxy-5,5,8,8-tetramethyl-5,6,7,8-tetrahydronaphthalen-2-yl)methyl]amino}-5-phenylpyrrolidine-2-carboxylic acid | MS (ESI+) m/z 603.3 (M + H)+. |
| Example III-120 | (2S,3S,4S,5S)-3-tert-butyl-1-(cyclohexanecarbonyl)-4-{[(3,4-dihydro-2H-1-benzopyran-6-yl)methyl]amino}-5-phenylpyrrolidine-2-carboxylic acid | MS (APCI+) m/z 519.1 (M + H)+. |
| Example III-121 | (2S,3S,4S,5S)-3-tert-butyl-4-{[(4-cyano-2-fluorophenyl)methyl]amino}-1-(cyclohexanecarbonyl)-5-phenylpyrrolidine-2-carboxylic acid | MS (APCI+) m/z 506.1 (M + H)+. |
| Example III-122 | (2S,3S,4S,5S)-3-tert-butyl-1-(cyclohexanecarbonyl)-4-{[(2,3-dihydro-1-benzofuran-5-yl)methyl]amino}-5-phenylpyrrolidine-2-carboxylic acid | MS (APCI+) m/z 505.1 (M + H)+. |
| Example III-123 | (2S,3S,4S,5S)-3-tert-butyl-1-(cyclohexanecarbonyl)-4-({[4-fluoro-2-(trifluoromethyl)phenyl]methyl}amino)-5-phenylpyrrolidine-2-carboxylic acid | MS (APCI+) m/z 549.1 (M + H)+. |
| Example III-124 | (2S,3S,4S,5S)-3-tert-butyl-4-[({5-chloro-2-[(propan-2-yl)oxy]phenyl}methyl)amino]-1-(cyclohexanecarbonyl)-5-phenylpyrrolidine-2-carboxylic acid | MS (APCI+) m/z 555.1 (M + H)+. |
| Example III-125 | (2S,3S,4S,5S)-3-tert-butyl-4-{[(3-cyano-4-fluorophenyl)methyl]amino}- | MS (APCI+) m/z 506.1 (M + H)+. |

TABLE 3-continued

| | | |
|---|---|---|
| | 1-(cyclohexanecarbonyl)-5-phenylpyrrolidine-2-carboxylic acid | |
| Example III-126 | (2S,3S,4S,5S)-3-tert-butyl-4-{[(3-chloro-4-methoxyphenyl)methyl]amino}-1-(cyclohexanecarbonyl)-5-phenylpyrrolidine-2-carboxylic acid | MS (APCI+) m/z 527.0 (M + H)+. |
| Example III-127 | (2S,3S,4S,5S)-3-tert-butyl-4-{[(2-cyano-4-fluorophenyl)methyl]amino}-1-(cyclohexanecarbonyl)-5-phenylpyrrolidine-2-carboxylic acid | MS (APCI+) m/z 506.0 (M + H)+. |
| Example III-128 | (2S,3S,4S,5S)-3-tert-butyl-1-(cyclohexanecarbonyl)-4-({[3-fluoro-4-(trifluoromethoxy)phenyl]methyl}amino)-5-phenylpyrrolidine-2-carboxylic acid | MS (APCI+) m/z 565.0 (M + H)+. |
| Example III-129 | (2S,3S,4S,5S)-3-tert-butyl-1-(cyclohexanecarbonyl)-4-{[(3,4-dihydro-2H-1,5-benzodioxepin-7-yl)methyl]amino}-5-phenylpyrrolidine-2-carboxylic acid | MS (APCI+) m/z 535.1 (M + H)+. |
| Example III-130 | (2S,3S,4S,5S)-3-tert-butyl-1-(cyclohexanecarbonyl)-4-{[(3,4-dichlorophenyl)methyl]amino}-5-phenylpyrrolidine-2-carboxylic acid | MS (APCI+) m/z 530.9 (M + H)+. |
| Example III-131 | (2S,3S,4S,5S)-4-({[5-bromo-2-(difluoromethoxy)phenyl]-methyl}amino)-3-tert-butyl-1-(cyclohexanecarbonyl)-5-phenylpyrrolidine-2-carboxylic acid | MS (APCI+) m/z 608.9 (M + H)+. |
| Example III-132 | (2S,3S,4S,5S)-3-tert-butyl-1-(cyclohexanecarbonyl)-4-{[(2,2-difluoro-2H-1,3-benzodioxol-5-yl)methyl]amino}-5-phenylpyrrolidine-2-carboxylic acid | MS (APCI+) m/z 543.1 (M + H)+. |
| Example III-133 | (2S,3S,4S,5S)-3-tert-butyl-1-(cyclohexanecarbonyl)-4-{[(3,5-dimethoxyphenyl)methyl]amino}-5-phenylpyrrolidine-2-carboxylic acid | MS (APCI+) m/z 523.1 (M + H)+. |
| Example III-134 | (2S,3S,4S,5S)-3-tert-butyl-1-(cyclohexanecarbonyl)-4-{[(3,4-dimethylphenyl)methyl]-amino}-5-phenylpyrrolidine-2-carboxylic acid | MS (APCI+) m/z 491.1 (M + H)+. |
| Example III-135 | (2S,3S,4S,5S)-4-{[(1-benzofuran-5-yl)methyl]amino}-3-tert-butyl-1-(cyclohexanecarbonyl)-5-phenylpyrrolidine-2-carboxylic acid | MS (APCI+) m/z 503.1 (M + H)+. |
| Example III-136 | (2S,3S,4S,5S)-3-tert-butyl-1-(cyclohexanecarbonyl)-4-({[2-fluoro-4-(trifluoromethyl)phenyl]-methyl}amino)-5-phenylpyrrolidine-2-carboxylic acid | MS (APCI+) m/z 549.1 (M + H)+II. |
| Example III-137 | (2S,3S,4S,5S)-3-tert-butyl-1-[1-(methanesulfonyl)cyclopropane-1-carbonyl]-4-({[2-methoxy-5- | LC/MS (ESI+) m/z 597.7 (M + H)+. |

TABLE 3-continued

| | | |
|---|---|---|
| Example III-138 | (2S,3S,4S,5S)-3-tert-butyl-1-(cyclohexanecarbonyl)-5-phenyl-4-({[4-(trifluoromethyl)phenyl]-methyl}amino)pyrrolidine-2-carboxylic acid | MS (APCI+) m/z 531.1 (M + H)+. |
| Example III-139 | (2S,3S,4S,5S)-3-tert-butyl-1-(cyclohexanecarbonyl)-4-({[2-(difluoromethyl)phenyl]-methyl}amino)-5-phenylpyrrolidine-2-carboxylic acid | MS (ESI+) m/z 513.2 (M + H)+. |
| Example III-140 | (2S,3S,4S,5S)-3-tert-butyl-4-{[(7-chloro-2H-1,3-benzodioxol-5-yl)methyl]amino}-1-(cyclohexanecarbonyl)-5-phenylpyrrolidine-2-carboxylic acid | MS (APCI+) m/z 541.0 (M + H)+. |
| Example III-141 | (2S,3S,4S,5S)-3-tert-butyl-1-(cyclohexanecarbonyl)-4-({[4-(difluoromethoxy)-3,5-dimethylphenyl]methyl}-amino)-5-phenylpyrrolidine-2-carboxylic acid | MS (APCI+) m/z 557.1 (M + H)+. |
| Example III-142 | (2S,3S,4S,5S)-3-tert-butyl-4-{[(6-chloro-2H-1,3-benzodioxol-5-yl)methyl]amino}-1-(cyclohexanecarbonyl)-5-phenylpyrrolidine-2-carboxylic acid | MS (APCI+) m/z 541.0 (M + H)+. |
| Example III-143 | rac-(2S,3S,4S,5R)-3-tert-butyl-4-{[(4-chloro-2-methoxyphenyl)methyl]-amino}-1-(cyclohexanecarbonyl)-5-(3-methoxypyridin-2-yl)pyrrolidine-2-carboxylic acid | LC/MS (ESI+) m/z 558.4 (M + H)+. |
| Example III-144 | (2S,3S,4S,5S)-3-tert-butyl-4-[(4-carbamoyl-6-chloropyridin-2-yl)amino]-1-(cyclohexanecarbonyl)-5-phenylpyrrolidine-2-carboxylic acid | $^1$HNMR (400 MHz, dimethyl sulfoxide-d$_6$) δ ppm 7.33 (d, J = 7.5 Hz, 2H), 7.11 (dd, J = 16.6, 7.3 Hz, 3H), 6.73 (s, 1H), 6.46 (s, 1H), 5.35 (d, J = 7.9 Hz, 2H), 4.93-4.85 (m, 1H), 4.56 (d, J = 3.7 Hz, 1H), 2.55-2.54 (m, 1H), 1.74-1.66 (m, 3H), 1.54-1.42 (m, 3H), 1.33-1.23 (m, 2H), 1.21-1.14 (m, 2H), 1.13-1.05 (m, 3H), 1.02 (s, 2H), 1.00 (s, 9H); MS (APCI+) m/z 526.4 (M + H)+. |
| Example III-145 | (2S,3S,4S,5S)-3-tert-butyl-4-[(6-chloro-3-cyano-5-fluoropyridin-2-yl)amino]-1-(cyclohexanecarbonyl)-5-phenylpyrrolidine-2-carboxylic acid | $^1$HNMR (400 MHz, dimethyl sulfoxide-d$_6$) 7.48-7.34 (m, 2H), 7.17-7.05 (m, 2H), 6.57 (s, 1H), 5.23-5.19 (m, 1H), 4.47-4.39 (m, 1H), 2.56-2.54 (m, 1H), 1.70-1.63 (m, 2H), 1.57-1.46 (m, 2H), 1.29 (s, 2H), 1.18 (s, 9H), 1.12 (d, J = 4.1 Hz, 3H), 1.03 (d, J = 5.2 Hz, 4H); MS (APCI+) m/z 527.4 (M + H )+. |
| Example III-146 | (2S,3S,4S,5S)-3-tert-butyl-4-[(6-chloro-4-cyanopyridin-2-yl)amino]-1-(cyclohexanecarbonyl)-5-phenylpyrrolidine-2-carboxylic acid | $^1$HNMR (400 MHz, dimethyl sulfoxide-d$_6$) δ ppm 7.45 (d, J = 7.5 Hz, 2H), 7.23-7.15 (m, 3H), 6.75 (s, 1H), 6.53 (s, 1H), 5.34 (d, J = 8.4 Hz, 1H), 4.86-4.82 (m, 1H), 4.39 (d, J = 5.8 Hz, 1H), 2.44 (t, J = 6.3 Hz, 1H), 2.25-2.20 (m, 1H), 1.71-1.65 (m, 2H), 1.52-1.40 (m, 2H), 1.34-1.26 (m, 2H) 1.19-1.16 (m, 1H), 1.15-1.04 (m, 6H), 1.01 (s, 9H), 0.77-0.66 (m, 1H); MS (APCI+) m/z 509.4 (M + H)+. |
| Example III-147 | (2S,3S,4S,5S)-3-tert-butyl-4-{[6-chloro-4-(2-hydroxypropan-2-yl)pyridin-2-yl]amino}-1-(cyclohexanecarbonyl)-5-phenylpyrrolidine-2-carboxylic acid | $^1$HNMR (400 MHz, dimethyl sulfoxide-d$_6$) δ ppm 7.45 (d, J = 7.4 Hz, 2H), 7.22-7.12 (m, 3H), 6.53 (d, J = 1.1 Hz, 1H)5 6.14 (d, J = 1.2 Hz, 1H), 5.33 (d, J = 8.2 Hz, 1H), 4.85 (t, J = 7.1 Hz, 1H), 4.41 (d, J = 5.5 Hz, 1H), 2.37 (t, J = 5.9 Hz, 1H), 2.27-2.18 (m, 1H), 1.72-1.65 (m, 2H), 1.52-1.43 (m, 2H), 1.29 (s, 6H), 1.28-1.22 (m, 1H), 1.21-1.15 (m, 1H). 1.15-1.05 (m, 3H), 1.03 (s, 9H), 0.76-0.68 (m, 1H); MS (APCI+) m/z 542.4 (M + H)+. |
| Example III-148 | (2S,3S,4S,5S)-3-tert-butyl-4-[(3-cyano-4,6-dimethylpyridin-2-yl)amino]-1-(cyclohexanecarbonyl)-5- | $^1$HNMR (400 MHz, dimethyl sulfoxide-d$_6$) δ ppm 7.45 (d, J 7.4 Hz, 2H), 7.24-7.12 (m, 3H), 6.37 (s, 1H), 5.35 (d, J = 7.7 Hz, 1H), 5.25 (dd, J = 7.7, 3.5 Hz, 1H), 4.49 (d, J = 3.6 Hz, 1H), 2.30 (t, J = 4.1 Hz, 1H), 2.28 (s, 3H), 2.26-2.18 (m, 1H), 2.14 (s, 3H), 1.71-1.64 |

TABLE 3-continued

| | | |
|---|---|---|
| | phenylpyrrolidine-2-carboxylic acid | (m, 2H), 1.52-1.45 (m, 2H), 1.32-1.16 (m, 3H), 1.12-1.07 (m, 1H), 1.06 (s, 9H), 0.77-0.65 (m, 1H);<br>MS (APCI+) m/z 503.5 (M + H)+. |
| Example III-149 | (2S,3S,4S,5S)-3-tert-butyl-4-[(7-chloro-3-ethylquinolin-2-yl)amino]-1-(cyclohexanecarbonyl)-5-phenylpyrrolidine-2-carboxylic acid | 1HNMR (400 MHz, dimethyl sulfoxide-d6) δ ppm 7.58-7.54 (m, 3H), 7.51 (d, J = 7.5 Hz, 2H), 7.19 (t, J = 7.4 Hz, 2H), 7.16-7.12 (m, 1H), 5.48 (d, J = 1.1 Hz, 1H), 5.40-5.35 (m, 1H), 2.47 (t, J = 3.9 Hz, 1H), 2.06 (dt, J = 33.6, 7.7 Hz, 1H), 1.76-1.64 (m, 2H), 1.54-1.46 (m, 2H), 1.36-1.20 (m, 2H), 1.12 (s, 9H), 1.07-1.02 (m, 1H) 0.90 (t, J = 7.4 Hz, 3H);<br>MS (APCI+) m/z 562.4 (M + H)+. |
| Example III-150 | \(2S,3S,4S,5S)-4-[(6-anilino-3-cyanopyridin-2-yl)amino]-3-tert-butyl-1-(cyclohexanecarbonyl)-5-phenylpyrrolidine-2-carboxylic acid | 1HNMR (400 MHz, dimethyl sulfoxide-d6) δ ppm 7.63-7.56 (m, 3H), 7.37 (d, J = 7.5 Hz, 2H), 7.33 (d, J = 7.9 Hz, 2H), 7.24 (d, J = 8.5 Hz, 1H), 7.15 (d, J = 7.5 Hz, 3H), 7.05 (t, J = 7.4 Hz, 1H), 6.00 (d, J = 8.5 Hz, 1H), 5.31-5.25 (m, 1H), 5.24-5.20 (m, 1H), 4.45 (d, J = 4.3 Hz, 1H), 2.36-2.32 (m, 2H), 1.67-1.57 (m, 2H), 1.51-1.42 (m, 2H), 1.32-1.16 (m, 2H), 1.15-1.05 (m, 2H), 1.01 (s, 9H);<br>MS (APCI+) m/z 566.5 (M + H)+. |
| Example III-151 | (2S,3S,4S,5S)-3-tert-butyl-1-(cyclohexanecarbonyl)-4-[(7-methoxy-4-methylquinolin-2-yl)amino]-5-phenylpyrrolidine-2-carboxylic acid | 1HNMR (400 MHz, dimethyl sulfoxide-d6) δ ppm 7.82 (d, J = 9.0 Hz, 1H). 7.52 (d, J = 7.4 Hz. 2H), 7.20-7.06 (m, 6H), 6.57 (s, 1H), 2.57 (t, J 6.4 Hz, 1H), 2.48 (s, 3H), 1.74-1.67 (m, 2H) 1.53-1.43 (m, 2H), 1.37-1.25 (m, 1H) 1.23-1.17 (m, 1H), 1.17-1.07 (m, 3H), 1.06 (s, 9H), 0.79-0.67 (m, 1H);<br>MS (APCI+) m/z 544.5 (M + H)+. |
| Example III-152 | (2S,3S,4S,5S)-3-tert-butyl-1-(cyclohexanecarbonyl)-4-[(4-ethoxyquinolin-2-yl)amino]-5-phenylpyrrolidine-2-carboxylic acid | 1HNMR (400 MHz, dimethyl sulfoxide-d6) δ ppm 7.96 (dd, J = 8.2, 1.3 Hz, 1H), 7.79-7.72 (m, 1H), 7.66 (d, J = 8.3 Hz, 1H), 7.54 (d, J = 7.5 Hz, 2H), 7.44 (t, J = 7.6 Hz, 1H), 7.21-7.10 (m, 3H), 6.23 (s, 1H), 5.52 (d, J = 8.3 Hz, 1H), 4.98 (dd, J = 8.4, 6.5 Hz, 1H), 4.46 (d, J = 6.1 Hz, 1H), 4.37-4.25 (m, 1H), 2.55 (t, J = 6.3 Hz, 1H), 2.30-2.21 (m, 1H), 1.75-1.67 (m, 2H), 1.53-1.48 (m, 1H) 1.46 (t, J = 7.0 Hz, 3H), 1.39-1.24 (m, 1H), 1.22-1.14 (m, 1H), 1.13-1.08 (m, 2H), 1.07 (s, 9H), 0.79-0.66 (m, 1H);<br>MS (APCI+) m/z 544.5 (M + H)+. |
| Example III-153 | (2S,3S,4S,5S)-3-tert-butyl-1-(cyclohexanecarbonyl)-4-({5-[(2-oxopyridin-1(2H)-yl)methyl]pyridin-2-yl}amino)-5-phenylpyrrolidine-2-carboxylic acid | 1HNMR (400 MHz, dimethyl sulfoxide-d6) δ ppm 7.90 (d, J = 2.3 Hz, 1H), 7.60 (dd, J = 6.7, 1.9 Hz, 1H), 7.46-7.37 (m, 4H), 7.18-7.08 (m, 3H), 6.44-6.39 (m, 2H), 6.23 (td, J = 6.7, 1.3 Hz, 1H), 5.35 (d, J = 8.3 Hz, 1H), 4.90 {s, 2H), 4.83 (t, J = 7.5 Hz, 1H), 4.39 (d, J = 6.0 Hz, 1H), 2.43 (t, J = 6.4 Hz, 1H), 2.26-2.16 (m, 1H), 1.71-1.65 (m, 2H), 1.52-1.41 (m, 2H), 1.35-1.23 (m, 1H), 1.21-1.04 (m, 5H), 1.01 (s, 9H), 0.78-0.63 (m, 1H);<br>MS (APCI+) m/z 557.5 (M + H)+. |
| Example III-154 | (2S,3S,4S,5S)-3-tert-butyl-1-(cyclohexanecarbonyl)-4-[(7-methoxy-3-methylisoquinolin-1-yl)amino]-5-phenylpyrrolidine-2-carboxylic acid | 1HNMR (400 MHz, dimethyl sulfoxide-d6) δ ppm 7.53 (dd, J = 8.3, 4.8 Hz, 3H), 7.30-7.25 (m, 1H), 7.11 (t, J = 7.5 Hz, 2H), 7.03 (t, J = 7.3 Hz, 1H), 6.95-6.90 (m, 1H), 6.72 (s, 1H), 5.48 (d, J = 7.5 Hz, 1H), 5.32-5.27 (m, 1H), 4.56 (d, J = 4.1 Hz, 1H), 3.82 (s, 3H), 2.68-2.65 (m, 1H), 2.38 (s, 3H), 2.30-2.22 (m, 1H), 1.74-1.66 (m, 2H), 1.54-1.46 (m, 2H), 1.36-1.17 (m, 4H), 1.11 (s, 9H);<br>MS (APCI+) m/z 544.5.5 (M + H)+. |
| Example III-155 | (2S,3S,4S,5S)-3-tert-butyl-4-{[5-{tert-butylcarbamoyl)pyridin-2-yl]amino}-1-(cyclohexanecarbonyl)-5-phenylpyrrolidine-2-carboxylic acid | 1HNMR (400 MHz, dimethyl sulfoxide-d6) δ ppm 8.38 (d, J = 2.4 Hz, 1H), 7.68 (dd, J = 8.8, 2.4 Hz, 1H), 7.47-7.43 (m, 2H), 7.24-7.13 (m, 3H), 6.27 (d, J = 8.9 Hz, 1H), 5.35 (d, J = 8.4 Hz, 1H), 4.97 (t, J = 7.9 Hz, 1H), 4.38 (d, J = 6.4 Hz, 1H), 2.44 (t, J = 6.9 Hz, 1H), 2.29-2.17 (m, 1H), 1.74-1.65 (m, 2H), 1.55-1.42 (m, 1H), 1.36 (s, 8H), 1.32-1.23 (m, 1H), 1.22-1.04 (m, 5H), 1.01 (s, 9H);<br>MS (APCI+) m/z 549.5 (M + H)+. |
| Example III-156 | (2S,3S,4S,5S)-3-tert-butyl-1-(cyclohexanecarbonyl)-4-[(isoquinolin-3-yl)amino]-5-phenylpyrrolidine-2-carboxylic acid | 1HNMR (400 MHz, dimethyl sulfoxide-d6) δ ppm 8.74 (s, 1H), 7.75 (d, J = 8.2 Hz, 1H), 7.52-7.42 (m, 4H), 7.19-7.07 (m, 4H), 5.39 (d, J = 8.0 Hz, 1H), 4.91 (t, J = 7.2 Hz, 1H), 4.43 (d, J = 5.6 Hz, 1H), 2.42 (t, J = 6.0 Hz, 1H), 2.29-2.18 (m, 1H), 1.75-1.65 (m, 2H), 1.51-1.41 (m, 2H), 1.36-1.24 (m, 1H), 1.22-1.15 (m, 1H), 1.13-1.06 (m, 2H), 1.05 (s, 9H);<br>MS (APCI+) m/z 500.4 (M + H)+. |
| Example III-157 | (2S,3S,4S,5S)-3-tert-butyl-1-(cyclohexanecarbonyl)-4-[(1,3-dimethyl-2,4-dioxo-1,2,3,4-tetrahydropyrido[4,3-d]pyrimidin-5-yl)amino]-5- | 1HNMR (400 MHz, dimethyl sulfoxide-d6) δ ppm 8.12 (d, J= 5.9 Hz, 1H), 7.44 (d, J = 7.4 Hz, 2H), 7.16-7.04 (m, 3H), 6.42 (d, J = 6.0 Hz, 1H), 5.39-5.30 (m, 2H), 4.41 (d, J = 6.0 Hz, 1H), 3.36 (s, 3H), 3.15 (s, 3H), 2.39 (t, J = 6,1 Hz, 1H), 2.28-2.20 (m, 1H), 1.73-1.65 (m, 2H), 1.52-1.40 (m, 2H), 1.36-1.23 (m, |

TABLE 3-continued

| | | |
|---|---|---|
| | phenylpyrrolidine-2-carboxylic acid | 1H), 1.13 (d, J = 39.0 Hz, 5H), 1.02 (s, 9H); MS (APCI+) m/z 562.4 (M + H)+. |
| Example III-158 | (2S,3S,4S,5S)-3-tert-butyl-4-{[5-(2-cyanopropan-2-yl)pyridin-2-yl]amino}-1-(cyclohexanecarbonyl)-5-phenylpyrrolidine-2-carboxylic acid | $^1$HNMR (400 MHz, dimethyl sulfoxide-d$_6$) δ ppm 8.00 (d, J = 2.6 Hz, 1H), 7.44 (dd, J = 8.0, 3.4 Hz, 3H), 7.21-7.11 (m, 3H), 6.34 (d, J = 8.9 Hz, 1H), 5.34 (d, J = 8.2 Hz, 1H), 4.91 (t, J = 7.5 Hz, 1H), 4.39 (d, J = 6.0 Hz, 1H), 2.43 (d, J = 6.5 Hz, 1H), 2.27-2.18 (m, 1H), 1.72-1.65 (m, 2H); 1,62 (s, 6H), 1.53-1.41 (m, 2H), 1.35-1.23 (m, 1H), 1.21-1.05 (m, 4H), 1.02 (s, 9H); MS (APCI+) m/z 417.5 (M + H)+. |
| Example III-159 | (2S,3S,4S,5S)-3-tert-butyl-4-{[5-(1-cyanocyclopropyl)pyridin-2-yl]amino}-1-(cyclohexanecarbonyl)-5-phenylpyrrolidine-2-carboxylic acid | $^1$HNMR (400 MHz, dimethyl sulfoxide-d$_6$) δ ppm 7.93 (d, J = 2.5 Hz, 1H) 7.48-7.41 (m, 2H), 7.29 (dd, J = 8.8, 2.5 Hz, 1H), 7.21-7.12 (m, 3H), 6.31 (d, J = 8.9 Hz, 1H), 5.33 (d, J = 8.2 Hz, 1H), 4.90 (t, J = 7.6 Hz, 1H), 4.38 (d, J = 6.1 Hz. 1H), 2.41 (t, J = 6.6 Hz, 1H), 2.27-2.18 (m, 1H), 1.73-1.64 (m, 2H), 1.61-1.56 (m, 2H), 1.53-1.40 (m, 2H), 1.34-1.29 (m; 2H), 1.22-1.04 (m, 5H), 1.01 (s, 9H); MS (APCI+) m/z 515.5 (M + H)+. |
| Example III-160 | (2S,3S,4S,5S)-4-{[3-(benzyloxy)pyridin-2-yl]amino}-3-tert-butyl-1-(cyclohexanecarbonyl)-5-phenylpyrrolidine-2-carboxylic acid | $^1$HNMR (400 MHz, dimethyl sulfoxide-d$_6$) δ ppm 7.51 (d, J = 5.3 Hz, 1H), 7.45 (d, J = 5.2 Hz, 2H), 7.35 (ddd, J = 13.9, 7.7, 6.0 Hz, 3H), 7.27-7.22 (m, 2H), 7.15-7.05 (m, 3H), 6.95 (d, J = 7.8 Hz, 1H), 6.47 (dd, J = 7.8, 5.3 Hz, 1H), 5.33 (d, J = 7.8 Hz, 1H), 5.13 (s, 1H), 4.95-4.81 (m, 2H), 4.46 (d, J = 4.5 Hz, 1H), 2.36 (t, J = 4.7 Hz, 1H), 2.27-2.16 (m, 1H), 1.71-1.63 (m, 2H), 1.53-1.43 (m, 2H), 1.36-1.16 (m, 3H), 1.11-1.06 (m, 2H), 1.04 (s, 9H); MS (APCI+) m/z 556.5 (M + H)+. |
| Example III-161 | (2S,3S,4S,5S)-3-tert-butyl-4-{[5-{tert-butylcarbamoyl)pyridin-3-yl]amino}-1-(cyclohexanecarbonyl)-5-phenylpyrrolidine-2-carboxylic acid | $^1$HNMR (400 MHz, dimethyl sulfoxide-d$_6$) δ ppm 8.09 (d, J = 1.8 Hz, 1H), 7.88 (d, J = 2.9 Hz, IH), 7.50 (d, J = 7.5 Hz, 2H), 7.28 (s, 1H), 7.17 (dt, J = 12.9, 7.1 Hz, 3H), 5.41 (d, J = 7.9 Hz, 1H), 4.48-4.43 (m, 1H), 4.40 (d, J = 6.0 Hz, 1H), 2.41 (t, J = 6.1 Hz, 1H), 2.28-2.19 (m, 1H), 1.75-1.65 (m, 2H), 1.52-1.46 (m, 1H), 1.39 (s, 9H), 1.31-1.21 (m, 1H), 1.21-1.05 (m, 5H), 1.03 (s, 9H); MS (APCI+) m/z 549.5 (M + H)+. |
| Example III-162 | (2S,3S,4S,5S)-3-tert-butyl-1-(cyclohexanecarbonyl)-4-[(isoquinolin-4-yl)amino]-5-phenylpyrrolidine-2-carboxylic acid | $^1$HNMR (400 MHz, dimethyl sulfoxide-d$_6$) δ ppm 8.70 (s, 1H), 8.14 (d, J = 7.9 Hz, 1H), 7.84 (d, J = 8.5 Hz, 3H), 7.79 (dd, J = 8.2, 3.7 Hz, 1H), 7.52 (d, J = 7.6 Hz, 2H), 7.04-6.91 (m, 3H), 5.53 (d, J = 7.6 Hz, 1H), 4.73-4.69 (m, 1H), 4.52 (d, J = 4.9 Hz, 1H), 2.70 (t, J = 5.1 Hz, 1H), 1.74-1.67 (m, 2H), 1.52-1.45 (m, 2H), 1.40 (dd, J = 16.3, 14.0 Hz, 1H), 1.20 (s, 2H), 1.17 (s, 2H), 1.09 (s, 9H), 1.06-1.03 (m, 1H); MS (APCI+) m/z 500.5 (M + H)+. |
| Example III-163 | (2S,3S,4S,5S)-3-tert-butyl-4-({[2-methoxy-4-(trifluoromethyl)phenyl]methyl}-amino)-5-phenyl-1-(pyridine-3-carbonyl)pyrrolidine-2-carboxylic acid | LC/MS (ESI+) m/z 556.5 (M + H)+. |
| Example III-164 | (2S,3S,4S,5R)-3-tert-butyl-5-(3-chloropyridin-2-yl)-1-(cyclohexanecarbonyl)-4-({[2-methoxy-5-(trifluoromethyl)phenyl]methyl}amino)pyrrolidine-2-carboxylic acid | LC/MS (ESI+) m/z 596.4 (M + H)+. |
| Example III-165 | (2R,3R,4R,5R)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid | MS (ESI+) m/z 564.2 (M + H)+. |
| Example III-166 | (2S,3S,4S,5S)-3-tert-butyl-4-{[(5-tert-butyl-2-methoxyphenyl)methyl]amino}-1-[(4-chlorophenyl)acetyl]-5-phenylpyrrolidine-2-carboxylic acid | MS (APCI+) m/z 591.1 (M + H)+. |

TABLE 3-continued

| Example III-167 | (2S,3S,4S,5S)-3-tert-butyl-4-{[(5-tert-butyl-2-methoxyphenyl)methyl]-amino}-1-(cyclohexylacetyl)-5-phenylpyrrolidine-2-carboxylic acid | MS (APCI+) m/z 563.1 (M + H)+. |
|---|---|---|
| Example III-168 | (2S,3S,4S;5,S)-4-({[5-(butan-2-yl)-2-methoxyphenyl]methyl}-amino)-3-tert-butyl-1-(cyclohexanecarbonyl)-5-phenylpyrrolidine-2-carboxylic acid | MS (APCI+) m/z 549.1 (M + H)+. |
| Example III-169 | (2S,3S,4S,5S)-3-tert-butyl-1-(cyclohexanecarbonyl)-4-({[5-(cyclohexylmethyl)-2-methoxyphenyl]methyl}amino)-5-phenylpyrrolidine-2-carboxylic acid | MS (APCI+) m/z 589.1 (M + H)+. |
| Example III-170 | (2S,3S,4S,5S)-3-ter-butyl-1-(cyclohexanecarbonyl)-4-({[5-(2-ethylbutyl)-2-methoxyphenyl]methyl}-amino)-5-phenylpyrrolidine-2-carboxylic acid | MS (APCI+) m/z 577.1 (M + H)+. |
| Example III-171 | (2S,3S,4S,5S)-3-tert-butyl-1-(cyclohexanecarbonyl)-4-({[2-methoxy-5-(1-phenylethyl)phenyl]methyl}-amino)-5-phenylpyrrolidine-2-carboxylic acid | MS (APCI+) m/z 597.1 (M + H)+. |
| Example III-172 | (2S,3S,4S,5S)-3-tert-butyl-4-{[(5-tert-butyl-2-methoxyphenyl)methyl]-amino}-1-[(3,4-difluorophenyl)acetyl]-5-phenylpyrrolidine-2-carboxylic acid | MS (APCI+) m/z 593.0 (M + H)+. |
| Example III-173 | (2S,3S,4S,5S)-3-tert-butyl-4-{[(5-tert-butyl-2-methoxyphenyl)methyl]-amino}-1-[(2,4-difluorophenyl)acetyl]-5-phenylpyrrolidine-2-carboxylic acid | MS (APCI+) m/z 593.0 (M + H)+. |
| Example III-174 | (2S,3S,4S,5S)-3-tert-butyl-4-{[(5-tert-butyl-2-methoxyphenyl)methyl]amino}-1-(4-methylcyclohexane-1-carbonyl)-5-phenylpyrrolidine-2-carboxylic acid | MS (APCI+) m/z 563.1 (M + H)+. |
| Example III-175 | (2S,3S,4S,5S)-3-tert-butyl-4-{[(5-tert-butyl-2-methoxyphenyl)methyl]amino}-1-carbonyl)-5-phenylpyrrolidine-2-carboxylic acid | MS (APCI+) m/z 563.1 (M + H)+. |
| Example III-176 | (2S,3S,4S,5S)-3-tert-butyl-4-{[(5-tert-butyl-2-methoxyphenyl)methyl]amino}-1-(1,5-dimethyl-4-oxo-1,4-dihydropyridine-3-carbonyl)-5-phenylpyrrolidine-2-carboxylic acid | MS (APCI+) m/z 588.1 (M + H)+. |
| Example III-177 | (2S,3S,4S,5S)-3-tert-butyl-4-{[(5-tert-butyl-2-methoxyphenyl)methyl]amino}-1-(1-methyl-1H-indole-3-carbonyl)-5-phenylpyrrolidine-2-carboxylic acid | MS (APCI+) m/z 596.1 (M + H)+. |
| Example III-178 | (2S,3S,4S,5S)-3-tert-butyl-4-{[(5-tert-butyl-2-methoxyphenyl)methyl]amino}-1-(6-fluoro-2H,4H-1,3-benzodioxine-8-carbonyl)-5-phenylpyrrolidine-2-carboxylic acid | MS (APCI+) m/z 619.1 (M + H)+. |

TABLE 3-continued

| Example III-179 | (2S,3S,4S,5S)-3-tert-butyl-4-{[(5-tert-butyl-2-methoxyphenyl)methyl]amino}-5-phenyl-1-[2-(propan-2-yl)oxane-4-carbonyl]pyrrolidine-2-carboxylic acid | MS (APCI+) m/z 593.1 (M + H)+. |
|---|---|---|
| Example III-180 | (2S,3S,4S,5S)-3-tert-butyl-1-(cyclohexanecarbonyl)-4-{[(2-hydroxyquinolin-3-yl)methyl]amino}-5-phenylpyrrolidine-2-carboxylic acid | MS (ESI+) m/z 530.3 (M + H)+. |
| Example III-181 | (2S,3S,4S,5S)-3-tert-butyl-1-(cyclohexanecarbonyl)-4-({[2-methoxy-5-(morpholin-4-yl)phenyl]methyl}amino)-5-phenylpyrrolidine-2-carboxylic acid | $^1$HNMR (400 MHz, dimethyl sulfoxide-$d_6$) δ ppm 7.61-7.55 (m, 2H), 7.41 (t, J = 7.5 Hz, 2H)5 7.35 (d, J = 7.3 Hz, 1H), 6.86-6.81 (m, 2H), 6.66-6.64 (m, 1H), 5.38 (d, J = 7.1 Hz, 1H), 4.55 (d, J = 1.9 Hz, 1H), 3.94-3.89 (m, 1H), 3.78 (d, J = 13.5 Hz, 1H), 3.73-3.70 (m, 4H), 3.55 (s, 3H), 3,46 (d, J = 13.5 Hz, 1H), 2.96-2.93 (m, 4H), 2.56-2.54 (m, 1H), 1.66-1.59 (m, 2H), 1.55-1.47 (m, 3H), 1.25-1.18 (m, 3H), 1.16 (s, 1H), 1.11-1.04 (m, 1H), 1.02 (s, 1H), 1.00 (s, 9H), 0.98 (s, 1H); MS (APCI+) m/z 606.6 (M + H)+. |
| Example III-182 | (2S,3S,4S,5S)-3-tert-butyl-4-{[(5-tert-butyl-2-methoxyphenyl)methyl]amino}-1-[(S*)-2-(4-chloro-3-methyl-1H-pyrazol-1-yl)propanoyl]-5-phenylpyrrolidine-2-carboxylic acid | MS (APCI+) m/z 609.0 (M + H)+. |
| Example III-183 | (2S,3S,4S,5S)-3-tert-butyl-1-(cyclohexanecarbonyl)-5-[2-(dimethylamino)pyridin-3-yl]-4-({[2-methoxy-5-(tricyclo[3.3.1.1$^{3,7}$]decan-1-yl)phenyl]methyl}amino)pyrrolidine-2-carboxylic acid | MS (APCI+) m/z 671.3 (M + H)+. |
| Example III-184 | (2S,3S,4S,5S)-3-tert-butyl-1-(cyclohexanecarbonyl)-4-({[2-methoxy-5-(4-methylpiperazin-1-yl)phenyl]methyl}amino)-5-phenylpyrrolidine-2-carboxylic acid | $^1$HNMR (400 MHz, dimethyl sulfoxide-$d_6$) δ ppm 7.57-7.49 (m, 2H), 7.38 (t, J = 7.4 Hz, 2H), 7.32 (t, J = 7.2 Hz, 1H), 6.85 (dd, J = 9.0, 2.9 Hz, 1H), 6.81 (d J = 8.9 Hz, 1H), 6.67-6.64 (m, 1H), 5.29 (d, J = 7.0 Hz, 1H), 4.53 (d, J = 2.0 Hz, 1H), 3.70 (d, J = 7.3 Hz, 1H), 3.53 (s, 3H), 3.35-3.31 (m, 4H), 3.25-3.20 (m, 3H), 2.88 (s, 3H), 2.43 (s, 1H), 1.68-1.61 (m, 2H), 1.57-1.49 (m, 2H), 1.29-1.17 (m, 3H), 1.13-1.05 (m, 2H), 1.03 (s, 1H), 1.01 (s, 9H); MS (APCI+) m/z 619.6 (M + H)+. |
| Example III-185 | (2S,3S,4S,5S)-3-tert-butyl-1-[(1S)-3,3-difluorocyclohexane-1-carbonyl]-4-({[2-methoxy-5-(trifluoromethyl)phenyl]methyl}amino)-5-phenylpyrrolidine-2-carboxylic acid | LC/MS (ESI+) m/z 597.5 (M + H)+. |
| Example III-186 | (2S,3S,4S,5S)-3-tert-butyl-1-(cyclohexanecarbonyl)-4-({[2-methoxy-5-(1-methyl-1H-pyrazol-4-yl)phenyl]methyl}amino)-5-phenylpyrrolidine-2-carboxylic acid | $^1$HNMR (400 MHz, dimethyl sulfoxide-$d_6$) δ ppm 7.77 (s, 1H), 7.59 (s, 1H), 7.58-7.53 (m, 2H)5 7.44-7.32 (m, 5H), 7.16 (s, 1H), 6.89 (d, J = 8.5 Hz, 1H), 5.36 (d, J = 7.0 Hz, 1H), 4.56 (d, J = 2.0 .Hz, 1H), 3.87-3.85 (m, 1H), 3.85 (s, 3H), 3.77 (d, J = 13.6 Hz, 1H), 3.59 (s, 3H), 3.49 (d, J = 13.4 Hz, 1H), 2.54-2.52 (m, 1H), 1.68-1.61 (m, 2H), 1.57-1.49 (m, 2H), 1.29-1.17 (m, 4H), 1.14-1.05 (m, 3H), 1.02 (s, 9H); MS (APCI+) m/z 573.5 (M + H)+. |
| Example III-187 | (2S,3S,4S,5S)-3-tert-butyl-1-(cyclohexanecarbonyl)-4-({[5-(1-cyclopropyl-1H-pyrazol-4-yl)-2-methoxyphenyl]methyl}amino)-5-phenylpyrrolidine-2-carboxylic acid | $^1$HNMR (400 MHz, dimethyl sulfoxide-$d_6$) δ ppm 7.84 (s, 1H), 7.59 (s, 1H), 7.57-7.53 (m, 2H), 7.43-7.31 (m, 4H), 7.17-7.15 (m, 1H), 6.89 (d, J = 8.5 Hz, 1H), 5.34 (d, J = 7.0 Hz, 1H), 4.55 (d, J = 2.0 Hz, 1H), 3.81 (d, J = 6.7 Hz, 1H), 3.76 (d, J = 13.7 Hz, 1H), 3.69 (ddd, J = 11.2, 7.4, 4.0 Hz, 1H), 3.60 (s, 3H), 3.49 (d, J = 13.5 Hz, 1H), 2.54-2.52 (m, 1H), 1.68-1.60 (m, 2H), 1.58-1.45 (m, 3H), 1.28-1.20 (m, 2H), 1.18 (s, 2H), 1.13-1.04 (m, 2H), 1.01 (s, 9H), 1.00-0.97 (m, 2H); MS (APCI+) m/z 599.5 (M + H)+. |

TABLE 3-continued

| Example III-188 | (2S,3S,4S,5S)-3-tert-butyl-1-(cyclohexanecarbonyl)-5-(2-fluorophenyl)-4-[({2-methoxy-5-[(1S,3S)-tricyclo[3.3.1.1$^{3,7}$]decan-1-yl]phenyl}methyl)amino]pyrrolidine-2-carboxylic acid | MS (ESI+) m/z 645.3 (M + H)$^+$. |
|---|---|---|
| Example III-189 | (2S,3S,4S,5S)-1-(cyclohexanecarbonyl)-4-({[2-methoxy-5-(trifluoromethyl)pyridin-3-yl]methyl}amino)-3-(1-methylcyclopropyl)-5-phenylpyrrolidine-2-carboxylic acid | MS (APCI+) m/z 560 (M + H)$^+$. |
| Example III-190 | (2S,3S,4S,5S)-3-tert-butyl-4-{[(5-tert-butyl-2-methoxyphenyl)methyl]amino}-1-[2-(3,5-dimethylphenoxy)propanoyl]-5-phenylpyrrolidine-2-carboxylic acid | MS (APCI+) m/z 615.1 (M + H)$^+$. |
| Example III-191 | (2S,3S,4S,5S)-3-tert~butyl-4-{[(5-tert-butyl-2-methoxyphenyl)methyl]amino}-5-phenyl-1-(1,2,3,4-tetrahydronaphthalene-2-carbonyl)pyrrolidine-2-carboxylic acid | MS (APCI+) m/z 597.1 (M + H)$^+$. |
| Example III-192 | (2S,3S,4S,5S)-3-tert-butyl-4-{[(5-tert-butyl-2-methoxyphenyl)methyl]amino}-5-phenyl-1-[(1R,5S)-tricyclo[3.2.1.0$^{2,4}$]octane-3-carbonyl]pyrrolidine-2-carboxylic acid | MS (APCI+) m/z 573.1 (M + H)$^+$. |
| Example III-193 | (2S3S,4S,5S)-3-tert-butyl-4-{[(5-tert-butyl-2-methoxyphenyl)methyl]amino}-5-phenyl-1-[2-(thiophen-2-yl)cyclopropane-1-carbonyl]pyrrolidine-2-carboxylic acid | MS (APCI+) m/z 589.1 (M + H)$^+$. |
| Example III-194 | (2S,3S,4S,5S)-3-tert-butyl-4-{[(5-tert-butyl-2-methoxyphenyl)methyl]amino}-1-[1-(3-methylphenyl)-5-(propan-2-yl)-1H-pyrazole-4-carbonyl]-5-phenylpyrrolidine-2-carboxylic acid | MS (APCI+) m/z 665.1 (M + H)$^+$. |
| Example III-195 | (2S,3S,4S,5S)-3-tert-butyl-4-{[(5-tert-butyl-2-methoxyphenyl)methyl]amino}-1-(2-methylcyclohexane-1-carbonyl)-5-phenylpyrrolidine-2-carboxylic acid | MS (APCI+) m/z 563.2 (M + H)$^+$. |
| Example III-196 | (2S,3S,4S,5S)-3-tert-butyl-1-(3,5-dimetliylcyclohexane-1-carbonyl)-4-({[2-methoxy-5-(trifluoromethyl)phenyl]methyl}amino)-5-phenylpyrrolidine-2-carboxylic acid | |
| Example III-197 | (2S,3S,4S,5S)-3-tert-butyl-1-(3,3-dimethylcyclopentane-1-carbonyl)-4-({[2-methoxy-5-(trifluoromethyl)phenyl]methyl}amino)-5-phenylpyrrolidine-2-carboxylic acid | LC/MS (ESI+) m/z 575.5 (M + H)$^+$. |
| Example III-198 | (2S,3S,4S,5S)-3-tert-butyl-4-({[2-methoxy-5-(trifluoromethyl)phenyl]methyl}amino)-1-(3- | LC/MS (ESI+) m/z 561.5 (M + H)$^+$. |

TABLE 3-continued

| | | |
|---|---|---|
| | methylcyclopentane-1-carbonyl)-5-phenylpyrrolidine-2-carboxylic acid | |
| Example III-199 | (2R,3R,4R,5S)-3-tert-butyl-1-(cyclohexanecarbonyl)-4-({[2-methoxy-5-(trifluoromethyl)phenyl]methyl}-amino)-5-phenylpyrrolidine-2-carboxylic acid | LC/MS (ESI+) m/z 561.7 (M + H)+. |
| Example III-200 | (2S,3S,4S,5S)-3-tert-butyl-4-({[2-methoxy-5-(trifluoromethyl)pyridin-3-yl]methyl}amino)-5-phenyl-1-{(2R,3R)-3-[(1H-pyrazol-1-yl)methyl]oxolane-2-carbonyl}pyrrolidine-2-carboxylic acid | LC/MS (ESI+) m/z 630.5 (M + H)+. |
| Example III-201 | (2S,3S,4S,5S)-3-tert-butyl-1-(3,5-dimethylcyclohexane-1-carbonyl)-4-({[2-methoxy-5-(trifluoromethyl)pyridin-3-yl]methyl}amino)-5-phenylpyrrolidine-2-carboxylic acid | LC/MS (ESI+) m/z 590.5 (M + H)+. |
| Example III-202 | (2S,3S,4S,5S)-4-({[5-(bicyclo[1.1.1]pentan-1-yl)-2-methoxyphenyl]methyl}-amino)-3-tert-butyl-1-(cyclohexanecarbonyl)-5-phenylpyrrolidine-2-carboxylic acid | MS (ESI+) m/z 559.3 (M + H)+. |
| Example III-203 | (2S,3S,4S,5S)-3-tert-butyl-4-{[(5-tert-butyl-2-methoxyphenyl)methyl]amino}-1-(3,3-dimethylcyclohexane-1-carbonyl)-5-phenylpyrrolidine-2-carboxylic acid | LC/MS (ESI+) m/z 577.6 (M + H)+. |
| Example III-204 | (2S,3S,4S,5S)-3-tert-butyl-4-{[(5-tert-butyl-2-methoxyphenyl)methyl]amino}-1-(2,2-dimethylcyclopentane-1-carbonyl)-5-phenylpyrrolidine-2-carboxylic acid | LC/MS (ESI+) m/z 563.9 (M + H)+. |
| Example III-205 | (2S,3S,4S,5S)-3-tert-butyl-4-{[(5-tert-butyl-2-methoxyphenyl)methyl]amino}-5-[2-(dimethylamino)pyridin-3-yl]-1-(2-methylcyclohexane-1-carbonyl)pyrrolidine-2-carboxylic acid | MS (APCI+) m/z 607.2 (M + H)+. |
| Example III-206 | (2S,3S,4S,5S)-3-tert-butyl-4-{[(5-tert-butyl-2-methoxyphenyl)methyl]amino}-5-[2-(dimethylamino)pyridin-3-yl]-1-[3-(trifluoromethyl)cyclohexane-1-carbonyl]pyrrolidine-2-carboxylic acid | MS (APCI+) m/z 661.2 (M + H)+. |
| Example III-207 | (2S,3S,4S,5S)-3-(tert-butyl)-4-(((5-cyclobutyl-2-methoxypyridin-3-yl)methyl)amino)-1-(3,5-dimethylcyclohexanecarbonyl)-5-phenylpyrrolidine-2-carboxylic acid | MS (APCI+) m/z 576.2 (M + H)+. |
| Example III-208 | (2S,3S,4S,5S)-3-tert-butyl-4-{[(5-cyclobutyl-2-methoxypyridin-3-yl)methyl]amino}-1-(2- | MS (APCI+) m/z 562.2 (M + H)+. |

TABLE 3-continued

| | | |
|---|---|---|
| Example III-209 | (2S,3S,4S,5S)-3-tert-butyl-4-{[(5-cyclobutyl-2-methoxypyridin-3-yl)methyl]amino}-5-phenyl-1-[3-(trifluoromethyl)cyclohexane-1-carbonyl]pyrrolidine-2-carboxylic acid | MS (APCI+) m/z 616.1 (M + H)+ |
| Example III-210 | (2S,3S,4S,5S)-3-tert-butyl-4-{[(5-tert-butyl-2-methoxyphenyl)methyl]amino}-5-[2-(dimethylamino)pyridin-3-yl]-1-[(2R*)-6-fluoro-3,4-dihydro-2H-1-benzopyran-2-carbonyl]pyrrolidine-2-carboxylic acid | MS (APCI+) m/z 661.3 (M + H)+ |
| Example III-211 | (2S,3S,4S,5S)-3-tertt-butyl-5-[2-(dimethylamino)pyridin-3-yl]-1-(cis-4-hydroxy-4-propylcyclohexane-1-carbonyl)-4-{[2-methoxy-5-(trifluoromethyl)pyridin-3-yl]amino}pyrrolidine-2-carboxylic acid | MS (APCI+) m/z 660 (M + H)+ |
| Example III-212 | (2S,3S,4S,5S)-3-tert-butyl-5-[2-(dimethylamino)pyridin-3-yl]-4-{[2-methoxy-5-(trifluoromethyl)pyridin-3-yl]amino}-1-[(1S,2S)-2-(trifluoromethyl)cyclohexane-1-carbonyl]pyrrolidine-2-carboxylic acid | MS (APCI+) m/z 594 (M + H)+ |
| Example III-213 | (2S,3S,4S,5S)-3-tert-butyl-5-[2-(dimethylamino)pyridin-3-yl]-4-{[2-methoxy-5-(trifluoromethyl)pyridin-3-yl]amino}-1-[(2R)-oxane-2-carbonyl]pyrrolidine-2-carboxylic acid | MS (APCI+) m/z 594 (M + H)+ |
| Example III-214 | (2S,3S,4S,5S)-3-tert-butyl-4-{[(5-cyclobutyl-2-methoxypyridin-3-yl)methyl]amino}-5-phenyl-1-[2-(trifluoromethyl)cyclohexane-1-carbonyl]pyrrolidine-2-carboxylic acid | MS (ESI+) m/z 616.2 (M + H)+ |
| Example III-215 | (2S,3S,4S,5S)-3-tert-butyl-4-{[(5-tert-butyl-2-methoxyphenyl)methyl]amino}-1-[(2R)-2-methoxy-2-phenylacetyl]-2-methyl-5-phenylpyrrolidine-2-carboxylic acid | LC/MS (ESI+) m/z 601.5 (M + H)+ |
| Example III-216 | (2S,3S,4S,5S)-3-tert-butyl-5-[2-(dimethylamino)pyridin-3-yl]-4-{[6-methyl-4-(trifluoromethyl)pyridin-2-yl]amino}-1-[(2R)-oxane-2-carbonyl]pyrrolidine-2-carboxylic acid | MS (APCI+) m/z 578 (M + H)+ |
| Example III-217 | (2S,3S,4S,5S)-3-tert-butyl-4-{[(5-tert-butyl-2-methoxyphenyl)methyl]amino}-1-[di(propan-2-yl)carbamoyl]-5-phenylpyrrolidine-2-carboxylic acid | MS (APCI+) m/z 566 (M + H)+ |
| Example III-218 | (2S,3S,4S,5S)-4-({[5-(bicyclo[1.1.1]pentan-1-yl)-2-methoxyphenyl]methyl}amino)-3-tert-butyl-5-[2-(difluoromethoxy)pyridin-3-yl]-1-{[(propan-2- | MS (ESI+) m/z 602.2 (M + H)+ |

TABLE 3-continued

| | | |
|---|---|---|
| | yl)oxy]carbonyl}pyrrolidine-2-carboxylic acid | |
| Example III-219 | (2S,3S,4S,5S)-3-tert-butyl-4-{[(6-tert-butyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid | MS (ESI+) m/z 570.2 (M + H)+ |
| Example III-220 | (2S,3S,4S,5S)-4-({[5-(bicyclo[1.1.1]pentan-1-yl)-2-methoxyphenyl]-methyl}amino)-3-tert-butyl-1-{[(propan-2-yl)oxy]carbonyl}-5-[2-(propan-2-yl)phenyl]pyrrolidine-2-carboxylic acid | MS (ESI+) m/z 577.3 (M + H)+ |
| Example III-221 | (2S,3S,4S,5S)-3-(bicyclo[1.1.1]pentan-1-yl)-4-({[2-methoxy-5-(trifluoromethyl)pyridin-3-yl]methyl}amino)-5-phenyl-1-{[(propan-2-yl)oxy]carbonyl}pyrrolidine-2-carboxylic acid | MS (ESI+) m/z 548 (M + H)+ |
| Example III-222 | (2S,3S,4S,5S)-3 (bicyclo[1.1.1]pentan 4-{[(5-tert-butyl-2-methoxyphenyl)methyl]amino}-5-(2-fluorophenyl)-1-{[(propan-2-yl)oxy]carbonyl}pyrrolidine-2-carboxylic acid | MS (ESI+) m/z 553 (M + H)+ |
| Example III-223 | (2S,3S,4S,5S)-3-tert-butyl-5-[2-(dimethylamino)pyridin-3-yl]-4-[({2-methoxy-5-[(3S,5S)-tricyclo[3.3.1.1^3,7]decan-1-yl]phenyl}methyl)amino]-1-{[(propan-2-yl)oxy]carbonyl}-pyrrolidine-2-carboxylic acid | MS (ESI+) m/z 647.3 (M + H)+ |
| Example III-224 | (2S,3S,4S,5S)-3-tert-butyl-4-{[(5-cyclobutyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid | MS (ESI+) m/z 568.2 (M + H)+ |
| Example III-225 | (2S,3S,4S,5S)-3-tert-butyl-5-[2-(dimethylamino)pyridin-3-yl]-4-[({2-methoxy-5-[(trifluoromethyl)sulfanyl]phenyl}methyl)amino]-1-{[(propan-2-yl)oxy]carbonyl}pyrrolidine-2-carboxylic acid | MS (ESI+) m/z 613.2 (M + H)+ |
| Example III-226 | (2S,3S,4S,5S)-3-tert-butyl-4-{[(6-methoxy-2,3-dihydro-1H-inden-5-yl)methyl]amino}-5-phenyl-1-{[(propan-2-yl)oxy]-carbonyl}pyrrolidine-2-carboxylic acid | MS (ESI+) m/z 509.1 (M + H)+ |
| Example III-227 | (2S,3S,4S,5S)-3-tert-butyl-4-{[(3-methoxy-5,5,8,8-tetramethyl-5,6,7,8-tetrahydronaphthalen-2-yl)methyl]amino}-5-phenyl-1-{[(propan-2-yl)oxy]carbonyl}pyrrolidine-2-carboxylic acid | MS (ESI+) m/z 579.2 (M + H)+ |
| Example III-228 | rac-(2S,3S,4S,5S)-3-tert-butyl-4-{[(5-tert-butyl-2-methoxyphenyl)methyl]amino}-1-(cyclohexanecarbonyl)- | |

TABLE 3-continued

| | | |
|---|---|---|
| | 5-(1-methyl-2-oxo-1,2-dihydropyridin-3-yl)pyrrolidine-2-carboxylic acid | |
| Example III-229 | (2S,3S,4S,5S)-3-tert-butyl-4-{[(5-tert-butyl-2-methoxyphenyl)methyl]amino}-1-{[(propan-2-yl)oxy]carbonyl}-5-{2-[(propan-2-yl)oxy]pyridin-3-yl}pyrrolidine-2-carboxylic acid | MS (ESI+) m/z 584.3 (M + H)+. |
| Example III-230 | (2S,3S,4S,5S)-3-tert-butyl-4-{[(5-tert-butyl-2-methoxyphenyl)methyl]amino}-1-[(7S)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid | MS (ESI+) m/z 710.2 (M + H)+. |
| Example III-231 | (2S,3S,4S,5S)-3-tert-butyl-4-({[2-methoxy-5-(trifluoromethoxy)phenyl]methyl}amino)-1-{[(propan-2-yl)oxy]carbonyl}-5-{2-[(propan-2-yl)oxy]pyridin-3-yl}pyrrolidine-2-carboxylic acid | MS (ESI+) m/z 612.2 (M + H)+. |
| Example III-232 | (2S,3S,4S,5S)-3-tert-butyl-5-[2-(dimethylamino)pyridin-3-yl]-4-({[2-methoxy-5-(2-methylbutan-2-yl)phenyl]methyl}amino)-1-{[(propan-2-yl)oxy]carbonyl}pyrrolidine-2-carboxylic acid | MS (ESI+) m/z 583.2 (M + H)+. |
| Example III-233 | (2S,3S,4S,5S)-3-tert-butyl-4-({[2-methoxy-5-(1-methylcyclobutyl)phenyl]methyl}amino)-5-(2-methoxypyridin-3-yl)-1-[(2S)-oxane-2-carbonyl]pyrrolidine-2-carboxylic acid | MS (ESI+) m/z 594.3 (M + H)+. |
| Example III-234 | (2S,3S,4S,5S)-3-tert-butyl-4-({[2-methoxy-5-(1-methylcyclobutyl)phenyl]methyl}amino)-5-(2-methoxypyridin-3-yl)-1-[(2R)-oxane-2-carbonyl]pyrrolidine-2-carboxylic acid | MS (ESI+) m/z 594.3 (M + H)+. |
| Example III-235 | (2S,3S,4S,5S)-3-tert-butyl-5-phenyl-1-{[(propan-2-yl)oxy]carbonyl}-4-({[1-(propan-2-yl)piperidin-4-yl]methyl}amino)pyrrolidine-2-carboxylic acid | MS (APCI+) m/z 488.2 (M + H)+. |
| Example III-236 | (2R93RAR95R)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid | MS (APCI+) m/z 570 (M + H)+. |
| Example III-237 | (2S,3S,4S,5S)-3-tert-butyl-4-({[2-hydroxy-5-(methoxycarbonyl)phenyl]methyl}amino)-1-[(2S)-oxolcinc-2-carbonyl]-5-[2-(propan-2-yl)phenyl]pyrrolidine-2-carboxylic acid | MS (ESI−) m/z 564.4 (M − H)−. |

Determination of Biological Activity

Cell Surface Expression-Horse Radish Peroxidase (CSE-HRP) Assay

A cellular assay for measuring the F508delCFTR cell surface expression after correction with test compounds either without or with a co-corrector (2 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid), was developed in human lung derived epithelial cell line (CFBE4lo-) (Veit G et al, (2012) Mol Biol Cell. 23(21): 4188-4202). The development was achieved by expressing the F508delCFTR mutation along with a horse-radish peroxidase (HRP) in the fourth exofacial loop, and then measuring the HRP activity using luminescence read-out from these cells, CFBE4lo-F508delCFTR-HRP, that were incubated overnight with the test corrector compounds, either without or with the co-corrector. For this primary assay, the CFBE4lo-F508delCFTR-HRP cells were plated in 384-well plates (Greiner Bio-one; Cat 781080) at 4,000 cells/well along with 0.5 μg/mL doxycycline to induce the F508delCFTR-HRP expression and further incubated at 37° C., 5% $CO_2$ for 72 hours. The test compounds were then added either without or with a co-corrector at the required concentrations and further incubated for 18-24 hours at 33° C. The highest concentration tested was 20 μM with an 8-point concentration response curve using a 3-fold dilution in both the test compound without or with the co-corrector. Three replicate plates were run to determine one $EC_{50}$. All plates contained negative controls (dimethyl sulfoxide, DMSO) and positive control (2 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 μL), and measuring the HRP activity using luminescence readout on EnVision® Multilabel Plate Reader (Perkin Elmer; product number 2104-0010). The raw counts from the experiment were analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}/Absolute\ (Mean_{Positive\ Control}-Mean_{Negative\ Control})]$$

wherein "SD" is standard deviation.

The % activity measured at each of the 8 test concentrations of the test compound added either without or with a co-corrector (2 μM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) was normalized to the on-plate positive control using the following formulae:

% activity(Test compound without co-corrector)=
[(test compound without co-corrector response−DMSO response)/(positive control response−DMSO response)]*100

% activity(Test compound with co-corrector)=[(test compound with co-corrector response−DMSO response)/(positive control response−DMSO response)]*100

The maximum % activity achieved for the test compound either without or with a co-corrector at any tested concentration is presented in Table 4 along with the respective $EC_{50}$'s calculated using the following general sigmoidal curve with variable Hill slope equation (described as Model 42 in the Accelrys® Assay Explorer v3.3 software):

$$y=(a-d)/(1+(x/c)\hat{\ }b)+d$$

General sigmoidal curve with concentration, response, top, bottom, $EC_{50}$ and Hill slope. This model describes a sigmoidal curve with an adjustable baseline, a. The equation can be used to fit curves where response is either increasing or decreasing with respect to the independent variable, "x".

"x" is a concentration of drug under test.
"y" is the response.
"a" is the maximum response, and "d" is the minimum response
"c" is the inflection point ($EC_{50}$) for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition).

The data is presented with the qualifiers shown below:

|  | Without/with co-corrector |
| --- | --- |
| EC50 (μM) | |
| <1 | +++ |
| ≥1 and <10 | ++ |
| ≥10 | + |
|  | Without co-corrector |
| Maximum % activity (%) | |
| <100 | + |
| ≥100 and <200 | ++ |
| ≥200 | +++ |
|  | With co-corrector |
| Maximum % activity (%) | |
| <150 | + |
| ≥150 and <350 | ++ |
| ≥350 | +++ |

TALBE 4

CSE-HRP data

| Example | EC50 (without co-corrector) (μM) | Maximum % activity (without co-corector) (%) | EC50 (with co-corrector) (μM) | Maximum % activity (with co-corrector) (%) |
| --- | --- | --- | --- | --- |
| 1 | ++ | + | ++ | +++ |
| 2 | ++ | + | ++ | +++ |
| 3 | ++ | + | ++ | ++ |
| 4 | ++ | + | ++ | +++ |
| 5 | ++ | + | ++ | +++ |
| 6 | ++ | +++ | ++ | +++ |
| 7 | +++ | +++ | +++ | +++ |
| 8 | ++ | ++ | +++ | +++ |
| 9 | +++ | ++ | +++ | +++ |
| 10 | ++ | +++ | ++ | +++ |
| 11 | ++ | ++ | ++ | +++ |
| 12 | +++ | ++ | +++ | +++ |

TABLE 4-continued

CSE-HRP data

| Example | EC50 (without co-corrector) (μM) | Maximum % activity (without co-corrector) (%) | EC50 (with co-corrector) (μM) | Maximum % activity (with co-corrector) (%) |
|---|---|---|---|---|
| 13 | ++ | ++ | ++ | +++ |
| 14 | ++ | + | ++ | +++ |
| 15 | ++ | ++ | ++ | +++ |
| 16 | +++ | +++ | +++ | +++ |
| 17 | ++ | +++ | +++ | +++ |
| 18 | ++ | +++ | ++ | +++ |
| 19 | ++ | +++ | ++ | +++ |
| 20 | ++ | ++ | ++ | +++ |
| 21 | ++ | ++ | ++ | +++ |
| 22 | +++ | ++ | +++ | +++ |
| 23 | ++ | +++ | +++ | +++ |
| 24 | +++ | +++ | +++ | +++ |
| 25 | +++ | ++ | +++ | +++ |
| 26 | +++ | ++ | +++ | +++ |
| 27 | ++ | +++ | ++ | +++ |
| 28 | +++ | +++ | +++ | +++ |
| 29 | +++ | ++ | +++ | +++ |
| 30 | ++ | +++ | ++ | +++ |
| 31 | +++ | +++ | +++ | +++ |
| 32 | ++ | +++ | +++ | +++ |
| 33 | ++ | +++ | +++ | +++ |
| 34 | ++ | +++ | ++ | +++ |
| 35 | ++ | +++ | +++ | +++ |
| 36 | +++ | ++ | +++ | +++ |
| 37 | +++ | + | +++ | ++ |
| 38 | ++ | +++ | +++ | +++ |
| 39 | ++ | ++ | ++ | +++ |
| 40 | ++ | +++ | ++ | +++ |
| 41 | ++ | +++ | +++ | +++ |
| 42 | +++ | +++ | +++ | +++ |
| 43 | ++ | ++ | +++ | +++ |
| 44 | ++ | +++ | ++ | +++ |
| 45 | ++ | ++ | ++ | +++ |
| 46 | ++ | +++ | +++ | +++ |
| 47 | +++ | +++ | +++ | +++ |
| 48 | ++ | ++ | ++ | +++ |
| 49 | ++ | +++ | +++ | +++ |
| 50 | ++ | ++ | ++ | +++ |
| 51 | ++ | +++ | +++ | +++ |
| 52 | ++ | ++ | ++ | +++ |
| 53 | ++ | +++ | +++ | +++ |
| 54 | ++ | +++ | +++ | +++ |
| 55 | ++ | + | ++ | ++ |
| 56 | ++ | ++ | +++ | +++ |
| 57 | +++ | ++ | +++ | +++ |
| 58 | ++ | + | ++ | ++ |
| 59 | ++ | +++ | +++ | +++ |
| 60 | ++ | +++ | ++ | +++ |
| 61 | +++ | +++ | +++ | +++ |
| 62 | +++ | +++ | +++ | +++ |
| 63 | ++ | + | ++ | +++ |
| 64 | ++ | +++ | ++ | +++ |
| 65 | ++ | ++ | ++ | +++ |
| 66 | ++ | ++ | ++ | +++ |
| 67 | +++ | +++ | +++ | +++ |
| 68 | ++ | +++ | +++ | +++ |
| 69 | +++ | +++ | +++ | +++ |
| 70 | ++ | ++ | ++ | +++ |
| 71 | ++ | +++ | ++ | +++ |
| 72 | ++ | +++ | +++ | +++ |
| 73 | +++ | +++ | +++ | +++ |
| 74 | ++ | +++ | +++ | +++ |
| 75 | ++ | +++ | +++ | +++ |
| 76 | ++ | ++ | ++ | +++ |
| 77 | ++ | +++ | ++ | +++ |
| 78 | ++ | +++ | ++ | +++ |
| 79 | ++ | +++ | ++ | +++ |
| 80 | ++ | +++ | ++ | +++ |
| 81 | ++ | ++ | ++ | +++ |
| 82 | ++ | + | ++ | ++ |
| 83 | ++ | +++ | +++ | +++ |
| 84 | +++ | +++ | +++ | +++ |
| 85 | ++ | +++ | +++ | +++ |
| 86 | ++ | +++ | +++ | +++ |
| 87 | ++ | +++ | ++ | +++ |
| 88 | +++ | +++ | +++ | +++ |
| 89 | ++ | +++ | +++ | +++ |
| 90 | ++ | +++ | ++ | +++ |
| 91 | +++ | +++ | +++ | +++ |
| 92 | +++ | +++ | +++ | +++ |
| 93 | ++ | +++ | +++ | +++ |
| 94 | ++ | +++ | +++ | +++ |
| 95 | +++ | +++ | +++ | +++ |
| 96 | ++ | ++ | ++ | +++ |
| 97 | +++ | +++ | +++ | +++ |
| 98 | +++ | +++ | +++ | +++ |
| 99 | ++ | +++ | ++ | +++ |
| 100 | ++ | +++ | +++ | +++ |
| 101 | ++ | +++ | +++ | +++ |
| 102 | ++ | ++ | ++ | +++ |
| 103 | ++ | ++ | ++ | +++ |
| 104 | ++ | +++ | +++ | +++ |
| 105 | ++ | +++ | +++ | +++ |
| 106 | ++ | ++ | ++ | +++ |
| 107 | ++ | +++ | +++ | +++ |
| 108 | ++ | +++ | ++ | +++ |
| 109 | +++ | +++ | +++ | +++ |
| 110 | ++ | +++ | +++ | +++ |
| 111 | ++ | +++ | ++ | +++ |
| 112 | ++ | +++ | +++ | +++ |
| 113 | ++ | +++ | +++ | +++ |
| 114 | +++ | + | +++ | +++ |
| 115 | ++ | +++ | +++ | +++ |
| 116 | ++ | +++ | +++ | +++ |
| 117 | +++ | +++ | +++ | +++ |
| 118 | +++ | ++ | +++ | +++ |
| 119 | +++ | +++ | +++ | +++ |
| I-1 | ++ | + | ++ | +++ |
| I-2 | ++ | + | ++ | +++ |
| I-3 | + | + | ++ | ++ |
| I-4 | + | + | ++ | + |
| I-5 | ++ | + | ++ | +++ |
| I-6 | ++ | +++ | ++ | +++ |
| I-7 | ++ | + | ++ | ++ |
| I-8 | ++ | + | ++ | ++ |
| I-9 | + | + | ++ | ++ |
| I-10 | ++ | + | ++ | +++ |
| I-11 | ++ | + | ++ | ++ |
| I-12 | ++ | +++ | ++ | +++ |
| I-13 | ++ | + | ++ | ++ |
| I-14 | + | + | ++ | ++ |
| I-15 | +++ | + | +++ | +++ |
| I-16 | ++ | + | ++ | +++ |
| I-17 | ++ | + | ++ | ++ |
| I-18 | ++ | + | ++ | +++ |
| I-19 | ++ | ++ | ++ | +++ |
| I-20 | ++ | +++ | +++ | +++ |
| I-21 | ++ | + | ++ | +++ |
| I-22 | ++ | +++ | +++ | +++ |
| I-23 | ++ | + | ++ | +++ |
| I-24 | ++ | +++ | ++ | +++ |
| I-25 | ++ | +++ | +++ | +++ |
| I-26 | ++ | ++ | ++ | +++ |
| I-27 | ++ | +++ | ++ | +++ |
| I-28 | ++ | +++ | ++ | +++ |
| I-29 | ++ | +++ | ++ | +++ |
| I-30 | + | + | + | + |
| I-31 | ++ | + | ++ | +++ |
| I-32 | ++ | + | ++ | +++ |
| I-33 | + | + | ++ | ++ |
| I-34 | ++ | +++ | ++ | +++ |
| I-35 | +++ | + | +++ | +++ |
| I-36 | ++ | ++ | ++ | +++ |
| I-37 | + | + | ++ | ++ |
| I-38 | ++ | + | ++ | ++ |
| I-39 | ++ | ++ | +++ | +++ |

TABLE 4-continued

CSE-HRP data

| Example | EC50 (without co-corrector) (μM) | Maximum % activity (without co-corrector) (%) | EC50 (with co-corrector) (μM) | Maximum % activity (with co-corrector) (%) |
|---|---|---|---|---|
| I-40 | + | + | + | + |
| I-41 | + | + | ++ | ++ |
| I-42 | ++ | +++ | +++ | +++ |
| I-43 | ++ | + | ++ | +++ |
| I-44 | ++ | ++ | ++ | +++ |
| I-45 | + | + | + | + |
| I-46 | ++ | + | ++ | ++ |
| I-47 | + | + | ++ | ++ |
| I-48 | +++ | +++ | +++ | +++ |
| I-49 | ++ | +++ | +++ | +++ |
| I-50 | ++ | + | ++ | ++ |
| I-51 | + | + | ++ | ++ |
| I-52 | +++ | +++ | +++ | +++ |
| I-53 | ++ | ++ | ++ | +++ |
| I-54 | ++ | + | ++ | ++ |
| I-55 | ++ | + | ++ | +++ |
| I-56 | +++ | + | +++ | +++ |
| I-57 | ++ | ++ | ++ | +++ |
| I-58 | ++ | +++ | ++ | +++ |
| I-59 | ++ | +++ | ++ | +++ |
| I-60 | ++ | +++ | ++ | +++ |
| I-61 | ++ | +++ | +++ | +++ |
| I-62 | ++ | ++ | ++ | +++ |
| I-63 | ++ | +++ | +++ | +++ |
| I-64 | ++ | + | ++ | +++ |
| I-65 | ++ | ++ | ++ | +++ |
| I-66 | ++ | +++ | ++ | +++ |
| I-67 | ++ | + | ++ | +++ |
| I-68 | +++ | +++ | +++ | +++ |
| I-69 | +++ | ++ | +++ | +++ |
| I-70 | ++ | +++ | ++ | +++ |
| I-71 | +++ | ++ | +++ | +++ |
| I-72 | +++ | +++ | +++ | +++ |
| I-73 | +++ | +++ | +++ | +++ |
| I-74 | +++ | +++ | +++ | +++ |
| I-75 | +++ | ++ | +++ | +++ |
| I-76 | ++ | +++ | +++ | +++ |
| I-77 | ++ | ++ | ++ | +++ |
| I-78 | ++ | +++ | +++ | +++ |
| I-79 | ++ | +++ | ++ | +++ |
| I-80 | + | + | + | + |
| I-81 | ++ | +++ | ++ | +++ |
| I-82 | ++ | + | ++ | +++ |
| I-83 | ++ | ++ | ++ | +++ |
| I-84 | ++ | ++ | ++ | +++ |
| I-85 | + | + | + | + |
| I-86 | +++ | ++ | +++ | +++ |
| I-87 | +++ | +++ | +++ | +++ |
| I-88 | ++ | ++ | ++ | +++ |
| I-89 | + | + | + | + |
| I-90 | ++ | ++ | ++ | +++ |
| I-91 | ++ | +++ | ++ | +++ |
| I-92 | ++ | +++ | ++ | +++ |
| I-93 | ++ | ++ | ++ | +++ |
| I-94 | +++ | +++ | +++ | +++ |
| I-95 | ++ | +++ | ++ | +++ |
| I-96 | ++ | +++ | ++ | +++ |
| I-97 | +++ | +++ | +++ | +++ |
| I-98 | ++ | + | ++ | ++ |
| I-99 | ++ | +++ | ++ | +++ |
| I-100 | ++ | +++ | ++ | +++ |
| I-101 | + | + | + | + |
| I-102 | ++ | ++ | ++ | +++ |
| I-103 | ++ | ++ | ++ | +++ |
| I-104 | ++ | ++ | ++ | +++ |
| I-105 | ++ | + | ++ | +++ |
| I-106 | ++ | +++ | ++ | +++ |
| I-107 | ++ | +++ | ++ | +++ |
| I-108 | ++ | ++ | ++ | +++ |
| I-109 | ++ | +++ | +++ | +++ |
| I-110 | +++ | + | +++ | +++ |
| I-111 | ++ | ++ | +++ | +++ |
| I-112 | +++ | +++ | +++ | +++ |
| I-113 | ++ | ++ | ++ | +++ |
| I-114 | ++ | + | ++ | ++ |
| I-115 | ++ | +++ | +++ | +++ |
| I-116 | +++ | ++ | +++ | +++ |
| I-117 | ++ | +++ | +++ | +++ |
| I-118 | +++ | +++ | +++ | +++ |
| I-119 | ++ | +++ | +++ | +++ |
| I-120 | ++ | ++ | ++ | +++ |
| I-121 | ++ | +++ | ++ | +++ |
| I-123 | ++ | +++ | ++ | +++ |
| I-124 | ++ | + | ++ | +++ |
| I-125 | + | + | + | + |
| I-126 | +++ | +++ | +++ | +++ |
| I-127 | ++ | ++ | ++ | +++ |
| I-128 | ++ | ++ | ++ | +++ |
| I-129 | ++ | ++ | ++ | +++ |
| I-130 | +++ | +++ | +++ | +++ |
| I-131 | ++ | +++ | ++ | +++ |
| I-132 | ++ | +++ | ++ | +++ |
| I-133 | ++ | +++ | ++ | +++ |
| I-134 | ++ | ++ | ++ | +++ |
| I-135 | ++ | +++ | ++ | +++ |
| I-136 | ++ | ++ | ++ | +++ |
| I-137 | ++ | +++ | ++ | +++ |
| I-138 | ++ | +++ | ++ | +++ |
| I-139 | ++ | +++ | ++ | +++ |
| I-140 | +++ | +++ | +++ | +++ |
| I-141 | ++ | +++ | +++ | +++ |
| I-142 | ++ | +++ | ++ | +++ |
| I-143 | ++ | + | ++ | +++ |
| I-144 | ++ | ++ | ++ | +++ |
| I-145 | ++ | ++ | ++ | +++ |
| I-146 | ++ | +++ | +++ | +++ |
| I-147 | ++ | + | ++ | +++ |
| I-148 | ++ | +++ | ++ | +++ |
| I-149 | ++ | +++ | ++ | +++ |
| I-150 | ++ | +++ | ++ | +++ |
| I-151 | ++ | +++ | ++ | +++ |
| I-152 | ++ | +++ | +++ | +++ |
| I-153 | ++ | +++ | +++ | +++ |
| I-154 | +++ | ++ | +++ | +++ |
| I-155 | ++ | ++ | ++ | +++ |
| I-156 | ++ | + | +++ | +++ |
| I-157 | +++ | + | ++ | +++ |
| I-158 | ++ | + | ++ | +++ |
| I-159 | +++ | +++ | +++ | +++ |
| I-160 | +++ | +++ | +++ | +++ |
| I-161 | ++ | +++ | ++ | +++ |
| I-162 | ++ | ++ | ++ | +++ |
| I-163 | ++ | ++ | ++ | +++ |
| I-164 | ++ | +++ | ++ | +++ |
| I-165 | +++ | ++ | +++ | +++ |
| I-166 | ++ | + | +++ | +++ |
| I-167 | ++ | +++ | +++ | +++ |
| I-168 | ++ | + | ++ | +++ |
| I-169 | ++ | ++ | ++ | +++ |
| I-170 | ++ | + | ++ | +++ |
| I-171 | +++ | +++ | +++ | +++ |
| I-172 | ++ | +++ | ++ | +++ |
| I-173 | ++ | + | ++ | ++ |
| I-174 | ++ | +++ | ++ | +++ |
| I-175 | +++ | + | +++ | +++ |
| I-176 | ++ | +++ | ++ | +++ |
| I-177 | +++ | +++ | +++ | +++ |
| I-178 | ++ | ++ | ++ | +++ |
| I-179 | ++ | ++ | ++ | +++ |
| I-180 | ++ | +++ | ++ | +++ |
| I-181 | +++ | + | +++ | +++ |
| I-182 | ++ | ++ | ++ | +++ |
| I-183 | ++ | ++ | +++ | +++ |
| I-184 | ++ | ++ | +++ | +++ |
| I-185 | +++ | +++ | +++ | +++ |
| I-186 | ++ | ++ | ++ | +++ |

TABLE 4-continued

CSE-HRP data

| Example | EC50 (without co-corrector) (µM) | Maximum % activity (without co-corector) (%) | EC50 (with co-corrector) (µM) | Maximum % activity (with co-corrector) (%) | Example | EC50 (without co-corrector) (µM) | Maximum % activity (without co-corector) (%) | EC50 (with co-corrector) (µM) | Maximum % activity (with co-corrector) (%) |
|---|---|---|---|---|---|---|---|---|---|
| I-187 | +++ | +++ | +++ | +++ | I-260 | ++ | + | ++ | ++ |
| I-188 | ++ | + | ++ | ++ | I-261 | ++ | +++ | ++ | +++ |
| I-189 | +++ | +++ | +++ | +++ | I-262 | ++ | +++ | ++ | +++ |
| I-190 | ++ | +++ | +++ | +++ | I-263 | ++ | + | ++ | ++ |
| I-191 | ++ | +++ | ++ | +++ | I-264 | ++ | + | ++ | ++ |
| I-192 | ++ | ++ | ++ | +++ | I-265 | ++ | +++ | ++ | +++ |
| I-193 | ++ | +++ | ++ | +++ | I-266 | ++ | +++ | ++ | +++ |
| I-194 | ++ | +++ | ++ | +++ | I-267 | + | + | ++ | + |
| I-195 | ++ | +++ | ++ | +++ | I-268 | ++ | + | ++ | +++ |
| I-196 | ++ | +++ | ++ | +++ | I-269 | ++ | ++ | ++ | +++ |
| I-197 | ++ | +++ | ++ | +++ | I-270 | +++ | +++ | +++ | +++ |
| I-198 | ++ | + | ++ | +++ | I-271 | ++ | +++ | ++ | +++ |
| I-199 | ++ | ++ | ++ | +++ | I-272 | ++ | ++ | +++ | +++ |
| I-200 | ++ | ++ | +++ | +++ | I-273 | ++ | +++ | +++ | +++ |
| I-201 | ++ | +++ | +++ | +++ | I-274 | ++ | ++ | ++ | +++ |
| I-202 | ++ | +++ | +++ | +++ | I-275 | ++ | +++ | ++ | +++ |
| I-203 | ++ | + | ++ | ++ | I-276 | ++ | ++ | ++ | +++ |
| I-204 | +++ | +++ | +++ | +++ | I-277 | ++ | ++ | ++ | +++ |
| I-205 | ++ | + | ++ | ++ | I-278 | ++ | + | ++ | ++ |
| I-206 | ++ | ++ | ++ | +++ | I-279 | ++ | ++ | ++ | +++ |
| I-207 | ++ | ++ | ++ | +++ | I-280 | ++ | + | ++ | ++ |
| I-208 | ++ | ++ | ++ | +++ | I-281 | ++ | ++ | ++ | +++ |
| I-209 | ++ | +++ | ++ | +++ | I-282 | ++ | ++ | ++ | +++ |
| I-210 | ++ | +++ | +++ | +++ | I-283 | ++ | +++ | ++ | +++ |
| I-211 | + | + | ++ | + | I-284 | ++ | +++ | ++ | +++ |
| I-212 | ++ | + | ++ | ++ | I-285 | + | + | +++ | + |
| I-213 | ++ | +++ | ++ | +++ | I-286 | ++ | ++ | +++ | +++ |
| I-214 | ++ | +++ | ++ | +++ | I-287 | ++ | +++ | +++ | +++ |
| I-215 | + | + | ++ | ++ | I-288 | ++ | ++ | +++ | +++ |
| I-216 | +++ | +++ | +++ | +++ | I-289 | ++ | ++ | +++ | +++ |
| I-217 | +++ | +++ | +++ | +++ | I-290 | ++ | +++ | ++ | +++ |
| I-218 | ++ | +++ | ++ | +++ | I-291 | +++ | ++ | +++ | +++ |
| I-219 | ++ | ++ | ++ | +++ | I-292 | ++ | ++ | +++ | +++ |
| I-220 | ++ | +++ | ++ | +++ | I-293 | ++ | +++ | ++ | +++ |
| I-221 | ++ | +++ | ++ | +++ | I-294 | ++ | +++ | +++ | +++ |
| I-222 | ++ | + | ++ | ++ | I-295 | ++ | +++ | +++ | +++ |
| I-223 | ++ | ++ | +++ | +++ | I-296 | ++ | +++ | ++ | +++ |
| I-224 | ++ | ++ | ++ | +++ | I-297 | ++ | +++ | +++ | +++ |
| I-225 | ++ | ++ | ++ | +++ | I-298 | ++ | ++ | ++ | +++ |
| I-226 | ++ | +++ | ++ | +++ | I-299 | ++ | ++ | ++ | +++ |
| I-227 | ++ | ++ | ++ | +++ | I-300 | ++ | +++ | ++ | +++ |
| I-228 | ++ | ++ | ++ | +++ | I-301 | ++ | +++ | ++ | +++ |
| I-229 | ++ | ++ | +++ | +++ | I-302 | ++ | ++ | ++ | +++ |
| I-230 | ++ | ++ | ++ | +++ | I-303 | ++ | + | ++ | +++ |
| I-231 | ++ | ++ | ++ | +++ | I-304 | +++ | +++ | +++ | +++ |
| I-232 | ++ | +++ | ++ | +++ | I-305 | ++ | ++ | ++ | +++ |
| I-233 | ++ | ++ | ++ | +++ | I-306 | +++ | +++ | +++ | +++ |
| I-234 | ++ | ++ | +++ | +++ | I-307 | +++ | +++ | +++ | +++ |
| I-235 | ++ | ++ | +++ | +++ | I-308 | ++ | + | +++ | +++ |
| I-236 | ++ | ++ | ++ | +++ | I-309 | ++ | ++ | ++ | +++ |
| I-237 | ++ | ++ | ++ | +++ | I-310 | ++ | +++ | +++ | +++ |
| I-238 | ++ | +++ | +++ | +++ | II-1 | ++ | + | ++ | ++ |
| I-239 | ++ | ++ | ++ | +++ | II-2 | ++ | + | ++ | +++ |
| I-240 | ++ | + | ++ | +++ | II-3 | ++ | + | ++ | ++ |
| I-241 | ++ | +++ | ++ | +++ | II-4 | ++ | ++ | ++ | +++ |
| I-242 | ++ | ++ | ++ | +++ | II-5 | ++ | + | ++ | +++ |
| I-243 | ++ | ++ | ++ | +++ | II-6 | ++ | ++ | ++ | +++ |
| I-244 | ++ | ++ | ++ | +++ | II-7 | ++ | + | ++ | +++ |
| I-245 | ++ | +++ | ++ | +++ | II-8 | ++ | + | ++ | +++ |
| I-246 | ++ | +++ | ++ | +++ | II-9 | ++ | + | ++ | +++ |
| I-247 | ++ | + | ++ | +++ | II-10 | ++ | ++ | ++ | +++ |
| I-248 | ++ | ++ | ++ | +++ | II-11 | ++ | + | ++ | +++ |
| I-249 | ++ | +++ | +++ | +++ | II-12 | ++ | ++ | ++ | +++ |
| I-250 | ++ | +++ | +++ | +++ | II-13 | ++ | + | ++ | +++ |
| I-251 | ++ | ++ | ++ | +++ | II-14 | ++ | +++ | ++ | +++ |
| I-252 | ++ | +++ | ++ | +++ | II-15 | +++ | + | +++ | +++ |
| I-253 | ++ | ++ | ++ | +++ | II-16 | ++ | + | ++ | +++ |
| I-254 | ++ | + | ++ | +++ | II-17 | ++ | ++ | ++ | +++ |
| I-255 | ++ | + | ++ | +++ | II-18 | ++ | + | ++ | +++ |
| I-256 | ++ | +++ | +++ | +++ | II-19 | ++ | ++ | ++ | +++ |
| I-257 | ++ | ++ | +++ | +++ | II-20 | ++ | +++ | ++ | +++ |
| I-258 | +++ | ++ | +++ | +++ | II-21 | ++ | +++ | ++ | +++ |
| I-259 | ++ | ++ | ++ | +++ | II-22 | ++ | ++ | ++ | +++ |

TABLE 4-continued

CSE-HRP data

| Example | EC50 (without co-corrector) (μM) | Maximum % activity (without co-corector) (%) | EC50 (with co-corrector) (μM) | Maximum % activity (with co-corrector) (%) |
|---|---|---|---|---|
| II-23 | ++ | ++ | ++ | +++ |
| II-24 | ++ | +++ | ++ | +++ |
| II-25 | ++ | +++ | ++ | +++ |
| II-26 | ++ | +++ | ++ | +++ |
| II-27 | ++ | +++ | ++ | +++ |
| II-28 | ++ | +++ | ++ | +++ |
| II-29 | ++ | +++ | ++ | +++ |
| II-30 | ++ | ++ | ++ | +++ |
| II-31 | ++ | + | ++ | +++ |
| II-32 | ++ | + | ++ | +++ |
| II-33 | ++ | ++ | ++ | +++ |
| II-34 | ++ | +++ | ++ | +++ |
| II-35 | ++ | +++ | ++ | +++ |
| II-36 | ++ | +++ | ++ | +++ |
| II-37 | ++ | ++ | ++ | +++ |
| II-38 | ++ | ++ | ++ | +++ |
| II-39 | ++ | ++ | ++ | +++ |
| II-40 | ++ | ++ | ++ | +++ |
| II-41 | ++ | +++ | ++ | +++ |
| II-42 | ++ | ++ | ++ | +++ |
| II-43 | ++ | +++ | ++ | +++ |
| II-44 | ++ | +++ | ++ | +++ |
| II-45 | ++ | +++ | ++ | +++ |
| II-46 | ++ | ++ | ++ | +++ |
| II-47 | ++ | ++ | ++ | +++ |
| II-48 | ++ | ++ | ++ | +++ |
| II-49 | ++ | ++ | ++ | +++ |
| II-50 | +++ | ++ | +++ | +++ |
| II-51 | ++ | ++ | ++ | +++ |
| II-52 | ++ | ++ | ++ | +++ |
| II-53 | ++ | + | ++ | ++ |
| II-54 | ++ | +++ | ++ | +++ |
| II-55 | + | + | ++ | ++ |
| II-56 | ++ | ++ | ++ | +++ |
| II-57 | ++ | ++ | ++ | +++ |
| II-58 | ++ | + | ++ | ++ |
| II-59 | ++ | ++ | ++ | +++ |
| II-60 | ++ | ++ | ++ | +++ |
| II-61 | ++ | ++ | ++ | +++ |
| II-62 | ++ | +++ | ++ | +++ |
| II-63 | ++ | +++ | ++ | +++ |
| II-64 | + | + | ++ | ++ |
| II-65 | ++ | ++ | ++ | +++ |
| II-66 | ++ | + | ++ | ++ |
| II-67 | ++ | + | ++ | ++ |
| II-68 | ++ | + | ++ | +++ |
| II-69 | ++ | + | ++ | ++ |
| II-70 | ++ | + | ++ | ++ |
| II-71 | ++ | + | ++ | ++ |
| II-72 | +++ | + | ++ | ++ |
| II-73 | ++ | +++ | ++ | +++ |
| II-74 | ++ | + | ++ | ++ |
| II-75 | +++ | + | ++ | ++ |
| II-76 | ++ | + | ++ | +++ |
| II-77 | ++ | ++ | ++ | +++ |
| II-79 | ++ | +++ | ++ | +++ |
| II-80 | ++ | ++ | ++ | +++ |
| II-81 | ++ | ++ | ++ | +++ |
| II-82 | ++ | ++ | ++ | +++ |
| II-83 | ++ | +++ | +++ | +++ |
| II-84 | ++ | ++ | ++ | +++ |
| II-85 | ++ | + | ++ | ++ |
| II-86 | ++ | + | ++ | ++ |
| II-87 | ++ | ++ | ++ | +++ |
| II-88 | ++ | ++ | ++ | +++ |
| II-89 | ++ | + | ++ | ++ |
| II-90 | ++ | +++ | ++ | +++ |
| II-91 | ++ | ++ | ++ | +++ |
| II-92 | ++ | ++ | ++ | +++ |
| II-93 | ++ | ++ | ++ | +++ |
| II-94 | ++ | ++ | ++ | +++ |
| II-95 | ++ | + | ++ | +++ |
| II-96 | ++ | ++ | ++ | +++ |
| II-97 | ++ | +++ | +++ | +++ |
| II-98 | ++ | ++ | ++ | +++ |
| II-99 | ++ | ++ | ++ | +++ |
| II-100 | ++ | + | ++ | ++ |
| II-101 | ++ | ++ | ++ | +++ |
| II-102 | ++ | ++ | +++ | +++ |
| II-103 | ++ | ++ | ++ | +++ |
| II-104 | ++ | + | ++ | ++ |
| II-105 | ++ | + | ++ | +++ |
| II-106 | ++ | + | ++ | ++ |
| II-107 | +++ | + | ++ | +++ |
| II-108 | ++ | + | ++ | +++ |
| II-109 | +++ | + | ++ | ++ |
| II-110 | ++ | + | ++ | +++ |
| II-111 | ++ | + | ++ | ++ |
| II-112 | + | + | ++ | ++ |
| II-113 | +++ | + | ++ | +++ |
| II-114 | +++ | + | ++ | +++ |
| II-115 | + | + | ++ | ++ |
| II-116 | ++ | ++ | ++ | +++ |
| II-117 | ++ | + | ++ | +++ |
| II-118 | ++ | ++ | ++ | +++ |
| II-119 | ++ | + | ++ | ++ |
| II-120 | ++ | ++ | ++ | +++ |
| II-121 | ++ | + | ++ | ++ |
| II-122 | ++ | + | ++ | ++ |
| II-123 | ++ | + | ++ | ++ |
| II-124 | +++ | ++ | +++ | +++ |
| II-125 | ++ | +++ | +++ | +++ |
| II-126 | ++ | ++ | ++ | +++ |
| II-127 | ++ | + | ++ | ++ |
| II-128 | ++ | ++ | ++ | +++ |
| II-129 | ++ | ++ | ++ | +++ |
| II-130 | ++ | + | ++ | ++ |
| II-131 | ++ | ++ | ++ | ++ |
| II-132 | ++ | + | ++ | +++ |
| II-133 | ++ | + | ++ | ++ |
| II-134 | ++ | +++ | ++ | +++ |
| II-135 | ++ | ++ | ++ | +++ |
| II-136 | ++ | ++ | ++ | +++ |
| II-137 | ++ | ++ | ++ | +++ |
| II-138 | ++ | ++ | ++ | +++ |
| II-139 | ++ | + | ++ | ++ |
| II-140 | ++ | ++ | +++ | +++ |
| II-141 | ++ | ++ | +++ | +++ |
| II-142 | ++ | + | ++ | +++ |
| II-143 | ++ | ++ | ++ | +++ |
| II-144 | ++ | ++ | ++ | +++ |
| II-145 | ++ | ++ | ++ | +++ |
| II-146 | ++ | + | ++ | +++ |
| II-147 | ++ | + | ++ | ++ |
| II-148 | +++ | ++ | +++ | +++ |
| II-149 | ++ | +++ | ++ | +++ |
| II-150 | ++ | +++ | +++ | +++ |
| II-151 | ++ | ++ | ++ | +++ |
| II-152 | ++ | + | ++ | +++ |
| II-153 | ++ | +++ | ++ | +++ |
| II-154 | ++ | ++ | ++ | +++ |
| II-155 | ++ | + | ++ | ++ |
| II-156 | ++ | + | ++ | ++ |
| II-157 | ++ | +++ | +++ | +++ |
| II-158 | +++ | ++ | +++ | +++ |
| II-159 | ++ | + | ++ | ++ |
| II-160 | ++ | +++ | +++ | +++ |
| II-161 | ++ | ++ | +++ | +++ |
| II-162 | ++ | ++ | ++ | +++ |
| II-163 | ++ | + | +++ | +++ |
| II-164 | +++ | +++ | +++ | +++ |
| II-165 | ++ | +++ | +++ | +++ |
| II-166 | +++ | ++ | +++ | +++ |
| II-167 | ++ | + | ++ | ++ |
| II-168 | ++ | +++ | +++ | +++ |
| II-169 | ++ | +++ | ++ | +++ |

TABLE 4-continued

CSE-HRP data

| Example | EC50 (without co-corrector) (μM) | Maximum % activity (without co-corrector) (%) | EC50 (with co-corrector) (μM) | Maximum % activity (with co-corrector) (%) |
|---|---|---|---|---|
| II-170 | ++ | +++ | ++ | +++ |
| II-171 | ++ | +++ | ++ | +++ |
| II-172 | ++ | +++ | +++ | +++ |
| II-173 | ++ | +++ | ++ | +++ |
| II-174 | ++ | +++ | ++ | +++ |
| II-175 | ++ | ++ | ++ | +++ |
| II-176 | ++ | ++ | ++ | +++ |
| II-177 | ++ | +++ | +++ | +++ |
| II-178 | ++ | +++ | +++ | +++ |
| II-179 | ++ | +++ | ++ | +++ |
| II-180 | ++ | +++ | +++ | +++ |
| II-181 | ++ | ++ | ++ | +++ |
| II-182 | ++ | +++ | ++ | +++ |
| II-183 | +++ | +++ | +++ | +++ |
| II-184 | ++ | ++ | ++ | +++ |
| II-185 | +++ | + | +++ | +++ |
| II-186 | +++ | +++ | +++ | +++ |
| II-187 | ++ | + | ++ | ++ |
| II-188 | ++ | +++ | ++ | +++ |
| II-189 | ++ | +++ | ++ | +++ |
| II-190 | ++ | +++ | +++ | +++ |
| II-191 | ++ | +++ | +++ | +++ |
| II-192 | +++ | +++ | +++ | +++ |
| II-193 | +++ | +++ | +++ | +++ |
| II-194 | +++ | +++ | +++ | +++ |
| II-195 | ++ | +++ | ++ | +++ |
| II-196 | ++ | +++ | ++ | +++ |
| II-197 | ++ | + | ++ | ++ |
| II-198 | ++ | + | ++ | ++ |
| II-199 | ++ | +++ | ++ | +++ |
| II-200 | ++ | ++ | +++ | +++ |
| II-201 | +++ | +++ | +++ | +++ |
| II-202 | +++ | +++ | +++ | +++ |
| II-203 | ++ | ++ | +++ | +++ |
| II-204 | +++ | ++ | +++ | +++ |
| II-205 | +++ | +++ | +++ | +++ |
| II-206 | +++ | +++ | +++ | +++ |
| II-207 | ++ | ++ | ++ | +++ |
| II-208 | ++ | +++ | +++ | +++ |
| II-209 | ++ | ++ | ++ | +++ |
| II-210 | ++ | +++ | ++ | +++ |
| II-211 | ++ | +++ | ++ | +++ |
| II-212 | ++ | +++ | ++ | +++ |
| II-213 | ++ | ++ | ++ | +++ |
| II-214 | ++ | +++ | ++ | +++ |
| II-215 | ++ | +++ | +++ | +++ |
| II-216 | ++ | ++ | ++ | +++ |
| II-217 | ++ | +++ | +++ | +++ |
| II-218 | ++ | ++ | ++ | +++ |
| II-219 | ++ | +++ | +++ | +++ |
| II-220 | ++ | ++ | ++ | +++ |
| II-221 | ++ | ++ | ++ | +++ |
| II-222 | ++ | ++ | +++ | +++ |
| II-223 | ++ | + | ++ | +++ |
| II-224 | ++ | +++ | +++ | +++ |
| II-225 | ++ | ++ | ++ | +++ |
| II-226 | +++ | ++ | +++ | +++ |
| II-227 | ++ | +++ | +++ | +++ |
| II-228 | +++ | +++ | +++ | +++ |
| II-229 | ++ | +++ | ++ | +++ |
| II-230 | ++ | ++ | ++ | +++ |
| II-231 | +++ | ++ | +++ | +++ |
| II-232 | ++ | ++ | +++ | +++ |
| II-233 | ++ | +++ | +++ | +++ |
| II-234 | ++ | +++ | ++ | +++ |
| II-235 | ++ | +++ | ++ | +++ |
| II-236 | ++ | +++ | +++ | +++ |
| II-237 | ++ | + | ++ | +++ |
| II-238 | ++ | ++ | ++ | +++ |
| II-239 | ++ | ++ | ++ | +++ |
| II-240 | ++ | +++ | +++ | +++ |
| II-241 | ++ | ++ | ++ | +++ |
| II-242 | ++ | ++ | ++ | +++ |
| II-243 | ++ | +++ | +++ | +++ |
| II-244 | ++ | +++ | +++ | +++ |
| II-245 | +++ | ++ | +++ | +++ |
| II-246 | ++ | ++ | ++ | +++ |
| II-247 | ++ | ++ | +++ | +++ |
| II-248 | ++ | +++ | +++ | +++ |
| II-249 | +++ | +++ | +++ | +++ |
| II-250 | ++ | ++ | ++ | +++ |
| II-251 | +++ | ++ | +++ | +++ |
| II-252 | +++ | +++ | +++ | +++ |
| II-253 | +++ | ++ | +++ | +++ |
| II-254 | ++ | +++ | ++ | +++ |
| II-255 | +++ | +++ | +++ | +++ |
| II-256 | +++ | +++ | +++ | +++ |
| II-257 | +++ | +++ | +++ | +++ |
| II-258 | ++ | +++ | +++ | +++ |
| II-259 | ++ | ++ | ++ | +++ |
| II-260 | ++ | ++ | ++ | +++ |
| II-261 | ++ | + | ++ | +++ |
| II-262 | ++ | ++ | ++ | +++ |
| II-263 | ++ | + | ++ | +++ |
| II-264 | ++ | +++ | ++ | +++ |
| II-265 | ++ | + | ++ | ++ |
| II-266 | ++ | ++ | +++ | +++ |
| II-267 | ++ | +++ | ++ | +++ |
| II-268 | ++ | +++ | ++ | +++ |
| II-269 | ++ | +++ | ++ | +++ |
| II-270 | +++ | +++ | +++ | +++ |
| II-271 | ++ | +++ | +++ | +++ |
| II-272 | ++ | ++ | ++ | +++ |
| II-273 | ++ | +++ | ++ | +++ |
| II-274 | ++ | +++ | ++ | +++ |
| II-275 | +++ | +++ | +++ | +++ |
| II-276 | ++ | +++ | +++ | +++ |
| II-277 | ++ | +++ | +++ | +++ |
| II-278 | ++ | ++ | ++ | +++ |
| II-279 | +++ | +++ | +++ | +++ |
| II-280 | ++ | + | ++ | +++ |
| II-281 | ++ | ++ | ++ | +++ |
| II-282 | +++ | +++ | +++ | +++ |
| II-283 | +++ | +++ | +++ | +++ |
| II-284 | ++ | + | ++ | +++ |
| II-285 | ++ | ++ | ++ | +++ |
| II-286 | +++ | +++ | +++ | +++ |
| II-287 | ++ | ++ | ++ | +++ |
| II-288 | ++ | + | ++ | +++ |
| II-289 | +++ | + | ++ | +++ |
| II-290 | ++ | + | ++ | ++ |
| II-291 | ++ | +++ | ++ | +++ |
| II-292 | ++ | ++ | ++ | +++ |
| II-293 | ++ | ++ | ++ | +++ |
| II-294 | ++ | +++ | ++ | +++ |
| II-295 | ++ | ++ | ++ | +++ |
| II-296 | ++ | ++ | ++ | +++ |
| II-297 | ++ | + | ++ | +++ |
| II-298 | ++ | ++ | ++ | +++ |
| II-299 | ++ | ++ | ++ | +++ |
| II-300 | +++ | +++ | +++ | +++ |
| II-301 | ++ | +++ | +++ | +++ |
| II-302 | ++ | +++ | ++ | +++ |
| II-303 | ++ | + | ++ | +++ |
| II-304 | ++ | +++ | ++ | +++ |
| II-305 | +++ | ++ | +++ | +++ |
| II-306 | ++ | +++ | ++ | +++ |
| II-307 | +++ | +++ | +++ | +++ |
| II-308 | ++ | ++ | ++ | +++ |
| II-309 | ++ | +++ | ++ | +++ |
| II-310 | ++ | +++ | +++ | +++ |
| II-311 | ++ | +++ | ++ | +++ |
| II-312 | +++ | ++ | +++ | +++ |
| II-313 | ++ | +++ | ++ | +++ |
| II-314 | ++ | +++ | +++ | +++ |

TABLE 4-continued

CSE-HRP data

| Example | EC50 (without co-corrector) (µM) | Maximum % activity (without co-corrector) (%) | EC50 (with co-corrector) (µM) | Maximum % activity (with co-corrector) (%) |
|---|---|---|---|---|
| II-315 | +++ | +++ | +++ | +++ |
| II-316 | ++ | +++ | ++ | +++ |
| II-317 | +++ | +++ | +++ | +++ |
| II-318 | ++ | +++ | ++ | +++ |
| II-319 | ++ | +++ | +++ | +++ |
| II-320 | ++ | +++ | +++ | +++ |
| II-321 | ++ | +++ | +++ | +++ |
| II-322 | ++ | ++ | ++ | +++ |
| II-323 | ++ | ++ | +++ | +++ |
| II-324 | ++ | +++ | +++ | +++ |
| II-325 | +++ | +++ | +++ | +++ |
| II-326 | ++ | +++ | +++ | +++ |
| II-327 | ++ | ++ | ++ | +++ |
| II-328 | ++ | +++ | ++ | +++ |
| II-329 | ++ | +++ | ++ | +++ |
| II-330 | ++ | +++ | +++ | +++ |
| II-331 | ++ | ++ | ++ | +++ |
| II-332 | ++ | +++ | +++ | +++ |
| II-333 | ++ | +++ | ++ | +++ |
| II-334 | ++ | +++ | ++ | +++ |
| II-335 | ++ | +++ | ++ | +++ |
| II-336 | ++ | ++ | ++ | +++ |
| II-337 | +++ | +++ | +++ | +++ |
| II-339 | ++ | +++ | +++ | +++ |
| II-340 | ++ | ++ | ++ | +++ |
| II-341 | +++ | +++ | +++ | +++ |
| II-342 | +++ | +++ | +++ | +++ |
| II-343 | +++ | ++ | +++ | +++ |
| II-344 | ++ | ++ | +++ | +++ |
| II-345 | ++ | + | ++ | +++ |
| II-346 | ++ | +++ | ++ | +++ |
| II-347 | +++ | ++ | +++ | +++ |
| II-348 | ++ | + | ++ | +++ |
| II-349 | ++ | + | ++ | +++ |
| II-350 | ++ | ++ | ++ | +++ |
| II-351 | +++ | ++ | +++ | +++ |
| II-352 | ++ | +++ | +++ | +++ |
| II-353 | ++ | +++ | +++ | +++ |
| II-354 | +++ | +++ | +++ | +++ |
| II-355 | ++ | ++ | +++ | +++ |
| II-356 | ++ | +++ | +++ | +++ |
| II-357 | ++ | +++ | +++ | +++ |
| II-358 | ++ | + | ++ | +++ |
| II-359 | ++ | +++ | ++ | +++ |
| II-360 | ++ | ++ | +++ | +++ |
| II-361 | ++ | +++ | +++ | +++ |
| II-362 | ++ | ++ | ++ | +++ |
| II-363 | ++ | ++ | ++ | +++ |
| II-364 | ++ | ++ | ++ | +++ |
| II-365 | +++ | +++ | +++ | +++ |
| II-366 | ++ | ++ | ++ | +++ |
| II-367 | ++ | ++ | ++ | +++ |
| II-368 | ++ | ++ | ++ | +++ |
| II-369 | +++ | +++ | +++ | +++ |
| II-370 | +++ | + | +++ | +++ |
| II-371 | ++ | +++ | ++ | +++ |
| II-372 | ++ | +++ | ++ | +++ |
| II-373 | ++ | ++ | ++ | +++ |
| II-374 | ++ | ++ | +++ | +++ |
| II-375 | +++ | +++ | +++ | +++ |
| II-376 | ++ | +++ | ++ | +++ |
| II-377 | ++ | ++ | ++ | +++ |
| II-378 | +++ | +++ | +++ | +++ |
| II-379 | ++ | ++ | ++ | +++ |
| II-380 | ++ | + | ++ | +++ |
| II-381 | ++ | ++ | ++ | +++ |
| II-382 | ++ | + | ++ | +++ |
| II-383 | ++ | +++ | ++ | +++ |
| II-384 | ++ | +++ | ++ | +++ |
| II-385 | +++ | +++ | +++ | +++ |
| II-386 | +++ | +++ | +++ | +++ |
| II-387 | ++ | +++ | ++ | +++ |
| II-388 | ++ | +++ | ++ | +++ |
| II-389 | ++ | ++ | ++ | +++ |
| II-390 | ++ | +++ | ++ | +++ |
| II-391 | ++ | +++ | ++ | +++ |
| II-392 | +++ | +++ | +++ | +++ |
| II-393 | ++ | + | ++ | ++ |
| II-394 | ++ | ++ | ++ | +++ |
| II-395 | ++ | + | ++ | ++ |
| II-396 | ++ | ++ | ++ | +++ |
| II-397 | ++ | ++ | +++ | +++ |
| II-398 | ++ | + | ++ | +++ |
| II-399 | +++ | ++ | +++ | +++ |
| II-400 | ++ | ++ | ++ | +++ |
| II-401 | ++ | +++ | +++ | +++ |
| II-402 | ++ | +++ | +++ | +++ |
| II-403 | ++ | ++ | ++ | +++ |
| II-404 | ++ | + | ++ | +++ |
| II-405 | ++ | +++ | ++ | +++ |
| II-406 | +++ | ++ | +++ | +++ |
| II-407 | ++ | ++ | ++ | +++ |
| II-408 | ++ | ++ | ++ | +++ |
| II-409 | ++ | ++ | +++ | +++ |
| II-410 | +++ | ++ | +++ | +++ |
| II-411 | ++ | +++ | +++ | +++ |
| II-412 | ++ | + | ++ | ++ |
| II-413 | ++ | + | ++ | ++ |
| II-414 | +++ | +++ | +++ | +++ |
| II-415 | ++ | +++ | +++ | +++ |
| II-416 | +++ | ++ | +++ | +++ |
| II-417 | ++ | ++ | ++ | +++ |
| II-418 | ++ | + | ++ | +++ |
| II-419 | ++ | +++ | ++ | +++ |
| II-420 | ++ | ++ | ++ | +++ |
| II-421 | ++ | + | ++ | ++ |
| II-422 | +++ | ++ | +++ | +++ |
| II-423 | +++ | ++ | +++ | +++ |
| II-424 | +++ | ++ | +++ | +++ |
| II-425 | ++ | +++ | ++ | +++ |
| II-426 | ++ | + | +++ | +++ |
| II-427 | +++ | +++ | +++ | +++ |
| II-428 | ++ | ++ | ++ | +++ |
| II-429 | +++ | ++ | +++ | +++ |
| II-430 | +++ | + | +++ | ++ |
| II-431 | +++ | ++ | +++ | +++ |
| II-432 | ++ | + | ++ | +++ |
| II-433 | +++ | ++ | +++ | +++ |
| II-434 | ++ | ++ | ++ | +++ |
| II-435 | ++ | + | ++ | ++ |
| II-436 | ++ | ++ | ++ | +++ |
| II-437 | ++ | +++ | ++ | +++ |
| II-438 | ++ | + | +++ | ++ |
| II-439 | ++ | +++ | +++ | +++ |
| II-440 | ++ | ++ | ++ | +++ |
| II-441 | +++ | +++ | +++ | +++ |
| II-442 | ++ | + | ++ | +++ |
| II-443 | ++ | +++ | ++ | +++ |
| II-444 | ++ | + | ++ | ++ |
| II-445 | ++ | ++ | ++ | +++ |
| II-446 | ++ | + | ++ | ++ |
| II-447 | ++ | ++ | ++ | +++ |
| II-448 | ++ | +++ | ++ | +++ |
| II-449 | ++ | +++ | +++ | +++ |
| II-450 | ++ | +++ | +++ | +++ |
| II-451 | ++ | +++ | ++ | +++ |
| II-452 | ++ | ++ | ++ | +++ |
| II-453 | + | + | +++ | ++ |
| II-454 | ++ | ++ | ++ | +++ |
| II-455 | ++ | +++ | ++ | +++ |
| II-456 | ++ | +++ | ++ | +++ |
| II-457 | ++ | +++ | ++ | +++ |
| II-458 | ++ | +++ | ++ | +++ |
| II-459 | ++ | + | ++ | +++ |
| II-460 | ++ | +++ | +++ | +++ |
| II-461 | ++ | + | ++ | ++ |

TABLE 4-continued

CSE-HRP data

| Example | EC50 (without co-corrector) (μM) | Maximum % activity (without co-corrector) (%) | EC50 (with co-corrector) (μM) | Maximum % activity (with co-corrector) (%) |
|---|---|---|---|---|
| II-462 | +++ | +++ | +++ | +++ |
| II-463 | ++ | ++ | ++ | +++ |
| II-464 | +++ | ++ | +++ | +++ |
| II-465 | ++ | +++ | +++ | +++ |
| II-466 | +++ | +++ | +++ | +++ |
| II-467 | +++ | ++ | +++ | +++ |
| II-468 | ++ | ++ | ++ | +++ |
| II-469 | ++ | ++ | ++ | +++ |
| II-470 | ++ | ++ | +++ | +++ |
| II-471 | + | + | +++ | ++ |
| II-472 | ++ | + | ++ | ++ |
| II-473 | ++ | +++ | +++ | +++ |
| II-474 | ++ | ++ | ++ | +++ |
| II-475 | ++ | + | ++ | ++ |
| II-476 | ++ | ++ | ++ | +++ |
| II-477 | +++ | ++ | ++ | +++ |
| II-478 | ++ | + | ++ | ++ |
| II-479 | ++ | +++ | ++ | +++ |
| II-480 | ++ | + | ++ | +++ |
| II-481 | ++ | ++ | ++ | +++ |
| II-482 | ++ | ++ | ++ | +++ |
| II-483 | ++ | + | ++ | ++ |
| II-484 | +++ | ++ | +++ | +++ |
| II-485 | ++ | + | ++ | ++ |
| II-486 | ++ | +++ | +++ | +++ |
| II-487 | ++ | +++ | ++ | +++ |
| II-488 | ++ | + | ++ | ++ |
| II-489 | ++ | ++ | ++ | +++ |
| II-490 | ++ | ++ | ++ | +++ |
| II-491 | ++ | +++ | ++ | +++ |
| II-492 | ++ | +++ | +++ | +++ |
| II-493 | ++ | +++ | ++ | +++ |
| II-494 | ++ | + | ++ | ++ |
| II-495 | ++ | +++ | ++ | +++ |
| II-496 | ++ | + | ++ | ++ |
| II-497 | ++ | + | ++ | ++ |
| II-498 | ++ | ++ | ++ | +++ |
| II-499 | ++ | ++ | ++ | +++ |
| II-500 | ++ | ++ | ++ | +++ |
| II-501 | ++ | +++ | ++ | +++ |
| II-502 | ++ | + | ++ | ++ |
| II-503 | ++ | + | ++ | +++ |
| II-504 | ++ | + | ++ | ++ |
| II-505 | ++ | +++ | +++ | +++ |
| II-506 | ++ | +++ | +++ | +++ |
| II-507 | +++ | ++ | +++ | +++ |
| II-508 | ++ | ++ | +++ | +++ |
| II-509 | +++ | +++ | +++ | +++ |
| II-510 | ++ | +++ | ++ | +++ |
| II-511 | ++ | ++ | ++ | +++ |
| II-512 | ++ | ++ | ++ | +++ |
| II-513 | ++ | ++ | ++ | +++ |
| II-514 | ++ | ++ | ++ | +++ |
| II-515 | ++ | ++ | ++ | +++ |
| II-516 | ++ | +++ | +++ | +++ |
| II-517 | ++ | +++ | +++ | +++ |
| II-518 | ++ | ++ | ++ | +++ |
| II-519 | ++ | ++ | +++ | +++ |
| II-520 | ++ | +++ | +++ | +++ |
| II-521 | ++ | + | ++ | ++ |
| II-522 | ++ | + | ++ | +++ |
| II-523 | ++ | +++ | ++ | +++ |
| II-524 | ++ | ++ | ++ | +++ |
| II-525 | ++ | ++ | ++ | +++ |
| II-526 | ++ | ++ | ++ | +++ |
| II-527 | ++ | ++ | ++ | +++ |
| II-528 | ++ | ++ | ++ | +++ |
| II-529 | ++ | +++ | ++ | +++ |
| II-530 | ++ | ++ | ++ | +++ |
| II-531 | ++ | ++ | ++ | +++ |
| II-532 | ++ | +++ | +++ | +++ |
| II-533 | ++ | ++ | ++ | +++ |
| II-534 | +++ | +++ | +++ | +++ |
| II-535 | ++ | +++ | ++ | +++ |
| II-536 | | | | |
| II-537 | ++ | +++ | ++ | +++ |
| II-538 | ++ | ++ | ++ | +++ |
| II-539 | ++ | + | ++ | ++ |
| II-540 | ++ | +++ | +++ | +++ |
| II-541 | ++ | ++ | ++ | +++ |
| II-542 | ++ | ++ | ++ | +++ |
| II-543 | ++ | +++ | ++ | +++ |
| II-544 | ++ | ++ | ++ | +++ |
| II-545 | ++ | +++ | ++ | +++ |
| II-546 | ++ | +++ | ++ | +++ |
| II-547 | ++ | +++ | ++ | +++ |
| II-548 | ++ | ++ | ++ | +++ |
| II-549 | ++ | +++ | +++ | +++ |
| II-550 | ++ | +++ | ++ | +++ |
| II-551 | ++ | +++ | ++ | +++ |
| II-552 | ++ | +++ | ++ | +++ |
| II-553 | ++ | +++ | ++ | +++ |
| II-554 | ++ | ++ | ++ | +++ |
| II-555 | ++ | + | ++ | ++ |
| II-556 | ++ | + | ++ | ++ |
| II-557 | ++ | ++ | +++ | +++ |
| II-558 | ++ | ++ | ++ | +++ |
| II-559 | ++ | +++ | ++ | +++ |
| II-560 | ++ | +++ | +++ | +++ |
| II-561 | ++ | +++ | +++ | +++ |
| II-562 | ++ | ++ | ++ | +++ |
| II-563 | ++ | ++ | ++ | +++ |
| II-564 | ++ | +++ | ++ | +++ |
| II-565 | ++ | ++ | ++ | +++ |
| II-566 | ++ | ++ | ++ | +++ |
| II-567 | ++ | +++ | ++ | +++ |
| II-568 | ++ | ++ | ++ | ++ |
| II-569 | ++ | + | ++ | +++ |
| II-570 | ++ | + | ++ | ++ |
| II-571 | ++ | +++ | ++ | +++ |
| II-572 | ++ | ++ | +++ | +++ |
| II-573 | ++ | ++ | ++ | +++ |
| II-574 | ++ | +++ | ++ | +++ |
| II-575 | ++ | ++ | ++ | +++ |
| II-576 | +++ | +++ | +++ | +++ |
| II-577 | ++ | ++ | ++ | +++ |
| II-578 | ++ | +++ | +++ | +++ |
| II-579 | ++ | +++ | +++ | +++ |
| II-580 | ++ | +++ | ++ | +++ |
| II-581 | ++ | +++ | +++ | +++ |
| II-582 | ++ | +++ | +++ | +++ |
| II-583 | ++ | ++ | ++ | +++ |
| II-584 | ++ | + | ++ | ++ |
| II-585 | ++ | +++ | +++ | +++ |
| II-586 | ++ | + | ++ | ++ |
| II-587 | ++ | ++ | ++ | +++ |
| II-588 | ++ | ++ | ++ | +++ |
| II-589 | +++ | ++ | +++ | +++ |
| II-590 | ++ | ++ | +++ | +++ |
| II-591 | ++ | +++ | +++ | +++ |
| II-592 | ++ | +++ | ++ | +++ |
| II-593 | ++ | +++ | +++ | +++ |
| II-594 | ++ | +++ | +++ | +++ |
| II-595 | +++ | +++ | +++ | +++ |
| II-596 | ++ | + | ++ | ++ |
| II-597 | ++ | ++ | ++ | +++ |
| II-598 | ++ | +++ | +++ | +++ |
| II-599 | ++ | + | ++ | ++ |
| II-600 | ++ | + | ++ | ++ |
| III-1 | ++ | + | ++ | +++ |
| III-2 | + | + | ++ | ++ |
| III-3 | + | + | ++ | ++ |
| III-4 | ++ | + | ++ | +++ |
| III-5 | ++ | + | ++ | ++ |
| III-6 | + | + | ++ | ++ |
| III-7 | ++ | + | ++ | +++ |

TABLE 4-continued

CSE-HRP data

| Example | EC50 (without co-corrector) (μM) | Maximum % activity (without co-corector) (%) | EC50 (with co-corrector) (μM) | Maximum % activity (with co-corector) (%) |
|---|---|---|---|---|
| III-8 | ++ | + | ++ | +++ |
| III-9 | + | + | ++ | ++ |
| III-10 | + | + | ++ | ++ |
| III-11 | ++ | + | ++ | ++ |
| III-12 | ++ | + | ++ | +++ |
| III-13 | + | + | + | + |
| III-14 | + | + | ++ | ++ |
| III-15 | ++ | + | +++ | ++ |
| III-16 | + | + | + | + |
| III-17 | + | + | ++ | ++ |
| III-18 | ++ | + | ++ | ++ |
| III-19 | ++ | + | ++ | ++ |
| III-20 | ++ | + | ++ | ++ |
| III-21 | + | + | ++ | ++ |
| III-22 | + | + | + | + |
| III-23 | + | + | + | + |
| III-24 | + | + | + | + |
| III-25 | + | + | ++ | ++ |
| III-26 | ++ | + | ++ | ++ |
| III-27 | ++ | +++ | ++ | +++ |
| III-28 | ++ | + | ++ | ++ |
| III-29 | ++ | + | ++ | ++ |
| III-30 | ++ | +++ | ++ | +++ |
| III-31 | + | + | ++ | ++ |
| III-32 | ++ | + | ++ | ++ |
| III-33 | ++ | + | ++ | ++ |
| III-34 | ++ | + | ++ | ++ |
| III-35 | ++ | ++ | +++ | +++ |
| III-36 | + | + | ++ | ++ |
| III-37 | + | + | ++ | ++ |
| III-38 | ++ | + | ++ | +++ |
| III-39 | + | + | ++ | ++ |
| III-40 | ++ | ++ | +++ | +++ |
| III-41 | ++ | ++ | ++ | +++ |
| III-42 | ++ | + | ++ | ++ |
| III-44 | ++ | + | ++ | ++ |
| III-45 | ++ | + | ++ | ++ |
| III-46 | ++ | + | ++ | ++ |
| III-47 | ++ | + | ++ | ++ |
| III-48 | + | + | ++ | ++ |
| III-49 | + | + | ++ | ++ |
| III-50 | + | + | ++ | ++ |
| III-51 | ++ | + | ++ | ++ |
| III-52 | + | + | +++ | ++ |
| III-53 | + | + | ++ | ++ |
| III-54 | ++ | + | ++ | ++ |
| III-55 | + | + | ++ | ++ |
| III-56 | + | + | ++ | ++ |
| III-57 | + | + | ++ | ++ |
| III-58 | + | + | ++ | ++ |
| III-59 | + | + | ++ | + |
| III-60 | ++ | + | ++ | +++ |
| III-61 | ++ | + | ++ | +++ |
| III-62 | ++ | + | ++ | ++ |
| III-63 | + | + | + | + |
| III-64 | ++ | + | ++ | ++ |
| III-65 | + | + | ++ | ++ |
| III-66 | + | + | ++ | ++ |
| III-67 | ++ | ++ | ++ | +++ |
| III-68 | + | + | ++ | ++ |
| III-69 | ++ | + | ++ | +++ |
| III-70 | + | + | ++ | ++ |
| III-71 | ++ | +++ | ++ | +++ |
| III-72 | + | + | ++ | ++ |
| III-73 | + | + | ++ | ++ |
| III-74 | + | + | ++ | ++ |
| III-75 | ++ | + | ++ | ++ |
| III-76 | + | + | ++ | ++ |
| III-77 | ++ | + | ++ | +++ |
| III-78 | + | + | ++ | ++ |
| III-79 | + | + | + | + |
| III-80 | + | + | ++ | ++ |
| III-81 | ++ | ++ | ++ | +++ |
| III-82 | ++ | + | ++ | ++ |
| III-83 | + | + | + | + |
| III-84 | + | + | ++ | + |
| III-85 | + | + | ++ | ++ |
| III-86 | + | + | ++ | ++ |
| III-87 | + | + | ++ | ++ |
| III-88 | + | + | ++ | ++ |
| III-89 | + | + | + | + |
| III-90 | + | + | ++ | + |
| III-91 | ++ | + | ++ | ++ |
| III-92 | + | + | + | + |
| III-93 | ++ | + | ++ | ++ |
| III-94 | ++ | ++ | ++ | +++ |
| III-95 | + | + | ++ | ++ |
| III-96 | ++ | +++ | ++ | +++ |
| III-97 | ++ | + | ++ | ++ |
| III-98 | + | + | ++ | ++ |
| III-99 | + | + | ++ | ++ |
| III-100 | + | + | ++ | ++ |
| III-101 | + | + | ++ | ++ |
| III-102 | + | + | ++ | ++ |
| III-103 | + | + | ++ | + |
| III-104 | + | + | ++ | ++ |
| III-105 | ++ | + | ++ | ++ |
| III-106 | ++ | + | ++ | ++ |
| III-107 | +++ | +++ | +++ | +++ |
| III-108 | + | + | ++ | + |
| III-109 | + | + | ++ | ++ |
| III-110 | + | + | ++ | ++ |
| III-111 | ++ | + | ++ | ++ |
| III-112 | ++ | + | ++ | ++ |
| III-113 | ++ | + | ++ | ++ |
| III-114 | ++ | ++ | ++ | +++ |
| III-115 | ++ | ++ | ++ | +++ |
| III-116 | ++ | ++ | +++ | +++ |
| III-117 | + | + | ++ | ++ |
| III-118 | +++ | +++ | +++ | +++ |
| III-119 | +++ | ++ | +++ | +++ |
| III-120 | + | + | ++ | ++ |
| III-121 | + | + | ++ | ++ |
| III-122 | + | + | ++ | ++ |
| III-123 | +++ | + | +++ | ++ |
| III-124 | ++ | + | +++ | +++ |
| III-125 | + | + | ++ | ++ |
| III-126 | ++ | + | ++ | ++ |
| III-127 | + | + | + | + |
| III-128 | + | + | ++ | ++ |
| III-129 | + | + | ++ | ++ |
| III-130 | + | + | ++ | ++ |
| III-131 | +++ | + | ++ | +++ |
| III-132 | + | + | ++ | ++ |
| III-133 | + | + | ++ | ++ |
| III-134 | ++ | + | ++ | ++ |
| III-135 | + | + | ++ | ++ |
| III-136 | + | + | ++ | ++ |
| III-137 | ++ | + | ++ | ++ |
| III-138 | + | + | ++ | ++ |
| III-139 | +++ | + | +++ | ++ |
| III-140 | + | + | ++ | ++ |
| III-141 | ++ | + | ++ | ++ |
| III-142 | ++ | + | ++ | ++ |
| III-143 | + | + | + | + |
| III-144 | + | + | +++ | + |
| III-145 | ++ | + | ++ | ++ |
| III-146 | + | + | ++ | ++ |
| III-147 | + | + | ++ | ++ |
| III-148 | ++ | + | ++ | +++ |
| III-149 | ++ | ++ | ++ | +++ |
| III-150 | + | + | + | + |
| III-151 | ++ | + | ++ | ++ |
| III-152 | + | + | ++ | ++ |
| III-153 | + | + | + | + |
| III-154 | ++ | + | ++ | ++ |

TALBE 4-continued

CSE-HRP data

| Example | EC50 (without co-corrector) (µM) | Maximum % activity (without co-corector) (%) | EC50 (with co-corrector) (µM) | Maximum % activity (with co-corrector) (%) |
|---|---|---|---|---|
| III-155 | + | + | ++ | + |
| III-156 | +++ | + | ++ | ++ |
| III-157 | + | + | ++ | ++ |
| III-158 | + | + | ++ | ++ |
| III-159 | + | + | ++ | ++ |
| III-160 | ++ | + | ++ | ++ |
| III-161 | + | + | + | + |
| III-162 | ++ | + | ++ | ++ |
| III-163 | ++ | + | ++ | ++ |
| III-164 | + | + | ++ | ++ |
| III-165 | ++ | + | ++ | ++ |
| III-166 | ++ | ++ | +++ | +++ |
| III-167 | ++ | +++ | +++ | +++ |
| III-168 | +++ | +++ | +++ | +++ |
| III-169 | +++ | +++ | +++ | +++ |
| III-170 | +++ | +++ | +++ | +++ |
| III-171 | ++ | +++ | +++ | +++ |
| III-172 | ++ | ++ | +++ | +++ |
| III-173 | ++ | +++ | +++ | +++ |
| III-174 | +++ | +++ | +++ | +++ |
| III-175 | +++ | +++ | +++ | +++ |
| III-176 | + | + | + | + |
| III-177 | ++ | + | ++ | ++ |
| III-178 | ++ | ++ | ++ | +++ |
| III-179 | ++ | +++ | +++ | +++ |
| III-180 | + | + | ++ | ++ |
| III-181 | ++ | + | ++ | ++ |
| III-183 | +++ | +++ | +++ | +++ |
| III-184 | + | + | ++ | + |
| III-185 | ++ | + | ++ | ++ |
| III-186 | ++ | + | ++ | ++ |
| III-187 | ++ | + | ++ | ++ |
| III-188 | +++ | ++ | +++ | +++ |
| III-189 | ++ | + | ++ | ++ |
| III-190 | ++ | +++ | +++ | +++ |
| III-191 | +++ | +++ | +++ | +++ |
| III-192 | +++ | +++ | +++ | +++ |
| III-193 | +++ | +++ | +++ | +++ |
| III-194 | ++ | ++ | +++ | +++ |
| III-195 | +++ | +++ | +++ | +++ |
| III-196 | +++ | ++ | +++ | +++ |
| III-197 | +++ | ++ | +++ | +++ |
| III-198 | ++ | +++ | +++ | +++ |
| III-199 | ++ | + | ++ | ++ |
| III-200 | + | + | ++ | ++ |
| III-201 | +++ | ++ | +++ | +++ |
| III-202 | +++ | +++ | +++ | +++ |
| III-203 | +++ | +++ | +++ | +++ |
| III-204 | +++ | +++ | +++ | +++ |
| III-205 | ++ | +++ | +++ | +++ |
| III-206 | ++ | +++ | +++ | +++ |
| III-207 | ++ | ++ | +++ | +++ |
| III-208 | ++ | ++ | +++ | +++ |
| III-209 | ++ | ++ | +++ | +++ |
| III-210 | ++ | + | ++ | ++ |
| III-211 | + | + | + | + |
| III-212 | + | + | ++ | ++ |
| III-213 | + | + | + | + |
| III-214 | +++ | ++ | +++ | +++ |
| III-215 | ++ | + | ++ | ++ |
| III-216 | ++ | + | ++ | ++ |
| III-217 | + | + | ++ | + |
| III-218 | ++ | ++ | ++ | +++ |
| III-219 | ++ | ++ | +++ | +++ |
| III-220 | +++ | +++ | +++ | +++ |
| III-221 | ++ | ++ | ++ | +++ |
| III-222 | ++ | ++ | ++ | +++ |
| III-223 | ++ | +++ | +++ | +++ |
| III-224 | ++ | +++ | ++ | +++ |
| III-225 | ++ | +++ | ++ | +++ |
| III-226 | ++ | +++ | ++ | +++ |
| III-227 | ++ | ++ | +++ | +++ |
| III-228 | + | + | + | + |
| III-229 | ++ | +++ | +++ | +++ |
| III-230 | ++ | + | ++ | ++ |
| III-231 | ++ | +++ | ++ | +++ |
| III-232 | ++ | +++ | ++ | +++ |
| III-233 | ++ | +++ | ++ | +++ |
| III-234 | ++ | ++ | ++ | +++ |
| III-235 | + | + | +++ | + |
| III-236 | ++ | + | ++ | ++ |
| III-237 | ++ | + | ++ | ++ |

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed:
1. A compound of Formula (I), or a pharmaceutically acceptable salt thereof,

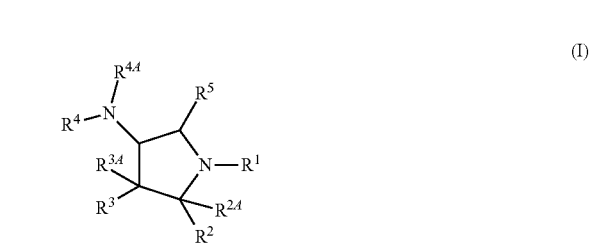

(I)

wherein
R$^1$ is selected from the group consisting of SO$_2$R$^6$, C(O)R$^6$, C(O)OR$^6$, and C(O)NR$^7$R$^8$;
R$^2$ is C(O)OH or a bioisostere thereof;
R$^{2A}$ is selected from the group consisting of hydrogen, C$_1$-C$_6$ alkyl, C$_1$-C$_6$ haloalkyl, and C$_3$-C$_6$ cycloalkyl;
R$^3$ is selected from the group consisting of C$_1$-C$_6$ alkyl, C$_3$-C$_6$ cycloalkyl, phenyl, and 5-6 membered heteroaryl; wherein the R$^3$ C$_1$-C$_6$ alkyl is optionally substituted with one or more substituents independently selected from the group consisting of C$_1$-C$_6$ alkoxy, OH, oxo, CN, NO$_2$, F, Cl, Br and I; wherein the R$^3$ C$_3$-C$_6$ cycloalkyl, phenyl, and 5-6 membered heteroaryl are optionally substituted with one or more substituents independently selected from the group consisting of C$_1$-C$_6$ alkyl, C$_1$-C$_6$ alkoxy, C$_1$-C$_6$ haloalkyl, OH, oxo, CN, NO$_2$, F, Cl, Br and I; and $R^{3A}$ is selected from the group consisting of hydrogen, $C_1$-$C_6$ alkyl, and $C_1$-$C_6$ haloalkyl; or $R^3$ and $R^{3A}$, together with the carbon to which they are attached, form $C_3$-$C_6$ cycloalkyl; wherein the $C_3$-$C_6$ cycloalkyl formed from $R^3$ and $R^{3A}$ and the carbon to which they are attached is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I;

$R^4$ is selected from the group consisting of $L^1$-$C_6$-$C_{10}$ aryl, $L^1$-5-11 membered heteroaryl, L-4-12 membered heterocyclyl, $L^1$-$C_3$-$C_{11}$ cycloalkyl, and $L^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of $R^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen, $C_1$-$C_6$ alkyl, and $C_1$-$C_6$ haloalkyl; or $R^4$ and $R^{4A}$, together with the carbon to which they are attached, form 4-12 membered heterocyclyl; wherein the 4-12 membered heterocyclyl is optionally substituted with one or more substituents independently selected from the group consisting of $R^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of $R^{12}$, OR$^{12}$, NR$^{13}$R$^{14}$, OH, oxo, CN, NO$_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of $R^{15}$, OR$^{15}$, SR$^{15}$, NR$^{16}$R$^{17}$, OH, CN, NO$_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of R's, OR$^{18}$, C(O)R$^{18}$, OC(O)R$^{18}$, C(O)OR$^{18}$, SO$_2$R$^{18}$, NR$^{19}$R$^{20}$, OH, oxo, CN, NO$_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{21}$, OR$^{21}$, C(O)R$^{21}$, OC(O)R$^{21}$, C(O)OR$^{21}$, C(O)NR$^{22}$R$^{23}$, SO$_2$R$^{21}$, NR$^{22}$R$^{23}$, OH, oxo, CN, NO$_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{24}$, OR$^{24}$, C(O)R$^{24}$, OC(O)R$^{24}$, C(O)OR$^{24}$, SO$_2$R$^{24}$, NR$^{25}$R$^{26}$, OH, oxo, CN, NO$_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, NO$_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, N($C_1$-$C_6$ alkyl)$_2$, OH, oxo, CN, NO$_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, NO$_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, NO$_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, NO$_2$, F, Cl, Br and I;

$R^{19}$ and $R^{20}$, at each occurrence, are each independently hydrogen or $C_1$-$C_6$ alkyl;

R²¹, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

2. The compound of claim 1, or a pharmaceutically acceptable salt thereof, wherein
$R^2$ is C(O)OH; and
$R^{24}$ is hydrogen.

3. The compound of claim 1, or a pharmaceutically acceptable salt thereof, wherein
$R^2$ is —C(O)NHSO$_2$R$^{G3a}$ or —C(O)NHSO$_2$N(R$^{G3a}$)$_2$;
$R^{G3a}$, at each occurrence, is independently $C_1$-$C_6$ alkyl, $C_1$-$C_6$ alkyl-O—$C_1$-$C_6$ alkyl, or $G^4$;
$G^4$, at each occurrence, is independently cycloalkyl, which is independently unsubstituted or substituted with 1, 2, or 3 independently selected $R^u$ groups;
$R^u$, at each occurrence, is independently $C_1$-$C_6$ alkyl; and
$R^{24}$ is hydrogen.

4. The compound of claim 1, or a pharmaceutically acceptable salt thereof, wherein
$R^5$ is phenyl; wherein the $R^5$ phenyl is unsubstituted.

5. A compound of Formula (III), or a pharmaceutically acceptable salt thereof,

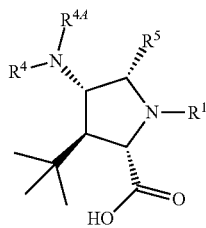

(III)

wherein
$R^1$ is selected from the group consisting of SO$_2$R$^6$, C(O)R$^6$, C(O)OR$^6$, and C(O)NR$^7$R$^8$;
$R^2$ is C(O)OH or a bioisostere thereof;
$R^4$ is selected from the group consisting of L$^1$-$C_6$-$C_{10}$ aryl, L$^1$-5-11 membered heteroaryl, L-4-12 membered heterocyclyl, L$^1$-$C_3$-$C_{11}$ cycloalkyl, and L$^1$-$C_4$-$C_{11}$ cycloalkenyl; wherein the $R^4$ $C_6$-$C_{10}$ aryl, 5-11 membered heteroaryl, 4-12 membered heterocyclyl, $C_3$-$C_{11}$ cycloalkyl, and $C_4$-$C_{11}$ cycloalkenyl are optionally substituted with one or more substituents independently selected from the group consisting of R$^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I; wherein L$^1$ is absent, or is selected from the group consisting of $C_1$-$C_6$ alkylene, $C_2$-$C_6$ alkenylene, $C_2$-$C_6$ alkynylene, and $C_1$-$C_6$ alkylene-O—; wherein the L$^1$ $C_1$-$C_6$ alkylene, $C_2$-$C_6$ alkenylene, and $C_2$-$C_6$ alkynylene, alone or as part of a group, are optionally substituted with one or more substituents independently selected from the group consisting of $C_1$-$C_6$ alkoxy, OH, and oxo; and $R^{4A}$ is selected from the group consisting of hydrogen, $C_1$-$C_6$ alkyl, and $C_1$-$C_6$ haloalkyl; or $R^4$ and $R^{4A}$, together with the carbon to which they are attached, form 4-12 membered heterocyclyl; wherein the 4-12 membered heterocyclyl is optionally substituted with one or more substituents independently selected from the group consisting of R$^9$, OR$^9$, C(O)OR$^9$, C(O)NR$^{10}$R$^{11}$, SR$^9$, NR$^{10}$R$^{11}$, Si(R$^9$)$_3$, SF$_5$, SO$_2$R$^9$, OH, oxo, CN, NO$_2$, F, Cl, Br and I;

$R^5$ is selected from the group consisting of $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl; wherein the $R^5$ $C_6$-$C_{10}$ membered aryl, 5-11 membered heteroaryl, 4-6 membered monocyclic heterocycle fused to a phenyl group, $C_3$-$C_{11}$ cycloalkyl, and $C_4$-$C_{11}$ cycloalkenyl are optionally substituted with one or more substituents independently selected from the group consisting of R$^{12}$, OR$^{12}$, NR$^{13}$R$^{14}$, OH, oxo, CN, NO$_2$, F, Cl, Br and I;

$R^6$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^6$ $C_1$-$C_6$ alkyl, $C_2$-$C_6$ alkenyl, and $C_2$-$C_6$ alkynyl are optionally substituted with one or more substituents independently selected from the group consisting of R$^{15}$, OR$^{15}$, SR$^{15}$, NR$^{16}$R$^{17}$, OH, CN, NO$_2$, F, Cl, Br and I; wherein the $R^6$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of R$^{18}$, OR$^{18}$, C(O)R$^{18}$, OC(O)R$^{18}$, C(O)OR$^{18}$, SO$_2$R$^{18}$, NR$^{19}$R$^{20}$, OH, oxo, CN, NO$_2$, F, Cl, Br and I;

$R^7$ and $R^8$ are each independently hydrogen or $C_1$-$C_6$ alkyl;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of R$^{21}$, OR$^{21}$, C(O)R$^{21}$, OC(O)R$^{21}$, C(O)OR$^{21}$, C(O)NR$^{22}$R$^{23}$, SO$_2$R$^{21}$, NR$^{22}$R$^{23}$, OH, oxo, CN, NO$_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of R$^{24}$, OR$^{24}$, C(O)R$^{24}$, OC(O)R$^{24}$, C(O)OR$^{24}$, SO$_2$R$^{24}$, NR$^{25}$R$^{26}$, OH, oxo, CN, NO$_2$, F, Cl, Br and I;

$R^{10}$ and $R^{11}$, at each occurrence, are each independently selected from the group consisting of hydrogen, $C_1$-$C_6$ alkyl, phenyl, and 5-6 membered heteroaryl; wherein each $R^{10}$ and $R^{11}$ phenyl and 5-6 membered heteroaryl is optionally substituted with one or more substituents independently selected from the group consisting of $C_1$-$C_6$ alkyl, $C_1$-$C_6$ alkoxy, $C_1$-$C_6$ haloalkyl, OH, oxo, CN, $NO_2$, F, Cl, Br and I;

$R^{12}$, at each occurrence, is independently selected from the group consisting of $C_1$-$C_6$ alkyl, $C_1$-$C_6$ haloalkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{12}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, $C_1$-$C_6$ haloalkoxy, $N(C_1$-$C_6$ alkyl$)_2$, OH, oxo, CN, $NO_2$, F, Cl, Br and I;

$R^{13}$ and $R^{14}$, at each occurrence, are each independently hydrogen or $C_1$-$C_6$ alkyl;

$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, $C_1$-$C_6$ haloalkyl, oxo, OH, CN, $NO_2$, F, Cl, Br and I;

$R^{16}$ and $R^{17}$, at each occurrence, are each independently hydrogen or $C_1$-$C_6$ alkyl;

$R^{18}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{18}$ $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I;

$R^{19}$ and $R^{20}$, at each occurrence, are each independently hydrogen or $C_1$-$C_6$ alkyl;

$R^{21}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{21}$ $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of OH, oxo, CN, $NO_2$, F, Cl, Br and I;

$R^{22}$ and $R^{23}$, at each occurrence, are each independently hydrogen or $C_1$-$C_6$ alkyl;

$R^{24}$, at each occurrence, is independently selected from the group consisting of $C_1$-$C_6$ alkyl, $C_1$-$C_6$ haloalkyl, $C_1$-$C_6$ alkoxy-$C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; and $R^{25}$ and $R^{26}$, at each occurrence, are each independently hydrogen or $C_1$-$C_6$ alkyl.

6. The compound of claim 5 or a pharmaceutically acceptable salt thereof, wherein
$R^1$ is $C(O)OR^6$;
$R^6$ is $C_1$-$C_6$ alkyl; wherein the $R^6$ $C_1$-$C_6$ alkyl is optionally substituted with one or more substituents independently selected from the group consisting of $R^{15}$, $OR^{15}$, $SR^{15}$, OH, and F; and
$R^{15}$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^{15}$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, OH, CN, F, and Cl.

7. The compound of claim 5 or a pharmaceutically acceptable salt thereof, wherein
$R^5$ is phenyl; wherein the $R^5$ phenyl is unsubstituted.

8. The compound of claim 5 or a pharmaceutically acceptable salt thereof, wherein
$R^5$ is pyridinyl; wherein the $R^5$ pyridinyl is optionally substituted with one or more substituents independently selected from the group consisting of $R^{12}$, $OR^{12}$, $NR^{13}R^{14}$, F, Cl, and Br;
$R^{12}$, at each occurrence, is independently selected from the group consisting of $C_1$-$C_6$ alkyl, $C_1$-$C_6$ haloalkyl, $C_3$-$C_{11}$ cycloalkyl, and 4-12 membered heterocyclyl; and
$R^{13}$ and $R^{14}$, at each occurrence, are each independently $C_1$-$C_6$ alkyl.

9. The compound of claim 1, or a pharmaceutically acceptable salt thereof, wherein the compound is selected from the group consisting of:
rac-(2R,3R,4R,5R)-3-tert-butyl-1-(cyclohexanecarbonyl)-4-{[6-methyl-4-(trifluoromethyl)pyridin-2-yl]amino}-5-phenylpyrrolidine-2-carboxylic acid;
rac-(2R,3R,4R,5R)-3-tert-butyl-1-(cyclohexanecarbonyl)-4-{[6-methoxy-4-(trifluoromethyl)pyridin-2-yl]amino}-5-phenylpyrrolidine-2-carboxylic acid;
(2R,3R,4R,5R)-3-tert-butyl-1-(cyclohexanecarbonyl)-4-{[6-methyl-4-(trifluoromethyl)pyridin-2-yl]amino}-5-phenylpyrrolidine-2-carboxylic acid;
(2S,3S,4S,5S)-3-tert-butyl-1-(cyclohexanecarbonyl)-4-{[6-methyl-4-(trifluoromethyl)pyridin-2-yl]amino}-5-phenylpyrrolidine-2-carboxylic acid;
rac-(2R,3R,4R,5R)-1-(cyclohexanecarbonyl)-3-(2-methoxypropan-2-yl)-4-{[6-methyl-4-(trifluoromethyl)pyridin-2-yl]amino}-5-phenylpyrrolidine-2-carboxylic acid;
rac-(2R,3R,4R,5R)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid;
(2S,3S,4S,5S)-3-tert-butyl-4-{[(5-tert-butyl-2-methoxyphenyl)methyl]amino}-1-(cyclohexanecarbonyl)-5-phenylpyrrolidine-2-carboxylic acid;
(2S,3S,4S,5S)-3-tert-butyl-1-(cyclohexanecarbonyl)-4-({[2-methoxy-4-(trifluoromethyl)phenyl]methyl}amino)-5-phenylpyrrolidine-2-carboxylic acid;
(2S,3S,4S,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid;

(2S,3S,4S,5S)-3-tert-butyl-4-({[2-methoxy-4-(trifluoromethyl)phenyl]methyl}amino)-5-phenyl-1-[(2R*)-2-phenylpropanoyl]pyrrolidine-2-carboxylic acid;

(2S,3S,4S,5S)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-1-(cyclohexanecarbonyl)-5-[2-(difluoromethoxy)phenyl]-4-({[2-methoxy-5-(trifluoromethyl)pyridin-3-yl]methyl}amino)pyrrolidine-2-carboxylic acid;

(2S,3S,4S,5S)-1-(benzenesulfonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R)-oxane-2-carbonyl]pyrrolidine-2-carboxylic acid;

(2S,3S,4S,5)-3-tert-butyl-4-{[(5-tert-butyl-2-methoxyphenyl)methyl]amino}-1-[(oxan-2-yl)acetyl]-5-phenylpyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid;

(2S,3S,4S,5S)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2S*,3S*)-3-(propan-2-yl)oxolane-2-carbonyl]pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-fluorophenyl)pyrrolidine-2-carboxylic acid;

(2S,3S,4S,5S)-3-tert-butyl-1-(cyclohexanecarbonyl)-4-{[(2-methoxy-5-phenylpyridin-3-yl)methyl]amino}-5-phenylpyrrolidine-2-carboxylic acid;

(2S,3S,4S,5S)-3-tert-butyl-1-(cyclohexanecarbonyl)-5-(4-fluorophenyl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1S)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(1R)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-methoxy-3-phenylpropanoyl]-5-phenylpyrrolidine-2-carboxylic acid;

(2S,3S,4S,5S)-3-tert-butyl-1-(cyclohexanecarbonyl)-4-[({2-methoxy-5-[1-(trifluoromethyl)cyclopropyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(2S)-oxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(cis-4-hydroxy-4-propylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-[2-(dimethylamino)pyridin-3-yl]pyrrolidine-2-carboxylic acid;

(2S,3S,4S,5S)-3-tert-butyl-1-[(2R*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid;

(2S,3S,4S,5S)-3-tert-butyl-4-{[(6-tert-butyl-2-methoxypyridin-3-yl)methyl]amino}-1-[(2S)-oxane-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R)-oxane-2-carbonyl]-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(2-methoxypropan-2-yl)-5-(2-methoxypyridin-3-yl)pyrrolidine-2-carboxylic acid;

(2S,3S,4S,5S)-4-{[(5-tert-butyl-2-methoxyphenyl)methyl]amino}-1-(cyclohexanecarbonyl)-5-[2-(dimethylamino)pyridin-3-yl]-3-(2-methoxypropan-2-yl)pyrrolidine-2-carboxylic acid;

(2S,3S,4S,5S)-3-tert-butyl-4-{[(5-tert-butyl-2-methoxyphenyl)methyl]amino}-1-[(1R*)-3,3-difluorocyclohexane-1-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(1S*)-3,3-difluorocyclohexane-1-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(2R)-oxane-2-carbonyl]pyrrolidine-2-carboxylic acid;

(2S,3S,4S,5S)-1-(bicyclo[3.1.0]hexane-6-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-1-(cyclohexanecarbonyl)-4-({[2-methoxy-5-(trimethylsilyl)pyridin-3-yl]methyl}amino)-5-phenylpyrrolidine-2-carboxylic acid;

(2S,3S,4S,5S)-3-tert-butyl-4-{[(2-tert-butyl-5-methoxypyridin-4-yl)methyl]amino}-1-(cyclohexanecarbonyl)-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-[(2R)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2S)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-[(2R)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-[(1R*)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(2,2,6,6-tetramethyloxane-4-carbonyl)pyrrolidine-2-carboxylic acid;

(2S,3S,4S,5S)-3-tert-butyl-4-[(5-tert-butyl-2-methoxypyridin-3-yl)amino]-1-(cyclohexanecarbonyl)-5-phenylpyrrolidine-2-carboxylic acid;

(2S,3S,4S,5S)-3-(bicyclo[1.1.1]pentan-1-yl)-1-(cyclohexanecarbonyl)-4-({[2-hydroxy-5-(trifluoromethyl)phenyl]methyl}amino)-5-phenylpyrrolidine-2-carboxylic acid;

(2S,3S,4S,5S)-3-(bicyclo[1.1.1]pentan-1-yl)-1-(cyclohexanecarbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-N-(methanesulfonyl)-5-phenylpyrrolidine-2-carboxamide;

(2S,3S,4S,5S)-3-tert-butyl-4-{[(5-tert-butyl-2-methoxyphenyl)methyl]amino}-5-[2-(difluoromethoxy)phenyl]-1-[(2S)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(2S*)-oxane-2-carbonyl]-5-[2-(propan-2-yl)phenyl]pyrrolidine-2-carboxylic acid;

(2S,3S,4S,5S)-3-tert-butyl-4-({[4-(3-chlorophenyl)oxan-4-yl]methyl}amino)-1-(cyclohexanecarbonyl)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(dimethylamino)pyridin-3-yl]-1-{[(propan-2-yl)oxy]carbonyl}pyrrolidine-2-carboxylic acid;

(2S,3S,4S,5S)-1-(bicyclo[3.1.0]hexane-6-carbonyl)-3-tert-butyl-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1R)-3,3-difluorocyclohexane-1-carbonyl]-5-phenylpyrrolidine-2-carboxylic acid;

(2S,3S,4S,5S)-3-tert-butyl-4-{[(5-cyclobutyl-2-methoxypyridin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-[(1R)-3,3-difluorocyclohexane-1-carbonyl]-5-phenylpyrrolidine-2-carboxylic acid;

(2S,3S,4S,5S)-3-(bicyclo[1.1.1]pentan-1-yl)-4-{[(6-tert-butyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-(bicyclo[1.1.1]pentan-1-yl)-4-{[(5-tert-butyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-[(2R)-oxane-2-carbonyl]-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-[2-(propan-2-yl)phenyl]pyrrolidine-2-carboxylic acid;

(2S,3S,4S,5S)-3-tert-butyl-1-[(1R)-3,3-difluorocyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-(bicyclo[1.1.1]pentan-1-yl)-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-({[2-methoxy-5-(trifluoromethyl)pyridin-3-yl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-{[(propan-2-yl)oxy]carbonyl}pyrrolidine-2-carboxylic acid;

(2S,3S,4S,5S)-3-tert-butyl-4-({[2-methoxy-4-(trifluoromethyl)phenyl]methyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-{[6-methyl-4-(trifluoromethyl)pyridin-2-yl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxane-2-carbonyl]-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-[(2R)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-(3-chlorophenyl)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-1-(cyclohexanecarbonyl)-4-({[2-methoxy-4-(trifluoromethyl)phenyl]methyl}amino)-5-(2-methylphenyl)pyrrolidine-2-carboxylic acid;

(2S,3S,4S,5S)-3-tert-butyl-4-{[(5-cyclobutyl-2-methoxypyridin-3-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-4-{[(6-methoxy-2,3-dihydro-1H-inden-5-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-5-(2-cyclopropylphenyl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-(2-methylphenyl)pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylphenyl)-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-1-[(2S)-oxolane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-(2-cyclopropylpyridin-3-yl)-1-[(2S)-oxolane-2-carbonyl]pyrrolidine-2-carboxylic acid;

(2S,3S,4S,5S)-3-tert-butyl-1-(ethoxycarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-1-(cyclopenanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-{[(5-tert-butyl-2-methoxyphenyl)methyl]amino}-1-{[(propan-2-yl)oxy]carbonyl}pyrrolidine-2-carboxylic acid;

(2S,3S,4S,5S)-3-tert-butyl-4-{[(2-methoxyquinolin-3-yl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-4-{[(5-cyclopropyl-2-methoxypyridin-3-yl)methyl]amino}-1-[(2S)-oxolane-2-carbonyl]-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-{[(5-tert-butyl-2-methoxyphenyl)methyl]amino}-1-(cyclobutanecarbonyl)pyrrolidine-2-carboxylic acid;

(2S,3S,4S,5S)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid;

(2S,3S,4S,5S)-3-tert-butyl-4-{[(5-tert-butyl-2-methoxyphenyl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-1-(cyclohexanecarbonyl)-4-{[(5-cyclopropyl-2-methoxypyridin-3-yl)methyl]amino}-5-(2-methylphenyl)pyrrolidine-2-carboxylic acid;

(2S,3S,4S,5S)-5-(2-bromophenyl)-3-tert-butyl-4-{[(5-cyclobutyl-2-methoxypyridin-3-yl)methyl]amino}-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylphenyl)-1-[(2S)-oxolane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-cyclopropylphenyl)-1-[(2S)-oxolane-2-carbonyl]pyrrolidine-2-carboxylic acid;

(2S,3S,4S,5S)-3-tert-butyl-4-({[2-methoxy-5-(1-methylcyclobutyl)phenyl]methyl}amino)-5-(2-methylphenyl)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methylphenyl)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-ethylphenyl)-1-[(2S)-oxolane-2-carbonyl]pyrrolidine-2-carboxylic acid;

(2S,3S,4S,5S)-3-tert-butyl-5-(2-cyclopropylphenyl)-4-({[2-methoxy-5-(1-methylcyclobutyl)phenyl]methyl}amino)-1-[(2S)-oxolane-2-carbonyl]pyrrolidine-2-carboxylic acid;

(2S,3S,4S,5S)-5-(2-bromophenyl)-3-tert-butyl-4-{[(5-tert-butyl-2-methoxyphenyl)methyl]amino}-1-[(2S)-oxane-2-carbonyl]pyrrolidine-2-carboxylic acid;

(2S,3S,4S,5S)-3-tert-butyl-1-(cyclohexanecarbonyl)-4-{[2-methoxy-5-(trifluoromethyl)pyridin-3-yl]amino}-5-phenylpyrrolidine-2-carboxylic acid;

(2S,3S,4S,5S)-3-tert-butyl-4-{[(5-cyclopropyl-2-methoxypyridin-3-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-5-(2-cyclopropylphenyl)-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-[2-(propan-2-yl)phenyl]pyrrolidine-2-carboxylic acid;

(2S,3S,4S,5S)-3-tert-butyl-1-(cyclohexanecarbonyl)-5-(2,2-dimethyl-2,3-dihydro-1-benzofuran-7-yl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-cyclobutyl-2-methoxypyridin-3-yl)methyl](methyl)amino}-1-[(2S)-oxane-2-carbonyl]-5-[2-(propan-2-yl)phenyl]pyrrolidine-2-carboxylic acid;

rac-(2R,3R,4R,5R)-3-tert-butyl-1-(cyclohexanecarbonyl)-4-[(4,6-dimethoxypyrimidin-2-yl)amino]-5-phenylpyrrolidine-2-carboxylic acid;

rac-(2R,3R,4R,5R)-3-tert-butyl-4-[(4-chloro-6-methoxypyrimidin-2-yl)amino]-1-(cyclohexanecarbonyl)-5-phenylpyrrolidine-2-carboxylic acid;

rac-(2R,3R,4R,5R)-3-tert-butyl-1-(cyclohexanecarbonyl)-4-{[1-(2,2-difluoro-2H-1,3-benzodioxol-5-yl)ethyl]amino}-5-phenylpyrrolidine-2-carboxylic acid;

rac-(2R,3R,4R,5R)-3-tert-butyl-1-(cyclohexanecarbonyl)-4-{[(5-methoxy-1,3-dimethyl-1H-pyrazol-4-yl)methyl]amino}-5-phenylpyrrolidine-2-carboxylic acid;

rac-(2R,3R,4R,5R)-3-tert-butyl-1-(cyclohexanecarbonyl)-5-phenyl-4-{[4-(trifluoromethyl)pyrimidin-2-yl]amino}pyrrolidine-2-carboxylic acid;

rac-(2R,3R,4R,5R)-3-tert-butyl-1-(cyclohexanecarbonyl)-4-({[2-methoxy-5-(trifluoromethyl)phenyl]methyl}amino)-5-phenylpyrrolidine-2-carboxylic acid;

rac-(2R,3R,4R,5R)-1-(cyclohexanecarbonyl)-3-cyclopropyl-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(cyclohexanecarbonyl)-4-({1-[2-methoxy-5-(trifluoromethyl)phenyl]ethyl}amino)-5-phenylpyrrolidine-2-carboxylic acid;

rac-(2S,3S,4S,5S)-3-tert-butyl-1-(cyclohexanecarbonyl)-4-[(2,6-dimethoxypyrimidin-4-yl)amino]-5-phenylpyrrolidine-2-carboxylic acid;

rac-(2R,3R,4R,5R)-3-tert-butyl-4-{[6-methoxy-4-(trifluoromethyl)pyridin-2-yl]amino}-5-phenyl-1-{[(propan-2-yl)oxy]carbonyl}pyrrolidine-2-carboxylic acid;

rac-(2R,3R,4R,5S)-3-tert-butyl-1-(cyclohexanecarbonyl)-4-({[2-(difluoromethoxy)phenyl]methyl}amino)-5-(pyridin-2-yl)pyrrolidine-2-carboxylic acid;

rac-(2R,3R,4R,5R)-3-tert-butyl-4-{[(5-chloro-2-methoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[4-methyl-6-(trifluoromethyl)pyrimidin-2-yl]amino}-5-phenyl-1-{[(propan-2-yl)oxy]carbonyl}pyrrolidine-2-carboxylic acid;

rac-(2R,3R,4R,5R)-3-tert-butyl-1-(cyclohexanecarbonyl)-4-({[2-(difluoromethoxy)-5-methoxyphenyl]methyl}amino)-5-phenylpyrrolidine-2-carboxylic acid;

rac-(2R,3R,4R,5R)-3-tert-butyl-1-(cyclohexanecarbonyl)-4-{[2-methoxy-5-(trifluoromethyl)pyridin-3-yl]amino}-5-phenylpyrrolidine-2-carboxylic acid;

rac-(2R,3R,4R,5S)-3-tert-butyl-1-(cyclohexanecarbonyl)-4-({[2-(difluoromethoxy)phenyl]methyl}amino)-5-(6-methoxypyridin-2-yl)pyrrolidine-2-carboxylic acid;

rac-(4R,6R,7R)-5-(cyclohexane carbonyl)-7-{[6-methyl-4-(trifluoromethyl)pyridin-2-yl]amino}-6-phenyl-5-azaspiro[2.4]heptane-4-carboxylic acid;

rac-(2R,3R,4R,5S)-3-tert-butyl-4-({[2-(difluoromethoxy)phenyl]methyl}amino)-5-(6-methoxypyridin-2-yl)-1-(oxane-2-carbonyl)pyrrolidine-2-carboxylic acid;

rac-(2R,3R,4R,5S)-3-tert-butyl-1-(cyclohexanecarbonyl)-5-(6-methoxypyridin-2-yl)-4-({[2-methoxy-5-(trifluoromethyl)phenyl]methyl}amino)pyrrolidine-2-carboxylic acid;

(2S,3S,4S,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-4-{[6-(difluoromethoxy)pyridin-2-yl]amino}-5-phenylpyrrolidine-2-carboxylic acid;

rac-(2R,3R,4R,5R)-3-tert-butyl-1-(cyclohexanecarbonyl)-5-[2-(dimethylamino)phenyl]-4-({[2-methoxy-5-(trifluoromethyl)phenyl]methyl}amino)pyrrolidine-2-carboxylic acid;

rac-(2R,3R,4R,5S)-3-tert-butyl-5-(6-methoxypyridin-2-yl)-4-({[2-methoxy-5-(trifluoromethyl)phenyl]methyl}amino)-1-[oxane-2-carbonyl]pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-(3-oxabicyclo[3.1.0]hexane-6-carbonyl)pyrrolidine-2-carboxylic acid;

rac-(2R,3R,4R,5R)-3-tert-butyl-5-[2-(dimethylamino)phenyl]-4-({[2-methoxy-4-(trifluoromethyl)phenyl]methyl}amino)-1-[oxane-2-carbonyl]pyrrolidine-2-carboxylic acid;

rac-(2R,3R,4R,5R)-3-tert-butyl-5-[2-(dimethylamino)phenyl]-1-[(2,2-dimethyloxane-4-carbonyl]-4-({[2-methoxy-4-(trifluoromethyl)phenyl]methyl}amino)pyrrolidine-2-carboxylic acid;

rac-(2R,3R,4R,5R)-3-tert-butyl-1-[(3R)-1-(methoxycarbonyl)piperidine-3-carbonyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid;

rac-(2R,3R,4R,5R)-3-tert-butyl-1-(cyclohexanecarbonyl)-4-({[5-(methanesulfonyl)-2-methoxyphenyl]methyl}amino)-5-phenylpyrrolidine-2-carboxylic acid;

rac-(2R,3R,4R,5R)-3-tert-butyl-1-[(1R,3R)-3-methoxycyclohexane-1-carbonyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-4-({[2-methoxy-5-(trifluoromethyl)phenyl]methyl}amino)-1-[(2S*)-2-phenoxypropanoyl]-5-phenylpyrrolidine-2-carboxylic acid;

(2R*,3R*,4R*,5R*)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid;

(2S,3S,4S,5S)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-5-phenyl-4-({[2-(propan-2-yl)phenyl]methyl}amino)pyrrolidine-2-carboxylic acid;

rac-(2R,3R,4R,5R)-3-tert-butyl-4-{[(5-chloro-2-methoxypyridin-3-yl)methyl]amino}-1-(cyclohexanecarbonyl)-5-phenylpyrrolidine-2-carboxylic acid;

rac-(2R,3R,4R,5R)-3-tert-butyl-4-{[6-methyl-4-(trifluoromethyl)pyridin-2-yl]amino}-5-phenyl-1-(spiro[2.5]octane-6-carbonyl)pyrrolidine-2-carboxylic acid;

rac-(2R,3R,4R,5R)-1-(cyclohexanecarbonyl)-3-(2-methoxypropan-2-yl)-4-{[6-methoxy-4-(trifluoromethyl)pyridin-2-yl]amino}-5-phenylpyrrolidine-2-carboxylic acid;

(2S,3S,4S,5S)-3-tert-butyl-1-(cyclohexanecarbonyl)-5-(2-methoxypyridin-3-yl)-4-({[2-methoxy-4-(trifluoromethyl)phenyl]methyl}amino)pyrrolidine-2-carboxylic acid;

rac-(2S,3S,4S,5R)-3-tert-butyl-4-{[(5-chloro-2-methoxyphenyl)methyl]amino}-1-(cyclohexanecarbonyl)-5-(3-methoxypyridin-2-yl)pyrrolidine-2-carboxylic acid;

rac-(2R,3R,4R,5R)-3-tert-butyl-1-(2-methoxy-2-methylpropanoyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-{[(3-methoxynaphthalen-2-yl)methyl]amino}-5-phenylpyrrolidine-2-carboxylic acid;

(2S,3S,4S,5S)-3-tert-butyl-1-(cyclohexanecarbonyl)-5-[2-(difluoromethoxy)phenyl]-4-({[2-methoxy-4-(trifluoromethyl)phenyl]methyl}amino)pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-4-(trifluoromethyl)phenyl]methyl}amino)pyrrolidine-2-carboxylic acid;

(2R,3R,4R,5R)-3-tert-butyl-4-({[2-methoxy-4-(trifluoromethyl)phenyl]methyl}amino)-5-phenyl-1-[(2R)-2-phenylpropanoyl]pyrrolidine-2-carboxylic acid;

(2S,3S,4S,5S)-4-{[(1-benzofuran-2-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2,3-dihydro-1,4-benzodioxin-6-yl)methyl]amino}-5-phenylpyrrolidine-2-carboxylic acid;

(2S,3S,4S,5S)-3-tert-butyl-1-(cyclohexanecarbonyl)-4-{[(4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-{[(6-methoxy-2,3-dihydro-1H-inden-5-yl)methyl]amino}-5-phenylpyrrolidine-2-carboxylic acid;

(2S,3S,4S,5S)-3-tert-butyl-1-(cyclohexanecarbonyl)-4-({[2-(cyclopropylmethoxy)-4-fluorophenyl]methyl}amino)-5-phenylpyrrolidine-2-carboxylic acid;

(2S,3S,4S,5S)-3-tert-butyl-4-{[(5-chloro-2-hydroxyphenyl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(trifluoromethyl)phenyl]methyl}amino)pyrrolidine-2-carboxylic acid;

(2S,3S,4S,5S)-3-tert-butyl-1-(cyclohexanecarbonyl)-5-phenyl-4-{[6-(propan-2-yl)-4-(trifluoromethyl)pyridin-2-yl]amino}pyrrolidine-2-carboxylic acid;

(2S,3S,4S,5S)-3-tert-butyl-4-[(3-cyano-4-methoxyquinolin-2-yl)amino]-1-(cyclohexanecarbonyl)-5-phenylpyrrolidine-2-carboxylic acid;

(2S,3S,4S,5S)-3-tert-butyl-1-(cyclohexanecarbonyl)-5-phenyl-4-[3-(trifluoromethyl)anilino]pyrrolidine-2-carboxylic acid;

(2S,3S,4S,5S)-3-tert-butyl-4-{[(5-chloro-2-methoxyphenyl)methyl]amino}-1-(cyclohexanecarbonyl)-5-(2-methoxyphenyl)pyrrolidine-2-carboxylic acid;

(2S,3S,4S,5S)-3-tert-butyl-4-{[(5-tert-butyl-2-methoxyphenyl)methyl]amino}-1-[(1S,3S)-3-methoxycyclohexane-1-carbonyl]-5-phenylpyrrolidine-2-carboxylic acid;

(2S,3S,4S,5S)-3-tert-butyl-1-[(1R,3R)-3-methoxycyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-[(1S,3S)-3-methoxycyclohexane-1-carbonyl]-4-({[2-methoxy-5-(trifluoromethyl)phenyl]methyl}amino)-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-4-{[(4-tert-butyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-3-(2-methoxypropan-2-yl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(pyridine-3-carbonyl)pyrrolidine-2-carboxylic acid;

(2S,3S,4S,5S)-1-benzoyl-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1$\lambda^6$-thiane-3-carbonyl)-5-phenylpyrrolidine-2-carboxylic acid;

(2S,3S,4S,5S)-3-tert-butyl-4-{[6-cyclobutyl-4-(trifluoromethyl)pyridin-2-yl]amino}-1-(cyclohexanecarbonyl)-5-phenylpyrrolidine-2-carboxylic acid;

(2S,3S,4S,5S)-3-tert-butyl-4-{[(5-cyclobutyl-2-methoxyphenyl)methyl]amino}-1-(cyclohexanecarbonyl)-5-phenylpyrrolidine-2-carboxylic acid;

(2S,3S,4S,5S)-4-{[(5-benzyl-2-methoxypyridin-3-yl)methyl]amino}-3-tert-butyl-1-(cyclohexanecarbonyl)-5-phenylpyrrolidine-2-carboxylic acid;

(2S,3S,4S,5S)-4-({[5-(butan-2-yl)-2-methoxypyridin-3-yl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[5-(cyclohexylmethyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-{[(5-cyclohexyl-2-methoxypyridin-3-yl)methyl]amino}-5-phenylpyrrolidine-2-carboxylic acid;

(2S,3S,4S,5S)-3-tert-butyl-1-(cyclohexanecarbonyl)-4-{[(5-cyclopentyl-2-methoxypyridin-3-yl)methyl]amino}-5-phenylpyrrolidine-2-carboxylic acid;

(2S,3S,4S,5S)-3-tert-butyl-1-(cyclohexanecarbonyl)-4-({[5-(2-ethylbutyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-
({[2-methoxy-5-(1-phenylethyl)pyridin-3-yl]
methyl}amino)-5-phenylpyrrolidine-2-carboxylic acid;

(2S,3S,4S,5S)-3-tert-butyl-1-(cyclohexanecarbonyl)-4-
({[2-methoxy-5-(2-methylpropyl)pyridin-3-yl]
methyl}amino)-5-phenylpyrrolidine-2-carboxylic acid;

(2S,3S,4S,5S)-3-tert-butyl-4-[({5-[(3-cyanophenyl)
methyl]-2-methoxypyridin-3-yl}methyl)amino]-1-(cyclohexanecarbonyl)-5-phenylpyrrolidine-2-carboxylic
acid;

(2S,3S,4S,5S)-3-tert-butyl-4-{[(4-methoxy[1,1'-biphenyl]-3-yl)methyl]amino}-1-[(1R,3R)-3-methoxycyclohexane-1-carbonyl]-5-phenylpyrrolidine-2-carboxylic
acid;

(2S,3S,4S,5S)-3-tert-butyl-1-[(1R,3R)-3-methoxycyclohexane-1-carbonyl]-4-({[2-methoxy-5-(trifluoromethyl)pyridin-3-yl]methyl}amino)-5-phenylpyrrolidine-2-carboxylic acid;

(2S,3S,4S,5S)-3-tert-butyl-4-{[(5-tert-butyl-2-hydroxyphenyl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{[(propan-2-yl)
oxy]carbonyl}pyrrolidine-2-carboxylic acid;

(2S,3S,4S,5S)-3-tert-butyl-4-(5-tert-butyl-2-methoxyanilino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-phenylpyrrolidine-2-carboxylic acid;

(2S,3S,4S,5S)-3-tert-butyl-4-({[2-methoxy-5-(trifluoromethyl)phenyl]methyl}amino)-1-[(oxan-2-yl)
acetyl]-5-phenylpyrrolidine-2-carboxylic acid;

(2S,3S,4S,5S)-3-tert-butyl-1-(cyclohexanecarbonyl)-4-
[({5-[(dimethylamino)methyl]-2-
methoxyphenyl}methyl)amino]-5-phenylpyrrolidine-2-carboxylic acid;

(2S,3S,4S,5S)-3-tert-butyl-1-(cyclohexanecarbonyl)-4-
({[2-methoxy-5-(pentafluoro-$\lambda^6$-sulfanyl)phenyl]
methyl}amino)-5-phenylpyrrolidine-2-carboxylic acid;

(2S,3S,4S,5S)-1-(cyclohexanecarbonyl)-4-{[(4-methoxy
[1,1'-biphenyl]-3-yl)methyl]amino}-3-(2-methoxypropan-2-yl)-5-phenylpyrrolidine-2-carboxylic acid;

(2S,3S,4S,5S)-3-tert-butyl-4-({[5-(2-cyanopropan-2-yl)-
2-methoxyphenyl]methyl}amino)-1-(cyclohexanecarbonyl)-5-phenylpyrrolidine-2-carboxylic acid;

(2S,3S,4S,5S)-3-tert-butyl-1-(cyclohexanecarbonyl)-4-
({[4-(2-hydroxypropan-2-yl)-2-methoxyphenyl]
methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(5-cyano-2-methoxybenzoyl)-5-phenylpyrrolidine-2-carboxylic acid;

(2S,3S,4S,5S)-3-tert-butyl-4-{[(5-tert-butyl-2-methoxyphenyl)methyl]amino}-1-[(1,3-dihydro-2H-isoindol-2-
yl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(thiophen-3-yl)
acetyl]pyrrolidine-2-carboxylic acid;

(2S,3S,4S,5S)-3-tert-butyl-4-{[(5-tert-butyl-2-methoxyphenyl)methyl]amino}-1-(8-fluoroquinoline-2-carbonyl)-5-phenylpyrrolidine-2-carboxylic acid;

(2S,3S,4S,5S)-3-tert-butyl-1-(cyclohexanecarbonyl)-4-
({[2-methoxy-5-(2-methylpropyl)phenyl]
methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-cyclopropyl-2-methoxyacetyl]-5-phenylpyrrolidine-2-carboxylic
acid;

(2S,3S,4S,5S)-3-tert-butyl-4-{[(5-tert-butyl-2-methoxyphenyl)methyl]amino}-1-[(2S*)-2-cyclopropyl-2-methoxyacetyl]-5-phenylpyrrolidine-2-carboxylic
acid;

(2S,3S,4S,5S)-3-tert-butyl-1-(cyclohexanecarbonyl)-4-
[({2-methoxy-5-[(1S,3 s)-tricyclo[3.3.1.1$^{3,7}$]decan-1-
yl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(1H-imidazol-4-yl)acetyl]-
5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclopentyl)
acetyl]-5-phenylpyrrolidine-2-carboxylic acid;

(2S,3S,4S,5S)-1-[(azepan-1-yl)acetyl]-3-tert-butyl-4-
{[(5-tert-butyl-2-methoxyphenyl)methyl]amino}-5-
phenylpyrrolidine-2-carboxylic acid;

(2S,3S,4S,5S)-3-tert-butyl-4-{[(5-tert-butyl-2-methoxyphenyl)methyl]amino}-1-(1-ethyl-4-oxo-1,4-dihydropyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(4-methyl-4H-furo[3,2-b]
pyrrole-5-carbonyl)-5-phenylpyrrolidine-2-carboxylic
acid;

(2S,3S,4S,5S)-3-tert-butyl-4-{[(5-tert-butyl-2-methoxyphenyl)methyl]amino}-1-[2-(4-chloro-1H-pyrazol-1-
yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2R*,3R*)-3-(propan-2-yl)oxolane-2-carbonyl]pyrrolidine-2-carboxylic
acid;

(2S,3S,4S,5S)-3-tert-butyl-4-({[2-methoxy-5-(trifluoromethyl)phenyl]methyl}amino)-5-phenyl-1-[(2R*,
3R*)-3-(propan-2-yl)oxolane-2-carbonyl]pyrrolidine-
2-carboxylic acid;

(2S,3S,4S,5S)-3-tert-butyl-4-({[2-methoxy-5-(trifluoromethyl)phenyl]methyl}amino)-5-phenyl-1-[(2S*,
3S*)-3-(propan-2-yl)oxolane-2-carbonyl]pyrrolidine-
2-carboxylic acid;

(2S,3S,4S,5S)-3-tert-butyl-4-{[(5-tert-butyl-2-methoxyphenyl)methyl]amino}-1-[(3aR*,6aS*)-hexahydro-
1H-cyclopenta[c]furan-1-carbonyl]-5-phenylpyrrolidine-2-carboxylic acid;

(2S,3S,4S,5S)-3-tert-butyl-1-[(3aR*,6aS*)-hexahydro-
1H-cyclopenta[c]furan-1-carbonyl]-4-({[2-methoxy-5-
(trifluoromethyl)phenyl]methyl}amino)-5-phenylpyrrolidine-2-carboxylic acid;

(2S,3S,4S,5S)-3-tert-butyl-1-(cyclohexanecarbonyl)-5-
(4-fluorophenyl)-4-({[2-methoxy-5-(propan-2-yl)phenyl]methyl}amino)pyrrolidine-2-carboxylic acid;

(2S,3S,4S,5S)-3-tert-butyl-1-(cyclohexanecarbonyl)-5-
(2-fluorophenyl)-4-({[2-methoxy-5-(trifluoromethyl)
pyridin-3-yl]methyl}amino)pyrrolidine-2-carboxylic
acid;

(2S,3S,4S,5S)-3-tert-butyl-1-(cyclohexanecarbonyl)-5-
(2-fluorophenyl)-4-({[2-methoxy-5-(propan-2-yl)phenyl]methyl}amino)pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(4-
fluorophenyl)pyrrolidine-2-carboxylic acid;

(2S,3S,4S,5S)-3-tert-butyl-1-(cyclohexanecarbonyl)-4-({[2-methoxy-5-(2-methoxypropan-2-yl)pyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(pyrimidin-5-yl)phenyl]methyl}amino)-5-phenylpyrrolidine-2-carboxylic acid;

(2S,3S,4S,5S)-4-{[(5-cyclobutyl-2-methoxypyridin-3-yl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclopentyl-2-methoxypyridin-3-yl)methyl]amino}-3-(2-methoxypropan-2-yl)-5-phenylpyrrolidine-2-carboxylic acid;

(2S,3S,4S,5S)-4-({[5-(bicyclo[2.2.1]heptan-2-yl)-2-methoxyphenyl]methyl}amino)-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-({[5-(cyclohexylmethyl)-2-methoxyphenyl]methyl}amino)-3-(2-methoxypropan-2-yl)-5-phenylpyrrolidine-2-carboxylic acid;

(2S,3S,4S,5S)-3-tert-butyl-4-{[(5-tert-butyl-2-methoxyphenyl)methyl]amino}-1-[(cyclopentyloxy)carbonyl]-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(trifluoromethyl)pyridin-3-yl]methyl}amino)pyrrolidine-2-carboxylic acid;

(2S,3S,4S,5S)-3-tert-butyl-1-(cyclohexanecarbonyl)-4-({[2-methoxy-5-(pyrrolidin-1-yl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(piperidin-1-yl)phenyl]methyl}amino)-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(pyridazin-4-yl)phenyl]methyl}amino)-5-phenylpyrrolidine-2-carboxylic acid;

(2S,3S,4S,5S)-3-tert-butyl-1-(cyclohexanecarbonyl)-4-{[(2'-fluoro-4-methoxy[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[5-(2,4-dimethyl-1,3-thiazol-5-yl)-2-methoxyphenyl]methyl}amino)-5-phenylpyrrolidine-2-carboxylic acid;

(2S,3S,4S,5S)-3-tert-butyl-4-{[(2'-cyano-4-methoxy[1,1'-biphenyl]-3-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[5-(3,6-dihydro-2H-pyran-4-yl)-2-methoxyphenyl]methyl}amino)-5-phenylpyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-(4-fluorophenyl)pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-1-(cyclohexanecarbonyl)-4-{[(5-cyclopentyl-2-methoxypyridin-3-yl)methyl]amino}-5-[2-(dimethylamino)pyridin-3-yl]pyrrolidine-2-carboxylic acid;

(2S,3S,4S,5S)-4-({[5-(bicyclo[2.2.1]heptan-2-yl)-2-methoxypyridin-3-yl]methyl}amino)-3-tert-butyl-1-(cyclohexanecarbonyl)-5-[2-(dimethylamino)pyridin-3-yl]pyrrolidine-2-carboxylic acid;

(2S,3S,4S,5S)-4-{[(6-bromo-3-methoxypyridin-2-yl)methyl]amino}-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-1-(cyclohexanecarbonyl)-4-({[2-methoxy-5-(trifluoromethyl)phenyl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-phenoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-[1-(methanesulfonyl)piperidine-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(trans)-2-(pyridin-3-yl)cyclopropane-1-carbonyl]pyrrolidine-2-carboxylic acid;

(2S,3S,4S,5S)-3-tert-butyl-1-(cyclohexanecarbonyl)-4-({[5-(2-fluorophenyl)-2-methoxypyridin-3-yl]methyl}amino)-5-phenylpyrrolidine-2-carboxylic acid;

(2S,3S,4S,5S)-3-tert-butyl-4-[({2-methoxy-5-[1-(trifluoromethyl)cyclopropyl]phenyl}methyl)amino]-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-(pyrazolo[1,5-a]pyridine-3-carbonyl)pyrrolidine-2-carboxylic acid;

(2S,3S,4S,5S)-3-tert-butyl-4-{[(5-tert-butyl-2-methoxyphenyl)methyl]amino}-1-[5-ethyl-1-(6-methoxypyridazin-3-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-tert-butyl-5-(propan-2-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[1-(2-fluorophenyl)-3,5-dimethyl-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclobutyl)acetyl]-5-phenylpyrrolidine-2-carboxylic acid;

(2S,3S,4S,5S)-1-[2-(azetidine-1-carbonyl)cyclohexane-1-carbonyl]-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(prop-2-en-1-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(cis-4-ethyl-4-hydroxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(propan-2-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(phenoxycarbonyl)-5-phenylpyrrolidine-2-carboxylic acid;

(2S,3S,4S,5S)-3-tert-butyl-4-{[(5-tert-butyl-2-methoxyphenyl)methyl]amino}-1-{[(2-chlorophenyl)methoxy]carbonyl}-5-phenylpyrrolidine-2-carboxylic acid;

(2S,3S,4S,5S)-3-tert-butyl-4-({[5-(1-cyanocyclobutyl)-2-methoxyphenyl]methyl}amino)-1-(cyclohexanecarbonyl)-5-phenylpyrrolidine-2-carboxylic acid;

(2S,3S,4S,5S)-3-tert-butyl-4-[(4-chloro-2,3-dihydro-1H-inden-2-yl)amino]-1-(cyclohexanecarbonyl)-5-phenylpyrrolidine-2-carboxylic acid;

(2S,3S,4S,5S)-3-tert-butyl-4-[(5-chloro-2,3-dihydro-1H-inden-2-yl)amino]-1-(cyclohexanecarbonyl)-5-phenylpyrrolidine-2-carboxylic acid;

(2S,3S,4S,5S)-3-tert-butyl-4-[(5-chloro-2, 3-dihydro-1H-inden-1-yl)amino]-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-(3,4-difluorophenyl)-2-methoxyacetyl]-5-phenylpyrrolidine-2-carboxylic acid;

(2S,3S,4S,5S)-3-tert-butyl-4-{[(5-tert-butyl-2-methoxyphenyl)methyl]amino}-1-[cyclohexyl(methoxy)acetyl]-5-phenylpyrrolidine-2-carboxylic acid;

(2S,3S,4S,5S)-1-(bicyclo[3.1.0]hexane-6-carbonyl)-3-tert-butyl-4-({[2-methoxy-5-(trifluoromethyl)phenyl]methyl}amino)-5-phenylpyrrolidine-2-carboxylic acid;

(2S,3S,4S,5S)-1-(bicyclo[3.1.0]hexane-3-carbonyl)-3-tert-butyl-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)phenyl]methyl}amino)-5-phenyl-1-[3-(trifluoromethyl)cyclopentane-1-carbonyl]pyrrolidine-2-carboxylic acid;

(2S,3S,4S,5S)-3-tert-butyl-1-(5,5-dimethyloxolane-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1-benzofuran-2-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(2R)-2,3-dihydro-1,4-benzodioxine-2-carbonyl]-5-phenylpyrrolidine-2-carboxylic acid;

(2S,3S,4S,5S)-3-tert-butyl-4-{[(2-cyclobutyl-5-methoxypyridin-4-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2-cyclopentyl-5-methoxypyridin-4-yl)methyl]amino}-5-phenylpyrrolidine-2-carboxylic acid;

(2S,3S,4S,5S)-3-tert-butyl-1-(cyclohexanecarbonyl)-4-[({3-methoxy-6-[1-(trifluoromethyl)cyclopropyl]pyridin-2-yl}methyl)amino]-5-phenylpyrrolidine-2-carboxylic acid;

(2S,3S,4S,5S)-3-tert-butyl-1-(cyclohexanecarbonyl)-4-({[2-methoxy-5-(trimethylsilyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(8-oxabicyclo[3.2.1]octane-3-carbonyl)-5-phenylpyrrolidine-2-carboxylic acid;

(2R,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid;

(2S,3S,4S,5S)-3-(2-methoxypropan-2-yl)-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-[(2S*)-2,3-dihydro-1-benzofuran-2-carbonyl]-5-[2-(dimethylamino)pyridin-3-yl]-4-[({2-methoxy-5-[1-(trifluoromethyl)cyclopropyl]phenyl}methyl)amino]pyrrolidine-2-carboxylic acid;

(2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-[(2S)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-(oxane-2-carbonyl)-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-phenyl-1-[(2R*,3R*)-3-phenyloxolne-2-carbonyl]pyrrolidine-2-carboxyic acid;

(2S,3S,4S,5S)-3-tert-butyl-4-{[(5-tert-butyl-2-methoxyphenyl)methyl]amino}-5-phenyl-1-[(2S*,3S*)-3-phenyloxolane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-(3,3-difluorocyclohexane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2S*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-5-phenyl-1-[(2R)-2-phenylpropanoyl]pyrrolidine-2-carboxylic acid;

(2S,3S,4S,5S)-3-tert-butyl-1-(3,3-difluorocyclohexane-1-carbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-1-(cyclohexanecarbonyl)-4-[({2-methoxy-5-[(trifluoromethyl)sulfanyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(propan-2-yl)phenyl]pyrrolidine-2-carboxylic acid;

(2S,3S,4S,5S)-1-(bicyclo[3.1.0]hexane-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-[2-(propan-2-yl)phenyl]pyrrolidine-2-carboxylic acid;

(2S,3S,4S,5S)-3-tert-butyl-1-(cyclohexanecarbonyl)-4-{[(2-methoxynaphthalen-1-yl)methyl]amino}-5-phenylpyrrolidine-2-carboxylic acid;

(2S,3S,4S,5S)-3-tert-butyl-1-[(1R)-3,3-difluorocyclohexane-1-carbonyl]-4-({[2-methoxy-5-(trimethylsilyl)pyridin-3-yl]methyl}amino)-5-phenylpyrrolidine-2-carboxylic acid;

(2S,3S,4S,5S)-3-tert-butyl-1-[(1R)-3,3-difluorocyclohexane-1-carbonyl]-4-{[(6-methoxy-2,3-dihydro-1H-inden-5-yl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(3S*)-1-methyl-2-oxopiperidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1$\lambda^6$-thiolane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-oxane-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-{(2S*)-2-[(2S*)-oxan-2-yl]propanoyl}-5-phenylpyrrolidine-2-carboxylic acid;

(2S,3S,4S,5S)-3-tert-butyl-4-{[(5-tert-butyl-2-methoxyphenyl)methyl]amino}-1-{(2R*)-2-[(2R*)-oxan-2-yl]propanoyl}-5-phenylpyrrolidine-2-carboxylic acid;

(2S,3S,4S,5S)-3-tert-butyl-4-{[(6-tert-butyl-2-methoxypyridin-3-yl)methyl]amino}-1-(3-methoxycyclohexane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1R*,3S*)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(2,3-dihydro-1,4-benzodioxine-6-carbonyl)-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[4-(cyclohexyloxy)benzoyl]-5-[2-(dimethylamino)pyridin-3-yl]pyrrolidine-2-carboxylic acid;

(2S,3S,4S,5S)-1-(bicyclo[3.1.0]hexane-6-carbonyl)-3-tert-butyl-4-{[(5-tert-butyl-2-methoxyphenyl)methyl]amino}-5-[2-(dimethylamino)pyridin-3-yl]pyrrolidine-2-carboxylic acid;

(2S,3S,4S,5S)-3-(bicyclo[1.1.1]pentan-1-yl)-4-{[(5-tert-butyl-2-methoxyphenyl)methyl]amino}-1-(cyclohexanecarbonyl)-5-phenylpyrrolidine-2-carboxylic acid;

(2R,3R,4R,5R)-3-tert-butyl-4-{[(5-tert-butyl-2-methoxyphenyl)methyl]amino}-1-(cyclohexanecarbonyl)-N-(methane sulfonyl)-5-phenylpyrrolidine-2-carboxamide;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-[(2S*)-2,3-dihydro-1,4-benzodioxine-carbonyl]-5-phenylpyrrolidine-2-carboxylic acid;

(2S,3S,4S,5S)-3-tert-butyl-4-{[(5-cyclobutyl-2-methoxypyridin-3-yl)methyl]amino}-1-(3,4-dihydro-1H-2-benzopyran-3-carbonyl)-5-phenylpyrrolidine-2-carboxylic acid;

(2S,3S,4S,5S)-3-tert-butyl-4-{[(2-tert-butyl-4-methoxypyrimidin-5-yl)methyl]amino}-1-(cyclohexanecarbonyl)-5-phenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-phenyl-1-{[(propan-2-yl)oxy]carbonyl}pyrrolidine-2-carboxylic acid;

rac-(2S,3S,4S,5S)-3-tert-butyl-4-{[(5-tert-butyl-2-methoxyphenyl)methyl]amino}-1-(cyclohexanecarbonyl)-2-methyl-5-phenylpyrrolidine-2-carboxylic acid;

(2S,3S,4S,5S)-3-tert-butyl-1-(cyclohexanecarbonyl)-4-({[5-methoxy-2-(pyrrolidin-1-yl)pyridin-4-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(1,1,1-trifluoro-2-methylpropan-2-yl)phenyl]methyl}amino)-5-phenylpyrrolidine-2-carboxylic acid;

(2S,3S,4S,5S)-3-tert-butyl-4-{[(5-cyclobutyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(2S)-oxane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-1-[(2R*)-oxane-2-carbonyl]-5-[2-(propan-2-yl)phenyl]pyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)oxolane-3-carbonyl]pyrrolidine-2-carboxylic acid;

(2S,3S,4S,5S)-3-tert-butyl-4-({[4-(2-chlorophenyl)oxan-4-yl]methyl}amino)-1-(cyclohexanecarbonyl)-5-phenylpyrrolidine-2-carboxylic acid;

(2S,3S,4S,5S)-4-{[(5-tert-butyl-2-methoxyphenyl)methyl]amino}-5-[2-(dimethylamino)pyridin-3-yl]-3-(2-methoxypropan-2-yl)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-{[(propan-2-yl)oxy]carbonyl}pyrrolidine-2-carboxylic acid;

(2S,3S,4S,5S)-1-(bicyclo[3.1.0]hexane-6-carbonyl)-3-tert-butyl-5-[2-(dimethylamino)pyridin-3-yl]-4-{[6-methyl-4-(trifluoromethyl)pyridin-2-yl]amino}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(1S*,2S*,3S*,4R*)-3-(trifluoromethyl)-7-oxabicyclo[2.2.1]heptane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-(2- methoxypyridin-3-yl)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(difluoromethoxy)pyridin-3-yl]pyrrolidine-2-carboxylic acid;

(2S,3S,4S,5S)-3-(bicyclo[1.1.1]pentan-1-yl)-4l-{[(5-tert-butyl-2-methoxyphenyl)methyl]amino}-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(difluoromethoxy)pyridin-3-yl]pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-[2-(difluoromethoxy)phenyl]pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(6-tert-butyl-2-methoxypyridin-3-yl)methyl]amino}-5-(2-fluorophenyl)-1-[(2S)-oxane-2-carbonyl]pyrrolidine-2-carboxylic acid;

(2S,3S,4S,5S)-1-(tert-butoxycarbonyl)-3-tert-butyl-4-{[(5-tert-butyl-2-methoxyphenyl)methyl]amino}-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R)-2-phenylpropanoyl]pyrrolidine-2-carboxylic acid;

(2S,3S,4S,5S)-3-tert-butyl-4-{[(6-tert-butyl-2-methoxypyridin-3-yl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)pyridin-3-yl]-1-[(2S)-oxane-2-carbonyl]pyrrolidine-2-carboxylic acid;

(2S,3S,4S,5S)-3-(bicyclo[1.1.1]pentan-1-yl)-4-{[(5-cyclobutyl-2-methoxypyridin-3-yl)methyl]amino}-5-phenyl-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-(2-methoxypyridin-3-yl)pyrrolidine-2-carboxylic acid;

(2S,3S,4S,5S)-3-tert-butyl-1-(cyclohexanecarbonyl)-4-({[2-methoxy-5-(1-methylcyclobutyl)phenyl]methyl}amino)-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2R)-2-phenylpropanoyl]pyrrolidine-2-carboxylic acid;

(2S,3S,4S,5S)-3-tert-butyl-5-(2-methoxypyridin-3-yl)-4-({[2-methoxy-5-(trifluoromethyl)pyridin-3-yl]methyl}amino)-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[(1S*,2R*,4R*)-7-oxabicyclo[2.2.1]heptane-2-carbonyl]-5-phenylpyrrolidine-2-carboxylic acid;

(2S,3S,4S,5S)-3-tert-butyl-4-{[(6-cyclobutyl-2-methoxypyridin-3-yl)methyl]amino}-1-(cyclohexanecarbonyl)-5-phenylpyrrolidine-2-carboxylic acid;

(2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-{[(oxetan-3-yl)oxy]carbonyl}-5-phenylpyrrolidine-2-carboxylic acid;

(2S,3S,4S,5S)-3-tert-butyl-5-[2-(dimethylamino)pyridin-3-yl]-4-({[2-methoxy-5-(pentafluoro-$\lambda^6$-sulfanyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-phenyl-1-[(3R)-1-{[(propan-2-yl)oxy]carbonyl}piperidine-3-carbonyl]pyrrolidine-2-carboxylic acid;

(2S,3S,4S,5S)-3-tert-butyl-4-{[(6-tert-butyl-2-chloropyridin-3-yl)methyl]amino}-1-[(1R)-3,3-difluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-(1-phenylcyclopropane-1-carbonyl)pyrrolidine-2-carboxylic acid;

(2S,3S,4S,5S)-3-tert-butyl-4-{[(6-methoxy-2,3-dihydro-1H-inden-5-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(2-methoxyquinolin-3-yl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(3-methoxy-5,5,8,8-tetramethyl-5,6,7,8-tetrahydronaphthalen-2-yl)methyl]amino}-1-{[(propan-2-yl)oxy]carbonyl}pyrrolidine-2-carboxylic acid;

(2S,3S,4S,5S)-3-tert-butyl-5-(3-chlorophenyl)-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-2-phenylbutanoyl]pyrrolidine-2-carboxylic acid;

(2S,3S,4S,5S)-3-tert-butyl-4-{[(5-tert-butyl-2-methoxyphenyl)methyl]amino}-1-[(7R)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid;

(2S,3S,4S,5S)-3-tert-butyl-1-[(1R,3R)-3-methoxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-[(1R*)-3,3-difluorocyclohexane-1-carbonyl]-5-(2-methoxypyridin-3-yl)-4-({[2-methoxy-5-(trifluoromethyl)phenyl]methyl}amino)pyrrolidine-2-carboxylic acid;

(2S,3S,4S,5S)-3-tert-butyl-1-[(1R*)-3,3-difluorocyclohexane-1-carbonyl]-5-(2-methoxypyridin-3-yl)-4-({[2-methoxy-4-(trifluoromethyl)phenyl]methyl}amino)pyrrolidine-2-carboxylic acid;

(2S,3S,4S,5S)-3-tert-butyl-1-(cyclohexanecarbonyl)-4-({[2-methoxy-5-(trifluoromethyl)pyridin-3-yl]methyl}amino)-5-(2-methylphenyl)pyrrolidine-2-carboxylic acid;

(2S,3S,4S,5S)-3-tert-butyl-4-{[(5-cyclobutyl-2-methoxypyridin-3-yl)methyl]amino}-5-phenyl-1-[(1R*,3S*)-3-(trifluoromethyl)cyclohexane-1-carbonyl]pyrrolidine-2-carboxylic acid;

(2S,3S,4S,5S)-3-tert-butyl-4-{[(5-cyclobutyl-2-methoxypyridin-3-yl)methyl]amino}-5-phenyl-1-[(1S*,3R*)-3-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-(2-methylphenyl)-1-[(2S)-oxolane-2-carbonyl]pyrrolidine-2-carboxylic acid;

(2S,3S,4S,5S)-3-tert-butyl-4-({[2-methoxy-5-(trifluoromethyl)pyridin-3-yl]methyl}amino)-5-(2-methylphenyl)-1-[(2S)-oxolane-2-carbonyl]pyrrolidine-2-carboxylic acid;

(2S,3S,4S,5S)-3-tert-butyl-5-phenyl-4-[(2-phenylethyl)amino]-1-1-{[(propan-2-yl)oxy]carbonyl}pyrrolidine-2-carboxylic acid;

(2S,3S,4S,5S)-3-tert-butyl-4-[(2-methyl-2-phenylpropyl)amino]-5-phenyl-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-[(2R)-oxane-2-carbonyl]pyrrolidine-2-carboxylic acid;

(2S,3S,4S,5S)-3-tert-butyl-4-({[4-(2-methoxyphenyl)oxan-4-yl]methyl}amino)-5-phenyl-1-{[propan-2-yl)oxy]carbonyl}pyrrolidine-2-carboxylic acid;

(2S,3S,4S,5S)-3-tert-butyl-5-phenyl-1-{[(propan-2-yl)oxy]carbonyl}-4-[({1-[4-(trifluoromethyl)phenyl]piperidin-3-yl}methyl)amino]pyrrolidine-2-carboxylic acid;

(2S,3S,4S,5S)-3-tert-butyl-5-(2-cyclopropylpyridin-3-yl)-4-({[2-methoxy-5-(trifluoromethyl)phenyl]methyl}amino)-1-[(2S)-oxolane-2-carbonyl]pyrrolidine-2-carboxylic acid;

(2S,3S,4S,5S)-3-tert-butyl-4-({[2-methoxy-5-(trifluoromethyl)pyridin-3-yl]methyl}amino)-1-[rel-(1R,2S,4S)-7-oxabicyclo[2.2.1]heptane-2-carbonyl]-5-[2-(propan-2-yl)phenyl]pyrrolidine-2-carboxylic acid;

(2S,3S,4S,5S)-3-tert-butyl-1-(cyclopropanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-1-(bicyclo[1.1.1]pentane-1-carbonyl)-3-tert-butyl-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-1-(cyclobutanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-5-[2-(azetidin-1-yl)pyridin-3-yl]-4-{[(5-bromo-2-ethoxyphenyl)methyl]amino}-3-tert-butyl-1-{[(propan-2-yl)oxy]carbonyl}pyrrolidine-2-carboxylic acid;

(2S,3S,4S,5S)-5-[2-(azetidin-1-yl)pyridin-3-yl]-3-tert-butyl-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-5-(2-cyclopropylphenyl)-4-({3-[(2-methoxypyridin-3-yl)amino]cyclobutyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-(cyclobutanecarbonyl)-5-[2-(trifluoromethyl)phenyl]pyrrolidine-2-carboxylic acid;

(2S,3S,4S,5S)-3-tert-butyl-1-(cyclobutanecarbonyl)-4-{[(5-cyclobutyl-2-methoxypyridin-3-yl)methyl]amino}-5-[2-(trifluoromethyl)phenyl]pyrrolidine-2-carboxylic acid;

(2S,3S,4S,5S)-3-tert-butyl-1-(cyclobutanecarbonyl)-4-({[2-methoxy-5-(1-methylcyclobutyl)phenyl]methyl}amino)-5-[2-(trifluoromethyl)phenyl]pyrrolidine-2-carboxylic acid;

(2S,3S,4S,5S)-3-tert-butyl-1-(cyclobutanecarbonyl)-4-({[2-methoxy-5-(trifluoromethyl)pyridin-3-yl]methyl}amino)-5-[2-(trifluoromethyl)phenyl]pyrrolidine-2-carboxylic acid;

(2S,3S,4S,5S)-3-tert-butyl-4-{[(5-cyclobutyl-2-methoxypyridin-3-yl)methyl]amino}-5-[2-(dimethylamino)pyridin-3-yl]-1-[(2S)-oxolane-2-carbonyl]pyrrolidine-2-carboxylic acid;

(2S,3S,4S,5S)-3-tert-butyl-5-(2-chlorophenyl)-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2S)-oxolane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S)-oxolane-2-carbonyl]pyrrolidine-2-carboxylic acid;

(2S,3S,4S,5S)-3-tert-butyl-4-{[(5-tert-butyl-2-hydroxyphenyl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-[(2S)-oxolane-2-carbonyl]-5-[2-(trifluoromethyl)phenyl]pyrrolidine-2-carboxylic acid;

(2S,3S,4S,5S)-4-{[(5-bromo-2-methoxypyridin-3-yl)methyl]amino}-3-tert-butyl-5-(2-methylphenyl)-1-[(2S)-oxane-2-carbonyl]pyrrolidine-2-carboxylic acid;

(2S,3S,4S,5S)-5-(2-bromophenyl)-3-tert-butyl-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-5-(2-bromophenyl)-3-tert-butyl-4-({[2-methoxy-4-(trifluoromethyl)phenyl]methyl}amino)-1-[(2S)-oxane-2-carbonyl]pyrrolidine-2-carboxylic acid;

(2S,3S,4S,5S)-5-(2-bromophenyl)-3-tert-butyl-4-({[2-methoxy-5-(trifluoromethyl)phenyl]methyl}amino)-1-[(2S)-oxane-2-carbonyl]pyrrolidine-2-carboxylic acid;

(2S,3S,4S,5S)-5-(2-bromophenyl)-3-tert-butyl-4-{[(5-cyclobutyl-2-methoxypyridin-3-yl)methyl]amino}-1-[(2S)-oxane-2-carbonyl]pyrrolidine-2-carboxylic acid;

(2S,3S,4S,5S)-5-(2-bromophenyl)-3-tert-butyl-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-5-(2-bromophenyl)-3-tert-butyl-4-{[(5-cyclopropyl-2-methoxypyridin-3-yl)methyl]amino}-1-[(2S)-oxolane-2-carbonyl]pyrrolidine-2-carboxylic acid;

(2S,3S,4S,5S)-5-(2-bromophenyl)-3-tert-butyl-4-{[(5-tert-butyl-2-methoxyphenyl)methyl]amino}-1-[(2S)-oxolane-2-carbonyl]pyrrolidine-2-carboxylic acid;

(2S,3S,4S,5S)-5-(2-bromophenyl)-3-tert-butyl-4-({[2-methoxy-5-(1-methylcyclobutyl)phenyl]methyl}amino)-1-[(2S)-oxolane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-cyclopropylphenyl)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2-ethylphenyl)-1-[(2S)-oxane-2-carbonyl]pyrrolidine-2-carboxylic acid;

(2S,3S,4S,5S)-3-tert-butyl-5-(2,3-dihydro-1-benzofuran-7-yl)-4-({[2-methoxy-5-(trifluoromethyl)pyridin-3-yl]methyl}amino)-1-[(2S)-oxane-2-carbonyl]pyrrolidine-2-carboxylic acid;

(2S,3S,4S,5S)-3-tert-butyl-5-(2,3-dihydro-1-benzofuran-7-yl)-4-({[2-methoxy-5-(trifluoromethyl)phenyl]methyl}amino)-1-[(2S)-oxane-2-carbonyl]pyrrolidine-2-carboxylic acid;

(2S,3S,4S,5S)-3-tert-butyl-5-(2,3-dihydro-1-benzofuran-7-yl)-4-({[2-methoxy-4-(trifluoromethyl)phenyl]methyl}amino)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-(2,3-dihydro-1-benzofuran-7-yl)-1-[(2S)-oxane-2-carbonyl]pyrrolidine-2-carboxylic acid;

(2S,3S,4S,5S)-3-tert-butyl-5-(2,3-dihydro-1-benzofuran-7-yl)-4-{[(3-methoxy-5,6,7,8-tetrahydronaphthalen-2-yl)methyl]amino}-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-(6-methoxypyridine-2-sulfonyl)-5-[2-(propan-2-yl)phenyl]pyrrolidine-2-carboxylic acid;

(2S,3S,4S,5S)-3-tert-butyl-4-({[2-methoxy-5-(1-methylcyclobutyl)phenyl]methyl}amino)-1-[(2S)-oxane-2-carbonyl]-5-[2-(propan-2-yl)phenyl]pyrrolidine-2-carboxylic acid;

(2S,3S,4S,5S)-3-tert-butyl-4-{[(2, 2-dimethyl-2, 3-dihydro-1-benzofuran-7-yl)methyl]amino}-1-[(2S)-oxolane-2-carbonyl]-5-[2-(propan-2-yl)phenyl]pyrrolidine-2-carboxylic acid;

(2S,3S,4S,5S)-3-tert-butyl-4-{[(2,2-dimethyl-2,3-dihydro-1-benzofuran-7-yl)methyl]amino}-1-[(2S)-oxane-2-carbonyl]-5-[2-(propan-2-yl)phenyl]pyrrolidine-2-carboxylic acid;

(2S,3S,4S,5S)-3-tert-butyl-4-{[(5-cyclobutyl-2-methoxypyridin-3-yl)methyl]amino}-1-(cyclohexanecarbonyl)-5-(2,2-dimethyl-2, 3-dihydro-1-benzofuran-7-yl)pyrrolidine-2-carboxylic acid;

(2S,3S,4S,5S)-3-tert-butyl-4-(4-chloro-7-methoxy-1,3-dihydro-2H-isoindol-2-yl)-1-[(2S)-oxane-2-carbonyl]-5-[2-(propan-2-yl)phenyl]pyrrolidine-2-carboxylic acid;

(2S,3S,4S,5S)-3-tert-butyl-4-({2-[2-methoxy-5-(trifluoromethyl)phenoxy]ethyl}amino)-1-{[(propan-2-yl)oxy]carbonyl}-5-{2-[(propan-2-yl)oxy]pyridin-3-yl}pyrrolidine-2-carboxylic acid;

(2S,3S,4S,5)-3-tert-butyl-4-{[(5-tert-butyl-2-methoxyphenyl)methyl]amino}-1-(cyclohexanecarbonyl)-5-(2-hydroxyphenyl)pyrrolidine-2-carboxylic acid;

rac-(2R,3R,4R,5R)-3-tert-butyl-4-[(5-chloropyridin-2-yl)amino]-1-(cyclohexanecarbonyl)-5-phenylpyrrolidine-2-carboxylic acid;

rac-(2R,3R,4R,5R)-3-tert-butyl-4-{[6-chloro-4-(trifluoromethyl)pyridin-2-yl]amino}-1-(cyclohexanecarbonyl)-5-phenylpyrrolidine-2-carboxylic acid;

rac-(2R,3R,4R,5R)-3-tert-butyl-4-{[(3-chloro-2,4-dimethoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-5-phenyl-4-[({2-[(propan-2-yl)oxy]phenyl}methyl)amino]pyrrolidine-2-carboxylic acid;

rac-(2R,3R,4R,5R)-3-tert-butyl-1-(cyclohexanecarbonyl)-4-({[2-(2-methylpropoxy)phenyl]methyl}amino)-5-phenylpyrrolidine-2-carboxylic acid;

rac-(2R,3R,4R,5R)-3-tert-butyl-1-(cyclohexanecarbonyl)-4-{[(2-methoxypyridin-3-yl)methyl]amino}-5-phenylpyrrolidine-2-carboxylic acid;

rac-(2R,3R,4R,5R)-3-tert-butyl-4-{[(3-chloro-2-methoxyphenyl)methyl]amino}-1-(cyclohexanecarbonyl)-5-phenylpyrrolidine-2-carboxylic acid;

rac-(2R,3R,4R,5R)-3-tert-butyl-4-({[5-chloro-2-(difluoromethoxy)phenyl]methyl}amino)-1-(cyclohexanecarbonyl)-5-phenylpyrrolidine-2-carboxylic acid;

rac-(2R,3R,4R,5R)-3-tert-butyl-4-{[(5-chloro-2-ethoxyphenyl)methyl]amino}-1-(cyclohexanecarbonyl)-5-phenylpyrrolidine-2-carboxylic acid;

rac-(2R,3R,4R,5R)-3-tert-butyl-4-{[(2-chloro-6-methoxyphenyl)methyl]amino}-1-(cyclohexanecarbonyl)-5-phenylpyrrolidine-2-carboxylic acid;

(2R,3R,4R,5R)-1-[di(propan-2-yl)carbamoyl]-3-methyl-4-{[6-methyl-4-(trifluoromethyl)pyridin-2-yl]amino}-5-phenylpyrrolidine-2-carboxylic acid;

rac-(2R,3R,4R,5R)-4-{[(5-chloro-2-methoxyphenyl)methyl]amino}-1-(cyclohexanecarbonyl)-3-cyclopropyl-5-phenylpyrrolidine-2-carboxylic acid;

rac-(2R,3R,4R,5R)-3-tert-butyl-4-{[6-methyl-4-(trifluoromethyl)pyridin-2-yl]amino}-5-phenyl-1-{[(propan-2-yl)oxy]carbonyl}pyrrolidine-2-carboxylic acid;

rac-(2R,3R,4R,5R)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;

rac-(2R,3R,4R,5R)-3-tert-butyl-4-({[2-chloro-5-(trifluoromethyl)pyridin-3-yl]methyl}amino)-1-(cyclohexanecarbonyl)-5-phenylpyrrolidine-2-carboxylic acid;

rac-(2R,3R,4R,5R)-3-tert-butyl-4-({[2-chloro-5-(trifluoromethyl)pyridin-3-yl]methyl}amino)-1-(cyclohexanecarbonyl)-5-(2-methoxyphenyl)pyrrolidine-2-carboxylic acid;

rac-(2R,3R,4R,5R)-3-tert-butyl-1-(cyclohexanecarbonyl)-5-(2-methoxyphenyl)-4-({[2-methoxy-5-(trifluoromethyl)phenyl]methyl}amino)pyrrolidine-2-carboxylic acid;

rac-(2R,3R,4R,5R)-3-tert-butyl-1-(cyclohexanecarbonyl)-4-({[2-(difluoromethoxy)-4-methoxyphenyl]methyl}amino)-5-phenylpyrrolidine-2-carboxylic acid;

rac-(2R,3R,4R,5S)-3-tert-butyl-4-{[(5-chloro-2-methoxyphenyl)methyl]amino}-1-(cyclohexanecarbonyl)-5-(6-methoxypyridin-2-yl)pyrrolidine-2-carboxylic acid;

rac-(2R,3R,4R,5R)-3-tert-butyl-5-[2-(dimethylamino)phenyl]-4-({[2-methoxy-5-(trifluoromethyl)phenyl]methyl}amino)-1-[oxane-2-carbonyl]pyrrolidine-2-carboxylic acid;

rac-(2R,3R,4R,5R)-3-tert-butyl-5-[2-(dimethylamino)
   phenyl]-4-({[2-methoxy-5-(trifluoromethyl)phenyl]
   methyl}amino)-1-[oxane-3-carbonyl]pyrrolidine-2-
   carboxylic acid;
rac-(2R,3R,4R,5R)-3-tert-butyl-5-[2-(dimethylamino)
   phenyl]-4-({[2-methoxy-4-(trifluoromethyl)phenyl]
   methyl}amino)-1-[oxane-3-carbonyl]pyrrolidine-2-
   carboxylic acid;
rac-(2R,3R,4R,5R)-3-tert-butyl-4-{[(4-chloro-2-
   methoxyphenyl)methyl]amino}-5-[2-(dimethylamino)
   phenyl]-1-[oxane-3-carbonyl]pyrrolidine-2-carboxylic
   acid;
rac-(2R,3R,4R,5R)-3-tert-butyl-5-[2-(dimethylamino)
   phenyl]-1-[2,2-dimethyloxane-4-carbonyl]-4-({[2-
   methoxy-5-(trifluoromethyl)phenyl]methyl}amino)
   pyrrolidine-2-carboxylic acid;
rac-(2R,3R,4R,5R)-3-tert-butyl-4-{[(5-chloro-2-
   methoxyphenyl)methyl]amino}-5-[2-(dimethylamino)
   phenyl]-1-[2,2-dimethyloxane-4-carbonyl]pyrrolidine-
   2-carboxylic acid;
rac-(2R,3R,4R,5R)-3-tert-butyl-4-{[(4-chloro-2-
   methoxyphenyl)methyl]amino}-5-[2-(dimethylamino)
   phenyl]-1-[2,2-dimethyloxane-4-carbonyl]pyrrolidine-
   2-carboxylic acid;
rac-(2R,3R,4R,5R)-3-tert-butyl-1-[(3S)-1-(methoxycar-
   bonyl)piperidine-3-carbonyl]-4-{[6-methyl-4-(trifluo-
   romethyl)pyridin-2-yl]amino}-5-phenylpyrrolidine-2-
   carboxylic acid;
rac-(2R,3R,4R,5R)-3-tert-butyl-4-{[(5-chloro-2-
   methoxyphenyl)methyl]amino}-5-[2-(dimethylamino)
   pyridin-3-yl]-1-{[(propan-2-yl)oxy]
   carbonyl}pyrrolidine-2-carboxylic acid;
rac-(2R,3R,4R,5R)-3-tert-butyl-4-{[(4-chloro-2-
   methoxyphenyl)methyl]amino}-5-[2-(dimethylamino)
   pyridin-3-yl]-1-{[(propan-2-yl)oxy]
   carbonyl}pyrrolidine-2-carboxylic acid;
rac-(2R,3R,4R,5R)-3-tert-butyl-1-(cyclohexanecarbo-
   nyl)-4-{[(5-fluoro-2-methoxypyridin-3-yl)methyl]
   amino}-5-phenylpyrrolidine-2-carboxylic acid;
rac-(2R,3R,4R,5R)-3-tert-butyl-1-(cyclohexanecarbo-
   nyl)-5-phenyl-4-({[2-(trifluoromethyl)phenyl]
   methyl}amino)pyrrolidine-2-carboxylic acid;
rac-(2R,3R,4R,5R)-3-tert-butyl-4-({[2-methoxy-5-(trif-
   luoromethyl)phenyl]methyl}amino)-5-phenyl-1-(phe-
   nylacetyl)pyrrolidine-2-carboxylic acid;
rac-(2S,3S,4S,5S)-3-tert-butyl-5-[2-(dimethylamino)
   pyridin-3-yl]-1-[(2R)-2-methoxy-2-phenylacetyl]-4-
   ({[2-methoxy-5-(trifluoromethyl)phenyl]
   methyl}amino)pyrrolidine-2-carboxylic acid;
rac-(2R,3R,4R,5R)-3-tert-butyl-4-({[2-methoxy-5-(trif-
   luoromethyl)phenyl]methyl}amino)-1-[(2R,3R)-2-
   methyloxane-3-carbonyl]-5-phenylpyrrolidine-2-car-
   boxylic acid;
rac-(2R,3R,4R,5R)-3-tert-butyl-4-({[2-methoxy-5-(trif-
   luoromethyl)phenyl]methyl}amino)-1-[(2S,3S)-2-
   methyloxane-3-carbonyl]-5-phenylpyrrolidine-2-car-
   boxylic acid;
rac-(2R,3R,4R,5R)-3-(tert-butyl)-4-((2-methoxy-5-(trif-
   luoromethyl)benzyl)amino)-1-((1R,3R)-3-methoxycy-
   clohexanecarbonyl)-5-phenylpyrrolidine-2-carboxylic
   acid;
rac-(2R,3R,4R,5R)-3-(tert-butyl)-4-((2-methoxy-4-(trif-
   luoromethyl)benzyl)amino)-1-((1R,3R)-3-methoxycy-
   clohexanecarbonyl)-5-phenylpyrrolidine-2-carboxylic
   acid;

rac-(2R,3R,4R,5R)-3-(tert-butyl)-4-((4-chloro-2-
   methoxybenzyl)amino)-1-((1R,3R)-3-methoxycyclo-
   hexanecarbonyl)-5-phenylpyrrolidine-2-carboxylic
   acid;
rac-(2R,3R,4R,5R)-3-tert-butyl-4-{[(4-fluoro-2-
   methoxyphenyl)methyl]amino}-5-phenyl-1-{[propan-
   2-yl)oxy]carbonyl}pyrrolidine-2-carboxylic acid;
rac-(2R,3R,4R,5R)-3-tert-butyl-4-{[(2-methoxy-5-meth-
   ylphenyl)methyl]amino}-5-phenyl-1-{[(propan-2-yl)
   oxy]carbonyl}pyrrolidine-2-carboxylic acid;
rac-(2R,3R,4R,5R)-3-tert-butyl-4-({[2-methoxy-4-(trif-
   luoromethoxy)phenyl]methyl}amino)-5-phenyl-1-
   {[(propan-2-yl)oxy]carbonyl}pyrrolidine-2-carboxylic
   acid;
rac-(2R,3R,4R,5R)-3-tert-butyl-4-{[(5-fluoro-2-
   methoxyphenyl)methyl]amino}-5-phenyl-1-{[(propan-
   2-yl)oxy]carbonyl}pyrrolidine-2-carboxylic acid;
rac-(2R,3R,4R,5R)-3-tert-butyl-4-{[(5-tert-butyl-2-
   methoxyphenyl)methyl]amino}-5-phenyl-1-{[(propan-
   2-yl)oxy]carbonyl}pyrrolidine-2-carboxylic acid;
rac-(2R,3R,4R,5R)-3-tert-butyl-4-({[2-methoxy-5-(pro-
   pan-2-yl)phenyl]methyl}amino)-5-phenyl-1-{[(pro-
   pan-2-yl)oxy]carbonyl}pyrrolidine-2-carboxylic acid;
rac-(2R,3R,4R,5R)-3-tert-butyl-4-{[(4-chloro-2-
   methoxyphenyl)methyl]amino}-5-phenyl-1-{[(propan-
   2-yl)oxy]carbonyl}pyrrolidine-2-carboxylic acid;
rac-(2R,3R,4R,5R)-3-tert-butyl-4-{[(2-methoxyphenyl)
   methyl]amino}-5-phenyl-1-{[(propan-2-yl)oxy]
   carbonyl}pyrrolidine-2-carboxylic acid;
rac-(2S,3S,4S,5S)-3-tert-butyl-4-{[(4-chloro-2-methoxy-
   phenyl)methyl]amino}-5-[2-(dimethylamino)pyridin-
   3-yl]-1-[(2R)-2-methoxy-2-phenylacetyl]pyrrolidine-
   2-carboxylic acid;
rac-(2S,3S,4S,5S)-3-tert-butyl-5-[2-(dimethylamino)
   pyridin-3-yl]-1-[(2R)-2-methoxy-2-phenylacetyl]-4-
   ({[2-methoxy-4-(trifluoromethyl)phenyl]
   methyl}amino)pyrrolidine-2-carboxylic acid;
rac-(2R,3R,4R,5R)-3-tert-butyl-4-({[2-methoxy-4-(trif-
   luoromethyl)phenyl]methyl}amino)-1-((2S)-oxane-2-
   carbonyl)-5-phenylpyrrolidine-2-carboxylic acid;
rac-(2S,3S,4S,5S)-3-tert-butyl-1-(cyclohexanecarbonyl)-
   5-(2-methoxyphenyl)-4-({[2-methoxy-4-(trifluorom-
   ethyl)phenyl]methyl}amino)pyrrolidine-2-carboxylic
   acid;
rac-(2R,3R,4R,5R)-3-tert-butyl-1-(cyclohexanecarbo-
   nyl)-5-[2-(dimethylamino)pyridin-3-yl]-4-({[2-
   methoxy-4-(trifluoromethyl)phenyl]methyl}amino)
   pyrrolidine-2-carboxylic acid;
rac-(2R,3R,4R,5R)-3-tert-butyl-1-(cyclohexanecarbo-
   nyl)-5-[2-(dimethylamino)pyridin-3-yl]-4-({[2-
   methoxy-5-(trifluoromethyl)pyridin-3-yl]
   methyl}amino)pyrrolidine-2-carboxylic acid;
rac-(2S,3S,4S,5R)-3-tert-butyl-1-(cyclohexanecarbonyl)-
   4-{[6-methyl-4-(trifluoromethyl)pyridin-2-yl]amino}-
   5-(pyridin-2-yl)pyrrolidine-2-carboxylic acid;
(2S*,3S*,4S*,5S*)-3-tert-butyl-4-{[(4-chloro-2-
   methoxyphenyl)methyl]amino}-1-[(2R)-2-methoxy-2-
   phenylacetyl]-5-phenylpyrrolidine-2-carboxylic acid;
rac-(2R,3R,4R,5R)-3-tert-butyl-4-{[6-methyl-4-(trifluo-
   romethyl)pyridin-2-yl]amino}-5-phenyl-1-(pheny-
   lacetyl)pyrrolidine-2-carboxylic acid;
rac-(2R,3R,4R,5R)-3-tert-butyl-5-[2-(dimethylamino)
   phenyl]-4-({[2-methoxy-5-(trifluoromethyl)phenyl]
   methyl}amino)-1-{[(propan-2-yl)oxy]
   carbonyl}pyrrolidine-2-carboxylic acid;
rac-(2R,3R,4R,5R)-3-tert-butyl-5-[2-(dimethylamino)
   phenyl]-4-({[2-methoxy-4-(trifluoromethyl)phenyl]

methyl}amino)-1-{[(propan-2-yl)oxy]
carbonyl}pyrrolidine-2-carboxylic acid;
rac-(2R,3R,4R,5R)-3-tert-butyl-4-({[2-methoxy-4-(trifluoromethyl)phenyl]methyl}amino)-1-[(2S*)-2-phenoxypropanoyl]-5-phenylpyrrolidine-2-carboxylic acid;
rac-(2S,3S,4S,5S)-3-tert-butyl-4-({[2-methoxy-5-(trifluoromethyl)phenyl]methyl}amino)-1-(oxolane-2-carbonyl)-5-phenylpyrrolidine-2-carboxylic acid;
rac-(2S,3S,4S,5S)-3-tert-butyl-4-({[2-methoxy-4-(trifluoromethyl)phenyl]methyl}amino)-1-(oxolane-2-carbonyl)-5-phenylpyrrolidine-2-carboxylic acid;
rac-(2S,3S,4S,5S)-3-tert-butyl-4-{[(5-chloro-2-methoxyphenyl)methyl]amino}-1-(oxolane-2-carbonyl)-5-phenylpyrrolidine-2-carboxylic acid;
(2S,3S,4S,5S)-3-tert-butyl-5-[2-(dimethylamino)phenyl]-1-[(2R)-2-methoxy-2-phenylacetyl]-4-({[2-methoxy-5-(trifluoromethyl)phenyl]methyl}amino)pyrrolidine-2-carboxylic acid;
(2S,3S,4S,5S)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid;
(2R,3R,4R,5R)-3-tert-butyl-1-[(2S)-2-methoxy-2-phenylacetyl]-4-({[2-methoxy-5-(trifluoromethyl)phenyl]methyl}amino)-5-phenylpyrrolidine-2-carboxylic acid;
(2S,3S,4S,5S)-3-tert-butyl-1-[(2S)-2-methoxy-2-phenylacetyl]-4-({[2-methoxy-4-(trifluoromethyl)phenyl]methyl}amino)-5-phenylpyrrolidine-2-carboxylic acid;
rac-(2R,3R,4R,5R)-3-tert-butyl-4-({[2-methoxy-5-(trifluoromethyl)phenyl]methyl}amino)-1-[(2R)-2-phenoxypropanoyl]-5-phenylpyrrolidine-2-carboxylic acid;
rac-(2R,3R,4R,5R)-3-tert-butyl-4-({[2-methoxy-4-(trifluoromethyl)phenyl]methyl}amino)-1-[(2R*)-2-phenoxypropanoyl]-5-phenylpyrrolidine-2-carboxylic acid;
rac-(2R,3R,4R,5R)-3-tert-butyl-1-(4,4-difluorocyclohexane-1-carbonyl)-4-({[2-methoxy-5-(trifluoromethyl)phenyl]methyl}amino)-5-phenylpyrrolidine-2-carboxylic acid;
rac-(2R,3R,4R,5R)-3-tert-butyl-1-(4,4-difluorocyclohexane-1-carbonyl)-4-({[2-methoxy-4-(trifluoromethyl)phenyl]methyl}amino)-5-phenylpyrrolidine-2-carboxylic acid;
rac-(2R,3R,4R,5R)-3-tert-butyl-4-({[2-methoxy-5-(trifluoromethyl)phenyl]methyl}amino)-5-phenyl-1-(spiro[2.5]octane-6-carbonyl)pyrrolidine-2-carboxylic acid;
rac-(2R,3R,4R,5R)-3-tert-butyl-4-{[(5-cyano-2-methoxyphenyl)methyl]amino}-1-(cyclohexanecarbonyl)-5-phenylpyrrolidine-2-carboxylic acid;
rac-(2R,3R,4R,5R)-3-tert-butyl-1-(cyclohexanecarbonyl)-4-({[2-methyl-5-(trifluoromethyl)phenyl]methyl}amino)-5-phenylpyrrolidine-2-carboxylic acid;
rac-(2R,3R,4R,5R)-3-tert-butyl-1-(cyclohexanecarbonyl)-4-({[2-methoxy-5-(propan-2-yl)phenyl]methyl}amino)-5-phenylpyrrolidine-2-carboxylic acid;
rac-(2R,3R,4R,5R)-3-tert-butyl-4-{[(4-cyano-2-methoxyphenyl)methyl]amino}-1-(cyclohexanecarbonyl)-5-phenylpyrrolidine-2-carboxylic acid;
rac-(2R,3R,4R,5R)-3-tert-butyl-4-({[5-chloro-2-(trifluoromethoxy)phenyl]methyl}amino)-1-(cyclohexanecarbonyl)-5-phenylpyrrolidine-2-carboxylic acid;
rac-(2R,3R,4R,5R)-3-tert-butyl-1-(cyclohexanecarbonyl)-5-phenyl-4-({[2-(trifluoromethoxy)phenyl]methyl}amino)pyrrolidine-2-carboxylic acid;
rac-(2R,3R,4R,5R)-3-tert-butyl-1-(cyclohexanecarbonyl)-4-({[2-methoxy-6-(trifluoromethyl)pyridin-3-yl]methyl}amino)-5-phenylpyrrolidine-2-carboxylic acid;
rac-(2R,3R,4R,5R)-4-{[(5-chloro-2-methoxyphenyl)methyl]amino}-1-(cyclohexanecarbonyl)-3-(2-methoxypropan-2-yl)-5-phenylpyrrolidine-2-carboxylic acid;
rac-(2R,3R,4R,5R)-3-tert-butyl-4-({[2-methoxy-4-(trifluoromethyl)phenyl]methyl}amino)-5-phenyl-1-[(2S*)-2-phenylpropanoyl]pyrrolidine-2-carboxylic acid;
(2S,3S,4S,5S)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid;
(2R,3R,4R,5R)-3-tert-butyl-4-({[2-methoxy-4-(trifluoromethyl)phenyl]methyl}amino)-1-[(2S)-oxane-2-carbonyl]-5-phenylpyrrolidine-2-carboxylic acid;
(2S,3S,4S,5S)-3-tert-butyl-1-[(2R)-2-methoxy-2-phenylacetyl]-4-({[2-methoxy-5-(trifluoromethyl)pyridin-3-yl]methyl}amino)-5-phenylpyrrolidine-2-carboxylic acid;
(2S,3S,4S,5S)-3-tert-butyl-1-[(2R)-2-methoxy-2-phenylacetyl]-5-(2-methoxypyridin-3-yl)-4-({[2-methoxy-4-(trifluoromethyl)phenyl]methyl}amino)pyrrolidine-2-carboxylic acid;
rac-(2R,3R,4R,5R)-3-tert-butyl-1-(1,4-dioxane-2-carbonyl)-4-({[2-methoxy-5-(trifluoromethyl)phenyl]methyl}amino)-5-phenylpyrrolidine-2-carboxylic acid;
rac-(2R,3R,4R,5R)-3-tert-butyl-4-{[(5-chloro-2-methoxyphenyl)methyl]amino}-1-(1,4-dioxane-2-carbonyl)-5-phenylpyrrolidine-2-carboxylic acid;
(2S,3S,4S,5S)-3-tert-butyl-5-[2-(dimethylamino)pyridin-3-yl]-1-[(2R)-2-methoxy-2-phenylacetyl]-4-({[2-methoxy-4-(trifluoromethyl)phenyl]methyl}amino)pyrrolidine-2-carboxylic acid;
rac-(2R,3R,4R,5R)-1-(cyclohexanecarbonyl)-3-(2-methoxypropan-2-yl)-4-({[2-methoxy-4-(trifluoromethyl)phenyl]methyl}amino)-5-phenylpyrrolidine-2-carboxylic acid;
rac-(2R,3R,4R,5R)-1-(cyclohexanecarbonyl)-3-(2-methoxypropan-2-yl)-4-{[2-methoxy-5-(trifluoromethyl)pyridin-3-yl]amino}-5-phenylpyrrolidine-2-carboxylic acid;
rac-(2R,3R,4R,5R)-3-tert-butyl-4-{[(5-tert-butyl-2-methoxyphenyl)methyl]amino}-1-[(cyclobutyloxy)carbonyl]-5-phenylpyrrolidine-2-carboxylic acid;
(2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid;
(2S,3S,4S,5S)-3-tert-butyl-5-(2-methoxypyridin-3-yl)-4-({[2-methoxy-4-(trifluoromethyl)phenyl]methyl}amino)-1-[(2S)-oxane-2-carbonyl]pyrrolidine-2-carboxylic acid;
(2S,3S,4S,5S)-3-tert-butyl-1-(cyclohexanecarbonyl)-4-({[2-methoxy-5-(trifluoromethyl)phenyl]methyl}amino)-5-(2-methylpyridin-3-yl)pyrrolidine-2-carboxylic acid;
(2S,3S,4S,5S)-3-tert-butyl-1-(cyclohexanecarbonyl)-4-({[2-methoxy-4-(trifluoromethyl)phenyl]methyl}amino)-5-(2-methylpyridin-3-yl)pyrrolidine-2-carboxylic acid;
(2S,3S,4S,5S)-3-tert-butyl-4-{[(5-chloro-2-methoxyphenyl)methyl]amino}-1-(cyclohexanecarbonyl)-5-(2-methylpyridin-3-yl)pyrrolidine-2-carboxylic acid;
(2S,3S,4S,5S)-3-tert-butyl-4-{[(4-chloro-2-methoxyphenyl)methyl]amino}-1-(cyclohexanecarbonyl)-5-(2-methylpyridin-3-yl)pyrrolidine-2-carboxylic acid;

(2S,3S,4S,5S)-3-tert-butyl-4-{[(5-chloro-2-methoxyphenyl)methyl]amino}-1-(cyclohexanecarbonyl)-5-phenylpyrrolidine-2-carboxylic acid;

(2S,3S,4S,5S)-3-tert-butyl-5-(2-methoxypyridin-3-yl)-4-({[2-methoxy-4-(trifluoromethyl)phenyl]methyl}amino)-1-[(2R*)-oxane-2-carbony]pyrolidine-2-carboxylic acid;

(2S,3S,4S,5S)-3-tert-butyl-4-{[(4-chloro-2-methoxyphenyl)methyl]amino}-1-(cyclohexanecarbonyl)-5-phenylpyrrolidine-2-carboxylic acid;

(2S,3S,4S,5S)-4-{[(1-benzofuran-3-yl)methyl]amino}-3-tert-butyl-1-(cyclohexanecarbonyl)-5-phenylpyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-[2-(dimethylamino)pyridin-3-yl]pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-phenylpyrrolidine-2-carboxylic acid;

(2S,3S,4S,5S)-3-tert-butyl-4-{[(4-chloro-2-fluoro-5-methoxyphenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2,5-dichlorophenyl)methyl]amino}-5-phenylpyrrolidine-2-carboxylic acid;

(2S,3S,4S,5S)-3-tert-butyl-1-(cyclohexanecarbonyl)-4-{[(2-fluoro-5-methoxyphenyl)methyl]amino}-5-phenylpyrrolidine-2-carboxylic acid;

(2S,3S,4S,5S)-3-tert-butyl-4-({[5-chloro-2-(difluoromethoxy)phenyl]methyl}amino)-1-(cyclohexanecarbonyl)-5-phenylpyrrolidine-2-carboxylic acid;

(2S,3S,4S,5S)-4-({[3,5-bis(trifluoromethyl)phenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[4-methoxy-2-(trifluoromethyl)phenyl]methyl}amino)-5-phenylpyrrolidine-2-carboxylic acid;

(2S,3S,4S,5S)-4-{[(2-bromo-5-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3,5-dichlorophenyl)methyl]amino}-5-phenylpyrrolidine-2-carboxylic acid;

(2S,3S,4S,5S)-3-tert-butyl-1-(cyclohexanecarbonyl)-4-{[(4-fluoro-3-methoxyphenyl)methyl]amino}-5-phenylpyrrolidine-2-carboxylic acid;

(2S,3S,4S,5S)-3-tert-butyl-1-(cyclohexanecarbonyl)-4-{[(2,4-dichlorophenyl)methyl]amino}-5-phenylpyrrolidine-2-carboxylic acid;

(2S,3S,4S,5S)-4-{[(2-bromo-4-fluoro-5-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3,5-difluorophenyl)methyl]amino}-5-phenylpyrrolidine-2-carboxylic acid;

(2S,3S,4S,5S)-3-tert-butyl-1-(cyclohexanecarbonyl)-4-{[(6-methoxy-2H-1,3-benzodioxol-5-yl)methyl]amino}-5-phenylpyrrolidine-2-carboxylic acid;

(2S,3S,4S,5S)-3-tert-butyl-1-(cyclohexanecarbonyl)-4-{[(2,5-dimethylphenyl)methyl]amino}-5-phenylpyrrolidine-2-carboxylic acid;

(2S,3S,4S,5S)-3-tert-butyl-1-(cyclohexanecarbonyl)-4-{[(4-fluoro-2-methoxyphenyl)methyl]amino}-5-phenylpyrrolidine-2-carboxylic acid;

(2S,3S,4S,5S)-3-tert-butyl-1-(cyclohexanecarbonyl)-4-{[(4-ethoxy-2-methylphenyl)methyl]amino}-5-phenylpyrrolidine-2-carboxylic acid;

(2S,3S,4S,5S)-3-tert-butyl-1-[(2R)-2-methoxypropanoyl]-4-({[2-methoxy-5-(trifluoromethyl)phenyl]methyl}amino)-5-phenylpyrrolidine-2-carboxylic acid;

(2S,3S,4S,5S)-3-tert-butyl-4-{[(3-tert-butylphenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-5-phenyl-4-({[3-(trifluoromethyl)phenyl]methyl}amino)pyrrolidine-2-carboxylic acid;

(2S,3S,4S,5S)-3-tert-butyl-4-{[(2-methoxy-4-methylphenyl)methyl]amino}-5-(2-methoxypyridin-3-yl)-1-[(2S)-oxane-2-carbonyl]pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-[2-(difluoromethoxy)phenyl]pyrrolidine-2-carboxylic acid;

(2S,3S,4S,5S)-3-tert-butyl-1-(cyclohexanecarbonyl)-4-{[(3-methoxy-5,6,7,8-tetrahydronaphthalen-2-yl)methyl]amino}-5-phenylpyrrolidine-2-carboxylic acid;

(2S,3S,4S,5S)-4-{[(5-bromo-2-ethoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[4-methoxy-3-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-{[(4,5-difluoro-2-methoxyphenyl)methyl]amino}-5-phenylpyrrolidine-2-carboxylic acid;

(2S,3S,4S,5S)-3-tert-butyl-1-(cyclohexanecarbonyl)-4-{[(6-ethoxy-2,3-dihydro-1H-inden-5-yl)methyl]amino}-5-phenylpyrrolidine-2-carboxylic acid;

(2S,3S,4S,5S)-3-tert-butyl-1-(cyclohexanecarbonyl)-4-{[(4-fluoro-3-phenoxyphenyl)methyl]amino}-5-phenylpyrrolidine-2-carboxylic acid;

(2S,3S,4S,5S)-3-tert-butyl-1-(cyclohexanecarbonyl)-4-{[(2,4-dimethylphenyl)methyl]amino}-5-phenylpyrrolidine-2-carboxylic acid;

(2S,3S,4S,5S)-3-tert-butyl-1-(cyclohexanecarbonyl)-4-{[(3,5-dimethylphenyl)methyl]amino}-5-phenylpyrrolidine-2-carboxylic acid;

(2S,3S,4S,5S)-3-tert-butyl-1-(cyclohexanecarbonyl)-4-{[(3,5-di-tert-butylphenyl)methyl]amino}-5-phenylpyrrolidine-2-carboxylic acid;

(2S,3S,4S,5S)-3-tert-butyl-5-(2-methoxyphenyl)-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(4-tert-butyl-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-5-(2-methoxyphenyl)-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-chloro-2-methoxyphenyl)methyl]amino}-5-(2-methoxyphenyl)-1-{[(propan-2-yl)oxy]carbonyl}pyrrolidine-2-carboxylic acid;

(2S,3S,4S,5S)-3-tert-butyl-1-(cyclohexanecarbonyl)-4-{[(2-methoxy-4-methylphenyl)methyl]amino}-5-(2-methoxypyridin-3-yl)pyrrolidine-2-carboxylic acid;

(2S,3S,4S,5S)-3-tert-butyl-4-({[5-chloro-2-(cyclopropylmethoxy)phenyl]methyl}amino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methoxyphenyl)pyrrolidine-2-carboxylic acid;

(2S,3S,4S,5S)-3-tert-butyl-4-{[(4-tert-butyl-2-methoxyphenyl)methyl]amino}-1-(cyclohexanecarbonyl)-5-(2-methoxyphenyl)pyrrolidine-2-carboxylic acid;

rac-(2S,3S,4S,5S)-3-tert-butyl-4-{[(4-chloro-2-methoxyphenyl)methyl]amino}-1-(cyclohexanecarbonyl)-5-(2-methoxypyridin-3-yl)pyrrolidine-2-carboxylic acid;

rac-(2S,3S,4S,5S)-3-tert-butyl-4-{[(5-chloro-2-methoxyphenyl)methyl]amino}-1-(cyclohexanecarbonyl)-5-(2-methoxypyridin-3-yl)pyrrolidine-2-carboxylic acid;

(2S,3S,4S,5S)-3-tert-butyl-4-[(2-chloro-6-fluoro-4-methylquinolin-3-yl)amino]-1-(cyclohexanecarbonyl)-5-phenylpyrrolidine-2-carboxylic acid;

(2S,3S,4S,5S)-3-tert-butyl-4-[(2-chloro-5-cyanopyridin-3-yl)amino]-1-(cyclohexanecarbonyl)-5-phenylpyrrolidine-2-carboxylic acid;

(2S,3S,4S,5S)-3-tert-butyl-4-[(3-cyano-6-methylpyridin-2-yl)amino]-1-(cyclohexanecarbonyl)-5-phenylpyrrolidine-2-carboxylic acid;

(2S,3S,4S,5S)-3-tert-butyl-4-{[3-cyano-4-(methoxymethyl)-6-methylpyridin-2-yl]amino}-1-(cyclohexanecarbonyl)-5-phenylpyrrolidine-2-carboxylic acid;

(2S,3S,4S,5S)-4-[3,5-bis(trifluoromethyl)anilino]-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(1R,3R)-3-methoxycyclohexane-1-carbonyl]-5-phenylpyrrolidine-2-carboxylic acid;

(2S,3S,4S,5S)-1-(cyclohexanecarbonyl)-3-(2-methoxypropan-2-yl)-4-({[2-methoxy-4-(trifluoromethyl)phenyl]methyl}amino)-5-phenylpyrrolidine-2-carboxylic acid;

rac-(2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-1-benzoyl-3-tert-butyl-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(1,1-dioxo-1λ⁶-thiane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-1H-pyrazole-3-sulfonyl)-5-phenylpyrrolidine-2-carboxylic acid;

(2S,3S,4S,5S)-1-(benzenesulfonyl)-3-tert-butyl-4-({[2-methoxy-5-(trifluoromethyl)phenyl]methyl}amino)-5-phenylpyrrolidine-2-carboxylic acid;

(2S,3S,4S,5S)-3-tert-butyl-1-(2,3-dihydro-1,4-benzodioxine-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(propan-2-yl)pyridin-3-yl]methyl}amino)-5-phenylpyrrolidine-2-carboxylic acid;

(2S,3S,4S,5S)-4-{[(5-bromo-2-methoxypyridin-3-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-[({2-methoxy-5-[(2R)-3-methoxy-2-methyl-3-oxopropyl]pyridin-3-yl}methyl)amino]-5-phenylpyrrolidine-2-carboxylic acid;

(2S,3S,4S,5S)-3-tert-butyl-4-{[(4-methoxy[1,1'-biphenyl]-3-yl)methyl]amino}-5-phenyl-1-{[(propan-2-yl)oxy]carbonyl}pyrrolidine-2-carboxylic acid;

(2S,3S,4S,5S)-3-tert-butyl-4-({[2-methoxy-4-(trifluoromethyl)phenyl]methyl}amino)-1-[(2-methylpropoxy)carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(oxan-4-yl)acetyl]-5-phenylpyrrolidine-2-carboxylic acid;

(2S,3S,4S,5S)-3-tert-butyl-1-(3,4-dihydro-2H-1-benzopyran-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-3,4-dihydro-2H-1-benzopyran-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-1H-2-benzopyran-1-carbonyl)-5-phenylpyrrolidine-2-carboxylic acid;

(2S,3S,4S,5S)-3-tert-butyl-1-(cyclohexanecarbonyl)-5-phenyl-4-({[2-(propan-2-yl)phenyl]methyl}amino)pyrrolidine-2-carboxylic acid;

(2S,3S,4S,5S)-3-tert-butyl-4-[(6-chloro-3,4-dihydro-2H-1-benzopyran-4-yl)amino]-1-(cyclohexanecarbonyl)-5-phenylpyrrolidine-2-carboxylic acid;

(2S,3S,4S,5S)-3-tert-butyl-1-(cyclohexanecarbonyl)-4-({[2-methoxy-5-(propan-2-yl)phenyl]methyl}amino)-5-phenylpyrrolidine-2-carboxylic acid;

(2S,3S,4S,5S)-3-tert-butyl-4-({[2-methoxy-5-(propan-2-yl)phenyl]methyl}amino)-5-phenyl-1-{[(propan-2-yl)oxy]carbonyl}pyrrolidine-2-carboxylic acid;

(2S,3S,4S,5S)-4-{[(5-bromo-2-methoxypyridin-3-yl)methyl]amino}-3-tert-butyl-5-phenyl-1-{[(propan-2-yl)oxy]carbonyl}pyrrolidine-2-carboxylic acid;

(2S,3S,4S,5S)-4-{[(5-bromo-2-methoxyphenyl)methyl]amino}-3-tert-butyl-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1-ethyl-2-methyl-1H-indol-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(1S,2R,4R)-4-(2-cyanoethyl)-2-methylcyclopentane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methyloxane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(4-cyanocyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(6,6-dimethyloxan-3-yl)acetyl]-5-phenylpyrrolidine-2-carboxylic acid;

(2S,3S,4S,5S)-1-[(bicyclo[1.1.1]pentan-1-yl)acetyl]-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-{[(1R)-3,4-dihydro-1H-2-benzopyran-1-yl]acetyl}-5-phenylpyrrolidine-2-carboxylic acid;

(2S,3S,4S,5S)-3-tert-butyl-4-{[(5-tert-butyl-2-methoxyphenyl)methyl]amino}-1-[(oxan-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(phenylacetyl)pyrrolidine-2-carboxylic acid;

(2S,3S,4S,5S)-3-tert-butyl-4-{[(5-tert-butyl-2-methoxyphenyl)methyl]amino}-1-[(4-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(thiophen-2-yl)acetyl]pyrrolidine-2-carboxylic acid;

(2S,3S,4S,5S)-3-tert-butyl-4-{[(5-tert-butyl-2-methoxyphenyl)methyl]amino}-1-[(2-chlorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(pyridin-3-yl)acetyl]pyrrolidine-2-carboxylic acid;

(2S,3S,4S,5S)-1-(1-benzofuran-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[3-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(pyrrolidin-1-yl)acetyl]pyrrolidine-2-carboxylic acid;

(2S,3S,4S,5S)-3-tert-butyl-4-{[(5-tert-butyl-2-methoxyphenyl)methyl]amino}-1-[(4,4-difluorocyclohexyl)acetyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[1-(pyridin-2-yl)cyclopropane-1-carbonyl]pyrrolidine-2-carboxylic acid;

(2S,3S,4S,5S)-3-tert-butyl-1-(cyclohexanecarbonyl)-4-({[2-methoxy-5-(trifluoromethoxy)phenyl]methyl}amino)-5-phenylpyrrolidine-2-carboxylic acid;

(2S,3S,4S,5S)-4-{[(5-benzyl-2-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(5-cyclohexyl-2-methoxyphenyl)methyl]amino}-5-phenylpyrrolidine-2-carboxylic acid;

(2S,3S,4S,5S)-3-tert-butyl-1-(cyclohexanecarbonyl)-4-{[(5-cyclopentyl-2-methoxyphenyl)methyl]amino}-5-phenylpyrrolidine-2-carboxylic acid;

(2S,3S,4S,5S)-4-({[5-(bicyclo[2.2.1]heptan-2-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(4-hydroxyphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-hydroxyphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(2,6-dimethylpyridine-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2-methylpyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,5-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,6-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,5-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(4-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2-methylphenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2-fluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methoxy-1-methyl-1H-pyrazole-5-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2,5-dimethylthiophen-3-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(morpholin-4-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(1-hydroxycyclohexyl)acetyl]-5-phenylpyrrolidine-2-carboxylic acid;

(2S,3S,4S,5S)-1-(bicyclo[2.2.1]hept-5-ene-2-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(cyclohex-2-en-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,4-dihydro-2H-1-benzopyran-4-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methoxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(2-phenylpropanoyl)pyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)-1,3-dioxane-5-carbonyl]pyrrolidine-2-carboxylic acid;

(2S,3S,4S,5S)-3-tert-butyl-4-{[(5-tert-butyl-2-methoxyphenyl)methyl]amino}-1-[(3-oxo-2,3-dihydro-1H-inden-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,3-difluorocyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,2-difluorocyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3,3-difluoro-1-methylcyclopentyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(3-methyl-4-oxo-3,4-dihydrophthalazin-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(2,3-dihydro-1-benzofuran-7-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[5-chloro-6-oxo-1-(propan-2-yl)-1,6-dihydropyridine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{4-[(pyridin-2-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-phenyl-1-{3-[(1H-1,2,4-triazol-1-yl)methyl]benzoyl}pyrrolidine-2-carboxylic acid;

(2S,3S,4S,5S)-3-tert-butyl-4-{[(5-tert-butyl-2-methoxyphenyl)methyl]amino}-1-(1-methyl-3-phenyl-1H-pyrazole-5-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-5-phenyl-1H-pyrazole-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[5-methyl-1-(2-methylphenyl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3,5-dimethyl-1-phenyl-1H-pyrazole-4-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-2H-1,5-benzodioxepine-7-carbonyl)-5-phenylpyrrolidine-2-carboxylic acid;

(2S,3S,4S,5S)-1-(2,1-benzoxazole-3-carbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-2H-1-benzopyran-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2,3-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(cyclopent-1-en-1-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(oxolan-2-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(5-chloro-3-fluoropyridin-2-yl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(R*)-2-(4-chloro-3-methyl-1H-pyrazol-1-yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[5-oxo-1-(propan-2-yl)pyrrolidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1-cyclopropyl-5-oxopyrrolidine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3-cyanophenyl)acetyl]-5-phenylpyrrolidine-2-carboxylic acid;

(2S,3S,4S,5S)-3-tert-butyl-1-[(3aR,6aS)-hexahydro-1H-cyclopenta[c]furan-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(methoxymethyl)phenyl]methyl}amino)-5-phenylpyrrolidine-2-carboxylic acid;

(2S,3S,4S,5S)-3-tert-butyl-1-(cyclohexanecarbonyl)-5-(4-fluorophenyl)-4-[({2-methoxy-5-[(1S,3s)-tricyclo[3.3.1.1$^{3,7}$]decan-1-yl]phenyl}methyl)amino]pyrrolidine-2-carboxylic acid;

(2S,3S,4S,5S)-3-tert-butyl-1-(cyclohexanecarbonyl)-4-{[(2-methoxyquinolin-3-yl)methyl]amino}-5-phenylpyrrolidine-2-carboxylic acid;

(2S,3S,4S,5S)-3-tert-butyl-1-(cyclohexanecarbonyl)-5-(2-fluorophenyl)-4-{[(4-methoxy[1,1'-biphenyl]-3-yl)methyl]amino}pyrrolidine-2-carboxylic acid;

(2S,3S,4S,5S)-3-tert-butyl-1-(cyclohexanecarbonyl)-4-({[2-methoxy-5-(pyrrolidin-1-yl)pyridin-3-yl]methyl}amino)-5-phenylpyrrolidine-2-carboxylic acid;

(2S,3S,4S,5S)-4-{[(5-bromo-2-methoxypyridin-3-yl)methyl]amino}-1-(cyclohexanecarbonyl)-3-(2-methoxypropan-2-yl)-5-phenylpyrrolidine-2-carboxylic acid;

(2S,3S,4S,5S)-4-{[(5-bromo-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-3-tert-butyl-1-(cyclohexanecarbonyl)-4-{[(4-methoxy-4'-methyl[1,1'-biphenyl]-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(2-methoxypyridin-3-yl)phenyl]methyl}amino)-5-phenylpyrrolidine-2-carboxylic acid;

(2S,3S,4S,5S)-4-({[5-(bicyclo[2.2.1]heptan-2-yl)-2-methoxypyridin-3-yl]methyl}amino)-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclohexyl-2-methoxypyridin-3-yl)methyl]amino}-3-(2-methoxypropan-2-yl)-5-phenylpyrrolidine-2-carboxylic acid;

(2S,3S,4S,5S)-1-(cyclohexanecarbonyl)-4-({[5-(cyclohexylmethyl)-2-methoxypyridin-3-yl]methyl}amino)-3-(2-methoxypropan-2-yl)-5-phenylpyrrolidine-2-carboxylic acid;

(2S,3S,4S,5S)-1-(cyclohexanecarbonyl)-3-(2-methoxypropan-2-yl)-4-({[2-methoxy-5-(propan-2-yl)pyridin-3-yl]methyl}amino)-5-phenylpyrrolidine-2-carboxylic acid;

(2S,3S,4S,5S)-4-{[(5-cyclobutyl-2-methoxyphenyl)methyl]amino}-1-(cyclohexanecarbonyl)-3-(2-methoxypropan-2-yl)-5-phenylpyrrolidine-2-carboxylic acid;

(2S,3S,4S,5S)-1-(cyclohexanecarbonyl)-4-{[(5-cyclopentyl-2-methoxyphenyl)methyl]amino}-3-(2-methoxypropan-2-yl)-5-phenylpyrrolidine-2-carboxylic acid;
(2S,3S,4S,5S)-1-(cyclohexanecarbonyl)-4-{[(5-cyclohexyl-2-methoxyphenyl)methyl]amino}-3-(2-methoxypropan-2-yl)-5-phenylpyrrolidine-2-carboxylic acid;
(2S,3S,4S,5S)-1-(cyclohexanecarbonyl)-3-(2-methoxypropan-2-yl)-4-({[2-methoxy-5-(propan-2-yl)phenyl]methyl}amino)-5-phenylpyrrolidine-2-carboxylic acid;
(2S,3S,4S,5S)-3-tert-butyl-1-(cyclohexanecarbonyl)-4-{[(5-cyclopropyl-2-methoxypyridin-3-yl)methyl]amino}-5-phenylpyrrolidine-2-carboxylic acid;
(2S,3S,4S,5S)-3-tert-butyl-1-(cyclohexanecarbonyl)-5-(2-fluorophenyl)-4-({[2-methoxy-5-(trifluoromethyl)phenyl]methyl}amino)pyrrolidine-2-carboxylic acid;
(2S,3S,4S,5S)-3-tert-butyl-1-(cyclohexanecarbonyl)-5-(2-fluorophenyl)-4-({[2-methoxy-4-(trifluoromethyl)phenyl]methyl}amino)pyrrolidine-2-carboxylic acid;
(2S,3S,4S,5S)-4-{[(5-bromo-2-methoxyphenyl)methyl]amino}-3-tert-butyl-1-(cyclohexanecarbonyl)-5-(2-fluorophenyl)pyrrolidine-2-carboxylic acid;
(2S,3S,4S,5S)-4-{[(5-bromo-2-methoxypyridin-3-yl)methyl]amino}-3-tert-butyl-1-(cyclohexanecarbonyl)-5-(2-fluorophenyl)pyrrolidine-2-carboxylic acid;
(2S,3S,4S,5S)-3-tert-butyl-4-{[(5-tert-butyl-2-methoxyphenyl)methyl]amino}-1-[(2-methylpropoxy)carbonyl]-5-phenylpyrrolidine-2-carboxylic acid;
(2S,3S,4S,5S)-3-tert-butyl-1-[(2R*)-2,3-dihydro-1-benzofuran-2-carbonyl]-4-({[2-methoxy-5-(trifluoromethyl)phenyl]methyl}amino)-5-phenylpyrrolidine-2-carboxylic acid;
(2S,3S,4S,5S)-3-tert-butyl-1-[(2S*)-2,3-dihydro-1-benzofuran-2-carbonyl]-4-({[2-methoxy-5-(trifluoromethyl)phenyl]methyl}amino)-5-phenylpyrrolidine-2-carboxylic acid;
(2S,3S,4S,5S)-3-tert-butyl-4-{[(5-tert-butyl-2-methoxyphenyl)methyl]amino}-1-(2-methoxy-3-methylbutanoyl)-5-phenylpyrrolidine-2-carboxylic acid;
(2S,3S,4S,5S)-3-tert-butyl-4-{[(5-tert-butyl-2-methoxyphenyl)methyl]amino}-1-[(2R*,3S*)-3-methyloxolane-2-carbonyl]-5-phenylpyrrolidine-2-carboxylic acid;
(2S,3S,4S,5S)-3-tert-butyl-4-{[(5-tert-butyl-2-methoxyphenyl)methyl]amino}-1-[(2S*,3R*)-3-methyloxolane-2-carbonyl]-5-phenylpyrrolidine-2-carboxylic acid;
(2S,3S,4S,5S)-3-tert-butyl-4-{[(5-tert-butyl-2-methoxyphenyl)methyl]amino}-1-[(2R*)-2-(3-chlorophenyl)-2-methoxyacetyl]-5-phenylpyrrolidine-2-carboxylic acid;
(2S,3S,4S,5S)-3-tert-butyl-4-{[(5-tert-butyl-2-methoxyphenyl)methyl]amino}-1-[(2S*)-2-(3-chlorophenyl)-2-methoxyacetyl]-5-phenylpyrrolidine-2-carboxylic acid;
(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-phenylpyrrolidine-2-carboxylic acid;
(2S,3S,4S,5S)-3-tert-butyl-1-(2-methoxy-3-methylbutanoyl)-4-({[2-methoxy-5-(trifluoromethyl)phenyl]methyl}amino)-5-phenylpyrrolidine-2-carboxylic acid;
(2S,3S,4S,5S)-3-tert-butyl-4-({[2-methoxy-5-(trifluoromethyl)phenyl]methyl}amino)-1-[(2R*,3S*)-3-methyloxolane-2-carbonyl]-5-phenylpyrrolidine-2-carboxylic acid;
(2S,3S,4S,5S)-3-tert-butyl-1-(cyclohexanecarbonyl)-4-({[2-methoxy-5-(thiophen-2-yl)phenyl]methyl}amino)-5-phenylpyrrolidine-2-carboxylic acid;
(2S,3S,4S,5S)-3-tert-butyl-1-(cyclohexanecarbonyl)-4-({[5-(furan-3-yl)-2-methoxyphenyl]methyl}amino)-5-phenylpyrrolidine-2-carboxylic acid;
(2S,3S,4S,5S)-3-tert-butyl-1-(cyclohexanecarbonyl)-4-{[(3',4-dimethoxy[1,1'-biphenyl]-3-yl)methyl]amino}-5-phenylpyrrolidine-2-carboxylic acid;
(2S,3S,4S,5S)-3-tert-butyl-1-(cyclohexanecarbonyl)-4-({[2-methoxy-5-(6-methylpyridin-3-yl)phenyl]methyl}amino)-5-phenylpyrrolidine-2-carboxylic acid;
(2S,3S,4S,5S)-3-tert-butyl-1-(cyclohexanecarbonyl)-4-{[(4-methoxy-2'-methyl[1,1'-biphenyl]-3-yl)methyl]amino}-5-phenylpyrrolidine-2-carboxylic acid;
(2S,3S,4S,5S)-3-tert-butyl-1-(cyclohexanecarbonyl)-4-({[2-methoxy-5-(4-methylpyridin-3-yl)phenyl]methyl}amino)-5-phenylpyrrolidine-2-carboxylic acid;
(2S,3S,4S,5S)-3-tert-butyl-4-{[(3'-cyano-4-methoxy[1,1'-biphenyl]-3-yl)methyl]amino}-1-(cyclohexanecarbonyl)-5-phenylpyrrolidine-2-carboxylic acid;
(2S,3S,4S,5S)-3-tert-butyl-1-(cyclohexanecarbonyl)-4-{[(4'-fluoro-4-methoxy-2'-methyl[1,1'-biphenyl]-3-yl)methyl]amino}-5-phenylpyrrolidine-2-carboxylic acid;
(2S,3S,4S,5S)-3-tert-butyl-1-(cyclohexanecarbonyl)-4-{[(2',4'-difluoro-4-methoxy[1,1'-biphenyl]-3-yl)methyl]amino}-5-phenylpyrrolidine-2-carboxylic acid;
(2S,3S,4S,5S)-3-tert-butyl-1-(cyclohexanecarbonyl)-4-({[2-methoxy-5-(pyridin-3-yl)phenyl]methyl}amino)-5-phenylpyrrolidine-2-carboxylic acid;
(2S,3S,4S,5S)-3-tert-butyl-1-(cyclohexanecarbonyl)-4-({[5-(3,5-dimethyl-1,2-oxazol-4-yl)-2-methoxyphenyl]methyl}amino)-5-phenylpyrrolidine-2-carboxylic acid;
(2S,3S,4S,5S)-3-tert-butyl-1-(cyclohexanecarbonyl)-4-{[(2',3'-difluoro-4-methoxy[1,1'-biphenyl]-3-yl)methyl]amino}-5-phenylpyrrolidine-2-carboxylic acid;
(2S,3S,4S,5S)-3-tert-butyl-1-(cyclohexanecarbonyl)-4-({[5-(5-fluoropyridin-3-yl)-2-methoxyphenyl]methyl}amino)-5-phenylpyrrolidine-2-carboxylic acid;
(2S,3S,4S,5S)-3-tert-butyl-1-(cyclohexanecarbonyl)-4-({[2-methoxy-5-(2-methylpyridin-3-yl)phenyl]methyl}amino)-5-phenylpyrrolidine-2-carboxylic acid;
(2S,3S,4S,5S)-3-tert-butyl-4-{[(4'-cyano-4-methoxy[1,1'-biphenyl]-3-yl)methyl]amino}-1-(cyclohexanecarbonyl)-5-phenylpyrrolidine-2-carboxylic acid;
(2S,3S,4S,5S)-3-tert-butyl-4-({[5-(1-cyclobutyl-1H-pyrazol-4-yl)-2-methoxyphenyl]methyl}amino)-1-(cyclohexanecarbonyl)-5-phenylpyrrolidine-2-carboxylic acid;
(2S,3S,4S,5S)-3-tert-butyl-1-(cyclohexanecarbonyl)-4-({[5-(furan-2-yl)-2-methoxyphenyl]methyl}amino)-5-phenylpyrrolidine-2-carboxylic acid;
(2S,3S,4S,5S)-3-tert-butyl-1-(cyclohexanecarbonyl)-4-({[5-(difluoromethoxy)-2-methoxyphenyl]methyl}amino)-5-phenylpyrrolidine-2-carboxylic acid;
(2S,3S,4S,5S)-3-tert-butyl-1-(cyclohexanecarbonyl)-4-({[5-(2,5-dihydrofuran-3-yl)-2-methoxyphenyl]methyl}amino)-5-phenylpyrrolidine-2-carboxylic acid;
(2S,3S,4S,5S)-4-{[(5-tert-butyl-2-methoxyphenyl)methyl]amino}-1-(cyclohexanecarbonyl)-5-(2-methoxyphenyl)-3-(2-methoxypropan-2-yl)pyrrolidine-2-carboxylic acid;
(2S,3S,4S,5S)-1-(cyclohexanecarbonyl)-5-(2-methoxyphenyl)-3-(2-methoxypropan-2-yl)-4-({[2-methoxy-5-(trifluoromethyl)phenyl]methyl}amino)pyrrolidine-2-carboxylic acid;

(2S,3S,4S,5S)-3-tert-butyl-1-(cyclohexanecarbonyl)-4-{[(3-methoxy-6-phenylpyridin-2-yl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-[(2S*)-2-methoxy-3,3-dimethylbutanoyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2-methoxy-3,3-dimethylbutanoyl]-5-phenylpyrrolidine-2-carboxylic acid;

(2S,3S,4S,5S)-3-tert-butyl-1-(3,4-dihydro-1H-2-benzopyran-3-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(3,4-dihydro-1H-2-benzopyran-3-carbonyl)-5-phenylpyrrolidine-2-carboxylic acid;

(2S,3S,4S,5S)-3-tert-butyl-4-{[(5-tert-butyl-2-methoxypyridin-3-yl)methyl]amino}-1-[(2,6-difluorophenyl)acetyl]-5-phenylpyrrolidine-2-carboxylic acid;

(2S,3S,4S,5S)-4-{[(5-tert-butyl-2-methoxyphenyl)methyl]amino}-1-(cyclohexanecarbonyl)-3-(1-methylcyclopropyl)-5-phenylpyrrolidine-2-carboxylic acid;

(2S,3S,4S,5S)-1-(cyclohexanecarbonyl)-4-({[2-methoxy-4-(trifluoromethyl)phenyl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(4,4,4-trifluoro-2-methylbutanoyl)pyrrolidine-2-carboxylic acid;

(2S,3S,4S,5S)-3-tert-butyl-4-{[(5-tert-butyl-2-methoxyphenyl)methyl]amino}-1-[2-(3-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-(3-methylcyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(4-fluorophenyl)cyclopropane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-methoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-(2,2-dimethylcyclopropane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(4-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[(2R)-2-methoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2-chlorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-(cyclobutanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2,3-dihydro-1-benzothiophene-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[1-(cyclopropanecarbonyl)piperidine-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(8-methoxy-1,2,3,4-tetrahydronaphthalene-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(oxane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-phenoxypropanoyl]-5-phenylpyrrolidine-2-carboxylic acid;

(2S,3S,4S,5S)-3-tert-butyl-4-{[(5-tert-butyl-2-methoxyphenyl)methyl]amino}-1-(6-fluoro-3,4-dihydro-2H-1-benzopyran-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclopent-3-ene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(2R)-oxolane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2,3-dimethylphenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(2-fluorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(phenylsulfanyl)propanoyl]pyrrolidine-2-carboxylic acid;

(2S,3S,4S,5S)-3-tert-butyl-4-{[(5-tert-butyl-2-methoxyphenyl)methyl]amino}-5-phenyl-1-[(2S)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-(2,2-difluorocyclopropane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2-ethylbutanoyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(3-chlorophenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(pyridin-4-yl)cyclopropane-1-carbonyl]pyrrolidine-2-carboxylic acid;

(2S,3S,4S,5S)-3-tert-butyl-4-{[(5-tert-butyl-2-methoxyphenyl)methyl]amino}-1-(cyclopentanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(cyclopropanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-difluorocyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3-fluorocyclobutane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-difluorocyclobutane-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-1-(2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-5-phenyl-1-[trans-2-phenylcy-clopropane-1-carbonyl]pyrrolidine-2-carboxylic acid;

(2S,3S,4S,5S)-3-tert-butyl-1-(cyclohexanecarbonyl)-4-({[2-methoxy-5-(oxan-4-yl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(3-methoxyphenyl)pyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(2-methylphenyl)pyridin-3-yl]methyl}amino)-5-phenylpyrrolidine-2-carboxylic acid;

(2S,3S,4S,5S)-3-tert-butyl-1-(cyclohexanecarbonyl)-4-({[5-(4-fluoro-2-methylphenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[5-(2,4-difluorophenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-{[(6-methoxy[3,3'-bipyridin]-5-yl)methyl]amino}-5-phenylpyrrolidine-2-carboxylic acid;

(2S,3S,4S,5S)-3-tert-butyl-1-(cyclohexanecarbonyl)-4-({[5-(2,3-difluorophenyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[2-methoxy-5-(4-methylphenyl)pyridin-3-yl]methyl}amino)-5-phenylpyrrolidine-2-carboxylic acid;

(2S,3S,4S,5S)-3-tert-butyl-1-(cyclohexanecarbonyl)-4-{[(6-methoxy-2'-methyl[3,3'-bipyridin]-5-yl)methyl]amino}-5-phenylpyrrolidine-2-carboxylic acid;

(2S,3S,4S,5S)-3-tert-butyl-1-(cyclohexanecarbonyl)-4-({[5-(3,6-dihydro-2H-pyran-4-yl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-4-({[5-(2,5-dihydrofuran-3-yl)-2-methoxypyridin-3-yl]methyl}amino)-5-phenylpyrrolidine-2-carboxylic acid;

(2S,3S,4S,5S)-3-tert-butyl-4-{[(5-tert-butyl-2-methoxy-pyridin-3-yl)methyl]amino}-1-(cyclohexanecarbonyl)-5-(2-fluorophenyl)pyrrolidine-2-carboxylic acid;

(2S,3S,4S,5S)-3-tert-butyl-1-(cyclohexanecarbonyl)-4-{[(5-cyclopropyl-2-methoxyphenyl)methyl]amino}-5-phenylpyrrolidine-2-carboxylic acid;

(2S,3S,4S,5S)-3-tert-butyl-1-(cyclohexanecarbonyl)-5-(2-fluorophenyl)-4-[({2-methoxy-5-[1-(trifluorom-ethyl)cyclopropyl]phenyl}methyl)amino]pyrrolidine-2-carboxylic acid;

(2S,3S,4S,5S)-3-tert-butyl-4-{[(5-tert-butyl-2-methoxy-phenyl)methyl]amino}-1-[1-(4-fluorophenyl)-5-methyl-1H-pyrazole-4-carbonyl]-5-phenylpyrrolidine-2-carboxylic acid;

(2S,3S,4S,5S)-3-tert-butyl-1-(1-tert-butyl-5-cyano-1H-pyrazole-4-carbonyl)-4-{[(5-tert-butyl-2-methoxyphe-nyl)methyl]amino}-5-phenylpyrrolidine-2-carboxylic acid;

(2S,3S,4S,5S)-3-tert-butyl-4-{[(5-tert-butyl-2-methoxy-phenyl)methyl]amino}-1-[1-(2,4-difluorophenyl)-5-methyl-1H-pyrazole-4-carbonyl]-5-phenylpyrrolidine-2-carboxylic acid;

(2S,3S,4S,5S)-3-tert-butyl-4-{[(5-tert-butyl-2-methoxy-phenyl)methyl]amino}-1-[1-(4-methoxyphenyl)-5-methyl-1H-pyrazole-4-carbonyl]-5-phenylpyrrolidine-2-carboxylic acid;

(2S,3S,4S,5S)-3-tert-butyl-4-{[(5-tert-butyl-2-methoxy-phenyl)methyl]amino}-1-(1-methyl-5-phenyl-1H-pyrazole-4-carbonyl)-5-phenylpyrrolidine-2-carbox-ylic acid;

(2S,3S,4S,5S)-3-tert-butyl-4-{[(5-tert-butyl-2-methoxy-phenyl)methyl]amino}-1-[5-ethyl-1-(4-fluorophenyl)-3-methyl-1H-pyrazole-4-carbonyl]-5-phenylpyrroli-dine-2-carboxylic acid;

(2S,3S,4S,5S)-3-tert-butyl-4-{[(5-tert-butyl-2-methoxy-phenyl)methyl]amino}-1-[1-tert-butyl-5-(trifluorom-ethyl)-1H-pyrazole-4-carbonyl]-5-phenylpyrrolidine-2-carboxylic acid;

(2S,3S,4S,5S)-3-tert-butyl-4-{[(5-tert-butyl-2-methoxy-phenyl)methyl]amino}-1-(5-methyl-1-phenyl-1H-pyrazole-4-carbonyl)-5-phenylpyrrolidine-2-carbox-ylic acid;

(2S,3S,4S,5S)-3-tert-butyl-4-{[(5-tert-butyl-2-methoxy-phenyl)methyl]amino}-1-(1-ethyl-3,5-dimethyl-1H-pyrazole-4-carbonyl)-5-phenylpyrrolidine-2-carbox-ylic acid;

(2S,3S,4S,5S)-3-tert-butyl-4-{[(5-tert-butyl-2-methoxy-phenyl)methyl]amino}-1-(2-methyl-4,5,6,7-tetrahy-dropyrazolo[1,5-a]pyridine-3-carbonyl)-5-phenylpyr-rolidine-2-carboxylic acid;

(2S,3S,4S,5S)-3-tert-butyl-4-{[(5-tert-butyl-2-methoxy-phenyl)methyl]amino}-5-phenyl-1-(4,5,6,7-tetrahy-dropyrazolo[1,5-a]pyridine-3-carbonyl)pyrrolidine-2-carboxylic acid;

(2S,3S,4S,5S)-3-tert-butyl-4-{[(5-tert-butyl-2-methoxy-phenyl)methyl]amino}-1-(5-methoxy-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-1-[(1R)-4-methoxy-1-methyl-2,3-dihydro-1H-indene-1-carbonyl]-5-phenylpyrroli-dine-2-carboxylic acid;

(2S,3S,4S,5S)-3-tert-butyl-4-{[(5-tert-butyl-2-methoxy-phenyl)methyl]amino}-1-(4-chloro-1-methyl-2,3-di-hydro-1H-indene-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-1-(1-methyl-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-1-(5-chloro-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxy-phenyl)methyl]amino}-5-phenyl-1-(3-phenyl-2,3-di-hydro-1-benzofuran-3-carbonyl)pyrrolidine-2-carbox-ylic acid;

(2S,3S,4S,5S)-3-tert-butyl-4-{[(5-tert-butyl-2-methoxy-phenyl)methyl]amino}-1-(3-hydroxy-3-methylpen-tanoyl)-5-phenylpyrrolidine-2-carboxylic acid;

(2S,3S,4S,5S)-3-tert-butyl-4-{[(5-tert-butyl-2-methoxy-phenyl)methyl]amino}-1-(3-hydroxy-3,4-dimethyl-pentanoyl)-5-phenylpyrrolidine-2-carboxylic acid;

(2S,3S,4S,5S)-3-tert-butyl-4-{[(6-tert-butyl-3-methoxy-pyridin-2-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxy-phenyl)methyl]amino}-5-phenyl-1-[4-(trifluorom-ethyl)cyclohexane-1-carbonyl]pyrrolidine-2-carbox-ylic acid;

(2S,3S,4S,5S)-3-tert-butyl-4-{[(5-tert-butyl-2-methoxyphenyl)methyl]amino}-1-[(1 s,3R,5S)-3,5-dimethylcyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(4,7,7-trimethylbicyclo[4.1.0]heptane-3-carbonyl)pyrrolidine-2-carboxylic acid;

(2S,3S,4S,5S)-3-tert-butyl-4-{[(5-tert-butyl-2-methoxyphenyl)methyl]amino}-1-(4,4-difluorocyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(prop-2-en-1-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(trans-4-ethyl-4-hydroxycyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(propan-2-yl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(trans-4-hydroxy-4-propylcyclohexane-1-carbonyl)-5-phenylpyrrolidine-2-carboxylic acid;

(2S,3S,4S,5S)-1-(butoxycarbonyl)-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-{[(prop-2-yn-1-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(pentyloxy)carbonyl]-5-phenylpyrrolidine-2-carboxylic acid;

(2S,3S,4S,5S)-3-tert-butyl-4-{[(5-tert-butyl-2-methoxyphenyl)methyl]amino}-1-({[(1S,2R,5S)-5-methyl-2-(propan-2-yl)cyclohexyl]oxy}carbonyl)-5-phenylpyrrolidine-2-carboxylic acid;

(2S,3S,4S,5S)-1-{[(but-3-en-1-yl)oxy]carbonyl}-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-4-{[(5-tert-butyl-2-methoxyphenyl)methyl]amino}-1-(methoxycarbonyl)-5-phenylpyrrolidine-2-carboxylic acid;

(2S,3S,4S,5S)-3-tert-butyl-4-{[(5-tert-butyl-2-methoxyphenyl)methyl]amino}-1-{[(but-2-yn-1-yl)oxy]carbonyl}-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(propoxycarbonyl)pyrrolidine-2-carboxylic acid;

(2S,3S,4S,5SS)-3-tert-butyl-4-{[(5-tert-butyl-2-methoxyphenyl)methyl]amino}-5-phenyl-1-{[(prop-2-en-1-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(2,2-dimethylpropoxy)carbonyl]-5-phenylpyrrolidine-2-carboxylic acid;

(2S,3R,4R,5S)-3-tert-butyl-4-{[(5-tert-butyl-2-methoxyphenyl)methyl]amino}-1-[(2R)-2-methoxy-2-phenylacetyl]-5-phenylpyrrolidine-2-carboxylic acid;

(2S,3S,4S,5S)-3-tert-butyl-1-(cyclohexanecarbonyl)-4-{[(1-methoxycyclohexyl)methyl]amino}-5-phenylpyrrolidine-2-carboxylic acid;

(2S,3R,4R,5S)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2S)-2-(3,4-difluorophenyl)-2-methoxyacetyl]-5-phenylpyrrolidine-2-carboxylic acid;

(2S,3S,4S,5S)-3-tert-butyl-4-({[2-methoxy-5-(trifluoromethyl)phenyl]methyl}amino)-1-(6-methyl-3,4-dihydro-2H-1-benzopyran-2-carbonyl)-5-phenylpyrrolidine-2-carboxylic acid;

(2S,3S,4S,5S)-3-tert-butyl-1-(7-fluoro-3,4-dihydro-2H-1-benzopyran-2-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-[2-(4-chlorophenoxy)-3-methylbutanoyl]-4-({[2-methoxy-5-(trifluoromethyl)phenyl]methyl}amino)-5-phenylpyrrolidine-2-carboxylic acid;

(2S,3S,4S,5S)-3-tert-butyl-4-({[5-(1-cyanocyclopropyl)-2-methoxyphenyl]methyl}amino)-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(8-methoxy-3,4-dihydro-2H-1-benzopyran-3-carbonyl)-5-phenylpyrrolidine-2-carboxylic acid;

(2S,3S,4S,5S)-4-({[2-(bicyclo[2.2.1]heptan-2-yl)-5-methoxypyridin-4-yl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2-cyclohexyl-5-methoxypyridin-4-yl)methyl]amino}-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[5-(2-fluorophenyl)-2-methoxypyridin-3-yl]methyl}amino)pyrrolidine-2-carboxylic acid;

(2S,3S,4S,5S)-3-tert-butyl-1-(cyclohexanecarbonyl)-4-({[5-(2,4-difluorophenyl)-2-methoxypyridin-3-yl]methyl}amino)-5-[2-(dimethylamino)pyridin-3-yl]pyrrolidine-2-carboxylic acid;

(2S,3S,4S,5S)-3-tert-butyl-1-(cyclohexanecarbonyl)-4-{[(2,6-dimethoxyphenyl)methyl]amino}-5-phenylpyrrolidine-2-carboxylic acid;

(2S,3S,4S,5S)-3-tert-butyl-1-(cyclohexanecarbonyl)-4-({[3-methoxy-6-(trifluoromethyl)pyridin-2-yl]methyl}amino)-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[5-(4-fluoro-2-methylphenyl)-2-methoxypyridin-3-yl]methyl}amino)pyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(4-methylphenyl)pyridin-3-yl]methyl}amino)pyrrolidine-2-carboxylic acid;

(2S,3S,4S,5S)-3-tert-butyl-4-{[(5-tert-butyl-2-methoxyphenyl)methyl]amino}-1-(2-fluorocyclohex-1-ene-1-carbonyl)-5-phenylpyrrolidine-2-carboxylic acid;

(2S,3R,4R,5S)-3-tert-butyl-4-{[(5-tert-butyl-2-methoxyphenyl)methyl]amino}-1-(cyclohexanecarbonyl)-5-phenylpyrrolidine-2-carboxylic acid;

(2S,3R,4R,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(6-chloro-2,3-dihydro-1H-indene-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[3-methyl-2-(2-methylphenoxy)butanoyl]-5-phenylpyrrolidine-2-carboxylic acid;

(2S,3S,4S,5S)-3-tert-butyl-1-(cyclohexanecarbonyl)-4-({[2-(2-fluoro-4-methylphenyl)-5-methoxypyridin-4-yl]methyl}amino)-5-phenylpyrrolidine-2-carboxylic acid;

(2S,3S,4S,5S)-3-tert-butyl-1-(cyclohexanecarbonyl)-4-({[2-(2-fluorophenyl)-5-methoxypyridin-4-yl]methyl}amino)-5-phenylpyrrolidine-2-carboxylic acid;

(2S,3S,4S,5S)-3-tert-butyl-1-(cyclohexanecarbonyl)-4-({[5-methoxy-2-(3-methoxyphenyl)pyridin-4-yl]methyl}amino)-5-phenylpyrrolidine-2-carboxylic acid;

(2S,3S,4S,5S)-4-{[(5-tert-butyl-2-methoxyphenyl)methyl]amino}-3-(2-methoxypropan-2-yl)-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-4-[({2-methoxy-5-[1-(methoxymethyl)cyclopropyl]phenyl}methyl)amino]-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1-benzofuran-2-carbonyl]-5-[2-(dimethylamino)pyridin-3-yl]pyrrolidine-2-carboxylic acid;

(2S,3S,4S,5S)-3-tert-butyl-1-(cyclohexanecarbonyl)-4-({[5-(2,2-difluoro-1-methylcyclopropyl)-2-methoxypyridin-3-yl]methyl}amino)-5-phenylpyrrolidine-2-carboxylic acid;

(2S,3S,4S,5S)-3-tert-butyl-1-(cyclohexanecarbonyl)-5-(2-fluorophenyl)-4-{[(2-methoxy-5-phenylpyridin-3-yl)methyl]amino}pyrrolidine-2-carboxylic acid;

(2S,3S,4S,5S)-3-tert-butyl-1-(cyclohexanecarbonyl)-5-(2-fluorophenyl)-4-({[5-(2-fluorophenyl)-2-methoxypyridin-3-yl]methyl}amino)pyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-[(2R*,5S*)-5-phenyloxolane-2-carbonyl]pyrrolidine-2-carboxylic acid;

(2S,3S,4S,5S)-3-tert-butyl-4-{[(6-tert-butyl-2-methoxypyridin-3-yl)methyl]amino}-1-[(2-methylphenyl)acetyl]-5-[2-(propan-2-yl)phenyl]pyrrolidine-2-carboxylic acid;

(2S,3S,4S,5S)-3-tert-butyl-4-{[(6-tert-butyl-2-methoxypyridin-3-yl)methyl]amino}-1-(3,3-dimethylcyclopentane-1-carbonyl)-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2-methylphenyl)acetyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R*)-2,3-dihydro-1-benzofuran-2-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1R*,3aR*,6a*)hexahydro-1H-cyclopenta[c]furan-1-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1S*,3aS*,6aR*)-hexahydro-1H-cyclopenta[c]furan-1-carbonyl]-5-phenylpyrrolidine-2-carboxylic acid;

(2S,3S,4S,5S)-3-tert-butyl-4-{[(6-tert-butyl-2-methoxypyridin-3-yl)methyl]amino}-1-[(2R)-2-methoxy-2-phenylacetyl]-5-phenylpyrrolidine-2-carboxylic acid;

(2S,3S,4S,5S)-3-tert-butyl-1-(5,5-dimethyloxolane-2-carbonyl)-4-({[2-methoxy-5-(trifluoromethyl)pyridin-3-yl]methyl}amino)-5-phenylpyrrolidine-2-carboxylic acid;

(2S,3S,4S,5S)-3-tert-butyl-1-(7-fluoro-3,4-dihydro-2H-1-benzopyran-2-carbonyl)-4-({[2-methoxy-5-(trifluoromethyl)pyridin-3-yl]methyl}amino)-5-phenylpyrrolidine-2-carboxylic acid;

(2S,3S,4S,5S)-1-(cyclohexanecarbonyl)-3-(2-methoxypropan-2-yl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-1-(cyclohexanecarbonyl)-5-[2-(dimethylamino)pyridin-3-yl]-3-(2-methoxypropan-2-yl)-4-({[2-methoxy-5-(trifluoromethyl)phenyl]methyl}amino)pyrrolidine-2-carboxylic acid;

(2S,3S,4S,5S)-3-tert-butyl-4-{[(5-tert-butyl-2-methoxyphenyl)methyl]amino}-1-[(2R*)-3,4-dihydro-2H-1-benzopyran-2-carbonyl]-5-[2-(dimethylamino)pyridin-3-yl]pyrrolidine-2-carboxylic acid;

(2S,3S,4S,5S)-1-{(4E)-2-[(2E)-but-2-en-1-yl]hex-4-enoyl}-3-tert-butyl-4-{[(5-tert-butyl-2-methoxyphenyl)methyl]amino}-5-phenylpyrrolidine-2-carboxylic acid;

(2S,3S,4S,5S)-3-tert-butyl-1-(cyclohexanecarbonyl)-4-({[2-methoxy-5-(1-methylcyclopropyl)pyridin-3-yl]methyl}amino)-5-phenylpyrrolidine-2-carboxylic acid;

(2S,3S,4S,5S)-3-tert-butyl-1-[(1S)-3,3-difluorocyclohexane-1-carbonyl]-4-({[2-methoxy-5-(trimethylsilyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-(6-oxaspiro[2.5]octane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(oxetane-2-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-[(3R*)-1-methyl-2-oxopiperidine-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-1H-pyrazole-3-carbonyl)-5-phenylpyrrolidine-2-carboxylic acid;

(2S,3S,4S,5S)-3-tert-butyl-4-({[2-methoxy-5-(trifluoromethyl)pyridin-3-yl]methyl}amino)-1-(7-methyl-2,3-dihydro-1-benzofuran-2-carbonyl)-5-phenylpyrrolidine-2-carboxylic acid;

(2S,3S,4S,5S)-3-tert-butyl-5-[2-(dimethylamino)pyridin-3-yl]-4-{[(4-methoxy[1,1'-biphenyl]-3-yl)methyl]amino}-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1S*,3S*)-3-methoxycyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,3R*)-3-methoxycyclohexane-1-carbonyl]pyrrolidine-2-carboxylic acid;

(2S,3S,4S,5S)-3-tert-butyl-5-[2-(dimethylamino)pyridin-3-yl]-4-{[(4-methoxy[1,1'-biphenyl]-3-yl)methyl]amino}-1-[(2S)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-[(2R)-oxane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S*)-7-fluoro-3,4-dihydro-2H-1-benzopyran-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R*)-7-fluoro-3,4-dihydro-2H-1-benzopyran-2-carbonyl]pyrrolidine-2-carboxylic acid;

(2S,3S,4S,5S)-3-tert-butyl-4-{[(5-tert-butyl-2-methoxyphenyl)methyl]amino}-1-{(2R*)-2-[(2S*)-oxan-2-yl]propanoyl}-5-phenylpyrrolidine-2-carboxylic acid;

(2S,3S,4S,5S)-3-tert-butyl-4-{[(5-tert-butyl-2-methoxyphenyl)methyl]amino}-1-{(2S*)-2-[(2R*)-oxan-2-yl]propanoyl}-5-phenylpyrrolidine-2-carboxylic acid;

(2S,3S,4S,5S)-3-tert-butyl-4-{[(6-tert-butyl-2-methoxypyridin-3-yl)methyl]amino}-1-[(1S*,3R*)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[2-(oxan-2-yl)propanoyl]-5-phenylpyrrolidine-2-carboxylic acid;

(2S,3S,4S,5S)-3-tert-butyl-4-{[(5-tert-butyl-2-methoxyphenyl)methyl]amino}-1-[cis-4-hydroxy-4-(trifluoromethyl)cyclohexane-1-carbonyl]phenylpyrrolidine-2-carboxylic acid;

(2S,3S,4S,5S)-3-tert-butyl-4-{[(5-tert-butyl-2-methoxyphenyl)methyl]amino}-1-[trans-4-hydroxy-4-(trifluoromethyl)cyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-5-(2-fluorophenyl)-1-[(2S)-oxane-2-carbonyl]pyrrolidine-2-carboxylic acid;

(2S,3S,4S,5S)-3-tert-butyl-1-(cyclohexanecarbonyl)-5-[2-(dimethylamino)pyridin-3-yl]-4-{[2-methoxy-5-(trifluoromethyl)pyridin-3-yl]amino}pyrrolidine-2-carboxylic acid;

(2S,3S,4S,5S)-3-tert-butyl-1-(cyclohexanecarbonyl)-4-({[2-methoxy-5-(1-methylcyclobutyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[4-hydroxy-4-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(4-phenoxybenzoyl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{4-[(oxan-4-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-{4-[(pyridin-2-yl)oxy]benzoyl}pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[4-(trifluoromethoxy)benzoyl]pyrrolidine-2-carboxylic acid;

(2S,3S,4S,5S)-3-tert-butyl-4-{[(5-tert-butyl-2-methoxyphenyl)methyl]amino}-1-(4,4-difluorocyclohexane-1-carbonyl)-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(3,5-dimethylcyclohexane-1-carbonyl)pyrrolidine-2-carboxylic acid;

(2S,3S,4S,5S)-3-(bicyclo[1.1.1]pentan-1-yl)-1-(cyclohexanecarbonyl)-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(2R*)-2,3-dihydro-1,4-benzodioxine-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(2S*)-2,3-dihydro-1,4-benzodioxine-2-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(1R*,2R*,3S*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-[(2R*)-2,3-dihydro-1,4-benzodioxine-2-carbonyl]-5-phenylpyrrolidine-2-carboxylic acid;

(2S,3S,4S,5S)-3-tert-butyl-4-{[(5-cyclobutyl-2-methoxypyridin-3-yl)methyl]amino}-1-(2,3-dihydro-1,4-benzodioxine-6-carbonyl)-5-phenylpyrrolidine-2-carboxylic acid;

(2S,3S,4S,5S)-3-tert-butyl-4-{[(5-cyclobutyl-2-methoxypyridin-3-yl)methyl]amino}-1-(6-fluoro-3,4-dihydro-2H-1-benzopyran-2-carbonyl)-5-phenylpyrrolidine-2-carboxylic acid;

(2S,3S,4S,5S)-3-tert-butyl-4-{[(2-tert-butyl-4-methoxypyrimidin-5-yl)methyl]amino}-1-[(1R*)-3,3-difluorocyclohexane-1-carbonyl]-5-phenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2R)-oxane-2-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1R,3R)-3-methoxycyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(3R*)-3,4-dihydro-1H-2-benzopyran-3-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-1-[(3S*)-3,4-dihydro-1H-2-benzopyran-3-carbonyl]-5-[2-(dimethylamino)pyridin-3-yl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2S*)-6-fluoro-3,4-dihydro-2H-1-benzopyran-2-carbonyl]pyrrolidine-2-carboxylic acid;

(2S,3S,4S,5S)-1-(bicyclo[3.1.0]hexane-6-carbonyl)-3-tert-butyl-5-[2-(dimethylamino)pyridin-3-yl]-4-{[2- methoxy-5-(trifluoromethyl)pyridin-3-yl]
amino}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxyphenyl)pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(1R,2R)-2-(trifluoromethyl)cyclohexane-1-carbonyl]pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-methoxypyridin-3-yl)pyrrolidine-2-carboxylic acid;

(2S,3S,4S,5S)-3-tert-butyl-4-({[2-methoxy-4-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-(3,3-difluorocyclohexane-1-carbonyl)-5-[2-(dimethylamino)pyridin-3-yl]-4-{[2-methoxy-5-(trifluoromethyl)pyridin-3-yl]amino}pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-[(2R*)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)pyridin-3-yl]-1-[(2S*)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-[2-(dimethylamino)pyridin-3-yl]-1-(oxane-2-carbonyl)pyrrolidine-2-carboxylic acid;

(2S,3S,4S,5S)-3-tert-butyl-4-{[(5-cyclobutyl-2-methoxypyridin-3-yl)methyl]amino}-1-(3,3-difluorocyclohexane-1-carbonyl)-5-phenylpyrrolidine-2-carboxylic acid;

(2S,3S,4S,5S)-3-tert-butyl-5-[2-(dimethylamino)pyridin-3-yl]-4-({[2-methoxy-5-(1-methylcyclobutyl)phenyl]methyl}amino)-1-[(2R)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-[(2R)-oxane-2-carbonyl]pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-[(2S)-oxane-2-carbonyl]pyrrolidine-2-carboxylic acid;

(2S,3S,4S,5S)-3-tert-butyl-4-{[(6-cyclobutyl-3-methoxypyridazin-4-yl)methyl]amino}-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-[3-(3-chlorophenyl)oxetane-3-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(3-fluorobicyclo[1.1.1]pentane-1-carbonyl)-5-phenylpyrrolidine-2-carboxylic acid;

(2S,3S,4S,5S)-3-tert-butyl-1-(cyclohexanecarbonyl)-4-({[1-(2,2-difluoro-2H-1,3-benzodioxol-5-yl)cyclopropyl]methyl}amino)-5-phenylpyrrolidine-2-carboxylic acid;

(2S,3S,4S,5S)-3-tert-butyl-4-{[2-(4-chlorophenyl)-2-methylpropyl]amino}-1-(cyclohexanecarbonyl)-5-phenylpyrrolidine-2-carboxylic acid;

(2S,3S,4S,5S)-4-({[5-(bicyclo[1.1.1]pentan-1-yl)-2-methoxyphenyl]methyl}amino)-5-[2-(dimethylamino)pyridin-3-yl]-3-(2-methoxypropan-2-yl)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[2-(trifluoromethyl)cyclohexane-1-carbonyl]pyrrolidine-2-carboxylic acid;

(2S,3S,4S,5S)-3-tert-butyl-1-(3,3-difluorocyclohexane-1-carbonyl)-5-[2-(dimethylamino)pyridin-3-yl]-4-{[6-methyl-4-(trifluoromethyl)pyridin-2-yl]amino}pyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[(2S*)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[(1S*,2S*,3S*,4R*)-3-(trifluoromethyl)-7-oxabicyclo[2.2.1]heptane-2-carbonyl]pyrrolidine-2-carboxylic acid;

(2S,3S,4S,5S)-3-tert-butyl-4-{[(5-tert-butyl-2-methoxyphenyl)methyl]amino}-5-[2-(difluoromethoxy)phenyl]-1-[(1R*,2R*,3R*,4S*)-3-(trifluoromethyl)-7-oxabicyclo[2.2.1]heptane-2-carbonyl]pyrrolidine-2-carboxylic acid;

(2S,3S,4S,5S)-3-tert-butyl-1-(3,3-difluorocyclohexane-1-carbonyl)-4-({[2-methoxy-4-(trifluoromethyl)phenyl]methyl}amino)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1S)-3,3-difluorocyclohexane-1-carbonyl]-5-phenylpyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-{[(propan-2-yl)oxy]carbonyl}pyrrolidine-2-carboxylic acid;

(2S,3S,4S,5S)-3-tert-butyl-5-(2-methoxypyridin-3-yl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-5-(2-methoxypyridin-3-yl)-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-4-(trifluoromethyl)phenyl]methyl}amino)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1R,3S)-3-hydroxycyclohexane-1-carbonyl]-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-[(1S,3S)-3-methoxycyclohexane-1-carbonyl]-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-(2-fluorophenyl)pyrrolidine-2-carboxylic acid;

(2S,3S,4S,5S)-1-(bicyclo[3.1.0]hexane-6-carbonyl)-3-tert-butyl-4-{[(5-cyclobutyl-2-methoxypyridin-3-yl)methyl]amino}-5-[2-(dimethylamino)pyridin-3-yl]pyrrolidine-2-carboxylic acid;

(2S,3S,4S,5S)-3-tert-butyl-4-{[(6-tert-butyl-2-methoxypyridin-3-yl)methyl]amino}-5-(2-fluorophenyl)-1-{[(propan-2-yl)oxy]carbonyl}pyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-[2-(dimethylamino)pyridin-3-yl]pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)pyridin-3-yl]-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(1S*,2R*,4R*)-7-oxabicyclo[2.2.1]heptane-2-carbonyl]pyrrolidine-2-carboxylic acid;

(2S,3S,4S,5S)-3-tert-butyl-4-({[2-methoxy-5-(trifluoromethoxy)phenyl]methyl}amino)-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethoxy)phenyl]methyl}amino)pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-(2-fluorophenyl)pyrrolidine-2-carboxylic acid;

(2S,3S,4S,5S)-3-tert-butyl-4-{[(5-tert-butyl-2-methoxyphenyl)methyl]amino}-1-[(1R,3S)-3-hydroxy-3-methylcyclohexane-1-carbonyl]-5-phenylpyrrolidine-2-carboxylic acid;

(2S,3S,4S,5S)-3-tert-butyl-1-(cyclohexanecarbonyl)-5-(2-methoxypyridin-3-yl)-4-[({2-methoxy-5-[(trifluoromethyl)sulfanyl]phenyl}methyl)amino]pyrrolidine-2-carboxylic acid;

(2S,3S,4S,5S)-3-tert-butyl-4-{[(6-tert-butyl-2-methoxypyridin-3-yl)methyl]amino}-1-(cyclohexanecarbonyl)-5-[2-(difluoromethoxy)phenyl]pyrrolidine-2-carboxylic acid;

(2S,3S,4S,5S)-3-tert-butyl-4-[({2-methoxy-5-[(trifluoromethyl)sulfanyl]phenyl}methyl)amino]-5-phenyl-1-{[(propan-2-yl)oxy]carbonyl}pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethyl)pyridin-3-yl]methyl}amino)pyrrolidine-2-carboxylic acid;

(2S,3S,4S,5S)-3-tert-butyl-4-{[(5-cyclobutyl-2-methoxypyridin-3-yl)methyl]amino}-5-(2-fluorophenyl)-1-[(2S)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-1-[(1R,3R)-3-fluorocyclohexane-1-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(1R,3R)-3-hydroxy-3-methylcyclohexane-1-carbonyl]-5-phenylpyrrolidine-2-carboxylic acid;

(2S,3S,4S,5S)-3-tert-butyl-4-[({2-methoxy-5-[(1S,3s)-tricyclo[3.3.1.1³,⁷]decan-1-yl]phenyl}methyl)amino]-5-phenyl-1-{[(propan-2-yl)oxy]carbonyl}pyrrolidine-2-carboxylic acid;

(2S,3S,4S,5S)-3-tert-butyl-4-({[2-methoxy-5-(pentafluoro-λ⁶-sulfanyl)phenyl]methyl}amino)-5-phenyl-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1R,2S,4S)-7-oxabicyclo[2.2.1]heptane-2-carbonyl]-5-[2-(propan-2-yl)phenyl]pyrrolidine-2-carboxylic acid;

(2S,3S,4S,5S)-3-tert-butyl-4-({[2-methoxy-5-(1-methylcyclobutyl)phenyl]methyl}amino)-5-phenyl-1-{[(propan-2-yl)oxy]carbonyl}pyrrolidine-2-carboxylic acid;

(2S,3S,4S,5S)-3-tert-butyl-1-[(1R,3S)-3-hydroxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(2S)-2-phenylpropanoyl]pyrrolidine-2-carboxylic acid;

(2S,3S,4S,5S)-3-tert-butyl-4-{[(5-tert-butyl-2-methoxyphenyl)methyl]amino}-5-(2-methoxypyridin-3-yl)-1-[(1R,3R)-3-(trifluoromethoxy)cyclohexane-1-carbonyl]pyrrolidine-2-carboxylic acid;

(2S,3S,4S,5S)-3-tert-butyl-5-(2-methoxypyridin-3-yl)-4-({[2-methoxy-5-(trifluoromethyl)phenyl]methyl}amino)-1-[(2R)-2-phenylpropanoyl]pyrrolidine-2-carboxylic acid;

(2S,3S,4S,5S)-3-tert-butyl-5-(2-methoxypyridin-3-yl)-4-({[2-methoxy-5-(trifluoromethoxy)phenyl]methyl}amino)-1-[(2R)-2-phenylpropanoyl]pyrrolidine-2-carboxylic acid;

(2S,3S,4S,5S)-3-tert-butyl-4-{[(5-tert-butyl-2-methoxyphenyl)methyl]amino}-1-[(1R,2S,4S)-7-oxabicyclo[2.2.1]heptane-2-carbonyl]-5-phenylpyrrolidine-2-carboxylic acid;

(2S,3S,4S,5S)-3-(bicyclo[1.1.1]pentan-1-yl)-5-(2-fluorophenyl)-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-1-(cyclohexanecarbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-5-(2-fluorophenyl)-4-({[2-methoxy-5-(1-methylcyclobutyl)phenyl]methyl}amino)-1-[(2S)-oxane-2-carbonyl]pyrrolidine-2-carboxylic acid;

(2S,3S,4S,5S)-3-tert-butyl-5-[2-(dimethylamino)pyridin-3-yl]-4-{[(4-methoxy[1,1'-biphenyl]-3-yl)methyl]amino}-1-{[(propan-2-yl)oxy]carbonyl}pyrrolidine-2-carboxylic acid;

(2S,3S,4S,5S)-3-tert-butyl-4-{[(6-cyclobutyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-cyclobutyl-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-5-(trifluoromethyl)phenyl]methyl}amino)-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-({[2-methoxy-5-(trifluoromethoxy)phenyl]methyl}amino)-1-[[(propan-2-yl)oxy]carbonyl}pyrrolidine-2-carboxylic acid;

(2S,3S,4S,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4R,5S)-3-tert-butyl-4-{[(3-methoxynaphthalen-2-yl)methyl]amino}-5-phenyl-1-{[(propan-2-yl)oxy]carbonyl}pyrrolidine-2-carboxylic acid;

(2S,3S,4R,5S)-3-tert-butyl-4-{[(6-methoxy-2,3-dihydro-1H-inden-5-yl)methyl]amino}-5-phenyl-1-{[(propan-2-yl)oxy]carbonyl}pyrrolidine-2-carboxylic acid;

(2S,3S,4R,5S)-3-tert-butyl-4-({[2-methoxy-5-(trifluoromethyl)phenyl]methyl}amino)-5-phenyl-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-4-({[2-methoxy-4-(trifluoromethyl)phenyl]methyl}amino)-1-(3-methylbutanoyl)-5-phenylpyrrolidine-2-carboxylic acid;

(2S,3S,4S,5S)-3-tert-butyl-5-[2-(dimethylamino)pyridin-3-yl]-4-[({2-methoxy-5-[1-(trifluoromethyl)cyclopropyl]phenyl}methyl)amino]-1-{[(propan-2-yl)oxy]carbonyl}pyrrolidine-2-carboxylic acid;

(2S,3S,4S,5S)-3-tert-butyl-4-({[2-methoxy-5-(trifluoromethoxy)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-4-({[2-methoxy-4-(trifluoromethyl)phenyl]methyl}amino)-1-{[(propan-2-yl)oxy]carbonyl}-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(3-methoxynaphthalen-2-yl)methyl]amino}-1-{[(propan-2-yl)oxy]carbonyl}pyrrolidine-2-carboxylic acid;

(2S,3S,4S,5S)-3-tert-butyl-5-[2-(dimethylamino)pyridin-3-yl]-4-{[(6-methoxy-2,3-dihydro-1H-inden-5-yl)methyl]amino}-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-(3-methylbutanoyl)-5-phenylpyrrolidine-2-carboxylic acid;

(2S,3S,4S,5S)-3-tert-butyl-5-[2-(dimethylamino)pyridin-3-yl]-4l-[[(3-methoxy-5,6,7,8-tetrahydronaphthalen-2-yl)methyl]amino}-1-{[(propan-2-yl)oxy]carbonyl}pyrrolidine-2-carboxylic acid;

(2S,3S,4S,5S)-3-tert-butyl-4-{[(5-cyclobutyl-2-methoxypyridin-3-yl)methyl]amino}-5-(2-fluorophenyl)-1-[(2R)-oxane-2-carbonyl]pyrrolidine-2-carboxylic acid;

(2S,3S,4S,5S)-3-tert-butyl-4-{[(5-chloro-2-methoxyphenyl)methyl]amino}-1-{[(propan-2-yl)oxy]carbonyl}-5-[2-(propan-2-yl)phenyl]pyrrolidine-2-carboxylic acid;

(2S,3S,4S,5S)-3-tert-butyl-4-{[(5-chloro-2-methoxyphenyl)methyl]amino}-5-[2-(dimethylamino)pyridin-3-yl]-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-1-[(1S)-6-methoxy-1-methyl-2,3-dihydro-1H-indene-1-carbonyl]-5-(2-methoxypyridin-3-yl)pyrrolidine-2-carboxylic acid;

(2S,3S,4S,5S)-3-tert-butyl-4-{[(5-tert-butyl-2-methoxyphenyl)methyl]amino}-1-[(1R)-6-methoxy-1-methyl-2,3-dihydro-1H-indene-1-carbonyl]-5-(2-methoxypyridin-3-yl)pyrrolidine-2-carboxylic acid;

(2S,3S,4S,5S)-3-tert-butyl-1-[(1S,3S)-3-methoxycyclohexane-1-carbonyl]-4-({[2-methoxy-4-(trifluoromethyl)phenyl]methyl}amino)-5-phenylpyrrolidine-2-carboxylic acid;

(2S,3S,4S,5S)-3-tert-butyl-1-[(1R)-3,3-difluorocyclohexane-1-carbonyl]-5-(2-methoxypyridin-3-yl)-4-({[2-methoxy-5-(trifluoromethyl)pyridin-3-yl]methyl}amino)pyrrolidine-2-carboxylic acid;

(2S,3S,4S,5S)-3-tert-butyl-1-(cyclohexanecarbonyl)-5-(2-methoxypyridin-3-yl)-4-({[2-methoxy-5-(trifluoromethyl)phenyl]methyl}amino)pyrrolidine-2-carboxylic acid;

(2S,3S,4S,5S)-3-tert-butyl-4-{[(6-methoxy-2,3-dihydro-1H-inden-5-yl)methyl]amino}-1-{[(propan-2-yl)oxy]carbonyl}-5-{2-[(propan-2-yl)oxy]pyridin-3-yl}pyrrolidine-2-carboxylic acid;

(2S,3S,4S,5S)-3-tert-butyl-1-(cyclohexanecarbonyl)-5-(2-methylphenyl)-4-{[6-methyl-4-(trifluoromethyl)pyridin-2-yl]amino}pyrrolidine-2-carboxylic acid;

(2S,3S,4S,5S)-3-tert-butyl-4-{[(5-tert-butyl-2-methoxyphenyl)methyl]amino}-1-(cyclohexanecarbonyl)-5-(2-methylphenyl)pyrrolidine-2-carboxylic acid;

(2S,3S,4S,5S)-3-tert-butyl-5-[2-(dimethylamino)pyridin-3-yl]-4-({[2-methoxy-5-(pyrrolidin-1-yl)pyridin-3-yl]methyl}amino)-1-{[(propan-2-yl)oxy]carbonyl}pyrrolidine-2-carboxylic acid;

(2S,3S,4S,5S)-3-tert-butyl-4-({[2-methoxy-5-(1-methylcyclobutyl)phenyl]methyl}amino)-5-(2-methylphenyl)-1-[(2S)-oxolane-2-carbonyl]pyrrolidine-2-carboxylic acid;

(2S,3S,4S,5S)-3-tert-butyl-4-{[(2-methoxyquinolin-3-yl)methyl]amino}-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)pyridin-3-yl]methyl}amino)-5-(2-methylphenyl)-1-{[(propan-2-yl)oxy]carbonyl}pyrrolidine-2-carboxylic acid;

(2S,3S,4S,5S)-3-tert-butyl-4-({[2-methoxy-5-(trifluoromethyl)phenyl]methyl}amino)-5-(2-methylphenyl)-1-{[(propan-2-yl)oxy]carbonyl}pyrrolidine-2-carboxylic acid;

(2S,3S,4S,5S)-3-tert-butyl-4-{[(5-tert-butyl-2-methoxyphenyl)methyl]amino}-5-(2-methylphenyl)-1-{[(propan-2-yl)oxy]carbonyl}pyrrolidine-2-carboxylic acid;

(2S,3S,4S,5S)-4-[({1-[(benzyloxy)carbonyl]piperidin-3-yl}methyl)amino]-3-tert-butyl-5-phenyl-1-{[(propan-2-yl)oxy]carbonyl}pyrrolidine-2-carboxylic acid;

(2S,3S,4S,5S)-3-tert-butyl-5-phenyl-1-{[(propan-2-yl)oxy]carbonyl}-4-({[3-(trifluoromethyl)cyclohexyl]methyl}amino)pyrrolidine-2-carboxylic acid;

(2S,3S,4S,5S)-3-tert-butyl-4-{[(5-cyclobutyl-2-methoxypyridin-3-yl)methyl]amino}-5-(2-methylphenyl)-1-[(2S)-oxane-2-carbonyl]pyrrolidine-2-carboxylic acid;

(2S,3S,4S,5S)-3-tert-butyl-5-(2-cyclopropylpyridin-3-yl)-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-3-tert-butyl-5-(2-cyclopropylpyridin-3-yl)-4-({[2-methoxy-4-(trifluoromethyl)phenyl]methyl}amino)-1-[(2S)-oxolane-2-carbonyl]pyrrolidine-2-carboxylic acid;

(2S,3S,4S,5S)-3-tert-butyl-4-{[(5-cyclobutyl-2-methoxy-pyridin-3-yl)methyl]amino}-5-(2-cyclopropylpyridin-3-yl)-1-[(2S)-oxolane-2-carbonyl]pyrrolidine-2-carboxylic acid;

(2S,3S,4S,5S)-3-tert-butyl-1-(3,3-difluorocyclopentane-1-carbonyl)-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-1-[(2S)-2-methoxypropanoyl]-4-({[2-methoxy-5-(trifluoromethyl)pyridin-3-yl]methyl}amino)-5-[2-(propan-2-yl)phenyl]pyrrolidine-2-carboxylic acid;

(2S,3S,4S,5S)-3-tert-butyl-4-({[2-methoxy-5-(trifluoromethyl)pyridin-3-yl]methyl}amino)-1-(oxane-4-carbonyl)-5-[2-(propan-2-yl)phenyl]pyrrolidine-2-carboxylic acid;

(2S,3S,4S,5S)-5-[2-(azetidin-1-yl)pyridin-3-yl]-3-tert-butyl-4-({[2-methoxy-5-(trifluoromethyl)pyridin-3-yl]methyl}amino)-1-{[(propan-2-yl)oxy]carbonyl}pyrrolidine-2-carboxylic acid;

(2S,3S,4S,5S)-3-tert-butyl-4-({[2-methoxy-5-(1-methylcyclobutyl)phenyl]methyl}amino)-1-[(2S)-oxolane-2-carbonyl]-5-[2-(propan-2-yl)phenyl]pyrrolidine-2-carboxylic acid;

(2S,3S,4S,5S)-4-{[(5-bromo-2-methoxypyridin-3-yl)methyl]amino}-3-tert-butyl-1-[(2S)-oxolane-2-carbonyl]-5-[2-(propan-2-yl)phenyl]pyrrolidine-2-carboxylic acid;

(2S,3S,4S,5S)-3-tert-butyl-4-({[2-methoxy-5-(trifluoromethyl)phenyl]methyl}amino)-1-[(2S)-oxolane-2-carbonyl]-5-[2-(propan-2-yl)phenyl]pyrrolidine-2-carboxylic acid;

(2S,3S,4S,5S)-3-tert-butyl-5-[2-(dimethylamino)pyridin-3-yl]-4-({[2-methoxy-5-(trifluoromethyl)pyridin-3-yl]methyl}amino)-1-[(2S)-oxolane-2-carbonyl]pyrrolidine-2-carboxylic acid;

(2S,3S,4S,5S)-3-tert-butyl-4-{[(5-cyclobutyl-2-methoxy-pyridin-3-yl)methyl]amino}-5-[2-(difluoromethyl)phenyl]-1-[(2S)-oxolane-2-carbonyl]pyrrolidine-2-carboxylic acid;

(2S,3S,4S,5S)-3-tert-butyl-4-{[(2-methoxyquinolin-3-yl)methyl]amino}-1-(oxane-4-carbonyl)-5-[2-(propan-2-yl)phenyl]pyrrolidine-2-carboxylic acid;

(2S,3S,4S,5S)-3-tert-butyl-5-[2-(dimethylamino)pyridin-3-yl]-4-{[(2-methoxyquinolin-3-yl)methyl]amino}-1-[(2S)-oxolane-2-carbonyl]pyrrolidine-2-carboxylic acid;

(2S,3S,4S,5S)-3-tert-butyl-5-[2-(dimethylamino)pyridin-3-yl]-4-{[(2-methoxyquinolin-3-yl)methyl]amino}-1-(oxane-4-carbonyl)pyrrolidine-2-carboxylic acid;

rac-(2R,3R,4R,5R)-3-tert-butyl-4-{[(2-chlorophenyl)methyl]amino}-1-(cyclopentylacetyl)-5-phenylpyrrolidine-2-carboxylic acid;

rac-(2R,3R,4R,5R)-3-tert-butyl-1-(cyclopentylacetyl)-4-{[(2-methylphenyl)methyl]amino}-5-phenylpyrrolidine-2-carboxylic acid;

rac-(2R,3R,4R,5R)-3-tert-butyl-1-(cyclopentylacetyl)-4-{[(2,4-dichlorophenyl)methyl]amino}-5-phenylpyrrolidine-2-carboxylic acid;

rac-(2R,3R,4R,5R)-3-tert-butyl-1-(cyclohexanecarbonyl)-5-phenyl-4-{[4-(trifluoromethyl)pyridin-2-yl]amino}pyrrolidine-2-carboxylic acid;

rac-(2R,3R,4R,5R)-3-tert-butyl-1-(cyclohexanecarbonyl)-5-phenyl-4-{[5-(trifluoromethyl)pyridin-2-yl]amino}pyrrolidine-2-carboxylic acid;

rac-(2R,3R,4R,5R)-3-tert-butyl-4-[(4-chloropyridin-2-yl)amino]-1-(cyclohexanecarbonyl)-5-phenylpyrrolidine-2-carboxylic acid;

rac-(2R,3R,4R,5R)-3-tert-butyl-1-(cyclohexanecarbonyl)-4-({[2-(difluoromethoxy)phenyl]methyl}amino)-5-phenylpyrrolidine-2-carboxylic acid;

rac-(2R,3R,4R,5R)-3-tert-butyl-1-(cyclohexanecarbonyl)-4-[(6-methoxypyridin-2-yl)amino]-5-phenylpyrrolidine-2-carboxylic acid;

rac-(2R,3R,4R,5R)-3-tert-butyl-4-{[(3-chloro-2-hydroxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-[({6-[(oxan-4-yl)oxy]pyridin-2-yl}methyl)amino]-5-phenylpyrrolidine-2-carboxylic acid;

rac-(2R,3R,4R,5R)-3-tert-butyl-1-(cyclohexanecarbonyl)-4-{[(2,5-dimethoxyphenyl)methyl]amino}-5-phenylpyrrolidine-2-carboxylic acid;

rac-(2R,3R,4R,5R)-3-tert-butyl-1-(cyclohexanecarbonyl)-4-{[(2-methoxyphenyl)methyl]amino}-5-phenylpyrrolidine-2-carboxylic acid;

rac-(2R,3R,4R,5R)-3-tert-butyl-1-(cyclohexanecarbonyl)-4-{[(2,3-dimethoxyphenyl)methyl]amino}-5-phenylpyrrolidine-2-carboxylic acid;

rac-(2R,3R,4R,5R)-3-tert-butyl-1-(cyclohexanecarbonyl)-4-{[(3-methoxyphenyl)methyl]amino}-5-phenylpyrrolidine-2-carboxylic acid;

rac-(2R,3R,4R,5R)-3-tert-butyl-4-{[(3-chloro-2,4-dimethoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[(4-methoxypyridin-3-yl)methyl]amino}-5-phenylpyrrolidine-2-carboxylic acid;

rac-(2R,3R,4R,5R)-3-tert-butyl-1-(cyclohexanecarbonyl)-4-{[6-methoxy-4-(trifluoromethyl)pyridin-2-yl](methyl)amino}-5-phenylpyrrolidine-2-carboxylic acid;

rac-(2R,3R,4R,5R)-3-tert-butyl-1-(cyclohexanecarbonyl)-4-[(2,2-difluoro-2H-1,3-benzodioxol-5-yl)amino]-5-phenylpyrrolidine-2-carboxylic acid;

rac-(2R,3R,4R,5R)-3-tert-butyl-1-(cyclohexanecarbonyl)-4-{[(6-methoxypyridin-2-yl)methyl]amino}-5-phenylpyrrolidine-2-carboxylic acid;

rac-(2R,3R,4R,5R)-3-tert-butyl-4-{[(5-chloro-2,4-dimethoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[(3-methoxypyridin-2-yl)methyl]amino}-5-phenylpyrrolidine-2-carboxylic acid;

rac-(2R,3R,4R,5R)-3-tert-butyl-1-(cyclohexanecarbonyl)-4-{[(4-methoxypyrimidin-2-yl)methyl]amino}-5-phenylpyrrolidine-2-carboxylic acid;

rac-(2R,3R,4R,5R)-3-tert-butyl-1-(cyclohexanecarbonyl)-4-{[6-oxo-4-(trifluoromethyl)-1,6-dihydropyridin-2-yl]amino}-5-phenylpyrrolidine-2-carboxylic acid;

rac-(2R,3R,4R,5R)-3-tert-butyl-1-(cyclohexanecarbonyl)-4-({[1-(2-methoxyethyl)-1H-imidazol-2-yl]methyl}amino)-5-phenylpyrrolidine-2-carboxylic acid;

rac-(2R,3R,4R,5R)-3-tert-butyl-1-(cyclohexanecarbonyl)-4-{[(6-methoxypyridin-3-yl)methyl]amino}-5-phenylpyrrolidine-2-carboxylic acid;

rac-(2R,3R,4R,5R)-3-tert-butyl-4-{[(5-chloro-2,3-dimethoxyphenyl)methyl]amino}-1-(cyclohexanecarbonyl)-5-phenylpyrrolidine-2-carboxylic acid;

rac-(2R,3R,4R,5R)-3-tert-butyl-4-{[(5-chloro-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-({[2-(morpholin-4-yl)pyridin-3-yl]methyl}amino)-5-phenylpyrrolidine-2-carboxylic acid;

rac-(2R,3R,4R,5R)-3-tert-butyl-1-(cyclohexanecarbonyl)-4-{[(2,4-dimethoxypyrimidin-5-yl)methyl]amino}-5-phenylpyrrolidine-2-carboxylic acid;

rac-(2R,3R,4R,5R)-3-tert-butyl-4-{[(4-chloro-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-{[1-oxo-4-(trifluoromethyl)-1$\lambda^5$-pyridin-2-yl]amino}-5-phenylpyrrolidine-2-carboxylic acid;

rac-(2R,3R,4R,5R)-3-tert-butyl-1-(cyclohexanecarbonyl)-4-{[6-methyl-1-oxo-4-(trifluoromethyl)-1-pyridin-2-yl]amino}-5-phenylpyrrolidine-2-carboxylic acid;

rac-(2R,3R,4R,5R)-1-(cyclohexanecarbonyl)-3-cyclopropyl-5-phenyl-4-{[4-(trifluoromethyl)pyridin-2-yl]amino}pyrrolidine-2-carboxylic acid;

rac-(2R,3R,4R,5R)-4-({[2-(difluoromethoxy)phenyl]methyl}amino)-1-[di(propan-2-yl)carbamoyl]-3-methyl-5-phenylpyrrolidine-2-carboxylic acid;

rac-(2R,3R,4R,5R)-3-tert-butyl-1-(cyclohexanecarbonyl)-4-({[2-methoxy-4-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-4-({[2-(dimethylamino)-5-(trifluoromethyl)pyridin-3-yl]methyl}amino)-5-phenylpyrrolidine-2-carboxylic acid;

rac-(2R,3R,4R,5R)-4-{[(5-chloro-2-methoxyphenyl)methyl]amino}-1-[di(propan-2-yl)carbamoyl]-3-methyl-5-phenylpyrrolidine-2-carboxylic acid;

rac-(2R,3R,4R,5R)-3-tert-butyl-5-phenyl-1-{[(propan-2-yl)oxy]carbonyl}-4-{[4-(trifluoromethyl)pyridin-2-yl]amino}pyrrolidine-2-carboxylic acid;

rac-(2R,3R,4R,5R)-4-{[(4-chloro-2-methoxyphenyl)methyl]amino}-1-[di(propan-2-yl)carbamoyl]-3-methyl-5-phenylpyrrolidine-2-carboxylic acid;

rac-(2R,3R,4R,5R)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid;

rac-(2R,3R,4R,5R)-3-tert-butyl-1-(cyclohexanecarbonyl)-5-[2-(dimethylamino)pyridin-3-yl]-4-({[2-methoxy-5-(trifluoromethyl)phenyl]methyl}amino)pyrrolidine-2-carboxylic acid;

rac-(2R,3R,4R,5R)-3-tert-butyl-4-[(4-cyanopyridin-2-yl)amino]-1-(cyclohexanecarbonyl)-5-phenylpyrrolidine-2-carboxylic acid;

rac-(2R,3R,4R,5R)-3-tert-butyl-5-phenyl-1-{[(propan-2-yl)oxy]carbonyl}-4-{[6-(trifluoromethyl)pyridin-2-yl]amino}pyrrolidine-2-carboxylic acid;

rac-(2R,3R,4R,5R)-3-tert-butyl-1-(cyclohexanecarbonyl)-4-{[(2,2-difluoro-2H-1,3-benzodioxol-4-yl)methyl]amino}-5-(2-methoxyphenyl)pyrrolidine-2-carboxylic acid;

rac-(2R,3R,4R,5R)-3-tert-butyl-1-(cyclohexanecarbonyl)-5-[2-(dimethylamino)pyridin-3-yl]-4-{[6-methyl-4-(trifluoromethyl)pyridin-2-yl]amino}pyrrolidine-2-carboxylic acid;

rac-(2R,3R,4R)-3-cyclopropyl-1-[di(propan-2-yl)carbamoyl]-4-{[6-methyl-4-(trifluoromethyl)pyridin-2-yl]amino}-5-phenylpyrrolidine-2-carboxylic acid;

rac-(2R,3R,4R,5R)-4-{[(5-chloro-2-methoxyphenyl)methyl]amino}-3-cyclopropyl-1-[di(propan-2-yl)carbamoyl]-5-phenylpyrrolidine-2-carboxylic acid;

rac-(2R,3R,4R,5R)-3-tert-butyl-1-(cyclohexanecarbonyl)-N-(2-methoxyethanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(2-methylpropane-2-sulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(1-methylcyclopropane-1-sulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(cyclopropanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(ethanesulfonyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(dimethylsulfamoyl)-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-[ethyl(methyl)sulfamoyl]-4-{[6-methyl-4-(trifluoromethyl)pyridin-2-yl]amino}-5-phenylpyrrolidine-2-carboxamide;

rac-(2R,3R,4R,5R)-3-tert-butyl-1-(cyclohexanecarbonyl)-N-(methanesulfonyl)-4-{[6-methyl-4-(trifluoromethyl)pyridin-2-yl]amino}-5-phenylpyrrolidine-2-carboxamide;

rac-(4R,6R,7R)-5-(cyclohexanecarbonyl)-7-({[2-(difluoromethoxy)phenyl]methyl}amino)-6-phenyl-5-azaspiro[2.4]heptane-4-carboxylic acid;

rac-(2R,3R,4R,5S)-3-tert-butyl-4-({[2-(difluoromethoxy)phenyl]methyl}amino)-5-(6-methoxypyridin-2-yl)-1-[(1R,5S,6S)-3-oxabicyclo[3.1.0]hexane-6-carbonyl]pyrrolidine-2-carboxylic acid;

rac-(2R,3R,4R,5S)-3-tert-butyl-4-({[2-(difluoromethoxy)phenyl]methyl}amino)-1-[di(propan-2-yl)carbamoyl]-5-(6-methoxypyridin-2-yl)pyrrolidine-2-carboxylic acid;

rac-(2R,3R,4R,5S)-3-tert-butyl-1-(cyclohexanecarbonyl)-4-({[2-methoxy-5-(trifluoromethyl)phenyl]methyl}amino)-5-(pyridin-2-yl)pyrrolidine-2-carboxylic acid;

rac-(2R,3R,4R,5S)-3-tert-butyl-4-{[(5-chloro-2-methoxyphenyl)methyl]amino}-1-(cyclohexanecarbonyl)-5-(pyridin-2-yl)pyrrolidine-2-carboxylic acid;

rac-(2R,3R,4R,5S)-3-tert-butyl-5-(6-methoxypyridin-2-yl)-4-{[6-methyl-4-(trifluoromethyl)pyridin-2-yl]amino}-1-(3-oxabicyclo[3.1.0]hexane-6-carbonyl)pyrrolidine-2-carboxylic acid;

rac-(2R,3R,4R,5S)-3-tert-butyl-5-(6-methoxypyridin-2-yl)-4-{[6-methyl-4-(trifluoromethyl)pyridin-2-yl]amino}-1-(oxane-2-carbonyl)pyrrolidine-2-carboxylic acid;

rac-(2R,3R,4R,5R)-3-tert-butyl-1-(cyclohexanecarbonyl)-4-({[2-(2-methoxyethoxy)-5-(trifluoromethyl)phenyl]methyl}amino)-5-phenylpyrrolidine-2-carboxylic acid;

rac-(2S,3S,4S,5S)-3-tert-butyl-1-(cyclohexanecarbonyl)-4-({[1-(2-methoxyethyl)-2-oxo-5-(trifluoromethyl)-1,2-dihydropyridin-3-yl]methyl}amino)-5-phenylpyrrolidine-2-carboxylic acid;

rac-(2R,3R,4R,5R)-3-tert-butyl-1-(cyclohexanecarbonyl)-4-({[2-(2-hydroxyethoxy)-5-(trifluoromethyl)phenyl]methyl}amino)-5-phenylpyrrolidine-2-carboxylic acid;

rac-(2R,3R,4R,5S)-3-tert-butyl-4-{[(4-chloro-2-methoxyphenyl)methyl]amino}-1-(cyclohexanecarbonyl)-5-(6-methoxypyridin-2-yl)pyrrolidine-2-carboxylic acid;

(2R,3R,4R,5R)-3-tert-butyl-1-[(2R)-2-methoxy-2-phenylacetyl]-4-({[2-methoxy-5-(trifluoromethyl)phenyl]methyl}amino)-5-phenylpyrrolidine-2-carboxylic acid;

rac-(2S,3S,4S,5R)-3-tert-butyl-5-(6-methoxypyridin-2-yl)-4-({[2-methoxy-5-(trifluoromethyl)phenyl]methyl}amino)-1-(oxane-3-carbonyl)pyrrolidine-2-carboxylic acid;

rac-(2S,3S,4S,5R)-3-tert-butyl-5-(6-methoxypyridin-2-yl)-4-({[2-methoxy-5-(trifluoromethyl)phenyl]methyl}amino)-1-[(3R*)-3-methyloxane-3-carbonyl]pyrrolidine-2-carboxylic acid;

rac-(2R,3R,4R,5R)-3-tert-butyl-5-[2-(dimethylamino)phenyl]-4-({[2-methoxy-5-(trifluoromethyl)phenyl]methyl}amino)-1-(3-oxabicyclo[3.1.0]hexane-6-carbonyl)pyrrolidine-2-carboxylic acid;

rac-(2R,3R,4R,5R)-3-tert-butyl-4-({[2-chloro-5-(2-methoxyethoxy)pyridin-4-yl]methyl}amino)-1-(cyclohexanecarbonyl)-5-phenylpyrrolidine-2-carboxylic acid;

rac-(2R,3R,4R,5R)-3-tert-butyl-4-{[(2-chloro-5-hydroxypyridin-4-yl)methyl]amino}-1-(cyclohexanecarbonyl)-5-phenylpyrrolidine-2-carboxylic acid;

rac-(2R,3R,4R,5R)-4-({[2-amino-5-(trifluoromethyl)pyridin-3-yl]methyl}amino)-3-tert-butyl-1-(cyclohexanecarbonyl)-5-phenylpyrrolidine-2-carboxylic acid;

(2R,3R,4R,5R)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid;

rac-(2S,3S,4S,5R)-3-tert-butyl-4-{[6-(difluoromethoxy)pyridin-2-yl]amino}-5-(6-methoxypyridin-2-yl)-1-(3-methyloxane-3-carbonyl)pyrrolidine-2-carboxylic acid;

rac-(2S,3S,4S,5S)-3-tert-butyl-5-[2-(dimethylamino)phenyl]-4-({[2-methoxy-5-(trifluoromethyl)phenyl]methyl}amino)-1-(3-methyloxane-3-carbonyl)pyrrolidine-2-carboxylic acid;

(2S,3S,4S,5S)-3-tert-butyl-1-[(2R)-2-methoxy-2-phenylacetyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(cyclohexanecarbonyl)-4-({[2-hydroxy-5-(methanesulfonyl)phenyl]methyl}amino)-5-phenylpyrrolidine-2-carboxylic acid;

rac-(2R,3R,4R,5R)-3-tert-butyl-1-(cyclohexanecarbonyl)-4-({[2-(2-methoxyethoxy)-5-(trifluoromethyl)pyridin-3-yl]methyl}amino)-5-phenylpyrrolidine-2-carboxylic acid;

rac-(2R,3R,4R,5R)-3-tert-butyl-1-(cyclohexanecarbonyl)-4-({[2-methoxy-5-(trifluoromethyl)pyridin-3-yl]methyl}amino)-5-phenylpyrrolidine-2-carboxylic acid;

rac-(2R,3R,4R,5S)-3-tert-butyl-4-{[(4-chloro-2-methoxyphenyl)methyl]amino}-1-(cyclohexanecarbonyl)-5-(pyridin-2-yl)pyrrolidine-2-carboxylic acid;

rac-(2R,3R,4R,5R)-3-tert-butyl-4-{[(2-cyanophenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-[({2-[3-(methanesulfonyl)propoxy]-5-(trifluoromethyl)phenyl}methyl)amino]-5-phenylpyrrolidine-2-carboxylic acid;

rac-(2R,3R,4R,5R)-3-tert-butyl-1-(cyclohexanecarbonyl)-4-({[2-(3-fluoropropoxy)-5-(trifluoromethyl)phenyl]methyl}amino)-5-phenylpyrrolidine-2-carboxylic acid;

rac-(2R,3R,4R,5R)-3-tert-butyl-1-(cyclohexanecarbonyl)-5-phenyl-4-[({2-[2-(trifluoromethoxy)ethoxy]-5-(trifluoromethyl)phenyl}methyl)amino]pyrrolidine-2-carboxylic acid;

rac-(2R,3R,4R,5R)-3-tert-butyl-1-(cyclohexanecarbonyl)-4-({[2-(2-hydroxyethoxy)-5-(trifluoromethyl)pyridin-3-yl]methyl}amino)-5-phenylpyrrolidine-2-carboxylic acid;

rac-(2R,3R,4R,5R)-3-tert-butyl-5-[2-(dimethylamino)pyridin-3-yl]-1-[(2R*)-2-methoxy-2-phenylacetyl]-4-({[2-methoxy-5-(trifluoromethyl)phenyl]methyl}amino)pyrrolidine-2-carboxylic acid;

rac-(2R,3R,4R,5R)-3-tert-butyl-5-[2-(dimethylamino)pyridin-3-yl]-1-[(2R)-2-methoxy-2-phenylacetyl]-4-{[6-methyl-4-(trifluoromethyl)pyridin-2-yl]amino}pyrrolidine-2-carboxylic acid;

rac-(2R,3R,4R,5R)-3-tert-butyl-5-[2-(dimethylamino)pyridin-3-yl]-1-[(2S)-2-methoxy-2-phenylacetyl]-4-{[6-methyl-4-(trifluoromethyl)pyridin-2-yl]amino}pyrrolidine-2-carboxylic acid;

rac-(2R,3R,4R,5R)-3-tert-butyl-4-{[(2,4-dimethoxyphenyl)methyl]amino}-5-phenyl-1-{[(propan-2-yl)oxy]carbonyl}pyrrolidine-2-carboxylic acid;

rac-(2R,3R,4R,5R)-3-tert-butyl-4-{[(3-methoxy[1,1'-biphenyl]-4-yl)methyl]amino}-5-phenyl-1-{[(propan-2-yl)oxy]carbonyl}pyrrolidine-2-carboxylic acid;

rac-(2R,3R,4R,5R)-3-tert-butyl-5-[2-(dimethylamino)pyridin-3-yl]-4-{[6-methyl-4-(trifluoromethyl)pyridin-2-yl]amino}-1-{[(propan-2-yl)oxy]carbonyl}pyrrolidine-2-carboxylic acid;

rac-(2R,3R,4R,5R)-3-tert-butyl-4-{[(5-chloro-2-methoxyphenyl)methyl]amino}-1-(cyclohexanecarbonyl)-5-[2-(dimethylamino)pyridin-3-yl]pyrrolidine-2-carboxylic acid;

(2R,3R,4R,5R)-3-tert-butyl-1-(cyclohexanecarbonyl)-5-(2-methoxyphenyl)-4-({[2-methoxy-4-(trifluoromethyl)phenyl]methyl}amino)pyrrolidine-2-carboxylic acid;

rac-(2R,3R,4R,5R)-3-tert-butyl-4-{[(5-chloro-2-methoxyphenyl)methyl]amino}-1-[(cyclobutyloxy)carbonyl]-5-phenylpyrrolidine-2-carboxylic acid;

rac-(2S,3S,4S,5R)-3-tert-butyl-1-(cyclohexanecarbonyl)-5-(6-methoxypyridin-2-yl)-4-{[6-methyl-4-(trifluoromethyl)pyridin-2-yl]amino}pyrrolidine-2-carboxylic acid;

(2R,3R,4R,5R)-3-tert-butyl-5-[2-(dimethylamino)phenyl]-1-[(2R)-2-methoxy-2-phenylacetyl]-4-({[2-methoxy-5-(trifluoromethyl)phenyl]methyl}amino)pyrrolidine-2-carboxylic acid;

(2R,3R,4R,5R)-3-tert-butyl-4-{[(5-chloro-2-methoxyphenyl)methyl]amino}-5-[2-(dimethylamino)phenyl]-1-[(2R)-2-methoxy-2-phenylacetyl]pyrrolidine-2-carboxylic acid;

(2S,3S,4S,5S)-3-tert-butyl-4-({[2-methoxy-5-(trifluoromethyl)phenyl]methyl}amino)-5-phenyl-1-[(2R)-3,3,3-trifluoro-2-methoxy-2-phenylpropanoyl]pyrrolidine-2-carboxylic acid;

(2R,3R,4R,5R)-3-tert-butyl-1-[(2S)-2-methoxy-2-phenylacetyl]-4-({[2-methoxy-4-(trifluoromethyl)phenyl]methyl}amino)-5-phenylpyrrolidine-2-carboxylic acid;

(2R,3R,4R,5R)-3-tert-butyl-4-({[2-methoxy-5-(trifluoromethyl)phenyl]methyl}amino)-5-phenyl-1-[(2R)-3,3,3-trifluoro-2-methoxy-2-phenylpropanoyl]pyrrolidine-2-carboxylic acid;

(2S,3S,4S,5S)-3-tert-butyl-1-[(2S)-2-methoxy-2-phenylacetyl]-4-{[6-methyl-4-(trifluoromethyl)pyridin-2-yl]amino}-5-phenylpyrrolidine-2-carboxylic acid;

rac-(2R,3R,4R,5R)-3-tert-butyl-1-(4,4-difluorocyclohexane-1-carbonyl)-4-{[6-methyl-4-(trifluoromethyl)pyridin-2-yl]amino}-5-phenylpyrrolidine-2-carboxylic acid;

rac-(2R,3R,4R,5R)-3-tert-butyl-4-({[2-methoxy-4-(trifluoromethyl)phenyl]methyl}amino)-5-phenyl-1-(spiro[2.5]octane-6-carbonyl)pyrrolidine-2-carboxylic acid;

rac-(2R,3R,4R,5R)-3-tert-butyl-1-(cyclohexanecarbonyl)-4-({[5-methoxy-2-(trifluoromethyl)phenyl]methyl}amino)-5-phenylpyrrolidine-2-carboxylic acid;

rac-(2R,3R,4R,5R)-3-tert-butyl-4-{[(5-tert-butyl-2-methoxyphenyl)methyl]amino}-1-(cyclohexanecarbonyl)-5-phenylpyrrolidine-2-carboxylic acid;

rac-(2R,3R,4R,5R)-3-tert-butyl-1-(cyclohexanecarbonyl)-4-({[5-fluoro-2-(methanesulfonyl)phenyl]methyl}amino)-5-phenylpyrrolidine-2-carboxylic acid;

rac-(2R,3R,4R,5R)-4-{[(5-bromo-2-cyanophenyl)methyl]amino}-3-tert-butyl-1-(cyclohexanecarbonyl)-5-phenylpyrrolidine-2-carboxylic acid;

rac-(2R,3R,4R,5R)-1-[(1R,2S,4S)-bicyclo[2.2.1]heptane-2-carbonyl]-3-tert-butyl-4-{[6-methyl-4-(trifluoromethyl)pyridin-2-yl]amino}-5-phenylpyrrolidine-2-carboxylic acid;

rac-(2R,3R,4R,5R)-4-[(5-chloro-3-methoxypyridin-2-yl)amino]-1-(cyclohexanecarbonyl)-3-(2-methoxypropan-2-yl)-5-phenylpyrrolidine-2-carboxylic acid;

rac-(2R,3R,4R,5R)-3-tert-butyl-4-[[2-methoxy-4-(trifluoromethyl)phenyl]methylamino]-5-phenyl-1-[(2R*)-2-phenylpropanoyl]pyrrolidine-2-carboxylic acid;

rac-(2R,3R,4R,5R)-3-tert-butyl-1-(1,4-dioxane-2-carbonyl)-4-({[2-methoxy-4-(trifluoromethyl)phenyl]methyl}amino)-5-phenylpyrrolidine-2-carboxylic acid;

rac-(2R,3R,4R,5R)-3-tert-butyl-1-[(cyclobutyloxy)carbonyl]-4-({[2-methoxy-4-(trifluoromethyl)phenyl]methyl}amino)-5-phenylpyrrolidine-2-carboxylic acid;

rac-(2R,3R,4R,5R)-4-{[(4-chloro-2-methoxyphenyl)methyl]amino}-1-(cyclohexanecarbonyl)-3-(2-methoxypropan-2-yl)-5-phenylpyrrolidine-2-carboxylic acid;

rac-(2R,3R,4R,5R)-1-(cyclohexanecarbonyl)-3-(2-methoxypropan-2-yl)-4-({[2-methoxy-5-(trifluoromethyl)pyridin-3-yl]methyl}amino)-5-phenylpyrrolidine-2-carboxylic acid;

(2R,3R,4R,5R)-3-tert-butyl-4-({[2-methoxy-4-(trifluoromethyl)phenyl]methyl}amino)-1-[(2R)-oxane-2-carbonyl]-5-phenylpyrrolidine-2-carboxylic acid;

(2S,3S,4S,5S)-4-{[(5-bromo-2-methoxyphenyl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(3-methoxy-5,5,8,8-tetramethyl-5,6,7,8-tetrahydronaphthalen-2-yl)methyl]amino}-5-phenylpyrrolidine-2-carboxylic acid;

(2S,3S,4S,5S)-3-tert-butyl-1-(cyclohexanecarbonyl)-4-{[(3,4-dihydro-2H-1-benzopyran-6-yl)methyl]amino}-5-phenylpyrrolidine-2-carboxylic acid;

(2S,3S,4S,5S)-3-tert-butyl-4-{[(4-cyano-2-fluorophenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-{[(2,3-dihydro-1-benzofuran-5-yl)methyl]amino}-5-phenylpyrrolidine-2-carboxylic acid;

(2S,3S,4S,5S)-3-tert-butyl-1-(cyclohexanecarbonyl)-4-({[4-fluoro-2-(trifluoromethyl)phenyl]methyl}amino)-5-phenylpyrrolidine-2-carboxylic acid;

(2S,3S,4S,5S)-3-tert-butyl-4-[({5-chloro-2-[(propan-2-yl)oxy]phenyl}methyl)amino]-1-(cyclohexanecarbonyl)-5-phenylpyrrolidine-2-carboxylic acid;

(2S,3S,4S,5S)-3-tert-butyl-4-{[(3-cyano-4-fluorophenyl)methyl]amino}-1-(cyclohexanecarbonyl)-5-phenylpyrrolidine-2-carboxylic acid;

(2S,3S,4S,5S)-3-tert-butyl-4-{[(3-chloro-4-methoxyphenyl)methyl]amino}-1-(cyclohexanecarbonyl)-5-phenylpyrrolidine-2-carboxylic acid;

(2S,3S,4S,5S)-3-tert-butyl-4-{[(2-cyano-4-fluorophenyl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[3-fluoro-4-(trifluoromethoxy)phenyl]methyl}amino)-5-phenylpyrrolidine-2-carboxylic acid;

(2S,3S,4S,5S)-3-tert-butyl-1-(cyclohexanecarbonyl)-4-{[(3,4-dihydro-2H-1,5-benzodioxepin-7-yl)methyl]amino}-5-phenylpyrrolidine-2-carboxylic acid;

(2S,3S,4S,5S)-3-tert-butyl-1-(cyclohexanecarbonyl)-4-{[(3,4-dichlorophenyl)methyl]amino}-5-phenylpyrrolidine-2-carboxylic acid;

(2S,3S,4S,5S)-4-({[5-bromo-2-(difluoromethoxy)phenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-{[(2,2-difluoro-2H-1,3-benzodioxol-5-yl)methyl]amino}-5-phenylpyrrolidine-2-carboxylic acid;

(2S,3S,4S,5S)-3-tert-butyl-1-(cyclohexanecarbonyl)-4-{[(3,5-dimethoxyphenyl)methyl]amino}-5-phenylpyrrolidine-2-carboxylic acid;

(2S,3S,4S,5S)-3-tert-butyl-1-(cyclohexanecarbonyl)-4-{[(3,4-dimethylphenyl)methyl]amino}-5-phenylpyrrolidine-2-carboxylic acid;

(2S,3S,4S,5S)-4-{[(1-benzofuran-5-yl)methyl]amino}-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[2-fluoro-4-(trifluoromethyl)phenyl]methyl}amino)-5-phenylpyrrolidine-2-carboxylic acid;

(2S,3S,4S,5S)-3-tert-butyl-1-[1-(methanesulfonyl)cyclopropane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-5-phenyl-4-({[4-(trifluoromethyl)phenyl]methyl}amino)pyrrolidine-2-carboxylic acid;

(2S,3S,4S,5S)-3-tert-butyl-1-(cyclohexanecarbonyl)-4-({[2-(difluoromethyl)phenyl]methyl}amino)-5-phenylpyrrolidine-2-carboxylic acid;

(2S,3S,4S,5S)-3-tert-butyl-4-{[(7-chloro-2H-1,3-benzodioxol-5-yl)methyl]amino}-1-(cyclohexanecarbonyl)-5-phenylpyrrolidine-2-carboxylic acid;

(2S,3S,4S,5S)-3-tert-butyl-1-(cyclohexanecarbonyl)-4-({[4-(difluoromethoxy)-3,5-dimethylphenyl]methyl}amino)-5-phenylpyrrolidine-2-carboxylic acid;

(2S,3S,4S,5S)-3-tert-butyl-4-{[(6-chloro-2H-1,3-benzo-dioxol-5-yl)methyl]amino}-1-(cyclohexanecarbonyl)-5-phenylpyrrolidine-2-carboxylic acid;

rac-(2S,3S,4S,5R)-3-tert-butyl-4-{[(4-chloro-2-methoxyphenyl)methyl]amino}-1-(cyclohexanecarbonyl)-5-(3-methoxypyridin-2-yl)pyrrolidine-2-carboxylic acid;

(2S,3S,4S,5S)-3-tert-butyl-4-[(4-carbamoyl-6-chloropyridin-2-yl)amino]-1-(cyclohexanecarbonyl)-5-phenylpyrrolidine-2-carboxylic acid;

(2S,3S,4S,5S)-3-tert-butyl-4-[(6-chloro-3-cyano-5-fluoropyridin-2-yl)amino]-1-(cyclohexanecarbonyl)-5-phenylpyrrolidine-2-carboxylic acid;

(2S,3S,4S,5S)-3-tert-butyl-4-[(6-chloro-4-cyanopyridin-2-yl)amino]-1-(cyclohexanecarbonyl)-5-phenylpyrrolidine-2-carboxylic acid;

(2S,3S,4S,5S)-3-tert-butyl-4-{[6-chloro-4-(2-hydroxypropan-2-yl)pyridin-2-yl]amino}-1-(cyclohexanecarbonyl)-5-phenylpyrrolidine-2-carboxylic acid;

(2S,3S,4S,5S)-3-tert-butyl-4-[(3-cyano-4,6-dimethylpyridin-2-yl)amino]-1-(cyclohexanecarbonyl)-5-phenylpyrrolidine-2-carboxylic acid;

(2S,3S,4S,5S)-3-tert-butyl-4-[(7-chloro-3-ethylquinolin-2-yl)amino]-1-(cyclohexanecarbonyl)-5-phenylpyrrolidine-2-carboxylic acid;

(2S,3S,4S,5S)-4-[(6-anilino-3-cyanopyridin-2-yl)amino]-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-[(7-methoxy-4-methylquinolin-2-yl)amino]-5-phenylpyrrolidine-2-carboxylic acid;

(2S,3S,4S,5S)-3-tert-butyl-1-(cyclohexanecarbonyl)-4-[(4-ethoxyquinolin-2-yl)amino]-5-phenylpyrrolidine-2-carboxylic acid;

(2S,3S,4S,5S)-3-tert-butyl-1-(cyclohexanecarbonyl)-4-({5-[(2-oxopyridin-1(2H)-yl)methyl]pyridin-2-yl}amino)-5-phenylpyrrolidine-2-carboxylic acid;

(2S,3S,4S,5S)-3-tert-butyl-1-(cyclohexanecarbonyl)-4-[(7-methoxy-3-methylisoquinolin-1-yl)amino]-5-phenylpyrrolidine-2-carboxylic acid;

(2S,3S,4S,5S)-3-tert-butyl-4-{[5-(tert-butylcarbamoyl)pyridin-2-yl]amino}-1-(cyclohexanecarbonyl)-5-phenylpyrrolidine-2-carboxylic acid;

(2S,3S,4S,5S)-3-tert-butyl-1-(cyclohexanecarbonyl)-4-[(isoquinolin-3-yl)amino]-5-phenylpyrrolidine-2-carboxylic acid;

(2S,3S,4S,5S)-3-tert-butyl-1-(cyclohexanecarbonyl)-4-[(1,3-dimethyl-2,4-dioxo-1,2,3,4-tetrahydropyrido[4,3-d]pyrimidin-5-yl)amino]-5-phenylpyrrolidine-2-carboxylic acid;

(2S,3S,4S,5S)-3-tert-butyl-4-{[5-(2-cyanopropan-2-yl)pyridin-2-yl]amino}-1-(cyclohexanecarbonyl)-5-phenylpyrrolidine-2-carboxylic acid;

(2S,3S,4S,5S)-3-tert-butyl-4-{[5-(1-cyanocyclopropyl)pyridin-2-yl]amino}-1-(cyclohexanecarbonyl)-5-phenylpyrrolidine-2-carboxylic acid;

(2S,3S,4S,5S)-4-{[3-(benzyloxy)pyridin-2-yl]amino}-3-tert-butyl-1-(cyclohexanecarbonyl)-5-phenylpyrrolidine-2-carboxylic acid;

(2S,3S,4S,5S)-3-tert-butyl-4-{[5-(tert-butylcarbamoyl)pyridin-3-yl]amino}-1-(cyclohexanecarbonyl)-5-phenylpyrrolidine-2-carboxylic acid;

(2S,3S,4S,5S)-3-tert-butyl-1-(cyclohexanecarbonyl)-4-[(isoquinolin-4-yl)amino]-5-phenylpyrrolidine-2-carboxylic acid;

(2S,3S,4S,5S)-3-tert-butyl-4-({[2-methoxy-4-(trifluoromethyl)phenyl]methyl}amino)-5-phenyl-1-(pyridine-3-carbonyl)pyrrolidine-2-carboxylic acid;

(2S,3S,4S,5R)-3-tert-butyl-5-(3-chloropyridin-2-yl)-1-(cyclohexanecarbonyl)-4-({[2-methoxy-5-(trifluoromethyl)phenyl]methyl}amino)pyrrolidine-2-carboxylic acid;

(2R,3R,4R,5R)-3-tert-butyl-4-({[2-methoxy-5-(trifluoromethyl)pyridin-3-yl]methyl}amino)-1-[(2S)-oxane-2-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-[(4-chlorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(cyclohexylacetyl)-5-phenylpyrrolidine-2-carboxylic acid;

(2S,3S,4S,5S)-4-({[5-(butan-2-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-1-(cyclohexanecarbonyl)-4-({[5-(cyclohexylmethyl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[5-(2-ethylbutyl)-2-methoxyphenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(1-phenylethyl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(3,4-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-[(2,4-difluorophenyl)acetyl]-5-phenylpyrrolidine-2-carboxylic acid;

(2S,3S,4S,5S)-3-tert-butyl-4-{[(5-tert-butyl-2-methoxyphenyl)methyl]amino}-1-(4-methylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3-methylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1,5-dimethyl-4-oxo-1,4-dihydropyridine-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(1-methyl-1H-indole-3-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(6-fluoro-2H,4H-1,3-benzodioxine-8-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-[2-(propan-2-yl)oxane-4-carbonyl]pyrrolidine-2-carboxylic acid;

(2S,3S,4S,5S)-3-tert-butyl-1-(cyclohexanecarbonyl)-4-{[(2-hydroxyquinolin-3-yl)methyl]amino}-5-phenylpyrrolidine-2-carboxylic acid;

(2S,3S,4S,5S)-3-tert-butyl-1-(cyclohexanecarbonyl)-4-({[2-methoxy-5-(morpholin-4-yl)phenyl]methyl}amino)-5-phenylpyrrolidine-2-carboxylic acid;

(2S,3S,4S,5S)-3-tert-butyl-4-{[(5-tert-butyl-2-methoxyphenyl)methyl]amino}-1-[(S*)-2-(4-chloro-3-methyl-1H-pyrazol-1-yl)propanoyl]-5-phenylpyrrolidine-2-carboxylic acid;

(2S,3S,4S,5S)-3-tert-butyl-1-(cyclohexanecarbonyl)-5-[2-(dimethylamino)pyridin-3-yl]-4-({[2-methoxy-5-(tricyclo[3.3.1.1$^{3,7}$]decan-1-yl)phenyl]methyl}amino)pyrrolidine-2-carboxylic acid;

(2S,3S,4S,5S)-3-tert-butyl-1-(cyclohexanecarbonyl)-4-({[2-methoxy-5-(4-methylpiperazin-1-yl)phenyl]methyl}amino)-5-phenylpyrrolidine-2-carboxylic acid;

(2S,3S,4S,5S)-3-tert-butyl-1-[(1S)-3,3-difluorocyclohexane-1-carbonyl]-4-({[2-methoxy-5-(trifluoromethyl)phenyl]methyl}amino)-5-phenylpyrrolidine-2-carboxylic acid;

(2S,3S,4S,5S)-3-tert-butyl-1-(cyclohexanecarbonyl)-4-({[2-methoxy-5-(1-methyl-1H-pyrazol-4-yl)phenyl]methyl}amino)-5-phenylpyrrolidine-2-carboxylic acid;

(2S,3S,4S,5S)-3-tert-butyl-1-(cyclohexanecarbonyl)-4-({[5-(1-cyclopropyl-1H-pyrazol-4-yl)-2-methoxyphenyl]methyl}amino)-5-phenylpyrrolidine-2-carboxylic acid;

(2S,3S,4S,5S)-3-tert-butyl-1-(cyclohexanecarbonyl)-5-(2-fluorophenyl)-4-[({2-methoxy-5-[(1S,3S)-tricyclo[3.3.1.1$^{3,7}$]decan-1-yl]phenyl}methyl)amino]pyrrolidine-2-carboxylic acid;

(2S,3S,4S,5S)-1-(cyclohexanecarbonyl)-4-({[2-methoxy-5-(trifluoromethyl)pyridin-3-yl]methyl}amino)-3-(1-methylcyclopropyl)-5-phenylpyrrolidine-2-carboxylic acid;

(2S,3S,4S,5S)-3-tert-butyl-4-{[(5-tert-butyl-2-methoxyphenyl)methyl]amino}-1-[2-(3,5-dimethylphenoxy)propanoyl]-5-phenylpyrrolidine-2-carboxylic acid;

(2S,3S,4S,5S)-3-tert-butyl-4-{[(5-tert-butyl-2-methoxyphenyl)methyl]amino}-5-phenyl-1-(1,2,3,4-tetrahydronaphthalene-2-carbonyl)pyrrolidine-2-carboxylic acid;

(2S,3S,4S,5S)-3-tert-butyl-4-{[(5-tert-butyl-2-methoxyphenyl)methyl]amino}-5-phenyl-1-[(1R,5S)-tricyclo[3.2.1.0$^{2,4}$]octane-3-carbonyl]pyrrolidine-2-carboxylic acid;

(2S,3S,4S,5S)-3-tert-butyl-4-{[(5-tert-butyl-2-methoxyphenyl)methyl]amino}-5-phenyl-1-[2-(thiophen-2-yl)cyclopropane-1-carbonyl]pyrrolidine-2-carboxylic acid;

(2S,3S,4S,5S)-3-tert-butyl-4-{[(5-tert-butyl-2-methoxyphenyl)methyl]amino}-1-[1-(3-methylphenyl)-5-(propan-2-yl)-1H-pyrazole-4-carbonyl]-5-phenylpyrrolidine-2-carboxylic acid;

(2S,3S,4S,5S)-3-tert-butyl-4-{[(5-tert-butyl-2-methoxyphenyl)methyl]amino}-1-(2-methylcyclohexane-1-carbonyl)-5-phenylpyrrolidine-2-carboxylic acid;

(2S,3S,4S,5S)-3-tert-butyl-1-(3,5-dimethylcyclohexane-1-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-1-(3,3-dimethylcyclopentane-1-carbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)phenyl]methyl}amino)-1-(3-methylcyclopentane-1-carbonyl)-5-phenylpyrrolidine-2-carboxylic acid;

(2R,3R,4R,5S)-3-tert-butyl-1-(cyclohexanecarbonyl)-4-({[2-methoxy-5-(trifluoromethyl)phenyl]methyl}amino)-5-phenylpyrrolidine-2-carboxylic acid;

(2S,3S,4S,5S)-3-tert-butyl-4-({[2-methoxy-5-(trifluoromethyl)pyridin-3-yl]methyl}amino)-5-phenyl-1-{(2R,3R)-3-[(1H-pyrazol-1-yl)methyl]oxolane-2-carbonyl}pyrrolidine-2-carboxylic acid;

(2S,3S,4S,5S)-3-tert-butyl-1-(3,5-dimethylcyclohexane-1-carbonyl)-4-({[2-methoxy-5-(trifluoromethyl)pyridin-3-yl]methyl}amino)-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-1-(cyclohexanecarbonyl)-5-phenylpyrrolidine-2-carboxylic acid;

(2S,3S,4S,5S)-3-tert-butyl-4-{[(5-tert-butyl-2-methoxyphenyl)methyl]amino}-1-(3,3-dimethylcyclohexane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-1-(2,2-dimethylcyclopentane-1-carbonyl)-5-phenylpyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-(2-methylcyclohexane-1-carbonyl)pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[3-(trifluoromethyl)cyclohexane-1-carbonyl]pyrrolidine-2-carboxylic acid;

(2S,3S,4S,5S)-3-(tert-butyl)-4-(((5-cyclobutyl-2-methoxypyridin-3-yl)methyl)amino)-1-(3,5-dimethylcyclohexanecarbonyl)-5-phenylpyrrolidine-2-carboxylic acid;

(2S,3S,4S,5S)-3-tert-butyl-4-{[(5-cyclobutyl-2-methoxypyridin-3-yl)methyl]amino}-1-(2-methylcyclohexane-1-carbonyl)-5-phenylpyrrolidine-2-carboxylic acid;

(2S,3S,4S,5S)-3-tert-butyl-4-{[(5-cyclobutyl-2-methoxypyridin-3-yl)methyl]amino}-5-phenyl-1-[3-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-5-[2-(dimethylamino)pyridin-3-yl]-1-[(2R*)-6-fluoro-3,4-dihydro-2H-1-benzopyran-2-carbonyl]pyrrolidine-2-carboxylic acid;

(2S,3S,4S,5S)-3-tert-butyl-5-[2-(dimethylamino)pyridin-3-yl]-1-(cis-4-hydroxy-4-propylcyclohexane-1-carbonyl)-4-{[2-methoxy-5-(trifluoromethyl)pyridin-3-yl]amino}pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(1S,2S)-2-(trifluoromethyl)cyclohexane-1-carbonyl]pyrrolidine-2-carboxylic acid;

(2S,3S,4S,5S)-3-tert-butyl-5-[2-(dimethylamino)pyridin-3-yl]-4-{[2-methoxy-5-(trifluoromethyl)pyridin-3-yl]amino}-1-[(2R)-oxane-2-carbonyl]pyrrolidine-2-carboxylic acid;

(2S,3S,4S,5S)-3-tert-butyl-4-{[(5-cyclobutyl-2-methoxypyridin-3-yl)methyl]amino}-5-phenyl-1-[2-(trifluoromethyl)cyclohexane-1-carbonyl]pyrrolidine-2-carboxylic acid;

(2S,3S,4S,5S)-3-tert-butyl-4-{[(5-tert-butyl-2-methoxyphenyl)methyl]amino}-1-[(2R)-2-methoxy-2-phenylacetyl]-2-methyl-5-phenylpyrrolidine-2-carboxylic acid;

(2S,3S,4S,5S)-3-tert-butyl-5-[2-(dimethylamino)pyridin-3-yl]-4-{[6-methyl-4-(trifluoromethyl)pyridin-2-yl]amino}-1-[(2R)-oxane-2-carbonyl]pyrrolidine-2-carboxylic acid;

(2S,3S,4S,5S)-3-tert-butyl-4-{[(5-tert-butyl-2-methoxyphenyl)methyl]amino}-1-[di(propan-2-yl)carbamoyl]-5-phenylpyrrolidine-2-carboxylic acid;

(2S,3S,4S,5S)-4-({[5-(bicyclo[1.1.1]pentan-1-yl)-2-methoxyphenyl]methyl}amino)-3-tert-butyl-5-[2-(difluoromethoxy)pyridin-3-yl]-1-{[(propan-2-yl)oxy]carbonyl}pyrrolidine-2-carboxylic acid;

(2S,3S,4S,5S)-3-tert-butyl-4-{[(6-tert-butyl-2-methoxypyridin-3-yl)methyl]amino}-5-[2-(dimethylamino)

pyridin-3-yl]-1-{[(propan-2-yl)oxy]
carbonyl}pyrrolidine-2-carboxylic acid;
(2S,3S,4S,5S)-4-({[5-(bicyclo[1.1.1]pentan-1-yl)-2-methoxyphenyl]methyl}amino)-3-tert-butyl-1-{[(propan-2-yl)oxy]carbonyl}-5-[2-(propan-2-yl)phenyl]pyrrolidine-2-carboxylic acid;
(2S,3S,4S,5S)-3-(bicyclo[1.1.1]pentan-1-yl)-4-({[2-methoxy-5-(trifluoromethyl)pyridin-3-yl]methyl}amino)-5-phenyl-1-{[(propan-2-yl)oxy]carbonyl}pyrrolidine-2-carboxylic acid;
(2S,3S,4S,5S)-3-(bicyclo[1.1.1]pentan-1-yl)-4-{[(5-tert-butyl-2-methoxyphenyl)methyl]amino}-5-(2-fluorophenyl)-1-{[(propan-2-yl)oxy]carbonyl}pyrrolidine-2-carboxylic acid;
(2S,3S,4S,5S)-3-tert-butyl-5-[2-(dimethylamino)pyridin-3-yl]-4-[({2-methoxy-5-[(3S,5S)-tricyclo[3.3.1.1$^{3,7}$]decan-1-yl]phenyl}methyl)amino]-1-{[(propan-2-yl)oxy]carbonyl}pyrrolidine-2-carboxylic acid;
(2S,3S,4S,5S)-3-tert-butyl-4-{[(5-cyclobutyl-2-methoxypyridin-3-yl)methyl]amino}-5-[2-(dimethylamino)pyridin-3-yl]-1-{[(propan-2-yl)oxy]carbonyl}pyrrolidine-2-carboxylic acid;
(2S,3S,4S,5S)-3-tert-butyl-5-[2-(dimethylamino)pyridin-3-yl]-4-[({2-methoxy-5-[(trifluoromethyl)sulfanyl]phenyl}methyl)amino]-1-{[(propan-2-yl)oxy]carbonyl}pyrrolidine-2-carboxylic acid;
(2S,3S,4S,5S)-3-tert-butyl-4-{[(6-methoxy-2,3-dihydro-1H-inden-5-yl)methyl]amino}-5-phenyl-1-{[(propan-2-yl)oxy]carbonyl}pyrrolidine-2-carboxylic acid;
(2S,3S,4S,5S)-3-tert-butyl-4-{[(3-methoxy-5,5,8,8-tetramethyl-5,6,7,8-tetrahydronaphthalen-2-yl)methyl]amino}-5-phenyl-1-{[(propan-2-yl)oxy]carbonyl}pyrrolidine-2-carboxylic acid;
rac-(2S,3S,4S,5S)-3-tert-butyl-4-{[(5-tert-butyl-2-methoxyphenyl)methyl]amino}-1-(cyclohexanecarbonyl)-5-(1-methyl-2-oxo-1,2-dihydropyridin-3-yl)pyrrolidine-2-carboxylic acid;
(2S,3S,4S,5S)-3-tert-butyl-4-{[(5-tert-butyl-2-methoxyphenyl)methyl]amino}-1-{[(propan-2-yl)oxy]carbonyl}-5-{2-[(propan-2-yl)oxy]pyridin-3-yl}pyrrolidine-2-carboxylic acid;
(2S,3S,4S,5S)-3-tert-butyl-4-{[(5-tert-butyl-2-methoxyphenyl)methyl]amino}-1-[(7S)-2,2-difluoro-7-methyl-6,7-dihydro-2H-furo[2,3-f][1,3]benzodioxole-7-carbonyl]-5-(2-methoxypyridin-3-yl)pyrrolidine-2-carboxylic acid;
(2S,3S,4S,5S)-3-tert-butyl-4-({[2-methoxy-5-(trifluoromethoxy)phenyl]methyl}amino)-1-{[(propan-2-yl)oxy]carbonyl}-5-{2-[(propan-2-yl)oxy]pyridin-3-yl}pyrrolidine-2-carboxylic acid;
(2S,3S,4S,5S)-3-tert-butyl-5-[2-(dimethylamino)pyridin-3-yl]-4-({[2-methoxy-5-(2-methylbutan-2-yl)phenyl]methyl}amino)-1-{[(propan-2-yl)oxy]carbonyl}pyrrolidine-2-carboxylic acid;
(2S,3S,4S,5S)-3-tert-butyl-4-({[2-methoxy-5-(1-methylcyclobutyl)phenyl]methyl}amino)-5-(2-methoxypyridin-3-yl)-1-[(2S)-oxane-2-carbonyl]pyrrolidine-2-carboxylic acid;
(2S,3S,4S,5S)-3-tert-butyl-4-({[2-methoxy-5-(1-methylcyclobutyl)phenyl]methyl}amino)-5-(2-methoxypyridin-3-yl)-1-[(2R)-oxane-2-carbonyl]pyrrolidine-2-carboxylic acid;
(2S,3S,4S,5S)-3-tert-butyl-5-phenyl-1-{[(propan-2-yl)oxy]carbonyl}-4-({[1-(propan-2-yl)piperidin-4-yl]methyl}amino)pyrrolidine-2-carboxylic acid;
(2R,3R,4R,5R)-3-tert-butyl-5-(2-chlorophenyl)-4-{[(5-cyclobutyl-2-methoxypyridin-3-yl)methyl]amino}-1-[(2S)-oxolane-2-carbonyl]pyrrolidine-2-carboxylic acid; and
(2S,3S,4S,5S)-3-tert-butyl-4-({[2-hydroxy-5-(methoxycarbonyl)phenyl]methyl}amino)-1-[(2S)-oxolane-2-carbonyl]-5-[2-(propan-2-yl)phenyl]pyrrolidine-2-carboxylic acid.

10. A pharmaceutical composition comprising a therapeutically effective amount of a compound of Formula (I) according to claim 1, or a pharmaceutically acceptable salt thereof, in combination with a pharmaceutically acceptable carrier.

11. A compound of claim 1, or a pharmaceutically acceptable salt thereof for use in medicine.

12. A compound of claim 1, or a pharmaceutically acceptable salt thereof for use in the treatment of cystic fibrosis.

13. A method for treating cystic fibrosis in a subject comprising administering a therapeutically effective amount of a compound of Formula (I) according to claim 1, or a pharmaceutically acceptable salt thereof, to a subject in need thereof.

14. A pharmaceutical composition comprising a compound of claim 1, or a pharmaceutically acceptable salt thereof, one potentiator, and one or more additional correctors.

15. A method for treating cystic fibrosis in a subject comprising administering a compound of claim 1, or a pharmaceutically acceptable salt thereof, one potentiator, and one or more additional correctors, to a subject in need thereof.

16. A pharmaceutical composition comprising a compound of claim 1, or a pharmaceutically acceptable salt thereof, and one or more additional therapeutic agents.

17. The pharmaceutical composition of claim 16 wherein the additional therapeutic agents are selected from the group consisting of CFTR modulators and CFTR amplifiers.

18. The pharmaceutical composition of claim 16 wherein the additional therapeutic agents are CFTR modulators.

19. A method for treating cystic fibrosis in a subject comprising administering a compound of claim 1, or a pharmaceutically acceptable salt thereof, and one or more additional therapeutic agents.

20. The method of claim 19 wherein the additional therapeutic agents are selected from the group consisting of CFTR modulators and CFTR amplifiers.

21. The method of claim 19 the wherein the additional therapeutic agents are CFTR modulators.

22. A pharmaceutical composition of claim 10 for use in medicine.

23. A pharmaceutical composition of claim 10 for use in the treatment of cystic fibrosis.

* * * * *

UNITED STATES PATENT AND TRADEMARK OFFICE
CERTIFICATE OF CORRECTION

PATENT NO. : 9,981,910 B2
APPLICATION NO. : 15/726075
DATED : May 29, 2018
INVENTOR(S) : Robert J. Altenbach et al.

It is certified that error appears in the above-identified patent and that said Letters Patent is hereby corrected as shown below:

Column 12, Line 18, "$[3.3.1.1^{3,7}]$" should be --$[3.3.1.1^{3,7}]$--.

Column 12, Line 19, "$[3.3.1.1^{3,7}]$" should be --$[3.3.1.1^{3,7}]$--.

Column 12, Line 49, "Sand" should be --S and--.

Column 12, Line 50, "Sand" should be --S and--.

Column 16, Line 17, "RU" should be --$R^u$--.

Column 16, Line 21, "-OC(O)N(R')$_2$" should be -- -OC(O)N(R$^j$)$_2$--.

Column 16, Line 21, "-S(O)$_2$R" should be -- -S(O)$_2$R$^j$--.

Column 26, Line 27, "$R^{3A}$together" should be --$R^{3A}$, together--.

Column 30, Line 66, "$C_3$-$C_1$" should be --$C_3$-$C_{11}$--.

Column 32, Line 63, "$C_3$-$C_1$" should be --$C_3$-$C_{11}$--.

Column 39, Line 59, "buty" should be --butyl--.

Column 43, Line 50, "-4l-" should be -- -4- --.

Column 58, Line 40, "4-[pyridin-2-yl)" should be --4-[(pyridin-2-yl)--.

Column 93, Line 37, "1-pyridin" should be --$1\lambda^5$-pyridin--.

Column 94, Line 60, "[3.1.O]" should be --[3.1.0]--.

Signed and Sealed this
Twenty-eighth Day of August, 2018

Andrei Iancu
*Director of the United States Patent and Trademark Office*

CERTIFICATE OF CORRECTION (continued)
U.S. Pat. No. 9,981,910 B2

Column 95, Line 37, "[3.1. O]" should be --[3.1.0]--.

Column 101, Line 13, "[3.3.1.1$^{37}$]" should be --[3.3.1.1$^{3,7}$]--.

Column 128, Line 32, "L-4-12" should be --L$^1$-4-12--.

Column 131, Line 18, "R's" should be --R$^{18}$--.

Column 132, Line 56, "L-5-11" should be --L$^1$-5-11--.

Column 133, Line 62, "($C_1$-$C_6$ alkylene)" should be --($C_1$-$C_6$ alkylene)$_x$--.

Column 133, Line 63, "($C_1$-$C_6$ alkylene)" should be --($C_1$-$C_6$ alkylene)$_x$--.

Column 133, Line 64, "($C_1$-$C_6$ alkylene)" should be --($C_1$-$C_6$ alkylene)$_x$--.

Column 135, Line 41, "OR$^2$" should be --OR$^{12}$--.

Column 135, Line 41, "NR$^{13R14}$" should be --NR$^{13}$R$^{14}$--.

Column 135, Line 46, "$C_3$-$C_1$" should be --$C_3$-$C_{11}$--.

Column 137, Line 28, "$C_3$-$C_1$" should be --$C_3$-$C_{11}$--.

Column 137, Line 67, "$C_3$-$C_1$" should be --$C_3$-$C_{11}$--.

Column 138, Line 24, "OR$^{15}$" should be --OR$^{15}$,--.

Column 142, Line 58, "alkylene)-4-12" should be --alkylene)$_x$-4-12--.

Column 143, Line 11, "R$^5$" should be --R$^{15}$--.

Column 145, Line 23, "R$^2$" should be --R$^{12}$--.

Column 154, Line 31, "[2,3-J]" should be --[2,3-*f*]--.

Column 163, Line 63, "diazabicycioundec" should be --diazabicycloundec--.

Column 182, Line 46, "00" should be --0°--.

Column 203, Line 37, "3A" should be --3Å--.

Column 237, Line 57, "60 mol" should be --60 μmol--.

Column 268, Line 25, "2*R*,3*S*,4*R*,5*RS*" should be --2*R*,3*S*,4*R*,5*R*--.

CERTIFICATE OF CORRECTION (continued)
U.S. Pat. No. 9,981,910 B2

Column 297, Line 16, "5.77" should be --5,77--.

Column 327, Line 33, "[1.1.1.1]" should be --[1.1.1]--.

Column 402, Line 8, "84 mol" should be --84 µmol--.

Column 629, Line 19, "II-182" should be --III-182--.

Column 644, Line 37, Claim 9, "(2S,3S,4S,5)" should be --(2S,3S,4S,5S)--.

Column 651, Line 53, Claim 9, "1-{[propan" should be --1-{[(propan--.

Column 662, Line 31, Claim 9, "1-{[propan" should be --1-{[(propan--.

Column 665, Line 34, Claim 9, "1-{[propan" should be --1-{[(propan--.

Column 667, Line 57, Claim 9, "(2S,3S,4S,55)" should be --(2S,3S,4S,5S)--.

Column 667, Line 61, Claim 9, "(2S,3S,4S,55)" should be --(2S,3S,4S,5S)--.

Column 667, Line 65, Claim 9, "(2S,3S,4S,5)" should be --(2S,3S,4S,5S)--.

Column 670, Line 6, Claim 9, "1-{[propan" should be --1-{[(propan--.

Column 678, Line 59, Claim 9, "(2S,3S,4S,5SS)" should be --(2S,3S,4S,5S)--.

Column 690, Line 2, Claim 9, "6a*" should be --6aS*--.

Column 697, Line 13, Claim 9, "1-{[propan" should be --1-{[(propan--.

Column 699, Line 35, Claim 9, "(2S,3S,4S,55)" should be --(2S,3S,4S,5S)--.

Column 701, Line 18, Claim 9, "-1-pyridin" should be -- -1$\lambda^5$-pyridin--.

Column 704, Line 35, Claim 9, "1-{[propan" should be --1-{[(propan--.